US010799523B2

(12) United States Patent
Olson et al.

(10) Patent No.: US 10,799,523 B2
(45) Date of Patent: Oct. 13, 2020

(54) TAU ANTISENSE OLIGOMERS AND USES THEREOF

(71) Applicant: F. Hoffmann-La Roche AG, Basel (CH)

(72) Inventors: Richard E. Olson, Orange, CT (US); Angela M. Cacace, Higganum, CT (US); Peter Hagedorn, Horsholm (DK); Anja Mølhart Høg, Hillerød (DK); Dong Li, East Lyme, CT (US); Jeffrey M. Brown, Medway, MA (US); Marianne Lerbech Jensen, Køge (DK); Niels Fisker Nielsen, Kgs. Lyngby (DK); Stephen E. Mercer, Middleton, CT (US)

(73) Assignee: F. HOFFMANN-LA ROCHE AG, Basel (CH)

( * ) Notice: Subject to any disclaimer, the term of this patent is extended or adjusted under 35 U.S.C. 154(b) by 0 days.

(21) Appl. No.: 15/016,169

(22) Filed: Feb. 4, 2016

(65) Prior Publication Data

US 2016/0237427 A1 Aug. 18, 2016

Related U.S. Application Data

(60) Provisional application No. 62/112,058, filed on Feb. 4, 2015, provisional application No. 62/156,684, filed on May 4, 2015, provisional application No. 62/237,922, filed on Oct. 6, 2015, provisional application No. 62/238,941, filed on Oct. 8, 2015, provisional application No. 62/279,612, filed on Jan. 15, 2016, provisional application No. 62/279,614, filed on Jan. 15, 2016, provisional application No. 62/279,610, filed on Jan. 15, 2016.

(51) Int. Cl.

| | |
|---|---|
| ***A61K 31/712*** | (2006.01) |
| ***C12N 15/113*** | (2010.01) |
| ***A61P 25/28*** | (2006.01) |

(52) U.S. Cl.

CPC ............ *A61K 31/712* (2013.01); *A61P 25/28* (2018.01); *C12N 15/113* (2013.01); *A61K 2121/00* (2013.01); *C12N 2310/11* (2013.01); *C12N 2310/315* (2013.01); *C12N 2310/3231* (2013.01); *C12N 2310/341* (2013.01); *C12N 2310/343* (2013.01); *C12N 2310/346* (2013.01)

(58) Field of Classification Search

None

See application file for complete search history.

(56) References Cited

U.S. PATENT DOCUMENTS

| | | | |
|---|---|---|---|
| 4,683,195 A | 7/1987 | Mullis et al. | |
| 5,166,195 A | 11/1992 | Ecker | |
| 5,248,670 A | 9/1993 | Draper et al. | |
| 5,264,423 A | 11/1993 | Cohen et al. | |
| 5,271,941 A | 12/1993 | Cho-chung | |
| 6,582,908 B2 * | 6/2003 | Fodor | B01J 19/0046 435/288.3 |
| 6,617,442 B1 | 9/2003 | Crooke et al. | |
| 7,015,315 B1 | 3/2006 | Cook et al. | |
| 7,399,845 B2 | 7/2008 | Seth et al. | |
| 7,919,472 B2 | 4/2011 | Monia et al. | |
| 8,580,756 B2 | 11/2013 | Hansen et al. | |
| 8,703,728 B2 | 4/2014 | Swayze et al. | |
| 9,243,291 B1 | 1/2016 | Burel | |
| 2010/0197762 A1 * | 8/2010 | Swayze | C12N 15/111 514/44 A |
| 2011/0130441 A1 | 6/2011 | Seth et al. | |
| 2012/0322851 A1 | 12/2012 | Hardee et al. | |
| 2014/0107330 A1 | 4/2014 | Freier et al. | |
| 2015/0275205 A1 * | 10/2015 | Miller | C07H 21/02 514/44 A |
| 2016/0032285 A1 | 2/2016 | Rigo et al. | |
| 2016/0138014 A1 | 5/2016 | Kordasiewicz et al. | |
| 2016/0145617 A1 * | 5/2016 | Kordasiewicz | C07H 21/02 514/44 A |

FOREIGN PATENT DOCUMENTS

| | | |
|---|---|---|
| EP | 2092065 B1 | 1/2012 |
| EP | 2410054 A1 | 1/2012 |
| EP | 1799859 B1 | 7/2014 |
| EP | 2410053 B1 | 10/2014 |
| EP | 1670896 B1 | 1/2015 |
| WO | WO 00/40614 A2 | 7/2000 |
| WO | WO 2004/046160 A2 | 6/2004 |
| WO | WO 2004/069992 A2 | 8/2004 |
| WO | WO 2007/031091 A2 | 3/2007 |
| WO | WO 2007/134181 A2 | 11/2007 |
| WO | WO 2007/146511 A2 | 12/2007 |
| WO | WO 2008/113832 A2 | 9/2008 |

(Continued)

OTHER PUBLICATIONS

Bojarski, L., et al., "Calcium dysregulation in Alzheimer's disease," *Neurochemistry International* 52(4-5):621-633, Elsevier Ltd., England (2008).

Gordon, D., et al., "Antisense Suppression of Tau in Cultured Rat Oligodendrocytes Inhibits Process Formation," *Journal of Neuroscience Research* 86(12):2591-2601, Wiley-Liss, Inc., United States (2008).

Takagi-Sato, M., et al., "Fine-Tuning of ENA® Gapmers as Antisense Oligonucleotides for Sequence-Specific Inhibition," *Oligonucleotides* 17(3):291-301, Maly Ann Liebert, Inc., United States (2007).

(Continued)

*Primary Examiner* — Richard A Schnizer

(74) *Attorney, Agent, or Firm* — Holland & Hart LLP

(57) ABSTRACT

The present invention relates to oligomer compounds (oligomers), which target Tau mRNA in a cell, leading to reduced expression of Tau protein. Reduction of Tau protein expression is beneficial for the treatment of certain medical disorders, e.g., a neurological disorder.

8 Claims, 234 Drawing Sheets

Specification includes a Sequence Listing.

(56) References Cited

FOREIGN PATENT DOCUMENTS

| | | |
|---|---|---|
| WO | WO 2008/150729 A2 | 12/2008 |
| WO | WO 2008/154401 A2 | 12/2008 |
| WO | WO 2009/006478 A2 | 1/2009 |
| WO | WO 2009/067647 A1 | 5/2009 |
| WO | WO 2009/090182 A1 | 7/2009 |
| WO | WO 2009/100320 A2 | 8/2009 |
| WO | WO 2009/124295 A2 | 10/2009 |
| WO | WO 2010/036698 A1 | 4/2010 |
| WO | WO 2011/017521 A2 | 2/2011 |
| WO | WO 2011/085102 A1 | 7/2011 |
| WO | WO 2011/115818 A1 | 9/2011 |
| WO | WO 2012/109395 A1 | 8/2012 |
| WO | WO 2013/148260 A1 | 10/2013 |
| WO | WO 2013/148283 A1 | 10/2013 |
| WO | WO 2013/159108 A2 | 10/2013 |
| WO | WO 2014/059341 A2 | 4/2014 |
| WO | WO 2014/153236 A1 | 9/2014 |
| WO | WO 2015/006705 A2 | 1/2015 |
| WO | WO 2015/010135 A2 | 1/2015 |
| WO | WO 2016/019063 A1 | 2/2016 |

OTHER PUBLICATIONS

Yu, J.T., et al., "Calcium dysregulation in Alzheimer's disease: From mechanisms to therapeutic opportunities," *Progress in Neurobiology* 89(3):240-255, Elsevier Ltd., England (2009).

Partial International Search Report for International Application No. PCT/US2016/016646, International Searching Authority, European Patent Office, Rijswijk, Netherlands, dated May 2, 2016, 4 pages.

Boehmerle, W., et al., "Paclitaxel induces calcium oscillations via an inositol 1,4,5-trisphosphate receptor and neuronal calcium sensor 1-dependent mechanism," *Proceedings of the National Academy of Sciences USA* 103(48):18356-18361, National Academy of Sciences, United States (2006).

Cao, Z., et al., "Tetramethylenedisulfotetramine Alters $Ca^{2+}$ Dynamics in Cultured Hippocampal Neurons: Mitigation by NMDA Receptor Blockade and $GABA_A$ Receptor-Positive Modulation," *Toxicological Sciences* 130(2):362-372, Oxford University Press, England (2012).

Frieden, M., et al., "Expanding the design horizon of antisense oligonucleotides with alpha-L-LNA," *Nucleic Acids Research* 31(21):6365-6372, Oxford University Press, England (2003).

He, S.J., et al., "Caffeine-dependent stimulus-triggered oscillations in the CA3 region of hippocampal slices from rats chronically exposed to lead," *Experimental Neurology* 190(2):525-534, Elsevier Inc., United States (2004).

Jepsen, J.S., "Downregulation of $p21^{(WAF1/CIP1)}$ and Estrogen Receptor α in MCF-7 Cells by Antisense Oligonucleotides Containing Locked Nucleic Acid (LNA)," *Oligonucleotides* 14(2):147-156, Maly Ann Liebert, Inc., United States (2004).

Kurreck, J., et al., "Design of antisense oligonucleotides stabilized by locked nucleic acids," *Nucleic Acids Res.* 30(9):1911-1918, Oxford University Press, England (2002).

Obika, S., et al., "Inhibition of ICAM-I gene expression by antisense 2',4'-BNA oligonucleotides," Nucleic Acids Symposium Series 1(1):145-146, Oxford University Press, England (2001).

Silahtaroglu, A.N., et al., "FISHing with locked nucleic acids (LNA): evaluation of different LNA/DNA mixmers," *Molecular and Cellular Probes* 17(4):165-169, Elsevier Ltd., England (2003).

Stanton, R., et al., "Chemical Modification Study of Antisense Gapmers," *Nucleic Acid Therapeutics* 22(5):344-359, Mary Ann Liebert, Inc., United States (2012).

Takagi-Sato, M., et al., "Design of ENA® gapmers as fine-tuning antisense oligonucleotides with sequence-specific inhibitory activity on mouse PADI4 mRNA expression," *Nucleic Acids Symposium Series* (*Oxford*) 50:319-320, Oxford University Press, England (2006).

International Search Report and Written Opinion for International Application No. PCT/US2016/016646, International Searching Authority, European Patent Office, Rijswijk, Netherlands, dated Jul. 8, 2016, 19 pages.

International Search Report and Written Opinion for International Application No. PCT/US2016/016652, International Searching Authority, European Patent Office, Rijswijk, Netherlands, dated Jul. 11, 2016, 17 pages.

International Search Report and Written Opinion for International Application No. PCT/US2016/016657, International Searching Authority, European Patent Office, Rijswijk, Netherlands, dated Apr. 28, 2016, 15 pages.

Altschul, S.F. and Gish, W., "Local Alignment Statistics," *Methods in Enzymology* 266:460-480, Academic Press, United States (1996).

Altschul, S.F., et al., "Gapped BLAST and PSI-BLAST: A New Generation of Protein Database Search Programs," *Nucleic Acids Research* 25(17):3389-3402, Oxford University Press, England (1997).

Andorfer, C., et al., "Hyperphosphorylation and Aggregation of Tau in Mice Expressing Normal Human Tau Isoforms," *Journal of Neurochemistry* 86(3):582-590, Wiley on behalf of the International Society for Neurochemistry, England (2003).

Barciszewski, J., et al., "Locked Nucleic Acid Aptamers," in *Nucleic Acid and Peptide Aptamers; Methods and Protocols,* Chapter 10, vol. 535, Mayer, G., ed., pp. 165-186, Humana Press, United States (2009).

Barten, D.M., et al., "Tau Transgenic Mice as Models for Cerebrospinal Fluid Tau Biomarkers," *Journal of Alzheimer's Disease* 24(Suppl 2):127-141, IOS Press, Netherlands (2011).

Christensen, U.B. and Pedersen, E.B., "Intercalating Nucleic Acids Containing Insertions of 1-o-(1-pyrenylmethyl)glycerol: Stabilisation of dsDNA and Discrimination of DNA over RNA," *Nucleic Acids Research* 30(22):4918-4925, Oxford University Press, England (2002).

Dass, C.R., "Vehicles for Oligonucleotide Delivery to Tumours," *The Journal of Pharmacy and Pharmacology* 54(1):3-27, Wiley, England (2002).

Dodart, J.C., et al., "Scopolamine-induced Deficits in a Two-trial Object Recognition Task in Mice," *NeuroReport* 8(5):1173-1178, Rapid Science Publishers, England (1997).

Dravid, S.M and Murray, T.F., "Spontaneous Synchronized Calcium Oscillations in Neocortical Neurons in the Presence of Physiological $[Mg^{2+}]$: Involvement of AMPA/kainate and Metabotropic Glutamate Receptors," *Brain Research* 1006(1):8-17, Elsevier B.V., Netherlands (2004).

Dyment, D.A., et al., "Homozygous nonsense mutation in SYNJ1 associated with intractable epilepsy and tau pathology," *Neurobiology of Aging* 36(2):1222.e1-1222.e5, Elsevier Inc., United States (published online Sep. 6 2014) (Feb. 2015).

Ennaceur, A. and Delacour, J., "A New One-trial Test for Neurobiological Studies of Memory in Rats. 1: Behavioral Data," *Behavioural Brain Research* 31(1):47-59, Elsevier/North-Holland Biomedical Press, Netherlands (1988).

Fluiter, K., et al., "Filling the Gap in LNA Antisense Oligo Gapmers: the Effects of Unlocked Nucleic Acid (UNA) and 4'-c-hydroxymethyl-DNA Modifications on Rnase H Recruitment and Efficacy of an LNA Gapmer," *Molecular BioSystems* 5(8):838-843, Royal Society of Chemistry, England (2009).

Freier, S.M. and Altmann, K.H., "The Ups and Downs of Nucleic Acid Duplex Stability: Structure-stability Studies on Chemically-modified DNA:RNA Duplexes," *Nucleic Acids Research* 25(22):4429-4443, Oxford University Press, England (1997).

Freshney, R.I., "Quantitation and Experimental Design," in *Culture of Animal Cells,* pp. 227-296, Alan R. Liss, Inc., United States (1987).

Frost, B., et al., "Connecting the dots between tau dysfunction and neurodegeneration," *Trends in Cell Biology* 25(1):46-53, Elsevier Ltd., England (Jan. 2015).

Genbank, "*Homo sapiens* chromosome 17, GRCh38.p2 Primary Assembly," Accession NC_000017.11, accessed at https://www.ncbi.nlm.nih.gov/nuccore/NC_000017, accessed on Apr. 18, 2016, 3 pages.

Genbank, "*Homo sapiens* microtubule associated protein tau (MAPT), RefSeqGene on chromosome 17," Accession NG_007398.1, accessed at https://www.ncbi.nlm.nih.gov/nuccore/NG_007398.1, accessed on Apr. 18, 2016, 37 pages.

(56) References Cited

OTHER PUBLICATIONS

Genbank, "*Homo sapiens* microtubule associated protein tau (MAPT), transcript variant 1, mRNA," Accession NM_016835.4, accessed at https://www.ncbi.nlm.nih.gov/nuccore/NM_016835, accessed on Apr. 18, 2016, 16 pages.
Genbank, "Microtubule-associated protein tau," Accession Q6QT54, accessed at https://www.ncbi.nlm.nih.gov/protein/Q6QT54?report=genpept, accessed on Apr. 18, 2016, 2 pages.
Genbank, "PREDICTED: Macaca fascicularis microtubule associated protein tau (MAPT), transcript variant X13, mRNA," Accession XM_005584540.1, accessed at https://www.ncbi.nlm.nih.gov/nuccore/XM 005584540.1, accessed on Apr. 18, 2016, 4 pages.
Genbank, "PREDICTED: Macaca fascicularis microtubule-associated protein tau (MAPT), transcript variant X1, mRNA," Accession XM_005584529.1, accessed at https://www.ncbi.nlm.nih.gov/nuccore/XM_005584529.1?report=genbank, accessed on Apr. 18, 2016, 4 pages.
Genbank, "RecName: Full=Microtubule-associated protein tau; AltName: Full=Neurofibrillary tangle protein; AltName: Full=Paired helical filament-tau; Short=PHF-tau," Accession P10636.5, accessed at http://www.ncbi.nlm.nih.gov/protein/P10636, accessed on Apr. 18, 2016, 38 pages.
Genbank, "Microtubule-associated protein tau," Accession No. Q5CZI7, accessed at http://www.ncbi.nlm.nih.gov/protein/Q5CZI7?report=genpept, accessed on Apr. 18, 2016, 2 pages.
Genbank, "Microtubule-associated Protein Tau, Fetal," Accession No. P18518, accessed at http://www.ncbi.nlm.nih.gov/protein/P18518?report=genpept, accessed on Apr. 18, 2016, 2 pages.
Genbank, "Microtubule-associated protein tau (Microtubule-associated protein tau, isoform 4)," Accession No. Q53YB1, accessed at http://www.ncbi.nlm.nih.gov/protein/Q53YB1?report=genpept, accessed on Apr. 18, 2016, 2 pages.
Gheyara, A.L., et al., "Tau Reduction Prevents Disease in a Mouse Model of Dravet Syndrome," *Annals of Neurology* 76(3):443-456, Wiley-Liss, United States (2014).
Holm, S., "A Simple Sequentially Rejective Multiple Test Procedure," *Scandinavian Journal of Statistics* 6:65-70, John Wiley & Sons, Inc., United States (1979).
Hou, C.E., et al., "Non-alzheimer's Disease Dementias: Anatomic, Clinical, and Molecular Correlates," *Canadian Journal of Psychiatry* 49(3):164-171, Sage, United States (2004).
Inoue, H., et al., "Elevation of Tau Protein Levels in the Cerebrospinal Fluid of Children with West Syndrome," *Epilepsy Research* 102(1-2):8-12, Elsevier B.V., Netherlands (2012).
Karlin, S. and Altschul, S.E., "Methods for Assessing the Statistical Significance of Molecular Sequence Features by using General Scoring Schemes," *Proceedings of the National Academy of Sciences of the USA* 87(6):2264-2268, National Academy of Sciences, United States (1990).
Karlin, S, and Altschul, S.F., "Applications and Statistics for Multiple High-Scoring Segments in Molecular Sequences," *Proceedings of the National Academy of Sciences USA* 90(12):5873-5877, National Academy of Sciences, United States (1993).
Laird, N.M. and Ware, J.H., "Random-effects Models for Longitudinal Data," *Biometrics* 38(4):963-974, Biometric Society, United States (1982).
Morris, R., "Developments of a Water-maze Procedure for Studying Spatial Learning in the Rat," *Journal of Neuroscience Methods* 11(1):47-60, Elsevier Science Publishers B.V., Netherlands (1984).
Moussaud, S., et al., "Alpha-synuclein and Tau: Teammates in Neurodegeneration?," *Molecular Neurodegeneration* 9:43, BioMed Central, England (2014).
Murphy, T.H., et al., "Spontaneous Synchronous Synaptic Calcium Transients in Cultured Cortical Neurons," *The Journal of Neuroscience* 12(12):4834-4845, Society for Neuroscience, United States (1992).
Myers, E.W. and Miller, W., "Optimal alignments in linear space," *Comput Appl Biosci.* 4(1):11-17, Oxford University Press, England (1988).
Needleman, S.B. and Wunsch, C.D., "A General Method Applicable to the Search for Similarities in the Amino Acid Sequence of Two Proteins," *Journal of Molecular Biology* 48(3):443-453, Academic Press, England (1970).
Oakley, J.C., et al., "Temperature- and Age-dependent Seizures in a Mouse Model of Severe Myoclonic Epilepsy in Infancy," *Proceedings of the National Academy of Sciences of the USA* 106(10:3994-3999, National Academy of Sciences, United States (2009).
Pasti, L., et al., "Cytosolic Calcium Oscillations in Astrocytes May Regulate Exocytotic Release of Glutamate," *The Journal of Neuroscience* 21(2):477-484, Society for Neuroscience, United States (2001).
Polydoro, M., et al., "Age-dependent Impairment of Cognitive and Synaptic Function in the Htau Mouse Model of Tau Pathology," *The Journal of Neuroscience* 29(34):10747-10749, Society for Neuroscience, United States (2009).
Rose, C.R. and Konnerth, A., "Exciting Glial Oscillations," *Nature Neuroscience* 4(8):773-74, Nature America Inc., United States (2001).
Ross, W.T. and Olsen, M., "Care of the Adult Patient with Down Syndrome," *Southern Medical Journal* 107(11):715-721, Southern Medical Association, United States (2014).
Seth, P.P., et al., "Synthesis and Biophysical Evaluation of 2',4'-constrained 2'O-methoxyethyl and 2',4'-constrained 2'O-ethyl Nucleic Acid Analogues," *Journal of Organic Chemistry* 75(5):1569-1581, American Chemical Society, United States (2010).
Stowe, R.P., et al., "Detection and Quantification of Epstein-Barr Virus EBER1 in EBV-infected Cells by Fluorescent in situ Hybridization and Flow Cytometry," *Journal of Virological Methods* 75(1):83-91, Elsevier Science B.V., Netherlands (1998).
Thom, M., et al., "Neurofibrillary Tangle Pathology and Braak Staging in Chronic Epilepsy in Relation to Traumatic Brain Injury and Hippocampal Sclerosis: a Post-mortem Study," *Brain : a Journal of Neurology* 134(Pt 10):2969-2981, Oxford University Press, England (2011).
Touboul, M., et al., "Early Detection of Chemoresistance In Vivo through the Use of a Radiolabeled Antisense Oligonucleotide," *Anticancer Research* 22(6A):3349-3356, International Institute of Anticancer Research, Greece (2002).
Uhlmann, E., "Recent Advances in the Medicinal Chemistry of Antisense Oligonucleotides," *Current Opinion in Drug Discovery and Development* 3(2):203-213, PharmaPress Ltd., England (2000).
Verjat, T., et al., "Detection of 8-oxoG DNA glycosylase activity and OGG1 transcripts in the rat CNS," *Mutation Research/DNA Repair* 460(2):127-138, Elsevier Science B.V., Netherlands (2000).
Vester, B., et al., "Chemically Modified Oligonucleotides with Efficient RNase H Response," *Bioorganic & Medicinal Chemistry Letters* 18(7):2296-2300, Elsevier Ltd., England (2008).
Vickers, T.A., et al., "Fully Modified 2' MOE Oligonucleotides Redirect Polyadenylation," *Nucleic Acids Research* 29(6):1293-1299, Oxford University Press, England (2001).
Xi, Z.Q., et al., "Is Intractable Epilepsy a Tauopathy?," *Medical Hypotheses* 76(6):897-900, Elsevier Ltd., England (2011).
Yaksh, T.L. and Rudy, T.A., "Chronic Catheterization of the Spinal Subarachnoid Space," *Physiology & Behavior* 17(6):1031-1036, Pergamon Press and Brain Research Publ., United States (1976).
Zheng, P., et al., "Hyperphosphorylated Tau Is Implicated in Acquired Epilepsy and Neuropsychiatric Comorbidities," *Molecular Neurobiology* 49(3):1532-1539, Humana Press, United States (2014).
Zonta, M. and Carmignoto, G., "Calcium Oscillations Encoding Neuron-to-astrocyte Communication," *Journal of Physiology* 96(3-4):193-198, Elsevier Science Ltd., England (2002).

* cited by examiner

Figure 1A. *MAPT* Genomic Sequence (SEQ ID NO: 1)

```
   1 gggattacag gcgtgagcca ccacacccag cccagaatgt ttattagaat gcacaattaa
  61 taccagaggc agtggggaag gaaggactga gcagaggagg aagttgagtt gtgattcaac
 121 ccaacaactg cctggctggc atggggagct ctggagttaa atagggccat cagactttcc
 181 cagtgtgggg ccaacatgac tgggtcttta taccccacc tctgtcagtc actcaacgtg
 241 gtctccctgc aacaaggtga ctcttgcagc cgagacaatc cctgaaggga cagaggctga
 301 agcctgtctg ccaacagcac tcccagtggc tggaacaagt ccttccctat aggggaatct
 361 gggcggcaca cctccatctc catgtccatc acatacgata tcacagacat ttaaatattt
 421 tgataactgt acataagagt ttcctttata atcttataga tcttatttta tgcatttgaa
 481 aatattcttc tgagacaggg cttttatcat attgccatag ggtgccacga tataaaaaag
 541 gttaaatact ctctgattca gaagtatcca atgatgactt ctctctcatg catttaattg
 601 aaaatctggt ttttctcctt ctctgctagt tctctacctc tctccccacc tcccacatca
 661 tagcctattc acatatgtct gaatctcatg atagacaagt tcaggttctt ttcccaggtt
 721 cttttttacca catccccccca cccccacata aaaagtatat atggcacagc ctaggttcca
 781 cccaaatcct ttctcctctt cttcctgggc ccacaactct cctacataca ttggtatacc
 841 ttgcgcttag ggatggccat gtgactaagt tctaacagtg gaacatgatc agatgccact
 901 tccagcctct aagacagcca gtgtgtttcc tccataagct ccttctcttc ctcccaactg
 961 gagactctaa atgatgaccc tgcctcaagc aagcaaacaa caagtccctc aggggtggtg
1021 taggctgcaa atggaaggag cttgagtccc aaaccttcca cggagaaggc tggctaccaa
1081 cctggatcac tcacccaaga ctgctcgaag agttggtttg aaccattgtg ttttggggtc
1141 tatttattac aacagtttag cttgctttgt gaatagattt agtggcagag cctccaaatt
1201 ctatagatac attgatctca gtcctaaccg catctggaac accattaaat aaaggaattg
1261 caaacccaga gaaggtaatg aatttgtcta aggtcataca agatggctag gatcaggacc
1321 caactctcca gttttctttc ttctctgcta ttctgccttc tgtgatccta cataagtggg
1381 catgattgta taacatatgc ggccatgaga tttctctttc agcaagagaa agggacagga
1441 agaaagagag ggaatgcatt ttcttggcct gaattagtgt gagccattag ttacctacat
1501 tgactaaatt atctggaatg aacattcaac tctacatcac atatagttaa aatgacagat
1561 ctgcttaaga ttgtttctag catacgttat ttcaatttag gcaaatgtga ccattcagtg
1621 tgaggggacc atactgtcat taggtccctg tcagttctca attatactgt tatcttagag
1681 ggggaaaaat gtgaaatttg aatgtagacg agtgttgatt tgactgctac agtttatttt
1741 acgtatagaa ataaaataat gtgtagcaaa agcattatta caaagatgat aatgaaataa
1801 ctagtattta taatagtata atagtatagt atttataata gtatgatagt ttaatgacta
1861 tttgtcagat gttgtgtaag aaactttata cacacacaca cacacacctc atttaattcc
1921 tgtatcaatc aggatacagg acgctgtggt aacaactcct caaatctcgg tggcttgcac
1981 aacaaatgct tatttctttt ttttttttga caccaagtct tgctctgtaa caggctggag
2041 tgcaatggtg caatctcggc tcactgcagc ctctgcctcc tgggttcaag cgattctcct
2101 gcctcagtct ctcgagtagc tgggaacaca ggcacgcgcc accacatctg gctaattttt
2161 gtgattttag tagagatggg atttcaccat gttgctcagg ctggccttga actcctgacc
2221 tcaagcgatc cacccacctc agcctcccaa agtgctggga ttacaggcat gagccactgc
2281 gcccagcccc aaatgtttat ttcttgctca tgtgacatgt acttcctcga gtttttcctt
2341 cctgagatct aagctgaagg aacagctctc tggagccacg ccattctggt ggcggaaagg
2401 aagagtaaaa gtggtagaac cttgcaatgc tcttgaagcg cctatttgga atgtctacat
2461 catgtaaatg gtaatggaca agtatgtata atccccacac caaaaaaagg ggacactatt
2521 ggggacaata accacatttc aatgctgcaa gacggatatt gactgcaccc ccttcccact
2581 ttcagaaaga agaagagtaa ttttgctgaa ctccttctag agactggaaa tgtcccttcc
2641 agttggggtg attagggaag gctttggtaa aatttgagct agagtttgaa ggttaggtag
2701 actactggtg ggtgaagaaa gaacaaggac ctttgtaggc aaaggaaaac ctcagaatta
2761 cagaggtgga aaaagagttc tagtcaagcc acttcagctg gctacagagt aggtgggaaa
2821 gaaaatggga ggacaagggc tcagatgatg gggggttggg gcattggggg gacacttgaa
2881 agctaaacta aggggttgaa cttaatttag gaggcagtta gaagctttta catattttg
2941 agcaagagag tgacataatt aaaatgatct gggccaggtg tggtggctca cacctgtaat
```

Figure 1B

```
3001 cccagcactt tgggaggctg aggagcttgg gtcacctgag gtcaggagat cgagaccagc
3061 ctggccaaca tggtgaaatc ccgtcctact aaaaatacaa aaattagccg ggagtggtgg
3121 catatgcctg taatcccagt agctgggagg ctgagacagg aaaatcgctt gaacccggga
3181 aacaggttgc agtgagccga gatcgtgcca ctgcactcca gcctgggcaa cagagcgaga
3241 ctccatctca aaaaaacaaa acaaacacac acaaaaaacc aaaaataaat aaataaaatg
3301 atcacttctg aatactgatc taactagggg ttgcagggtg ggctgatata gggagaaact
3361 ggagagcaag gagatcacta aggtccctac atgtccagaa ccaagataga ggtcttgaac
3421 taggatggtg gcagttagaa caacaacaac aaaaagtcaa ttccaggctg agtgcagtgg
3481 ctcatgcttg taatcccaac gctttgggag gctgaggtgg gagttagaaa gcagcctggg
3541 caacactgca agacctcctc tctaaaaaaa aaaaaaaaaa aaagttagcc aggtgtggtg
3601 gtgcccacct gtagtcccag caactcagaa ggctgaggtg ggaagattgc ttgagcccca
3661 ggagttcaag cttgccgtga gctacgattg tgccactgca ctccagcctg agcaagacct
3721 tgtctccaaa aaaaggtcaa ttccactgac ttttctaagg tgtacaccat caaggggcag
3781 ctccatctcc aggccattgg ctcatgagac attctgtagt cagaaggcta gggcagattg
3841 ctttgagcaa gcccccatgg tggttctcac tcctacttct ttgggtatat gcccctctgt
3901 ttaaaaataa agttaatatg catttaaaaa aaaaaaggag aaaaaggtca gttccagaaa
3961 ctgtgtgaat aaagcatttt acttgctttt tctattaatc tataacatat gttgattttt
4021 taaaaagaat ataagagcta tgcaaattgg agcttcaaga caacttccca tctccctagg
4081 aggagatggc tgccctaaac ccccctacat agaaatcatc ccactgcttg ggcttaaact
4141 tgatgttggg gaaatgaaaa atccaagcta aggccgaagc ctggggcctg ggcgaccagc
4201 agaatgagga ccactggtca gtttcaggct gaggtgcgtc ttccagggga caatctctag
4261 ctggccctta aacattcaga cttcaagctc tatttacagc ataaaggtgt ttcaaaagac
4321 gtgatacaaa taactgcaaa tgctctgcga tgtgttaagc actgtttgaa attcgtctaa
4381 tttaagattt ttttttctga cgtaacggtt agattcacgt ttcttttttt ttaagtacag
4441 ttctactgta ttgtaactga gttagcttgc tttaagccga tttgttaagg aaaggattca
4501 ccttggtcag taacaaaaaa ggtgggaaaa aagcaaggag aaaggaagca gcctggggga
4561 aagagacctt agccaggggg gcggtttcgg gactacgaag ggtcggggcg gacggactcg
4621 agggccggcc acgtggaagg ccgctcagga cttctgtagg agaggacacc gccccaggct
4681 gactgaaagt aaagggcagc ggacccagcg gcggagccac tggccttgcc ccgaccccgc
4741 atggcccgaa ggaggacacc cacccccaca acgacacaaa gactccaact acaggaggtg
4801 gagaaagcgc gtgcgccacg gaacgcgcgt gcgcgctgcg gtcagcgccg cggcctgagg
4861 cgtagcggga gggggaccgc gaaagggcag cgccgagagg aacgagccgg gagacgccgg
4921 acggccgagc ggcagggcgc tcgcgcgcgc ccactagtgg ccggaggaga aggctcccgc
4981 ggaggccgcg ctgcccgccc cctcccctgg ggaggctcgc gttcccgctg ctcgcgcctg
5041 cgccgcccgc cggcctcagg aacgcgccct cttcgccggc gcgcgccctc gcagtcaccg
5101 ccacccacca gctccggcac caacagcagc gccgctgcca ccgcccacct tctgccgccg
5161 ccaccacagc caccttctcc tcctccgctg tcctctcccg tcctcgcctc tgtcgactat
5221 caggtaagcg ccgcggctcc gaaatctgcc tcgccgtccg cctctgtgca cccctgcgcc
5281 gccgcccctc gccctccctc tccgcagact ggggcttcgt gcgccgggca tcggtcgggg
5341 ccaccgcagg gcccctccct gcctcccctg ctcgggggct ggggccaggg cggcctggaa
5401 agggacctga gcaagggatg cacgcacgcg tgagtgcgcg cgtgtgtgtg tgctggaggg
5461 tcttcaccac cagattcgcg cagaccccag gtggaggctg tgccggcagg gtggggcgcg
5521 gcggcggtga cttgggggag gggctgccc ttcactctcg actgcagcct tttgccgcaa
5581 tgggcgtgtg tgtgtgtgtg tgtgtgtgtg tgtgtgtgtg tgtgtgtgtg gaggggtccg
5641 ataacgaccc ccgaaaccga atctgaaatc cgctgtccct gccgctgttc gccatcagct
5701 ctaagaaaga cgtggatcgg gttctagaaa agatgactcc ctgcacgccc ctccctgcac
5761 ctcccgagca gtgattccga cagggccttc actgcccctg attttaggcg gggccggcc
5821 ccctcccctt ttcctccttc agaaacccgt aggggacatt tgggggctgg gagaaatcga
5881 ggagatgggg aggggtccac gcgctgtcac tttagttgcc cttccccctg cgcacgcctg
5941 gcacagagac gcgagcagcg ccgtgcctga gaacagtgcg cggatcccac tgtgcacgct
6001 cgcaaaggca gggttcacct ggcctggcga tgtggacgga ctcggcggcc gctggtcccc
6061 gttcgcgggc acgcacagcc gcagccacgc acggatgggc gcggggctgc aggtgcatct
```

Figure 1C

```
6121 cggggcggat ttctttctca gcgctcggag cgcagggcgc ccggcgtgtg cgctccctgc
6181 cggaggcgcg gggctggcgc gcagggctcg cccctcactg cggcagtggg tgtggaccct
6241 ggtgggcgag gaagggggag gataggctgt gcctcctccc actcccgccc ccagcccccc
6301 tttttttccc cctcggaacg cgaggtgcca tcttttttcg gcgtgtcacg tctttacggt
6361 gccatgccaa accgggtggc cgggcttcat aggacagggc ggggcctggc attaaaggga
6421 gggggacaat cagcgctgaa atcttggcgt tttgctgctg cgggcgtgag cactgggggc
6481 gttcgcccag caccttcttc gggggctctt tgctttgtct gtagaggtta cgtgatctgc
6541 gctcccagcc ctggtttctg gcttttattc tgagggtgtt cagtcaacct cccccctacg
6601 cccatgcgcc tctctttcct ttttcgctcc tcatttccga gcccattgtt ggatctcgag
6661 gcttgctggg ttcgatgaac tcgagtcaac cccccgaccc ccggcacgca tggaacgggc
6721 gtgaccgcgc gcagcctcgt ctcggagtct gccggcgccg ggaagcttct gaagggatgg
6781 gattcgagtc tccgtgcgcg ctgcgggcgg cggcagaggg atctcgcccc tccctacacc
6841 ccaagtgtcc tgagggccac gccacaccag gttgcccagc gagggacgct ggctacccat
6901 ccggggatgg gtggggagcc ctggcggggc ctctccggct ttacgccctg ttgcttcgcc
6961 tggccggaga atgtgaggaa ggggcataag gttactggtg cttcggccac acccatcttt
7021 ctgagcccac tggactgggc gcagaggggg gattgccatg gaaaccacag gtgtccggag
7081 aggggatctt ggggctggcc tcaccccttc cctgcggaga ttggggaccc tggggtaggg
7141 ggagccgcgc ccagtcggcc tcctggagga cacgggagga agccccgaac cccgcgcct
7201 gaggctgttt ctgattggcc cctggaggcc gcagacacgc agataggcgg ccctgggtgt
7261 atttttatta atattatgtc cgtactgatt aatattattt atcttaaata aatttcaccc
7321 gtgtccaagt tcaccgcgcc cccaaaaccg agtctggggc ggcaggggga actcctggcc
7381 aacgaatcca tgcctcgccc tcctgtgatg aacctggtac gcacggtttt ctggttaatt
7441 ctatcgctga aaactggtgc ggggggcgca cttctgagac ggaagagcat ctaggagctg
7501 aatcctccac gcgggtcgcc caggttgatc tgaatttctg gggaatggct tggctgcccg
7561 cccgggacca ggccgaccct ccttgacggt ggcgtagagg gctggagcct gggtactgcg
7621 aggctcctcg catggctggg cccgccgcga ggggttgcag agcggctcag ggatcgattc
7681 aagcatcgtc tctcctccct cgcccccaga cagagctggg cgcggggttc cccttccaga
7741 tggagcgagg gtctcggggt ggccccggaa aaggggagcc cgcggccacg gctacgtatt
7801 gccatctcgc gagcagagat gtcacctcct gcctttggag gaaagggagc ccggtgggga
7861 tgagcgcatt tagcccaatg ctgggaacaa agcgcactcc gcgcttctgc gatttcgctc
7921 cattttgaaa tgtgttggcg ctttggtggg gccgctgcgg tgggcaaggc cgggggcgct
7981 gttaatggag gaacctcagg gggacggtcc ttcgtaggaa actctatcct ggctctgcgc
8041 gcgctttaag gaaatggctt ccctccagga cctcgaggga tgcagctttt gcgcggatga
8101 cggtggggtg ctgaaccagc cggtgcgcct ctggaaatgt ctgggcacgg atcctggggc
8161 catcgacgac tcctccccat tcccagcagg cgggagctct tacattccga gcgagtgacc
8221 cctctcaccc tctggcgctc acacacctgt aactccaaac ctccgtctca gaatggtcca
8281 ggctggaagg gatgatgggg gctccgacag cgactgccta gctcacccct ctgcgtgctc
8341 aggctccagg ctcagcagga ccaatttgag ttctatctga tccccctcgg ccccttaact
8401 gacccatcct acaggagaca gggaaatgtc tttcctaccg cggttgattc tggggtgtca
8461 ttttgtgttt tgtgatggct gcttatattt actgtataag cattgtattt actgtataag
8521 cattgtatta taattactgt ataagctgct tatatttact gtataagcat ctccaaatcc
8581 tccctctacg taaacaaatt aatggataaa cagataagtg tatcccctgc ccccacccct
8641 gctacgcagg tccggagtga ctcttgaagc tcatacattc cttggccaag tttgcttctc
8701 taacagatgt ttatatagca ataacctggc ttggctcttg ggttcacctt tggacgattt
8761 ggggaagggg cttgttggct ttgctgggtt ttggatgagt gacagtccat gactgttcct
8821 gctggaaggg cgtgactttt aagtggtttc taatatcagg cattgctcct ccgacaggaa
8881 caaaagaaat ggatactgcc cataaattgt tagaaaactt agaatcgctt tgattgagga
8941 aaggttagat ttattccggt tggaaaaagt ggcctttcta ttaaacgtgc cctttgaccc
9001 tcatgccctt ggaggtcggt gccagcctgg agatgggata agattgtggt tttccttctg
9061 cctttttaac atctgttgtt acagtccatt tgttgaaaat ttaaagaaac tgttttattc
9121 cactttccct cagcatttat gtgtgtggtt tcagtagctc tgtggctata tgtacgaaca
9181 cgtgttattt ttccaattgg acatgtgata attttccaac tggaccttgc cttctattga
```

Figure 1D

```
 9241 tgtatttatt tagcatcttc cttactccct ccttgaaaaa gaatcactca aaaacaaata
 9301 aaaacagccg taggggccta atacagtgct agacatacaa gaggtattcg gtccatacca
 9361 aatggatttt atccatgaag gataaatggg gaaatacagt gggaagcagg tgggaaactg
 9421 cgtttgactc tgctctttcc tccaccacca ctttcctcat caccgtgttc agagaccccc
 9481 aaagccccct cacactccca gaaacacccc cctggccact cctaacttgc catgcccagg
 9541 agttaggtgc ttccactagt gacatggagc tggcgtttgg ggggcacctc agcaggtgac
 9601 gggaagagaa gaccccagcc tcaccagctg ggctgcagca gggagaggag tcctcatgtt
 9661 ccagcaggga ctctcagctg ttttcctgta aaaccatggt tctcaactgg gggccactga
 9721 gatgtctaga gagatgtttt tgttttcaca actcggggag ggtgctactg acatcttgtg
 9781 ggtagaggcc aggaatgctg ttaaacatcc tacaaggaag gcacaggaca gtctcctaca
 9841 tcaaaatatg acccagtccc aatgtcacca ctgctggggt tgacactggc actgctatct
 9901 taattacatt cattgagtgt cttttaggag gccctattct aagtgcttgc taagattatc
 9961 tcatttaatc ctcacaacac ttccgctatg tagcaggtgc tgttattatc tccgtgatgg
10021 ggaaactgaa gcacagagag ggttagtaac ttgctaaagg tcacagagcc agtgggtggt
10081 ggagctggtt gcctgacact agttccctcc cctctcagcc acatgtgggt ttacttggcc
10141 attgtggact agtctgggaa cccagatatg atctataaca ttgacccagt agaatattga
10201 ttccaaaacc actgtctcac aaatgaattt ttacaagagt ctgtaatcgg agcatgaccc
10261 agaataaggt tagggagatg tggagttaaa gctctcaatt tcttatctgg ccccgacaca
10321 gagagcaagg catttcactc tacattggtg ctctgtttat aaaacaaaga gcaaatatct
10381 cttcctaagg tccttaaacc tcttcccccca atccagggtt tctggactgc tctgccatat
10441 gacggggcag ctggtttgat tgacccaggg aaggctggaa atcaagactg ggggatcaag
10501 acgtagattc agtgtggcca aggtcaagtc tctgaggttt agggacatca gatccccagc
10561 ttaggttctg tacctcggca aggtgaaagc gttggcgccc actgatgagg cctgctctga
10621 gattgtgggt gtgggttgag ttgggtgggc ataggcaagt cctcttgtaa gaatcttttg
10681 gcaaagatgg gcctgggagg cttttctcac ttcctggggc ccaggctttg caataagtat
10741 tccattatac tgtggtacct tggggctacc tgagaatcct ctgtctcgcc cctgttgcct
10801 tgccaaagag tttgctgtcc aagaattcct ttcctgtctc caggtgccat gctcctgcca
10861 cctctgccag gttccctgcc tgcccagatg gctcccaact gagtgtgagg aggaatttga
10921 gacaggtttt gagctttctg ggttctccag ttaggaaact ttctgtaagc atgcagatag
10981 aatgggcttc agcaaaatac aaactcgaac aacttccatg tatagtccct taattttctt
11041 tgcttttttc atatttcatc aggctccatg ctgagcccaa tcagggaccc gatagaaatc
11101 caaacaccat gtcagcgagt ccccaagaaa tgcattttgt gccaaggcta ttcaaggaag
11161 gtttgggagc agctcaaggg cagacactgt taccctcccc caggtcccca gtgcagggca
11221 gtgttctgca tgtggaggca gtttggccta atggttaagg aggtaggctc tgatcgggcc
11281 tcctgggcac aaatcccagc tccctgctca ctgtgagacc taagccatat tgtttagctg
11341 cttggagagt tttttgtcat ccacaacttg gagtatgatg gtacctgtct cacgggttgc
11401 catggggttc acacaagcta acccggtact cactagggcc aagcacatag taactgctca
11461 gtaaatggca tcatcggcgg tgtcctgtgg atgagtgctt gtgattggct gaatgaccag
11521 aggggtctaa agatcctggt gatggaatca gttgtacaga taaattgtta cactgagtag
11581 ggatcaagat aggaaaagtc ggcaactacc cagctcccct gcaccaaact gggcagaagt
11641 ggatcctctg aaaattgcac acacccatgt ttaaatgtac acacagaact cttgccacag
11701 gcaagcggag atttgtcatc tgctgtccct gcctcatctt cttcctgaaa tccactccat
11761 gccaggaata aactgcatgc tctccaccag cccaaactga cctgccttcc cgccagccat
11821 cccgggcagg gtgacctggc ttagtacatc gggttcagag atctttccag tttactcgtt
11881 gaataaaaag tgagggctga tcgagaaagt aatggcagtc agggaaggcg aaggaggtaa
11941 agaagagatt ttacaaatga agtaattcaa cagagtgctg acattggtaa actggcaaac
12001 agatttcagg gtggttggtt gagagtagag tagaaaagga ttaaataaag caaacttgtg
12061 gtgtactgaa tcttaggaat tccatgtatc caataagtat agtcatttat gaattaataa
12121 attcggccta agaagccttc ttatcgctta aatcaagact aagtaacaat atatcagttt
12181 taaaaagtca ttatatcaga aaatcattta aatgatacac atagatttcc aagattttac
12241 tttaaccgaa actatataaa tgtgaatttg ttcacccatc ttttgacaca gggctcaggt
12301 cttctcttgg tgtctggatc agccagttga aatttcttgt ctgttttgcc tatgccacat
```

Figure 1E

```
12361 taataatgca ctgtctgggt cctccgattt cagtttggat tttgggttta cattgtggag
12421 tcatctgaat gcagaatcct tcagggattt tacttttttt tttttttttc atggtcttta
12481 ccatcccatt tgatagtaaa tattactcac ctttatgaag tctttccaaa acattcaact
12541 aaattttctt aaaatcattg aatgatttga agagcttatt cctcagcact tttactccat
12601 cagcttgcac cttatttttt aatctttttt tgagacggag tctcgctcta tcgcccaggc
12661 ttaagtgcaa tggcgcgatc ttggctcact gcgacctcca cctcctgggt tcaagcaatt
12721 ccgcctcagc ctccgccgta gccgggacta caggtacaca ccataatgct cggctgattt
12781 ttgtattttt gtagggatgg ggtatcgcca tgttggccag gctggtcccg aacttctgac
12841 ccaagtgatc cacccacctc ggcctcccaa agtgctggga ttacaggtgt gagccaccgc
12901 gcccggccag cttgcacctt atttaggata tgtgattatt atagcaagtc tggtgtacat
12961 acaagatttt gaatgggcac agatgacctt tagtaagtgc ttggctgtga taagaggcag
13021 tcctgactgc agatcaggct gtgtggaccc cagccttgca tgtttacaga ccttcatgtc
13081 ttattcttac agggtatcag aagaacacct actggggaaa cttataaatt agtaaaaggt
13141 gggcattctc cccgcccatc ttctgtctgt ctgccaggac tagcacagca ctttgaagtc
13201 attcacatag aatcccaact taagagggta aaatcctcct caacagactg aaaataagtt
13261 taaattccct ttgctatatt aactcccctg aggaaagagt cttagatcaa tgtccaacac
13321 taaaaacagt tttaaatcag caagtgagaa ttaaatctga agcaattgat aataatgttt
13381 cattcattcc tctcctttgg ccccgtccac cctactgcta aatccaggca tcaaagagaa
13441 gagggacata attatctcta gtcccagctg ctggttttcc ttccagccta tggcccagtt
13501 ttctgtttta ctgagaaggc tggtgatgtt atcttgggat ctaagtctgc agtttcacca
13561 caaaaagtcc agggatgcac tttcatgctt gtgtcctcct ccctgggata gcaaggatat
13621 tagaagaccc ctggctctgt aattgcttgt catgtgctct acagacgcca cagaatgcca
13681 agaacgaagt gctgggaagg acaaattcat ggaaccgtgg gacggtgctc ctcccccagc
13741 gtaaaggaca gctcctcctc ctgaattgga gccagcgttc taaatcatgt gtcaacagag
13801 ttgtcctgga tcggatccag ttctgccatt gatttgcagg tcatttcagt ggtacctgtt
13861 tccagttgtt cttaattgaa cagtggcacc aaactattgt cttgcctcat cccccctcca
13921 tggcctgtcc cccaaaaaga gacttcttgg gtaattaatc agggcaacat caggcagtct
13981 gggcgcggtg gctcacgcct gtaatcccag cactttggga ggccgaggcg ggcagatcat
14041 gaggttagga gattgagacc atcctggctt tgtgaaaccc cgtctctact aaaaatacaa
14101 aaaattagcc gggcgtggtg gcgggcgcct gtagtcccag ctactcgaga ggctgaggca
14161 ggggaatggc gtgaacccgg gaggtggagg ttgcagtgag ccgagatcgc accactgcac
14221 tctagcctgg gcgacagagc tagacttctt ctcaaaaaaa aaaaaaaaaa ggaatctctt
14281 tggttttata tatttttttt tatatatata atatatatta aaatataata tatatattta
14341 tataatataa tatataaata tattatatat tatatatttt tatatattat atattatata
14401 tattatatat tatatattta tatatttata tattatatat atttatatat tatatattta
14461 tatatattat atatttatat ataatatata ttatatatta tatattatat attatatatt
14521 atatatttat atatattata tattatatat attatatatt atatatttat atattatata
14581 tttatatata ttatatatta tatattatat atttatatat tatatattta tatattatat
14641 atatttatat atattatata ttatatatta tatatgtata tattatatat gttatatatt
14701 atatatattt atatatataa tatattgtat atattatata tctaatatat tatatatatt
14761 atatatatta tatattataa tatatattat atattatata tatttttata tatataatat
14821 gtataatata taatatatat aaaaacatat ataatatata ttatatatta tatatatatt
14881 atatatatta tatatattaa atatatttta tatatattat atatattata tatattaaat
14941 atattttata tatattatat atatatacac atatatatat ataaatgagg ccaggctcgg
15001 tggctcacac ttgtaatccc agcactgtgg gaggatcact tgaagccagg agtctgagac
15061 tagcctgggc aacaaaacaa gatcctgtct ctacaaaagg aaactgtaaa aattagctgg
15121 gcatgatggc atgtgtctgt agccctagct acttgggagg ccgaagcagg aggatcgctt
15181 gagcccagga gttcaaggct acagtgagct atgattgtcc catagcactc cagcctgggt
15241 aacacagcaa ggccctgtct ctaaactttt tttttttaat tctatttata tttacatgta
15301 tttaaatgtg aatattcact acctatttgt tgcatgcctg catttttttat actgggcttg
15361 ccaaaaaccc gaacagcttt ctactttgac aatgtatcag aatttaaatc agcaatatgt
15421 taataagcca agcaaaggtt atatatgcaa ataaaactgt tgtctataac ctcctgttac
```

Figure 1F

```
15481 actggggcac agcaaaagtc atggtgtagt cgcatgtgaa cctgtccctt tcatagctgc
15541 tcattgccag gaaacatcag gaatagccat ttggaagagt catcagccct cccaccatcc
15601 gttttctgtc ttgtcttttc cctatgagca ggggaaattc cacgctggcc ccaatcccca
15661 gtgcagcggc tcagcctctg cctctgctgc tggtccccat gaggccagct tagaaacgga
15721 ggattttgca gaacatccct aaatccgctt gaataatgaa gtgatcattc ataaactcac
15781 ctgaacctta ttaaaaccta tttaatattt ttcctggata atcctatagg gataacttgc
15841 ctcctgggct tctctccacc gggttcagtt cttcctttag tggtgaagtt cctcccttct
15901 tagcatctca actgtgcctg agaaaaggcc agtggcggct gcactctgtt ccctgtggag
15961 tgttaataaa gactgaataa attgaaataa atccctttca atgtcattaa gtgctataaa
16021 taatcatgaa ccaatgttcg atggctgatg agaaatgcaa gaaaaaattt ttaatcagta
16081 ggattcataa gttgacaatc tgggccaagt taaaaaaaat aaaaataaaa agacttttaa
16141 aaagatctta tcgtttgtta ccagtaagac tgaattccag aagcaagcta ctccctcatt
16201 tgtgggcccc tgttatcact ggctgcttag ggttgccaag ccctgaattc atttgtcaac
16261 taagagattt ttggccaaga ttaagatttc ccatgcctcc atatttccat ctgagaaatg
16321 gagattatac tgtcttcccc ctcagaatgg atgataatgt ggtctctctt ctgttcgcat
16381 agtcatagaa ctgaaataaa acaacttaag agaattcctt tgagcttctc agaagtgctg
16441 cagggctggg ggatgcctcc caggagccgc agtcaggtgc tgatctgaag tctttggtgg
16501 gctgacttta gcctgacctg aaatagtata gctgctgcca cctggctccc ttagcgtcag
16561 tcagacggtg cagctggttc ctaggggtga gggctgagcc agcagggtcc gtgcccagga
16621 gggatgcatg ggtggccaca gcccagcctg cactgatctt gtctgtcccc ttctttggaa
16681 ggaaggagcc ccaaaccagg gtgcaagaca gtgggtgggg gtgccttgag catgacctca
16741 agtgatttcc agcccctgcc agtgctgact tctctgggga agggctggga cttccttctg
16801 ggctcaagtc acgacccttg gatggaattt cctgggagct tttctgtttt ttctggagtt
16861 ttcagttttt tcctaaccag acagggactt ggtacagaat ctcatattct aattatgcct
16921 aggagcagcc tctccccacc actcacagtg tttagcatgt gacaggaatc gattaaggca
16981 tgagtgatta aattaaagcc aggcattgac ttggatggtg taatattctg acatctgttt
17041 ggtgtcaaag gcacggggca ggcgcgttaa ttgaactgct tgcacctggc atttgaattg
17101 agccagagcg gggctaaagt cagtttgcct tcaccctgta aatggagggt ttctccggag
17161 cgtggatggt gggaggtatt tcagggtgta tgcataaccc ccaccctgac aatggcccat
17221 ctcttctcca gcgtggccag gtttgagtgc cagtcctggg tgtccagtgg ccccatagcc
17281 ttgcgtttta gtaaaatgct gcccccatta ccacctggtc tgtgcacttc ggtcactgga
17341 atttgccatc ttccagtccc gaatgtggca agccatggag ccttaagctc ttctccctcc
17401 acatcctgga acagacccgc cagtttcttc caggcattgc ctcagtttgc ccctctgttt
17461 ccagtcacac tctcaccagc gataaaatga ttttagacct tatcatctca ccctcggatc
17521 cttatggaaa caataatgag ttgttccctg tttcaattcc aaaattcata tccaatccgt
17581 tttgcatgcc attgccaaat tcctcccaga gcaaccccgt cacctgccct ggccctctcc
17641 aagtgtggtc ctgccatggg catcgcctgc taagccaagc tggcctcgag ctgcctgccc
17701 gggtccccac accttggctc acctccctgc ccagtcccgc ctcctgccag cctgccctgt
17761 ggctccttca tagatgccgt gctctttctg ccccttgctc acccatggca gccttgcccc
17821 tctctccctg ccccaccccc tatttaaatt gacctgacct tcctcagtgt ccatcttccc
17881 cgaagctttc cccagccttg gcactcaagg tccagaggct acgcgtttcc tctcacctgt
17941 ggcagcgccg tgctccccag tgcctcacag tttccttctt gcccccgctt cctgtgtagg
18001 actcatctgc ccacaggttg cacgtcctgt gagggcaagg actgtgtctt atgtgacttt
18061 ccttctccag tcacagagct gggcacatag atagctcaaa accctcttta ttaacacagt
18121 tggatgttga gaaatcaaac aggccaatgt caaatgagct ctccttattt aaatcaagtc
18181 agttctccac ctcctagcac tcagttccag tactctatat acatggaaat aataaaaaac
18241 acatttcctt tgaaacattc tataatcgtt cctttgccct acttcagacc aacttaacgc
18301 actccccatt ggtccaaatg agttttgcta tacgaagatg ctgataataa tagcagcagt
18361 ggattattct gctaaaacca ttgcctcgtt aatcctcagt cccgaggtgg ggattattat
18421 cctcattttg cagagaagca aactgagact cagagatttc acagctgggg agggagccag
18481 ctcatccctc tgtccaggcc caagctctct cccgcttgcc ttcctgcctc tgcaacctca
18541 gagcatcccc catctggttc tactgcctgt gctagtcgtg caggagccaa aagacacgtc
```

Figure 1G

18601 tttagtgcta aggactggag aagccatgcc ctccagcctc tgtgaatggg tcatatgtaa
18661 catgagcctg gagaaattat ttgaaaccaa aggcaagcct ctaaaccagg ctgctgcttc
18721 atggcgccgg tgacggcaga accaaattta gtgctgtggg caggtccaca cttatcaaat
18781 agagaagctc atttttcttc cggctcacat caagcatgaa aaatgttcac acataccccc
18841 cacacacaca tgctttccgg aggggtccat gtggctagag gctggaagat gtggatgaga
18901 ggagcctggc aggtaagccc agggaagatg acattcagct tcccagacag catctacagg
18961 gagaaattta attaaaagtg gggcggtttc cctgagcaag gcagacaaag tcagccctct
19021 actgttaaga aaaagggtca cagtgagagg ggaggtgagg agactgagtc tgtattttct
19081 agtctgttgg gctacactac ctgatccccc ttcctcaaaa atccacttta ctttccccat
19141 gtctacacca atgtggttca cactctggga ccaggaaaag gggagtgat ggggaacaga
19201 gaagggagga gctcacacag ctgaggctgg ggttatgcat atcgaattac ttagaatttg
19261 caacctcaca gggtactttc atggcgttga aatacacttc ccacagccac cctccctcta
19321 actaaaagca agagtcattt ctcagttctg gtcttgcctc ccacgttctc ctccacattt
19381 aagaaaatcc accagctaca aagtgaagat accatatgtg atatcccacc ctagtttctg
19441 ttttatcagg gtttggagca ggtggagcag gcagagggat catttcagcc tataaattgt
19501 attaagggtg agtactgagt cattcttcaa gaaaagtttt agaagcatcc aaaactgaag
19561 ggtggagcca cctggagaca gtatcatcag tcctggcccc gagcatggcc tgcataggcc
19621 cccatggatc ccagcgggag ctgcagagtg cgggcacctt ggcacacagc cctgagtgca
19681 aaattaggag ctgggcagag ggcatctctc tgtcgccatt gggcagccca gggcacactg
19741 gtcatagcct tagaccacga acaccctgtg cccgggggac agatgcaacc agtgtgccct
19801 gggctgccca atggcaacag agagatcgac acctggaccc catgtcacgg ggactccact
19861 actaaggctc ctaagactgc caccttccag tgggataagc cctgcctcct actgggccca
19921 caatgtgcag agaacacttg ggactacctg gctttctgga tacacaaata ttgatccaat
19981 ctggactaat tagaaggtca gtcccaataa caaatcgaag tcagctgggc gtgatggctc
20041 actcctataa tcccagcact ttgggaggct gaggtgggca gatcatttga agccagaagt
20101 tcaagaccag cctgggcaac atagcaaaac cctgtctcta ctaaaaatac aaataattag
20161 gctgggtgtg gtggctcatg cctgtaatcc caacagtttg ggaggctgag gcaggtggtc
20221 acctgaggtc aggagtttga gaccagcctg gccaacaggg tgaaaccccg tgtctactaa
20281 aaacataaaa attagccaag catgatggca tgtgcctata atcctggcta ctagggaggc
20341 tgagacagga gagaatcgct tgaatccagg aggtggttgc agtgagctga gatggtgcca
20401 ctgcactcca gcctggttga cagagcaaga ctctgtctca aaaaaaaaaa aaaaaaaaaa
20461 aaaagccatg cctggtggag cactacgtgt aatctcagct atttgggagg ctgaggcacg
20521 agaatcactt gaacctggga ggcagtggtt gcagtgagct gagatcgcgc cactgcactc
20581 cagcctgggc gacagagtga gtgagactcc atttcaaaaa aataataaat ctgagtcact
20641 ttaatattgt tatttggatg tcaacctcta ggtgtttgag acaggagagt gatatggggg
20701 cactggaaac acacaggcac ggggtgtcct cacacttggg tagcccacac gatgtgattt
20761 cagggtgctg ggaggtcccc ccactcccca aattactaac aagtggatag tactttacag
20821 tttatatgat ctcatttgat tcttaacatg agcctgtgag tgaaaaattc cttcccctct
20881 tctacagatt aggacgttga gattcaggga ggttcagagg gattcaggga agtcaagtgg
20941 cacctggagt cccgtggcta atttgaggcc ggtaggggat tcgaacccag gatttgtgct
21001 tcttatgcct gggcttctgc tccctggggc atggtcttcc ccctagcttt cccattcact
21061 gctttagcct aggggtccta ccctttatta aactgccagt gcctcactgc ttttctcccc
21121 caaagacaaa aaaaaagtgt ttttgctttt gttttgtttt tcatgggcag agacctggaa
21181 tttcagcttg agaatttgtg ccatatgata aataaatcaa cagatggctt tttccttaaa
21241 aaaaaaaaaa aaaaaaacta agatgtattt gcagtgaggc ataatttgta ccaaaaagtg
21301 ctcaccacac tgtagtcatg gggcaggag gcagccgcgg gtgaagggag aaatcttgga
21361 gtccaggcag ccccttctg ggctgaactg gggagctggg ggtgctgcca gccctgccag
21421 gttctcctag gaggcggcag ctcatatggc tgtgggagga ggcagaggga gcctcatatg
21481 cacccacatt tccagggatc tagaagacag aaggaggaaa accaccatca tgttaaagca
21541 gacagttagg taacacatcc tgtaatacaa gttatttttt ccacatctaa aggctaaaaa
21601 tagttgttag aatttaaaga taattggtaa atgagtttct atccttctag tttcacatca
21661 aatggaatca tgctgccttc acatcactag tgcccgttat ttgtgtttaa tttccacaat

Figure 1H

```
21721 gttgtctaat tccactcttt gggcttcccc agggatccag cctccctcac tcgcccatcg
21781 cagggagatg ctttattcat ctttgtgtct tctgtgccgg gcatagcgca tggcacagaa
21841 taagcactca gtaattgatt cacgagtgaa taaatggatg agtgggtgag ttcaatattg
21901 actacaaaaa ccctaaggcc acactggtga gtggctgcgc ctgtagtccc agctgctggg
21961 gaatctgagg caggaggatc tcttgagccc aggagtttga aactagcctg ggcgatatag
22021 cgagaacctg tctcaaatga caaaaacagg gccaggtgca gtggctcacg cctggaatcc
22081 cagcacttta ggaggccaag atgggaggat cacttgaggc caggagtccg agaccagcct
22141 gggcaacata gggagaccct gtctctacaa aaaatttttt aaaaattagc tgggcatggc
22201 ggtgtgcgct tgtagtccca gctactcagg aggctgaggc aggaggatca cttgagccca
22261 ggaaattgag gctgcagcga gccatgatgg caccactgca ctgcagcctg ggcgtcagaa
22321 cgagacctgc tctcaaaaaa acaaacaaac aacaaaaaaa aaggctttct taaagagact
22381 tgagaacaga aaggggaaca gatacataac ttatatattt atttgttcat ctttccacct
22441 tcctggaggg tggaggggaa caggtctgta tttggagttt tgaatgctaa aagtgggaat
22501 acatgtactg tttgccatga tctgttcaaa agttaagcca aatgccttag attctcctga
22561 aaactggaat gccactgtaa actataagcc ccacttcaaa gataaaagat cttgatgaac
22621 agggctgggt ctgtggactg ggcctctccc caccacacaa ggaagggtgg tgccagttga
22681 aggaaaatca cttaaatcct tgctgtctcc taataaggtg tggtcccagg tagggctgtc
22741 agaattagca aattaaaaca cagggcatct gtgaaaatta gaatttcaga taacaacaaa
22801 taattggcat aggctgcata atgtccctca aagatatcag gtcctaatct ccagaacctg
22861 taaatgtgat cttatttgga aaaggggtct ttgtagatgt ggttaaatta aggattttga
22921 gatgggggga ttatcctgta ttatctaggt aggtcctaaa tgcagtcaca ctcatccttg
22981 taagaggaag gaagagagag atggaaaaca cagaagagaa gacaatgtgg tgatggaggc
23041 agagattgga gtgaggtggc cacaagccaa ggactgctgg cagctaccag cagccagaaa
23101 agtccaggaa ccaattctct cttggagctc cagagggagt gtggccctgc tgacacctta
23161 gcttcaacct agtgatcctg attttggact ttggccttca gaagtgtgag ggaatgaata
23221 tctgttgttt taagccacca agtttatggt catttcctac agcagccaca ggaatcaaaa
23281 acagtaagta tgtcccatgc aatgtttgtg acacacacca aaaatattac ttgttgttca
23341 cctgaaattc aaatttaact gggtctcctg tattttattt ggccaaccta gttcccaggc
23401 ccaaagaaag aggcttttga aatttgcaag aaagctggtt ggagctgtca gaaagtggac
23461 tttgtaaaca cagtaccacc gaaccaattt gaactgtact acctctagac aaaagagagg
23521 gcagtcagac agttgttcgt gatttcttct ttcaacagtc atttgagcac ttactacaaa
23581 acagaagcta tgtgtaaggg tggaggcgtt agctgttaat caggacctcc aggctaagtt
23641 tctgtattag tccgttttca cgctgctgat aaagacatac ccgagactgg ggaatttaca
23701 aaagaaagag gtttaattgg acttacagtt ccaagtggct ggggaagcct cacaatcatg
23761 gcagaaggca aggaggagca agccacatct tacatggatg gcagcagaca gacagggaga
23821 gagagcttgt gcaggggaac tcctcttttt aaaaccatca gatctcgtta gacttattca
23881 ctatcaagag aacagcacag aaaagacctg cccccatgat tcagttactt cccaccagat
23941 ccctcccaca acatgtggga attcaagatg agatttgtta ccatatcagt taccaaccct
24001 tccagataaa tcacgtgaaa tatcgccatt aacagagtga gctcaggtgg ttcttcagtg
24061 catttctgat acctgaacct tccctgggaa tttcacagac catcaggctc tccacccttt
24121 gatagcagga tagcagggcc caggttctgc aggaggagat gttaccacag gcctgaaagg
24181 gagggagggg cagatgctac aggaagatgc tggctctgga ttcgctggag gagctttcaa
24241 gggaagtaga tacacactgt ctccatcatt tcatgtccat cacactctaa aatgctttgg
24301 acaagaagca aatgttaaag acaaatgtgg cccattttcc tgtacaaaga gggctgctcc
24361 catgccaggc tattggcact ggtgggcatg aggcttctct gctgccctgg ccggggggtt
24421 ctctcactca ccattggctc tctgacacct ggagagacca ccacccttgg gctttcatga
24481 tgctcacaga atccacactg ttggagcttt aaggagcctg gatcaactgg aacaggcagg
24541 gagtactagg acagcccagc attgccccaa aatatccagg cctgataaaa gagaaaaaca
24601 ggtagctcac aggaaaagga taaaaaaagg aggagggatt taacatgaaa aggtgcttga
24661 tctccctcat aataaaaaga ctgctgattc catccaggca agtgacagaa aaaaaaaatt
24721 taatttaaaa agactgctga taaaaccaca gcgagacact gctgctcagg gatctgaggg
24781 tgtgggcagc caggctgcca cgcatcatgg gtcggagagg aagaccacac ccctggagca
```

Figure 1I

```
24841 gagggcggct gatctgtcag atgccctttg acagcacctc agcttccaag aattaaccct
24901 ttctatgtga gcagaggcat ccatgggggg acacactggt gaatcatctg ttatgtagaa
24961 gtctggaaaa catcaggatg gaactggtga aataagtgtg gcctctgacg gaatggagcg
25021 gtccgtctgc actgctgcgg gtgcccctca gatcctgtgg gtcagtgaga aaagcagtga
25081 ggaacaaggc aggtactgtg tactgtcctc tgcgtgcaag gaaggccagc gcatgcaaca
25141 gagtccacac agacatagcc taactctgga aggaagaatg agaatgcagt ttcagtggtg
25201 gcctctggtg ggagagaact gggtgaaggg agatgtcatt tccatttctc tactattaat
25261 tttgtattac catgcttaaa tgttactttt tacctttttt tttttttttg agacagggtc
25321 tctctctgtt gcccaggcag gagtgcagtg gtacaatcat ggttcactgc agcctgaacc
25381 tcccaggctc aagcaatcct cccacctcag cctcctgagt agctgggact ataggcacgc
25441 ataccaccgt gcccagctat ttttttaat caagatggag tttttctatg ttgcccaggc
25501 tggtctcaag ctcctggact caagcaatcc tcctgcctca gcctcccaaa gggctgagat
25561 taaaacgtga gtcaccctgc ccagccaatt gctttttaaa aaagattaaa tgcatgtata
25621 cgctcaggca tcagcacact tggaaaggat gaaaatatcc ggaagaaggg ttcttttaaa
25681 aggctcctca agtgatgctg gcaggcatga cgaatgtccc tggtcacaaa agctctgatc
25741 tggcctaacc ctgtcatgtt agagactgga gtgcgtgtgt gtgcgcgcaa agtgtggggg
25801 gatgggggtg agtgtgtgtg gtgtgtaagc atgagtgtgt atgtgtgtgg tgtggggtg
25861 tgtgctgtgt gagcgtgtgt gagtctgtgt gtgtagtgtg tgtgtgaagt atgtggtgtg
25921 tatgtgtgac gtgaggtgtg tgtggtgtgt gagttgtgta tggtgtgtgc atgagcatgt
25981 gtgtgggcat gtgatgtgtg tgtggtgtgt aagcatgtgt gagtgtgtat gtttgagcat
26041 gtgtggtgtg ttgtgatatg tgtgtggtgt gtgagcatgt gtgtgtgatg tgtctgtgtg
26101 tggtgtgtgt gagcatgtgt gttgtgtgtg tggtgcatgt gtgtggcgtg tgagcgtgtg
26161 tgtgcattgt gtctgtgagc atgtgtgagt gtgtgtgtgt tcagcatata taaggcatgt
26221 aactgaacac agcactttag agggctctcc tggagtcaga gggggtgggt aggaggagaa
26281 gggaggtggg ctagtgtgct gaagtatcta ctccttgtca tagtctgtga caacccagac
26341 tagcccatga gccaccctgt tccctgcatt tccaatgaga cctcggtgga catgttccct
26401 gaggtgaggc tgactgatgt catttgacga tcttgatgcc aaatcctttt atatcaaaaa
26461 caaccagaac actctctttt ctcttagtgc tttcacccag atgaccacat ttcatcctcc
26521 cagccactct gggccaggtg gcactgctgg tttgaaaggg aggtctcccc tggagtaact
26581 tccgtgggcg gattcacacc ctgcccacag tcctgtccca gtcagcccac catggtggtc
26641 tccggttcct ccagaattcc cgcttttcag ctcatcccca cattcccgga gggactgaga
26701 gcgcagcccc agggccctgc tctttggggg ccgtctctac acccagagaa gcagcaaggc
26761 attcctaggt ttctctttca gatgcagaac ttcagtgttc agagatgttc ccactggtcc
26821 tgagagggct cagttcagct ttaatgactg cgctgttgcg tgtgctctgc agagggcggg
26881 tggcccagcg tggctgactg cagttttcct gacgtggagc ccgagcctgc cccgctgttt
26941 attaattaag gatcactctg cttgcagaac cctgaactcc ccagaactgt gaggtgggag
27001 aaccccgaga ggccacctgg ccccacttcc cacctgctgc ccaaaccccc tctctgcctt
27061 cctgacagtc accccaactc ccagtgatcc ccatcaacca tctgacaagg ggactgagag
27121 ggaagagaaa ggaggggccc aaagaggaag gtaaaactgt cgggaacagc ccccaaatgt
27181 gtgacagcct tcagtggagt tgcccacttt ccctttctc ctccctgcag gacctccctt
27241 ctccccagtc ctccccaact tctgaggtta cattgagaaa agtctgcaga gaggtgccag
27301 catcacaagg tgttaaggac cacgagtttg gcattttaac agatgccaga gccacttgag
27361 aaatgtggta actaagccca gagaggtaca gttaacctcc ccagagtcac acagcaggtt
27421 catggcaaag ctggactagc acaggtgtcc ttcccctgca gatccccttc tgtgccccac
27481 atcacctccc tccagtgtct gggccacctg gagatgggcc ctcagactca cccggccaga
27541 ggtgccatct catgggagag gtctggccag gaagcatcga tatttgagat cccaagaaat
27601 gaagacttgg cctgtcagat gacagacttc ggtcatggga acacgtgatc tgttttacac
27661 atgcgtcccc tcagcagcag ctttccagaa cattccccact ttcttctgta gtgagaagaa
27721 ctctttccct gcagcctcct gcccaactcc tccttcagtg tctttgcttc agtgtctttg
27781 ataaaccatt ctgctttgca gagtgcgagc tctgccttgc agggttcgca tctgcctgtg
27841 ctgagtaacc aacgctaagg tcgagtggtc ggtcacctct cataagagct agggttgtct
27901 catgctgatg actaggactt gccctcaagg agaaaaataa atcaaaacaa aagcaaaaac
```

Figure 1J

```
27961 agcaaacatg catctcttaa agaaggctct gagtccaggt aaatttcctt ccactgaagc
28021 agccaggctg aattcgaatt atctttgccc ctgcttaaaa actaatgcaa attttcctag
28081 agaatatcca ctaattcctg gagggggcat gggcattcct gatgcccatg agaggaccat
28141 ttgctcttcc ctcagtatgc taaataacag aagcgacatt tgttgctgga aagtatcagt
28201 gaagttaata aggtttttct tgcccagggt gagggaacag ttcccaatga caaatgctgt
28261 atgggaaggg gctgtagaac tgccagcccc tttggtccat ccgtaaagtg aactctgtgg
28321 atcctggagg attccagcgt cttttttttt ttttcttttt ttttaagaca gagccttgct
28381 gtcacccagg ctggagtgca gtggcacgat ctcagttcac tgcaacctcc gcctcccggg
28441 ttcaagcgat tctcatgtct cggcctcccg agcagcaaga ctacaggtgc gcaccaccat
28501 gcccgactaa tttttgtatt attagtagag acggggtttt cactctgttg gccaggctgg
28561 tctcaaactc ctgacctcag gtgatccacc cgcctcagcc tcccaaagtg ctgggattac
28621 aggcatgagc caccatgccc agccagcatc tttcattttt ctgtctgctt tggccctttc
28681 ctctctcact gtcttccttt tccatttcca aagtcagtcc atctcactat tagcacaaaa
28741 actgctagag cgcttgtcat tggtcatctc tccctgcacc tggctggtct gttcttggcc
28801 actgaagcgt ttcccccagc tgttgcttta atcattttat tgttattatg ccttacttaa
28861 gaaatggata tgagatgcat ttacctgtct cttcctgcca ctctgcagag ccagtaagat
28921 gtggtggaaa gggcccaggc tttggaggag ggctggctgg ggttggatct tggctgcccc
28981 ctactagctg tgtgaccttg ggtaagtagc tggacctctc tgagcctggt tcggaatcat
29041 agcacctctc tttcagggct gctgtaagga atagcagtgg tgtgtataaa gcagagcgca
29101 cagccagcaa ctggccccta gccacactgc tgagcaccta ctgtgataag ctgccattgt
29161 ggtgtgtgaa gcaaagggga aacatgcctg ctgtagtgag cttcctgtag ggcaggttgt
29221 agaaccagag gtgggttcca aggttacaaa gggactctta gtgtattagt ctgttctcac
29281 attactataa agacctacct gagactggat catttataaa gaaaagaggt ttaattggct
29341 cacattggct gggtgcggtg gctcacgcct gtaatcccag cattttggga ggccaaggcc
29401 ggcggatcac ttgaggtcag gaatttgaga ccagcctggc caacatggtg aaaccctgtc
29461 tcttctaaaa taaaatacaa aaattagctg gccatggtgg tgtgcgcctg gaatcccagc
29521 tactcaggag gctgaggtgg aagaattgct tgagcccggg aggtggaggt tgcagtgagc
29581 caagatcgcc ccactgcact ctagcctggg cagcagactg agactctgtc tcaataaaaa
29641 aaaaaaaaaa gaaaagaaaa agaattgcaa gaaataaatt attgtttatg agctatatgg
29701 tctgtggtac cttgttgtgg gactgggagt cttggcgtct ccctgaccct gcctgttgct
29761 gcagcaccgc tcagccctgc ctgctcccta cctgcctccc ctcggcctct cctgcctcca
29821 ccgggcccct ggtgcctcct ctagagacag tcctcctggg accgattgtg ttctcactta
29881 cacgaggcat ccaggactac agataaccag aggaaggggc gcccccccgg cctgccctcc
29941 tccctggcat cctcacgctg cagaggtcag agcctcatcc cagcccctta cctgccccta
30001 ctctgtggag aaccgtggtc agttcgccag gccggatcca cgaacggcct tgtggaagat
30061 ggtgagctca cacccagagc tggctccgat gaccctgtct cctttacatg tttctacctt
30121 cccctcccta ccttccccca ctgctgggcg cagagtggag gcagatgagg tttaaagctc
30181 agaagggctt aaacgggttg gggcgcagtg gctcatgcct gtaatcccgg cactttggga
30241 ggccaaggca gaggatcact tgagcccagg agttcgagac caacctgagc aacatagtga
30301 gaccgcgtct ctacaaaaaa taaaataaat aaaattagct ttgcagggtg gcatgcacct
30361 gcagtccctg ctactcagaa ggctgaggtg ggaggatcgc ttgtgcccag gagtttgagg
30421 ctgcagtgag ctatgctggc accacagcac tccagcctga gtaacagaat gagatcctgt
30481 ctcaaaacaa acaaacaaac aaacaaaaga aggcttaaag gggctccag gtgggcttgg
30541 cagcacaaag ctatgaagtt ctatcttaga cacaagttct gttactgggc ctttgcaggc
30601 tggcctgggt acctggctgc catagacagg gaaccttcca gatgagctgc aggcgtggag
30661 cacaggagcc agggtgctct tcctgggctc tgtccacagg cagaacgtac acagtctttg
30721 tacacgtccg gcggctctgg tgcctatttt tgtttgtgtt tttcttttgt ttgggggat
30781 ggatttggtt tcccccgagc cctctgtcct cctgtcacct ggctggtgct cggcaatgtt
30841 gaccagctgc ctggctggag ttggcagtgg ctaaggctgt gacagctaac atgttcctga
30901 gtcctctcat ttcttcacca taatgccctg ttgagtttgc agatactgtc tctgttttta
30961 tctcccgggg aaactgaggc tcagagtggc taggccacct tcccatggtc cctcagctca
31021 tgagggccac acagggcatt gcggtggcct tctcctcagc cttgaccctc cggccccagc
```

Figure 1K

```
31081 attgctgcct caaggggtct cctctgctga gccgtgcacc ttctgcctgg cagctccaac
31141 tctgtggctg tgttcagtgg ctcagcactg ccccttgacc ctccctggcc ttctgcggat
31201 gccagactgg agcactctga caaggtctgg ggtggttgta tgggtcctgt gacctctata
31261 cacctcccag tgcctgggaa tcctgcagat acaccctcct tagccgtccc taaccataga
31321 ggacatttct gaggtccccg agagagtggg gcacccctgc aggatccaac tgctgggccc
31381 aggaaggata gcagcagcat gaggggttcc attagccaca aactcacggc atggaacctt
31441 cacccacctc gcccctcatc tgctgtttag cacctggcac gccgtgtata cttactgatt
31501 attacatttt aatggcaaat tatagtggca aacgtatgca tctttgcaca attgttgtac
31561 agcatgatga acaagtcatt aatagtaaag aataaatgtg aaagtgagaa aaatctgact
31621 gccaaagttt ttactccttc cttccctccc cagactttta aatgaaagtt tagggataat
31681 cccttagttg tcctgctagt aggacttgca attaaaagaa ttgggccaag aacacttcta
31741 cgcttctcct tttaggtttg ggtgtaaatt cggggtattt ctcactgatg aaagcctggt
31801 gcagggcaga ccgtgggaag ctttcatttc cggaatggac catcaacatc ccttggagaa
31861 gaattctctt ctccagaccc agacctggtg tcctggcacc cattgggcaa gtgggtccta
31921 gaagacaaac ctggtcagag cctggaggct gcttagcatt ccccacgcac attagcagct
31981 cggagagctc aggaagccgc agcccctcct tgcctcacca gcctggatca ggacagcatc
32041 ccctggaaga cacacagggc ctggcctctg attacccagc ctggagggaa agctcaatcg
32101 agcatcatgt caccccggtgc ccccatgcag ggtggcactg gtgagacccc caagccaatg
32161 ataccacctc acaggagtgc aggcccattg tggccagatc atcttgactt ttcaagataa
32221 atcagaaatc gtatttccat gagatatccc tatttgcaag tgatggtgac taaattagaa
32281 gtttttgaat attgtaacat gttcgtaggc tgtttgtctg gtttaaactc tatctggagg
32341 aattcaagct agacttcagg aataacttct tgaggcaagg attttgagac cttagggaaa
32401 gaaggacgtc ttgggggtat tctgactgtt gtcctcctgg aagggaagaa cagagaacta
32461 gaagactgcc cttagcgaag ttcaaagcac ctaagcccgg gaccctcagc aagtgttctt
32521 gagtcacaga ttctccctga ggcgcctctt tctggctcca tagaatggct gattctgtaa
32581 ctcggtgagt ttgctttttt tttttcctcc atcacccagg ctggagtgca gtgaagctgg
32641 agtgccgtgg agcgatcact gcaacctctg tctcccaggt tcaagcaatt ctccttcctc
32701 agcctcccaa gtagctggga ttacaagcat gcagcaccac acctggctaa tttttgtgtt
32761 tttaatagag acggcccgaa gtgctaggat tacaggcatg agccaccgcg gccagccata
32821 actctgtgac tcttgttaca aaggccttat attttgctct ttgagggtgg ttttggtttg
32881 atgcctgttg gttgccatct tttaactagg gatgttttat caaaatgccc agccaaagtg
32941 tccaaacaaa ttataactta aagtttgaaa atgtctggca cttctaattc aatgcctgtt
33001 gtgccaggca ctgggctgct gaggaactga gtcccgtccc tgcaggctag ctagagaaca
33061 cacacacaca cacacacaca cacacacaca gagtggtctt acaagtcagt tttatattct
33121 acctatatgc aataaaggta ttattatgtt gaggtgcctt gatataaaaa tttttcttaa
33181 aggagaggat gcctaaaaca ggcattacct gaaacctcct ctctccagca ttggttgtct
33241 tctgtcatga ctcagggttt tcactgagaa tgggatggaa atgtggtcta aagatagggc
33301 caatgttggg actggatccc ctctgggaag tcagaccagg ctagggcagg tccttgaagc
33361 catcaggaaa agcctctgga gccagaaaca aaacaaaaaa aaaatggtgt taactaaact
33421 cagtctcaaa tcctgaatag gactcaagtc aagcaaaata attaaaggag ttagcaaagg
33481 gcaagtcaga gagaccgagc aacaccaatg tcttccggga gccctgtggc gagtgacaga
33541 gcctggactc tggagtagaa ctcatcttgt gtcttcttct gccactcgtt agctgggtga
33601 ccttgagcca agccccttaa cctcttggac cctatgttct tatctctaag taggggctgg
33661 taatatcttc ccctttgagg aatgccctct aaggggtgtt gtgaagattc ggtaaggtgg
33721 caggggtagg actcctggcc agaaacaggc acataataaa tgctaagtct ctccttctct
33781 ccacctgctg gatgctgtag atactaagga tttcgatgtg aatgagacaa aacccctgcc
33841 ttccaggagc ctttgagaat cagagaacta gacccatttc cagaacaagg ggatgcaggg
33901 tctggataaa gttttgggga tcaatagagc agagggctcc cagaggatcc catagggttg
33961 actcctaact caagggcatg agacaacccc caggaagggc accctggaag gggtccggct
34021 gtccctgatt tacttgtggg cactggggga atgcccggag ccatccagcc ctcagggctc
34081 tgtgtgattc tgggttcctc ccataaaaga taatcagatt ctttcacgtt aatgtctttc
34141 tccacctcat tgcacatcat gcagctattc attgactcag caagtatcag ctttgcatgc
```

Figure 1L

```
34201 gaccttggcc tacccacttt agcttttagt aatagctccc ttcttgaata atacaaccag
34261 tggggaaaca gaacctaact cttacctctg ggaggcttat ttgctttgag aacatatgtc
34321 ctgcagtttt gttcatatgg cagtgaagtt tcgtgcacac actctagagc caggcagcct
34381 gggttcaaag cgcagctctg ccaggtccta actgcatgaa tttgggcaag tcgctcaacc
34441 tctccatgcc tgagtttcct catctgtaag attggagcaa tggtaatacc tgctttttag
34501 ggttgagaag agaattaaat gaattaagat gggtaaagtg cttagagtgg agctttgcaa
34561 gtagtaagtg ctatgtaagt gttcgattta aaatgaaaga cccttaaata cattctttgt
34621 tcatttcaca agcccttcat ttcacaacct tacatttcac aaccaagctc tgtctcccct
34681 ggaatccagc cataactctg ctcacaagtg tgagacaggc cccagcagag ctgcacgaag
34741 aggagagaag gcagcccccc agactcccaa ccccctgtcc aagatggcaa aaccagaaca
34801 cagcctctgt accaccccag caggtattca gaatctgcaa tctccaaagc ccacttcaat
34861 tgtaaatgta gagccacgtg cgctttaagt cacctgtcac tctggaggct cttttgctca
34921 gttcctcacc attagcaggg atgacaggga gtgcaggagt gcggtcgact cccagatatt
34981 ggagagcgct gggctagctg cccattctcc cggcctccac tcctctttgc tgtccagcca
35041 tcacttgctc tttgaaggca aacaaaacag aaaacagtgc caaaagtatg ggaagaaagc
35101 cagcttctcc cctggggtgc ctgtgatgcc atgcccaccc tccctgacca cgcagcccct
35161 gtggaccctc agggccccaa gcccccattt ccatcacatg cgtacaccca tgtgtgtcca
35221 tagccgccca tctcagtcaa taaggctgct cctgcccact tggaatagtg gtgacaacca
35281 ggagtggctt atgggaacta tcccaatggc ctgacagcat gtccgctgca aaccgctgag
35341 gtaggacact gccctcatgt ctagctgatc agcaagaggc gcagttgctt tcttaggtaa
35401 cattgctgct gtgtcctggc cattgctggg gggtggcact taatctacac cagatttttc
35461 cctcctgtat cttccaagct gcttggatct tggtgctgaa ttaggttgga ctttgtcttg
35521 tggggaaggg aggactatag accctcaacg taagcaatgg tcagactatt ctaagaaaac
35581 tcgccgaatt aaagcatgag gtaaatttag ttctgacttc tgtccacccc actgccactg
35641 tccccttta tcccatgatc ccttgctttt cttttcctcc tctctcccta tctcttgtgt
35701 ttgacgcatg ataggaattc agaaatatat gtttgtggat ttgtttattc acgtagcaaa
35761 ccatttcttg agtgcctacc atgggccagg tagaatgggc ggcccgggc tgcagtggtt
35821 tcttcagccc ctctccaggg tttacactgt gcaagacggt ttgtgatggg tcctcccatc
35881 gaggaccaca ctcttctttc tctgtgcccc ttggtcctca gtctctgacc ccacttcaaa
35941 ggcagcattc actcagggaa gctcccatac aatgctagtc agagtaaaag tttggacaaa
36001 ttgccaggaa gcagcttgtc agtatgcata aacagccttt aaaatattac tactctttga
36061 cccagaattt cacttctagg aatctgtcct aaggaagtag tcacatgcaa aagatttatg
36121 taccaagatg ttcatcaaag tgttgtttta taacaggaag tctcagaagc tggataaata
36181 tccaacctct ggaaatggtt agatagaata gtatgtagcc attagaaaat tatgtctatg
36241 gggtttaaaa tgtcatggga aaacacttct gacataaaag agcatgagaa ctgtatattt
36301 agcataatct taactatgtt ttagaatgca caggaaaaaa atgtacaaac atattcatag
36361 tgatgtctct ggtggtagga ttatgatcag taagtacttc tgtctcttca tattttcctg
36421 tatttgataa tacatgcata tgttgttttt aaaataagaa aaattttaag tttaaaattg
36481 gagctgaaaa gtgtttttag gtcaggcgag gtggctcaca cctgtaatag caccactttg
36541 ggaggctgag gcagtcagat cacttgagcc caggagttcg agaccagcct ggccaacatg
36601 gtgaaacccc atctctacta aaaataaaaa aattagccat gtgtggtggc acacatctgt
36661 aatcccagct acttgggagg ctgaggcatg agaattgctt gaacccagga ggtggaggtt
36721 gcagtgagcc aagatcgtgc cactgcactc tagtctgggc aacagagtaa gactctatgt
36781 caaagaaaaa aaaaaaagaa aagccttttt aaacagtagc agacataact atataatcct
36841 tactaagctg tcggtcaaat ttttatttat atatttattt tattcattta ttatttttag
36901 acagggtctc actctgttgc ccaggctgga gtacagtggc gtgatcatgg ctctcttcaa
36961 acttgacctc ccgggctcaa gtgatcctcc catcttagcc tcccaagtag atgggaccac
37021 aggtgcatac caccacacct ggctaatttt ttttattttt tatttttaga gatggtgttt
37081 actatgttgc ccaggctagt ctcaaactcc tgggctcaag ctatcctccc acctcggcct
37141 cccgaagtgc tggggttacc agcatgagcc actgtaccca gccctcaaat ttttaaaaat
37201 ctataagaga cattattgga caattagaga aattcacata tggacttata atagtatcag
37261 agtgtgtggt gtgatggttc tggagggaat ggactttttc tttggagaca ggcttttcta
```

Figure 1M

```
37321 tgcccacccct tttatcttgc taacttatca tcatccaggt tccagcagaa acattacttc
37381 ccccaggaaa tttcttaagg gtgcagtatc atgatgtctg cagcaaattc tcaaatagct
37441 caggaaaaaa gtacgtgtgt ggtatgagtg tgtgtatgta tgtgtgtata tatatacaca
37501 tatatacaca tatatataca tatatgtgta tatatataca tatatgtgta tatatataca
37561 cacacataca catatatata cacacacaca tacatacatg tatttttata taattatata
37621 tgcagagagt gcaaatgttg ccaagttaaa gattggtgag tctaggtgaa gggaatatgg
37681 tatttattgt attatttgtg caacttttct taagtttgaa aattttcaaa acaaaaaatt
37741 ggaggaagaa ggcatgccag tctaccccaa gccctccatt ggaatgctga aaatctaaac
37801 aatgtgattt ggcaatttca tttcttttct gttgtgggcc agtagtcctt agatgttggg
37861 gaagggggta gtcgctgagg tgtggttgac ttaggatgga agaagcagaa gtcaagactc
37921 ccagggtcaa agtggtttgc tctgctgacc caagtgtggg aggcccagag tcagcgtttc
37981 aggtgtgcta attcagcatg gttctattca cggccaaagt ccaccctggg cacctctctg
38041 gcagcaatct tgggtgactc tactaaggcc aggcctccat gaccctatgt ctggatccca
38101 tatctccacc tctcccactg tctcaggaac ggtgcttagc tttttctttt ccctctcctg
38161 tcttctttgc cagcatgtag aaagtttaaa taattcccct ctttacaaca aaacaaaaca
38221 taccccccttc agtcaaccac cctagctctc ttctcctttt cccagccaga tttttttaaa
38281 agcatcctag gccaggcgcg gtgactcacg cctgtaattc cagcactttg ggaggccaag
38341 gtgggtggat cacaaggtca ggagatcgag accatcctgg ctaacatggt gaaaccccat
38401 ctctactaaa aatacaaaaa agtagccggg agtggtggca ggtgcctgta gtcccagcta
38461 ctcgggaggc tgaggcagga gaatggcgtg aacctggtag gcggaggttg cagtgagccg
38521 agatggcgcc actgcactcc agcctgggtg acagagtgag actccgtctc aggaaaaaaa
38581 aaaaaaaaaa aaaaaaaagc atcctcagca ctttggcaac tccatctcct cccaacatgt
38641 ccctgttact ggaatccagc caggactcag ccccgatctt tctactctaa ccagttgtct
38701 cagttaacaa ggacaggttt atgctgcagt gacaaacaag atcccaaatt cttgtggctt
38761 cacacatctg gcaccacctc atcttccagc cttaggagtc atcttttagt tccttgaaaa
38821 ctctttacag ttttctgttg gggccttgtc atatactatt cccctggaat gttctttcct
38881 atcccctccc tttcaccttg ctaacttgtg cccatccttc aggtctcagc agaaacatca
38941 cttccttggg gaagttttct ccaacaccca cactacacag gtgtcccatc tacactccta
39001 tgactttgtg gtacttgtct cacttcattt tccactgcct tcccccacaag gcacctgcac
39061 aagggcaagg accgtaccac tgtacctatg tcactcattg ctgtggtcac ctgcactctg
39121 gctgcctacc ttaactacac attagaatca cctgaggagc ttttaaagcc acaatgcaag
39181 actccaccct aggccaattg gatccaaatc cctggggtag ggccagacat cagtggagtt
39241 atatatacat atatatattt tgtttgtttg tttgtttgtt ttttgagaca gagttttgct
39301 ctgtcaccca ggctggagtg cagtggcgcg atcttggctc actgcaagct ccgcctctcg
39361 ggttcacacc attctcctgc ctcagcctcc tgagtggctg gaactacaag tgctcgccac
39421 cacgcccagc taattttttt gtgtttttag tagagatggg gtttcaccgt gttagccagg
39481 atggtctcga tctcctgacc tcatgatctg cctgcctcat cagcctccca gagtgctggg
39541 attacaggca tgagccactg cacccggcca tcagtggata tatttttaaa gcactgcaga
39601 gaattctgtt gcatcagctt gagaaccact gatctgcctt gtgcttcaca tttaaaactt
39661 tttttttaatg aataaataaa ccccaaaaaa ttaatctccc taagcctccc tagaagatag
39721 gatggtaagg atattttcct aggtaaaaat atgttaattt catatttcat gaaatttcat
39781 gtttcatttc aatcaagctc tgtcatacac cttacatggg gcaagcccag tgcctgggca
39841 gggtgtaatt atactcatta cacaggcaag gaaaagtcac attaggtgat ggagcacaaa
39901 taggcagtta atggtttcag ggctagttag gatatgtttg tctttcaatt gcaagtaata
39961 gaagcccaaa gaaattggtt atttatataa tataattgat tggttcccaa atttgaaaaa
40021 ttcaggaata gacccagctt aggtacagct ggatccagtc actcaaacaa tgtcacaaag
40081 aacccctttga caggaatgta tcctgtgttg actctacttt gctctgagta gtctttcccc
40141 aggtgatgat aaaaatggtc atcatcgcca ggcttgtgtc ctgtttagta ggaatataca
40201 agaagagctc agtaaatgct ggccccacca ctaagcaaaa acaaaacttt tgttgttgtt
40261 attgttgttt taaataacag cttagacctt tcttctttcc ttgttattct ctttcatctg
40321 taatccagtt ttctacttct gaagtataga atgttctgat gatttattct tcattaccca
40381 caacttgcac atgtttattt aaaaatgcca ggattgcctg gccgttgtgt gctgttaacc
```

Figure 1N

```
40441 tttgtttgct gttagtggat ccctgaagtt caggctccca ggggagcaga taatgggtat
40501 ccagttcctg caatatccac cctctggcaa gccaagttcc ttcctgggta aggttttgcc
40561 tacctgcatt cctagggaag tttctgggcc tgaccaccaa gccagctctg agaaggggtg
40621 cataagcccc accatgcttt ggctctgtcc ctatagaata ttttatgttg ttactgaaaa
40681 ctaaaggaag atgggtgcgg tggctcatgc ctgtaatccc agcactttgg gaggccaaga
40741 cagattgatc actcgatgcc aggagttcaa gaccagcctg gccaacatgg tgaaaccttg
40801 tctctacaaa aacaaaacaa aacaaaaatt agccgggtat ggtggcatgc acctgtggta
40861 ccagctactc aagaggctga ggcacaagaa tctcttgaac ctgggaggta gaggttgcag
40921 tgagccgaga tcgcactact gcattccagc ctgggtgaca gagcaagatt ctgtctccaa
40981 aaaaaaaaaa aaaaagaaaa ggaaagctaa aggagagaga ctaaaatgat atcaggttcc
41041 tggagaacaa acagacatga ttttgcttca tggcaggaca gccggaagaa gtgggattat
41101 atcctcacat tacaaataag aaaactgaga ctcagaatgg ttaagtcact tgtcccaggc
41161 cacacagcca gtaaattaca gaaacagaat ttgaacccaa atcttccagc tccaaagctt
41221 gtgttctttt cactacctcc tgcttaattt tttaatttct aagattagac ccttcatcta
41281 tccatgacac ctgcctgtca tcccctgaaa aaaggtgaac gccgttcaga aatttttcta
41341 gcctgagctc actcccagtt cacttatttt tgctttgtca tggctgccca gtccccactt
41401 gtagaccagg aataggtcat ggctgcgggg actacacgct gtcgctgctg caagggccgg
41461 cctctgtttc cggggctgag tgggggccag acctgccagg agcaccatct tctgtgggtc
41521 ctgcctggat gtcacatccc ggccccaaga agtcactgca aaccttcgta ttattgagct
41581 tcacatccta gaatttgctg tcactgtggc tgctgcatga agttgtcctg agagaaacgg
41641 gcattgtcat taacagggaa attgatggtc tggggaaaa gtcatcctca ttctcttgca
41701 gatctatggg tgattgagac tggctgatgt tgaaggggtt tctcagccat cgtgtgccat
41761 gttatggaac agtggtgtag ccagccattt gacacccagc gctgaccttt gtttaacaac
41821 ctcacctata tatgacaaaa tgattgtcag aaataatcgt gtaatgaaat gactgtaata
41881 atggccagaa aagaaacgca gatagtaaaa tgtttctctt gttgaactct gtacatataa
41941 ttgcaccagg atttttttca aataaaaagt aaatattata ctacaaaaaa gggaaaaagc
42001 acaagcattt attaaatagc tttctatatc tttctgagtt ttgatccttt gattgcagac
42061 tgatgtaata ttttatgtaa atcattgctt ggttactaag tgaactttaa gaaaagtgag
42121 acgtctgcag aagttgccca taatttagca gctactgtat tgtaccattg atgtacggct
42181 ttattttctt gattaattat ttaaacaata taattcacaa ttttaaaata ataaatttcc
42241 acttaaaatg gtatttaaac tcagcaaaat atatcatcta tgagtaaaat ttgtatttac
42301 caagcaaaaa tattacagtt tgtggttcac atgctgtctc actgttttaa attttaaata
42361 caaaaactcc aagtaggctg ggtgtggtgg ctcacacctg taatcccagt actttgggag
42421 gctgaggcag gcatatcgct tgagttcagg agttcaagat ttgcctgggc aacatagtga
42481 gatcctgtct ctactgaaaa caattagctg ggtgtggtgg cacatgcctg cggtcccagc
42541 tactcaggag gctgagatag gaggatcact tgaaccctgg gggacagagg ttgcagtgag
42601 gcaagattgc accactgcac tccagcctgg gtgacagatt gagaccctgt ctcaaaaaaa
42661 gaaaaaaaaa aaagaaacac aaaaactcca ggtggtcgca cagaatgaca ggactgaagt
42721 aacttagctc caatttctgt cttcataatc actgtcctac cattgtctgt gcttagaatc
42781 tacttgctta atgcaggaac atgtgttctc acagagatgg aaaatgcaaa tggcgccaga
42841 agcaagctgg aaattctgaa ccattaagaa tttactctct gccaggcacg gtggctcacg
42901 cctgtaatcc caggactttg ggaggctgag gcaggcagat catctgaggt caggagttca
42961 agaccagcct ggccaacatg gtgaaacttc atctctacaa aaatacaaaa attagccagg
43021 catgatggtg ggtgcctgta atcccagcta ctcgggaggc tgaggcagga gaatcgcttg
43081 cacctgagag gtggaggttg cagtgagccg agatctatct gcaccattgc acttcagcct
43141 gggagacaga gtaagactcc atctcaaaaa aaaaaaaaaa aaaaaagaac ttactctcaa
43201 aataaatacg tgtggctgac tccacatatg gtagggccaa ctgtataact agaagttctc
43261 caaataactt ctgtggagaa aaaaaagttt attaaaggtt aacttttta aagtgctaac
43321 tagaacctta ctaacactga gatcgcacca attgtttata acttagacag ggccgggtgc
43381 agtggctcat gcctataatc ccaacacttt gggaggccga ggcaggtgga tcacttgatg
43441 tcaggagttc gagaccagcc taaccaacat gatgaaaccc catctctact aaaaatacaa
43501 aaattagcca ggcacggtgg tacacgcctg taatcccagc tactggggag ggtgaggcag
```

Figure 1O

```
43561 gagaatctct tgaacccagg aggcggagat tgcagtgggc caagatcgca ccattgcact
43621 ctagccccag caacaagagt gaaactctgt ttcaaacaaa caaacaaaaa aaaaaacctc
43681 ttggaccagg aaaatatttt ttaagggagg agtattttat cactggcatt gtttaggatt
43741 gcaggcacat gatgctaatg aaaagcagac taactattag ttggttttat tactgttttt
43801 gaactctctc tctccctttt tttttttttt gagacagagt ctctctctct gtcacccagg
43861 ctggaatgca gtgactgcag tctcagctca ctacatcctc tgcctcctca gttcaagtga
43921 ttctcgtgcc tcagcctccc gagtagctgg gattacaggg caccacacca ggctaagttt
43981 ttgtattttt agtagaggca gggtttcacc atgttgccca ggctggtctc aaactcctgg
44041 cctcaagcga tctgcccatc ttgacctccc aaagtgttgg gattacaggc gtgagccacc
44101 gtgcctagcc ctgtttttga actctctaga gacagtccag ccccttatta cttgtcctga
44161 ggcagctgct cccttcacct ggccccccgc attgtgttcc ggacccttgt cctggtggtg
44221 ctaaagaata tctctgtcga tcctttgggg actggggaaa ctgaggccca gtgccacgcg
44281 atgccatttg ttcagggaag attaggtcat ctgctaggtc cccagtcact tgaccttctt
44341 cccagacagg aagaagctgc tctgggtctc tcagtgctcc acgtgtcttt gcacattgaa
44401 atgttttctg attttttttt tttttttttt gctgttacat ttacttttaa aaaataacaa
44461 gcaataaaat gttacatttg agaaggttga aatgagaatt gatttgagtt aaattctagc
44521 agatttttct tagaagaatg atatcatcat ctccagctac ctgcaattga tctactctga
44581 attaagaaag agacttccat ttgttgttta tattttgcac tcttgatgtg tttctttaaa
44641 ttatggtcat gggccaggtg taggagctca cacctgtaat cccagcacct tgggactctg
44701 aggagggagg atcactggag gccaggagtt caagacctcg tctgtacagt aaattttaaa
44761 aattagccag gcatggtagc attcacctgt agtcttagct acttgggagg ctgagatggg
44821 aggattgctt gagccagaac tttgaggcta cagtgagtta ttttcacgcc actgccctct
44881 agcctggctg acagagcaag acctgcctca aaaaaataag taaaaaataa attaaatttc
44941 aatcattagc agtcattagg atatttaaat acagtatgtt gaatcaaagt tacgcatgtg
45001 tgtatttttt tttccagaga gttgtttatc atgtgggttt taatttaact ttaaaaaaat
45061 gttggctgga cagttgccca aatggtatca tcagccattt ggttgagaac gtatgtcctg
45121 cgggctcctc tgtcactgga gttttgctag ctgacagcca ctggctagtt agagactgca
45181 gtcagcacag atgcaggcgt ggacttgcgc acgtaaccat gtcaatgcaa agccatcact
45241 tcttaaaaat tctgaaccct gctgtctgag atggtggtgc agcggataga actctgctct
45301 aagaggcagt agctaattcc atgtcttctt tgcccttgac tagctgagtg actttgcaca
45361 tggggcttgc ctctctgttg ccttgtctgc aaagtggaat catcttttcc ttgctagaca
45421 gaaggtggac cctggaccta tggccttttt gagtttcccc cccgcttctt agaaggacct
45481 ctgatcctac tgagtttaat acccacgggt taataattgg gaaaagcaaa ggaagcgctt
45541 ctgtttaggt aattatatgc atgtttttgt ctttttctgg ctggaaagat atccaagcca
45601 ctgggaaggt ccgtggctac ccagggtagc cctctctggg gagggctgct atatccaaga
45661 gcccctcatg agaatttgaa aatcgaccat ggtagggcct gctgactttt gacagctaat
45721 ggtgtgctga gaattgtccc tccaaagatg cctttccatt ccctcgggag agtctgggca
45781 gcccctactg gggctggga tgctggctct tccctcagcc tccaccccaa ctgctctctt
45841 ccctcctccc ctccccagcc ccctaatttc tctcacaagg ctttgttctg cagcaacctt
45901 tcctaatgca gtcctggcct cttcgcagct tcattacata accttccgtg gactcctggt
45961 ccaaggatca ccccagaaag ccagtcagag gtaggcacgc agctggggtc catttactta
46021 ccttccccac cccctcggaa ctcagaggtg gtgcaggaat ttggactcca agaattaaca
46081 gctccaccac catcaccaga gccaaaactc aggatgcatg tgcttcatct gctgcttatt
46141 tccagctgag agccagtggt gccatggttc cttagggagc cggtcccctg atgccggctc
46201 ctggccccaa atctctctga tccgggctct tccagaatgt cttgtctcca ccatcgcctt
46261 tgaccaatgg tgtccctttg cctggtaatg tcccctttgc ctgatgatgg ccctgtcact
46321 cctctcttta gcacagagga ggctgtttca tcccttcaag cctgccctcc cttcaagtct
46381 tagctcaagt tcaccttctc cgcagagcct tctccaatct tcttgactac gtctcctctc
46441 agctccagca acctctgtct ctggcactga ttccttactt agctaagaga atcacagaca
46501 cttggggctc aggacaatct gctttctctc ttcttaccca tggccttgga ctgtgtgtac
46561 ctctttgtct ccactcccaa acccaacccc cagagggcag agagcatgtt gtctgtccct
46621 ttgctcagca tgaagccatg cgtgtggtag atcggcagag ttccataact tgtgttgacc
```

Figure 1P

```
46681 gaggggtcac tttgctctga aattacccct gtgtccttca gtatttgcac agatagcttc
46741 ctggccagac cgaatatatc caagggcatg gcccacctct gctcctgttt ccaggtccct
46801 ggtgggggtt agttcatgcc ttcctcataa tctgcccact ggcctggtcc tcaaggtctt
46861 cccaactgct cagccagagt tgagaaaatg ggtcgctcca tcctgtttgt gtcgttctct
46921 ccttcctggc ccactctcct gcccacaggt atccaggggc tgcctgtagc attagaggac
46981 atacatgcac atgcgtgggc atgggacact cacgtagcct ccaagcacag catcaataat
47041 gcattctgtg ctttatagca tggaaagctg ctctaaactt tattacacag tggacatgtc
47101 tgaagcagct cccaaatcca cccctgagtg tgttggaatt ggcaagccta tcacttggga
47161 gtctagtttt tttgttcgtt aataatagat gcttcctgtg gccccagctt ggcaattttg
47221 atttaaagtg atcttaactg aagagactaa tggacgggtc tgaatttgtg ccttttaagc
47281 acaaagtatt gctcttaatt aactggattc tatcctttga gcaggcagag gccttccccc
47341 aagggcgtca ttaacgatcc acatctggac atcttccaaa gccttcttct gtttcaggcc
47401 aaccgcaggt gtgttcctga acacccagga ggctatgaga gccacatatg cctcccaaat
47461 acacacagtg tgcatgccca gggacataga gcagtgtgca aagtcccatt ccatctctct
47521 ccacctggga gaggatggct cttctgtctg attcatggct caaagtggta aaggagctcc
47581 ccactccccg tcccacgcct actcagagtc tgcaaatatg tatgcgatat gagagctcgt
47641 cagttagctg tcttcagtgt ggcgcacatt tgaggagtct gactcccctc cagcacaggc
47701 caatgtgcac tgctctccta tctttgtacc cccactgttg cactgtgcag aggttggagc
47761 catagaagta ccagagctgt gaaaggagag gccccctctc acctctgccc tggtctccat
47821 ccccactttc tctaggaagc tagtaggtgc tgacagggga gagaagggag gggaggggtc
47881 cagaaacagt ggctcatgcc tgcaatccta gcactttggg aggctgaggc aggaggatca
47941 tttgaggtca ggagtttgag accagcctgg gcaatgtagc aagaccctat ctctacaaaa
48001 agaaaaaatg taattagctg ggtgtggtgg tgggcacctg tagtcctagc tacttgggag
48061 gatgaggtgg gaggattgct tgagcccaag agtttgaggt tacagtaagc tgtgattgca
48121 ccactgcact ccagcctggg caacagagct gagaccctat ctcaaaaaaa gaaaaaaaaa
48181 aagaaaggag agagagagaa agaaaagaaa agaaaaaaaa aaaagaaggg aagggaaagc
48241 ccagaagagt gtggggagag gaggcggccg tcattctggg gccctcagtg tgcacaacca
48301 gataacacat gctctgtggg cttttgtacc attttgcttg agcataaaga aaggaaggct
48361 gcccctaaat agaaagcact ctggaggcaa acaaatctga ctccaatcct ggccctgcca
48421 ctttcccagc tgaggactta gacaagcacc ctagcctctt ggacattctc agagccatct
48481 gctgcaagtg ggtgctgcca tacccacctt actgggcagg cttgggggac caagggtggt
48541 aaatggctca gtctttcatg atgcggccac acagcaggtg cgccatccag gtccatttct
48601 ttccttcctt tcccccaaat caagttgtca ttaaagtact agtccacatt aatgaaatca
48661 actgtattaa ttttctattt gctgctataa taaatcatca gaaatttagt ggcttaaacc
48721 aacacaaatg tattacctta cagttctgga ggccagaagc cctccatagg tgtcactggg
48781 ctgaaatcaa ggttttggca aggttgcggt cctttctgga gggtccaggg gagaatccat
48841 tttcttcctt tttccagctt ctaaaggttt catgcattcc ttggctcatg atcttctata
48901 gctatagtca gaaaaatttt ccatcaatca tcttcaaagc cagcaatggc aggatgagtc
48961 ctcacatcac cttgctctga caccagttct ctgcctccct cttccacatg tcaggaccct
49021 catgattact ttgggctcac tctgataatc tgggatgatc tctctatttt agagtcagct
49081 gactgggaac cttaattcca tctacaaccc caattcctct ttgccatgta cagtgacata
49141 ttcacaggtt ctggggatta ggacgagcct gtctctgaaa ggctacttta catgaaaatt
49201 catttttta attaagattt ttttttcctc ttgagacaag gtctcactct atggttcagg
49261 ctggagtgca gtggtatgat cacagctcac tgcagcctcg acgtctctgg gctcaggtga
49321 tcctcccacc tcagcttccc tagtagctgg aactacaggg gtgagccccc atgcccagct
49381 aatttttttt tttttttttt tttgagacag agtctcactc agtcacccag gctggtgtgc
49441 agtggtgcaa tctcagctca cagcaacctc cgcctcctgg gttcaagtga ttcttgtgcc
49501 tcagcctccc aaggagctgg gactacaggt gtgcaccacc acgcccgact aatttttgta
49561 tttttagtaa agatggggtt tcaccatgtt ggccaggctg gtctcaaact cctgatctca
49621 agtgatccac caacctcagc ctctcaaagt gctgggatta caggtgtaag ccaacatgcc
49681 cggccccagc taattttaa atattttttt tgtagagatg ggttttacc attttgtcta
49741 ggctggtctt gaactcctgg gctcaagcaa acctcccacc ttggtctccc aaagtgctgg
```

Figure 1Q

```
49801 gattacagca tgagccactg cactcggcct taagagaaga tttaataatt aatactttac
49861 aacaagatct ggaagaggtg ggatgagtaa ctaaatgagg atacaagtaa cccgggtcat
49921 atttgctaat accettggtc acattgaact tgatatetta tcagattttc ctaatcagct
49981 cctttagcag cagtgttgca gcatcttatc tcattttgtt ttttgttttt ttgcctagca
50041 catgcctgta aatcactgga ttgaggtgtt tagatgtttg ttgtcctttg gatgcttctt
50101 ataaatccat atttcatggc tccctggaaa gtgctatgca aatgataagc tgcaaggatg
50161 gaaaggaaat tgcagtgctc ctgaattgta aatgggcttt tacgaggagg tttctaatta
50221 ctcgctcttt ctcttgaact gaggagttga agtgtaggtg gcagatccat aacagataat
50281 catgtgtgtg atgtgacttc agcctgagcg tcgaggacca agtcacagag caggaacagc
50341 cactctccag tgtccttggg gctacgtctg aggagaacct gggatttcat atatgacctg
50401 cactggctgg ggggctctct tgacgtaacg tgttccctct gagcatgtta cagattctga
50461 cattcttatg ttccttctgt ggagagacat gtacttagtg acctaactca ctttagcata
50521 tttttgctca tcgtttgtgt agcttaaagg aatcagataa ttacccccto cccactactt
50581 tcggaagcac aaatgcaatg ccctagaatt gtactgggga ctcaaaaaga aaagagagta
50641 gtaaaatcta ttaaagggga caaagacagc ctatatacta caagctttct atttttatgg
50701 cagagaatgc cattttctaa gtaaacagag aactgcattt gacctgcaat atcaaatgca
50761 tggatttgat gctttggaaa gcaactgttt tctgcgttaa tctgggtgtc ttccgtgaaa
50821 tgtcctcctg cctttggctt aaacactagc tttgtctaca gccattccat cctgaacctg
50881 cccaatcttg tctgaatcct ggtttcacca ctgacaagct gtgtgtcctt gggcaagtta
50941 cttcacctgt ctgtgcttca gagtcctcat ctgtgagttg gggaatctgg acagaatcta
51001 ccccataggg cgtagtgagg atgtgttgaa ttatcccaag tggctacaca gagtaagcac
51061 tcaaatgatg tcatcgttgt catgattgct gttaccagag cctagagttc attctgatac
51121 tcgagtctgt ggcccatcca gcccaggtaa ggaatagttg gaggagttgg gcatgttcag
51181 cttgaagagg agacgacagg ggatatggga tagttgaatc tgtgaagggc cccctgggat
51241 gaagaactgg catgttctgt gtggctccag ggcactgagc aggacccatt tgccaaagtc
51301 tcagggacac agtttctagc tatagacaga aaaattttct gtcactcaga ggatgaaaat
51361 agaatgagcc cccttaagag gtaatgagct ccctgtcatt ggaaggattc cagaagagct
51421 aggtaaccac tttaggtgct atcaaggggc ttttttcttt aaagtccttt ccaaaagctt
51481 ctgagattgc ataaacaata ggaagccatc ttggtgcttt aacacaaact ctccccagtg
51541 atgagggttg agccaaagcc agattggcaa gcagagagga gacttgtgta caaggagttc
51601 ctcgagtcaa ttgctttttc cttgttctag ccagccagag ggctcctgtt ggaaaacagg
51661 agaccggaga ggctgaggcc tgaccaaacc agcttctgca ggccagctgg gaggccacaa
51721 ctcctaccta cgggaaaact gaagggcatc tctattttta gattagcaaa agaaaataaa
51781 tttaagtttg agtctccttt gcaactttta aaagacatct ttattgagat gatcattcac
51841 attctataaa attcccccac tttgagttac aattcagtgg ttttagtctt ccttgatgat
51901 tttgatggtc ttttcttaag gctcttggaa gacccagaag cctctcagac acaggtgggt
51961 gtggagggcg tagcacagag gcagacttct catttcctgg gtctcccctt taatgactct
52021 cagagacccc tccttccccc tgcccctggc ttctacccca ggggtgtaga gttttgccat
52081 tttccaagca gaacttcatt tcctcttctg tgtctacact ctttgtgctt ctttcttgcc
52141 agctttttct cctttgcccg cccttccttc cttccttccc tccctccctc cttccctcct
52201 tccctctttc cctccttccc cccttccacc cttcccccct tcccccctto cctccttcct
52261 tccttccctc cttccttcct tccttcctgc cttccttcct tcctgccttc cttccttcct
52321 gccttccttc cttccttcct tccttccttc cttccttcct ggtatgtgac taatttctgt
52381 ttcaggacat aaatgttgtc caggctgttc tttggtcttt ctgttggata atggacattt
52441 ggcattgaga gaggctgctt tttctgaaat catgttcttg ggcccccagaa cctaggtgtg
52501 tgcttctgac tttgttttct tcctgatcca aattctgata tgtccattta aattgatcta
52561 gacccacagg gcactgtggg acagatcctc agtggaacat gactctgtaa cgagagcatt
52621 ttgttttgtc aaaatgagaa catattattg cctttcatct gattgtaaac ataatacatg
52681 tttataaaac agtataatga gacaaaaatg tagacactaa taagggaaaa tctccctaat
52741 tgtatttctc ttcacagaga aagcccctgt tgggcatata tactctagtt tgtttatttg
52801 tttgactaca catatatgta ttctttttctt atgtataaaa attctgaaca tgcacatttc
52861 tgcaactact gttttcactt gatgatgcat ggacctctct agagtgtacg tttcttcttc
```

Figure 1R

```
52921 cttacaaagc agttggcttc gcccagggta caccaggaca cggttttggc tctgtcccca
52981 gggtgtcacg ggaccagggg atgatctcac agggtctgcc atctgccctg cctggccgga
53041 ggctgcatcg agagggccaa ggggcaccac gtgtcgtggg tactgtcaaa caagagcctt
53101 cagagccttc cacagtcttt cttttgcttc ccagcattgc ttccccgctg gtggactctg
53161 aatctagaac tagctccagg cgcctctcca aattcagacg ggagctgggg cactattata
53221 atgcaaatct aggcaaagcc ctcccaatac caggatccag aatggggtgg ggccctttgc
53281 cctgaaaagc tgtttagttt gaaaatacaa acaggagaca gaaaagtttg gctaaattaa
53341 tggataaagt tttaacgatg gtaaccatag tagggttcat cgacagccag cgatggttct
53401 gaacacttga catgtattaa ctcacctaat ccccacattt tacagacaat gcaaaggagg
53461 ctctgggagg ttgagtgact tgccccaaag tcgcacagct cctaagtgaa ggattcggag
53521 tggactccag gcagcctggt ctgactccct gcactgcgct gtgcttatct ctggccccaa
53581 tgccgccatg cagaagtgtc tgggggcact ttgtctctgt cagacagaat tcggagatgt
53641 gtatgcttgc cctggtatgg cacttctctt tttttgagac agaatctcac tctgtcaccc
53701 tggctggagt gcagtggcat gatctcagct cactgcaacc tccgcctccc aggttcaagc
53761 aattcttgtg cctcagcctc ccaagtagct gggattatag atgtgcacca tcgtgcctag
53821 ctaaattttt gtacttttag taaagatgtt gttttgctgt gttggccaag ctgatctcga
53881 actttggcc tcaagtgatc tgcctacctc agcctcccaa agtgctggga ttacaggcat
53941 gagccaccat gcctggcagt gtggcacttc ttacgtgtgt tcagcggaca ctgtttatct
54001 tctgtccctc caagacggtg ctgagctcag gtcgttcatt actggcagac aactgctgat
54061 ttccaacaga attgccatcc tcttctcccc tgcgactttc agagtgtgac ctcagactca
54121 aaaattagaa gtgaaaacat cttaaaaact atcacctttt cttcctaatc ctcctctccc
54181 ctccctgtct tccttgttgt ccccatctaa tgaactatca tggcaaaaag agcccatttc
54241 tggtcatttt ctgtggcctt tcaaactccc acctacccca ctgctcctgg gtgcattacc
54301 cgaaagctga gacttcagtg cagaaagtgc caggccctct gtccccccag atcgccttcc
54361 ttgtcttccc tgtgcttgcc tgtcacattg tgtgggttcc agcgctggaa ggaatgagga
54421 acagattctc tggttctcct tttgaagttt accttcgctc caccacttct gagaccttcc
54481 cggaagttgc cccttgtttc tctcctctcc agggctgccc cagagctgcc tctcacctct
54541 tcctgctgtc accccaccac catcagggca gaagttggga caaagcctct cctactggct
54601 cctgcttttc tcccttaggt ccagcctcct cttctccatc ttcaggagtc tccttctcca
54661 ctcacacgtc atgacttcag cacctcgcat cagtccagaa tatgactgct tgttcaagtg
54721 ccacctttct catgcatttt tttctagtga caatcacagc caccctgtgg ggcaggagtg
54781 tcatcatccc catgtttcaa atgaagaatt gcagttcaga gagggcaagt gactggccca
54841 gcctcaacag ctagccagtg gaccccacca gggcttctga ctccagtccg ggttcccttt
54901 ccacccaaat ccatggaggg agctgagccg agaacaggtg tccttcagga agacgtgaag
54961 ccaaagcctc cacctccaaa ctcaggggcc cagggagtcc aggcacccat ccactcacaa
55021 ggctggatat ggtgcattcc aggagagggg ttgggggcga gtggcctctc tgtgtacccg
55081 tggggataga tgcgcaagtg gcatcgccac atcgtgagtc ctggcttcat gggtgagctc
55141 caggtccaac gagaagccaa gcaggggggc cttcaagctc agctttgggc ccgggtcggg
55201 gtacagggta gagcgggcct ccccagcccc tgccatgagg ccaaggcagt gcatcgttcg
55261 cagcgtacat tcagaaacca aagcctagga gctggttatc attccggttt acagctgatg
55321 gaagagcagg tgcttccgag aacccacagt gctctttggc cagtgaccca agggtgcctc
55381 tgagaggcct cgcagcaccc ggaggtgctg ctgaggcaac gccctgactg taagaaggac
55441 cattcatcct cagagagtgg ccgtgatgct gctgcgacag tcccaccatc cctcccgact
55501 ctcactccca acagacttcc cactgtaaag ctgaactctc cagcaaatca cctctcgcca
55561 gactctctcc tcactctctc tgggtccact agaggttcct cagcctctct ttgccttggt
55621 tttcccagct gtaaaatgga gcaaagaggg cctatgtacc cacaaaggtg tggttggagc
55681 gactcctcct acattagggc ctcgagtggg gcttcatgat tggttggtgg aggtctccaa
55741 acccacccag tgccaccgaa ggctgagact gcagatgcaa tgccacaggt gtccttcctc
55801 agcctgggca gctgaacatc atgtgtaaaa cggggataat aagataataa cagccccttg
55861 cacctatgtg gctgtgagga ttaaacaaga taaatgtgta acagtgcctg gctatagaaa
55921 tatttactct tgttattaag ggaagaatat gtgtggctaa aaagggatcg aagatgtaaa
55981 agccaatccc tccccctcta gcatatttaa gggtaatgtt gagttggttt gtggaccatt
```

Figure 1S

```
56041 tgctgcctgt tagagctgga aggtagggac cccctctcaa cagcgatgct acaaattata
56101 cccattggag gtcaaccaaa agacaaagct tattggctgg acatggtggc tcacacctgt
56161 aatcctagca ctttgggagg ccaaggcagg cggatcactt gagatcagga gttcgagacc
56221 agcctggcca acatggtgaa accccatccc tactaaaaat acaaaaatta gctgggcgtg
56281 gtggtgcaca cctgtaatcc cagctactca ggaggctgag gcaggagaat cactagaacc
56341 caggaggtga aggttgcagt gagccgagat cgcaccactg tactcaaacc gaggcaacag
56401 agggagacgc aatctcaaaa aaaagaaaaa aagacaaagc ttgttaatac cagcatattg
56461 ttaagggaat aaagtaggct gcagaacaac tggtgtaata tggtgccatg tagggaaaat
56521 tacatgtgtg cataggagag gggtctgcaa ggttgtgccc taagatgtta gagtggttcc
56581 tttgcttttc tcttttataa ttttgtattt gacttttaaa taaggaccat aaatcacttt
56641 tataaaatac attctctcca gcccctacta ctcctttaaa gaataagagt ggtttgccca
56701 agaaagacag tttttttgc tctggttttc ttgattctga catcagagga aactccttct
56761 catccacttg gggctctggg ttcaggggat tcatttcagg cagattaaag tggtgaccag
56821 gggcattcgt ggacacaggg agggacagga gcaccatcag tttgtctcac acaaccactg
56881 tcatcctcac tgaaggctgt tgcctgatca aaaacagtat tgggccaggc acggtggctc
56941 acacctgtaa taccaccact ttgggaggct gaggtgagtg gatcacttga ggtcaggagt
57001 tcgagatcaa cctggccaac atggtgaaac cttgtctcta ctaaaagttc aaaaattagc
57061 caggcgtggt gggtgcctgt agtcccagct acttgggagg ctgaggcagg agaattgctt
57121 gaacccgaga ggtagaggtt gcagtgagcc gagatggcac caccacactc cagcctgggc
57181 gaccgagggg gactctgtct taaaaaaaaa aaaaaaaaaa aaaaatatat atatatatat
57241 atgtcaaaaa tggggtagtt tttagatcta tagtagttct aaaaacaaag gccatccaag
57301 catgacagat ttacaagcac tattggctat tccagtagtt acaatggagg agagaagctt
57361 ttagttaaaa caaacaaaca acacaacaaa cccagaaacc ttaggtcaaa accaaaattg
57421 tcctctcaga cacaatctgg gaattttctc atgacagtgg gcattagcca actgacatca
57481 gcagcaacca tccgtgtgca cacagtggca ccacctcctc ccaaaaagca gccttcatct
57541 atgccctcat acaatcgttg attattctct ttggattgag gcccggaatt atttaagttt
57601 cttcttgcca gcatgagtct ttcctttctg tatgctcctt atcttctctc tttaatttgg
57661 cagttctgct tgaaatctgg gtctttcatt agtagtagtt caatttggtt ccagaacatt
57721 ctgtggtgtg atgcaatgtg accagagctc acacttcaga gctcttcaag ggccagtctt
57781 actgagcacc tcccagtggc tgcctgtgtg ctgggcgcca cttgtggtgg gcaggagaga
57841 ggaggggaca caaaaggaga cacagctcct tcttagaagc tcaaagttgg ggaccagctg
57901 ccacagaaga gtatgtttag catctgagac accaagatcc agcgtcacaa gggtgtttat
57961 taagcctcct catctctttc tttttctttt ttttttttt tttcctcagg cagtcttact
58021 ctgtcaccca ggctggagtg cagtggcatg atctcggctc actgcatgca accaccacct
58081 cccgggttta agcaattctc ctgcctcagc ctccccagta gctgggatta caggtgccca
58141 ccaccacacc cagctaattt ttgtgttttt agtagagaca gggtttcacc atgttggtca
58201 ggctggtctc gaactcctga cctcagatga ttcacccacc tcggcctccc agtgtgctgg
58261 gattacaggt gtgagccacc gcgcctggcc ttgctgttga ttcatctata gtatgtttga
58321 cttgatgacc tccagttacc ttagacagag gttctcatct aagctccaac tttccatttc
58381 ctttgtcctc gtctttcccc ttaacccctc cacatttctc tcaaaatcac cccacttcta
58441 aaaaatactg tttatttttc ttttaaattt caaattatct atactcattg aaataaatca
58501 aaatagcatg gaataagcga aaaaaatgga tcccaccctt ccccactccc attccctagg
58561 gctaaccata gttaaccatt taatgactag gttttttgt tgttgttatt ttttatttat
58621 ttattttgag acagagtctt actctgtcac ccaggctgga gtgcagtggt gtgatctcgg
58681 ctcactgcaa cctctgcctc ccaggttcaa gcattctcct gcctctgcct cctgagtagc
58741 tgggattaca ggtgcctgcc accacacctg gctaattttt gtacttttgg tagagacagg
58801 gtttctcaat gttagccagg ctggtctcga actcctggcc tcaagtgatc tgcccacctt
58861 ggccttccaa aatactggga ttaaggtatg agccaccgca cccagccctc ctgggctctt
58921 ttcctttagt tgcactcgct ccccgctcct ggagtagagg gatttccgag agactgtggg
58981 ctccagcctt cacctaggcc caggactagg atgcctgccc taacatttat ctttatacct
59041 taaagcaaaa cagctggacc ataagcattc aagaacaaac tgtgaataag gagaaagttc
59101 tcccaggaaa caagagcttt agttatgttg ggccagccct tatattcctt agctgttacc
```

Figure 1T

```
59161 agtcactgct tgatttaatc tcggctatca cttggcctga caggtctgct gctggtgcca
59221 ggatgtctgg gttttgaagc ctggctccat tacatacttc ctgtgtgacc ttgggcaact
59281 tactcaacct gtctgttcct cagtttcccc agctgtatta tgtcagcata atagtttgtt
59341 gtgtgaatta aatgaggtaa taactggaaa tgcttcaaac atggttccta tcatgagaaa
59401 tcctgctttc cgcctaaatg tgctggaaaa ttcctggtgg tgcagaacag gagaccagag
59461 caaaggaaag acagggtgca gaagccaaaa attaccttgg agaacaaagc gcatgttaag
59521 gttatttttg gattctaggt ttatctctgc ttggtcttca gttacctaca agagatccat
59581 ttaggggatt tttgtttgtt tttaacgata gctttattga gatataattc atatgccata
59641 aaagtcactc ttttaaaatg tttccggtat attcacaagg ctgtgcagcc ttccctgtcc
59701 ttgattccag tctgagtttt taactgaagg gataaggagg accacgcttt ccccagacca
59761 gaaccgcggg ccaggggcgg attccgctga gtcaccgcgg gcgcctggtg cgcggcggcg
59821 gagcccggga ccttccttgg ctgcccccta gcgagggccg cagcgcagcc tgagacaccc
59881 gccggggccg ctccacggcc gtcggattta gactggaagc tcggtccagg tccccagctt
59941 gatgcgcccg cggtgtagga gaccagcccg actcgagctt cccctgagcc cctggactct
60001 tgactccagc agggcctggg taatgaacgt cagctcccct ttcccaaagg ggttgctctg
60061 ttgggaaggc acccgtttga tacagtagca tagagatggg ttttagcatc aaaatatcag
60121 aattcaagcc ttgctctctg cttactagct gtgtgaccct aaaaaggttt ctgaacgtct
60181 ctgagcttca gtttcctcat cattccttct cacggggtgg ttgtgagcat tacagagatc
60241 ctctctgtga agcccctgtg agtggctcat cctgagggct gaaataaaca tgttattaat
60301 aatccaaaac tggcaaggga tgttgactgg tccccctccc ttgcccaagg agctttctag
60361 aacctgagtt atcattacca aactgtactg ccttgagtaa gaaagttaga aggaatggga
60421 aggatggtgg caggtggagg aaggcggatt ggtcatcacc tccttgcagc aagaaacagc
60481 cccagatcgt gggaaaccta cagacctgct agacagacta ggagcaaaag ctggggcttt
60541 aagaatcccc agggaggttc tcctgagaga gtagccagtt ggattttgta agcagagatt
60601 tgtttgggga ggaggtgaca acgtagggag cagaggggca aagctgtcgg gaatcctgcc
60661 ttgagggcag ggatgtgtgt tggggggagt tgggtcactg ggctcggtg gccttgggca
60721 agtttctacc tctcaggtcc tttacccacc tagggtcgcc atcctgccca cctcacaggt
60781 tacagtgagc ctggatgcac tgtcatgggc aggtgcccag gaaaatggca gacatgttcc
60841 aaacagcacg cagcattccc cagtgatgcc cagggtcacc ttggaggtgg gcgagatgcc
60901 tggggtttct cgtccacccc acaacacctc aggggacagc caaagctgtc ccttcaggta
60961 agctgcacag aagatgtgaa ctctgctgca aagactctat tctttgggag caaaagggac
61021 ccagggtctc acctgcacat ccctgtccct gagggcctag gggttcttgg aggccccagc
61081 cttggcaaaa tgaggaagaa ggtgaaggtt gtctgggccc ctgccaggct ccttcctcgg
61141 ccacgcactc cccttcctgc acacacaccc ttctccctcc accccatctc cattgttgtc
61201 agaaaagtca caataaaaag gtccatattg tctagttccc atacttttaa tttttaaaat
61261 tttatttatt tatttattta tgtatttttt gagacagagt cttaacccag gctggagttc
61321 agtggcatga tctaggctca ctgcaacctc tccctcctgg gttcaagtga ttctcatgcc
61381 tcagcctccc gagtagctga gattacagat atgtgccact atgcccagct aatttttgta
61441 tttttagtag agacggggtt tcaccatgtt ggccaggctg gtctcgaact cctggcctca
61501 agtgatctgc ctgcctgagc ctccggaagt gctgggattt caggtgtgag ccaccgcact
61561 cggctccaca cttttcactt attaaaagac tgtggtgtcc atcaatggat gaatgaataa
61621 accaatgtgg actatccctc ccattaccca aggaatgaag cacggagccg tgccaagatc
61681 tggattcaca gtgaaagaag ccagtcacca aaagccacgt gctgtgtgac ttcccttata
61741 cgaaatatcc agaagagata catccatggt gacagaaagt agatgagcag ctggggactg
61801 gcgaagggga gaagggggag cagctgtcta tgaggtccag cctttcttct gggtttggtg
61861 agaatgtttt ggaactagat agaggtgata gttgtacaac attgtgaatg tactaaatgc
61921 cactgaatca ttcattttaa atcgttcttt acgttgcatg aattttaagt caatcaaaaa
61981 cagttgtttg aaaagagaaa agcctatggg tagcggcagc agtgattgga tttatgattc
62041 gattccatgg ctcatccctc ccctgcctca ccccctcgcc ctccgacgtc ttcttctttt
62101 actctgaact gttatctttg ttctcatctc tctctctctc tctcaaccct gcagacactt
62161 ttccctttct ttgtctgccc ccaccctcca gatttccgtg tctccagtgt ctccctacga
62221 ggcatgaatt gagactggga gggtgtgatt ctgaagaagg caccaacagt gactcagcta
```

Figure 1U

```
62281 gcccccttccc ccaccccgcc ccccgggcct caatttagct aaaaaaccac agggacggac
62341 tcaggaggca ataccctttcc aagggtccct aaaaaatgtc ccattttagt gtccaggttt
62401 cactcaactt tagtgcctcc cctaaaatgt gttccttacc tcccacccca ctgcatctaa
62461 gtcactgcct gagaaaacag gattgaggaa aggagaaagg aagagagaga gagaggagga
62521 gagagagaga gagggaggaa ggctgatgga tttagaaaag aagaaaacaa gtggtctgag
62581 gaaaacagcc ttggtgtgtt tattttcctg tctgtgtatc gcttctcggc cttttggcta
62641 agatcaagtg tattttcctg tctgtgtgtc tcgcttagat tacagggatc tgtgggtgat
62701 gacacgtctg gtccaggctg cgtagtcacc tcaagggcat gcttattgat gtgtttttca
62761 attcactatc tttgcatggg agtcccaggc caagaggcac agctgcgcca tttgtctgtt
62821 ggtttagata tcctttatcc agttcttcca gagaaatcat cctgcccttc tggaggaggt
62881 gggcagcagg ggtcagagat gggagggaaa ggaaggagcc aggtccttgg ctaggatgcc
62941 agggtcccct gcctctcacc tggcctgggc tggaggcctc ctgctgtcct gtcactgatc
63001 actaccccgc cccagcctcc tgagttagaa gacacaggct aaagtagagt atttcttcat
63061 tgaaaaaccc atacaaaata aaggttcata aaaaataaaa atttagactg ggtgctgtgg
63121 ctcacacctg tgatcccagc actttgggag gccaaggcag gtggatcgct tgagccctgg
63181 ggttcatgac cagcctgggc aacatagtga aaccccatct ctacaaaaaa tacaaaaaat
63241 tagccaggca tggtggtgca tacctgtggt cccagcttct cagcctatgg acccacatag
63301 aatacaatgt cagcataaga agggagccct ggggtcacca aatggtttgg gcggcaaaga
63361 acctgaaggt tgagagaagt ggcttggtta cccagctgtt ggatgtgaga cctggccact
63421 gcttcttcca taccctagac ctgcaccctg acatctcaag taaaaagttg ggggatgttt
63481 tatggtccag gatgaaggaa gggcagtgag gggcagcgga gcatcacttt gcatttctgt
63541 ctgcctctta ctggctgtgt gacctggggc aggtaacttc ccagactcct gggaatcata
63601 acacctatga tgatgatgat gatgatgatg atgatgatga tgacacctac ctcaaggatt
63661 gccctgaagg gtcacagaga tgcctgcaag gcacctgcat ggagcaagcg ccccttctct
63721 ggcaggtgct gggtgagcac tacctgctgc caggccctgg ggctatggca ctgcgtgacc
63781 ctgcaagtcc tacctggcga agctgtcgtt cttgtgctca gtcagtgttg gttgtaagac
63841 tgagaagagt cacttcattt tgctctccag ggacatcttt ctgggtccta ttttctgcct
63901 atgtcaagta gcgcctcaag gatgctcctg aaaatgggct tgtctttctt aacatggcag
63961 gtaggtccca aagcattagc atggggcagc tgacctagcc cagccaatgc agtgcagtga
64021 ctcttgcaac cgagtctaat cagaaggtcc atgaacctac gagcatttcc tgtcccagga
64081 tcagggtgga ggctgagcct ccctgcttag agattcttcc catgcattcc actttttcc
64141 ccaaaagaaa atattgaccc ttgagaggca cacagtttat ttattttgca tagtaaatag
64201 tagcctgtat tttaaggatg agttgatttc tgcatcagcc cctgtaggtc atcagccttc
64261 tattggtgca tctgactctc tctagccctg cagggatggt ggagggggag gggaaggagg
64321 gatctttatt ggaaaccagg acagtgagac tcattgccct gtcatctgct ctgtggtgct
64381 gaatgaggca gcccaacaga gaaataccct gagcgagcat ccccagcctc caaaacagtg
64441 gcgcattgcc ctgagtcctg ggaatgacct ttgattctcc tgctcctgac ttggaaccca
64501 tggaaacctc tagaagcagc tgaggaaaac ccaacatgaa aagcagaact ccacactgag
64561 aatataggag gtgatcggaa catacaatga ttcttgctaa gaccgattca cagtttttct
64621 tttttttcga tcgaagaaat actggagaag cctaaagaag gagtctaaaa actctggcac
64681 gtgggccaaa actgtccttg agctaagaat gattttcaca tttttaagtg gttgaaaaat
64741 gaaataaaat aagatgatgt tttgtgacac atgaaagcta tgggaaattc aaattctaat
64801 atctataaat agtgttttat cagaacacag tcatgctcat ttatttatgc tcgatggctg
64861 ctttcccgct acaattacgt tgagcagtta caacagagac cacgtggccc acaaagcctt
64921 acaatattta ctatctggcc ctttccagaa aaaaatgtgc cgactcttga ccttaacctc
64981 agcaatttgg gaggccgagg caggcggatc gcttgagctc tggagttcat gaccagcctg
65041 ggcaacatag taagactcca tctctacaaa aaatacaaaa cattagccag gcatggtggt
65101 gcacacctgt ggtcctagcc actcgggaga ctgaggtggg aggatcgcct gagcccagga
65161 agtcgaggct gcagtgagct gtgatggcac cactgcacct cagcctgggc gacagagcaa
65221 gaccttgtct ccaaataaat aaataatgca aagtaaaata aataaaacca tataaaaagg
65281 aatcaattta aaattataat gaaagctggc cgggcatggt ggctcacgcc tgtaatccca
65341 gcactttggg aggctgaggt gggtggatca cgaggccagg agatcgagac catcttggct
```

Figure 1V

```
65401 aacacggtga aaccccgtct ctactaaaaa tacaaaaaaa aaattagccg ggcacagtgg
65461 cgggcgcctg tagtcccagc tactcgggag gctgaggcag gagaatgtct tgaacccggg
65521 aggtggagct tgcagtgagc cgagatcgtg ccacttgcag tccagcctgg gcgaaagagc
65581 gagactccgt ctcaaaaaca aaaacaaaaa caaaaacaaa aaaaaattat aatgaaagcc
65641 aaggggcata gtagaacaaa ttttctagag ctcattaagt caaatgagtc accagttagt
65701 aaaacgcagt cacggggaag agagggcagg attctttgaa gcagcggctc tcctaaaaac
65761 aacccaccct tgtccagctg ccttccctcc tgagggtgtt ccctttgact gtgtgacccc
65821 catcccctat ttcccaaccg tccaagccca cctctagcat aatacgagct tttaatccct
65881 ctccctgacc ccaacccgat tttgaagccc agtctagtat tttctcaaat acacttcttg
65941 gctccattcc ttcctttcca tcacctctgc cttttcactg catgcttgga ccactgcagt
66001 cagctcccta tgaacagttg ctctctaccc atccaatcgg ccccgcctgc tgctgccaaa
66061 ttcaccgagg gcacctctgt ggtgctgcct gtggacaaag tccaagccag ccacctcacc
66121 cacctacagg tgagtgggga gcagccagcg tgtccagtgg tttaccccat cgccacagac
66181 ttggtgatgt gtcgatgtgc agagaagggg tgttggcagc cacaacacaa gcaaccccgc
66241 cccatgtgag atctaagatg ggcgtgctgg gagccacctc tgagaatcca acagaaggca
66301 gaggggagaa cggctcacac ggcacaaaca ctccttcctt tttttttttt ctttttcctt
66361 tttgaaagga gtctcactct attgcccagg caggagtgca gtggtgcaat ctcagctcac
66421 tgcaacctcc gcctcctagg ttcaagcgat tctccagcct cagcttccca agtagctggg
66481 attacaggta cactccacca tgcccggcta atttttgtgt ttttagtaga gacggggttt
66541 ccctatgttg gccaggctgg tcttgagctc ctgacctcag gtgatctgcc tgccttggcc
66601 tcccaaagtg ctgggattac aggtgtgagc catggggcct agcctccttc catttaaatg
66661 tatgcctaat ttgcccattg agaacggctg agacgcattt taagtggcca gggtctactt
66721 agagttagtg ctcatgacca ggcccaggtc aagcctggct ggccagatgg tgcctttgac
66781 ctgctctgtc tctgtgcaaa ggaatgagct gaaggatggg ggtgcagtgt gtgggcagtg
66841 ggctggggct ggcaggactc agtgactaag ggaagagaac tttcctcact accagcctgt
66901 cttttcaggg caccgcgggg ggctttggga cttggtgatg aacacagcac agagagctgt
66961 ccagcatgcg ggtccctggc ttctcacact tcccaggctc cttcagaggc tctctccaaa
67021 gggagctgct ctctctagaa cccatgaatt tggaatatag gcaaccactg cattggggac
67081 cactgacctc aaacatagag accagagcaa atggggctca tcacgtgaaa ctcatctgga
67141 actctagcag gttcttttat atatatatat atatatatat atttttttatt attatacttt
67201 aagttctagg gtacatgtgc acaacatgca ggtttgttac atatgtatac atgtgccatg
67261 ttggtgtgct gcacccatta attcatcatt tacattaggt atatctccta atgctatccc
67321 tccccactcc ccccacccca caacaggccc cagtgtgtga tgttcccctt cctgtgtcca
67381 agtgttctca ttgttcaatt cccacctacg agtgagaaca tgctgtgttt ggtttttttg
67441 tccttgcgat agtttgctga gaatgatggt ttccagcttc atccatgtcc ctacaaagga
67501 catgaactca tcattttta tggctgcata gtattccatg gtgtatatgt gccacatttt
67561 cttaatccag tctatcattg ttggacattt gggttggttc caagtctttg ctattgtgaa
67621 tagtgccgca ataaacatac gtgtgcatgt gtctttataa cagcatgatt tatattcctt
67681 tggttatata cccagtaatg agatggctgg gtcaaatggt atttctagtt ctagatccct
67741 gaggaatcgc cacactgtct tccacaatgg ttgaactagt ttacagtcct accaacagtg
67801 taaaagtgtt cctatttctc cacatcctct ccagcagctg ttgtttcctg actttttaat
67861 gatcgccatt ctaactggtg tgagatgtta tctcatggtg gttttgattt gcatttctct
67921 gatggccagt gatgatgagc atttttcac atgtctgttg gcgaactcta gcagcttctt
67981 ttcacaagtt catggagaga ggtttcccac tgagggaatc acatctgtct gatcaaaaga
68041 ggcttgggaa atggctctcc tgttcattcc ctgaaaacct ctgatggaac cactgccact
68101 gtggcagccc cagcactggc accccagcca tgattggtgc cccagccaca tctctgctgt
68161 gagccccaga gccctggtta attaatcatc cacgtgttga tggggagagg cccattcaca
68221 aaagcgacat aaagcccagg gagacgtggc cgtggcaaga agggtgtggg actacattcc
68281 gcccccaact gagagattca gaaaccagaa aaaaatggaa aaacatactg tgctcttggg
68341 tgggaaaact aaatatcatg aagggagcaa tttttatagt tttggcctat aatacaattc
68401 cagccgaaat cccagtggaa ctttgagaat ttgcaggaaa aaaaaaaatg tctaaagtac
68461 atctggaaga caaacttaca agaaggtcaa ataattttga aaaagaaaat gatatctaag
```

Figure 1W

```
68521 cccacctaga gaataagact tgagatccaa agctaaatca ggaggctcta gcaaaattga
68581 cagataagca ggacagagtg catggtgcat tcacctgggg aagagggcag attggtctac
68641 aaataggcct gggtccactg actttagctg ttatatttgg ggagaaactt ttcaacctca
68701 ctccatctta aacctaaaaa tattccagat gaattaataa atataaaaaa ttagaccact
68761 aaaaatgtag aagaaaatgg atgatctttc tataccatag agcaatggaa taaatcacaa
68821 aggaaaacag atttgactat ataaaactta aaccctgccc atcaaaaacc atcagaaacc
68881 aaaataaaag gcaaccaact ggagaagata gttgccacaa atatgatcaa gggttaatgt
68941 tattcataaa ttaagagccc acacaagtca ttagaataag cactgagacc tgaacagaca
69001 agcaaaaaga atgagagtgg gtcggcgcgg cggctcatgc ctgtaatccc agcactttgg
69061 aaggctgaag caggcggatc acttgatccc aggagttcca acaccagcct gagcaacatg
69121 gtgaaacccct gcctctacaa aagtcataaa tattagccgg gtgtgatggc acacgcctgt
69181 agtcccagct actcaggagg ctgaggtggg tggatcactt gagcccggga ggtagagtct
69241 gcagtgagcc aagatcacac cgctgcactc cagctggagc aacagagtga gaccctgact
69301 taaaagaaaa aaaaaaaaaa agaggagaaa aatgctgatc tcactagtaa ttaaaacatc
69361 aggccaggcg cagtggctca cacctttaat cccagcactc tgggaggctg aggcaggcag
69421 atcacttgag atcaggagtt ctagaccagc ttggccaaca tggtgaaatc ccgtctctac
69481 aaaaaataca aaaattcgcc aagcgtggtg gcacatgcct gtgatcccag ctactcggga
69541 ggctgagaca ggagaattgc ttgaacacgg gaggcagagg ttgcagtaag ctgagatcgt
69601 accattccag tccagcctgg gctacagagc gagactctgt cccagaaaaa attaaaacat
69661 cacatattta aacaactcta ggatatcatt taaaaaaaca ttaatagact gtttttttaga
69721 gcacttttag gttcacagtg aaactgagtg gaaggtacag agacttcccg tatgttccct
69781 gccctccacg tacagcctcc cccactgcca acgtcctgca ccagagtggt acacttgtta
69841 caaccaatga atcctcatta acatatcatt atcacccaag ttcatagttt acattagtaa
69901 aacatcatct ttcatctata agcacaaaaa tttttggca tttatttagg tgtatgatta
69961 actcagtgtt gacaagactc acacttcata cccacttgca ctgcatctga gaagcaattg
70021 gtgtctacag ccgctacacc ctcaacaagc ccgatcttgt ttgaaaagca attggtgatg
70081 cttctcaaaa ttctatggac aaagtcagcc gggcatggtg gctcatgcct gtaatcccta
70141 aactttggga ggccgaggca ggcagatcac ctgaggtctg gtgaaacccct gtctctacta
70201 aaaatgcaaa aattacccag gcatggtggc tggggcctgt aatcccagct actcgggagg
70261 ctgaggcagg agaatcgctt gaagcaagga ggcggaggtt tcagtgagcc aagattgcac
70321 cactgcactc cagcctgggt gacaagagtg aaactccatc taaaaaaaaa aaattatgga
70381 caaagttttt caaaaagata tttaatgcaa ctttatttgt aatattggaa catctgaggc
70441 catttcagtg ctaactatta ggggatggtt aggaaaatat ggtacatatg tggaaaggaa
70501 catttggtag ttagtgcccc tgatgtttac aaaggctttt agtgaccaac aaatgctcat
70561 gctataatct tatgtgaaaa aagcaagtag cataattgca actatatttt taatgcatag
70621 aataaaaggc tagaaggaaa tatcacagat ccttgacata cattcccaaa cctttgtaaa
70681 tccgcggatt catgaaaaca gacacatttg cacaagtgcc tgatcttttc tgttatacat
70741 tcattagaag tcaagccctg gtgccacaaa gtatctgcct tttcaaatgt gatcagaatg
70801 ttctcttttg cttcaaggcc atttttcacg aagcagtggc atttttgcct cttcatcaga
70861 gtcaccgtgt gccctggagg actgagaaca gcagagccgt tttaggatgg gacagggcag
70921 ccaggaggat tgggctcact ccctactgag tgcctcactc ccgtacagcc cccatagagg
70981 aagaggggtt caaatttatt cctcagccag atggcatgtg ccgcctgtcc tggaatttca
71041 catcacttat gatggaccaa aattccaaaa gctgaatcca tgattgtcaa agtctggtat
71101 ggcaggatgt caacagtaat cgtttctggg cagagggatg attttctctt cccatcttgc
71161 tttgtataaa tacattttct ataataaggt tgtattactt ttctcatcaa gaaatagcaa
71221 agtactgttt tactcaaaat atgaatagag ccaggcatgg tggcagctta tgcctgtaat
71281 cccaacactt tgagaggcgg atatgggagg atcactttag cccaggagtt tgagaccagc
71341 ctgggcaaca tagtgagacc cccgtcccca ctccccccaaa gaaaacccac aaagcattta
71401 tcctggatta ttcacagggg ccaaaaaaaa aaaaaaattc aggcctccta tagccatgag
71461 ctacgaatat gaaaatatgc aaatgtgtaa gaaaagccag cacatccgat ttttactttt
71521 actttcacac ctctgtccac catgttccaa gagaagaaac ttggtcattg aaaggaatag
71581 atcaaatcca aagaacaaaa ccactgtgct cattaaactt cttagtgttc acaaagcttt
```

Figure 1X

```
71641 agctgcaggt tgaatggggc aacccgaatt ggctggctca cctgggctgc agggagcaga
71701 gatcgcgaca ctgcactcca gcctgggcaa caaagcgaga ctctatctca aaaaaaaaaa
71761 agttcataaa ttcaaagtta tgaattattt ttaaaataat aataatttac aataaagatg
71821 aggacaaagt gtgagtaaat ggtggtttct atccagctct gttgagctga agtggcatct
71881 ccctgctggg gcttttgggg aagaagggtg tgtgttgctc ttcagatccc aagcctcatg
71941 cccctactgg gccctgtggg gtgcttctca gcccaccagg agagccaccg ttggaacaca
72001 cacgtggggg acctggtggg tgccggtgtg gtgaatgggg gccacagcct gactccagga
72061 agccagcaaa ctcggagctg gaggagtcag gacacccccg atgagtcaag agttggtttt
72121 gctgccagtt gacatctgat tgaaccatct cttcacttct ccgtgcctca ctttccttac
72181 cagacaggct ctgctgatgc tgtccctctc ctgttcagtc gtgccctcac cgttaaagag
72241 aaagagcaaa ctgctgggca gcagcattga tttttttaat gaagtggaaa gagagctggg
72301 aataacaagt cgggcccacc tcacctgcct cacctggtgg gtttatttgt tttgtttttt
72361 tttttttgtt ttgagacaga gtttcaccct gtcacccagg ctggagtgca gtggtgtaat
72421 ctcagctcac tgcaacctcc acctgccagg ttcaattgat tctcctgcct cagcctcccc
72481 agtagctggg attacaggca cctgccacat gcctggctaa ttattgtatt tttagtagag
72541 atggggtttt accatgttgg ccaggctggt ctcgatctcc tgacctcagg tgatccaccc
72601 acctcggcct cccaaagtgc tgagatcaca ggcgtgagcc accatgcctg gccgtcacct
72661 ggtggtgttg aatatgaact gctgcggtgt tggtaaatta agcaagcaga tagatgtaaa
72721 taacgcttgg gcaggaatat ggagcacggg atgaggatgg gcggccaact gttagagagg
72781 gtagcaggga ggctgagatc tgcctgccat gaactgggag gagaggctcc tctctctctt
72841 cacccccact ctgcccccca acactcctca gaacttatcc tctcctcttc tttccccagg
72901 tgaactttga accaggatgg ctgagccccg ccaggagttc gaagtgatgg aagatcacgc
72961 tgggacgtac gggttggggg acaggaaaga tcagggggc tacaccatgc accaagacca
73021 agagggtgac acggacgctg gcctgaaagg ttagtggaca gccatgcaca gcaggcccag
73081 atcactgcaa gccaaggggt ggcgggaaca gtttgcatcc agaattgcaa agaaatttta
73141 aatacattat tgtcttagac tgtcagtaaa gtaaagcctc attaatttga gtgggccaag
73201 ataactcaag cagtgagata atggccagac acggtggctc acgcctgtaa tcccagcact
73261 ttggaaggcc caggcaggag gatcccttga ggccaggaat ttgagaccgg cctgggcaac
73321 atagcaagac cccgtctcta aaataattta aaaattagcc aggtgttgtg gtgcatgtct
73381 atagtcctag ctactcagga tgctgaggca gaaggatcac ttgagcccag gagttcaagg
73441 ttgcagtaag ctgtgattat aaaactgcac tccagcctga gcaacagagc aagaccctgt
73501 caaaaaaaaa agaaaagaaa aaagaaagaa agaaatttac cttgagttac ccacatgagt
73561 gaatgtaggg acagagattt tagggcctta acaatctctc aaatacaggg tacttttga
73621 ggcattagcc acacctgtta gcttataaat cagtggtatt gattagcatg taaaatatgt
73681 gactttaaac attgcttttt atctcttact tagatcaggc ctgagtggcc tctctttagc
73741 aagagttggt tagccctggg attcttactg tagccacatt aataaacaac atcgacttct
73801 aaacattcta taataccatc ttttggccaa attgacttcg cctcttcctc tctctttcca
73861 aatgaaatgt gtttcatttc actgtcagac cacatggttg gggaccccac agagcacaca
73921 gccctccctc tgccttccca tgctggccct tcacccactg ctggagtgcc aggttggtcc
73981 aagggttgga ccaagttgtc tgaggttgtc tcaaggttgg tcgaggctgt ctccgcgctg
74041 ggttgtgcta caaggagccc ttctttccat gggtgtggct ggcagtgagt gctcacagca
74101 acagcccaca gtgcagcccg agggcaggat ggactcagtc cctgcctcca tacccatttc
74161 taaggaggca aaatggcaaa cactctactt ttctctttta atgctaaaaa taagaaaaca
74221 ccttgcagcc cagggtatgg gtagtgcatg gaagccgtgg agttgtgagg tgggaagtga
74281 cctctgctgg atatgtctat tcaggaagat tgctggagtg ggtggggtct ctgggaggtc
74341 ccctgagtgt gggaagctgg gaccaccagc tttctcgcac agggagtggc catcccagct
74401 tggagaggtt ccaggactgg ttgggaggca cgtttcagat ttctatctgt tgaatcagcg
74461 aagatattgg attatgagga atttgggaat taggaaagtg ggtgcaggtg ggttggggt
74521 aggtgaagga agacatgggc gtattggggg agcaggggct gctcagaggt gttccagaag
74581 ctctgggtga ggaggtgaga gggaccgggg aatgcagctc ggcccagcct ccctgcctga
74641 ggtcagccat cacgtggtga tggcaagatg gaaatgtgct ttctgactgc tccagccagt
74701 gctgccagat tcagctcccc agggagggca cctgagaggc tccaagccag gagatctgtt
```

Figure 1Y

```
74761 ttctcctttg ttttgttttt ttttgttttg ttttgtttta ttatacttta agttctaggg
74821 tacatgtgca caacgtgcag gtttgttaca tatgtataca tgtgccatgt tggtgtgctg
74881 cacccatcaa cttgtcattt acattaggta tatctcctaa tgctatccct cccccctccc
74941 cccacccccct gttttctcct ttgaatcctt cttagaggcc gggtgcggtg gctcacgcct
75001 gtaatcccag cactttggga ggctgcggca ggaggattgc ttgagcccag gagttccaga
75061 ccagcctggg caacatagtg agacctcgtc tctacagata ataattttaa aaattatccg
75121 ggcatagtgg catgcaccta tagtcccagc tactcaagag gcagaggcag gaggatcact
75181 tgagcccagg aggcggaggt tgccgtgagc caagatccca ccactgcact ccagcctggg
75241 cgacagagac ccccatgtca aataataata ataataaata aatccttctc agtcccttcc
75301 tcactgtgtc cccctccact gaatttttcc acctcctctc ccacttcccc cactcccgct
75361 ttccctctcc ttctctcccc actccatctt tttctttctc tgctgtttct cgtccctccc
75421 tcctctccat cccacaacac tgcctaccct gtccctgccc caccctggtg ctcaggatgt
75481 gtgaagtgag ggtggtagc ccccaagacc tcaaccccga aggttagcct gttgaaacca
75541 ctttctccca gctgcccccc tggcagttgg tgctgctggg ggaaactggg attgggggcc
75601 agattttgcc tctttttcctg acaaagagag atgaagagtt ctctcaccag gtgcctggga
75661 ctggggtgtg ggtgtcccag cctatcccag cgcatctgtt ctgcatcatg attaatagtg
75721 ctgctttcag ccgggcgcgg tggctcacac ctgtaatccc agcactttgg gaggctaagg
75781 tgggcagatc acaaggtcag gagttcgaga ccagcctggc caacatggtg aaacctcgtc
75841 tctactaaaa atacaaaaat taaccaggtg tggtggtggg tgcctgtagt cccagctact
75901 tgggaggctg aggcaggaga atcacttgaa tctgggaagc agaggttgca gtgagccaag
75961 atcgtgccac tgcactccag cctgggtgac agagcgagac tccgtcctaa aaaaaaagga
76021 gttttgctct gtcgcccagg ctggagtgta gtggcgccat ctcggctcac cgcaacctgc
76081 gcctcccggg tgcaagcgat tctcctgcct cagcctccca agtagctagg attacaggcg
76141 cctaccacca cgcccggcca gttcttgtat ttttagaaga gacggggttt caccctgttg
76201 gccaggctcg tctgggactc ctgacctcag gtaatccgcc cacctcagcc tcccaaagtg
76261 ctgggattgc aggcatgagc caccgtgccc agtcaactcc ttctcaaaaa aaaaaaaata
76321 gtgctgcttt ctctttcaag tgtcctgatt tgggtgatag taaatgccac tctacttata
76381 agggatctac ctcagaatgc taattgggac atttttgtag cactctactg ttggcagcag
76441 gtgatgctca caacagcccg tgagggtgga tgacgtccgc ttcacagatg acaaaggagc
76501 ctcatgctca gaccgtgggc tgccagagca ggtccatggc tgcagcccca catggaccat
76561 atttccccct tgtcactctt tccaccaagc tcccttggaa cttcagttat taagctctct
76621 tgggtggaat ccaagttaga atcacaacat gtgcctcata tggattgtgc cagtgaaaaa
76681 tgacattcta tttagaggca gggcagcctg gcttagagtc agtttaaaat atgtattatg
76741 ctgcaacaaa tgtaccatga tcctgtaaga tgttcacaac aagggaactg gatgtggggt
76801 atactgtctg tactaacttc acaagttttc tgtaaatcta aaactgttcc aaaataacaa
76861 gttcgtttaa aattaactcc aggagaccag gtacggtagc taatgcctat aatcccagca
76921 cttcggaagg ctgaggcagg tggattgctt gagcccagga gtttgagaca agcctgggca
76981 acatggtgaa atcctgtctc taaaaaaaat cacaaaaatt agccaggtgt ggtggcgcat
77041 tcctgtagtc ccagctactt gcggggctga ggtgggagaa tcatctgagc ccaggagttt
77101 gaggctgcag tgagctgtga ttgtaccact gcactccaac ctgggcaaca gagcaagacc
77161 ctgtctcaaa aaacaaaaat gaaataaagt ccaggaaaga agtaggtttt accactctta
77221 ttttctgaag agaaaactaa atttaatgtg taaagtgagg acaagttcac caagttagtg
77281 tttgagttgc ctaaaatatg tttgctaaaa ctattcaaag ctttcacata aaacatgatc
77341 agaagttcta tgccaaaaca tatgtgtgtg tatatatata tgcactatat atactgtata
77401 taaaaatgca aaatctaaat tgccaacctt ttagaaattg ctctgaaagg aaagcatttc
77461 aagataattt gcttacccaa agaatatact ttccaagaaa gcaagtaata cttaaggtgt
77521 tcataatcct catcaaatta attcttgcta ctgaaagctt acaaggagct gttttgatgt
77581 cgggtgtgac aggtttgact tggcagaagg tgtcacttta ctaacaacat tttaaataag
77641 tgacagaaga caagaaacta cacgttaaat gccagaacaa agagtgtcta agtggatgct
77701 aagagttgaa atatggctgg atacctgccc aagagagctg aaaagtagat gaaagttggt
77761 tacctataaa ctagtgcacc ctaatgaatt aaaaggtgtt gatgagttaa cttgttatgc
77821 cttccagata agacatgcaa atggggcttc ttcctccttc actacttcca agggatttaa
```

Figure 1Z

```
77881 caaggagacc aatgcaaatg ataaggactg tagggctcaa gctggggaca gattggggaa
77941 agggggacca tcatgcccat atagatgtcc ctgtgccctg gcagtcaagg ctgctgaaaa
78001 ataacaaaac ccagaagtct gcgtgatgct gcctctccat ttgtccaaag ccttcttgcg
78061 gcagtttgca ggcttttgca aaagctccag gaccaaggag ctatgttcat gctggaagct
78121 tgttcaggat tagctgttct ttgtgggatg ggtgcagcca gggccaggtg tccagggaca
78181 gtgttttaac aaagggcatg aggtgtctga tctcacagtg gaactccact tgcctttttt
78241 tcatcttctc attctgcttc atgcacagaa ccagccccat cctgaaactg actctaaatt
78301 actcccgccc caggtggagt gcctttctcg gagttcaaca gagccttcct gtcgcccaag
78361 ggacaactcc actgaatgcc caagccacac ccaaaaccta acaagtaaaa accaaattct
78421 gtgctccccc atcctgggcc attcctggtt tctctactgc tgttggtgat accaccatca
78481 gcttgtccat catgaccctg gccagttcct ccccacaaccc tccacagcac ccagggacct
78541 cacctccatt ccatccgaca cagatctcct caccacaaac cttggttttg caacagcagc
78601 catgagacct ttacaccctc cgcccttcat cctgtccccc actgaggccc cagagccatt
78661 ccttaaagca gcgcgccaca aactataacc cacaagccaa ttctggtacc cagcctgttt
78721 tgcacagcca gtgaactgac aatgatcttt tcatacagcc agaaaaacaa aacaaaacaa
78781 aaaacaacaa aaaaaaaccc caccattctg agcatgtgac ttccatgttc aagatgtctc
78841 atgttcagaa aggcccctgg aaaaggagga aggggagctg ggcacaaagg gagaccctct
78901 cagctgagct cctcccatcc agacattttc ctggacttcc tatccaatga cttcccttag
78961 cttcttatca gccacccctg tctgcccagg aggctggaag atgtggcctt ttaactgggc
79021 acagctctgt cctctatcat atcagggctc tgttcccaag gagggtagag agaatggaca
79081 ccaggtggac cctcagcagt ctgtgccaca gagggagtgt ttgcaatttc cagactaaaa
79141 gtccccatgt gcttgacggg gtatgtgact acaacgtgat gcttgacttt tcctcatatg
79201 accagagcca ctttgtccat ctggtacaat gtcagctatc tgctaggggc cctccaggat
79261 tcccagtcaa ttccatatct gcatcaccac cattggcact aaataaaata aaatactcaa
79321 gttcctgctg gtgagcatga gcagtgctac actgggccct tcaaccaagg tgacatgata
79381 atgactgaaa ataatcactg ccacttattg gggacgtctc atctgccagg catggtacaa
79441 agtgctttaa ataagcattc aacaatttca tgctgacaga agccctgtga gccagtggag
79501 ctactactat gcccattata caggggagaa aactgaggca gagagaggtt aggtaattcg
79561 ctcagcctca cacaaccaat aggtggtgga gccaggattt gggccccatc tgcctgactc
79621 tctagaggct ctatcttcca gtcttccaga gttgagtcta agccatgaat aggacaatta
79681 gacagcagag gaaacccatt cagccaccat gtgcatgaag agtaaggaat ttctgtcata
79741 cagaggggag tgaattcact gagctgagag ctgaggaacc attgatctga tggctgagac
79801 accactggga agactggaga ggcttttctg ggcatgcagt gccaggcaca ggaggagctg
79861 agggaagatg actaagaggt actggcaaag aattcagaaa ttctgatgga agctttacat
79921 gttaccatca catccatcca tctatccacc catccatcca cccatatctt cctccctcca
79981 cccaatcatg catacatcca gtcatctata caccacccac ccacccatcc atccatccat
80041 ccatcccttc atccatccca tcatccatcc aattatacat acatccaatc atatatctgt
80101 acataatcca ttcttccctc ggttcatcca tccatccatt catccatcca tccacccatc
80161 ccttccttca tccttcctat catccatcca atcatatatc tgtacataat ccattcttcc
80221 ctcggttcat ccatccatcc attcatccat ccatccaccc atcccttcct tcatccttcc
80281 tatcatccat ccaatcatac atatatccaa tcatacatct gcacatcacc agctcatcca
80341 tctatccatt tatccatcca tccttccttc catccatcat tcatccatca tacatacatc
80401 taaccataca tctctacatc attcattctt ccatcgattc atccaattat ccatcattcc
80461 ttcctccatc catcccatta tccatttgat catacatata tcatctatac atcatccatt
80521 catccatcca tccatccatc cacccatatc ttcatccaat caatcataca tacatcgaat
80581 catctacaca tcacccatcc atccatccat ccattcatct atccacccat ccatccatcc
80641 atccatccat tcatctatcc acccatccat ccatccatcc atccatccat ccatgtaacc
80701 atccagtcat atatccaatt acacatccat ccagttatac attcatacat gcatctaatc
80761 attcaattat acatacacac atccatataa ttctacatcc aattatacct ccatccaatt
80821 acacattcat acacccacct aataaattat taattcatat atccatccat ataattatac
80881 atcaattata catccatcta atcattcagt aattcaccca ccatccagtc atctatccaa
80941 taatacattc atccaatcat ccatccatcc atccacccat tcatccatcc atccgtccgt
```

Figure 1AA

```
81001 ccacccatca tggtatgagc catgatttac cacgatggtc ccctgtggac agcccaggtg
81061 gggcagaact gaagggaagc ccagggctgc ccccataaac atttgcctcc tttacatgga
81121 tgagaactag atccacatgt ataaatcctc atgatttgaa ggtgctttta ccaacattca
81181 ctcatgggat tctcccagga gctctaggag gaggcaggta gagttgaggt catctcacgc
81241 attttacaga tgaggaaacg gaggccctga gaggcaggtc caaggccacc tgaccagaaa
81301 gaagtggaac tgggacttga acccagccat cttgcccctt ggtcccatgc tctctagcct
81361 gtaactcctg cttcctggtg gggcatctcc aggaggaccc tatcggctgg ccatgggcct
81421 gccctggagt cttttgctct gtgtggccat ccttcctccc tcaggagagt gtgtgctccc
81481 agagcacagg ctgtatcttc tgagcatttt gtcccttccc agtacctagc actcagctct
81541 gtatacattg ggctctcaag aattctcaac cttccagagt gtaaggcctt gacctgctca
81601 gccctggata ctgcatgatg cattgataag cccataaaat aaccagggca gattgactcc
81661 cagtggccaa agtgccacag ggaagggaca attcagccct tctaggagga ggaggaggta
81721 gttttctcat ttctattaag gcaacaaaag ctgccttact aaggacattc ttggtggagg
81781 gcgtgactgt caaccactgt gatcatttgg gcctctcttg cccaggcttc ccattctgaa
81841 aggacagttt tattgtaggt acacatggct gccatttcaa atgtaactca cagcttgtcc
81901 atcagtcctt ggaggtcttt ctatgaaagg agcttggtgg cgtccaaaca ccacccaatg
81961 tccacttaga agtaagcacc gtgtctgccc tgagctgact ccttttccaa ggaaggggtt
82021 ggatcgctga gtgtttttcc aggtgtctac ttgttgttaa ttaatagcaa tgacaaagca
82081 gaaggttcat gcgtagctcg gctttctggt atttgctgcc cgttgaccaa tggaagataa
82141 acctttgcct caggtggcac cactagctgg ttaagaggca ctttgtcctt tcacccagga
82201 gcaaacgcac atcacctgtg tcctcatctg atggccctgg tgtggggcac agtcgtgttg
82261 gcagggaggg aggtggggtt ggtccccttt gtgggtttgt tgcgaggccg tgttccagct
82321 gtttccacag ggagcgattt tcagctccac aggacactgc tccccagttc ctcctgagaa
82381 caaaaggggg cgctggggag aggccaccgt tctgagggct cactgtatgt gttccagaat
82441 ctcccctgca gacccccact gaggacggat ctgaggaacc gggctctgaa acctctgatg
82501 ctaagagcac tccaacagcg gaaggtgggc cccccttcag acgccccctc catgcctcca
82561 gcctgtgctt agccgtgctt tgagcctccc tcctggctgc atctgctgct ccccctggct
82621 gagagatgtg ctcactcctt cggtgctttg caggacagcg tggtgggagc tgagccttgc
82681 gtcgatgcct tgcttgctgg tgctgagtgt gggcaccttc atcccgtgtg tgctctggag
82741 gcagccaccc ttggacagtc ccgcgcacag ctccacaaag ccccgctcca tacgattgtc
82801 ctcccacacc cccttcaaaa gcccccctcct ctctctttct tcaggggcca gtaggtccca
82861 gagcagccat ttggctgagg gaaggggcag gtcagtggac atctgatctt ggtttagtat
82921 ccttcatttt gggggctctg ggtgtggcct gggcctctgg actttggcca cggtgtttgt
82981 tccagccctt ctcctaacct gtcctttcca gacactcggc atctaggtta ttagcacctc
83041 gcatactttc tgacatgctc ctcagtcctg attttgacca tcttctcttg cttcccatct
83101 gtgtcagtca agactgcatt tggctgtaag aaacagaaac cccaactaac tgtggcattt
83161 acatgaagag gtttactttt ctcacataat cagatgtcta gacttggcca gcacctcaag
83221 ggtcattgat gctctcctgt ctttattttc tgtcatcttt agtggttgga ttgttgcctc
83281 atggttacaa agtggctgct gcacttccag gcatcacatc tgcctttgaa gcaggaacaa
83341 gttgcaaagt aaagtggcca aaagggccct gaaactaaat gtgtcccctt aggaaagcag
83401 gagttttctt gcaagtggca atcttctgct tatgtctcat tggccagagc tgggtcttac
83461 ggccacccct tgctgcgagc aaggctggga cattgagcat tttgccgtcc aacctcttta
83521 gcagaataaa ccaaggggga agaacgttaa tagtggcttt tgagtcacta gttggcagta
83581 tctgcccctc tatctttcca tcctccccat ggagtttcaa ggttcctttc tcagtacttc
83641 ttcaggctct gcacgttcat ttggatcttg tgtcttgggg tgaaaaactg gcccaagtgt
83701 ctccccaagc atccaccttt ggattaattt ggaaaatggc tgtcaagtgc ccgcctcttg
83761 cttggtataa tgctacagct ttagaggacg cagcaggcat gggccttgcc gctgaggttc
83821 ttagcctcat gagaatatcc agatcagatt ctcttggctc cttcttagag ccagtgatgc
83881 aagacacttc ctgctcatct tgtcgggacg gttttacaag ttgcctgcca tcctgagaaa
83941 gtctacaaaa cgatgccaga cctcatgcca gcttcccaag ccttgactct cagtgctccc
84001 tcaacaggat tctggaagaa tctcccaaac aagtcgcaat cccctctgga ccctgtgcag
84061 gcatgagact caagagcatt ggctcccacc cctggtggag ggaacactgc tggggctggg
```

Figure 1BB

```
84121 atcttgcctg gttgctccgc ctgcacccaa gacaaccata attaaaatgt ccttcattga
84181 acttggaaag ccttcaaagc tgacaactcc ttatgtgtac ccggaaaggc ctgggagtgt
84241 gccagggcat tgctcgggag ggacgctgat ttggaagcat ttacctgatg agagactgac
84301 agcagctcct ggtagccgag ctttccctcc tgcctctgct gtgaaggtgg acccatccaa
84361 cagtcaaatg cctgactctg gacaggagcg gacctattta ttgccatgca agggactctg
84421 cacttttgaa ttgtgggtca tgggcttgga tttaggggtt agagctggga gaagtcttgg
84481 aagtcaccta gagatgacac tgccattttg cagatgagga aaccgtccaa tcaaaatgga
84541 ccaaggactt gcccaaagcc tcacagcaaa accataggcc cccgcactaa ccccagagtc
84601 cctgtgctgt cttaagaatc aaatagttgt aagcaatcat ctggttttca gtatttcttc
84661 ttttaaaatg cctggggcca tgcccagcag tctgtttcac tgcagcgttt acacagggct
84721 gccgggcttt cctggtggat gagctgggcg gttcatgagc cagaaccact cagcagcatg
84781 tcagtgtgct tcctggggag ctggtagcag gggctccggg ccctacttca gggctgcttt
84841 ctggcatatg gctgatcccc tcctcactcc tcctccctgc attgctcctg cgcaagaagc
84901 aaaggtgagg ggctgggtat ggctcgtcct ggcccctcta aggtggatct cggtggtttc
84961 tagatgtgac agcaccctta gtggatgagg gagctcccgg caagcaggct gccgcgcagc
85021 cccacacgga gatcccagaa ggaaccacag gtgagggtaa gccccagaga cccccaggca
85081 gtcaaggccc tgctgggtgc cccagctgac ctgtgacaga agtgagggag ctttgcgtgt
85141 ttatcctcct gtggggcagg aacatgggtg gattctggct cctgggaatc ttgggttgtg
85201 agtagctcga tgccttggtg ctcagttacc tccctggctg cctgccagcc tctcagagca
85261 tttagggcct tctggacttc tagatgctcc tcatcttgcc tcagtcagcg cgtcagttcc
85321 agagacttct ctgcagggtt ttctggggca ggtggtggca gacccgtgcc ttcttgacac
85381 ctgaggtcag tccaccctcc tgctcagact gcccagcaca gggtcacctc ccaaggggtg
85441 gaccccaaga tcacctgagc gcacagaggg tgcagatgac tggaccacac cttttggtga
85501 tcttaatgag gtggtcccag aggagctcag acatgcaatc tagcatccag ttctgggact
85561 ctgtctcctt ttcaaacgta ttcatgtaga acaggcatga cgagaatgcc ttgtcaacat
85621 gggtgatggg gaatcaatca gacagggcgc cgggctcaag gctgcagtca cccaagagtg
85681 gctcagccca ccaggcccta ggaaacgcct gcacagcctg gagctcctgg agtcatttcc
85741 ttcatgtctt cttcactgca cttacgtaaa gatgccagcc attggtttgg tgatttggag
85801 ggtgcccagt tgcccaacaa gaaatgcaga agaggcctag ccaggatttc accagcagtg
85861 gagagtagag aagatgtggc cagaaaagag tttcctttcc ctcctaaaga tggtactccc
85921 tgcagctact ggggaagcct gcagcattct ctagggctct gtgtgttgag agcagcccca
85981 ccctggcccc ttctgagtgc atttctgctt tgtgacttga tccgtgaagt cccctgagat
86041 gggcagaggg gatgtcctcg aagctggggc agagcctcat ccttgaacgt gaaggacgtt
86101 tgaagactgt ggcatgatca caggatgaga tcacagggaa cttgagtttc tctcctcctc
86161 tcccttcaca gttatttcac tgagggaaat ccctcccctg cccagaatga aaactctagc
86221 caactcttga cttttccatc actccaaagt agttgaaagt acattagtct ccacagtggc
86281 aaaacagtgt gcaaaagcta aataattaga acagccagtc ccatgtgaca gtcaaagctt
86341 ctaactccat tcaaagttgc agccattccc ctcgagggct ggcagggagg ggaggggtaa
86401 gagaaacagg aaggttctta ctgagttggt cctggtgtga gctgcgtcac actccctgca
86461 gaggtttcaa ggagactctc tctctctctg tctccatggg gaccttattt gaattcttct
86521 actcttaccc cagcctgcca tctccagcta tcctcccctg aagagccctt ctgctgcgct
86581 ggattctggt ggccatgtca tctcctcggc cccgtgggag tctgaagatc tggctgcagc
86641 ctcacctctg aggtcctgct agttgccacc tcttaaacat gatctgaggc tcccatgcac
86701 tctgacctgt gcccacatgg ggcccacggg aaacacgctg gcaagcaaac tgtgggtgtg
86761 cagacggttc tcagggctgc agcacctgtc ctttgctctg cccccaaagc aaggccagcc
86821 catcttccat cctctagtgt tccttggtgg ggccctgacc acagtccacc aggtccctaa
86881 ccagagggga cacacaccag gtgtcctcaa tgtattgcct tgaaacagtt gtgctgggac
86941 tgtgatgggg ggtggccatg tagccacccc caccaccccc aagccactct ctccaaggaa
87001 atcctcctaa agatcccttt acatcctcca tgtggtgggg aggttctaga gttgggtgca
87061 tgtgtcttca gctactgaca atgcagacct tagttggcac ctcgctctgg cctatcctgt
87121 ttgctgttct tggcgctcca gtgaaactcc ccatgggcca tccagttggg gtgcagtgtg
87181 gccaccccct tgcaggttcc tgccttgctg gagagcacag ggccctcctg gctcttgtaa
```

Figure 1CC

```
87241 aacactcccc atggtacaga gaggccagca gtgatgtgag gcccaacctc cctccatggt
87301 gttcccaagc agctcccttt ctggggtcaa ggggtggcaa agacagtgca gcgtccaatt
87361 tctgactcaa gccgggcctg gctatcgcag ctctgcactg tgtgtgacag caaggcaact
87421 cacccagtgc cgtggcagtg accgtgtccg aggaagcctc ctcacaccct ctgtctcaag
87481 gactctggca tttagctgga cttgctgtag ctctgagcct ttctgccatt gccatcacct
87541 tgtcagaaac tcaggccgaa tctgcactca gagttgtgcc caggcagttg agccaacact
87601 tgctcagcga tattgtcaca tgacaaggca ctgtcaccac tgggcgtcgt gggtagcgca
87661 gtgtcggctg gatggacccg gagggtgtct gtgtcatgct agtgctagtg atgggagccc
87721 cgtgagccca ttgcccgccc tcccatgccc tcagcagctg cctggggaca gccaatggcc
87781 tgggtgtttc tgaggctacc acatggcttc caggaaactc gagaaccttt ctctcccttg
87841 cctacactct tcacacaggc ctgtgctggc cagcggtggg gatccggcat tcctatctta
87901 ggtgcagaaa gtgactgact cattgcaggc ctgggagata agactgatgg cccagccagc
87961 aagatgtatg gatttctcag aggcagtggc ctctgtcatt gtcctcagga aatgctggtg
88021 attctggtgg cctgaggtca atgcatgtca acgtggccaa cttgccttat aaactttttt
88081 tctggacaat tgcgtgcact gtcctgtaac agtgtcctgt tgtttatgat gcagaaatag
88141 gtgtttttaa agcctattga ttttggtact attaatgtgg tcaggaactt tctcagtctt
88201 tcttgtttgg ggtgagctgt ggcttcctaa acaggaaccc aagacacccc caaaagctgc
88261 tcaccagcac tgccagcctc cctcttacca agtagcaccc gttcaggaca ttctgcgaaa
88321 ggcatttgcc cagaagttgg gaggaaggaa atgtaacatt ttggggcacc taccatatgc
88381 caggcaccag gctaaacgtg ttcacacaaa ttctcttact aaccctcacc atccttctac
88441 aagacaaact agtatcttca tcttggggtt caagatgagg aaatggaggc tcagagaggt
88501 tgaatgaatg ccggtgcctg gatatgaacc ccatctgcct gactccgcaa cccaggcaaa
88561 gtctttcctt gaacttccca gcagccactg cttagacaca gcctccacaa ccatggctca
88621 gcagcaaatt gcttctctga cctcactcag cctgtgtgtc cttgttgagt gaggcattca
88681 ggaccctggt cccaaagtgg agaaagtctt tcctactagg tcatagctac acctgcatgt
88741 gggtgctgtg ccttttgttt agtgaacttt tatcaccagc atcctcagca atgacatttg
88801 cagagaagcc agagctgagg caccttggta ttcttgggat gtgactttcc tgaatgttta
88861 agggaaaatg cccgaaggta cagagagctt ggtttctagt aaacaataac tgtcttgctt
88921 ttaccccccct tcatttgctg acacatacac cagctgaaga agcaggcatt ggagacaccc
88981 ccagcctgga agacgaagct gctggtcacg tgacccaagg tcagtgaact ggaattgcct
89041 gccatgactt gggggttggg gggagggaca tggggtgggc tctgccctga aaagatcatt
89101 tggacctgag ctctaattca caagtccagg agattttagg gagttggttc ttatcaaagg
89161 ttggctactc agatatagaa agagccctag tggttttttt ctaataccat ttctgggtaa
89221 ttcctaaggc atttagtgtt ctgaaagatg ctagccttgt ccagcctggg agttgagaat
89281 gaatgtctaa cagaaactct aggccgggcg tggtggctca cgcctctaat cccagcacta
89341 tgggagaccc aggtgggcag atcacctgag gtcaggagtt tgagaccagc ctggccaaca
89401 tgtgaaatcc tgtctcacta caaataaaaa aattagccgg gtgtggtggt aggtgcctat
89461 aatcccagct actcaggagg ctgaggcagg acaatcgctc gaacccagga ggtggacgtt
89521 gcagtgagcc gagatcgcat cattgcactc cagcctgggc aacaaaagca aaactccgtc
89581 tcaaaaaaaa aaaagaaact caaatatgtg tgacaggcga ttctcactgc aggctgccct
89641 gtggctgatc caggagcaag gccttaacca tgtcatcccc aagcgattgc ttgtaaactt
89701 tcttctgtgc agccttcaac ccttattatg attttcttct caggaaccaa actgctgtat
89761 tcaagaaagg cagctttgtg taatcattta tcataaatat cttaagaaaa atcctagaga
89821 ttcctaattt taggaaatgg gagacctatg gtactgatat aatgtgggct gggcttgttt
89881 tctgtcattt gctagataaa tgaacttgag agcctactgt aaaatgtgga agcttctaga
89941 ttgcagaagg gctggaaaga cactgttctt ttctcccgag tgatgggatc tgtccagtat
90001 ttagagctgc ctctgaggcc atctgattct aggagactct gcctcgttga ggatatttg
90061 aggcctaact acacattcct gcccccagag aggtcacagc ctatagcagg ctgatgtttc
90121 tcatgtcaca tggcacagaa aggcacattt tcgttctcag gctaacaaag agcttcaaaa
90181 actattagaa gggacagtgg ctataagaga agaacctcag tcaatgtgtg aaattaacta
90241 ggaacctggc tcctgtttct tttaggtcat gtttttcagc ttaggtaaaa ctagaggctt
90301 tgataaagca tgacctctag aaatcattgc ttttcataaa tggaagtggg tttgagtttt
```

Figure 1DD

```
90361 ttctactgat tgttagtgca ggtgatgtct acatgccccc agaacatatt ccatgcaaca
90421 aaaaaagccc aggtcaccgt ctttgctggg aacttgactt ttgtgctcac tgaattttaa
90481 gctttctgac agcagcctgg aatcatggag ggataaagta cctattagta agatggaaaa
90541 aggtgtttca ggttggagct gcagtctgtt gagagtaagc tatgggaagg cctgtatacg
90601 aggggtggac ttttcttctg taagtgtcca gagaccaggc ctcctgaaga gggcatgggg
90661 gcttaactta cctggactac tgtgtttaca atactcattt atcttgaact cctcctaacc
90721 cctgagaatt gctacattta gtatttgctg agtacttcct agcatcctag ggaatcaata
90781 gaacattctc ccaaccaggc tgggtgcggt ggctcatgtc tgtaatccca gcactttggg
90841 aggccaaggt aggcagatcc cttgaggcca ggagtgcaag actagcctgg ctgacatggt
90901 gaaaccccgt ctttactaaa aatacaaaag ttagccaggc atggtggtac acacctgtaa
90961 tcccagctac atgggaggag taggaggcag gagaattgct tgaacctggg aggtggaggt
91021 tgctgtgagc cgagatcatg ccactgcact ccagcctggg cgacagagtg agtgagactc
91081 tgtttaaaaa aaaaaaaaaa aaagaacatt ctcctaacct ggcttcttcc tccaggggtg
91141 taattaatca tgtcagtttc ctcattgata cacacacaca cacactacaa tcctgtatcc
91201 attacttttc aaggtacatt tactatttac gtttggggtc cttgtctctt ttttaatagt
91261 gtttcttaaa gtcttgtatt atatcagagt acagtaacat cccagtcaag agcactctag
91321 taagctctag gaggaaagcg acttccggaa ggcagtggag acctgtcctg ttggggcagc
91381 ataggggcag cccctgcctc tggtcagttc tggcgctcag gctcagggtt gcctctgggc
91441 tgttcttccc agagactgac aaagggctcc cataaggcac ctgcagagcc tgtgagaagc
91501 tgaagtcaat gttttcctga caccagttga tctgtgcagg atccattgat ttaaccacct
91561 gctgtgtggc atgcactgtg gtcgatgcca ggaacaggaa ttggaggggc ccatgagcat
91621 ggccagtatc acaggctgga ggtgctgctg cgctctgacc gggcctcttg gggatgagcc
91681 catgtcaacc accttgcctc cgatggggtc gggcccacag gttacctttg tgtgtccatg
91741 accacacctt cctccccgac ctcatccaaa tctctttctt ttccaagccc ctgaatcctt
91801 cagggctgca ggttttgttt aaagcagagc tggtgagttg cataggttgt tgcgttggga
91861 ctagatgggg tgttcaaaga gttgggagtt aaaaaacata aagggtattt attaggagaa
91921 ccaaggagtg taattctcct gttcttaata tgcggccagg ttaatgaatg tcacgtgaat
91981 gaaccagaaa aaaatgaagt gtgcccttga tcagctgggt tggtgtgcag caagctgtgt
92041 gaccagggga cagcagtggt cctgagggcc gtcactgtct gccgtgcaga gcccttcctc
92101 ccacgggggc ctacctcacc tgtgccaagg gcttgtctgt ggtcagtgac ctggatagat
92161 ctgaatgggg cttctttttc gaggagtctt atggcaggtc tctcagtaaa gactccattc
92221 ttgatgatca cacattttgg attttccaaa tctgtcagag aatgggcttg aggcggggtt
92281 tgtgggcact agtttcactg gtttcattta ccaaaaaggg gagcagaagt caagtatggt
92341 ggctcatccc tgtaatccca gaggcaagag aattgcttga gcccaggagt tcgagaccag
92401 cctgagcaac ataaggagac cccgtctcca caaaaatgaa aaataacatt ttagtcagac
92461 gtggtggcat gcatctgtgg tcccagctgc ttgggagggt gagatgggag ggttgtttga
92521 gccctggagt taaagttgca atgagctgtg attgcaccac tgcactctag cctgggtgac
92581 agaacgagac cctgtctcaa aaaaaaaaaa aaagaaagaa aaaaaggaaa aaaaaaactc
92641 atgcctgtaa tcccagcact ttggggaccg gggtgggcag atcacgaggt caggagatca
92701 agactatcct agccaacatg gtgaaacccc gtttctacta aaaatacaaa aattagccag
92761 gtgtggtggc acgtgcctgt aatcccagtt actcgggagg ctgaggcagg agaatcgctt
92821 gaaccaggga gtcagaggtt gcagtgagct gagatcgtgc cactgtactc cagcctgggc
92881 gacagagtga gactctgtct caaaccaaaa aaaaggggtg gggggcgggg gcaggagaac
92941 agtgagaggt agggagagga aaggggattc tcgctacacc caaaccagat accatctaga
93001 ggctagaatc tttgggaggc tcaaattccc tagaaagcag gagaagcttc tgtagccctc
93061 ccgctttccc agtagattaa gcccagggcg gctccagatg tgtgacatgc tctgtgccca
93121 accagagccc atcataggca gaggaataac acccacacca gaagggccct cggaggtcac
93181 cacgtccaag aaccctcttt acagatgagg aaactgaggc ccagagaggg gagagccacc
93241 tagcgagctg gtggcggcta gaccaggaga gctgtcattc caagcaagca aaggcaacga
93301 gacgagccca gagctgtgct cccatctctt tgttaggggg cctgggatgc cctctcagtg
93361 tcattttgtc caggatgatg ctccctctct taagcgatta atgcgccctt gctaaccttt
93421 tgctatcgct gcctcttcaa accagaggag ttgagagttc cgggccggca gaggaaggcg
```

Figure 1EE

```
93481 cctgaaaggc ccctggccaa tgagattagc gcccacgtcc agcctggacc ctgcggagag
93541 gcctctgggg tctctgggcc gtgcctcggg gagaaagagc cagaagctcc cgtcccgctg
93601 accgcgagcc ttcctcagca ccgtcccgtt tgcccagcgc ctcctccaac aggaggccct
93661 caggagccct ccctggagtg gggacaaaaa ggcggggact gggccgagaa gggtccggcc
93721 tttccgaagc ccgccaccac tgcgtatctc cacacagagc ctgaaagtgg taaggtggtc
93781 caggaaggct tcctccgaga gccaggcccc ccaggtctga gccaccagct catgtccggc
93841 atgcctgggg ctcccctcct gcctgagggc cccagagagg ccacacgcca accttcgggg
93901 acaggacctg aggacacaga gggcggccgc cacgcccctg agctgctcaa gcaccagctt
93961 ctaggagacc tgcaccagga ggggccgccg ctgaaggggg caggggggcaa agagaggccg
94021 gggagcaagg aggaggtgga tgaagaccgc gacgtcgatg agtcctcccc ccaagactcc
94081 cctccctcca aggcctcccc agcccaagat gggcggcctc cccagacagc cgccagagaa
94141 gccaccagca tcccaggctt cccagcggag ggtgccatcc ccctccctgt ggatttcctc
94201 tccaaagttt ccacagagat cccagcctca gagcccgacg ggcccagtgt agggcgggcc
94261 aaagggcagg atgccccccct ggagttcacg tttcacgtgg aaatcacacc caacgtgcag
94321 aaggagcagg cgcactcgga ggagcatttg ggaagggctg catttccagg ggcccctgga
94381 gaggggccag aggcccgggg cccctctttg ggagaggaca caaaagaggc tgaccttcca
94441 gagccctctg aaaagcagcc tgctgctgct ccgcgggggga agcccgtcag ccgggtccct
94501 caactcaaag gtctgtgtct tgagcttctt cgctccttcc ctggggacct cccaggcctc
94561 ccaggctgcg ggcactgcca ctgagcttcc aggcctcccg actcctgctg cttctgacgt
94621 tcctaggacg ccactaaatc gacacctggg tgcagctgct ccactccctc ggcctcctcc
94681 cgtgctcagg ctgtggccgc acgcgcccct cacgcttgcc cgccactctg catgtcacca
94741 gcaccccccgc tccgtgctcc ccaccttgtt tgactctctg gccacttgat ttgtccacaa
94801 cggcccatca gcccacagga ggtttggtgg gtgccttcca ccgacaggat gacgggtgcc
94861 ctcatggtgt ctagaactct ccaaccctcc catgtaggca taagcagccc cactttgcag
94921 atgaggaaac ggaggctcag agaagtacag taacttgccg aaggccaatg agtagtaagt
94981 gacagagcca ggtttgggat ccaggtaggt tgtctctgaa agacacgcct gtcctgcatc
95041 ccacaacgcc tcccaggagg tgctggagtg tggacgccta acacagagat gtgcagggca
95101 cacacagcag gtgacacaca cagcatccag aggtggccca gagctcatgc tgtgcctttg
95161 gcccagtgcc ctgcccccac ccactctgcc ttgtggcagg aagacaagga gcagacacaa
95221 gatctccctg gtccacatgc caccacctcc ctctgcagag gacaagggga tcctcatgct
95281 ggcattggag gggttgagc agggcccacc ttgagccctc aggagcacga ccacagcagc
95341 cctgcaggga gggattggtg ggaggagagt cccaagtatc agggagagga gagttggtgt
95401 cccacaggag acctcagagc cacaaggcga gcttgttcat aaatttggga cccttagcat
95461 ttcacagtta tttgcagagc ccagaaatgg atgttactga agctcacagt tgcaagcatc
95521 tgttaaattt ttattagatt ttacttttag ggaaaacttt gaaatgctat aaagaagcct
95581 gtgtttaaaa gttaagacag aggctggggg cgatggctca cgcctgtaat ctcagcactt
95641 tgggaggcca aggcaggtgg atcatttgag gttaggagtt cgagaccagc ctggccaaca
95701 tggtgagacc ctgtctctac taaaattaca aaaaattagc tgggcgtggt ggcgggcacc
95761 tgtagtccca gctactgggg aggctgaagc aggataagtg cttgaaccca ggaggcggag
95821 gttacagtga gccaagatca caccactgta ccctaagcct gggcgacaga gtgagactct
95881 gtctcaaaaa ataaaataaa ataaagttaa gagagaaaaa aatatatcct atatcctttg
95941 ttaaattcca aaacagtagg ggacaaataa ctgacttgac aggttactac aatatttcct
96001 gaaatgatgt tttcttgaat actggcctac tagaggttca taggtgtgtt tggattaaaa
96061 aagagttcca tggcccagtg actgggggaa aaaaataaaa gactaaagta agttaaacag
96121 gcttttctgc tgcaggactt gtcagagcct ttaatgtact aatggccatt gtgaccctct
96181 gagaaggtca cagagtgggt ttcccaaact tacttgattc tacctgctaa catttcctgg
96241 aggaagtttg ggaaatgccg atttagcaga ttcttttgtt gtgccgtgga tggtgctggt
96301 tgatgtgggc aaaacaaaga acacgtgagt cagatccgcc tggggctctt actaaagtgc
96361 aggttcccag gtgccacttt aggcttacag acccagttgt ggggtaagcc tgggagtctt
96421 ttagcaggtg attctgccac atagtatagt tggaaaacct ctgggcatac tcattgctgg
96481 tccctctaga aatccaggtg acaatagcca atgagaagct ccaagagacc cagttgtcca
96541 tggggtagag ggaatgtgat attgaaacca aagaagaaaa tctatgatca gttttcagca
```

Figure 1FF

```
96601 gtgactgtca agagaaggag aagggtgagt tagcgctgat gctggctgac aggtcagcgg
96661 gttggtttca ccaaggagtg tgatgaaggc tgatgttgtc tgtgggaatg tatgatggta
96721 actggtttgt agctaatttg gggaagcagt gagaattcgt gccctttgaa gaccagtaag
96781 tggcaagaaa cccaccaggc ctggctcagg gctgggctgg gcttggctcg tctcagagca
96841 gctggggctg gtggccaaag ccaccattag tgaggggcag gccctggggg tacaaccagc
96901 aactagggga caaagacaac cctgccagcc tctcctattc tggaggcgtg tgaccagaaa
96961 tggagatggg ttggtcagca taagatggcc aggaaggtgg aaatcaggac tgctggcaat
97021 ctagccacat gggcagggga gccgggtggt tccaggcagt ttccaaggcc aagagggtga
97081 gcaggcacct cacagggaat cagggccaag cctggctgca gtgtggagac aatgcaccca
97141 cccccatcct tggatcttgc aggaggctgg gtcctcactg agctaccaac atccatggcc
97201 ctgaggcttt taaaacaccc atccatggag tggggctggt cccagtgggg tgaggctgac
97261 cctggcagaa acagggcagg agcctgtggg ttagggagac tgcaccttcc ttagatagcc
97321 tccatgccat catgtccccg tgacagtttc tgctgcgtcc cctctgcatg gtcccacccct
97381 cggccagcct gctgccccct cttgccaggt tgcgctaatc agtgacccca gtgtgctgtg
97441 ttgatactaa caatgcgagg cctagcagat tcaagggaaa agagaaccaa ctgggtttcc
97501 accagaccca actaaacaaa catggaccta tcccagagaa atccagcttc accacagctg
97561 gctttctgtg aacagtgaaa atggagtgtg acaagcattc ttattttata ttttatcagc
97621 tcgcatggtc agtaaaagca aagacgggac tggaagcgat gacaaaaaag ccaaggtaag
97681 ctgacgatgc cacggagctc tgcagctggt caagtttaca gagaagctgt gctttatgtc
97741 tgattcattc tcatatataa tgtggggagt atttgtcact aaagtacagc tgtcatttaa
97801 agtgctttgt attttggggc aggcttttaa aaagtccagc atttattagt tttgatactt
97861 accccaggga agagcagttg gcaggttcat gaagtcatgc tcctaattcc agctttctta
97921 gtgtactttc agtgagaccc tgacagtaaa tgaaggtgtg tttgaaaacc aaacccagga
97981 cagtaaatga aggtgtgttt gaaaaccagc cctaggacag taaatgaagc catcttctca
98041 ctgcataaac tgcacccaga tctttgccca tccttctcag tatttcactt caccccattgt
98101 ttactgtctc aatgactggg gaaatgtctg gggaaatgct cccgtaattg cacagtggcg
98161 tttttcctgg aaaatcccac catggctcta gataagacct atttttctta aaggtatcta
98221 aaatttccag cataaattct gtctgaaaca cctgaatttt aatcagtact ggagcccgga
98281 gggcatctcc agttgccaca tagctctgag cattcagtgg tgtgttgagg gctgctcccg
98341 gaagtgcctg cagagtcagg gctccccagc ctcatctagt gaggcagtgg aagggcctgt
98401 ggggatttgg agagctggcc tgggtctctg aagtgatagt gacagctgct tgtcaatcac
98461 ggtgcacatt tagtgccggg ggcagggggc agggaatacc agcctcatgc atgcatgcat
98521 tcatttgttc cttccttcat tcattcattc agtacacatg ggtacaacat ccctgccctg
98581 gagttgccca gagtctaggg aggggaaaga tctattaccc tgggcctcgg ccagctgggg
98641 agtgctgctg gtggagaggg gccgtgtgca gcgagggaag gaggagtcgt caataccccc
98701 accccagctt tgctttcttg tcatcagccc cagggcccca gcctgtgtcc ctcctctccc
98761 attgctactt catctcctgg gtcctcctta ccaagcctga ccacacagag ggccttggcc
98821 gcttccatgg ggaattggaa agcaataaga tagcatcccc tagaagccca gtgaagtctg
98881 ggacaggacc cttctctgag ctctgacttg ctcttggaaa cacttcgagg cttagcctcc
98941 ccactttgtt tcccaagagt gtgacctgtt cccctccaaa cacccccttc tcctccaggg
99001 ccatgcccac ccgtcaaaat cccccacggg caggacgaac tgtgggtgtc agtcaccatc
99061 tatcctgcat cctggttcca gggccccccc cagccccgcc tccataggga caggcgtgca
99121 gacacccgtc cctggctgct tcctcttgtg gaatgggttc aaaagtaagc agtgttgttt
99181 acactgacaa actgaaaaaa aaagaaaaag agataacatt ggaggcttgg cacagtggct
99241 catgcctgta atcccagcac tttgggaggc taaggtggga ggatgtcccc agcccaagag
99301 ttctagacca gcctgggcaa catagcaaga ccccatctca aaaaaaaaat ttaattggcc
99361 aggcagaggt gggaggatca cttgaaccca aagggtggag gctgcagtga gccgtgatgg
99421 caccactgca ctccagccag ggcaacagag ggagaccctg tctctaaaac aaacaaacaa
99481 acaaacaaac aaaagagtta acattggcca gattaggatt caccagatag tgttaatatt
99541 agtttgattt gagactttaa tcagaaagca catgtgtggt gggggtgggt gtaacctaag
99601 tcaggtagaa tctttccaac ttgggggggg cacactcctg attgtagcca tatgagtctg
99661 tcagtgtggt ggaagagacc atgggttaat gggcaggtaa aaaagcacct tgcctggaat
```

Figure 1GG

```
 99721 tgagtagaaa gtaaggccct tcagaccccg tgacacactt ggggacattt tcttgagtaa
 99781 catcctaaga ttcatgtacc ttgatgatct ccatcaactt actcatgtga agcaccttta
 99841 aaccagtcgt ctccaaattc aggggcacag taacatccaa caggctggag aaagaacgta
 99901 ctagaacttc cattcctttt tcatgtcctc ttctaaaagc tttgtcaggg ccaggcgcgg
 99961 tggctcacgc ctgtaatccc agcactttgg gaggccgaga cgggtggatc acgaggtcag
100021 gagatcgaga ccatcctggc taacacagtg aaaccccatc tctactaaaa atacaaaaaa
100081 acgagccggg cgtggtggtg ggcgcctgta gtcccagcta ctcgggaggc tgaggcagga
100141 gaatggcgtg aacccaggag gcagagcttg cagtgagccg agattgcacc actgcagtcc
100201 agcctgggcg acagagcgag actccgtctc aaaaaagaaa aagaaaaaga aaaagaactg
100261 tgattgggga ggacggtcac tttcctgttc ttactgatca gaagggatat taagggtacc
100321 tgattcaaac agcctggaga tcactgcttt caaccattac ctgccttatt tatttttagt
100381 tactgtcctt ttttcagttt gtttccctcc tccatgtgct gacttttatt ttgattttat
100441 ttatgtttat gtttaagaca tccacacgtt cctctgctaa aaccttgaaa aataggcctt
100501 gccttagccc caaacacccc actcctggta gctcagaccc tctgatccaa ccctccagcc
100561 ctgctgtgtg cccagagcca ccttcctctc ctaaacacgt ctcttctgtc acttcccgaa
100621 ctggcagttc tggagcaaag gagatgaaac tcaaggtaag gaaaccacct ttgaaaagaa
100681 ccaggctgct ctgctgtggt ttgcaaatgt ggggtttgtt tatttgtttt ttagcctcaa
100741 agacctttct tcaaatgagt tctggcatag aagcaccgtg taaaatagtt agaattctgg
100801 gcaaagggga aaagagagct gggggccatc cctctcagca ccccacaggc tctcatagca
100861 gcagctccta agacacctgg tgggaccttg gtttcgaaat cgctactcta aggctgggca
100921 cggtggctca cacctgtaat cccagctctt taggaggccg aggagggtgg atcacctgag
100981 atcaggagtt cgagaccagc ctggctaaca tggcaaaacc ctgtctctac taaaaataca
101041 aaaattagcc gggcgtggtg ttatgcgtgg tggtaatcgc agctactcgg gaggctgagg
101101 cacaaggatt gcttgaaccc cagaggcaga ggttgtagtt agctccagct tgggcgacag
101161 agcaagaccc tgtcgcaaaa attgtttaaa aaacaaaccc aaaattgcta ctctcattgg
101221 gttcctttgc ccattcctga ttttggcaag agaaatgctt ccagattgcc ctgatctggg
101281 taggacagca tcacgccata gcaacactgc cccgtgagct cactgccccc tcaactagct
101341 tgtggtcctt ggttaatgtc agtttctttt ttgagtttgt gttatgtcta agggtcatct
101401 gctgggtaac ggaacccagg gactgcccta gtccctagac tgtgccatgc ccgactctgc
101461 cagctttgtc agtgatgctg gtgctcgcct cctcgggtgc tcgcctggtc tgagcacacc
101521 caaggagttc ttgaggcctt agggttgttt gcgagagaat gaaagaacac gacctagctc
101581 tctttagcat ccttggtcag gttcaacact gcccccaggg gcctctggtg gagccaacca
101641 ccatcagcca aataaatcca taattagagt cagaaaatgg atgtctgcat atgtgtagtg
101701 cactaatgtc ctgccgatga ttgacatgga gtggagagtg acctgatcat tgctgtgagc
101761 tctgctggcc ttggcacaac tcatgctgat aactaatgca cacagttcct ctgggaggaa
101821 atgtcctcag ggaacttgga gtttgggtgg ggatgtgggt ttgtgtgccc agcaagccct
101881 tgtggttgta gcagacacta gtggcatcta ggaggcaaag ggtcacccca gtcttagcca
101941 cgttttgagt caaggtggcg gagtggggct ggtgttgact cttggtggca gtaacttttc
102001 ccaatggtga aaaacccctc tatcatgttt catttacagg gggctgatgg taaaacgaag
102061 atcgccacac cgcggggagc agcccctcca ggccagaagg gccaggccaa cgccaccagg
102121 attccagcaa aaaccccgcc cgctccaaag acaccaccca gctctggtaa gaagaacgtt
102181 ctcttgaatc ttagaggaag ctgaagctct cagaggtaca gccttcattt taggaggcct
102241 taggccactg agaatgaata acccctggca gctggtcagc agcttgcagt ttactaagca
102301 ctggagtctt cattgccttc tcagtccttt tgatttctga ggcaaatgtt gaatccctac
102361 cttttttttt ttttttcttt tgagacagag tttcgctttt gttatccagg ccggagtgca
102421 gtggtgtgat ctcagctcac tgcatcctcc acctcccagg ttcaagcgat tctcctacct
102481 cagcctccct agtagctggg attacaggca cctgccacta tgcccggcta atttttttgta
102541 tttttagtag agacagggtt tcaccatgtt ggccaggctg gtctcgaacg cctgacctca
102601 ggtgatccac ctgcctcggc ctcccaaagt gctgggatta caggcatgag ccaccactcc
102661 cagcctgaat cctcactttt tatcaatgaa gaaattgagg ctgattctgc agcatgataa
102721 aaaaaaatac agaaaaagga aaaaaaagaa agaaatcgag cctctgagag tttgcttgac
102781 tgagtctaac cagctcattt taaaccccgag gaaaatgcag tcacatgact actaagtggc
```

Figure 1HH

```
102841 agctctcgga gcctctctgg ccccaagtcc agggttccat agaggcagcc ccagcatggc
102901 atgttttcag tccccaaatg agactctgga gacaaatgtc tctggagaca gagcagcagc
102961 ctggataagt cacaatgggt gacgtcactc agggctcaac cctgggcag cttaacttgc
103021 tagggacgtt aggagtctgc tgcaaaacct gagggtctta gctgagcagt cacaggctgg
103081 gcccgttgcc ctgggctcct gtgagtaaaa cccagtcaat tttgagtacc cagtaaggca
103141 tccattgagt tattttgcag ccaggagtgc tattaagaac agtcgcggct gggcgtggtg
103201 gctcatgcct gtaatcccag cactttggga ggccaaggtg ggcggatcac ctgaggtcag
103261 gagttcgaga ccagcttggc caacatggca aaaccccgtc tctaataaaa atacaaaata
103321 attagctggg cgtggtggcg ggcgcctgta atcccagctt ctcaggaggg tgaggaagga
103381 gaatcacttg aacccaggag gcagaggttg cagtgagctg agatcgcacc attgcactcc
103441 agcctggatg acaaaagtga gattccttct caaaaaaaaa aaaaaaaaaa cagtcgtcct
103501 ctttggggat tagggacagc ctgcctgcct gcccgagcac ttctctcttc cattgcccca
103561 gtgaagtatt ccaggcccct gggtttagac tctgcaccat gtaggggtgt ctgacctgca
103621 cttgctcctt ggtggcacgg gcagcctatg gcacttgctg cgggctgtga ccaaagcctg
103681 gcctggatct tggatcttgg tgactctgct tctccctggc ctgagggagc tgcccagagc
103741 ctgcccacca cctgctgcgt gtctttgcgg tggcatttct cgcacacatg ccgtgcggtg
103801 gcacccccaa ggatggccat tcactaaggc ccattgtttt tgtcttttcg cttcgtgttt
103861 tctggcctgg tgtttttctc atatacatgt gatccaggga taattcccag aattttgaca
103921 ggattttaag tagcgtttgg atcctgctgt tttttttca cttaacatcg ggccagttga
103981 ctcacactct gttttttgtt gttgtttttt tgagacggag tctcactgtg tcacccaggc
104041 tgaagtgcag tggcacaatc ttggcatact gcaacctctg cttcccaaat tcaagcagtt
104101 ttcctgcctc agcctcctga gtagctggga ctacaggcac aggccaccac gccctgctaa
104161 tttttgtatt tttagtaaag acagggtttc accattttgg ccagcctagt ctcgaactcc
104221 tgacctcaag tgatccgccc acctcggcct cccaaagtgc tgggattaca ggggactcac
104281 actttgtaac aacctgaaac aacgtgatgc atttcccttt gggtcttacc tgctcttcgg
104341 tggctgcctg caggtggaga gaccctcccc cttgggcccc tcgaccttgt ttcagaatgg
104401 ggcccctgct gggccagctg tgggtgcctg ccacgtgaag gactcattaa ggccctgttt
104461 aagcctgatg ataataaggc tttcgtggat ttttctcttt aagcgactaa gcaagtccag
104521 agaagaccac cccctgcagg gcccagatct gagagaggta ctcgggagcc tacttcgctg
104581 ggagcagcct ccctttgcgt gtgtggccat tcactggctt gtgtttctag agccgggagg
104641 accctttctct gcaatgcagg gttcacacag ggttcgcagc ctgaagatgg agcagtccga
104701 attctcttcc ctgtgcagtt tgcgcagctg tgtttgtctg atgggctttc taatcctgtg
104761 tgctctcctt gacttcaggg acaatggcat tacaggcatg agccaccatg cctggctgtc
104821 tccctatgtt tcagatgaag acataggctt aaggaggtca ggtgacttgc ccacgaccac
104881 tctgtaaata agaggcatga aaagtatttg gagccaccac caccaagccc actggtcacc
104941 ctgggtctct gaagtcaggg aggcaggagg atgggaggtc tgaggaggca gagaggctga
105001 gcctggaggc cctggaggcc gaggccccat ctgttgtttc cttatgtgga aaataagagg
105061 cttcatttgt cctattgcca cagagcgtac tacttcagga acatccaaga catggaaatc
105121 cgcagggcac ggtggctcac gtctataatc ccggcacttt gggaggttga ggtgggagaa
105181 tcgcttgagg ccagaagttc aagaccagcc tgagcaacat agtcagaccc cgtctctata
105241 aaaaacatta tttttaaaaa agacatggaa gtcaaattct aaaaactggt gctggctggg
105301 tgcggtggct catgcctata atcccagcac tttgggaggc cgaggcgggt ggatcacctg
105361 aggtcaggag ttcaagacca gcctggccaa catggtaaaa cctctactaa agaaatcttt
105421 actgaaaata caaaaatcca gtctctacta aaataagtct ctactaaaaa tacaaaaatt
105481 agccaggcgt ggtgctgcac acctgtaata tcagctactc gggaggctga ggcaggagac
105541 tcgcttgatc ccatgcagcg gaggttgcag tgagccgaga tcacgccatt gcactccagc
105601 ctgggcatca gaataagact ccgtctcaaa aaaaaaacca caaaaaaaca aaacaacaac
105661 aaaagaaaac tagtgcttat tcgtcactgg ccaagctgcc cattggctac atgggtgctt
105721 caaagagctg cccttctcca ggtctggcca gcaggtatgt gttacagcaa atgcctgggg
105781 cagcggcagg ggcattgctg cgggaagctt ctggacttgc aggaaagcta agttctcaga
105841 ctgcagggga gctaagcaca cctcggcaca gggtgaggcc tgcggttctc agacttcagt
105901 ctttgtggag cttgagaaaa atgaggcttt gcaggtccca cccctagaga ttctgctcta
```

Figure 1ll

```
105961 tccactcttg aaggggatcg agaaatttgc attttgcaac tcccactttc ctccttgaaa
106021 gctccggaga ttctgacgca gggttccgtg ggccacactt tggaaaatac agacccatga
106081 gatagaatac cagactgttg aagtgtaacg gggcctggg aagtgcagta acagaagcaa
106141 gtttgagggt aaaggacacc cagaggaggg agggacagca tctgcatgga gaggagaaga
106201 gaccccccag cagcttccag ggtgttggaa gggtgcgcta gtaactgcta tgcatggcag
106261 gtggggaact gtacgtcagg gcacagcagc atgaagcggt atggctcgtg tggacagcta
106321 gggacaggca ggcgtggagc aggcatcctg ttctgaaggc caaatcccac agaggagcca
106381 gggtgctggc aggagccctg aactagccga acagctgaac agctgaacat tcaccctgtg
106441 gggaaagggt cagaagcgtc caggcttgag ggcacagctg ggtctcgtca ctgcatcacc
106501 cttatttagg ataaaggccc tgaagaattg tattagaggt tggcaaagca tatctaccac
106561 ctcctggagc cacgctggcc gcagggatta taattatttc cattttcaaa ttaaggcctc
106621 tgagctcaga gaggggaagt tacttgtctg aggccacaca gcttgttgga gcccatctct
106681 tgacccaaag actgtggagc cgagttggcc acctctctgg gagcgggtat tggatggtgg
106741 ttgatggttt tccattgctt tcctgggaaa ggggtgtctc tgtccctaag caaaaaggca
106801 gggaggaaga gatgcttccc cagggcagcc gtctgctgta gctgcgcttc caacctggct
106861 tccacctgcc taacccagtg gtgagcctgg gaatggaccc acgggacagg cagcccccag
106921 ggccttttct gaccccaccc actcgagtcc tggcttcact cccttccttc cttcccaggt
106981 gaacctccaa aatcagggga tcgcagcggc tacagcagcc ccggctcccc aggcactccc
107041 ggcagccgct cccgcacccc gtcccttcca accccaccca cccgggagcc caagaaggtg
107101 gcagtggtcc gtactccacc caagtcgccg tcttccgcca agagccgcct gcagacagcc
107161 cccgtgccca tgccagacct gaagaatgtc aagtccaaga tcggctccac tgagaacctg
107221 aagcaccagc cgggaggcgg gaaggtgaga gtggctggct gcgcgtggag gtgtgggggg
107281 ctgcgcctgg aggggtaggg ctgtgcctgg aagggtaggg ctgcgcctgg aggtgcgcgg
107341 ttgagcgtgg agtcgtggga ctgtgcatgg aggtgtgggg ctccccgcac ctgagcaccc
107401 ccgcataaca ccccagtccc ctctggaccc tcttcaagga agttcagttc tttattgggc
107461 tctccactac actgtgagtg ccctcctcag gcgagagaac gttctggctc ttctcttgcc
107521 ccttcagccc ctgttaatcg gacagagatg gcagggctgt gtctccacgg ccggaggctc
107581 tcatagtcag ggcacccaca gcggttcccc acctgccttc tgggcagaat acactgccac
107641 ccataggtca gcatctccac tcgtgggcca tctgcttagg ttgggttcct ctggattctg
107701 gggagattgg gggttctgtt ttgatcagct gattcttctg ggagcaagtg ggtgctcgcg
107761 agctctccag cttcctaaag gtggagaagc acagacttcg gggcctggc ctggatccct
107821 ttccccattc ctgtccctgt gcccctcgtc tgggtgcgtt agggctgaca tacaaagcac
107881 cacagtgaaa gaacagcagt atgcctcctc actagccagg tgtgggcggg tgggtttctt
107941 ccaaggcctc tctgtggccg tgggtagcca cctctgtcct gcaccgctgc agtcttccct
108001 ctgtgtgtgc tcctggtagc tctgcgcatg ctcatcttct tataagaaca ccatggcagc
108061 tgggcgtagt ggctcacgcc tataatccca gcactttggg aggctgaggc aggcagatca
108121 cgaggtcagg agttcgagac caacctgacc aacagggtga aacctcgtct ctactaaaaa
108181 tacaaaaata cctgggcgtg gtggtggtgc gcgcctataa tcccagctac tcaggaggct
108241 gaggcaggag aatcgcttga acccaggagg cagaggttgc agtgagccga gatagtgcca
108301 ctgcactcca gtttgagcaa cagagcgaga ctctgtctca aaacaaaata aaacaaacca
108361 aaaaaaccca ccatggctta gggcccagcc tgatgacctc atttttcact tagtcacctc
108421 tctaaaggcc ctgtctccaa atagagtcac attctaaggt acgggggtgt tggggagggg
108481 ggttagggct tcaacatgtg aatttgcggg gaccacaatt cagcccagga ccccgctccc
108541 gccacccagc actggggagc tggggaaggg tgaagaggag gctgggggtg agaaggacca
108601 cagctcactc tgaggctgca gatgtgctgg gccttctggg cactgggcct cggggagcta
108661 gggggctttc tggaaccctg ggcctgcgtg tcagcttgcc tcccccacgc aggcgctctc
108721 cacaccattg aagttcttat cacttgggtc tgagcctggg gcatttggac ggagggtggc
108781 caccagtgca catgggcacc ttgcctcaaa ccctgccacc tccccccacc caggatcccc
108841 cctgccccccg aacaagcttg tgagtgcagt gtcacatccc atcgggatgg aaatggacgg
108901 tcgggttaaa agggacgcat gtgtagaccc tgcctctgtg catcaggcct cttttgagag
108961 tccctgcgtg ccaggcggtg cacagaggtg gagaagactc ggctgtgccc cagagcacct
109021 cctctcatcg aggaaaggac agacagtggc tcccctgtgg ctgtggggac aagggcagag
```

Figure 1JJ

```
109081 ctccctggaa cacaggaggg agggaaggaa gagaacatct cagaatctcc ctcctgatgg
109141 caaacgatcc gggttaaatt aaggtccggc cttttcctgc tcaggcatgt ggagcttgta
109201 gtggaagagg ctctctggac cctcatccac cacagtggcc tggttagaga ccttggggaa
109261 ataactcaca ggtgacccag ggcctctgtc ctgtaccgca gctgagggaa actgtcctgc
109321 gcttccactg gggacaatgc gctccctcgt ctccagactt tccagtcctc attcggttct
109381 cgaaagtcgc ctccagaagc cccatcttgg gaccaccgtg actttcattc tccagggtgc
109441 ctggccttgg tgctgcccaa gaccccagag gggccctcac tggcctttcc tgccttttct
109501 cccattgccc acccatgcac ccccatcctg ctccagcacc cagactgcca tccaggatct
109561 cctcaagtca cataacaagc agcacccaca aggtgctccc ttccccctag cctgaatctg
109621 ctgctccccg tctggggttc cccgcccatg cacctctggg ggcccctggg ttctgccata
109681 ccctgccctg tgtcccatgg tggggaatgt ccttctctcc ttatctcttc ccttccctta
109741 aatccaagtt cagttgccat ctcctccagg aagtcttcct ggattcccct ctctcttctt
109801 aaagcccctg taaactctga ccacactgag catgtgtctg ctgctcccta gtctgggcca
109861 tgagtgaggg tggaggccaa gtctcatgca tttttgcagc ccccacaaga ctgtgcaggt
109921 ggccggccct cattgaatgc ggggttaatt taactcagcc tctgtgtgag tggatgattc
109981 aggttgccag agacagaacc ctcagcttag catgggaagt agcttccctg ttgaccctga
110041 gttcatctga ggttggcttg gaaggtgtgg gcaccatttg gcccagttct tacagctctg
110101 aagagagcag caggaatggg gctgagcagg gaagacaact ttccattgaa ggccccttc
110161 agggccagaa ctgtccctcc caccctgcag ctgccctgcc tctgcccatg aggggtgaga
110221 gtcaggcgac ctcatgccaa gtgtagaaag gggcagacgg gagccccagg ttatgacgtc
110281 accatgctgg gtggaggcag cacgtccaaa tctactaaag ggttaaagga gaaagggtga
110341 cttgactttt cttgagatat tttgggggac gaagtgtgga aaagtggcag aggacacagt
110401 cacagcctcc cttaaatgcc aggaaagcct agaaaaattg tctgaaacta aacctcagcc
110461 ataacaaaga ccaacacatg aatctccagg aaaaaagaaa aagaaaaatg tcatacaggg
110521 tccatgcaca agagccttta aaatgacccg ctgaagggtg tcaggcctcc tcctcctgga
110581 ctggcctgaa ggctccacga gcttttgctg agacctttgg gtccctgtgg cctcatgtag
110641 tacccagtat gcagtaagtg ctcaataaat gtttggctac aaaagaggca aagctggcgg
110701 agtctgaaga atccctcaac cgtgccggaa cagatgctaa caccaaaggg aaaagagcag
110761 gagccaagtc acgtttggga acctgcagag gctgaaaact gccgcagatt gctgcaaatc
110821 attgggggaa aaacggaaaa cgtctgtttt ccccttttgtg cttttctctg ttttcttctt
110881 tgtgcttttc tctgttttca ggatttgcta cagtgaacat agattgcttt ggggccccaa
110941 atggaattat tttgaaagga aaatgcagat aatcaggtgg ccgcactgga gcaccagctg
111001 ggtaggggta gagattgcag gcaaggagga ggagctgggt ggggtgccag gcaggaagag
111061 cccgtaggcc ccgccgatct tgtgggagtc gtgggtggca gtgttccctc cagactgtaa
111121 aagggagcac ctggcgggaa gagggaattc ttttaaacat cattccagtg cccgagcctc
111181 ctggacctgt tgtcatcttg aggtgggcct cccctgggtg actctagtgt gcagcctggc
111241 tgagactcag tggccctggg ttcttactgc tgacacctac cctcaacctc aaccactgcg
111301 gcctcctgtg caccctgatc cagtggctca ttttccactt tcagtcccag ctctatccct
111361 atttgcagtt tccaagtgcc tggtcctcag tcagctcaga cccagccagg ccagcccctg
111421 gttcccacat ccccttttgcc aagctcatcc ccgccctgtt tggcctgcgg gagtgggagt
111481 gtgtccagac acagagacaa aggaccagct tttaaaacat tttgttgggg ccaggtgtgg
111541 tggctcacac ctaatcccaa cacctgggga ggccaaggca gaaggatcac ttgagtccag
111601 gagttcaaga ccagcctggg caacataggg agaccctgtc tctacaattt tttttttaat
111661 tagctgggcc tgttggcact ctcctgtagt tccagctact ctagaggctg aggtgggagg
111721 actgcttgag cctgggaggt cagggctgca atgagccatg ttcacaccac tgaacgccag
111781 cctgggcgag accctgtatc aaaaaagtaa agtaaaatga atcctgtacg ttatattaag
111841 gtgccccaaa ttgtacttag aaggatttca tagttttaaa tacttttgtt atttaaaaaa
111901 ttaaatgact gcagcatata aattaggttc ttaatggagg ggaaaaagag tacaagaaaa
111961 gaaataagaa tctagaaaca aagataagag cagaaataaa ccagaaaaca caaccttgca
112021 ctcctaactt aaaaaaaaaa atgaagaaaa cacaaccagt aaaacaacat ataacagcat
112081 taagagctgg ctcctggctg ggcgcggtgg cgcatgcctg taatcccaac actttgggag
112141 gccgatgctg gaggatcact tgagaccagg agttcaaggt tgcagtgagc tatgatcata
```

Figure 1KK

```
112201 ccactacacc ctagcctggg caacacagtg agactgagac tctattaaaa aaaaaatgct
112261 ggttccttcc ttatttcatt cctttattca ttcattcaga caacatttat ggggcacttc
112321 tgagcaccag gctctgtgct aagagctttt gcccccaggg tccaggccag gggacagggg
112381 caggtgagca gagaaacagg gccagtcaca gcagcaggag gaatgtagga tggagagctt
112441 ggccaggcaa ggacatgcag gggagcagc ctgcacaagt cagcaagcca gagaagacag
112501 gcagaccctt gtttgggacc tgttcagtgg cctttgaaag gacagccccc acccggagtg
112561 ctgggtgcag gagctgaagg aggatagtgg aacactgcaa cgtggagctc ttcagagcaa
112621 aagcaaaata aacaactgga ggcagctggg gcagcagagg gtgtgtgttc agcactaagg
112681 ggtgtgaagc ttgagcgcta ggagagttca cactggcaga agagaggttg gggcagctgc
112741 aagcctctgg acatcgcccg acaggacaga gggtggtgga cggtggccct gaagagaggc
112801 tcagttcagc tggcagtggc cgtgggagtg ctgaagcagg caggctgtcg gcatctgctg
112861 gggacggtta agcaggggtg agggcccagc ctcagcagcc cttcttgggg ggtcgctggg
112921 aaacatagag gagaactgaa gaagcaggga gtcccagggt ccatgcaggg cgagagagaa
112981 gttgctcatg tggggcccag gctgcaggat caggagaact ggggaccctg tgactgccag
113041 cggggagaag gggtgtgca ggatcatgcc cagggaaggg cccaggggcc caagcatggg
113101 ggggcctggt tggctctgag aagatggagc taaagtcact ttctcggagg atgtccaggc
113161 caatagttgg gatgtgaaga cgtgaagcag cacagagcct ggaagcccag gatggacaga
113221 aacctacctg agcagtgggg ctttgaaagc cttggggcgg ggggtgcaat attcaagatg
113281 gccacaagat ggcaatagaa tgctgtaact ttcttggttc tgggccgcag cctgggtggc
113341 tgcttccttc cctgtgtgta ttgatttgtt tctctttttt gagacagagt cttgctgggt
113401 tgcccaggct ggagtgcagt ggtgcgatca tagctcactg cagccttgaa gtcctgagct
113461 caagagatcc ttccacctca gcctcctgag tagttgggac cacaggcttg caccacagtg
113521 cccaactaat ttcttatatt ttttgtagag atggggtttc actgtgtcgc ccaggatggt
113581 cttgaactcc tgggctcaag tgatcctcct gcctcagcct cgcaaattgc tgggattaca
113641 ggtgtgagcc accatgcccg accttctctt tttaagggcg tgtgtgtgtg tgtgtgtgtg
113701 tgggcgcact ctcgtcttca ccttccccca gccttgctct gtctctaccc agtcacctct
113761 gcccatctct ccgatctgtt tctctctcct tttacccctc tttcctcccct cctcatacac
113821 cactgaccat tatagagaac tgagtattct aaaaatacat tttatttatt tattttgaga
113881 cagagtctca ctctgtcacc caggctggag tgcagtggtg caatctcggc tcactgcaac
113941 ctccgcctcc caggttgaag caactctcct gcctcagcct ccctagtagc tgggattaca
114001 agcacacacc accatgccta gcaaattttt atatttttag tagaggagga gtgtcaccat
114061 gtttgccaag ctggtctcaa actcctggcc tcaggtgatc tgcctacctt ggtctcccaa
114121 agtgctggga ttacaggtgt gagccaccac gcctgccctt aaaaatacat tatatttaat
114181 agcaaagccc cagttgtcac tttaaaaagc atctatgtag aacatttatg tggaataaat
114241 acagtgaatt tgtacgtgga atcgtttgcc tctcctcaat cagggccagg gatgcaggtg
114301 agcttgggct gagatgtcag accccacagt aagtgggggg cagagccagg ctgggacccct
114361 cctctaggac agctctgtaa ctctgagacc ctccaggcat cttttcctgt acctcagtgc
114421 ttctgaaaaa tctgtgtgaa tcaaatcatt ttaaaggagc ttgggttcat cactgtttaa
114481 aggacagtgt aaataattct gaaggtgact ctaccctgtt atttgatctc ttctttggcc
114541 agctgactta acaggacata gacaggtttt cctgtgtcag ttcctaagct gatcaccttg
114601 gacttgaaga ggaggcttgt gtgggcatcc agtgcccacc ccgggttaaa ctcccagcag
114661 agtattgcac tgggcttgct gagcctggtg aggcaaagca cagcacagcg agcaccaggc
114721 agtgctggag acaggccaag tctgggccag cctgggagcc aactgtgagg cacggacggg
114781 gctgtggggc tgtggggctg caggcttggg gccagggagg gagggctggg ctctttggaa
114841 cagccttgag agaactgaac ccaaacaaaa ccagatcaag gtctagtgag agcttagggc
114901 tgctttgggt gctccaggaa attgattaaa ccaagtggac acacaccccc agccccacct
114961 caccacagcc tctccttcag ggtcaaactc tgaccacaga catttctccc ctgactagga
115021 gttccctgga tcaaaattgg gagcttgcaa cacatcgttc tctcccttga tggtttttgt
115081 cagtgtctat ccagagctga agtgtaatat atatgttact gtagctgaga aattaaattt
115141 caggattctg atttcataat gacaaccatt cctcttttct ctcccttctg taaatctaag
115201 attctataaa cggtgttgac ttaatgtgac aattggcagt agttcaggtc tgctttgtaa
115261 ataccccttgt gtctattgta aaatctcaca aaggcttgtt gccttttttg tggggttaga
```

Figure 1LL

```
115321 acaagaaaaa gccacatgga aaaaaaattt ctttttttgtt tttttgtttg cttgtttttt
115381 tgagacagag tttcactctg tcgcccaggc tggagtgcag tggtgcgatc tccgcccact
115441 gcaagctcca cctcccgggt tcatgctatt ctcctgtctc agcctcccaa gtagctggga
115501 ctgcaggtgc ccgccaccac acctggctaa ttttttgta tttttagtag agacggggtt
115561 tcaccgtgtt agccaggatg gtctcaatct cctgacctcg tcatctgcct gcctcggcct
115621 cccaaagtgc tgagattaca ggcgtgagcc accgtgcccg gccagaaaaa aacatttcta
115681 agtatgtggc agatactgaa ttattgctta atgtcctttg attcatttgt ttaatttctt
115741 taatggatta gtacagaaaa caaagttctc ttccttgaaa aactggtaag ttttctttgt
115801 cagataagga gagttaaata acccatgaca tttccctttt tgcctcggct tccaggaagc
115861 tcaaagttaa atgtaatgat cactcttgta attatcagtg ttgatgccct tcccttcttc
115921 taatgttact ctttacattt tcctgcttta ttattgtgtg tgttttctaa ttctaagctg
115981 ttcccactcc tttctgaaag caggcaaatc ttctaagcct tatccactga aaagttatga
116041 ataaaaaatg atcgtcaagc ctacaggtgc tgaggctact ccagaggctg aggccagagg
116101 accacttgag cccaggaatt tgagacctgg gctgggcagc atagcaagac tctatctcca
116161 ttaaaactat ttttttttat ttaaaaaata atccgcaaag aaggagttta tgtgggattc
116221 cttaaaatcg gagggtggca tgaattgatt caaagacttg tgcagagggc gacagtgact
116281 ccttgagaag cagtgtgaga aagcctgtcc cacctccttc cgcagctcca gcctgggctg
116341 aggcactgtc acagtgtctc cttgctggca ggagagaatt tcaacattca ccaaaaagta
116401 gtattgtttt tattaggttt atgaggctgt agccttgagg acagcccagg acaactttgt
116461 tgtcacatag atagcctgtg gctacaaact ctgagatcta gattcttctg cggctgcttc
116521 tgacctgaga aagttgcgga acctcagcga gcctcacatg gcctccttgt ccttaacgtg
116581 gggacggtgg gcaagaaagg tgatgtggca ctagagattt atccatctct aaaggaggag
116641 tggattgtac attgaaacac cagagaagga attacaaagg aagaatttga gtatctaaaa
116701 atgtaggtca ggcgctcctg tgttgattgc agggctattc acaatagcca agatttggaa
116761 gcaacccaag tgtccatcaa cagacaaatg gataaagaaa atgtggtgca tatacacaat
116821 ggaatactat tcagccatga aaaagaatga gaatctgtca tttgaaacaa catggatgga
116881 actggaggac attatgttaa gtgaaataag ccagacagaa ggacagactt cacatgttct
116941 cacacatttg tgggagctaa aaattaaact catggagata gagagtagaa ggatggttac
117001 cagaggctga ggagggtgga ggggagcagg gagaaagtag ggatggttaa tgggtacaaa
117061 aacgtagtta gcatgcatag atctagtatt ggatagcaca gcagggtgac gacagccaac
117121 agtaatttat agtacattta aaaacaacta aaagagtgta actggactgg ctaacatggt
117181 gaaaccccgt ctctactaaa aatacaaaaa ttagctgggc acggtggctc acgcctgtaa
117241 tcccagcact ttgggaggcc gaggcgggcc gatcacgagg tcaggagatc gagaccatcc
117301 tagctaacat ggtgaaaccc cgtctctact acaaatacaa aaaaaagaaa aaattagccg
117361 ggcatggtgg tgggcgcctg tagtcccagc tactcgggag gctgaggcag gagaatggcg
117421 tgaacccggg aggcggagct tgcagtgagc cgagatcgcg ccactgcact ccagcctggg
117481 cgacaaggca agattctatc tcaaaaaaat aaaaataaaa taaaataaaa taataaaata
117541 aaataaaata aaataaaata aaataaataa aataaaatgt ataattggaa tgtttataac
117601 acaagaaatg ataaatgctt gaggtgatag ataccccatt caccgtgatg tgattattgc
117661 acaatgtatg tctgtatcta aatatctcat gtaccccaca agtatataca cctactatgt
117721 acccatataa atttaaaatt aaaaaattat aaaacaaaaa taaataagta aattaaaatg
117781 taggctggac accgtggttc acgcctgtaa tcccagtgct ttgtgaggct gaggtgagag
117841 aatcacttga gcccaggagt ttgagaccgg cctgggtgac atagcgagac cccatcatca
117901 caaagaattt ttaaaaatta gctgggcgtg gtagcacata ccggtagttc cagctacttg
117961 ggagaccgag gcaggaggat tgcttgagcc caggagttta aggctgcagt gagctacgat
118021 ggcgccactg cattccagcc tgggtgacag agtgagagct tgtctctatt ttaaaaataa
118081 taaaaagaat aaataaaaat aaattaaaat gtaaatatgt gcatgttaga aaaaatacac
118141 ccatcagcaa aaagggggta aaggagcgat ttcagtcata attggagaga tgcagaataa
118201 gccagcaatg cagtttcttt tattttggtc aaaaaaaata agcaaaacaa tgttgtaaac
118261 acccagtgct ggcagcaatg tggtgaggct ggctctctca ccagggctca cagggaaaac
118321 tcatgcaacc cttttagaaa gccatgtgga gagttgtacc gagaggtttt agaatattta
118381 taactttgac ccagaaattc tattctagga ctctgtgtta tgaaaataac ccatcatatg
```

Figure 1MM

```
118441 gaaaaagctc ctttcagaaa gaggttcatg ggaggctgtt tgtatttttt ttttctttgc
118501 atcaaatcca gctcctgcag gactgtttgt attattgaag tacaaagtgg aatcaataca
118561 aatgttggat agcaggggaa caatattcac aaaatggaat gggacatagt attaaacata
118621 gtgcttctga tgaccgtaga ccatagacaa tgcttaggat atgatatcac ttcttttgtt
118681 gtttttgta ttttgagacg aagtctcatt ctgtcaccca ggctggagtt cagtggcgcc
118741 atctcagctc actgcaacct ccatctcccg ggttcaagct attctccttc ctcaacctcc
118801 cgagtagctg ggttgcgcac caccatgcct ggctaacttt tgtattttta gtacagacgg
118861 ggtttcacca cgttggccag gctgctcttg aactcctgac gtcaggtgat ccaccagcct
118921 tgacctccca aagtgctagg attacaggag ccactgtacc cagcctagga tatgatatca
118981 cttcttagag caagatacaa aattgcatgt gcacaataat tctaccaagt ataggtatac
119041 aggggtagtt atatataaat gagacttcaa ggaaatacaa caaaatgcaa tcgtgattgt
119101 gttagggtgg taagaaaacg gtttttgctt tgatgagctc tgttttttaa aatcgttata
119161 ttttctaata aaaatacata gtcttttgaa ggaacataaa agattatgaa gaaatgagtt
119221 agatattgat tcctattgaa gattcagaca agtaaaatta aggggaaaaa aaacgggatg
119281 aaccagaagt caggctggag ttccaacccc agatccgaca gcccaggctg atggggcctc
119341 cagggcagtg gtttccaccc agcattctca aaagagccac tgaggtctca gtgccatttt
119401 caagatttcg gaagcggcct gggcacggct ggtccttcac tgggatcacc acttggcaat
119461 tatttacacc tgagacgaat gaaaaccaga gtgctgagat tacaggcatg gtggcttacg
119521 cttgtaatcg gctttgggaa gccgaggtgg gctgattgct tgagcccagg agtttcaaac
119581 tatcctggac aacatagcat gacctcgtct ctacaaaaaa tacaaaaaat ttgccaggtg
119641 tggtggcatg tgcctgtggt cccagctact tgggaggctg aagtaggaga atcccctgag
119701 ccctgggaag tcgaggctgc actgagccgt gatggtgtca ctgcactcca gcctgggtga
119761 caaagtgaga ccctatctca caaagaaaaa aaacaaaaca aaaaacccaa agcacactgt
119821 ttccactgtt tccagagttc ctgagaggaa aggtcaccgg gtgaggaaga cgttctcact
119881 gatctggcag agaaaatgtc cagtttttcc aactccctaa accatggttt tctatttcat
119941 agttcttagg caaattggta aaaatcattt ctcatcaaaa cgctgatatt ttcacacctc
120001 cctggtgtct gcagaaagaa ccttccagaa atgcagtcgt gggagaccca tccaggccac
120061 ccctgcttat ggaagagctg agaaaaagcc ccacgggagc atttgctcag cttccgttac
120121 gcacctagtg gcattgtggg tgggagaggg ctggtgggtg gatggaagga gaaggcacag
120181 ccccccccttg cagggacaga gccctcgtac agaagggaca ccccacattt gtcttcccca
120241 caaagcggcc tgtgtcctgc ctacggggtc agggcttctc aaacctggct gtgtgtcaga
120301 atcaccaggg gaacttttca aaactagaga gactgaagcc agactcctag attctaattc
120361 taggtcaggg ctaggggctg agattgtaaa aatccacagg tgattctgat gcccggcagg
120421 cttgagaaca gccgcaggga gttctctggg aatgtgccgg tgggtctagc caggtgtgag
120481 tggagatgcc ggggaacttc ctattactca ctcgtcagtg tggccgaaca catttttcac
120541 ttgacctcag gctggtgaac gctcccctct ggggttcagg cctcacgatg ccatcctttt
120601 gtgaagtgag gacctgcaat cccagcttcg taaagcccgc tggaaatcac tcacacttct
120661 gggatgcctt cagagcagcc ctctatccct tcagctcccc tgggatgtga ctcgacctcc
120721 cgtcactccc cagactgcct ctgccaagtc cgaaagtgga ggcatccttg cgagcaagta
120781 ggcgggtcca gggtggcgca tgtcactcat cgaaagtgga ggcgtccttg cgagcaagca
120841 ggcgggtcca gggtggcgtg tcactcatcc tttttctgg ctaccaaagg tgcagataat
120901 taataagaag ctggatctta gcaacgtcca gtccaagtgt ggctcaaagg ataatatcaa
120961 acacgtcccg ggaggcggca gtgtgagtac cttcacacgt cccatgcgcc gtgctgtggc
121021 ttgaattatt aggaagtggt gtgagtgcgt acacttgcga gacactgcat agaataaatc
121081 cttcttgggc tctcaggatc tggctgcgac ctctgggtga atgtagcccg gctccccaca
121141 ttcccccaca cggtccactg ttcccagaag ccccttcctc atattctagg aggggtgtc
121201 ccagcatttc tgggtccccc agcctgcgca ggctgtgtgg acagaatagg gcagatgacg
121261 gaccctctct ccggaccctg cctgggaagc tgagaatacc catcaaagtc tccttccact
121321 catgcccagc cctgtcccca ggagccccat agcccattgg aagttgggct gaaggtggtg
121381 gcacctgaga ctgggctgcc gcctcctccc ccgacacctg ggcaggttga cgttgagtgg
121441 ctccactgtg gacaggtgac ccgtttgttc tgatgagcgg acaccaaggt cttactgtcc
121501 tgctcagctg ctgctcctac acgttcaagg caggagccga ttcctaagcc tccagcttat
```

Figure 1NN

```
121561 gcttagcctg cgccaccctc tggcagagac tccagatgca aagagccaaa ccaaagtgcg
121621 acaggtccct ctgcccagcg ttgaggtgtg gcagagaaat gctgcttttg gccctttag
121681 atttggctgc ctcttgccag gagtggtggc tcgtgcctgt aattccagca ctttgggaga
121741 ctaaggcggg aggttcgctt gagcccagga gttcaagacc agcctgggca acaatgagac
121801 ccctgtgtct acaaaaagaa ttaaaattag ccaggtgtgg tggcacgcac ctgtagtccc
121861 agctacttgg gaggctgagg tgggaggatt gcctgagtcc gggaggcgga agttgcaagg
121921 agccatgatc gcgccactgc acttcaacct aggcaacaga gtgagacttt gtctcaaaaa
121981 acaatcatat aataatttta aaataaatag atttggcttc ctctaaatgt ccccggggac
122041 tccgtgcatc ttctgtggag tgtctccgtg agattcggga ctcagatcct caagtgcaac
122101 tgacccaccc gataagctga ggcttcatca tcccctggcc ggtctatgtc gactgggcac
122161 ccgaggctcc tctcccacca gctctcttgg tcagctgaaa gcaaactgtt aacaccctgg
122221 ggagctggac gtatgagacc cttggggtgg gaggcgttga tttttgagag caatcacctg
122281 gccctggctg gcagtaccgg gacactgctg tggctccggg gtgggctgtc tccagaaaat
122341 gcctggcctg aggcagccac ccgcatccag cccagagggt ttattcttgc aatgtgctgc
122401 tgcttcctgc cctgagcacc tggatcccgg cttctgccct gaggcccctt gagtcccaca
122461 ggtagcaagc gcttgccctg cggctgctgc atggggctaa ctaacgcttc ctcaccagtg
122521 tctgctaagt gtctcctctg tctcccacgc cctgctctcc tgtcccccca gtttgtctgc
122581 tgtgaggga cagaagaggt gtgtgccgcc cccacccctg cccgggccct tgttcctggg
122641 attgctgttt tcagctgttt gagctttgat cctggttctc tggcttcctc aaagtgagct
122701 cggccagagg aggaaggcca tgtgctttct ggttgaagtc aagtctggtg ccctggtgga
122761 ggctgtgctg ctgaggcgga gctggggaga gagtgcacac gggctgcgtg gccaacccct
122821 ctgggtagct gatgcccaaa gacgctgcag tgcccaggac atctgggacc tccctggggc
122881 ccgcccgtgt gtcccgcgct gtgttcatct gcgggctagc ctgtgacccg cgctgtgctc
122941 gtctgcgggc tagcctgtgt cccgcgctct gcttgtctgc ggtctagcct gtgacctggc
123001 agagagccac cagatgtccc gggctgagca ctgccctctg agcaccttca caggaagccc
123061 ttctcctggt gagaagagat gccagcccct ggcatctggg ggcactggat ccctggcctg
123121 agccctagcc tctccccagc ctgggggccc cttcccagca ggctggccct gctccttctc
123181 tacctgggac ccttctgcct cctggctgga ccctggaagc tctgcagggc ctgctgtccc
123241 cctccctgcc ctccaggtat cctgaccacc ggccctggct cccactgcca tccactcctc
123301 tcctttctgg ccgttccctg gtccctgtcc cagcccccct ccccctctca cgagttacct
123361 cacccaggcc agagggaaga gggaaggagg ccctggtcat accagcacgt cctcccacct
123421 ccctcggccc tggtccaccc cctcagtgct ggcctcagag cacagctctc tccaagccag
123481 gccgcgcgcc atccatcctc cctgtccccc aacgtccttg ccacagatca tgtccgccct
123541 gacacacatg ggtctcagcc atctctgccc cagttaactc cccatccata aagagcacat
123601 gccagccgac accaaaataa ttcgggatgg ttccagttta gacctaagtg gaaggagaaa
123661 ccaccacctg ccctgcacct tgttttttgg tgaccttgat aaaccatctt cagccatgaa
123721 gccagctgtc tcccaggaag ctccagggcg gtgcttcctc gggagctgac tgataggtgg
123781 gaggtggctg ccccccttgca ccctcaggtg accccacaca aggccactgc tggaggccct
123841 ggggactcca ggaatgtcaa tcagtgacct gccccccagg ccccacacag ccatggctgc
123901 atagaggcct gcctccaagg gacctgtctg tctgccactg tggagtccct acagcgtgcc
123961 ccccacaggg gagctggttc tttgactgag atcagctggc agctcagggt catcattccc
124021 agagggagcg gtgccctgga ggccacaggc ctcctcatgt gtgtctgcgt ccgctcgagc
124081 ttactgagac actaaatctg ttggtttctg ctgtgccacc tacccaccct gttggtgttg
124141 ctttgttcct attgctaaag acaggaatgt ccaggacact gagtgtgcag gtgcctgctg
124201 gttctcacgt ccgagctgct gaactccgct gggtcctgct tactgatggt ctttgctcta
124261 gtgctttcca gggtccgtgg aagcttttcc tggaataaag cccacgcatc gaccctcaca
124321 gcgcctcccc tctttgaggc ccagcagata ccccactcct gcctttccag caagattttt
124381 cagatgctgt gcatactcat catattgatc acttttttct tcatgcctga ttgtgatctg
124441 tcaatttcat gtcaggaaag ggagtgacat ttttacactt aagcgtttgc tgagcaaatg
124501 tctgggtctt gcacaatgac aatgggtccc tgtttttccc agaggctctt ttgttctgca
124561 gggattgaag acactccagt cccacagtcc ccagctcccc tggggcaggg ttggcagaat
124621 ttcgacaaca catttttcca ccctgactag gatgtgctcc tcatggcagc tgggaaccac
```

Figure 10O

```
124681 tgtccaataa gggcctgggc ttacacagct gcttctcatt gagttacacc cttaataaaa
124741 taatcccatt ttatcctttt tgtctctctg tcttcctctc tctctgcctt tcctcttctc
124801 tctcctcctc tctcatctcc aggtgcaaat agtctacaaa ccagttgacc tgagcaaggt
124861 gacctccaag tgtggctcat taggcaacat ccatcataaa ccaggtagcc ctgtggaagg
124921 tgagggttgg gacgggaggg tgcagggggt ggaggagtcc tggtgaggct ggaactgctc
124981 cagacttcag aaggggctgg aaaggatatt ttaggtagac ctacatcaag gaaagtgttg
125041 agtgtgaaac ttgcgggagc ccaggaggcg tggtggctcc agctcgctcc tgcccaggcc
125101 atgctgccca agacaaggtg aggcgggagt gaagtgaaat aaggcaggca cagaaagaaa
125161 gcacatattc tcggccgggc gctgtggctc acgcctgtaa ttccagcact ttgggaggcc
125221 aaggtgggtg gatcatgagg tcaggagatt gagaccatcc tggctaacac agtgaaaccc
125281 cgtctctact aaaaatacaa aaaattagcc gggcgtggtg gtgggcgcct gtagtcccag
125341 ctactccgga ggctgaggca ggaaaatggc gtgaacccgg aaggcggagc ttgcagtgag
125401 cggagtgagc agagatcgcg ccactgcact ccagcctggg cgacagagcg agactccgtc
125461 tcaaaaaaaa aaagcacatg ttctcgcttc tttgtgggat ccaggagata gagaatagaa
125521 ggatggttac cagaggctgg gaagggtagt gaggggatgg tgggggggatg gtcaatgggt
125581 acaaaaaaaa tagaataaga cctagtattt gatagtgcaa cagggtgact atagtcaata
125641 ataatttaat tgtacattta aaaataacta aaagatagcc gggtgcagtg gcttacgtct
125701 gtaatcccag tactttggga ggctgaggtg ggcgtttgag accagcctgg ccaacatggt
125761 gaaaccccat ctctactaaa aatacaaaaa ttagccaggc atggtggcgg gcgcctgtaa
125821 tcccagctac tcgggaggct gaggcaggag aatcacttga acctgggagg cagaggttgc
125881 agtgagccga gatcttgcca ctgcactcca gcctgggtga cagtgaaact ccgtctcaaa
125941 aataaaaata aaaatacagc tgggcacggt ggctcacgcc tgtaatccca gcactttggg
126001 aggccgaggc gagcggatca caaggtcagg agatatagac catcctggct aacacggtga
126061 aaccccgtct ctactaaaaa tacaaaaaat tagccaggcg tggtggcagg tgcctatagt
126121 cccagctact cacaaggctg aggcaggaga atggcatgaa cctgggaggc ggagcttgca
126181 gtgagccgag attgtgccac tgcactccag cctgggcgag agagtgagac tccgtctcaa
126241 aacaaaaaca aaaacaaaaa caaaaacaaa cacacaacaa aaacctaaaa gaatataaat
126301 ggattgtttg taacacaaag gacaaatgtt tgaggggatg gataccccat tttccatgat
126361 gtgattatta tacattgtgt gtctgtatca aaacatctca tgagccccat aaatatatac
126421 acctaactat gtacccacaa aaattaaaaa aatatatttt ttaaggtgaa gagggaggcg
126481 agatgctggc cttaacccct aacccgttgt tctccctgca agctgtccac agggcctctc
126541 agactcgagg ttcagctata tggatgcatg agcttggtcc ccagccaaca tgggagacac
126601 ttcaccatcg gcagcagcta cagcacagga accctgggtc actgccatgt cccctctgtg
126661 actttgttta aacagaaaat gatgctctgg gccggctgtg gtggcccaca cctataatcc
126721 cagcaccttg ggaggcgggg gtgggcagat tgcctgaggt caggagttgg agatcagcct
126781 ggccgacatg gcgaaacccc atgtctacta aaaatacaaa aactagccag gcatggtggc
126841 acatgcctgt aatcccagct acttgggagg ctgaagcagg agaatcactt gaacccagga
126901 ggcagaggct gagtgagcca agatcgtgcc aatgcactcc agcttgggtg agggagtgag
126961 actccgtctc aaaaaaaaaa aaaaagaaag aaaaagaaaa gaaagtgatc ctactggaac
127021 catgcttact cccctcccca cctcacactg tgtagaaatt agtgctgtcg gccaggcgcg
127081 gtggctcatg cctgtaatcg cagcactttg ggaggccaag gcaggcggat cacgaggtca
127141 ggagatcaag accatcctgg ctaacacagt gaaaccctgt ctctactaaa aatacaaaaa
127201 attagccggg catggtggca ggcacctgta gtcccaacta cttgggaggc tgaggcagga
127261 gaatggcatg aacctgggag gcggagcttg cagtgagcca agatcgcgcc actgcatacc
127321 agcctaggtg acagagtgag actcagcaaa aaaagaaaga aagaaagaaa gaaatcagtg
127381 ctgtctatac ttctttctgc agtgatggaa atattctgta tctgtgctgt ccagtatagt
127441 agccactagc tacatgtggc acttgaaaca tggctggtac agttgaggaa gagtggctgc
127501 catatcggac gacacagcta tagattctgt caccccaccc cgagagtcca gagcggggac
127561 ttctgcctta ggccctattc agggctgatt tttacttgaa cccttactgt gggaagagaa
127621 ggccatgaga agttcagtct agaatgtgac tccttatttt ctggctccct tggacacttt
127681 gtgggattta gtctccctgt ggaaagtatt ccacaagtgg tgccactacc ccagctgtga
127741 gagcagctgg gagctgcttt tgtcatcttt ccctggaaag tcctgtgggc tgtctcttcc
```

Figure 1PP

```
127801 tcatgccttg tcccatgctt gggcatggtg tcaagcgtca ggagggagaa agggtcctta
127861 tttatttatt tagagaggga cccttcttct gttcccaggc tggagtgcag tggtgcgatc
127921 tcggctcact gcaacctccg cctcctgggt tcaagtgatt ctcctgcctc agcctcctga
127981 gtagctgaga ttacaggcac atgccaacat gcccggctaa tttttttttt tttttttttt
128041 tttttttttt tttttttttt gagatggagt tgtactctca ttgcccaggc tggaatgtaa
128101 tggcacaatc tcggctcact gcaacctcca cctcctggat tcaagcaatt ctcctgtctc
128161 agcttcccaa gtagctggga ttacaggtgc ccgccaccat gctcaactaa tttttgtatt
128221 tttttttag tagagacgag gtttcaccat gttggtcaga ctggtctcaa actcctgacc
128281 tcaggtgatc cacctgcctc ggcctcccaa agtgctagga ttacaggcat gagccaccac
128341 gcccggcctg aaagggttct tatttagtgt gcattttgac attcaattta attccaaggt
128401 cttgtggggt catggtttac aggatgttga tatagaaaag acttcactta atgggccggg
128461 cgcagtggct catgcctgta atcccagcac tttgggaggc cgaggcaggc agatcaggag
128521 gtcaggagat tgagaccatc ctggctaaca cagtgaaacc ccatctctac tgaaaataca
128581 aaaaattagc tgggcgtggt ggcaggcacc tgtagtccca gccactcggt tggctgaggc
128641 aggagaatgg catgaacccg ggaggcggag cttgcagtga gcagagacca tgccactgca
128701 ctccagcctg ggcgacagag caagactctg tctcaagaaa aaaaaaaaaa aacagacttt
128761 acttactgga agccaaccaa tgtatattta gagtaatttt tcctgggctg agctgtcatt
128821 tacttttgca gtatctcaag aagaagagtt tacagtgtaa atatttgatg cacactttga
128881 ttatatagat gaagcaaact attttcaaga gctttgcaag gacttacttg tatccaaaca
128941 ccattctaaa aggagtctta cctacttcta aaggctggtc tctacttgga accacttgct
129001 tggccctggt tcaagtcctg ctgcaaacct ggaagtcctg tcattgtctt cttccctcca
129061 gagcagtggc acccaatcta atttttgctg tgccccagca gcccctggca ctttgccctg
129121 tagactgcag acctcatgta atgtatgtta agtccacaga accacagaag atgatggcaa
129181 gatgctcttg tgtgtgttgt gttctaggag gtggccaggt ggaagtaaaa tctgagaagc
129241 ttgacttcaa ggacagagtc cagtcgaaga ttgggtccct ggacaatatc acccacgtcc
129301 ctggcggagg aaataaaaag gtaaaggggg tagggtgggt tggatgctgc ccttgggtat
129361 atgggcatta atcaagttga gtggacaaag gctggtccag ttcccagagg aggaaaacag
129421 aggcttctgt gttgactggc tggatgtggg ccctcagcag catccagtgg gtctccactg
129481 cctgtctcaa tcacctggag ctttagcacg tttcacacct gggccccaac ctggagaggc
129541 tgaccaatgg gtctcagggg cagctcggtt gctggagttt ttgtttttat ttattttat
129601 gtatttaagg cagggtctct gtattagtcc attctcacac tgctaataaa gacataccca
129661 agactgggta atttataaag gaaagaggtt taatggactc acagttccac atggctgggg
129721 aggcctcaaa atcatggcgg aaggcaaagg agaagcaaag gcatttctta catggcgaca
129781 ggcaagagag cgtgtgcagg ggaactccca tttataaaac catcagacct catgagattt
129841 attcactatc atgagaacag catgggaaag acccgccccc atgattcagt tacctcccac
129901 tgggtccctc ccatgacaca tggaattatg ggagctacaa ttcaagatga gatttgggtg
129961 gggacacagc caaaccatat cagtctccct ctgtcatcca ggctggagtg cactggcatg
130021 atctcggctc actgcagcct ctacctccct gggtcaggtg atcttcccac ctcagcctcc
130081 caggtagctg gaactacagg tacctgccac tatgcctggc taaatatttt gtatttcctg
130141 tggagacgag gttttgccac gttgcccagg ctggtcttga actcctgagg tcaagcaata
130201 tgcccacctc ggcctcccaa ggtgctggga ttacaggtgt gagccacagt gctcggccta
130261 agtcactgca gtttttaaag ctcccaggtg attcttcagt gcagtcaaaa gtgagaactg
130321 gctgggtgcg gtggctcatg cctgtaatcc cagcaccttg ggaggcgaag gtgggcagat
130381 ggcttgaggt caggagttca agaccagcct ggccaacatg gtaaaacccc atctctacta
130441 aaaatacaaa agttagctgg gtgtggtggt gcgtgcctgt aatcccagct acttgggagg
130501 ctgaggcatg agaattgctt gaacccaggg gacagaggtt gtagtgagcc gagatcgtgc
130561 cactgcactc cagcctgggc aacagagtga gattccatct cacaaaaaaa aaaaaaagcg
130621 agaaccactg tcctaggccc tgatgtttgc aggcaactaa aaaaggaagt ggacatcccc
130681 agtcagctgt ggcgcaccaa gaacaagtca tgggaacata acctaatttt ctaaatgggt
130741 tactaggcac ttagagcaaa acaatgatgc cgaaatcctg atttcagcaa agcctctgcc
130801 tgcctgtctt ggaagtatcc acatgaggct gctggggcct tggtgtcccc agcagtttct
130861 agtctctagg tcttgctgtg ggtgtctgtg cagtgagggt gtgtgtggcg ctgggtgagc
```

Figure 1QQ

```
130921 tctgtctagg cctggcacag gatgcggtct ggtagctgct gcttctcttc tgcagaagcg
130981 cagccaagca ccctctgggg tttcaggccc acacccagcc tgaagttctg ggagtggctc
131041 actttccaac cttcagggtc tcccagcagc tgactgggga gtggtggagg gaaaagggat
131101 tgtattagtc cgttttcacg ccgctgatga agacataccc gatactgggc agtctaaaag
131161 atagaggtct gatggactca cagttccacg tgactgggga ggcctgacaa tcatggtgga
131221 aggtgaaagg cttgtctcac acggtggcag acaagagaaa agagcttgtg caggggaact
131281 cccctttata aaaccatcag atctcgggag acttattcac tatcatgaga acagcacggg
131341 aaagaccctc ctctatgatt caattacctc ccaccaggtc cctcccacaa catgtaggaa
131401 ttgtgggaac tacaattcaa gatgacattt gggtggggac acagccaaac catatcaggg
131461 cgtcccagaa agggtatagg gtctgagacc caagtcagca tgagaaagta tgcttctcat
131521 ggtggcccag ttgggtggaa gtggcagccg ggccgtcttt ccaccaggcc actcaagtag
131581 cagctgagag acccctgccc tggccagtcc ccgccctccc ctcttgccac tgcctctggt
131641 tctgaacaga tgggcaccct catcttgtat ttgtgattaa tgtctaacaa tgtagttttg
131701 tgagaagggt ttgctgatac agccttgctg cagatgctgc gaactgtggc ctggggcaga
131761 ccttacctcc agacacgccc tgaggcaggg gagggcactg gcccgtagct ggccgagagc
131821 tctcgggttg cgcgacaggg atacttttca gcggctgggt cgctatccaa agtgagaaaa
131881 cgaggaggga ccaggaggct gtccgcctca agagatgtgg gggccaggtc cagttatctg
131941 gggaagcagt aagcttctct gctgtttcta accccaggcc tcccctggtc taaggcaggg
132001 cctcccagcc tcggggcact ttaaagatat ctgggcctgg ccccatcccc acagtctgac
132061 tgagtgggtc tggatagggc ctgagcattg gtgatttcct gggtgaaagg aggcccctca
132121 cagtctctgg aagcttctct gtgttaggaa aagctctggg cttgactctg ctttgaaagt
132181 caagatccgc aaatcctctc agcctcagtt tctccttcag caagatgaaa tggaaatgct
132241 gtacctacgt cccggggtgg ttgtgagacc caaaaaagac aatgttctgg aaggttcctg
132301 gtgcgttgca gtcctctaag aacctgagtt agagccacgc tgagtctcag cttcttggct
132361 ccttctgttt caaactcgtc catgtgatag ctcaggaagg gtaggcaggg ccctgccccc
132421 tactcagaaa acaccatcct ggtcctgggg atccccgcag cattagtccc ctgttttccc
132481 agtgtattga gaaaaattgc taacaagcag tggggcacac caccagcctc ctgggttcct
132541 ttcagtttgg ggatttttgg acattcccag gaatgtctta aaaaacactt caaaaaacat
132601 taacataaat atttttatca aagcctgtat taaatggtct ttcaagaaaa tacagtaaca
132661 ggtcaggcat ggtggctcat gcctgtaacc ccagcacttt gggaggccaa ggcaggcaga
132721 tcacctgaaa tcaggagttc aagaccaacc tggccaacac agccaaatcc catctctaca
132781 aaaaatacaa aaattagctg ggtgtggtgg cacacacctg tagtcccagc tacttgggag
132841 gccgaggcag gagaattgct tgatcccgga ggcggaggtt gcagtgagcc gagatcgtgc
132901 cactgcactc cagcgtgggt gacaaggtga atctttgtct caaaaaaaaa aaaaaaaaaa
132961 agataaaata cagtatacag taatagagaa caatcctttt ttcaaagtag tgaccccaaa
133021 tgaacaaaat atgcatctag cttaaatgcg aacctggttt tctctacgcc cattcaagcc
133081 cctgcaatag gggcccttca ccccgcatcc atggactcct aaaattatat ggaaaatggc
133141 tgtgtgtgag tgtggatgga catgtgcaca catattttg gctttaccag atgctcaaag
133201 agcctaggac ccaaaaaggg ctgagaatga ccgtgtcggc cacttcaggg tcatcaggaa
133261 ttgctgtgca ctgctcactt ctccagtgaa cactttctgc ttctgtgttt cctggtatcc
133321 tttgggactc ctggctaggt catgtgtttc tctactttca aaagggcttc agccaggcac
133381 gatggcatga gcctgtagtc ccagttgctc tggaggttaa ggtgggaaga ttgcttgagc
133441 ccaggaattt gaggccagcc tgggcaagta gataggtaga tgattgatag atagatagat
133501 agataaatag atggatagat aagtcgctag acagtcatcc atccacccat ccacacataa
133561 aaaggccttt gtcatgtcat gttttgtggc ccacctgcca gtgttgccca cagttgctgc
133621 ccctccaaac tcatcagtca ctggcaaaca ggaggaatgt gtggctcatg tctgggcatc
133681 agtggctgtg ggagacatcc ttgatcttct ccagcttctc cttccacatt ttcctttgca
133741 atctggcaat atctattaaa ataaaatgtg catgcctttt gacctaagag cttcacttct
133801 aggacccact tacacgtgtg tgacatgatg ttcatacggg tttatttatc tgaggttgtt
133861 catacacacc attgcctgta atcactaaag gcgggagcag cctacacatc catccacaga
133921 ggagtagatg ccttttggta catccgtggc gacggaatac taagcagcct gtgtatctat
133981 acactcacac gtgtttgttt atgtgtggaa tatctctgga gggtacacaa gaaacttaaa
```

Figure 1RR

```
134041 atgatcactg tctctgggga gggtacctgg gtgcctggga ggcaggtcag ggaaggagtg
134101 ggcacaggta ttaccaattg gaagacaata aaaacaacag ctcctggcca ggcgcagtgg
134161 ctcacgcctg taatggcagc actctgagag gctgaggcgg gcagattgct tgcgtccagg
134221 agttcaagac cagcctgggc aacatagcaa aaccccgttt ctattaaaaa tacaaaaaat
134281 tagccaggtg tggtggcatg cacctgtaat cccagctact cgggaggctg aggtgggaga
134341 atcacctgag cctgggaggt caaggctgca gtgaggtgag attgtgccac cgcactctag
134401 cctgggcgat agagcaagac cctgtctcaa aaacaaacaa aaaacagtcc ctggcactct
134461 gggccaggcc tggcagggca gttggcaggg ctggtctttc tctggcactt catctcaccc
134521 tccctccctt cctcttcttg cagattgaaa cccacaagct gaccttccgc gagaacgcca
134581 aagccaagac agaccacggg gcggagatcg tgtacaagtc gccagtggtg tctggggaca
134641 cgtctccacg gcatctcagc aatgtctcct ccaccggcag catcgacatg gtagactcgc
134701 cccagctcgc cacgctagct gacgaggtgt ctgcctccct ggccaagcag ggtttgtgat
134761 caggcccctg ggcggtcaa taattgtgga gaggagagaa tgagagagtg tggaaaaaaa
134821 aagaataatg acccggcccc cgccctctgc ccccagctgc tcctcgcagt tcggttaatt
134881 ggttaatcac ttaacctgct tttgtcactc ggctttggct cgggacttca aaatcagtga
134941 tgggagtaag agcaaatttc atctttccaa attgatgggt gggctagtaa taaaatattt
135001 aaaaaaaaac attcaaaaac atggccacat ccaacatttc ctcaggcaat tccttttgat
135061 tctttttttct tccccctcca tgtagaagag ggagaaggag aggctctgaa agctgcttct
135121 gggggatttc aagggactgg gggtgccaac cacctctggc cctgttgtgg gggtgtcaca
135181 gaggcagtgg cagcaacaaa ggatttgaaa cttggtgtgt tcgtggagcc acaggcagac
135241 gatgtcaacc ttgtgtgagt gtgacggggg ttggggtggg gcgggaggcc acgggggagg
135301 ccgaggcagg ggctgggcag aggggagagg aagcacaaga agtgggagtg ggagaggaag
135361 ccacgtgctg gagagtagac atccccctcc ttgccgctgg gagagccaag gcctatgcca
135421 cctgcagcgt ctgagcggcc gcctgtcctt ggtggccggg ggtgggggcc tgctgtgggt
135481 cagtgtgcca ccctctgcag ggcagcctgt gggagaaggg acagcgggta aaaagagaag
135541 gcaagctggc aggagggtgg cacttcgtgg atgacctcct tagaaaagac tgaccttgat
135601 gtcttgagag cgctggcctc ttcctccctc cctgcagggt agggggcctg agttgagggg
135661 cttccctctg ctccacagaa accctgtttt attgagttct gaaggttgga actgctgcca
135721 tgattttggc cactttgcag acctgggact ttagggctaa ccagttctct ttgtaaggac
135781 ttgtgcctct tgggagacgt ccacccgttt ccaagcctgg gccactggca tctctggagt
135841 gtgtgggggt ctgggaggca ggtcccgagc cccctgtcct tcccacggcc actgcagtca
135901 cccctgtctg cgccgctgtg ctgttgtctg ccgtgagagc ccaatcactg cctatacccc
135961 tcatcacacg tcacaatgtc ccgaattccc agcctcacca cccettctca gtaatgaccc
136021 tggttggttg caggaggtac ctactccata ctgagggtga aattaaggga aggcaaagtc
136081 caggcacaag agtgggaccc cagcctctca ctctcagttc cactcatcca actgggaccc
136141 tcaccacgaa tctcatgatc tgattcggtt ccctgtctcc tcctcccgtc acagatgtga
136201 gccagggcac tgctcagctg tgaccctagg tgtttctgcc ttgttgacat ggagagagcc
136261 ctttcccctg agaaggcctg gccccttcct gtgctgagcc cacagcagca ggctgggtgt
136321 cttggttgtc agtggtggca ccaggatgga agggcaaggc acccagggca ggccccacagt
136381 cccgctgtcc cccacttgca ccctagcttg tagctgccaa cctcccagac agcccagccc
136441 gctgctcagc tccacatgca tagtatcagc cctccacacc cgacaaaggg gaacacaccc
136501 ccttggaaat ggttcttttc ccccagtccc agctggaagc catgctgtct gttctgctgg
136561 agcagctgaa catatacata gatgttgccc tgccctcccc atctgcaccc tgttgagttg
136621 tagttggatt tgtctgttta tgcttggatt caccagagtg actatgatag tgaaaagaaa
136681 aaaaaaaaaa aaaaaggacg catgtatctt gaaatgcttg taaagaggtt tctaacccac
136741 cctcacgagg tgtctctcac ccccacactg ggactcgtgt ggcctgtgtg gtgccacccct
136801 gctgggggcct cccaagtttt gaaaggcttt cctcagcacc tgggacccaa cagagaccag
136861 cttctagcag ctaaggaggc cgttcagctg tgacgaaggc ctgaagcaca ggattaggac
136921 tgaagcgatg atgtcccctt ccctacttcc ccttggggct ccctgtgtca gggcacagac
136981 taggtcttgt ggctggtctg gcttgcggcg cgaggatggt tctctctggt catagcccga
137041 agtctcatgg cagtcccaaa ggaggcttac aactcctgca tcacaagaaa aaggaagcca
137101 ctgccagctg gggggatctg cagctcccag aagctccgtg agcctcagcc acccctcaga
```

Figure 1SS

```
137161 ctgggttcct ctccaagctc gccctctgga ggggcagcgc agcctcccac caagggccct
137221 gcgaccacag cagggattgg gatgaattgc ctgtcctgga tctgctctag aggcccaagc
137281 tgcctgcctg aggaaggatg acttgacaag tcaggagaca ctgttcccaa agccttgacc
137341 agagcacctc agcccgctga ccttgcacaa actccatctg ctgccatgag aaaagggaag
137401 ccgcctttgc aaaacattgc tgcctaaaga aactcagcag cctcaggccc aattctgcca
137461 cttctggttt gggtacagtt aaaggcaacc ctgagggact tggcagtaga aatccagggc
137521 ctcccctggg gctggcagct tcgtgtgcag ctagagcttt acctgaaagg aagtctctgg
137581 gcccagaact ctccaccaag agcctccctg ccgttcgctg agtcccagca attctcctaa
137641 gttgaaggga tctgagaagg agaaggaaat gtggggtaga tttggtggtg gttagagata
137701 tgccccccctc attactgcca acagtttcgg ctgcatttct tcacgcacct cggttcctct
137761 tcctgaagtt cttgtgccct gctcttcagc accatgggcc ttcttatacg gaaggctctg
137821 ggatctcccc cttgtggggg caggctcttg gggccagcct aagatcatgg tttagggtga
137881 tcagtgctgg cagataaatt gaaaaggcac gctggcttgt gatcttaaat gaggacaatc
137941 cccccagggc tgggcactcc tcccctcccc tcacttctcc cacctgcaga gccagtgtcc
138001 ttgggtgggc tagataggat atactgtatg ccggctcctt caagctgctg actcacttta
138061 tcaatagttc catttaaatt gacttcagtg gtgagactgt atcctgtttg ctattgcttg
138121 ttgtgctatg gggggagggg ggaggaatgt gtaagatagt taacatgggc aaagggagat
138181 cttggggtgc agcacttaaa ctgcctcgta accctttcca tgatttcaac cacatttgct
138241 agagggaggg agcagccacg gagttagagg cccttggggt ttctcttttc cactgacagg
138301 ctttcccagg cagctggcta gttcattccc tccccagcca ggtgcaggcg taggaatatg
138361 gacatctggt tgctttggcc tgctgccctc tttcaggggt cctaagccca caatcatgcc
138421 tccctaagac cttggcatcc ttccctctaa gccgttggca cctctgtgcc acctctcaca
138481 ctggctccag acacacagcc tgtgcttttg gagctgagat cactcgcttc accctcctca
138541 tctttgttct ccaagtaaag ccacgaggtc ggggcgaggg cagaggtgat cacctgcgtg
138601 tcccatctac agacctgcgg cttcataaaa cttctgattt ctcttcagct ttgaaaaggg
138661 ttaccctggg cactggccta gagcctcacc tcctaataga cttagcccca tgagtttgcc
138721 atgttgagca ggactatttc tggcacttgc aagtcccatg atttcttcgg taattctgag
138781 ggtgggggga gggacatgaa atcatcttag cttagctttc tgtctgtgaa tgtctatata
138841 gtgtattgtg tgttttaaca aatgatttac actgactgtt gctgtaaaag tgaatttgga
138901 aataaagtta ttactctgat taaataaggt ctccattcat ggattccaag gacaagaaag
138961 tcatatagaa tgtctatttt ttaagttctt tcccacgcac ccttagataa tttagctcag
139021 aacaggaaat gatagtatta ataaaagctg gacatcagga ttaacagctc tctctggggc
139081 cctgaaggtg agagttctca gacttgctca tttgcagttg cttctttgtg atgctggcaa
139141 accatcctag tcccattcaa agggcaatac aaagccttgt ggctgacctc acgatgcagc
139201 actcagtttg caagaccggc accagtgtat gcaaacctga gaaggttggg gatgaggata
139261 tgggatcttt catccctgga aatttagtcc agaggcctgg ggctggagca gaacaccaag
139321 ccaatcagct taatgaatgg cttagattcc tgctaggttt gcagagctgc cttctttcct
139381 ttggtacctt attatagatt gaggagtatt tctgctaaac caagataggg ataaccagat
139441 agcatcttca tagcaatgcc acaaaggaaa acaaaaacaa aacagtaatc catcatatta
139501 ttccttagta actatgccaa ggtcatgata ctgaatcctt agattgtttc aaaatactac
139561 ttttctttgc tcttcctgat gtgtttgcca ccgcaggcag atgtttaagt aaaacagatt
139621 ttaactgcag ctacaaaagc agcaacaggc cagcaaaaga gaagtgctat ctcagagagc
139681 atggctttca gagccacaag agacagcctc actggctgtt tcagcttgac tgccatgcaa
139741 agaagagagc agagggagaa ccagccccac ccacttattc atcttgtaca aaaaaaaagc
139801 acctaccagc ctaggctaca tagtgagaca ctatctccac aaaaaaccca cgaaaactag
139861 ctgggtatgg tggcacatgc ctacagtccc agctactggt aaggctgtgg tgggaggatc
139921 tcttgaggcc aggaaggaga tccaggctgc agtgagccaa gattgcacca ctgcactcca
139981 gtctggacaa tcgagcaaga tcccatctca aacaataaaa aaaaaaagcg tgtaacctcc
140041 tcagaagaaa gatgttataa tctcaggcag caggcaagaa ccaatccagg ctctaagcaa
140101 attatgtatc tcactgaccc caccaaacct cagaaaaatt taacagtgag aagcaaaatc
140161 tcctttaaag agcaacttag aacagataga aaatatcata cagctgactt cactagagag
140221 aaagtgcatc aactgctttc actcaacaaa aagaaaaaag agatgatcaa tgcagatccc
```

Figure 1TT

```
140281 ctctcctcct ggcagccctt accctcagtg aaaagccacc accattctct ctctggtggc
140341 catcagatca acctgcggcg ttcccacaag acagaatgga gattttccaa ggtatagagc
140401 aagtcagagt accccaaaga acggcggcag agagccagct ccgaaactgc caacactacc
140461 atgcatacac agttcagtaa gtcaagaaag gcctggtaca cagcattctg taactttttt
140521 ttttattttt ttcaattttt ccttcttttt tttttttaag cactagtctg tgctttgcga
140581 acagaatcaa gacattaaca aagatcagct tctctgaaga aaagcatttc tatagaacaa
140641 agacagctac atgtttcgct gccattacac agctccaaag caggaaaaga aaatatttac
140701 aaaatacaag gttttttttt tccatttttt gtttttgttt ttttttttcaa tgctaaaagg
140761 gttattcaga attttcaacc ttataaatag aagaagcact ttatgcatag ggatatggtg
140821 cattattgta ttttttttta aagaaacaat gacaaacccct ttaacttgca aacagaaaaa
140881 aaaatcacta atgttgaaaa ttgtgaaaaa accccaacca ttaa
```

Figure 1UU. *MAPT* cDNA Sequence (SEQ ID NO: 2)

```
1    acggccgagc ggcagggcgc tcgcgcgcgc ccactagtgg ccggaggaga aggctcccgc
61   ggaggccgcg ctgcccgccc cctcccctgg ggaggctcgc gttcccgctg ctcgcgcctg
121  cgccgcccgc cggcctcagg aacgcgccct cttcgccggc gcgcgccctc gcagtcaccg
181  ccacccacca gctccggcac caacagcagc gccgctgcca ccgcccacct tctgccgccg
241  ccaccacagc caccttctcc tcctccgctg tcctctcccg tcctcgcctc tgtcgactat
301  caggtgaact ttgaaccagg atggctgagc cccgccagga gttcgaagtg atggaagatc
361  acgctgggac gtacgggttg gggacagga aagatcaggg gggctacacc atgcaccaag
421  accaagaggg tgacacggac gctggcctga aagaatctcc cctgcagacc cccactgagg
481  acggatctga ggaaccgggc tctgaaacct ctgatgctaa gagcactcca acagcggaag
541  atgtgacagc acccttagtg gatgagggag ctcccggcaa gcaggctgcc gcgcagcccc
601  acacggagat cccagaagga accacagctg aagaagcagg cattggagac acccccagcc
661  tggaagacga agctgctggt cacgtgaccc aagagcctga aagtggtaag gtggtccagg
721  aaggcttcct ccgagagcca ggcccccag gtctgagcca ccagctcatg tccggcatgc
781  ctggggctcc cctcctgcct gagggcccca gagaggccac acgccaacct tcggggacag
841  gacctgagga cacagagggc ggccgccacg cccctgagct gctcaagcac cagcttctag
901  gagacctgca ccaggagggg ccgccgctga agggggcagg gggcaaagag aggccgggga
961  gcaaggagga ggtggatgaa gaccgcgacg tcgatgagtc ctcccccaa gactcccctc
1021 cctccaaggc ctccccagcc caagatgggc ggcctcccca gacagccgcc agagaagcca
1081 ccagcatccc aggcttccca gcggagggtg ccatcccct ccctgtggat ttcctctcca
1141 aagtttccac agagatccca gcctcagagc ccgacgggcc cagtgtaggg cgggccaaag
1201 ggcaggatgc ccccctggag ttcacgtttc acgtggaaat cacacccaac gtgcagaagg
1261 agcaggcgca ctcggaggag catttgggaa gggctgcatt tccaggggcc cctggagagg
1321 ggccagaggc ccggggcccc tctttgggag aggacacaaa agaggctgac cttccagagc
1381 cctctgaaaa gcagcctgct gctgctccgc gggggaagcc cgtcagccgg gtccctcaac
1441 tcaaagctcg catggtcagt aaaagcaaag acgggactgg aagcgatgac aaaaaagcca
1501 agacatccac acgttcctct gctaaaacct tgaaaaatag gccttgcctt agccccaaac
1561 accccactcc tggtagctca gaccctctga tccaaccctc cagccctgct gtgtgcccag
1621 agccaccttc ctctcctaaa cacgtctctt ctgtcacttc ccgaactggc agttctggag
1681 caaaggagat gaaactcaag gggctgatg gtaaaacgaa gatcgccaca ccgcggggag
1741 cagcccctcc aggccagaag ggccaggcca acgccaccag gattccagca aaaaccccgc
1801 ccgctccaaa gacaccaccc agctctggtg aacctccaaa atcaggggat cgcagcggct
1861 acagcagccc cggctcccca ggcactcccg gcagccgctc ccgcaccccg tcccttccaa
1921 ccccacccac ccgggagccc aagaaggtgg cagtggtccg tactccaccc aagtcgccgt
1981 cttccgccaa gagccgcctg cagacagccc ccgtgcccat gccagacctg aagaatgtca
2041 agtccaagat cggctccact gagaacctga agcaccagcc gggaggcggg aaggtgcaga
2101 taattaataa gaagctggat cttagcaacg tccagtccaa gtgtggctca aaggataata
2161 tcaaacacgt cccgggaggc ggcagtgtgc aaatagtcta caaaccagtt gacctgagca
2221 aggtgacctc caagtgtggc tcattaggca acatccatca taaaccagga ggtggccagg
2281 tggaagtaaa atctgagaag cttgacttca aggacagagt ccagtcgaag attgggtccc
2341 tggacaatat cacccacgtc cctggcggag gaaataaaaa gattgaaacc cacaagctga
2401 ccttccgcga gaacgccaaa gccaagacag accacggggc ggagatcgtg tacaagtcgc
2461 cagtggtgtc tggggacacg tctccacggc atctcagcaa tgtctcctcc accggcagca
2521 tcgacatggt agactcgccc cagctcgcca cgctagctga cgaggtgtct gcctccctgg
2581 ccaagcaggg tttgtgatca ggcccctggg gcggtcaata attgtggaga ggagagaatg
2641 agagagtgtg gaaaaaaaaa gaataatgac ccggcccccg ccctctgccc ccagctgctc
2701 ctcgcagttc ggttaattgg ttaatcactt aacctgcttt tgtcactcgg ctttggctcg
2761 ggacttcaaa atcagtgatg ggagtaagag caaatttcat ctttccaaat tgatgggtgg
2821 gctagtaata aaatatttaa aaaaaaacat tcaaaaacat ggccacatcc aacatttcct
2881 caggcaattc cttttgattc tttttcttc cccctccatg tagaagaggg agaaggagag
2941 gctctgaaag ctgcttctgg gggatttcaa gggactgggg gtgccaacca cctctggccc
```

Figure 1VV

```
3001 tgttgtgggg gtgtcacaga ggcagtggca gcaacaaagg atttgaaact tggtgtgttc
3061 gtggagccac aggcagacga tgtcaacctt gtgtgagtgt gacgggggtt ggggtggggc
3121 gggaggccac gggggaggcc gaggcagggg ctgggcagag gggagaggaa gcacaagaag
3181 tgggagtggg agaggaagcc acgtgctgga gagtagacat ccccctcctt gccgctggga
3241 gagccaaggc ctatgccacc tgcagcgtct gagcggccgc ctgtccttgg tggccggggg
3301 tgggggcctg ctgtgggtca gtgtgccacc ctctgcaggg cagcctgtgg gagaagggac
3361 agcgggtaaa aagagaaggc aagctggcag gagggtggca cttcgtggat gacctcctta
3421 gaaaagactg accttgatgt cttgagagcg ctggcctctt cctccctccc tgcagggtag
3481 ggggcctgag ttgaggggct tccctctgct ccacagaaac cctgttttat tgagttctga
3541 aggttggaac tgctgccatg attttggcca ctttgcagac ctgggacttt agggctaacc
3601 agttctcttt gtaaggactt gtgcctcttg ggagacgtcc acccgtttcc aagcctgggc
3661 cactggcatc tctggagtgt gtgggggtct gggaggcagg tcccgagccc cctgtccttc
3721 ccacggccac tgcagtcacc cctgtctgcg ccgctgtgct gttgtctgcc gtgagagccc
3781 aatcactgcc tataccoctc atcacacgtc acaatgtccc gaattcccag cctcaccacc
3841 ccttctcagt aatgaccctg gttggttgca ggaggtacct actccatact gagggtgaaa
3901 ttaagggaag gcaaagtcca ggcacaagag tgggacccca gcctctcact ctcagttcca
3961 ctcatccaac tgggaccctc accacgaatc tcatgatctg attcggttcc ctgtctcctc
4021 ctcccgtcac agatgtgagc cagggcactg ctcagctgtg accctaggtg tttctgcctt
4081 gttgacatgg agagagccct ttcccctgag aaggcctggc cccttcctgt gctgagccca
4141 cagcagcagg ctgggtgtct tggttgtcag tggtggcacc aggatggaag ggcaaggcac
4201 ccagggcagg cccacagtcc cgctgtcccc cacttgcacc ctagcttgta gctgccaacc
4261 tcccagacag cccagcccgc tgctcagctc cacatgcata gtatcagccc tccacacccg
4321 acaaagggga acacaccccc ttggaaatgg ttcttttccc ccagtcccag ctggaagcca
4381 tgctgtctgt tctgctggag cagctgaaca tatacataga tgttgccctg ccctccccat
4441 ctgcaccctg ttgagttgta gttggatttg tctgtttatg cttggattca ccagagtgac
4501 tatgatagtg aaaagaaaaa aaaaaaaaaa aaaggacgca tgtatcttga aatgcttgta
4561 aagaggtttc taacccaccc tcacgaggtg tctctcaccc ccacactggg actcgtgtgg
4621 cctgtgtggt gccaccctgc tggggcctcc caagttttga aaggctttcc tcagcacctg
4681 ggacccaaca gagaccagct tctagcagct aaggaggccg ttcagctgtg acgaaggcct
4741 gaagcacagg attaggactg aagcgatgat gtccccttcc ctacttcccc ttggggctcc
4801 ctgtgtcagg gcacagacta ggtcttgtgg ctggtctggc ttgcggcgcg aggatggttc
4861 tctctggtca tagcccgaag tctcatggca gtcccaaagg aggcttacaa ctcctgcatc
4921 acaagaaaaa ggaagccact gccagctggg gggatctgca gctcccagaa gctccgtgag
4981 cctcagccac ccctcagact gggttcctct ccaagctcgc cctctggagg ggcagcgcag
5041 cctcccacca agggccctgc gaccacagca gggattggga tgaattgcct gtcctggatc
5101 tgctctagag gcccaagctg cctgcctgag gaaggatgac ttgacaagtc aggagacact
5161 gttcccaaag ccttgaccag agcacctcag cccgctgacc ttgcacaaac tccatctgct
5221 gccatgagaa aagggaagcc gcctttgcaa aacattgctg cctaaagaaa ctcagcagcc
5281 tcaggcccaa ttctgccact tctggtttgg gtacagttaa aggcaaccct gagggacttg
5341 gcagtagaaa tccagggcct cccctggggc tggcagcttc gtgtgcagct agagctttac
5401 ctgaaaggaa gtctctgggc ccagaactct ccaccaagag cctccctgcc gttcgctgag
5461 tcccagcaat tctcctaagt tgaagggatc tgagaaggag aaggaaatgt ggggtagatt
5521 tggtggtggt tagagatatg ccccccctcat tactgccaac agtttcggct gcatttcttc
5581 acgcacctcg gttcctcttc ctgaagttct tgtgccctgc tcttcagcac catgggcctt
5641 cttatacgga aggctctggg atctcccccct tgtgggggca ggctcttggg gccagcctaa
5701 gatcatggtt tagggtgatc agtgctggca gataaattga aaaggcacgc tggcttgtga
5761 tcttaaatga ggacaatccc cccagggctg ggcactcctc ccctcccctc acttctccca
5821 cctgcagagc cagtgtcctt gggtgggcta gataggatat actgtatgcc ggctccttca
5881 agctgctgac tcactttatc aatagttcca tttaaattga cttcagtggt gagactgtat
5941 cctgtttgct attgcttgtt gtgctatggg gggagggggg aggaatgtgt aagatagtta
6001 acatgggcaa agggagatct tggggtgcag cacttaaact gcctcgtaac ccttttcatg
6061 atttcaacca catttgctag agggagggag cagccacgga gttagaggcc cttggggttt
```

Figure 1WW

```
6121 ctcttttcca ctgacaggct ttcccaggca gctggctagt tcattccctc cccagccagg
6181 tgcaggcgta ggaatatgga catctggttg ctttggcctg ctgccctctt tcaggggtcc
6241 taagcccaca atcatgcctc cctaagacct tggcatcctt ccctctaagc cgttggcacc
6301 tctgtgccac ctctcacact ggctccagac acacagcctg tgcttttgga gctgagatca
6361 ctcgcttcac cctcctcatc tttgttctcc aagtaaagcc acgaggtcgg ggcgagggca
6421 gaggtgatca cctgcgtgtc ccatctacag acctgcggct tcataaaact tctgatttct
6481 cttcagcttt gaaaagggtt accctgggca ctggcctaga gcctcacctc ctaatagact
6541 tagccccatg agtttgccat gttgagcagg actatttctg gcacttgcaa gtcccatgat
6601 ttcttcggta attctgaggg tgggggagg gacatgaaat catcttagct tagctttctg
6661 tctgtgaatg tctatatagt gtattgtgtg ttttaacaaa tgatttacac tgactgttgc
6721 tgtaaaagtg aatttggaaa taaagttatt actctgatta aa
```

Figure 1XX. Microtubule-associated protein tau (Tau) protein sequence (SEQ ID NO: 3)

```
MAEPRQEFEVMEDHAGTYGLGDRKDQGGYTMHQDQEGDTDAGLKESPLQTPTEDGSEEPGSETSDAKSTPTAEDV
TAPLVDEGAPGKQAAAQPHTEIPEGTTAEEAGIGDTPSLEDEAAGHVTQEPESGKVVQEGFLREPGPPGLSHQLMSG
MPGAPLLPEGPREATRQPSGTGPEDTEGGRHAPELLKHQLLGDLHQEGPPLKGAGGKERPGSKEEVDEDRDVDESSP
QDSPPSKASPAQDGRPPQTAAREATSIPGFPAEGAIPLPVDFLSKVSTEIPASEPDGPSVGRAKGQDAPLEFTFHVEITP
NVQKEQAHSEEHLGRAAFPGAPGEGPEARGPSLGEDTKEADLPEPSEKQPAAAPRGKPVSRVPQLKARMVSKSKDG
TGSDDKKAKTSTRSSAKTLKNRPCLSPKHPTPGSSDPLIQPSSPAVCPEPPSSPKHVSSVTSRTGSSGAKEMKLKGADG
KTKIATPRGAAPPGQKGQANATRIPAKTPPAPKTPPSSGEPPKSGDRSGYSSPGSPGTPGSRSRTPSLPTPPTREPKKV
AVVRTPPKSPSSAKSRLQTAPVPMPDLKNVKSKIGSTENLKHQPGGGKVQIINKKLDLSNVQSKCGSKDNIKHVPGGG
SVQIVYKPVDLSKVTSKCGSLGNIHHKPGGGQVEVKSEKLDFKDRVQSKIGSLDNITHVPGGGNKKIETHKLTFRENAK
AKTDHGAEIVYKSPVVSGDTSPRHLSNVSSTGSIDMVDSPQLATLADEVSASLAKQGL
```

Figure 2A

| Oligomer Name | ASO Number | ASO Sequence | SEQ ID NO | premRNA start NG_007398 | premRNA end NG_007398 | Chemical Structure |
|---|---|---|---|---|---|---|
| ASO-001167 | ASO-001167 | AAAgatgaaatttgctcTTA | 4 | 134947 | 134966 | OxyAs OxyAs OxyAs DNAgs DNAas DNAts DNAgs DNAas DNAas DNAas DNAts DNAts DNAts DNAgs DNAcs DNAts DNAcs OxyTs OxyTs OxyA |
| ASO-001168 | ASO-001168 | GAAagatgaaatttgctCTT | 5 | 134948 | 134967 | OxyGs OxyAs OxyAs DNAas DNAgs DNAas DNAts DNAgs DNAas DNAas DNAas DNAts DNAts DNAts DNAgs DNAcs DNAts OxyMCs OxyTs OxyT |
| ASO-001169 | ASO-001169 | GGAaagatgaaatttgcTCT | 6 | 134949 | 134968 | OxyGs OxyGs OxyAs DNAas DNAas DNAgs DNAas DNAts DNAgs DNAas DNAas DNAas DNAts DNAts DNAts DNAgs DNAcs OxyTs OxyMCs OxyT |
| ASO-000829 | ASO-000829 | AAGatgaaatttgCTC | 7 | 134950 | 134965 | OxyAs OxyAs OxyGs DNAas DNAts DNAgs DNAas DNAas DNAas DNAts DNAts DNAts DNAgs OxyMCs OxyTs OxyMC |
| ASO-001170 | ASO-001170 | TGGaaagatgaaatttgCTC | 8 | 134950 | 134969 | OxyTs OxyGs OxyGs DNAas DNAas DNAas DNAgs DNAas DNAts DNAgs DNAas DNAas DNAas DNAts DNAts DNAts DNAgs OxyMCs OxyTs OxyMC |
| ASO-001171 | ASO-001171 | TTGgaaagatgaaatttGCT | 9 | 134951 | 134970 | OxyTs OxyTs OxyGs DNAgs DNAas DNAas DNAas DNAgs DNAas DNAts DNAgs DNAas DNAas DNAas DNAts DNAts DNAts OxyGs OxyMCs OxyT |
| ASO-001172 | ASO-001172 | TTTggaaagatgaaattTGC | 10 | 134952 | 134971 | OxyTs OxyTs OxyTs DNAgs DNAgs DNAas DNAas DNAas DNAgs DNAas DNAts DNAgs DNAas DNAas DNAas DNAts DNAts OxyTs OxyGs OxyMC |
| ASO-001173 | ASO-001173 | ATTtggaaagatgaaatTTG | 11 | 134953 | 134972 | OxyAs OxyTs OxyTs DNAts DNAgs DNAgs DNAas DNAas DNAas DNAgs DNAas DNAts DNAgs DNAas DNAas DNAas DNAts OxyTs OxyTs OxyG |

Figure 2B

| Oligomer Name | ASO Number | ASO Sequence | SEQ ID NO | premRNA start NG_007398 | premRNA end NG_007398 | Chemical Structure |
|---|---|---|---|---|---|---|
| ASO-001174 | ASO-001174 | AATttggaaagatgaaaTTT | 12 | 134954 | 134973 | OxyAs OxyAs OxyTs DNAts DNAts DNAgs DNAgs DNAas DNAas DNAas DNAgs DNAas DNAts DNAgs DNAas DNAas DNAas OxyTs OxyTs OxyT |
| ASO-001175 | ASO-001175 | CAAtttggaaagatgaaATT | 13 | 134955 | 134974 | OxyMCs OxyAs OxyAs DNAts DNAts DNAts DNAgs DNAgs DNAas DNAas DNAas DNAgs DNAas DNAts DNAgs DNAas DNAas OxyAs OxyTs OxyT |
| ASO-001176 | ASO-001176 | TCAatttggaaagatgaAAT | 14 | 134956 | 134975 | OxyTs OxyMCs OxyAs DNAas DNAts DNAts DNAts DNAgs DNAgs DNAas DNAas DNAas DNAgs DNAas DNAts DNAgs DNAas OxyAs OxyAs OxyT |
| ASO-001177 | ASO-001177 | ATCaatttggaaagatgAAA | 15 | 134957 | 134976 | OxyAs OxyTs OxyMCs DNAas DNAas DNAts DNAts DNAts DNAgs DNAgs DNAas DNAas DNAas DNAgs DNAas DNAts DNAgs OxyAs OxyAs OxyA |
| ASO-001178 | ASO-001178 | CATcaatttggaaagatGAA | 16 | 134958 | 134977 | OxyMCs OxyAs OxyTs DNAcs DNAas DNAas DNAts DNAts DNAts DNAgs DNAgs DNAas DNAas DNAas DNAgs DNAas DNAts OxyGs OxyAs OxyA |
| ASO-001179 | ASO-001179 | CCAtcaatttggaaagaTGA | 17 | 134959 | 134978 | OxyMCs OxyMCs OxyAs DNAts DNAcs DNAas DNAas DNAts DNAts DNAts DNAgs DNAgs DNAas DNAas DNAas DNAgs DNAas OxyTs OxyGs OxyA |
| ASO-001180 | ASO-001180 | CCCatcaatttggaaagATG | 18 | 134960 | 134979 | OxyMCs OxyMCs OxyMCs DNAas DNAts DNAcs DNAas DNAas DNAts DNAts DNAts DNAgs DNAgs DNAas DNAas DNAas DNAgs OxyAs OxyTs OxyG |
| ASO-001181 | ASO-001181 | ACCcatcaatttggaaaGAT | 19 | 134961 | 134980 | OxyAs OxyMCs OxyMCs DNAcs DNAas DNAts DNAcs DNAas DNAas DNAts DNAts DNAts DNAgs DNAgs DNAas DNAas DNAas OxyGs OxyAs OxyT |
| ASO-001182 | ASO-001182 | CACccatcaatttggaaAGA | 20 | 134962 | 134981 | OxyMCs OxyAs OxyMCs DNAcs DNAcs DNAas DNAts DNAcs DNAas DNAas DNAts DNAts DNAts DNAgs DNAgs DNAas DNAas OxyAs OxyGs OxyA |

Figure 2C

| Oligomer Name | ASO Number | ASO Sequence | SEQ ID NO | premRNA start NG_007398 | premRNA end NG_007398 | Chemical Structure |
|---|---|---|---|---|---|---|
| ASO-001183 | ASO-001183 | CCAcccatcaatttggaAAG | 21 | 134963 | 134982 | OxyMCs OxyMCs OxyAs DNAcs DNAcs DNAcs DNAas DNAts DNAcs DNAas DNAas DNAts DNAts DNAts DNAgs DNAgs DNAas OxyAs OxyAs OxyG |
| ASO-001184 | ASO-001184 | CCCacccatcaatttggAAA | 22 | 134964 | 134983 | OxyMCs OxyMCs OxyMCs DNAas DNAcs DNAcs DNAcs DNAas DNAts DNAcs DNAas DNAas DNAts DNAts DNAts DNAgs DNAgs OxyAs OxyAs OxyA |
| ASO-001062 | ASO-001062 | GCCcacccatcaatttgGAA | 23 | 134965 | 134984 | OxyGs OxyMCs OxyMCs DNAcs DNAas DNAcs DNAcs DNAcs DNAas DNAts DNAcs DNAas DNAas DNAts DNAts DNAts DNAgs OxyGs OxyAs OxyA |
| ASO-001063 | ASO-001063 | TAGcccacccatcaattTGG | 24 | 134967 | 134986 | OxyTs OxyAs OxyGs DNAcs DNAcs DNAcs DNAas DNAcs DNAcs DNAcs DNAas DNAts DNAcs DNAas DNAas DNAts DNAts OxyTs OxyGs OxyG |
| ASO-001064 | ASO-001064 | CTAgcccacccatcaatTTG | 25 | 134968 | 134987 | OxyMCs OxyTs OxyAs DNAgs DNAcs DNAcs DNAcs DNAas DNAcs DNAcs DNAcs DNAas DNAts DNAcs DNAas DNAas DNAts OxyTs OxyTs OxyG |
| ASO-001065 | ASO-001065 | ACTagcccacccatcaaTTT | 26 | 134969 | 134988 | OxyAs OxyMCs OxyTs DNAas DNAgs DNAcs DNAcs DNAcs DNAas DNAcs DNAcs DNAcs DNAas DNAts DNAcs DNAas DNAas OxyTs OxyTs OxyT |
| ASO-001066 | ASO-001066 | TACtagcccacccatcaATT | 27 | 134970 | 134989 | OxyTs OxyAs OxyMCs DNAts DNAas DNAgs DNAcs DNAcs DNAcs DNAas DNAcs DNAcs DNAcs DNAas DNAts DNAcs DNAas OxyAs OxyTs OxyT |
| ASO-000830 | ASO-000830 | TACtagcccacccATC | 28 | 134974 | 134989 | OxyTs OxyAs OxyMCs DNAts DNAas DNAgs DNAcs DNAcs DNAcs DNAas DNAcs DNAcs DNAcs OxyAs OxyTs OxyMC |
| ASO-000260 | ASO-000260 | CCCtcttctacatGGA | 29 | 135077 | 135092 | OxyMCs OxyMCs OxyMCs DNAts DNAcs DNAts DNAts DNAcs DNAts DNAas DNAcs DNAas DNAts OxyGs OxyGs OxyA |

Figure 2D

| Oligomer Name | ASO Number | ASO Sequence | SEQ ID NO | premRNA start NG_007398 | premRNA end NG_007398 | Chemical Structure |
|---|---|---|---|---|---|---|
| ASO-000305 | ASO-000305 | TGCctctgtgacaCCC | 30 | 135171 | 135186 | OxyTs OxyGs OxyMCs DNAcs DNAts DNAcs DNAts DNAgs DNAts DNAgs DNAas DNAcs DNAas OxyMCs OxyMCs OxyMC |
| ASO-000304 | ASO-000304 | TTCaaatcctttgTTG | 31 | 135194 | 135209 | OxyTs OxyTs OxyMCs DNAas DNAas DNAas DNAts DNAcs DNAcs DNAts DNAts DNAts DNAgs OxyTs OxyTs OxyG |
| ASO-000324 | ASO-000324 | CACacaaggttgaCAT | 32 | 135242 | 135257 | OxyMCs OxyAs OxyMCs DNAas DNAcs DNAas DNAas DNAgs DNAgs DNAts DNAts DNAgs DNAas OxyMCs OxyAs OxyT |
| ASO-000268 | ASO-000268 | CGTcacactcacaCAA | 33 | 135251 | 135266 | OxyMCs OxyGs OxyTs DNAcs DNAas DNAcs DNAas DNAcs DNAts DNAcs DNAas DNAcs DNAas OxyMCs OxyAs OxyA |
| ASO-000223 | ASO-000223 | GCCaccaaggacaGGC | 34 | 135441 | 135456 | OxyGs OxyMCs OxyMCs DNAas DNAcs DNAcs DNAas DNAas DNAgs DNAgs DNAas DNAcs DNAas OxyGs OxyGs OxyMC |
| ASO-000224 | ASO-000224 | CAGcttgccttctCTT | 35 | 135533 | 135548 | OxyMCs OxyAs OxyGs DNAcs DNAts DNAts DNAgs DNAcs DNAcs DNAts DNAts DNAcs DNAts OxyMCs OxyTs OxyT |
| ASO-000319 | ASO-000319 | ATCaaggtcagtcTTT | 36 | 135585 | 135600 | OxyAs OxyTs OxyMCs DNAas DNAas DNAgs DNAgs DNAts DNAcs DNAas DNAgs DNAts DNAcs OxyTs OxyTs OxyT |
| ASO-000208 | ASO-000208 | CCTtcagaactcaATA | 37 | 135690 | 135705 | OxyMCs OxyMCs OxyTs DNAts DNAcs DNAas DNAgs DNAas DNAas DNAcs DNAts DNAcs DNAas OxyAs OxyTs OxyA |
| ASO-000689 | ASO-000689 | AAAgtcccaggtcTGC | 38 | 135737 | 135752 | OxyAs OxyAs OxyAs DNAgs DNAts DNAcs DNAcs DNAcs DNAas DNAgs DNAgs DNAts DNAcs OxyTs OxyGs OxyMC |

Figure 2E

| Oligomer Name | ASO Number | ASO Sequence | SEQ ID NO | premRNA start NG_007398 | premRNA end NG_007398 | Chemical Structure |
|---|---|---|---|---|---|---|
| ASO-000434 | ASO-000434 | CTAaagtcccaggTCT | 39 | 135739 | 135754 | OxyMCs OxyTs OxyAs DNAas DNAas DNAgs DNAts DNAcs DNAcs DNAcs DNAas DNAgs DNAgs OxyTs OxyMCs OxyT |
| ASO-000409 | ASO-000409 | TAAagtcccaggTCT | 40 | 135739 | 135753 | OxyTs OxyAs OxyAs DNAas DNAgs DNAts DNAcs DNAcs DNAcs DNAas DNAgs DNAgs OxyTs OxyMCs OxyT |
| ASO-000432 | ASO-000432 | CCTaaagtcccagGTC | 41 | 135740 | 135755 | OxyMCs OxyMCs OxyTs DNAas DNAas DNAas DNAgs DNAts DNAcs DNAcs DNAcs DNAas DNAgs OxyGs OxyTs OxyMC |
| ASO-000391 | ASO-000391 | TAAagtcccagGTC | 42 | 135740 | 135753 | OxyTs OxyAs OxyAs DNAas DNAgs DNAts DNAcs DNAcs DNAcs DNAas DNAgs OxyGs OxyTs OxyMC |
| ASO-001779 | ASO-001779 | TAGccctaaagtcccagGTC | 43 | 135740 | 135759 | OxyTs OxyAs OxyGs DNAcs DNAcs DNAcs DNAts DNAas DNAas DNAas DNAgs DNAts DNAcs DNAcs DNAcs DNAas DNAgs OxyGs OxyTs OxyMC |
| ASO-000899 | ASO-000899 | CTAaagtcccagGTC | 44 | 135740 | 135754 | OxyMC OxyT OxyA DNAa DNAa DNAg DNAt DNAc DNAc DNAc DNAa DNAg OxyG OxyT OxyMC |
| ASO-000398 | ASO-000398 | CCCtaaagtcccaGGT | 45 | 135741 | 135756 | OxyMCs OxyMCs OxyMCs DNAts DNAas DNAas DNAas DNAgs DNAts DNAcs DNAcs DNAcs DNAas OxyGs OxyGs OxyT |
| ASO-001778 | ASO-001778 | TTAgccctaaagtcccaGGT | 46 | 135741 | 135760 | OxyTs OxyTs OxyAs DNAgs DNAcs DNAcs DNAcs DNAts DNAas DNAas DNAas DNAgs DNAts DNAcs DNAcs DNAcs DNAas OxyGs OxyGs OxyT |
| ASO-000414 | ASO-000414 | GCCctaaagtcccAGG | 47 | 135742 | 135757 | OxyGs OxyMCs OxyMCs DNAcs DNAts DNAas DNAas DNAas DNAgs DNAts DNAcs DNAcs DNAcs OxyAs OxyGs OxyG |
| ASO-000403 | ASO-000403 | CCCtaaagtcccAGG | 48 | 135742 | 135756 | OxyMCs OxyMCs OxyMCs DNAts DNAas DNAas DNAas DNAgs DNAts DNAcs DNAcs DNAcs OxyAs OxyGs OxyG |

Figure 2F

| Oligomer Name | ASO Number | ASO Sequence | SEQ ID NO | premRNA start NG_007398 | premRNA end NG_007398 | Chemical Structure |
|---|---|---|---|---|---|---|
| ASO-001780 | ASO-001780 | GTTagccctaaagtcccAGG | 49 | 135742 | 135761 | OxyGs OxyTs OxyTs DNAas DNAgs DNAcs DNAcs DNAcs DNAts DNAas DNAas DNAas DNAgs DNAts DNAcs DNAcs DNAcs OxyAs OxyGs OxyG |
| ASO-000433 | ASO-000433 | GCCctaaagtccCAG | 50 | 135743 | 135757 | OxyGs OxyMCs OxyMCs DNAcs DNAts DNAas DNAas DNAas DNAgs DNAts DNAcs DNAcs OxyMCs OxyAs OxyG |
| ASO-000411 | ASO-000411 | CCCtaaagtccCAG | 51 | 135743 | 135756 | OxyMCs OxyMCs OxyMCs DNAts DNAas DNAas DNAas DNAgs DNAts DNAcs DNAcs OxyMCs OxyAs OxyG |
| ASO-001781 | ASO-001781 | GGTtagccctaaagtccCAG | 52 | 135743 | 135762 | OxyGs OxyGs OxyTs DNAts DNAas DNAgs DNAcs DNAcs DNAcs DNAts DNAas DNAas DNAas DNAgs DNAts DNAcs DNAcs OxyMCs OxyAs OxyG |
| ASO-000389 | ASO-000389 | TAGccctaaagtcCCA | 53 | 135744 | 135759 | OxyTs OxyAs OxyGs DNAcs DNAcs DNAcs DNAts DNAas DNAas DNAas DNAgs DNAts DNAcs OxyMCs OxyMCs OxyA |
| ASO-001939 | ASO-001939 | TAGccctaaagtcCCA | 54 | 135744 | 135759 | OxyTs OxyAs OxyG DNAcs DNAcs DNAcs DNAts DNAas DNAas DNAas DNAgs DNAts DNAcs OxyMCs OxyMC OxyA |
| ASO-001932 | ASO-001932 | TAGccctaaagtcCCA | 55 | 135744 | 135759 | OxyTs OxyA OxyGs DNAcs DNAcs DNAcs DNAts DNAas DNAas DNAas DNAgs DNAts DNAcs OxyMCs OxyMC OxyA |
| ASO-001925 | ASO-001925 | TAGccctaaagtcCCA | 56 | 135744 | 135759 | OxyT OxyAs OxyGs DNAcs DNAcs DNAcs DNAts DNAas DNAas DNAas DNAgs DNAts DNAcs OxyMCs OxyMC OxyA |
| ASO-001924 | ASO-001924 | TAGccctaaagtcCCA | 57 | 135744 | 135759 | OxyT OxyAs OxyGs DNAcs DNAcs DNAcs DNAts DNAas DNAas DNAas DNAgs DNAts DNAcs OxyMCs OxyMCs OxyA |

Figure 2G

| Oligomer Name | ASO Number | ASO Sequence | SEQ ID NO | premRNA start NG_007398 | premRNA end NG_007398 | Chemical Structure |
|---|---|---|---|---|---|---|
| ASO-001952 | ASO-001952 | TAGccctaaagtcCCA | 58 | 135744 | 135759 | OxyTs OxyAs OxyGs DNAcs DNAcs DNAcs DNAts DNAas DNAas DNAas DNAgs DNAts DNAcs OxyMCs OxyMC OxyA |
| ASO-001931 | ASO-001931 | TAGccctaaagtcCCA | 59 | 135744 | 135759 | OxyTs OxyA OxyGs DNAcs DNAcs DNAcs DNAts DNAas DNAas DNAas DNAgs DNAts DNAcs OxyMCs OxyMCs OxyA |
| ASO-001953 | ASO-001953 | TAGccctaaagtcCCA | 60 | 135744 | 135759 | OxyTs OxyA OxyGs DNAcs DNAcs DNAcs DNAts DNAas DNAas DNAas DNAgs DNAts DNAcs OxyMC OxyMC OxyA |
| ASO-001945 | ASO-001945 | TAGccctaaagtcCCA | 61 | 135744 | 135759 | OxyTs OxyAs OxyGs DNAcs DNAcs DNAcs DNAts DNAas DNAas DNAas DNAgs DNAts DNAcs OxyMC OxyMCs OxyA |
| ASO-001946 | ASO-001946 | TAGccctaaagtcCCA | 62 | 135744 | 135759 | OxyT OxyAs OxyG DNAcs DNAcs DNAcs DNAts DNAas DNAas DNAas DNAgs DNAts DNAcs OxyMCs OxyMC OxyA |
| ASO-001971 | ASO-001971 | TAGccctaaagtcCCA | 63 | 135744 | 135759 | OxyTs OxyAs OxyG DNAcs DNAcs DNAcs DNAts DNAas DNAas DNAas DNAgs DNAts DNAcs OxyMC OxyMCs OxyA |
| ASO-001938 | ASO-001938 | TAGccctaaagtcCCA | 64 | 135744 | 135759 | OxyTs OxyAs OxyG DNAcs DNAcs DNAcs DNAts DNAas DNAas DNAas DNAgs DNAts DNAcs OxyMCs OxyMCs OxyA |
| ASO-001959 | ASO-001959 | TAGccctaaagtcCCA | 65 | 135744 | 135759 | OxyT OxyAs OxyGs DNAcs DNAcs DNAcs DNAts DNAas DNAas DNAas DNAgs DNAts DNAcs OxyMC OxyMCs OxyA |
| ASO-001965 | ASO-001965 | TAGccctaaagtcCCA | 66 | 135744 | 135759 | OxyTs OxyA OxyGs DNAcs DNAcs DNAcs DNAts DNAas DNAas DNAas DNAgs DNAts DNAcs OxyMC OxyMCs OxyA |

Figure 2H

| Oligomer Name | ASO Number | ASO Sequence | SEQ ID NO | premRNA start NG_007398 | premRNA end NG_007398 | Chemical Structure |
|---|---|---|---|---|---|---|
| ASO-001782 | ASO-001782 | TGGttagccctaaagtcCCA | 67 | 135744 | 135763 | OxyTs OxyGs OxyGs DNAts DNAts DNAas DNAgs DNAcs DNAcs DNAcs DNAts DNAas DNAas DNAas DNAgs DNAts DNAcs OxyMCs OxyMCs OxyA |
| ASO-000900 | ASO-000900 | TAGccctaaagtcCCA | 68 | 135744 | 135759 | OxyT OxyA OxyG DNAc DNAc DNAc DNAt DNAa DNAa DNAa DNAg DNAt DNAc OxyMC OxyMC OxyA |
| ASO-000435 | ASO-000435 | TTAgccctaaagtCCC | 69 | 135745 | 135760 | OxyTs OxyTs OxyAs DNAgs DNAcs DNAcs DNAcs DNAts DNAas DNAas DNAas DNAgs DNAts OxyMCs OxyMCs OxyMC |
| ASO-000423 | ASO-000423 | GTTagccctaaagTCC | 70 | 135746 | 135761 | OxyGs OxyTs OxyTs DNAas DNAgs DNAcs DNAcs DNAcs DNAts DNAas DNAas DNAas DNAgs OxyTs OxyMCs OxyMC |
| ASO-000442 | ASO-000442 | TAGccctaaagTCC | 71 | 135746 | 135759 | OxyTs OxyAs OxyGs DNAcs DNAcs DNAcs DNAts DNAas DNAas DNAas DNAgs OxyTs OxyMCs OxyMC |
| ASO-000416 | ASO-000416 | GGTtagccctaaaGTC | 72 | 135747 | 135762 | OxyGs OxyGs OxyTs DNAts DNAas DNAgs DNAcs DNAcs DNAcs DNAts DNAas DNAas DNAas OxyGs OxyTs OxyMC |
| ASO-000438 | ASO-000438 | GTTagccctaaAGT | 73 | 135748 | 135761 | OxyGs OxyTs OxyTs DNAas DNAgs DNAcs DNAcs DNAcs DNAts DNAas DNAas OxyAs OxyGs OxyT |
| ASO-000581 | ASO-000581 | ACTggttagccctAAA | 74 | 135750 | 135765 | OxyAs OxyMCs OxyTs DNAgs DNAgs DNAts DNAts DNAas DNAgs DNAcs DNAcs DNAcs DNAts OxyAs OxyAs OxyA |
| ASO-000639 | ASO-000639 | AACtggttagcccTAA | 75 | 135751 | 135766 | OxyAs OxyAs OxyMCs DNAts DNAgs DNAgs DNAts DNAts DNAas DNAgs DNAcs DNAcs DNAcs OxyTs OxyAs OxyA |

Figure 2I

| Oligomer Name | ASO Number | ASO Sequence | SEQ ID NO | premRNA start NG_007398 | premRNA end NG_007398 | Chemical Structure |
|---|---|---|---|---|---|---|
| ASO-000558 | ASO-000558 | GAActggttagccCTA | 76 | 135752 | 135767 | OxyGs OxyAs OxyAs DNAcs DNAts DNAgs DNAgs DNAts DNAts DNAas DNAgs DNAcs DNAcs OxyMCs OxyTs OxyA |
| ASO-000597 | ASO-000597 | GAGaactggttagCCC | 77 | 135754 | 135769 | OxyGs OxyAs OxyGs DNAas DNAas DNAcs DNAts DNAgs DNAgs DNAts DNAts DNAas DNAgs OxyMCs OxyMCs OxyMC |
| ASO-000245 | ASO-000245 | TACaaagagaactGGT | 78 | 135760 | 135775 | OxyTs OxyAs OxyMCs DNAas DNAas DNAas DNAgs DNAas DNAgs DNAas DNAas DNAcs DNAts OxyGs OxyGs OxyT |
| ASO-000897 | ASO-000897 | CACaagtccttacAAA | 79 | 135770 | 135785 | OxyMC OxyA OxyMC DNAa DNAa DNAg DNAt DNAc DNAc DNAt DNAt DNAa DNAc OxyA OxyA OxyA |
| ASO-000185 | ASO-000185 | GGCacaagtccttACA | 80 | 135772 | 135787 | OxyGs OxyGs OxyMCs DNAas DNAcs DNAas DNAas DNAgs DNAts DNAcs DNAcs DNAts DNAts OxyAs OxyMCs OxyA |
| ASO-000426 | ASO-000426 | AGGcacaagtccTTA | 81 | 135774 | 135788 | OxyAs OxyGs OxyGs DNAcs DNAas DNAcs DNAas DNAas DNAgs DNAts DNAcs DNAcs OxyTs OxyTs OxyA |
| ASO-000417 | ASO-000417 | GAGgcacaagtccTTA | 82 | 135774 | 135789 | OxyGs OxyAs OxyGs DNAgs DNAcs DNAas DNAcs DNAas DNAas DNAgs DNAts DNAcs DNAcs OxyTs OxyTs OxyA |
| ASO-000393 | ASO-000393 | AGAggcacaagtcCTT | 83 | 135775 | 135790 | OxyAs OxyGs OxyAs DNAgs DNAgs DNAcs DNAas DNAcs DNAas DNAas DNAgs DNAts DNAcs OxyMCs OxyTs OxyT |
| ASO-000449 | ASO-000449 | AAGaggcacaagtCCT | 84 | 135776 | 135791 | OxyAs OxyAs OxyGs DNAas DNAgs DNAgs DNAcs DNAas DNAcs DNAas DNAas DNAgs DNAts OxyMCs OxyMCs OxyT |

Figure 2J

| Oligomer Name | ASO Number | ASO Sequence | SEQ ID NO | premRNA start NG_007398 | premRNA end NG_007398 | Chemical Structure |
|---|---|---|---|---|---|---|
| ASO-000406 | ASO-000406 | AGAggcacaagtCCT | 85 | 135776 | 135790 | OxyAs OxyGs OxyAs DNAgs DNAgs DNAcs DNAas DNAcs DNAas DNAas DNAgs DNAts OxyMCs OxyMCs OxyT |
| ASO-000392 | ASO-000392 | CCAagaggcacaaGTC | 86 | 135778 | 135793 | OxyMCs OxyMCs OxyAs DNAas DNAgs DNAas DNAgs DNAgs DNAcs DNAas DNAcs DNAas DNAas OxyGs OxyTs OxyMC |
| ASO-000444 | ASO-000444 | CAAgaggcacaaGTC | 87 | 135778 | 135792 | OxyMCs OxyAs OxyAs DNAgs DNAas DNAgs DNAgs DNAcs DNAas DNAcs DNAas DNAas OxyGs OxyTs OxyMC |
| ASO-000443 | ASO-000443 | CCCaagaggcacaAGT | 88 | 135779 | 135794 | OxyMCs OxyMCs OxyMCs DNAas DNAas DNAgs DNAas DNAgs DNAgs DNAcs DNAas DNAcs DNAas OxyAs OxyGs OxyT |
| ASO-000450 | ASO-000450 | CAAgaggcacaAGT | 89 | 135779 | 135792 | OxyMCs OxyAs OxyAs DNAgs DNAas DNAgs DNAgs DNAcs DNAas DNAcs DNAas OxyAs OxyGs OxyT |
| ASO-000258 | ASO-000258 | CTCccaagaggcaCAA | 90 | 135781 | 135796 | OxyMCs OxyTs OxyMCs DNAcs DNAcs DNAas DNAas DNAgs DNAas DNAgs DNAgs DNAcs DNAas OxyMCs OxyAs OxyA |
| ASO-000205 | ASO-000205 | TGGccgtgggaagGAC | 91 | 135876 | 135891 | OxyTs OxyGs OxyGs DNAcs DNAmcs DNAgs DNAts DNAgs DNAgs DNAgs DNAas DNAas DNAgs OxyGs OxyAs OxyMC |
| ASO-000213 | ASO-000213 | GGTgaggctgggaATT | 92 | 135984 | 135999 | OxyGs OxyGs OxyTs DNAgs DNAas DNAgs DNAgs DNAcs DNAts DNAgs DNAgs DNAgs DNAas OxyAs OxyTs OxyT |
| ASO-000293 | ASO-000293 | GTGaggctgggaATT | 93 | 135984 | 135998 | OxyGs OxyTs OxyGs DNAas DNAgs DNAgs DNAcs DNAts DNAgs DNAgs DNAgs DNAas OxyAs OxyTs OxyT |

Figure 2K

| Oligomer Name | ASO Number | ASO Sequence | SEQ ID NO | premRNA start NG_007398 | premRNA end NG_007398 | Chemical Structure |
|---|---|---|---|---|---|---|
| ASO-000321 | ASO-000321 | TGGtgaggctgggAAT | 94 | 135985 | 136000 | OxyTs OxyGs OxyGs DNAts DNAgs DNAas DNAgs DNAgs DNAcs DNAts DNAgs DNAgs DNAgs OxyAs OxyAs OxyT |
| ASO-000226 | ASO-000226 | CTCagtatggagtAGG | 95 | 136040 | 136055 | OxyMCs OxyTs OxyMCs DNAas DNAgs DNAts DNAas DNAts DNAgs DNAgs DNAas DNAgs DNAts OxyAs OxyGs OxyG |
| ASO-000682 | ASO-000682 | AATttcaccctcaGTA | 96 | 136049 | 136064 | OxyAs OxyAs OxyTs DNAts DNAts DNAcs DNAas DNAcs DNAcs DNAcs DNAts DNAcs DNAas OxyGs OxyTs OxyA |
| ASO-000673 | ASO-000673 | TTAatttcaccctCAG | 97 | 136051 | 136066 | OxyTs OxyTs OxyAs DNAas DNAts DNAts DNAts DNAcs DNAas DNAcs DNAcs DNAcs DNAts OxyMCs OxyAs OxyG |
| ASO-000578 | ASO-000578 | CTTaatttcacccTCA | 98 | 136052 | 136067 | OxyMCs OxyTs OxyTs DNAas DNAas DNAts DNAts DNAts DNAcs DNAas DNAcs DNAcs DNAcs OxyTs OxyMCs OxyA |
| ASO-000540-21 | ASO-002180 | CCTTaatttcaccCTCA | 99 | 136052 | 136068 | OxyMCs OxyMCs OxyTs OxyTs DNAas DNAas DNAts DNAts DNAts DNAcs DNAas DNAcs DNAcs OxyMCs OxyTs OxyMCs OxyAs |
| ASO-000540-22 | ASO-002192 | CCTTaatttcacCctCA | 100 | 136052 | 136068 | OxyMCs OxyMCs OxyTs OxyTs DNAas DNAas DNAts DNAts DNAts DNAcs DNAas DNAcs OxyMCs DNAcs DNAts OxyMCs OxyAs |
| ASO-000540-23 | ASO-002109 | CCTTAatttcacCctCA | 101 | 136052 | 136068 | OxyMCs OxyMCs OxyTs OxyTs OxyAs DNAas DNAts DNAts DNAts DNAcs DNAas DNAcs OxyMCs DNAcs DNAts OxyMCs OxyAs |
| ASO-000540-24 | ASO-002121 | TcCCtTaatttcaccCT | 102 | 136054 | 136070 | OxyTs DNAcs OxyMCs OxyMCs DNAts OxyTs DNAas DNAas DNAts DNAts DNAts DNAcs DNAas DNAcs DNAcs OxyMCs OxyTs |

Figure 2L

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-25 | ASO-002133 | TcCCTtaatttcaccCT | 103 | 136054 | 136070 | OxyTs DNAcs OxyMCs OxyMCs OxyTs DNAts DNAas DNAas DNAts DNAts DNAts DNAcs DNAas DNAcs DNAcs OxyMCs OxyTs |
| ASO-000540-26 | ASO-002145 | TcCCTtaatttcAccCT | 104 | 136054 | 136070 | OxyTs DNAcs OxyMCs OxyMCs OxyTs DNAts DNAas DNAas DNAts DNAts DNAts DNAcs OxyAs DNAcs DNAcs OxyMCs OxyTs |
| ASO-000540-27 | ASO-002157 | TcCCTTaatttcaccCT | 105 | 136054 | 136070 | OxyTs DNAcs OxyMCs OxyMCs OxyTs OxyTs DNAas DNAas DNAts DNAts DNAts DNAcs DNAas DNAcs DNAcs OxyMCs OxyTs |
| ASO-000540-28 | ASO-002169 | TCcCTTaatttcaccCT | 106 | 136054 | 136070 | OxyTs OxyMCs DNAcs OxyMCs OxyTs OxyTs DNAas DNAas DNAts DNAts DNAts DNAcs DNAas DNAcs DNAcs OxyMCs OxyTs |
| ASO-000540-29 | ASO-002181 | TCCcttaatttcacCCT | 107 | 136054 | 136070 | OxyTs OxyMCs OxyMCs DNAcs DNAts DNAts DNAas DNAas DNAts DNAts DNAts DNAcs DNAas DNAcs OxyMCs OxyMCs OxyTs |
| ASO-000540-3 | ASO-002154 | CCCttaatttcacCcTC | 108 | 136053 | 136069 | OxyMCs OxyMCs OxyMCs DNAts DNAts DNAas DNAas DNAts DNAts DNAts DNAcs DNAas DNAcs OxyMCs DNAcs OxyTs OxyMCs |
| ASO-000540-42 | ASO-002147 | CCCTtaatttcacccTCA | 109 | 136052 | 136069 | OxyMCs OxyMCs OxyMCs OxyTs DNAts DNAas DNAas DNAts DNAts DNAts DNAcs DNAas DNAcs DNAcs DNAcs OxyTs OxyMCs OxyAs |
| ASO-000540-43 | ASO-002159 | CCCTtaatttcaccCtCA | 110 | 136052 | 136069 | OxyMCs OxyMCs OxyMCs OxyTs DNAts DNAas DNAas DNAts DNAts DNAts DNAcs DNAas DNAcs DNAcs OxyMCs DNAts OxyMCs OxyAs |
| ASO-000540-44 | ASO-002171 | CCCTtaatttcaccCTCA | 111 | 136052 | 136069 | OxyMCs OxyMCs OxyMCs OxyTs DNAts DNAas DNAas DNAts DNAts DNAts DNAcs DNAas DNAcs DNAcs OxyMCs OxyTs OxyMCs OxyAs |

Figure 2M

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-45 | ASO-002183 | CCCTtaatttcacCctCA | 112 | 136052 | 136069 | OxyMCs OxyMCs OxyMCs OxyTs DNAts DNAas DNAas DNAts DNAts DNAts DNAcs DNAas DNAcs OxyMCs DNAcs DNAts OxyMCs OxyAs |
| ASO-000540-46 | ASO-002195 | CCCTtaatttcacCcTCA | 113 | 136052 | 136069 | OxyMCs OxyMCs OxyMCs OxyTs DNAts DNAas DNAas DNAts DNAts DNAts DNAcs DNAas DNAcs OxyMCs DNAcs OxyTs OxyMCs OxyAs |
| ASO-000540-47 | ASO-002196 | CCCTtaatttcaCcctCA | 114 | 136052 | 136069 | OxyMCs OxyMCs OxyMCs OxyTs DNAts DNAas DNAas DNAts DNAts DNAts DNAcs DNAas OxyMCs DNAcs DNAcs DNAts OxyMCs OxyAs |
| ASO-000540-48 | ASO-002200 | CCCTtaatttcaCccTCA | 115 | 136052 | 136069 | OxyMCs OxyMCs OxyMCs OxyTs DNAts DNAas DNAas DNAts DNAts DNAts DNAcs DNAas OxyMCs DNAcs DNAcs OxyTs OxyMCs OxyAs |
| ASO-000540-49 | ASO-002204 | CCCTtaatttcaCcCtCA | 116 | 136052 | 136069 | OxyMCs OxyMCs OxyMCs OxyTs DNAts DNAas DNAas DNAts DNAts DNAts DNAcs DNAas OxyMCs DNAcs OxyMCs DNAts OxyMCs OxyAs |
| ASO-000540-5 | ASO-002178 | CCCttaatttcAcccTC | 117 | 136053 | 136069 | OxyMCs OxyMCs OxyMCs DNAts DNAts DNAas DNAas DNAts DNAts DNAts DNAcs OxyAs DNAcs DNAcs DNAcs OxyTs OxyMCs |
| ASO-000540-50 | ASO-002208 | CCCTtaatttcAccCtCA | 118 | 136052 | 136069 | OxyMCs OxyMCs OxyMCs OxyTs DNAts DNAas DNAas DNAts DNAts DNAts DNAcs OxyAs DNAcs DNAcs OxyMCs DNAts OxyMCs OxyAs |
| ASO-000540-51 | ASO-002212 | CCCTtaatttcAcCctCA | 119 | 136052 | 136069 | OxyMCs OxyMCs OxyMCs OxyTs DNAts DNAas DNAas DNAts DNAts DNAts DNAcs OxyAs DNAcs OxyMCs DNAcs DNAts OxyMCs OxyAs |
| ASO-000540-52 | ASO-002216 | TcCCTtaatttcacCcTC | 120 | 136053 | 136070 | OxyTs DNAcs OxyMCs OxyMCs OxyTs DNAts DNAas DNAas DNAts DNAts DNAts DNAcs DNAas DNAcs OxyMCs DNAcs OxyTs OxyMCs |

Figure 2N

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-53 | ASO-002220 | TCcCTtaatttcacccTC | 121 | 136053 | 136070 | OxyTs OxyMCs DNAcs OxyMCs OxyTs DNAts DNAas DNAas DNAts DNAts DNAts DNAcs DNAas DNAcs DNAcs DNAcs OxyTs OxyMCs |
| ASO-000540-54 | ASO-002224 | TCcCTTaatttcacCcTC | 122 | 136053 | 136070 | OxyTs OxyMCs DNAcs OxyMCs OxyTs OxyTs DNAas DNAas DNAts DNAts DNAts DNAcs DNAas DNAcs OxyMCs DNAcs OxyTs OxyMCs |
| ASO-000540-55 | ASO-002197 | TCCcttaatttcaccCTC | 123 | 136053 | 136070 | OxyTs OxyMCs OxyMCs DNAcs DNAts DNAts DNAas DNAas DNAts DNAts DNAts DNAcs DNAas DNAcs DNAcs OxyMCs OxyTs OxyMCs |
| ASO-000540-69 | ASO-002222 | TCCcTtaatttcacCctCA | 124 | 136052 | 136070 | OxyTs OxyMCs OxyMCs DNAcs OxyTs DNAts DNAas DNAas DNAts DNAts DNAts DNAcs DNAas DNAcs OxyMCs DNAcs DNAts OxyMCs OxyAs |
| ASO-000540-70 | ASO-002226 | TCCCttaatttcaccCTCA | 125 | 136052 | 136070 | OxyTs OxyMCs OxyMCs OxyMCs DNAts DNAts DNAas DNAas DNAts DNAts DNAts DNAcs DNAas DNAcs DNAcs OxyMCs OxyTs OxyMCs OxyAs |
| ASO-000540-71 | ASO-002199 | TCCCttaatttcacCcTCA | 126 | 136052 | 136070 | OxyTs OxyMCs OxyMCs OxyMCs DNAts DNAts DNAas DNAas DNAts DNAts DNAts DNAcs DNAas DNAcs OxyMCs DNAcs OxyTs OxyMCs OxyAs |
| ASO-000540-72 | ASO-002203 | TCCCttaatttcacCCtCA | 127 | 136052 | 136070 | OxyTs OxyMCs OxyMCs OxyMCs DNAts DNAts DNAas DNAas DNAts DNAts DNAts DNAcs DNAas DNAcs OxyMCs OxyMCs DNAts OxyMCs OxyAs |
| ASO-000540-73 | ASO-002207 | TCCCttaatttcaCcCtCA | 128 | 136052 | 136070 | OxyTs OxyMCs OxyMCs OxyMCs DNAts DNAts DNAas DNAas DNAts DNAts DNAts DNAcs DNAas OxyMCs DNAcs OxyMCs DNAts OxyMCs OxyAs |
| ASO-000540-74 | ASO-002211 | TCCCttaatttcACcCtCA | 129 | 136052 | 136070 | OxyTs OxyMCs OxyMCs OxyMCs DNAts DNAts DNAas DNAas DNAts DNAts DNAts DNAcs OxyAs OxyMCs DNAcs OxyMCs DNAts OxyMCs OxyAs |

Figure 2O

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-75 | ASO-002215 | TCCCTtaatttcaccCTCA | 130 | 136052 | 136070 | OxyTs OxyMCs OxyMCs OxyMCs OxyTs DNAts DNAas DNAas DNAts DNAts DNAts DNAcs DNAas DNAcs DNAcs OxyMCs OxyTs OxyMCs OxyAs |
| ASO-000540-76 | ASO-002219 | TCCCTtaatttcacCCtCA | 131 | 136052 | 136070 | OxyTs OxyMCs OxyMCs OxyMCs OxyTs DNAts DNAas DNAas DNAts DNAts DNAts DNAcs DNAas DNAcs OxyMCs OxyMCs DNAts OxyMCs OxyAs |
| ASO-000540-77 | ASO-002223 | TCCCTtaatttcacCCTCA | 132 | 136052 | 136070 | OxyTs OxyMCs OxyMCs OxyMCs OxyTs DNAts DNAas DNAas DNAts DNAts DNAts DNAcs DNAas DNAcs OxyMCs OxyMCs OxyTs OxyMCs OxyAs |
| ASO-000540-8 | ASO-002119 | CCCtTaatttcaccCTC | 133 | 136053 | 136069 | OxyMCs OxyMCs OxyMCs DNAts OxyTs DNAas DNAas DNAts DNAts DNAts DNAcs DNAas DNAcs DNAcs OxyMCs OxyTs OxyMCs |
| ASO-000540-9 | ASO-002131 | CCCtTaatttcacCcTC | 134 | 136053 | 136069 | OxyMCs OxyMCs OxyMCs DNAts OxyTs DNAas DNAas DNAts DNAts DNAts DNAcs DNAas DNAcs OxyMCs DNAcs OxyTs OxyMCs |
| TBD-mm10 | ASO-002382 | CCttgATttcgccctCA | 135 | 136053 | 136069 | OxyMCs OxyMCs DNAts DNAts DNAgs OxyAs OxyTs DNAts DNAts DNAcs DNAgs DNAcs DNAcs DNAcs DNAts OxyMCs OxyAs |
| TBD-mm11 | ASO-002299 | CCttgATttcaccctCT | 136 | 136052 | 136068 | OxyMCs OxyMCs DNAts DNAts DNAgs OxyAs OxyTs DNAts DNAts DNAcs DNAas DNAcs DNAcs DNAcs DNAts OxyMCs OxyTs |
| TBD-mm12 | ASO-002311 | CCttaGTttcaccctCG | 137 | 136054 | 136070 | OxyMCs OxyMCs DNAts DNAts DNAas OxyGs OxyTs DNAts DNAts DNAcs DNAas DNAcs DNAcs DNAcs DNAts OxyMCs OxyGs |
| TBD-mm19 | ASO-002300 | CCCttgatttcaccctCA | 138 | 136052 | 136069 | OxyMCs OxyMCs OxyMCs DNAts DNAts DNAgs DNAas DNAts DNAts DNAts DNAcs DNAas DNAcs DNAcs DNAcs DNAts OxyMCs OxyAs |

Figure 2P

| Oligomer Name | ASO Number | ASO Sequence | SEQ ID NO | premRNA start NG_007398 | premRNA end NG_007398 | Chemical Structure |
|---|---|---|---|---|---|---|
| TBD-mm20 | ASO-002312 | CCCttaatttcaccctCG | 139 | 136054 | 136071 | OxyMCs OxyMCs OxyMCs DNAts DNAts DNAas DNAas DNAts DNAts DNAts DNAcs DNAas DNAcs DNAcs DNAcs DNAts OxyMCs OxyGs |
| TBD-mm21 | ASO-002324 | CCCttagtttcaccctCA | 140 | 136052 | 136069 | OxyMCs OxyMCs OxyMCs DNAts DNAts DNAas DNAgs DNAts DNAts DNAts DNAcs DNAas DNAcs DNAcs DNAcs DNAts OxyMCs OxyAs |
| TBD-mm22 | ASO-002336 | CCCttgatttcgccctCA | 141 | 136052 | 136069 | OxyMCs OxyMCs OxyMCs DNAts DNAts DNAgs DNAas DNAts DNAts DNAts DNAcs DNAgs DNAcs DNAcs DNAcs DNAts OxyMCs OxyAs |
| TBD-mm23 | ASO-002348 | CCCttgatttcaccctCG | 142 | 136053 | 136070 | OxyMCs OxyMCs OxyMCs DNAts DNAts DNAgs DNAas DNAts DNAts DNAts DNAcs DNAas DNAcs DNAcs DNAcs DNAts OxyMCs OxyGs |
| TBD-mm24 | ASO-002360 | CCCttgatttcaccctCT | 143 | 136052 | 136069 | OxyMCs OxyMCs OxyMCs DNAts DNAts DNAgs DNAas DNAts DNAts DNAts DNAcs DNAas DNAcs DNAcs DNAcs DNAts OxyMCs OxyTs |
| TBD-mm31 | ASO-002349 | TCcCTtgatttcacCctCA | 144 | 136053 | 136071 | OxyTs OxyMCs DNAcs OxyMCs OxyTs DNAts DNAgs DNAas DNAts DNAts DNAts DNAcs DNAas DNAcs OxyMCs DNAcs DNAts OxyMCs OxyAs |
| TBD-mm32 | ASO-002361 | TCcCTtaatttcacCctCG | 145 | 136052 | 136070 | OxyTs OxyMCs DNAcs OxyMCs OxyTs DNAts DNAas DNAas DNAts DNAts DNAts DNAcs DNAas DNAcs OxyMCs DNAcs DNAts OxyMCs OxyGs |
| TBD-mm33 | ASO-002373 | ACcCTtaatttcacCctCA | 146 | 136053 | 136071 | OxyAs OxyMCs DNAcs OxyMCs OxyTs DNAts DNAas DNAas DNAts DNAts DNAts DNAcs DNAas DNAcs OxyMCs DNAcs DNAts OxyMCs OxyAs |
| TBD-mm34 | ASO-002385 | TCcCTtgatttcgcCctCA | 147 | 136052 | 136070 | OxyTs OxyMCs DNAcs OxyMCs OxyTs DNAts DNAgs DNAas DNAts DNAts DNAts DNAcs DNAgs DNAcs OxyMCs DNAcs DNAts OxyMCs OxyAs |

Figure 2Q

| Oligomer Name | ASO Number | ASO Sequence | SEQ ID NO | premRNA start NG_007398 | premRNA end NG_007398 | Chemical Structure |
|---|---|---|---|---|---|---|
| TBD-mm35 | ASO-002302 | TCcCTtagtttcacCctCG | 148 | 136054 | 136072 | OxyTs OxyMCs DNAcs OxyMCs OxyTs DNAts DNAas DNAgs DNAts DNAts DNAts DNAcs DNAas DNAcs OxyMCs DNAcs DNAts OxyMCs OxyGs |
| TBD-mm36 | ASO-002314 | ACcCTtgatttcacCctCA | 149 | 136054 | 136072 | OxyAs OxyMCs DNAcs OxyMCs OxyTs DNAts DNAgs DNAas DNAts DNAts DNAts DNAcs DNAas DNAcs OxyMCs DNAcs DNAts OxyMCs OxyAs |
| TBD-mm7 | ASO-002346 | CCttgATttcaccctCA | 150 | 136053 | 136069 | OxyMCs OxyMCs DNAts DNAts DNAgs OxyAs OxyTs DNAts DNAts DNAcs DNAas DNAcs DNAcs DNAcs DNAts OxyMCs OxyAs |
| TBD-mm8 | ASO-002358 | CCttaGTttcaccctCA | 151 | 136053 | 136069 | OxyMCs OxyMCs DNAts DNAts DNAas OxyGs OxyTs DNAts DNAts DNAcs DNAas DNAcs DNAcs DNAcs DNAts OxyMCs OxyAs |
| TBD-mm9 | ASO-002370 | CCttaATttcaccctCG | 152 | 136052 | 136068 | OxyMCs OxyMCs DNAts DNAts DNAas OxyAs OxyTs DNAts DNAts DNAcs DNAas DNAcs DNAcs DNAcs DNAts OxyMCs OxyGs |
| ASO-000540 | ASO-000540 | CCTtaatttcaccCTC | 153 | 136053 | 136068 | OxyMCs OxyMCs OxyTs DNAts DNAas DNAas DNAts DNAts DNAts DNAcs DNAas DNAcs DNAcs OxyMCs OxyTs OxyMC |
| ASO-000555 | ASO-000555 | CTTaatttcaccCTC | 154 | 136053 | 136067 | OxyMCs OxyTs OxyTs DNAas DNAas DNAts DNAts DNAts DNAcs DNAas DNAcs DNAcs OxyMCs OxyTs OxyMC |
| ASO-000579 | ASO-000579 | TTAatttcaccCTC | 155 | 136053 | 136066 | OxyTs OxyTs OxyAs DNAas DNAts DNAts DNAts DNAcs DNAas DNAcs DNAcs OxyMCs OxyTs OxyMC |
| ASO-000540-1 | ASO-002130 | CCCttaatttcacccTC | 156 | 136053 | 136069 | OxyMCs OxyMCs OxyMCs DNAts DNAts DNAas DNAas DNAts DNAts DNAts DNAcs DNAas DNAcs DNAcs DNAcs OxyTs OxyMCs |

Figure 2R

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-10 | ASO-002143 | CCCTtaatttcaccCTC | 157 | 136053 | 136069 | OxyMCs OxyMCs OxyMCs OxyTs DNAts DNAas DNAas DNAts DNAts DNAts DNAcs DNAas DNAcs DNAcs OxyMCs OxyTs OxyMCs |
| ASO-000540-11 | ASO-002155 | CCCTtaatttcacCcTC | 158 | 136053 | 136069 | OxyMCs OxyMCs OxyMCs OxyTs DNAts DNAas DNAas DNAts DNAts DNAts DNAcs DNAas DNAcs OxyMCs DNAcs OxyTs OxyMCs |
| ASO-000540-12 | ASO-002167 | CCCTtaatttcacCCTC | 159 | 136053 | 136069 | OxyMCs OxyMCs OxyMCs OxyTs DNAts DNAas DNAas DNAts DNAts DNAts DNAcs DNAas DNAcs OxyMCs OxyMCs OxyTs OxyMCs |
| ASO-000540-13 | ASO-002179 | CCCTtaatttcaCccTC | 160 | 136053 | 136069 | OxyMCs OxyMCs OxyMCs OxyTs DNAts DNAas DNAas DNAts DNAts DNAts DNAcs DNAas OxyMCs DNAcs DNAcs OxyTs OxyMCs |
| ASO-000540-14 | ASO-002191 | CCttaATttcaccctCA | 161 | 136052 | 136068 | OxyMCs OxyMCs DNAts DNAts DNAas OxyAs OxyTs DNAts DNAts DNAcs DNAas DNAcs DNAcs DNAcs DNAts OxyMCs OxyAs |
| ASO-000540-15 | ASO-002108 | CCTtaatttcacccTCA | 162 | 136052 | 136068 | OxyMCs OxyMCs OxyTs DNAts DNAas DNAas DNAts DNAts DNAts DNAcs DNAas DNAcs DNAcs DNAcs OxyTs OxyMCs OxyAs |
| ASO-000540-16 | ASO-002120 | CCTtaaTttcaccctCA | 163 | 136052 | 136068 | OxyMCs OxyMCs OxyTs DNAts DNAas DNAas OxyTs DNAts DNAts DNAcs DNAas DNAcs DNAcs DNAcs DNAts OxyMCs OxyAs |
| ASO-000540-17 | ASO-002132 | CCTtaAtttcaccctCA | 164 | 136052 | 136068 | OxyMCs OxyMCs OxyTs DNAts DNAas OxyAs DNAts DNAts DNAts DNAcs DNAas DNAcs DNAcs DNAcs DNAts OxyMCs OxyAs |
| ASO-000540-18 | ASO-002144 | CCTtaATttcaccctCA | 165 | 136052 | 136068 | OxyMCs OxyMCs OxyTs DNAts DNAas OxyAs OxyTs DNAts DNAts DNAcs DNAas DNAcs DNAcs DNAcs DNAts OxyMCs OxyAs |

Figure 2S

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-19 | ASO-002156 | CCTtaATttcacccTCA | 166 | 136052 | 136068 | OxyMCs OxyMCs OxyTs DNAts DNAas OxyAs OxyTs DNAts DNAts DNAcs DNAas DNAcs DNAcs DNAcs OxyTs OxyMCs OxyAs |
| ASO-000540-2 | ASO-002142 | CCCttaatttcaccCTC | 167 | 136053 | 136069 | OxyMCs OxyMCs OxyMCs DNAts DNAts DNAas DNAas DNAts DNAts DNAts DNAcs DNAas DNAcs DNAcs OxyMCs OxyTs OxyMCs |
| ASO-000540-20 | ASO-002168 | CCTTaatttcaccCtCA | 168 | 136052 | 136068 | OxyMCs OxyMCs OxyTs OxyTs DNAas DNAas DNAts DNAts DNAts DNAcs DNAas DNAcs DNAcs OxyMCs DNAts OxyMCs OxyAs |
| ASO-000540-56 | ASO-002201 | TCCcttaatttcacCcTC | 169 | 136053 | 136070 | OxyTs OxyMCs OxyMCs DNAcs DNAts DNAts DNAas DNAas DNAts DNAts DNAts DNAcs DNAas DNAcs OxyMCs DNAcs OxyTs OxyMCs |
| ASO-000540-57 | ASO-002205 | TCCcTtaatttcacccTC | 170 | 136053 | 136070 | OxyTs OxyMCs OxyMCs DNAcs OxyTs DNAts DNAas DNAas DNAts DNAts DNAts DNAcs DNAas DNAcs DNAcs DNAcs OxyTs OxyMCs |
| ASO-000540-58 | ASO-002209 | TCCcTtaatttcacCcTC | 171 | 136053 | 136070 | OxyTs OxyMCs OxyMCs DNAcs OxyTs DNAts DNAas DNAas DNAts DNAts DNAts DNAcs DNAas DNAcs OxyMCs DNAcs OxyTs OxyMCs |
| ASO-000540-59 | ASO-002213 | TCCcTtaatttcaCccTC | 172 | 136053 | 136070 | OxyTs OxyMCs OxyMCs DNAcs OxyTs DNAts DNAas DNAas DNAts DNAts DNAts DNAcs DNAas OxyMCs DNAcs DNAcs OxyTs OxyMCs |
| ASO-000540-6 | ASO-002190 | CCCttaatttcAcCcTC | 173 | 136053 | 136069 | OxyMCs OxyMCs OxyMCs DNAts DNAts DNAas DNAas DNAts DNAts DNAts DNAcs OxyAs DNAcs OxyMCs DNAcs OxyTs OxyMCs |
| ASO-000540-60 | ASO-002217 | TCCcTtaatttcAcCcTC | 174 | 136053 | 136070 | OxyTs OxyMCs OxyMCs DNAcs OxyTs DNAts DNAas DNAas DNAts DNAts DNAts DNAcs OxyAs DNAcs OxyMCs DNAcs OxyTs OxyMCs |

Figure 2T

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-61 | ASO-002221 | TCCCttaatttcacCCTC | 175 | 136053 | 136070 | OxyTs OxyMCs OxyMCs OxyMCs DNAts DNAts DNAas DNAas DNAts DNAts DNAts DNAcs DNAas DNAcs OxyMCs OxyMCs OxyTs OxyMCs |
| ASO-000540-62 | ASO-002225 | TCCCttaatttcaCcCTC | 176 | 136053 | 136070 | OxyTs OxyMCs OxyMCs OxyMCs DNAts DNAts DNAas DNAas DNAts DNAts DNAts DNAcs DNAas OxyMCs DNAcs OxyMCs OxyTs OxyMCs |
| ASO-000540-63 | ASO-002198 | TCCCttaatttcaCCcTC | 177 | 136053 | 136070 | OxyTs OxyMCs OxyMCs OxyMCs DNAts DNAts DNAas DNAas DNAts DNAts DNAts DNAcs DNAas OxyMCs OxyMCs DNAcs OxyTs OxyMCs |
| ASO-000540-64 | ASO-002202 | TCCCttaatttcAccCTC | 178 | 136053 | 136070 | OxyTs OxyMCs OxyMCs OxyMCs DNAts DNAts DNAas DNAas DNAts DNAts DNAts DNAcs OxyAs DNAcs DNAcs OxyMCs OxyTs OxyMCs |
| ASO-000540-65 | ASO-002206 | TCCCttaatttCaccCTC | 179 | 136053 | 136070 | OxyTs OxyMCs OxyMCs OxyMCs DNAts DNAts DNAas DNAas DNAts DNAts DNAts OxyMCs DNAas DNAcs DNAcs OxyMCs OxyTs OxyMCs |
| ASO-000540-66 | ASO-002210 | TCcCTtaatttcacCctCA | 180 | 136052 | 136070 | OxyTs OxyMCs DNAcs OxyMCs OxyTs DNAts DNAas DNAas DNAts DNAts DNAts DNAcs DNAas DNAcs OxyMCs DNAcs DNAts OxyMCs OxyAs |
| ASO-000540-67 | ASO-002214 | TCCcttaatttcacccTCA | 181 | 136052 | 136070 | OxyTs OxyMCs OxyMCs DNAcs DNAts DNAts DNAas DNAas DNAts DNAts DNAts DNAcs DNAas DNAcs DNAcs DNAcs OxyTs OxyMCs OxyAs |
| ASO-000540-68 | ASO-002218 | TCCcTtaatttcaccCtCA | 182 | 136052 | 136070 | OxyTs OxyMCs OxyMCs DNAcs OxyTs DNAts DNAas DNAas DNAts DNAts DNAts DNAcs DNAas DNAcs DNAcs OxyMCs DNAts OxyMCs OxyAs |
| ASO-000540-mm1 | ASO-002297 | CCTtgatttcaccCTC | 183 | 136053 | 136068 | OxyMCs OxyMCs OxyTs DNAts DNAgs DNAas DNAts DNAts DNAts DNAcs DNAas DNAcs DNAcs OxyMCs OxyTs OxyMCs |

Figure 2U

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-mm2 | ASO-002309 | CCTtaatttcgccCTC | 184 | 136053 | 136068 | OxyMCs OxyMCs OxyTs DNAts DNAas DNAas DNAts DNAts DNAts DNAcs DNAgs DNAcs DNAcs OxyMCs OxyTs OxyMCs |
| ASO-000540-mm3 | ASO-002321 | CCTtagtttcaccCTC | 185 | 136053 | 136068 | OxyMCs OxyMCs OxyTs DNAts DNAas DNAgs DNAts DNAts DNAts DNAcs DNAas DNAcs DNAcs OxyMCs OxyTs OxyMCs |
| ASO-000540-mm4 | ASO-002333 | CCTtgatttcgccCTC | 186 | 136053 | 136068 | OxyMCs OxyMCs OxyTs DNAts DNAgs DNAas DNAts DNAts DNAts DNAcs DNAgs DNAcs DNAcs OxyMCs OxyTs OxyMCs |
| ASO-000540-mm5 | ASO-002345 | CCTtggtttcaccCTC | 187 | 136053 | 136068 | OxyMCs OxyMCs OxyTs DNAts DNAgs DNAgs DNAts DNAts DNAts DNAcs DNAas DNAcs DNAcs OxyMCs OxyTs OxyMCs |
| ASO-000540-mm6 | ASO-002357 | CCTtagtttcgccCTC | 188 | 136053 | 136068 | OxyMCs OxyMCs OxyTs DNAts DNAas DNAgs DNAts DNAts DNAts DNAcs DNAgs DNAcs DNAcs OxyMCs OxyTs OxyMCs |
| TBD-mm1 | ASO-002369 | CCCttgatttcacccTC | 189 | 136052 | 136068 | OxyMCs OxyMCs OxyMCs DNAts DNAts DNAgs DNAas DNAts DNAts DNAts DNAcs DNAas DNAcs DNAcs DNAcs OxyTs OxyMCs |
| TBD-mm2 | ASO-002381 | CCCttagtttcacccTC | 190 | 136053 | 136069 | OxyMCs OxyMCs OxyMCs DNAts DNAts DNAas DNAgs DNAts DNAts DNAts DNAcs DNAas DNAcs DNAcs DNAcs OxyTs OxyMCs |
| TBD-mm25 | ASO-002372 | TcCCTtgatttcacCcTC | 191 | 136052 | 136069 | OxyTs DNAcs OxyMCs OxyMCs OxyTs DNAts DNAgs DNAas DNAts DNAts DNAts DNAcs DNAas DNAcs OxyMCs DNAcs OxyTs OxyMCs |
| TBD-mm26 | ASO-002384 | TcCCTtaatttcgcCcTC | 192 | 136052 | 136069 | OxyTs DNAcs OxyMCs OxyMCs OxyTs DNAts DNAas DNAas DNAts DNAts DNAts DNAcs DNAgs DNAcs OxyMCs DNAcs OxyTs OxyMCs |

Figure 2V

| Oligomer Name | ASO Number | ASO Sequence | SEQ ID NO | premRNA start NG_007398 | premRNA end NG_007398 | Chemical Structure |
|---|---|---|---|---|---|---|
| TBD-mm27 | ASO-002301 | TcCCTtagtttcacCcTC | 193 | 136052 | 136069 | OxyTs DNAcs OxyMCs OxyMCs OxyTs DNAts DNAas DNAgs DNAts DNAts DNAts DNAcs DNAas DNAcs OxyMCs DNAcs OxyTs OxyMCs |
| TBD-mm28 | ASO-002313 | TcCCTtgatttcgcCcTC | 194 | 136054 | 136071 | OxyTs DNAcs OxyMCs OxyMCs OxyTs DNAts DNAgs DNAas DNAts DNAts DNAts DNAcs DNAgs DNAcs OxyMCs DNAcs OxyTs OxyMCs |
| TBD-mm29 | ASO-002325 | TcCCTtagtttcgcCcTC | 195 | 136052 | 136069 | OxyTs DNAcs OxyMCs OxyMCs OxyTs DNAts DNAas DNAgs DNAts DNAts DNAts DNAcs DNAgs DNAcs OxyMCs DNAcs OxyTs OxyMCs |
| TBD-mm3 | ASO-002298 | CCCttaatttcgcccTC | 196 | 136053 | 136069 | OxyMCs OxyMCs OxyMCs DNAts DNAts DNAas DNAas DNAts DNAts DNAts DNAcs DNAgs DNAcs DNAcs DNAcs OxyTs OxyMCs |
| TBD-mm30 | ASO-002337 | AcCCTtgatttcacCcTC | 197 | 136053 | 136070 | OxyAs DNAcs OxyMCs OxyMCs OxyTs DNAts DNAgs DNAas DNAts DNAts DNAts DNAcs DNAas DNAcs OxyMCs DNAcs OxyTs OxyMCs |
| TBD-mm4 | ASO-002310 | CCCttgatttcgcccTC | 198 | 136054 | 136070 | OxyMCs OxyMCs OxyMCs DNAts DNAts DNAgs DNAas DNAts DNAts DNAts DNAcs DNAgs DNAcs DNAcs DNAcs OxyTs OxyMCs |
| TBD-mm5 | ASO-002322 | CCCttggtttcacccTC | 199 | 136052 | 136068 | OxyMCs OxyMCs OxyMCs DNAts DNAts DNAgs DNAgs DNAts DNAts DNAts DNAcs DNAas DNAcs DNAcs DNAcs OxyTs OxyMCs |
| TBD-mm6 | ASO-002334 | CCCttagtttcgcccTC | 200 | 136052 | 136068 | OxyMCs OxyMCs OxyMCs DNAts DNAts DNAas DNAgs DNAts DNAts DNAts DNAcs DNAgs DNAcs DNAcs DNAcs OxyTs OxyMCs |
| ASO-000662 | ASO-000662 | CCCttaatttcacCCT | 201 | 136054 | 136069 | OxyMCs OxyMCs OxyMCs DNAts DNAts DNAas DNAas DNAts DNAts DNAts DNAcs DNAas DNAcs OxyMCs OxyMCs OxyT |

Figure 2W

| Oligomer Name | ASO Number | ASO Sequence | SEQ ID NO | premRNA start NG_007398 | premRNA end NG_007398 | Chemical Structure |
|---|---|---|---|---|---|---|
| ASO-000566 | ASO-000566 | CCTtaatttcacCCT | 202 | 136054 | 136068 | OxyMCs OxyMCs OxyTs DNAts DNAas DNAas DNAts DNAts DNAts DNAcs DNAas DNAcs OxyMCs OxyMCs OxyT |
| ASO-000540-30 | ASO-002193 | TCCcTtaatttcaccCT | 203 | 136054 | 136070 | OxyTs OxyMCs OxyMCs DNAcs OxyTs DNAts DNAas DNAas DNAts DNAts DNAts DNAcs DNAas DNAcs DNAcs OxyMCs OxyTs |
| ASO-000540-31 | ASO-002110 | TCCcTtaatttcAccCT | 204 | 136054 | 136070 | OxyTs OxyMCs OxyMCs DNAcs OxyTs DNAts DNAas DNAas DNAts DNAts DNAts DNAcs OxyAs DNAcs DNAcs OxyMCs OxyTs |
| ASO-000540-32 | ASO-002122 | TCCcTTaatttcaccCT | 205 | 136054 | 136070 | OxyTs OxyMCs OxyMCs DNAcs OxyTs OxyTs DNAas DNAas DNAts DNAts DNAts DNAcs DNAas DNAcs DNAcs OxyMCs OxyTs |
| ASO-000540-33 | ASO-002134 | TCCCttaatttcacCCT | 206 | 136054 | 136070 | OxyTs OxyMCs OxyMCs OxyMCs DNAts DNAts DNAas DNAas DNAts DNAts DNAts DNAcs DNAas DNAcs OxyMCs OxyMCs OxyTs |
| ASO-000540-34 | ASO-002146 | TCCCttaatttcaCcCT | 207 | 136054 | 136070 | OxyTs OxyMCs OxyMCs OxyMCs DNAts DNAts DNAas DNAas DNAts DNAts DNAts DNAcs DNAas OxyMCs DNAcs OxyMCs OxyTs |
| ASO-000540-35 | ASO-002158 | TCCCttaatttcaCCCT | 208 | 136054 | 136070 | OxyTs OxyMCs OxyMCs OxyMCs DNAts DNAts DNAas DNAas DNAts DNAts DNAts DNAcs DNAas OxyMCs OxyMCs OxyMCs OxyTs |
| ASO-000540-36 | ASO-002170 | TCCCttaatttCaccCT | 209 | 136054 | 136070 | OxyTs OxyMCs OxyMCs OxyMCs DNAts DNAts DNAas DNAas DNAts DNAts DNAts OxyMCs DNAas DNAcs DNAcs OxyMCs OxyTs |
| ASO-000540-37 | ASO-002182 | CCCttaatttcaccctCA | 210 | 136052 | 136069 | OxyMCs OxyMCs OxyMCs DNAts DNAts DNAas DNAas DNAts DNAts DNAts DNAcs DNAas DNAcs DNAcs DNAcs DNAts OxyMCs OxyAs |

Figure 2X

| Oligomer Name | ASO Number | ASO Sequence | SEQ ID NO | premRNA start NG_007398 | premRNA end NG_007398 | Chemical Structure |
|---|---|---|---|---|---|---|
| ASO-000540-38 | ASO-002194 | CCCttaatttcacccTCA | 211 | 136052 | 136069 | OxyMCs OxyMCs OxyMCs DNAts DNAts DNAas DNAas DNAts DNAts DNAts DNAcs DNAas DNAcs DNAcs DNAcs OxyTs OxyMCs OxyAs |
| ASO-000540-39 | ASO-002111 | CCCttaatttcacCctCA | 212 | 136052 | 136069 | OxyMCs OxyMCs OxyMCs DNAts DNAts DNAas DNAas DNAts DNAts DNAts DNAcs DNAas DNAcs OxyMCs DNAcs DNAts OxyMCs OxyAs |
| ASO-000540-4 | ASO-002166 | CCCttaatttcaCccTC | 213 | 136053 | 136069 | OxyMCs OxyMCs OxyMCs DNAts DNAts DNAas DNAas DNAts DNAts DNAts DNAcs DNAas OxyMCs DNAcs DNAcs OxyTs OxyMCs |
| ASO-000540-40 | ASO-002123 | CCCttaatttcaCcctCA | 214 | 136052 | 136069 | OxyMCs OxyMCs OxyMCs DNAts DNAts DNAas DNAas DNAts DNAts DNAts DNAcs DNAas OxyMCs DNAcs DNAcs DNAts OxyMCs OxyAs |
| ASO-000540-41 | ASO-002135 | CCCttaatttcAcCctCA | 215 | 136052 | 136069 | OxyMCs OxyMCs OxyMCs DNAts DNAts DNAas DNAas DNAts DNAts DNAts DNAcs OxyAs DNAcs OxyMCs DNAcs DNAts OxyMCs OxyAs |
| TBD-mm13 | ASO-002323 | TcCCtTgatttcaccCT | 216 | 136053 | 136069 | OxyTs DNAcs OxyMCs OxyMCs DNAts OxyTs DNAgs DNAas DNAts DNAts DNAts DNAcs DNAas DNAcs DNAcs OxyMCs OxyTs |
| TBD-mm14 | ASO-002335 | TcCCtTaatttcaccCA | 217 | 136052 | 136068 | OxyTs DNAcs OxyMCs OxyMCs DNAts OxyTs DNAas DNAas DNAts DNAts DNAts DNAcs DNAas DNAcs DNAcs OxyMCs OxyAs |
| TBD-mm15 | ASO-002347 | TcCCtTaatttcgccCT | 218 | 136053 | 136069 | OxyTs DNAcs OxyMCs OxyMCs DNAts OxyTs DNAas DNAas DNAts DNAts DNAts DNAcs DNAgs DNAcs DNAcs OxyMCs OxyTs |
| TBD-mm16 | ASO-002359 | TcCCtTgatttcaccCA | 219 | 136053 | 136069 | OxyTs DNAcs OxyMCs OxyMCs DNAts OxyTs DNAgs DNAas DNAts DNAts DNAts DNAcs DNAas DNAcs DNAcs OxyMCs OxyAs |

Figure 2Y

| Oligomer Name | ASO Number | ASO Sequence | SEQ ID NO | premRNA start NG_007398 | premRNA end NG_007398 | Chemical Structure |
|---|---|---|---|---|---|---|
| TBD-mm17 | ASO-002371 | TcCCtTgatttcaccCG | 220 | 136052 | 136068 | OxyTs DNAcs OxyMCs OxyMCs DNAts OxyTs DNAgs DNAas DNAts DNAts DNAts DNAcs DNAas DNAcs DNAcs OxyMCs OxyGs |
| TBD-mm18 | ASO-002383 | TcCCtTagtttcgccCT | 221 | 136052 | 136068 | OxyTs DNAcs OxyMCs OxyMCs DNAts OxyTs DNAas DNAgs DNAts DNAts DNAts DNAcs DNAgs DNAcs DNAcs OxyMCs OxyTs |
| ASO-000628 | ASO-000628 | CCTtaatttcaCCC | 222 | 136055 | 136068 | OxyMCs OxyMCs OxyTs DNAts DNAas DNAas DNAts DNAts DNAts DNAcs DNAas OxyMCs OxyMCs OxyMC |
| ASO-000642 | ASO-000642 | CCCttaatttcaCCC | 223 | 136055 | 136069 | OxyMCs OxyMCs OxyMCs DNAts DNAts DNAas DNAas DNAts DNAts DNAts DNAcs DNAas OxyMCs OxyMCs OxyMC |
| ASO-000274 | ASO-000274 | TCCcttaatttcaCCC | 224 | 136055 | 136070 | OxyTs OxyMCs OxyMCs DNAcs DNAts DNAts DNAas DNAas DNAts DNAts DNAts DNAcs DNAas OxyMCs OxyMCs OxyMC |
| ASO-000339 | ASO-000339 | CCttaatttcaCCC | 225 | 136055 | 136068 | OxyMCs OxyMCs DNAts DNAts DNAas DNAas DNAts DNAts DNAts DNAcs DNAas OxyMCs OxyMCs OxyMC |
| ASO-000536 | ASO-000536 | TTCccttaatttcACC | 226 | 136056 | 136071 | OxyTs OxyTs OxyMCs DNAcs DNAcs DNAts DNAts DNAas DNAas DNAts DNAts DNAts DNAcs OxyAs OxyMCs OxyMC |
| ASO-000603 | ASO-000603 | TCCcttaatttcACC | 227 | 136056 | 136070 | OxyTs OxyMCs OxyMCs DNAcs DNAts DNAts DNAas DNAas DNAts DNAts DNAts DNAcs OxyAs OxyMCs OxyMC |
| ASO-000666 | ASO-000666 | TCCcttaatttCAC | 228 | 136057 | 136070 | OxyTs OxyMCs OxyMCs DNAcs DNAts DNAts DNAas DNAas DNAts DNAts DNAts OxyMCs OxyAs OxyMC |

Figure 2Z

| Oligomer Name | ASO Number | ASO Sequence | SEQ ID NO | premRNA start NG_007398 | premRNA end NG_007398 | Chemical Structure |
|---|---|---|---|---|---|---|
| ASO-000272 | ASO-000272 | AGAgtgagaggctGGG | 229 | 136099 | 136114 | OxyAs OxyGs OxyAs DNAgs DNAts DNAgs DNAas DNAgs DNAas DNAgs DNAgs DNAcs DNAts OxyGs OxyGs OxyG |
| ASO-000255 | ASO-000255 | TGGatgagtggaaCTG | 230 | 136115 | 136130 | OxyTs OxyGs OxyGs DNAas DNAts DNAgs DNAas DNAgs DNAts DNAgs DNAgs DNAas DNAas OxyMCs OxyTs OxyG |
| ASO-000336 | ASO-000336 | GGAtgagtggaACT | 231 | 136116 | 136129 | OxyGs OxyGs OxyAs DNAts DNAgs DNAas DNAgs DNAts DNAgs DNAgs DNAas OxyAs OxyMCs OxyT |
| ASO-000206 | ASO-000206 | GTTggatgagtgGAA | 232 | 136118 | 136132 | OxyGs OxyTs OxyTs DNAgs DNAgs DNAas DNAts DNAgs DNAas DNAgs DNAts DNAgs OxyGs OxyAs OxyA |
| ASO-000271 | ASO-000271 | AGTtggatgagtGGA | 233 | 136119 | 136133 | OxyAs OxyGs OxyTs DNAts DNAgs DNAgs DNAas DNAts DNAgs DNAas DNAgs DNAts OxyGs OxyGs OxyA |
| ASO-000340 | ASO-000340 | GTTggatgagtGGA | 234 | 136119 | 136132 | OxyGs OxyTs OxyTs DNAgs DNAgs DNAas DNAts DNAgs DNAas DNAgs DNAts OxyGs OxyGs OxyA |
| ASO-000229 | ASO-000229 | CAGggaaccgaatCAG | 235 | 136160 | 136175 | OxyMCs OxyAs OxyGs DNAgs DNAgs DNAas DNAas DNAcs DNAmcs DNAgs DNAas DNAas DNAts OxyMCs OxyAs OxyG |
| ASO-000273 | ASO-000273 | GCCctggctcacaTCT | 236 | 136193 | 136208 | OxyGs OxyMCs OxyMCs DNAcs DNAts DNAgs DNAgs DNAcs DNAts DNAcs DNAas DNAcs DNAas OxyTs OxyMCs OxyT |
| ASO-000264 | ASO-000264 | ACAaggcagaaacACC | 237 | 136229 | 136244 | OxyAs OxyMCs OxyAs DNAas DNAgs DNAgs DNAcs DNAas DNAgs DNAas DNAas DNAas DNAcs OxyAs OxyMCs OxyMC |
| ASO-000341 | ASO-000341 | TGTcaacaaggCAG | 238 | 136236 | 136249 | OxyTs OxyGs OxyTs DNAcs DNAas DNAas DNAcs DNAas DNAas DNAgs DNAgs OxyMCs OxyAs OxyG |

Figure 2AA

| Oligomer Name | ASO Number | ASO Sequence | SEQ ID NO | premRNA start NG_007398 | premRNA end NG_007398 | Chemical Structure |
|---|---|---|---|---|---|---|
| ASO-000198 | ASO-000198 | TGCcctgggtgccTTG | 239 | 136355 | 136370 | OxyTs OxyGs OxyMCs DNAcs DNAcs DNAts DNAgs DNAgs DNAgs DNAts DNAgs DNAcs DNAcs OxyTs OxyTs OxyG |
| ASO-000210 | ASO-000210 | AGCgggactgtggGCC | 240 | 136371 | 136386 | OxyAs OxyGs OxyMCs DNAgs DNAgs DNAgs DNAas DNAcs DNAts DNAgs DNAts DNAgs DNAgs OxyGs OxyMCs OxyMC |
| ASO-000342 | ASO-000342 | GGgacagcgggACT | 241 | 136378 | 136391 | OxyGs OxyGs DNAgs DNAas DNAcs DNAas DNAgs DNAmcs DNAgs DNAgs DNAgs OxyAs OxyMCs OxyT |
| ASO-000333 | ASO-000333 | GCGggctgggctgTCT | 242 | 136427 | 136442 | OxyGs OxyMCs OxyGs DNAgs DNAgs DNAcs DNAts DNAgs DNAgs DNAgs DNAcs DNAts DNAgs OxyTs OxyMCs OxyT |
| ASO-000199 | ASO-000199 | CAGaacagacagcATG | 243 | 136541 | 136556 | OxyMCs OxyAs OxyGs DNAas DNAas DNAcs DNAas DNAgs DNAas DNAcs DNAas DNAgs DNAcs OxyAs OxyTs OxyG |
| ASO-000280 | ASO-000280 | TCTatgtatatgtTCA | 244 | 136567 | 136582 | OxyTs OxyMCs OxyTs DNAas DNAts DNAgs DNAts DNAas DNAts DNAas DNAts DNAgs DNAts OxyTs OxyMCs OxyA |
| ASO-000211 | ASO-000211 | ATCtatgtatatgTTC | 245 | 136568 | 136583 | OxyAs OxyTs OxyMCs DNAts DNAas DNAts DNAgs DNAts DNAas DNAts DNAas DNAts DNAgs OxyTs OxyTs OxyMC |
| ASO-000347 | ASO-000347 | CATctatgtataTGT | 246 | 136570 | 136584 | OxyMCs OxyAs OxyTs DNAcs DNAts DNAas DNAts DNAgs DNAts DNAas DNAts DNAas OxyTs OxyGs OxyT |
| ASO-000352 | ASO-000352 | ACAtctatgtataTGT | 247 | 136570 | 136585 | OxyAs OxyMCs OxyAs DNAts DNAcs DNAts DNAas DNAts DNAgs DNAts DNAas DNAts DNAas OxyTs OxyGs OxyT |

Figure 2BB

| Oligomer Name | ASO Number | ASO Sequence | SEQ ID NO | premRNA start NG_007398 | premRNA end NG_007398 | Chemical Structure |
|---|---|---|---|---|---|---|
| ASO-000232 | ASO-000232 | CAAcagggtgcagATG | 248 | 136600 | 136615 | OxyMCs OxyAs OxyAs DNAcs DNAas DNAgs DNAgs DNAgs DNAts DNAgs DNAcs DNAas DNAgs OxyAs OxyTs OxyG |
| ASO-000257 | ASO-000257 | AGCataaacagacAAA | 249 | 136629 | 136644 | OxyAs OxyGs OxyMCs DNAas DNAts DNAas DNAas DNAas DNAcs DNAas DNAgs DNAas DNAcs OxyAs OxyAs OxyA |
| ASO-000388 | ASO-000388 | ATAgtcactctggTGA | 250 | 136650 | 136665 | OxyAs OxyTs OxyAs DNAgs DNAts DNAcs DNAas DNAcs DNAts DNAcs DNAts DNAgs DNAgs OxyTs OxyGs OxyA |
| ASO-000390 | ASO-000390 | TAGtcactctggTGA | 251 | 136650 | 136664 | OxyTs OxyAs OxyGs DNAts DNAcs DNAas DNAcs DNAts DNAcs DNAts DNAgs DNAgs OxyTs OxyGs OxyA |
| ASO-000413 | ASO-000413 | AGTcactctggTGA | 252 | 136650 | 136663 | OxyAs OxyGs OxyTs DNAcs DNAas DNAcs DNAts DNAcs DNAts DNAgs DNAgs OxyTs OxyGs OxyA |
| ASO-000405 | ASO-000405 | CATagtcactctgGTG | 253 | 136651 | 136666 | OxyMCs OxyAs OxyTs DNAas DNAgs DNAts DNAcs DNAas DNAcs DNAts DNAcs DNAts DNAgs OxyGs OxyTs OxyG |
| ASO-000430 | ASO-000430 | TAGtcactctgGTG | 254 | 136651 | 136664 | OxyTs OxyAs OxyGs DNAts DNAcs DNAas DNAcs DNAts DNAcs DNAts DNAgs OxyGs OxyTs OxyG |
| ASO-000447 | ASO-000447 | TCAtagtcactctGGT | 255 | 136652 | 136667 | OxyTs OxyMCs OxyAs DNAts DNAas DNAgs DNAts DNAcs DNAas DNAcs DNAts DNAcs DNAts OxyGs OxyGs OxyT |
| ASO-000396 | ASO-000396 | TACatgcgtccTTT | 256 | 136693 | 136706 | OxyTs OxyAs OxyMCs DNAas DNAts DNAgs DNAmcs DNAgs DNAts DNAcs DNAcs OxyTs OxyTs OxyT |
| ASO-000395 | ASO-000395 | GATacatgcgtccTTT | 257 | 136693 | 136708 | OxyGs OxyAs OxyTs DNAas DNAcs DNAas DNAts DNAgs DNAmcs DNAgs DNAts DNAcs DNAcs OxyTs OxyTs OxyT |

Figure 2CC

| Oligomer Name | ASO Number | ASO Sequence | SEQ ID NO | premRNA start NG_007398 | premRNA end NG_007398 | Chemical Structure |
|---|---|---|---|---|---|---|
| ASO-000394 | ASO-000394 | AAGatacatgcgtCCT | 258 | 136695 | 136710 | OxyAs OxyAs OxyGs DNAas DNAts DNAas DNAcs DNAas DNAts DNAgs DNAmcs DNAgs DNAts OxyMCs OxyMCs OxyT |
| ASO-000421 | ASO-000421 | TTCaagatacatgCGT | 259 | 136698 | 136713 | OxyTs OxyTs OxyMCs DNAas DNAas DNAgs DNAas DNAts DNAas DNAcs DNAas DNAts DNAgs OxyMCs OxyGs OxyT |
| ASO-000400 | ASO-000400 | ATTtcaagatacaTGC | 260 | 136700 | 136715 | OxyAs OxyTs OxyTs DNAts DNAcs DNAas DNAas DNAgs DNAas DNAts DNAas DNAcs DNAas OxyTs OxyGs OxyMC |
| ASO-000248 | ASO-000248 | GCAtttcaagataCAT | 261 | 136702 | 136717 | OxyGs OxyMCs OxyAs DNAts DNAts DNAts DNAcs DNAas DNAas DNAgs DNAas DNAts DNAas OxyMCs OxyAs OxyT |
| ASO-000451 | ASO-000451 | AAGcatttcaagaTAC | 262 | 136704 | 136719 | OxyAs OxyAs OxyGs DNAcs DNAas DNAts DNAts DNAts DNAcs DNAas DNAas DNAgs DNAas OxyTs OxyAs OxyMC |
| ASO-000707 | ASO-000707 | ACAagcatttcaaGAT | 263 | 136706 | 136721 | OxyAs OxyMCs OxyAs DNAas DNAgs DNAcs DNAas DNAts DNAts DNAts DNAcs DNAas DNAas OxyGs OxyAs OxyT |
| ASO-000619 | ASO-000619 | TTAcaagcatttcAAG | 264 | 136708 | 136723 | OxyTs OxyTs OxyAs DNAcs DNAas DNAas DNAgs DNAcs DNAas DNAts DNAts DNAts DNAcs OxyAs OxyAs OxyG |
| ASO-000671 | ASO-000671 | AACctctttacaaGCA | 265 | 136715 | 136730 | OxyAs OxyAs OxyMCs DNAcs DNAts DNAcs DNAts DNAts DNAts DNAas DNAcs DNAas DNAas OxyGs OxyMCs OxyA |
| ASO-000221 | ASO-000221 | GTTagaaacctctTTA | 266 | 136721 | 136736 | OxyGs OxyTs OxyTs DNAas DNAgs DNAas DNAas DNAas DNAcs DNAcs DNAts DNAcs DNAts OxyTs OxyTs OxyA |

Figure 2DD

| Oligomer Name | ASO Number | ASO Sequence | SEQ ID NO | premRNA start NG_007398 | premRNA end NG_007398 | Chemical Structure |
|---|---|---|---|---|---|---|
| ASO-000298 | ASO-000298 | CCAcacaggccacACG | 267 | 136776 | 136791 | OxyMCs OxyMCs OxyAs DNAcs DNAas DNAcs DNAas DNAgs DNAgs DNAcs DNAcs DNAas DNAcs OxyAs OxyMCs OxyG |
| ASO-000311 | ASO-000311 | GTCtctgttgggtCCC | 268 | 136842 | 136857 | OxyGs OxyTs OxyMCs DNAts DNAcs DNAts DNAgs DNAts DNAts DNAgs DNAgs DNAgs DNAts OxyMCs OxyMCs OxyMC |
| ASO-000290 | ASO-000290 | TGAacggcctcctTAG | 269 | 136871 | 136886 | OxyTs OxyGs OxyAs DNAas DNAmcs DNAgs DNAgs DNAcs DNAcs DNAts DNAcs DNAcs DNAts OxyTs OxyAs OxyG |
| ASO-000437 | ASO-000437 | CTGtgcttcaggcCTT | 270 | 136896 | 136911 | OxyMCs OxyTs OxyGs DNAts DNAgs DNAcs DNAts DNAts DNAcs DNAas DNAgs DNAgs DNAcs OxyMCs OxyTs OxyT |
| ASO-000446 | ASO-000446 | TCCtgtgcttcagGCC | 271 | 136898 | 136913 | OxyTs OxyMCs OxyMCs DNAts DNAgs DNAts DNAgs DNAcs DNAts DNAts DNAcs DNAas DNAgs OxyGs OxyMCs OxyMC |
| ASO-000685 | ASO-000685 | AATcctgtgcttcAGG | 272 | 136900 | 136915 | OxyAs OxyAs OxyTs DNAcs DNAcs DNAts DNAgs DNAts DNAgs DNAcs DNAts DNAts DNAcs OxyAs OxyGs OxyG |
| ASO-000410 | ASO-000410 | TCCtgtgcttcAGG | 273 | 136900 | 136913 | OxyTs OxyMCs OxyMCs DNAts DNAgs DNAts DNAgs DNAcs DNAts DNAts DNAcs OxyAs OxyGs OxyG |
| ASO-000604 | ASO-000604 | AATcctgtgcttCAG | 274 | 136901 | 136915 | OxyAs OxyAs OxyTs DNAcs DNAcs DNAts DNAgs DNAts DNAgs DNAcs DNAts DNAts OxyMCs OxyAs OxyG |
| ASO-000490 | ASO-000490 | TAAtcctgtgcttCAG | 275 | 136901 | 136916 | OxyTs OxyAs OxyAs DNAts DNAcs DNAcs DNAts DNAgs DNAts DNAgs DNAcs DNAts DNAts OxyMCs OxyAs OxyG |

Figure 2EE

| Oligomer Name | ASO Number | ASO Sequence | SEQ ID NO | premRNA start NG_007398 | premRNA end NG_007398 | Chemical Structure |
|---|---|---|---|---|---|---|
| ASO-000529 | ASO-000529 | AATcctgtgctTCA | 276 | 136902 | 136915 | OxyAs OxyAs OxyTs DNAcs DNAcs DNAts DNAgs DNAts DNAgs DNAcs DNAts OxyTs OxyMCs OxyA |
| ASO-000532 | ASO-000532 | CTAatcctgtgctTCA | 277 | 136902 | 136917 | OxyMCs OxyTs OxyAs DNAas DNAts DNAcs DNAcs DNAts DNAgs DNAts DNAgs DNAcs DNAts OxyTs OxyMCs OxyA |
| ASO-000508 | ASO-000508 | TAAtcctgtgctTCA | 278 | 136902 | 136916 | OxyTs OxyAs OxyAs DNAts DNAcs DNAcs DNAts DNAgs DNAts DNAgs DNAcs DNAts OxyTs OxyMCs OxyA |
| ASO-000219 | ASO-000219 | CCTaatcctgtgcTTC | 279 | 136903 | 136918 | OxyMCs OxyMCs OxyTs DNAas DNAas DNAts DNAcs DNAcs DNAts DNAgs DNAts DNAgs DNAcs OxyTs OxyTs OxyMC |
| ASO-000656 | ASO-000656 | TAAtcctgtgcTTC | 280 | 136903 | 136916 | OxyTs OxyAs OxyAs DNAts DNAcs DNAcs DNAts DNAgs DNAts DNAgs DNAcs OxyTs OxyTs OxyMC |
| ASO-000522 | ASO-000522 | CTAatcctgtgcTTC | 281 | 136903 | 136917 | OxyMCs OxyTs OxyAs DNAas DNAts DNAcs DNAcs DNAts DNAgs DNAts DNAgs DNAcs OxyTs OxyTs OxyMC |
| ASO-000513 | ASO-000513 | CCTaatcctgtgCTT | 282 | 136904 | 136918 | OxyMCs OxyMCs OxyTs DNAas DNAas DNAts DNAcs DNAcs DNAts DNAgs DNAts DNAgs OxyMCs OxyTs OxyT |
| ASO-000640 | ASO-000640 | TCCtaatcctgtgCTT | 283 | 136904 | 136919 | OxyTs OxyMCs OxyMCs DNAts DNAas DNAas DNAts DNAcs DNAcs DNAts DNAgs DNAts DNAgs OxyMCs OxyTs OxyT |
| ASO-000661 | ASO-000661 | CTAatcctgtgCTT | 284 | 136904 | 136917 | OxyMCs OxyTs OxyAs DNAas DNAts DNAcs DNAcs DNAts DNAgs DNAts DNAgs OxyMCs OxyTs OxyT |
| ASO-000478 | ASO-000478 | GTCctaatcctgtGCT | 285 | 136905 | 136920 | OxyGs OxyTs OxyMCs DNAcs DNAts DNAas DNAas DNAts DNAcs DNAcs DNAts DNAgs DNAts OxyGs OxyMCs OxyT |

Figure 2FF

| Oligomer Name | ASO Number | ASO Sequence | SEQ ID NO | premRNA start NG_007398 | premRNA end NG_007398 | Chemical Structure |
|---|---|---|---|---|---|---|
| ASO-000500 | ASO-000500 | TCCtaatcctgtGCT | 286 | 136905 | 136919 | OxyTs OxyMCs OxyMCs DNAts DNAas DNAas DNAts DNAcs DNAcs DNAts DNAgs DNAts OxyGs OxyMCs OxyT |
| ASO-000601 | ASO-000601 | CCTaatcctgtGCT | 287 | 136905 | 136918 | OxyMCs OxyMCs OxyTs DNAas DNAas DNAts DNAcs DNAcs DNAts DNAgs DNAts OxyGs OxyMCs OxyT |
| ASO-000643 | ASO-000643 | AGTcctaatcctgTGC | 288 | 136906 | 136921 | OxyAs OxyGs OxyTs DNAcs DNAcs DNAts DNAas DNAas DNAts DNAcs DNAcs DNAts DNAgs OxyTs OxyGs OxyMC |
| ASO-000600 | ASO-000600 | GTCctaatcctgTGC | 289 | 136906 | 136920 | OxyGs OxyTs OxyMCs DNAcs DNAts DNAas DNAas DNAts DNAcs DNAcs DNAts DNAgs OxyTs OxyGs OxyMC |
| ASO-000525 | ASO-000525 | TCCtaatcctgTGC | 290 | 136906 | 136919 | OxyTs OxyMCs OxyMCs DNAts DNAas DNAas DNAts DNAcs DNAcs DNAts DNAgs OxyTs OxyGs OxyMC |
| ASO-000453 | ASO-000453 | TCAgtcctaatccTGT | 291 | 136908 | 136923 | OxyTs OxyMCs OxyAs DNAgs DNAts DNAcs DNAcs DNAts DNAas DNAas DNAts DNAcs DNAcs OxyTs OxyGs OxyT |
| ASO-000553 | ASO-000553 | CTTcagtcctaatCCT | 292 | 136910 | 136925 | OxyMCs OxyTs OxyTs DNAcs DNAas DNAgs DNAts DNAcs DNAcs DNAts DNAas DNAas DNAts OxyMCs OxyMCs OxyT |
| ASO-000622 | ASO-000622 | GCTtcagtcctaATC | 293 | 136912 | 136926 | OxyGs OxyMCs OxyTs DNAts DNAcs DNAas DNAgs DNAts DNAcs DNAcs DNAts DNAas OxyAs OxyTs OxyMC |
| ASO-000325 | ASO-000325 | CTGacacagggagCCC | 294 | 136956 | 136971 | OxyMCs OxyTs OxyGs DNAas DNAcs DNAas DNAcs DNAas DNAgs DNAgs DNAgs DNAas DNAgs OxyMCs OxyMCs OxyMC |

Figure 2GG

| Oligomer Name | ASO Number | ASO Sequence | SEQ ID NO | premRNA start NG_007398 | premRNA end NG_007398 | Chemical Structure |
|---|---|---|---|---|---|---|
| ASO-000215 | ASO-000215 | GCCagaccagccaCAA | 295 | 136987 | 137002 | OxyGs OxyMCs OxyMCs DNAas DNAgs DNAas DNAcs DNAcs DNAas DNAgs DNAcs DNAcs DNAas OxyMCs OxyAs OxyA |
| ASO-000482 | ASO-000482 | CAGgagttgtaAGC | 296 | 137065 | 137078 | OxyMCs OxyAs OxyGs DNAgs DNAas DNAgs DNAts DNAts DNAgs DNAts DNAas OxyAs OxyGs OxyMC |
| ASO-000337 | ASO-000337 | TGCaggagttgtaAGC | 297 | 137065 | 137080 | OxyTs OxyGs OxyMCs DNAas DNAgs DNAgs DNAas DNAgs DNAts DNAts DNAgs DNAts DNAas OxyAs OxyGs OxyMC |
| ASO-000480 | ASO-000480 | ATGcaggagttgtAAG | 298 | 137066 | 137081 | OxyAs OxyTs OxyGs DNAcs DNAas DNAgs DNAgs DNAas DNAgs DNAts DNAts DNAgs DNAts OxyAs OxyAs OxyG |
| ASO-000644 | ASO-000644 | GATgcaggagttgTAA | 299 | 137067 | 137082 | OxyGs OxyAs OxyTs DNAgs DNAcs DNAas DNAgs DNAgs DNAas DNAgs DNAts DNAts DNAgs OxyTs OxyAs OxyA |
| ASO-000695 | ASO-000695 | TGCaggagttgTAA | 300 | 137067 | 137080 | OxyTs OxyGs OxyMCs DNAas DNAgs DNAgs DNAas DNAgs DNAts DNAts DNAgs OxyTs OxyAs OxyA |
| ASO-000455 | ASO-000455 | TGAtgcaggagttGTA | 301 | 137068 | 137083 | OxyTs OxyGs OxyAs DNAts DNAgs DNAcs DNAas DNAgs DNAgs DNAas DNAgs DNAts DNAts OxyGs OxyTs OxyA |
| ASO-000531 | ASO-000531 | GTGatgcaggagtTGT | 302 | 137069 | 137084 | OxyGs OxyTs OxyGs DNAas DNAts DNAgs DNAcs DNAas DNAgs DNAgs DNAas DNAgs DNAts OxyTs OxyGs OxyT |
| ASO-000651 | ASO-000651 | TGTgatgcaggagTTG | 303 | 137070 | 137085 | OxyTs OxyGs OxyTs DNAgs DNAas DNAts DNAgs DNAcs DNAas DNAgs DNAgs DNAas DNAgs OxyTs OxyTs OxyG |

Figure 2HH

| Oligomer Name | ASO Number | ASO Sequence | SEQ ID NO | premRNA start NG_007398 | premRNA end NG_007398 | Chemical Structure |
|---|---|---|---|---|---|---|
| ASO-00007 | ASO-00007 | TGTgatgcaggaGTT | 304 | 137071 | 137085 | OxyTs OxyGs OxyTs DNAgs DNAas DNAts DNAgs DNAcs DNAas DNAgs DNAgs DNAas OxyGs OxyTs OxyT |
| ASO-000419 | ASO-000419 | GTGatgcaggaGTT | 305 | 137071 | 137084 | OxyGs OxyTs OxyGs DNAas DNAts DNAgs DNAcs DNAas DNAgs DNAgs DNAas OxyGs OxyTs OxyT |
| ASO-000730 | ASO-000730 | TGTgatgcaggaGTT | 306 | 137071 | 137085 | OxyT OxyGs OxyT DNAgs DNAas DNAts DNAgs DNAcs DNAas DNAgs DNAgs DNAas OxyG OxyTs OxyT |
| ASO-000728 | ASO-000728 | TGTgatgcaggaGTT | 307 | 137071 | 137085 | OxyTs OxyG OxyTs DNAgs DNAas DNAts DNAgs DNAcs DNAas DNAgs DNAgs DNAas OxyG OxyTs OxyT |
| ASO-000729 | ASO-000729 | TGTgatgcaggaGTT | 308 | 137071 | 137085 | OxyT OxyG OxyT DNAgs DNAas DNAts DNAgs DNAcs DNAas DNAgs DNAgs DNAas OxyGs OxyTs OxyT |
| ASO-000727 | ASO-000727 | TGTgatgcaggaGTT | 309 | 137071 | 137085 | OxyT OxyG OxyT DNAgs DNAas DNAts DNAgs DNAcs DNAas DNAgs DNAgs DNAas OxyG OxyT OxyT |
| ASO-000715 | ASO-000715 | TGtgatgcaggagTT | 310 | 137071 | 137085 | OxyTs OxyGs DNAts DNAgs DNAas DNAts DNAgs DNAcs DNAas DNAgs DNAgs DNAas DNAgs OxyTs OxyT |
| ASO-000716 | ASO-000716 | GAtgcaggagTT | 311 | 137071 | 137082 | OxyGs OxyAs DNAts DNAgs DNAcs DNAas DNAgs DNAgs DNAas DNAgs OxyTs OxyT |
| ASO-000721 | ASO-000721 | TGTgatgcaggaGTT | 312 | 137071 | 137085 | AminoTs OxyGs OxyTs DNAgs DNAas DNAts DNAgs DNAcs DNAas DNAgs DNAgs DNAas OxyGs OxyTs OxyT |
| ASO-000722 | ASO-000722 | TGTgatgcaggaGTT | 313 | 137071 | 137085 | AminoTs OxyGs OxyTs DNAgs DNAas DNAts DNAgs DNAcs DNAas DNAgs DNAgs DNAas OxyGs OxyTs AminoT |

Figure 2II

| Oligomer Name | ASO Number | ASO Sequence | SEQ ID NO | premRNA start NG_007398 | premRNA end NG_007398 | Chemical Structure |
|---|---|---|---|---|---|---|
| ASO-000723 | ASO-000723 | TGTgatgcaggaGTT | 314 | 137071 | 137085 | AminoTs OxyGs AminoTs DNAgs DNAas DNAts DNAgs DNAcs DNAas DNAgs DNAgs DNAas OxyGs AminoTs AminoT |
| ASO-000724 | ASO-000724 | TGTgatgcaggaGTT | 315 | 137071 | 137085 | OxyTs OxyGs AminoTs DNAgs DNAas DNAts DNAgs DNAcs DNAas DNAgs DNAgs DNAas OxyGs OxyTs OxyT |
| ASO-000725 | ASO-000725 | TGTgatgcaggaGTT | 316 | 137071 | 137085 | OxyTs OxyGs OxyTs DNAgs DNAas DNAts DNAgs DNAcs DNAas DNAgs DNAgs DNAas OxyGs OxyTs AminoT |
| ASO-000726 | ASO-000726 | TGTgatgcaggaGTT | 317 | 137071 | 137085 | AminoT OxyG AminoT DNAgs DNAas DNAts DNAgs DNAcs DNAas DNAgs DNAgs DNAas OxyG AminoT AminoT |
| ASO-000731 | ASO-000731 | TGTgatgcaggaGTT | 318 | 137071 | 137085 | OxyT OxyG OxyT DNAg DNAa DNAt DNAg DNAc DNAa DNAg DNAg DNAa OxyG OxyT OxyT |
| ASO-000718 | ASO-000718 | TGatgcaggaGT | 319 | 137072 | 137083 | OxyTs OxyGs DNAas DNAts DNAgs DNAcs DNAas DNAgs DNAgs DNAas OxyGs OxyT |
| ASO-000445 | ASO-000445 | TTGtgatgcagGAG | 320 | 137073 | 137086 | OxyTs OxyTs OxyGs DNAts DNAgs DNAas DNAts DNAgs DNAcs DNAas DNAgs OxyGs OxyAs OxyG |
| ASO-000436 | ASO-000436 | CTTgtgatgcagGAG | 321 | 137073 | 137087 | OxyMCs OxyTs OxyTs DNAgs DNAts DNAgs DNAas DNAts DNAgs DNAcs DNAas DNAgs OxyGs OxyAs OxyG |
| ASO-000717 | ASO-000717 | GTgatgcaggAG | 322 | 137073 | 137084 | OxyGs OxyTs DNAgs DNAas DNAts DNAgs DNAcs DNAas DNAgs DNAgs OxyAs OxyG |
| ASO-000570 | ASO-000570 | TTCttgtgatgcaGGA | 323 | 137074 | 137089 | OxyTs OxyTs OxyMCs DNAts DNAts DNAgs DNAts DNAgs DNAas DNAts DNAgs DNAcs DNAas OxyGs OxyGs OxyA |
| ASO-000408 | ASO-000408 | TCTtgtgatgcaGGA | 324 | 137074 | 137088 | OxyTs OxyMCs OxyTs DNAts DNAgs DNAts DNAgs DNAas DNAts DNAgs DNAcs DNAas OxyGs OxyGs OxyA |

Figure 2JJ

| Oligomer Name | ASO Number | ASO Sequence | SEQ ID NO | premRNA start NG_007398 | premRNA end NG_007398 | Chemical Structure |
|---|---|---|---|---|---|---|
| ASO-000401 | ASO-000401 | CTTgtgatgcaGGA | 325 | 137074 | 137087 | OxyMCs OxyTs OxyTs DNAgs DNAts DNAgs DNAas DNAts DNAgs DNAcs DNAas OxyGs OxyGs OxyA |
| ASO-000719 | ASO-000719 | TGtgatgcagGA | 326 | 137074 | 137085 | OxyTs OxyGs DNAts DNAgs DNAas DNAts DNAgs DNAcs DNAas DNAgs OxyGs OxyA |
| ASO-000313 | ASO-000313 | CAGagggcgagctTGG | 327 | 137173 | 137188 | OxyMCs OxyAs OxyGs DNAas DNAgs DNAgs DNAgs DNAmcs DNAgs DNAas DNAgs DNAcs DNAts OxyTs OxyGs OxyG |
| ASO-000331 | ASO-000331 | AATccctgctgtgGTC | 328 | 137223 | 137238 | OxyAs OxyAs OxyTs DNAcs DNAcs DNAcs DNAts DNAgs DNAcs DNAts DNAgs DNAts DNAgs OxyGs OxyTs OxyMC |
| ASO-000251 | ASO-000251 | AGGcaattcatCCC | 329 | 137239 | 137252 | OxyAs OxyGs OxyGs DNAcs DNAas DNAas DNAts DNAts DNAcs DNAas DNAts OxyMCs OxyMCs OxyMC |
| ASO-000574 | ASO-000574 | TGGtcaaggctttGGG | 330 | 137326 | 137341 | OxyTs OxyGs OxyGs DNAts DNAcs DNAas DNAas DNAgs DNAgs DNAcs DNAts DNAts DNAts OxyGs OxyGs OxyG |
| ASO-000218 | ASO-000218 | TCTggtcaaggctTTG | 331 | 137328 | 137343 | OxyTs OxyMCs OxyTs DNAgs DNAgs DNAts DNAcs DNAas DNAas DNAgs DNAgs DNAcs DNAts OxyTs OxyTs OxyG |
| ASO-000634 | ASO-000634 | CTCtggtcaaggcTTT | 332 | 137329 | 137344 | OxyMCs OxyTs OxyMCs DNAts DNAgs DNAgs DNAts DNAcs DNAas DNAas DNAgs DNAgs DNAcs OxyTs OxyTs OxyT |
| ASO-000497 | ASO-000497 | GGTgctctggtcaAGG | 333 | 137333 | 137348 | OxyGs OxyGs OxyTs DNAgs DNAcs DNAts DNAcs DNAts DNAgs DNAgs DNAts DNAcs DNAas OxyAs OxyGs OxyG |
| ASO-000569 | ASO-000569 | GGTgctctggtCAA | 334 | 137335 | 137348 | OxyGs OxyGs OxyTs DNAgs DNAcs DNAts DNAcs DNAts DNAgs DNAgs DNAts OxyMCs OxyAs OxyA |

Figure 2KK

| Oligomer Name | ASO Number | ASO Sequence | SEQ ID NO | premRNA start NG_007398 | premRNA end NG_007398 | Chemical Structure |
|---|---|---|---|---|---|---|
| ASO-000565 | ASO-000565 | GCTgaggtgctctGGT | 335 | 137338 | 137353 | OxyGs OxyMCs OxyTs DNAgs DNAas DNAgs DNAgs DNAts DNAgs DNAcs DNAts DNAcs DNAts OxyGs OxyGs OxyT |
| ASO-000296 | ASO-000296 | AGTttgtgcaaggTCA | 336 | 137358 | 137373 | OxyAs OxyGs OxyTs DNAts DNAts DNAgs DNAts DNAgs DNAcs DNAas DNAas DNAgs DNAgs OxyTs OxyMCs OxyA |
| ASO-000663 | ASO-000663 | GAGtttgtgcaagGTC | 337 | 137359 | 137374 | OxyGs OxyAs OxyGs DNAts DNAts DNAts DNAgs DNAts DNAgs DNAcs DNAas DNAas DNAgs OxyGs OxyTs OxyMC |
| ASO-000670 | ASO-000670 | AGTttgtgcaagGTC | 338 | 137359 | 137373 | OxyAs OxyGs OxyTs DNAts DNAts DNAgs DNAts DNAgs DNAcs DNAas DNAas DNAgs OxyGs OxyTs OxyMC |
| ASO-000261 | ASO-000261 | GGAgtttgtgcaaGGT | 339 | 137360 | 137375 | OxyGs OxyGs OxyAs DNAgs DNAts DNAts DNAts DNAgs DNAts DNAgs DNAcs DNAas DNAas OxyGs OxyGs OxyT |
| ASO-000262 | ASO-000262 | GGAgtttgtgcaAGG | 340 | 137361 | 137375 | OxyGs OxyGs OxyAs DNAgs DNAts DNAts DNAts DNAgs DNAts DNAgs DNAcs DNAas OxyAs OxyGs OxyG |
| ASO-000275 | ASO-000275 | TGGagtttgtgcaAGG | 341 | 137361 | 137376 | OxyTs OxyGs OxyGs DNAas DNAgs DNAts DNAts DNAts DNAgs DNAts DNAgs DNAcs DNAas OxyAs OxyGs OxyG |
| ASO-000247 | ASO-000247 | ATGgagtttgtgcAAG | 342 | 137362 | 137377 | OxyAs OxyTs OxyGs DNAgs DNAas DNAgs DNAts DNAts DNAts DNAgs DNAts DNAgs DNAcs OxyAs OxyAs OxyG |
| ASO-000303 | ASO-000303 | TGGagtttgtgcAAG | 343 | 137362 | 137376 | OxyTs OxyGs OxyGs DNAas DNAgs DNAts DNAts DNAts DNAgs DNAts DNAgs DNAcs OxyAs OxyAs OxyG |

Figure 2LL

| Oligomer Name | ASO Number | ASO Sequence | SEQ ID NO | premRNA start NG_007398 | premRNA end NG_007398 | Chemical Structure |
|---|---|---|---|---|---|---|
| ASO-000299 | ASO-000299 | ATGgagtttgtgCAA | 344 | 137363 | 137377 | OxyAs OxyTs OxyGs DNAgs DNAas DNAgs DNAts DNAts DNAts DNAgs DNAts DNAgs OxyMCs OxyAs OxyA |
| ASO-000270 | ASO-000270 | AGAtggagtttgtGCA | 345 | 137364 | 137379 | OxyAs OxyGs OxyAs DNAts DNAgs DNAgs DNAas DNAgs DNAts DNAts DNAts DNAgs DNAts OxyGs OxyMCs OxyA |
| ASO-000297 | ASO-000297 | AGCagatggagttTGT | 346 | 137367 | 137382 | OxyAs OxyGs OxyMCs DNAas DNAgs DNAas DNAts DNAgs DNAgs DNAas DNAgs DNAts DNAts OxyTs OxyGs OxyT |
| ASO-000259 | ASO-000259 | TTCtttaggcagcAAT | 347 | 137416 | 137431 | OxyTs OxyTs OxyMCs DNAts DNAts DNAts DNAas DNAgs DNAgs DNAcs DNAas DNAgs DNAcs OxyAs OxyAs OxyT |
| ASO-000220 | ASO-000220 | TGTacccaaaccaGAA | 348 | 137462 | 137477 | OxyTs OxyGs OxyTs DNAas DNAcs DNAcs DNAcs DNAas DNAas DNAas DNAcs DNAcs DNAas OxyGs OxyAs OxyA |
| ASO-000278 | ASO-000278 | GTTgcctttaacTGT | 349 | 137475 | 137489 | OxyGs OxyTs OxyTs DNAgs DNAcs DNAcs DNAts DNAts DNAts DNAas DNAas DNAcs OxyTs OxyGs OxyT |
| ASO-000334 | ASO-000334 | GCCctggatttctACT | 350 | 137505 | 137520 | OxyGs OxyMCs OxyMCs DNAcs DNAts DNAgs DNAgs DNAas DNAts DNAts DNAts DNAcs DNAts OxyAs OxyMCs OxyT |
| ASO-000241 | ASO-000241 | TGGtggagagttcTGG | 351 | 137583 | 137598 | OxyTs OxyGs OxyGs DNAts DNAgs DNAgs DNAas DNAgs DNAas DNAgs DNAts DNAts DNAcs OxyTs OxyGs OxyG |
| ASO-000289 | ASO-000289 | TTCtcagatccctTCA | 352 | 137643 | 137658 | OxyTs OxyTs OxyMCs DNAts DNAcs DNAas DNAgs DNAas DNAts DNAcs DNAcs DNAcs DNAts OxyTs OxyMCs OxyA |

Figure 2MM

| Oligomer Name | ASO Number | ASO Sequence | SEQ ID NO | premRNA start NG_007398 | premRNA end NG_007398 | Chemical Structure |
|---|---|---|---|---|---|---|
| ASO-000233 | ASO-000233 | CTCtaaccaccacCAA | 353 | 137682 | 137697 | OxyMCs OxyTs OxyMCs DNAts DNAas DNAas DNAcs DNAcs DNAas DNAcs DNAcs DNAas DNAcs OxyMCs OxyAs OxyA |
| ASO-000201 | ASO-000201 | AGGgcacaagaacTTC | 354 | 137765 | 137780 | OxyAs OxyGs OxyGs DNAgs DNAcs DNAas DNAcs DNAas DNAas DNAgs DNAas DNAas DNAcs OxyTs OxyTs OxyMC |
| ASO-000645 | ASO-000645 | ATCttaggctggCCC | 355 | 137851 | 137865 | OxyAs OxyTs OxyMCs DNAts DNAts DNAas DNAgs DNAgs DNAcs DNAts DNAgs DNAgs OxyMCs OxyMCs OxyMC |
| ASO-000546 | ASO-000546 | GATcttaggctggCCC | 356 | 137851 | 137866 | OxyGs OxyAs OxyTs DNAcs DNAts DNAts DNAas DNAgs DNAgs DNAcs DNAts DNAgs DNAgs OxyMCs OxyMCs OxyMC |
| ASO-000692 | ASO-000692 | TGAtcttaggctgGCC | 357 | 137852 | 137867 | OxyTs OxyGs OxyAs DNAts DNAcs DNAts DNAts DNAas DNAgs DNAgs DNAcs DNAts DNAgs OxyGs OxyMCs OxyMC |
| ASO-000511 | ASO-000511 | GATcttaggctgGCC | 358 | 137852 | 137866 | OxyGs OxyAs OxyTs DNAcs DNAts DNAts DNAas DNAgs DNAgs DNAcs DNAts DNAgs OxyGs OxyMCs OxyMC |
| ASO-000538 | ASO-000538 | TGAtcttaggctGGC | 359 | 137853 | 137867 | OxyTs OxyGs OxyAs DNAts DNAcs DNAts DNAts DNAas DNAgs DNAgs DNAcs DNAts OxyGs OxyGs OxyMC |
| ASO-000214 | ASO-000214 | ATGatcttaggctGGC | 360 | 137853 | 137868 | OxyAs OxyTs OxyGs DNAas DNAts DNAcs DNAts DNAts DNAas DNAgs DNAgs DNAcs DNAts OxyGs OxyGs OxyMC |
| ASO-000653 | ASO-000653 | GATcttaggctGGC | 361 | 137853 | 137866 | OxyGs OxyAs OxyTs DNAcs DNAts DNAts DNAas DNAgs DNAgs DNAcs DNAts OxyGs OxyGs OxyMC |

Figure 2NN

| Oligomer Name | ASO Number | ASO Sequence | SEQ ID NO | premRNA start NG_007398 | premRNA end NG_007398 | Chemical Structure |
|---|---|---|---|---|---|---|
| ASO-000615 | ASO-000615 | CATgatcttaggcTGG | 362 | 137854 | 137869 | OxyMCs OxyAs OxyTs DNAgs DNAas DNAts DNAcs DNAts DNAts DNAas DNAgs DNAgs DNAcs OxyTs OxyGs OxyG |
| ASO-000524 | ASO-000524 | CCAtgatcttaggCTG | 363 | 137855 | 137870 | OxyMCs OxyMCs OxyAs DNAts DNAgs DNAas DNAts DNAcs DNAts DNAts DNAas DNAgs DNAgs OxyMCs OxyTs OxyG |
| ASO-000492 | ASO-000492 | CATgatcttaggCTG | 364 | 137855 | 137869 | OxyMCs OxyAs OxyTs DNAgs DNAas DNAts DNAcs DNAts DNAts DNAas DNAgs DNAgs OxyMCs OxyTs OxyG |
| ASO-000468 | ASO-000468 | ACCatgatcttagGCT | 365 | 137856 | 137871 | OxyAs OxyMCs OxyMCs DNAas DNAts DNAgs DNAas DNAts DNAcs DNAts DNAts DNAas DNAgs OxyGs OxyMCs OxyT |
| ASO-000698 | ASO-000698 | CCAtgatcttagGCT | 366 | 137856 | 137870 | OxyMCs OxyMCs OxyAs DNAts DNAgs DNAas DNAts DNAcs DNAts DNAts DNAas DNAgs OxyGs OxyMCs OxyT |
| ASO-000593 | ASO-000593 | CATgatcttagGCT | 367 | 137856 | 137869 | OxyMCs OxyAs OxyTs DNAgs DNAas DNAts DNAcs DNAts DNAts DNAas DNAgs OxyGs OxyMCs OxyT |
| ASO-000519 | ASO-000519 | AAAccatgatcttAGG | 368 | 137858 | 137873 | OxyAs OxyAs OxyAs DNAcs DNAcs DNAas DNAts DNAgs DNAas DNAts DNAcs DNAts DNAts OxyAs OxyGs OxyG |
| ASO-000582 | ASO-000582 | CTAaaccatgatcTTA | 369 | 137860 | 137875 | OxyMCs OxyTs OxyAs DNAas DNAas DNAcs DNAcs DNAas DNAts DNAgs DNAas DNAts DNAcs OxyTs OxyTs OxyA |
| ASO-000635 | ASO-000635 | CCCtaaaccatgaTCT | 370 | 137862 | 137877 | OxyMCs OxyMCs OxyMCs DNAts DNAas DNAas DNAas DNAcs DNAcs DNAas DNAts DNAgs DNAas OxyTs OxyMCs OxyT |

Figure 2OO

| Oligomer Name | ASO Number | ASO Sequence | SEQ ID NO | premRNA start NG_007398 | premRNA end NG_007398 | Chemical Structure |
|---|---|---|---|---|---|---|
| ASO-000471 | ASO-000471 | CACcctaaaccatGAT | 371 | 137864 | 137879 | OxyMCs OxyAs OxyMCs DNAcs DNAcs DNAts DNAas DNAas DNAas DNAcs DNAcs DNAas DNAts OxyGs OxyAs OxyT |
| ASO-000701 | ASO-000701 | ATCaccctaaaccATG | 372 | 137866 | 137881 | OxyAs OxyTs OxyMCs DNAas DNAcs DNAcs DNAcs DNAts DNAas DNAas DNAas DNAcs DNAcs OxyAs OxyTs OxyG |
| ASO-000533 | ASO-000533 | TGAtcaccctaaaCCA | 373 | 137868 | 137883 | OxyTs OxyGs OxyAs DNAts DNAcs DNAas DNAcs DNAcs DNAcs DNAts DNAas DNAas DNAas OxyMCs OxyMCs OxyA |
| ASO-000323 | ASO-000323 | GAGgagtgcccagCCC | 374 | 137947 | 137962 | OxyGs OxyAs OxyGs DNAgs DNAas DNAgs DNAts DNAgs DNAcs DNAcs DNAcs DNAas DNAgs OxyMCs OxyMCs OxyMC |
| ASO-000329 | ASO-000329 | TGCaggtgggagaAGT | 375 | 137973 | 137988 | OxyTs OxyGs OxyMCs DNAas DNAgs DNAgs DNAts DNAgs DNAgs DNAgs DNAas DNAgs DNAas OxyAs OxyGs OxyT |
| ASO-000194 | ASO-000194 | TATctagcccaCCC | 376 | 138003 | 138016 | OxyTs OxyAs OxyTs DNAcs DNAts DNAas DNAgs DNAcs DNAcs DNAcs DNAas OxyMCs OxyMCs OxyMC |
| ASO-000192 | ASO-000192 | CTAtctagcccaCCC | 377 | 138003 | 138017 | OxyMCs OxyTs OxyAs DNAts DNAcs DNAts DNAas DNAgs DNAcs DNAcs DNAcs DNAas OxyMCs OxyMCs OxyMC |
| ASO-000343 | ASO-000343 | TAtcctatctaGCC | 378 | 138008 | 138021 | OxyTs OxyAs DNAts DNAcs DNAcs DNAts DNAas DNAts DNAcs DNAts DNAas OxyGs OxyMCs OxyMC |
| ASO-000212 | ASO-000212 | TTGataaagtgaGTC | 379 | 138050 | 138064 | OxyTs OxyTs OxyGs DNAas DNAts DNAas DNAas DNAas DNAgs DNAts DNAgs DNAas OxyGs OxyTs OxyMC |

Figure 2PP

| Oligomer Name | ASO Number | ASO Sequence | SEQ ID NO | premRNA start NG_007398 | premRNA end NG_007398 | Chemical Structure |
|---|---|---|---|---|---|---|
| ASO-000230 | ASO-000230 | ATTgataaagtgAGT | 380 | 138051 | 138065 | OxyAs OxyTs OxyTs DNAgs DNAas DNAts DNAas DNAas DNAas DNAgs DNAts DNAgs OxyAs OxyGs OxyT |
| ASO-000188 | ASO-000188 | AACtattgataaAGT | 381 | 138055 | 138069 | OxyAs OxyAs OxyMCs DNAts DNAas DNAts DNAts DNAgs DNAas DNAts DNAas DNAas OxyAs OxyGs OxyT |
| ASO-000415 | ASO-000415 | GAActattgatAAA | 382 | 138057 | 138070 | OxyGs OxyAs OxyAs DNAcs DNAts DNAas DNAts DNAts DNAgs DNAas DNAts OxyAs OxyAs OxyA |
| ASO-000448 | ASO-000448 | GGAactattgaTAA | 383 | 138058 | 138071 | OxyGs OxyGs OxyAs DNAas DNAcs DNAts DNAas DNAts DNAts DNAgs DNAas OxyTs OxyAs OxyA |
| ASO-000190 | ASO-000190 | AAAtggaactattGAT | 384 | 138060 | 138075 | OxyAs OxyAs OxyAs DNAts DNAgs DNAgs DNAas DNAas DNAcs DNAts DNAas DNAts DNAts OxyGs OxyAs OxyT |
| ASO-000191 | ASO-000191 | AATggaactatTGA | 385 | 138061 | 138074 | OxyAs OxyAs OxyTs DNAgs DNAgs DNAas DNAas DNAcs DNAts DNAas DNAts OxyTs OxyGs OxyA |
| ASO-000348 | ASO-000348 | TCAAtttaaatGGAA | 386 | 138068 | 138082 | OxyTs OxyMCs OxyAs OxyAs DNAts DNAts DNAts DNAas DNAas DNAas DNAts OxyGs OxyGs OxyAs OxyA |
| ASO-000349 | ASO-000349 | GTcaatttaaaTGGA | 387 | 138069 | 138083 | OxyGs OxyTs DNAcs DNAas DNAas DNAts DNAts DNAts DNAas DNAas DNAas OxyTs OxyGs OxyGs OxyA |
| ASO-000200 | ASO-000200 | GGAtacagtctcaCCA | 388 | 138089 | 138104 | OxyGs OxyGs OxyAs DNAts DNAas DNAcs DNAas DNAgs DNAts DNAcs DNAts DNAcs DNAas OxyMCs OxyMCs OxyA |
| ASO-000630 | ASO-000630 | GCAaacaggatacAGT | 389 | 138096 | 138111 | OxyGs OxyMCs OxyAs DNAas DNAas DNAcs DNAas DNAgs DNAgs DNAas DNAts DNAas DNAcs OxyAs OxyGs OxyT |

Figure 2QQ

| Oligomer Name | ASO Number | ASO Sequence | SEQ ID NO | premRNA start NG_007398 | premRNA end NG_007398 | Chemical Structure |
|---|---|---|---|---|---|---|
| ASO-000614 | ASO-000614 | CAAacaggatacAGT | 390 | 138096 | 138110 | OxyMCs OxyAs OxyAs DNAas DNAcs DNAas DNAgs DNAgs DNAas DNAts DNAas DNAcs OxyAs OxyGs OxyT |
| ASO-000563 | ASO-000563 | AAAcaggatacAGT | 391 | 138096 | 138109 | OxyAs OxyAs OxyAs DNAcs DNAas DNAgs DNAgs DNAas DNAts DNAas DNAcs OxyAs OxyGs OxyT |
| ASO-000527 | ASO-000527 | TAGcaaacaggatACA | 392 | 138098 | 138113 | OxyTs OxyAs OxyGs DNAcs DNAas DNAas DNAas DNAcs DNAas DNAgs DNAgs DNAas DNAts OxyAs OxyMCs OxyA |
| ASO-000617 | ASO-000617 | ATAgcaaacaggaTAC | 393 | 138099 | 138114 | OxyAs OxyTs OxyAs DNAgs DNAcs DNAas DNAas DNAas DNAcs DNAas DNAgs DNAgs DNAas OxyTs OxyAs OxyMC |
| ASO-000539 | ASO-000539 | AATagcaaacaggATA | 394 | 138100 | 138115 | OxyAs OxyAs OxyTs DNAas DNAgs DNAcs DNAas DNAas DNAas DNAcs DNAas DNAgs DNAgs OxyAs OxyTs OxyA |
| ASO-000691 | ASO-000691 | CAAtagcaaacagGAT | 395 | 138101 | 138116 | OxyMCs OxyAs OxyAs DNAts DNAas DNAgs DNAcs DNAas DNAas DNAas DNAcs DNAas DNAgs OxyGs OxyAs OxyT |
| ASO-000589 | ASO-000589 | AATagcaaacagGAT | 396 | 138101 | 138115 | OxyAs OxyAs OxyTs DNAas DNAgs DNAcs DNAas DNAas DNAas DNAcs DNAas DNAgs OxyGs OxyAs OxyT |
| ASO-000509 | ASO-000509 | GCAatagcaaacaGGA | 397 | 138102 | 138117 | OxyGs OxyMCs OxyAs DNAas DNAts DNAas DNAgs DNAcs DNAas DNAas DNAas DNAcs DNAas OxyGs OxyGs OxyA |
| ASO-000674 | ASO-000674 | CAAtagcaaacaGGA | 398 | 138102 | 138116 | OxyMCs OxyAs OxyAs DNAts DNAas DNAgs DNAcs DNAas DNAas DNAas DNAcs DNAas OxyGs OxyGs OxyA |

Figure 2RR

| Oligomer Name | ASO Number | ASO Sequence | SEQ ID NO | premRNA start NG_007398 | premRNA end NG_007398 | Chemical Structure |
|---|---|---|---|---|---|---|
| ASO-000488 | ASO-000488 | GCAatagcaaacAGG | 399 | 138103 | 138117 | OxyGs OxyMCs OxyAs DNAas DNAts DNAas DNAgs DNAcs DNAas DNAas DNAas DNAcs OxyAs OxyGs OxyG |
| ASO-000507 | ASO-000507 | AGCaatagcaaacAGG | 400 | 138103 | 138118 | OxyAs OxyGs OxyMCs DNAas DNAas DNAts DNAas DNAgs DNAcs DNAas DNAas DNAas DNAcs OxyAs OxyGs OxyG |
| ASO-000521 | ASO-000521 | AGCaatagcaaaCAG | 401 | 138104 | 138118 | OxyAs OxyGs OxyMCs DNAas DNAas DNAts DNAas DNAgs DNAcs DNAas DNAas DNAas OxyMCs OxyAs OxyG |
| ASO-000288 | ASO-000288 | AAGcaatagcaaaCAG | 402 | 138104 | 138119 | OxyAs OxyAs OxyGs DNAcs DNAas DNAas DNAts DNAas DNAgs DNAcs DNAas DNAas DNAas OxyMCs OxyAs OxyG |
| ASO-000552 | ASO-000552 | AAGcaatagcaaACA | 403 | 138105 | 138119 | OxyAs OxyAs OxyGs DNAcs DNAas DNAas DNAts DNAas DNAgs DNAcs DNAas DNAas OxyAs OxyMCs OxyA |
| ASO-000250 | ASO-000250 | CAAatgtggttgaAAT | 404 | 138223 | 138238 | OxyMCs OxyAs OxyAs DNAas DNAts DNAgs DNAts DNAgs DNAgs DNAts DNAts DNAgs DNAas OxyAs OxyAs OxyT |
| ASO-000294 | ASO-000294 | GCAaatgtggttgAAA | 405 | 138224 | 138239 | OxyGs OxyMCs OxyAs DNAas DNAas DNAts DNAgs DNAts DNAgs DNAgs DNAts DNAts DNAgs OxyAs OxyAs OxyA |
| ASO-000318 | ASO-000318 | TAGcaaatgtggtTGA | 406 | 138226 | 138241 | OxyTs OxyAs OxyGs DNAcs DNAas DNAas DNAas DNAts DNAgs DNAts DNAgs DNAgs DNAts OxyTs OxyGs OxyA |
| ASO-000308 | ASO-000308 | CCCaagggcctctAAC | 407 | 138263 | 138278 | OxyMCs OxyMCs OxyMCs DNAas DNAas DNAgs DNAgs DNAgs DNAcs DNAcs DNAts DNAcs DNAts OxyAs OxyAs OxyMC |

Figure 2SS

| Oligomer Name | ASO Number | ASO Sequence | SEQ ID NO | premRNA start NG_007398 | premRNA end NG_007398 | Chemical Structure |
|---|---|---|---|---|---|---|
| ASO-000254 | ASO-000254 | AAAgcaaccagatGTC | 408 | 138361 | 138376 | OxyAs OxyAs OxyAs DNAgs DNAcs DNAas DNAas DNAcs DNAcs DNAas DNAgs DNAas DNAts OxyGs OxyTs OxyMC |
| ASO-000545 | ASO-000545 | AAGagggcagcagGCC | 409 | 138377 | 138392 | OxyAs OxyAs OxyGs DNAas DNAgs DNAgs DNAgs DNAcs DNAas DNAgs DNAcs DNAas DNAgs OxyGs OxyMCs OxyMC |
| ASO-000476 | ASO-000476 | GAAagagggcagcAGG | 410 | 138379 | 138394 | OxyGs OxyAs OxyAs DNAas DNAgs DNAas DNAgs DNAgs DNAgs DNAcs DNAas DNAgs DNAcs OxyAs OxyGs OxyG |
| ASO-000620 | ASO-000620 | CTGaaagagggcaGCA | 411 | 138381 | 138396 | OxyMCs OxyTs OxyGs DNAas DNAas DNAas DNAgs DNAas DNAgs DNAgs DNAgs DNAcs DNAas OxyGs OxyMCs OxyA |
| ASO-000477 | ASO-000477 | CCCtgaaagagggCAG | 412 | 138383 | 138398 | OxyMCs OxyMCs OxyMCs DNAts DNAgs DNAas DNAas DNAas DNAgs DNAas DNAgs DNAgs DNAgs OxyMCs OxyAs OxyG |
| ASO-000562 | ASO-000562 | TGAttgtgggcttAGG | 413 | 138401 | 138416 | OxyTs OxyGs OxyAs DNAts DNAts DNAgs DNAts DNAgs DNAgs DNAgs DNAcs DNAts DNAts OxyAs OxyGs OxyG |
| ASO-000547 | ASO-000547 | ATGattgtgggctTAG | 414 | 138402 | 138417 | OxyAs OxyTs OxyGs DNAas DNAts DNAts DNAgs DNAts DNAgs DNAgs DNAgs DNAcs DNAts OxyTs OxyAs OxyG |
| ASO-000696 | ASO-000696 | TGAttgtgggctTAG | 415 | 138402 | 138416 | OxyTs OxyGs OxyAs DNAts DNAts DNAgs DNAts DNAgs DNAgs DNAgs DNAcs DNAts OxyTs OxyAs OxyG |
| ASO-000279 | ASO-000279 | GATtgtgggctTAG | 416 | 138402 | 138415 | OxyGs OxyAs OxyTs DNAts DNAgs DNAts DNAgs DNAgs DNAgs DNAcs DNAts OxyTs OxyAs OxyG |

Figure 2TT

| Oligomer Name | ASO Number | ASO Sequence | SEQ ID NO | premRNA start NG_007398 | premRNA end NG_007398 | Chemical Structure |
|---|---|---|---|---|---|---|
| ASO-000543 | ASO-000543 | CATgattgtgggcTTA | 417 | 138403 | 138418 | OxyMCs OxyAs OxyTs DNAgs DNAas DNAts DNAts DNAgs DNAts DNAgs DNAgs DNAgs DNAcs OxyTs OxyTs OxyA |
| ASO-000626 | ASO-000626 | TGAttgtgggcTTA | 418 | 138403 | 138416 | OxyTs OxyGs OxyAs DNAts DNAts DNAgs DNAts DNAgs DNAgs DNAgs DNAcs OxyTs OxyTs OxyA |
| ASO-000650 | ASO-000650 | ATGattgtgggcTTA | 419 | 138403 | 138417 | OxyAs OxyTs OxyGs DNAas DNAts DNAts DNAgs DNAts DNAgs DNAgs DNAgs DNAcs OxyTs OxyTs OxyA |
| ASO-000599 | ASO-000599 | CATgattgtgggCTT | 420 | 138404 | 138418 | OxyMCs OxyAs OxyTs DNAgs DNAas DNAts DNAts DNAgs DNAts DNAgs DNAgs DNAgs OxyMCs OxyTs OxyT |
| ASO-000542 | ASO-000542 | GCAtgattgtgggCTT | 421 | 138404 | 138419 | OxyGs OxyMCs OxyAs DNAts DNAgs DNAas DNAts DNAts DNAgs DNAts DNAgs DNAgs DNAgs OxyMCs OxyTs OxyT |
| ASO-000463 | ASO-000463 | GGCatgattgtggGCT | 422 | 138405 | 138420 | OxyGs OxyGs OxyMCs DNAas DNAts DNAgs DNAas DNAts DNAts DNAgs DNAts DNAgs DNAgs OxyGs OxyMCs OxyT |
| ASO-000605 | ASO-000605 | GCAtgattgtggGCT | 423 | 138405 | 138419 | OxyGs OxyMCs OxyAs DNAts DNAgs DNAas DNAts DNAts DNAgs DNAts DNAgs DNAgs OxyGs OxyMCs OxyT |
| ASO-000479 | ASO-000479 | CATgattgtggGCT | 424 | 138405 | 138418 | OxyMCs OxyAs OxyTs DNAgs DNAas DNAts DNAts DNAgs DNAts DNAgs DNAgs OxyGs OxyMCs OxyT |
| ASO-000474 | ASO-000474 | GCAtgattgtgGGC | 425 | 138406 | 138419 | OxyGs OxyMCs OxyAs DNAts DNAgs DNAas DNAts DNAts DNAgs DNAts DNAgs OxyGs OxyGs OxyMC |
| ASO-000675 | ASO-000675 | GGCatgattgtgGGC | 426 | 138406 | 138420 | OxyGs OxyGs OxyMCs DNAas DNAts DNAgs DNAas DNAts DNAts DNAgs DNAts DNAgs OxyGs OxyGs OxyMC |

Figure 2UU

| Oligomer Name | ASO Number | ASO Sequence | SEQ ID NO | premRNA start NG_007398 | premRNA end NG_007398 | Chemical Structure |
|---|---|---|---|---|---|---|
| ASO-000537 | ASO-000537 | AGGcatgattgtgGGC | 427 | 138406 | 138421 | OxyAs OxyGs OxyGs DNAcs DNAas DNAts DNAgs DNAas DNAts DNAts DNAgs DNAts DNAgs OxyGs OxyGs OxyMC |
| ASO-000287 | ASO-000287 | AGGgaggcatgatTGT | 428 | 138410 | 138425 | OxyAs OxyGs OxyGs DNAgs DNAas DNAgs DNAgs DNAcs DNAas DNAts DNAgs DNAas DNAts OxyTs OxyGs OxyT |
| ASO-000292 | ASO-000292 | GGGaggcatgatTGT | 429 | 138410 | 138424 | OxyGs OxyGs OxyGs DNAas DNAgs DNAgs DNAcs DNAas DNAts DNAgs DNAas DNAts OxyTs OxyGs OxyT |
| ASO-000216 | ASO-000216 | TTAgggaggcatgATT | 430 | 138412 | 138427 | OxyTs OxyTs OxyAs DNAgs DNAgs DNAgs DNAas DNAgs DNAgs DNAcs DNAas DNAts DNAgs OxyAs OxyTs OxyT |
| ASO-000266 | ASO-000266 | TTAgggaggcatGAT | 431 | 138413 | 138427 | OxyTs OxyTs OxyAs DNAgs DNAgs DNAgs DNAas DNAgs DNAgs DNAcs DNAas DNAts OxyGs OxyAs OxyT |
| ASO-000256 | ASO-000256 | TCTtagggaggcaTGA | 432 | 138414 | 138429 | OxyTs OxyMCs OxyTs DNAts DNAas DNAgs DNAgs DNAgs DNAas DNAgs DNAgs DNAcs DNAas OxyTs OxyGs OxyA |
| ASO-000269 | ASO-000269 | GAGgtggcacagaGGT | 433 | 138460 | 138475 | OxyGs OxyAs OxyGs DNAgs DNAts DNAgs DNAgs DNAcs DNAas DNAcs DNAas DNAgs DNAas OxyGs OxyGs OxyT |
| ASO-000350 | ASO-000350 | CAGtgtgagaggtGG | 434 | 138469 | 138483 | OxyMCs OxyAs OxyGs DNAts DNAgs DNAts DNAgs DNAas DNAgs DNAas DNAgs DNAgs DNAts OxyGs OxyG |
| ASO-000353 | ASO-000353 | CAGtgtgagaggTG | 435 | 138470 | 138483 | OxyMCs OxyAs OxyGs DNAts DNAgs DNAts DNAgs DNAas DNAgs DNAas DNAgs DNAgs OxyTs OxyG |

Figure 2VV

| Oligomer Name | ASO Number | ASO Sequence | SEQ ID NO | premRNA start NG_007398 | premRNA end NG_007398 | Chemical Structure |
|---|---|---|---|---|---|---|
| ASO-000310 | ASO-000310 | ACAaagatgaggaGGG | 436 | 138532 | 138547 | OxyAs OxyMCs OxyAs DNAas DNAas DNAgs DNAas DNAts DNAgs DNAas DNAgs DNAgs DNAas OxyGs OxyGs OxyG |
| ASO-000309 | ASO-000309 | AACaaagatgaggAGG | 437 | 138533 | 138548 | OxyAs OxyAs OxyMCs DNAas DNAas DNAas DNAgs DNAas DNAts DNAgs DNAas DNAgs DNAgs OxyAs OxyGs OxyG |
| ASO-000263 | ASO-000263 | GAAgagaaatcagAAG | 438 | 138631 | 138646 | OxyGs OxyAs OxyAs DNAgs DNAas DNAgs DNAas DNAas DNAas DNAts DNAcs DNAas DNAgs OxyAs OxyAs OxyG |
| ASO-000197 | ASO-000197 | TCTaggccagtgcCCA | 439 | 138667 | 138682 | OxyTs OxyMCs OxyTs DNAas DNAgs DNAgs DNAcs DNAcs DNAas DNAgs DNAts DNAgs DNAcs OxyMCs OxyMCs OxyA |
| ASO-000239 | ASO-000239 | AGTctattaggAGG | 440 | 138689 | 138702 | OxyAs OxyGs OxyTs DNAcs DNAts DNAas DNAts DNAts DNAas DNAgs DNAgs OxyAs OxyGs OxyG |
| ASO-000267 | ASO-000267 | GCTcaacatggcaAAC | 441 | 138714 | 138729 | OxyGs OxyMCs OxyTs DNAcs DNAas DNAas DNAcs DNAas DNAts DNAgs DNAgs DNAcs DNAas OxyAs OxyAs OxyMC |
| ASO-000306 | ASO-000306 | TGCaagtgccagAAA | 442 | 138737 | 138751 | OxyTs OxyGs OxyMCs DNAas DNAas DNAgs DNAts DNAgs DNAcs DNAcs DNAas DNAgs OxyAs OxyAs OxyA |
| ASO-000345 | ASO-000345 | GCAagtgccagAAA | 443 | 138737 | 138750 | OxyGs OxyMCs OxyAs DNAas DNAgs DNAts DNAgs DNAcs DNAcs DNAas DNAgs OxyAs OxyAs OxyA |
| ASO-000193 | ASO-000193 | AATcatgggacttGCA | 444 | 138748 | 138763 | OxyAs OxyAs OxyTs DNAcs DNAas DNAts DNAgs DNAgs DNAgs DNAas DNAcs DNAts DNAts OxyGs OxyMCs OxyA |

Figure 2WW

| Oligomer Name | ASO Number | ASO Sequence | SEQ ID NO | premRNA start NG_007398 | premRNA end NG_007398 | Chemical Structure |
|---|---|---|---|---|---|---|
| ASO-000284 | ASO-000284 | GATttcatgtcccTCC | 445 | 138788 | 138803 | OxyGs OxyAs OxyTs DNAts DNAts DNAcs DNAas DNAts DNAgs DNAts DNAcs DNAcs DNAcs OxyTs OxyMCs OxyMC |
| ASO-000209 | ASO-000209 | GCTaagctaagaTGA | 446 | 138802 | 138816 | OxyGs OxyMCs OxyTs DNAas DNAas DNAgs DNAcs DNAts DNAas DNAas DNAgs DNAas OxyTs OxyGs OxyA |
| ASO-000207 | ASO-000207 | CTAagctaagaTGA | 447 | 138802 | 138815 | OxyMCs OxyTs OxyAs DNAas DNAgs DNAcs DNAts DNAas DNAas DNAgs DNAas OxyTs OxyGs OxyA |
| ASO-000301 | ASO-000301 | TAGacattcacaGAC | 448 | 138822 | 138836 | OxyTs OxyAs OxyGs DNAas DNAcs DNAas DNAts DNAts DNAcs DNAas DNAcs DNAas OxyGs OxyAs OxyMC |
| ASO-000234 | ASO-000234 | TATagacattcaCAG | 449 | 138824 | 138838 | OxyTs OxyAs OxyTs DNAas DNAgs DNAas DNAcs DNAas DNAts DNAts DNAcs DNAas OxyMCs OxyAs OxyG |
| ASO-000332 | ASO-000332 | AAAcacacaatacACT | 450 | 138840 | 138855 | OxyAs OxyAs OxyAs DNAcs DNAas DNAcs DNAas DNAcs DNAas DNAas DNAts DNAas DNAcs OxyAs OxyMCs OxyT |
| SPC-15693-01 | ASO-002268 | CAgcaacagtcagtGT | 451 | 138869 | 138884 | OxyMCs OxyAs DNAgs DNAcs DNAas DNAas DNAcs DNAas DNAgs DNAts DNAcs DNAas DNAgs DNAts OxyGs OxyTs |
| SPC-15692-01 | ASO-002260 | ACagcaacagtcagTG | 452 | 138870 | 138885 | OxyAs OxyMCs DNAas DNAgs DNAcs DNAas DNAas DNAcs DNAas DNAgs DNAts DNAcs DNAas DNAgs OxyTs OxyGs |
| SPC-15691-01 | ASO-002252 | TAcagcaacagtcaGT | 453 | 138871 | 138886 | OxyTs OxyAs DNAcs DNAas DNAgs DNAcs DNAas DNAas DNAcs DNAas DNAgs DNAts DNAcs DNAas OxyGs OxyTs |

Figure 2XX

| Oligomer Name | ASO Number | ASO Sequence | SEQ ID NO | premRNA start NG_007398 | premRNA end NG_007398 | Chemical Structure |
|---|---|---|---|---|---|---|
| SPC-15690-01 | ASO-002244 | TTAcagcaacagtcAG | 454 | 138872 | 138887 | OxyTs OxyTs OxyAs DNAcs DNAas DNAgs DNAcs DNAas DNAas DNAcs DNAas DNAgs DNAts DNAcs OxyAs OxyGs |
| SPC-15689-01 | ASO-002235 | TTTacagcaacagtCA | 455 | 138873 | 138888 | OxyTs OxyTs OxyTs DNAas DNAcs DNAas DNAgs DNAcs DNAas DNAas DNAcs DNAas DNAgs DNAts OxyMCs OxyAs |
| SPC-15688-01 | ASO-002290 | TTttacagcaacaGTC | 456 | 138874 | 138889 | OxyTs OxyTs DNAts DNAts DNAas DNAcs DNAas DNAgs DNAcs DNAas DNAas DNAcs DNAas OxyGs OxyTs OxyMCs |
| SPC-15687-01 | ASO-002282 | CTtttacagcaacaGT | 457 | 138875 | 138890 | OxyMCs OxyTs DNAts DNAts DNAts DNAas DNAcs DNAas DNAgs DNAcs DNAas DNAas DNAcs DNAas OxyGs OxyTs |
| SPC-15686-01 | ASO-002275 | ACttttacagcaaCAG | 458 | 138876 | 138891 | OxyAs OxyMCs DNAts DNAts DNAts DNAts DNAas DNAcs DNAas DNAgs DNAcs DNAas DNAas OxyMCs OxyAs OxyGs |
| SPC-15685-01 | ASO-002267 | CActtttacagcaaCA | 459 | 138877 | 138892 | OxyMCs OxyAs DNAcs DNAts DNAts DNAts DNAts DNAas DNAcs DNAas DNAgs DNAcs DNAas DNAas OxyMCs OxyAs |
| SPC-15684-01 | ASO-002259 | TCActtttacagcAAC | 460 | 138878 | 138893 | OxyTs OxyMCs OxyAs DNAcs DNAts DNAts DNAts DNAts DNAas DNAcs DNAas DNAgs DNAcs OxyAs OxyAs OxyMCs |
| SPC-15683-01 | ASO-002251 | TTCacttttacagCAA | 461 | 138879 | 138894 | OxyTs OxyTs OxyMCs DNAas DNAcs DNAts DNAts DNAts DNAts DNAas DNAcs DNAas DNAgs OxyMCs OxyAs OxyAs |
| SPC-15682-01 | ASO-002243 | ATTcacttttacagCA | 462 | 138880 | 138895 | OxyAs OxyTs OxyTs DNAcs DNAas DNAcs DNAts DNAts DNAts DNAts DNAas DNAcs DNAas DNAgs OxyMCs OxyAs |

Figure 2YY

| Oligomer Name | ASO Number | ASO Sequence | SEQ ID NO | premRNA start NG_007398 | premRNA end NG_007398 | Chemical Structure |
|---|---|---|---|---|---|---|
| SPC-15681-01 | ASO-002234 | AATtcacttttacaGC | 463 | 138881 | 138896 | OxyAs OxyAs OxyTs DNAts DNAcs DNAas DNAcs DNAts DNAts DNAts DNAts DNAas DNAcs DNAas OxyGs OxyMCs |
| SPC-15680-01 | ASO-002289 | AAATtcactttt ACAG | 464 | 138882 | 138897 | OxyAs OxyAs OxyAs OxyTs DNAts DNAcs DNAas DNAcs DNAts DNAts DNAts DNAts OxyAs OxyMCs OxyAs OxyGs |
| SPC-15679-01 | ASO-002281 | CAAattcactttTACA | 465 | 138883 | 138898 | OxyMCs OxyAs OxyAs DNAas DNAts DNAts DNAcs DNAas DNAcs DNAts DNAts DNAts OxyTs OxyAs OxyMCs OxyAs |
| ASO-002090 | ASO-002090 | ATTtcCaaattcactTtTAC | 466 | 138884 | 138903 | OxyAs OxyTs OxyTs DNAts DNAcs OxyMCs DNAas DNAas DNAas DNAts DNAts DNAcs DNAas DNAcs DNAts OxyTs DNAts OxyTs OxyAs OxyMC |
| ASO-002043 | ASO-002043 | ATtTCcaaattcacttTTAC | 467 | 138884 | 138903 | OxyAs OxyTs DNAts OxyTs OxyMCs DNAcs DNAas DNAas DNAas DNAts DNAts DNAcs DNAas DNAcs DNAts DNAts OxyTs OxyTs OxyAs OxyMC |
| ASO-002076 | ASO-002076 | ATtTCcaaattcacTTttAC | 468 | 138884 | 138903 | OxyAs OxyTs DNAts OxyTs OxyMCs DNAcs DNAas DNAas DNAas DNAts DNAts DNAcs DNAas DNAcs OxyTs OxyTs DNAts DNAts OxyAs OxyMC |
| ASO-002062 | ASO-002062 | ATTtcCaaattcactTTtAC | 469 | 138884 | 138903 | OxyAs OxyTs OxyTs DNAts DNAcs OxyMCs DNAas DNAas DNAas DNAts DNAts DNAcs DNAas DNAcs DNAts OxyTs OxyTs DNAts OxyAs OxyMC |
| ASO-002082 | ASO-002082 | ATtTcCaaattcactTtTAC | 470 | 138884 | 138903 | OxyAs OxyTs DNAts OxyTs DNAcs OxyMCs DNAas DNAas DNAas DNAts DNAts DNAcs DNAas DNAcs DNAts OxyTs DNAts OxyTs OxyAs OxyMC |
| ASO-000753 | ASO-000753 | ATTTCcaaattcactTTTA C | 471 | 138884 | 138903 | OxyAs OxyTs OxyTs OxyTs OxyMCs DNAcs DNAas DNAas DNAas DNAts DNAts DNAcs DNAas DNAcs DNAts OxyTs OxyTs OxyTs OxyAs OxyMC |

Figure 2ZZ

| Oligomer Name | ASO Number | ASO Sequence | SEQ ID NO | premRNA start NG_007398 | premRNA end NG_007398 | Chemical Structure |
|---|---|---|---|---|---|---|
| ASO-001940 | ASO-001940 | ATtTCcaaattcactTTtAC | 472 | 138884 | 138903 | OxyAs OxyTs DNAts OxyTs OxyMCs DNAcs DNAas DNAas DNAas DNAts DNAts DNAcs DNAas DNAcs DNAts OxyTs OxyTs DNAts OxyAs OxyMC |
| ASO-001933 | ASO-001933 | AtTTCcaaattcactTTtAC | 473 | 138884 | 138903 | OxyAs DNAts OxyTs OxyTs OxyMCs DNAcs DNAas DNAas DNAas DNAts DNAts DNAcs DNAas DNAcs DNAts OxyTs OxyTs DNAts OxyAs OxyMC |
| ASO-001919 | ASO-001919 | ATTTccaaattcactTTTAC | 474 | 138884 | 138903 | OxyAs OxyTs OxyTs OxyTs DNAcs DNAcs DNAas DNAas DNAas DNAts DNAts DNAcs DNAas DNAcs DNAts OxyTs OxyTs OxyTs OxyAs OxyMC |
| ASO-002094 | ASO-002094 | ATtTCcaaattcacTtTtAC | 475 | 138884 | 138903 | OxyAs OxyTs DNAts OxyTs OxyMCs DNAcs DNAas DNAas DNAas DNAts DNAts DNAcs DNAas DNAcs OxyTs DNAts OxyTs DNAts OxyAs OxyMC |
| ASO-002034 | ASO-002034 | ATTtCcaaattcactTtTAC | 476 | 138884 | 138903 | OxyAs OxyTs OxyTs DNAts OxyMCs DNAcs DNAas DNAas DNAas DNAts DNAts DNAcs DNAas DNAcs DNAts OxyTs DNAts OxyTs OxyAs OxyMC |
| ASO-002036 | ASO-002036 | ATttCcAaattcacttTTAC | 477 | 138884 | 138903 | OxyAs OxyTs DNAts DNAts OxyMCs DNAcs OxyAs DNAas DNAas DNAts DNAts DNAcs DNAas DNAcs DNAts DNAts OxyTs OxyTs OxyAs OxyMC |
| ASO-002084 | ASO-002084 | ATTtCcaaattcacTTttAC | 478 | 138884 | 138903 | OxyAs OxyTs OxyTs DNAts OxyMCs DNAcs DNAas DNAas DNAas DNAts DNAts DNAcs DNAas DNAcs OxyTs OxyTs DNAts DNAts OxyAs OxyMC |
| ASO-002037 | ASO-002037 | ATTTccaaattcaCtTttAC | 479 | 138884 | 138903 | OxyAs OxyTs OxyTs OxyTs DNAcs DNAcs DNAas DNAas DNAas DNAts DNAts DNAcs DNAas OxyMCs DNAts OxyTs DNAts DNAts OxyAs OxyMC |
| ASO-002058 | ASO-002058 | ATTtCcaaattcacTttTAC | 480 | 138884 | 138903 | OxyAs OxyTs OxyTs DNAts OxyMCs DNAcs DNAas DNAas DNAas DNAts DNAts DNAcs DNAas DNAcs OxyTs DNAts DNAts OxyTs OxyAs OxyMC |

Figure 2AAA

| Oligomer Name | ASO Number | ASO Sequence | SEQ ID NO | premRNA start NG_007398 | premRNA end NG_007398 | Chemical Structure |
|---|---|---|---|---|---|---|
| ASO-002057 | ASO-002057 | ATTTccaaattcaCttTtAC | 481 | 138884 | 138903 | OxyAs OxyTs OxyTs OxyTs DNAcs DNAcs DNAas DNAas DNAas DNAts DNAts DNAcs DNAas OxyMCs DNAts DNAts OxyTs DNAts OxyAs OxyMC |
| ASO-001926 | ASO-001926 | ATTTCcaaattcacttTTAC | 482 | 138884 | 138903 | OxyAs OxyTs OxyTs OxyTs OxyMCs DNAcs DNAas DNAas DNAas DNAts DNAts DNAcs DNAas DNAcs DNAts DNAts OxyTs OxyTs OxyAs OxyMC |
| ASO-002092 | ASO-002092 | ATttCCaaattcactTtTAC | 483 | 138884 | 138903 | OxyAs OxyTs DNAts DNAts OxyMCs OxyMCs DNAas DNAas DNAas DNAts DNAts DNAcs DNAas DNAcs DNAts OxyTs DNAts OxyTs OxyAs OxyMC |
| ASO-002023 | ASO-002023 | ATTTccaaattcacTTttAC | 484 | 138884 | 138903 | OxyAs OxyTs OxyTs OxyTs DNAcs DNAcs DNAas DNAas DNAas DNAts DNAts DNAcs DNAas DNAcs OxyTs OxyTs DNAts DNAts OxyAs OxyMC |
| ASO-000758 | ASO-000758 | ATTtccaaattcactttTAC | 485 | 138884 | 138903 | OxyAs OxyTs OxyTs DNAts DNAcs DNAcs DNAas DNAas DNAas DNAts DNAts DNAcs DNAas DNAcs DNAts DNAts DNAts OxyTs OxyAs OxyMC |
| ASO-002065 | ASO-002065 | ATttCCaaattcactTTtAC | 486 | 138884 | 138903 | OxyAs OxyTs DNAts DNAts OxyMCs OxyMCs DNAas DNAas DNAas DNAts DNAts DNAcs DNAas DNAcs DNAts OxyTs OxyTs DNAts OxyAs OxyMC |
| ASO-002038 | ASO-002038 | ATTtCcaaattcacTtTtAC | 487 | 138884 | 138903 | OxyAs OxyTs OxyTs DNAts OxyMCs DNAcs DNAas DNAas DNAas DNAts DNAts DNAcs DNAas DNAcs OxyTs DNAts OxyTs DNAts OxyAs OxyMC |
| ASO-002039 | ASO-002039 | ATtTCcaaattcacTttTAC | 488 | 138884 | 138903 | OxyAs OxyTs DNAts OxyTs OxyMCs DNAcs DNAas DNAas DNAas DNAts DNAts DNAcs DNAas DNAcs OxyTs DNAts DNAts OxyTs OxyAs OxyMC |
| ASO-000763 | ASO-000763 | ATttccaaattcacttttAC | 489 | 138884 | 138903 | OxyAs OxyTs DNAts DNAts DNAcs DNAcs DNAas DNAas DNAas DNAts DNAts DNAcs DNAas DNAcs DNAts DNAts DNAts DNAts OxyAs OxyMC |

Figure 2BBB

| Oligomer Name | ASO Number | ASO Sequence | SEQ ID NO | premRNA start NG_007398 | premRNA end NG_007398 | Chemical Structure |
|---|---|---|---|---|---|---|
| ASO-000768 | ASO-000768 | AtttccaaattcacttttAC | 490 | 138884 | 138903 | OxyAs DNAts DNAts DNAts DNAcs DNAcs DNAas DNAas DNAas DNAts DNAts DNAcs DNAas DNAcs DNAts DNAts DNAts DNAts OxyAs OxyMC |
| 17-18-19mer-1 | ASO-002390 | TCCaaattcacttTTAC | 491 | 138884 | 138900 | OxyTs OxyMCs OxyMCs DNAas DNAas DNAas DNAts DNAts DNAcs DNAas DNAcs DNAts DNAts OxyTs OxyTs OxyAs OxyMCs |
| 17-18-19mer-10 | ASO-002403 | TCCAaattcacttTTAC | 492 | 138884 | 138900 | OxyTs OxyMCs OxyMCs OxyAs DNAas DNAas DNAts DNAts DNAcs DNAas DNAcs DNAts DNAts OxyTs OxyTs OxyAs OxyMCs |
| 17-18-19mer-13 | ASO-002439 | TCCAAattcactttTAC | 493 | 138884 | 138900 | OxyTs OxyMCs OxyMCs OxyAs OxyAs DNAas DNAts DNAts DNAcs DNAas DNAcs DNAts DNAts DNAts OxyTs OxyAs OxyMCs |
| 17-18-19mer-16 | ASO-002473 | TTCcaaattcacttTTAC | 494 | 138884 | 138901 | OxyTs OxyTs OxyMCs DNAcs DNAas DNAas DNAas DNAts DNAts DNAcs DNAas DNAcs DNAts DNAts OxyTs OxyTs OxyAs OxyMCs |
| 17-18-19mer-22 | ASO-002440 | TTCcaaattcactTTTAC | 495 | 138884 | 138901 | OxyTs OxyTs OxyMCs DNAcs DNAas DNAas DNAas DNAts DNAts DNAcs DNAas DNAcs DNAts OxyTs OxyTs OxyTs OxyAs OxyMCs |
| 17-18-19mer-28 | ASO-002417 | TTCCaaattcactttTAC | 496 | 138884 | 138901 | OxyTs OxyTs OxyMCs OxyMCs DNAas DNAas DNAas DNAts DNAts DNAcs DNAas DNAcs DNAts DNAts DNAts OxyTs OxyAs OxyMCs |
| 17-18-19mer-34 | ASO-002394 | TTCCaaattcacttTTAC | 497 | 138884 | 138901 | OxyTs OxyTs OxyMCs OxyMCs DNAas DNAas DNAas DNAts DNAts DNAcs DNAas DNAcs DNAts DNAts OxyTs OxyTs OxyAs OxyMCs |
| 17-18-19mer-4 | ASO-002426 | TCCaaattcactTTTAC | 498 | 138884 | 138900 | OxyTs OxyMCs OxyMCs DNAas DNAas DNAas DNAts DNAts DNAcs DNAas DNAcs DNAts OxyTs OxyTs OxyTs OxyAs OxyMCs |

Figure 2CCC

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-40 | ASO-002454 | TTCCAaattcactttTAC | 499 | 138884 | 138901 | OxyTs OxyTs OxyMCs OxyMCs OxyAs DNAas DNAas DNAts DNAts DNAcs DNAas DNAcs DNAts DNAts DNAts OxyTs OxyAs OxyMCs |
| 17-18-19mer-46 | ASO-002431 | TTTccaaattcacttTTAC | 500 | 138884 | 138902 | OxyTs OxyTs OxyTs DNAcs DNAcs DNAas DNAas DNAas DNAts DNAts DNAcs DNAas DNAcs DNAts DNAts OxyTs OxyTs OxyAs OxyMCs |
| 17-18-19mer-52 | ASO-002408 | TTTccaaattcactTTTAC | 501 | 138884 | 138902 | OxyTs OxyTs OxyTs DNAcs DNAcs DNAas DNAas DNAas DNAts DNAts DNAcs DNAas DNAcs DNAts OxyTs OxyTs OxyTs OxyAs OxyMCs |
| 17-18-19mer-58 | ASO-002467 | TTTCcaaattcactttTAC | 502 | 138884 | 138902 | OxyTs OxyTs OxyTs OxyMCs DNAcs DNAas DNAas DNAas DNAts DNAts DNAcs DNAas DNAcs DNAts DNAts DNAts OxyTs OxyAs OxyMCs |
| 17-18-19mer-64 | ASO-002445 | TTTCcaaattcacttTTAC | 503 | 138884 | 138902 | OxyTs OxyTs OxyTs OxyMCs DNAcs DNAas DNAas DNAas DNAts DNAts DNAcs DNAas DNAcs DNAts DNAts OxyTs OxyTs OxyAs OxyMCs |
| 17-18-19mer-7 | ASO-002461 | TCCAaattcactttTAC | 504 | 138884 | 138900 | OxyTs OxyMCs OxyMCs OxyAs DNAas DNAas DNAts DNAts DNAcs DNAas DNAcs DNAts DNAts DNAts OxyTs OxyAs OxyMCs |
| 17-18-19mer-70 | ASO-002422 | TTTCCaaattcactttTAC | 505 | 138884 | 138902 | OxyTs OxyTs OxyTs OxyMCs OxyMCs DNAas DNAas DNAas DNAts DNAts DNAcs DNAas DNAcs DNAts DNAts DNAts OxyTs OxyAs OxyMCs |
| ASO-001933-mm1 | ASO-002291 | GtTTCcaaattcactTTtAC | 506 | 138884 | 138903 | OxyGs DNAts OxyTs OxyTs OxyMCs DNAcs DNAas DNAas DNAas DNAts DNAts DNAcs DNAas DNAcs DNAts OxyTs OxyTs DNAts OxyAs OxyMCs |
| ASO-001933-mm2 | ASO-002303 | AtTTCcagattcactTTtAC | 507 | 138884 | 138903 | OxyAs DNAts OxyTs OxyTs OxyMCs DNAcs DNAas DNAgs DNAas DNAts DNAts DNAcs DNAas DNAcs DNAts OxyTs OxyTs DNAts OxyAs OxyMCs |

Figure 2DDD

| Oligomer Name | ASO Number | ASO Sequence | SEQ ID NO | premRNA start NG_007398 | premRNA end NG_007398 | Chemical Structure |
|---|---|---|---|---|---|---|
| ASO-001933-mm3 | ASO-002315 | TtTTCcaaattcactTTtAC | 508 | 138884 | 138903 | OxyTs DNAts OxyTs OxyTs OxyMCs DNAcs DNAas DNAas DNAas DNAts DNAts DNAcs DNAas DNAcs DNAts OxyTs OxyTs DNAts OxyAs OxyMCs |
| ASO-001933-mm4 | ASO-002327 | GtTTCcagattcactTTtAC | 509 | 138884 | 138903 | OxyGs DNAts OxyTs OxyTs OxyMCs DNAcs DNAas DNAgs DNAas DNAts DNAts DNAcs DNAas DNAcs DNAts OxyTs OxyTs DNAts OxyAs OxyMCs |
| ASO-001933-mm5 | ASO-002339 | AtTTCcaagttcactTTtGC | 510 | 138884 | 138903 | OxyAs DNAts OxyTs OxyTs OxyMCs DNAcs DNAas DNAas DNAgs DNAts DNAts DNAcs DNAas DNAcs DNAts OxyTs OxyTs DNAts OxyGs OxyMCs |
| ASO-001933-mm6 | ASO-002351 | AtTTCcagattcgctTTtAC | 511 | 138884 | 138903 | OxyAs DNAts OxyTs OxyTs OxyMCs DNAcs DNAas DNAgs DNAas DNAts DNAts DNAcs DNAgs DNAcs DNAts OxyTs OxyTs DNAts OxyAs OxyMCs |
| SPC-15678-01 | ASO-002274 | CCaaattcactttTAC | 512 | 138884 | 138899 | OxyMCs OxyMCs DNAas DNAas DNAas DNAts DNAts DNAcs DNAas DNAcs DNAts DNAts DNAts OxyTs OxyAs OxyMCs |
| SPC-15857-01 | ASO-002326 | ATtTcCaaattcacttTTAC | 513 | 138884 | 138903 | OxyAs OxyTs DNAts OxyTs DNAcs OxyMCs DNAas DNAas DNAas DNAts DNAts DNAcs DNAas DNAcs DNAts DNAts OxyTs OxyTs OxyAs OxyMCs |
| SPC-15858-01 | ASO-002338 | ATTtcCaaattcacttTTAC | 514 | 138884 | 138903 | OxyAs OxyTs OxyTs DNAts DNAcs OxyMCs DNAas DNAas DNAas DNAts DNAts DNAcs DNAas DNAcs DNAts DNAts OxyTs OxyTs OxyAs OxyMCs |
| SPC-15860-01 | ASO-002362 | ATTtCcaaattcacttTTAC | 515 | 138884 | 138903 | OxyAs OxyTs OxyTs DNAts OxyMCs DNAcs DNAas DNAas DNAas DNAts DNAts DNAcs DNAas DNAcs DNAts DNAts OxyTs OxyTs OxyAs OxyMCs |
| SPC-15864-01 | ASO-002236 | ATTTccaaattcacTttTAC | 516 | 138884 | 138903 | OxyAs OxyTs OxyTs OxyTs DNAcs DNAcs DNAas DNAas DNAas DNAts DNAts DNAcs DNAas DNAcs OxyTs DNAts DNAts OxyTs OxyAs OxyMCs |

Figure 2EEE

| Oligomer Name | ASO Number | ASO Sequence | SEQ ID NO | premRNA start NG_007398 | premRNA end NG_007398 | Chemical Structure |
|---|---|---|---|---|---|---|
| SPC-15868-01 | ASO-002269 | ATtTCcaaattcactTtTAC | 517 | 138884 | 138903 | OxyAs OxyTs DNAts OxyTs OxyMCs DNAcs DNAas DNAas DNAas DNAts DNAts DNAcs DNAas DNAcs DNAts OxyTs DNAts OxyTs OxyAs OxyMCs |
| SPC-15872-01 | ASO-002237 | ATttCCaaattcacttTTAC | 518 | 138884 | 138903 | OxyAs OxyTs DNAts DNAts OxyMCs OxyMCs DNAas DNAas DNAas DNAts DNAts DNAcs DNAas DNAcs DNAts DNAts OxyTs OxyTs OxyAs OxyMCs |
| SPC-15873-01 | ASO-002246 | ATTtCcaaattcactTTtAC | 519 | 138884 | 138903 | OxyAs OxyTs OxyTs DNAts OxyMCs DNAcs DNAas DNAas DNAas DNAts DNAts DNAcs DNAas DNAcs DNAts OxyTs OxyTs DNAts OxyAs OxyMCs |
| SPC-15874-01 | ASO-002254 | ATTTccaaattcacTtTtAC | 520 | 138884 | 138903 | OxyAs OxyTs OxyTs OxyTs DNAcs DNAcs DNAas DNAas DNAas DNAts DNAts DNAcs DNAas DNAcs OxyTs DNAts OxyTs DNAts OxyAs OxyMCs |
| SPC-15878-01 | ASO-002284 | ATtTccAaattcacttTTAC | 521 | 138884 | 138903 | OxyAs OxyTs DNAts OxyTs DNAcs DNAcs OxyAs DNAas DNAas DNAts DNAts DNAcs DNAas DNAcs DNAts DNAts OxyTs OxyTs OxyAs OxyMCs |
| SPC-15879-01 | ASO-002229 | ATTTccaaattcacttTTAC | 522 | 138884 | 138903 | OxyAs OxyTs OxyTs OxyTs DNAcs DNAcs DNAas DNAas DNAas DNAts DNAts DNAcs DNAas DNAcs DNAts DNAts OxyTs OxyTs OxyAs OxyMCs |
| SPC-15880-01 | ASO-002238 | ATTTccaaattcactTtTAC | 523 | 138884 | 138903 | OxyAs OxyTs OxyTs OxyTs DNAcs DNAcs DNAas DNAas DNAas DNAts DNAts DNAcs DNAas DNAcs DNAts OxyTs DNAts OxyTs OxyAs OxyMCs |
| SPC-15883-01 | ASO-002263 | ATtTcCaaattcactTTtAC | 524 | 138884 | 138903 | OxyAs OxyTs DNAts OxyTs DNAcs OxyMCs DNAas DNAas DNAas DNAts DNAts DNAcs DNAas DNAcs DNAts OxyTs OxyTs DNAts OxyAs OxyMCs |
| SPC-15888-01 | ASO-002239 | ATTTccaaattcactTTtAC | 525 | 138884 | 138903 | OxyAs OxyTs OxyTs OxyTs DNAcs DNAcs DNAas DNAas DNAas DNAts DNAts DNAcs DNAas DNAcs DNAts OxyTs OxyTs DNAts OxyAs OxyMCs |

Figure 2FFF

| Oligomer Name | ASO Number | ASO Sequence | SEQ ID NO | premRNA start NG_007398 | premRNA end NG_007398 | Chemical Structure |
|---|---|---|---|---|---|---|
| ASO-000754 | ASO-000754 | TATTTccaaattcacTTTTA | 526 | 138885 | 138904 | OxyTs OxyAs OxyTs OxyTs OxyTs DNAcs DNAcs DNAas DNAas DNAas DNAts DNAts DNAcs DNAas DNAcs OxyTs OxyTs OxyTs OxyTs OxyA |
| ASO-002055 | ASO-002055 | TAtTtCcaaattcacTTtTA | 527 | 138885 | 138904 | OxyTs OxyAs DNAts OxyTs DNAts OxyMCs DNAcs DNAas DNAas DNAas DNAts DNAts DNAcs DNAas DNAcs OxyTs OxyTs DNAts OxyTs OxyA |
| ASO-002035 | ASO-002035 | TAtTtcCaaattcactTTTA | 528 | 138885 | 138904 | OxyTs OxyAs DNAts OxyTs DNAts DNAcs OxyMCs DNAas DNAas DNAas DNAts DNAts DNAcs DNAas DNAcs DNAts OxyTs OxyTs OxyTs OxyA |
| ASO-002048 | ASO-002048 | TATtTccaaattcaCttTTA | 529 | 138885 | 138904 | OxyTs OxyAs OxyTs DNAts OxyTs DNAcs DNAcs DNAas DNAas DNAas DNAts DNAts DNAcs DNAas OxyMCs DNAts DNAts OxyTs OxyTs OxyA |
| ASO-002053 | ASO-002053 | TAtTtCcaaattcactTTTA | 530 | 138885 | 138904 | OxyTs OxyAs DNAts OxyTs DNAts OxyMCs DNAcs DNAas DNAas DNAas DNAts DNAts DNAcs DNAas DNAcs DNAts OxyTs OxyTs OxyTs OxyA |
| ASO-002067 | ASO-002067 | TAtTTccaaattcaCTttTA | 531 | 138885 | 138904 | OxyTs OxyAs DNAts OxyTs OxyTs DNAcs DNAcs DNAas DNAas DNAas DNAts DNAts DNAcs DNAas OxyMCs OxyTs DNAts DNAts OxyTs OxyA |
| ASO-001954 | ASO-001954 | TATTTccaaattcactTTTA | 532 | 138885 | 138904 | OxyTs OxyAs OxyTs OxyTs OxyTs DNAcs DNAcs DNAas DNAas DNAas DNAts DNAts DNAcs DNAas DNAcs DNAts OxyTs OxyTs OxyTs OxyA |
| ASO-001947 | ASO-001947 | TATTtccaaattcacTTTTA | 533 | 138885 | 138904 | OxyTs OxyAs OxyTs OxyTs DNAts DNAcs DNAcs DNAas DNAas DNAas DNAts DNAts DNAcs DNAas DNAcs OxyTs OxyTs OxyTs OxyTs OxyA |
| ASO-002081 | ASO-002081 | TATttCcaaattcacTtTTA | 534 | 138885 | 138904 | OxyTs OxyAs OxyTs DNAts DNAts OxyMCs DNAcs DNAas DNAas DNAas DNAts DNAts DNAcs DNAas DNAcs OxyTs DNAts OxyTs OxyTs OxyA |

Figure 2GGG

| Oligomer Name | ASO Number | ASO Sequence | SEQ ID NO | premRNA start NG_007398 | premRNA end NG_007398 | Chemical Structure |
|---|---|---|---|---|---|---|
| ASO-001966 | ASO-001966 | TAtTTccaaattcacTTtTA | 535 | 138885 | 138904 | OxyTs OxyAs DNAts OxyTs OxyTs DNAcs DNAcs DNAas DNAas DNAas DNAts DNAts DNAcs DNAas DNAcs OxyTs OxyTs DNAts OxyTs OxyA |
| ASO-002025 | ASO-002025 | TAttTcCaaattcactTTTA | 536 | 138885 | 138904 | OxyTs OxyAs DNAts DNAts OxyTs DNAcs OxyMCs DNAas DNAas DNAas DNAts DNAts DNAcs DNAas DNAcs DNAts OxyTs OxyTs OxyTs OxyA |
| ASO-002033 | ASO-002033 | TATtTccaaattcacTtTTA | 537 | 138885 | 138904 | OxyTs OxyAs OxyTs DNAts OxyTs DNAcs DNAcs DNAas DNAas DNAas DNAts DNAts DNAcs DNAas DNAcs OxyTs DNAts OxyTs OxyTs OxyA |
| ASO-001960 | ASO-001960 | TaTTTccaaattcacTTtTA | 538 | 138885 | 138904 | OxyTs DNAas OxyTs OxyTs OxyTs DNAcs DNAcs DNAas DNAas DNAas DNAts DNAts DNAcs DNAas DNAcs OxyTs OxyTs DNAts OxyTs OxyA |
| ASO-002056 | ASO-002056 | TAttTCcaaattcacTTtTA | 539 | 138885 | 138904 | OxyTs OxyAs DNAts DNAts OxyTs OxyMCs DNAcs DNAas DNAas DNAas DNAts DNAts DNAcs DNAas DNAcs OxyTs OxyTs DNAts OxyTs OxyA |
| ASO-002063 | ASO-002063 | TATttCcaaattcacTTtTA | 540 | 138885 | 138904 | OxyTs OxyAs OxyTs DNAts DNAts OxyMCs DNAcs DNAas DNAas DNAas DNAts DNAts DNAcs DNAas DNAcs OxyTs OxyTs DNAts OxyTs OxyA |
| ASO-002089 | ASO-002089 | TATTtccaaattcaCttTTA | 541 | 138885 | 138904 | OxyTs OxyAs OxyTs OxyTs DNAts DNAcs DNAcs DNAas DNAas DNAas DNAts DNAts DNAcs DNAas OxyMCs DNAts DNAts OxyTs OxyTs OxyA |
| ASO-002073 | ASO-002073 | TAtTtCcaaattcacTtTTA | 542 | 138885 | 138904 | OxyTs OxyAs DNAts OxyTs DNAts OxyMCs DNAcs DNAas DNAas DNAas DNAts DNAts DNAcs DNAas DNAcs OxyTs DNAts OxyTs OxyTs OxyA |
| ASO-002027 | ASO-002027 | TATtTccaaattcaCtTtTA | 543 | 138885 | 138904 | OxyTs OxyAs OxyTs DNAts OxyTs DNAcs DNAcs DNAas DNAas DNAas DNAts DNAts DNAcs DNAas OxyMCs DNAts OxyTs DNAts OxyTs OxyA |

Figure 2HHH

| Oligomer Name | ASO Number | ASO Sequence | SEQ ID NO | premRNA start NG_007398 | premRNA end NG_007398 | Chemical Structure |
|---|---|---|---|---|---|---|
| ASO-002075 | ASO-002075 | TATtTccaaattcaCTttTA | 544 | 138885 | 138904 | OxyTs OxyAs OxyTs DNAts OxyTs DNAcs DNAcs DNAas DNAas DNAas DNAts DNAts DNAcs DNAas OxyMCs OxyTs DNAts DNAts OxyTs OxyA |
| ASO-002028 | ASO-002028 | TAtTTccaaattcaCttTTA | 545 | 138885 | 138904 | OxyTs OxyAs DNAts OxyTs OxyTs DNAcs DNAcs DNAas DNAas DNAas DNAts DNAts DNAcs DNAas OxyMCs DNAts DNAts OxyTs OxyTs OxyA |
| ASO-002085 | ASO-002085 | TAtTTccaaattcaCtTtTA | 546 | 138885 | 138904 | OxyTs OxyAs DNAts OxyTs OxyTs DNAcs DNAcs DNAas DNAas DNAas DNAts DNAts DNAcs DNAas OxyMCs DNAts OxyTs DNAts OxyTs OxyA |
| ASO-002083 | ASO-002083 | TAttTCcaaattcacTtTTA | 547 | 138885 | 138904 | OxyTs OxyAs DNAts DNAts OxyTs OxyMCs DNAcs DNAas DNAas DNAas DNAts DNAts DNAcs DNAas DNAcs OxyTs DNAts OxyTs OxyTs OxyA |
| ASO-000759 | ASO-000759 | TATttccaaattcactTTA | 548 | 138885 | 138904 | OxyTs OxyAs OxyTs DNAts DNAts DNAcs DNAcs DNAas DNAas DNAas DNAts DNAts DNAcs DNAas DNAcs DNAts DNAts OxyTs OxyTs OxyA |
| ASO-000769 | ASO-000769 | TatttccaaattcactttTA | 549 | 138885 | 138904 | OxyTs DNAas DNAts DNAts DNAts DNAcs DNAcs DNAas DNAas DNAas DNAts DNAts DNAcs DNAas DNAcs DNAts DNAts DNAts OxyTs OxyA |
| ASO-000764 | ASO-000764 | TAtttccaaattcactttTA | 550 | 138885 | 138904 | OxyTs OxyAs DNAts DNAts DNAts DNAcs DNAcs DNAas DNAas DNAas DNAts DNAts DNAcs DNAas DNAcs DNAts DNAts DNAts OxyTs OxyA |
| 17-18-19mer-11 | ASO-002415 | TTCCaaattcactTTTA | 551 | 138885 | 138901 | OxyTs OxyTs OxyMCs OxyMCs DNAas DNAas DNAas DNAts DNAts DNAcs DNAas DNAcs DNAts OxyTs OxyTs OxyTs OxyAs |
| 17-18-19mer-14 | ASO-002451 | TTCCAaattcacttTTA | 552 | 138885 | 138901 | OxyTs OxyTs OxyMCs OxyMCs OxyAs DNAas DNAas DNAts DNAts DNAcs DNAas DNAcs DNAts DNAts OxyTs OxyTs OxyAs |

Figure 2III

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-17 | ASO-002392 | TTTccaaattcactTTTA | 553 | 138885 | 138902 | OxyTs OxyTs OxyTs DNAcs DNAcs DNAas DNAas DNAas DNAts DNAts DNAcs DNAas DNAcs DNAts OxyTs OxyTs OxyTs OxyAs |
| 17-18-19mer-2 | ASO-002402 | TTCcaaattcactTTTA | 554 | 138885 | 138901 | OxyTs OxyTs OxyMCs DNAcs DNAas DNAas DNAas DNAts DNAts DNAcs DNAas DNAcs DNAts OxyTs OxyTs OxyTs OxyAs |
| 17-18-19mer-23 | ASO-002452 | TTTccaaattcacTTTTA | 555 | 138885 | 138902 | OxyTs OxyTs OxyTs DNAcs DNAcs DNAas DNAas DNAas DNAts DNAts DNAcs DNAas DNAcs OxyTs OxyTs OxyTs OxyTs OxyAs |
| 17-18-19mer-29 | ASO-002429 | TTTCcaaattcacttTTA | 556 | 138885 | 138902 | OxyTs OxyTs OxyTs OxyMCs DNAcs DNAas DNAas DNAas DNAts DNAts DNAcs DNAas DNAcs DNAts DNAts OxyTs OxyTs OxyAs |
| 17-18-19mer-35 | ASO-002406 | TTTCcaaattcactTTTA | 557 | 138885 | 138902 | OxyTs OxyTs OxyTs OxyMCs DNAcs DNAas DNAas DNAas DNAts DNAts DNAcs DNAas DNAcs DNAts OxyTs OxyTs OxyTs OxyAs |
| 17-18-19mer-41 | ASO-002465 | TTTCCaaattcacttTTA | 558 | 138885 | 138902 | OxyTs OxyTs OxyTs OxyMCs OxyMCs DNAas DNAas DNAas DNAts DNAts DNAcs DNAas DNAcs DNAts DNAts OxyTs OxyTs OxyAs |
| 17-18-19mer-47 | ASO-002443 | ATTtccaaattcactTTTA | 559 | 138885 | 138903 | OxyAs OxyTs OxyTs DNAts DNAcs DNAcs DNAas DNAas DNAas DNAts DNAts DNAcs DNAas DNAcs DNAts OxyTs OxyTs OxyTs OxyAs |
| 17-18-19mer-5 | ASO-002438 | TTCcaaattcacTTTTA | 560 | 138885 | 138901 | OxyTs OxyTs OxyMCs DNAcs DNAas DNAas DNAas DNAts DNAts DNAcs DNAas DNAcs OxyTs OxyTs OxyTs OxyTs OxyAs |
| 17-18-19mer-53 | ASO-002420 | ATTtccaaattcacTTTTA | 561 | 138885 | 138903 | OxyAs OxyTs OxyTs DNAts DNAcs DNAcs DNAas DNAas DNAas DNAts DNAts DNAcs DNAas DNAcs OxyTs OxyTs OxyTs OxyTs OxyAs |

Figure 2JJJ

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-59 | ASO-002478 | ATTTccaaattcacttTTA | 562 | 138885 | 138903 | OxyAs OxyTs OxyTs OxyTs DNAcs DNAcs DNAas DNAas DNAas DNAts DNAts DNAcs DNAas DNAcs DNAts DNAts OxyTs OxyTs OxyAs |
| 17-18-19mer-65 | ASO-002457 | ATTTccaaattcactTTTA | 563 | 138885 | 138903 | OxyAs OxyTs OxyTs OxyTs DNAcs DNAcs DNAas DNAas DNAas DNAts DNAts DNAcs DNAas DNAcs DNAts OxyTs OxyTs OxyTs OxyAs |
| 17-18-19mer-71 | ASO-002434 | ATTTCcaaattcacttTTA | 564 | 138885 | 138903 | OxyAs OxyTs OxyTs OxyTs OxyMCs DNAcs DNAas DNAas DNAas DNAts DNAts DNAcs DNAas DNAcs DNAts DNAts OxyTs OxyTs OxyAs |
| 17-18-19mer-8 | ASO-002472 | TTCCaaattcacttTTA | 565 | 138885 | 138901 | OxyTs OxyTs OxyMCs OxyMCs DNAas DNAas DNAas DNAts DNAts DNAcs DNAas DNAcs DNAts DNAts OxyTs OxyTs OxyAs |
| ASO-001954-mm1 | ASO-002340 | TATTTccagattcactTTTA | 566 | 138885 | 138904 | OxyTs OxyAs OxyTs OxyTs OxyTs DNAcs DNAcs DNAas DNAgs DNAas DNAts DNAts DNAcs DNAas DNAcs DNAts OxyTs OxyTs OxyTs OxyAs |
| ASO-001954-mm2 | ASO-002352 | TATTTccgaattcactTTTA | 567 | 138885 | 138904 | OxyTs OxyAs OxyTs OxyTs OxyTs DNAcs DNAcs DNAgs DNAas DNAas DNAts DNAts DNAcs DNAas DNAcs DNAts OxyTs OxyTs OxyTs OxyAs |
| ASO-001954-mm3 | ASO-002364 | GATTTccaaattcactTTTA | 568 | 138885 | 138904 | OxyGs OxyAs OxyTs OxyTs OxyTs DNAcs DNAcs DNAas DNAas DNAas DNAts DNAts DNAcs DNAas DNAcs DNAts OxyTs OxyTs OxyTs OxyAs |
| ASO-001954-mm4 | ASO-002376 | GGTTTccaaattcactTTTA | 569 | 138885 | 138904 | OxyGs OxyGs OxyTs OxyTs OxyTs DNAcs DNAcs DNAas DNAas DNAas DNAts DNAts DNAcs DNAas DNAcs DNAts OxyTs OxyTs OxyTs OxyAs |
| ASO-001954-mm5 | ASO-002293 | AATTTccagattcactTTTA | 570 | 138885 | 138904 | OxyAs OxyAs OxyTs OxyTs OxyTs DNAcs DNAcs DNAas DNAgs DNAas DNAts DNAts DNAcs DNAas DNAcs DNAts OxyTs OxyTs OxyTs OxyAs |

Figure 2KKK

| Oligomer Name | ASO Number | ASO Sequence | SEQ ID NO | premRNA start NG_007398 | premRNA end NG_007398 | Chemical Structure |
|---|---|---|---|---|---|---|
| ASO-001954-mm6 | ASO-002305 | TATTTccaagttcgctTTTA | 571 | 138885 | 138904 | OxyTs OxyAs OxyTs OxyTs OxyTs DNAcs DNAcs DNAas DNAas DNAgs DNAts DNAts DNAcs DNAgs DNAcs DNAts OxyTs OxyTs OxyTs OxyAs |
| SPC-15677-01 | ASO-002266 | TCCaaattcactttTA | 572 | 138885 | 138900 | OxyTs OxyMCs OxyMCs DNAas DNAas DNAas DNAts DNAts DNAcs DNAas DNAcs DNAts DNAts DNAts OxyTs OxyAs |
| SPC-15859-01 | ASO-002350 | TAtTTccaaattcactTTTA | 573 | 138885 | 138904 | OxyTs OxyAs DNAts OxyTs OxyTs DNAcs DNAcs DNAas DNAas DNAas DNAts DNAts DNAcs DNAas DNAcs DNAts OxyTs OxyTs OxyTs OxyAs |
| SPC-15861-01 | ASO-002374 | TAtTTccaaattcacTtTTA | 574 | 138885 | 138904 | OxyTs OxyAs DNAts OxyTs OxyTs DNAcs DNAcs DNAas DNAas DNAas DNAts DNAts DNAcs DNAas DNAcs OxyTs DNAts OxyTs OxyTs OxyAs |
| SPC-15862-01 | ASO-002386 | TATTtccaaattcaCTttTA | 575 | 138885 | 138904 | OxyTs OxyAs OxyTs OxyTs DNAts DNAcs DNAcs DNAas DNAas DNAas DNAts DNAts DNAcs DNAas OxyMCs OxyTs DNAts DNAts OxyTs OxyAs |
| SPC-15863-01 | ASO-002227 | TATtTccaaattcactTTTA | 576 | 138885 | 138904 | OxyTs OxyAs OxyTs DNAts OxyTs DNAcs DNAcs DNAas DNAas DNAas DNAts DNAts DNAcs DNAas DNAcs DNAts OxyTs OxyTs OxyTs OxyAs |
| SPC-15865-01 | ASO-002245 | TAttTCcaaattcactTTTA | 577 | 138885 | 138904 | OxyTs OxyAs DNAts DNAts OxyTs OxyMCs DNAcs DNAas DNAas DNAas DNAts DNAts DNAcs DNAas DNAcs DNAts OxyTs OxyTs OxyTs OxyAs |
| SPC-15867-01 | ASO-002261 | TATtTccaaattcacTTtTA | 578 | 138885 | 138904 | OxyTs OxyAs OxyTs DNAts OxyTs DNAcs DNAcs DNAas DNAas DNAas DNAts DNAts DNAcs DNAas DNAcs OxyTs OxyTs DNAts OxyTs OxyAs |
| SPC-15869-01 | ASO-002276 | TATttCcaaattcactTTTA | 579 | 138885 | 138904 | OxyTs OxyAs OxyTs DNAts DNAts OxyMCs DNAcs DNAas DNAas DNAas DNAts DNAts DNAcs DNAas DNAcs DNAts OxyTs OxyTs OxyTs OxyAs |

Figure 2LLL

| Oligomer Name | ASO Number | ASO Sequence | SEQ ID NO | premRNA start NG_007398 | premRNA end NG_007398 | Chemical Structure |
|---|---|---|---|---|---|---|
| SPC-15871-01 | ASO-002228 | TATTtccaaattcaCtTtTA | 580 | 138885 | 138904 | OxyTs OxyAs OxyTs OxyTs DNAts DNAcs DNAcs DNAas DNAas DNAas DNAts DNAts DNAcs DNAas OxyMCs DNAts OxyTs DNAts OxyTs OxyAs |
| SPC-15882-01 | ASO-002255 | TATTtccaaattcactTTTA | 581 | 138885 | 138904 | OxyTs OxyAs OxyTs OxyTs DNAts DNAcs DNAcs DNAas DNAas DNAas DNAts DNAts DNAcs DNAas DNAcs DNAts OxyTs OxyTs OxyTs OxyAs |
| SPC-15886-01 | ASO-002285 | TATTtccaaattcacTTtTA | 582 | 138885 | 138904 | OxyTs OxyAs OxyTs OxyTs DNAts DNAcs DNAcs DNAas DNAas DNAas DNAts DNAts DNAcs DNAas DNAcs OxyTs OxyTs DNAts OxyTs OxyAs |
| SPC-15887-01 | ASO-002230 | TATTtccaaattcacTtTTA | 583 | 138885 | 138904 | OxyTs OxyAs OxyTs OxyTs DNAts DNAcs DNAcs DNAas DNAas DNAas DNAts DNAts DNAcs DNAas DNAcs OxyTs DNAts OxyTs OxyTs OxyAs |
| SPC-15890-01 | ASO-002256 | TATTtccaaattcAcTttTA | 584 | 138885 | 138904 | OxyTs OxyAs OxyTs OxyTs DNAts DNAcs DNAcs DNAas DNAas DNAas DNAts DNAts DNAcs OxyAs DNAcs OxyTs DNAts DNAts OxyTs OxyAs |
| SPC-15893-01 | ASO-002279 | TATTtccaaattcActTtTA | 585 | 138885 | 138904 | OxyTs OxyAs OxyTs OxyTs DNAts DNAcs DNAcs DNAas DNAas DNAas DNAts DNAts DNAcs OxyAs DNAcs DNAts OxyTs DNAts OxyTs OxyAs |
| ASO-002072 | ASO-002072 | TTAttTccaaattcaCTtTT | 586 | 138886 | 138905 | OxyTs OxyTs OxyAs DNAts DNAts OxyTs DNAcs DNAcs DNAas DNAas DNAas DNAts DNAts DNAcs DNAas OxyMCs OxyTs DNAts OxyTs OxyT |
| ASO-000755 | ASO-000755 | TTATTtccaaattcaCTTTT | 587 | 138886 | 138905 | OxyTs OxyTs OxyAs OxyTs OxyTs DNAts DNAcs DNAcs DNAas DNAas DNAas DNAts DNAts DNAcs DNAas OxyMCs OxyTs OxyTs OxyTs OxyT |
| ASO-002071 | ASO-002071 | TTaTtTccaaattcacTTTT | 588 | 138886 | 138905 | OxyTs OxyTs DNAas OxyTs DNAts OxyTs DNAcs DNAcs DNAas DNAas DNAas DNAts DNAts DNAcs DNAas DNAcs OxyTs OxyTs OxyTs OxyT |

Figure 2MMM

| Oligomer Name | ASO Number | ASO Sequence | SEQ ID NO | premRNA start NG_007398 | premRNA end NG_007398 | Chemical Structure |
|---|---|---|---|---|---|---|
| ASO-000760 | ASO-000760 | TTAtttccaaattcactTTT | 589 | 138886 | 138905 | OxyTs OxyTs OxyAs DNAts DNAts DNAts DNAcs DNAcs DNAas DNAas DNAas DNAts DNAts DNAcs DNAas DNAcs DNAts OxyTs OxyTs OxyT |
| ASO-001920 | ASO-001920 | TTATttccaaattcaCTTTT | 590 | 138886 | 138905 | OxyTs OxyTs OxyAs OxyTs DNAts DNAts DNAcs DNAcs DNAas DNAas DNAas DNAts DNAts DNAcs DNAas OxyMCs OxyTs OxyTs OxyTs OxyT |
| ASO-002080 | ASO-002080 | TTatTTccaaattcacTTTT | 591 | 138886 | 138905 | OxyTs OxyTs DNAas DNAts OxyTs OxyTs DNAcs DNAcs DNAas DNAas DNAas DNAts DNAts DNAcs DNAas DNAcs OxyTs OxyTs OxyTs OxyT |
| ASO-001927 | ASO-001927 | TTATTtccaaattcacTTTT | 592 | 138886 | 138905 | OxyTs OxyTs OxyAs OxyTs OxyTs DNAts DNAcs DNAcs DNAas DNAas DNAas DNAts DNAts DNAcs DNAas DNAcs OxyTs OxyTs OxyTs OxyT |
| ASO-001941 | ASO-001941 | TTaTTtccaaattcaCTtTT | 593 | 138886 | 138905 | OxyTs OxyTs DNAas OxyTs OxyTs DNAts DNAcs DNAcs DNAas DNAas DNAas DNAts DNAts DNAcs DNAas OxyMCs OxyTs DNAts OxyTs OxyT |
| ASO-002045 | ASO-002045 | TTaTttCcaaattcacTTTT | 594 | 138886 | 138905 | OxyTs OxyTs DNAas OxyTs DNAts DNAts OxyMCs DNAcs DNAas DNAas DNAas DNAts DNAts DNAcs DNAas DNAcs OxyTs OxyTs OxyTs OxyT |
| ASO-001934 | ASO-001934 | TtATTtccaaattcaCTtTT | 595 | 138886 | 138905 | OxyTs DNAts OxyAs OxyTs OxyTs DNAts DNAcs DNAcs DNAas DNAas DNAas DNAts DNAts DNAcs DNAas OxyMCs OxyTs DNAts OxyTs OxyT |
| ASO-002074 | ASO-002074 | TTatTTccaaattcaCTtTT | 596 | 138886 | 138905 | OxyTs OxyTs DNAas DNAts OxyTs OxyTs DNAcs DNAcs DNAas DNAas DNAas DNAts DNAts DNAcs DNAas OxyMCs OxyTs DNAts OxyTs OxyT |
| ASO-002093 | ASO-002093 | TTAtTtccaaattcACttTT | 597 | 138886 | 138905 | OxyTs OxyTs OxyAs DNAts OxyTs DNAts DNAcs DNAcs DNAas DNAas DNAas DNAts DNAts DNAcs OxyAs OxyMCs DNAts DNAts OxyTs OxyT |

Figure 2NNN

| Oligomer Name | ASO Number | ASO Sequence | SEQ ID NO | premRNA start NG_007398 | premRNA end NG_007398 | Chemical Structure |
|---|---|---|---|---|---|---|
| ASO-002054 | ASO-002054 | TTaTTtccaaattcaCtTTT | 598 | 138886 | 138905 | OxyTs OxyTs DNAas OxyTs OxyTs DNAts DNAcs DNAcs DNAas DNAas DNAas DNAts DNAts DNAcs DNAas OxyMCs DNAts OxyTs OxyTs OxyT |
| ASO-002091 | ASO-002091 | TTaTtTccaaattcaCtTTT | 599 | 138886 | 138905 | OxyTs OxyTs DNAas OxyTs DNAts OxyTs DNAcs DNAcs DNAas DNAas DNAas DNAts DNAts DNAcs DNAas OxyMCs DNAts OxyTs OxyTs OxyT |
| ASO-002064 | ASO-002064 | TTaTtTccaaattcaCTtTT | 600 | 138886 | 138905 | OxyTs OxyTs DNAas OxyTs DNAts OxyTs DNAcs DNAcs DNAas DNAas DNAas DNAts DNAts DNAcs DNAas OxyMCs OxyTs DNAts OxyTs OxyT |
| ASO-002066 | ASO-002066 | TTATttccaaattCacTtTT | 601 | 138886 | 138905 | OxyTs OxyTs OxyAs OxyTs DNAts DNAts DNAcs DNAcs DNAas DNAas DNAas DNAts DNAts OxyMCs DNAas DNAcs OxyTs DNAts OxyTs OxyT |
| ASO-002044 | ASO-002044 | TTAtTtccaaattcaCtTTT | 602 | 138886 | 138905 | OxyTs OxyTs OxyAs DNAts OxyTs DNAts DNAcs DNAcs DNAas DNAas DNAas DNAts DNAts DNAcs DNAas OxyMCs DNAts OxyTs OxyTs OxyT |
| ASO-002047 | ASO-002047 | TTATttccaaattCaCttTT | 603 | 138886 | 138905 | OxyTs OxyTs OxyAs OxyTs DNAts DNAts DNAcs DNAcs DNAas DNAas DNAas DNAts DNAts OxyMCs DNAas OxyMCs DNAts DNAts OxyTs OxyT |
| ASO-002046 | ASO-002046 | TTatTtCcaaattcacTTTT | 604 | 138886 | 138905 | OxyTs OxyTs DNAas DNAts OxyTs DNAts OxyMCs DNAcs DNAas DNAas DNAas DNAts DNAts DNAcs DNAas DNAcs OxyTs OxyTs OxyTs OxyT |
| ASO-000765 | ASO-000765 | TTatttccaaattcacttTT | 605 | 138886 | 138905 | OxyTs OxyTs DNAas DNAts DNAts DNAts DNAcs DNAcs DNAas DNAas DNAas DNAts DNAts DNAcs DNAas DNAcs DNAts DNAts OxyTs OxyT |
| ASO-000770 | ASO-000770 | TtatttccaaattcacttTT | 606 | 138886 | 138905 | OxyTs DNAts DNAas DNAts DNAts DNAts DNAcs DNAcs DNAas DNAas DNAas DNAts DNAts DNAcs DNAas DNAcs DNAts DNAts OxyTs OxyT |

Figure 2OOO

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-12 | ASO-002427 | TTTCcaaattcacTTTT | 607 | 138886 | 138902 | OxyTs OxyTs OxyTs OxyMCs DNAcs DNAas DNAas DNAas DNAts DNAts DNAcs DNAas DNAcs OxyTs OxyTs OxyTs OxyTs |
| 17-18-19mer-15 | ASO-002462 | TTTCCaaattcactTTT | 608 | 138886 | 138902 | OxyTs OxyTs OxyTs OxyMCs OxyMCs DNAas DNAas DNAas DNAts DNAts DNAcs DNAas DNAcs DNAts OxyTs OxyTs OxyTs |
| 17-18-19mer-18 | ASO-002404 | ATTtccaaattcacTTTT | 609 | 138886 | 138903 | OxyAs OxyTs OxyTs DNAts DNAcs DNAcs DNAas DNAas DNAas DNAts DNAts DNAcs DNAas DNAcs OxyTs OxyTs OxyTs OxyTs |
| 17-18-19mer-24 | ASO-002463 | ATTtccaaattcaCTTTT | 610 | 138886 | 138903 | OxyAs OxyTs OxyTs DNAts DNAcs DNAcs DNAas DNAas DNAas DNAts DNAts DNAcs DNAas OxyMCs OxyTs OxyTs OxyTs OxyTs |
| 17-18-19mer-3 | ASO-002414 | TTTccaaattcacTTTT | 611 | 138886 | 138902 | OxyTs OxyTs OxyTs DNAcs DNAcs DNAas DNAas DNAas DNAts DNAts DNAcs DNAas DNAcs OxyTs OxyTs OxyTs OxyTs |
| 17-18-19mer-30 | ASO-002441 | ATTTccaaattcactTTT | 612 | 138886 | 138903 | OxyAs OxyTs OxyTs OxyTs DNAcs DNAcs DNAas DNAas DNAas DNAts DNAts DNAcs DNAas DNAcs DNAts OxyTs OxyTs OxyTs |
| 17-18-19mer-36 | ASO-002418 | ATTTccaaattcacTTTT | 613 | 138886 | 138903 | OxyAs OxyTs OxyTs OxyTs DNAcs DNAcs DNAas DNAas DNAas DNAts DNAts DNAcs DNAas DNAcs OxyTs OxyTs OxyTs OxyTs |
| 17-18-19mer-42 | ASO-002476 | ATTTCcaaattcactTTT | 614 | 138886 | 138903 | OxyAs OxyTs OxyTs OxyTs OxyMCs DNAcs DNAas DNAas DNAas DNAts DNAts DNAcs DNAas DNAcs DNAts OxyTs OxyTs OxyTs |
| 17-18-19mer-48 | ASO-002455 | TATttccaaattcacTTTT | 615 | 138886 | 138904 | OxyTs OxyAs OxyTs DNAts DNAts DNAcs DNAcs DNAas DNAas DNAas DNAts DNAts DNAcs DNAas DNAcs OxyTs OxyTs OxyTs OxyTs |

Figure 2PPP

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-54 | ASO-002432 | TATttccaaattcaCTTTT | 616 | 138886 | 138904 | OxyTs OxyAs OxyTs DNAts DNAts DNAcs DNAcs DNAas DNAas DNAas DNAts DNAts DNAcs DNAas OxyMCs OxyTs OxyTs OxyTs OxyTs |
| 17-18-19mer-6 | ASO-002450 | TTTccaaattcaCTTTT | 617 | 138886 | 138902 | OxyTs OxyTs OxyTs DNAcs DNAcs DNAas DNAas DNAas DNAts DNAts DNAcs DNAas OxyMCs OxyTs OxyTs OxyTs OxyTs |
| 17-18-19mer-60 | ASO-002397 | TATTtccaaattcactTTT | 618 | 138886 | 138904 | OxyTs OxyAs OxyTs OxyTs DNAts DNAcs DNAcs DNAas DNAas DNAas DNAts DNAts DNAcs DNAas DNAcs DNAts OxyTs OxyTs OxyTs |
| 17-18-19mer-66 | ASO-002468 | TATTtccaaattcacTTTT | 619 | 138886 | 138904 | OxyTs OxyAs OxyTs OxyTs DNAts DNAcs DNAcs DNAas DNAas DNAas DNAts DNAts DNAcs DNAas DNAcs OxyTs OxyTs OxyTs OxyTs |
| 17-18-19mer-72 | ASO-002446 | TATTTccaaattcactTTT | 620 | 138886 | 138904 | OxyTs OxyAs OxyTs OxyTs OxyTs DNAcs DNAcs DNAas DNAas DNAas DNAts DNAts DNAcs DNAas DNAcs DNAts OxyTs OxyTs OxyTs |
| 17-18-19mer-9 | ASO-002391 | TTTCcaaattcactTTT | 621 | 138886 | 138902 | OxyTs OxyTs OxyTs OxyMCs DNAcs DNAas DNAas DNAas DNAts DNAts DNAcs DNAas DNAcs DNAts OxyTs OxyTs OxyTs |
| ASO-001941-mm1 | ASO-002317 | ATaTTtccaaattcaCTtTT | 622 | 138886 | 138905 | OxyAs OxyTs DNAas OxyTs OxyTs DNAts DNAcs DNAcs DNAas DNAas DNAas DNAts DNAts DNAcs DNAas OxyMCs OxyTs DNAts OxyTs OxyTs |
| ASO-001941-mm2 | ASO-002329 | TTaTTtccaaattcaCTtTA | 623 | 138886 | 138905 | OxyTs OxyTs DNAas OxyTs OxyTs DNAts DNAcs DNAcs DNAas DNAas DNAas DNAts DNAts DNAcs DNAas OxyMCs OxyTs DNAts OxyTs OxyAs |
| ASO-001941-mm3 | ASO-002341 | TTaTTtccaaattcaCTtTG | 624 | 138886 | 138905 | OxyTs OxyTs DNAas OxyTs OxyTs DNAts DNAcs DNAcs DNAas DNAas DNAas DNAts DNAts DNAcs DNAas OxyMCs OxyTs DNAts OxyTs OxyGs |

Figure 2QQQ

| Oligomer Name | ASO Number | ASO Sequence | SEQ ID NO | premRNA start NG_007398 | premRNA end NG_007398 | Chemical Structure |
|---|---|---|---|---|---|---|
| ASO-001941-mm4 | ASO-002353 | ATaTTtccagattcaCTtTT | 625 | 138886 | 138905 | OxyAs OxyTs DNAas OxyTs OxyTs DNAts DNAcs DNAcs DNAas DNAgs DNAas DNAts DNAts DNAcs DNAas OxyMCs OxyTs DNAts OxyTs OxyTs |
| ASO-001941-mm5 | ASO-002365 | TTaTTtccaagttcaCTtTC | 626 | 138886 | 138905 | OxyTs OxyTs DNAas OxyTs OxyTs DNAts DNAcs DNAcs DNAas DNAas DNAgs DNAts DNAts DNAcs DNAas OxyMCs OxyTs DNAts OxyTs OxyMCs |
| ASO-001941-mm6 | ASO-002377 | TTaTTtccagattcgCTtTT | 627 | 138886 | 138905 | OxyTs OxyTs DNAas OxyTs OxyTs DNAts DNAcs DNAcs DNAas DNAgs DNAas DNAts DNAts DNAcs DNAgs OxyMCs OxyTs DNAts OxyTs OxyTs |
| SPC-15676-01 | ASO-002258 | TTCcaaattcactTTT | 628 | 138886 | 138901 | OxyTs OxyTs OxyMCs DNAcs DNAas DNAas DNAas DNAts DNAts DNAcs DNAas DNAcs DNAts OxyTs OxyTs OxyTs |
| SPC-15866-01 | ASO-002253 | TTAtTtccaaattcaCTtTT | 629 | 138886 | 138905 | OxyTs OxyTs OxyAs DNAts OxyTs DNAts DNAcs DNAcs DNAas DNAas DNAas DNAts DNAts DNAcs DNAas OxyMCs OxyTs DNAts OxyTs OxyTs |
| SPC-15870-01 | ASO-002283 | TTAttTccaaattcacTTTT | 630 | 138886 | 138905 | OxyTs OxyTs OxyAs DNAts DNAts OxyTs DNAcs DNAcs DNAas DNAas DNAas DNAts DNAts DNAcs DNAas DNAcs OxyTs OxyTs OxyTs OxyTs |
| SPC-15875-01 | ASO-002262 | TTATttccaaattcacTTTT | 631 | 138886 | 138905 | OxyTs OxyTs OxyAs OxyTs DNAts DNAts DNAcs DNAcs DNAas DNAas DNAas DNAts DNAts DNAcs DNAas DNAcs OxyTs OxyTs OxyTs OxyTs |
| SPC-15876-01 | ASO-002270 | TTATttccaaattcaCtTTT | 632 | 138886 | 138905 | OxyTs OxyTs OxyAs OxyTs DNAts DNAts DNAcs DNAcs DNAas DNAas DNAas DNAts DNAts DNAcs DNAas OxyMCs DNAts OxyTs OxyTs OxyTs |
| SPC-15877-01 | ASO-002277 | TTATttccaaattcACttTT | 633 | 138886 | 138905 | OxyTs OxyTs OxyAs OxyTs DNAts DNAts DNAcs DNAcs DNAas DNAas DNAas DNAts DNAts DNAcs OxyAs OxyMCs DNAts DNAts OxyTs OxyTs |

Figure 2RRR

| Oligomer Name | ASO Number | ASO Sequence | SEQ ID NO | premRNA start NG_007398 | premRNA end NG_007398 | Chemical Structure |
|---|---|---|---|---|---|---|
| SPC-15881-01 | ASO-002247 | TTaTTtccaaattcacTTTT | 634 | 138886 | 138905 | OxyTs OxyTs DNAas OxyTs OxyTs DNAts DNAcs DNAcs DNAas DNAas DNAas DNAts DNAts DNAcs DNAas DNAcs OxyTs OxyTs OxyTs OxyTs |
| SPC-15884-01 | ASO-002271 | TTAtTtccaaattcacTTTT | 635 | 138886 | 138905 | OxyTs OxyTs OxyAs DNAts OxyTs DNAts DNAcs DNAcs DNAas DNAas DNAas DNAts DNAts DNAcs DNAas DNAcs OxyTs OxyTs OxyTs OxyTs |
| SPC-15885-01 | ASO-002278 | TTaTTtccaaattcACttTT | 636 | 138886 | 138905 | OxyTs OxyTs DNAas OxyTs OxyTs DNAts DNAcs DNAcs DNAas DNAas DNAas DNAts DNAts DNAcs OxyAs OxyMCs DNAts DNAts OxyTs OxyTs |
| SPC-15889-01 | ASO-002248 | TTaTTtccaaattcActTTT | 637 | 138886 | 138905 | OxyTs OxyTs DNAas OxyTs OxyTs DNAts DNAcs DNAcs DNAas DNAas DNAas DNAts DNAts DNAcs OxyAs DNAcs DNAts OxyTs OxyTs OxyTs |
| SPC-15891-01 | ASO-002264 | TTAtTtccaaattcActTTT | 638 | 138886 | 138905 | OxyTs OxyTs OxyAs DNAts OxyTs DNAts DNAcs DNAcs DNAas DNAas DNAas DNAts DNAts DNAcs OxyAs DNAcs DNAts OxyTs OxyTs OxyTs |
| SPC-15892-01 | ASO-002272 | TTaTTtccaaattcAcTtTT | 639 | 138886 | 138905 | OxyTs OxyTs DNAas OxyTs OxyTs DNAts DNAcs DNAcs DNAas DNAas DNAas DNAts DNAts DNAcs OxyAs DNAcs OxyTs DNAts OxyTs OxyTs |
| SPC-15894-01 | ASO-002286 | TTAtTtccaaattcAcTtTT | 640 | 138886 | 138905 | OxyTs OxyTs OxyAs DNAts OxyTs DNAts DNAcs DNAcs DNAas DNAas DNAas DNAts DNAts DNAcs OxyAs DNAcs OxyTs DNAts OxyTs OxyTs |
| SPC-15895-01 | ASO-002231 | TTATttccaaattcActTTT | 641 | 138886 | 138905 | OxyTs OxyTs OxyAs OxyTs DNAts DNAts DNAcs DNAcs DNAas DNAas DNAas DNAts DNAts DNAcs OxyAs DNAcs DNAts OxyTs OxyTs OxyTs |
| SPC-15896-01 | ASO-002240 | TTATttccaaattcAcTtTT | 642 | 138886 | 138905 | OxyTs OxyTs OxyAs OxyTs DNAts DNAts DNAcs DNAcs DNAas DNAas DNAas DNAts DNAts DNAcs OxyAs DNAcs OxyTs DNAts OxyTs OxyTs |

Figure 2SSS

| Oligomer Name | ASO Number | ASO Sequence | SEQ ID NO | premRNA start NG_007398 | premRNA end NG_007398 | Chemical Structure |
|---|---|---|---|---|---|---|
| ASO-002020 | ASO-002020 | AcTTTatttccaaattcactTTtaC | 643 | 138884 | 138908 | OxyAs DNAcs OxyTs OxyTs OxyTs DNAas DNAts DNAts DNAts DNAcs DNAcs DNAas DNAas DNAas DNAts DNAts DNAcs DNAas DNAcs DNAts OxyTs OxyTs DNAts DNAas OxyMC |
| ASO-000756 | ASO-000756 | TTTATttccaaattcACTTT | 644 | 138887 | 138906 | OxyTs OxyTs OxyTs OxyAs OxyTs DNAts DNAts DNAcs DNAcs DNAas DNAas DNAas DNAts DNAts DNAcs OxyAs OxyMCs OxyTs OxyTs OxyT |
| ASO-001967 | ASO-001967 | TTtATttccaaattcACtTT | 645 | 138887 | 138906 | OxyTs OxyTs DNAts OxyAs OxyTs DNAts DNAts DNAcs DNAcs DNAas DNAas DNAas DNAts DNAts DNAcs OxyAs OxyMCs DNAts OxyTs OxyT |
| ASO-001955 | ASO-001955 | TTTATttccaaattcaCTTT | 646 | 138887 | 138906 | OxyTs OxyTs OxyTs OxyAs OxyTs DNAts DNAts DNAcs DNAcs DNAas DNAas DNAas DNAts DNAts DNAcs DNAas OxyMCs OxyTs OxyTs OxyT |
| ASO-001948 | ASO-001948 | TTTAtttccaaattcACTTT | 647 | 138887 | 138906 | OxyTs OxyTs OxyTs OxyAs DNAts DNAts DNAts DNAcs DNAcs DNAas DNAas DNAas DNAts DNAts DNAcs OxyAs OxyMCs OxyTs OxyTs OxyT |
| ASO-002086 | ASO-002086 | AcTTtatttccaaattcactTTTaC | 648 | 138884 | 138908 | OxyAs DNAcs OxyTs OxyTs DNAts DNAas DNAts DNAts DNAts DNAcs DNAcs DNAas DNAas DNAas DNAts DNAts DNAcs DNAas DNAcs DNAts OxyTs OxyTs OxyTs DNAas OxyMC |
| ASO-002029 | ASO-002029 | ACtTtatttccaaattcacttTTaC | 649 | 138884 | 138908 | OxyAs OxyMCs DNAts OxyTs DNAts DNAas DNAts DNAts DNAts DNAcs DNAcs DNAas DNAas DNAas DNAts DNAts DNAcs DNAas DNAcs DNAts DNAts OxyTs OxyTs DNAas OxyMC |
| ASO-001961 | ASO-001961 | TtTATttccaaattcACtTT | 650 | 138887 | 138906 | OxyTs DNAts OxyTs OxyAs OxyTs DNAts DNAts DNAcs DNAcs DNAas DNAas DNAas DNAts DNAts DNAcs OxyAs OxyMCs DNAts OxyTs OxyT |

Figure 2TTT

| Oligomer Name | ASO Number | ASO Sequence | SEQ ID NO | premRNA start NG_007398 | premRNA end NG_007398 | Chemical Structure |
|---|---|---|---|---|---|---|
| ASO-002095 | ASO-002095 | ACTttatttccaaattcactTtTaC | 651 | 138884 | 138908 | OxyAs OxyMCs OxyTs DNAts DNAts DNAas DNAts DNAts DNAts DNAcs DNAcs DNAas DNAas DNAas DNAts DNAts DNAcs DNAas DNAcs DNAts OxyTs DNAts OxyTs DNAas OxyMC |
| ASO-002059 | ASO-002059 | ACTttatttccaaattcacttTTAC | 652 | 138884 | 138908 | OxyAs OxyMCs OxyTs DNAts DNAts DNAas DNAts DNAts DNAts DNAcs DNAcs DNAas DNAas DNAas DNAts DNAts DNAcs DNAas DNAcs DNAts DNAts OxyTs OxyTs OxyAs OxyMC |
| ASO-002077 | ASO-002077 | ActttatttccaaattcactTTTAC | 653 | 138884 | 138908 | OxyAs DNAcs DNAts DNAts DNAts DNAas DNAts DNAts DNAts DNAcs DNAcs DNAas DNAas DNAas DNAts DNAts DNAcs DNAas DNAcs DNAts OxyTs OxyTs OxyTs OxyAs OxyMC |
| ASO-002021 | ASO-002021 | AcTTtatttccaaattcactttTAC | 654 | 138884 | 138908 | OxyAs DNAcs OxyTs OxyTs DNAts DNAas DNAts DNAts DNAts DNAcs DNAcs DNAas DNAas DNAas DNAts DNAts DNAcs DNAas DNAcs DNAts DNAts DNAts OxyTs OxyAs OxyMC |
| ASO-000761 | ASO-000761 | TTTatttccaaattcacTTT | 655 | 138887 | 138906 | OxyTs OxyTs OxyTs DNAas DNAts DNAts DNAts DNAcs DNAcs DNAas DNAas DNAas DNAts DNAts DNAcs DNAas DNAcs OxyTs OxyTs OxyT |
| ASO-002068 | ASO-002068 | ACtTtatttccaaattcactTtTAC | 656 | 138884 | 138908 | OxyAs OxyMCs DNAts OxyTs DNAts DNAas DNAts DNAts DNAts DNAcs DNAcs DNAas DNAas DNAas DNAts DNAts DNAcs DNAas DNAcs DNAts OxyTs DNAts OxyTs OxyAs OxyMC |
| ASO-000766 | ASO-000766 | TTtatttccaaattcactTT | 657 | 138887 | 138906 | OxyTs OxyTs DNAts DNAas DNAts DNAts DNAts DNAcs DNAcs DNAas DNAas DNAas DNAts DNAts DNAcs DNAas DNAcs DNAts OxyTs OxyT |

Figure 2UUU

| Oligomer Name | ASO Number | ASO Sequence | SEQ ID NO | premRNA start NG_007398 | premRNA end NG_007398 | Chemical Structure |
|---|---|---|---|---|---|---|
| ASO-000771 | ASO-000771 | TttatttccaaattcactTT | 658 | 138887 | 138906 | OxyTs DNAts DNAts DNAas DNAts DNAts DNAts DNAcs DNAcs DNAas DNAas DNAas DNAts DNAts DNAcs DNAas DNAcs DNAts OxyTs OxyT |
| 17-18-19mer-19 | ASO-002416 | TATttccaaattcaCTTT | 659 | 138887 | 138904 | OxyTs OxyAs OxyTs DNAts DNAts DNAcs DNAcs DNAas DNAas DNAas DNAts DNAts DNAcs DNAas OxyMCs OxyTs OxyTs OxyTs |
| 17-18-19mer-25 | ASO-002474 | TATttccaaattcACTTT | 660 | 138887 | 138904 | OxyTs OxyAs OxyTs DNAts DNAts DNAcs DNAcs DNAas DNAas DNAas DNAts DNAts DNAcs OxyAs OxyMCs OxyTs OxyTs OxyTs |
| 17-18-19mer-31 | ASO-002453 | TATTtccaaattcacTTT | 661 | 138887 | 138904 | OxyTs OxyAs OxyTs OxyTs DNAts DNAcs DNAcs DNAas DNAas DNAas DNAts DNAts DNAcs DNAas DNAcs OxyTs OxyTs OxyTs |
| 17-18-19mer-37 | ASO-002430 | TATTtccaaattcaCTTT | 662 | 138887 | 138904 | OxyTs OxyAs OxyTs OxyTs DNAts DNAcs DNAcs DNAas DNAas DNAas DNAts DNAts DNAcs DNAas OxyMCs OxyTs OxyTs OxyTs |
| 17-18-19mer-43 | ASO-002395 | TATTTccaaattcacTTT | 663 | 138887 | 138904 | OxyTs OxyAs OxyTs OxyTs OxyTs DNAcs DNAcs DNAas DNAas DNAas DNAts DNAts DNAcs DNAas DNAcs OxyTs OxyTs OxyTs |
| 17-18-19mer-49 | ASO-002466 | TTAtttccaaattcaCTTT | 664 | 138887 | 138905 | OxyTs OxyTs OxyAs DNAts DNAts DNAts DNAcs DNAcs DNAas DNAas DNAas DNAts DNAts DNAcs DNAas OxyMCs OxyTs OxyTs OxyTs |
| 17-18-19mer-55 | ASO-002444 | TTAtttccaaattcACTTT | 665 | 138887 | 138905 | OxyTs OxyTs OxyAs DNAts DNAts DNAts DNAcs DNAcs DNAas DNAas DNAas DNAts DNAts DNAcs OxyAs OxyMCs OxyTs OxyTs OxyTs |
| 17-18-19mer-61 | ASO-002409 | TTATttccaaattcacTTT | 666 | 138887 | 138905 | OxyTs OxyTs OxyAs OxyTs DNAts DNAts DNAcs DNAcs DNAas DNAas DNAas DNAts DNAts DNAcs DNAas DNAcs OxyTs OxyTs OxyTs |

Figure 2VVV

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-67 | ASO-002479 | TTATttccaaattcaCTTT | 667 | 138887 | 138905 | OxyTs OxyTs OxyAs OxyTs DNAts DNAts DNAcs DNAcs DNAas DNAas DNAas DNAts DNAts DNAcs DNAas OxyMCs OxyTs OxyTs OxyTs |
| 17-18-19mer-73 | ASO-002458 | TTATTtccaaattcacTTT | 668 | 138887 | 138905 | OxyTs OxyTs OxyAs OxyTs OxyTs DNAts DNAcs DNAcs DNAas DNAas DNAas DNAts DNAts DNAcs DNAas DNAcs OxyTs OxyTs OxyTs |
| ASO-001967-mm1 | ASO-002294 | ATtATttccaaattcACtTT | 669 | 138887 | 138906 | OxyAs OxyTs DNAts OxyAs OxyTs DNAts DNAts DNAcs DNAcs DNAas DNAas DNAas DNAts DNAts DNAcs OxyAs OxyMCs DNAts OxyTs OxyTs |
| ASO-001967-mm2 | ASO-002306 | TTtATttccaagttcACtTT | 670 | 138887 | 138906 | OxyTs OxyTs DNAts OxyAs OxyTs DNAts DNAts DNAcs DNAcs DNAas DNAas DNAgs DNAts DNAts DNAcs OxyAs OxyMCs DNAts OxyTs OxyTs |
| ASO-001967-mm3 | ASO-002318 | GTtATttccaaattcACtTT | 671 | 138887 | 138906 | OxyGs OxyTs DNAts OxyAs OxyTs DNAts DNAts DNAcs DNAcs DNAas DNAas DNAas DNAts DNAts DNAcs OxyAs OxyMCs DNAts OxyTs OxyTs |
| ASO-001967-mm4 | ASO-002330 | ATtATttccagattcACtTT | 672 | 138887 | 138906 | OxyAs OxyTs DNAts OxyAs OxyTs DNAts DNAts DNAcs DNAcs DNAas DNAgs DNAas DNAts DNAts DNAcs OxyAs OxyMCs DNAts OxyTs OxyTs |
| ASO-001967-mm5 | ASO-002342 | TTtATttccaggttcACtTT | 673 | 138887 | 138906 | OxyTs OxyTs DNAts OxyAs OxyTs DNAts DNAts DNAcs DNAcs DNAas DNAgs DNAgs DNAts DNAts DNAcs OxyAs OxyMCs DNAts OxyTs OxyTs |
| ASO-001967-mm6 | ASO-002354 | CTtATttccaagttcACtTT | 674 | 138887 | 138906 | OxyMCs OxyTs DNAts OxyAs OxyTs DNAts DNAts DNAcs DNAcs DNAas DNAas DNAgs DNAts DNAts DNAcs OxyAs OxyMCs DNAts OxyTs OxyTs |
| SPC-15675-01 | ASO-002250 | TTTCcaaattcacTTT | 675 | 138887 | 138902 | OxyTs OxyTs OxyTs OxyMCs DNAcs DNAas DNAas DNAas DNAts DNAts DNAcs DNAas DNAcs OxyTs OxyTs OxyTs |

Figure 2WWW

| Oligomer Name | ASO Number | ASO Sequence | SEQ ID NO | premRNA start NG_007398 | premRNA end NG_007398 | Chemical Structure |
|---|---|---|---|---|---|---|
| ASO-002006 | ASO-002006 | CTtTAtttccaaattcACTT | 676 | 138888 | 138907 | OxyMCs OxyTs DNAts OxyTs OxyAs DNAts DNAts DNAts DNAcs DNAcs DNAas DNAas DNAas DNAts DNAts DNAcs OxyAs OxyMCs OxyTs OxyT |
| ASO-000757 | ASO-000757 | CTTTAtttccaaattCACTT | 677 | 138888 | 138907 | OxyMCs OxyTs OxyTs OxyTs OxyAs DNAts DNAts DNAts DNAcs DNAcs DNAas DNAas DNAas DNAts DNAts OxyMCs OxyAs OxyMCs OxyTs OxyT |
| ASO-002017 | ASO-002017 | CTtTAtttccaaattcaCTT | 678 | 138888 | 138907 | OxyMCs OxyTs DNAts OxyTs OxyAs DNAts DNAts DNAts DNAcs DNAcs DNAas DNAas DNAas DNAts DNAts DNAcs DNAas OxyMCs OxyTs OxyT |
| ASO-001928 | ASO-001928 | CTTTAtttccaaattcACTT | 679 | 138888 | 138907 | OxyMCs OxyTs OxyTs OxyTs OxyAs DNAts DNAts DNAts DNAcs DNAcs DNAas DNAas DNAas DNAts DNAts DNAcs OxyAs OxyMCs OxyTs OxyT |
| ASO-001968 | ASO-001968 | ACTTTatttccaaattCACT T | 680 | 138888 | 138908 | OxyAs OxyMCs OxyTs OxyTs OxyTs DNAas DNAts DNAts DNAts DNAcs DNAcs DNAas DNAas DNAas DNAts DNAts OxyMCs OxyAs OxyMCs OxyTs OxyT |
| ASO-001921 | ASO-001921 | CTTTatttccaaattCACTT | 681 | 138888 | 138907 | OxyMCs OxyTs OxyTs OxyTs DNAas DNAts DNAts DNAts DNAcs DNAcs DNAas DNAas DNAas DNAts DNAts OxyMCs OxyAs OxyMCs OxyTs OxyT |
| ASO-001989 | ASO-001989 | CTTTatttccaaattcACTT | 682 | 138888 | 138907 | OxyMCs OxyTs OxyTs OxyTs DNAas DNAts DNAts DNAts DNAcs DNAcs DNAas DNAas DNAas DNAts DNAts DNAcs OxyAs OxyMCs OxyTs OxyT |
| ASO-001942 | ASO-001942 | CTtTAtttccaaattCAcTT | 683 | 138888 | 138907 | OxyMCs OxyTs DNAts OxyTs OxyAs DNAts DNAts DNAts DNAcs DNAcs DNAas DNAas DNAas DNAts DNAts OxyMCs OxyAs DNAcs OxyTs OxyT |
| ASO-000128 | ASO-000128 | TTTccaaattcaCTT | 684 | 138888 | 138902 | OxyTs OxyTs OxyTs DNAcs DNAcs DNAas DNAas DNAas DNAts DNAts DNAcs DNAas OxyMCs OxyTs OxyT |

Figure 2XXX

| Oligomer Name | ASO Number | ASO Sequence | SEQ ID NO | premRNA start NG_007398 | premRNA end NG_007398 | Chemical Structure |
|---|---|---|---|---|---|---|
| ASO-001935 | ASO-001935 | CtTTAtttccaaattCAcTT | 685 | 138888 | 138907 | OxyMCs DNAts OxyTs OxyTs OxyAs DNAts DNAts DNAts DNAcs DNAcs DNAas DNAas DNAas DNAts DNAts OxyMCs OxyAs DNAcs OxyTs OxyT |
| ASO-000013 | ASO-000013 | ATTtccaaattcaCTT | 686 | 138888 | 138903 | OxyAs OxyTs OxyTs DNAts DNAcs DNAcs DNAas DNAas DNAas DNAts DNAts DNAcs DNAas OxyMCs OxyTs OxyT |
| ASO-002002 | ASO-002002 | CTTtAtttccaaattcACTT | 687 | 138888 | 138907 | OxyMCs OxyTs OxyTs DNAts OxyAs DNAts DNAts DNAts DNAcs DNAcs DNAas DNAas DNAas DNAts DNAts DNAcs OxyAs OxyMCs OxyTs OxyT |
| ASO-000762 | ASO-000762 | CTTtatttccaaattcaCTT | 688 | 138888 | 138907 | OxyMCs OxyTs OxyTs DNAts DNAas DNAts DNAts DNAts DNAcs DNAcs DNAas DNAas DNAas DNAts DNAts DNAcs DNAas OxyMCs OxyTs OxyT |
| ASO-002010 | ASO-002010 | CTTtatttccaaatTcaCTT | 689 | 138888 | 138907 | OxyMCs OxyTs OxyTs DNAts DNAas DNAts DNAts DNAts DNAcs DNAcs DNAas DNAas DNAas DNAts OxyTs DNAcs DNAas OxyMCs OxyTs OxyT |
| ASO-002005 | ASO-002005 | CTtTatttccaaattcaCTT | 690 | 138888 | 138907 | OxyMCs OxyTs DNAts OxyTs DNAas DNAts DNAts DNAts DNAcs DNAcs DNAas DNAas DNAas DNAts DNAts DNAcs DNAas OxyMCs OxyTs OxyT |
| ASO-001998 | ASO-001998 | CTttAtttccaaattcACTT | 691 | 138888 | 138907 | OxyMCs OxyTs DNAts DNAts OxyAs DNAts DNAts DNAts DNAcs DNAcs DNAas DNAas DNAas DNAts DNAts DNAcs OxyAs OxyMCs OxyTs OxyT |
| ASO-002001 | ASO-002001 | CTTTatttccaaattcaCTT | 692 | 138888 | 138907 | OxyMCs OxyTs OxyTs OxyTs DNAas DNAts DNAts DNAts DNAcs DNAcs DNAas DNAas DNAas DNAts DNAts DNAcs DNAas OxyMCs OxyTs OxyT |
| ASO-001994 | ASO-001994 | CTtTatttccaaattcACTT | 693 | 138888 | 138907 | OxyMCs OxyTs DNAts OxyTs DNAas DNAts DNAts DNAts DNAcs DNAcs DNAas DNAas DNAas DNAts DNAts DNAcs OxyAs OxyMCs OxyTs OxyT |

Figure 2YYY

| Oligomer Name | ASO Number | ASO Sequence | SEQ ID NO | premRNA start NG_007398 | premRNA end NG_007398 | Chemical Structure |
|---|---|---|---|---|---|---|
| ASO-002013 | ASO-002013 | CTTtAtttccaaattcaCTT | 694 | 138888 | 138907 | OxyMCs OxyTs OxyTs DNAts OxyAs DNAts DNAts DNAts DNAcs DNAcs DNAas DNAas DNAas DNAts DNAts DNAcs DNAas OxyMCs OxyTs OxyT |
| ASO-002009 | ASO-002009 | CTttAtttccaaattcaCTT | 695 | 138888 | 138907 | OxyMCs OxyTs DNAts DNAts OxyAs DNAts DNAts DNAts DNAcs DNAcs DNAas DNAas DNAas DNAts DNAts DNAcs DNAas OxyMCs OxyTs OxyT |
| ASO-000767 | ASO-000767 | CTttatttccaaattcacTT | 696 | 138888 | 138907 | OxyMCs OxyTs DNAts DNAts DNAas DNAts DNAts DNAts DNAcs DNAcs DNAas DNAas DNAas DNAts DNAts DNAcs DNAas DNAcs OxyTs OxyT |
| ASO-000772 | ASO-000772 | Ctttatttccaaattcact T | 697 | 138888 | 138907 | OxyMCs DNAts DNAts DNAts DNAas DNAts DNAts DNAts DNAcs DNAcs DNAas DNAas DNAas DNAts DNAts DNAcs DNAas DNAcs OxyTs OxyT |
| BMT-214296 | ASO-214296 | CTTTActtccaaattCACTT | 698 | 138888 | 138907 | OxyMCs OxyTs OxyTs OxyTs OxyAs DNAcs DNAts DNAts DNAcs DNAcs DNAas DNAas DNAas DNAts DNAts OxyMCs OxyAs OxyMCs OxyTs OxtT |
| ASO-000013-mm1 | ASO-002366 | GTTtccaaattcaCTT | 699 | 138888 | 138903 | OxyGs OxyTs OxyTs DNAts DNAcs DNAcs DNAas DNAas DNAas DNAts DNAts DNAcs DNAas OxyMCs OxyTs OxyTs |
| ASO-000013-mm2 | ASO-002378 | ATTtccaagttcaCTT | 700 | 138888 | 138903 | OxyAs OxyTs OxyTs DNAts DNAcs DNAcs DNAas DNAas DNAgs DNAts DNAts DNAcs DNAas OxyMCs OxyTs OxyTs |
| ASO-000013-mm3 | ASO-002295 | ATTtccgaattcaCTT | 701 | 138888 | 138903 | OxyAs OxyTs OxyTs DNAts DNAcs DNAcs DNAgs DNAas DNAas DNAts DNAts DNAcs DNAas OxyMCs OxyTs OxyTs |
| ASO-000013-mm4 | ASO-002307 | GTTtccagattcaCTT | 702 | 138888 | 138903 | OxyGs OxyTs OxyTs DNAts DNAcs DNAcs DNAas DNAgs DNAas DNAts DNAts DNAcs DNAas OxyMCs OxyTs OxyTs |

Figure 2ZZZ

| Oligomer Name | ASO Number | ASO Sequence | SEQ ID NO | premRNA start NG_007398 | premRNA end NG_007398 | Chemical Structure |
|---|---|---|---|---|---|---|
| ASO-000013-mm5 | ASO-002319 | GTTtccaaattcaCTA | 703 | 138888 | 138903 | OxyGs OxyTs OxyTs DNAts DNAcs DNAcs DNAas DNAas DNAas DNAts DNAts DNAcs DNAas OxyMCs OxyTs OxyAs |
| ASO-000013-mm6 | ASO-002331 | ATTtccagattcaCTC | 704 | 138888 | 138903 | OxyAs OxyTs OxyTs DNAts DNAcs DNAcs DNAas DNAgs DNAas DNAts DNAts DNAcs DNAas OxyMCs OxyTs OxyMCs |
| ASO-000898 | ASO-000898 | ATTtccaaattcaCTT | 705 | 138888 | 138903 | OxyA OxyT OxyT DNAt DNAc DNAc DNAa DNAa DNAa DNAt DNAt DNAc DNAa OxyMC OxyT OxyT |
| ASO-001942-mm1 | ASO-002363 | CTtTAtttccagattCAcTT | 706 | 138888 | 138907 | OxyMCs OxyTs DNAts OxyTs OxyAs DNAts DNAts DNAts DNAcs DNAcs DNAas DNAgs DNAas DNAts DNAts OxyMCs OxyAs DNAcs OxyTs OxyTs |
| ASO-001942-mm2 | ASO-002375 | CTtTAtttccaaattCAcTG | 707 | 138888 | 138907 | OxyMCs OxyTs DNAts OxyTs OxyAs DNAts DNAts DNAts DNAcs DNAcs DNAas DNAas DNAas DNAts DNAts OxyMCs OxyAs DNAcs OxyTs OxyGs |
| ASO-001942-mm3 | ASO-002292 | CTtTAtttccaaattCGcTT | 708 | 138888 | 138907 | OxyMCs OxyTs DNAts OxyTs OxyAs DNAts DNAts DNAts DNAcs DNAcs DNAas DNAas DNAas DNAts DNAts OxyMCs OxyGs DNAcs OxyTs OxyTs |
| ASO-001942-mm4 | ASO-002304 | CTtTAtttccagattCAcTA | 709 | 138888 | 138907 | OxyMCs OxyTs DNAts OxyTs OxyAs DNAts DNAts DNAts DNAcs DNAcs DNAas DNAgs DNAas DNAts DNAts OxyMCs OxyAs DNAcs OxyTs OxyAs |
| ASO-001942-mm5 | ASO-002316 | CTtTAtttccaggttCAcTT | 710 | 138888 | 138907 | OxyMCs OxyTs DNAts OxyTs OxyAs DNAts DNAts DNAts DNAcs DNAcs DNAas DNAgs DNAgs DNAts DNAts OxyMCs OxyAs DNAcs OxyTs OxyTs |
| ASO-001942-mm6 | ASO-002328 | CTtTAtttccgaggttCAcTT | 711 | 138888 | 138907 | OxyMCs OxyTs DNAts OxyTs OxyAs DNAts DNAts DNAts DNAcs DNAcs DNAgs DNAas DNAgs DNAts DNAts OxyMCs OxyAs DNAcs OxyTs OxyTs |

Figure 2AAAA

| Oligomer Name | ASO Number | ASO Sequence | SEQ ID NO | premRNA start NG_007398 | premRNA end NG_007398 | Chemical Structure |
|---|---|---|---|---|---|---|
| SPC-15674-01 | ASO-002242 | ATTtccaaattcACTT | 712 | 138888 | 138903 | OxyAs OxyTs OxyTs DNAts DNAcs DNAcs DNAas DNAas DNAas DNAts DNAts DNAcs OxyAs OxyMCs OxyTs OxyTs |
| ASO-002004 | ASO-002004 | CTTTatttccaaatTcaCT | 713 | 138889 | 138907 | OxyMCs OxyTs OxyTs OxyTs DNAas DNAts DNAts DNAts DNAcs DNAcs DNAas DNAas DNAas DNAts OxyTs DNAcs DNAas OxyMCs OxyT |
| ASO-002012 | ASO-002012 | CTTtatttccaaatTcACT | 714 | 138889 | 138907 | OxyMCs OxyTs OxyTs DNAts DNAas DNAts DNAts DNAts DNAcs DNAcs DNAas DNAas DNAas DNAts OxyTs DNAcs OxyAs OxyMCs OxyT |
| ASO-001962 | ASO-001962 | ACTTTatttccaaattCACT | 715 | 138889 | 138908 | OxyAs OxyMCs OxyTs OxyTs OxyTs DNAas DNAts DNAts DNAts DNAcs DNAcs DNAas DNAas DNAas DNAts DNAts OxyMCs OxyAs OxyMCs OxyT |
| ASO-001956 | ASO-001956 | ACTTtatttccaaatTCACT | 716 | 138889 | 138908 | OxyAs OxyMCs OxyTs OxyTs DNAts DNAas DNAts DNAts DNAts DNAcs DNAcs DNAas DNAas DNAas DNAts OxyTs OxyMCs OxyAs OxyMCs OxyT |
| ASO-001949 | ASO-001949 | ACTTTatttccaaatTCACT | 717 | 138889 | 138908 | OxyAs OxyMCs OxyTs OxyTs OxyTs DNAas DNAts DNAts DNAts DNAcs DNAcs DNAas DNAas DNAas DNAts OxyTs OxyMCs OxyAs OxyMCs OxyT |
| ASO-001987 | ASO-001987 | CTTTAtttccaaatTcACT | 718 | 138889 | 138907 | OxyMCs OxyTs OxyTs OxyTs OxyAs DNAts DNAts DNAts DNAcs DNAcs DNAas DNAas DNAas DNAts OxyTs DNAcs OxyAs OxyMCs OxyT |
| ASO-001991 | ASO-001991 | CTTTatttccaaatTCACT | 719 | 138889 | 138907 | OxyMCs OxyTs OxyTs OxyTs DNAas DNAts DNAts DNAts DNAcs DNAcs DNAas DNAas DNAas DNAts OxyTs OxyMCs OxyAs OxyMCs OxyT |
| ASO-001995 | ASO-001995 | CTTtatttccaaatTCACT | 720 | 138889 | 138907 | OxyMCs OxyTs OxyTs DNAts DNAas DNAts DNAts DNAts DNAcs DNAcs DNAas DNAas DNAas DNAts OxyTs OxyMCs OxyAs OxyMCs OxyT |

Figure 2BBBB

| Oligomer Name | ASO Number | ASO Sequence | SEQ ID NO | premRNA start NG_007398 | premRNA end NG_007398 | Chemical Structure |
|---|---|---|---|---|---|---|
| ASO-001992 | ASO-001992 | CTTTAtttccaaatTcaCT | 721 | 138889 | 138907 | OxyMCs OxyTs OxyTs OxyTs OxyAs DNAts DNAts DNAts DNAcs DNAcs DNAas DNAas DNAas DNAts OxyTs DNAcs DNAas OxyMCs OxyT |
| ASO-002000 | ASO-002000 | CTTTatttccaaatTcACT | 722 | 138889 | 138907 | OxyMCs OxyTs OxyTs OxyTs DNAas DNAts DNAts DNAts DNAcs DNAcs DNAas DNAas DNAas DNAts OxyTs DNAcs OxyAs OxyMCs OxyT |
| ASO-001996 | ASO-001996 | CTTTatttccaaatTCaCT | 723 | 138889 | 138907 | OxyMCs OxyTs OxyTs OxyTs DNAas DNAts DNAts DNAts DNAcs DNAcs DNAas DNAas DNAas DNAts OxyTs OxyMCs DNAas OxyMCs OxyT |
| ASO-002008 | ASO-002008 | CTTtatttccaaatTCaCT | 724 | 138889 | 138907 | OxyMCs OxyTs OxyTs DNAts DNAas DNAts DNAts DNAts DNAcs DNAcs DNAas DNAas DNAas DNAts OxyTs OxyMCs DNAas OxyMCs OxyT |
| ASO-002015 | ASO-002015 | CTTTAtttccaaatTCaCT | 725 | 138889 | 138907 | OxyMCs OxyTs OxyTs OxyTs OxyAs DNAts DNAts DNAts DNAcs DNAcs DNAas DNAas DNAas DNAts OxyTs OxyMCs DNAas OxyMCs OxyT |
| ASO-002016 | ASO-002016 | CTTtatttccaaatTcaCT | 726 | 138889 | 138907 | OxyMCs OxyTs OxyTs DNAts DNAas DNAts DNAts DNAts DNAcs DNAcs DNAas DNAas DNAas DNAts OxyTs DNAcs DNAas OxyMCs OxyT |
| ASO-001986 | ASO-001986 | CTTTAtttccaaatTCACT | 727 | 138889 | 138907 | OxyMCs OxyTs OxyTs OxyTs OxyAs DNAts DNAts DNAts DNAcs DNAcs DNAas DNAas DNAas DNAts OxyTs OxyMCs OxyAs OxyMCs OxyT |
| 17-18-19mer-50 | ASO-002477 | CTTtatttccaaattCACT | 728 | 138889 | 138907 | OxyMCs OxyTs OxyTs DNAts DNAas DNAts DNAts DNAts DNAcs DNAcs DNAas DNAas DNAas DNAts DNAts OxyMCs OxyAs OxyMCs OxyTs |
| 17-18-19mer-62 | ASO-002421 | CTTTatttccaaattcACT | 729 | 138889 | 138907 | OxyMCs OxyTs OxyTs OxyTs DNAas DNAts DNAts DNAts DNAcs DNAcs DNAas DNAas DNAas DNAts DNAts DNAcs OxyAs OxyMCs OxyTs |

Figure 2CCCC

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-68 | ASO-002398 | CTTTatttccaaattCACT | 730 | 138889 | 138907 | OxyMCs OxyTs OxyTs OxyTs DNAas DNAts DNAts DNAts DNAcs DNAcs DNAas DNAas DNAas DNAts DNAts OxyMCs OxyAs OxyMCs OxyTs |
| 17-18-19mer-74 | ASO-002469 | CTTTAtttccaaattcACT | 731 | 138889 | 138907 | OxyMCs OxyTs OxyTs OxyTs OxyAs DNAts DNAts DNAts DNAcs DNAcs DNAas DNAas DNAas DNAts DNAts DNAcs OxyAs OxyMCs OxyTs |
| ASO-001995-mm1 | ASO-002343 | CTTtatttccagatTCACT | 732 | 138889 | 138907 | OxyMCs OxyTs OxyTs DNAts DNAas DNAts DNAts DNAts DNAcs DNAcs DNAas DNAgs DNAas DNAts OxyTs OxyMCs OxyAs OxyMCs OxyTs |
| ASO-001995-mm2 | ASO-002355 | CTTtgtttccaaatTCACT | 733 | 138889 | 138907 | OxyMCs OxyTs OxyTs DNAts DNAgs DNAts DNAts DNAts DNAcs DNAcs DNAas DNAas DNAas DNAts OxyTs OxyMCs OxyAs OxyMCs OxyTs |
| ASO-001995-mm3 | ASO-002367 | CTTtatttccaaatTCACG | 734 | 138889 | 138907 | OxyMCs OxyTs OxyTs DNAts DNAas DNAts DNAts DNAts DNAcs DNAcs DNAas DNAas DNAas DNAts OxyTs OxyMCs OxyAs OxyMCs OxyGs |
| ASO-001995-mm4 | ASO-002379 | CTTtgtttccagatTCACT | 735 | 138889 | 138907 | OxyMCs OxyTs OxyTs DNAts DNAgs DNAts DNAts DNAts DNAcs DNAcs DNAas DNAgs DNAas DNAts OxyTs OxyMCs OxyAs OxyMCs OxyTs |
| ASO-001995-mm5 | ASO-002296 | CTTtgtttccaagtTCACT | 736 | 138889 | 138907 | OxyMCs OxyTs OxyTs DNAts DNAgs DNAts DNAts DNAts DNAcs DNAcs DNAas DNAas DNAgs DNAts OxyTs OxyMCs OxyAs OxyMCs OxyTs |
| ASO-001995-mm6 | ASO-002308 | CTTtatttccgagtTCACT | 737 | 138889 | 138907 | OxyMCs OxyTs OxyTs DNAts DNAas DNAts DNAts DNAts DNAcs DNAcs DNAgs DNAas DNAgs DNAts OxyTs OxyMCs OxyAs OxyMCs OxyTs |
| SPC-15673-01 | ASO-002233 | TATttccaaattcACT | 738 | 138889 | 138904 | OxyTs OxyAs OxyTs DNAts DNAts DNAcs DNAcs DNAas DNAas DNAas DNAts DNAts DNAcs OxyAs OxyMCs OxyTs |

Figure 2DDDD

| Oligomer Name | ASO Number | ASO Sequence | SEQ ID NO | premRNA start NG_007398 | premRNA end NG_007398 | Chemical Structure |
|---|---|---|---|---|---|---|
| ASO-002003 | ASO-002003 | CTTTatttccaaatTCAC | 739 | 138890 | 138907 | OxyMCs OxyTs OxyTs OxyTs DNAas DNAts DNAts DNAts DNAcs DNAcs DNAas DNAas DNAas DNAts OxyTs OxyMCs OxyAs OxyMC |
| ASO-002007 | ASO-002007 | CTTtatttccaaatTCAC | 740 | 138890 | 138907 | OxyMCs OxyTs OxyTs DNAts DNAas DNAts DNAts DNAts DNAcs DNAcs DNAas DNAas DNAas DNAts OxyTs OxyMCs OxyAs OxyMC |
| ASO-002011 | ASO-002011 | CTtTatttccaaatTcAC | 741 | 138890 | 138907 | OxyMCs OxyTs DNAts OxyTs DNAas DNAts DNAts DNAts DNAcs DNAcs DNAas DNAas DNAas DNAts OxyTs DNAcs OxyAs OxyMC |
| ASO-001988 | ASO-001988 | CTTTAtttccaaatTcAC | 742 | 138890 | 138907 | OxyMCs OxyTs OxyTs OxyTs OxyAs DNAts DNAts DNAts DNAcs DNAcs DNAas DNAas DNAas DNAts OxyTs DNAcs OxyAs OxyMC |
| ASO-001999 | ASO-001999 | CTTTAtttccaaatTCAC | 743 | 138890 | 138907 | OxyMCs OxyTs OxyTs OxyTs OxyAs DNAts DNAts DNAts DNAcs DNAcs DNAas DNAas DNAas DNAts OxyTs OxyMCs OxyAs OxyMC |
| ASO-001993 | ASO-001993 | CTTTatttccaaatTcAC | 744 | 138890 | 138907 | OxyMCs OxyTs OxyTs OxyTs DNAas DNAts DNAts DNAts DNAcs DNAcs DNAas DNAas DNAas DNAts OxyTs DNAcs OxyAs OxyMC |
| ASO-001997 | ASO-001997 | CTTtatttccaaatTcAC | 745 | 138890 | 138907 | OxyMCs OxyTs OxyTs DNAts DNAas DNAts DNAts DNAts DNAcs DNAcs DNAas DNAas DNAas DNAts OxyTs DNAcs OxyAs OxyMC |
| 17-18-19mer-26 | ASO-002393 | CTTtatttccaaaTTCAC | 746 | 138890 | 138907 | OxyMCs OxyTs OxyTs DNAts DNAas DNAts DNAts DNAts DNAcs DNAcs DNAas DNAas DNAas OxyTs OxyTs OxyMCs OxyAs OxyMCs |
| 17-18-19mer-32 | ASO-002464 | CTTTatttccaaattCAC | 747 | 138890 | 138907 | OxyMCs OxyTs OxyTs OxyTs DNAas DNAts DNAts DNAts DNAcs DNAcs DNAas DNAas DNAas DNAts DNAts OxyMCs OxyAs OxyMCs |

Figure 2EEEE

| Oligomer Name | ASO Number | ASO Sequence | SEQ ID NO | premRNA start NG_007398 | premRNA end NG_007398 | Chemical Structure |
|---|---|---|---|---|---|---|
| 17-18-19mer-44 | ASO-002407 | CTTTAtttccaaattCAC | 748 | 138890 | 138907 | OxyMCs OxyTs OxyTs OxyTs OxyAs DNAts DNAts DNAts DNAcs DNAcs DNAas DNAas DNAas DNAts DNAts OxyMCs OxyAs OxyMCs |
| 17-18-19mer-51 | ASO-002396 | ACTttatttccaaatTCAC | 749 | 138890 | 138908 | OxyAs OxyMCs OxyTs DNAts DNAts DNAas DNAts DNAts DNAts DNAcs DNAcs DNAas DNAas DNAas DNAts OxyTs OxyMCs OxyAs OxyMCs |
| 17-18-19mer-57 | ASO-002456 | ACTttatttccaaaTTCAC | 750 | 138890 | 138908 | OxyAs OxyMCs OxyTs DNAts DNAts DNAas DNAts DNAts DNAts DNAcs DNAcs DNAas DNAas DNAas OxyTs OxyTs OxyMCs OxyAs OxyMCs |
| 17-18-19mer-63 | ASO-002433 | ACTTtatttccaaattCAC | 751 | 138890 | 138908 | OxyAs OxyMCs OxyTs OxyTs DNAts DNAas DNAts DNAts DNAts DNAcs DNAcs DNAas DNAas DNAas DNAts DNAts OxyMCs OxyAs OxyMCs |
| 17-18-19mer-69 | ASO-002410 | ACTTtatttccaaatTCAC | 752 | 138890 | 138908 | OxyAs OxyMCs OxyTs OxyTs DNAts DNAas DNAts DNAts DNAts DNAcs DNAcs DNAas DNAas DNAas DNAts OxyTs OxyMCs OxyAs OxyMCs |
| 17-18-19mer-75 | ASO-002480 | ACTTTatttccaaattCAC | 753 | 138890 | 138908 | OxyAs OxyMCs OxyTs OxyTs OxyTs DNAas DNAts DNAts DNAts DNAcs DNAcs DNAas DNAas DNAas DNAts DNAts OxyMCs OxyAs OxyMCs |
| ASO-001997-mm1 | ASO-002320 | CTTtatttccagatTcAC | 754 | 138890 | 138907 | OxyMCs OxyTs OxyTs DNAts DNAas DNAts DNAts DNAts DNAcs DNAcs DNAas DNAgs DNAas DNAts OxyTs DNAcs OxyAs OxyMCs |
| ASO-001997-mm2 | ASO-002332 | CTTtatttccgaatTcAC | 755 | 138890 | 138907 | OxyMCs OxyTs OxyTs DNAts DNAas DNAts DNAts DNAts DNAcs DNAcs DNAgs DNAas DNAas DNAts OxyTs DNAcs OxyAs OxyMCs |
| ASO-001997-mm3 | ASO-002344 | CTTtgtttccaaatTcAC | 756 | 138890 | 138907 | OxyMCs OxyTs OxyTs DNAts DNAgs DNAts DNAts DNAts DNAcs DNAcs DNAas DNAas DNAas DNAts OxyTs DNAcs OxyAs OxyMCs |

Figure 2FFFF

| Oligomer Name | ASO Number | ASO Sequence | SEQ ID NO | premRNA start NG_007398 | premRNA end NG_007398 | Chemical Structure |
|---|---|---|---|---|---|---|
| ASO-001997-mm4 | ASO-002356 | CTTtgtttccagatTcAC | 757 | 138890 | 138907 | OxyMCs OxyTs OxyTs DNAts DNAgs DNAts DNAts DNAts DNAcs DNAcs DNAas DNAgs DNAas DNAts OxyTs DNAcs OxyAs OxyMCs |
| ASO-001997-mm5 | ASO-002368 | CTTtatttccaggtTcAC | 758 | 138890 | 138907 | OxyMCs OxyTs OxyTs DNAts DNAas DNAts DNAts DNAts DNAcs DNAcs DNAas DNAgs DNAgs DNAts OxyTs DNAcs OxyAs OxyMCs |
| ASO-001997-mm6 | ASO-002380 | CTTtgtttccaagtTcAC | 759 | 138890 | 138907 | OxyMCs OxyTs OxyTs DNAts DNAgs DNAts DNAts DNAts DNAcs DNAcs DNAas DNAas DNAgs DNAts OxyTs DNAcs OxyAs OxyMCs |
| SPC-15672-01 | ASO-002288 | TTAtttccaaattCAC | 760 | 138890 | 138905 | OxyTs OxyTs OxyAs DNAts DNAts DNAts DNAcs DNAcs DNAas DNAas DNAas DNAts DNAts OxyMCs OxyAs OxyMCs |
| 17-18-19mer-21 | ASO-002428 | ACTttatttccaaaTTCA | 761 | 138891 | 138908 | OxyAs OxyMCs OxyTs DNAts DNAts DNAas DNAts DNAts DNAts DNAcs DNAcs DNAas DNAas DNAas OxyTs OxyTs OxyMCs OxyAs |
| 17-18-19mer-27 | ASO-002405 | ACTttatttccaaATTCA | 762 | 138891 | 138908 | OxyAs OxyMCs OxyTs DNAts DNAts DNAas DNAts DNAts DNAts DNAcs DNAcs DNAas DNAas OxyAs OxyTs OxyTs OxyMCs OxyAs |
| 17-18-19mer-33 | ASO-002475 | ACTTtatttccaaatTCA | 763 | 138891 | 138908 | OxyAs OxyMCs OxyTs OxyTs DNAts DNAas DNAts DNAts DNAts DNAcs DNAcs DNAas DNAas DNAas DNAts OxyTs OxyMCs OxyAs |
| 17-18-19mer-39 | ASO-002442 | ACTTtatttccaaaTTCA | 764 | 138891 | 138908 | OxyAs OxyMCs OxyTs OxyTs DNAts DNAas DNAts DNAts DNAts DNAcs DNAcs DNAas DNAas DNAas OxyTs OxyTs OxyMCs OxyAs |
| 17-18-19mer-45 | ASO-002419 | ACTTTatttccaaatTCA | 765 | 138891 | 138908 | OxyAs OxyMCs OxyTs OxyTs OxyTs DNAas DNAts DNAts DNAts DNAcs DNAcs DNAas DNAas DNAas DNAts OxyTs OxyMCs OxyAs |

Figure 2GGGG

| Oligomer Name | ASO Number | ASO Sequence | SEQ ID NO | premRNA start NG_007398 | premRNA end NG_007398 | Chemical Structure |
|---|---|---|---|---|---|---|
| SPC-15671-01 | ASO-002280 | TTTatttccaaatTCA | 766 | 138891 | 138906 | OxyTs OxyTs OxyTs DNAas DNAts DNAts DNAts DNAcs DNAcs DNAas DNAas DNAas DNAts OxyTs OxyMCs OxyAs |
| SPC-15670-01 | ASO-002273 | CTTtatttccaaATTC | 767 | 138892 | 138907 | OxyMCs OxyTs OxyTs DNAts DNAas DNAts DNAts DNAts DNAcs DNAcs DNAas DNAas OxyAs OxyTs OxyTs OxyMCs |
| SPC-15669-01 | ASO-002265 | ACTTtatttccaAATT | 768 | 138893 | 138908 | OxyAs OxyMCs OxyTs OxyTs DNAts DNAas DNAts DNAts DNAts DNAcs DNAcs DNAas OxyAs OxyAs OxyTs OxyTs |
| ASO-000139 | ASO-000139 | AACtttatttccaAAT | 769 | 138894 | 138909 | OxyAs OxyAs OxyMCs DNAts DNAts DNAts DNAas DNAts DNAts DNAts DNAcs DNAcs DNAas OxyAs OxyAs OxyT |
| SPC-15668-01 | ASO-002257 | AACTttatttccAAAT | 770 | 138894 | 138909 | OxyAs OxyAs OxyMCs OxyTs DNAts DNAts DNAas DNAts DNAts DNAts DNAcs DNAcs OxyAs OxyAs OxyAs OxyTs |
| SPC-15667-01 | ASO-002249 | TAACtttatttcCAAA | 771 | 138895 | 138910 | OxyTs OxyAs OxyAs OxyMCs DNAts DNAts DNAts DNAas DNAts DNAts DNAts DNAcs OxyMCs OxyAs OxyAs OxyAs |
| SPC-15666-01 | ASO-002241 | ATAActttatttcCAA | 772 | 138896 | 138911 | OxyAs OxyTs OxyAs OxyAs DNAcs DNAts DNAts DNAts DNAas DNAts DNAts DNAts DNAcs OxyMCs OxyAs OxyAs |
| ASO-000118 | ASO-000118 | AATaactttatttCCA | 773 | 138897 | 138912 | OxyAs OxyAs OxyTs DNAas DNAas DNAcs DNAts DNAts DNAts DNAas DNAts DNAts DNAts OxyMCs OxyMCs OxyA |
| SPC-15665-01 | ASO-002232 | AATaactttattTCCA | 774 | 138897 | 138912 | OxyAs OxyAs OxyTs DNAas DNAas DNAcs DNAts DNAts DNAts DNAas DNAts DNAts OxyTs OxyMCs OxyMCs OxyAs |

Figure 2HHHH

| Oligomer Name | ASO Number | ASO Sequence | SEQ ID NO | premRNA start NG_007398 | premRNA end NG_007398 | Chemical Structure |
|---|---|---|---|---|---|---|
| ASO-000101 | ASO-000101 | TAAtaactttattTCC | 775 | 138898 | 138913 | OxyTs OxyAs OxyAs DNAts DNAas DNAas DNAcs DNAts DNAts DNAts DNAas DNAts DNAts OxyTs OxyMCs OxyMC |
| SPC-15664-01 | ASO-002287 | TAAtaactttatTTCC | 776 | 138898 | 138913 | OxyTs OxyAs OxyAs DNAts DNAas DNAas DNAcs DNAts DNAts DNAts DNAas DNAts OxyTs OxyTs OxyMCs OxyMCs |
| ASO-000148 | ASO-000148 | GTAataactttatTTC | 777 | 138899 | 138914 | OxyGs OxyTs OxyAs DNAas DNAts DNAas DNAas DNAcs DNAts DNAts DNAts DNAas DNAts OxyTs OxyTs OxyMC |
| ASO-000184 | ASO-000184 | TAAtaactttatTTC | 778 | 138899 | 138913 | OxyTs OxyAs OxyAs DNAts DNAas DNAas DNAcs DNAts DNAts DNAts DNAas DNAts OxyTs OxyTs OxyMC |
| ASO-000112 | ASO-000112 | GTAataactttaTTT | 779 | 138900 | 138914 | OxyGs OxyTs OxyAs DNAas DNAts DNAas DNAas DNAcs DNAts DNAts DNAts DNAas OxyTs OxyTs OxyT |
| ASO-000170 | ASO-000170 | AGTaataactttaTTT | 780 | 138900 | 138915 | OxyAs OxyGs OxyTs DNAas DNAas DNAts DNAas DNAas DNAcs DNAts DNAts DNAts DNAas OxyTs OxyTs OxyT |
| ASO-000154 | ASO-000154 | GAGtaataactttATT | 781 | 138901 | 138916 | OxyGs OxyAs OxyGs DNAts DNAas DNAas DNAts DNAas DNAas DNAcs DNAts DNAts DNAts OxyAs OxyTs OxyT |
| ASO-000125 | ASO-000125 | AGTaataactttATT | 782 | 138901 | 138915 | OxyAs OxyGs OxyTs DNAas DNAas DNAts DNAas DNAas DNAcs DNAts DNAts DNAts OxyAs OxyTs OxyT |
| ASO-000167 | ASO-000167 | GAGtaataacttTAT | 783 | 138902 | 138916 | OxyGs OxyAs OxyGs DNAts DNAas DNAas DNAts DNAas DNAas DNAcs DNAts DNAts OxyTs OxyAs OxyT |

Figure 2IIIII

| Oligomer Name | ASO Number | ASO Sequence | SEQ ID NO | premRNA start NG_007398 | premRNA end NG_007398 | Chemical Structure |
|---|---|---|---|---|---|---|
| ASO-000134 | ASO-000134 | AGAgtaataacttTAT | 784 | 138902 | 138917 | OxyAs OxyGs OxyAs DNAgs DNAts DNAas DNAas DNAts DNAas DNAas DNAcs DNAts DNAts OxyTs OxyAs OxyT |
| ASO-000175 | ASO-000175 | CAGagtaataactTTA | 785 | 138903 | 138918 | OxyMCs OxyAs OxyGs DNAas DNAgs DNAts DNAas DNAas DNAts DNAas DNAas DNAcs DNAts OxyTs OxyTs OxyA |
| ASO-000178 | ASO-000178 | AGAgtaataactTTA | 786 | 138903 | 138917 | OxyAs OxyGs OxyAs DNAgs DNAts DNAas DNAas DNAts DNAas DNAas DNAcs DNAts OxyTs OxyTs OxyA |
| ASO-000138 | ASO-000138 | CAGagtaataacTTT | 787 | 138904 | 138918 | OxyMCs OxyAs OxyGs DNAas DNAgs DNAts DNAas DNAas DNAts DNAas DNAas DNAcs OxyTs OxyTs OxyT |
| ASO-000171 | ASO-000171 | TCAgagtaataacTTT | 788 | 138904 | 138919 | OxyTs OxyMCs OxyAs DNAgs DNAas DNAgs DNAts DNAas DNAas DNAts DNAas DNAas DNAcs OxyTs OxyTs OxyT |
| ASO-000236 | ASO-000236 | ATCagagtaataaCTT | 789 | 138905 | 138920 | OxyAs OxyTs OxyMCs DNAas DNAgs DNAas DNAgs DNAts DNAas DNAas DNAts DNAas DNAas OxyMCs OxyTs OxyT |
| ASO-000127 | ASO-000127 | TCAgagtaataaCTT | 790 | 138905 | 138919 | OxyTs OxyMCs OxyAs DNAgs DNAas DNAgs DNAts DNAas DNAas DNAts DNAas DNAas OxyMCs OxyTs OxyT |
| ASO-000177 | ASO-000177 | CAGagtaataaCTT | 791 | 138905 | 138918 | OxyMCs OxyAs OxyGs DNAas DNAgs DNAts DNAas DNAas DNAts DNAas DNAas OxyMCs OxyTs OxyT |
| ASO-000238 | ASO-000238 | AATcagagtaataACT | 792 | 138906 | 138921 | OxyAs OxyAs OxyTs DNAcs DNAas DNAgs DNAas DNAgs DNAts DNAas DNAas DNAts DNAas OxyAs OxyMCs OxyT |

Figure 2JJJJ

| Oligomer Name | ASO Number | ASO Sequence | SEQ ID NO | premRNA start NG_007398 | premRNA end NG_007398 | Chemical Structure |
|---|---|---|---|---|---|---|
| ASO-000222 | ASO-000222 | TAAtcagagtaatAAC | 793 | 138907 | 138922 | OxyTs OxyAs OxyAs DNAts DNAcs DNAas DNAgs DNAas DNAgs DNAts DNAas DNAas DNAts OxyAs OxyAs OxyMC |
| ASO-000307 | ASO-000307 | AATcagagtaatAAC | 794 | 138907 | 138921 | OxyAs OxyAs OxyTs DNAcs DNAas DNAgs DNAas DNAgs DNAts DNAas DNAas DNAts OxyAs OxyAs OxyMC |
| ASO-000204 | ASO-000204 | TTAatcagagtaaTAA | 795 | 138908 | 138923 | OxyTs OxyTs OxyAs DNAas DNAts DNAcs DNAas DNAgs DNAas DNAgs DNAts DNAas DNAas OxyTs OxyAs OxyA |
| ASO-000330 | ASO-000330 | TAAtcagagtaaTAA | 796 | 138908 | 138922 | OxyTs OxyAs OxyAs DNAts DNAcs DNAas DNAgs DNAas DNAgs DNAts DNAas DNAas OxyTs OxyAs OxyA |
| ASO-000326 | ASO-000326 | TTTaatcagagtaATA | 797 | 138909 | 138924 | OxyTs OxyTs OxyTs DNAas DNAas DNAts DNAcs DNAas DNAgs DNAas DNAgs DNAts DNAas OxyAs OxyTs OxyA |
| ASO-000249 | ASO-000249 | TTTaatcagagtAAT | 798 | 138910 | 138924 | OxyTs OxyTs OxyTs DNAas DNAas DNAts DNAcs DNAas DNAgs DNAas DNAgs DNAts OxyAs OxyAs OxyT |
| ASO-002022 | ASO-002022 | TTATttccaaattcaCTtTT | 799 | 138886 | 138905 | OxyTs OxyTs OxyAs OxyTs DNAts DNAts DNAcs DNAcs DNAas DNAas DNAas DNAts DNAts DNAcs DNAas OxyMCs OxyTs DNAts OxyTs OxyT |
| ASO-002026 | ASO-002026 | TTatTTccaaattcaCtTTT | 800 | 138886 | 138905 | OxyTs OxyTs DNAas DNAts OxyTs OxyTs DNAcs DNAcs DNAas DNAas DNAas DNAts DNAts DNAcs DNAas OxyMCs DNAts OxyTs OxyTs OxyT |
| ASO-002024 | ASO-002024 | TTAttTccaaattcaCtTTT | 801 | 138886 | 138905 | OxyTs OxyTs OxyAs DNAts DNAts OxyTs DNAcs DNAcs DNAas DNAas DNAas DNAts DNAts DNAcs DNAas OxyMCs DNAts OxyTs OxyTs OxyT |

Figure 2KKKK

| Oligomer Name | ASO Number | ASO Sequence | SEQ ID NO | premRNA start NG_007398 | premRNA end NG_007398 | Chemical Structure |
|---|---|---|---|---|---|---|
| ASO-002049 | ASO-002049 | ACTTtatttccaaattcactTTtAC | 802 | 138884 | 138908 | OxyAs OxyMCs OxyTs OxyTs DNAts DNAas DNAts DNAts DNAts DNAcs DNAcs DNAas DNAas DNAas DNAts DNAts DNAcs DNAas DNAcs DNAts OxyTs OxyTs DNAts OxyAs OxyMC |
| ASO-002019 | ASO-002019 | ActtTatttccaaattcactTTtaC | 803 | 138884 | 138909 | OxyAs OxyMCs DNAts DNAts OxyTs DNAas DNAts DNAts DNAts DNAcs DNAcs DNAas DNAas DNAas DNAts DNAts DNAcs DNAas DNAcs DNAts OxyTs OxyTs DNAts DNAas OxyMC |
| ASO-000069 | ASO-000069 | ATttcCaaaTtcacTT | 936 | 138888 | 138903 | OxyAs OxyTs DNAts DNAts DNAcs OxyMCs DNAas DNAas DNAas OxyTs DNAts DNAcs DNAas DNAcs OxyTs OxyT |
| ASO-000070 | ASO-000070 | ATTtccAaatTcaCTT | 937 | 138888 | 138903 | OxyAs OxyTs OxyTs DNAts DNAcs DNAcs OxyAs DNAas DNAas DNAts OxyTs DNAcs DNAas OxyMCs OxyTs OxyT |
| ASO-002107 | ASO-002107 | CCCttaatttCacccTC | 938 | 136053 | 136069 | OxyMCs OxyMCs OxyMCs DNAts DNAts DNAas DNAas DNAts DNAts DNAts OxyMCs DNAas DNAcs DNAcs DNAcs OxyTs OxyMC |
| ASO-002625 | ASO-002625 | TAGccctaaagtcCCA | 901 | 135744 | 135759 | OxyTs OxyA OxyG DNAc DNAcs DNAcs DNAts DNAas DNAas DNAas DNAgs DNAt DNAc OxyMC OxyMCs OxyA |
| ASO-002675 | ASO-002675 | TAGccctaaagtcCCA | 902 | 135744 | 135759 | OxyTs OxyA OxyG DNAc DNAcs DNAcs DNAts DNAas DNAas DNAas DNAgs DNAts DNAc OxyMC OxyMCs OxyA |
| ASO-002633 | ASO-002633 | TAGccctaaagtcCCA | 903 | 135744 | 135759 | OxyTs OxyA OxyG DNAc DNAc DNAcs DNAts DNAas DNAas DNAas DNAgs DNAts DNAc OxyMC OxyMCs OxyA |
| ASO-002640 | ASO-002640 | CCTtaATttcacccTCA | 904 | 136052 | 136068 | OxyMCs OxyMC OxyT DNAt DNAas OxyAs OxyTs DNAts DNAts DNAcs DNAas DNAcs DNAc DNAc OxyT OxyMCs OxyA |
| ASO-002632 | ASO-002632 | CCTtaATttcacccTCA | 905 | 136052 | 136068 | OxyMCs OxyMC OxyT DNAt DNAas OxyAs OxyTs DNAts DNAts DNAcs DNAas DNAcs DNAcs DNAc OxyT OxyMCs OxyA |

Figure 2LLLL

| Oligomer Name | ASO Number | ASO Sequence | SEQ ID NO | premRNA start NG_007398 | premRNA end NG_007398 | Chemical Structure |
|---|---|---|---|---|---|---|
| ASO-002647 | ASO-002647 | CCTtaATttcacccTCA | 906 | 136052 | 136068 | OxyMCs OxyMC OxyT DNAt DNAa OxyAs OxyTs DNAts DNAts DNAcs DNAas DNAcs DNAcs DNAc OxyT OxyMCs OxyA |
| ASO-002655 | ASO-002655 | CCTtaatttcaccCTC | 907 | 136053 | 136068 | OxyMCs OxyMC OxyT DNAt DNAa DNAas DNAts DNAts DNAts DNAcs DNAas DNAcs DNAc OxyMC OxyTs OxyMC |
| ASO-002641 | ASO-002641 | CCTtaatttcaccCTC | 908 | 136053 | 136068 | OxyMCs OxyMC OxyT DNAt DNAas DNAas DNAts DNAts DNAts DNAcs DNAas DNAcs DNAc OxyMC OxyTs OxyMC |
| ASO-002648 | ASO-002648 | CCTtaatttcaccCTC | 909 | 136053 | 136068 | OxyMCs OxyMC OxyT DNAt DNAas DNAas DNAts DNAts DNAts DNAcs DNAas DNAc DNAc OxyMC OxyTs OxyMC |
| ASO-002666 | ASO-002666 | AtTTCcaaattcactTTtAC | 910 | 138884 | 138903 | OxyAs DNAt OxyT OxyT OxyMCs DNAcs DNAas DNAas DNAas DNAts DNAts DNAcs DNAas DNAcs DNAts OxyT OxyT DNAt OxyAs OxyMC |
| ASO-002659 | ASO-002659 | AtTTCcaaattcactTTtAC | 911 | 138884 | 138903 | OxyAs DNAt OxyT OxyT OxyMCs DNAcs DNAas DNAas DNAas DNAts DNAts DNAcs DNAas DNAcs DNAts OxyTs OxyT DNAt OxyAs OxyMC |
| ASO-002652 | ASO-002652 | ATttCCaaattcactTtTAC | 912 | 138884 | 138903 | OxyAs OxyT DNAt DNAt OxyMC OxyMCs DNAas DNAas DNAas DNAts DNAts DNAcs DNAas DNAcs DNAts OxyTs DNAt OxyT OxyAs OxyMC |
| ASO-002645 | ASO-002645 | ATttCCaaattcactTtTAC | 913 | 138884 | 138903 | OxyAs OxyT DNAt DNAt OxyMCs OxyMCs DNAas DNAas DNAas DNAts DNAts DNAcs DNAas DNAcs DNAts OxyT DNAt OxyT OxyAs OxyMC |
| ASO-002638 | ASO-002638 | ATttCCaaattcactTtTAC | 914 | 138884 | 138903 | OxyAs OxyT DNAt DNAt OxyMCs OxyMCs DNAas DNAas DNAas DNAts DNAts DNAcs DNAas DNAcs DNAts OxyTs DNAt OxyT OxyAs OxyMC |
| ASO-003270 | ASO-003270 | AtTTCcaaattcactTTtAC | 915 | 138884 | 138903 | OxyAs DNAt OxyT OxyT OxyMCs DNAcs DNAas DNAas DNAas DNAts DNAts DNAcs DNAas DNAcs DNAts OxyT OxyT DNAts OxyAs OxyMC |
| ASO-003269 | ASO-003269 | AtTTCcaaattcactTTtAC | 916 | 138884 | 138903 | OxyAs DNAt OxyT OxyT OxyMCs DNAcs DNAas DNAas DNAas DNAts DNAts DNAcs DNAas DNAcs DNAt OxyT OxyT DNAts OxyAs OxyMC |
| ASO-003268 | ASO-003268 | AtTTCcaaattcactTTtAC | 917 | 138884 | 138903 | OxyAs DNAt OxyT OxyT OxyMC DNAcs DNAas DNAas DNAas DNAts DNAts DNAcs DNAas DNAcs DNAts OxyT OxyT DNAts OxyAs OxyMC |

Figure 2MMMM

| Oligomer Name | ASO Number | ASO Sequence | SEQ ID NO | premRNA start NG_007398 | premRNA end NG_007398 | Chemical Structure |
|---|---|---|---|---|---|---|
| ASO-002673 | ASO-002673 | AtTTCcaaattcactTTtAC | 918 | 138884 | 138903 | OxyAs DNAt OxyT OxyT OxyMC DNAcs DNAas DNAas DNAas DNAts DNAts DNAcs DNAas DNAcs DNAts OxyTs OxyT DNAt OxyAs OxyMC |
| ASO-002661 | ASO-002661 | TTtATttccaaattcACtTT | 919 | 138887 | 138906 | OxyTs OxyT DNAt OxyA OxyTs DNAts DNAts DNAcs DNAcs DNAas DNAas DNAas DNAts DNAts DNAcs OxyA OxyMC DNAt OxyTs OxyT |
| ASO-002654 | ASO-002654 | TTtATttccaaattcACtTT | 920 | 138887 | 138906 | OxyTs OxyT DNAt OxyA OxyTs DNAts DNAts DNAcs DNAcs DNAas DNAas DNAas DNAts DNAts DNAcs OxyAs OxyMC DNAt OxyTs OxyT |
| ASO-002668 | ASO-002668 | TTtATttccaaattcACtTT | 921 | 138887 | 138906 | OxyTs OxyT DNAt OxyA OxyT DNAts DNAts DNAcs DNAcs DNAas DNAas DNAas DNAts DNAts DNAcs OxyAs OxyMC DNAt OxyTs OxyT |
| ASO-002676 | ASO-002676 | ATTtccaaattcaCTT | 922 | 138888 | 138903 | OxyAs OxyT OxyT DNAt DNAc DNAcs DNAas DNAas DNAas DNAts DNAts DNAcs DNAa OxyMC OxyTs OxyT |
| ASO-002669 | ASO-002669 | ATTtccaaattcaCTT | 923 | 138888 | 138903 | OxyAs OxyT OxyT DNAt DNAcs DNAcs DNAas DNAas DNAas DNAts DNAts DNAc DNAa OxyMC OxyTs OxyT |
| ASO-002662 | ASO-002662 | ATTtccaaattcaCTT | 924 | 138888 | 138903 | OxyAs OxyT OxyT DNAt DNAcs DNAcs DNAas DNAas DNAas DNAts DNAts DNAcs DNAa OxyMC OxyTs OxyT |
| ASO-002672 | ASO-002672 | TAGccctaaagtcCCA | 925 | 135744 | 135759 | OxyTs OxyAs OxyGs DNAmcs DNAmcs DNAmcs DNAts DNAas DNAas DNAas DNAgs DNAts DNAmcs OxyMCs OxyMCs OxyA |
| ASO-002658 | ASO-002658 | CCTtaATttcacccTCA | 926 | 136052 | 136068 | OxyMCs OxyMCs OxyTs DNAts DNAas OxyAs OxyTs DNAts DNAts DNAmcs DNAas DNAmcs DNAmcs DNAmcs OxyTs OxyMCs OxyA |
| ASO-002622 | ASO-002622 | CCTtaatttcaccCTC | 927 | 136053 | 136068 | OxyMCs OxyMCs OxyTs DNAts DNAas DNAas DNAts DNAts DNAts DNAmcs DNAas DNAmcs DNAmcs OxyMCs OxyTs OxyMC |
| ASO-002629 | ASO-002629 | AtTTCcaaattcactTTtAC | 928 | 138884 | 138903 | OxyAs DNAts OxyTs OxyTs OxyMCs DNAmcs DNAas DNAas DNAas DNAts DNAts DNAmcs DNAas DNAmcs DNAts OxyTs OxyTs DNAts OxyAs OxyMC |

Figure 2NNNN

| Oligomer Name | ASO Number | ASO Sequence | SEQ ID NO | premRNA start NG_007398 | premRNA end NG_007398 | Chemical Structure |
|---|---|---|---|---|---|---|
| ASO-002621 | ASO-002621 | ATttCCaaattcactTtTAC | 929 | 138884 | 138903 | OxyAs OxyTs DNAts DNAts OxyMCs OxyMCs DNAas DNAas DNAas DNAts DNAts DNAmcs DNAas DNAmcs DNAts OxyTs DNAts OxyTs OxyAs OxyMC |
| ASO-002665 | ASO-002665 | TTtATttccaaattcACtTT | 930 | 138887 | 138906 | OxyTs OxyTs DNAts OxyAs OxyTs DNAts DNAts DNAmcs DNAmcs DNAas DNAas DNAas DNAts DNAts DNAmcs OxyAs OxyMCs DNAts OxyTs OxyT |
| ASO-002630 | ASO-002630 | ATTtccaaattcaCTT | 931 | 138888 | 138903 | OxyAs OxyTs OxyTs DNAts DNAmcs DNAmcs DNAas DNAas DNAas DNAts DNAts DNAmcs DNAas OxyMCs OxyTs OxyT |
| ASO-002399 | ASO-002399 | AtTTCcaAattcactTTtAC | 932 | 138884 | 138903 | OxyAs DNAts OxyTs OxyTs OxyMCs DNAcs DNAas OxyAs DNAas DNAts DNAts DNAcs DNAas DNAcs DNAts OxyTs OxyTs DNAts OxyAs OxyMC |
| ASO-002482 | ASO-002482 | ATtTcCaAattcactTtTAC | 933 | 138884 | 138903 | OxyAs OxyTs DNAts OxyTs DNAcs OxyMCs DNAas OxyAs DNAas DNAts DNAts DNAcs DNAas DNAcs DNAts OxyTs DNAts OxyTs OxyAs OxyMC |
| ASO-002437 | ASO-002437 | ATtTcCaaattcacTTtTAC | 934 | 138884 | 138903 | OxyAs OxyTs DNAts OxyTs DNAcs OxyMCs DNAas DNAas DNAas DNAts DNAts DNAcs DNAas DNAcs OxyTs OxyTs DNAts OxyTs OxyAs OxyMC |
| ASO-002425 | ASO-002425 | ATtTcCAaattcacTTtTAC | 935 | 138884 | 138903 | OxyAs OxyTs DNAts OxyTs DNAcs OxyMCs OxyAs DNAas DNAas DNAts DNAts DNAcs DNAas DNAcs OxyTs OxyTs DNAts OxyTs OxyAs OxyMC |
| ASO-000071 | ASO-000071 | ATttCcaaAttCacTT | 960 | 138888 | 138903 | OxyAs OxyTs DNAts DNAts OxyMCs DNAcs DNAas DNAas OxyAs DNAts DNAts OxyMCs DNAas DNAcs OxyTs OxyT |

ASO number indicates a unique designation for each oligomer.

The ASO sequence corresponds to the oligomer sequence, left corresponds to the 5'end and right corresponds to the 3'end.

SEQ ID Number corresponds to the sequence of the oligomer listed in the sequence listing.

Figure 3A

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 4 | ASO-001167 | ASO-001167 | AAAgatgaaatttgctcTTA | 134947 | 134966 | 2787 | 77 |
| 5 | ASO-001168 | ASO-001168 | GAAagatgaaatttgctCTT | 134948 | 134967 | 2788 | 89 |
| 6 | ASO-001169 | ASO-001169 | GGAaagatgaaatttgcTCT | 134949 | 134968 | 2789 | 99 |
| 7 | ASO-000829 | ASO-000829 | AAGatgaaatttgCTC | 134950 | 134965 | 2790 | 99 |
| 8 | ASO-001170 | ASO-001170 | TGGaaagatgaaatttgCTC | 134950 | 134969 | 2790 | 100 |
| 9 | ASO-001171 | ASO-001171 | TTGgaaagatgaaatttGCT | 134951 | 134970 | 2791 | 97 |
| 10 | ASO-001172 | ASO-001172 | TTTggaaagatgaaattTGC | 134952 | 134971 | 2792 | 96 |
| 11 | ASO-001173 | ASO-001173 | ATTtggaaagatgaaatTTG | 134953 | 134972 | 2793 | 43 |
| 12 | ASO-001174 | ASO-001174 | AATttggaaagatgaaaTTT | 134954 | 134973 | 2794 | 0 |
| 13 | ASO-001175 | ASO-001175 | CAAtttggaaagatgaaATT | 134955 | 134974 | 2795 | 3 |
| 14 | ASO-001176 | ASO-001176 | TCAatttggaaagatgaAAT | 134956 | 134975 | 2796 | 36 |
| 15 | ASO-001177 | ASO-001177 | ATCaatttggaaagatgAAA | 134957 | 134976 | 2797 | 45 |
| 16 | ASO-001178 | ASO-001178 | CATcaatttggaaagatGAA | 134958 | 134977 | 2798 | 26 |
| 17 | ASO-001179 | ASO-001179 | CCAtcaatttggaaagaTGA | 134959 | 134978 | 2799 | 79 |
| 18 | ASO-001180 | ASO-001180 | CCCatcaatttggaaagATG | 134960 | 134979 | 2800 | 77 |
| 19 | ASO-001181 | ASO-001181 | ACCcatcaatttggaaaGAT | 134961 | 134980 | 2801 | 82 |
| 20 | ASO-001182 | ASO-001182 | CACccatcaatttggaaAGA | 134962 | 134981 | 2802 | 85 |
| 21 | ASO-001183 | ASO-001183 | CCAcccatcaatttggaAAG | 134963 | 134982 | 2803 | 97 |
| 22 | ASO-001184 | ASO-001184 | CCCacccatcaatttggAAA | 134964 | 134983 | 2804 | 89 |
| 23 | ASO-001062 | ASO-001062 | GCCcacccatcaatttgGAA | 134965 | 134984 | 2805 | 79 |
| 24 | ASO-001063 | ASO-001063 | TAGcccacccatcaattTGG | 134967 | 134986 | 2807 | 98 |
| 25 | ASO-001064 | ASO-001064 | CTAgcccacccatcaatTTG | 134968 | 134987 | 2808 | 99 |
| 26 | ASO-001065 | ASO-001065 | ACTagcccacccatcaaTTT | 134969 | 134988 | 2809 | 100 |
| 27 | ASO-001066 | ASO-001066 | TACtagcccacccatcaATT | 134970 | 134989 | 2810 | 94 |
| 28 | ASO-000830 | ASO-000830 | TACtagcccacccATC | 134974 | 134989 | 2814 | 99 |
| 29 | ASO-000260 | ASO-000260 | CCCtcttctacatGGA | 135077 | 135092 | 2917 | 99 |
| 30 | ASO-000305 | ASO-000305 | TGCctctgtgacaCCC | 135171 | 135186 | 3011 | 99 |
| 31 | ASO-000304 | ASO-000304 | TTCaaatcctttgTTG | 135194 | 135209 | 3034 | 96 |
| 32 | ASO-000324 | ASO-000324 | CACacaaggttgaCAT | 135242 | 135257 | 3082 | 99 |
| 33 | ASO-000268 | ASO-000268 | CGTcacactcacaCAA | 135251 | 135266 | 3091 | 99 |
| 34 | ASO-000223 | ASO-000223 | GCCaccaaggacaGGC | 135441 | 135456 | 3281 | 8 |
| 35 | ASO-000224 | ASO-000224 | CAGcttgccttctCTT | 135533 | 135548 | 3373 | 99 |
| 36 | ASO-000319 | ASO-000319 | ATCaaggtcagtcTTT | 135585 | 135600 | 3425 | 99 |
| 37 | ASO-000208 | ASO-000208 | CCTtcagaactcaATA | 135690 | 135705 | 3530 | 97 |

Figure 3B

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 38 | ASO-000689 | ASO-000689 | AAAgtcccaggtcTGC | 135737 | 135752 | 3577 | 99 |
| 39 | ASO-000434 | ASO-000434 | CTAaagtcccaggTCT | 135739 | 135754 | 3579 | 99 |
| 40 | ASO-000409 | ASO-000409 | TAAagtcccaggTCT | 135739 | 135753 | 3579 | 98 |
| 41 | ASO-000432 | ASO-000432 | CCTaaagtcccagGTC | 135740 | 135755 | 3580 | 98 |
| 42 | ASO-000391 | ASO-000391 | TAAagtcccagGTC | 135740 | 135753 | 3580 | 98 |
| 43 | ASO-001779 | ASO-001779 | TAGccctaaagtcccagGTC | 135740 | 135759 | 3580 | 100 |
| 44 | ASO-000899 | ASO-000899 | CTAaagtcccagGTC | 135740 | 135754 | 3580 | 6 |
| 45 | ASO-000398 | ASO-000398 | CCCtaaagtcccaGGT | 135741 | 135756 | 3581 | 85 |
| 46 | ASO-001778 | ASO-001778 | TTAgccctaaagtcccaGGT | 135741 | 135760 | 3581 | 100 |
| 47 | ASO-000414 | ASO-000414 | GCCctaaagtcccAGG | 135742 | 135757 | 3582 | 58 |
| 48 | ASO-000403 | ASO-000403 | CCCtaaagtcccAGG | 135742 | 135756 | 3582 | 45 |
| 49 | ASO-001780 | ASO-001780 | GTTagccctaaagtcccAGG | 135742 | 135761 | 3582 | 100 |
| 50 | ASO-000433 | ASO-000433 | GCCctaaagtccCAG | 135743 | 135757 | 3583 | 99 |
| 51 | ASO-000411 | ASO-000411 | CCCtaaagtccCAG | 135743 | 135756 | 3583 | 99 |
| 52 | ASO-001781 | ASO-001781 | GGTtagccctaaagtccCAG | 135743 | 135762 | 3583 | 100 |
| 53 | ASO-000389 | ASO-000389 | TAGccctaaagtcCCA | 135744 | 135759 | 3584 | 100 |
| 54 | ASO-001939 | ASO-001939 | TAGccctaaagtcCCA | 135744 | 135759 | 3584 | 100 |
| 55 | ASO-001932 | ASO-001932 | TAGccctaaagtcCCA | 135744 | 135759 | 3584 | 100 |
| 56 | ASO-001925 | ASO-001925 | TAGccctaaagtcCCA | 135744 | 135759 | 3584 | 100 |
| 57 | ASO-001924 | ASO-001924 | TAGccctaaagtcCCA | 135744 | 135759 | 3584 | 100 |
| 58 | ASO-001952 | ASO-001952 | TAGccctaaagtcCCA | 135744 | 135759 | 3584 | 100 |
| 59 | ASO-001931 | ASO-001931 | TAGccctaaagtcCCA | 135744 | 135759 | 3584 | 100 |
| 60 | ASO-001953 | ASO-001953 | TAGccctaaagtcCCA | 135744 | 135759 | 3584 | 100 |
| 61 | ASO-001945 | ASO-001945 | TAGccctaaagtcCCA | 135744 | 135759 | 3584 | 100 |
| 62 | ASO-001946 | ASO-001946 | TAGccctaaagtcCCA | 135744 | 135759 | 3584 | 99 |
| 63 | ASO-001971 | ASO-001971 | TAGccctaaagtcCCA | 135744 | 135759 | 3584 | 100 |
| 64 | ASO-001938 | ASO-001938 | TAGccctaaagtcCCA | 135744 | 135759 | 3584 | 100 |
| 65 | ASO-001959 | ASO-001959 | TAGccctaaagtcCCA | 135744 | 135759 | 3584 | 100 |
| 66 | ASO-001965 | ASO-001965 | TAGccctaaagtcCCA | 135744 | 135759 | 3584 | 99 |
| 67 | ASO-001782 | ASO-001782 | TGGttagccctaaagtcCCA | 135744 | 135763 | 3584 | 99 |
| 68 | ASO-000900 | ASO-000900 | TAGccctaaagtcCCA | 135744 | 135759 | 3584 | 0 |
| 69 | ASO-000435 | ASO-000435 | TTAgccctaaagtCCC | 135745 | 135760 | 3585 | 98 |
| 70 | ASO-000423 | ASO-000423 | GTTagccctaaagTCC | 135746 | 135761 | 3586 | 99 |
| 71 | ASO-000442 | ASO-000442 | TAGccctaaagTCC | 135746 | 135759 | 3586 | 91 |
| 72 | ASO-000416 | ASO-000416 | GGTtagccctaaaGTC | 135747 | 135762 | 3587 | 100 |
| 73 | ASO-000438 | ASO-000438 | GTTagccctaaAGT | 135748 | 135761 | 3588 | 98 |

Figure 3C

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 74 | ASO-000581 | ASO-000581 | ACTggttagccctAAA | 135750 | 135765 | 3590 | 100 |
| 75 | ASO-000639 | ASO-000639 | AACtggttagcccTAA | 135751 | 135766 | 3591 | 100 |
| 76 | ASO-000558 | ASO-000558 | GAActggttagccCTA | 135752 | 135767 | 3592 | 100 |
| 77 | ASO-000597 | ASO-000597 | GAGaactggttagCCC | 135754 | 135769 | 3594 | 100 |
| 78 | ASO-000245 | ASO-000245 | TACaaagagaactGGT | 135760 | 135775 | 3600 | 100 |
| 79 | ASO-000897 | ASO-000897 | CACaagtccttacAAA | 135770 | 135785 | 3610 | 4 |
| 80 | ASO-000185 | ASO-000185 | GGCacaagtccttACA | 135772 | 135787 | 3612 | 99 |
| 81 | ASO-000426 | ASO-000426 | AGGcacaagtccTTA | 135774 | 135788 | 3614 | 52 |
| 82 | ASO-000417 | ASO-000417 | GAGgcacaagtccTTA | 135774 | 135789 | 3614 | 39 |
| 83 | ASO-000393 | ASO-000393 | AGAggcacaagtcCTT | 135775 | 135790 | 3615 | 75 |
| 84 | ASO-000449 | ASO-000449 | AAGaggcacaagtCCT | 135776 | 135791 | 3616 | 95 |
| 85 | ASO-000406 | ASO-000406 | AGAggcacaagtCCT | 135776 | 135790 | 3616 | 78 |
| 86 | ASO-000392 | ASO-000392 | CCAagaggcacaaGTC | 135778 | 135793 | 3618 | 99 |
| 87 | ASO-000444 | ASO-000444 | CAAgaggcacaaGTC | 135778 | 135792 | 3618 | 99 |
| 88 | ASO-000443 | ASO-000443 | CCCaagaggcacaAGT | 135779 | 135794 | 3619 | 100 |
| 89 | ASO-000450 | ASO-000450 | CAAgaggcacaAGT | 135779 | 135792 | 3619 | 99 |
| 90 | ASO-000258 | ASO-000258 | CTCccaagaggcaCAA | 135781 | 135796 | 3621 | 97 |
| 91 | ASO-000205 | ASO-000205 | TGGccgtgggaagGAC | 135876 | 135891 | 3716 | 90 |
| 92 | ASO-000213 | ASO-000213 | GGTgaggctgggaATT | 135984 | 135999 | 3823 | 100 |
| 93 | ASO-000293 | ASO-000293 | GTGaggctgggaATT | 135984 | 135998 | 3823 | 100 |
| 94 | ASO-000321 | ASO-000321 | TGGtgaggctgggAAT | 135985 | 136000 | 3824 | 99 |
| 95 | ASO-000226 | ASO-000226 | CTCagtatggagtAGG | 136040 | 136055 | 3879 | 90 |
| 96 | ASO-000682 | ASO-000682 | AATttcaccctcaGTA | 136049 | 136064 | 3888 | 79 |
| 97 | ASO-000673 | ASO-000673 | TTAatttcaccctCAG | 136051 | 136066 | 3890 | 84 |
| 98 | ASO-000578 | ASO-000578 | CTTaatttcacccTCA | 136052 | 136067 | 3891 | 99 |
| 99 | ASO-000540-21 | ASO-002180 | CCTTaatttcaccCTCA | 136052 | 136068 | 3891 | 98 |
| 100 | ASO-000540-22 | ASO-002192 | CCTTaatttcacCctCA | 136052 | 136068 | 3891 | 99 |
| 101 | ASO-000540-23 | ASO-002109 | CCTTAatttcacCctCA | 136052 | 136068 | 3891 | 97 |
| 102 | ASO-000540-24 | ASO-002121 | TcCCtTaatttcaccCT | 136054 | 136070 | 3893 | 98 |
| 103 | ASO-000540-25 | ASO-002133 | TcCCTtaatttcaccCT | 136054 | 136070 | 3893 | 97 |
| 104 | ASO-000540-26 | ASO-002145 | TcCCTtaatttcAccCT | 136054 | 136070 | 3893 | 90 |
| 105 | ASO-000540-27 | ASO-002157 | TcCCTTaatttcaccCT | 136054 | 136070 | 3893 | 95 |
| 106 | ASO-000540-28 | ASO-002169 | TCcCTTaatttcaccCT | 136054 | 136070 | 3893 | 91 |
| 107 | ASO-000540-29 | ASO-002181 | TCCcttaatttcacCCT | 136054 | 136070 | 3893 | 92 |
| 108 | ASO-000540-3 | ASO-002154 | CCCttaatttcacCcTC | 136053 | 136069 | 3892 | 97 |

Figure 3D

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 109 | ASO-000540-42 | ASO-002147 | CCCTtaatttcacccTCA | 136052 | 136069 | 3891 | 99 |
| 110 | ASO-000540-43 | ASO-002159 | CCCTtaatttcaccCtCA | 136052 | 136069 | 3891 | 97 |
| 111 | ASO-000540-44 | ASO-002171 | CCCTtaatttcaccCTCA | 136052 | 136069 | 3891 | 96 |
| 112 | ASO-000540-45 | ASO-002183 | CCCTtaatttcacCctCA | 136052 | 136069 | 3891 | 98 |
| 113 | ASO-000540-46 | ASO-002195 | CCCTtaatttcacCcTCA | 136052 | 136069 | 3891 | 91 |
| 114 | ASO-000540-47 | ASO-002196 | CCCTtaatttcaCcctCA | 136052 | 136069 | 3891 | 100 |
| 115 | ASO-000540-48 | ASO-002200 | CCCTtaatttcaCccTCA | 136052 | 136069 | 3891 | 95 |
| 116 | ASO-000540-49 | ASO-002204 | CCCTtaatttcaCcCtCA | 136052 | 136069 | 3891 | 82 |
| 117 | ASO-000540-5 | ASO-002178 | CCCttaatttcAcccTC | 136053 | 136069 | 3892 | 97 |
| 118 | ASO-000540-50 | ASO-002208 | CCCTtaatttcAccCtCA | 136052 | 136069 | 3891 | 93 |
| 119 | ASO-000540-51 | ASO-002212 | CCCTtaatttcAcCctCA | 136052 | 136069 | 3891 | 87 |
| 120 | ASO-000540-52 | ASO-002216 | TcCCTtaatttcacCcTC | 136053 | 136070 | 3892 | 97 |
| 121 | ASO-000540-53 | ASO-002220 | TCcCTtaatttcacccTC | 136053 | 136070 | 3892 | 99 |
| 122 | ASO-000540-54 | ASO-002224 | TCcCTTaatttcacCcTC | 136053 | 136070 | 3892 | 85 |
| 123 | ASO-000540-55 | ASO-002197 | TCCcttaatttcaccCTC | 136053 | 136070 | 3892 | 99 |
| 124 | ASO-000540-69 | ASO-002222 | TCCcTtaatttcacCctCA | 136052 | 136070 | 3891 | 97 |
| 125 | ASO-000540-70 | ASO-002226 | TCCCttaatttcaccCTCA | 136052 | 136070 | 3891 | 93 |
| 126 | ASO-000540-71 | ASO-002199 | TCCCttaatttcacCcTCA | 136052 | 136070 | 3891 | 83 |
| 127 | ASO-000540-72 | ASO-002203 | TCCCttaatttcacCCtCA | 136052 | 136070 | 3891 | 78 |
| 128 | ASO-000540-73 | ASO-002207 | TCCCttaatttcaCcCtCA | 136052 | 136070 | 3891 | 58 |
| 129 | ASO-000540-74 | ASO-002211 | TCCCttaatttcACcCtCA | 136052 | 136070 | 3891 | 26 |
| 130 | ASO-000540-75 | ASO-002215 | TCCCTtaatttcaccCTCA | 136052 | 136070 | 3891 | 84 |
| 131 | ASO-000540-76 | ASO-002219 | TCCCTtaatttcacCCtCA | 136052 | 136070 | 3891 | 44 |
| 132 | ASO-000540-77 | ASO-002223 | TCCCTtaatttcacCCTCA | 136052 | 136070 | 3891 | 30 |
| 133 | ASO-000540-8 | ASO-002119 | CCCtTaatttcaccCTC | 136053 | 136069 | 3892 | 98 |
| 134 | ASO-000540-9 | ASO-002131 | CCCtTaatttcacCcTC | 136053 | 136069 | 3892 | 96 |
| 135 | TBD-mm10 | ASO-002382 | CCttgATttcgccctCA | 136053 | 136069 | 3891 | 84 |
| 136 | TBD-mm11 | ASO-002299 | CCttgATttcaccctCT | 136052 | 136068 | 3891 | 98 |
| 137 | TBD-mm12 | ASO-002311 | CCttaGTttcaccctCG | 136054 | 136070 | 3891 | 98 |
| 138 | TBD-mm19 | ASO-002300 | CCCttgatttcaccctCA | 136052 | 136068 | 3891 | 50 |
| 139 | TBD-mm20 | ASO-002312 | CCCttaatttcaccctCG | 136054 | 136070 | 3891 | 50 |
| 140 | TBD-mm21 | ASO-002324 | CCCttagtttcaccctCA | 136052 | 136069 | 3891 | 50 |
| 141 | TBD-mm22 | ASO-002336 | CCCttgatttcgccctCA | 136052 | 136069 | 3891 | 57 |

Figure 3E

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 142 | TBD-mm23 | ASO-002348 | CCCttgatttcaccctCG | 136053 | 136070 | 3891 | 52 |
| 143 | TBD-mm24 | ASO-002360 | CCCttgatttcaccctCT | 136052 | 136070 | 3891 | 52 |
| 144 | TBD-mm31 | ASO-002349 | TCcCTtgatttcacCctCA | 136053 | 136070 | 3891 | 97 |
| 145 | TBD-mm32 | ASO-002361 | TCcCTtaatttcacCctCG | 136052 | 136070 | 3891 | 98 |
| 146 | TBD-mm33 | ASO-002373 | ACcCTtaatttcacCctCA | 136053 | 136069 | 3891 | 100 |
| 147 | TBD-mm34 | ASO-002385 | TCcCTtgatttcgcCctCA | 136052 | 136068 | 3891 | 92 |
| 148 | TBD-mm35 | ASO-002302 | TCcCTtagtttcacCctCG | 136054 | 136070 | 3891 | 50 |
| 149 | TBD-mm36 | ASO-002314 | ACcCTtgatttcacCctCA | 136054 | 136070 | 3891 | 95 |
| 150 | TBD-mm7 | ASO-002346 | CCttgATttcaccctCA | 136053 | 136070 | 3891 | 98 |
| 151 | TBD-mm8 | ASO-002358 | CCttaGTttcaccctCA | 136053 | 136069 | 3891 | 99 |
| 152 | TBD-mm9 | ASO-002370 | CCttaATttcaccctCG | 136052 | 136070 | 3891 | 100 |
| 153 | ASO-000540 | ASO-000540 | CCTtaatttcaccCTC | 136053 | 136068 | 3892 | 99 |
| 154 | ASO-000555 | ASO-000555 | CTTaatttcaccCTC | 136053 | 136067 | 3892 | 98 |
| 155 | ASO-000579 | ASO-000579 | TTAatttcaccCTC | 136053 | 136066 | 3892 | 94 |
| 156 | ASO-000540-1 | ASO-002130 | CCCttaatttcacccTC | 136053 | 136069 | 3892 | 97 |
| 157 | ASO-000540-10 | ASO-002143 | CCCTtaatttcaccCTC | 136053 | 136069 | 3892 | 98 |
| 158 | ASO-000540-11 | ASO-002155 | CCCTtaatttcacCcTC | 136053 | 136069 | 3892 | 96 |
| 159 | ASO-000540-12 | ASO-002167 | CCCTtaatttcacCCTC | 136053 | 136069 | 3892 | 88 |
| 160 | ASO-000540-13 | ASO-002179 | CCCTtaatttcaCccTC | 136053 | 136069 | 3892 | 95 |
| 161 | ASO-000540-14 | ASO-002191 | CCttaATttcaccctCA | 136052 | 136068 | 3891 | 99 |
| 162 | ASO-000540-15 | ASO-002108 | CCTtaatttcacccTCA | 136052 | 136068 | 3891 | 98 |
| 163 | ASO-000540-16 | ASO-002120 | CCTtaaTttcaccctCA | 136052 | 136068 | 3891 | 98 |
| 164 | ASO-000540-17 | ASO-002132 | CCTtaAtttcaccctCA | 136052 | 136068 | 3891 | 98 |
| 165 | ASO-000540-18 | ASO-002144 | CCTtaATttcaccctCA | 136052 | 136068 | 3891 | 99 |
| 166 | ASO-000540-19 | ASO-002156 | CCTtaATttcacccTCA | 136052 | 136068 | 3891 | 99 |
| 167 | ASO-000540-2 | ASO-002142 | CCCttaatttcaccCTC | 136053 | 136069 | 3892 | 98 |
| 168 | ASO-000540-20 | ASO-002168 | CCTTaatttcaccCtCA | 136052 | 136068 | 3891 | 99 |
| 169 | ASO-000540-56 | ASO-002201 | TCCcttaatttcacCcTC | 136053 | 136070 | 3892 | 98 |
| 170 | ASO-000540-57 | ASO-002205 | TCCcTtaatttcacccTC | 136053 | 136070 | 3892 | 98 |
| 171 | ASO-000540-58 | ASO-002209 | TCCcTtaatttcacCcTC | 136053 | 136070 | 3892 | 93 |
| 172 | ASO-000540-59 | ASO-002213 | TCCcTtaatttcaCccTC | 136053 | 136070 | 3892 | 84 |
| 173 | ASO-000540-6 | ASO-002190 | CCCttaatttcAcCcTC | 136053 | 136069 | 3892 | 80 |
| 174 | ASO-000540-60 | ASO-002217 | TCCcTtaatttcAcCcTC | 136053 | 136070 | 3892 | 3 |

Figure 3F

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 175 | ASO-000540-61 | ASO-002221 | TCCCttaatttcacCCTC | 136053 | 136070 | 3892 | 69 |
| 176 | ASO-000540-62 | ASO-002225 | TCCCttaatttcaCcCTC | 136053 | 136070 | 3892 | 36 |
| 177 | ASO-000540-63 | ASO-002198 | TCCCttaatttcaCCcTC | 136053 | 136070 | 3892 | 48 |
| 178 | ASO-000540-64 | ASO-002202 | TCCCttaatttcAccCTC | 136053 | 136070 | 3892 | 61 |
| 179 | ASO-000540-65 | ASO-002206 | TCCCttaatttCaccCTC | 136053 | 136070 | 3892 | 69 |
| 180 | ASO-000540-66 | ASO-002210 | TCcCTtaatttcacCctCA | 136052 | 136070 | 3891 | 99 |
| 181 | ASO-000540-67 | ASO-002214 | TCCcttaatttcacccTCA | 136052 | 136070 | 3891 | 99 |
| 182 | ASO-000540-68 | ASO-002218 | TCCcTtaatttcaccCtCA | 136052 | 136070 | 3891 | 99 |
| 183 | ASO-000540-mm1 | ASO-002297 | CCTtgatttcaccCTC | 136053 | 136068 | 3892 | 97 |
| 184 | ASO-000540-mm2 | ASO-002309 | CCTtaatttcgccCTC | 136053 | 136068 | 3892 | 87 |
| 185 | ASO-000540-mm3 | ASO-002321 | CCTtagtttcaccCTC | 136053 | 136068 | 3892 | 91 |
| 186 | ASO-000540-mm4 | ASO-002333 | CCTtgatttcgccCTC | 136053 | 136068 | 3892 | 89 |
| 187 | ASO-000540-mm5 | ASO-002345 | CCTtggtttcaccCTC | 136053 | 136068 | 3892 | 96 |
| 188 | ASO-000540-mm6 | ASO-002357 | CCTtagtttcgccCTC | 136053 | 136068 | 3892 | 13 |
| 189 | TBD-mm1 | ASO-002369 | CCCttgatttcacccTC | 136052 | 136070 | 3892 | 95 |
| 190 | TBD-mm2 | ASO-002381 | CCCttagtttcacccTC | 136053 | 136069 | 3892 | 98 |
| 191 | TBD-mm25 | ASO-002372 | TcCCTtgatttcacCcTC | 136052 | 136070 | 3892 | 51 |
| 192 | TBD-mm26 | ASO-002384 | TcCCTtaatttcgcCcTC | 136052 | 136068 | 3892 | 61 |
| 193 | TBD-mm27 | ASO-002301 | TcCCTtagtttcacCcTC | 136052 | 136068 | 3892 | 52 |
| 194 | TBD-mm28 | ASO-002313 | TcCCTtgatttcgcCcTC | 136054 | 136070 | 3892 | 51 |
| 195 | TBD-mm29 | ASO-002325 | TcCCTtagtttcgcCcTC | 136052 | 136069 | 3892 | 23 |
| 196 | TBD-mm3 | ASO-002298 | CCCttaatttcgcccTC | 136053 | 136069 | 3892 | 97 |
| 197 | TBD-mm30 | ASO-002337 | AcCCTtgatttcacCcTC | 136053 | 136070 | 3892 | 100 |
| 198 | TBD-mm4 | ASO-002310 | CCCttgatttcgcccTC | 136054 | 136070 | 3892 | 71 |
| 199 | TBD-mm5 | ASO-002322 | CCCttggtttcacccTC | 136052 | 136069 | 3892 | 91 |
| 200 | TBD-mm6 | ASO-002334 | CCCttagtttcgcccTC | 136052 | 136069 | 3892 | 51 |
| 201 | ASO-000662 | ASO-000662 | CCCttaatttcacCCT | 136054 | 136069 | 3893 | 96 |
| 202 | ASO-000566 | ASO-000566 | CCTtaatttcacCCT | 136054 | 136068 | 3893 | 94 |
| 203 | ASO-000540-30 | ASO-002193 | TCCcTtaatttcaccCT | 136054 | 136070 | 3893 | 89 |

Figure 3G

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 204 | ASO-000540-31 | ASO-002110 | TCCcTtaatttcAccCT | 136054 | 136070 | 3893 | 74 |
| 205 | ASO-000540-32 | ASO-002122 | TCCcTTaatttcaccCT | 136054 | 136070 | 3893 | 84 |
| 206 | ASO-000540-33 | ASO-002134 | TCCCttaatttcacCCT | 136054 | 136070 | 3893 | 75 |
| 207 | ASO-000540-34 | ASO-002146 | TCCCttaatttcaCcCT | 136054 | 136070 | 3893 | 60 |
| 208 | ASO-000540-35 | ASO-002158 | TCCCttaatttcaCCCT | 136054 | 136070 | 3893 | 33 |
| 209 | ASO-000540-36 | ASO-002170 | TCCCttaatttCaccCT | 136054 | 136070 | 3893 | 66 |
| 210 | ASO-000540-37 | ASO-002182 | CCCttaatttcaccctCA | 136052 | 136069 | 3891 | 98 |
| 211 | ASO-000540-38 | ASO-002194 | CCCttaatttcacccTCA | 136052 | 136069 | 3891 | 98 |
| 212 | ASO-000540-39 | ASO-002111 | CCCttaatttcacCctCA | 136052 | 136069 | 3891 | 98 |
| 213 | ASO-000540-4 | ASO-002166 | CCCttaatttcaCccTC | 136053 | 136069 | 3892 | 96 |
| 214 | ASO-000540-40 | ASO-002123 | CCCttaatttcaCcctCA | 136052 | 136069 | 3891 | 99 |
| 215 | ASO-000540-41 | ASO-002135 | CCCttaatttcAcCctCA | 136052 | 136069 | 3891 | 96 |
| 216 | TBD-mm13 | ASO-002323 | TcCCtTgatttcaccCT | 136053 | 136069 | 3893 | 95 |
| 217 | TBD-mm14 | ASO-002335 | TcCCtTaatttcaccCA | 136052 | 136069 | 3893 | 99 |
| 218 | TBD-mm15 | ASO-002347 | TcCCtTaatttcgccCT | 136053 | 136070 | 3893 | 91 |
| 219 | TBD-mm16 | ASO-002359 | TcCCtTgatttcaccCA | 136053 | 136070 | 3893 | 97 |
| 220 | TBD-mm17 | ASO-002371 | TcCCtTgatttcaccCG | 136052 | 136070 | 3893 | 95 |
| 221 | TBD-mm18 | ASO-002383 | TcCCtTagtttcgccCT | 136052 | 136068 | 3893 | 65 |
| 222 | ASO-000628 | ASO-000628 | CCTtaatttcaCCC | 136055 | 136068 | 3894 | 98 |
| 223 | ASO-000642 | ASO-000642 | CCCttaatttcaCCC | 136055 | 136069 | 3894 | 98 |
| 224 | ASO-000274 | ASO-000274 | TCCcttaatttcaCCC | 136055 | 136070 | 3894 | 99 |
| 225 | ASO-000339 | ASO-000339 | CCttaatttcaCCC | 136055 | 136068 | 3894 | 100 |
| 226 | ASO-000536 | ASO-000536 | TTCccttaatttcACC | 136056 | 136071 | 3895 | 91 |
| 227 | ASO-000603 | ASO-000603 | TCCcttaatttcACC | 136056 | 136070 | 3895 | 87 |
| 228 | ASO-000666 | ASO-000666 | TCCcttaatttCAC | 136057 | 136070 | 3896 | 63 |
| 229 | ASO-000272 | ASO-000272 | AGAgtgagaggctGGG | 136099 | 136114 | 3938 | 100 |
| 230 | ASO-000255 | ASO-000255 | TGGatgagtggaaCTG | 136115 | 136130 | 3954 | 99 |
| 231 | ASO-000336 | ASO-000336 | GGAtgagtggaACT | 136116 | 136129 | 3955 | 98 |
| 232 | ASO-000206 | ASO-000206 | GTTggatgagtgGAA | 136118 | 136132 | 3957 | 99 |
| 233 | ASO-000271 | ASO-000271 | AGTtggatgagtGGA | 136119 | 136133 | 3958 | 100 |
| 234 | ASO-000340 | ASO-000340 | GTTggatgagtGGA | 136119 | 136132 | 3958 | 100 |
| 235 | ASO-000229 | ASO-000229 | CAGggaaccgaatCAG | 136160 | 136175 | 3999 | 100 |
| 236 | ASO-000273 | ASO-000273 | GCCctggctcacaTCT | 136193 | 136208 | 4032 | 95 |
| 237 | ASO-000264 | ASO-000264 | ACAaggcagaaacACC | 136229 | 136244 | 4068 | 100 |

Figure 3H

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 238 | ASO-000341 | ASO-000341 | TGTcaacaaggCAG | 136236 | 136249 | 4075 | 56 |
| 239 | ASO-000198 | ASO-000198 | TGCcctgggtgccTTG | 136355 | 136370 | 4194 | 97 |
| 240 | ASO-000210 | ASO-000210 | AGCgggactgtggGCC | 136371 | 136386 | 4210 | 92 |
| 241 | ASO-000342 | ASO-000342 | GGgacagcgggACT | 136378 | 136391 | 4217 | |
| 242 | ASO-000333 | ASO-000333 | GCGggctgggctgTCT | 136427 | 136442 | 4266 | 99 |
| 243 | ASO-000199 | ASO-000199 | CAGaacagacagcATG | 136541 | 136556 | 4380 | 99 |
| 244 | ASO-000280 | ASO-000280 | TCTatgtatatgtTCA | 136567 | 136582 | 4406 | 100 |
| 245 | ASO-000211 | ASO-000211 | ATCtatgtatatgTTC | 136568 | 136583 | 4407 | 99 |
| 246 | ASO-000347 | ASO-000347 | CATctatgtataTGT | 136570 | 136584 | 4409 | 42 |
| 247 | ASO-000352 | ASO-000352 | ACAtctatgtataTGT | 136570 | 136585 | 4409 | 4 |
| 248 | ASO-000232 | ASO-000232 | CAAcagggtgcagATG | 136600 | 136615 | 4439 | 98 |
| 249 | ASO-000257 | ASO-000257 | AGCataaacagacAAA | 136629 | 136644 | 4468 | 99 |
| 250 | ASO-000388 | ASO-000388 | ATAgtcactctggTGA | 136650 | 136665 | 4489 | 99 |
| 251 | ASO-000390 | ASO-000390 | TAGtcactctggTGA | 136650 | 136664 | 4489 | 97 |
| 252 | ASO-000413 | ASO-000413 | AGTcactctggTGA | 136650 | 136663 | 4489 | 37 |
| 253 | ASO-000405 | ASO-000405 | CATagtcactctgGTG | 136651 | 136666 | 4490 | 100 |
| 254 | ASO-000430 | ASO-000430 | TAGtcactctgGTG | 136651 | 136664 | 4490 | 100 |
| 255 | ASO-000447 | ASO-000447 | TCAtagtcactctGGT | 136652 | 136667 | 4491 | 100 |
| 256 | ASO-000396 | ASO-000396 | TACatgcgtccTTT | 136693 | 136706 | 4532 | 100 |
| 257 | ASO-000395 | ASO-000395 | GATacatgcgtccTTT | 136693 | 136708 | 4532 | 99 |
| 258 | ASO-000394 | ASO-000394 | AAGatacatgcgtCCT | 136695 | 136710 | 4534 | 100 |
| 259 | ASO-000421 | ASO-000421 | TTCaagatacatgCGT | 136698 | 136713 | 4537 | 100 |
| 260 | ASO-000400 | ASO-000400 | ATTtcaagatacaTGC | 136700 | 136715 | 4539 | 99 |
| 261 | ASO-000248 | ASO-000248 | GCAtttcaagataCAT | 136702 | 136717 | 4541 | 100 |
| 262 | ASO-000451 | ASO-000451 | AAGcatttcaagaTAC | 136704 | 136719 | 4543 | 99 |
| 263 | ASO-000707 | ASO-000707 | ACAagcatttcaaGAT | 136706 | 136721 | 4545 | 100 |
| 264 | ASO-000619 | ASO-000619 | TTAcaagcatttcAAG | 136708 | 136723 | 4547 | 88 |
| 265 | ASO-000671 | ASO-000671 | AACctctttacaaGCA | 136715 | 136730 | 4554 | |
| 266 | ASO-000221 | ASO-000221 | GTTagaaacctctTTA | 136721 | 136736 | 4560 | 100 |
| 267 | ASO-000298 | ASO-000298 | CCAcacaggccacACG | 136776 | 136791 | 4615 | 98 |
| 268 | ASO-000311 | ASO-000311 | GTCtctgttgggtCCC | 136842 | 136857 | 4681 | 97 |
| 269 | ASO-000290 | ASO-000290 | TGAacggcctcctTAG | 136871 | 136886 | 4710 | 99 |
| 270 | ASO-000437 | ASO-000437 | CTGtgcttcaggcCTT | 136896 | 136911 | 4735 | 100 |
| 271 | ASO-000446 | ASO-000446 | TCCtgtgcttcagGCC | 136898 | 136913 | 4737 | 98 |
| 272 | ASO-000685 | ASO-000685 | AATcctgtgcttcAGG | 136900 | 136915 | 4739 | 65 |

Figure 3I

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 273 | ASO-000410 | ASO-000410 | TCCtgtgcttcAGG | 136900 | 136913 | 4739 | 23 |
| 274 | ASO-000604 | ASO-000604 | AATcctgtgcttCAG | 136901 | 136915 | 4740 | 94 |
| 275 | ASO-000490 | ASO-000490 | TAAtcctgtgcttCAG | 136901 | 136916 | 4740 | 89 |
| 276 | ASO-000529 | ASO-000529 | AATcctgtgctTCA | 136902 | 136915 | 4741 | 100 |
| 277 | ASO-000532 | ASO-000532 | CTAatcctgtgctTCA | 136902 | 136917 | 4741 | 99 |
| 278 | ASO-000508 | ASO-000508 | TAAtcctgtgctTCA | 136902 | 136916 | 4741 | 95 |
| 279 | ASO-000219 | ASO-000219 | CCTaatcctgtgcTTC | 136903 | 136918 | 4742 | 100 |
| 280 | ASO-000656 | ASO-000656 | TAAtcctgtgcTTC | 136903 | 136916 | 4742 | 99 |
| 281 | ASO-000522 | ASO-000522 | CTAatcctgtgcTTC | 136903 | 136917 | 4742 | 98 |
| 282 | ASO-000513 | ASO-000513 | CCTaatcctgtgCTT | 136904 | 136918 | 4743 | 97 |
| 283 | ASO-000640 | ASO-000640 | TCCtaatcctgtgCTT | 136904 | 136919 | 4743 | 93 |
| 284 | ASO-000661 | ASO-000661 | CTAatcctgtgCTT | 136904 | 136917 | 4743 | 85 |
| 285 | ASO-000478 | ASO-000478 | GTCctaatcctgtGCT | 136905 | 136920 | 4744 | 96 |
| 286 | ASO-000500 | ASO-000500 | TCCtaatcctgtGCT | 136905 | 136919 | 4744 | 94 |
| 287 | ASO-000601 | ASO-000601 | CCTaatcctgtGCT | 136905 | 136918 | 4744 | 93 |
| 288 | ASO-000643 | ASO-000643 | AGTcctaatcctgTGC | 136906 | 136921 | 4745 | 99 |
| 289 | ASO-000600 | ASO-000600 | GTCctaatcctgTGC | 136906 | 136920 | 4745 | 98 |
| 290 | ASO-000525 | ASO-000525 | TCCtaatcctgTGC | 136906 | 136919 | 4745 | 90 |
| 291 | ASO-000453 | ASO-000453 | TCAgtcctaatccTGT | 136908 | 136923 | 4747 | 60 |
| 292 | ASO-000553 | ASO-000553 | CTTcagtcctaatCCT | 136910 | 136925 | 4749 | 95 |
| 293 | ASO-000622 | ASO-000622 | GCTtcagtcctaATC | 136912 | 136926 | 4751 | 100 |
| 294 | ASO-000325 | ASO-000325 | CTGacacagggagCCC | 136956 | 136971 | 4795 | 99 |
| 295 | ASO-000215 | ASO-000215 | GCCagaccagccaCAA | 136987 | 137002 | 4826 | 97 |
| 296 | ASO-000482 | ASO-000482 | CAGgagttgtaAGC | 137065 | 137078 | 4904 | 60 |
| 297 | ASO-000337 | ASO-000337 | TGCaggagttgtaAGC | 137065 | 137080 | 4904 | 88 |
| 298 | ASO-000480 | ASO-000480 | ATGcaggagttgtAAG | 137066 | 137081 | 4905 | 57 |
| 299 | ASO-000644 | ASO-000644 | GATgcaggagttgTAA | 137067 | 137082 | 4906 | 97 |
| 300 | ASO-000695 | ASO-000695 | TGCaggagttgTAA | 137067 | 137080 | 4906 | 41 |
| 301 | ASO-000455 | ASO-000455 | TGAtgcaggagttGTA | 137068 | 137083 | 4907 | 94 |
| 302 | ASO-000531 | ASO-000531 | GTGatgcaggagtTGT | 137069 | 137084 | 4908 | 100 |
| 303 | ASO-000651 | ASO-000651 | TGTgatgcaggagTTG | 137070 | 137085 | 4909 | 96 |
| 304 | ASO-000007 | ASO-000007 | TGTgatgcaggaGTT | 137071 | 137085 | | |
| 305 | ASO-000419 | ASO-000419 | GTGatgcaggaGTT | 137071 | 137084 | 4910 | 100 |
| 306 | ASO-000730 | ASO-000730 | TGTgatgcaggaGTT | 137071 | 137085 | 4910 | 92 |
| 307 | ASO-000728 | ASO-000728 | TGTgatgcaggaGTT | 137071 | 137085 | 4910 | 91 |

Figure 3J

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 308 | ASO-000729 | ASO-000729 | TGTgatgcaggaGTT | 137071 | 137085 | 4910 | 12 |
| 309 | ASO-000727 | ASO-000727 | TGTgatgcaggaGTT | 137071 | 137085 | 4910 | 1 |
| 310 | ASO-000715 | ASO-000715 | TGtgatgcaggagTT | 137071 | 137085 | 4910 | 2 |
| 311 | ASO-000716 | ASO-000716 | GAtgcaggagTT | 137071 | 137082 | 4910 | 97 |
| 312 | ASO-000721 | ASO-000721 | TGTgatgcaggaGTT | 137071 | 137085 | 4910 | 99 |
| 313 | ASO-000722 | ASO-000722 | TGTgatgcaggaGTT | 137071 | 137085 | 4910 | 99 |
| 314 | ASO-000723 | ASO-000723 | TGTgatgcaggaGTT | 137071 | 137085 | 4910 | |
| 315 | ASO-000724 | ASO-000724 | TGTgatgcaggaGTT | 137071 | 137085 | 4910 | 99 |
| 316 | ASO-000725 | ASO-000725 | TGTgatgcaggaGTT | 137071 | 137085 | 4910 | 100 |
| 317 | ASO-000726 | ASO-000726 | TGTgatgcaggaGTT | 137071 | 137085 | 4910 | 12 |
| 318 | ASO-000731 | ASO-000731 | TGTgatgcaggaGTT | 137071 | 137085 | 4910 | |
| 319 | ASO-000718 | ASO-000718 | TGatgcaggaGT | 137072 | 137083 | 4911 | 100 |
| 320 | ASO-000445 | ASO-000445 | TTGtgatgcagGAG | 137073 | 137086 | 4912 | 100 |
| 321 | ASO-000436 | ASO-000436 | CTTgtgatgcagGAG | 137073 | 137087 | 4912 | 98 |
| 322 | ASO-000717 | ASO-000717 | GTgatgcaggAG | 137073 | 137084 | 4912 | 99 |
| 323 | ASO-000570 | ASO-000570 | TTCttgtgatgcaGGA | 137074 | 137089 | 4913 | 91 |
| 324 | ASO-000408 | ASO-000408 | TCTtgtgatgcaGGA | 137074 | 137088 | 4913 | 90 |
| 325 | ASO-000401 | ASO-000401 | CTTgtgatgcaGGA | 137074 | 137087 | 4913 | 88 |
| 326 | ASO-000719 | ASO-000719 | TGtgatgcagGA | 137074 | 137085 | 4913 | 100 |
| 327 | ASO-000313 | ASO-000313 | CAGagggcgagctTGG | 137173 | 137188 | 5012 | 100 |
| 328 | ASO-000331 | ASO-000331 | AATccctgctgtgGTC | 137223 | 137238 | 5062 | 100 |
| 329 | ASO-000251 | ASO-000251 | AGGcaattcatCCC | 137239 | 137252 | 5078 | 97 |
| 330 | ASO-000574 | ASO-000574 | TGGtcaaggctttGGG | 137326 | 137341 | 5165 | 99 |
| 331 | ASO-000218 | ASO-000218 | TCTggtcaaggctTTG | 137328 | 137343 | 5167 | 99 |
| 332 | ASO-000634 | ASO-000634 | CTCtggtcaaggcTTT | 137329 | 137344 | 5168 | 99 |
| 333 | ASO-000497 | ASO-000497 | GGTgctctggtcaAGG | 137333 | 137348 | 5172 | 99 |
| 334 | ASO-000569 | ASO-000569 | GGTgctctggtCAA | 137335 | 137348 | 5174 | 100 |
| 335 | ASO-000565 | ASO-000565 | GCTgaggtgctctGGT | 137338 | 137353 | 5177 | 99 |
| 336 | ASO-000296 | ASO-000296 | AGTttgtgcaaggTCA | 137358 | 137373 | 5197 | 98 |
| 337 | ASO-000663 | ASO-000663 | GAGtttgtgcaagGTC | 137359 | 137374 | 5198 | 100 |
| 338 | ASO-000670 | ASO-000670 | AGTttgtgcaagGTC | 137359 | 137373 | 5198 | 100 |
| 339 | ASO-000261 | ASO-000261 | GGAgtttgtgcaaGGT | 137360 | 137375 | 5199 | 100 |
| 340 | ASO-000262 | ASO-000262 | GGAgtttgtgcaAGG | 137361 | 137375 | 5200 | 99 |
| 341 | ASO-000275 | ASO-000275 | TGGagtttgtgcaAGG | 137361 | 137376 | 5200 | 7 |
| 342 | ASO-000247 | ASO-000247 | ATGgagtttgtgcAAG | 137362 | 137377 | 5201 | 98 |

Figure 3K

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 343 | ASO-000303 | ASO-000303 | TGGagtttgtgcAAG | 137362 | 137376 | 5201 | 99 |
| 344 | ASO-000299 | ASO-000299 | ATGgagtttgtgCAA | 137363 | 137377 | 5202 | 96 |
| 345 | ASO-000270 | ASO-000270 | AGAtggagtttgtGCA | 137364 | 137379 | 5203 | 100 |
| 346 | ASO-000297 | ASO-000297 | AGCagatggagttTGT | 137367 | 137382 | 5206 | 96 |
| 347 | ASO-000259 | ASO-000259 | TTCtttaggcagcAAT | 137416 | 137431 | 5255 | |
| 348 | ASO-000220 | ASO-000220 | TGTacccaaaccaGAA | 137462 | 137477 | 5301 | 98 |
| 349 | ASO-000278 | ASO-000278 | GTTgcctttaacTGT | 137475 | 137489 | 5314 | 99 |
| 350 | ASO-000334 | ASO-000334 | GCCctggatttctACT | 137505 | 137520 | 5344 | 61 |
| 351 | ASO-000241 | ASO-000241 | TGGtggagagttcTGG | 137583 | 137598 | 5422 | 99 |
| 352 | ASO-000289 | ASO-000289 | TTCtcagatccctTCA | 137643 | 137658 | 5482 | 99 |
| 353 | ASO-000233 | ASO-000233 | CTCtaaccaccacCAA | 137682 | 137697 | 5521 | 100 |
| 354 | ASO-000201 | ASO-000201 | AGGgcacaagaacTTC | 137765 | 137780 | 5604 | 90 |
| 355 | ASO-000645 | ASO-000645 | ATCttaggctggCCC | 137851 | 137865 | 5689 | 94 |
| 356 | ASO-000546 | ASO-000546 | GATcttaggctggCCC | 137851 | 137866 | 5689 | 92 |
| 357 | ASO-000692 | ASO-000692 | TGAtcttaggctgGCC | 137852 | 137867 | 5690 | 99 |
| 358 | ASO-000511 | ASO-000511 | GATcttaggctgGCC | 137852 | 137866 | 5690 | 76 |
| 359 | ASO-000538 | ASO-000538 | TGAtcttaggctGGC | 137853 | 137867 | 5691 | 99 |
| 360 | ASO-000214 | ASO-000214 | ATGatcttaggctGGC | 137853 | 137868 | 5691 | 99 |
| 361 | ASO-000653 | ASO-000653 | GATcttaggctGGC | 137853 | 137866 | 5691 | 98 |
| 362 | ASO-000615 | ASO-000615 | CATgatcttaggcTGG | 137854 | 137869 | 5692 | 89 |
| 363 | ASO-000524 | ASO-000524 | CCAtgatcttaggCTG | 137855 | 137870 | 5693 | 98 |
| 364 | ASO-000492 | ASO-000492 | CATgatcttaggCTG | 137855 | 137869 | 5693 | 95 |
| 365 | ASO-000468 | ASO-000468 | ACCatgatcttagGCT | 137856 | 137871 | 5694 | 99 |
| 366 | ASO-000698 | ASO-000698 | CCAtgatcttagGCT | 137856 | 137870 | 5694 | 100 |
| 367 | ASO-000593 | ASO-000593 | CATgatcttagGCT | 137856 | 137869 | 5694 | 55 |
| 368 | ASO-000519 | ASO-000519 | AAAccatgatcttAGG | 137858 | 137873 | 5696 | 96 |
| 369 | ASO-000582 | ASO-000582 | CTAaaccatgatcTTA | 137860 | 137875 | 5698 | 74 |
| 370 | ASO-000635 | ASO-000635 | CCCtaaaccatgaTCT | 137862 | 137877 | 5700 | 98 |
| 371 | ASO-000471 | ASO-000471 | CACcctaaaccatGAT | 137864 | 137879 | 5702 | 96 |
| 372 | ASO-000701 | ASO-000701 | ATCaccctaaaccATG | 137866 | 137881 | 5704 | 100 |
| 373 | ASO-000533 | ASO-000533 | TGAtcaccctaaaCCA | 137868 | 137883 | 5706 | 96 |
| 374 | ASO-000323 | ASO-000323 | GAGgagtgcccagCCC | 137947 | 137962 | 5785 | |
| 375 | ASO-000329 | ASO-000329 | TGCaggtgggagaAGT | 137973 | 137988 | 5811 | |
| 376 | ASO-000194 | ASO-000194 | TATctagcccaCCC | 138003 | 138016 | 5841 | 100 |
| 377 | ASO-000192 | ASO-000192 | CTAtctagcccaCCC | 138003 | 138017 | 5841 | 99 |

Figure 3L

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 378 | ASO-000343 | ASO-000343 | TAtcctatctaGCC | 138008 | 138021 | 5846 | |
| 379 | ASO-000212 | ASO-000212 | TTGataaagtgaGTC | 138050 | 138064 | 5888 | |
| 380 | ASO-000230 | ASO-000230 | ATTgataaagtgAGT | 138051 | 138065 | 5889 | 99 |
| 381 | ASO-000188 | ASO-000188 | AACtattgataaAGT | 138055 | 138069 | 5893 | 4 |
| 382 | ASO-000415 | ASO-000415 | GAActattgatAAA | 138057 | 138070 | 5895 | 21 |
| 383 | ASO-000448 | ASO-000448 | GGAactattgaTAA | 138058 | 138071 | 5896 | 100 |
| 384 | ASO-000190 | ASO-000190 | AAAtggaactattGAT | 138060 | 138075 | 5898 | |
| 385 | ASO-000191 | ASO-000191 | AATggaactatTGA | 138061 | 138074 | 5899 | 97 |
| 386 | ASO-000348 | ASO-000348 | TCAAtttaaatGGAA | 138068 | 138082 | 5906 | |
| 387 | ASO-000349 | ASO-000349 | GTcaatttaaaTGGA | 138069 | 138083 | 5907 | |
| 388 | ASO-000200 | ASO-000200 | GGAtacagtctcaCCA | 138089 | 138104 | 5927 | 100 |
| 389 | ASO-000630 | ASO-000630 | GCAaacaggatacAGT | 138096 | 138111 | 5934 | 100 |
| 390 | ASO-000614 | ASO-000614 | CAAacaggatacAGT | 138096 | 138110 | 5934 | 99 |
| 391 | ASO-000563 | ASO-000563 | AAAcaggatacAGT | 138096 | 138109 | 5934 | 90 |
| 392 | ASO-000527 | ASO-000527 | TAGcaaacaggatACA | 138098 | 138113 | 5936 | 99 |
| 393 | ASO-000617 | ASO-000617 | ATAgcaaacaggaTAC | 138099 | 138114 | 5937 | 99 |
| 394 | ASO-000539 | ASO-000539 | AATagcaaacaggATA | 138100 | 138115 | 5938 | 99 |
| 395 | ASO-000691 | ASO-000691 | CAAtagcaaacagGAT | 138101 | 138116 | 5939 | 99 |
| 396 | ASO-000589 | ASO-000589 | AATagcaaacagGAT | 138101 | 138115 | 5939 | 99 |
| 397 | ASO-000509 | ASO-000509 | GCAatagcaaacaGGA | 138102 | 138117 | 5940 | |
| 398 | ASO-000674 | ASO-000674 | CAAtagcaaacaGGA | 138102 | 138116 | 5940 | |
| 399 | ASO-000488 | ASO-000488 | GCAatagcaaacAGG | 138103 | 138117 | 5941 | 100 |
| 400 | ASO-000507 | ASO-000507 | AGCaatagcaaacAGG | 138103 | 138118 | 5941 | 99 |
| 401 | ASO-000521 | ASO-000521 | AGCaatagcaaaCAG | 138104 | 138118 | 5942 | 99 |
| 402 | ASO-000288 | ASO-000288 | AAGcaatagcaaaCAG | 138104 | 138119 | 5942 | |
| 403 | ASO-000552 | ASO-000552 | AAGcaatagcaaACA | 138105 | 138119 | 5943 | 98 |
| 404 | ASO-000250 | ASO-000250 | CAAatgtggttgaAAT | 138223 | 138238 | 6061 | |
| 405 | ASO-000294 | ASO-000294 | GCAaatgtggttgAAA | 138224 | 138239 | 6062 | |
| 406 | ASO-000318 | ASO-000318 | TAGcaaatgtggtTGA | 138226 | 138241 | 6064 | |
| 407 | ASO-000308 | ASO-000308 | CCCaagggcctctAAC | 138263 | 138278 | 6101 | |
| 408 | ASO-000254 | ASO-000254 | AAAgcaaccagatGTC | 138361 | 138376 | 6199 | |
| 409 | ASO-000545 | ASO-000545 | AAGagggcagcagGCC | 138377 | 138392 | 6215 | 92 |
| 410 | ASO-000476 | ASO-000476 | GAAagagggcagcAGG | 138379 | 138394 | 6217 | 100 |
| 411 | ASO-000620 | ASO-000620 | CTGaaagagggcaGCA | 138381 | 138396 | 6219 | 63 |
| 412 | ASO-000477 | ASO-000477 | CCCtgaaagagggCAG | 138383 | 138398 | 6221 | 39 |

Figure 3M

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 413 | ASO-000562 | ASO-000562 | TGAttgtgggcttAGG | 138401 | 138416 | 6239 | 100 |
| 414 | ASO-000547 | ASO-000547 | ATGattgtgggctTAG | 138402 | 138417 | 6240 | 100 |
| 415 | ASO-000696 | ASO-000696 | TGAttgtgggctTAG | 138402 | 138416 | 6240 | 99 |
| 416 | ASO-000279 | ASO-000279 | GATtgtgggctTAG | 138402 | 138415 | 6240 | |
| 417 | ASO-000543 | ASO-000543 | CATgattgtgggcTTA | 138403 | 138418 | 6241 | 100 |
| 418 | ASO-000626 | ASO-000626 | TGAttgtgggcTTA | 138403 | 138416 | 6241 | 100 |
| 419 | ASO-000650 | ASO-000650 | ATGattgtgggcTTA | 138403 | 138417 | 6241 | 100 |
| 420 | ASO-000599 | ASO-000599 | CATgattgtgggCTT | 138404 | 138418 | 6242 | 98 |
| 421 | ASO-000542 | ASO-000542 | GCAtgattgtgggCTT | 138404 | 138419 | 6242 | 96 |
| 422 | ASO-000463 | ASO-000463 | GGCatgattgtggGCT | 138405 | 138420 | 6243 | 79 |
| 423 | ASO-000605 | ASO-000605 | GCAtgattgtggGCT | 138405 | 138419 | 6243 | 61 |
| 424 | ASO-000479 | ASO-000479 | CATgattgtggGCT | 138405 | 138418 | 6243 | |
| 425 | ASO-000474 | ASO-000474 | GCAtgattgtgGGC | 138406 | 138419 | 6244 | 99 |
| 426 | ASO-000675 | ASO-000675 | GGCatgattgtgGGC | 138406 | 138420 | 6244 | 95 |
| 427 | ASO-000537 | ASO-000537 | AGGcatgattgtgGGC | 138406 | 138421 | 6244 | 89 |
| 428 | ASO-000287 | ASO-000287 | AGGgaggcatgatTGT | 138410 | 138425 | 6248 | |
| 429 | ASO-000292 | ASO-000292 | GGGaggcatgatTGT | 138410 | 138424 | 6248 | |
| 430 | ASO-000216 | ASO-000216 | TTAgggaggcatgATT | 138412 | 138427 | 6250 | 96 |
| 431 | ASO-000266 | ASO-000266 | TTAgggaggcatGAT | 138413 | 138427 | 6251 | |
| 432 | ASO-000256 | ASO-000256 | TCTtagggaggcaTGA | 138414 | 138429 | 6252 | |
| 433 | ASO-000269 | ASO-000269 | GAGgtggcacagaGGT | 138460 | 138475 | 6298 | |
| 434 | ASO-000350 | ASO-000350 | CAGtgtgagaggtGG | 138469 | 138483 | 6307 | |
| 435 | ASO-000353 | ASO-000353 | CAGtgtgagaggTG | 138470 | 138483 | 6308 | |
| 436 | ASO-000310 | ASO-000310 | ACAaagatgaggaGGG | 138532 | 138547 | 6370 | |
| 437 | ASO-000309 | ASO-000309 | AACaaagatgaggAGG | 138533 | 138548 | 6371 | |
| 438 | ASO-000263 | ASO-000263 | GAAgagaaatcagAAG | 138631 | 138646 | 6469 | |
| 439 | ASO-000197 | ASO-000197 | TCTaggccagtgcCCA | 138667 | 138682 | 6505 | 99 |
| 440 | ASO-000239 | ASO-000239 | AGTctattaggAGG | 138689 | 138702 | 6527 | 100 |
| 441 | ASO-000267 | ASO-000267 | GCTcaacatggcaAAC | 138714 | 138729 | 6552 | |
| 442 | ASO-000306 | ASO-000306 | TGCaagtgccagAAA | 138737 | 138751 | 6575 | |
| 443 | ASO-000345 | ASO-000345 | GCAagtgccagAAA | 138737 | 138750 | 6575 | |
| 444 | ASO-000193 | ASO-000193 | AATcatgggacttGCA | 138748 | 138763 | 6586 | 100 |
| 445 | ASO-000284 | ASO-000284 | GATttcatgtcccTCC | 138788 | 138803 | 6626 | |
| 446 | ASO-000209 | ASO-000209 | GCTaagctaagaTGA | 138802 | 138816 | 6640 | 99 |
| 447 | ASO-000207 | ASO-000207 | CTAagctaagaTGA | 138802 | 138815 | 6640 | 97 |

Figure 3N

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 448 | ASO-000301 | ASO-000301 | TAGacattcacaGAC | 138822 | 138836 | 6660 | |
| 449 | ASO-000234 | ASO-000234 | TATagacattcaCAG | 138824 | 138838 | 6662 | 100 |
| 450 | ASO-000332 | ASO-000332 | AAAcacacaatacACT | 138840 | 138855 | 6678 | |
| 451 | SPC-15693-01 | ASO-002268 | CAgcaacagtcagtGT | 138869 | 138884 | 6707 | 100 |
| 452 | SPC-15692-01 | ASO-002260 | ACagcaacagtcagTG | 138870 | 138885 | 6708 | 100 |
| 453 | SPC-15691-01 | ASO-002252 | TAcagcaacagtcaGT | 138871 | 138886 | 6709 | 99 |
| 454 | SPC-15690-01 | ASO-002244 | TTAcagcaacagtcAG | 138872 | 138887 | 6710 | 100 |
| 455 | SPC-15689-01 | ASO-002235 | TTTacagcaacagtCA | 138873 | 138888 | 6711 | 100 |
| 456 | SPC-15688-01 | ASO-002290 | TTttacagcaacaGTC | 138874 | 138889 | 6712 | 100 |
| 457 | SPC-15687-01 | ASO-002282 | CTtttacagcaacaGT | 138875 | 138890 | 6713 | 86 |
| 458 | SPC-15686-01 | ASO-002275 | ACttttacagcaaCAG | 138876 | 138891 | 6714 | 100 |
| 459 | SPC-15685-01 | ASO-002267 | CActtttacagcaaCA | 138877 | 138892 | 6715 | 93 |
| 460 | SPC-15684-01 | ASO-002259 | TCActtttacagcAAC | 138878 | 138893 | 6716 | 99 |
| 461 | SPC-15683-01 | ASO-002251 | TTCacttttacagCAA | 138879 | 138894 | 6717 | 100 |
| 462 | SPC-15682-01 | ASO-002243 | ATTcacttttacagCA | 138880 | 138895 | 6718 | 98 |
| 463 | SPC-15681-01 | ASO-002234 | AATtcacttttacaGC | 138881 | 138896 | 6719 | 77 |
| 464 | SPC-15680-01 | ASO-002289 | AAATtcacttttACAG | 138882 | 138897 | 6720 | 96 |
| 465 | SPC-15679-01 | ASO-002281 | CAAattcactttTACA | 138883 | 138898 | 6721 | 99 |
| 466 | ASO-002090 | ASO-002090 | ATTtcCaaattcactTtTAC | 138884 | 138903 | 6722 | 99 |
| 467 | ASO-002043 | ASO-002043 | ATtTCcaaattcacttTTAC | 138884 | 138903 | 6722 | 99 |
| 468 | ASO-002076 | ASO-002076 | ATtTCcaaattcacTTttAC | 138884 | 138903 | 6722 | 99 |
| 469 | ASO-002062 | ASO-002062 | ATTtcCaaattcactTTtAC | 138884 | 138903 | 6722 | 100 |
| 470 | ASO-002082 | ASO-002082 | ATtTcCaaattcactTtTAC | 138884 | 138903 | 6722 | 100 |
| 471 | ASO-000753 | ASO-000753 | ATTTCcaaattcactTTTAC | 138884 | 138903 | 6722 | 96 |
| 472 | ASO-001940 | ASO-001940 | ATtTCcaaattcactTTtAC | 138884 | 138903 | 6722 | 99 |
| 473 | ASO-001933 | ASO-001933 | AtTTCcaaattcactTTtAC | 138884 | 138903 | 6722 | 99 |
| 474 | ASO-001919 | ASO-001919 | ATTTccaaattcactTTTAC | 138884 | 138903 | 6722 | 99 |
| 475 | ASO-002094 | ASO-002094 | ATtTCcaaattcacTtTtAC | 138884 | 138903 | 6722 | 98 |
| 476 | ASO-002034 | ASO-002034 | ATTtCcaaattcactTtTAC | 138884 | 138903 | 6722 | 100 |
| 477 | ASO-002036 | ASO-002036 | ATttCcAaattcacttTTAC | 138884 | 138903 | 6722 | 100 |
| 478 | ASO-002084 | ASO-002084 | ATTtCcaaattcacTTttAC | 138884 | 138903 | 6722 | 99 |
| 479 | ASO-002037 | ASO-002037 | ATTTccaaattcaCtTttAC | 138884 | 138903 | 6722 | 99 |
| 480 | ASO-002058 | ASO-002058 | ATTtCcaaattcacTttTAC | 138884 | 138903 | 6722 | 99 |
| 481 | ASO-002057 | ASO-002057 | ATTTccaaattcaCttTtAC | 138884 | 138903 | 6722 | 99 |
| 482 | ASO-001926 | ASO-001926 | ATTTCcaaattcacttTTAC | 138884 | 138903 | 6722 | 99 |

Figure 3O

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 483 | ASO-002092 | ASO-002092 | ATttCCaaattcactTtTAC | 138884 | 138903 | 6722 | 99 |
| 484 | ASO-002023 | ASO-002023 | ATTTccaaattcacTTttAC | 138884 | 138903 | 6722 | 100 |
| 485 | ASO-000758 | ASO-000758 | ATTtccaaattcactttTAC | 138884 | 138903 | 6722 | 97 |
| 486 | ASO-002065 | ASO-002065 | ATttCCaaattcactTTtAC | 138884 | 138903 | 6722 | 99 |
| 487 | ASO-002038 | ASO-002038 | ATTtCcaaattcacTtTtAC | 138884 | 138903 | 6722 | 99 |
| 488 | ASO-002039 | ASO-002039 | ATtTCcaaattcacTttTAC | 138884 | 138903 | 6722 | 98 |
| 489 | ASO-000763 | ASO-000763 | ATttccaaattcactttAC | 138884 | 138903 | 6722 | 14 |
| 490 | ASO-000768 | ASO-000768 | AtttccaaattcactttAC | 138884 | 138903 | 6722 | 0 |
| 491 | 17-18-19mer-1 | ASO-002390 | TCCaaattcacttTTAC | 138884 | 138900 | 6722 | 100 |
| 492 | 17-18-19mer-10 | ASO-002403 | TCCAaattcacttTTAC | 138884 | 138900 | 6722 | 100 |
| 493 | 17-18-19mer-13 | ASO-002439 | TCCAAattcactttTAC | 138884 | 138900 | 6722 | 100 |
| 494 | 17-18-19mer-16 | ASO-002473 | TTCcaaattcacttTTAC | 138884 | 138901 | 6722 | 100 |
| 495 | 17-18-19mer-22 | ASO-002440 | TTCcaaattcactTTTAC | 138884 | 138901 | 6722 | |
| 496 | 17-18-19mer-28 | ASO-002417 | TTCCaaattcactttTAC | 138884 | 138901 | 6722 | |
| 497 | 17-18-19mer-34 | ASO-002394 | TTCCaaattcacttTTAC | 138884 | 138901 | 6722 | |
| 498 | 17-18-19mer-4 | ASO-002426 | TCCaaattcactTTTAC | 138884 | 138900 | 6722 | 100 |
| 499 | 17-18-19mer-40 | ASO-002454 | TTCCAaattcactttTAC | 138884 | 138901 | 6722 | |
| 500 | 17-18-19mer-46 | ASO-002431 | TTTccaaattcacttTTAC | 138884 | 138902 | 6722 | 94 |
| 501 | 17-18-19mer-52 | ASO-002408 | TTTccaaattcactTTTAC | 138884 | 138902 | 6722 | 98 |
| 502 | 17-18-19mer-58 | ASO-002467 | TTTCcaaattcactttTAC | 138884 | 138902 | 6722 | 99 |
| 503 | 17-18-19mer-64 | ASO-002445 | TTTCcaaattcacttTTAC | 138884 | 138902 | 6722 | 99 |
| 504 | 17-18-19mer-7 | ASO-002461 | TCCAaattcactttTAC | 138884 | 138900 | 6722 | 100 |
| 505 | 17-18-19mer-70 | ASO-002422 | TTTCCaaattcactttTAC | 138884 | 138902 | 6722 | 97 |
| 506 | ASO-001933-mm1 | ASO-002291 | GtTTCcaaattcactTTtAC | 138884 | 138903 | 6722 | 50 |
| 507 | ASO-001933-mm2 | ASO-002303 | AtTTCcagattcactTTtAC | 138884 | 138903 | 6722 | 50 |
| 508 | ASO-001933-mm3 | ASO-002315 | TtTTCcaaattcactTTtAC | 138884 | 138903 | 6722 | 50 |
| 509 | ASO-001933-mm4 | ASO-002327 | GtTTCcagattcactTTtAC | 138884 | 138903 | 6722 | 83 |
| 510 | ASO-001933-mm5 | ASO-002339 | AtTTCcaagttcactTTtGC | 138884 | 138903 | 6722 | 69 |
| 511 | ASO-001933-mm6 | ASO-002351 | AtTTCcagattcgctTTtAC | 138884 | 138903 | 6722 | 75 |
| 512 | SPC-15678-01 | ASO-002274 | CCaaattcactttTAC | 138884 | 138899 | 6722 | 79 |
| 513 | SPC-15857-01 | ASO-002326 | ATtTcCaaattcacttTTAC | 138884 | 138903 | 6722 | 99 |

Figure 3P

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 514 | SPC-15858-01 | ASO-002338 | ATTtcCaaattcacttTTAC | 138884 | 138903 | 6722 | 99 |
| 515 | SPC-15860-01 | ASO-002362 | ATTtCcaaattcacttTTAC | 138884 | 138903 | 6722 | 99 |
| 516 | SPC-15864-01 | ASO-002236 | ATTTccaaattcacTttTAC | 138884 | 138903 | 6722 | 100 |
| 517 | SPC-15868-01 | ASO-002269 | ATtTCcaaattcactTtTAC | 138884 | 138903 | 6722 | 100 |
| 518 | SPC-15872-01 | ASO-002237 | ATttCCaaattcacttTTAC | 138884 | 138903 | 6722 | 100 |
| 519 | SPC-15873-01 | ASO-002246 | ATTtCcaaattcactTTtAC | 138884 | 138903 | 6722 | 99 |
| 520 | SPC-15874-01 | ASO-002254 | ATTTccaaattcacTtTtAC | 138884 | 138903 | 6722 | 11 |
| 521 | SPC-15878-01 | ASO-002284 | ATtTccAaattcacttTTAC | 138884 | 138903 | 6722 | 100 |
| 522 | SPC-15879-01 | ASO-002229 | ATTTccaaattcacttTTAC | 138884 | 138903 | 6722 | 99 |
| 523 | SPC-15880-01 | ASO-002238 | ATTTccaaattcactTtTAC | 138884 | 138903 | 6722 | 100 |
| 524 | SPC-15883-01 | ASO-002263 | ATtTcCaaattcactTTtAC | 138884 | 138903 | 6722 | |
| 525 | SPC-15888-01 | ASO-002239 | ATTTccaaattcactTTtAC | 138884 | 138903 | 6722 | 100 |
| 526 | ASO-000754 | ASO-000754 | TATTTccaaattcacTTTTA | 138885 | 138904 | 6723 | 100 |
| 527 | ASO-002055 | ASO-002055 | TAtTtCcaaattcacTTtTA | 138885 | 138904 | 6723 | 99 |
| 528 | ASO-002035 | ASO-002035 | TAtTtcCaaattcactTTTA | 138885 | 138904 | 6723 | 100 |
| 529 | ASO-002048 | ASO-002048 | TATtTccaaattcaCttTTA | 138885 | 138904 | 6723 | 100 |
| 530 | ASO-002053 | ASO-002053 | TAtTtCcaaattcactTTTA | 138885 | 138904 | 6723 | 100 |
| 531 | ASO-002067 | ASO-002067 | TAtTTccaaattcaCTttTA | 138885 | 138904 | 6723 | 99 |
| 532 | ASO-001954 | ASO-001954 | TATTTccaaattcactTTTA | 138885 | 138904 | 6723 | 99 |
| 533 | ASO-001947 | ASO-001947 | TATTtccaaattcacTTTTA | 138885 | 138904 | 6723 | 99 |
| 534 | ASO-002081 | ASO-002081 | TATttCcaaattcacTtTTA | 138885 | 138904 | 6723 | 100 |
| 535 | ASO-001966 | ASO-001966 | TAtTTccaaattcacTTtTA | 138885 | 138904 | 6723 | 99 |
| 536 | ASO-002025 | ASO-002025 | TAttTcCaaattcactTTTA | 138885 | 138904 | 6723 | 100 |
| 537 | ASO-002033 | ASO-002033 | TATtTccaaattcacTtTTA | 138885 | 138904 | 6723 | 99 |
| 538 | ASO-001960 | ASO-001960 | TaTTTccaaattcacTTtTA | 138885 | 138904 | 6723 | 99 |
| 539 | ASO-002056 | ASO-002056 | TAttTCcaaattcacTTtTA | 138885 | 138904 | 6723 | 100 |
| 540 | ASO-002063 | ASO-002063 | TATttCcaaattcacTTtTA | 138885 | 138904 | 6723 | 99 |
| 541 | ASO-002089 | ASO-002089 | TATTtccaaattcaCttTTA | 138885 | 138904 | 6723 | 100 |
| 542 | ASO-002073 | ASO-002073 | TAtTtCcaaattcacTtTTA | 138885 | 138904 | 6723 | 99 |
| 543 | ASO-002027 | ASO-002027 | TATtTccaaattcaCtTtTA | 138885 | 138904 | 6723 | 99 |
| 544 | ASO-002075 | ASO-002075 | TATtTccaaattcaCTttTA | 138885 | 138904 | 6723 | 99 |
| 545 | ASO-002028 | ASO-002028 | TAtTTccaaattcaCttTTA | 138885 | 138904 | 6723 | 99 |
| 546 | ASO-002085 | ASO-002085 | TAtTTccaaattcaCtTtTA | 138885 | 138904 | 6723 | 99 |
| 547 | ASO-002083 | ASO-002083 | TAttTCcaaattcacTtTTA | 138885 | 138904 | 6723 | 99 |
| 548 | ASO-000759 | ASO-000759 | TATttccaaattcacttTTA | 138885 | 138904 | 6723 | 93 |

Figure 3Q

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 549 | ASO-000769 | ASO-000769 | TatttccaaattcactttTA | 138885 | 138904 | 6723 | 0 |
| 550 | ASO-000764 | ASO-000764 | TAtttccaaattcactttTA | 138885 | 138904 | 6723 | 0 |
| 551 | 17-18-19mer-11 | ASO-002415 | TTCCaaattcactTTTA | 138885 | 138901 | 6723 | 99 |
| 552 | 17-18-19mer-14 | ASO-002451 | TTCCAaattcacttTTA | 138885 | 138901 | 6723 | 100 |
| 553 | 17-18-19mer-17 | ASO-002392 | TTTccaaattcactTTTA | 138885 | 138902 | 6723 | 100 |
| 554 | 17-18-19mer-2 | ASO-002402 | TTCcaaattcactTTTA | 138885 | 138901 | 6723 | 100 |
| 555 | 17-18-19mer-23 | ASO-002452 | TTTccaaattcacTTTTA | 138885 | 138902 | 6723 | 100 |
| 556 | 17-18-19mer-29 | ASO-002429 | TTTCcaaattcacttTTA | 138885 | 138902 | 6723 | 99 |
| 557 | 17-18-19mer-35 | ASO-002406 | TTTCcaaattcactTTTA | 138885 | 138902 | 6723 | 100 |
| 558 | 17-18-19mer-41 | ASO-002465 | TTTCCaaattcacttTTA | 138885 | 138902 | 6723 | 97 |
| 559 | 17-18-19mer-47 | ASO-002443 | ATTtccaaattcactTTTA | 138885 | 138903 | 6723 | 100 |
| 560 | 17-18-19mer-5 | ASO-002438 | TTCcaaattcacTTTTA | 138885 | 138901 | 6723 | 100 |
| 561 | 17-18-19mer-53 | ASO-002420 | ATTtccaaattcacTTTTA | 138885 | 138903 | 6723 | 100 |
| 562 | 17-18-19mer-59 | ASO-002478 | ATTTccaaattcacttTTA | 138885 | 138903 | 6723 | 96 |
| 563 | 17-18-19mer-65 | ASO-002457 | ATTTccaaattcactTTTA | 138885 | 138903 | 6723 | 100 |
| 564 | 17-18-19mer-71 | ASO-002434 | ATTTCcaaattcacttTTA | 138885 | 138903 | 6723 | 63 |
| 565 | 17-18-19mer-8 | ASO-002472 | TTCCaaattcacttTTA | 138885 | 138901 | 6723 | 100 |
| 566 | ASO-001954-mm1 | ASO-002340 | TATTTccagattcactTTTA | 138885 | 138904 | 6723 | 98 |
| 567 | ASO-001954-mm2 | ASO-002352 | TATTTccgaattcactTTTA | 138885 | 138904 | 6723 | 99 |
| 568 | ASO-001954-mm3 | ASO-002364 | GATTTccaaattcactTTTA | 138885 | 138904 | 6723 | 97 |
| 569 | ASO-001954-mm4 | ASO-002376 | GGTTTccaaattcactTTTA | 138885 | 138904 | 6723 | 38 |
| 570 | ASO-001954-mm5 | ASO-002293 | AATTTccagattcactTTTA | 138885 | 138904 | 6723 | 96 |
| 571 | ASO-001954-mm6 | ASO-002305 | TATTTccaagttcgctTTTA | 138885 | 138904 | 6723 | 52 |
| 572 | SPC-15677-01 | ASO-002266 | TCCaaattcactttTA | 138885 | 138900 | 6723 | 99 |
| 573 | SPC-15859-01 | ASO-002350 | TAtTTccaaattcactTTTA | 138885 | 138904 | 6723 | 99 |
| 574 | SPC-15861-01 | ASO-002374 | TAtTTccaaattcacTtTTA | 138885 | 138904 | 6723 | 100 |
| 575 | SPC-15862-01 | ASO-002386 | TATTtccaaattcaCTttTA | 138885 | 138904 | 6723 | 99 |
| 576 | SPC-15863-01 | ASO-002227 | TATtTccaaattcactTTTA | 138885 | 138904 | 6723 | 99 |
| 577 | SPC-15865-01 | ASO-002245 | TAttTCcaaattcactTTTA | 138885 | 138904 | 6723 | 100 |
| 578 | SPC-15867-01 | ASO-002261 | TATtTccaaattcacTTtTA | 138885 | 138904 | 6723 | 99 |
| 579 | SPC-15869-01 | ASO-002276 | TATttCcaaattcactTTTA | 138885 | 138904 | 6723 | 100 |

Figure 3R

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 580 | SPC-15871-01 | ASO-002228 | TATTtccaaattcaCtTtTA | 138885 | 138904 | 6723 | 97 |
| 581 | SPC-15882-01 | ASO-002255 | TATTtccaaattcactTTTA | 138885 | 138904 | 6723 | 98 |
| 582 | SPC-15886-01 | ASO-002285 | TATTtccaaattcacTTtTA | 138885 | 138904 | 6723 | 83 |
| 583 | SPC-15887-01 | ASO-002230 | TATTtccaaattcacTtTTA | 138885 | 138904 | 6723 | 100 |
| 584 | SPC-15890-01 | ASO-002256 | TATTtccaaattcAcTtTA | 138885 | 138904 | 6723 | 99 |
| 585 | SPC-15893-01 | ASO-002279 | TATTtccaaattcActTtTA | 138885 | 138904 | 6723 | 100 |
| 586 | ASO-002072 | ASO-002072 | TTAttTccaaattcaCTtTT | 138886 | 138905 | 6724 | 99 |
| 587 | ASO-000755 | ASO-000755 | TTATTtccaaattcaCTTTT | 138886 | 138905 | 6724 | 99 |
| 588 | ASO-002071 | ASO-002071 | TTaTtTccaaattcacTTTT | 138886 | 138905 | 6724 | 100 |
| 589 | ASO-000760 | ASO-000760 | TTAtttccaaattcactTTT | 138886 | 138905 | 6724 | 96 |
| 590 | ASO-001920 | ASO-001920 | TTATtccaaattcaCTTTT | 138886 | 138905 | 6724 | 99 |
| 591 | ASO-002080 | ASO-002080 | TTatTTccaaattcacTTTT | 138886 | 138905 | 6724 | 100 |
| 592 | ASO-001927 | ASO-001927 | TTATTtccaaattcacTTTT | 138886 | 138905 | 6724 | 99 |
| 593 | ASO-001941 | ASO-001941 | TTaTTtccaaattcaCTtTT | 138886 | 138905 | 6724 | 99 |
| 594 | ASO-002045 | ASO-002045 | TTaTttCcaaattcacTTTT | 138886 | 138905 | 6724 | 100 |
| 595 | ASO-001934 | ASO-001934 | TtATTtccaaattcaCTtTT | 138886 | 138905 | 6724 | 98 |
| 596 | ASO-002074 | ASO-002074 | TTatTTccaaattcacTtTT | 138886 | 138905 | 6724 | 100 |
| 597 | ASO-002093 | ASO-002093 | TTAtTtccaaattcACttTT | 138886 | 138905 | 6724 | 100 |
| 598 | ASO-002054 | ASO-002054 | TTaTTtccaaattcaCtTTT | 138886 | 138905 | 6724 | 100 |
| 599 | ASO-002091 | ASO-002091 | TTaTtTccaaattcaCtTTT | 138886 | 138905 | 6724 | 99 |
| 600 | ASO-002064 | ASO-002064 | TTaTtTccaaattcaCTtTT | 138886 | 138905 | 6724 | 99 |
| 601 | ASO-002066 | ASO-002066 | TTATttccaaattCacTtTT | 138886 | 138905 | 6724 | 99 |
| 602 | ASO-002044 | ASO-002044 | TTAtTtccaaattcaCtTTT | 138886 | 138905 | 6724 | 99 |
| 603 | ASO-002047 | ASO-002047 | TTATttccaaattCaCttTT | 138886 | 138905 | 6724 | 99 |
| 604 | ASO-002046 | ASO-002046 | TTatTtCcaaattcacTTTT | 138886 | 138905 | 6724 | 96 |
| 605 | ASO-000765 | ASO-000765 | TTatttccaaattcacttTT | 138886 | 138905 | 6724 | 39 |
| 606 | ASO-000770 | ASO-000770 | TtatttccaaattcacttTT | 138886 | 138905 | 6724 | 0 |
| 607 | 17-18-19mer-12 | ASO-002427 | TTTCcaaattcacTTTT | 138886 | 138902 | 6724 | 98 |
| 608 | 17-18-19mer-15 | ASO-002462 | TTTCCaaattcactTTT | 138886 | 138902 | 6724 | 91 |
| 609 | 17-18-19mer-18 | ASO-002404 | ATTtccaaattcacTTTT | 138886 | 138903 | 6724 | |
| 610 | 17-18-19mer-24 | ASO-002463 | ATTtccaaattcaCTTTT | 138886 | 138903 | 6724 | |
| 611 | 17-18-19mer-3 | ASO-002414 | TTTccaaattcacTTTT | 138886 | 138902 | 6724 | 98 |
| 612 | 17-18-19mer-30 | ASO-002441 | ATTTccaaattcactTTT | 138886 | 138903 | 6724 | |
| 613 | 17-18-19mer-36 | ASO-002418 | ATTTccaaattcacTTTT | 138886 | 138903 | 6724 | |
| 614 | 17-18-19mer-42 | ASO-002476 | ATTTCcaaattcactTTT | 138886 | 138903 | 6724 | |

Figure 3S

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 615 | 17-18-19mer-48 | ASO-002455 | TATttccaaattcacTTTT | 138886 | 138904 | 6724 | 99 |
| 616 | 17-18-19mer-54 | ASO-002432 | TATttccaaattcaCTTTT | 138886 | 138904 | 6724 | 99 |
| 617 | 17-18-19mer-6 | ASO-002450 | TTTccaaattcaCTTTT | 138886 | 138902 | 6724 | 94 |
| 618 | 17-18-19mer-60 | ASO-002397 | TATTtccaaattcactTTT | 138886 | 138904 | 6724 | 100 |
| 619 | 17-18-19mer-66 | ASO-002468 | TATTtccaaattcacTTTT | 138886 | 138904 | 6724 | 100 |
| 620 | 17-18-19mer-72 | ASO-002446 | TATTTccaaattcactTTT | 138886 | 138904 | 6724 | 100 |
| 621 | 17-18-19mer-9 | ASO-002391 | TTTCcaaattcactTTT | 138886 | 138902 | 6724 | 99 |
| 622 | ASO-001941-mm1 | ASO-002317 | ATaTTtccaaattcaCTtTT | 138886 | 138905 | 6724 | 50 |
| 623 | ASO-001941-mm2 | ASO-002329 | TTaTTtccaaattcaCTtTA | 138886 | 138905 | 6724 | 99 |
| 624 | ASO-001941-mm3 | ASO-002341 | TTaTTtccaaattcaCTtTG | 138886 | 138905 | 6724 | 99 |
| 625 | ASO-001941-mm4 | ASO-002353 | ATaTTtccagattcaCTtTT | 138886 | 138905 | 6724 | 76 |
| 626 | ASO-001941-mm5 | ASO-002365 | TTaTTtccaagttcaCTtTC | 138886 | 138905 | 6724 | 87 |
| 627 | ASO-001941-mm6 | ASO-002377 | TTaTTtccagattcgCTtTT | 138886 | 138905 | 6724 | 79 |
| 628 | SPC-15676-01 | ASO-002258 | TTCcaaattcactTTT | 138886 | 138901 | 6724 | 100 |
| 629 | SPC-15866-01 | ASO-002253 | TTAtTtccaaattcaCTtTT | 138886 | 138905 | 6724 | 97 |
| 630 | SPC-15870-01 | ASO-002283 | TTAttTccaaattcacTTTT | 138886 | 138905 | 6724 | 99 |
| 631 | SPC-15875-01 | ASO-002262 | TTATttccaaattcacTTTT | 138886 | 138905 | 6724 | 100 |
| 632 | SPC-15876-01 | ASO-002270 | TTATttccaaattcaCtTTT | 138886 | 138905 | 6724 | 100 |
| 633 | SPC-15877-01 | ASO-002277 | TTATttccaaattcACttTT | 138886 | 138905 | 6724 | 100 |
| 634 | SPC-15881-01 | ASO-002247 | TTaTTtccaaattcacTTTT | 138886 | 138905 | 6724 | 100 |
| 635 | SPC-15884-01 | ASO-002271 | TTAtTtccaaattcacTTTT | 138886 | 138905 | 6724 | 100 |
| 636 | SPC-15885-01 | ASO-002278 | TTaTTtccaaattcACttTT | 138886 | 138905 | 6724 | 100 |
| 637 | SPC-15889-01 | ASO-002248 | TTaTTtccaaattcActTTT | 138886 | 138905 | 6724 | 100 |
| 638 | SPC-15891-01 | ASO-002264 | TTAtTtccaaattcActTTT | 138886 | 138905 | 6724 | 100 |
| 639 | SPC-15892-01 | ASO-002272 | TTaTTtccaaattcAcTtTT | 138886 | 138905 | 6724 | 100 |
| 640 | SPC-15894-01 | ASO-002286 | TTAtTtccaaattcAcTtTT | 138886 | 138905 | 6724 | 99 |
| 641 | SPC-15895-01 | ASO-002231 | TTATttccaaattcActTTT | 138886 | 138905 | 6724 | 100 |
| 642 | SPC-15896-01 | ASO-002240 | TTATttccaaattcAcTtTT | 138886 | 138905 | 6724 | 100 |
| 643 | ASO-002020 | ASO-002020 | ACttTatttccaaattcactTTtaC | 138884 | 138909 | 6722 | 99 |
| 644 | ASO-000756 | ASO-000756 | TTTATttccaaattcACTTT | 138887 | 138906 | 6725 | 100 |

Figure 3T

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 645 | ASO-001967 | ASO-001967 | TTtATttccaaattcACtTT | 138887 | 138906 | 6725 | 99 |
| 646 | ASO-001955 | ASO-001955 | TTTATttccaaattcaCTTT | 138887 | 138906 | 6725 | 99 |
| 647 | ASO-001948 | ASO-001948 | TTTAtttccaaattcACTTT | 138887 | 138906 | 6725 | 100 |
| 648 | ASO-002086 | ASO-002086 | AcTTtatttccaaattcactTTTaC | 138884 | 138908 | 6722 | 98 |
| 649 | ASO-002029 | ASO-002029 | ACtTtatttccaaattcacttTTaC | 138884 | 138908 | 6722 | 98 |
| 650 | ASO-001961 | ASO-001961 | TtTATttccaaattcACtTT | 138887 | 138906 | 6725 | 99 |
| 651 | ASO-002095 | ASO-002095 | ACTttatttccaaattcactTtTaC | 138884 | 138908 | 6722 | 94 |
| 652 | ASO-002059 | ASO-002059 | ACTttatttccaaattcacttTTAC | 138884 | 138908 | 6722 | 93 |
| 653 | ASO-002077 | ASO-002077 | ActttatttccaaattcactTTTAC | 138884 | 138908 | 6722 | 91 |
| 654 | ASO-002021 | ASO-002021 | AcTTtatttccaaattcactttTAC | 138884 | 138908 | 6722 | 91 |
| 655 | ASO-000761 | ASO-000761 | TTTatttccaaattcacTTT | 138887 | 138906 | 6725 | 93 |
| 656 | ASO-002068 | ASO-002068 | ACtTtatttccaaattcactTtTAC | 138884 | 138908 | 6722 | 86 |
| 657 | ASO-000766 | ASO-000766 | TTtatttccaaattcactTT | 138887 | 138906 | 6725 | 3 |
| 658 | ASO-000771 | ASO-000771 | TttatttccaaattcactTT | 138887 | 138906 | 6725 | 0 |
| 659 | 17-18-19mer-19 | ASO-002416 | TATttccaaattcaCTTT | 138887 | 138904 | 6725 | 100 |
| 660 | 17-18-19mer-25 | ASO-002474 | TATtccaaattcACTTT | 138887 | 138904 | 6725 | 100 |
| 661 | 17-18-19mer-31 | ASO-002453 | TATTtccaaattcacTTT | 138887 | 138904 | 6725 | 100 |
| 662 | 17-18-19mer-37 | ASO-002430 | TATTtccaaattcaCTTT | 138887 | 138904 | 6725 | 100 |
| 663 | 17-18-19mer-43 | ASO-002395 | TATTTccaaattcacTTT | 138887 | 138904 | 6725 | 100 |
| 664 | 17-18-19mer-49 | ASO-002466 | TTAtttccaaattcaCTTT | 138887 | 138905 | 6725 | 98 |
| 665 | 17-18-19mer-55 | ASO-002444 | TTAtttccaaattcACTTT | 138887 | 138905 | 6725 | 100 |
| 666 | 17-18-19mer-61 | ASO-002409 | TTATttccaaattcacTTT | 138887 | 138905 | 6725 | 93 |
| 667 | 17-18-19mer-67 | ASO-002479 | TTATttccaaattcaCTTT | 138887 | 138905 | 6725 | 98 |
| 668 | 17-18-19mer-73 | ASO-002458 | TTATTtccaaattcacTTT | 138887 | 138905 | 6725 | 100 |
| 669 | ASO-001967-mm1 | ASO-002294 | ATtATttccaaattcACtTT | 138887 | 138906 | 6725 | 50 |
| 670 | ASO-001967-mm2 | ASO-002306 | TTtATttccaagttcACtTT | 138887 | 138906 | 6725 | 50 |
| 671 | ASO-001967-mm3 | ASO-002318 | GTtATttccaaattcACtTT | 138887 | 138906 | 6725 | 99 |
| 672 | ASO-001967-mm4 | ASO-002330 | ATtATttccagattcACtTT | 138887 | 138906 | 6725 | 83 |

Figure 3U

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 673 | ASO-001967-mm5 | ASO-002342 | TTtATttccaggttcACtTT | 138887 | 138906 | 6725 | 48 |
| 674 | ASO-001967-mm6 | ASO-002354 | CTtATttccaagttcACtTT | 138887 | 138906 | 6725 | 87 |
| 675 | SPC-15675-01 | ASO-002250 | TTTCcaaattcacTTT | 138887 | 138902 | 6725 | 99 |
| 676 | ASO-002006 | ASO-002006 | CTtTAtttccaaattcACTT | 138888 | 138907 | 6726 | 99 |
| 677 | ASO-000757 | ASO-000757 | CTTTAtttccaaattCACTT | 138888 | 138907 | 6726 | 100 |
| 678 | ASO-002017 | ASO-002017 | CTtTAtttccaaattcaCTT | 138888 | 138907 | 6726 | 99 |
| 679 | ASO-001928 | ASO-001928 | CTTTAtttccaaattcACTT | 138888 | 138907 | 6726 | 100 |
| 680 | ASO-001968 | ASO-001968 | ACTTTatttccaaattCACTT | 138888 | 138908 | 6726 | 100 |
| 681 | ASO-001921 | ASO-001921 | CTTTatttccaaattCACTT | 138888 | 138907 | 6726 | 100 |
| 682 | ASO-001989 | ASO-001989 | CTTTatttccaaattcACTT | 138888 | 138907 | 6726 | 100 |
| 683 | ASO-001942 | ASO-001942 | CTtTAtttccaaattCAcTT | 138888 | 138907 | 6726 | 99 |
| 684 | ASO-000128 | ASO-000128 | TTTccaaattcaCTT | 138888 | 138902 | 6726 | 100 |
| 685 | ASO-001935 | ASO-001935 | CtTTAtttccaaattCAcTT | 138888 | 138907 | 6726 | 100 |
| 686 | ASO-000013 | ASO-000013 | ATTtccaaattcaCTT | 138888 | 138903 | 6726 | 95 |
| 687 | ASO-002002 | ASO-002002 | CTTtAtttccaaattcACTT | 138888 | 138907 | 6726 | 100 |
| 688 | ASO-000762 | ASO-000762 | CTTtatttccaaattcaCTT | 138888 | 138907 | 6726 | 97 |
| 689 | ASO-002010 | ASO-002010 | CTTtatttccaaatTcaCTT | 138888 | 138907 | 6726 | 98 |
| 690 | ASO-002005 | ASO-002005 | CTtTatttccaaattcaCTT | 138888 | 138907 | 6726 | 98 |
| 691 | ASO-001998 | ASO-001998 | CTttAtttccaaattcACTT | 138888 | 138907 | 6726 | 99 |
| 692 | ASO-002001 | ASO-002001 | CTTTatttccaaattcaCTT | 138888 | 138907 | 6726 | 97 |
| 693 | ASO-001994 | ASO-001994 | CTtTatttccaaattcACTT | 138888 | 138907 | 6726 | 95 |
| 694 | ASO-002013 | ASO-002013 | CTTtAtttccaaattcaCTT | 138888 | 138907 | 6726 | 98 |
| 695 | ASO-002009 | ASO-002009 | CTttAtttccaaattcaCTT | 138888 | 138907 | 6726 | 94 |
| 696 | ASO-000767 | ASO-000767 | CTttatttccaaattcacTT | 138888 | 138907 | 6726 | 32 |
| 697 | ASO-000772 | ASO-000772 | CtttatttccaaattcacTT | 138888 | 138907 | 6726 | 0 |
| 698 | BMT-214296 | ASO-214296 | CTTTActtccaaattCACTT | 138888 | 138907 | 6726 | |
| 699 | ASO-000013-mm1 | ASO-002366 | GTTtccaaattcaCTT | 138888 | 138903 | 6726 | 97 |
| 700 | ASO-000013-mm2 | ASO-002378 | ATTtccaagttcaCTT | 138888 | 138903 | 6726 | 55 |
| 701 | ASO-000013-mm3 | ASO-002295 | ATTtccgaattcaCTT | 138888 | 138903 | 6726 | 60 |
| 702 | ASO-000013-mm4 | ASO-002307 | GTTtccagattcaCTT | 138888 | 138903 | 6726 | 52 |

Figure 3V

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 703 | ASO-000013-mm5 | ASO-002319 | GTTtccaaattcaCTA | 138888 | 138903 | 6726 | 98 |
| 704 | ASO-000013-mm6 | ASO-002331 | ATTtccagattcaCTC | 138888 | 138903 | 6726 | 46 |
| 705 | ASO-000898 | ASO-000898 | ATTtccaaattcaCTT | 138888 | 138903 | 6726 | |
| 706 | ASO-001942-mm1 | ASO-002363 | CTtTAtttccagattCAcTT | 138888 | 138907 | 6726 | 98 |
| 707 | ASO-001942-mm2 | ASO-002375 | CTtTAtttccaaattCAcTG | 138888 | 138907 | 6726 | 99 |
| 708 | ASO-001942-mm3 | ASO-002292 | CTtTAtttccaaattCGcTT | 138888 | 138907 | 6726 | 50 |
| 709 | ASO-001942-mm4 | ASO-002304 | CTtTAtttccagattCAcTA | 138888 | 138907 | 6726 | 50 |
| 710 | ASO-001942-mm5 | ASO-002316 | CTtTAtttccaggttCAcTT | 138888 | 138907 | 6726 | 52 |
| 711 | ASO-001942-mm6 | ASO-002328 | CTtTAtttccgaggttCAcTT | 138888 | 138907 | 6726 | 96 |
| 712 | SPC-15674-01 | ASO-002242 | ATTtccaaattcACTT | 138888 | 138903 | 6726 | 100 |
| 713 | ASO-002004 | ASO-002004 | CTTTatttccaaatTcaCT | 138889 | 138907 | 6727 | 98 |
| 714 | ASO-002012 | ASO-002012 | CTTtatttccaaatTcACT | 138889 | 138907 | 6727 | 100 |
| 715 | ASO-001962 | ASO-001962 | ACTTTatttccaaattCACT | 138889 | 138908 | 6727 | 100 |
| 716 | ASO-001956 | ASO-001956 | ACTTtatttccaaatTCACT | 138889 | 138908 | 6727 | 99 |
| 717 | ASO-001949 | ASO-001949 | ACTTTatttccaaatTCACT | 138889 | 138908 | 6727 | 100 |
| 718 | ASO-001987 | ASO-001987 | CTTTAtttccaaatTcACT | 138889 | 138907 | 6727 | 99 |
| 719 | ASO-001991 | ASO-001991 | CTTTatttccaaatTCACT | 138889 | 138907 | 6727 | 100 |
| 720 | ASO-001995 | ASO-001995 | CTTtatttccaaatTCACT | 138889 | 138907 | 6727 | 99 |
| 721 | ASO-001992 | ASO-001992 | CTTTAtttccaaatTcaCT | 138889 | 138907 | 6727 | 100 |
| 722 | ASO-002000 | ASO-002000 | CTTTatttccaaatTcACT | 138889 | 138907 | 6727 | 100 |
| 723 | ASO-001996 | ASO-001996 | CTTTatttccaaatTCaCT | 138889 | 138907 | 6727 | 99 |
| 724 | ASO-002008 | ASO-002008 | CTTtatttccaaatTCaCT | 138889 | 138907 | 6727 | 99 |
| 725 | ASO-002015 | ASO-002015 | CTTTAtttccaaatTCaCT | 138889 | 138907 | 6727 | 98 |
| 726 | ASO-002016 | ASO-002016 | CTTtatttccaaatTcaCT | 138889 | 138907 | 6727 | 98 |
| 727 | ASO-001986 | ASO-001986 | CTTTAtttccaaatTCACT | 138889 | 138907 | 6727 | 95 |
| 728 | 17-18-19mer-50 | ASO-002477 | CTTtatttccaaattCACT | 138889 | 138907 | 6727 | 100 |
| 729 | 17-18-19mer-62 | ASO-002421 | CTTTatttccaaattcACT | 138889 | 138907 | 6727 | 98 |
| 730 | 17-18-19mer-68 | ASO-002398 | CTTTatttccaaattCACT | 138889 | 138907 | 6727 | 95 |
| 731 | 17-18-19mer-74 | ASO-002469 | CTTTAtttccaaattcACT | 138889 | 138907 | 6727 | 99 |

Figure 3W

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 732 | ASO-001995-mm1 | ASO-002343 | CTTtatttccagatTCACT | 138889 | 138907 | 6727 | 97 |
| 733 | ASO-001995-mm2 | ASO-002355 | CTTtgtttccaaatTCACT | 138889 | 138907 | 6727 | 98 |
| 734 | ASO-001995-mm3 | ASO-002367 | CTTtatttccaaatTCACG | 138889 | 138907 | 6727 | 100 |
| 735 | ASO-001995-mm4 | ASO-002379 | CTTtgtttccagatTCACT | 138889 | 138907 | 6727 | 86 |
| 736 | ASO-001995-mm5 | ASO-002296 | CTTtgtttccaagtTCACT | 138889 | 138907 | 6727 | 52 |
| 737 | ASO-001995-mm6 | ASO-002308 | CTTtatttccgagtTCACT | 138889 | 138907 | 6727 | 51 |
| 738 | SPC-15673-01 | ASO-002233 | TATttccaaattcACT | 138889 | 138904 | 6727 | 99 |
| 739 | ASO-002003 | ASO-002003 | CTTTatttccaaatTCAC | 138890 | 138907 | 6728 | 99 |
| 740 | ASO-002007 | ASO-002007 | CTTtatttccaaatTCAC | 138890 | 138907 | 6728 | 99 |
| 741 | ASO-002011 | ASO-002011 | CTtTatttccaaatTcAC | 138890 | 138907 | 6728 | 100 |
| 742 | ASO-001988 | ASO-001988 | CTTTAtttccaaatTcAC | 138890 | 138907 | 6728 | 99 |
| 743 | ASO-001999 | ASO-001999 | CTTTAtttccaaatTCAC | 138890 | 138907 | 6728 | 100 |
| 744 | ASO-001993 | ASO-001993 | CTTTatttccaaatTcAC | 138890 | 138907 | 6728 | 99 |
| 745 | ASO-001997 | ASO-001997 | CTTtatttccaaatTcAC | 138890 | 138907 | 6728 | 99 |
| 746 | 17-18-19mer-26 | ASO-002393 | CTTtatttccaaaTTCAC | 138890 | 138907 | 6728 | 99 |
| 747 | 17-18-19mer-32 | ASO-002464 | CTTTatttccaaattCAC | 138890 | 138907 | 6728 | 99 |
| 748 | 17-18-19mer-44 | ASO-002407 | CTTTAtttccaaattCAC | 138890 | 138907 | 6728 | 100 |
| 749 | 17-18-19mer-51 | ASO-002396 | ACTttatttccaaatTCAC | 138890 | 138908 | 6728 | 100 |
| 750 | 17-18-19mer-57 | ASO-002456 | ACTttatttccaaaTTCAC | 138890 | 138908 | 6728 | 97 |
| 751 | 17-18-19mer-63 | ASO-002433 | ACTTtatttccaaattCAC | 138890 | 138908 | 6728 | 100 |
| 752 | 17-18-19mer-69 | ASO-002410 | ACTTtatttccaaatTCAC | 138890 | 138908 | 6728 | 99 |
| 753 | 17-18-19mer-75 | ASO-002480 | ACTTTatttccaaattCAC | 138890 | 138908 | 6728 | 99 |
| 754 | ASO-001997-mm1 | ASO-002320 | CTTtatttccagatTcAC | 138890 | 138907 | 6728 | 83 |
| 755 | ASO-001997-mm2 | ASO-002332 | CTTtatttccgaatTcAC | 138890 | 138907 | 6728 | 85 |
| 756 | ASO-001997-mm3 | ASO-002344 | CTTtgtttccaaatTcAC | 138890 | 138907 | 6728 | 83 |
| 757 | ASO-001997-mm4 | ASO-002356 | CTTtgtttccagatTcAC | 138890 | 138907 | 6728 | 33 |
| 758 | ASO-001997-mm5 | ASO-002368 | CTTtatttccaggtTcAC | 138890 | 138907 | 6728 | 6 |

Figure 3X

| SEQ ID NO: | Oligomer Name | ASO Number | ASO Sequence | premRNA start NG_007398 | premRNA end NG_007398 | mRNA start NM_016835 | Tau/Tubulin % Inhibition |
|---|---|---|---|---|---|---|---|
| 759 | ASO-001997-mm6 | ASO-002380 | CTTtgtttccaagtTcAC | 138890 | 138907 | 6728 | 50 |
| 760 | SPC-15672-01 | ASO-002288 | TTAtttccaaattCAC | 138890 | 138905 | 6728 | 93 |
| 761 | 17-18-19mer-21 | ASO-002428 | ACTttatttccaaaTTCA | 138891 | 138908 | 6729 | 100 |
| 762 | 17-18-19mer-27 | ASO-002405 | ACTttatttccaaATTCA | 138891 | 138908 | 6729 | 100 |
| 763 | 17-18-19mer-33 | ASO-002475 | ACTTtatttccaaatTCA | 138891 | 138908 | 6729 | 99 |
| 764 | 17-18-19mer-39 | ASO-002442 | ACTTtatttccaaaTTCA | 138891 | 138908 | 6729 | 100 |
| 765 | 17-18-19mer-45 | ASO-002419 | ACTTTatttccaaatTCA | 138891 | 138908 | 6729 | 98 |
| 766 | SPC-15671-01 | ASO-002280 | TTTatttccaaatTCA | 138891 | 138906 | 6729 | 100 |
| 767 | SPC-15670-01 | ASO-002273 | CTTtatttccaaATTC | 138892 | 138907 | 6730 | 99 |
| 768 | SPC-15669-01 | ASO-002265 | ACTTtatttccaAATT | 138893 | 138908 | 6731 | 84 |
| 769 | ASO-000139 | ASO-000139 | AACtttatttccaAAT | 138894 | 138909 | 6732 | 23 |
| 770 | SPC-15668-01 | ASO-002257 | AACTttatttccAAAT | 138894 | 138909 | 6732 | 93 |
| 771 | SPC-15667-01 | ASO-002249 | TAACtttatttcCAAA | 138895 | 138910 | 6733 | 97 |
| 772 | SPC-15666-01 | ASO-002241 | ATAActttatttcCAA | 138896 | 138911 | 6734 | 97 |
| 773 | ASO-000118 | ASO-000118 | AATaactttatttCCA | 138897 | 138912 | 6735 | 92 |
| 774 | SPC-15665-01 | ASO-002232 | AATaactttattTCCA | 138897 | 138912 | 6735 | 99 |
| 775 | ASO-000101 | ASO-000101 | TAAtaactttattTCC | 138898 | 138913 | 6736 | 60 |
| 776 | SPC-15664-01 | ASO-002287 | TAAtaactttatTTCC | 138898 | 138913 | 6736 | 76 |
| 777 | ASO-000148 | ASO-000148 | GTAataactttatTTC | 138899 | 138914 | 6737 | 41 |
| 778 | ASO-000184 | ASO-000184 | TAAtaactttatTTC | 138899 | 138913 | 6737 | 7 |
| 779 | ASO-000112 | ASO-000112 | GTAataactttaTTT | 138900 | 138914 | 6738 | 1 |
| 780 | ASO-000170 | ASO-000170 | AGTaataactttaTTT | 138900 | 138915 | 6738 | 1 |
| 781 | ASO-000154 | ASO-000154 | GAGtaataactttATT | 138901 | 138916 | 6739 | 0 |
| 782 | ASO-000125 | ASO-000125 | AGTaataactttATT | 138901 | 138915 | 6739 | 1 |
| 783 | ASO-000167 | ASO-000167 | GAGtaataacttTAT | 138902 | 138916 | 6740 | 5 |
| 784 | ASO-000134 | ASO-000134 | AGAgtaataacttTAT | 138902 | 138917 | 6740 | 12 |
| 785 | ASO-000175 | ASO-000175 | CAGagtaataactTTA | 138903 | 138918 | 6741 | 43 |
| 786 | ASO-000178 | ASO-000178 | AGAgtaataactTTA | 138903 | 138917 | 6741 | 2 |
| 787 | ASO-000138 | ASO-000138 | CAGagtaataacTTT | 138904 | 138918 | 6742 | 43 |
| 788 | ASO-000171 | ASO-000171 | TCAgagtaataacTTT | 138904 | 138919 | 6742 | 39 |
| 789 | ASO-000236 | ASO-000236 | ATCagagtaataaCTT | 138905 | 138920 | 6743 | 65 |
| 790 | ASO-000127 | ASO-000127 | TCAgagtaataaCTT | 138905 | 138919 | 6743 | 29 |
| 791 | ASO-000177 | ASO-000177 | CAGagtaataaCTT | 138905 | 138918 | 6743 | 28 |
| 792 | ASO-000238 | ASO-000238 | AATcagagtaataACT | 138906 | 138921 | 6744 | 21 |

Figure 3Y

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 793 | ASO-000222 | ASO-000222 | TAAtcagagtaatAAC | 138907 | 138922 | 6745 | 15 |
| 794 | ASO-000307 | ASO-000307 | AATcagagtaatAAC | 138907 | 138921 | 6745 | 3 |
| 795 | ASO-000204 | ASO-000204 | TTAatcagagtaaTAA | 138908 | 138923 | 6746 | 1 |
| 796 | ASO-000330 | ASO-000330 | TAAtcagagtaaTAA | 138908 | 138922 | 6746 | 2 |
| 797 | ASO-000326 | ASO-000326 | TTTaatcagagtaATA | 138909 | 138924 | 6747 | 9 |
| 798 | ASO-000249 | ASO-000249 | TTTaatcagagtAAT | 138910 | 138924 | 6748 | 0 |
| 799 | ASO-002022 | ASO-002022 | TTATttccaaattcaCTtTT | 138886 | 138905 | 6724 | 99 |
| 800 | ASO-002026 | ASO-002026 | TTatTTccaaattcaCtTTT | 138886 | 138905 | 6724 | 100 |
| 801 | ASO-002024 | ASO-002024 | TTAttTccaaattcaCtTTT | 138886 | 138905 | 6724 | 99 |
| 802 | ASO-002049 | ASO-002049 | ACTTtatttccaaattcactTTtAC | 138884 | 138908 | 6722 | 99 |
| 803 | ASO-002019 | ASO-002019 | ACttTatttccaaattcactTTtaC | 138884 | 138908 | 6722 | 98 |
| 936 | ASO-000069 | ASO-000069 | ATttcCaaaTtcacTT | 138888 | 138903 | 6726 | 99 |
| 937 | ASO-000070 | ASO-000070 | ATTtccAaatTcaCTT | 138888 | 138903 | 6726 | 33 |
| 938 | ASO-002107 | ASO-002107 | CCCttaatttCacccTC | 136053 | 136069 | 3892 | 93 |
| 901 | ASO-002625 | ASO-002625 | TAGccctaaagtcCCA | 135744 | 135759 | 3584 | 0 |
| 902 | ASO-002675 | ASO-002675 | TAGccctaaagtcCCA | 135744 | 135759 | 3584 | 27 |
| 903 | ASO-002633 | ASO-002633 | TAGccctaaagtcCCA | 135744 | 135759 | 3584 | 1 |
| 904 | ASO-002640 | ASO-002640 | CCTtaATttcacccTCA | 136052 | 136068 | 3891 | 34 |
| 905 | ASO-002632 | ASO-002632 | CCTtaATttcacccTCA | 136052 | 136068 | 3891 | 65 |
| 906 | ASO-002647 | ASO-002647 | CCTtaATttcacccTCA | 136052 | 136068 | 3891 | 34 |
| 907 | ASO-002655 | ASO-002655 | CCTtaatttcaccCTC | 136053 | 136068 | 3892 | 12 |
| 908 | ASO-002641 | ASO-002641 | CCTtaatttcaccCTC | 136053 | 136068 | 3892 | 23 |
| 909 | ASO-002648 | ASO-002648 | CCTtaatttcaccCTC | 136053 | 136068 | 3892 | 6 |
| 910 | ASO-002666 | ASO-002666 | AtTTCcaaattcactTTtAC | 138884 | 138903 | 6722 | 70 |
| 911 | ASO-002659 | ASO-002659 | AtTTCcaaattcactTTtAC | 138884 | 138903 | 6722 | 77 |
| 912 | ASO-002652 | ASO-002652 | ATttCCaaattcactTtTAC | 138884 | 138903 | 6722 | 72 |
| 913 | ASO-002645 | ASO-002645 | ATttCCaaattcactTtTAC | 138884 | 138903 | 6722 | 75 |
| 914 | ASO-002638 | ASO-002638 | ATttCCaaattcactTtTAC | 138884 | 138903 | 6722 | 79 |
| 915 | ASO-003270 | ASO-003270 | AtTTCcaaattcactTTtAC | 138884 | 138903 | 6722 | 85 |
| 916 | ASO-003269 | ASO-003269 | AtTTCcaaattcactTTtAC | 138884 | 138903 | 6722 | 61 |
| 917 | ASO-003268 | ASO-003268 | AtTTCcaaattcactTTtAC | 138884 | 138903 | 6722 | 73 |
| 918 | ASO-002673 | ASO-002673 | AtTTCcaaattcactTTtAC | 138884 | 138903 | 6722 | 65 |
| 919 | ASO-002661 | ASO-002661 | TTtATttccaaattcACtTT | 138887 | 138906 | 6725 | 42 |

Figure 3Z

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 920 | ASO-002654 | ASO-002654 | TTtATttccaaattcACtTT | 138887 | 138906 | 6725 | 42 |
| 921 | ASO-002668 | ASO-002668 | TTtATttccaaattcACtTT | 138887 | 138906 | 6725 | 28 |
| 922 | ASO-002676 | ASO-002676 | ATTtccaaattcaCTT | 138888 | 138903 | 6726 | 26 |
| 923 | ASO-002669 | ASO-002669 | ATTtccaaattcaCTT | 138888 | 138903 | 6726 | 4 |
| 924 | ASO-002662 | ASO-002662 | ATTtccaaattcaCTT | 138888 | 138903 | 6726 | 46 |
| 925 | ASO-002672 | ASO-002672 | TAGccctaaagtcCCA | 135744 | 135759 | 3584 | 99 |
| 926 | ASO-002658 | ASO-002658 | CCTtaATttcacccTCA | 136052 | 136068 | 3891 | 99 |
| 927 | ASO-002622 | ASO-002622 | CCTtaatttcaccCTC | 136053 | 136068 | 3892 | 97 |
| 928 | ASO-002629 | ASO-002629 | AtTTCcaaattcactTTtAC | 138884 | 138903 | 6722 | 99 |
| 929 | ASO-002621 | ASO-002621 | ATttCCaaattcactTtTAC | 138884 | 138903 | 6722 | 100 |
| 930 | ASO-002665 | ASO-002665 | TTtATttccaaattcACtTT | 138887 | 138906 | 6725 | 99 |
| 931 | ASO-002630 | ASO-002630 | ATTtccaaattcaCTT | 138888 | 138903 | 6726 | 99 |
| 932 | ASO-002399 | ASO-002399 | AtTTCcaAattcactTTtAC | 138884 | 138903 | 6722 | 66 |
| 933 | ASO-002482 | ASO-002482 | ATtTcCaAattcactTtTAC | 138884 | 138903 | 6722 | 66 |
| 934 | ASO-002437 | ASO-002437 | ATtTcCaaattcacTTtTAC | 138884 | 138903 | 6722 | 66 |
| 935 | ASO-002425 | ASO-002425 | ATtTcCAaattcacTTtTAC | 138884 | 138903 | 6722 | 66 |
| 960 | ASO-000071 | ASO-000071 | ATttCcaaAttCacTT | 138888 | 138903 | 6726 | 7 |

ASO sequence corresponds to the oligomer sequence, left corresponds to the 5'end and right corresponds to the 3'end.

SEQ ID Number corresponds to the sequence of the oligomer listed in the sequence listing.

"mm" indicates "mismatches."

Figure 6A

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-001167 | ASO-001167 | AAAgatgaaatttgctcTTA | 4 | 134947 | 134966 | >100% | |
| ASO-001168 | ASO-001168 | GAAagatgaaatttgctCTT | 5 | 134948 | 134967 | 100% | |
| ASO-001169 | ASO-001169 | GGAaagatgaaatttgcTCT | 6 | 134949 | 134968 | 74% | |
| ASO-000829 | ASO-000829 | AAGatgaaatttgCTC | 7 | 134950 | 134965 | >100% | 0.08 |
| ASO-001170 | ASO-001170 | TGGaaagatgaaatttgCTC | 8 | 134950 | 134969 | 6% | |
| ASO-001171 | ASO-001171 | TTGgaaagatgaaatttGCT | 9 | 134951 | 134970 | 1% | |
| ASO-001172 | ASO-001172 | TTTggaaagatgaaattTGC | 10 | 134952 | 134971 | 8% | |
| ASO-001173 | ASO-001173 | ATTtggaaagatgaaatTTG | 11 | 134953 | 134972 | 0% | |
| ASO-001174 | ASO-001174 | AATttggaaagatgaaaTTT | 12 | 134954 | 134973 | 0% | |
| ASO-001175 | ASO-001175 | CAAtttggaaagatgaaATT | 13 | 134955 | 134974 | 4% | |
| ASO-001176 | ASO-001176 | TCAatttggaaagatgaAAT | 14 | 134956 | 134975 | 0% | |
| ASO-001177 | ASO-001177 | ATCaatttggaaagatgAAA | 15 | 134957 | 134976 | 10% | |
| ASO-001178 | ASO-001178 | CATcaatttggaaagatGAA | 16 | 134958 | 134977 | 62% | |
| ASO-001181 | ASO-001181 | ACCcatcaatttggaaaGAT | 16 | 134961 | 134980 | 73% | |

Figure 6B

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-001179 | ASO-001179 | CCAtcaatttggaaagaTGA | 17 | 134959 | 134978 | 52% | |
| ASO-001180 | ASO-001180 | CCCatcaatttggaaagATG | 18 | 134960 | 134979 | 58% | |
| ASO-001182 | ASO-001182 | CACccatcaatttggaaAGA | 20 | 134962 | 134981 | 92% | |
| ASO-001183 | ASO-001183 | CCAcccatcaatttggaAAG | 21 | 134963 | 134982 | 58% | |
| ASO-001184 | ASO-001184 | CCCacccatcaatttggAAA | 22 | 134964 | 134983 | 12% | |
| ASO-001062 | ASO-001062 | GCCcacccatcaatttgGAA | 23 | 134965 | 134984 | 1% | |
| ASO-001063 | ASO-001063 | TAGcccacccatcaattTGG | 24 | 134967 | 134986 | 8% | |
| ASO-001064 | ASO-001064 | CTAgcccacccatcaatTTG | 25 | 134968 | 134987 | 0% | |
| ASO-001065 | ASO-001065 | ACTagcccacccatcaaTTT | 26 | 134969 | 134988 | 13% | |
| ASO-001066 | ASO-001066 | TACtagcccacccatcaATT | 27 | 134970 | 134989 | 54% | |
| ASO-000830 | ASO-000830 | TACtagcccacccATC | 28 | 134974 | 134989 | >100% | 0.05 |
| ASO-000260 | ASO-000260 | CCCtcttctacatGGA | 29 | 135077 | 135092 | | |
| ASO-000305 | ASO-000305 | TGCctctgtgacaCCC | 30 | 135171 | 135186 | | |
| ASO-000304 | ASO-000304 | TTCaaatcctttgTTG | 31 | 135194 | 135209 | | |
| ASO-000324 | ASO-000324 | CACacaaggttgaCAT | 32 | 135242 | 135257 | | |

Figure 6C

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000268 | ASO-000268 | CGTcacactcacaCAA | 33 | 135251 | 135266 | | |
| ASO-000223 | ASO-000223 | GCCaccaaggacaGGC | 34 | 135441 | 135456 | | |
| ASO-000224 | ASO-000224 | CAGcttgccttctCTT | 35 | 135533 | 135548 | | |
| ASO-000319 | ASO-000319 | ATCaaggtcagtcTTT | 36 | 135585 | 135600 | | |
| ASO-000208 | ASO-000208 | CCTtcagaactcaATA | 37 | 135690 | 135705 | | |
| ASO-000689 | ASO-000689 | AAAgtcccaggtcTGC | 38 | 135737 | 135752 | | |
| ASO-000434 | ASO-000434 | CTAaagtcccaggTCT | 39 | 135739 | 135754 | 59% | |
| ASO-000409 | ASO-000409 | TAAagtcccaggTCT | 40 | 135739 | 135753 | >100% | |
| ASO-000432 | ASO-000432 | CCTaaagtcccagGTC | 41 | 135740 | 135755 | 63% | |
| ASO-000391 | ASO-000391 | TAAagtcccagGTC | 42 | 135740 | 135753 | 72% | |
| ASO-001779 | ASO-001779 | TAGccctaaagtcccagGTC | 43 | 135740 | 135759 | 54% | 0.05 |
| ASO-000899 | ASO-000899 | CTAaagtcccagGTC | 44 | 135740 | 135754 | | |
| ASO-000398 | ASO-000398 | CCCtaaagtcccaGGT | 45 | 135741 | 135756 | 76% | |
| ASO-001778 | ASO-001778 | TTAgccctaaagtcccaGGT | 46 | 135741 | 135760 | 86% | 0.04 |
| ASO-000414 | ASO-000414 | GCCctaaagtcccAGG | 47 | 135742 | 135757 | 42% | |
| ASO-000403 | ASO-000403 | CCCtaaagtcccAGG | 48 | 135742 | 135756 | 72% | |
| ASO-001780 | ASO-001780 | GTTagccctaaagtcccAGG | 49 | 135742 | 135761 | 28% | 0.07 |
| ASO-000433 | ASO-000433 | GCCctaaagtccCAG | 50 | 135743 | 135757 | 34% | |
| ASO-000411 | ASO-000411 | CCCtaaagtccCAG | 51 | 135743 | 135756 | 51% | 0.15 |
| ASO-001781 | ASO-001781 | GGTtagccctaaagtccCAG | 52 | 135743 | 135762 | 37% | 0.03 |
| ASO-000389 | ASO-000389 | TAGccctaaagtcCCA | 53 | 135744 | 135759 | 96% | 0.04 |
| ASO-001939 | ASO-001939 | TAGccctaaagtcCCA | 54 | 135744 | 135759 | >100% | |
| ASO-001932 | ASO-001932 | TAGccctaaagtcCCA | 55 | 135744 | 135759 | 86% | |
| ASO-001925 | ASO-001925 | TAGccctaaagtcCCA | 56 | 135744 | 135759 | >100% | |

Figure 6D

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-001924 | ASO-001924 | TAGccctaaagtcCCA | 57 | 135744 | 135759 | 100% | |
| ASO-001952 | ASO-001952 | TAGccctaaagtcCCA | 58 | 135744 | 135759 | 79% | |
| ASO-001931 | ASO-001931 | TAGccctaaagtcCCA | 59 | 135744 | 135759 | 83% | |
| ASO-001953 | ASO-001953 | TAGccctaaagtcCCA | 60 | 135744 | 135759 | 97% | 0.25 |
| ASO-001945 | ASO-001945 | TAGccctaaagtcCCA | 61 | 135744 | 135759 | 68% | |
| ASO-001946 | ASO-001946 | TAGccctaaagtcCCA | 62 | 135744 | 135759 | >100% | 0.13 |
| ASO-001971 | ASO-001971 | TAGccctaaagtcCCA | 63 | 135744 | 135759 | 81% | |
| ASO-001938 | ASO-001938 | TAGccctaaagtcCCA | 64 | 135744 | 135759 | 87% | |
| ASO-001959 | ASO-001959 | TAGccctaaagtcCCA | 65 | 135744 | 135759 | 83% | |
| ASO-001965 | ASO-001965 | TAGccctaaagtcCCA | 66 | 135744 | 135759 | 83% | |
| ASO-001782 | ASO-001782 | TGGttagccctaaagtcCCA | 67 | 135744 | 135763 | 75% | 0.09 |
| ASO-000900 | ASO-000900 | TAGccctaaagtcCCA | 68 | 135744 | 135759 | | |
| ASO-000435 | ASO-000435 | TTAgccctaaagtCCC | 69 | 135745 | 135760 | 29% | |
| ASO-000423 | ASO-000423 | GTTagccctaaagTCC | 70 | 135746 | 135761 | >100% | |
| ASO-000442 | ASO-000442 | TAGccctaaagTCC | 71 | 135746 | 135759 | 88% | 0.26 |
| ASO-000416 | ASO-000416 | GGTtagccctaaaGTC | 72 | 135747 | 135762 | | |
| ASO-000438 | ASO-000438 | GTTagccctaaAGT | 73 | 135748 | 135761 | 61% | |
| ASO-000581 | ASO-000581 | ACTggttagccctAAA | 74 | 135750 | 135765 | 4% | 0.06 |
| ASO-000639 | ASO-000639 | AACtggttagcccTAA | 75 | 135751 | 135766 | 31% | |
| ASO-000558 | ASO-000558 | GAActggttagccCTA | 76 | 135752 | 135767 | 80% | 0.06 |
| ASO-000597 | ASO-000597 | GAGaactggttagCCC | 77 | 135754 | 135769 | 2% | |
| ASO-000245 | ASO-000245 | TACaaagagaactGGT | 78 | 135760 | 135775 | | |
| ASO-000897 | ASO-000897 | CACaagtccttacAAA | 79 | 135770 | 135785 | | |
| ASO-000185 | ASO-000185 | GGCacaagtccttACA | 80 | 135772 | 135787 | | |

Figure 6E

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-000426 | ASO-000426 | AGGcacaagtccTTA | 81 | 135774 | 135788 | >100% | |
| ASO-000417 | ASO-000417 | GAGgcacaagtccTTA | 82 | 135774 | 135789 | 76% | |
| ASO-000393 | ASO-000393 | AGAggcacaagtcCTT | 83 | 135775 | 135790 | 78% | |
| ASO-000449 | ASO-000449 | AAGaggcacaagtCCT | 84 | 135776 | 135791 | 82% | 0.17 |
| ASO-000406 | ASO-000406 | AGAggcacaagtCCT | 85 | 135776 | 135790 | 74% | |
| ASO-000392 | ASO-000392 | CCAagaggcacaaGTC | 86 | 135778 | 135793 | 74% | |
| ASO-000444 | ASO-000444 | CAAgaggcacaaGTC | 87 | 135778 | 135792 | >100% | |
| ASO-000443 | ASO-000443 | CCCaagaggcacaAGT | 88 | 135779 | 135794 | 90% | |
| ASO-000450 | ASO-000450 | CAAgaggcacaAGT | 89 | 135779 | 135792 | 36% | |
| ASO-000258 | ASO-000258 | CTCccaagaggcaCAA | 90 | 135781 | 135796 | | |
| ASO-000205 | ASO-000205 | TGGccgtgggaagGAC | 91 | 135876 | 135891 | | |
| ASO-000213 | ASO-000213 | GGTgaggctgggaATT | 92 | 135984 | 135999 | | |
| ASO-000293 | ASO-000293 | GTGaggctgggaATT | 93 | 135984 | 135998 | | |
| ASO-000321 | ASO-000321 | TGGtgaggctgggAAT | 94 | 135985 | 136000 | | |
| ASO-000226 | ASO-000226 | CTCagtatggagtAGG | 95 | 136040 | 136055 | | |
| ASO-000682 | ASO-000682 | AATttcaccctcaGTA | 96 | 136049 | 136064 | 73% | |
| ASO-000673 | ASO-000673 | TTAatttcaccctCAG | 97 | 136051 | 136066 | 42% | |
| ASO-000578 | ASO-000578 | CTTaatttcacccTCA | 98 | 136052 | 136067 | 40% | |
| ASO-000540-21 | ASO-002180 | CCTTaatttcaccCTCA | 99 | 136052 | 136068 | | 0.04 |
| ASO-000540-22 | ASO-002192 | CCTTaatttcacCctCA | 100 | 136052 | 136068 | | 0.03 |
| ASO-000540-23 | ASO-002109 | CCTTAatttcacCctCA | 101 | 136052 | 136068 | | 0.03 |
| ASO-000540-24 | ASO-002121 | TcCCtTaatttcaccCT | 102 | 136054 | 136070 | | 0.11 |
| ASO-000540-25 | ASO-002133 | TcCCTtaatttcaccCT | 103 | 136054 | 136070 | | 0.16 |
| ASO-000540-26 | ASO-002145 | TcCCTtaatttcAccCT | 104 | 136054 | 136070 | | 0.31 |

Figure 6F

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000540-27 | ASO-002157 | TcCCTTaatttcaccCT | 105 | 136054 | 136070 | | 0.25 |
| ASO-000540-28 | ASO-002169 | TCcCTTaatttcaccCT | 106 | 136054 | 136070 | | 0.38 |
| ASO-000540-29 | ASO-002181 | TCCcttaatttcacCCT | 107 | 136054 | 136070 | | 0.48 |
| ASO-000540-3 | ASO-002154 | CCCttaatttcacCcTC | 108 | 136053 | 136069 | | 0.13 |
| ASO-000540-42 | ASO-002147 | CCCTtaatttcacccTCA | 109 | 136052 | 136069 | | 0.03 |
| ASO-000540-43 | ASO-002159 | CCCTtaatttcaccCtCA | 110 | 136052 | 136069 | | 0.08 |
| ASO-000540-44 | ASO-002171 | CCCTtaatttcaccCTCA | 111 | 136052 | 136069 | | 0.13 |
| ASO-000540-45 | ASO-002183 | CCCTtaatttcacCctCA | 112 | 136052 | 136069 | | 0.10 |
| ASO-000540-46 | ASO-002195 | CCCTtaatttcacCcTCA | 113 | 136052 | 136069 | | 0.40 |
| ASO-000540-47 | ASO-002196 | CCCTtaatttcaCcctCA | 114 | 136052 | 136069 | | 0.03 |
| ASO-000540-48 | ASO-002200 | CCCTtaatttcaCccTCA | 115 | 136052 | 136069 | | 0.17 |
| ASO-000540-49 | ASO-002204 | CCCTtaatttcaCcCtCA | 116 | 136052 | 136069 | | 0.60 |
| ASO-000540-5 | ASO-002178 | CCCttaatttcAcccTC | 117 | 136053 | 136069 | | 0.13 |
| ASO-000540-50 | ASO-002208 | CCCTtaatttcAccCtCA | 118 | 136052 | 136069 | | 0.23 |
| ASO-000540-51 | ASO-002212 | CCCTtaatttcAcCctCA | 119 | 136052 | 136069 | | 0.44 |
| ASO-000540-52 | ASO-002216 | TcCCTtaatttcacCcTC | 120 | 136053 | 136070 | | 0.14 |
| ASO-000540-53 | ASO-002220 | TCcCTtaatttcacccTC | 121 | 136053 | 136070 | | 0.09 |
| ASO-000540-54 | ASO-002224 | TCcCTTaatttcacCcTC | 122 | 136053 | 136070 | | 0.44 |
| ASO-000540-55 | ASO-002197 | TCCcttaatttcaccCTC | 123 | 136053 | 136070 | | 0.08 |
| ASO-000540-69 | ASO-002222 | TCCcTtaatttcacCctCA | 124 | 136052 | 136070 | | 0.13 |
| ASO-000540-70 | ASO-002226 | TCCCttaatttcaccCTCA | 125 | 136052 | 136070 | | 0.23 |
| ASO-000540-71 | ASO-002199 | TCCCttaatttcacCcTCA | 126 | 136052 | 136070 | | 0.72 |
| ASO-000540-72 | ASO-002203 | TCCCttaatttcacCCtCA | 127 | 136052 | 136070 | | 0.92 |
| ASO-000540-73 | ASO-002207 | TCCCttaatttcaCcCtCA | 128 | 136052 | 136070 | | 2.51 |

Figure 6G

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-000540-74 | ASO-002211 | TCCCttaatttcACcCtCA | 129 | 136052 | 136070 | | 10.00 |
| ASO-000540-75 | ASO-002215 | TCCCTtaatttcaccCTCA | 130 | 136052 | 136070 | | 0.62 |
| ASO-000540-76 | ASO-002219 | TCCCTtaatttcacCCtCA | 131 | 136052 | 136070 | | 4.18 |
| ASO-000540-77 | ASO-002223 | TCCCTtaatttcacCCTCA | 132 | 136052 | 136070 | | 7.96 |
| ASO-000540-8 | ASO-002119 | CCCtTaatttcaccCTC | 133 | 136053 | 136069 | | 0.05 |
| ASO-000540-9 | ASO-002131 | CCCtTaatttcacCcTC | 134 | 136053 | 136069 | | 0.14 |
| TBD-mm10 | ASO-002382 | CCttgATttcgccctCA | 135 | 136053 | 136069 | | 1.25 |
| TBD-mm11 | ASO-002299 | CCttgATttcaccctCT | 136 | 136052 | 136068 | | 0.27 |
| TBD-mm12 | ASO-002311 | CCttaGTttcaccctCG | 137 | 136054 | 136070 | | 0.22 |
| TBD-mm19 | ASO-002300 | CCCttgatttcaccctCA | 138 | 136052 | 136069 | | 0.34 |
| TBD-mm20 | ASO-002312 | CCCttaatttcaccctCG | 139 | 136054 | 136071 | | 0.09 |
| TBD-mm21 | ASO-002324 | CCCttagtttcaccctCA | 140 | 136052 | 136069 | | 0.28 |
| TBD-mm22 | ASO-002336 | CCCttgatttcgccctCA | 141 | 136052 | 136069 | | 2.39 |
| TBD-mm23 | ASO-002348 | CCCttgatttcaccctCG | 142 | 136053 | 136070 | | 0.78 |
| TBD-mm24 | ASO-002360 | CCCttgatttcaccctCT | 143 | 136052 | 136069 | | 0.99 |
| TBD-mm31 | ASO-002349 | TCcCTtgatttcacCctCA | 144 | 136053 | 136071 | | 0.20 |
| TBD-mm32 | ASO-002361 | TCcCTtaatttcacCctCG | 145 | 136052 | 136070 | | 0.12 |
| TBD-mm33 | ASO-002373 | ACcCTtaatttcacCctCA | 146 | 136053 | 136071 | | |
| TBD-mm34 | ASO-002385 | TCcCTtgatttcgcCctCA | 147 | 136052 | 136070 | | 1.28 |
| TBD-mm35 | ASO-002302 | TCcCTtagtttcacCctCG | 148 | 136054 | 136072 | | 0.27 |
| TBD-mm36 | ASO-002314 | ACcCTtgatttcacCctCA | 149 | 136054 | 136072 | | |

Figure 6H

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| TBD-mm7 | ASO-002346 | CCttgATttcaccctCA | 150 | 136053 | 136069 | | 0.16 |
| TBD-mm8 | ASO-002358 | CCttaGTttcaccctCA | 151 | 136053 | 136069 | | 0.16 |
| TBD-mm9 | ASO-002370 | CCttaATttcaccctCG | 152 | 136052 | 136068 | | 0.05 |
| ASO-000540 | ASO-000540 | CCTtaatttcaccCTC | 153 | 136053 | 136068 | >100% | 0.14 |
| ASO-000555 | ASO-000555 | CTTaatttcaccCTC | 154 | 136053 | 136067 | >100% | 0.21 |
| ASO-000579 | ASO-000579 | TTAatttcaccCTC | 155 | 136053 | 136066 | 44% | |
| ASO-000540-1 | ASO-002130 | CCCttaatttcacccTC | 156 | 136053 | 136069 | | 0.15 |
| ASO-000540-10 | ASO-002143 | CCCTtaatttcaccCTC | 157 | 136053 | 136069 | | 0.07 |
| ASO-000540-11 | ASO-002155 | CCCTtaatttcacCcTC | 158 | 136053 | 136069 | | 0.18 |
| ASO-000540-12 | ASO-002167 | CCCTtaatttcacCCTC | 159 | 136053 | 136069 | | 0.47 |
| ASO-000540-13 | ASO-002179 | CCCTtaatttcaCccTC | 160 | 136053 | 136069 | | 0.24 |
| ASO-000540-14 | ASO-002191 | CCttaATttcaccctCA | 161 | 136052 | 136068 | | 0.04 |
| ASO-000540-15 | ASO-002108 | CCTtaatttcacccTCA | 162 | 136052 | 136068 | | 0.08 |
| ASO-000540-16 | ASO-002120 | CCTtaaTttcaccctCA | 163 | 136052 | 136068 | | 0.07 |
| ASO-000540-17 | ASO-002132 | CCTtaAtttcaccctCA | 164 | 136052 | 136068 | | 0.19 |
| ASO-000540-18 | ASO-002144 | CCTtaATttcaccctCA | 165 | 136052 | 136068 | | 0.01 |
| ASO-000540-19 | ASO-002156 | CCTtaATttcacccTCA | 166 | 136052 | 136068 | | 0.01 |
| ASO-000540-2 | ASO-002142 | CCCttaatttcaccCTC | 167 | 136053 | 136069 | | 0.08 |
| ASO-000540-20 | ASO-002168 | CCTTaatttcaccCtCA | 168 | 136052 | 136068 | | 0.04 |
| ASO-000540-56 | ASO-002201 | TCCcttaatttcacCcTC | 169 | 136053 | 136070 | | 0.22 |
| ASO-000540-57 | ASO-002205 | TCCcTtaatttcacccTC | 170 | 136053 | 136070 | | 0.18 |
| ASO-000540-58 | ASO-002209 | TCCcTtaatttcacCcTC | 171 | 136053 | 136070 | | 0.40 |
| ASO-000540-59 | ASO-002213 | TCCcTtaatttcaCccTC | 172 | 136053 | 136070 | | 0.70 |

Figure 6I

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-000540-6 | ASO-002190 | CCCttaatttcAcCcTC | 173 | 136053 | 136069 | | 0.94 |
| ASO-000540-60 | ASO-002217 | TCCcTtaatttcAcCcTC | 174 | 136053 | 136070 | | 10.00 |
| ASO-000540-61 | ASO-002221 | TCCCttaatttcacCCTC | 175 | 136053 | 136070 | | 1.25 |
| ASO-000540-62 | ASO-002225 | TCCCttaatttcaCcCTC | 176 | 136053 | 136070 | | 5.08 |
| ASO-000540-63 | ASO-002198 | TCCCttaatttcaCCcTC | 177 | 136053 | 136070 | | 3.83 |
| ASO-000540-64 | ASO-002202 | TCCCttaatttcAccCTC | 178 | 136053 | 136070 | | 1.60 |
| ASO-000540-65 | ASO-002206 | TCCCttaatttCaccCTC | 179 | 136053 | 136070 | | 1.16 |
| ASO-000540-66 | ASO-002210 | TCcCTtaatttcacCctCA | 180 | 136052 | 136070 | | 0.07 |
| ASO-000540-67 | ASO-002214 | TCCcttaatttcacccTCA | 181 | 136052 | 136070 | | 0.03 |
| ASO-000540-68 | ASO-002218 | TCCcTtaatttcaccCtCA | 182 | 136052 | 136070 | | 0.11 |
| ASO-000540-mm1 | ASO-002297 | CCTtgatttcaccCTC | 183 | 136053 | 136068 | | 0.23 |
| ASO-000540-mm2 | ASO-002309 | CCTtaatttcgccCTC | 184 | 136053 | 136068 | | 1.01 |
| ASO-000540-mm3 | ASO-002321 | CCTtagtttcaccCTC | 185 | 136053 | 136068 | | 1.15 |
| ASO-000540-mm4 | ASO-002333 | CCTtgatttcgccCTC | 186 | 136053 | 136068 | | 1.05 |
| ASO-000540-mm5 | ASO-002345 | CCTtggtttcaccCTC | 187 | 136053 | 136068 | | 0.79 |
| ASO-000540-mm6 | ASO-002357 | CCTtagtttcgccCTC | 188 | 136053 | 136068 | | 8.70 |
| TBD-mm1 | ASO-002369 | CCCttgatttcacccTC | 189 | 136052 | 136068 | | 0.54 |
| TBD-mm2 | ASO-002381 | CCCttagtttcacccTC | 190 | 136053 | 136069 | | 0.38 |
| TBD-mm25 | ASO-002372 | TcCCTtgatttcacCcTC | 191 | 136052 | 136069 | | 0.57 |

Figure 6J

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| TBD-mm26 | ASO-002384 | TcCCTtaatttcgcCcTC | 192 | 136052 | 136069 | | 1.75 |
| TBD-mm27 | ASO-002301 | TcCCTtagtttcacCcTC | 193 | 136052 | 136069 | | 0.59 |
| TBD-mm28 | ASO-002313 | TcCCTtgatttcgcCcTC | 194 | 136054 | 136071 | | 1.33 |
| TBD-mm29 | ASO-002325 | TcCCTtagtttcgcCcTC | 195 | 136052 | 136069 | | 10.00 |
| TBD-mm3 | ASO-002298 | CCCttaatttcgcccTC | 196 | 136053 | 136069 | | 0.53 |
| TBD-mm30 | ASO-002337 | AcCCTtgatttcacCcTC | 197 | 136053 | 136070 | | |
| TBD-mm4 | ASO-002310 | CCCttgatttcgcccTC | 198 | 136054 | 136070 | | 2.46 |
| TBD-mm5 | ASO-002322 | CCCttggtttcacccTC | 199 | 136052 | 136068 | | 0.58 |
| TBD-mm6 | ASO-002334 | CCCttagtttcgcccTC | 200 | 136052 | 136068 | | 3.27 |
| ASO-000662 | ASO-000662 | CCCttaatttcacCCT | 201 | 136054 | 136069 | 81% | 0.36 |
| ASO-000566 | ASO-000566 | CCTtaatttcacCCT | 202 | 136054 | 136068 | >100% | 0.50 |
| ASO-000540-30 | ASO-002193 | TCCcTtaatttcaccCT | 203 | 136054 | 136070 | | 0.42 |
| ASO-000540-31 | ASO-002110 | TCCcTtaatttcAccCT | 204 | 136054 | 136070 | | 0.94 |
| ASO-000540-32 | ASO-002122 | TCCcTTaatttcaccCT | 205 | 136054 | 136070 | | 0.48 |
| ASO-000540-33 | ASO-002134 | TCCCttaatttcacCCT | 206 | 136054 | 136070 | | 1.30 |
| ASO-000540-34 | ASO-002146 | TCCCttaatttcaCcCT | 207 | 136054 | 136070 | | 2.19 |
| ASO-000540-35 | ASO-002158 | TCCCttaatttcaCCCT | 208 | 136054 | 136070 | | 6.94 |
| ASO-000540-36 | ASO-002170 | TCCCttaatttCaccCT | 209 | 136054 | 136070 | | 1.48 |
| ASO-000540-37 | ASO-002182 | CCCttaatttcaccctCA | 210 | 136052 | 136069 | | 0.08 |
| ASO-000540-38 | ASO-002194 | CCCttaatttcacccTCA | 211 | 136052 | 136069 | | 0.03 |
| ASO-000540-39 | ASO-002111 | CCCttaatttcacCctCA | 212 | 136052 | 136069 | | 0.06 |
| ASO-000540-4 | ASO-002166 | CCCttaatttcaCccTC | 213 | 136053 | 136069 | | 0.19 |

Figure 6K

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000540-40 | ASO-002123 | CCCttaatttcaCcctCA | 214 | 136052 | 136069 | | 0.05 |
| ASO-000540-41 | ASO-002135 | CCCttaatttcAcCctCA | 215 | 136052 | 136069 | | 0.29 |
| TBD-mm13 | ASO-002323 | TcCCtTgatttcaccCT | 216 | 136053 | 136069 | | 0.53 |
| TBD-mm14 | ASO-002335 | TcCCtTaatttcaccCA | 217 | 136052 | 136068 | | 0.08 |
| TBD-mm15 | ASO-002347 | TcCCtTaatttcgccCT | 218 | 136053 | 136069 | | 0.85 |
| TBD-mm16 | ASO-002359 | TcCCtTgatttcaccCA | 219 | 136053 | 136069 | | 0.49 |
| TBD-mm17 | ASO-002371 | TcCCtTgatttcaccCG | 220 | 136052 | 136068 | | 0.70 |
| TBD-mm18 | ASO-002383 | TcCCtTagtttcgccCT | 221 | 136052 | 136068 | | 5.56 |
| ASO-000628 | ASO-000628 | CCTtaatttcaCCC | 222 | 136055 | 136068 | 67% | |
| ASO-000642 | ASO-000642 | CCCttaatttcaCCC | 223 | 136055 | 136069 | >100% | 0.20 |
| ASO-000274 | ASO-000274 | TCCcttaatttcaCCC | 224 | 136055 | 136070 | | |
| ASO-000339 | ASO-000339 | CCttaatttcaCCC | 225 | 136055 | 136068 | | |
| ASO-000536 | ASO-000536 | TTCccttaatttcACC | 226 | 136056 | 136071 | >100% | 0.51 |
| ASO-000603 | ASO-000603 | TCCcttaatttcACC | 227 | 136056 | 136070 | 80% | 0.60 |
| ASO-000666 | ASO-000666 | TCCcttaatttCAC | 228 | 136057 | 136070 | >100% | |
| ASO-000272 | ASO-000272 | AGAgtgagaggctGGG | 229 | 136099 | 136114 | | |
| ASO-000255 | ASO-000255 | TGGatgagtggaaCTG | 230 | 136115 | 136130 | | |
| ASO-000336 | ASO-000336 | GGAtgagtggaACT | 231 | 136116 | 136129 | | |
| ASO-000206 | ASO-000206 | GTTggatgagtgGAA | 232 | 136118 | 136132 | | |
| ASO-000271 | ASO-000271 | AGTtggatgagtGGA | 233 | 136119 | 136133 | | |
| ASO-000340 | ASO-000340 | GTTggatgagtGGA | 234 | 136119 | 136132 | | |
| ASO-000229 | ASO-000229 | CAGggaaccgaatCAG | 235 | 136160 | 136175 | | |
| ASO-000273 | ASO-000273 | GCCctggctcacaTCT | 236 | 136193 | 136208 | | |

Figure 6L

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000264 | ASO-000264 | ACAaggcagaaacACC | 237 | 136229 | 136244 | | |
| ASO-000341 | ASO-000341 | TGTcaacaaggCAG | 238 | 136236 | 136249 | | |
| ASO-000198 | ASO-000198 | TGCcctgggtgccTTG | 239 | 136355 | 136370 | | |
| ASO-000210 | ASO-000210 | AGCgggactgtggGCC | 240 | 136371 | 136386 | | |
| ASO-000342 | ASO-000342 | GGgacagcgggACT | 241 | 136378 | 136391 | | |
| ASO-000333 | ASO-000333 | GCGggctgggctgTCT | 242 | 136427 | 136442 | | |
| ASO-000199 | ASO-000199 | CAGaacagacagcATG | 243 | 136541 | 136556 | | |
| ASO-000280 | ASO-000280 | TCTatgtatatgtTCA | 244 | 136567 | 136582 | | |
| ASO-000211 | ASO-000211 | ATCtatgtatatgTTC | 245 | 136568 | 136583 | | |
| ASO-000347 | ASO-000347 | CATctatgtataTGT | 246 | 136570 | 136584 | | |
| ASO-000352 | ASO-000352 | ACAtctatgtataTGT | 247 | 136570 | 136585 | | |
| ASO-000232 | ASO-000232 | CAAcagggtgcagATG | 248 | 136600 | 136615 | | |
| ASO-000257 | ASO-000257 | AGCataaacagacAAA | 249 | 136629 | 136644 | | |
| ASO-000388 | ASO-000388 | ATAgtcactctggTGA | 250 | 136650 | 136665 | 86% | 0.13 |
| ASO-000390 | ASO-000390 | TAGtcactctggTGA | 251 | 136650 | 136664 | 78% | 0.26 |
| ASO-000413 | ASO-000413 | AGTcactctggTGA | 252 | 136650 | 136663 | 97% | |
| ASO-000405 | ASO-000405 | CATagtcactctgGTG | 253 | 136651 | 136666 | 2% | |
| ASO-000430 | ASO-000430 | TAGtcactctgGTG | 254 | 136651 | 136664 | 82% | |
| ASO-000447 | ASO-000447 | TCAtagtcactctGGT | 255 | 136652 | 136667 | 86% | 0.03 |
| ASO-000396 | ASO-000396 | TACatgcgtccTTT | 256 | 136693 | 136706 | 92% | 0.04 |
| ASO-000395 | ASO-000395 | GATacatgcgtccTTT | 257 | 136693 | 136708 | >100% | 0.02 |
| ASO-000394 | ASO-000394 | AAGatacatgcgtCCT | 258 | 136695 | 136710 | >100% | 0.05 |
| ASO-000421 | ASO-000421 | TTCaagatacatgCGT | 259 | 136698 | 136713 | | |
| ASO-000400 | ASO-000400 | ATTtcaagatacaTGC | 260 | 136700 | 136715 | | |

Figure 6M

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000248 | ASO-000248 | GCAtttcaagataCAT | 261 | 136702 | 136717 | | |
| ASO-000451 | ASO-000451 | AAGcatttcaagaTAC | 262 | 136704 | 136719 | 67% | 0.10 |
| ASO-000707 | ASO-000707 | ACAagcatttcaaGAT | 263 | 136706 | 136721 | | |
| ASO-000619 | ASO-000619 | TTAcaagcatttcAAG | 264 | 136708 | 136723 | 37% | |
| ASO-000671 | ASO-000671 | AACctctttacaaGCA | 265 | 136715 | 136730 | | |
| ASO-000221 | ASO-000221 | GTTagaaacctctTTA | 266 | 136721 | 136736 | | |
| ASO-000298 | ASO-000298 | CCAcacaggccacACG | 267 | 136776 | 136791 | | |
| ASO-000311 | ASO-000311 | GTCtctgttgggtCCC | 268 | 136842 | 136857 | | |
| ASO-000290 | ASO-000290 | TGAacggcctcctTAG | 269 | 136871 | 136886 | | |
| ASO-000437 | ASO-000437 | CTGtgcttcaggcCTT | 270 | 136896 | 136911 | 51% | |
| ASO-000446 | ASO-000446 | TCCtgtgcttcagGCC | 271 | 136898 | 136913 | 76% | |
| ASO-000685 | ASO-000685 | AATcctgtgcttcAGG | 272 | 136900 | 136915 | 73% | |
| ASO-000410 | ASO-000410 | TCCtgtgcttcAGG | 273 | 136900 | 136913 | >100% | |
| ASO-000604 | ASO-000604 | AATcctgtgcttCAG | 274 | 136901 | 136915 | 57% | |
| ASO-000490 | ASO-000490 | TAAtcctgtgcttCAG | 275 | 136901 | 136916 | 76% | |
| ASO-000529 | ASO-000529 | AATcctgtgctTCA | 276 | 136902 | 136915 | 10% | |
| ASO-000532 | ASO-000532 | CTAatcctgtgctTCA | 277 | 136902 | 136917 | 100% | |
| ASO-000508 | ASO-000508 | TAAtcctgtgctTCA | 278 | 136902 | 136916 | 87% | |
| ASO-000219 | ASO-000219 | CCTaatcctgtgcTTC | 279 | 136903 | 136918 | | |
| ASO-000656 | ASO-000656 | TAAtcctgtgcTTC | 280 | 136903 | 136916 | 2% | |
| ASO-000522 | ASO-000522 | CTAatcctgtgcTTC | 281 | 136903 | 136917 | 73% | |
| ASO-000513 | ASO-000513 | CCTaatcctgtgCTT | 282 | 136904 | 136918 | 58% | |
| ASO-000640 | ASO-000640 | TCCtaatcctgtgCTT | 283 | 136904 | 136919 | 23% | |
| ASO-000661 | ASO-000661 | CTAatcctgtgCTT | 284 | 136904 | 136917 | 26% | |

Figure 6N

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000478 | ASO-000478 | GTCctaatcctgtGCT | 285 | 136905 | 136920 | 88% | 0.28 |
| ASO-000500 | ASO-000500 | TCCtaatcctgtGCT | 286 | 136905 | 136919 | >100% | |
| ASO-000601 | ASO-000601 | CCTaatcctgtGCT | 287 | 136905 | 136918 | 63% | |
| ASO-000643 | ASO-000643 | AGTcctaatcctgTGC | 288 | 136906 | 136921 | 25% | |
| ASO-000600 | ASO-000600 | GTCctaatcctgTGC | 289 | 136906 | 136920 | 37% | |
| ASO-000525 | ASO-000525 | TCCtaatcctgTGC | 290 | 136906 | 136919 | 65% | |
| ASO-000453 | ASO-000453 | TCAgtcctaatccTGT | 291 | 136908 | 136923 | 53% | |
| ASO-000553 | ASO-000553 | CTTcagtcctaatCCT | 292 | 136910 | 136925 | 96% | |
| ASO-000622 | ASO-000622 | GCTtcagtcctaATC | 293 | 136912 | 136926 | 11% | |
| ASO-000325 | ASO-000325 | CTGacacagggagCCC | 294 | 136956 | 136971 | | |
| ASO-000215 | ASO-000215 | GCCagaccagccaCAA | 295 | 136987 | 137002 | | |
| ASO-000482 | ASO-000482 | CAGgagttgtaAGC | 296 | 137065 | 137078 | 78% | |
| ASO-000337 | ASO-000337 | TGCaggagttgtaAGC | 297 | 137065 | 137080 | | |
| ASO-000480 | ASO-000480 | ATGcaggagttgtAAG | 298 | 137066 | 137081 | 41% | |
| ASO-000644 | ASO-000644 | GATgcaggagttgTAA | 299 | 137067 | 137082 | 0% | |
| ASO-000695 | ASO-000695 | TGCaggagttgTAA | 300 | 137067 | 137080 | | |
| ASO-000455 | ASO-000455 | TGAtgcaggagttGTA | 301 | 137068 | 137083 | 8% | |
| ASO-000531 | ASO-000531 | GTGatgcaggagtTGT | 302 | 137069 | 137084 | 14% | |
| ASO-000651 | ASO-000651 | TGTgatgcaggagTTG | 303 | 137070 | 137085 | 29% | |
| ASO-000419 | ASO-000419 | GTGatgcaggaGTT | 305 | 137071 | 137084 | 65% | |
| ASO-000730 | ASO-000730 | TGTgatgcaggaGTT | 306 | 137071 | 137085 | | 0.25 |
| ASO-000728 | ASO-000728 | TGTgatgcaggaGTT | 307 | 137071 | 137085 | | 0.51 |
| ASO-000729 | ASO-000729 | TGTgatgcaggaGTT | 308 | 137071 | 137085 | | 10.00 |
| ASO-000727 | ASO-000727 | TGTgatgcaggaGTT | 309 | 137071 | 137085 | | 10.00 |

Figure 6O

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000715 | ASO-000715 | TGtgatgcaggagTT | 310 | 137071 | 137085 | | |
| ASO-000716 | ASO-000716 | GAtgcaggagTT | 311 | 137071 | 137082 | | |
| ASO-000721 | ASO-000721 | TGTgatgcaggaGTT | 312 | 137071 | 137085 | | |
| ASO-000722 | ASO-000722 | TGTgatgcaggaGTT | 313 | 137071 | 137085 | | |
| ASO-000723 | ASO-000723 | TGTgatgcaggaGTT | 314 | 137071 | 137085 | | |
| ASO-000724 | ASO-000724 | TGTgatgcaggaGTT | 315 | 137071 | 137085 | | |
| ASO-000725 | ASO-000725 | TGTgatgcaggaGTT | 316 | 137071 | 137085 | | |
| ASO-000726 | ASO-000726 | TGTgatgcaggaGTT | 317 | 137071 | 137085 | | |
| ASO-000731 | ASO-000731 | TGTgatgcaggaGTT | 318 | 137071 | 137085 | | |
| ASO-000718 | ASO-000718 | TGatgcaggaGT | 319 | 137072 | 137083 | | |
| ASO-000445 | ASO-000445 | TTGtgatgcagGAG | 320 | 137073 | 137086 | 0% | |
| ASO-000436 | ASO-000436 | CTTgtgatgcagGAG | 321 | 137073 | 137087 | 88% | |
| ASO-000717 | ASO-000717 | GTgatgcaggAG | 322 | 137073 | 137084 | | |
| ASO-000570 | ASO-000570 | TTCttgtgatgcaGGA | 323 | 137074 | 137089 | 61% | |
| ASO-000408 | ASO-000408 | TCTtgtgatgcaGGA | 324 | 137074 | 137088 | 92% | |
| ASO-000401 | ASO-000401 | CTTgtgatgcaGGA | 325 | 137074 | 137087 | 70% | |
| ASO-000719 | ASO-000719 | TGtgatgcagGA | 326 | 137074 | 137085 | | |
| ASO-000313 | ASO-000313 | CAGagggcgagctTGG | 327 | 137173 | 137188 | | |
| ASO-000331 | ASO-000331 | AATccctgctgtgGTC | 328 | 137223 | 137238 | | |
| ASO-000251 | ASO-000251 | AGGcaattcatCCC | 329 | 137239 | 137252 | | |
| ASO-000574 | ASO-000574 | TGGtcaaggctttGGG | 330 | 137326 | 137341 | 0% | |
| ASO-000218 | ASO-000218 | TCTggtcaaggctTTG | 331 | 137328 | 137343 | | |
| ASO-000634 | ASO-000634 | CTCtggtcaaggcTTT | 332 | 137329 | 137344 | 0% | |
| ASO-000497 | ASO-000497 | GGTgctctggtcaAGG | 333 | 137333 | 137348 | 15% | |

Figure 6P

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000569 | ASO-000569 | GGTgctctggtCAA | 334 | 137335 | 137348 | >100% | |
| ASO-000565 | ASO-000565 | GCTgaggtgctctGGT | 335 | 137338 | 137353 | 19% | |
| ASO-000296 | ASO-000296 | AGTttgtgcaaggTCA | 336 | 137358 | 137373 | | |
| ASO-000663 | ASO-000663 | GAGtttgtgcaagGTC | 337 | 137359 | 137374 | 0% | |
| ASO-000670 | ASO-000670 | AGTttgtgcaagGTC | 338 | 137359 | 137373 | 0% | |
| ASO-000261 | ASO-000261 | GGAgtttgtgcaaGGT | 339 | 137360 | 137375 | | |
| ASO-000262 | ASO-000262 | GGAgtttgtgcaAGG | 340 | 137361 | 137375 | | |
| ASO-000275 | ASO-000275 | TGGagtttgtgcaAGG | 341 | 137361 | 137376 | | |
| ASO-000247 | ASO-000247 | ATGgagtttgtgcAAG | 342 | 137362 | 137377 | | |
| ASO-000303 | ASO-000303 | TGGagtttgtgcAAG | 343 | 137362 | 137376 | | |
| ASO-000299 | ASO-000299 | ATGgagtttgtgCAA | 344 | 137363 | 137377 | | |
| ASO-000270 | ASO-000270 | AGAtggagtttgtGCA | 345 | 137364 | 137379 | | |
| ASO-000297 | ASO-000297 | AGCagatggagttTGT | 346 | 137367 | 137382 | | |
| ASO-000259 | ASO-000259 | TTCtttaggcagcAAT | 347 | 137416 | 137431 | | |
| ASO-000220 | ASO-000220 | TGTacccaaaccaGAA | 348 | 137462 | 137477 | | |
| ASO-000278 | ASO-000278 | GTTgcctttaacTGT | 349 | 137475 | 137489 | | |
| ASO-000334 | ASO-000334 | GCCctggatttctACT | 350 | 137505 | 137520 | | |
| ASO-000241 | ASO-000241 | TGGtggagagttcTGG | 351 | 137583 | 137598 | | |
| ASO-000289 | ASO-000289 | TTCtcagatccctTCA | 352 | 137643 | 137658 | | |
| ASO-000233 | ASO-000233 | CTCtaaccaccacCAA | 353 | 137682 | 137697 | | |
| ASO-000201 | ASO-000201 | AGGgcacaagaacTTC | 354 | 137765 | 137780 | | |
| ASO-000645 | ASO-000645 | ATCttaggctggCCC | 355 | 137851 | 137865 | 51% | |
| ASO-000546 | ASO-000546 | GATcttaggctggCCC | 356 | 137851 | 137866 | 91% | |
| ASO-000692 | ASO-000692 | TGAtcttaggctgGCC | 357 | 137852 | 137867 | | |

Figure 6Q

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000511 | ASO-000511 | GATcttaggctgGCC | 358 | 137852 | 137866 | 8% | |
| ASO-000538 | ASO-000538 | TGAtcttaggctGGC | 359 | 137853 | 137867 | 44% | |
| ASO-000214 | ASO-000214 | ATGatcttaggctGGC | 360 | 137853 | 137868 | | |
| ASO-000653 | ASO-000653 | GATcttaggctGGC | 361 | 137853 | 137866 | 5% | |
| ASO-000615 | ASO-000615 | CATgatcttaggcTGG | 362 | 137854 | 137869 | 8% | |
| ASO-000524 | ASO-000524 | CCAtgatcttaggCTG | 363 | 137855 | 137870 | 18% | |
| ASO-000492 | ASO-000492 | CATgatcttaggCTG | 364 | 137855 | 137869 | 46% | |
| ASO-000468 | ASO-000468 | ACCatgatcttagGCT | 365 | 137856 | 137871 | 88% | 0.09 |
| ASO-000698 | ASO-000698 | CCAtgatcttagGCT | 366 | 137856 | 137870 | | |
| ASO-000593 | ASO-000593 | CATgatcttagGCT | 367 | 137856 | 137869 | 25% | |
| ASO-000519 | ASO-000519 | AAAccatgatcttAGG | 368 | 137858 | 137873 | 81% | |
| ASO-000582 | ASO-000582 | CTAaaccatgatcTTA | 369 | 137860 | 137875 | 21% | |
| ASO-000635 | ASO-000635 | CCCtaaaccatgaTCT | 370 | 137862 | 137877 | 90% | 0.13 |
| ASO-000471 | ASO-000471 | CACcctaaaccatGAT | 371 | 137864 | 137879 | 71% | |
| ASO-000701 | ASO-000701 | ATCaccctaaaccATG | 372 | 137866 | 137881 | | |
| ASO-000533 | ASO-000533 | TGAtcaccctaaaCCA | 373 | 137868 | 137883 | >100% | |
| ASO-000323 | ASO-000323 | GAGgagtgcccagCCC | 374 | 137947 | 137962 | | |
| ASO-000329 | ASO-000329 | TGCaggtgggagaAGT | 375 | 137973 | 137988 | | |
| ASO-000194 | ASO-000194 | TATctagcccaCCC | 376 | 138003 | 138016 | | |
| ASO-000192 | ASO-000192 | CTAtctagcccaCCC | 377 | 138003 | 138017 | | |
| ASO-000343 | ASO-000343 | TAtcctatctaGCC | 378 | 138008 | 138021 | | |
| ASO-000212 | ASO-000212 | TTGataaagtgaGTC | 379 | 138050 | 138064 | | |
| ASO-000230 | ASO-000230 | ATTgataaagtgAGT | 380 | 138051 | 138065 | | |
| ASO-000188 | ASO-000188 | AACtattgataaAGT | 381 | 138055 | 138069 | | |

Figure 6R

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000415 | ASO-000415 | GAActattgatAAA | 382 | 138057 | 138070 | 86% | |
| ASO-000448 | ASO-000448 | GGAactattgaTAA | 383 | 138058 | 138071 | 0% | |
| ASO-000190 | ASO-000190 | AAAtggaactattGAT | 384 | 138060 | 138075 | | |
| ASO-000191 | ASO-000191 | AATggaactatTGA | 385 | 138061 | 138074 | | |
| ASO-000348 | ASO-000348 | TCAAtttaaatGGAA | 386 | 138068 | 138082 | | |
| ASO-000349 | ASO-000349 | GTcaatttaaaTGGA | 387 | 138069 | 138083 | | |
| ASO-000200 | ASO-000200 | GGAtacagtctcaCCA | 388 | 138089 | 138104 | | |
| ASO-000630 | ASO-000630 | GCAaacaggatacAGT | 389 | 138096 | 138111 | 0% | |
| ASO-000614 | ASO-000614 | CAAacaggatacAGT | 390 | 138096 | 138110 | 50% | 0.04 |
| ASO-000563 | ASO-000563 | AAAcaggatacAGT | 391 | 138096 | 138109 | >100% | |
| ASO-000527 | ASO-000527 | TAGcaaacaggatACA | 392 | 138098 | 138113 | 50% | 0.04 |
| ASO-000617 | ASO-000617 | ATAgcaaacaggaTAC | 393 | 138099 | 138114 | 28% | |
| ASO-000539 | ASO-000539 | AATagcaaacaggATA | 394 | 138100 | 138115 | 82% | |
| ASO-000691 | ASO-000691 | CAAtagcaaacagGAT | 395 | 138101 | 138116 | | |
| ASO-000589 | ASO-000589 | AATagcaaacagGAT | 396 | 138101 | 138115 | 4% | |
| ASO-000509 | ASO-000509 | GCAatagcaaacaGGA | 397 | 138102 | 138117 | | |
| ASO-000674 | ASO-000674 | CAAtagcaaacaGGA | 398 | 138102 | 138116 | | |
| ASO-000488 | ASO-000488 | GCAatagcaaacAGG | 399 | 138103 | 138117 | 41% | |
| ASO-000507 | ASO-000507 | AGCaatagcaaacAGG | 400 | 138103 | 138118 | 49% | |
| ASO-000521 | ASO-000521 | AGCaatagcaaaCAG | 401 | 138104 | 138118 | 53% | |
| ASO-000288 | ASO-000288 | AAGcaatagcaaaCAG | 402 | 138104 | 138119 | | |
| ASO-000552 | ASO-000552 | AAGcaatagcaaACA | 403 | 138105 | 138119 | >100% | |
| ASO-000250 | ASO-000250 | CAAatgtggttgaAAT | 404 | 138223 | 138238 | | |
| ASO-000294 | ASO-000294 | GCAaatgtggttgAAA | 405 | 138224 | 138239 | | |

Figure 6S

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000318 | ASO-000318 | TAGcaaatgtggtTGA | 406 | 138226 | 138241 | | |
| ASO-000308 | ASO-000308 | CCCaagggcctctAAC | 407 | 138263 | 138278 | | |
| ASO-000254 | ASO-000254 | AAAgcaaccagatGTC | 408 | 138361 | 138376 | | |
| ASO-000545 | ASO-000545 | AAGagggcagcagGCC | 409 | 138377 | 138392 | 73% | |
| ASO-000476 | ASO-000476 | GAAagagggcagcAGG | 410 | 138379 | 138394 | 0% | |
| ASO-000620 | ASO-000620 | CTGaaagagggcaGCA | 411 | 138381 | 138396 | 37% | |
| ASO-000477 | ASO-000477 | CCCtgaaagagggCAG | 412 | 138383 | 138398 | 18% | |
| ASO-000562 | ASO-000562 | TGAttgtgggcttAGG | 413 | 138401 | 138416 | 3% | |
| ASO-000547 | ASO-000547 | ATGattgtgggctTAG | 414 | 138402 | 138417 | 24% | |
| ASO-000696 | ASO-000696 | TGAttgtgggctTAG | 415 | 138402 | 138416 | | |
| ASO-000279 | ASO-000279 | GATtgtgggctTAG | 416 | 138402 | 138415 | | |
| ASO-000543 | ASO-000543 | CATgattgtgggcTTA | 417 | 138403 | 138418 | 0% | 0.07 |
| ASO-000626 | ASO-000626 | TGAttgtgggcTTA | 418 | 138403 | 138416 | 29% | |
| ASO-000650 | ASO-000650 | ATGattgtgggcTTA | 419 | 138403 | 138417 | 8% | |
| ASO-000599 | ASO-000599 | CATgattgtgggCTT | 420 | 138404 | 138418 | 0% | |
| ASO-000542 | ASO-000542 | GCAtgattgtgggCTT | 421 | 138404 | 138419 | 47% | |
| ASO-000463 | ASO-000463 | GGCatgattgtggGCT | 422 | 138405 | 138420 | 6% | |
| ASO-000605 | ASO-000605 | GCAtgattgtggGCT | 423 | 138405 | 138419 | 0% | |
| ASO-000479 | ASO-000479 | CATgattgtggGCT | 424 | 138405 | 138418 | | |
| ASO-000474 | ASO-000474 | GCAtgattgtgGGC | 425 | 138406 | 138419 | 86% | |
| ASO-000675 | ASO-000675 | GGCatgattgtgGGC | 426 | 138406 | 138420 | 5% | |
| ASO-000537 | ASO-000537 | AGGcatgattgtgGGC | 427 | 138406 | 138421 | 0% | |
| ASO-000287 | ASO-000287 | AGGgaggcatgatTGT | 428 | 138410 | 138425 | | |
| ASO-000292 | ASO-000292 | GGGaggcatgatTGT | 429 | 138410 | 138424 | | |

Figure 6T

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000216 | ASO-000216 | TTAgggaggcatgATT | 430 | 138412 | 138427 | | |
| ASO-000266 | ASO-000266 | TTAgggaggcatGAT | 431 | 138413 | 138427 | | |
| ASO-000256 | ASO-000256 | TCTtagggaggcaTGA | 432 | 138414 | 138429 | | |
| ASO-000269 | ASO-000269 | GAGgtggcacagaGGT | 433 | 138460 | 138475 | | |
| ASO-000350 | ASO-000350 | CAGtgtgagaggtGG | 434 | 138469 | 138483 | | |
| ASO-000353 | ASO-000353 | CAGtgtgagaggTG | 435 | 138470 | 138483 | | |
| ASO-000310 | ASO-000310 | ACAaagatgaggaGGG | 436 | 138532 | 138547 | | |
| ASO-000309 | ASO-000309 | AACaaagatgaggAGG | 437 | 138533 | 138548 | | |
| ASO-000263 | ASO-000263 | GAAgagaaatcagAAG | 438 | 138631 | 138646 | | |
| ASO-000197 | ASO-000197 | TCTaggccagtgcCCA | 439 | 138667 | 138682 | | |
| ASO-000239 | ASO-000239 | AGTctattaggAGG | 440 | 138689 | 138702 | | |
| ASO-000267 | ASO-000267 | GCTcaacatggcaAAC | 441 | 138714 | 138729 | | |
| ASO-000306 | ASO-000306 | TGCaagtgccagAAA | 442 | 138737 | 138751 | | |
| ASO-000345 | ASO-000345 | GCAagtgccagAAA | 443 | 138737 | 138750 | | |
| ASO-000193 | ASO-000193 | AATcatgggacttGCA | 444 | 138748 | 138763 | | |
| ASO-000284 | ASO-000284 | GATttcatgtcccTCC | 445 | 138788 | 138803 | | |
| ASO-000209 | ASO-000209 | GCTaagctaagaTGA | 446 | 138802 | 138816 | | |
| ASO-000207 | ASO-000207 | CTAagctaagaTGA | 447 | 138802 | 138815 | | |
| ASO-000301 | ASO-000301 | TAGacattcacaGAC | 448 | 138822 | 138836 | | |
| ASO-000234 | ASO-000234 | TATagacattcaCAG | 449 | 138824 | 138838 | | |
| ASO-000332 | ASO-000332 | AAAcacacaatacACT | 450 | 138840 | 138855 | | |
| SPC-15693-01 | ASO-002268 | CAgcaacagtcagtGT | 451 | 138869 | 138884 | | |
| SPC-15692-01 | ASO-002260 | ACagcaacagtcagTG | 452 | 138870 | 138885 | | |
| SPC-15691-01 | ASO-002252 | TAcagcaacagtcaGT | 453 | 138871 | 138886 | | |

Figure 6U

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| SPC-15690-01 | ASO-002244 | TTAcagcaacagtcAG | 454 | 138872 | 138887 | | |
| SPC-15689-01 | ASO-002235 | TTTacagcaacagtCA | 455 | 138873 | 138888 | | |
| SPC-15688-01 | ASO-002290 | TTttacagcaacaGTC | 456 | 138874 | 138889 | | |
| SPC-15687-01 | ASO-002282 | CTtttacagcaacaGT | 457 | 138875 | 138890 | | |
| SPC-15686-01 | ASO-002275 | ACttttacagcaaCAG | 458 | 138876 | 138891 | | |
| SPC-15685-01 | ASO-002267 | CActtttacagcaaCA | 459 | 138877 | 138892 | | |
| SPC-15684-01 | ASO-002259 | TCActtttacagcAAC | 460 | 138878 | 138893 | | |
| SPC-15683-01 | ASO-002251 | TTCacttttacagCAA | 461 | 138879 | 138894 | | |
| SPC-15682-01 | ASO-002243 | ATTcacttttacagCA | 462 | 138880 | 138895 | | 0.24 |
| SPC-15681-01 | ASO-002234 | AATtcacttttacaGC | 463 | 138881 | 138896 | | |
| SPC-15680-01 | ASO-002289 | AAATtcacttttACAG | 464 | 138882 | 138897 | | |
| SPC-15679-01 | ASO-002281 | CAAattcactttTACA | 465 | 138883 | 138898 | | |
| ASO-002090 | ASO-002090 | ATTtcCaaattcactTtTAC | 466 | 138884 | 138903 | >100% | 0.04 |
| ASO-002043 | ASO-002043 | ATtTCcaaattcacttTTAC | 467 | 138884 | 138903 | >100% | 0.02 |
| ASO-002076 | ASO-002076 | ATtTCcaaattcacTTttAC | 468 | 138884 | 138903 | >100% | 0.04 |
| ASO-002062 | ASO-002062 | ATTtcCaaattcactTTtAC | 469 | 138884 | 138903 | >100% | 0.02 |
| ASO-002082 | ASO-002082 | ATtTcCaaattcactTtTAC | 470 | 138884 | 138903 | >100% | 0.01 |
| ASO-000753 | ASO-000753 | ATTTCcaaattcactTTTAC | 471 | 138884 | 138903 | >100% | 0.11 |
| ASO-001940 | ASO-001940 | ATtTCcaaattcactTTtAC | 472 | 138884 | 138903 | 85% | 0.03 |
| ASO-001933 | ASO-001933 | AtTTCcaaattcactTTtAC | 473 | 138884 | 138903 | >100% | 0.05 |
| ASO-001919 | ASO-001919 | ATTTccaaattcactTTTAC | 474 | 138884 | 138903 | >100% | 0.04 |
| ASO-002094 | ASO-002094 | ATtTCcaaattcacTtTtAC | 475 | 138884 | 138903 | 83% | 0.05 |
| ASO-002034 | ASO-002034 | ATTtCcaaattcactTtTAC | 476 | 138884 | 138903 | >100% | 0.02 |
| ASO-002036 | ASO-002036 | ATttCcAaattcacttTTAC | 477 | 138884 | 138903 | >100% | 0.02 |

Figure 6V

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-002084 | ASO-002084 | ATTtCcaaattcacTTttAC | 478 | 138884 | 138903 | >100% | 0.03 |
| ASO-002037 | ASO-002037 | ATTTccaaattcaCtTttAC | 479 | 138884 | 138903 | >100% | 0.04 |
| ASO-002058 | ASO-002058 | ATTtCcaaattcacTttTAC | 480 | 138884 | 138903 | >100% | 0.03 |
| ASO-002057 | ASO-002057 | ATTTccaaattcaCttTtAC | 481 | 138884 | 138903 | >100% | 0.03 |
| ASO-001926 | ASO-001926 | ATTTCcaaattcacttTTAC | 482 | 138884 | 138903 | 79% | 0.09 |
| ASO-002092 | ASO-002092 | ATttCCaaattcactTtTAC | 483 | 138884 | 138903 | >100% | 0.02 |
| ASO-002023 | ASO-002023 | ATTTccaaattcacTTttAC | 484 | 138884 | 138903 | >100% | 0.02 |
| ASO-000758 | ASO-000758 | ATTtccaaattcactttTAC | 485 | 138884 | 138903 | >100% | 0.15 |
| ASO-002065 | ASO-002065 | ATttCCaaattcactTTtAC | 486 | 138884 | 138903 | >100% | 0.02 |
| ASO-002038 | ASO-002038 | ATTtCcaaattcacTtTtAC | 487 | 138884 | 138903 | >100% | 0.02 |
| ASO-002039 | ASO-002039 | ATtTCcaaattcacTttTAC | 488 | 138884 | 138903 | 35% | 0.05 |
| ASO-000763 | ASO-000763 | ATttccaaattcacttttAC | 489 | 138884 | 138903 | >100% | |
| ASO-000768 | ASO-000768 | AtttccaaattcacttttAC | 490 | 138884 | 138903 | >100% | |
| ASO-001933-mm1 | ASO-002291 | GtTTCcaaattcactTTtAC | 506 | 138884 | 138903 | | 0.10 |
| ASO-001933-mm2 | ASO-002303 | AtTTCcagattcactTTtAC | 507 | 138884 | 138903 | | 0.11 |
| ASO-001933-mm3 | ASO-002315 | TtTTCcaaattcactTTtAC | 508 | 138884 | 138903 | | 0.03 |
| ASO-001933-mm4 | ASO-002327 | GtTTCcagattcactTTtAC | 509 | 138884 | 138903 | | 0.88 |
| ASO-001933-mm5 | ASO-002339 | AtTTCcaagttcactTTtGC | 510 | 138884 | 138903 | | 2.70 |
| ASO-001933-mm6 | ASO-002351 | AtTTCcagattcgctTTtAC | 511 | 138884 | 138903 | | 1.88 |
| SPC-15678-01 | ASO-002274 | CCaaattcactttTAC | 512 | 138884 | 138899 | | |

Figure 6W

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| SPC-15857-01 | ASO-002326 | ATtTcCaaattcacttTTAC | 513 | 138884 | 138903 | | 0.03 |
| SPC-15858-01 | ASO-002338 | ATTtcCaaattcacttTTAC | 514 | 138884 | 138903 | | 0.04 |
| SPC-15860-01 | ASO-002362 | ATTtCcaaattcacttTTAC | 515 | 138884 | 138903 | | 0.04 |
| SPC-15864-01 | ASO-002236 | ATTTccaaattcacTttTAC | 516 | 138884 | 138903 | | |
| SPC-15868-01 | ASO-002269 | ATtTCcaaattcactTtTAC | 517 | 138884 | 138903 | | 0.04 |
| SPC-15872-01 | ASO-002237 | ATttCCaaattcacttTTAC | 518 | 138884 | 138903 | | |
| SPC-15873-01 | ASO-002246 | ATTtCcaaattcactTTtAC | 519 | 138884 | 138903 | | 0.03 |
| SPC-15874-01 | ASO-002254 | ATTTccaaattcacTtTtAC | 520 | 138884 | 138903 | | |
| SPC-15878-01 | ASO-002284 | ATtTccAaattcacttTTAC | 521 | 138884 | 138903 | | |
| SPC-15879-01 | ASO-002229 | ATTTccaaattcacttTTAC | 522 | 138884 | 138903 | | |
| SPC-15880-01 | ASO-002238 | ATTTccaaattcactTtTAC | 523 | 138884 | 138903 | | |
| SPC-15883-01 | ASO-002263 | ATtTcCaaattcactTTtAC | 524 | 138884 | 138903 | | |
| SPC-15888-01 | ASO-002239 | ATTTccaaattcactTTtAC | 525 | 138884 | 138903 | | |
| ASO-000754 | ASO-000754 | TATTTccaaattcacTTTTA | 526 | 138885 | 138904 | >100% | |
| ASO-002055 | ASO-002055 | TAtTtCcaaattcacTTtTA | 527 | 138885 | 138904 | >100% | 0.09 |
| ASO-002035 | ASO-002035 | TAtTtcCaaattcactTTTA | 528 | 138885 | 138904 | >100% | 0.03 |
| ASO-002048 | ASO-002048 | TATtTccaaattcaCttTTA | 529 | 138885 | 138904 | >100% | 0.07 |
| ASO-002053 | ASO-002053 | TAtTtCcaaattcactTTTA | 530 | 138885 | 138904 | >100% | 0.04 |
| ASO-002067 | ASO-002067 | TAtTTccaaattcaCTttTA | 531 | 138885 | 138904 | >100% | 0.07 |
| ASO-001954 | ASO-001954 | TATTTccaaattcactTTTA | 532 | 138885 | 138904 | >100% | 0.05 |
| ASO-001947 | ASO-001947 | TATTtccaaattcacTTTTA | 533 | 138885 | 138904 | >100% | 0.07 |
| ASO-002081 | ASO-002081 | TATttCcaaattcacTtTTA | 534 | 138885 | 138904 | >100% | 0.07 |
| ASO-001966 | ASO-001966 | TAtTTccaaattcacTTtTA | 535 | 138885 | 138904 | >100% | 0.05 |
| ASO-002025 | ASO-002025 | TAttTcCaaattcactTTTA | 536 | 138885 | 138904 | >100% | 0.03 |

Figure 6X

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-002033 | ASO-002033 | TATtTccaaattcacTtTTA | 537 | 138885 | 138904 | >100% | 0.05 |
| ASO-001960 | ASO-001960 | TaTTTccaaattcacTTtTA | 538 | 138885 | 138904 | >100% | 0.08 |
| ASO-002056 | ASO-002056 | TAttTCcaaattcacTTtTA | 539 | 138885 | 138904 | >100% | 0.07 |
| ASO-002063 | ASO-002063 | TATttCcaaattcacTTtTA | 540 | 138885 | 138904 | >100% | 0.08 |
| ASO-002089 | ASO-002089 | TATTtccaaattcaCttTTA | 541 | 138885 | 138904 | >100% | 0.06 |
| ASO-002073 | ASO-002073 | TAtTtCcaaattcacTtTTA | 542 | 138885 | 138904 | >100% | 0.06 |
| ASO-002027 | ASO-002027 | TATtTccaaattcaCtTtTA | 543 | 138885 | 138904 | >100% | 0.09 |
| ASO-002075 | ASO-002075 | TATtTccaaattcaCTttTA | 544 | 138885 | 138904 | >100% | 0.14 |
| ASO-002028 | ASO-002028 | TAtTTccaaattcaCttTTA | 545 | 138885 | 138904 | 77% | 0.08 |
| ASO-002085 | ASO-002085 | TAtTTccaaattcaCtTtTA | 546 | 138885 | 138904 | >100% | 0.09 |
| ASO-002083 | ASO-002083 | TAttTCcaaattcacTtTTA | 547 | 138885 | 138904 | >100% | 0.04 |
| ASO-000759 | ASO-000759 | TATttccaaattcacttTTA | 548 | 138885 | 138904 | >100% | 0.55 |
| ASO-000769 | ASO-000769 | TatttccaaattcactttTA | 549 | 138885 | 138904 | >100% | |
| ASO-000764 | ASO-000764 | TAtttccaaattcactttTA | 550 | 138885 | 138904 | >100% | |
| ASO-001954-mm1 | ASO-002340 | TATTTccagattcactTTTA | 566 | 138885 | 138904 | | 0.04 |
| ASO-001954-mm2 | ASO-002352 | TATTTccgaattcactTTTA | 567 | 138885 | 138904 | | 0.04 |
| ASO-001954-mm3 | ASO-002364 | GATTTccaaattcactTTTA | 568 | 138885 | 138904 | | 0.13 |
| ASO-001954-mm4 | ASO-002376 | GGTTTccaaattcactTTTA | 569 | 138885 | 138904 | | 5.46 |
| ASO-001954-mm5 | ASO-002293 | AATTTccagattcactTTTA | 570 | 138885 | 138904 | | |
| ASO-001954-mm6 | ASO-002305 | TATTTccaagttcgctTTTA | 571 | 138885 | 138904 | | 0.31 |

Figure 6Y

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| SPC-15677-01 | ASO-002266 | TCCaaattcactttTA | 572 | 138885 | 138900 | | |
| SPC-15859-01 | ASO-002350 | TAtTTccaaattcactTTTA | 573 | 138885 | 138904 | | 0.03 |
| SPC-15861-01 | ASO-002374 | TAtTTccaaattcacTtTTA | 574 | 138885 | 138904 | | |
| SPC-15862-01 | ASO-002386 | TATTtccaaattcaCTttTA | 575 | 138885 | 138904 | | 0.18 |
| SPC-15863-01 | ASO-002227 | TATtTccaaattcactTTTA | 576 | 138885 | 138904 | | 0.04 |
| SPC-15865-01 | ASO-002245 | TAttTCcaaattcactTTTA | 577 | 138885 | 138904 | | 0.04 |
| SPC-15867-01 | ASO-002261 | TATtTccaaattcacTTtTA | 578 | 138885 | 138904 | | 0.09 |
| SPC-15869-01 | ASO-002276 | TATttCcaaattcactTTTA | 579 | 138885 | 138904 | | 0.05 |
| SPC-15871-01 | ASO-002228 | TATTtccaaattcaCtTtTA | 580 | 138885 | 138904 | | 0.11 |
| SPC-15882-01 | ASO-002255 | TATTtccaaattcactTTTA | 581 | 138885 | 138904 | | 0.03 |
| SPC-15886-01 | ASO-002285 | TATTtccaaattcacTTtTA | 582 | 138885 | 138904 | | 0.08 |
| SPC-15887-01 | ASO-002230 | TATTtccaaattcacTtTTA | 583 | 138885 | 138904 | | 0.07 |
| SPC-15890-01 | ASO-002256 | TATTtccaaattcAcTttTA | 584 | 138885 | 138904 | | 0.11 |
| SPC-15893-01 | ASO-002279 | TATTtccaaattcActTtTA | 585 | 138885 | 138904 | | 0.12 |
| ASO-002072 | ASO-002072 | TTAttTccaaattcaCTtTT | 586 | 138886 | 138905 | >100% | 0.13 |
| ASO-000755 | ASO-000755 | TTATTtccaaattcaCTTTT | 587 | 138886 | 138905 | >100% | 0.03 |
| ASO-002071 | ASO-002071 | TTaTtTccaaattcacTTTT | 588 | 138886 | 138905 | 89% | 0.05 |
| ASO-000760 | ASO-000760 | TTAtttccaaattcactTTT | 589 | 138886 | 138905 | >100% | 0.39 |
| ASO-001920 | ASO-001920 | TTATttccaaattcaCTTTT | 590 | 138886 | 138905 | >100% | 0.06 |
| ASO-002080 | ASO-002080 | TTatTTccaaattcacTTTT | 591 | 138886 | 138905 | >100% | 0.04 |
| ASO-001927 | ASO-001927 | TTATTtccaaattcacTTTT | 592 | 138886 | 138905 | >100% | 0.07 |
| ASO-001941 | ASO-001941 | TTaTTtccaaattcaCTtTT | 593 | 138886 | 138905 | >100% | 0.10 |
| ASO-002045 | ASO-002045 | TTaTttCcaaattcacTTTT | 594 | 138886 | 138905 | >100% | 0.06 |
| ASO-001934 | ASO-001934 | TtATTtccaaattcaCTtTT | 595 | 138886 | 138905 | 70% | 0.13 |

Figure 6Z

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-002074 | ASO-002074 | TTatTTccaaattcaCTtTT | 596 | 138886 | 138905 | 89% | 0.06 |
| ASO-002093 | ASO-002093 | TTAtTtccaaattcACttTT | 597 | 138886 | 138905 | >100% | 0.09 |
| ASO-002054 | ASO-002054 | TTaTTtccaaattcaCtTTT | 598 | 138886 | 138905 | 81% | 0.06 |
| ASO-002091 | ASO-002091 | TTaTtTccaaattcaCtTTT | 599 | 138886 | 138905 | >100% | 0.07 |
| ASO-002064 | ASO-002064 | TTaTtTccaaattcaCTtTT | 600 | 138886 | 138905 | >100% | 0.09 |
| ASO-002066 | ASO-002066 | TTATttccaaattCacTtTT | 601 | 138886 | 138905 | 96% | 0.05 |
| ASO-002044 | ASO-002044 | TTAtTtccaaattcaCtTTT | 602 | 138886 | 138905 | >100% | 0.11 |
| ASO-002047 | ASO-002047 | TTATttccaaattCaCttTT | 603 | 138886 | 138905 | >100% | 0.05 |
| ASO-002046 | ASO-002046 | TTatTtCcaaattcacTTTT | 604 | 138886 | 138905 | >100% | 0.11 |
| ASO-000765 | ASO-000765 | TTatttccaaattcacttTT | 605 | 138886 | 138905 | >100% | |
| ASO-000770 | ASO-000770 | TtatttccaaattcacttTT | 606 | 138886 | 138905 | >100% | |
| ASO-001941-mm1 | ASO-002317 | ATaTTtccaaattcaCTtTT | 622 | 138886 | 138905 | | 0.09 |
| ASO-001941-mm2 | ASO-002329 | TTaTTtccaaattcaCTtTA | 623 | 138886 | 138905 | | 0.06 |
| ASO-001941-mm3 | ASO-002341 | TTaTTtccaaattcaCTtTG | 624 | 138886 | 138905 | | 0.12 |
| ASO-001941-mm4 | ASO-002353 | ATaTTtccagattcaCTtTT | 625 | 138886 | 138905 | | 1.44 |
| ASO-001941-mm5 | ASO-002365 | TTaTTtccaagttcaCTtTC | 626 | 138886 | 138905 | | 0.53 |
| ASO-001941-mm6 | ASO-002377 | TTaTTtccagattcgCTtTT | 627 | 138886 | 138905 | | 1.27 |
| SPC-15676-01 | ASO-002258 | TTCcaaattcactTTT | 628 | 138886 | 138901 | | |
| SPC-15866-01 | ASO-002253 | TTAtTtccaaattcaCTtTT | 629 | 138886 | 138905 | | 0.20 |
| SPC-15870-01 | ASO-002283 | TTAttTccaaattcacTTTT | 630 | 138886 | 138905 | | 0.12 |

Figure 6AA

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| SPC-15875-01 | ASO-002262 | TTATttccaaattcacTTTT | 631 | 138886 | 138905 | | 0.07 |
| SPC-15876-01 | ASO-002270 | TTATttccaaattcaCtTTT | 632 | 138886 | 138905 | | 0.14 |
| SPC-15877-01 | ASO-002277 | TTATttccaaattcACttTT | 633 | 138886 | 138905 | | 0.06 |
| SPC-15881-01 | ASO-002247 | TTaTTtccaaattcacTTTT | 634 | 138886 | 138905 | | 0.04 |
| SPC-15884-01 | ASO-002271 | TTAtTtccaaattcacTTTT | 635 | 138886 | 138905 | | 0.11 |
| SPC-15885-01 | ASO-002278 | TTaTTtccaaattcACttTT | 636 | 138886 | 138905 | | 0.05 |
| SPC-15889-01 | ASO-002248 | TTaTTtccaaattcActTTT | 637 | 138886 | 138905 | | 0.04 |
| SPC-15891-01 | ASO-002264 | TTAtTtccaaattcActTTT | 638 | 138886 | 138905 | | 0.11 |
| SPC-15892-01 | ASO-002272 | TTaTTtccaaattcAcTtTT | 639 | 138886 | 138905 | | 0.06 |
| SPC-15894-01 | ASO-002286 | TTAtTtccaaattcAcTtTT | 640 | 138886 | 138905 | | 0.13 |
| SPC-15895-01 | ASO-002231 | TTATttccaaattcActTTT | 641 | 138886 | 138905 | | 0.05 |
| SPC-15896-01 | ASO-002240 | TTATttccaaattcAcTtTT | 642 | 138886 | 138905 | | 0.06 |
| ASO-002020 | ASO-002020 | AcTTTatttccaaattcactTTtaC | 643 | 138884 | 138908 | 18% | 0.18 |
| ASO-000756 | ASO-000756 | TTTATttccaaattcACTTT | 644 | 138887 | 138906 | >100% | 0.01 |
| ASO-001967 | ASO-001967 | TTtATttccaaattcACtTT | 645 | 138887 | 138906 | >100% | 0.04 |
| ASO-001955 | ASO-001955 | TTTATttccaaattcaCTTT | 646 | 138887 | 138906 | >100% | 0.05 |
| ASO-001948 | ASO-001948 | TTTAtttccaaattcACTTT | 647 | 138887 | 138906 | >100% | 0.04 |
| ASO-002086 | ASO-002086 | AcTTtatttccaaattcactTTTaC | 648 | 138884 | 138908 | 77% | 0.25 |
| ASO-002029 | ASO-002029 | ACtTtatttccaaattcacttTTaC | 649 | 138884 | 138908 | 29% | 0.37 |
| ASO-001961 | ASO-001961 | TtTATttccaaattcACtTT | 650 | 138887 | 138906 | 83% | 0.07 |
| ASO-002095 | ASO-002095 | ACTttatttccaaattcactTtTaC | 651 | 138884 | 138908 | 18% | 0.67 |
| ASO-002059 | ASO-002059 | ACTttatttccaaattcacttTTAC | 652 | 138884 | 138908 | 35% | 0.60 |
| ASO-002077 | ASO-002077 | ActttatttccaaattcactTTTAC | 653 | 138884 | 138908 | 87% | 0.89 |
| ASO-002021 | ASO-002021 | AcTTtatttccaaattcactttTAC | 654 | 138884 | 138908 | 24% | 0.64 |

Figure 6BB

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000761 | ASO-000761 | TTTatttccaaattcacTTT | 655 | 138887 | 138906 | >100% | 0.22 |
| ASO-002068 | ASO-002068 | ACtTtatttccaaattcactTtTAC | 656 | 138884 | 138908 | 35% | 0.43 |
| ASO-000766 | ASO-000766 | TTtatttccaaattcactTT | 657 | 138887 | 138906 | >100% | |
| ASO-000771 | ASO-000771 | TttatttccaaattcactTT | 658 | 138887 | 138906 | >100% | |
| ASO-001967-mm1 | ASO-002294 | ATtATttccaaattcACtTT | 669 | 138887 | 138906 | | 0.03 |
| ASO-001967-mm2 | ASO-002306 | TTtATttccaagttcACtTT | 670 | 138887 | 138906 | | 0.25 |
| ASO-001967-mm3 | ASO-002318 | GTtATttccaaattcACtTT | 671 | 138887 | 138906 | | 0.06 |
| ASO-001967-mm4 | ASO-002330 | ATtATttccagattcACtTT | 672 | 138887 | 138906 | | 1.37 |
| ASO-001967-mm5 | ASO-002342 | TTtATttccaggttcACtTT | 673 | 138887 | 138906 | | 6.28 |
| ASO-001967-mm6 | ASO-002354 | CTtATttccaagttcACtTT | 674 | 138887 | 138906 | | 0.75 |
| SPC-15675-01 | ASO-002250 | TTTCcaaattcacTTT | 675 | 138887 | 138902 | | |
| ASO-002006 | ASO-002006 | CTtTAtttccaaattcACTT | 676 | 138888 | 138907 | 0% | 0.02 |
| ASO-000757 | ASO-000757 | CTTTAtttccaaattCACTT | 677 | 138888 | 138907 | >100% | 0.01 |
| ASO-002017 | ASO-002017 | CTtTAtttccaaattcaCTT | 678 | 138888 | 138907 | >100% | 0.10 |
| ASO-001928 | ASO-001928 | CTTTAtttccaaattcACTT | 679 | 138888 | 138907 | >100% | 0.01 |
| ASO-001968 | ASO-001968 | ACTTTatttccaaattCACTT | 680 | 138888 | 138908 | >100% | 0.02 |
| ASO-001921 | ASO-001921 | CTTTatttccaaattCACTT | 681 | 138888 | 138907 | >100% | 0.02 |
| ASO-001989 | ASO-001989 | CTTTatttccaaattcACTT | 682 | 138888 | 138907 | 0% | 0.02 |
| ASO-001942 | ASO-001942 | CTtTAtttccaaattCAcTT | 683 | 138888 | 138907 | >100% | 0.03 |
| ASO-000128 | ASO-000128 | TTTccaaattcaCTT | 684 | 138888 | 138902 | | |

Figure 6CC

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-001935 | ASO-001935 | CtTTAtttccaaattCAcTT | 685 | 138888 | 138907 | >100% | 0.03 |
| ASO-000013 | ASO-000013 | ATTtccaaattcaCTT | 686 | 138888 | 138903 | 91% | 0.13 |
| ASO-002002 | ASO-002002 | CTTtAtttccaaattcACTT | 687 | 138888 | 138907 | >100% | 0.04 |
| ASO-000762 | ASO-000762 | CTTtatttccaaattcaCTT | 688 | 138888 | 138907 | >100% | 0.15 |
| ASO-002010 | ASO-002010 | CTTtatttccaaatTcaCTT | 689 | 138888 | 138907 | >100% | 0.14 |
| ASO-002005 | ASO-002005 | CTtTatttccaaattcaCTT | 690 | 138888 | 138907 | >100% | 0.11 |
| ASO-001998 | ASO-001998 | CTttAtttccaaattcACTT | 691 | 138888 | 138907 | 75% | 0.13 |
| ASO-002001 | ASO-002001 | CTTTatttccaaattcaCTT | 692 | 138888 | 138907 | >100% | 0.07 |
| ASO-001994 | ASO-001994 | CTtTatttccaaattcACTT | 693 | 138888 | 138907 | 45% | 0.06 |
| ASO-002013 | ASO-002013 | CTTtAtttccaaattcaCTT | 694 | 138888 | 138907 | 30% | 0.14 |
| ASO-002009 | ASO-002009 | CTttAtttccaaattcaCTT | 695 | 138888 | 138907 | >100% | 0.49 |
| ASO-000767 | ASO-000767 | CTttatttccaaattcacTT | 696 | 138888 | 138907 | >100% | |
| ASO-000772 | ASO-000772 | CtttatttccaaattcacTT | 697 | 138888 | 138907 | >100% | |
| BMT-214296 | ASO-214296 | CTTTActtccaaattCACTT | 698 | 138888 | 138907 | | 0.03 |
| ASO-000013-mm1 | ASO-002366 | GTTtccaaattcaCTT | 699 | 138888 | 138903 | | 0.18 |
| ASO-000013-mm2 | ASO-002378 | ATTtccaagttcaCTT | 700 | 138888 | 138903 | | 4.52 |
| ASO-000013-mm3 | ASO-002295 | ATTtccgaattcaCTT | 701 | 138888 | 138903 | | 3.17 |
| ASO-000013-mm4 | ASO-002307 | GTTtccagattcaCTT | 702 | 138888 | 138903 | | 0.80 |
| ASO-000013-mm5 | ASO-002319 | GTTtccaaattcaCTA | 703 | 138888 | 138903 | | 0.14 |
| ASO-000013-mm6 | ASO-002331 | ATTtccagattcaCTC | 704 | 138888 | 138903 | | 6.02 |

Figure 6DD

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-000898 | ASO-000898 | ATTtccaaattcaCTT | 705 | 138888 | 138903 | | |
| ASO-001942-mm1 | ASO-002363 | CTtTAtttccagattCAcTT | 706 | 138888 | 138907 | | 0.19 |
| ASO-001942-mm2 | ASO-002375 | CTtTAtttccaaattCAcTG | 707 | 138888 | 138907 | | 0.06 |
| ASO-001942-mm3 | ASO-002292 | CTtTAtttccaaattCGcTT | 708 | 138888 | 138907 | | 0.07 |
| ASO-001942-mm4 | ASO-002304 | CTtTAtttccagattCAcTA | 709 | 138888 | 138907 | | 0.13 |
| ASO-001942-mm5 | ASO-002316 | CTtTAtttccaggttCAcTT | 710 | 138888 | 138907 | | 0.50 |
| ASO-001942-mm6 | ASO-002328 | CTtTAtttccgaggttCAcTT | 711 | 138888 | 138907 | | 0.28 |
| SPC-15674-01 | ASO-002242 | ATTtccaaattcACTT | 712 | 138888 | 138903 | | |
| ASO-002004 | ASO-002004 | CTTTatttccaaatTcaCT | 713 | 138889 | 138907 | >100% | 0.03 |
| ASO-002012 | ASO-002012 | CTTtatttccaaatTcACT | 714 | 138889 | 138907 | >100% | 0.04 |
| ASO-001962 | ASO-001962 | ACTTTatttccaaattCACT | 715 | 138889 | 138908 | >100% | 0.02 |
| ASO-001956 | ASO-001956 | ACTTtatttccaaatTCACT | 716 | 138889 | 138908 | >100% | 0.01 |
| ASO-001949 | ASO-001949 | ACTTTatttccaaatTCACT | 717 | 138889 | 138908 | 98% | 0.02 |
| ASO-001987 | ASO-001987 | CTTTAtttccaaatTcACT | 718 | 138889 | 138907 | >100% | 0.02 |
| ASO-001991 | ASO-001991 | CTTTatttccaaatTCACT | 719 | 138889 | 138907 | >100% | 0.01 |
| ASO-001995 | ASO-001995 | CTTtatttccaaatTCACT | 720 | 138889 | 138907 | >100% | 0.02 |
| ASO-001992 | ASO-001992 | CTTTAtttccaaatTcaCT | 721 | 138889 | 138907 | >100% | 0.03 |
| ASO-002000 | ASO-002000 | CTTTatttccaaatTcACT | 722 | 138889 | 138907 | >100% | 0.02 |
| ASO-001996 | ASO-001996 | CTTTatttccaaatTCaCT | 723 | 138889 | 138907 | 93% | 0.01 |
| ASO-002008 | ASO-002008 | CTTtatttccaaatTCaCT | 724 | 138889 | 138907 | >100% | 0.05 |

Figure 6EE

| Oligomer Name | ASO Number | ASO Sequence | SEQ ID NO: | premRNA start NG_007398 | premRNA end NG_007398 | Oscillation data % control | $IC_{50}$ (µM) hTau neurons |
|---|---|---|---|---|---|---|---|
| ASO-002015 | ASO-002015 | CTTTAtttccaaatTCaCT | 725 | 138889 | 138907 | >100% | 0.02 |
| ASO-002016 | ASO-002016 | CTTtatttccaaatTcaCT | 726 | 138889 | 138907 | >100% | 0.12 |
| ASO-001986 | ASO-001986 | CTTTAtttccaaatTCACT | 727 | 138889 | 138907 | >100% | 0.02 |
| ASO-001995-mm1 | ASO-002343 | CTTtatttccagatTCACT | 732 | 138889 | 138907 | | 0.13 |
| ASO-001995-mm2 | ASO-002355 | CTTtgtttccaaatTCACT | 733 | 138889 | 138907 | | 0.11 |
| ASO-001995-mm3 | ASO-002367 | CTTtatttccaaatTCACG | 734 | 138889 | 138907 | | 0.02 |
| ASO-001995-mm4 | ASO-002379 | CTTtgtttccagatTCACT | 735 | 138889 | 138907 | | 1.21 |
| ASO-001995-mm5 | ASO-002296 | CTTtgtttccaagtTCACT | 736 | 138889 | 138907 | | 0.99 |
| ASO-001995-mm6 | ASO-002308 | CTTtatttccgagtTCACT | 737 | 138889 | 138907 | | 0.62 |
| SPC-15673-01 | ASO-002233 | TATttccaaattcACT | 738 | 138889 | 138904 | | |
| ASO-002003 | ASO-002003 | CTTTatttccaaatTCAC | 739 | 138890 | 138907 | >100% | 0.01 |
| ASO-002007 | ASO-002007 | CTTtatttccaaatTCAC | 740 | 138890 | 138907 | >100% | 0.02 |
| ASO-002011 | ASO-002011 | CTtTatttccaaatTcAC | 741 | 138890 | 138907 | >100% | 0.06 |
| ASO-001988 | ASO-001988 | CTTTAtttccaaatTcAC | 742 | 138890 | 138907 | >100% | 0.02 |
| ASO-001999 | ASO-001999 | CTTTAtttccaaatTCAC | 743 | 138890 | 138907 | >100% | 0.01 |
| ASO-001993 | ASO-001993 | CTTTatttccaaatTcAC | 744 | 138890 | 138907 | 6% | 0.01 |
| ASO-001997 | ASO-001997 | CTTtatttccaaatTcAC | 745 | 138890 | 138907 | >100% | 0.07 |
| ASO-001997-mm1 | ASO-002320 | CTTtatttccagatTcAC | 754 | 138890 | 138907 | | 1.06 |
| ASO-001997-mm2 | ASO-002332 | CTTtatttccgaatTcAC | 755 | 138890 | 138907 | | 0.97 |

Figure 6FF

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-001997-mm3 | ASO-002344 | CTTtgtttccaaatTcAC | 756 | 138890 | 138907 | | 1.54 |
| ASO-001997-mm4 | ASO-002356 | CTTtgtttccagatTcAC | 757 | 138890 | 138907 | | 4.36 |
| ASO-001997-mm5 | ASO-002368 | CTTtatttccaggtTcAC | 758 | 138890 | 138907 | | 3.33 |
| ASO-001997-mm6 | ASO-002380 | CTTtgtttccaagtTcAC | 759 | 138890 | 138907 | | 3.57 |
| SPC-15672-01 | ASO-002288 | TTAtttccaaattCAC | 760 | 138890 | 138905 | | |
| SPC-15671-01 | ASO-002280 | TTTatttccaaatTCA | 766 | 138891 | 138906 | | |
| SPC-15670-01 | ASO-002273 | CTTtatttccaaATTC | 767 | 138892 | 138907 | | |
| SPC-15669-01 | ASO-002265 | ACTTtatttccaAATT | 768 | 138893 | 138908 | | |
| ASO-000139 | ASO-000139 | AACtttatttccaAAT | 769 | 138894 | 138909 | | |
| SPC-15668-01 | ASO-002257 | AACTttatttccAAAT | 770 | 138894 | 138909 | | |
| SPC-15667-01 | ASO-002249 | TAACtttatttcCAAA | 771 | 138895 | 138910 | | |
| SPC-15666-01 | ASO-002241 | ATAActttatttcCAA | 772 | 138896 | 138911 | | 0.20 |
| ASO-000118 | ASO-000118 | AATaactttatttCCA | 773 | 138897 | 138912 | | 1.51 |
| SPC-15665-01 | ASO-002232 | AATaactttattTCCA | 774 | 138897 | 138912 | | |
| ASO-000101 | ASO-000101 | TAAtaactttattTCC | 775 | 138898 | 138913 | | |
| SPC-15664-01 | ASO-002287 | TAAtaactttatTTCC | 776 | 138898 | 138913 | | 1.89 |
| ASO-000148 | ASO-000148 | GTAataactttatTTC | 777 | 138899 | 138914 | | |
| ASO-000184 | ASO-000184 | TAAtaactttatTTC | 778 | 138899 | 138913 | | 10.00 |
| ASO-000112 | ASO-000112 | GTAataactttaTTT | 779 | 138900 | 138914 | | |
| ASO-000170 | ASO-000170 | AGTaataactttaTTT | 780 | 138900 | 138915 | | |
| ASO-000154 | ASO-000154 | GAGtaataactttATT | 781 | 138901 | 138916 | | |

Figure 6GG

| Oligomer Name | ASO Number | ASO Sequence | SEQ ID NO: | premRNA start NG_007398 | premRNA end NG_007398 | Oscillation data % control | $IC_{50}$ (μM) hTau neurons |
|---|---|---|---|---|---|---|---|
| ASO-000125 | ASO-000125 | AGTaataactttATT | 782 | 138901 | 138915 | | |
| ASO-000167 | ASO-000167 | GAGtaataacttTAT | 783 | 138902 | 138916 | | |
| ASO-000134 | ASO-000134 | AGAgtaataacttTAT | 784 | 138902 | 138917 | | |
| ASO-000175 | ASO-000175 | CAGagtaataactTTA | 785 | 138903 | 138918 | | |
| ASO-000178 | ASO-000178 | AGAgtaataactTTA | 786 | 138903 | 138917 | | |
| ASO-000138 | ASO-000138 | CAGagtaataacTTT | 787 | 138904 | 138918 | | |
| ASO-000171 | ASO-000171 | TCAgagtaataacTTT | 788 | 138904 | 138919 | | |
| ASO-000236 | ASO-000236 | ATCagagtaataaCTT | 789 | 138905 | 138920 | | |
| ASO-000127 | ASO-000127 | TCAgagtaataaCTT | 790 | 138905 | 138919 | | |
| ASO-000177 | ASO-000177 | CAGagtaataaCTT | 791 | 138905 | 138918 | | |
| ASO-000238 | ASO-000238 | AATcagagtaataACT | 792 | 138906 | 138921 | | |
| ASO-000222 | ASO-000222 | TAAtcagagtaatAAC | 793 | 138907 | 138922 | | |
| ASO-000307 | ASO-000307 | AATcagagtaatAAC | 794 | 138907 | 138921 | | |
| ASO-000204 | ASO-000204 | TTAatcagagtaaTAA | 795 | 138908 | 138923 | | |
| ASO-000330 | ASO-000330 | TAAtcagagtaaTAA | 796 | 138908 | 138922 | | |
| ASO-000326 | ASO-000326 | TTTaatcagagtaATA | 797 | 138909 | 138924 | | |
| ASO-000249 | ASO-000249 | TTTaatcagagtAAT | 798 | 138910 | 138924 | | |
| ASO-002022 | ASO-002022 | TTATttccaaattcaCTtTT | 799 | 138886 | 138905 | >100% | 0.09 |
| ASO-002026 | ASO-002026 | TTatTTccaaattcaCtTTT | 800 | 138886 | 138905 | >100% | 0.06 |
| ASO-002024 | ASO-002024 | TTAttTccaaattcaCtTTT | 801 | 138886 | 138905 | >100% | 0.11 |
| ASO-002049 | ASO-002049 | ACTTtatttccaaattcactTTtAC | 802 | 138884 | 138908 | 29% | 0.20 |
| ASO-002019 | ASO-002019 | ActtTatttccaaattcactTTtaC | 803 | 138884 | 138908 | 18% | 0.39 |

Figure 7A

| ASO Number | ASO Sequence | SEQ ID NO: | premRNA start NG_007398 | premRNA end NG_007398 | In vivo acute tolerability score | brain tau mRNA % remaining |
|---|---|---|---|---|---|---|
| ASO-000013 | ATTtccaaattcaCTT | 686 | 138888 | 138903 | 0 | 29 |
| ASO-000118 | AATaactttatttCCA | 773 | 138897 | 138912 | 0.17 | 59 |
| ASO-000125 | AGTaataactttATT | 782 | 138901 | 138915 | | |
| ASO-000128 | TTTccaaattcaCTT | 684 | 138888 | 138902 | | |
| ASO-000134 | AGAgtaataacttTAT | 784 | 138902 | 138917 | | |
| ASO-000170 | AGTaataactttaTTT | 780 | 138900 | 138915 | | |
| ASO-000178 | AGAgtaataactTTA | 786 | 138903 | 138917 | | |
| ASO-000204 | TTAatcagagtaaTAA | 795 | 138908 | 138923 | | |
| ASO-000249 | TTTaatcagagtAAT | 798 | 138910 | 138924 | | |
| ASO-000307 | AATcagagtaatAAC | 794 | 138907 | 138921 | | |
| ASO-000326 | TTTaatcagagtaATA | 797 | 138909 | 138924 | | |
| ASO-000330 | TAAtcagagtaaTAA | 796 | 138908 | 138922 | | |
| ASO-000388 | ATAgtcactctggTGA | 250 | 136650 | 136665 | 20 | |
| ASO-000389 | TAGccctaaagtcCCA | 53 | 135744 | 135759 | 3.83 | 32 |
| ASO-000390 | TAGtcactctggTGA | 251 | 136650 | 136664 | 16.67 | |
| ASO-000394 | AAGatacatgcgtCCT | 258 | 136695 | 136710 | 11.67 | |
| ASO-000396 | TACatgcgtccTTT | 256 | 136693 | 136706 | 20 | |
| ASO-000411 | CCCtaaagtccCAG | 51 | 135743 | 135756 | 13.33 | |
| ASO-000435 | TTAgccctaaagtCCC | 69 | 135745 | 135760 | 7.17 | |
| ASO-000442 | TAGccctaaagTCC | 71 | 135746 | 135759 | 10 | |
| ASO-000447 | TCAtagtcactctGGT | 255 | 136652 | 136667 | 13.67 | |
| ASO-000449 | AAGaggcacaagtCCT | 84 | 135776 | 135791 | 3.83 | |
| ASO-000451 | AAGcatttcaagaTAC | 262 | 136704 | 136719 | 7.33 | |
| ASO-000468 | ACCatgatcttagGCT | 365 | 137856 | 137871 | 18 | |
| ASO-000478 | GTCctaatcctgtGCT | 285 | 136905 | 136920 | 16 | |
| ASO-000520 | CGTgatcttccatCAC | 811 | 72944 | 72959 | 1.17 | 69 |
| ASO-000527 | TAGcaaacaggatACA | 392 | 138098 | 138113 | 8.33 | |
| ASO-000540 | CCTtaatttcaccCTC | 153 | 136053 | 136068 | 0.33 | 29 |
| ASO-000543 | CATgattgtgggcTTA | 417 | 138403 | 138418 | 20 | |
| ASO-000555 | CTTaatttcaccCTC | 154 | 136053 | 136067 | 4.17 | 38 |
| ASO-000558 | GAActggttagccCTA | 76 | 135752 | 135767 | 17.67 | |
| ASO-000566 | CCTtaatttcacCCT | 202 | 136054 | 136068 | 0 | 42 |
| ASO-000581 | ACTggttagccctAAA | 74 | 135750 | 135765 | 20 | |
| ASO-000603 | TCCcttaatttcACC | 227 | 136056 | 136070 | 0 | 48 |
| ASO-000614 | CAAacaggatacAGT | 390 | 138096 | 138110 | 10.67 | |

Figure 7B

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-000635 | CCCtaaaccatgaTCT | 370 | 137862 | 137877 | 2.33 | 71 |
| ASO-000642 | CCCttaatttcaCCC | 223 | 136055 | 136069 | 0.7 | 30 |
| ASO-000662 | CCCttaatttcacCCT | 201 | 136054 | 136069 | 0.5 | 20 |
| ASO-000753 | ATTTCcaaattcactTTTAC | 471 | 138884 | 138903 | 2.33 | 29 |
| ASO-000755 | TTATTtccaaattcaCTTTT | 587 | 138886 | 138905 | 1.67 | 18 |
| ASO-000756 | TTTATttccaaattcACTTT | 644 | 138887 | 138906 | 0.83 | 10 |
| ASO-000757 | CTTTAtttccaaattCACTT | 677 | 138888 | 138907 | 0.17 | 6 |
| ASO-000758 | ATTtccaaattcactttTAC | 485 | 138884 | 138903 | 0.17 | 49 |
| ASO-000759 | TATttccaaattcactttTTA | 548 | 138885 | 138904 | 0.33 | 77 |
| ASO-000760 | TTAtttccaaattcactTTT | 589 | 138886 | 138905 | 0 | 63 |
| ASO-000761 | TTTatttccaaattcacTTT | 655 | 138887 | 138906 | 0.33 | 44 |
| ASO-000762 | CTTtatttccaaattcaCTT | 688 | 138888 | 138907 | 0 | 30 |
| ASO-000773 | ATCacttcgaactCCT | 817 | 72933 | 72948 | 3.33 | 21 |
| ASO-000774 | CATcacttcgaacTCC | 818 | 72934 | 72949 | 3 | 18 |
| ASO-000775 | CCAtcacttcgaaCTC | 819 | 72935 | 72950 | 6.3 | |
| ASO-000829 | AAGatgaaatttgCTC | 7 | 134950 | 134965 | 4.67 | 28 |
| ASO-000830 | TACtagcccacccATC | 28 | 134974 | 134989 | 6.67 | |
| ASO-000898 | ATTtccaaattcaCTT | 705 | 138888 | 138903 | | |
| ASO-001778 | TTAgccctaaagtcccaGGT | 46 | 135741 | 135760 | 20 | |
| ASO-001779 | TAGccctaaagtcccagGTC | 43 | 135740 | 135759 | 20 | |
| ASO-001780 | GTTagccctaaagtcccAGG | 49 | 135742 | 135761 | 20 | |
| ASO-001781 | GGTtagccctaaagtccCAG | 52 | 135743 | 135762 | 20 | |
| ASO-001782 | TGGttagccctaaagtcCCA | 67 | 135744 | 135763 | 12.33 | |
| ASO-001919 | ATTTccaaattcactTTTAC | 474 | 138884 | 138903 | 4.33 | 16 |
| ASO-001920 | TTATttccaaattcaCTTTT | 590 | 138886 | 138905 | 1.5 | 27 |
| ASO-001921 | CTTTatttccaaattCACTT | 681 | 138888 | 138907 | 1 | 10 |
| ASO-001925 | TAGccctaaagtcCCA | 56 | 135744 | 135759 | 11 | |
| ASO-001926 | ATTTCcaaattcacttTTAC | 482 | 138884 | 138903 | 0.67 | 46 |
| ASO-001927 | TTATTtccaaattcacTTTT | 592 | 138886 | 138905 | 1.17 | 44 |
| ASO-001928 | CTTTAtttccaaattcACTT | 679 | 138888 | 138907 | 1.33 | 6 |
| ASO-001933 | AtTTCcaaattcactTTtAC | 473 | 138884 | 138903 | 0.83 | 20 |
| ASO-001934 | TtATTtccaaattcaCTtTT | 595 | 138886 | 138905 | 0.67 | 43 |
| ASO-001935 | CtTTAtttccaaattCAcTT | 685 | 138888 | 138907 | 1.33 | 19 |
| ASO-001940 | ATtTCcaaattcactTTtAC | 472 | 138884 | 138903 | 0.29 | 22 |
| ASO-001941 | TTaTTtccaaattcaCTtTT | 593 | 138886 | 138905 | 2 | 14 |
| ASO-001942 | CTtTAtttccaaattCAcTT | 683 | 138888 | 138907 | 2 | 16 |

Figure 7C

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-001947 | TATTtccaaattcacTTTTA | 533 | 138885 | 138904 | 3.83 | 26 |
| ASO-001948 | TTTAtttccaaattcACTTT | 647 | 138887 | 138906 | 0.33 | 11 |
| ASO-001953 | TAGccctaaagtcCCA | 60 | 135744 | 135759 | 4 | |
| ASO-001954 | TATTTccaaattcactTTTA | 532 | 138885 | 138904 | 1.17 | 23 |
| ASO-001955 | TTTATttccaaattcaCTTT | 646 | 138887 | 138906 | 0.5 | 19 |
| ASO-001956 | ACTTtatttccaaatTCACT | 716 | 138889 | 138908 | 0 | 15 |
| ASO-001960 | TaTTTccaaattcacTTtTA | 538 | 138885 | 138904 | 5 | 23 |
| ASO-001961 | TtTATttccaaattcACtTT | 650 | 138887 | 138906 | 2.17 | 25 |
| ASO-001962 | ACTTTatttccaaattCACT | 715 | 138889 | 138908 | 2 | 9 |
| ASO-001966 | TAtTTccaaattcacTTtTA | 535 | 138885 | 138904 | 4.33 | 23 |
| ASO-001967 | TTtATttccaaattcACtTT | 645 | 138887 | 138906 | 1 | 22 |
| ASO-001968 | ACTTTatttccaaattCACT T | 680 | 138888 | 138908 | 0.67 | 19 |
| ASO-001995 | CTTtatttccaaatTCACT | 720 | 138889 | 138907 | 0.17 | 57 |
| ASO-001997 | CTTtatttccaaatTcAC | 745 | 138890 | 138907 | | |
| ASO-001998 | CTttAtttccaaattcACTT | 691 | 138888 | 138907 | | |
| ASO-002002 | CTTtAtttccaaattcACTT | 687 | 138888 | 138907 | | |
| ASO-002005 | CTtTatttccaaattcaCTT | 690 | 138888 | 138907 | | |
| ASO-002007 | CTTtatttccaaatTCAC | 740 | 138890 | 138907 | 0.13 | 26 |
| ASO-002008 | CTTtatttccaaatTCaCT | 724 | 138889 | 138907 | 0.67 | 34 |
| ASO-002009 | CTttAtttccaaattcaCTT | 695 | 138888 | 138907 | | |
| ASO-002010 | CTTtatttccaaatTcaCTT | 689 | 138888 | 138907 | | |
| ASO-002011 | CTtTatttccaaatTcAC | 741 | 138890 | 138907 | | |
| ASO-002012 | CTTtatttccaaatTcACT | 714 | 138889 | 138907 | 0 | 36 |
| ASO-002016 | CTTtatttccaaatTcaCT | 726 | 138889 | 138907 | | |
| ASO-002022 | TTATttccaaattcaCTtTT | 799 | 138886 | 138905 | | |
| ASO-002023 | ATTTccaaattcacTTttAC | 484 | 138884 | 138903 | | |
| ASO-002024 | TTAttTccaaattcaCtTTT | 801 | 138886 | 138905 | | |
| ASO-002025 | TAttTcCaaattcactTTTA | 536 | 138885 | 138904 | | |
| ASO-002026 | TTatTTccaaattcaCtTTT | 800 | 138886 | 138905 | | |
| ASO-002027 | TATtTccaaattcaCtTtTA | 543 | 138885 | 138904 | | |
| ASO-002028 | TAtTTccaaattcaCttTTA | 545 | 138885 | 138904 | | |
| ASO-002033 | TATtTccaaattcacTtTTA | 537 | 138885 | 138904 | | |
| ASO-002034 | ATTtCcaaattcactTtTAC | 476 | 138884 | 138903 | 0.83 | 34 |
| ASO-002035 | TAtTtcCaaattcactTTTA | 528 | 138885 | 138904 | 0.5 | 42 |
| ASO-002036 | ATttCcAaattcacttTTAC | 477 | 138884 | 138903 | 0.33 | 34 |

Figure 7D

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-002037 | ATTTccaaattcaCtTttAC | 479 | 138884 | 138903 | | |
| ASO-002038 | ATTtCcaaattcacTtTtAC | 487 | 138884 | 138903 | 0 | 42 |
| ASO-002043 | ATtTCcaaattcacttTTAC | 467 | 138884 | 138903 | 0.83 | 48 |
| ASO-002044 | TTAtTtccaaattcaCtTTT | 602 | 138886 | 138905 | | |
| ASO-002045 | TTaTttCcaaattcacTTTT | 594 | 138886 | 138905 | | |
| ASO-002046 | TTatTtCcaaattcacTTTT | 604 | 138886 | 138905 | | |
| ASO-002047 | TTATttccaaattCaCttTT | 603 | 138886 | 138905 | | |
| ASO-002048 | TATtTccaaattcaCttTTA | 529 | 138885 | 138904 | 1.17 | 59 |
| ASO-002053 | TAtTtCcaaattcactTTTA | 530 | 138885 | 138904 | 1 | 47 |
| ASO-002054 | TTaTTtccaaattcaCtTTT | 598 | 138886 | 138905 | | |
| ASO-002055 | TAtTtCcaaattcacTTtTA | 527 | 138885 | 138904 | | |
| ASO-002056 | TAttTCcaaattcacTTtTA | 539 | 138885 | 138904 | | |
| ASO-002057 | ATTTccaaattcaCttTtAC | 481 | 138884 | 138903 | | |
| ASO-002058 | ATTtCcaaattcacTttTAC | 480 | 138884 | 138903 | 0.83 | 39 |
| ASO-002062 | ATTtcCaaattcactTTtAC | 469 | 138884 | 138903 | | |
| ASO-002063 | TATttCcaaattcacTTtTA | 540 | 138885 | 138904 | | |
| ASO-002064 | TTaTtTccaaattcaCTtTT | 600 | 138886 | 138905 | | |
| ASO-002065 | ATttCCaaattcactTTtAC | 486 | 138884 | 138903 | 0 | 36 |
| ASO-002066 | TTATttccaaattCacTtTT | 601 | 138886 | 138905 | | |
| ASO-002067 | TAtTTccaaattcaCTttTA | 531 | 138885 | 138904 | | |
| ASO-002071 | TTaTtTccaaattcacTTTT | 588 | 138886 | 138905 | 1 | 33 |
| ASO-002072 | TTAttTccaaattcaCTtTT | 586 | 138886 | 138905 | | |
| ASO-002073 | TAtTtCcaaattcacTtTTA | 542 | 138885 | 138904 | | |
| ASO-002074 | TTatTTccaaattcaCTtTT | 596 | 138886 | 138905 | | |
| ASO-002075 | TATtTccaaattcaCTttTA | 544 | 138885 | 138904 | | |
| ASO-002076 | ATtTCcaaattcacTTttAC | 468 | 138884 | 138903 | 0.33 | 60 |
| ASO-002077 | ActttatttccaaattcactTTT AC | 653 | 138884 | 138908 | | |
| ASO-002080 | TTatTTccaaattcacTTTT | 591 | 138886 | 138905 | 0 | 36 |
| ASO-002081 | TATttCcaaattcacTtTTA | 534 | 138885 | 138904 | | |
| ASO-002082 | ATtTcCaaattcactTtTAC | 470 | 138884 | 138903 | 0.13 | 31 |
| ASO-002083 | TAttTCcaaattcacTtTTA | 547 | 138885 | 138904 | 0.83 | 54 |
| ASO-002084 | ATTtCcaaattcacTTttAC | 478 | 138884 | 138903 | 0.33 | 52 |
| ASO-002085 | TAtTTccaaattcaCtTtTA | 546 | 138885 | 138904 | | |
| ASO-002086 | AcTTtatttccaaattcactTT TaC | 648 | 138884 | 138908 | | |
| ASO-002089 | TATTtccaaattcaCttTTA | 541 | 138885 | 138904 | | |

Figure 7E

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-002090 | ATTtcCaaattcactTtTAC | 466 | 138884 | 138903 | | |
| ASO-002091 | TTaTtTccaaattcaCtTTT | 599 | 138886 | 138905 | | |
| ASO-002092 | ATttCCaaattcactTtTAC | 483 | 138884 | 138903 | 0.48 | 14 |
| ASO-002093 | TTAtTtccaaattcACttTT | 597 | 138886 | 138905 | | |
| ASO-002094 | ATtTCcaaattcacTtTtAC | 475 | 138884 | 138903 | 0.5 | 61 |

Figure 12

| RhoA | a | c | t | t | t | a | t | t | t | c | c | a | a | a | t | a | c | a | c | t | t | c | t | t | t | | | | |
|---|---|---|---|---|---|---|---|---|---|---|---|---|---|---|---|---|---|---|---|---|---|---|---|---|---|---|---|---|---|
| | ASO Sequence | | | | | | | | | | | | | | | | | | | | | | | | | | | | |
| ASO Number | | | | | | | | | | | | | | | | | | | | | | | | | | CRC hTau (nM) | Tuj 1 Screening 5uM (% inhibition) | Rho CDI neurons 5uM (% inhibition) | 4 wk+ tolerability |
| ASO-000757 | | C | T | T | T | A | t | t | t | c | c | a | a | a | t | t | C | A | C | T | T | | | | | 12 | 77% | 74% | No |
| **ASO-0001967** | | | T | T | t | A | T | t | t | c | c | a | a | a | t | t | c | A | C | t | T | T | | | | **36** | **13%** | **20%** | **Yes** |
| ASO-000755 | | | | T | T | A | T | T | t | c | c | a | a | a | t | t | c | a | C | T | T | T | T | | | 34 | 53% | 25% | No |
| **ASO-001941** | | | | T | T | a | T | T | t | c | c | a | a | a | t | t | c | a | C | T | t | T | T | | | **102** | **30%** | **22%** | **Yes** |
| ASO-000753 | | | | | | A | T | T | T | C | c | a | a | a | t | t | c | a | c | t | T | T | T | A | C | 110 | 72% | 30% | No |
| **ASO-002038** | | | | | | A | T | T | t | C | c | a | a | a | t | t | c | a | c | T | t | T | t | A | C | **24** | **0%** | **11%** | **Yes** |
| **ASO-001933** | | | | | | A | t | T | T | C | c | a | a | a | t | t | c | a | c | t | T | T | t | A | C | **53** | **27%** | **12%** | **Yes** |
| **ASO-001940** | | | | | | A | T | t | T | C | c | a | a | a | t | t | c | a | c | t | T | T | t | A | C | **27** | **10%** | **0%** | **Yes** |

Figure 16A

| ASO Number | SEQ ID NO: | ASO Sequence | tau Human Transcript start (SEQID NO : 1) | Human Transcript tau end (SEQID NO : 1) | hTau Neurons Tau HC IC50 (uM) | Tau % inhibition (htau neurons) |
|---|---|---|---|---|---|---|
| ASO-000050 | 804 | GCGtgatcttcCAT | 72,947 | 72,960 | 0.14 | 100 |
| ASO-000054 | 805 | AGCgtgatcttccATC | 72,946 | 72,961 | 0.10 | 100 |
| ASO-000237 | 806 | AGCcatcctggttCAA | 72,907 | 72,922 | | 99 |
| ASO-000461 | 807 | CCAgcgtgatcttCCA | 72,948 | 72,963 | 0.05 | 99 |
| ASO-000462 | 808 | CCAgcgtgatcTTC | 72,950 | 72,963 | | 97 |
| ASO-000472 | 809 | GCGtgatcttccaTCA | 72,945 | 72,960 | | |
| ASO-000495 | 810 | TCCcagcgtgatcTTC | 72,950 | 72,965 | | |
| ASO-000520 | 811 | CGTgatcttccatCAC | 72,944 | 72,959 | 6.79 | 43 |
| ASO-000573 | 812 | CAGcgtgatcttcCAT | 72,947 | 72,962 | | 99 |
| ASO-000587 | 813 | TCCcagcgtgaTCT | 72,952 | 72,965 | | 91 |
| ASO-000596 | 814 | CGTgatcttccATC | 72,946 | 72,959 | 0.16 | 97 |
| ASO-000633 | 815 | CCCagcgtgatctTCC | 72,949 | 72,964 | | 99 |
| ASO-000659 | 816 | CCCagcgtgatCTT | 72,951 | 72,964 | | 94 |
| ASO-000773 | 817 | ATCacttcgaactCCT | 72,933 | 72,948 | 0.02 | 100 |
| ASO-000774 | 818 | CATcacttcgaacTCC | 72,934 | 72,949 | 0.02 | 100 |
| ASO-000775 | 819 | CCAtcacttcgaaCTC | 72,935 | 72,950 | 0.10 | 99 |
| ASO-000945 | 820 | TCCatcacttcgaactcCTG | 72,932 | 72,951 | | |
| ASO-000946 | 821 | TTCcatcacttcgaactCCT | 72,933 | 72,952 | | 99 |
| ASO-000947 | 822 | CTTccatcacttcgaacTCC | 72,934 | 72,953 | | 99 |
| ASO-000948 | 823 | TCTtccatcacttcgaaCTC | 72,935 | 72,954 | | 99 |
| ASO-001783 | 824 | CCAgcgtgatcttccatCAC | 72,944 | 72,963 | 0.15 | 98 |
| ASO-001784 | 825 | CCCagcgtgatcttccaTCA | 72,945 | 72,964 | 0.19 | 95 |
| ASO-001922 | 826 | CCAGcgtgatcttccATCAC | 72,944 | 72,963 | 0.55 | 91 |
| ASO-001923 | 827 | TCCCagcgtgatcttCCATC | 72,946 | 72,965 | | 41 |
| ASO-001929 | 828 | CCAGCgtgatcttccaTCAC | 72,944 | 72,963 | | 45 |
| ASO-001930 | 829 | TCCCAgcgtgatcttcCATC | 72,946 | 72,965 | | 37 |
| ASO-001936 | 830 | CcAGCgtgatcttccATcAC | 72,944 | 72,963 | | 83 |
| ASO-001937 | 831 | TcCCAgcgtgatcttCCaTC | 72,946 | 72,965 | | 67 |
| ASO-001943 | 832 | CCaGCgtgatcttccATcAC | 72,944 | 72,963 | | 64 |
| ASO-001944 | 833 | TCcCAgcgtgatcttCCaTC | 72,946 | 72,965 | | 59 |
| ASO-001950 | 834 | CCCAgcgtgatcttcCATCA | 72,945 | 72,964 | | 44 |
| ASO-001951 | 835 | CGTCccagcgtgatcTTCCA | 72,948 | 72,967 | | 38 |
| ASO-001957 | 836 | CCCAGcgtgatcttccATCA | 72,945 | 72,964 | | 53 |
| ASO-001958 | 837 | CGTCCcagcgtgatctTCCA | 72,948 | 72,967 | | 16 |
| ASO-001963 | 838 | CcCAGcgtgatcttcCAtCA | 72,945 | 72,964 | 1.05 | 89 |
| ASO-001964 | 839 | CgTCCcagcgtgatcTTcCA | 72,948 | 72,967 | | 29 |
| ASO-001969 | 840 | CCcAGcgtgatcttcCAtCA | 72,945 | 72,964 | 0.89 | 82 |

Figure 16B

| ASO Number | SEQ ID NO: | ASO Sequence | tau Human Transcript start (SEQID NO.: 1) | Human Transcript tau end (SEQID NO.: 1) | hTau Neurons Tau HC IC50 (uM) | Tau % inhibition (htau neurons) |
|---|---|---|---|---|---|---|
| ASO-001970 | 841 | CGtCCcagcgtgatcTTcCA | 72,948 | 72,967 | | 58 |
| ASO-001978 | 842 | TCCcagcgtgatcttccATC | 72,946 | 72,965 | 0.27 | 97 |
| ASO-002100 | 843 | CATCacttcgaaCtCC | 72,934 | 72,949 | 0.02 | 100 |
| ASO-002101 | 844 | CCatcacttCGaacTC | 72,935 | 72,950 | 0.10 | 100 |
| ASO-002102 | 845 | CaTCACttcgaacTcCT | 72,933 | 72,949 | 0.07 | 99 |
| ASO-002103 | 846 | TCCatCacttcgaaCTC | 72,935 | 72,951 | 0.15 | 98 |
| ASO-002104 | 847 | CttCcatcacttCgaaCT | 72,936 | 72,953 | 0.22 | 99 |
| ASO-002105 | 848 | CtTcCATcacttcgaaCTCC | 72,934 | 72,953 | 0.97 | 76 |
| ASO-002106 | 849 | TCTtcCAtcacttcgaacTCCT | 72,933 | 72,954 | 0.49 | 94 |
| ASO-002112 | 850 | CAtCActtcgaaCtCC | 72,934 | 72,949 | 0.02 | 100 |
| ASO-002113 | 851 | CCatcacttCgaaCTC | 72,935 | 72,950 | 0.08 | 100 |
| ASO-002114 | 852 | CCaTCacttcgaaCtCC | 72,934 | 72,950 | 0.20 | 97 |
| ASO-002115 | 853 | TcCATcacttcgaaCTC | 72,935 | 72,951 | 0.04 | 100 |
| ASO-002116 | 854 | TCCatCacttcgaaCTCC | 72,934 | 72,951 | 1.31 | 72 |
| ASO-002117 | 855 | CTTCcatcacttcgaaCTCC | 72,934 | 72,953 | 0.86 | 83 |
| ASO-002118 | 856 | TCTTCcatcacttcgaaCTCCT | 72,933 | 72,954 | 5.91 | 16 |
| ASO-002124 | 857 | CATCacttcgaacTCC | 72,934 | 72,949 | 0.01 | 98 |
| ASO-002125 | 858 | CcAtCActtcgaaCTC | 72,935 | 72,950 | 0.10 | 98 |
| ASO-002126 | 859 | CCaTCacttcgaacTCC | 72,934 | 72,950 | 0.09 | 100 |
| ASO-002127 | 860 | TCCatcacttcgaaCTC | 72,935 | 72,951 | 0.04 | 98 |
| ASO-002128 | 861 | TCcAtCacttcgaaCtCC | 72,934 | 72,951 | 0.23 | 96 |
| ASO-002129 | 862 | TCttCcatcacttCGaaCTC | 72,935 | 72,954 | 0.14 | 99 |
| ASO-002136 | 863 | CATCacTtcgaactCC | 72,934 | 72,949 | 0.01 | 99 |
| ASO-002137 | 864 | CcaTCacttcgaaCTC | 72,935 | 72,950 | 0.02 | 100 |
| ASO-002138 | 865 | CCaTcACttcgaacTCC | 72,934 | 72,950 | 0.06 | 99 |
| ASO-002139 | 866 | CCATcacttcgaaCTcCT | 72,933 | 72,950 | 0.20 | 99 |
| ASO-002140 | 867 | TCCAtcacttcgaaCTCC | 72,934 | 72,951 | 0.13 | 98 |
| ASO-002141 | 868 | TCttCcatcacttCgaaCTC | 72,935 | 72,954 | 0.10 | 99 |
| ASO-002148 | 869 | CATCacttcgaactCC | 72,934 | 72,949 | 0.01 | 100 |
| ASO-002149 | 870 | CcatCActtcgaaCTC | 72,935 | 72,950 | 0.04 | 100 |
| ASO-002150 | 871 | CcaTCaCttcgaactCC | 72,934 | 72,950 | 0.02 | 100 |
| ASO-002151 | 872 | CcATcACttcgaacTcCT | 72,933 | 72,950 | 0.03 | 100 |
| ASO-002152 | 873 | TCCatcacttcgaacTCC | 72,934 | 72,951 | 0.02 | 100 |
| ASO-002153 | 874 | TTCCatCacttcgaaCtCCT | 72,933 | 72,952 | 5.37 | 40 |
| ASO-002160 | 875 | CAtCAcTtcgaactCC | 72,934 | 72,949 | 0.01 | 100 |
| ASO-002161 | 876 | CATCaCttcgaacTcCT | 72,933 | 72,949 | 0.09 | 99 |
| ASO-002162 | 877 | CCAtcacttcgaacTCC | 72,934 | 72,950 | 0.06 | 99 |
| ASO-002163 | 878 | CCATcacttcgaacTCCT | 72,933 | 72,950 | 0.13 | 100 |
| ASO-002164 | 879 | TtCCatcacttCGaaCTC | 72,935 | 72,952 | 0.12 | 95 |

Figure 16C

| ASO Number | SEQ ID NO: | ASO Sequence | tau Human Transcript start (SEQID NO.: 1) | Human Transcript tau end (SEQID NO.: 1) | hTau Neurons Tau HC IC50 (uM) | Tau % inhibition (htau neurons) |
|---|---|---|---|---|---|---|
| ASO-002165 | 880 | TtCCAtCacttcgaaCtCCT | 72,933 | 72,952 | 2.61 | 58 |
| ASO-002172 | 881 | CAtCaCTtcgaactCC | 72,934 | 72,949 | 0.02 | 100 |
| ASO-002173 | 882 | CATcACttcgaacTcCT | 72,933 | 72,949 | 0.02 | 100 |
| ASO-002174 | 883 | TCCatcacttCGaaCTC | 72,935 | 72,951 | 0.22 | 99 |
| ASO-002175 | 884 | CCAtcacttcgaactCCT | 72,933 | 72,950 | 0.07 | 99 |
| ASO-002176 | 885 | TtCCatcacttCgaaCTC | 72,935 | 72,952 | 0.07 | 97 |
| ASO-002177 | 886 | TtCCaTCacttcgaaCtCCT | 72,933 | 72,952 | 3.00 | 52 |
| ASO-002184 | 887 | CCatcacttCGaaCTC | 72,935 | 72,950 | 0.21 | 99 |
| ASO-002185 | 888 | CAtCACttcgaacTcCT | 72,933 | 72,949 | 0.04 | 100 |
| ASO-002186 | 889 | TCCatcacttCgaaCTC | 72,935 | 72,951 | 0.04 | 98 |
| ASO-002187 | 890 | CttCcatcacttCGaaCT | 72,936 | 72,953 | 0.14 | 100 |
| ASO-002188 | 891 | TTCcatcacttcgaaCTC | 72,935 | 72,952 | 0.07 | 99 |
| ASO-002189 | 892 | TTCCatcacttcgaacTCCT | 72,933 | 72,952 | 0.23 | 99 |
| ASO-002623 | 893 | CATcacttcgaacTCC | 72934 | 72949 | | 6 |
| ASO-002667 | 894 | CATCacttcgaactCC | 72934 | 72949 | | 41 |
| ASO-002674 | 895 | CATCacttcgaactCC | 72934 | 72949 | | 7 |
| ASO-002631 | 896 | CATcacttcgaacTCC | 72934 | 72949 | | 4 |
| ASO-002639 | 897 | CATcacttcgaacTCC | 72934 | 72949 | | 13 |
| ASO-002624 | 898 | CATCacttcgaactCC | 72934 | 72949 | | 36 |
| ASO-002637 | 899 | CATcacttcgaacTCC | 72934 | 72949 | | 100 |
| ASO-002651 | 900 | CATCacttcgaactCC | 72934 | 72949 | | 100 |

Figure 16D

| ASO Number | ASO Sequence | tau Human Transcript start (SEQID NO.: 1) | Human Transcript tau end (SEQID NO.: 1) | Chemical Structure |
|---|---|---|---|---|
| ASO-000050 | GCGtgatcttcCAT | 72,947 | 72,960 | OxyGs OxyMCs OxyGs DNAts DNAgs DNAas DNAts DNAcs DNAts DNAts DNAcs OxyMCs OxyAs OxyT |
| ASO-000054 | AGCgtgatcttccATC | 72,946 | 72,961 | OxyAs OxyGs OxyMCs DNAgs DNAts DNAgs DNAas DNAts DNAcs DNAts DNAts DNAcs DNAcs OxyAs OxyTs OxyMC |
| ASO-000237 | AGCcatcctggttCAA | 72,907 | 72,922 | OxyAs OxyGs OxyMCs DNAcs DNAas DNAts DNAcs DNAcs DNAts DNAgs DNAgs DNAts DNAts OxyMCs OxyAs OxyA |
| ASO-000461 | CCAgcgtgatcttCCA | 72,948 | 72,963 | OxyMCs OxyMCs OxyAs DNAgs DNAmcs DNAgs DNAts DNAgs DNAas DNAts DNAcs DNAts DNAts OxyMCs OxyMCs OxyA |
| ASO-000462 | CCAgcgtgatcTTC | 72,950 | 72,963 | OxyMCs OxyMCs OxyAs DNAgs DNAmcs DNAgs DNAts DNAgs DNAas DNAts DNAcs OxyTs OxyTs OxyMC |
| ASO-000472 | GCGtgatcttccaTCA | 72,945 | 72,960 | OxyGs OxyMCs OxyGs DNAts DNAgs DNAas DNAts DNAcs DNAts DNAts DNAcs DNAcs DNAas OxyTs OxyMCs OxyA |
| ASO-000495 | TCCcagcgtgatcTTC | 72,950 | 72,965 | OxyTs OxyMCs OxyMCs DNAcs DNAas DNAgs DNAmcs DNAgs DNAts DNAgs DNAas DNAts DNAcs OxyTs OxyTs OxyMC |
| ASO-000520 | CGTgatcttccatCAC | 72,944 | 72,959 | OxyMCs OxyGs OxyTs DNAgs DNAas DNAts DNAcs DNAts DNAts DNAcs DNAcs DNAas DNAts OxyMCs OxyAs OxyMC |
| ASO-000573 | CAGcgtgatcttcCAT | 72,947 | 72,962 | OxyMCs OxyAs OxyGs DNAmcs DNAgs DNAts DNAgs DNAas DNAts DNAcs DNAts DNAts DNAcs OxyMCs OxyAs OxyT |
| ASO-000587 | TCCcagcgtgaTCT | 72,952 | 72,965 | OxyTs OxyMCs OxyMCs DNAcs DNAas DNAgs DNAmcs DNAgs DNAts DNAgs DNAas OxyTs OxyMCs OxyT |
| ASO-000596 | CGTgatcttccATC | 72,946 | 72,959 | OxyMCs OxyGs OxyTs DNAgs DNAas DNAts DNAcs DNAts DNAts DNAcs DNAcs OxyAs OxyTs OxyMC |
| ASO-000633 | CCCagcgtgatctTCC | 72,949 | 72,964 | OxyMCs OxyMCs OxyMCs DNAas DNAgs DNAmcs DNAgs DNAts DNAgs DNAas DNAts DNAcs DNAts OxyTs OxyMCs OxyMC |

Figure 16E

| ASO Number | ASO Sequence | tau Human Transcript start (SEQID NO.: 1) | Human Transcript tau end (SEQID NO.: 1) | Chemical Structure |
|---|---|---|---|---|
| ASO-000659 | CCCagcgtgatCTT | 72,951 | 72,964 | OxyMCs OxyMCs OxyMCs DNAas DNAgs DNAmcs DNAgs DNAts DNAgs DNAas DNAts OxyMCs OxyTs OxyT |
| ASO-000773 | ATCacttcgaactCCT | 72,933 | 72,948 | OxyAs OxyTs OxyMCs DNAas DNAcs DNAts DNAts DNAmcs DNAgs DNAas DNAas DNAcs DNAts OxyMCs OxyMCs OxyT |
| ASO-000774 | CATcacttcgaacTCC | 72,934 | 72,949 | OxyMCs OxyAs OxyTs DNAcs DNAas DNAcs DNAts DNAts DNAmcs DNAgs DNAas DNAas DNAcs OxyTs OxyMCs OxyMC |
| ASO-000775 | CCAtcacttcgaaCTC | 72,935 | 72,950 | OxyMCs OxyMCs OxyAs DNAts DNAcs DNAas DNAcs DNAts DNAts DNAmcs DNAgs DNAas DNAas OxyMCs OxyTs OxyMC |
| ASO-000945 | TCCatcacttcgaactcCTG | 72,932 | 72,951 | OxyTs OxyMCs OxyMCs DNAas DNAts DNAcs DNAas DNAcs DNAts DNAts DNAmcs DNAgs DNAas DNAas DNAcs DNAts DNAcs OxyMCs OxyTs OxyG |
| ASO-000946 | TTCcatcacttcgaactCCT | 72,933 | 72,952 | OxyTs OxyTs OxyMCs DNAcs DNAas DNAts DNAcs DNAas DNAcs DNAts DNAts DNAmcs DNAgs DNAas DNAas DNAcs DNAts OxyMCs OxyMCs OxyT |
| ASO-000947 | CTTccatcacttcgaacTCC | 72,934 | 72,953 | OxyMCs OxyTs OxyTs DNAcs DNAcs DNAas DNAts DNAcs DNAas DNAcs DNAts DNAts DNAmcs DNAgs DNAas DNAas DNAcs OxyTs OxyMCs OxyMC |
| ASO-000948 | TCTtccatcacttcgaaCTC | 72,935 | 72,954 | OxyTs OxyMCs OxyTs DNAts DNAcs DNAcs DNAas DNAts DNAcs DNAas DNAcs DNAts DNAts DNAmcs DNAgs DNAas DNAas OxyMCs OxyTs OxyMC |
| ASO-001783 | CCAgcgtgatcttccatCAC | 72,944 | 72,963 | OxyMCs OxyMCs OxyAs DNAgs DNAcs DNAgs DNAts DNAgs DNAas DNAts DNAcs DNAts DNAts DNAcs DNAcs DNAas DNAts OxyMCs OxyAs OxyMC |
| ASO-001784 | CCCagcgtgatcttccaTCA | 72,945 | 72,964 | OxyMCs OxyMCs OxyMCs DNAas DNAgs DNAcs DNAgs DNAts DNAgs DNAas DNAts DNAcs DNAts DNAts DNAcs DNAcs DNAas OxyTs OxyMCs OxyA |
| ASO-001922 | CCAGcgtgatcttccATCAC | 72,944 | 72,963 | OxyMCs OxyMCs OxyAs OxyGs DNAcs DNAgs DNAts DNAgs DNAas DNAts DNAcs DNAts DNAts DNAcs DNAcs OxyAs OxyTs OxyMCs OxyAs OxyMC |
| ASO-001923 | TCCCagcgtgatcttCCATC | 72,946 | 72,965 | OxyTs OxyMCs OxyMCs OxyMCs DNAas DNAgs DNAcs DNAgs DNAts DNAgs DNAas DNAts DNAcs DNAts DNAts OxyMCs OxyMCs OxyAs OxyTs OxyMC |
| ASO-001929 | CCAGCgtgatcttccaTCAC | 72,944 | 72,963 | OxyMCs OxyMCs OxyAs OxyGs OxyMCs DNAgs DNAts DNAgs DNAas DNAts DNAcs DNAts DNAts DNAcs DNAcs DNAas OxyTs OxyMCs OxyAs OxyMC |

Figure 16F

| ASO Number. | ASO Sequence | tau Human Transcript start (SEQID NO.: 1) | Human Transcript tau end (SEQID NO.: 1) | Chemical Structure |
|---|---|---|---|---|
| ASO-001930 | TCCCAgcgtgatcttcCATC | 72,946 | 72,965 | OxyTs OxyMCs OxyMCs OxyMCs OxyAs DNAgs DNAcs DNAgs DNAts DNAgs DNAas DNAts DNAcs DNAts DNAts DNAcs OxyMCs OxyAs OxyTs OxyMC |
| ASO-001936 | CcAGCgtgatcttccATcAC | 72,944 | 72,963 | OxyMCs DNAcs OxyAs OxyGs OxyMCs DNAgs DNAts DNAgs DNAas DNAts DNAcs DNAts DNAts DNAcs DNAcs OxyAs OxyTs DNAcs OxyAs OxyMC |
| ASO-001937 | TcCCAgcgtgatcttCCaTC | 72,946 | 72,965 | OxyTs DNAcs OxyMCs OxyMCs OxyAs DNAgs DNAcs DNAgs DNAts DNAgs DNAas DNAts DNAcs DNAts DNAts OxyMCs OxyMCs DNAas OxyTs OxyMC |
| ASO-001943 | CCaGCgtgatcttccATcAC | 72,944 | 72,963 | OxyMCs OxyMCs DNAas OxyGs OxyMCs DNAgs DNAts DNAgs DNAas DNAts DNAcs DNAts DNAts DNAcs DNAcs OxyAs OxyTs DNAcs OxyAs OxyMC |
| ASO-001944 | TCcCAgcgtgatcttCCaTC | 72,946 | 72,965 | OxyTs OxyMCs DNAcs OxyMCs OxyAs DNAgs DNAcs DNAgs DNAts DNAgs DNAas DNAts DNAcs DNAts DNAts OxyMCs OxyMCs DNAas OxyTs OxyMC |
| ASO-001950 | CCCAgcgtgatcttcCATCA | 72,945 | 72,964 | OxyMCs OxyMCs OxyMCs OxyAs DNAgs DNAcs DNAgs DNAts DNAgs DNAas DNAts DNAcs DNAts DNAts DNAcs OxyMCs OxyAs OxyTs OxyMCs OxyA |
| ASO-001951 | CGTCccagcgtgatcTTCCA | 72,948 | 72,967 | OxyMCs OxyGs OxyTs OxyMCs DNAcs DNAcs DNAas DNAgs DNAcs DNAgs DNAts DNAgs DNAas DNAts DNAcs OxyTs OxyTs OxyMCs OxyMCs OxyA |
| ASO-001957 | CCCAGcgtgatcttccATCA | 72,945 | 72,964 | OxyMCs OxyMCs OxyMCs OxyAs OxyGs DNAcs DNAgs DNAts DNAgs DNAas DNAts DNAcs DNAts DNAts DNAcs DNAcs OxyAs OxyTs OxyMCs OxyA |
| ASO-001958 | CGTCCcagcgtgatctTCCA | 72,948 | 72,967 | OxyMCs OxyGs OxyTs OxyMCs OxyMCs DNAcs DNAas DNAgs DNAcs DNAgs DNAts DNAgs DNAas DNAts DNAcs DNAts OxyTs OxyMCs OxyMCs OxyA |
| ASO-001963 | CcCAGcgtgatcttcCAtCA | 72,945 | 72,964 | OxyMCs DNAcs OxyMCs OxyAs OxyGs DNAcs DNAgs DNAts DNAgs DNAas DNAts DNAcs DNAts DNAts DNAcs OxyMCs OxyAs DNAts OxyMCs OxyA |
| ASO-001964 | CgTCCcagcgtgatcTTcCA | 72,948 | 72,967 | OxyMCs DNAgs OxyTs OxyMCs OxyMCs DNAcs DNAas DNAgs DNAcs DNAgs DNAts DNAgs DNAas DNAts DNAcs OxyTs OxyTs DNAcs OxyMCs OxyA |
| ASO-001969 | CCcAGcgtgatcttcCAtCA | 72,945 | 72,964 | OxyMCs OxyMCs DNAcs OxyAs OxyGs DNAcs DNAgs DNAts DNAgs DNAas DNAts DNAcs DNAts DNAts DNAcs OxyMCs OxyAs DNAts OxyMCs OxyA |
| ASO-001970 | CGtCCcagcgtgatcTTcCA | 72,948 | 72,967 | OxyMCs OxyGs DNAts OxyMCs OxyMCs DNAcs DNAas DNAgs DNAcs DNAgs DNAts DNAgs DNAas DNAts DNAcs OxyTs OxyTs DNAcs OxyMCs OxyA |

Figure 16G

| ASO Number | ASO Sequence | tau Human Transcript start (SEQID NO.: 1) | Human Transcript tau end (SEQID NO.: 1) | Chemical Structure |
|---|---|---|---|---|
| ASO-001978 | TCCcagcgtgatcttccATC | 72,946 | 72,965 | OxyTs OxyMCs OxyMCs DNAcs DNAas DNAgs DNAcs DNAgs DNAts DNAgs DNAas DNAts DNAcs DNAts DNAts DNAcs DNAcs OxyAs OxyTs OxyMC |
| ASO-002100 | CATCacttcgaaCtCC | 72,934 | 72,949 | OxyMCs OxyAs OxyTs OxyMCs DNAas DNAcs DNAts DNAts DNAcs DNAgs DNAas DNAas OxyMCs DNAts OxyMCs OxyMC |
| ASO-002101 | CCatcacttCGaacTC | 72,935 | 72,950 | OxyMCs OxyMCs DNAas DNAts DNAcs DNAas DNAcs DNAts DNAts OxyMCs OxyGs DNAas DNAas DNAcs OxyTs OxyMC |
| ASO-002102 | CaTCACttcgaacTcCT | 72,933 | 72,949 | OxyMCs DNAas OxyTs OxyMCs OxyAs OxyMCs DNAts DNAts DNAcs DNAgs DNAas DNAas DNAcs OxyTs DNAcs OxyMCs OxyT |
| ASO-002103 | TCCatCacttcgaaCTC | 72,935 | 72,951 | OxyTs OxyMCs OxyMCs DNAas DNAts OxyMCs DNAas DNAcs DNAts DNAts DNAcs DNAgs DNAas DNAas OxyMCs OxyTs OxyMC |
| ASO-002104 | CttCcatcacttCgaaCT | 72,936 | 72,953 | OxyMCs DNAts DNAts OxyMCs DNAcs DNAas DNAts DNAcs DNAas DNAcs DNAts DNAts OxyMCs DNAgs DNAas DNAas OxyMCs OxyT |
| ASO-002105 | CtTcCATcacttcgaaCTCC | 72,934 | 72,953 | OxyMCs DNAts OxyTs DNAcs OxyMCs OxyAs OxyTs DNAcs DNAas DNAcs DNAts DNAts DNAcs DNAgs DNAas DNAas OxyMCs OxyTs OxyMCs OxyMC |
| ASO-002106 | TCTtcCAtcacttcgaacTCCT | 72,933 | 72,954 | OxyTs OxyMCs OxyTs DNAts DNAcs OxyMCs OxyAs DNAts DNAcs DNAas DNAcs DNAts DNAts DNAcs DNAgs DNAas DNAas DNAcs OxyTs OxyMCs OxyMCs OxyT |
| ASO-002112 | CAtCActtcgaaCtCC | 72,934 | 72,949 | OxyMCs OxyAs DNAts OxyMCs OxyAs DNAcs DNAts DNAts DNAcs DNAgs DNAas DNAas OxyMCs DNAts OxyMCs OxyMC |
| ASO-002113 | CCatcacttCgaaCTC | 72,935 | 72,950 | OxyMCs OxyMCs DNAas DNAts DNAcs DNAas DNAcs DNAts DNAts OxyMCs DNAgs DNAas DNAas OxyMCs OxyTs OxyMC |
| ASO-002114 | CCaTCacttcgaaCtCC | 72,934 | 72,950 | OxyMCs OxyMCs DNAas OxyTs OxyMCs DNAas DNAcs DNAts DNAts DNAcs DNAgs DNAas DNAas OxyMCs DNAts OxyMCs OxyMC |
| ASO-002115 | TcCATcacttcgaaCTC | 72,935 | 72,951 | OxyTs DNAcs OxyMCs OxyAs OxyTs DNAcs DNAas DNAcs DNAts DNAts DNAcs DNAgs DNAas DNAas OxyMCs OxyTs OxyMC |

Figure 16H

| ASO Number | ASO Sequence | tau Human Transcript start (SEQID NO.: 1) | Human Transcript tau end (SEQID NO.: 1) | Chemical Structure |
|---|---|---|---|---|
| ASO-002116 | TCCatCacttcgaaCTCC | 72,934 | 72,951 | OxyTs OxyMCs OxyMCs DNAas DNAts OxyMCs DNAas DNAcs DNAts DNAts DNAcs DNAgs DNAas DNAas OxyMCs OxyTs OxyMCs OxyMC |
| ASO-002117 | CTTCcatcacttcgaaCTCC | 72,934 | 72,953 | OxyMCs OxyTs OxyTs OxyMCs DNAcs DNAas DNAts DNAcs DNAas DNAcs DNAts DNAts DNAcs DNAgs DNAas DNAas OxyMCs OxyTs OxyMCs OxyMC |
| ASO-002118 | TCTTCcatcacttcgaaCTCCT | 72,933 | 72,954 | OxyTs OxyMCs OxyTs OxyTs OxyMCs DNAcs DNAas DNAts DNAcs DNAas DNAcs DNAts DNAts DNAcs DNAgs DNAas DNAas OxyMCs OxyTs OxyMCs OxyMCs OxyT |
| ASO-002124 | CATCacttcgaacTCC | 72,934 | 72,949 | OxyMCs OxyAs OxyTs OxyMCs DNAas DNAcs DNAts DNAts DNAcs DNAgs DNAas DNAas DNAcs OxyTs OxyMCs OxyMC |
| ASO-002125 | CcAtCActtcgaaCTC | 72,935 | 72,950 | OxyMCs DNAcs OxyAs DNAts OxyMCs OxyAs DNAcs DNAts DNAts DNAcs DNAgs DNAas DNAas OxyMCs OxyTs OxyMC |
| ASO-002126 | CCaTCacttcgaacTCC | 72,934 | 72,950 | OxyMCs OxyMCs DNAas OxyTs OxyMCs DNAas DNAcs DNAts DNAts DNAcs DNAgs DNAas DNAas DNAcs OxyTs OxyMCs OxyMC |
| ASO-002127 | TCCatcacttcgaaCTC | 72,935 | 72,951 | OxyTs OxyMCs OxyMCs DNAas DNAts DNAcs DNAas DNAcs DNAts DNAts DNAcs DNAgs DNAas DNAas OxyMCs OxyTs OxyMC |
| ASO-002128 | TCcAtCacttcgaaCtCC | 72,934 | 72,951 | OxyTs OxyMCs DNAcs OxyAs DNAts OxyMCs DNAas DNAcs DNAts DNAts DNAcs DNAgs DNAas DNAas OxyMCs DNAts OxyMCs OxyMC |
| ASO-002129 | TCttCcatcacttCGaaCTC | 72,935 | 72,954 | OxyTs OxyMCs DNAts DNAts OxyMCs DNAcs DNAas DNAts DNAcs DNAas DNAcs DNAts DNAts OxyMCs OxyGs DNAas DNAas OxyMCs OxyTs OxyMC |
| ASO-002136 | CATCacTtcgaactCC | 72,934 | 72,949 | OxyMCs OxyAs OxyTs OxyMCs DNAas DNAcs OxyTs DNAts DNAcs DNAgs DNAas DNAas DNAcs DNAts OxyMCs OxyMC |
| ASO-002137 | CcaTCacttcgaaCTC | 72,935 | 72,950 | OxyMCs DNAcs DNAas OxyTs OxyMCs DNAas DNAcs DNAts DNAts DNAcs DNAgs DNAas DNAas OxyMCs OxyTs OxyMC |
| ASO-002138 | CCaTcACttcgaacTCC | 72,934 | 72,950 | OxyMCs OxyMCs DNAas OxyTs DNAcs OxyAs OxyMCs DNAts DNAts DNAcs DNAgs DNAas DNAas DNAcs OxyTs OxyMCs OxyMC |

Figure 16I

| ASO Number. | ASO Sequence | tau Human Transcript start (SEQID NO.: 1) | Human Transcript tau end (SEQID NO.: 1) | Chemical Structure |
|---|---|---|---|---|
| ASO-002139 | CCATcacttcgaaCTcCT | 72,933 | 72,950 | OxyMCs OxyMCs OxyAs OxyTs DNAcs DNAas DNAcs DNAts DNAts DNAcs DNAgs DNAas DNAas OxyMCs OxyTs DNAcs OxyMCs OxyT |
| ASO-002140 | TCCAtcacttcgaaCTCC | 72,934 | 72,951 | OxyTs OxyMCs OxyMCs OxyAs DNAts DNAcs DNAas DNAcs DNAts DNAts DNAcs DNAgs DNAas DNAas OxyMCs OxyTs OxyMCs OxyMC |
| ASO-002141 | TCttCcatcacttCgaaCTC | 72,935 | 72,954 | OxyTs OxyMCs DNAts DNAts OxyMCs DNAcs DNAas DNAts DNAcs DNAas DNAcs DNAts DNAts OxyMCs DNAgs DNAas DNAas OxyMCs OxyTs OxyMC |
| ASO-002148 | CATCacttcgaactCC | 72,934 | 72,949 | OxyMCs OxyAs OxyTs OxyMCs DNAas DNAcs DNAts DNAts DNAcs DNAgs DNAas DNAas DNAcs DNAts OxyMCs OxyMC |
| ASO-002149 | CcatCActtcgaaCTC | 72,935 | 72,950 | OxyMCs DNAcs DNAas DNAts OxyMCs OxyAs DNAcs DNAts DNAts DNAcs DNAgs DNAas DNAas OxyMCs OxyTs OxyMC |
| ASO-002150 | CcaTCaCttcgaactCC | 72,934 | 72,950 | OxyMCs DNAcs DNAas OxyTs OxyMCs DNAas OxyMCs DNAts DNAts DNAcs DNAgs DNAas DNAas DNAcs DNAts OxyMCs OxyMC |
| ASO-002151 | CcATcACttcgaacTcCT | 72,933 | 72,950 | OxyMCs DNAcs OxyAs OxyTs DNAcs OxyAs OxyMCs DNAts DNAts DNAcs DNAgs DNAas DNAas DNAcs OxyTs DNAcs OxyMCs OxyT |
| ASO-002152 | TCCatcacttcgaacTCC | 72,934 | 72,951 | OxyTs OxyMCs OxyMCs DNAas DNAts DNAcs DNAas DNAcs DNAts DNAts DNAcs DNAgs DNAas DNAas DNAcs OxyTs OxyMCs OxyMC |
| ASO-002153 | TTCCatCacttcgaaCtCCT | 72,933 | 72,952 | OxyTs OxyTs OxyMCs OxyMCs DNAas DNAts OxyMCs DNAas DNAcs DNAts DNAts DNAcs DNAgs DNAas DNAas OxyMCs DNAts OxyMCs OxyMCs OxyT |
| ASO-002160 | CAtCAcTtcgaactCC | 72,934 | 72,949 | OxyMCs OxyAs DNAts OxyMCs OxyAs DNAcs OxyTs DNAts DNAcs DNAgs DNAas DNAas DNAcs DNAts OxyMCs OxyMC |
| ASO-002161 | CATCaCttcgaacTcCT | 72,933 | 72,949 | OxyMCs OxyAs OxyTs OxyMCs DNAas OxyMCs DNAts DNAts DNAcs DNAgs DNAas DNAas DNAcs OxyTs DNAcs OxyMCs OxyT |
| ASO-002162 | CCAtcacttcgaacTCC | 72,934 | 72,950 | OxyMCs OxyMCs OxyAs DNAts DNAcs DNAas DNAcs DNAts DNAts DNAcs DNAgs DNAas DNAas DNAcs OxyTs OxyMCs OxyMC |
| ASO-002163 | CCATcacttcgaacTCCT | 72,933 | 72,950 | OxyMCs OxyMCs OxyAs OxyTs DNAcs DNAas DNAcs DNAts DNAts DNAcs DNAgs DNAas DNAas DNAcs OxyTs OxyMCs OxyMCs OxyT |

Figure 16J

| ASO Number | ASO Sequence | tau Human Transcript start (SEQID NO.: 1) | Human Transcript tau end (SEQID NO.: 1) | Chemical Structure |
|---|---|---|---|---|
| ASO-002164 | TtCCatcacttCGaaCTC | 72,935 | 72,952 | OxyTs DNAts OxyMCs OxyMCs DNAas DNAts DNAcs DNAas DNAcs DNAts DNAts OxyMCs OxyGs DNAas DNAas OxyMCs OxyTs OxyMC |
| ASO-002165 | TtCCAtCacttcgaaCtCCT | 72,933 | 72,952 | OxyTs DNAts OxyMCs OxyMCs OxyAs DNAts OxyMCs DNAas DNAcs DNAts DNAts DNAcs DNAgs DNAas DNAas OxyMCs DNAts OxyMCs OxyMCs OxyT |
| ASO-002172 | CAtCaCTtcgaactCC | 72,934 | 72,949 | OxyMCs OxyAs DNAts OxyMCs DNAas OxyMCs OxyTs DNAts DNAcs DNAgs DNAas DNAas DNAcs DNAts OxyMCs OxyMC |
| ASO-002173 | CATcACttcgaacTcCT | 72,933 | 72,949 | OxyMCs OxyAs OxyTs DNAcs OxyAs OxyMCs DNAts DNAts DNAcs DNAgs DNAas DNAas DNAcs OxyTs DNAcs OxyMCs OxyT |
| ASO-002174 | TCCatcacttCGaaCTC | 72,935 | 72,951 | OxyTs OxyMCs OxyMCs DNAas DNAts DNAcs DNAas DNAcs DNAts DNAts OxyMCs OxyGs DNAas DNAas OxyMCs OxyTs OxyMC |
| ASO-002175 | CCAtcacttcgaactCCT | 72,933 | 72,950 | OxyMCs OxyMCs OxyAs DNAts DNAcs DNAas DNAcs DNAts DNAts DNAcs DNAgs DNAas DNAas DNAcs DNAts OxyMCs OxyMCs OxyT |
| ASO-002176 | TtCCatcacttCgaaCTC | 72,935 | 72,952 | OxyTs DNAts OxyMCs OxyMCs DNAas DNAts DNAcs DNAas DNAcs DNAts DNAts OxyMCs DNAgs DNAas DNAas OxyMCs OxyTs OxyMC |
| ASO-002177 | TtCCaTCacttcgaaCtCCT | 72,933 | 72,952 | OxyTs DNAts OxyMCs OxyMCs DNAas OxyTs OxyMCs DNAas DNAcs DNAts DNAts DNAcs DNAgs DNAas DNAas OxyMCs DNAts OxyMCs OxyMCs OxyT |
| ASO-002184 | CCatcacttCGaaCTC | 72,935 | 72,950 | OxyMCs OxyMCs DNAas DNAts DNAcs DNAas DNAcs DNAts DNAts OxyMCs OxyGs DNAas DNAas OxyMCs OxyTs OxyMC |
| ASO-002185 | CAtCACttcgaacTcCT | 72,933 | 72,949 | OxyMCs OxyAs DNAts OxyMCs OxyAs OxyMCs DNAts DNAts DNAcs DNAgs DNAas DNAas DNAcs OxyTs DNAcs OxyMCs OxyT |
| ASO-002186 | TCCatcacttCgaaCTC | 72,935 | 72,951 | OxyTs OxyMCs OxyMCs DNAas DNAts DNAcs DNAas DNAcs DNAts DNAts OxyMCs DNAgs DNAas DNAas OxyMCs OxyTs OxyMC |
| ASO-002187 | CttCcatcacttCGaaCT | 72,936 | 72,953 | OxyMCs DNAts DNAts OxyMCs DNAcs DNAas DNAts DNAcs DNAas DNAcs DNAts DNAts OxyMCs OxyGs DNAas DNAas OxyMCs OxyT |
| ASO-002188 | TTCcatcacttcgaaCTC | 72,935 | 72,952 | OxyTs OxyTs OxyMCs DNAcs DNAas DNAts DNAcs DNAas DNAcs DNAts DNAts DNAcs DNAgs DNAas DNAas OxyMCs OxyTs OxyMC |

Figure 16K

| ASO Number. | ASO Sequence | tau Human Transcript start (SEQID NO.: 1) | Human Transcript tau end (SEQID NO.: 1) | Chemical Structure |
|---|---|---|---|---|
| ASO-002189 | TTCCatcacttcgaacTCCT | 72,933 | 72,952 | OxyTs OxyTs OxyMCs OxyMCs DNAas DNAts DNAcs DNAas DNAcs DNAts DNAts DNAcs DNAgs DNAas DNAas DNAcs OxyTs OxyMCs OxyMCs OxyT |
| ASO-002623 | CATcacttcgaacTCC | 72934 | 72949 | OxyMCs OxyA OxyT DNAc DNAas DNAcs DNAts DNAts DNAmcs DNAgs DNAas DNAas DNAc OxyT OxyMCs OxyMC |
| ASO-002667 | CATCacttcgaactCC | 72934 | 72949 | OxyMCs OxyA OxyT OxyMC DNAas DNAcs DNAts DNAts DNAmcs DNAgs DNAas DNAas DNAc DNAt OxyMCs OxyMC |
| ASO-002674 | CATCacttcgaactCC | 72934 | 72949 | OxyMCs OxyA OxyT OxyMC DNAas DNAcs DNAts DNAts DNAmcs DNAgs DNAas DNAa DNAc DNAt OxyMCs OxyMC |
| ASO-002631 | CATcacttcgaacTCC | 72934 | 72949 | OxyMCs OxyA OxyT DNAc DNAas DNAcs DNAts DNAts DNAmcs DNAgs DNAas DNAa DNAc OxyT OxyMCs OxyMC |
| ASO-002639 | CATcacttcgaacTCC | 72934 | 72949 | OxyMCs OxyA OxyT DNAc DNAa DNAcs DNAts DNAts DNAmcs DNAgs DNAas DNAas DNAc OxyT OxyMCs OxyMC |
| ASO-002624 | CATCacttcgaactCC | 72934 | 72949 | OxyMCs OxyA OxyT OxyMC DNAa DNAcs DNAts DNAts DNAmcs DNAgs DNAas DNAas DNAc DNAt OxyMCs OxyMC |
| ASO-002637 | CATcacttcgaacTCC | 72934 | 72949 | OxyMCs OxyAs OxyTs DNAmcs DNAas DNAmcs DNAts DNAts DNAmcs DNAgs DNAas DNAas DNAmcs OxyTs OxyMCs OxyMC |
| ASO-002651 | CATCacttcgaactCC | 72934 | 72949 | OxyMCs OxyAs OxyTs OxyMCs DNAas DNAmcs DNAts DNAts DNAmcs DNAgs DNAas DNAas DNAmcs DNAts OxyMCs OxyMC |

PSP Tau Pathology

NHP Tau mRNA

NHP Brain Tau Protein

Figure 20A

| ASO Number. | SEQ ID NO. | ASO Sequence | tau Human Transcript start (SEQID NO.: 1) | Human Transcript tau end (SEQID NO.: 1) | mRNA start NM_016835 | Tau/Tubulin % inhibition |
|---|---|---|---|---|---|---|
| ASO-257283 | 939 | AtTTCcaaattcactTTtAC | 138884 | 138903 | 6722 | 11 |
| ASO-257284 | 940 | AtTTCcaaattcactTTtAC | 138884 | 138903 | 6722 | 8 |
| ASO-002263 | 524 | ATtTcCaaattcactTTtAC | 138884 | 138903 | 6722 | 92 |
| ASO-002627 | 941 | CcaaattcactTTtAC | 138884 | 138899 | 6722 | 51 |
| ASO-002677 | 942 | TCcaaattcactTTtAC | 138884 | 138900 | 6722 | 12 |
| ASO-002670 | 943 | TTCcaaattcactTTtAC | 138884 | 138901 | 6722 | 8 |
| ASO-002663 | 944 | tTTCcaaattcactTTtAC | 138884 | 138902 | 6722 | 11 |
| ASO-002635 | 945 | caaattcactTTtAC | 138884 | 138898 | 6722 | 96 |
| ASO-002643 | 946 | tTTCcaaattcactTTtA | 138885 | 138902 | 6723 | 11 |
| ASO-002671 | 947 | TCcaaattcactTTtA | 138885 | 138900 | 6723 | 40 |
| ASO-002664 | 948 | TTCcaaattcactTTtA | 138885 | 138901 | 6723 | 14 |
| ASO-002626 | 949 | AtTTCcaaattcactTTtA | 138885 | 138903 | 6723 | 8 |
| ASO-002634 | 950 | AtTTCcaaattcactTTt | 138886 | 138903 | 6724 | 8 |
| ASO-002678 | 956 | TTCcaaattcactTTt | 138886 | 138901 | 6724 | 14 |
| ASO-002650 | 957 | tTTCcaaattcactTTt | 138886 | 138902 | 6724 | 12 |
| ASO-002657 | 958 | tTTCcaaattcactTT | 138887 | 138902 | 6725 | 14 |
| ASO-002642 | 951 | AtTTCcaaattcactTT | 138887 | 138903 | 6725 | 7 |
| ASO-002649 | 952 | AtTTCcaaattcactT | 138888 | 138903 | 6726 | 9 |
| ASO-002656 | 953 | AtTTCcaaattcact | 138889 | 138903 | 6727 | 16 |

FIGURE 20B

| ASO Number. | ASO Sequence | tau Human Transcript start (SEQID NO.: 1) | Human Transcript tau end (SEQID NO.: 1) | Chemical Structure |
|---|---|---|---|---|
| ASO-257283 | AtTTCcaaattcactTTtAC | 138884 | 138903 | OxyA DNAts OxyTs OxyTs OxyMCs DNAcs DNAas DNAas DNAas DNAts DNAts DNAcs DNAas DNAcs DNAts OxyTs OxyTs DNAts OxyAs OxyMC |
| ASO-257284 | AtTTCcaaattcactTTtAC | 138884 | 138903 | OxyAs DNAts OxyTs OxyTs OxyMCs DNAcs DNAas DNAas DNAas DNAt DNAts DNAcs DNAas DNAcs DNAts OxyTs OxyTs DNAts OxyAs OxyMC |
| ASO-002263 | ATtTcCaaattcactTTtAC | 138884 | 138903 | OxyAs OxyTs DNAts OxyTs DNAcs OxyMCs DNAas DNAas DNAas DNAts DNAts DNAcs DNAas DNAcs DNAts OxyTs OxyTs DNAts OxyAs OxyMC |
| ASO-002627 | CcaaattcactTTtAC | 138884 | 138899 | OxyMCs DNAcs DNAas DNAas DNAas DNAts DNAts DNAcs DNAas DNAcs DNAts OxyTs OxyTs DNAts OxyAs OxyMC |
| ASO-002677 | TCcaaattcactTTtAC | 138884 | 138900 | OxyTs OxyMCs DNAcs DNAas DNAas DNAas DNAts DNAts DNAcs DNAas DNAcs DNAts OxyTs OxyTs DNAts OxyAs OxyMC |
| ASO-002670 | TTCcaaattcactTTtAC | 138884 | 138901 | OxyTs OxyTs OxyMCs DNAcs DNAas DNAas DNAas DNAts DNAts DNAcs DNAas DNAcs DNAts OxyTs OxyTs DNAts OxyAs OxyMC |
| ASO-002663 | tTTCcaaattcactTTtAC | 138884 | 138902 | DNAts OxyTs OxyTs OxyMCs DNAcs DNAas DNAas DNAas DNAts DNAts DNAcs DNAas DNAcs DNAts OxyTs OxyTs DNAts OxyAs OxyMC |
| ASO-002635 | caaattcactTTtAC | 138884 | 138898 | DNAcs DNAas DNAas DNAas DNAts DNAts DNAcs DNAas DNAcs DNAts OxyTs OxyTs DNAts OxyAs OxyMC |
| ASO-002643 | tTTCcaaattcactTTtA | 138885 | 138902 | DNAts OxyTs OxyTs OxyMCs DNAcs DNAas DNAas DNAas DNAts DNAts DNAcs DNAas DNAcs DNAts OxyTs OxyTs DNAts OxyA |
| ASO-002671 | TCcaaattcactTTtA | 138885 | 138900 | OxyTs OxyMCs DNAcs DNAas DNAas DNAas DNAts DNAts DNAcs DNAas DNAcs DNAts OxyTs OxyTs DNAts OxyA |
| ASO-002664 | TTCcaaattcactTTtA | 138885 | 138901 | OxyTs OxyTs OxyMCs DNAcs DNAas DNAas DNAas DNAts DNAts DNAcs DNAas DNAcs DNAts OxyTs OxyTs DNAts OxyA |
| ASO-002626 | AtTTCcaaattcactTTtA | 138885 | 138903 | OxyAs DNAts OxyTs OxyTs OxyMCs DNAcs DNAas DNAas DNAas DNAts DNAts DNAcs DNAas DNAcs DNAts OxyTs OxyTs DNAts OxyA |
| ASO-002634 | AtTTCcaaattcactTTt | 138886 | 138903 | OxyAs DNAts OxyTs OxyTs OxyMCs DNAcs DNAas DNAas DNAas DNAts DNAts DNAcs DNAas DNAcs DNAts OxyTs OxyTs DNAt |
| ASO-002678 | TTCcaaattcactTTt | 138886 | 138901 | OxyTs OxyTs OxyMCs DNAcs DNAas DNAas DNAas DNAts DNAts DNAcs DNAas DNAcs DNAts OxyTs OxyTs DNAt |

FIGURE 20C

| ASO Number. | ASO Sequence | tau Human Transcript start (SEQID NO.: 1) | Human Transcript tau end (SEQID NO.: 1) | Chemical Structure |
|---|---|---|---|---|
| ASO-002650 | tTTCcaaattcactTTt | 138886 | 138902 | DNAts OxyTs OxyTs OxyMCs DNAcs DNAas DNAas DNAas DNAts DNAts DNAcs DNAas DNAcs DNAts OxyTs OxyTs DNAt |
| ASO-002657 | tTTCcaaattcactTT | 138887 | 138902 | DNAts OxyTs OxyTs OxyMCs DNAcs DNAas DNAas DNAas DNAts DNAts DNAcs DNAas DNAcs DNAts OxyTs OxyT |
| ASO-002642 | AtTTCcaaattcactTT | 138887 | 138903 | OxyAs DNAts OxyTs OxyTs OxyMCs DNAcs DNAas DNAas DNAas DNAts DNAts DNAcs DNAas DNAcs DNAts OxyTs OxyT |
| ASO-002649 | AtTTCcaaattcactT | 138888 | 138903 | OxyAs DNAts OxyTs OxyTs OxyMCs DNAcs DNAas DNAas DNAas DNAts DNAts DNAcs DNAas DNAcs DNAts OxyT |
| ASO-002656 | AtTTCcaaattcact | 138889 | 138903 | OxyAs DNAts OxyTs OxyTs OxyMCs DNAcs DNAas DNAas DNAas DNAts DNAts DNAcs DNAas DNAcs DNAt |

TAU ANTISENSE OLIGOMERS AND USES THEREOF

REFERENCE TO EARLIER FILED APPLICATIONS

This application is a non-provisional application claiming the benefit of U.S. Provisional Application No. 62/112,058, filed Feb. 4, 2015, U.S. Provisional Application No. 62/156,684, filed May 4, 2015, U.S. Provisional Application No. 62/237,922, filed Oct. 6, 2015, U.S. Provisional Application No. 62/238,941, filed Oct. 8, 2015, U.S. Provisional Application No. 62/279,612, filed Jan. 15, 2016, U.S. Provisional Application No. 62/279,614, filed Jan. 15, 2016, and U.S. Provisional Application No. 62/279,610, filed Jan. 15, 2016, all of which are incorporated herein by reference in their entireties.

REFERENCE TO SEQUENCE LISTING SUBMITTED ELECTRONICALLY VIA EFS-WEB

The content of the electronically submitted sequence listing (Name: 3338.0190007 SL.TXT, Size: 377,140 bytes; and Date of Creation: Feb. 2, 2016) submitted in this application is incorporated herein by reference in its entirety.

FIELD OF INVENTION

The present invention relates to oligomeric compounds (oligomers) that target microtubule-associated protein tau (MAPT) transcript in a cell, leading to reduced expression of MAPT mRNA and/or Tau protein. Reduction of MAPT mRNA and/or Tau protein expression is beneficial for a range of medical disorders, such as tauopathies, Down syndrome, depression, seizure disorders, and movement disorders.

BACKGROUND

Tau protein is a microtubule-associated protein (MAP) that interacts with tubulin to stabilize, and promote assembly into, microtubules. Microtubules are critical structural components of the cellular cytoskeleton and are involved in various cellular processes, including mitosis, cytokinesis, and vesicular transport. Tau protein is present in multiple cell and tissue types, but is particularly abundant in neurons compared to non-neuronal cells.

Due to Tau's role in stabilizing microtubules, alteration of Tau expression levels and/or function can disrupt critical cellular processes, which is thought to contribute to various neurodegenerative disorders such as tauopathies. For example, it has been found that neurofibrillary inclusions in Alzheimer's disease (AD) contain aggregates of hyperphosphorylated Tau protein.

In addition, abnormal Tau expression and/or function has been associated with other diseases of the brain (also included in the family of pathologically and genetically defined tauopathies), including Frontotemporal dementia (FTD), progressive supranuclear palsy (PSP), corticobasal degeneration (CBD), corticobasal ganglionic degeneration, dementia pugilistica, Frontotemporal dementia with parkinsonism linked to chromosome 17 (FTDP-17), Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration, and others. Abnormal Tau expression and/or function can also play a role in additional diseases such as Down Syndrome, seizure disorders (e.g., epilepsy), network dysfunction (e.g., depression), and movement disorders (e.g., Parkinson's disease).

Tau-associated disorders such as AD are the most common cause of dementia in the elderly, and robust and effective agents for the treatment of neurodegenerative diseases, including tauopathies, seizure disorders, and movement disorders, are greatly needed.

Antisense molecules that can decrease protein expression have been studied in the development of human therapeutics. Antisense molecules that target pre-mRNA or mRNA can reduce the RNA level thereby reducing the protein level. Antisense molecules can act on a target sequence through various mechanisms of action: degradation of mRNA through RNaseH, steric hindrance of ribosomal subunit binding, altering maturation of mRNA, splicing activation, 5'-cap formation inhibition, arrest of translation and/or double strand RNase activation. In some cases, however, antisense molecules targeting regions nearby polyadenylation sites are known to increase mRNA stability. See Vickers et al., NAR (2001) 29(6) 1293-1299.

SUMMARY OF INVENTION

The present invention provides an oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 134,947-138,940 of SEQ ID NO: 1.

The present invention also provides an oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 135,050-138,940 of SEQ ID NO: 1.

The present invention further provides an oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 72,802-73,072 of SEQ ID NO: 1.

The present invention also provides an oligomer of from 10 to 50 nucleotides in length comprising a contiguous nucleotide sequence that hybridizes to a nucleic acid sequence within a microtubule-associated protein tau (MAPT) transcript, wherein the oligomer has at least one property selected from: (1) reduces expression of Tau mRNA in a cell, compared to a control cell that has not been exposed to the oligomer; and (2) reduces expression of Tau protein in a cell, compared to a control cell that has not been exposed to the oligomer.

The present invention also provides an oligomer of from 10 to 50 nucleotides in length comprising a contiguous nucleotide sequence that hybridizes to a nucleic acid sequence within a microtubule-associated protein tau (MAPT) transcript, wherein the oligomer has an in vivo tolerability less than or equal to a total score of 4, wherein the total score is the sum of a unit score of five categories, which are 1) hyperactivity; 2) decreased activity and arousal; 3) motor dysfunction and/or ataxia; 4) abnormal posture and breathing; and 5) tremor and/or convulsions, and wherein the unit score for each category is measured on a scale of 0-4.

The present invention also provides a conjugate comprising an oligomer of from 10 to 50 nucleotides in length comprising a contiguous nucleotide sequence that hybridizes to a nucleic acid sequence within a microtubule-associated protein tau (MAPT) transcript, wherein the oligomer is covalently attached to at least one non-nucleotide or non-polynucleotide moiety.

The present invention also provides a pharmaceutical composition comprising an oligomer of from 10 to 50 nucleotides in length comprising a contiguous nucleotide sequence that hybridizes to a nucleic acid sequence within a microtubule-associated protein tau (MAPT) transcript and a pharmaceutically acceptable carrier.

The present invention also provides a kit comprising an oligomer of from 10 to 50 nucleotides in length comprising a contiguous nucleotide sequence that hybridizes to a nucleic acid sequence within a microtubule-associated protein tau (MAPT) transcript and instructions for use.

The present invention further provides a method of inhibiting or reducing Tau protein expression in a cell, the method comprising administering an oligomer of from 10 to 50 nucleotides in length comprising a contiguous nucleotide sequence that hybridizes to a nucleic acid sequence within a microtubule-associated protein tau (MAPT) transcript to a cell expressing Tau protein, wherein the Tau protein expression in the cell is inhibited or reduced after the administration.

The present invention further provides a method for treating a seizure disorder in a subject in need thereof, the method comprising administering an oligomer of from 10 to 50 nucleotides in length comprising a contiguous nucleotide sequence that hybridizes to a nucleic acid sequence within a microtubule-associated protein tau (MAPT) transcript to a cell expressing Tau protein to the subject.

The present invention further provides a method for treating a seizure disorder in a subject in need thereof, the method comprising administering an oligomer of from 10 to 50 nucleotides in length comprising a contiguous nucleotide sequence that hybridizes to a nucleic acid sequence within a microtubule-associated protein tau (MAPT) transcript to a cell expressing Tau protein to the subject.

The present invention further provides the use of an oligomer of from 10 to 50 nucleotides in length comprising a contiguous nucleotide sequence that hybridizes to a nucleic acid sequence within a microtubule-associated protein tau (MAPT) transcript for the manufacture of a medicament for the treatment of a neurological disorder, e.g., a tauopathy, a neurodegenerative disease with tauopathy (a neurodegenerative disease which involves accumulation of tau protein in the brain), an epileptic disorder with tauopathy (an epileptic disorder which involves accumulation of tau protein in the brain), an epileptic disorder without tauopathy (an epileptic disorder which does not involve accumulation of tau protein in the brain), an idiopathic adult epileptic disorder without tauopathy (an idiopathic adult epileptic disorder which does not involve accumulation of tau protein in the brain), a seizure disorder, or any combination thereof.

EMBODIMENTS

E1. An oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 134,947-138,940 of SEQ ID NO: 1.

E2. An oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 135,050-138,940 of SEQ ID NO: 1.

E3. An oligomer of from 10 to 50 nucleotides in length comprising a contiguous nucleotide sequence that hybridizes to a nucleic acid sequence within a microtubule-associated protein tau (MAPT) transcript, wherein the nucleic acid sequence corresponds to nucleotides 72,802-73,072 of SEQ ID NO: 1.

E4. The oligomer of any one of embodiments 1 or 3, wherein the nucleotide sequence comprises at least one nucleotide analog.

E5. The oligomer of any one of embodiments 1 to 4, which is a gapmer, a blockmer, a mixmer, a headmer, a tailmer, or a totalmer.

E6. The oligomer of any one of embodiments 1 to 5, which is a gapmer.

E7. The oligomer of embodiment 6, which has the formula of 5'-A-B-C-3' (II), wherein (i) B is a contiguous sequence of 7 to 23 DNA units;

(ii) A is a first wing sequence of 1 to 10 nucleotides, wherein the first wing sequence comprises one or more nucleotide analogs and optionally one or more DNA units and wherein at least one of the nucleotide analogs is located at the 5' end of A; and (iii) C is a second wing sequence of 1 to 10 nucleotides, wherein the second wing sequence comprises one or more nucleotide analogs and optionally one or more DNA units and wherein at least one of the nucleotide analogs is located at the 3' end of C.

E8. The oligomer of embodiment 7, wherein A has the formula of LmDnLoDpLq (III) and C has the formula of Lm'Dn'Lo'Dp'Lq' (IV) and wherein L is a nucleotide analog;

D is a DNA unit;

m and q' are 1 to 6 units;

n, p, n', and p' are 0 to 2 units; and o, q, m', and o' are 0 to 5 units.

E9. The oligomer of embodiment 7 or 8, wherein the first wing sequence comprises a combination of nucleotide analogs and DNA unit selected from (i) 1-9 nucleotide analogs and 1 DNA unit; (ii) 1-8 nucleotide analogs and 1-2 DNA units; (iii) 1-7 nucleotide analogs and 1-3 DNA units; (iv) 1-6 nucleotide analogs and 1-4 DNA units; (v) 1-5 nucleotide analogs and 1-5 DNA units; (vi) 1-4 nucleotide analogs and 1-6 DNA units; (vii) 1-3 nucleotide analogs and 1-7 DNA units; (viii) 1-2 nucleotide analogs and 1-8 DNA units; and (ix) 1 nucleotide analog and 1-9 DNA units.

E10. The oligomer of any one of embodiments 7 to 9, wherein the second wing sequence comprises a combination of nucleotide analogs and DNA unit selected from (i) 1-9 nucleotide analogs and 1 DNA unit; (ii) 1-8 nucleotide analogs and 1-2 DNA units; (iii) 1-7 nucleotide analogs and 1-3 DNA units; (iv) 1-6 nucleotide analogs and 1-4 DNA units; (v) 1-5 nucleotide analogs and 1-5 DNA units; (vi) 1-4 nucleotide analogs and 1-6 DNA units; (vii) 1-3 nucleotide analogs and 1-7 DNA units; (viii) 1-2 nucleotide analogs and 1-8 DNA units; and (ix) 1 nucleotide analog and 1-9 DNA units.

E11. The oligomer of any one of embodiments 8 to 10, wherein A is selected from L, LL, LDL, LLL, LLLL, LLDL, LDLL, LDDL, LLDD, LLLLL, LLLDL, LLDLL, LDLLL, LLDDL, LDDLL, LLDLD, LDLLD, LDLDL, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD, and C is selected from L, LL, LDL, LLL, LLLL, LLDL, LDLL, LDDL, LLDD, LLLLL, LLLDL, LLDLL, LDLLL, LLDDL, LDDLL, LLDLD, LDLLD, LDLDL, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD.

E12. The oligomer of any one of embodiments 1 to 11, which comprises at least two, at least three, at least four, at least five, at least six, at least seven, at least eight, at least nine, or at least ten nucleotide analogs.

E13. The oligomer of any one of embodiments 1 to 12, wherein the nucleotide analog or analogs are selected from Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), and any combination thereof.

E14. The oligomer of any one of embodiments 1 to 13, wherein the nucleotide analog or analogs comprise a bicyclic sugar.

E15. The oligomer of embodiment 14, wherein the bicyclic sugar comprises cEt, 2',4'-constrained 2'-O-methoxyethyl (cMOE), LNA, α-LNA, β-LNA, 2'-0,4'-C-ethylene-bridged nucleic acids (ENA), amino-LNA, oxy-LNA, or thio-LNA.

E16. The oligomer of any one of embodiments 1 to 15, wherein the nucleotide analog or analogs comprise an LNA.

E17. The oligomer of embodiment 16, which comprises three to five LNAs on the 5' portion of the oligomer and three to five LNAs on the 3' portion of the oligomer.

E18, The oligomer of any one of embodiments 1 and 4-17, wherein the nucleic acid sequence corresponds to nucleotides 134,947-138,924 of SEQ ID NO: 1.

E19. The oligomer of any one of embodiments 1 to 18, wherein the MAPT transcript comprises SEQ ID NO: 1.

E20. The oligomer of embodiment 19, wherein the nucleotide sequence hybridizes to a nucleic acid sequence within nucleotides 135,700-138,940; 136,000-138,940; 136,620-138,940; 136,860-138,940; 137,060-138,940; 137,300-138,940; 137,830-138,940; 138,030-138,940; 138,350-138,940; 134,821-135,020; 135,700-135,820; 136,000-136,110; 136,620-136,760; 136,860-136,960; 137,060-137,110; 137,300-137,400; 137,830-137,900; 138,030-138,140; 138,350-138,450; or 138,860-138,940 of SEQ ID NO: 1.

E21. The oligomer of embodiment 19, wherein the nucleotide sequence has at least about 80%, at least about 90%, at least about 95%, at least about 96%, at least about 97%, at least about 98%, at least about 99%, or 100% sequence identity to a region within the complement of a nucleic acid sequence selected from nucleotides 134,947-138,940 of SEQ ID NO: 1.

E22. The oligomer of embodiment 21, wherein the nucleotide sequence has at least about 80%, at least about 90%, at least about 95%, at least about 96%, at least about 97%, at least about 98%, at least about 99%, or 100% sequence identity to a region within the complement of nucleotides 135,700-138,940; 136,000-138,940; 136,620-138,940; 136,860-138,940; 137,060-138,940; 137,300-138,940; 137,830-138,940; 138,030-138,940; 138,350-138,940; 134,821-135,020; 135,700-135,820; 136,000-136,110; 136,620-136,760; 136,860-136,960; 137,060-137,110; 137,300-137,400; 137,830-137,900; 138,030-138,140; 138,350-138,450; or 138,860-138,940 of SEQ ID NO: 1.

E23. The oligomer of any one of embodiments 3 to 17, wherein the nucleic acid sequence corresponds to nucleotides 72,802-73,072; 72,812-73,062; 72,822-73,052; 72,832-73,042; 72,842-73,032; 72,852-73,022; 72,862-73,012; 72,872-73,002; 72,882-72,992; 72,892-72,982; or 72,902-72,972 of SEQ ID NO: 1.

E24. The oligomer of embodiment 22, wherein the nucleotide sequence hybridizes to a nucleic acid sequence within nucleotides 72,802-73,072; 72,812-73,062; 72,822-73,052; 72,832-73,042; 72,842-73,032; 72,852-73,022; 72,862-73,012; 72,872-73,002; 72,882-72,992; 72,892-72,982; or 72,902-72,972 of SEQ ID NO: 1.

E25. The oligomer of embodiment 23, wherein the nucleotide sequence has at least about 80%, at least about 90%, at least about 95%, at least about 96%, at least about 97%, at least about 98%, at least about 99%, or 100% sequence identity to a region within the complement of nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; or 72,902-72,972 of SEQ ID NO: 1.

E26. The oligomer of embodiment 24, wherein the nucleotide sequence has at least about 80%, at least about 90%, at least about 95%, at least about 96%, at least about 97%, at least about 98%, at least about 99%, or 100% sequence identity to a region within the complement of nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; or 72,902-72,972 of SEQ ID NO: 1.

E27. The oligomer of embodiment 24, wherein the nucleotide sequence has at least about 80%, at least about 90%, at least about 95%, at least about 96%, at least about 97%, at least about 98%, at least about 99%, or 100% sequence identity to a region within the complement of nucleotides 72,947-72,960; 72,946-72,961; 72,907-72,922; 72,948-72,963; 72,950-72,963; 72,945-72,960; 72,950-72,965; 72,944-72,959; 72,947-72,962; 72,952-72,965; 72,946-72,959; 72,949-72,964; 72,951-72,964; 72,933-72,948; 72,934-72,949; 72,935-72,950; 72,932-72,951; 72,933-72,952; 72,934-72,953; 72,945-72,964; 72,944-72,963; 72,948-72,967; 72,946-72,965; 72,935-72,951; 72,936-72,953; 72,933-72,934; 72,933-72,954; 72,933-72,950; 72,935-72,954; 72,934-72,951; 72,934-72,950; 72,933-72,949; or 72,935-72,952 of SEQ ID NO: 1.

E28. The oligomer of any one of embodiments 1 to 27, wherein the nucleotide sequence comprises no mismatches or no more than one or two mismatches with the region.

E29. The oligomer of any one of embodiments 1, 2, 4-22, and 28, wherein the nucleotide sequence has at least about 80%, at least about 90%, at least about 95%, at least about 96%, at least about 97%, at least about 98%, at least about 99%, or 100% sequence identity to a region within the complement of nucleotides 136,000-136,110 or 138,860-138,940 of SEQ ID NO: 1.

E30. The oligomer of embodiment 29, wherein the nucleotide sequence has at least about 80%, at least about 90%, at least about 95%, at least about 96%, at least about 97%, at least about 98%, at least about 99%, or 100% sequence identity to a region within the complement of nucleotides 136,053-136,068 or 138,884-138,908 of SEQ ID NO: 1.

E31. The oligomer of any one of embodiments 1, 2, 4-22, and 28, wherein the nucleotide sequence comprises a nucleotide sequence at least about 80%, at least about 90%, at least about 95%, at least about 96%, at least about 97%, at least about 98%, at least about 99%, or 100% sequence identity to a nucleic acid sequence selected from: SEQ ID NO: 4 to SEQ ID NO: 803.

E32. The oligomer of any one of embodiments 1, 2, 4-22, and 28, wherein the nucleotide sequence has at least about 80%, at least about 90%, at least about 95%, at least about 96%, at least about 97%, at least about 98%, at least about 99%, or 100% sequence identity to a nucleic acid sequence selected from the sequences in FIGS. 2A to 2NNNN, 3A to 3Z, 6A to 6GG, and 7A to 7E, wherein the upper case letter is LNA and the lower case letter is DNA.

E33. The oligomer of any one of embodiments 1 to 17, wherein the nucleotide sequence has at least about 80%, at least about 90%, at least about 95%, at least about 96%, at least about 97%, at least about 98%, at least about 99%, or 100% sequence identity to a nucleic acid sequence selected from: ctttatttccaaattcactt (SEQ ID NO: 676); actttatttccaaattcact (SEQ ID NO: 715); tttatttccaaattcacttt (SEQ ID NO: 644); ttatttccaaattcactttt (SEQ ID NO: 799); atttccaaattcacttttac (SEQ ID NO: 466); atttccaaattcactttta (SEQ ID NO: 559); actttatttccaaattcactt (SEQ ID NO: 680); or atttccaaattcactt (SEQ ID NO: 686).

E34. The oligomer of embodiment 32, wherein the nucleotide sequence has at least about 80%, at least about 90%, at least about 95%, at least about 96%, at least about 97%, at least about 98%, at least about 99%, or 100% sequence identity to a nucleic acid sequence selected from: tatttccaaattcactttta (SEQ ID NO: 526); aataactttatttcca (SEQ ID NO: 773); agtaataactttatt (SEQ ID NO: 782); tttccaaattcactt (SEQ ID NO: 684); agagtaataactttat (SEQ ID NO: 784); agtaataactttattt (SEQ ID NO: 780); agagtaataacttta (SEQ ID NO: 786); ttaatcagagtaataa (SEQ ID NO: 795); tttaatcagagtaat (SEQ ID NO: 798); aatcagagtaataac (SEQ ID NO: 794); tttaatcagagtaata (SEQ ID NO: 797); taatcagagtaataa (SEQ ID NO: 796); ctttatttccaaattcact (SEQ ID NO: 713); and ctttatttccaaattcac (SEQ ID NO: 739).

E35. The oligomer of embodiment 32, wherein the nucleotide sequence has at least about 80%, at least about 90%, at least about 95%, at least about 96%, at least about 97%, at least about 98%, at least about 99%, or 100% sequence identity to a nucleic acid sequence selected from: atttccaaattcacttttac (SEQ ID NOs: 466 to 490, 513 to 525, 910 to 918, 928, 929, or 932 to 935); tatttccaaattcactttta (SEQ ID NOs: 526 to 550, or 573 to 585); ttatttccaaattcactttt (SEQ ID NOs: 586-606, 629 to 642,799 to 801); tttatttccaaattcacttt (SEQ ID NOs: 644 to 647, 657 to 658, 919 to 921, or 930); ctttatttccaaattcactt (SEQ ID NOs: 676 to 679, 681 to 683, 685, or 687 to 697); actttatttccaaattcactt (SEQ ID NO: 680); tttccaaattcactt (SEQ ID NO: 684); atttccaaattcactt (SEQ ID NOs: 686, 705, 712, 936, or 937, 922, 924, or 931); actttatttccaaattcact (SEQ ID NOs: 715 to 717); ctttatttccaaattcact (SEQ ID NOs: 713, 714 or 718 to 731,); ctttatttccaaattcac (SEQ ID NOs: 739 to 748); aataactttatttcca (SEQ ID NO: 773 or 774); agtaataactttattt (SEQ ID NO: 780); agtaataactttatt (SEQ ID NO: 782); agagtaataactttat (SEQ ID NO: 784); agagtaataacttta (SEQ ID NO: 786); aatcagagtaataac (SEQ ID NO: 794); ttaatcagagtaataa (SEQ ID NO: 795); taatcagagtaataa (SEQ ID NO: 796); tttaatcagagtaata (SEQ ID NO: 797); and tttaatcagagtaat (SEQ ID NO: 798)

E36. The oligomer of any one of embodiments 3 to 17, wherein the nucleotide sequence has at least about 80%, at least about 90%, at least about 95%, at least about 96%, at least about 97%, at least about 98%, at least about 99%, or 100% sequence identity to a nucleic acid sequence selected from the sequences in FIGS. 16A to 16C and 16D to 16K, wherein the upper case letter is LNA and the lower case letter is DNA.

E37. The oligomer of any one of embodiments 3 to 17, wherein the nucleotide sequence has at least about 80%, at least about 90%, at least about 95%, at least about 96%, at least about 97%, at least about 98%, at least about 99%, or 100% sequence identity to a nucleic acid sequence selected from: SEQ ID NO: 804 to SEQ ID NO: 892.

E38. The oligomer of any one of embodiments 1 to 37, which is single-stranded.

E39. The oligomer of any one of embodiments 1 to 38, which has at least one property selected from: (1) reduces expression of Tau mRNA in a cell, compared to a control cell that has not been exposed to the oligomer; and (2) reduces expression of Tau protein in a cell, compared to a control cell that has not been exposed to the oligomer.

E40. The oligomer of any one of embodiments 1 to 39, wherein the oligomer has an in vivo tolerability less than or equal to a total score of 4, wherein the total score is the sum of a unit score of five categories, which are 1) hyperactivity; 2) decreased activity and arousal; 3) motor dysfunction and/or ataxia; 4) abnormal posture and breathing; and 5) tremor and/or convulsions, and wherein the unit score for each category is measured on a scale of 0-4.

E41. The oligomer of embodiment 40, wherein the in vivo tolerability is less than or equal to the total score of 3, the total score of 2, the total score of 1, or the total score of 0.

E42. The oligomer of any one of embodiments 1 to 41, wherein calcium oscillations of neuronal cells which are in contact with the oligomer are greater than or equal to 95%, greater than or equal to 90%, greater than or equal to 85%, greater than or equal to 80%, greater than or equal to 75%, or greater than or equal to 70% of oscillations in neuronal cells that are not in contact with the oligomer.

E43. The oligomer of any one of embodiments 1 to 42, which reduces expression of Tau mRNA in a cell by at least about 20%, at least about 30%, at least about 40%, at least about 50%, at least about 60%, at least about 70%, at least about 80%, at least about 90%, or about 100% compared to a cell not exposed to the oligomer.

E44. The oligomer of any one of embodiments 1 to 43, which reduces expression of Tau protein in a cell by at least about 60%, at least about 70%, at least about 80%, at least about 90%, or at least about 95% compared to a cell not exposed to the oligomer.

E45. The oligomer of any one embodiments 1 to 44, which comprises the nucleotides A, T, C, and G and at least one analog of the nucleotides A, T, C, and G, and has a sequence score greater than or equal to 0.2, wherein the sequence score is calculated by formula I:

$$\frac{\#\text{ of } C \text{ nucleotides and analogs thereof} - \#\text{ of } G \text{ nucleotides and analogs thereof}}{\text{Total nucleotide length}}. \qquad (I)$$

E46. The oligomer of any one of embodiments 1 to 45, which has from 10 to 24 nucleotides in length or from 14 to 21 nucleotides in length.

E47. The oligomer of any one of embodiments 1 to 46, which has 14, 15, 16, 17, 20, or 21 nucleotides in length.

E48. The oligomer of embodiment 1, 2, 4-22, and 28, which comprises, consists essentially of, or consists of a nucleotide sequence selected from FIGS. 2A to 2NNNN, 3A to 3Z, 6A to 6GG, and 7A to 7E, wherein the upper case letter is LNA and the lower case letter is DNA.

E49. The oligomer of embodiment 48, which comprises, consists essentially of, or consists of: ATTtCcaaattcacTtTtAC (SEQ ID NO: 487); CTTTAtttccaaattCACTT (SEQ ID NO: 677); ACTTTatttccaaattCACT (SEQ ID NO: 715); TTTATttccaaattcACTTT (SEQ ID NO: 644); TTtATttccaaattcACtTT (SEQ ID NO: 645); TTaTTtccaaattcaCTtTT (SEQ ID NO: 593); ATTTccaaattcactTTTAC (SEQ ID NO: 474); ACTTTatttccaaattCACTT (SEQ ID NO: 680); ATTtccaaattcaCTT (SEQ ID NO: 686); TATTTccaaattcactTTTA (SEQ ID NO: 532); AATaactttatttCCA (SEQ ID NO: 773); AGTaataactttATT (SEQ ID NO: 782); TTTccaaattcaCTT (SEQ ID NO: 684); AGAgtaataacttTAT (SEQ ID NO: 784); AGTaataactttaTTT (SEQ ID NO: 780); AGAgtaataactTTA (SEQ ID NO: 786); TTAatcagagtaaTAA (SEQ ID NO: 795); TTTaatcagagtAAT (SEQ ID NO: 798); AATcagagtaatAAC (SEQ ID NO: 794); TTTaatcagagtaATA (SEQ ID NO: 797); TAAtcagagtaaTAA (SEQ ID NO: 796); CTTtatttccaaatTCACT (SEQ ID NO: 720); ATtTCcaaattcactTTtAC (SEQ ID NO: 472); AtTTCcaaattcactTTtAC (SEQ ID NO: 473); ATTtCcaaattcacTtTtAC (SEQ ID NO: 487); or CTTtatttccaaatTcAC (SEQ ID NO: 745), wherein the upper case letter is LNA and the lower case letter is DNA.

E50. The oligomer of embodiment 48, which comprises, consists essentially of, or consists of: ATtTCcaaattcactTTtAC (SEQ ID NO: 472); AtTTCcaaattcactTTtAC (SEQ ID NO: 473); ATTTccaaattcactTTTAC (SEQ ID NO: 474); ATTTCcaaattcacttTTAC (SEQ ID NO: 482); ATTtCcaaattcacTtTtAC (SEQ ID NO: 487); ATtTCcaaattcactTTtAC (SEQ ID NO: 524), AtTTCcaaattcactTTtAC (SEQ ID NO: 493), TATTTccaaattcactTTTA (SEQ ID NO: 532); TTaTTtccaaattcaCTtTT (SEQ ID NO: 593); TTTATttccaaattcACTTT (SEQ ID NO: 644); TTtATttccaaattcACtTT (SEQ ID NO: 645); TTTATttccaaattcaCTTT (SEQ ID NO: 646), TTTAtttccaaattcACTTT (SEQ ID NO: 647); CTTTAtttccaaattCACTT (SEQ ID NO: 677); CTTTAtttccaaattcACTT (SEQ ID NO: 679); ACTTTatttccaaattCACTT (SEQ ID NO: 680); CTTTatttccaaattCACTT (SEQ ID NO: 681); CTtTAtttccaaattCAcTT (SEQ ID NO: 683); TTTccaaattcaCTT (SEQ ID NO: 684); CtTTAtttccaaattCAcTT (SEQ ID NO: 685); ATTtccaaattcaCTT (SEQ ID NO: 686); CTTtatttccaaatTcACT (SEQ ID NO: 714); ACTTTatttccaaattCACT (SEQ ID NO: 715); ACTTtatttccaaatTCACT (SEQ ID NO: 716); CTTtatttccaaatTCACT (SEQ ID NO: 720); CTTtatttccaaatTCAC (SEQ ID NO: 740); CTTtatttccaaatTcAC (SEQ ID NO: 745); AATaactttatttCCA (SEQ ID NO: 773); AGTaataactttaTTT (SEQ ID NO: 780); AGTaataactttATT (SEQ ID NO: 782); AGAgtaataacttTAT (SEQ ID NO: 784); AGAgtaataactTTA (SEQ ID NO: 786); AATcagagtaatAAC (SEQ ID NO: 794); TTAatcagagtaaTAA (SEQ ID NO: 795); TAAtcagagtaaTAA (SEQ ID NO: 796); TTTaatcagagtaATA (SEQ ID NO: 797); or TTTaatcagagtAAT (SEQ ID NO: 798), wherein the upper case letter is LNA and the lower case letter is DNA.

E51. The oligomer of embodiment 48, which comprises, consists essentially of, or consists of CTTTAtttccaaattcACTT (SEQ ID NO: 679, ASO-001928), ATTTCcaaattcacttTTAC (SEQ ID NO: 482, ASO-001962); CTTTatttccaaattCACTT (SEQ ID NO: 681, ASO-001921), TTtATttccaaattcACtTT (SEQ ID NO: 645, ASO-001967); TTTAtttccaaattcACTTT (SEQ ID NO: 647, ASO-001948), TTaTTtccaaattcaCTtTT (SEQ ID NO: 593, ASO-001941), ACTTtatttccaaatTCACT (SEQ ID NO: 716, ASO-001956), CTtTAtttccaaattCAcTT (SEQ ID NO: 683, ASO-001942), TTTATttccaaattcaCTTT (SEQ ID NO: 646, ASO-001955), ACTTTatttccaaattCACTT (SEQ ID NO: 680, ASO-001968); CtTTAtttccaaattCAcTT (SEQ ID NO: 685, ASO-001935), AtTTCcaaattcactTTtAC (SEQ ID NO: 473, ASO-001933), TTtATttccaaattcACtTT (SEQ ID NO: 645, ASO-001967), ATtTCcaaattcactTTtAC (SEQ ID NO: 492), ATTtCcaaattcacTtTtAC (SEQ ID NO: 487, ASO-002038), or AtTTCcaaattcactTTtAC (SEQ ID NO: 493), wherein the upper case letter is LNA and the lower case letter is DNA.

E52. The oligomer of embodiment 50, which comprises, consists essentially of, or consists of ATtTCcaaattcactTTtAC (SEQ ID NO: 472, ASO-001940); AtTTCcaaattcactTTtAC (SEQ ID NO: 473, ASO-001933), ATTTccaaattcactTTTAC (SEQ ID NO: 474; ASO-001919); ATTTCcaaattcacttTTAC (SEQ ID NO: 482, ASO-001962); ATTtCcaaattcacTtTtAC (SEQ ID NO: 487, ASO-002038), ATtTCcaaattcactTTtAC (SEQ ID NO: 524, ASO-002263), AtTTCcaaattcactTTtAC (SEQ ID NO: 493, ASO-002439), TATTTccaaattcactTTTA (SEQ ID NO: 532, ASO-001954); TTaTTtccaaattcaCTtTT (SEQ ID NO: 593, ASO-001941), TTTATttccaaattcACTTT (SEQ ID NO: 644, ASO-000756); TTtATttccaaattcACtTT (SEQ ID NO: 645, ASO-001967); TTTATttccaaattcaCTTT (SEQ ID NO: 646, ASO-001955), TTTAtttccaaattcACTTT (SEQ ID NO: 647, ASO-001948), CTTTAtttccaaattCACTT (SEQ ID NO: 677, ASO-000757); CTTTAtttccaaattcACTT (SEQ ID NO: 679, ASO-001928), ACTTTatttccaaattCACTT (SEQ ID NO: 680, ASO-001968); CTTTatttccaaattCACTT (SEQ ID NO: 681, ASO-001921), CTtTAtttccaaattCAcTT (SEQ ID NO: 683, ASO-001942), TTTccaaattcaCTT (SEQ ID NO: 684, ASO-000128); CtTTAtttccaaattCAcTT (SEQ ID NO: 685, ASO-001935), ATTtccaaattcaCTT (SEQ ID NO: 686, ASO-000013); CTTtatttccaaatTcACT (SEQ ID NO: 714, ASO-002012); ACTTTatttccaaattCACT (SEQ ID NO: 715, ASO-001962); ACTTtatttccaaatTCACT (SEQ ID NO: 716, ASO-001956), CTTtatttccaaatTCACT (SEQ ID NO: 720, ASO-001995); CTTtatttccaaatTCAC (SEQ ID NO: 740, ASO-002007); CTTtatttccaaatTcAC (SEQ ID NO: 745, ASO-001997); AATaactttatttCCA (SEQ ID NO: 773, ASO-000118); AGTaataactttaTTT (SEQ ID NO: 780, ASO-000170); AGTaataactttATT (SEQ ID NO: 782, ASO-000125); AGAgtaataacttTAT (SEQ ID NO: 784, ASO-000134); AGAgtaataactTTA (SEQ ID NO: 786, ASO-000178); AATcagagtaatAAC (SEQ ID NO: 794, ASO-000307); TTAatcagagtaaTAA (SEQ ID NO: 795, ASO-000204); TAAtcagagtaaTAA (SEQ ID NO: 796, ASO-000330); TTTaatcagagtaATA (SEQ ID NO: 797, ASO-000326); and TTTaatcagagtAAT (SEQ ID NO: 798, ASO-000249).

E53. The oligomer of embodiment 1 to 48, which comprises, consists essentially of, or consists of a nucleotide sequence selected from FIGS. 16A to 16C and 16D to 16K.

E54. The oligomer of embodiment 53, which comprises, consists essentially of, or consists of a nucleotide sequence selected from FIGS. 16A to 16C and 16D to 16K, wherein the upper case letter is LNA and the lower case letter is DNA.

E55. The oligomer of any one of embodiments 1 to 54, which comprises an internucleoside linkage selected from: a phosphodiester linkage, a phosphotriester linkage, a methylphosphonate linkage, a phosphoramidate linkage, a phosphorothioate linkage, and combinations thereof.

E56. The oligomer of any one of embodiments 1 to 55, wherein the oligomer comprises a nucleotide analog.

E57. The oligomer of embodiment 56, wherein the nucleotide analog comprises 5'methyl cytosine.

E58. A conjugate comprising the oligomer of any one of embodiments 1 to 57, wherein the oligomer is covalently attached to at least one non-nucleotide or non-polynucleotide moiety.

E59. The conjugate of embodiment 58, wherein the non-nucleotide or non-polynucleotide moiety comprises a protein, a fatty acid chain, a sugar residue, a glycoprotein, a polymer, or any combinations thereof.

E60. A pharmaceutical composition comprising the oligomer of any one embodiments 1 to 57 or the conjugate of embodiment 58 or 59 and a pharmaceutically acceptable carrier.

E61. The composition of embodiment 60, which further comprises a therapeutic agent.

E62. The composition of embodiment 61, wherein the therapeutic agent is a Tau antagonist.

E63. The composition of embodiment 62, wherein the Tau antagonist is an anti-Tau antibody or fragment thereof.

E64. A kit comprising the oligomer of any one embodiments 1 to 57, the conjugate of embodiment 58 or 59, or the composition of any one of embodiments 60 to 63 and instructions for use.

E65. A diagnostic kit comprising the oligomer of any one embodiments 1 to 57, the conjugate of embodiment 58 or 59, or the composition of any one of embodiments 60 to 63 and instructions for use.

E66. A method of inhibiting or reducing Tau protein expression in a cell, the method comprising administering the oligomer of any one embodiments 1 to 57, the conjugate of embodiment 58 or 59, or the composition of any one of embodiments 60 to 63 to the cell expressing Tau protein, wherein the Tau protein expression in the cell is inhibited or reduced after the administration.

E67. The method of embodiment 66 wherein the oligomer inhibits or reduces expression of Tau mRNA in the cell after the administration.

E68. The method of embodiment 66 or 67, wherein the expression of Tau mRNA is reduced by at least about 20%, at least about 30%, at least about 40%, at least about 50%, at least about 60%, at least about 70%, at least about 80%, at least about 90%, or about 100% after the administration compared to a cell not exposed to the oligomer.

E69. The method of any one of embodiments 66 to 68, wherein the oligomer reduces expression of Tau protein in the cell after the administration by at least about 60%, at least about 70%, at least about 80%, or at least about 90% compared to a cell not exposed to the oligomer.

E70. The method of any one of embodiments 66 to 69, wherein the cell is a neuron.

E71. A method for treating a tauopathy in a subject in need thereof, comprising administering an effective amount of the oligomer of any one embodiments 1 to 57, the conjugate of embodiment 58 or 59, or the composition of any one of embodiments 60 to 63 to the subject.

E72. The method of embodiment 71, wherein the tauopathy is a disease selected from Alzheimer's disease, progressive supranuclear palsy, dementia pugilistica (chronic traumatic encephalopathy), frontal temporal dementia, parkinsonism linked to chromosome 17, Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, frontotemporal lobar degeneration, and any combination thereof.

E73. The method of embodiment 71, wherein the tauopathy is progressive supranuclear palsy.

E74. The method of embodiment 71, wherein the tauopathy is Alzheimer's disease.

E75. The method of embodiment 71, wherein the tauopathy is frontal temporal dementia.

E76. A method of regulating neuronal hyperexcitability in a subject in need thereof comprising administering an effective amount of the oligomer of any one embodiments 1 to 57, the conjugate of embodiment 58 or 59, or the composition of any one of embodiments 60 to 63 to the subject.

E77. A method for treating a seizure disorder in a subject in need thereof, comprising administering an effective amount of the oligomer of any one embodiments 1 to 57, the conjugate of embodiment 58 or 59, or the composition of any one of embodiments 60 to 61 to the subject.

E78. The method of embodiment 77, wherein the seizure disorder is a disease selected from epilepsy, juvenile myoclonic epilepsy, reflex epilepsy, benign familial infantile epilepsy (BFIE), infantile convulsions, infantile spasms, choreoathetosis (ICCA) syndrome, injury-associated seizures, brain injury, brain strokes, meningitis, and febrile seizures.

E79. A method for treating or preventing a neurological disorder comprising administering an effective amount of the oligomer of any one of embodiments 1 to 57, the conjugate of embodiment 58 or 59, or the composition of any one of embodiments 60 to 63.

E80. The method of embodiment 79, wherein the neurological disorder is selected from progressive supranuclear palsy, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Parkinson's disease, Huntington's disease, Hemimegalencephaly, Tuberous sclerosis complex, Focal cortical dysplasia type 2b, or Ganglion cell tumors. In certain embodiments, the disease or condition is an epileptic disorder without tauopathy, e.g., Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, Landau Kleffner syndrome, focal seizures, simple focal seizures (no loss of consciousness), focal dyscognitive seizures (impairment of consciousness), focal seizure evolving to generalized tonic-clonic (GTC) convulsions, generalized seizures (convulsive or non-convulsive with bilateral discharges involving subcortical structures), absence seizures, myoclonic seizures, clonic seizures, tonic seizures, tonic-clonic seizures, atonic seizures, an autistic disorder, an autism spectrum disorder (e.g., as defined in the Diagnostic and Statistical Manual of Mental Disorders V (DSM-V)), an Asperger's disorder, a pervasive developmental disorder, and any combination thereof.

E81. The method of any one of embodiments 71 to 80, wherein the subject is a human.

E82. Use of the oligomer according to any one of the embodiments 1 to 57 for the manufacture of a medicament for the treatment of a neurological disorder.

E83. The oligomer of any one of embodiments 1 to 57 for use in therapy of a disease or condition.

E84. The oligomer for use of embodiment 83, wherein the disease or condition is a neurological disorder.

E85. The oligomer of embodiment 50, wherein the oligomer is ATtTCcaaattcactTTtAC (SEQ ID NO: 472) with the chemical structure of OxyAs OxyTs DNAts OxyTs OxyMCs DNAcs DNAas DNAas DNAas DNAts DNAts DNAcs DNAas DNAcs DNAts OxyTs OxyTs DNAts OxyAs OxyMC (ASO-001940); AtTTCcaaattcactTTtAC (SEQ ID NO: 473) with the chemical structure of OxyAs DNAts OxyTs OxyTs OxyMCs DNAcs DNAas DNAas DNAas DNAts DNAts DNAcs DNAas DNAcs DNAts OxyTs OxyTs DNAts OxyAs OxyMC (ASO-001933); ATTTccaaattcactTTTAC (SEQ ID NO: 474) with the chemical structure of OxyAs OxyTs OxyTs OxyTs DNAcs DNAcs DNAas DNAas DNAas DNAts DNAts DNAcs DNAas DNAcs DNAts OxyTs OxyTs OxyTs OxyAs OxyMC (ASO-001919); ATTTCcaaattcacttTTAC (SEQ ID NO: 482) with the chemical structure of OxyAs OxyTs DNAts OxyTs DNAcs OxyMCs DNAas OxyAs DNAas DNAts DNAts DNAcs DNAas DNAcs DNAts OxyTs DNAts OxyTs OxyAs OxyMC (ASO-001962); ATTtCcaaattcacTtTtAC (SEQ ID NO: 487) with the chemical structure of OxyAs OxyTs OxyTs DNAts OxyMCs DNAcs DNAas DNAas DNAas DNAts DNAts DNAcs DNAas DNAcs OxyTs DNAts OxyTs DNAts OxyAs OxyMC (ASO-002038); AtTTCcaaattcactTTtAC (SEQ ID NO: 493) with the chemical structure of OxyTs OxyMCs OxyMCs OxyAs OxyAs DNAas DNAts DNAts DNAcs DNAas DNAcs DNAts DNAts DNAts OxyTs OxyAs OxyMCs (ASO-002439); ATtTCcaaattcactTTtAC (SEQ ID NO: 524) with the chemical structure of OxyAs OxyTs DNAts OxyTs DNAcs OxyMCs DNAas DNAas DNAas DNAts DNAts DNAcs DNAas DNAcs DNAts OxyTs OxyTs DNAts OxyAs OxyMCs (ASO-002263); TATTTccaaattcactTTTA (SEQ ID NO: 532) with the chemical structure of OxyTs OxyAs OxyTs OxyTs OxyTs DNAcs DNAcs DNAas DNAas DNAas DNAts DNAts DNAcs DNAas DNAcs DNAts OxyTs OxyTs OxyTs OxyA (ASO-001954); TTaTTtccaaattcaCTtTT (SEQ ID NO: 593) with the chemical structure of OxyTs OxyTs DNAas OxyTs OxyTs DNAts DNAcs DNAcs DNAas DNAas DNAas DNAts DNAts DNAcs DNAas OxyMCs OxyTs DNAts OxyTs OxyT (ASO-001941); TTTATtccaaattcACTTT (SEQ ID NO: 644) with the chemical structure of OxyTs OxyTs OxyTs OxyAs OxyTs DNAts DNAts DNAcs DNAcs DNAas DNAas DNAas DNAts DNAts DNAcs OxyAs OxyMCs OxyTs OxyTs OxyT (ASO-000756); TTtATttccaaattcACtTT (SEQ ID NO: 645) with the chemical structure of OxyTs OxyTs DNAts OxyAs OxyTs DNAts DNAts DNAcs DNAcs DNAas DNAas DNAas DNAts DNAts DNAcs OxyAs OxyMCs DNAts OxyTs OxyT (ASO-001967); TTTATttccaaattcaCTTT (SEQ ID NO: 646) with the chemical structure of OxyTs OxyTs OxyTs OxyAs OxyTs DNAts DNAts DNAcs DNAcs DNAas DNAas DNAas DNAts DNAts DNAcs DNAas OxyMCs OxyTs OxyTs OxyT (ASO-001955); TTTAtttccaaattcACTTT (SEQ ID NO: 647) with the chemical structure of OxyTs OxyTs OxyTs OxyAs DNAts DNAts DNAts DNAcs DNAcs DNAas DNAas DNAas DNAts DNAts DNAcs OxyAs OxyMCs OxyTs OxyTs OxyT (ASO-001948); CTTTAtttccaaattCACTT (SEQ ID NO: 677) with the chemical structure of OxyMCs OxyTs OxyTs OxyTs OxyAs DNAts DNAts DNAts DNAcs DNAcs DNAas DNAas DNAas DNAts DNAts OxyMCs OxyAs OxyMCs OxyTs OxyT (ASO-000757); CTTTAtttccaaattcACTT (SEQ ID NO: 679) with the chemical structure of OxyMCs OxyTs OxyTs OxyTs OxyAs DNAts DNAts DNAts DNAcs DNAcs DNAas DNAas DNAas DNAts DNAts DNAcs OxyAs OxyMCs OxyTs OxyT (ASO-001928); ACTTTatttccaaattCACTT (SEQ ID NO: 680) with the chemical structure of OxyAs OxyMCs OxyTs OxyTs OxyTs DNAas DNAts DNAts DNAts DNAcs DNAcs DNAas DNAas DNAas DNAts DNAts OxyMCs OxyAs OxyMCs OxyTs OxyT (ASO-001968); CTTTatttccaaattCACTT (SEQ ID NO: 681) with the chemical structure of OxyMCs OxyTs OxyTs OxyTs DNAas DNAts DNAts DNAts DNAcs DNAcs DNAas DNAas DNAas DNAts DNAts OxyMCs OxyAs OxyMCs OxyTs OxyT (ASO-001921); CTtTAtttccaaattCAcTT (SEQ ID NO: 683) with the chemical structure of OxyMCs OxyTs DNAts OxyTs OxyAs DNAts DNAts DNAts DNAcs DNAcs DNAas DNAas DNAas DNAts DNAts OxyMCs OxyAs DNAcs OxyTs OxyT (ASO-001942); TTTccaaattcaCTT (SEQ ID NO: 684) with the chemical structure of OxyTs OxyTs OxyTs DNAcs DNAcs DNAas DNAas DNAas DNAts DNAts DNAcs DNAas OxyMCs OxyTs OxyT (ASO-000128); CtTTAtttccaaattCAcTT (SEQ ID NO: 685) with the chemical structure of OxyMCs DNAts OxyTs OxyTs OxyAs DNAts DNAts DNAts DNAcs DNAcs DNAas DNAas DNAas DNAts DNAts OxyMCs OxyAs DNAcs OxyTs OxyT (ASO-001935); ATTtccaaattcaCTT (SEQ ID NO: 686) with the chemical structure of OxyAs OxyTs OxyTs DNAts DNAcs DNAcs DNAas DNAas DNAas DNAts DNAts DNAcs DNAas OxyMCs OxyTs OxyT (ASO-000013); CTTtatttccaaatTcACT (SEQ ID NO: 714) with the chemical structure of OxyMCs OxyTs OxyTs DNAts DNAas DNAts DNAts DNAts DNAcs DNAcs DNAas DNAas DNAas DNAts OxyTs DNAcs OxyAs OxyMCs OxyT (ASO-002012); ACTTTatttccaaattCACT (SEQ ID NO: 715) with the chemical structure of OxyAs OxyMCs OxyTs OxyTs OxyTs DNAas DNAts DNAts DNAts DNAcs DNAcs DNAas DNAas DNAas DNAts DNAts OxyMCs OxyAs OxyMCs OxyT (ASO-001962); ACTTtatttccaaatTCACT (SEQ ID NO: 716) with the chemical structure of OxyAs OxyMCs OxyTs OxyTs DNAts DNAas DNAts DNAts DNAts DNAcs DNAcs DNAas DNAas DNAas DNAts OxyTs OxyMCs OxyAs OxyMCs OxyT (ASO-001956), CTTtatttccaaatTCACT (SEQ ID NO: 720) with the chemical structure of OxyMCs OxyTs OxyTs DNAts DNAas DNAts DNAts DNAts DNAcs DNAcs DNAas DNAas DNAas DNAts OxyTs OxyMCs OxyAs OxyMCs OxyT (ASO-1995); CTTtatttccaaatTCAC (SEQ ID NO: 740) with the chemical structure of OxyMCs OxyTs OxyTs DNAts DNAas DNAts DNAts DNAts DNAcs DNAcs DNAas DNAas DNAas DNAts OxyTs OxyMCs OxyAs OxyMC (ASO-002007); CTTtatttccaaatTcAC (SEQ ID NO: 745) with the chemical structure of OxyMCs OxyTs OxyTs DNAts DNAas DNAts DNAts DNAts DNAcs DNAcs DNAas DNAas DNAas DNAts OxyTs DNAcs OxyAs OxyMC (ASO-001997); AATaactttatttCCA (SEQ ID NO: 773) with the chemical structure of OxyAs OxyAs OxyTs DNAas DNAas DNAcs DNAts DNAts DNAts DNAas DNAts DNAts DNAts OxyMCs OxyMCs OxyA (ASO-000118); AGTaataactttaTTT (SEQ ID NO: 780) with the chemical structure of OxyAs OxyGs OxyTs DNAas DNAas DNAts DNAas DNAas DNAcs DNAts DNAts DNAts DNAas OxyTs OxyTs OxyT (ASO-000170); AGTaataactttATT (SEQ ID NO: 782) with the chemical structure of OxyAs OxyGs OxyTs DNAas DNAas DNAts DNAas DNAas DNAcs DNAts DNAts DNAts OxyAs OxyTs OxyT (ASO-000125); AGAgtaataacttTAT (SEQ ID NO: 784) with the chemical structure of OxyAs OxyGs OxyAs DNAgs DNAts DNAas DNAas DNAts DNAas DNAas DNAcs DNAts DNAts OxyTs OxyAs OxyT (ASO-000134); AGAgtaataactTTA (SEQ ID NO: 786) with the chemical structure of OxyAs OxyGs OxyAs DNAgs DNAts DNAas DNAas DNAts DNAas DNAas DNAcs DNAts OxyTs OxyTs OxyA (ASO-000178); AATcagagtaatAAC (SEQ ID NO: 794) with the chemical structure of OxyAs OxyAs OxyTs DNAcs DNAas DNAgs DNAas DNAgs DNAts DNAas DNAas DNAts OxyAs OxyAs OxyMC (ASO-000307); TTAatcagagtaaTAA (SEQ ID NO: 795) with the chemical structure of OxyTs OxyTs OxyAs DNAas DNAts DNAcs DNAas DNAgs DNAas DNAgs DNAts DNAas DNAas OxyTs OxyAs OxyA (ASO-000204); TAAtcagagtaaTAA (SEQ ID NO: 796) with the chemical structure of OxyTs OxyAs OxyAs DNAts DNAcs DNAas DNAgs DNAas DNAgs DNAts DNAas DNAas OxyTs OxyAs OxyA (ASO-000330); TTTaatcagagtaATA (SEQ ID NO: 797) with the chemical structure of OxyTs OxyTs OxyTs DNAas DNAas DNAts DNAcs DNAas DNAgs DNAas DNAgs DNAts DNAas OxyAs OxyTs OxyA (ASO-000326); or TTTaatcagagtAAT (SEQ ID NO: 798) with the chemical structure of OxyTs OxyTs OxyTs DNAas DNAas DNAts DNAcs DNAas DNAgs DNAas DNAgs DNAts OxyAs OxyAs OxyT (ASO-000249).

BRIEF DESCRIPTION OF FIGURES

FIGS. 1A to 1XX show Tau genomic, mRNA, and protein sequences. SEQ ID NO: 1 in FIG. 1A to 1TT represents a MAPT genomic sequence. SEQ ID NO: 1 is identical to a MAPT pre-mRNA sequence except that nucleotide "t" in SEQ ID NO: 1 is shown as "u" in pre-mRNA. SEQ ID NO: 2 in FIG. 1UU to 1WW represents a MAPT mRNA sequence except that nucleotide "t" in SEQ ID NO: 2 is shown as "u" in mRNA. The Tau protein sequence encoded by the MAPT mRNA is shown as SEQ ID NO: 3 in FIG. 1XX.

FIG. 2A to 2NNNN shows exemplary oligomers, designs (ASO Sequence), and chemical structure of the oligomers. FIG. 2A to 2NNNN lists the oligomer name, antisense oligomer (ASO) identification number, ASO sequence, SEQ ID Number, target start and end positions on the MAPT pre-mRNA sequence and chemical structure. Examples of oligomers with mismatched bases are provided in FIG. 2A to 2NNNN as "mm." The specific mismatched base-pairs are bolded, underlined, italicized, and highlighted.

FIG. 3A to 3Z shows exemplary oligomers targeting nucleotides 134,947 to 138,940 of SEQ ID NO: 1. FIG. 3A to 3Z lists the SEQ ID number, oligomer name, ASO identification number, ASO sequence, target start and end positions on the MAPT pre-mRNA sequence, target start on the mature mRNA sequence and normalized Tau/Tuj-1 and Tuj-1 immunocytochemistry values (as discussed in Example 2 below). Examples of oligomers with mismatched bases are provided in FIG. 3A to 3Z as "mm." The specific mismatched base-pairs are bolded, underlined, italicized, and highlighted.

FIG. 6A to 6GG shows the impact of Tau antisense oligonucleotides on spontaneous calcium oscillations in primary neurons. FIG. 6A to 6GG lists the ASO identification number, ASO sequence, SEQ ID Number, target start and end positions on the MAPT pre-mRNA sequence, calcium oscillation data as a percent of control (as discussed in Example 3 below) and $IC_{50}$ values of Tau neurons (as discussed in Example 2 below). Examples of oligomers with mismatched bases are provided in FIG. 6A to 6GG as "mm." The specific mismatched base-pairs are bolded, underlined, italicized, and highlighted.

FIG. 7A to 7E shows the in vivo tolerability of exemplary oligomers. FIG. 7A to 7E lists the ASO identification number, ASO sequence, SEQ ID Number, target start and end positions on the MAPT pre-mRNA sequence, in vivo acute tolerability score (as discussed in Example 5 below) and the percent of brain MAPT mRNA remaining after administration (as also discussed in Example 5 below).

FIG. 12 shows the comparison of the sequence of selected oligomers and the sequence of Rho A which aligns with a portion of the MAPT genomic sequence (SEQ ID NO: 1). The RhoA sequence is listed as actttatttccaaatacacttcttt (SEQ ID NO: 959). The mismatches between the selected oligomers and the Rho A sequence were highlighted. The sequence of ASO-000757 has one mismatch compared to the corresponding RhoA sequence; the sequences of ASO-0001967, ASO-000755, and ASO-001941 have two mismatches compared to the corresponding RhoA sequence; and the sequences of ASO-000753, ASO-002038, ASO-001933, and ASO-001940 have four mismatches compared to the corresponding RhoA sequence. FIG. 12 shows that the traditional gapmers (i.e., ASO-000757, ASO-000755, and ASO-000753) are not tolerated beyond 4 weeks following a single 100 μg ICV bolus dose while the alternating flank gapmers (i.e., ASO-001941, ASO-002038, ASO-001933, and ASO-001940) exhibit tolerability beyond 4 weeks. Tubulin inhibition was highly correlated, in this data set, to long term tolerability. Rho A reduction greater than 25% (i.e., ASO-000757, ASO-000755, and ASO-000753) was also correlated with lack of long term tolerability (greater than 4 weeks following a single ICV bolus injection of 100 μg of each ASO shown).

FIG. 14A shows that a single 100 μg ICV bolus reduces total Tau protein using BT-2 and HT-7 ELISA. The left panel shows the total Tau protein expression (% of control) when a vehicle is administered (i.e., 100%), and the right panel shows the total Tau protein expression when ASO-000774 was administered. FIG. 14B shows the total wheel counts assessed in a running wheel assay in Tg4510 (tauopathy mouse model) and double negative littermate controls (Dbl Neg) as described in the Example 7.

FIG. 15A shows survival plots of Dravet mice and littermate controls treated with a single ICV administration of 20 or 37 μg of Tau ASO-000762 targeting the 3'-UTR region of Tau mRNA. The oligomer has been shown to reduce 20-50% of Tau protein (data not shown) at 10 days postnatally. The upper line in FIG. 15A shows the percent survival of the Dravet mice treated with a single ICV administration of 37 μg of Tau ASO-000762. The middle line in FIG. 15A shows the percent survival of the Dravet mice treated with a single ICV administration of 20 μg of Tau ASO-000762. The lower line in FIG. 15A shows the percent survival of the Dravet mice treated with a single ICV administration of saline. FIG. 15B shows the percent mice without hyperthermia-induced Generalized Tonic-Clonic Seizures (GTCS) in Dravet mice. The GTCS was measured 8-9 weeks post-injection of ASO-000762 at 20 μg. The percent mice without GTCS after administration of vehicle is shown in circle, and the percent mice without GTCS after administration of ASO-000762 is shown as square.

FIGS. 16A to 16C and 16D to 16K show exemplary oligomers, designs, and their chemical structures. FIG. 16A to 16C lists the antisense oligomer (ASO) identification number, SEQ ID number, ASO sequence, target start and end positions on the Tau pre-mRNA sequence, $IC_{50}$ values of Tau neurons (as discussed in Example 8 below) and percent Tau inhibition (as also discussed in Example 8 below). FIG. 16D to 16K shows the specific chemical structure of the oligomers shown in FIG. 16A to 16C and lists the antisense oligomer (ASO) identification number, ASO sequence, target start and end positions on the Tau pre-mRNA sequence and chemical structure.

FIGS. 20A and 20B to 20C show exemplary oligomers, designs, and chemical structures tested by QUANTIGENE® analysis. FIG. 20A lists the antisense oligomer (ASO) identification number, SEQ ID number, ASO sequence, target start and end positions on the Tau pre-mRNA sequence, start position on the mature mRNA sequence, and QUANTIGENE® expression of mRNA (as discussed in Example 10 below). FIG. 20B to 20C shows the specific chemical structure of the oligomers shown in FIG. 20A and lists the antisense oligomer (ASO) identification number, ASO sequence, target start and end positions on the Tau pre-mRNA sequence and chemical structure.

DETAILED DESCRIPTION OF INVENTION

I. Definitions

Figure 4:
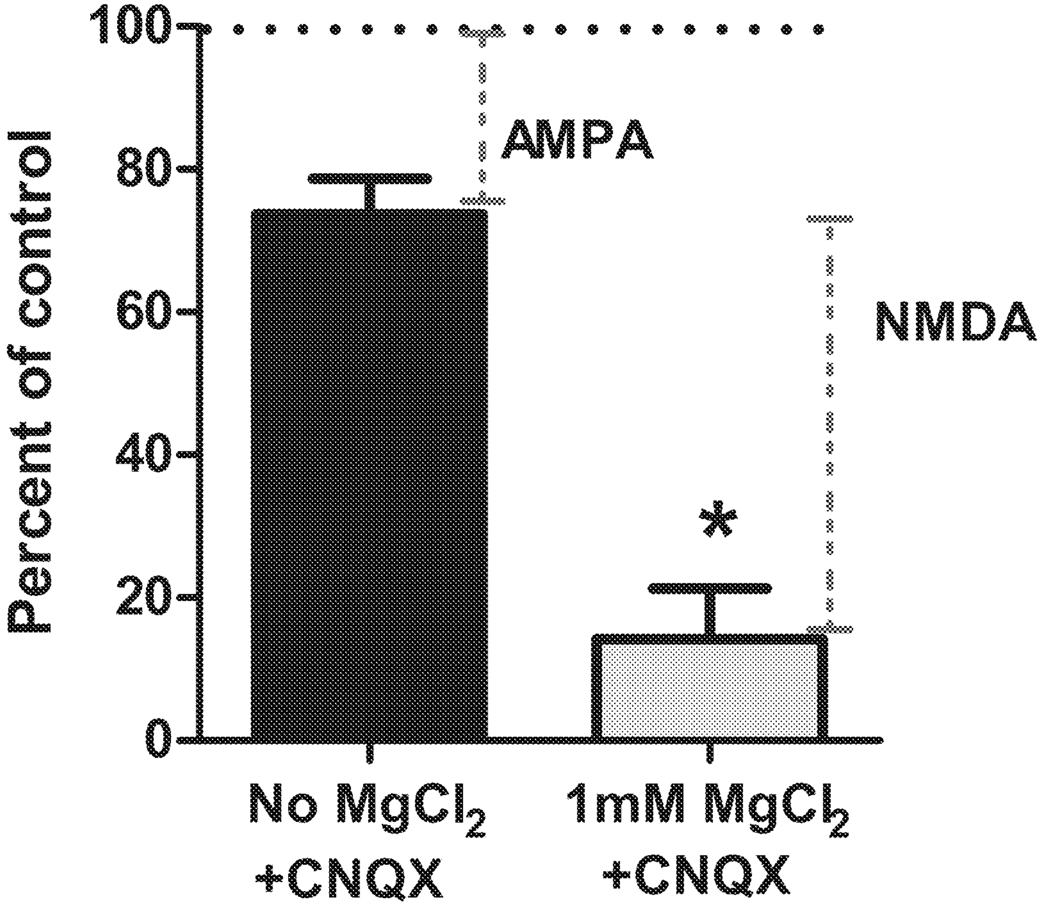
FIG. 4 is a graph demonstrating primary neuronal spontaneous calcium oscillations. Primary neuronal spontaneous calcium oscillations were measured as described previously (Murphy et. al., 1992, 1 Neurosci. 12:4834-4845). Addition of the α-amino-3-hydroxy-5-methyl-4-isoxazolepropionic acid (AMPA) receptor antagonist, 6-Cyano-7-nitroquinoxaline-2,3-dione (CNQX; 3 μM), reduced calcium oscillations by 20% representing the total AMPA response in the assay (AMPA labeled bar shown). Calcium oscillations were reduced further, by about 80%, when N-methyl-D-aspartate (NMDA) receptor function was blocked by 1 mM $MgCl_2$ (NMDA labeled bar shown).

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). For example, if it is stated that "the oligomer reduces expression of Tau protein in a cell following administration of the oligomer by at least about 60%," it is implied that the Tau levels are reduced by a range of 50% to 70%.

The term "nucleic acids" or "nucleotides" is intended to encompass plural nucleic acids. In some embodiments, the term "nucleic acids" or "nucleotides" refers to a target sequence, e.g., pre-mRNAs, mRNAs, or DNAs in vivo or in vitro. When the term refers to the nucleic acids or nucleotides in a target sequence, the nucleic acids or nucleotides can be naturally occurring sequences within a cell. In other embodiments, "nucleic acids" or "nucleotides" refers to a sequence in the oligomers of the invention. When the term refers to a sequence in the oligomers, the nucleic acids or nucleotides are not naturally occurring. In one embodiment, the nucleic acids or nucleotides in the oligomers are produced synthetically or recombinantly, but are not a naturally occurring sequence or a fragment thereof. In another embodiment, the nucleic acids or nucleotides in the oligomers contain at least one nucleotide analog that is not naturally occurring in nature. The term "nucleic acid" or "nucleoside" refers to a single nucleic acid segment, e.g., a DNA, an RNA, or an analog thereof, present in a polynucleotide. "Nucleic acid" or "nucleoside" includes naturally occurring nucleic acids or non-naturally occurring nucleic acids. In some embodiments, the terms "nucleotide", "unit" and "monomer" are used interchangeably. It will be recognized that when referring to a sequence of nucleotides or monomers, what is referred to is the sequence of bases, such as A, T, G, C or U, and analogs thereof.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogs" herein. Herein, a single nucleotide (unit) can also be referred to as a monomer or nucleic acid unit. In certain embodiments, the term "nucleotide analogs" refers to nucleotides having modified sugar moieties. Non-limiting examples of the nucleotides having modified sugar moieties (e.g., LNA) are disclosed elsewhere herein. In other embodiments, the term "nucleotide analogs" refers to nucleotides having modified base moieties. The nucleotides having modified base moieties include, but are not limited to, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

The term "nucleoside" as used herein is used to refer to a glycoside comprising a sugar moiety and a base moiety, and can therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide can refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" can refer to a "nucleoside" for example the term "nucleotide" can be used, even when specifying the presence or nature of the linkages between the nucleosides.

The term "nucleotide length" as used herein means the total number of the nucleotides (monomers) in a given sequence. For example, the sequence of AAAgatgaaatttgctcTTA (SEQ ID NO: 4) has 20 nucleotides; thus the nucleotide length of the sequence is 20. The term "nucleotide length" is therefore used herein interchangeably with "nucleotide number."

As one of ordinary skill in the art would recognize, the 5' terminal nucleotide of an oligonucleotide does not comprise a 5' internucleotide linkage group, although it can comprise a 5' terminal group.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, untranslated regions ("UTRs"), and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide.

The term "non-coding region" as used herein means a nucleotide sequence that is not a coding region. Examples of non-coding regions include, but are not limited to, promoters, ribosome binding sites, transcriptional terminators, introns, untranslated regions ("UTRs"), non-coding exons and the like. Some of the exons can be wholly or part of the 5' untranslated region (5' UTR) or the 3' untranslated region (3' UTR) of each transcript. The untranslated regions are important for efficient translation of the transcript and for controlling the rate of translation and half-life of the transcript.

The term "region" when used in the context of a nucleotide sequence refers to a section of that sequence. For example, the phrase "region within a nucleotide sequence" or "region within the complement of a nucleotide sequence" refers to a sequence shorter than the nucleotide sequence, but longer than at least 10 nucleotides located within the particular nucleotide sequence or the complement of the nucleotides sequence, respectively. The term "sub-sequence" or "subsequence" can also refer to a region of a nucleotide sequence.

The term "downstream," when referring to a nucleotide sequence, means that a nucleic acid or a nucleotide sequence is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, UTRs, and stem-loop structures. If a coding region is intended for expression in a eukaryotic cell, a polyadenylation signal and transcription termination sequence will usually be located 3' to the coding sequence.

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms to produce different proteins and RNAs such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, a RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

The terms "identical" or percent "identity" in the context of two or more nucleic acids refer to two or more sequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., 1990, Proc. Natl. Acad. Sci., 87:2264-2268, as modified in Karlin et al., 1993, Proc. Natl. Acad. Sci., 90:5873-5877, and incorporated into the NBLAST and XBLAST programs (Altschul et al., 1997, Nucleic Acids Res., 25:3389-3402). In certain embodiments, Gapped BLAST can be used as described in Altschul et al., 1997, Nucleic Acids Res. 25:3389-3402. BLAST-2, WU-BLAST-2 (Altschul et al., 1996, Methods in Enzymology, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first nucleotide sequence to a second nucleotide sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

Different regions within a single polynucleotide target sequence that align with a polynucleotide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

As used herein, the terms "homologous" and "homology" are interchangeable with the terms "identity" and "identical."

The term "naturally occurring variant thereof" refers to variants of the Tau polypeptide sequence or MAPT nucleic acid sequence (e.g., transcript) which exist naturally within the defined taxonomic group, such as mammalian, such as mouse, monkey, and human. Typically, when referring to "naturally occurring variants" of a polynucleotide the term also can encompass any allelic variant of the MAPT-encoding genomic DNA which is found at Chromosomal position 17q21 by chromosomal translocation or duplication, and the RNA, such as mRNA derived therefrom. "Naturally occurring variants" can also include variants derived from alternative splicing of the MAPT mRNA. When referenced to a specific polypeptide sequence, e.g., the term also includes naturally occurring forms of the protein, which can therefore be processed, e.g., by co- or post-translational modifications, such as signal peptide cleavage, proteolytic cleavage, glycosylation, etc.

In determining the degree of "complementarity" between oligomers of the invention (or regions thereof) and the target region of the nucleic acid which encodes mammalian Tau (e.g., the MAPT gene), such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the two sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

The term "complement" as used herein indicates a sequence that is complementary to a reference sequence. It is well known that complementarity is the base principle of DNA replication and transcription as it is a property shared between two DNA or RNA sequences, such that when they are aligned antiparallel to each other, the nucleotide bases at each position in the sequences will be complementary, much like looking in the mirror and seeing the reverse of things. Therefore, for example, the complement of a sequence of 5' "ATGC"3' can be written as 3' "TACG"5' or 5' "GCAT"3'. The terms "reverse complement", "reverse complementary" and "reverse complementarity" as used herein are interchangeable with the terms "complement", "complementary" and "complementarity."

The terms "corresponding to" and "corresponds to," when referencing two separate nucleic acid or nucleotide sequences can be used to clarify regions of the sequences that correspond or are similar to each other based on homology and/or functionality, although the nucleotides of the specific sequences can be numbered differently. For example, different isoforms of a gene transcript can have similar or conserved portions of nucleotide sequences whose numbering can differ in the respective isoforms based on alternative splicing and/or other modifications. In addition, it is recognized that different numbering systems can be employed when characterizing a nucleic acid or nucleotide sequence (e.g., a gene transcript and whether to begin numbering the sequence from the translation start codon or to include the 5'UTR). Further, it is recognized that the nucleic acid or nucleotide sequence of different variants of a gene or gene transcript can vary. As used herein, however, the regions of the variants that share nucleic acid or nucleotide sequence homology and/or functionality are deemed to "correspond" to one another. For example, a nucleotide sequence of a MAPT transcript corresponding to nucleotides X to Y of SEQ ID NO: 1 ("reference sequence") refers to an MAPT transcript sequence (e.g., MAPT pre-mRNA or mRNA) that has an identical sequence or a similar sequence to nucleotides X to Y of SEQ ID NO: 1. A person of ordinary skill in the art can identify the corresponding X and Y residues in the MAPT transcript sequence by aligning the MAPT transcript sequence with SEQ ID NO: 1.

The terms "corresponding nucleotide analog" and "corresponding nucleotide" are intended to indicate that the nucleobase in the nucleotide analog and the naturally occurring nucleotide have the same pairing, or hybridizing, ability. For example, when the 2-deoxyribose unit of the nucleotide is linked to an adenine, the "corresponding nucleotide analog" contains a pentose unit (different from 2-deoxyribose) linked to an adenine.

The term "design" or "oligomer design" or "ASO Sequence" as used herein refers to a pattern of nucleotides (e.g., DNA) and nucleotide analogs (e.g., LNA) in a given sequence. As used herein, the design of an oligomer is shown by a combination of upper case letters and lower case letters. For example, an oligomer sequence of tatttccaaattcactttta (SEQ ID NO: 573) can have oligomer designs of ASO-002350 (TAtTTccaaattcactTTTA), ASO-002374 (TAtTTccaaattcacTtTTA), ASO-002386 (TATTtccaaattcaCTttTA), ASO-002227 (TATtTccaaattcactTTTA), ASO-002245 (TAttTCcaaattcactTTTA), ASO-002261 (TATtTccaaattcacTTtTA), ASO-002276 (ATttCcaaattcactTTTA), ASO-002228 (TATTtccaaattcaCtTtTA), ASO-002255 (TATTtccaaattcactTTTA), ASO-002285 (TATTtccaaattcacTTtTA), ASO-002230 (TATTtccaaattcacTtTTA), ASO-002256 (TATTtccaaattcAcTttTA), or ASO-002279 (TATTtccaaattcActTtTA), wherein the upper case letter indicates a nucleotide analog (e.g., LNA) and the lower case letter indicates a nucleotide (e.g., DNA)

The term "chemical structure" of an oligomer as used herein refers to a detailed description of the components of the oligomers, e.g., nucleotides (e.g., DNA), nucleotide analogs (e.g., beta-D-oxy-LNA), nucleotide base (e.g., A, T, G, C, U, or MC), and backbone structure (e.g., phosphorothioate or phosphorodiester). For example, a chemical structure of ASO-002350 can be OxyTs OxyAs DNAts OxyTs OxyTs DNAcs DNAcs DNAas DNAas DNAas DNAts DNAts DNAcs DNAas DNAcs DNAts OxyTs OxyTs OxyTs OxyAs. FIGS. 2, 16D to 16K, and 20B to 20C lists non-limiting examples of chemical structures that can be applied to any one of the oligomers disclosed herein.

"Potency" is normally expressed as an $IC_{50}$ or $EC_{50}$ value, in μM, nM or pM unless otherwise stated. Potency can also be expressed in terms of percent inhibition. $IC_{50}$ is the median inhibitory concentration of a therapeutic molecule. $EC_{50}$ is the median effective concentration of a therapeutic molecule relative to a vehicle or saline control. In functional assays, $IC_{50}$ is the concentration that reduces a biological response, e.g., transcription of mRNA or protein expression, by 50% of the biological response that is achieved by the therapeutic molecule. In functional assays, $EC_{50}$ is the concentration of a therapeutic molecule that produces 50% of the biological response, eg., transcription of mRNA or protein expression. $IC_{50}$ or $EC_{50}$ can be calculated by any number of means known in the art.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an oligomer as disclosed herein is an amount sufficient to carry out a specifically stated purpose. An "effective amount" can be determined empirically and in a routine manner, in relation to the stated purpose.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for a disease or condition disclosed elsewhere herein according to the methods provided herein if the patient shows, e.g., total, partial, or transient alleviation or elimination of symptoms associated with the disease or disorder.

II. The Oligomer

The present invention employs oligomeric compounds (referred herein as oligomers), for use in modulating the function of nucleic acid molecules encoding mammalian Tau, such as the MAPT nucleic acid, e.g., MAPT transcript, including MAPT pre-mRNA, and MAPT mRNA, or naturally occurring variants of such nucleic acid molecules encoding mammalian Tau. The term "oligomer" in the context of the present invention, refers to a molecule formed by covalent linkage of two or more nucleotides (i.e., an oligonucleotide).

The oligomer comprises a contiguous nucleotide sequence of from about 10 to about 50, such as 10-20, 16-20, 15-25, 10-30, 10-35, 10-40, or 10-45 nucleotides in length. The terms "antisense oligomer," "antisense oligonucleotide," and "ASO" as used herein are interchangeable with the term "oligomer."

A reference to a SEQ ID number includes a particular nucleobase sequence, but does not include an oligomer design as shown in FIG. 2A to 2NNNN, 3A to 3Z, 6A to 6GG, 7A to 7E, 16A to 16C, 16D to 16K, 20A, or 20B to 20C. Furthermore, the oligomers disclosed in the figures herein show a representative design, but are not limited to the specific design shown in the tables. Herein, a single nucleotide (unit) can also be referred to as a monomer or unit. When this specification refers to a specific ASO number (or oligomer name), the reference includes the specific oligomer design. For example, when a claim (or this specification) recites SEQ ID NO: 803, it includes the nucleotide sequence of actttatttccaaattcacttttac. When a claim (or the specification) recites ASO-002019, it includes the nucleotide sequence of actttatttccaaattcacttttac with the oligomer design shown in the figures (i.e., ActtTatttccaaattcactTTtaC). Alternatively, ASO-002019 can be written as ActtTatttccaaattcactTTtaC, wherein the upper case letter is a modified nucleotide (e.g., LNA) and the lower case letter is a non-modified nucleotide (e.g., DNA). ASO-002019 can also be written as SEQ ID NO: 803, wherein each of the first nucleotide, the fifth nucleotide, the $21^{st}$ nucleotide, the $22^{nd}$ nucleotide, and the $25^{th}$ nucleotide from the 5' end is a modified nucleotide, e.g., LNA, and each of the other nucleotides is a non-modified nucleotide (e.g., DNA). The oligomers of the invention can also be written as SEQ ID NO: 803 with the chemical structure shown in FIG. 2A to 2NNNN, i.e., OxyAs OxyMCs DNAts DNAts OxyTs DNAas DNAts DNAts DNAts DNAcs DNAcs DNAas DNAas DNAas DNAts DNAts DNAcs DNAas DNAcs DNAts OxyTs OxyTs DNAts DNAas OxyMC.

In various embodiments, the oligomer of the invention does not comprise RNA (units). In some embodiments, the oligomer comprises one or more DNA units. In one embodiment, the oligomer according to the invention is a linear molecule or is synthesized as a linear molecule. In some embodiments, the oligomer is a single stranded molecule, and does not comprise short regions of, for example, at least 3, 4 or 5 contiguous nucleotides, which are complementary to equivalent regions within the same oligomer (i.e. duplexes)—in this regard, the oligomer is not (essentially) double stranded. In some embodiments, the oligomer is essentially not double stranded. In some embodiments, the oligomer is not a siRNA. In various embodiments, the oligomer of the invention can consist entirely of the contiguous nucleotide region. Thus, in some embodiments the oligomer is not substantially self-complementary.

In other embodiments, the present invention includes fragments of oligomers. For example, the invention includes at least one nucleotide, at least two contiguous nucleotides, at least three contiguous nucleotides, at least four contiguous nucleotides, at least five contiguous nucleotides, at least six contiguous nucleotides, at least seven contiguous nucleotides, at least eight contiguous nucleotides, or at least nine contiguous nucleotides of the oligomers disclosed herein.

Fragments of any of the sequences disclosed herein are contemplated as part of the invention.

II.A. The Target

Suitably the oligomer of the invention is capable of down-regulating (e.g., reducing or removing) expression of the MAPT mRNA or protein. In this regard, the oligomer of the invention can affect indirect inhibition of Tau protein through the reduction in Tau mRNA levels, typically in a mammalian cell, such as a human cell, such as a neuronal cell.

Microtubule-associated protein tau (MAPT), in a pathologic state associated with disease, is also known as neurofibrillary tangle protein or paired helical filament-tau (PHF-tau). Synonyms of MAPT are known and include DDPAC, FTDP-17L, MSTD, MTBT1, MTBT2, PPND, PPP1R103, MAPTL, and TAU. The sequence for the MAPT gene can be found under publicly available Accession Number NC_000017.11 and the sequence for the MAPT pre-mRNA transcript can be found under publicly available Accession Number NG 007398 (SEQ ID NO: 1). The sequence for Tau protein can be found under publicly available Accession Numbers: P10636, P18518, Q14799, Q15549, Q15550, Q15551, Q1RMF6, Q53YB1, Q5CZI7, Q5XWFO, Q6QT54, Q9UDJ3, Q9UMHO, Q9UQ96, each of which is incorporated by reference herein in its entirety. Natural variants of the MAPT gene product are known. For example, natural variants of Tau protein can contain one or more amino acid substitutions selected from: RSH, RSL, D285N, V289A, K574T, L583V, G589V, N596K, N613H, P618L, P618S, G620V, S622N, K634M, S637F, V654M, E659V, K6861, G706R, R723W, and any combinations thereof. Therefore, the oligomers of the present invention can be designed to reduce or inhibit expression of the natural variants of the Tau protein.

Mutations in Tau are known to cause one or more pathological conditions. The oligomers of the invention can be used to reduce or inhibit the expression of a SNP or alternatively spliced MAPT transcript containing one or more mutations and consequently reduce the formation of a mutated Tau protein. Examples of Tau protein mutants include, but are not limited to a Tau protein comprising one or more mutations selected from: S515E, S516E, S519E, S531A, T548A, T548E, S552A, S552E, S579A, S713E, S721E, S726E, S730E, S739E, and any combination thereof. The oligomer of the invention can be designed to reduce or inhibit expression of any mutants of Tau proteins.

An example of a target nucleic acid sequence of the oligomers is MAPT pre-mRNA or MAPT mRNA. SEQ ID NO: 1 in FIG. 1A to 1TT represents a MAPT genomic sequence. SEQ ID NO: 1 is identical to a MAPT pre-mRNA sequence except that nucleotide "t" in SEQ ID NO: 1 is shown as "u" in pre-mRNA. SEQ ID NO: 2 in FIG. 1UU to 1WW represents a MAPT mRNA sequence except that nucleotide 1 in SEQ ID NO: 2 is shown as "u" in mRNA. In certain embodiments, the "target nucleic acid" comprises a Tau protein-encoding nucleic acids or naturally occurring variants thereof, and RNA nucleic acids derived therefrom, e.g., pre-mRNA or mature mRNA. In some embodiments, for example when used in research or diagnostics the "target nucleic acid" can be a cDNA or a synthetic oligonucleotide derived from the above DNA or RNA nucleic acid targets. In one embodiment, the MAPT genomic sequence is shown as GenBank Accession No. NG_007398.1 (SEQ ID NO: 1). The 3' UTR region of the MAPT pre-mRNA is known to correspond to nucleotides 134,947-140,924 of SEQ ID NO: 1. The 5' UTR region of the MAPT pre-mRNA is known to correspond to nucleotides 1-72,917 of SEQ ID NO: 1. MAPT cDNA which corresponds to MAPT mRNA is known as GenBank Accession No. NM_016835.3 (SEQ ID NO: 2). See FIG. 1UU to 1WW. The Tau protein sequence encoded by the MAPT mRNA is shown as SEQ ID NO: 3. See FIG. 1XX.

In some embodiments, an oligomer of the invention hybridizes to a region within the 3' UTR of a MAPT transcript, e.g., SEQ ID NO: 1. In some embodiments, an oligomer of the invention hybridizes to a region within the 3' UTR of a MAPT transcript, e.g., SEQ ID NO: 1, wherein the oligomer has a design according to formula: 5' A-B-C 3' as described elsewhere herein (e.g., Section II.G, e.g., Section II.G.I) or a chemical structure shown elsewhere herein (e.g., FIGS. 2A to 2NNNN, 16D to 16K, and 20B to 20C). In certain embodiments, the oligomers hybridize to a region within a 3' UTR of a MAPT transcript, e.g., SEQ ID NO: 1, and have a sequence score equal to or greater than about 0.1, 0.2, 0.3, 0.4, 0.5, 0.6, 0.7, 0.8, 0.9, or 1.0. Calculation methods of the sequence score are disclosed elsewhere herein.

In one embodiment, the oligomer according to the invention comprises a contiguous nucleotide sequence that hybridizes to a region within 3' UTR in a microtubule-associated protein MAPT transcript, e.g., a region corresponding to the 3' UTR of SEQ ID NO: 1. In another embodiment, the oligomer of the invention comprises a contiguous nucleotide sequence that hybridizes to a nucleic acid sequence, or a region within the sequence, of a MAPT transcript ("target region"), wherein the nucleic acid sequence corresponds to nucleotides 134,947-138,940 of SEQ ID NO: 1. In another embodiment, the oligomer of the invention comprises a contiguous nucleotide sequence that hybridizes to a nucleic acid sequence, or a region within the sequence, of a MAPT transcript, wherein the nucleic acid sequence corresponds to nucleotides 134,947-138,940 of SEQ ID NO: 1, and wherein the oligomer has one of the designs described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 134,947-138,924 of SEQ ID NO: 1. In another embodiment, the target region corresponds to nucleotides 135,050-138,940; 135,700-138,940; 136,000-138,940; 136,620-138,940; 136,860-138,940; 137,060-138,940; 137,300-138,940; 137,830-138,940; 138,030-138,940; 138,350-138,940; 134,821-135,020; 135,050-135,820; 135,700-135,820; 136,000-136,110; 136,010-136,100; 136,020-136,090; 136,030-136,080; 136,040-136,070; 136,620-136,760; 136,860-136,960; 137,060-137,110; 137,300-137,400; 137,830-137,900; 138,030-138,140; 138,350-138,450; 138,860-138,940; 138,870-138,930; 138,880-138,920; or 138,890-138,920 of SEQ ID NO: 1, wherein optionally, the oligomer has a design described herein (e.g., Section II.G.I, e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 135,050-138,940 of SEQ ID NO: 1. In another embodiment, the target region corresponds to nucleotides 135,700-138,940 of SEQ ID NO: 1. In another embodiment, the target region corresponds to nucleotides 136,000-138,940 of SEQ ID NO: 1. In another embodiment, the target region corresponds to nucleotides 136,620-138,940 of SEQ ID NO: 1. In another embodiment, the target region corresponds to nucleotides 136,860-138,940 of SEQ ID NO: 1. In another embodiment, the target region corresponds to nucleotides 137,060-138,940 of SEQ ID NO: 1. In another embodiment, the target region corresponds to nucleotides 137,300-138,940 of SEQ ID NO: 1. In another embodiment, the target region corresponds to nucleotides 137,830-138,940 of SEQ ID NO: 1. In another embodiment, the target region corresponds to nucleotides 138,030-138,940 of SEQ ID NO: 1. In another embodiment, the target region corresponds to nucleotides 138,350-138,940 of SEQ ID NO: 1. In another embodiment, the target region corresponds to nucleotides 134,821-135,020 of SEQ ID NO: 1. In another embodiment, the target region corresponds to nucleotides 135,050-138,820 of SEQ ID NO: 1. In another embodiment, the target region corresponds to nucleotides 135,700-135,820 of SEQ ID NO: 1. In other embodiments, the target region corresponds to nucleotides 136,620-136,760 of SEQ ID NO: 1. In some embodiments, the target region corresponds to nucleotides 136,860-136,960 of SEQ ID NO: 1. In certain embodiments, the target region corresponds to nucleotides 137,060-137,110 of SEQ ID NO: 1. In other embodiments, the target region corresponds to nucleotides 137,300-137,400 of SEQ ID NO: 1. In yet other embodiments, the target region corresponds to nucleotides 137,830-137,900 of SEQ ID NO: 1. In still other embodiments, the target region corresponds to nucleotides 138,030-138,140 of SEQ ID NO: 1. In certain embodiments, the target region corresponds to nucleotides 138,350-138,450 of SEQ ID NO: 1. In other embodiments, the target region corresponds to nucleotides 138,860-138,940 of SEQ ID NO: 1.

In some embodiments, the target region corresponds to nucleotides 134,947-134,989, 135,533-135,550, 135,585-135,605, 135,690-135,710, 135,739-135,769, 135,775-135,792, 136,049-136,070, 136,053-136,068; 136,650-136,667, 136,693-136,723, 136,896-136,926, 137,067-137,089, 137,326-137,373, 137,851-137,883, 138,058-138,119, 138,377-138,394, 138,401-138,420, 138,884-138,908; 138,401-138,908; 138,377-138,908; 138,058-138,908; 137,851-138,908; 137,326-138,908; 137,067-138,908; 136,896-138,908; 136,693-138,908; 136,650-138,908; 136,049-138,908; 135,775-138,908; 135,739-138,908; or 134,947-138,908 of SEQ ID NO: 1, wherein optionally, the oligomer has a design described elsewhere herein (e.g., Section II.G, e.g., a gapmer design, e.g., an alternating flank gapmer design). In another embodiment, the target region corresponds to nucleotides 134,947-134,989 of SEQ ID NO: 1. In another embodiment, the target region corresponds to nucleotides 135,533-135,550 of SEQ ID NO: 1. In another embodiment, the target region corresponds to nucleotides 135,585-135,605 of SEQ ID NO: 1. In another embodiment, the target region corresponds to nucleotides 135,690-135,710 of SEQ ID NO: 1. In another embodiment, the target region corresponds to nucleotides 135,739-135,769 of SEQ ID NO: 1. In another embodiment, the target region corresponds to nucleotides 135,775-135,792 of SEQ ID NO: 1. In another embodiment, the target region corresponds to nucleotides 136,049-136,070 of SEQ ID NO: 1. In another embodiment, the target region corresponds to nucleotides 136,053-136,068 of SEQ ID NO: 1. In another embodiment, the target region corresponds to nucleotides 136,650-136,667 of SEQ ID NO: 1. In another embodiment, the target region corresponds to nucleotides 136,693-136,723 of SEQ ID NO: 1. In another embodiment, the target region corresponds to nucleotides 136,896-136,926 of SEQ ID NO: 1. In another embodiment, the target region corresponds to nucleotides 137,067-137,089 of SEQ ID NO: 1. In another embodiment, the target region corresponds to nucleotides 137,326-137,373 of SEQ ID NO: 1. In another embodiment, the target region corresponds to nucleotides 137,851-137,883 of SEQ ID NO: 1. In another embodiment, the target region corresponds to nucleotides 138,058-138,119 of SEQ ID NO: 1. In another embodiment, the target region corresponds to nucleotides 138,377-138,394 of SEQ ID NO: 1. In another embodiment, the target region corresponds to nucleotides 138,401-138,420 of SEQ ID NO: 1. In another embodiment, the target region corresponds to nucleotides 138,884-138,908 of SEQ ID NO: 1.

In other embodiments, the target region corresponds to nucleotides 138,401-138,908 of SEQ ID NO: 1. In other embodiments, the target region corresponds to nucleotides 138,377-138,908 of SEQ ID NO: 1. In other embodiments, the target region corresponds to nucleotides 138,058-138,908 of SEQ ID NO: 1. In other embodiments, the target region corresponds to nucleotides 137,851-138,908 of SEQ ID NO: 1. In other embodiments, the target region corresponds to nucleotides 137,326-138,908 of SEQ ID NO: 1. In other embodiments, the target region corresponds to nucleotides 137,067-138,908 of SEQ ID NO: 1. In other embodiments, the target region corresponds to nucleotides 136,896-138,908 of SEQ ID NO: 1. In other embodiments, the target region corresponds to nucleotides 136,693-138,908 of SEQ ID NO: 1. In other embodiments, the target region corresponds to nucleotides 136,650-138,908 of SEQ ID NO: 1. In other embodiments, the target region corresponds to nucleotides 136,049-138,908 of SEQ ID NO: 1. In other embodiments, the target region corresponds to nucleotides 135,775-138,908 of SEQ ID NO: 1. In other embodiments, the target region corresponds to nucleotides 135,739-138,908 of SEQ ID NO: 1.

In other embodiments, the target region corresponds to nucleotides 136,053-136,068 of SEQ ID NO: 1+1, +2, +3, +4, +5, +6, +7, +8, +9, +10, +11, +12, +13, +14, +15, +20, +25, +30, +35, +40, +45, or +50 nucleotides at the 3' end, the 5' end, or both. In certain embodiments, the target region corresponds to nucleotides 138,884-138,908 of SEQ ID NO: 1+1, +2, +3, +4, +5, +6, +7, +8, +9, +10, +11, +12, +13, +14, +15, +20, +25, +30, +35, +40, +45, or +50 nucleotides of SEQ ID NO: 1 at the 3' end, the 5' end, or both.

In some embodiments, an oligomer of the invention hybridizes to a region within the 5' UTR of a MAPT transcript, e.g., SEQ ID NO: 1. In some embodiments, an oligomer of the invention hybridizes to a region within the 5' UTR of a MAPT transcript, e.g., SEQ ID NO: 1, wherein the oligomer has a design according to formula: 5' A-B-C 3' as described elsewhere herein (e.g., Section II.G, e.g., Section II.G.I) or a chemical structure shown elsewhere herein (e.g., FIGS. 2A to 2NNNN, 16D to 16K, and 20B to 20C). In certain embodiments, the oligomers hybridize to a region within a 5' UTR of a MAPT transcript, e.g., SEQ ID NO: 1, and have a sequence score equal to or greater than about 0.1, 0.2, 0.3, 0.4, 0.5, 0.6, 0.7, 0.8, 0.9, or 1.0. Calculation methods of the sequence score are disclosed elsewhere herein.

In some embodiments, an oligomer of the invention hybridizes to a region within exon 2 of a MAPT transcript, e.g., SEQ ID NO: 1. In some embodiments, an oligomer of the invention hybridizes to a region within exon 2 of a MAPT transcript, e.g., SEQ ID NO: 1, wherein the oligomer has a design according to formula: 5' A-B-C 3' as described elsewhere herein (e.g., Section II.G, e.g., Section II.G.I) or a chemical structure shown elsewhere herein (e.g., FIGS. 2A to 2NNNN, 16D to 16K, and 20B to 20C). In certain embodiments, the oligomers hybridize to a region within exon 2 of a MAPT transcript, e.g., SEQ ID NO: 1, and have a sequence score equal to or greater than about 0.1, 0.2, 0.3, 0.4, 0.5, 0.6, 0.7, 0.8, 0.9, or 1.0. Calculation methods of the sequence score are disclosed elsewhere herein.

In one embodiment, the oligomer according to the invention comprises a contiguous nucleotide sequence that hybridizes to a region within 5' UTR and/or exon 2 in a microtubule-associated protein MAPT transcript, e.g., a region corresponding to the 5' UTR and/or exon 2 of SEQ ID NO: 1. In the MAPT transcript, the 5' UTR and exon 2 overlap but are not contiguous. In another embodiment, the oligomer of the invention comprises a contiguous nucleotide sequence that hybridizes to a nucleic acid sequence, or a region within the sequence, of a MAPT transcript ("target region"), wherein the nucleic acid sequence corresponds to nucleotides 72,802-73,072 of SEQ ID NO: 1. In another embodiment, the oligomer of the invention comprises a contiguous nucleotide sequence that hybridizes to a nucleic acid sequence, or a region within the sequence, of a MAPT transcript ("target region"), wherein the nucleic acid sequence corresponds to nucleotides 72,802-73,072 of SEQ ID NO: 1, and wherein the oligomer has one of the designs described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 72,802-73,072; 72,812-73,062; 72,822-73,052; 72,832-73,042; 72,842-73,032; 72,852-73,022; 72,862-73,012; 72,872-73,002; 72,882-72,992; 72,892-72,982; or 72,902-72,972 of SEQ ID NO: 1, wherein optionally, the oligomer has a design described herein (e.g., Section II.G.I, e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 72 802-73,072 of SEQ ID NO: 1. In another embodiment, the target region corresponds to nucleotides 72,812-73,062 of SEQ ID NO: 1. In another embodiment, the target region corresponds to nucleotides 72,822-73,052 of SEQ ID NO: 1. In another embodiment, the target region corresponds to nucleotides 72,832-73,042 of SEQ ID NO: 1. In another embodiment, the target region corresponds to nucleotides 72,842-73,032 of SEQ ID NO: 1. In another embodiment, the target region corresponds to nucleotides 72,852-73,022 of SEQ ID NO: 1. In another embodiment, the target region corresponds to nucleotides 72,862-73,012 of SEQ ID NO: 1. In another embodiment, the target region corresponds to nucleotides 72,872-73,002 of SEQ ID NO: 1. In another embodiment, the target region corresponds to nucleotides 72,882-72,992 of SEQ ID NO: 1. In another embodiment, the target region corresponds to nucleotides 72,892-72,982 of SEQ ID NO: 1. In another embodiment, the target region corresponds to nucleotides 72,902-72,972 of SEQ ID NO: 1.

In some embodiments, the target region corresponds to nucleotides 72,802-73,072; 72,812-73,072; 72,822-73,072; 72,832-73,072; 72,842-73,072; 72,852-73,072; 72,862-73,072; 72,872-73,072; 72,882-73,072; 72,892-73,072; 72,902-73,072; 72,802-73,062; 72,802-73,052; 72,802-73,042; 72,802-73,032; 72,802-73,022; 72,802-73,012; 72,802-73,002; 72,802-72,992; 72,802-73,982; or 72,802-73,972 of SEQ ID NO: 1, wherein optionally, the oligomer has a design described elsewhere herein (e.g., Section II.G, e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 72,802-73,072 of SEQ ID NO: 1. In another embodiment, the target region corresponds to nucleotides 72,812-73,072 of SEQ ID NO: 1. In another embodiment, the target region corresponds to nucleotides 72,822-73,072 of SEQ ID NO: 1. In another embodiment, the target region corresponds to nucleotides 72,832-73,072 of SEQ ID NO: 1. In another embodiment, the target region corresponds to nucleotides 72,842-73,072 of SEQ ID NO: 1. In another embodiment, the target region corresponds to nucleotides 72,852-73,072 of SEQ ID NO: 1. In another embodiment, the target region corresponds to nucleotides 72,862-73,072 of SEQ ID NO: 1. In another embodiment, the target region corresponds to nucleotides 72,872-73,072 of SEQ ID NO: 1. In another embodiment, the target region corresponds to nucleotides 72,882-73,072 of SEQ ID NO: 1. In another embodiment, the target region corresponds to nucleotides 72,892-73,072 of SEQ ID NO: 1. In another embodiment, the target region corresponds to nucleotides 72,902-73,072 of SEQ ID NO: 1. In another embodiment, the target region corresponds to nucleotides 72,802-73,062 of SEQ ID NO: 1. In another embodiment, the target region corresponds to nucleotides 72,802-73,052 of SEQ ID NO: 1. In another embodiment, the target region corresponds to nucleotides 72,802-73,042 of SEQ ID NO: 1. In another embodiment, the target region corresponds to nucleotides 72,802-73,032 of SEQ ID NO: 1. In another embodiment, the target region corresponds to nucleotides 72,802-73,022 of SEQ ID NO: 1. In another embodiment, the target region corresponds to nucleotides 72,802-73,012 of SEQ ID NO: 1. In another embodiment, the target region corresponds to nucleotides 72,802-73,002 of SEQ ID NO: 1. In another embodiment, the target region corresponds to nucleotides 72,802-72,992 of SEQ ID NO: 1. In another embodiment, the target region corresponds to nucleotides 72,802-73,982 of SEQ ID NO: 1. In another embodiment, the target region corresponds to nucleotides 72,802-73,972 of SEQ ID NO: 1.

In some embodiments, the target region corresponds to nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; or 72,902-72,972 of SEQ ID NO: 1, wherein optionally, the oligomer has a design described elsewhere herein (e.g., Section II.G, e.g., a gapmer design, e.g., an alternating flank gapmer design) or a chemical structure shown elsewhere herein (e.g., FIGS. 2A to 2NNNN, 16D to 16K, and 20B to 20C). In another embodiment, the target region corresponds to nucleotides 72,872-73,012 of SEQ ID NO: 1. In another embodiment, the target region corresponds to nucleotides 72,882-73,012 of SEQ ID NO: 1. In another embodiment, the target region corresponds to nucleotides 72,892-73,012 of SEQ ID NO: 1. In another embodiment, the target region corresponds to nucleotides 72,902-73,012 of SEQ ID NO: 1. In another embodiment, the target region corresponds to nucleotides 72,862-73,002 of SEQ ID NO: 1. In another embodiment, the target region corresponds to nucleotides 72,872-73,002 of SEQ ID NO: 1. In another embodiment, the target region corresponds to nucleotides 72,882-73,002 of SEQ ID NO: 1. In another embodiment, the target region corresponds to nucleotides 72,892-73,002 of SEQ ID NO: 1. In another embodiment, the target region corresponds to nucleotides 72,902-73,002 of SEQ ID NO: 1. In another embodiment, the target region corresponds to nucleotides 72,862-72,992 of SEQ ID NO: 1. In another embodiment, the target region corresponds to nucleotides 72,872-72,992 of SEQ ID NO: 1. In another embodiment, the target region corresponds to nucleotides 72,882-72,992 of SEQ ID NO: 1. In another embodiment, the target region corresponds to nucleotides 72,892-72,992 of SEQ ID NO: 1. In another embodiment, the target region corresponds to nucleotides 72,902-72,992 of SEQ ID NO: 1. In another embodiment, the target region corresponds to nucleotides 72,862-72,982 of SEQ ID NO: 1. In another embodiment, the target region corresponds to nucleotides 72,872-72,982 of SEQ ID NO: 1. In another embodiment, the target region corresponds to nucleotides 72,882-72,982 of SEQ ID NO: 1. In another embodiment, the target region corresponds to nucleotides 72,892-72,982 of SEQ ID NO: 1. In another embodiment, the target region corresponds to nucleotides 72,902-72,982 of SEQ ID NO: 1. In another embodiment, the target region corresponds to nucleotides 72,862-72,972 of SEQ ID NO: 1. In another embodiment, the target region corresponds to nucleotides 72,872-72,972 of SEQ ID NO: 1. In another embodiment, the target region corresponds to nucleotides 72,882-72,972 of SEQ ID NO: 1. In another embodiment, the target region corresponds to nucleotides 72,892-72,972 of SEQ ID NO: 1. In another embodiment, the target region corresponds to nucleotides 72,902-72,972 of SEQ ID NO: 1.

In other embodiments, the target region corresponds to nucleotides 72,947-72,960 of SEQ ID NO: 1. In other embodiments, the target region corresponds to nucleotides 72,946-72,961 of SEQ ID NO: 1. In other embodiments, the target region corresponds to nucleotides 72,907-72,922 of SEQ ID NO: 1. In other embodiments, the target region corresponds to nucleotides 72,948-72,963 of SEQ ID NO: 1. In other embodiments, the target region corresponds to nucleotides 72,950-72,963 of SEQ ID NO: 1. In other embodiments, the target region corresponds to nucleotides 72,945-72,960 of SEQ ID NO: 1. In other embodiments, the target region corresponds to nucleotides 72,950-72,965 of SEQ ID NO: 1. In other embodiments, the target region corresponds to nucleotides 72,944-72,959 of SEQ ID NO: 1. In other embodiments, the target region corresponds to nucleotides 72,947-72,962 of SEQ ID NO: 1. In other embodiments, the target region corresponds to nucleotides 72,952-72,965 of SEQ ID NO: 1.

In other embodiments, the target region corresponds to nucleotides 72,946-72,959 of SEQ ID NO: 1. In other embodiments, the target region corresponds to nucleotides 72,949-72,964 of SEQ ID NO: 1. In other embodiments, the target region corresponds to nucleotides 72,951-72,964 of SEQ ID NO: 1. In other embodiments, the target region corresponds to nucleotides 72,933-72,948 of SEQ ID NO: 1. In other embodiments, the target region corresponds to nucleotides 72,934-72,949 of SEQ ID NO: 1. In other embodiments, the target region corresponds to nucleotides 72,935-72,950 of SEQ ID NO: 1. In other embodiments, the target region corresponds to nucleotides 72,932-72,951 of SEQ ID NO: 1. In other embodiments, the target region corresponds to nucleotides 72,933-72,952 of SEQ ID NO: 1. In other embodiments, the target region corresponds to nucleotides 72,934-72,953 of SEQ ID NO: 1. In other embodiments, the target region corresponds to nucleotides 72,935-72,954 of SEQ ID NO: 1.

In other embodiments, the target region corresponds to nucleotides 72,944-72,963 of SEQ ID NO: 1. In other embodiments, the target region corresponds to nucleotides 72,945-72,964 of SEQ ID NO: 1. In other embodiments, the target region corresponds to nucleotides 72,946-72,965 of SEQ ID NO: 1.

In other embodiments, the target region corresponds to nucleotides 72,948-72,967 of SEQ ID NO: 1. In other embodiments, the target region corresponds to nucleotides 72,933-72,949 of SEQ ID NO: 1. In other embodiments, the target region corresponds to nucleotides 72,935-72,951 of SEQ ID NO: 1. In other embodiments, the target region corresponds to nucleotides 72,936-72,953 of SEQ ID NO: 1. In other embodiments, the target region corresponds to nucleotides 72,933-72,934 of SEQ ID NO: 1. In other embodiments, the target region corresponds to nucleotides 72,934-72,950 of SEQ ID NO: 1. In other embodiments, the target region corresponds to nucleotides 72,934-72,951 of SEQ ID NO: 1. In other embodiments, the target region corresponds to nucleotides 72,933-72,954 of SEQ ID NO: 1. In other embodiments, the target region corresponds to nucleotides 72,933-72,950 of SEQ ID NO: 1.

In other embodiments, an oligomer of the invention comprises a contiguous nucleotide sequence that hybridizes to a nucleic acid sequence, or a region within the sequence, of a MAPT transcript ("target region"), wherein the nucleic acid sequence corresponds to nucleotides 97,648-97,661 of SEQ ID NO: 1, and wherein the oligomer optionally has one of the designs described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In yet other embodiments, an oligomer of the invention comprises a contiguous nucleotide sequence that hybridizes to a nucleic acid sequence, or a region within the sequence, of a MAPT transcript ("target region"), wherein the nucleic acid sequence corresponds to nucleotides 134,749-134,764 of SEQ ID NO: 1, and wherein the oligomer optionally has one of the designs described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, the oligomer of the invention is capable of hybridizing to the target nucleic acid (e.g., MAPT transcript) under physiological condition, i.e., in vivo condition. In some embodiments, the oligomer of the invention is capable of hybridizing to the target nucleic acid (e.g., MAPT transcript) in vitro. In some embodiments, the oligomer of the invention is capable of hybridizing to the target nucleic acid (e.g., MAPT transcript) in vitro under stringent conditions. Stringency conditions for hybridization in vitro are dependent on, inter alia, productive cell uptake, RNA accessibility, temperature, free energy of association, salt concentration, and time (see, e.g., Stanley T Crooks, Antisense Drug Technology: Principles, Strategies and Applications, $2^{nd}$ Edition, CRC Press (2007))). Generally, conditions of high to moderate stringency are used for in vitro hybridization to enable hybridization between substantially similar nucleic acids, but not between dissimilar nucleic acids. An example of stringent hybridization conditions include hybridization in 5× saline-sodium citrate (SSC) buffer (0.75 M sodium chloride/0.075 M sodium citrate) for 1 hour at 40° C., followed by washing the sample 10 times in 1×SSC at 40° C. and 5 times in 1×SSC buffer at room temperature. In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. A wash solution containing 4×SSC, 0.1% SDS can be used at 37° C., with a final wash in 1×SSC at 45° C.

II.B. Oligomer Sequences

The oligomers of the invention comprise a contiguous nucleotide sequence which corresponds to the complement of a region of MAPT transcript, e.g., a nucleotide sequence corresponding to SEQ ID NO: 1.

In certain embodiments, the invention provides an oligomer from 10-50, such as 10-30 nucleotides in length which comprises a contiguous nucleotide sequence of a total of from 10-30 nucleotides, wherein the contiguous nucleotide sequence has at least 85%, 90%, 95%, 98%, or 99%) sequence identity to a region within the complement of a mammalian microtubule-associated protein tau (MAPT) transcript, such as SEQ ID NO: 1 or naturally occurring variant thereof. Thus, for example, the oligomer hybridizes to a single stranded nucleic acid molecule having the sequence of a portion of SEQ ID NO: 1.

The oligomer can comprise a contiguous nucleotide sequence which is fully complementary (perfectly complementary) to the equivalent region of a nucleic acid which encodes a mammalian Tau protein (e.g., SEQ ID NO: 1). The oligomer can comprise a contiguous nucleotide sequence which is fully complementary (perfectly complementary) to a nucleic acid sequence, or a region within the sequence, corresponding to nucleotides 134,947-138,940, 135,050-138,940; 135,700-138,940; 136,000-138,940; 136,620-138,940; 136,860-138,940; 137,060-138,940; 137,300-138,940; 137,830-138,940; 138,030-138,940; 138,350-138,940; 134,821-135,020; 135,050-135,820; 135,700-135,820; 136,000-136,110; 136,620-136,760; 136,860-136,960; 137,060-137,110; 137,300-137,400; 137,830-137,900; 138,030-138,140; 138,350-138,450; or 138,860-138,940 of SEQ ID NO: 1. Furthermore, the oligomer can have a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

The oligomer can also comprise a contiguous nucleotide sequence which is fully complementary (perfectly complementary) to the equivalent region of a nucleic acid which encodes a mammalian Tau protein (e.g., SEQ ID NO: 1). The oligomer can comprise a contiguous nucleotide sequence which is fully complementary (perfectly complementary) to a nucleic acid sequence, or a region within the sequence, corresponding to nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; or 72,902-72,972 of SEQ ID NO: 1. Furthermore, the oligomer can have a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, the nucleotide sequence of the oligomers of the invention or the contiguous nucleotide sequence has at least about 80% sequence identity to a sequence selected from SEQ ID NOs: 4 to 803, and 901 to 935 (i.e., the sequences in FIGS. 2A to 2NNNN, 3A to 3Z, 6A to 6GG, and 7A to 7E), such as at least 85%, at least 90%, at least 91%, at least 92%, at least 93%, at least 94%, at least 95%, at least 96% sequence identity, at least 97% sequence identity, at least 98% sequence identity, at least 99% sequence identity, such as 100% sequence identity (homologous). In some embodiments, the oligomer has a design described elsewhere herein (e.g., Section II.G.I, e.g., a gapmer design, e.g., an alternating flank gapmer design) or a chemical structure shown elsewhere herein (e.g., FIGS. 2A to 2NNNN, 16D to 16K, and 20B to 20C).

In other embodiments, the oligomer of the invention comprises at least one oligomer sequence (e.g., ASO number) disclosed in FIGS. 2A to 2NNNN, 3A to 3Z, 6A to 6GG, 7A to 7E, 16A to 16C, 16D to 16K, 20A or 20B to 20C. In some embodiments, the oligomer of the invention comprises at least one oligomer sequence (e.g., ASO number) disclosed in FIGS. 2A to 2NNNN, 3A to 3Z, 6A to 6GG, 7A to 7E, 16A to 16C, 16D to 16K, 20A or 20B to 20C wherein the oligomer is one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, or 15 nucleotides shorter at the 3' end than the ASOs disclosed in FIGS. 2A to 2NNNN, 3A to 3Z, 6A to 6GG, 7A to 7E, 16A to 16C, 16D to 16K, 20A or 20B to 20C. In other embodiments, the oligomer of the invention comprises at least one oligomer sequence (e.g., ASO number) disclosed in FIGS. 2A to 2NNNN, 3A to 3Z, 6A to 6GG, 7A to 7E, 16A to 16C, 16D to 16K, 20A or 20B to 20C, wherein the oligomer is one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, or 15 nucleotides shorter at the 5' end than the ASOs disclosed in FIGS. 2A to 2NNNN, 3A to 3Z, 6A to 6GG, 7A to 7E, 16A to 16C, 16D to 16K, 20A or 20B to 20C. In yet other embodiments, the oligomer of the invention comprises at least one oligomer sequence (e.g., ASO number) disclosed in FIGS. 2A to 2NNNN, 3A to 3Z, 6A to 6GG, 7A to 7E, 16A to 16C, 16D to 16K, 20A or 20B to 20C, wherein the oligomer is one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, or 15 nucleotides shorter at the 5' end and/or the 3' end than the ASOs disclosed in FIGS. 2A to 2NNNN, 3A to 3Z, 6A to 6GG, 7A to 7E, 16A to 16C, 16D to 16K, 20A or 20B to 20C.

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of a nucleic acid sequence selected from nucleotides 134,947-134,989, 135,739-135,769, 135,775-135,792, 136,049-136,070, 136,053-136,068; 136,650-136,667, 136,693-136,723, 136,896-136,926, 137,067-137,089, 137,326-137,373, 137,851-137,883, 138,058-138,119, 138,377-138,394, 138,401-138,420, 138,884-138,924; 138,401-138,924; 138,377-138,924; 138,058-138,924; 137,851-138,924; 137,326-138,924; 137,067-138,924; 136,896-138,924; 136,693-138,924; 136,650-138,924; 136,049-138,924; 135,775-138,924; 135,739-138,924; 134,947-138,924; 134,947-138,940; 134,909-138,924; 134,871-138,924; and 134,854-138,924 of SEQ ID NO: 1. In some embodiments, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, the nucleotide sequence of the oligomers of the invention or the contiguous nucleotide sequence has at least about 80% sequence identity to a sequence selected from SEQ ID NOs: 804 to 900 (i.e., the sequences in FIG. 16A to 16C or 16D to 16K), such as at least 85%, at least 90%, at least 91%, at least 92%, at least 93%, at least 94%, at least 95%, at least 96% sequence identity, at least 97% sequence identity, at least 98% sequence identity, at least 99% sequence identity, such as 100% sequence identity (homologous). In some embodiments, the oligomer has a design described elsewhere herein (e.g., Section II.G.I, e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of a nucleic acid sequence selected from nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; and 72,902-72,972 of SEQ ID NO: 1. In some embodiments, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 134,947-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 135,700-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 136,000-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 136,620-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 136,860-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 137,060-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 137,300-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 137,830-138,940 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 138,030-138,940 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 138,350-138,940 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 136,000-136,110 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In other embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 138,860-138,940 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 138,884-138,908 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In other embodiments, an oligomer of the invention has at least about 60%, at least about 70%, at least about 80%, at least about 90%, at least about 95%, at least about 96%, at least about 97%, at least about 98%, at least about 99%, or 100% sequence identity to a region within the complement of nucleotides 134,854-138,924 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In some embodiments, an oligomer of the invention has at least about 60%, at least about 70%, at least about 80%, at least about 90%, at least about 95%, at least about 96%, at least about 97%, at least about 98%, at least about 99%, or 100% sequence identity to a region within the complement of a nucleic acid sequence selected from nucleotides 134,947-134,989, 135,739-135,769, 135,775-135,792, 136,049-136,070, 136,053-136,068; 136,650-136,667, 136,693-136,723, 136,896-136,926, 137,067-137,089, 137,326-137,373, 137,851-137,883, 138,058-138,119, 138,377-138,394, 138,401-138,420, 138,884-138,924; 138,401-138,924; 138,377-138,924; 138,058-138,924; 137,851-138,924; 137,326-138,924; 137,067-138,924; 136,896-138,924; 136,693-138,924; 136,650-138,924; 136,049-138,924; 135,775-138,924; 135,739-138,924; and 134,947-138,924 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In some embodiments, the region is within the complement of nucleotides 134,947-134,989 of SEQ ID NO: 1. In some embodiments, the region is within the complement of nucleotides 135,739-135,769 of SEQ ID NO: 1. In some embodiments, the region is within the complement of nucleotides 135,775-135,792 of SEQ ID NO: 1. In some embodiments, the region is within the complement of nucleotides 136,049-136,070 of SEQ ID NO: 1. In some embodiments, the region is within the complement of nucleotides 136,053-136,068 of SEQ ID NO: 1. In some embodiments, the region is within the complement of nucleotides 136,650-136,667 of SEQ ID NO: 1. In some embodiments, the region is within the complement of nucleotides 136,693-136,723 of SEQ ID NO: 1. In some embodiments, the region is within the complement of nucleotides 136,896-136,926 of SEQ ID NO: 1. In some embodiments, the region is within the complement of nucleotides 137,067-137,089 of SEQ ID NO: 1.

In other embodiments, the region is within the complement of nucleotides 137,326-137,373 of SEQ ID NO: 1. In some embodiments, the region is within the complement of nucleotides 137,851-137,883 of SEQ ID NO: 1. In some embodiments, the region is within the complement of nucleotides 138,058-138,119 of SEQ ID NO: 1. In some embodiments, the region is within the complement of nucleotides 138,377-138,394 of SEQ ID NO: 1. In some embodiments, the region is within the complement of nucleotides 138,401-138,420 of SEQ ID NO: 1.

In some embodiments, the region is within the complement of nucleotides 138,884-138,924 of SEQ ID NO: 1. In some embodiments, the region is within the complement of nucleotides 138,401-138,924 of SEQ ID NO: 1. In some embodiments, the region is within the complement of nucleotides 138,377-138,924 of SEQ ID NO: 1. In some embodiments, the region is within the complement of nucleotides 138,058-138,924 of SEQ ID NO: 1. In some embodiments, the region is within the complement of nucleotides 137,851-138,924 of SEQ ID NO: 1. In some embodiments, the region is within the complement of nucleotides 137,326-138,924 of SEQ ID NO: 1. In some embodiments, the region is within the complement of nucleotides 137,067-138,924 of SEQ ID NO: 1. In some embodiments, the region is within the complement of nucleotides 136,896-138,924 of SEQ ID NO: 1. In some embodiments, the region is within the complement of nucleotides 136,693-138,924 of SEQ ID NO: 1. In some embodiments, the region is within the complement of nucleotides 136,650-138,924 of SEQ ID NO: 1. In some embodiments, the region is within the complement of nucleotides 136,049-138,924 of SEQ ID NO: 1. In some embodiments, the region is within the complement of nucleotides 135,775-138,924 of SEQ ID NO: 1. In some embodiments, the region is within the complement of nucleotides 135,739-138,924 of SEQ ID NO: 1. In some embodiments, the region is within the complement of nucleotides 134,947-138,924 of SEQ ID NO: 1.

In some embodiments the oligomer (or contiguous nucleotide portion thereof) is selected from, or comprises, one of the sequences selected from the group consisting of SEQ ID NOs: 4 to 803, 901 to 953, 956 to 958, and 960 or a region of at least 10 contiguous nucleotides thereof, wherein the oligomer (or contiguous nucleotide portion thereof) can optionally comprise one, two, three, or four mismatches when compared to the corresponding MAPT transcript.

In one embodiment, the oligomer can comprise a sequence selected from the group consisting of ctttatttccaaattcactt [138888-138907] (SEQ ID NO: 676); actttatttccaaattcact [138889-138908] (SEQ ID NO: 715); tttatttccaaattcacttt [138887-138906] (SEQ ID NO: 644); ttatttccaaattcacttttt [138886-138905] (SEQ ID NO: 799); atttccaaattcactttac [138884-138903](SEQ ID NO: 466); atttccaaattcactttta [138885-138903] (SEQ ID NO: 559); actttatttccaaattcactt [138888-138908] (SEQ ID NO: 680); atttccaaattcactt [138888-138903] (SEQ ID NO: 686); tatttccaaattcactttta [13885-138904] (SEQ ID NO: 526); aataactttatttcca [138897-138912] (SEQ ID NO: 773); agtaataactttatt [138901-138915] (SEQ ID NO: 782); tttccaaattcactt [138888-138902] (SEQ ID NO: 684); agagtaataactttat [138902-138917] (SEQ ID NO: 784); agtaataactttattt [138900-138915] (SEQ ID NO: 780); agagtaataacttta [138903-138917] (SEQ ID NO: 786); ttaatcagagtaataa [138908-138923] (SEQ ID NO: 795); tttaatcagagtaat [138910-138924] (SEQ ID NO: 798); aatcagagtaataac [138907-138921] (SEQ ID NO: 794); tttaatcagagtaata [138909-139924] (SEQ ID NO: 797); taatcagagtaataa [138908-138922] (SEQ ID NO: 796); ctttatttccaaattcact [138889-138907] (SEQ ID NO: 713); or ctttatttccaaattcac [138890-138907] (SEQ ID NO: 739). In a particular embodiment, the oligomer comprises atttccaaattcactttac [138884-138903] (SEQ ID NO: 466). In one embodiment, the oligomer (or contiguous nucleotide portion thereof) optionally has one, two, three, or four mismatches against the selected sequence. In another embodiment, the oligomer optionally comprises one or more nucleotide analogs. In other embodiments, the oligomer has a design described elsewhere herein (e.g., Section II.G.I, e.g., a gapmer design, e.g., an alternating flank gapmer design) or a chemical structure shown elsewhere herein (e.g., FIGS. 2A to 2NNNN, 16D to 16K, and 20B to 20C). Non-limiting examples of the nucleotide analogs useful for the invention are disclosed elsewhere herein.

In other embodiments, an oligomer of the invention comprises, consists essentially of, or consists of a nucleotide sequence having at least about 60%, at least about 70%, at least about 80%, at least about 90%, at least about 95%, at least about 96%, at least about 97%, at least about 98%, at least about 99%, or 100% sequence identity to SEQ ID NOs: 939, 940, 524, 941, 942, 943, 944, 945, 946, 947, 948, 949, 950, 956, 957, 958, 951, 952, or 953. In some embodiments, the oligomer having a sequence identity to SEQ ID NOs: 939, 940, 524, 941, 942, 943, 944, 945, 946, 947, 948, 949, 950, 956, 957, 958, 951, 952, or 953 has the design of ASO-257283, ASO-257284, ASO-002263, ASO-002627, ASO-002677, ASO-002670, ASO-002663, ASO-002635, ASO-002643, ASO-002671, ASO-002664, ASO-002626, ASO-002634, ASO-002678, ASO-002650, ASO-002657, ASO-002642, ASO-002649, or ASO-002656, respectively.

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,812-73,062 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,822-73,052 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement nucleotides 72,832-73,042 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,842-73,032 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,852-73,022 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,862-73,012 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,872-73,002 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,882-72,992 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,892-72,982 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,902-72,972 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,812-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,822-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,832-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,842-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,852-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,862-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,872-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,882-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,892-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,902-73,072 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,062 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,052 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,042 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,032 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,022 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,012 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,002 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-72,992 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,982 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In certain embodiments, an oligomer of the invention comprises a nucleotide sequence having at least about 60%, at least about 70%, at least about 80%, at least about 90%, at least about 95%, at least about 96%, at least about 97%, at least about 98%, at least about 99%, or 100% sequence identity to a region within the complement of nucleotides 72,802-73,972 of SEQ ID NO: 1, wherein optionally, the oligomer has a design described herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C).

In some embodiments, an oligomer of the invention has at least about 60%, at least about 70%, at least about 80%, at least about 90%, at least about 95%, at least about 96%, at least about 97%, at least about 98%, at least about 99%, or 100% sequence identity to a region within the complement of a nucleic acid sequence selected from nucleotides 72,862-73,012; 72,872-73,012; 72,882-73,012; 72,892-73,012; 72,902-73,012; 72,862-73,002; 72,872-73,002; 72,882-73,002; 72,892-73,002; 72,902-73,002; 72,862-72,992; 72,872-72,992; 72,882-72,992; 72,892-72,992; 72,902-72,992; 72,862-72,982; 72,872-72,982; 72,882-72,982; 72,892-72,982; 72,902-72,982; 72,862-72,972; 72,872-72,972; 72,882-72,972; 72,892-72,972; and 72,902-72,972 of SEQ ID NO: 1, wherein optionally, the oligomer has a design described elsewhere herein (e.g., Section II.G. e.g., a gapmer design, e.g., an alternating flank gapmer design) or a chemical structure shown elsewhere herein (e.g., FIGS. 2A to 2NNNN, 16D to 16K, and 20B to 20C). In some embodiments, the region is within the complement of nucleotides 72,862-73,012 of SEQ ID NO: 1. In some embodiments, the region is within the complement of nucleotides 72,872-73,012 of SEQ ID NO: 1. In some embodiments, the region is within the complement of nucleotides 72,882-73,012 of SEQ ID NO: 1. In some embodiments, the region is within the complement of nucleotides 72,892-73,012 of SEQ ID NO: 1. In some embodiments, the region is within the complement of nucleotides 72,902-73,012 of SEQ ID NO: 1. In some embodiments, the region is within the complement of nucleotides 72,862-73,002 of SEQ ID NO: 1. In some embodiments, the region is within the complement of nucleotides 72,872-73,002 of SEQ ID NO: 1. In some embodiments, the region is within the complement of nucleotides 72,882-73,002 of SEQ ID NO: 1. In some embodiments, the region is within the complement of nucleotides 72,892-73,002 of SEQ ID NO: 1.

In other embodiments, the region is within the complement of nucleotides 72,902-73,002 of SEQ ID NO: 1. In some embodiments, the region is within the complement of nucleotides 72,862-72,992 of SEQ ID NO: 1. In some embodiments, the region is within the complement of nucleotides 72,872-72,992 of SEQ ID NO: 1. In some embodiments, the region is within the complement of nucleotides 72,882-72,992 of SEQ ID NO: 1. In some embodiments, the region is within the complement of nucleotides 72,892-72,992 of SEQ ID NO: 1.

In some embodiments, the region is within the complement of nucleotides 72,902-72,992 of SEQ ID NO: 1. In some embodiments, the region is within the complement of nucleotides 72,862-72,982 of SEQ ID NO: 1. In some embodiments, the region is within the complement of nucleotides 72,872-72,982 of SEQ ID NO: 1. In some embodiments, the region is within the complement of nucleotides 72,882-72,982 of SEQ ID NO: 1. In some embodiments, the region is within the complement of nucleotides 72,892-72,982 of SEQ ID NO: 1. In some embodiments, the region is within the complement of nucleotides 72,902-72,982 of SEQ ID NO: 1. In some embodiments, the region is within the complement of nucleotides 72,862-72,972 of SEQ ID NO: 1. In some embodiments, the region is within the complement of nucleotides 72,872-72,972 of SEQ ID NO: 1. In some embodiments, the region is within the complement of nucleotides 72,882-72,972 of SEQ ID NO: 1. In some embodiments, the region is within the complement of nucleotides 72,892-72,972 of SEQ ID NO: 1. In some embodiments, the region is within the complement of nucleotides 72,902-72,972 of SEQ ID NO: 1.

In one embodiment, the oligomer can comprise a sequence selected from the group consisting of SEQ ID NOs: 804 to 900. In one embodiment, the oligomer (or contiguous nucleotide portion thereof) optionally has one, two, or three mismatches against the selected sequence. In another embodiment, the oligomer optionally comprises one or more nucleotide analogs. In other embodiments, the oligomer has a design described elsewhere herein (e.g., Section II.G.I, e.g., a gapmer design, e.g., an alternating flank gapmer design) or a chemical structure described elsewhere herein. Non-limiting examples of the nucleotide analogs useful for the invention are disclosed elsewhere herein.

When the oligomer sequences are listed only with lower case letters (e.g., ctttatttccaaattcactt (SEQ ID NO: 676), the nucleic acids included in the oligomer can be either naturally occurring nucleic acids or nucleotide analogs. If an oligomer sequence is described as a combination of lower case letters and upper case letters (e.g., CTTtatttccaaattcaCTT), the upper case letters in the sequence are nucleotide analogs (e.g, LNA) while the lower case letters are naturally occurring nucleic acids (e.g., DNA). Therefore, for example, when a sequence "CTTtatttccaaattcaCTT" is provided herein, also provided is "ctttatttccaaattcactt (or SEQ ID NO: 676), wherein the three nucleic acids at the 3' end are nucleotide analogs (e.g., LNA) and the three nucleic acids at the 5' end are naturally occurring nucleic acids (e.g., DNA)" or "ctttatttccaaattcactt (or SEQ ID NO: 676) with a design of LLLDDDDDDDDDDDDDDLLL, wherein L is a nucleotide analog and D is a DNA unit."

In certain embodiments, the oligomer of the invention comprises a nucleotide sequence selected from SEQ ID NO: 4 to 953, 956 to 958, and 960. See FIGS. 2A to 2NNNN, 3A to 3Z, 6A to 6GG, 7A to 7E, 16A to 16C, 16D to 16K, 20A, and 20B to 20C. In certain embodiments, the oligomer of the invention comprises a nucleotide sequence selected from the sequences listed in FIGS. 2A to 2NNNN, 3A to 3Z, 6A to 6GG, 7A to 7E, 16A to 16C, 16D to 16K, 20A, and 20B to 20C. Nonetheless, the design of the oligomers is not limited to the design shown in FIGS. 2A to 2NNNN, 3A to 3Z, 6A to 6GG, 7A to 7E, 16A to 16C, 16D to 16K, 20A, and 20B to 20C. The oligomers of the invention can have any oligomer design, e.g., gapmer, mixmer, blockmer, or fully modified, as described elsewhere herein. Thus, in some embodiments, the oligomer of the invention comprises a nucleotide sequence selected from SEQ ID NO: 4 to 953, 956 to 958, and 960, wherein at least one nucleotide is modified. In other embodiments, the oligomer of the invention comprises a nucleotide sequence selected from SEQ ID NOs: 4 to 953, 956 to 958, and 960, wherein the one to five nucleotides at the 5' end and the one to five nucleotides at the 3' end are nucleotide analogs (e.g., LNA) and the other nucleotides in the middle are naturally occurring nucleic acids. In still other embodiments, the oligomer comprises a nucleotide sequence selected from SEQ ID NO: 4 to 953, 956 to 958, and 960, wherein the nucleotide design for the oligomer is as described in FIGS. 2A to 2NNNN, 3A to 3Z, 6A to 6GG, and 7A to 7E (the upper case letter indicates a nucleotide analog, e.g., LNA, and the lower case letter indicates a naturally occurring nucleic acid (e.g., DNA). In yet other embodiments, the oligomer of the invention comprises a nucleotide sequence selected from SEQ ID NOs: 4 to 953, 956 to 958, and 960, wherein the backbone comprises at least one phosphorothioate bond. In a particular embodiment, the oligomer comprises a nucleotide sequence selected from the sequences in FIG. 7A to 7E, e.g., SEQ ID NOs: 677, 679, 715, 681 644, 647, 593, 716, 474, 683, 587, 685, 646, 680, 201, 473, 645, 532, 538, 535, 650, 533, 590, 7, 153, 686, 471, 223, 688, 53, 154, 202, 595, 655, 482, 227, 485, 589, 370, 548, 250, 251, 258, 256, 51, 69, 71, 255, 84, 262, 365, 285, 392, 417, 76, 74, 390, 28, 46, 43, 49, 52, 67, 56, 60, 698, 773, 782, 684, 784, 780, 786, 795, 798, 794, 797, 796, 705, 592, 472, 720, 745, 691, 687, 690, 740, 724, 695, 689, 741, 714, 726, 799, 484, 801, 536, 800, 543, 545, 537, 476, 528, 477, 479, 487, 467, 602, 594, 604, 603, 529, 530, 598, 527, 539, 481, 480, 469, 540, 600, 486, 601, 531, 588, 586, 542, 596, 544, 468, 653, 591, 534, 470, 547, 478, 546, 648, 541, 466, 599, 483, 597, and 475, wherein the oligomer is designed as described in FIG. 7A to 7E, and wherein the upper case letters are nucleotide analogs, e.g., LNAs, and the lower case letters are DNAs. Non-limiting examples of the oligomers are shown in FIGS. 2A to 2NNNN, 3A to 3Z, 6A to 6GG, 7A to 7E, 16A to 16C, and 16D to 16K. In some embodiments, the oligomers of the invention bind to the target nucleic acid sequence (e.g., MAPT transcript) and inhibit or reduce expression of the MAPT transcript by at least 10% or 20% compared to the normal (i.e., control) expression level in the cell, e.g., at least 30%, 40%, 50%, 60%, 70%, 80%, 90% or 95% compared to the normal expression level (such as the expression level in the absence of the oligomer(s) or conjugate(s)) in the cell.

In certain embodiments, the oligomers of the invention bind to the MAPT transcript and inhibit or reduce expression of the MAPT mRNA by at least about 10% or about 20% compared to the normal (i.e. control) expression level in the cell, e.g., at least about 30%, about 40%, about 50%, about 60%, about 70%, about 80%, about 90% or about 95% compared to the normal expression level (such as the expression level in the absence of the oligomer(s) or conjugate(s)) in the cell. In certain embodiments, the oligomer reduces expression of Tau protein in a cell following administration of the oligomer by at least 60%, at least 70%, at least 80%, or at least 90% compared to a cell not exposed to the oligomer (i.e., control). In some embodiments, the oligomer reduces expression of Tau protein in a cell following administration of the oligomer by at least about 60%, at least about 70%, at least about 80%, or at least about 90% compared to a cell not exposed to the oligomer (i.e., control).

In certain embodiments, the oligomer of the invention has at least one property selected from: (1) reduces expression of Tau mRNA in a cell, compared to a control cell that has not been exposed to the oligomer; (2) does not significantly reduce calcium oscillations in a cell; (3) does not significantly reduce tubulin intensity in a cell; (4) reduces expression of Tau protein in a cell; and (5) any combinations thereof compared to a control cell that has not been exposed to the oligomer.

In some embodiments, the oligomer of the invention does not significantly reduce calcium oscillations in a cell, e.g., neuronal cells. If the oligomer does not significantly reduce calcium oscillations in a cell, this property of the oligomer corresponds with a reduced neurotoxicity of the oligomer. In some embodiments, calcium oscillations are greater than or equal to 95%, greater than or equal to 90%, greater than or equal to 85%, greater than or equal to 80%, greater than or equal to 75%, or greater than or equal to 70% of oscillations in a cell not exposed to the oligomer.

Calcium oscillations are important for the proper functions of neuronal cells. Networks of cortical neurons have been shown to undergo spontaneous calcium oscillations resulting in the release of the neurotransmitter glutamate. Calcium oscillations can also regulate interactions of neurons with associated glia, in addition to other associated neurons in the network, to release other neurotransmitters in addition to glutamate. Regulated calcium oscillations are required for homeostasis of neuronal networks for normal brain function. (See, Shashank et al., *Brain Research,* 1006 (1): 8-17 (2004); Rose et al., *Nature Neurosci.,* 4:773-774 (2001); Zonta et al., *Physiol Paris.,* 96(3-4):193-8 (2002); Pasti et al., *J. Neurosci.,* 21(2): 477-484 (2001).) Glutamate also activates two distinct ion channels, α-amino-3-hydroxy-5-methyl-4-isoxazolepropionic acid (AMPA) receptors and N-methyl-D-aspartate (NMDA) receptors.

In some embodiments, the calcium oscillations measured in the present methods are AMPA-dependent calcium oscillations. In some embodiments, the calcium oscillations are NMDA-dependent calcium oscillations. In some embodiments, the calcium oscillations are gamma-aminobutyric acid (GABA)-dependent calcium oscillations. In some embodiments, the calcium oscillations can be a combination of two or more of AMPA-dependent, NMDA-dependent or GABA-dependent calcium oscillations.

In certain embodiments, the calcium oscillations measured in the present methods are AMPA-dependent calcium oscillations. In order to measure AMPA-dependent calcium oscillations, the calcium oscillations can be measured in the presence of $Mg^{2+}$ ions (e.g., $MgCl_2$). In certain embodiments, the method further comprises adding $Mg^{2+}$ ions (e.g., $MgCl_2$) at an amount that allows for detection of AMPA-dependent calcium oscillations. In some embodiments, the effective ion concentration allowing for detection of AMPA-dependent calcium oscillations is at least about 0.5 mM. In other embodiments, the effective ion concentration to induce AMPA-dependent calcium oscillations is at least about 0.6 mM, at least about 0.7 mM, at least about 0.8 mM, at least about 0.9 mM, at least about 1 mM, at least about 1.5 mM, at least about 2.0 mM, at least about 2.5 mM, at least about 3.0 mM, at least about 4 mM, at least about 5 mM, at least about 6 mM, at least about 7 mM, at least about 8 mM, at least about 9 mM, or at least about 10 mM. In a particular embodiment, the concentration of $Mg^{2+}$ ions (e.g., $MgCl_2$) useful for the methods is 1 mM. In certain embodiments, the concentration of $Mg^{2+}$ ions (e.g., $MgCl_2$) useful for the present methods is about 1 mM to about 10 mM, about 1 mM to about 15 mM, about 1 mM to about 20 mM, or about 1 mM to about 25 mM. $Mg^{2+}$ ions can be added by the addition of magnesium salts, such as magnesium carbonate, magnesium chloride, magnesium citrate, magnesium hydroxide, magnesium oxide, magnesium sulfate, and magnesium sulfate heptahydrate.

In some embodiments, calcium oscillations are measured in the present method through the use of fluorescent probes which detect the fluctuations of intracellular calcium levels. For example, detection of intracellular calcium flux can be achieved by staining the cells with fluorescent dyes which bind to calcium ions (known as fluorescent calcium indicators) with a resultant, detectable change in fluorescence (e.g., Fluo-4 AM and Fura Red AM dyes available from Molecular Probes. Eugene, Oreg., United States of America).

In other embodiments, the oligomers of the invention do not significantly reduce the tubulin intensity in a cell. In some embodiments, tubulin intensity is greater than or equal to 95%, greater than or equal to 90%, greater than or equal to 85%, greater than or equal to 80%, greater than or equal to 75%, or greater than or equal to 70% of tubulin intensity in a cell not exposed to the oligomer (or exposed to saline).

In some embodiments, such property is observed when using from 0.04 nM to 400 μM concentration of the oligomer of the invention. In the same or a different embodiment, the inhibition or reduction of expression of MAPT mRNA and/or Tau protein in the cell results in less than 100%, such as less than 98%, less than 95%, less than 90%, less than 80%, such as less than 70%, mRNA or protein levels compared to cells not exposed to the oligomer. Modulation of expression level can be determined by measuring Tau protein levels, e.g., by methods such as SDS-PAGE followed by western blotting using suitable antibodies raised against the target protein. Alternatively, modulation of expression levels can be determined by measuring levels of MAPT mRNA, e.g., by northern blot or quantitative RT-PCR. When measuring inhibition via mRNA levels, the level of down-regulation when using an appropriate dosage, such as from about 0.04 nM to about 400 μM concentration, is, in some embodiments typically to a level of from about 10-20% the normal levels in the cell in the absence of the oligomer.

In certain embodiments, the oligomer of the invention has an in vivo tolerability less than or equal to a total score of 4, wherein the total score is the sum of a unit score of five categories, which are 1) hyperactivity; 2) decreased activity and arousal; 3) motor dysfunction and/or ataxia; 4) abnormal posture and breathing; and 5) tremor and/or convulsions, and wherein the unit score for each category is measured on a scale of 0-4. In certain embodiments, the in vivo tolerability is less than or equal to the total score of 3, the total score of 2, the total score of 1, or the total score of 0. In some embodiment, the assessment for in vivo tolerability is determined as described in Example 5 below.

In some embodiments, the oligomer can tolerate 1, 2, 3, or 4 (or more) mismatches, when hybridizing to the target sequence and still sufficiently bind to the target to show the desired effect, i.e., down-regulation of the target mRNA and/or protein. Mismatches can, for example, be compensated by increased length of the oligomer nucleotide sequence and/or an increased number of nucleotide analogs, which are disclosed elsewhere herein.

In some embodiments, the oligomer of the invention comprises no more than 3 mismatches when hybridizing to the target sequence. In other embodiments, the contiguous nucleotide sequence comprises no more than 2 mismatches when hybridizing to the target sequence. In other embodiments, the contiguous nucleotide sequence comprises no more than 1 mismatch when hybridizing to the target sequence. In some embodiments, the target sequence is a region within nucleotides 134,947-138,940 of SEQ ID NO: 1. In some embodiments, the contiguous nucleotide sequence comprises no more than a single mismatch when hybridizing to the target sequence, a region within nucleotides 134,947-138,940 of SEQ ID NO: 1. In some embodiments, the target sequence is a region within nucleotides 135,050-138,940 of SEQ ID NO: 1. In some embodiments, the contiguous nucleotide sequence comprises no more than a single mismatch when hybridizing to the target sequence, a region within nucleotides 135,050-138,940 of SEQ ID NO: 1. In some embodiments, the target sequence is a region within nucleotides 72,802-73,072 of SEQ ID NO: 1. In some embodiments, the contiguous nucleotide sequence comprises no more than a single mismatch when hybridizing to the target sequence, a region within nucleotides 72,802-73,072 of SEQ ID NO: 1.

In some embodiments the region within the complement or the region can consist of 11, 12, 13, 14, 15, 16, 17, 18, 19, 20, 21, 22, 23, 24, 25, 26, 27, 28, or 29 contiguous nucleotides, such as from 12-22, such as from 14-21 nucleotides. Suitably, in some embodiments, the region is of the same length as the contiguous nucleotide sequence of the oligomer of the invention.

In some embodiments the oligomer according to the invention comprises a nucleotide sequence, or a region within the sequence, according to any one of SEQ ID NOs: 4 to 953, 956 to 958, and 960.

In other embodiments the oligomer according to the invention comprises a nucleotide sequence, or a region within the sequence, according to any one of SEQ ID NOs: 804 to 900. In other embodiments the oligomer according to the invention comprises a nucleotide sequence, or a region within the sequence, according to any one of SEQ ID NOs: 936 to 953,956 to 958, and 960.

However, it is recognized that, in some embodiments, the nucleotide sequence of the oligomer can comprise additional 5' or 3' nucleotides, such as, independently, 1, 2, 3, 4 or 5 additional nucleotides 5' and/or 3', which are non-complementary to the target sequence. In this respect the oligomer of the invention, can, in some embodiments, comprise a contiguous nucleotide sequence which is flanked 5' and/or 3' by additional nucleotides. In some embodiments the additional 5' and/or 3' nucleotides are naturally occurring nucleotides, such as DNA or RNA.

In some embodiments the oligomer according to the invention comprises a nucleotide sequence according to SEQ ID NO: 677 (e.g., ASO-000757), or a region thereof. In some embodiments the oligomer according to the invention comprises a nucleotide sequence according to SEQ ID NO: 679 (e.g., ASO-001928), or a region thereof. In some embodiments the oligomer according to the invention comprises a nucleotide sequence according to SEQ ID NO: 715 (e.g., ASO-001962), or a region thereof. In some embodiments the oligomer according to the invention comprises a nucleotide sequence according to SEQ ID NO: 681 (e.g., ASO-001921), or a region thereof. In some embodiments the oligomer according to the invention comprises a nucleotide sequence according to SEQ ID NO: 644 (e.g., ASO-000756), or a region thereof. In some embodiments the oligomer according to the invention comprises a nucleotide sequence according to SEQ ID NO: 647 (e.g., ASO-001948), or a region thereof. In some embodiments the oligomer according to the invention comprises a nucleotide sequence according to SEQ ID NO: 593 (e.g., ASO-001941), or a region thereof. In some embodiments the oligomer according to the invention comprises a nucleotide sequence according to SEQ ID NO: 716 (e.g., ASO-001956), or a region thereof. In some embodiments the oligomer according to the invention comprises a nucleotide sequence according to SEQ ID NO: 474 (e.g., ASO-001919), or a region thereof. In some embodiments the oligomer according to the invention comprises a nucleotide sequence according to SEQ ID NO: 683 (e.g., ASO-001942), or a region thereof. In some embodiments the oligomer according to the invention comprises a nucleotide sequence according to SEQ ID NO: 587 (e.g., ASO-000755), or a region thereof. In some embodiments the oligomer according to the invention comprises a nucleotide sequence according to SEQ ID NO: 685 (e.g., ASO-001935), or a region thereof. In some embodiments the oligomer according to the invention comprises a nucleotide sequence according to SEQ ID NO: 472 (e.g., ASO-001940), or a region thereof. In some embodiments the oligomer according to the invention comprises a nucleotide sequence according to SEQ ID NO: 646 (e.g., ASO-001955), or a region thereof. In some embodiments the oligomer according to the invention comprises a nucleotide sequence according to SEQ ID NO: 680 (e.g., ASO-001968) or a region thereof. In some embodiments the oligomer according to the invention comprises a nucleotide sequence according to SEQ ID NO: 201 (e.g., ASO-000662), or a region thereof. In some embodiments the oligomer according to the invention comprises a nucleotide sequence according to SEQ ID NO: 473 (e.g., ASO-001933), or a region thereof. In some embodiments the oligomer according to the invention comprises a nucleotide sequence according to SEQ ID NO: 645 (e.g., ASO-001967), or a region thereof. In some embodiments the oligomer according to the invention comprises a nucleotide sequence according to SEQ ID NO: 532 (e.g., ASO-001954), or a region thereof. In some embodiments the oligomer according to the invention comprises a nucleotide sequence according to SEQ ID NO: 538 (e.g., ASO-001960), or a region thereof. In some embodiments the oligomer according to the invention comprises a nucleotide sequence according to SEQ ID NO: 535 (e.g., ASO-001966), or a region thereof. In some embodiments the oligomer according to the invention comprises a nucleotide sequence according to SEQ ID NO: 650 (e.g., ASO-001961), or a region thereof. In some embodiments the oligomer according to the invention comprises a nucleotide sequence according to SEQ ID NO: 533 (e.g., ASO-001947), or a region thereof. In some embodiments the oligomer according to the invention comprises a nucleotide sequence according to SEQ ID NO: 590 (e.g., ASO-001920), or a region thereof. In some embodiments the oligomer according to the invention comprises a nucleotide sequence according to SEQ ID NO: 7 (e.g., ASO-000829), or a region thereof. In some embodiments the oligomer according to the invention comprises a nucleotide sequence according to SEQ ID NO: 740 (e.g., ASO-002007), or a region thereof. In some embodiments the oligomer according to the invention comprises a nucleotide sequence according to SEQ ID NO: 714 (e.g., ASO-002012), or a region thereof. In some embodiments the oligomer according to the invention comprises a nucleotide sequence according to SEQ ID NO: 487 (e.g., ASO-002038), or a region thereof.

In some embodiments the oligomer according to the invention comprises a nucleotide sequence according to SEQ ID NO: 153 (e.g., ASO-000540), or a region thereof. In some embodiments the oligomer according to the invention comprises a nucleotide sequence according to SEQ ID NO: 686 (e.g., ASO-000013), or a region thereof. In some embodiments the oligomer according to the invention comprises a nucleotide sequence according to SEQ ID NO: 471 (e.g., ASO-000753), or a region thereof. In some embodiments the oligomer according to the invention comprises a nucleotide sequence according to SEQ ID NO: 223 (e.g., ASO-000642), or a region thereof. In some embodiments the oligomer according to the invention comprises a nucleotide sequence according to SEQ ID NO: 688 (e.g., ASO-000762), or a region thereof. In some embodiments the oligomer according to the invention comprises a nucleotide sequence according to SEQ ID NO: 53 (e.g., ASO-000389), or a region thereof. In some embodiments the oligomer according to the invention comprises a nucleotide sequence according to SEQ ID NO: 154 (e.g., ASO-000555), or a region thereof. In some embodiments the oligomer according to the invention comprises a nucleotide sequence according to SEQ ID NO: 202 (e.g., ASO-000566), or a region thereof. In some embodiments the oligomer according to the invention comprises a nucleotide sequence according to SEQ ID NO: 595 (e.g., ASO-001934), or a region thereof. In some embodiments the oligomer according to the invention comprises a nucleotide sequence according to SEQ ID NO: 655 (e.g., ASO-000761), or a region thereof. In some embodiments the oligomer according to the invention comprises a nucleotide sequence according to SEQ ID NO: 482 (e.g., ASO-001926), or a region thereof. In some embodiments the oligomer according to the invention comprises a nucleotide sequence according to SEQ ID NO: 485 (e.g., ASO-000758), or a region thereof. In some embodiments the oligomer according to the invention comprises a nucleotide sequence according to SEQ ID NO: 589 (e.g., ASO-000760), or a region thereof. In some embodiments the oligomer according to the invention comprises a nucleotide sequence according to SEQ ID NO: 370 (e.g., ASO-000635), or a region thereof. In some embodiments the oligomer according to the invention comprises a nucleotide sequence according to SEQ ID NO: 548 (e.g., ASO-000759), or a region thereof. In some embodiments the oligomer according to the invention comprises a nucleotide sequence according to SEQ ID NO: 250 (e.g., ASO-000388), or a region thereof. In some embodiments the oligomer according to the invention comprises a nucleotide sequence according to SEQ ID NO: 251 (e.g., ASO-000390), or a region thereof. In some embodiments the oligomer according to the invention comprises a nucleotide sequence according to SEQ ID NO: 258 (e.g., ASO-000394), or a region thereof. In some embodiments the oligomer according to the invention comprises a nucleotide sequence according to SEQ ID NO: 256 (e.g., ASO-000396), or a region thereof. In some embodiments the oligomer according to the invention comprises a nucleotide sequence according to SEQ ID NO: 51 (e.g., ASO-000411), or a region thereof. In some embodiments the oligomer according to the invention comprises a nucleotide sequence according to SEQ ID NO: 69 (e.g., ASO-000435), or a region thereof. In some embodiments the oligomer according to the invention comprises a nucleotide sequence according to SEQ ID NO: 71 (e.g., ASO-000442), or a region thereof. In some embodiments the oligomer according to the invention comprises a nucleotide sequence according to SEQ ID NO: 255 (e.g., ASO-000447), or a region thereof. In some embodiments the oligomer according to the invention comprises a nucleotide sequence according to SEQ ID NO: 84 (e.g., ASO-000449), or a region thereof. In some embodiments the oligomer according to the invention comprises a nucleotide sequence according to SEQ ID NO: 262 (e.g., ASO-000451), or a region thereof. In some embodiments the oligomer according to the invention comprises a nucleotide sequence according to SEQ ID NO: 365 (e.g., ASO-000468), or a region thereof. In some embodiments the oligomer according to the invention comprises a nucleotide sequence according to SEQ ID NO: 285 (e.g., ASO-000478), or a region thereof. In some embodiments the oligomer according to the invention comprises a nucleotide sequence according to SEQ ID NO: 392 (e.g., ASO-000527), or a region thereof. In some embodiments the oligomer according to the invention comprises a nucleotide sequence according to SEQ ID NO: 417 (e.g., ASO-000543), or a region thereof. In some embodiments the oligomer according to the invention comprises a nucleotide sequence according to SEQ ID NO: 76 (e.g., ASO-000558), or a region thereof. In some embodiments the oligomer according to the invention comprises a nucleotide sequence according to SEQ ID NO: 74 (e.g., ASO-000581), or a region thereof. In some embodiments the oligomer according to the invention comprises a nucleotide sequence according to SEQ ID NO: 390 (e.g., ASO-000614), or a region thereof. In some embodiments the oligomer according to the invention comprises a nucleotide sequence according to SEQ ID NO: 28 (e.g., ASO-000830), or a region thereof. In some embodiments the oligomer according to the invention comprises a nucleotide sequence according to SEQ ID NO: 46 (e.g., ASO-001778), or a region thereof. In some embodiments the oligomer according to the invention comprises a nucleotide sequence according to SEQ ID NO: 43 (e.g., ASO-001779), or a region thereof. In some embodiments the oligomer according to the invention comprises a nucleotide sequence according to SEQ ID NO: 49 (e.g., ASO-001780), or a region thereof. In some embodiments the oligomer according to the invention comprises a nucleotide sequence according to SEQ ID NO: 52 (e.g., ASO-001781), or a region thereof. In some embodiments the oligomer according to the invention comprises a nucleotide sequence according to SEQ ID NO: 67 (e.g., ASO-001782), or a region thereof. In some embodiments the oligomer according to the invention comprises a nucleotide sequence according to SEQ ID NO: 56 (e.g., ASO-001925, or a region thereof. In some embodiments the oligomer according to the invention comprises a nucleotide sequence according to SEQ ID NO: 60 (e.g., ASO-001953), or a region thereof. In some embodiments the oligomer according to the invention comprises a nucleotide sequence according to SEQ ID NO: 698 (e.g., ASO-214296), or a region thereof. In some embodiments the oligomer according to the invention comprises a nucleotide sequence according to SEQ ID NO: 773 (e.g., ASO-000118), or a region thereof. In some embodiments the oligomer according to the invention comprises a nucleotide sequence according to SEQ ID NO: 782 (e.g., ASO-000125), or a region thereof.

In some embodiments the oligomer according to the invention comprises a nucleotide sequence according to SEQ ID NO: 807 (e.g., ASO-000461), or a region thereof. In some embodiments the oligomer according to the invention comprises a nucleotide sequence according to SEQ ID NO: 824 (e.g., ASO-001783), or a region thereof. In some embodiments the oligomer according to the invention comprises a nucleotide sequence according to SEQ ID NO: 825 (e.g., ASO-001784), or a region thereof. In some embodiments the oligomer according to the invention comprises a nucleotide sequence according to SEQ ID NO: 811 (e.g., ASO-000520), or a region thereof. In some embodiments the oligomer according to the invention comprises a nucleotide sequence according to SEQ ID NO: 818 (e.g., ASO-000774), or a region thereof. In some embodiments the oligomer according to the invention comprises a nucleotide sequence according to SEQ ID NO: 817 (e.g., ASO-000773), or a region thereof.

In some embodiments, the oligomer of the invention has a sequence score greater than or equal to 0.2, wherein the sequence score is calculated by formula I:

$$\frac{\#\text{ of } C \text{ nucleotides and analogs thereof} - \#\text{ of } G \text{ nucleotides and analogs thereof}}{\text{Total nucleotide length}}. \quad \text{(I)}$$

In other embodiments, the oligomer of the invention has a sequence score greater than or equal to 0.2, wherein the sequence score is calculated by formula IA:

$$\frac{\#\text{ of } C \text{ nucleotides and 5-methylcytosine nucleotides} - \#\text{ of } G \text{ nucleotides}}{\text{Total nucleotide length}}. \quad \text{(IA)}$$

In these embodiments, a sequence score of greater than or equal to a cut off value corresponds to a reduced neurotoxicity of the oligomer.

In certain embodiments, the oligomer of the invention has a sequence score greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In one embodiment, the oligomer of the invention comprises a contiguous nucleotide sequence hybridizing to a non-coding region of a MAPT transcript, wherein the sequence score of the oligomer is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, the oligomer of the invention comprises a contiguous nucleotide sequence hybridizing to a 3' UTR of a MAPT transcript, wherein the sequence score of the oligomer is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, the oligomer of the invention comprises a contiguous nucleotide sequence hybridizing to a 5' UTR of a MAPT transcript, wherein the sequence score of the oligomer is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, the oligomer of the invention comprises a contiguous nucleotide sequence hybridizing to exon 2 of a MAPT transcript, wherein the sequence score of the oligomer is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In all of these embodiments, when the sequence score is greater than or equal to the cut off value, the oligomer is considered to have reduced neurotoxicity.

II.C. Oligomer Length

The oligomers can comprise a contiguous nucleotide sequence of a total of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides in length.

In some embodiments, the oligomers comprise a contiguous nucleotide sequence of a total of about 10-22, such as 10-21 or 12-18, such as 13-17 or 12-16, such as 13, 14, 15, 16, 17, 18, 19, 20, or 21 contiguous nucleotides in length.

In some embodiments, the oligomers comprise a contiguous nucleotide sequence of a total of 10, 11, 12, 13, or 14 contiguous nucleotides in length.

In some embodiments, the oligomer according to the invention consists of no more than 22 nucleotides, such as no more than 21 or 20 nucleotides, such as no more than 18 nucleotides, such as 15, 16 or 17 nucleotides. In some embodiments the oligomer of the invention comprises less than 22 nucleotides. It should be understood that when a range is given for an oligomer, or contiguous nucleotide sequence length, the range includes the lower and upper lengths provided in the range, for example from (or between) 10-50, includes both 10 and 50.

II.D. Nucleosides and Nucleoside Analogs

In one aspect of the invention, the oligomers comprise one or more non-naturally occurring nucleotide analogs.

“Nucleotide analogs” as used herein are variants of natural nucleotides, such as DNA or RNA nucleotides, by virtue of modifications in the sugar and/or base moieties. Analogs could in principle be merely “silent” or “equivalent” to the natural nucleotides in the context of the oligonucleotide, i.e. have no functional effect on the way the oligonucleotide works to inhibit target gene expression. Such “equivalent” analogs can nevertheless be useful if, for example, they are easier or cheaper to manufacture, or are more stable to storage or manufacturing conditions, or represent a tag or label. In some embodiments, however, the analogs will have a functional effect on the way in which the oligomer works to inhibit expression; for example by producing increased binding affinity to the target and/or increased resistance to intracellular nucleases and/or increased ease of transport into the cell. Specific examples of nucleoside analogs are described by e.g. Freier & Altmann; *Nucl. Acid Res.,* 1997, 25, 4429-4443 and Uhlmann; *Curr. Opinion in Drug Development,* 2000, 3(2), 293-213, and in Scheme 1:

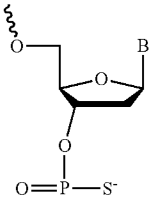

Phosphorthioate

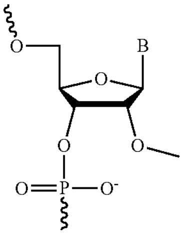

2'-O-Methyl

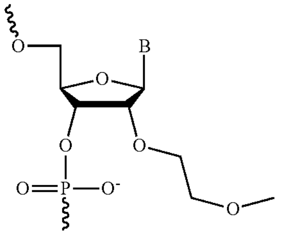

2'-MOE

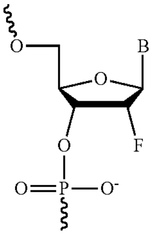

2'-Fluoro

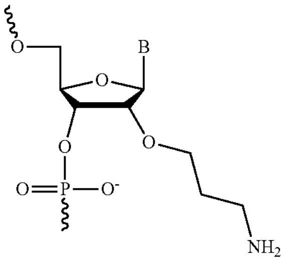

2'-AP

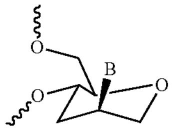

HNA

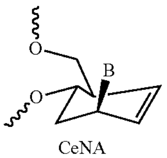

CeNA

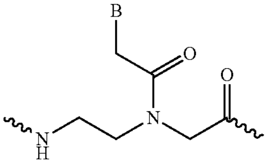

PNA

-continued

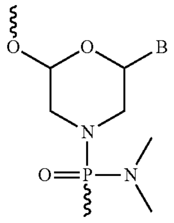

Morpholino

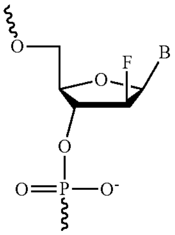

2'-F-ANA

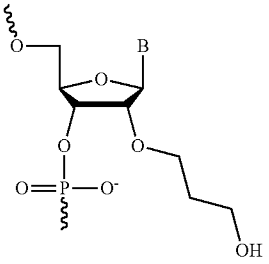

2'-(3-hydroxy)propyl

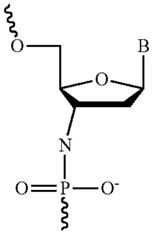

3'-Phosphoramidate

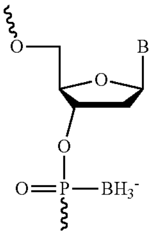

Boranophosphates

In one embodiment, the oligomer includes at least one, at least two, at least three, at least four, at least five, at least six, at least seven, at least eight, at least nine, or at least ten nucleotide analogs. In another embodiment, the oligomer includes four, six, eight, or ten nucleotide analogs.

Examples of the nucleotide analogs include, but are not limited to, Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), or any combination thereof.

“Hexitol nucleic acids” or “HNA” are composed of phosphorylated 2,3-dideoxy-D-arabino-hexitol units with a nucleobase situated in the 2-[S]-position.

“cEt” or “constrained ethyl” means a bicyclic nucleoside having a sugar moiety comprising a bridge connecting the 4'-carbon and the 2'-carbon, wherein the bridge has the formula: 4'-CH(CH3)-0-2'.

“2'-O-methoxyethyl” (also 2'-MOE and 2'-O(CH2)2-OCH3 and MOE) refers to an 0-methoxy-ethyl modification at the 2' position of a furanosyl ring. A 2'-O-methoxyethyl modified sugar is a modified sugar.

As used herein, “2'-F” refers to modification of the 2' position of the furanosyl sugar ring to comprise a fluoro group.

As used herein, “2'-OMe” or “2'-OCH3” or “2'-O-methyl” each refers to modification at the 2' position of the furanosyl sugar ring to comprise a —OCH3 group.

The oligomer can thus comprise a simple sequence of natural occurring nucleotides—for example, 2'-deoxynucleotides (referred to herein generally as “DNA”), but also possibly ribonucleotides (referred to herein generally as "RNA"), or a combination of such naturally occurring nucleotides and one or more non-naturally occurring nucleotides, i.e. nucleotide analogs. Such nucleotide analogs can suitably enhance the affinity of the oligomer for the target sequence.

Examples of suitable nucleotide analogs are provided by WO2007/031091, which is incorporated by reference in its entirety, or are referenced therein.

Incorporation of affinity-enhancing nucleotide analogs in the oligomer, such as LNA or 2'-substituted sugars, can allow the size of the specifically binding oligomer to be reduced, and can also reduce the upper limit to the size of the oligomer before non-specific or aberrant binding takes place.

In some embodiments, the oligomer comprises at least one LNA. Additional details of the LNA compound are disclosed elsewhere herein. In some embodiments the oligomer comprises at least 2 LNAs. In some embodiments, the oligomer comprises from 3-10 LNAs, e.g., 6 or 7 LNAs, e.g., at least 3 or at least 4, or at least 5, or at least 6, or at least 7, or 8 LNAs. In some embodiments all the nucleotides analogs can be LNA.

In a specific embodiment, the oligomer of the invention includes a bicyclic sugar. Non-limiting examples of the bicyclic sugar includes cEt, 2',4'-constrained 2'-O-methoxyethyl (cMOE), LNA, α-LNA, β-LNA, 2'-0,4'-C-ethylene-bridged nucleic acids (ENA), amino-LNA, oxy-LNA, or thio-LNA.

The term "thio-LNA" comprises a locked nucleotide in which Y in general Formula VI below is selected from S or $—CH_2—S—$. Thio-LNA can be in both beta-D and alpha-L-configuration.

The term "amino-LNA" comprises a locked nucleotide in which Y in general Formula VI below is selected from —N(H)—, N(R)—, $CH_2—N(H)—$, and $—CH_2—N(R)—$ where R is selected from hydrogen and $C_{1-4}$-alkyl. Amino-LNA can be in both beta-D and alpha-L-configuration.

The term "oxy-LNA" comprises a locked nucleotide in which Y in general Formula VI below represents —O—. Oxy-LNA can be in both beta-D and alpha-L-configuration.

The term "ENA" comprises a locked nucleotide in which Y in general Formula VI below is $—CH_2—O—$ (where the oxygen atom of $—CH_2—O—$ is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

It will be recognized that when referring to a nucleotide sequence motif or nucleotide sequence, which consists of only nucleotides, the oligomers of the invention which are defined by that sequence, can comprise a corresponding nucleotide analog in place of one or more of the nucleotides present in the sequence, such as LNA units or other nucleotide analogs, including cEt, cMOE, α-LNA, β-LNA, ENA, amino-LNA, oxy-LNA, thio-LNA, which raise the duplex stability/$T_m$ of the oligomer/target duplex (i.e. affinity enhancing nucleotide analogs).

In some embodiments, any mismatches between the nucleotide sequence of the oligomer and the target sequence are found in regions outside the affinity enhancing nucleotide analogs, such as region B as referred to herein, and/or region D as referred to herein, and/or at the site of non-modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and can also provide increased nuclease resistance.

In one embodiment, a nucleotide analog is oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In a particular embodiment, a nucleotide analog is beta-D-oxy-LNA.

In some embodiments the nucleotide analogs present within the oligomer of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'-MOE units. In some embodiments there is only one of the above types of nucleotide analogs present in the oligomer of the invention, or contiguous nucleotide sequence thereof.

In some embodiments the nucleotide analogs are 2'-O-methoxyethyl-RNA (2'-MOE), 2'-fluoro-DNA monomers, LNA nucleotide analogs, cEt, cMOE, α-LNA, β-LNA, ENA, amino-LNA, oxy-LNA, or thio-LNA units, and as such the oligonucleotide of the invention can comprise nucleotide analogs which are independently selected from these types of analog, or can comprise only one type of analog selected from those above. In some embodiments at least one of the nucleotide analogs is 2'-MOE-RNA, such as 2, 3, 4, 5, 6, 7, 8, 9 or 10 2'-MOE-RNA nucleotide units. In some embodiments at least one of the nucleotide analogs is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, 8, 9, or 10 LNA units, such as from 3-7 or 4-8 LNA units, or 3, 4, 5, 6, 7, or 8 LNA units. In some embodiments, all the nucleotide analogs are LNA. In some embodiments, the oligomer can comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'-methylcytosine. In some embodiments of the invention, the oligomer can comprise both LNA and DNA units. In certain embodiments, the combined total of LNA and DNA units is 10-50, 10-30, such as 10-25, e.g., 10-22, such as 10-21. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogs and naturally occurring nucleotides (such as RNA or DNA, e.g., DNA nucleotides), optionally with modified internucleotide linkages such as phosphorothioate.

The term "nucleobase" refers to the base moiety of a nucleotide and covers both naturally occurring as well as non-naturally occurring variants. Thus, "nucleobase" covers not only the known purine and pyrimidine heterocycles but also heterocyclic analogs and tautomeres thereof.

Examples of nucleobases include, but are not limited to adenine, guanine, cytosine, thymidine, uracil, xanthine, hypoxanthine, 5-methyl cytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In certain embodiments, the present invention includes oligomers comprising nucleotide analogs. In some embodiments, the nucleotide analog comprises a modified nucleobase such as 5-methylcytosine. In other embodiments, the nucleotide analog comprise a modified nucleobases such as 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In certain embodiments, the oligomers have a chemical structure as disclosed in FIG. 2A to 2NNNN or FIG. 16D to 16K.

II.E. LNA

The term "LNA" refers to a bicyclic nucleoside analog, known as "Locked Nucleic Acid". It can refer to an LNA monomer, or, when used in the context of an "LNA oligonucleotide," LNA refers to an oligonucleotide containing one or more such bicyclic nucleotide analogs. LNA nucleotides are characterized by the presence of a linker group (such as a bridge) between CT and C4' of the ribose sugar ring—for example as shown as the biradical $R^{4*}$-$R^{2*}$ as described below.

In certain embodiments, the LNA used in the oligonucleotide compounds of the invention has the structure of the general formula V:

(V)

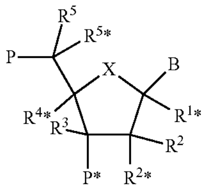

wherein for all chiral centers, asymmetric groups can be found in either R or S orientation; wherein X is selected from —O—, —S—, —N(RN*)—, —C(R6R6*)-, such as, in some embodiments —O—;

B is selected from hydrogen, optionally substituted C1-4-alkoxy, optionally substituted C1-4-alkyl, optionally substituted C1-4-acyloxy, nucleobases including naturally occurring and nucleobase analogs, DNA intercalators, photochemically active groups, thermochemically active groups, chelating groups, reporter groups, and ligands; in some embodiments, B is a nucleobase or nucleobase analog;

P designates an internucleotide linkage to an adjacent monomer, or a 5'-terminal group, such internucleotide linkage or 5'-terminal group optionally including the substituent R5 or equally applicable the substituent R5*;

P* designates an internucleotide linkage to an adjacent monomer, or a 3'-terminal group;

R4* and R2* together designate a bivalent linker group consisting of 1-4 groups/atoms selected from —C(RaRb)—, —C(Ra)═C(Rb)-, —C(Ra)=N—, —O—, —Si(Ra)2-, —S—, —SO2-, —N(Ra)—, and >C═Z, wherein Z is selected from —O—, —S—, and —N(Ra)—, and Ra and Rb each is independently selected from hydrogen, optionally substituted C1-12-alkyl, optionally substituted C2-12-alkenyl, optionally substituted C2-12-alkynyl, hydroxy, optionally substituted C1-12-alkoxy, C2-12-alkoxyalkyl, C2-12-alkenyloxy, carboxy, C1-12-alkoxycarbonyl, C1-12-alkylcarbonyl, formyl, aryl, aryloxy-carbonyl, aryloxy, aryl carbonyl, heteroaryl, heteroaryloxy-carbonyl, heteroaryloxy, heteroarylcarbonyl, amino, mono- and di(C1-6-alkyl) amino, carbamoyl, mono- and di(C1-6-alkyl)-amino-carbonyl, amino-C1-6-alkyl-aminocarbonyl, mono- and di(C1-6-alkyl)amino-C1-6-alkyl-aminocarbonyl, C1-6-alkyl-carbonylamino, carbamido, C1-6-alkanoyloxy, sulphono, C1-6-alkylsulphonyloxy, nitro, azido, sulphanyl, C1-6-alkylthio, halogen, DNA intercalators, photochemically active groups, thermochemically active groups, chelating groups, reporter groups, and ligands, where aryl and heteroaryl can be optionally substituted and where two geminal substituents Ra and Rb together can designate optionally substituted methylene (═CH2), wherein for all chiral centers, asymmetric groups can be found in either R or S orientation, and;

each of the substituents R1*, R2, R3, R5, R5*, R6 and R6*, which are present is independently selected from hydrogen, optionally substituted C1-12-alkyl, optionally substituted C2-12-alkenyl, optionally substituted C2-12-alkynyl, hydroxy, C1-12-alkoxy, C2-12-alkoxyalkyl, C2-12-alkenyloxy, carboxy, C1-12-alkoxycarbonyl, C1-12-alkyl-carbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C1-6-alkyl) amino, carbamoyl, mono- and di(C1-6-alkyl)-amino-carbonyl, amino-C1-6-alkyl-aminocarbonyl, mono- and di(C1-6-alkyl)amino-C1-6-alkyl-aminocarbonyl, C1-6-alkyl-carbonylamino, carbamido, C1-6-alkanoyloxy, sulphono, C1-6-alkylsulphonyloxy, nitro, azido, sulphanyl, C1-6-alkylthio, halogen, DNA intercalators, photochemically active groups, thermochemically active groups, chelating groups, reporter groups, and ligands, where aryl and heteroaryl can be optionally substituted, and where two geminal substituents together can designate oxo, thioxo, imino, or optionally substituted methylene; wherein RN is selected from hydrogen and C1-4-alkyl, and where two adjacent (non-geminal) substituents can designate an additional bond resulting in a double bond; and RN*, when present and not involved in a biradical, is selected from hydrogen and C1-4-alkyl; and basic salts and acid addition salts thereof. For all chiral centers, asymmetric groups can be found in either R or S orientation.

In some embodiments, R4* and R2* together designate a biradical consisting of a groups selected from the group consisting of C(RaRb)—C(RaRb)-, C(RaRb)—O—, C(RaRb)—NRa—, C(RaRb)—S—, and C(RaRb)—C(RaRb)—O—, wherein each Ra and Rb can optionally be independently selected. In some embodiments, Ra and Rb can be, optionally independently selected from the group consisting of hydrogen and C1-6alkyl, such as methyl, such as hydrogen.

In some embodiments, $R^{4*}$ and $R^{2*}$ together designate the biradical —O—CH($CH_2OCH_3$)— (2'O-methoxyethyl bicyclic nucleic acid—Seth at al., 2010, J. Org. Chem)—in either the R- or S-configuration. In some embodiments, $R^{4*}$ and $R^{2*}$ together designate the biradical —O—CH($CH_2CH_3$)— (2'O-ethyl bicyclic nucleic acid—Seth at al., 2010, J. Org. Chem). —in either the R- or S-configuration.

In some embodiments, $R^{4*}$ and $R^{2*}$ together designate the biradical —O—CH($CH_3$)—. —in either the R- or S-configuration. In some embodiments, $R^{4*}$ and $R^{2*}$ together designate the biradical —O—$CH_2$—O—$CH_2$— (Seth at al., 2010, J. Org. Chem).

In some embodiments, $R^{4*}$ and $R^{2*}$ together designate the biradical —O—NR—$CH_3$— Seth at al., 2010, J. Org. Chem).

In some embodiments, the LNA units have a structure selected from the following group:

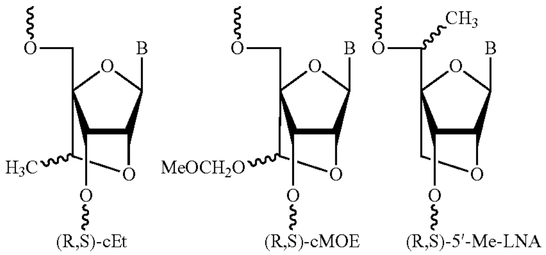

(R,S)-cEt (R,S)-cMOE (R,S)-5'-Me-LNA in which the orientation of the $CH_3$— substituent in the cEt LNA units can independently be R or S, and in which the orientation of the $MeOCH_2$— substituent in the cMOE LNA units can independently be R or S, and in which the orientation of the $CH_3$-substituent in the 5'-Me-LNA units can independently be R or S.

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups can be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups can be found in either R or S orientation.

In some embodiments, $R^{1*}$, $R^2$, $R^3$ are hydrogen.

In some embodiments, $R^5$ and $R^{5*}$ are each independently selected from the group consisting of H, —$CH_3$, —$CH_2$—$CH_3$, —$CH_2$—O—$CH_3$, and —CH═$CH_2$. Suitably in some embodiments, either $R^5$ or $R^{5*}$ are hydrogen, whereas the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(═O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(═O)$NJ_1J_2$, N(H)C(═NH)$NJ_1J_2$ or N(H)C(═X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(═O)$NJ_1J_2$, N(H)C(═NH)$NJ_1J_2$or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(═O)$NJ_1J_2$. For all chiral centers, asymmetric groups can be found in either R or S orientation. Such 5' modified bicyclic nucleotides are disclosed in WO 2007/134181, which is hereby incorporated by reference in its entirety.

In some embodiments B is a nucleobase, including nucleobase analogs and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)═C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, aryl carbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl can be optionally substituted and where two geminal substituents $R^a$ and $R^b$ together can designate optionally substituted methylene (═$CH_2$). For all chiral centers, asymmetric groups can be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH═CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH═CH— For all chiral centers, asymmetric groups can be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical $C(R^aR^b)$—O—$C(R^cR^d)$—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ^3C(=X)NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments the substituent group is $C_{1-6}$ alkoxy. In some embodiments Z is $CH_3OCH_2$—. For all chiral centers, asymmetric groups can be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^{3*}$ are hydrogen, and one or both of $R^5$, $R^{5*}$ can be other than hydrogen as referred to above and in WO 2007/134181, which is incorporated by reference herein in its entirety.

In some embodiments, $R^{4*}$ and $R^{2*}$ together designate a biradical which comprise a substituted amino group in the bridge such as consist of or comprise the biradical —$CH_2$—$N(R^c)$—, wherein $R^c$ is $C_{1-12}$ alkyloxy. In some embodiments $R^{4*}$ and $R^{2*}$ together designate a biradical —$Cq_3q_4$—NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $NJ_1J_2$, $COOJ_1$, CN, O—$C(=O)NJ_1J_2$, $N(H)C(=NH)NJ_1J_2$ or $N(H)C(=X=N(H)J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups can be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ can be other than hydrogen as referred to above and in WO 2007/134181. In some embodiments $R^{4*}$ and $R^{2*}$ together designate a biradical (bivalent group) $C(R^aR^b)$—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1SJ_1$, $SOJ_1$, $SO_2J_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=NH)NJ_1J_2$, $N(H)C(=O)NJ_1J_2$ or $N(H)C(=S)NJ_1J_2$; or $R^a$ and $R^b$ together are =C(q3)(q4); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$ or $N(H)C(=S)NJ_1J_2$, and; each $J_1$ and $J_2$ is, independently, H, C1-$C_6$ alkyl, substituted C1-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C1-$C_6$ aminoalkyl, substituted C1-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is $C(q_1)(q_2)C(q_3)(q_4)$, $C(q_1)=C(q_3)$, $C[=C(q_1)(q_2)]$—$C(q_3)(q_4)$ or $C(q_1)(q_2)$—$C[=C(q_3)(q_4)]$; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$alkoxy, $OJ_1$, $SJ_1$, $SOJ_1$, $SO_2J_1$, $NJ_1J_2$, $N_3$, CN, $C(=O)OJ_1$, $C(=O)$—$NJ_1J_2$, $C(=O)$ $J_1$-$C(=O)NJ_1J_2$, $N(H)C(=NH)NJ_1J_2$, $N(H)C(=O)NJ_1J_2$ or $N(H)C(=S)NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups can be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ can be other than hydrogen as referred to above and in WO 2007/134181 or WO2009/067647 (alpha-L-bicyclic nucleic acids analogs).

Further bicyclic nucleoside analogs and their use in antisense oligonucleotides are disclosed in WO2011/115818, WO2011/085102, WO2011/017521, WO09/100320, WO10/036698, WO09/124295 & WO09/006478, each of which are incorporated by reference herein in their entireties. Such nucleoside analogs can in some aspects be useful in the compounds of present invention.

In some embodiments the LNA used in the oligonucleotide compounds of the invention has the structure of the general formula VI:

(VI)

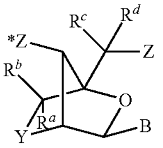

wherein Y is selected from the group consisting of —O—, —$CH_2$O—, —S—, —NH—, N($R^e$) and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^bR^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, aryl carbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl can be optionally substituted and where two geminal substituents $R^a$ and $R^b$ together can designate optionally substituted methylene (═$CH_2$); and $R^H$ is selected from hydrogen and $C_{1-4}$-alkyl. In some embodiments $R^a$, $R^bR^c$, $R^d$ and $R^e$ are, optionally independently, selected from the group consisting of hydrogen and $C_{1-6}$ alkyl, such as methyl. For all chiral centers, asymmetric groups can be found in either R or S orientation, for example, two exemplary stereochemical isomers include the beta-D and alpha-L isoforms, which can be illustrated as follows:

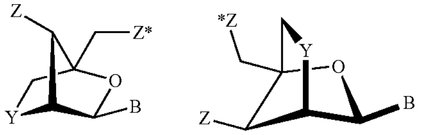

Specific exemplary LNA units are shown below:

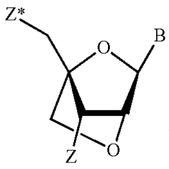

β-D-oxy-LNA

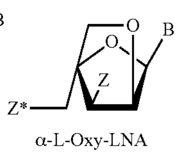

α-L-Oxy-LNA

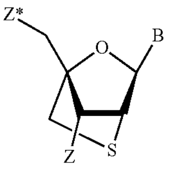

β-D-thio-LNA

-continued

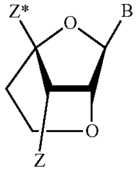

β-D-ENA

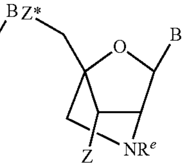

β-D-amino-LNA

In other embodiments, the oligomers of the invention comprise nucleotides with modified sugar moieties as described in FIGS. 2A to 2NNNN, 3A to 3Z, 6A to 6GG, 7A to 7E, 16A to 16C, 16D to 16K, 20A, and 20B to 20C.

II.F. RNase Recruitment

It is recognized that an oligomeric compound can function via non RNase mediated degradation of target mRNA, such as by steric hindrance of translation, or other methods, however, in one aspect, the oligomers of the invention are capable of recruiting an endoribonuclease (RNase), such as RNaseH.

In one aspect, the oligomer, or contiguous nucleotide sequence, comprises a region of at least 7 consecutive nucleotide units, such as at least 8 or at least 9 consecutive nucleotide units (residues), in certain embodiments including 7, 8, 9, 10, 11, 12, 13, 14, 15, 16, 17, 18, 19, 20, 21, 22, or 23 consecutive nucleotides, which, when formed in a duplex with the complementary target RNA is capable of recruiting RNase. The contiguous sequence which is capable of recruiting RNase can be region B as referred to in the context of a gapmer as described herein. In some embodiments the size of the contiguous sequence which is capable of recruiting RNase, such as region B, can be higher, such as 10, 11, 12, 13, 14, 15, 16, 17, 18, 19, 20, 21, 22, or 23 nucleotide units.

U.S. Pat. No. 6,617,442, which is incorporated by reference herein in its entirety, provides in vitro methods for determining RNaseH activity, which can be used to determine the ability to recruit RNaseH. Therefore, in one embodiment, an oligomer of the invention is capable of recruiting RNaseH. In another embodiment, the invention includes a method of identifying an oligomer which is capable of utilizing RNaseH mechanism, e.g., recruiting RNaseH.

Oligomers can be screened to identify those which are effective in recruiting RNaseH. The ability of oligomers to recruit RNaseH can be determined by measuring the binding of the oligomers to RNaseH. The methods of determining binding of the oligomers to RNaseH are well known in the art. For example, the oligomers can be radiolabeled and binding of the oligomers to RNaseH can be detected by autoradiography. In some embodiments, fusion proteins of RNaseH with glutathione-S-transferase or small peptide tags can be prepared and immobilized to a solid phase such as beads. Labeled or unlabeled oligomers to be screened for binding to this enzyme can then be incubated with the solid phase. Oligomers which bind to the enzyme immobilized to the solid phase can then be identified either by detection of bound label or by eluting specifically the bound oligomers from the solid phase. Another method involves screening of oligomer libraries for binding partners. Recombinant tagged or labeled RNaseH is used to select oligomers from the library which interact with the enzyme. Sequencing of the oligomers leads to identification of those oligomers which will be more effective as antisense molecules.

An oligomer is deemed capable of recruiting RNaseH if, when provided with the complementary RNA target, it has an initial rate, as measured in pmol/l/min, of at least 1%, such as at least 5%, such as at least 10% or, more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of U.S. Pat. No. 6,617,442.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of U.S. Pat. No. 6,617,442.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of U.S. Pat. No. 6,617,442.

Typically the region of the oligomer which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

In some embodiments, the monomers which are capable of recruiting RNase are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference in its entirety), and UNA (unlinked nucleic acid) nucleotides (see Fluiter et al., Mol. Biosyst., 2009, 10, 1039, hereby incorporated by reference). UNA is unlocked nucleic acid, typically where the C2-C3 C—C bond of the ribose has been removed, forming an unlocked "sugar" residue.

II.G. Oligomer Design

The oligomer of the invention can comprise a nucleotide sequence which comprises both nucleotides and nucleotide analogs, and can be in the form of a gapmer, blockmer, mixmer, headmer, tailmer, or totalmer. Examples of configurations of a gapmer, blockmer, mixmer, headmer, tailmer, or totalmer that can be used with the oligomer of the invention are described in U.S. Patent Appl. Publ. No. 2012/0322851, which is incorporated by reference herein in its entirety.

A gapmer oligomer is an oligomer which comprises a contiguous stretch of nucleotides which is capable of recruiting an RNase, such as RNaseH, such as a region of at least 7 DNA nucleotides, which is flanked both 5' and 3' by regions of affinity enhancing 1-6 nucleotide analogs 5' and 3' to the contiguous stretch of nucleotides which is capable of recruiting RNase.

A "headmer" is defined as an oligomer that comprises a region X and a region Y that is contiguous thereto, with the 5'-most monomer of region Y linked to the 3'-most monomer of region X. Region X comprises a contiguous stretch of non-RNase recruiting nucleoside analogs and region Y comprises a contiguous stretch (such as at least 7 contiguous monomers) of DNA monomers or nucleoside analog monomers recognizable and cleavable by the RNase.

A "tailmer" is defined as an oligomer that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analog monomers recognizable and cleavable by the RNase, and region Y comprises a contiguous stretch of non-RNase recruiting nucleoside analogs.

Other "chimeric" oligomers, called "mixmers", consist of an alternating composition of (i) DNA monomers or nucleoside analog monomers recognizable and cleavable by RNase, and (ii) non-RNase recruiting nucleoside analog monomers.

A "totalmer" is a single stranded oligomer which only comprises non-naturally occurring nucleotides or nucleotide analogs.

In some embodiments, in addition to enhancing affinity of the oligomer for the target region, some nucleoside analogs also mediate RNase (e.g., RNaseH) binding and cleavage. Since α-L-LNA monomers recruit RNaseH activity to a certain extent, in some embodiments, gap regions (e.g., region B as referred to herein) of oligomers containing α-L-LNA monomers consist of fewer monomers recognizable and cleavable by the RNaseH, and more flexibility in the mixmer construction is introduced.

II.G.1. Gapmer Design

In one embodiment, the oligomer of the invention is a gapmer. A gapmer oligomer is an oligomer which comprises a contiguous stretch of nucleotides which is capable of recruiting an RNase, such as RNaseH, such as a region of at least 7 DNA nucleotides, referred to herein in as region B (B), wherein region B is flanked both 5' and 3' by regions of affinity enhancing nucleotide analogs, such as from 1-10 nucleotide analogs 5' and 3' to the contiguous stretch of nucleotides which is capable of recruiting RNase—these regions are referred to as regions A (A) and C (C) respectively.

In certain embodiments, the gapmer is an alternating flank gapmer, examples of which are discussed below. In certain embodiments, the alternating flank gapmer exhibits less off target binding than a traditional gapmer. In certain embodiments, the alternating flank gapmer has better long term tolerability than a traditional gapmer.

An alternating flank gapmer can comprises a (poly) nucleotide sequence of formula (5' to 3'), A-B-C, wherein: region A (A) (5' region or a first wing sequence) comprises at least one nucleotide analog, such as at least one LNA unit, such as from 1-10 nucleotide analogs, such as LNA units, and; region B (B) comprises at least seven consecutive nucleotides which are capable of recruiting RNase (when formed in a duplex with a complementary RNA molecule, such as the pre-mRNA or mRNA target), such as DNA nucleotides, and; region C (C) (3'region or a second wing sequence) comprises at least one nucleotide analog, such as at least one LNA unit, such as from 1-10 nucleotide analogs, such as LNA units; wherein regions A and C can include at any position in A and C 1-2 insertions of DNA nucleotide regions (e.g., DNA gapmers), in which these DNA insertions can each be 1-3 DNA units long.

In certain other embodiments, the gapmer, e.g., an alternating flank gapmer, comprises a (poly)nucleotide sequence of formula (5' to 3'), A-B-C, or optionally A-B-C-D or D-A-B-C, wherein: region A (A) (5' region) comprises at least one nucleotide analog, such as at least one LNA unit, such as from 1-10 nucleotide analogs, such as LNA units, and; region B (B) comprises at least seven consecutive nucleotides which are capable of recruiting RNase (when formed in a duplex with a complementary RNA molecule, such as the mRNA target), such as DNA nucleotides, and; region C (C) (3'region) comprises at least one nucleotide analog, such as at least one LNA unit, such as from 1-10 nucleotide analogs, such as LNA units, and; region D (D), when present comprises 1, 2 or 3 nucleotide units, such as DNA nucleotides.

In some embodiments, region A comprises 1, 2, 3, 4, 5, 6, 7, 8, 9, or 10 nucleotide analogs, such as LNA units, such as from 2-5 nucleotide analogs, such as 2-5 LNA units, such as 2-5 nucleotide analogs, such as 3-5 LNA units; and/or region C consists of 1, 2, 3, 4, 5, 6, 7, 8, 9, or 10 nucleotide analogs, such as LNA units, such as from 2-5 nucleotide analogs, such as 2-5 LNA units, such as 2-5 nucleotide analogs, such as 3-5 LNA units.

In some embodiments B comprises 7, 8, 9, 10, 11, 12, 13, 14, 15, 16, 17, 18, 19, 20, 21, 22, or 23 consecutive nucleotides which are capable of recruiting RNase, or from 8-14, or from 7-10, or from 7-9, such as 8, such as 9, such as 10, or such as 14 consecutive nucleotides which are capable of recruiting RNase. In some embodiments region B comprises at least seven DNA nucleotide unit, such as 7-23 DNA units, such as from 7-20 DNA units, such as from 7-14 DNA units, such as from 8-14 DNA units, such as 7, 8, 9, 10, 11, 12, 13, or 14 DNA units.

In some embodiments region A comprises 3, 4, or 5 nucleotide analogs, such as LNA, region B consists of 7, 8, 9, 10, 11, 12, 13, or 14 DNA units, and region C consists of 3, 4, or 5 nucleotide analogs, such as LNA. Such designs include (A-B-C) 5-10-5, 3-14-3, 3-10-3, 3-10-4, 4-10-3, 3-9-3, 3-9-4, 4-9-3, 3-8-3, 3-8-4, 4-8-3, 3-7-3, 3-7-4, and 4-7-3, and can further include region D, which can have one to 3 nucleotide units, such as DNA units.

In some embodiments, the oligomer of the invention, e.g., an alternating flank gapmer, has the formula of 5'-A-B-C-3', wherein (i) B is a contiguous sequence of 7 to 23 DNA units;

(ii) A is a first wing sequence of 1 to 10 nucleotides, wherein the first wing sequence comprises one or more nucleotide analogs and optionally one or more DNA units (e.g., DNA gapmer) and wherein at least one of the nucleotide analogs is located at the 5' end of A; and (iii) C is a second wing sequence of 1 to 10 nucleotides, wherein the second wing sequence comprises one or more nucleotide analogs and optionally one or more DNA units (e.g., DNA gapmer) and wherein at least one of the nucleotide analogs is located at the 3' end of C.

In other embodiments, the oligomer, e.g., an alternating flank gapmer, has the formula of 5'-A-B-C-3', wherein B is a contiguous sequence of 7 to 23 DNA units, A is LmDnLoDpLq and C is Lm'Dn'Lo'Dp'Lq' and wherein L is a nucleotide analog; D is a DNA unit; m and q' are 1 to 6 units; n, p, n', and p' are 0 to 2 units; and o, q, m', and o' are 0 to 5.

In some embodiments, the first wing sequence (A in the formula) comprises a combination of nucleotide analogs and DNA units selected from (i) 1-9 nucleotide analogs and 1 DNA unit; (ii) 1-8 nucleotide analogs and 1-2 DNA units; (iii) 1-7 nucleotide analogs and 1-3 DNA units; (iv) 1-6 nucleotide analogs and 1-4 DNA units; (v) 1-5 nucleotide analogs and 1-5 DNA units; (vi) 1-4 nucleotide analogs and 1-6 DNA units; (vii) 1-3 nucleotide analogs and 1-7 DNA units; (viii) 1-2 nucleotide analogs and 1-8 DNA units; and (ix) 1 nucleotide analog and 1-9 DNA units.

In certain embodiments, the second wing sequence (C in the formula) comprises a combination of nucleotide analogs and DNA unit selected from (i) 1-9 nucleotide analogs and 1 DNA unit; (ii) 1-8 nucleotide analogs and 1-2 DNA units; (iii) 1-7 nucleotide analogs and 1-3 DNA units; (iv) 1-6 nucleotide analogs and 1-4 DNA units; (v) 1-5 nucleotide analogs and 1-5 DNA units; (vi) 1-4 nucleotide analogs and 1-6 DNA units; (vii) 1-3 nucleotide analogs and 1-7 DNA units; (viii) 1-2 nucleotide analogs and 1-8 DNA units; and (ix) 1 nucleotide analog and 1-9 DNA units.

In some embodiments, A in the oligomer formula has a sub-formula selected from L, LL, LDL, LLL, LLDL, LDLL, LDDL, LLLL, LLLLL, LLLDL, LLDLL, LDLLL, LLDDL, LDDLL, LLDLD, LDLLD, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD, and C in the oligomer formula has a sub-formula selected from L, LL, LDL, LLL, LLDL, LLLL, LDLL, LDDL, LLDD, LLLLL, LLLLD, LLLDL, LLDLL, LDLLL, LLDDL, LDDLL, LLDLD, LDLLD, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD.

In certain embodiments, the oligomer, e.g., an alternating flank gapmer, has the formula of 5' A-B-C 3', wherein B is a contiguous sequence of 7 to 23 DNA units, A has a formula of LLDLL, LDLLL, or LLLDL and C has the formula of LLDLL or LDLDLL, and wherein L is an LNA unit and D is a DNA unit.

In other embodiments, the oligomers of the invention are alternating flank gapmers having the formula of 5' A-B-C 3', wherein the oligomer has 12 to 25 nucleotides in length, A is a first wing sequence having the formula of $L_m d_n L_o d_p L_q$, C is a second wing sequence having the formula of $L_{q'} d_{p'} L_{o'} d_{n'} L_{m'}$, wherein each wing independently has 1-17 nucleotides in length and is optionally interrupted by DNA spacers $d_n$, $d_p$, $d_{n'}$ and $d_{p'}$, each of which independently has 0 to 3 DNA units, with each wing flanking an all DNA gap of 7 to 23 nucleotides;

wherein m and m' are at least 1;

and n, n', p and p' are independently 0-3 units;

such that m+n+o+p+q=1-17; and independently m'+n'+o'+p'+q'=1-17;

or (m+n+o+p+q) and (m'+n'+o'+p'+q') are independently 1, 2, 3, 4, 5, 6, 7, 8, 9, 10, 11, 12, 13, 14, 15, 16 or 17;

or B comprises a DNA gap of 7, 8, 9, 10, 11, 12, 13, 14, 15, 16, 17, 18, 19, 20, 21, 22 or 23.

Further gapmer designs are disclosed in WO2004/046160, which is hereby incorporated by reference in its entirety. WO2008/113832 hereby incorporated by reference in its entirety, refers to 'shortmer' gapmer oligomers. In some embodiments, oligomers presented herein can be such shortmer gapmers.

In some embodiments the oligomer, e.g., an alternating flank gapmer, comprises a contiguous nucleotide sequence of a total of 10, 11, 12, 13, 14, 15, 16, 17, 18, 19, or 20 nucleotide units, wherein the contiguous nucleotide sequence is of formula (5'-3'), A-B-C, or optionally A-B-C-D or D-A-B-C, wherein; A consists of 1, 2, 3, 4, or 5 nucleotide analog units, such as LNA units; B consists of 7, 8, 9, 10, 11, 12, 13, or 14 contiguous nucleotide units which are capable of recruiting RNase when formed in a duplex with a complementary RNA molecule (such as a mRNA target); and C consists of 1, 2,3, 4, or 5 nucleotide analog units, such as LNA units. When present, D consists of a single DNA unit.

In some embodiments A comprises 1 LNA unit. In some embodiments A comprises 2 LNA units. In some embodiments A comprises 3 LNA units. In some embodiments A comprises 4 LNA units. In some embodiments A comprises 5 LNA units. In some embodiments C comprises 1 LNA unit. In some embodiments C comprises 2 LNA units. In some embodiments C comprises 3 LNA units. In some embodiments C comprises 4 LNA units. In some embodiments C comprises 5 LNA units. In some embodiments B comprises 7 nucleotide units. In some embodiments B comprises 8 nucleotide units. In some embodiments B comprises 9 nucleotide units. In certain embodiments, B comprises 10 nucleoside units. In certain embodiments, B comprises 11 nucleoside units. In certain embodiments, B comprises 12 nucleoside units. In certain embodiments, B comprises 13 nucleoside units. In certain embodiments, B comprises 14 nucleoside units. In certain embodiments, B comprises 7-23 DNA monomers. In some embodiments B comprises from 7-23 DNA units, such as 7, 8, 9, 10, 11, 12, 13, 14, 15, 16, 17, 18, 19, 20, 21, 22, or 23 DNA units. In some embodiments B consists of DNA units. In some embodiments B comprises at least one LNA unit which is in the alpha-L configuration, such as 2, 3, 4, 5, 6, 7, 8, 9, 10, 11, 12, 13, 14, 15, 16, 17, 18, 19, 20, 21, 22, or 23 LNA units in the alpha-L-configuration. In some embodiments B comprises at least one alpha-L-oxy LNA unit or wherein all the LNA units in the alpha-L-configuration are alpha-L-oxy LNA units. In some embodiments the number of nucleotides present in A-B-C are selected from (nucleotide analog units—region B—nucleotide analog units):): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, and 3-10-1. In some embodiments the number of nucleotides in A-B-C is selected from: 2-7-1, 1-7-2, 2-7-2, 3-7-3, 2-7-3, 3-7-2, 3-7-4, and 4-7-3. In other embodiments, the oligomer contains 10 DNA units in B, LDLLL in A (first wing) and LLDLL in C (second wing). In yet other embodiments, the oligomer contains 9 DNA units in B, LDDLL in A, and LDLDLL in C. In still other embodiments, the oligomer contains 10 DNA units in B, LLDLL in A, and LLDLL in C. In further embodiments, the oligomer contains 9 DNA units in B, LLLLL in A, and LDDLL in C. In certain embodiments, each of regions A and C comprises three LNA monomers, and region B consists of 7, 8, 9, 10, 11, 12, 13, or 14 nucleoside monomers, for example, DNA monomers. In some embodiments both A and C consist of two LNA units each, and B consists of 7, 8, or 9 nucleotide units, for example DNA units. In various embodiments, other gapmer designs include those where regions A and/or C consists of 3, 4, 5 or 6 nucleoside analogs, such as monomers containing a 2'-O-methoxyethyl-ribose sugar (2'-MOE) or monomers containing a 2'-fluoro-deoxyribose sugar, and region B consists of 7, 8, 9, 10, 11, 12, 13, 14, 15, 16, 17, 18, 19, 20, 21, 22, or 23 nucleosides, such as DNA monomers, where regions A-B-C have 3-8-3, 3-9-3, 3-10-3, 5-10-5 or 4-12-4 monomers. Further gapmer designs are disclosed in WO 2007/146511A2, hereby incorporated by reference in its entirety.

In some embodiments, the alternating flank oligomer has at least 10 contiguous nucleotides, comprising region A, region B, and region C (A-B-C), wherein region B comprises at least 5 consecutive nucleoside units and is flanked at 5' by region A of 1-8 contiguous nucleoside units and at 3' by region C of 1-8 contiguous nucleoside units, wherein region B, when formed in a duplex with a complementary RNA, is capable of recruiting RNaseH, and wherein region A and region C are selected from the group consisting of:

(i) region A comprises a 5' LNA nucleoside unit and a 3' LNA nucleoside unit, and at least one DNA nucleoside unit between the 5' LNA nucleoside unit and the 3' LNA nucleoside unit, and, region C comprises at least two 3' LNA nucleosides; or (ii) region A comprises at least one 5' LNA nucleoside and region C comprises a 5' LNA nucleoside unit, at least two terminal 3' LNA nucleoside units, and at least one DNA nucleoside unit between the 5' LNA nucleoside unit and the 3' LNA nucleoside units, and (iii) region A comprises a 5' LNA nucleoside unit and a 3' LNA nucleoside unit, and at least one DNA nucleoside unit between the 5' LNA nucleoside unit and the 3' LNA nucleoside unit; and region C comprises a 5' LNA nucleoside unit, at least two terminal 3' LNA nucleoside units, and at least one DNA nucleoside unit between the 5' LNA nucleoside unit and the 3' LNA nucleoside units.

In some embodiments, region A or region C comprises 1, 2, or 3 DNA nucleoside units. In other embodiments, region A and region C comprise 1, 2, or 3 DNA nucleoside units. In yet other embodiments, region B comprises at least five consecutive DNA nucleoside units. In certain embodiments, region B comprises 6, 7, 8, 9, 10, 11, 12, 13 or 14 consecutive DNA nucleoside units. In some embodiments, region B is 8, 9 10, 11, or 12 nucleotides in length. In other embodiments, region A comprises two 5' terminal LNA nucleoside units. In some embodiments, region A has formula 5' $[LNA]_{1-3}[DNA]_{1-3}$ $[LNA]_{1-3}$, or 5' $[LNA]_{1-2}$ $[DNA]_1$-2$[LNA]_{1-2}[DNA]_{1-2}[LNA]_{1-2}$. In other embodiments, region C has formula $[LNA]_{1-3}[DNA]$ 3$[LNA]_{2-3}$3', or $[LNA]_{1-2}[DNA]_{1-2}[LNA]_{1-2}[DNA]_{1-2}[LNA]_{2-3}$3' In yet other embodiments, region A has formula 5' $[LNA]_{1-3}$ $[DNA]_{1-3}$ $[LNA]_{1-3}$, or 5' $[LNA]_{1-2}$ $[DNA]_{1-2}$ $[LNA]_{1-2}$ $[DNA]_{1-2}[LNA]_{1-2}$, and region C comprises 2, 3, 4 or 5 consecutive LNA nucleoside units. In some embodiments, region C has formula $[LNA]_{1-3}[DNA]_{1-3}[LNA]_{2-3}$3' or $[LNA]_{1-2}$ $[DNA]_{1-2}[LNA]_{1-2}[DNA]_{1-2}[LNA]_{2-3}$3', and region A comprises 1, 2, 3, 4 or 5 consecutive LNA nucleoside units. In still other embodiments, region A has a sequence of LNA and DNA nucleosides, 5'-3' selected from the group consisting of L, LL, LDL, LLL, LLDL, LDLL, LDDL, LLLL, LLLLL, LLLDL, LLDLL, LDLLL, LLDDL, LDDLL, LLDLD, LDLLD, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD, wherein L represents a LNA nucleoside, and D represents a DNA nucleoside. In yet other embodiments, region C has a sequence of LNA and DNA nucleosides, 5'-3' selected from the group consisting of LL, LLL, LLLL, LDLL, LLLLL, LLDLL, LDLLL, LDDLL, LDDLLL, LLDDLL, LDLDLL, LDDDLL, LDLDDLL, LDDLDLL, LDDDLLL, and LLDLDLL. In a further embodiment, region A has a sequence of LNA and DNA nucleosides, 5'-3' selected from the group consisting of LDL, LLDL, LDLL, LDDL, LLLDL, LLDLL, LDLLL, LLDDL, LDDLL, LLDLD, LDLLD, LDDDL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD, and region C has a sequence of LNA and DNA nucleosides, 5'-3' selected from the group consisting of LDLL, LLLLL, LLDLL, LDLLL, LDDLL, LDDLLL, LLDDLL, LDLDLL, LDDDLL, LDLDDLL, LDDLDLL, LDDDLLL, and LLDLDLL.

In certain embodiments, the alternating flank oligomer has contiguous nucleotides comprising a sequence of nucleosides, 5'-3', selected from the group consisting of LLDDDLLDDDDDDDDLL, LDLLDLDDDDDDDDDLL, LLLDDDDDDDDDLDLL, LLLDDDDDDDDLDDLL, LLLDDDDDDDLDDDLL, LLLDDDDDDDLDLDLL, LLLDLDDDDDDDDLLL, LLLDLDDDDDDDLDLL, LLLLDDDDDDDDLDLL, LLLLDDDDDDDLDDLL, LLLDDDLDDDDDDDLL, LLLDDLDDDDDDDDLL, LLLDDLLDDDDDDDLL, LLLDDLLDDDDDDLLL, LLLLLDDDDDDLDDLL, LDLLLDDDDDDDDDLL, LDLLLDDDDDDLDDLL, LDLLLLDDDDDDDDLL, LLDLLLDDDDDDDDLL, LLLDLDDDDDDDDDLL, LLLDLDDDDDDLDDLL, LLLDLLDDDDDDDDLL, LLLLDDDDDDLDDDLL, LLLLLDDDDDDDDLDLL, LLLLDDDDDDDDDLDLL, LLLDDDDDDDDDDLDLL, LLDLDDDDDDDDDLDLL, LDLLLDDDDDDDDDLDLL, LLLDDDDDDDDDDLDDLL, LLLDDDDDDDDLDDDLL, LLLDDDDDDDDLDLDDLL, LLLLDDDDDDDDLDDLL, LLLLDDDDDDDDDLDLLL, LLLLDDDDDDDLDDDLL, LLLLDDDDDDDLDDLLL, LLLLDDDDDDDLDLDLL, LLLLDDDDDDLDDLDLL, LLLLDDDDDDDLDLDDLL, LLDLLDDDDDDDDDDDLL, LLDLLLDDDDDDDDLDLL, LLLDLDDDDDDDDDDLL, LLLDLDDDDDDDDDLDLL, LLLDLDDDDDDDDLDDLL, LLLDLDDDDDDDLDLDLL, LLLLDDDDDDDDDLLDLL, LLLLLDDDDDDDDDLDLLL, LLLLLDDDDDDDDDLDDLL, LLLLDDDDDDDDDDLLDLL, LLLLDDDDDDDDDDLDLLL, LLLLDDDDDDDDDDLDDLL, LLLDDDDDDDDDDDLLDLL, LLLDDDDDDDDDDDLDLLL, LLLLLDDDDDDDDDLLDLL, LLLDDDDDDDDDDDLDDLL, LLDLLDDDDDDDDDLDDLL, LLLDLDDDDDDDDDLDLL, LLLDLDDDDDDDDDLDDLL, LLLLDDDDDDDDDDLDLDLL, LLLLDDDDDDDDLLDLDLL, LDLLLDDDDDDDDDDLLDLL, LLDLLDDDDDDDDDDLLDLL, LLDLDDDDDDDDDDDDLLLL, LLDDLDDDDDDDDDDDLLLL, LLLDLDDDDDDDDDDLLLL, LLDLDDDDDDDDDDDDDLLL, LLDLLDDDDDDDDDDDLLLL, LLDDLDDDDDDDDDDDDLLL, LLLDDDDDDDDDDDDLDDLLL, LLLDLDDDDDDDDDDDDDLLL, LLDLLDDDDDDDDDDDDLLL, LLLLDDDDDDDDDDDLLDLL, LLLLDDDDDDDDDDDLLDDLL, LLLDDLDDDDDDDDDLDLLL, LLDDLDLDDDDDDDDDLLLL, LLDDLLDDDDDDDDDDLDLLL, LLLDLDDDDDDDDDLDLDLL, LLDLLDDDDDDDDDLDDLLL, LLLDLDDDDDDDDDDLDLLL, LLDLDDLDDDDDDDDDLLLL, LLLLDDDDDDDDDLDLDDLL, LLLDLDDDDDDDDDLDDLLL, LLDLDLDDDDDDDDDDLLLL, LLDLLDDDDDDDDDDDLDLLL, LLDLDLDDDDDDDDDLLDLL, LLDDLLDDDDDDDDDDDLLDLL, LLLLDDDDDDDDDLDDLDLL, LLLDDLDDDDDDDDDDLLDLL, LLDLLDDDDDDDDDDLLDDLL, LLDLDLDDDDDDDDDLDLLL, LLLDLDDDDDDDDDDLLDDLL, LLDDLLDDDDDDDDDDDLLLL, LLDLLDDDDDDDDDDLDLDLL, LLLLDDDDDDDDDDDLDDLLL, LLLDDLDDDDDDDDDDLLLL, LLLDLDDDDDDDDDDLLDLL, LLLLDDDDDDDDDDDLDLDLL, LLLLDDDDDDDDDDDDLDLLL, and LLDDLLDDDDDDDDDDLDLL; wherein L represents a LNA nucleoside, and D represents a DNA nucleoside. In other embodiments, the LNA nucleoside is beta-D-oxy LNA.

In yet other embodiments, an alternating flank oligomer has contiguous nucleotides comprising an alternating sequence of LNA and DNA nucleoside units, 5'-3', selected from the group consisting of: 2-3-2-8-2, 1-1-2-1-1-9-2, 3-10-1-1-2, 3-9-1-2-2, 3-8-1-3-2, 3-8-1-1-1-1-2, 3-1-1-9-3, 3-1-1-8-1-1-2, 4-9-1-1-2, 4-8-1-2-2, 3-3-1-8-2, 3-2-1-9-2, 3-2-2-8-2, 3-2-2-7-3, 5-7-1-2-2, 1-1-3-10-2, 1-1-3-7-1-2-2, 1-1-4-9-2, 2-1-3-9-2, 3-1-1-10-2, 3-1-1-7-1-2-2, 3-1-2-9-2, 4-7-1-3-2, 5-9-1-1-2, 4-10-1-1-2, 3-11-1-1-2, 2-1-1-10-1-1-2, 1-1-3-9-1-1-2, 3-10-1-2-2, 3-9-1-3-2, 3-8-1-1-1-2-2, 4-9-1-2-2, 4-9-1-1-3, 4-8-1-3-2, 4-8-1-2-3, 4-8-1-1-1-1-2, 4-7-1-2-1-1-2, 4-7-1-1-1-2-2, 2-1-2-11-2, 2-1-3-8-1-1-2, 3-1-1-11-2, 3-1-1-9-1-1-2, 3-1-1-8-1-2-2, 3-1-1-7-1-1-1-1-2, 4-9-2-1-2, 4-7-1-3-3, 5-9-1-1-3, 5-9-1-2-2, 4-10-2-1-2, 4-10-1-1-3, 4-10-1-2-2, 3-11-2-1-2, 3-11-1-1-3, 5-9-2-1-2, 3-11-1-2-2, 2-1-2-9-1-2-2, 3-1-1-10-1-1-2, 3-1-1-9-1-2-2, 4-9-1-1-1-1-2, 4-8-2-1-1-1-2, 1-1-3-10-2-1-2, 2-1-2-10-2-1-2, 2-1-1-12-4, 2-2-1-11-4, 3-1-1-11-4, 2-1-1-13-3, 2-1-2-11-4, 2-2-1-12-3, 3-11-1-2-3, 3-1-1-12-3, 2-1-2-12-3, 4-11-2-1-2, 4-10-2-2-2, 3-2-1-9-1-1-3, 2-2-1-1-1-9-4, 2-2-2-9-1-1-3, 3-1-1-9-1-1-1-1-2, 2-1-2-9-1-2-3, 3-1-1-10-1-1-3, 2-1-1-2-1-9-4, 4-9-1-1-1-2-2, 3-1-1-9-1-2-3, 2-1-1-1-1-10-4, 2-1-2-10-1-1-3, 2-1-1-1-1-9-2-1-2, 2-2-2-9-2-1-2, 4-9-1-2-1-1-2, 3-2-1-9-2-1-2, 2-1-2-9-2-2-2, 2-1-1-1-1-9-1-1-3, 3-1-1-9-2-2-2, 2-2-2-10-4, 2-1-2-9-1-1-1-1-2, 4-10-1-2-3, 3-2-1-10-4, 3-1-1-10-2-1-2, 4-10-1-1-1-1-2, 4-11-1-1-3, and 2-2-2-10-1-1-2; wherein the first numeral represents an number of LNA units, the next a number of DNA units, and alternating LNA and DNA regions thereafter.

In other embodiments, the oligomers of the invention has the design described in FIGS. 2A to 2NNNN, 3A to 3Z, 6A to 6GG, 7A to 7E, 16A to 16C, 16D to 16K, 20A, and 20B to 20C.

II.H. Internucleotide Linkages

The monomers of the oligomers described herein are coupled together via linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference in its entirety).

Examples of suitable internucleotide linkages that can be used with the invention include phosphodiester linkage, a phosphotriester linkage, a methylphosphonate linkage, a phosphoramidate linkage, a phosphorothioate linkage, and combinations thereof.

It is, in some embodiments, preferred to modify the internucleotide linkage from its normal phosphodiester to one that is more resistant to nuclease attack, such as phosphorothioate or boranophosphate—these two, being cleavable by RNaseH, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages can also be used for the flanking regions (A and C, and for linking A or C to D, and within region D, as appropriate).

Regions A, B and C, can, however, comprise internucleotide linkages other than phosphorothioate, such as phosphodiester linkages, particularly, for instance when the use of nucleotide analogs protects the internucleotide linkages within regions A and C from endo-nuclease degradation—such as when regions A and C comprise LNA nucleotides.

The internucleotide linkages in the oligomer can be phosphodiester, phosphorothioate or boranophosphate so as to allow RNaseH cleavage of targeted RNA. Phosphorothioate is preferred, for improved nuclease resistance and other reasons, such as ease of manufacture.

In one aspect of the oligomer of the invention, the nucleotides and/or nucleotide analogs are linked to each other by means of phosphorothioate groups.

It is recognized that the inclusion of phosphodiester linkages, such as one or two linkages, into an otherwise phosphorothioate oligomer, particularly between or adjacent to nucleotide analog units (typically in region A and or C) can modify the bioavailability and/or bio-distribution of an oligomer—see WO2008/113832, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein can be used, for example phosphate (phosphodiester) linkages can be used, particularly for linkages between nucleotide analogs, such as LNA, units. Likewise, when referring to specific gapmer oligonucleotide sequences, such as those provided herein, when the C residues are annotated as 5'methyl modified cytosine, in various embodiments, one or more of the Cs present in the oligomer can be unmodified C residues.

US Publication No. 2011/0130441, which was published Jun. 2, 2011 and is incorporated by reference herein in its entirety, refers to oligomeric compounds having at least one bicyclic nucleoside attached to the 3' or 5' termini by a neutral internucleoside linkage. The oligomers of the invention can therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages can be phosphorothioate.

In some embodiments, the oligomers of the invention have internucleotide linkages described in FIG. 2A to 2NNNN, 16D to 16K, or 20B to 20C. As used herein, e.g., FIGS. 2A to 2NNNN, 16D to 16K, or 20B to 20C, phosphorothioate linkages are indicated as "s", and phosphorodiester linkages are indicated by the absence of "s."

In some embodiments, the internucleotide linkages are combinations of phosphorothioate linkages and phosphodiester linkages. Non-limiting examples of combination linkages are shown in ASO-002623, ASO-002667, ASO-002674, ASO-002631, ASO-002639, and ASO-002624.

III. Conjugates

In the context the term "conjugate" is intended to indicate a heterogeneous molecule formed by the covalent or non-covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins can be antibodies for a target protein. In some embodiments, typical polymers are polyethylene glycol.

Therefore, in various embodiments, the oligomer of the invention comprises both a polynucleotide region which typically consists of a contiguous sequence of nucleotides, and a further non-nucleotide region. When referring to the oligomer of the invention comprising a contiguous nucleotide sequence, the compound can comprise non-nucleotide components, such as a conjugate component.

The invention also provides for a conjugate comprising the oligomer according to the invention as herein described, and at least one non-nucleotide or non-polynucleotide moiety covalently attached to the oligomer. Therefore, in various embodiments where the oligomer of the invention comprises a specified nucleic acid or nucleotide sequence, as herein disclosed, the compound can also comprise at least one non-nucleotide or non-polynucleotide moiety (e.g., not comprising one or more nucleotides or nucleotide analogs) covalently attached to the oligomer.

Conjugation (to a conjugate moiety) can enhance the activity, cellular distribution or cellular uptake of the oligomer of the invention. Such moieties include, but are not limited to, antibodies, polypeptides, lipid moieties such as a cholesterol moiety, cholic acid, a thioether.

The oligomers of the invention can also be conjugated to active drug substances, for example, aspirin, ibuprofen, a sulfa drug, an antidiabetic, an antibacterial or an antibiotic.

In certain embodiments the conjugated moiety is a sterol, such as cholesterol.

III.A. Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that can be hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999).

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

IV. Pharmaceutical Compositions and Administration Routes

The oligomer of the invention can be used in pharmaceutical formulations and compositions. Suitably, such compositions comprise a pharmaceutically acceptable diluent, carrier, salt or adjuvant.

The oligomer of the invention can be included in a unit formulation such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The formulated drug may comprise pharmaceutically acceptable binding agents and adjuvants. Capsules, tablets, or pills can contain for example the following compounds: microcrystalline cellulose, gum or gelatin as binders; starch or lactose as excipients; stearates as lubricants; various sweetening or flavoring agents. For capsules the dosage unit may contain a liquid carrier like fatty oils. Likewise coatings of sugar or enteric agents may be part of the dosage unit. The oligonucleotide formulations can also be emulsions of the active pharmaceutical ingredients and a lipid forming a micellular emulsion.

The pharmaceutical compositions of the present invention can be administered in a number of ways depending upon whether local or systemic treatment is desired and upon the area to be treated. Administration can be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal, intra-cerebroventricular, or intraventricular, administration. In one embodiment the oligomer is administered IV, IP, orally, topically or as a bolus injection or administered directly in to the target organ. In another embodiment, the oligomer is administered intrathecal or intra-cerebroventricular as a bolus injection.

Pharmaceutical compositions and formulations for topical administration can include transdermal patches, ointments, lotions, creams, gels, drops, sprays, suppositories, liquids and powders. Conventional pharmaceutical carriers, aqueous, powder or oily bases, thickeners and the like may be necessary or desirable. Examples of topical formulations include those in which the oligomer of the invention are in admixture with a topical delivery agent such as lipids, liposomes, fatty acids, fatty acid esters, steroids, chelating agents and surfactants. Compositions and formulations for oral administration include but are not limited to powders or granules, microparticulates, nanoparticulates, suspensions or solutions in water or non-aqueous media, capsules, gel capsules, sachets, tablets or minitablets. Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to the target tissue can be enhanced by carrier-mediated delivery including, but not limited to, cationic liposomes, cyclodextrins, porphyrin derivatives, branched chain dendrimers, polyethylenimine polymers, nanoparticles and microspheres (Dass C R. *J Pharm Pharmacol* 2002; 54(1):3-27).

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

For parenteral, subcutaneous, intradermal or topical administration the formulation can include a sterile diluent, buffers, regulators of tonicity and antibacterials. The active oligomers can be prepared with carriers that protect against degradation or immediate elimination from the body, including implants or microcapsules with controlled release properties. For intravenous administration the carriers can be physiological saline or phosphate buffered saline. International Publication No. WO2007/031091 (A2), published Mar. 22, 2007, further provides suitable pharmaceutically acceptable diluent, carrier and adjuvants—which are hereby incorporated by reference.

V. Diagnostics

This disclosure further provides a diagnostic method useful during diagnosis of Tau related diseases, e.g., a tauopathy. Non-limiting examples of tauopathy include, but are not limited to, Alzheimer's disease, progressive supranuclear palsy, dementia pugilistica (chronic traumatic encephalopathy), frontal temporal dementia, parkinsonism linked to chromosome 17, Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, or frontotemporal lobar degeneration.

The oligomers of the invention can be used to measure expression of Tau transcript in a tissue or body fluid from an individual and comparing the measured expression level with a standard Tau transcript expression level in normal tissue or body fluid, whereby an increase in the expression level compared to the standard is indicative of a disorder treatable by an oligomer of the invention.

The oligomer of the invention can be used to assay Tau transcript levels in a biological sample using any methods known to those of skill in the art. (Touboul et. al., Anticancer Res. (2002) 22 (6A): 3349-56; Verjout et. al., Mutat. Res. (2000) 640: 127-38); Stowe et. al., J. Virol. Methods (1998) 75 (1): 93-91).

By "biological sample" is intended any biological sample obtained from an individual, cell line, tissue culture, or other source of cells potentially expressing Tau transcript. Methods for obtaining tissue biopsies and body fluids from mammals are well known in the art.

VI. Kits Comprising Oligomers

This disclosure further provides kits that comprise an oligomer of the invention described herein and that can be used to perform the methods described herein. In certain embodiments, a kit comprises at least one oligomer in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed oligomer can be readily incorporated into one of the established kit formats which are well known in the art.

VII. Methods of Using

The oligomers of the invention can be utilized as research reagents for, for example, diagnostics, therapeutics and prophylaxis.

In research, such oligomers can be used to specifically inhibit the synthesis of Tau protein (typically by degrading or inhibiting the mRNA and thereby prevent protein formation) in cells and experimental animals thereby facilitating functional analysis of the target or an appraisal of its usefulness as a target for therapeutic intervention. Further provided are methods of down-regulating the expression of MAPT mRNA and/or Tau protein in cells or tissues comprising contacting the cells or tissues, in vitro or in vivo, with an effective amount of one or more of the oligomers, conjugates or compositions of the invention.

In diagnostics the oligomers can be used to detect and quantitate MAPT transcript expression in cell and tissues by northern blotting, in-situ hybridization or similar techniques.

For therapeutics, an animal or a human, suspected of having a disease or disorder, which can be treated by modulating the expression of MAPT transcript and/or Tau protein is treated by administering oligomeric compounds in accordance with this invention. Further provided are methods of treating a mammal, such as treating a human, suspected of having or being prone to a disease or condition, associated with expression of MAPT transcript and/or Tau protein by administering a therapeutically or prophylactically effective amount of one or more of the oligomers or compositions of the invention. The oligomer, a conjugate or a pharmaceutical composition according to the invention is typically administered in an effective amount. In some embodiments, the oligomer or conjugate of the invention is used in therapy.

The invention further provides for an oligomer according to the invention, for use for the treatment of one or more of the diseases referred to herein, such as a disease selected from Alzheimer's disease, progressive supranuclear palsy, Down syndrome, dementia pugilistica (chronic traumatic encephalopathy and other traumatic brain injury), frontal temportal dementia, frontal temporal dementia with parkinsonism linked to chromosome 17 (FTDP-17), Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, Hemimegalencephaly, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration (reviewed in Frost et. al., *Trends Cell Biol* (2015) 25: 216-53; Dyment et. al., *Neurobiol. Aging* (2014) September 6: S0197-4580; Moussaud et. al., *Mol. Neurodeg* (2014) 29:43 Ross et. al., *South Med. J.* (2014) 107: 715-21). In addition, the invention provides for oligomer use for the treatment diseases of brain network dysfunction including all forms of epilepsy and depression (Inoue et. al., *Epilepsy* (2012) 102: 8-12; Xi et. al., *Med Hypotheses* (2011) 76: 897-900; Hou et. al., *Can. J. Psychiatry* (2004) 3: 164-71). The invention further provides for a method for treating tauopathies, the method comprising administering an effective amount of one or more oligomers, conjugates, or pharmaceutical compositions thereof to an animal in need thereof (such as a patient in need thereof).

In certain embodiments, the disease, disorder, or condition is associated with overexpression of MAPT gene transcript and/or Tau protein.

The invention also provides for methods of inhibiting (e.g., by reducing) the expression of MAPT gene transcript and/or Tau protein in a cell or a tissue, the method comprising contacting the cell or tissue, in vitro or in vivo, with an effective amount of one or more oligomers, conjugates, or pharmaceutical compositions thereof, of the invention to affect degradation of expression of MAPT gene transcript thereby reducing Tau protein.

The invention also provides for the use of the oligomer or conjugate of the invention as described for the manufacture of a medicament for the treatment of a disorder as referred to herein, or for a method of the treatment of as a disorder as referred to herein.

The invention further provides for a method for inhibiting Tau protein in a cell which is expressing Tau comprising administering an oligomer or a conjugate according to the invention to the cell so as to affect the inhibition of Tau protein in the cell.

The invention includes a method of reducing, ameliorating, preventing, or treating neuronal hyperexcitability in a subject in need thereof comprising administering an oligomer or a conjugate according to the invention.

The invention also provides for a method for treating a disorder as referred to herein the method comprising administering an oligomer or a conjugate according to the invention as herein described and/or a pharmaceutical composition according to the invention to a patient in need thereof.

The oligomers and other compositions according to the invention can be used for the treatment of conditions associated with over expression or expression of mutated version of Tau protein.

The invention provides for the oligomer or the conjugate according to invention, for use as a medicament, such as for the treatment of tauopathies. In some embodiments the tauopathy is a disease selected from Alzheimer's disease, progressive supranuclear palsy, dementia pugilistica (chronic traumatic encephalopathy), frontal temporal dementia, frontal temporal dementia with parkinsonism linked to chromosome 17, Lytico-Bodig disease (Parkinson-dementia complex of Guam), Down syndrome, Hemimegalencephaly, Tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration (reviewed in Frost et al, *Trends Cell Biol* (2015) 25: 216-53; Thom et al., *Brain* (2011) 134:2969-81; Zheng et al., *Mol. Neurobiol.* (2014) 49: 1532-9).

The invention provides for the oligomer or the conjugate according to invention, for use as a medicament, such as for the treatment of seizure disorders (Dyment et. al., *Neurobiol. Aging* (2014) September 6 S0197-4580; Inoue et. al., *Epilepsy* (2012) 102:8-12; Gheyera et. al., *Ann Neurol* (2014-76: 443-56). In some embodiments, the seizure disorder is selected from epilepsy, juvenile myoclonic epilepsy, reflex epilepsy, benign focal epilepsy of childhood (BFEC), generalized epilepsy with febrile seizures plus (GEFS+), migrating partial seizures in infancy (MPSI), Mendelian epilepsy syndromes, infantile convulsions, infantile spasms, severe myoclonic epilepsy of infancy (SMEI or Dravet syndrome), Juvenile myoclonic epilepsy (JME or Janz syndrome), Angelman syndrome, Rett syndrome, epilepsy in fragile X syndrome, choreoathetosis (ICCA) syndrome, injury-associated seizures, brain injury, brain strokes, meningitis, and febrile seizures. In certain embodiments, the epilepsy is benign familial infantile epilepsy (BFIE).

In other embodiments, the seizure disorder is selected from idiopathic generalized epilepsy, idiopathic partial epilepsy, symptomatic generalized epilepsy, or symptomatic partial epilepsy. In some embodiments, the seizure disorder is idiopathic epilepsy selected from childhood absence epilepsy, juvenile myoclonic epilepsy, epilepsy with grand mal seizures on awakening others, benign focal epilepsy of childhood. In certain embodiments, the seizure disorder is symptomatic epilepsy selected from West syndrome, Lennox-Gastaut syndrome, temporal lobe epilepsy, or frontal lobe epilepsy. In other embodiments, the seizure disorder is idiopathic generalized epilepsy selected from myoclonic seizures (sudden and very short duration jerking of the extremities), absence seizures (staring spells), or generalized tonic-clonic seizures (grand mal seizures). In still other embodiments, the seizure disorder is idiopathic partial epilepsy including benign focal epilepsy of childhood (BFEC).

The invention also provides for the oligomer or the conjugate according to the invention, for use as a medicament, such as for the treatment of movement disorders. In some embodiments, the movement disorder is selected from Akathisia (inability to sit still), Akinesia (lack of movement), Associated Movements (Mirror Movements or Homolateral Synkinesis), Athetosis (contorted torsion or twisting), Ataxia (gross lack of coordination of muscle movements), Ballismus (violent involuntary rapid and irregular movements), Hemiballismus (affecting only one side of the body), Bradykinesia (slow movement), Cerebral palsy, Chorea (rapid, involuntary movement), Sydenham's chorea, Rheumatic chorea, Huntington's disease, Dyskinesia (abnormal, involuntary movement), Tardive dyskinesia, Dystonia (sustained torsion), Dystonia muscularum, Blepharospasm, Writer's cramp, Spasmodic torticollis (twisting of head and neck), Dopamine-responsive dystonia (hereditary progressive dystonia with diurnal fluctuation or Segawa's disease), Essential tremor, Geniospasm (episodic involuntary up and down movements of the chin and lower lip), Myoclonus (brief, involuntary twitching of a muscle or a group of muscles), Metabolic General Unwellness Movement Syndrome (MGUMS), Mirror movement disorder (involuntary movements on one side of the body mirroring voluntary movements of the other side), Parkinson's disease, Paroxysmal kinesigenic dyskinesia, Restless Legs Syndrome RLS (WittMaack-Ekboms disease), Spasms (contractions), Stereotypic movement disorder, Stereotypy (repetition), Tic disorders (involuntary, compulsive, repetitive, stereotyped), Tourette's syndrome, Tremor (oscillations), Rest tremor (4-8 Hz), Postural tremor, Kinetic tremor, Essential tremor (6-8 Hz variable amplitude), Cerebellar tremor (6-8 Hz variable amplitude), Parkinsonian tremors (4-8 Hz variable amplitude), Physiological tremor (10-12 Hz low amplitude), Wilson's disease, and tics.

The invention further provides use of an oligomer of the invention in the manufacture of a medicament for the treatment of a disease, disorder or condition as referred to herein. In some embodiments, the oligomer or conjugate of the invention is used for the manufacture of a medicament for the treatment of a tauopathy, a seizure disorder, or a combination thereof.

Generally stated, one aspect of the invention is directed to a method of treating a mammal suffering from or susceptible to conditions associated with abnormal levels of Tau i.e., a tauopathy), comprising administering to the mammal and therapeutically effective amount of an oligomer targeted to MAPT transcript that comprises one or more LNA units. The oligomer, a conjugate or a pharmaceutical composition according to the invention is typically administered in an effective amount.

The disease or disorder, as referred to herein, can, in some embodiments be associated with a mutation in the MAPT gene or a gene whose protein product is associated with or interacts with Tau protein. Therefore, in some embodiments, the target mRNA is a mutated form of the MAPT sequence.

An interesting aspect of the invention is directed to the use of an oligomer (compound) as defined herein or a conjugate as defined herein for the preparation of a medicament for the treatment of a disease, disorder or condition as referred to herein.

The methods of the invention can be employed for treatment or prophylaxis against diseases caused by abnormal levels of Tau protein. In some embodiments, diseases caused by abnormal levels of Tau protein are tauopathies. In certain embodiments, tauopathies include Alzheimer's disease, progressive supranuclear palsy, dementia pugilistica (chronic traumatic encephalopathy), frontal temporal dementia, parkinsonism linked to chromosome 17, Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, down syndrome, and frontotemporal lobar degeneration.

In certain embodiments, the disease or condition for treatment or prophylaxis is a neurological disorder. In other embodiments, the neurological disorder is selected from progressive supranuclear palsy, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Parkinson's disease, Huntington's disease, Hemimegalencephaly, Tuberous sclerosis complex, Focal cortical dysplasia type 2b, or Ganglion cell tumors. In certain embodiments, the disease or condition is an epileptic disorder without tauopathy, e.g., Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, Landau Kleffner syndrome, focal seizures, simple focal seizures (no loss of consciousness), focal dyscognitive seizures (impairment of consciousness), focal seizure evolving to generalized tonic-clonic (GTC) convulsions, generalized seizures (convulsive or non-convulsive with bilateral discharges involving subcortical structures), absence seizures, myoclonic seizures, clonic seizures, tonic seizures, tonic-clonic seizures, atonic seizures, an autistic disorder, an autism spectrum disorder (e.g., as defined in the Diagnostic and Statistical Manual of Mental Disorders V (DSM-V)), an Asperger's disorder, a pervasive developmental disorder, or any combination thereof.

In certain embodiments, the neurological disorder is a neurodegenerative disorder, an epileptic disorder, an idiopathic adult epileptic disorder, or any combination thereof. In other embodiments, the disease or condition is a neurodegenerative disorder with tauopathy (i.e., a neurodegenerative disease which involves accumulation of tau protein in the brain), an epileptic disorder with tauopathy (an epileptic disorder which involves accumulation of tau protein in the brain), an epileptic disorder without tauopathy (an epileptic disorder which does not involve accumulation of tau protein in the brain), an idiopathic adult epileptic disorder without tauopathy (an idiopathic adult epileptic disorder which does not involve accumulation of tau protein in the brain), or any combination thereof. In certain other embodiments, the disease or condition for treatment or prophylaxis is a neurodegenerative disease with tauopathy, e.g., progressive supranuclear palsy, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Parkinson's disease or Huntington's disease. In certain embodiments, the disease or condition for treatment or prophylaxis is an epileptic disorder with tauopathy, e.g., Hemimegalencephaly, Tuberous sclerosis complex, Focal cortical dysplasia type 2b, or Ganglion cell tumors. In certain embodiments, the disease or condition is an epileptic disorder without tauopathy, e.g., Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, or Landau Kleffner syndrome. In certain embodiments, the disease or condition for treatment or prophylaxis is an idiopathic adult epileptic disorder without tauopathy, e.g., focal seizures, simple focal seizures (no loss of consciousness), focal dyscognitive seizures (impairment of consciousness), focal seizure evolving to generalized tonic-clonic (GTC) convulsions, generalized seizures (convulsive or non-convulsive with bilateral discharges involving subcortical structures), absence seizures, myoclonic seizures, clonic seizures, tonic seizures, tonic-clonic seizures or atonic seizures. In certain embodiments, the neurological disorder for treatment or prophylaxis is an autistic disorder, an autism spectrum disorder (e.g., as defined in the Diagnostic and Statistical Manual of Mental Disorders V (DSM-V)), an Asperger's disorder or a pervasive developmental disorder.

Alternatively stated, in some embodiments, the invention is furthermore directed to a method for treating abnormal levels of Tau protein, the method comprising administering a oligomer of the invention, or a conjugate of the invention or a pharmaceutical composition of the invention to a patient in need thereof.

The invention also relates to an oligomer, a composition or a conjugate as defined herein for use as a medicament.

The invention further relates to use of a compound, composition, or a conjugate as defined herein for the manufacture of a medicament for the treatment of abnormal levels of Tau protein or expression of mutant forms of Tau protein (such as allelic variants, such as those associated with one of the diseases referred to herein).

A patient who is in need of treatment is a patient suffering from or likely to suffer from the disease or disorder.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1

Construction of Oligomers

A number of oligomers were designed to target the 3' UTR of MAPT pre-mRNA. See FIG. 1A to 1TT for genomic MAPT sequence. For example, the oligomers were constructed to target nucleotides 134,821-138,940 of SEQ ID NO: 1. The exemplary sequences of the oligomers are described in FIGS. 2A to 2NNNN, 3A to 3Z, 6A to 6GG, and 7A to 7E. In some embodiments, the oligomers were designed to be gapmers or mixmers. FIG. 2A to 2NNNN shows non-limiting examples of the oligomer design for selected sequences. The same methods can be applied to any other sequences disclosed herein. The gapmers were constructed to contain locked nucleic acids—LNAs (upper case letters). For example, a gapmer can have Beta-deoxy LNA at the 5' end and the 3' end and have a phosphorothioate backbone. But the LNAs can also be substituted with any other nucleotide analog and the backbone can be other type of backbone (e.g., a phosphodiester linkage, a phosphotriester linkage, a methylphosphonate linkage, a phosphoramidate linkage, or combinations thereof).

The oligomers were synthesized using methods well known in the art. Exemplary methods of preparing such oligomers are described in Barciszewski et al., Chapter 10—"Locked Nucleic Acid Aptamers" in *Nucleic Acid and Peptide Aptamers: Methods and Protocols*, vol. 535, Gunter Mayer (ed.) (2009), the entire contents of which is hereby expressly incorporated by reference herein.

In FIG. 2A to 2NNNN, in the Sequence designation, upper case designates a modified nucleotide such as an LNA nucleotide (either Beta-D-Oxy, Alpha-L-Oxy, Beta-D-Amino or Beta-D-Thio LNA or other modified nucleotide such as cEt, cMOE, UNA or ENA) and lower case designates a DNA nucleotide. Thus a sequence represented by TAGccctaaagtcCCA (SEQ ID NO: 53, i.e., ASO-000389) represents a 3-10-3 16mer modified nucleotide-DNA-modified nucleotide gapmer with a 5'-T and 3'-A, such as a 3-10-3 LNA-DNA-LNA gapmer. Some oligomers can be an alternating flank gapmer as described elsewhere herein. In some embodiments, selected examples of alternating flank gapmers having a 7 nucleotide gap are ASO-002399, ASO-002482, ASO-002437, and ASO-002425. Any one of the oligomer sequences disclosed herein can have the alternating flank gapmer design shown in the figures. In addition, any one of the oligomer sequences disclosed herein can have the chemical structure shown in FIGS. 2A to 2NNNN, 16D to 16K, and 20B to 20C.

In FIG. 2A to 2NNNN, the following designate the components of the oligonucleotides of the present invention, with oligonucleotides always depicted in the 5' to 3' direction. Therefore, the 5' end of an oligomer hybridizes to the pre-mRNA end number in the table and the 3' end of the oligomer hybridizes to the pre-mRNA start number in the figure. A reference to a SEQ ID number includes a particular sequence, but does not include an oligomer design or its chemical structure.

Beta-D-oxy LNA nucleotides are designated by OxyB where B designates a nucleotide base such as thymine (T), uridine (U), cytosine (C), methylcytosine (MC), adenine (A) or guanine (G), and thus include OxyA, OxyT, OxyMC, OxyC and OxyG.

Alpha-L-oxy LNA nucleotides are designated by AlfaOxyB where B designates a nucleotide base such as thymine (T), uridine (U), cytosine (C), methylcytosine (MC), adenine (A) or guanine (G), and thus include AlfaOxyA, AlfaOxyT, AlfaOxyMC, AlfaOxyC and AlfaOxyG. The letter M or m before C or c indicates 5-methylcytosine.

Beta-D-Amino LNA nucleotides are designated by AminoB where B designates a nucleotide base such as thymine (T), uridine (U), cytosine (C), methylcytosine (MC), adenine (A) or guanine (G), and thus include AminoA, AminoT, AminoMC, AminoC and AminoG. The letter M or m before C or c indicates 5-methylcytosine. Some examples of the oligomers including 5 methylcytosine include ASO-002672, ASO-002658, ASO-002622, ASO-002629, ASO-002621, ASO-002665, and ASO-002630. See FIG. 2A to 2NNNN.

Beta-D-Thio-LNA nucleotides are designated by ThioB where B designates a nucleotide base such as thymine (T), uridine (U), cytosine (C), methylcytosine (MC), adenine (A) or guanine (G), and thus include ThioA, ThioT, ThioMC, ThioC and ThioG. The letter M or m before C or c indicates 5-methylcytosine.

DNA nucleotides are designated by DNAb, where the lower case b designates a nucleotide base such as thymine (T), uridine (U), cytosine (C), 5-methylcytosine (MC), adenine (A) or guanine (G), and thus include DNAa, DNAt, DNAc, DNAmc and DNAg. The letter M or m before C or c indicates 5-methylcytosine.

The letter "s" after the nucleotide designation indicates phosphorothioate linkage whereas absence of "s" indicates phosphodiester linkage.

Thus a 3-10-3 beta-D-oxy LNA-DNA-beta-D-oxy LNA gapmer with sequence ATTtccaaattcaCTT, with full phosphorothioate internucleotide linkages would be designated OxyAs OxyTs OxyTs DNAts DNAcs DNAcs DNAas DNAas DNAas DNAts DNAts DNAcs DNAas OxyMCs OxyTs OxyT. In some embodiments, the oligomers have a mix of phosphorothioate and phosphodiester internucleotide linkages. Examples of the oligomers having a mix of phosphorothioate and phosphodiester internucleotide linkages include, but are not limited to, ASO-002625, ASO-002675, ASO-002633, ASO-002640, ASO-002632, ASO-002647, ASO-002655, ASO-002641, ASO-002648, ASO-002666, ASO-002659, ASO-002652, ASO-002645, ASO-002638, ASO-003270, ASO-003269, ASO-003268, ASO-002673, ASO-002661, ASO-002654, ASO-002668, ASO-002676, AS-002669 and ASO-002662. See FIG. 2A to 2NNNN.

Preparation of Oligos with Mismatches

Oligos having mismatched bases at different locations were also prepared using standard methods well known in the art. Examples of oligomers with mismatched bases are provided in FIG. 2A to 2NNNN or 3A to 3Z as "mm." The specific mismatched basepair are bolded, underlined, italicized, and highlighted.

Example 2

In Vitro Reduction in Tau Protein

Each of the oligomers targeting the 3' UTR of an MAPT transcript was tested for its ability to decrease Tau protein in mouse primary neurons expressing the entire human MAPT gene as a bacmid containing transgene (C57-b16 BAC-Tg hTau; Polydoro et. al., *J. Neurosci.* (2009) 29 (34): 10747-9). Primary hTau mouse embryonic forebrain neuronal cultures do not express endogenous mouse tau as mouse tau was knocked out. Primary neurons were generated by papain digestion according to manufacturer's protocol (Worthington Biochemical Corporation, LK0031050). Briefly, forebrains were dissected from hTau mouse E18 BAC-Tg embryos expressing the entire human microtubule-associated protein Tau (MAPT) gene on a murine MAPT-null background and were incubated at 37° C. for 30-45 minutes in papain/DNase/Earle's balanced salt solution (EBSS) solution. After trituration and centrifugation of cell pellet, the reaction was stopped by incubation with EBSS containing protease inhibitors, bovine serum albumin (BSA) and DNase. The cells were triturated and washed with Neurobasal (NB, Invitrogen) supplemented with 2% B-27, 100 m/ml penicillin, 85 μg/ml streptomycin, and 0.5 mM glutamine. The cells were plated in supplemented NB media onto poly-D-lysine-coated 96-well optical imaging plates (BD Biosciences) at 15,000 cells/well.

After obtaining the primary hTau mouse embryonic forebrain neuronal cultures expressing a human MAPT gene, the cultures were treated with oligomers to inhibit the Tau mRNA and protein expression. The cultures were then subject to immunocytochemistry and imaging to measure the inhibition. One day post plating (DIV 1), half of the supplemented neurobasal (NB) media on the primary hTau mouse embryonic forebrain neuronal cultures was removed and replaced with supplemented NB media containing various concentrations of LNA oligomers. Primary hTau neuronal cultures were cultured with LNA oligomers until 13 days post plating (DIV 13). On DIV 13, the cultures were rinsed with Dulbecco's phosphate-buffered saline lacking calcium and magnesium (DPBS, Invitrogen) and fixed in 4% paraformaldehyde/4% sucrose/DPBS for 15 min. Cultures were rinsed and then blocked and permeabilized in DPBS plus 0.1% Triton X-100 (TX-100) and 3% BSA for one hour at room temperature. Cultures were rinsed and then incubated for two hours at room temperature with primary antibody 1:500, Tau5 antibody to measure Tau protein, Invitrogen AHB0042; and 1:500, β-III tubulin (TuJ-1) antibody to measure neurite area, Abcam ab41489) in DPBS plus 3% BSA and 0.1% TX-100. Cultures were rinsed and incubated with Hoeschst 33342 nuclear dye (1:800, Invitrogen) and AlexaFluor fluorescence-conjugated secondary antibodies (Invitrogen, 1:500) in DPBS plus 3% BSA and 0.1% TX-100 for one hour at room temperature. Cultures were rinsed abundantly and stored in DPBS until imaging. Imaging was conducted using the Cellomics VTi automated immunofluorescence imaging system. In brief, using untreated wells, saturation levels for each fluorophore channel were set to 70%. Then 12 sequential images were acquired from each well, and total fluorescence intensity and total fluorescence area were calculated for both Tau and TuJ-1 proteins using the Cellomics VTi SpotDetector (version 4) image analysis software. To evaluate Tau protein reduction resulting from oligomer treatment, a Tau5 total fluorescence intensity-to-Tuj-1 total fluorescence area ratio (Tau/TuJ-1) was created for each well and then all data were normalized to the average Tau/Tuj-1 ratio of the untreated wells. TuJ-1 intensity acts as an internal standard for each sample. To evaluate neurite/neuronal toxicity from oligomer treatment, the Tuj-1 total fluorescence area from each well was normalized to the average Tuj-1 total fluorescence area of the untreated wells. Nuclei counts from each well were also acquired as an alternative measure of toxicity associated with LNA oligomer treatment. Data are expressed as mean±S.D. For immunocytochemistry, data points represent the mean±S.D. from wells treated in triplicate. Potency values were generated using wells treated with a broad concentration range of LNA oligomer, from which the resulting normalized Tau/Tuj-1 and Tuj-1 values were analyzed compared to normalized values from saline control samples. Analysis was done using non-linear regression with top and bottom values set at fixed values of 100% and 0%, respectively, where 100% inhibition represents a complete reduction of signal compared to the control sample (FIG. 3A to 3Z). For qPCR, data were analyzed using a one-way ANOVA with a Dunnett's multiple comparison test to compare saline- and LNA oligomer-treated groups. Statistical significance was set at a value of $p<0.05$.

The reduction of Tau protein by each oligomer was compared with saline. The results of the Tau protein reduction compared to Saline are shown in FIG. 3A to 3Z. If the Tau protein level in antisense oligonucleotide treated neurons was equal to or higher than in control cells, percent inhibition is expressed as zero inhibition. The target regions to which antisense oligomers are inhibitory are considered 'hot-spots' on the Tau transcript.

Oligomers were diluted in water and added to cells at 1 day post plating (DIV01) to a final concentration of 5 μM. For $IC_{50}$ determinations, neurons were treated with a top concentration of 5 μM and a concentration response dilution of 1:3 was used to define the $IC_{50}$ value. The calculated $IC_{50}$ value for certain oligomers is shown in FIG. 6A to 6GG.

Example 3

Spontaneous Calcium Oscillation Measurement

The present application shows that a reduction of oscillations in intracellular free calcium concentration (calcium oscillation) corresponds to increased neurotoxicity of an oligomer to a cell. The amount of reduction and how it corresponds to an increase in neurotoxicity can be determined as described herein. To measure primary cortical neuron spontaneous calcium oscillation, rat primary cortical neurons were prepared from Sprague-Dawley rat embryos (E19). Cells were plated 25,000 cells/well onto 384 well poly-D-lysine coated fluorescent imaging plate reader (FLIPR plates) (Greiner Bio-One) in 25 Neurobasal media containing B27 supplement and 2 mM glutamine. Cells were grown for 11 days at 37° C. in 5% $CO_2$ and fed with 25 μl of additional media on DIV04 and DIV08 for use on DIV11. On the day of the experiment, media was removed from the plate and the cells were washed once with 50 of 37° C. assay buffer (Hank's Balanced Salt Solution with 2 mM $CaCl_2$ and 10 mM Hopes pH 7.4). Oscillations were tested in the presence and absence of 1 mM $MgCl_2$ (FIG. 4). Cells were loaded with a cell permanent fluorescent calcium dye, fluo-4 AM (Life Technologies). Fluo-4 AM was prepared at 2.5 mm in DMSO containing 20% plutonic F-127 then diluted 1:1000 in assay buffer. Cells were incubated 1 hr with 20 μl of 2.5 μM fluo-4 AM at 37° C. in 5% $CO_2$. After 1 hr 20 μl of room temperature assay buffer was added and the cells were allowed to equilibrate to room temperature for 10 additional minutes and placed in the FLIPR. Baseline signal (measurement of intracellular calcium) was read for 100 seconds (1 reading/second) before the addition of anti-sense oligomers. Oligomers were added with a 384 well head in the FLIPR in 20 μl of assay buffer at 75 μM for a final concentration of 25 μM. FLIPR signal was read for an additional 200 seconds (1 reading/second) after the addition of oligomer. A second 5 minute post addition plate read (300 one second points) on the FLIPR was conducted to allow for additional data capture. Raw data from the 5 minute read was exported and, using Excel, spike amplitude and frequency was calculated. Calculations were performed by measuring the average FLIPR signal over the 300 second read for control (non-treated) wells. For treated wells, a scoring system was developed where a score of 1 was given for each 1 second read where signal increase greater than 50% of the average control value (calculated above). A score of 0 was given for each 1 second read that increased less than 50% of average control value. For each treatment a total score was calculated and converted to percent control for graphical purposes. If the antisense oligomer produced a calcium oscillation response greater than that of AMPA alone, percent of control is expressed as greater than 100% (FIG. 6A to 6GG).

Effect of oligomers on primary neuronal spontaneous calcium oscillations was measured under two conditions, in the presence and absence of 1 mM $MgCl_2$ as a source of $Mg^{2+}$ ions, as described previously (Murphy et. al., *J. Neurosci.* 12, 4834-4845 (1992)). This was done to isolated N-methyl-D-aspartate (NMDA)- and α-amino-3-hydroxy-5-methyl-4-isoxazolepropionic acid (AMPA)-receptor mediated calcium oscillations. Data presented in FIG. 4 show that, addition of the AMPA receptor antagonist 6-Cyano-7-nitroquinoxaline-2,3-dione (CNQX; 3 μM) reduced calcium oscillations by 20%, representing the total AMPA response in the assay (FIG. 4 AMPA labeled bar shown). Calcium oscillations were reduced further, by about 80%, when (NMDA) receptor function was blocked by 1 mM $MgCl_2$ (FIG. 4 NMDA labeled bar shown).

Figure 5:
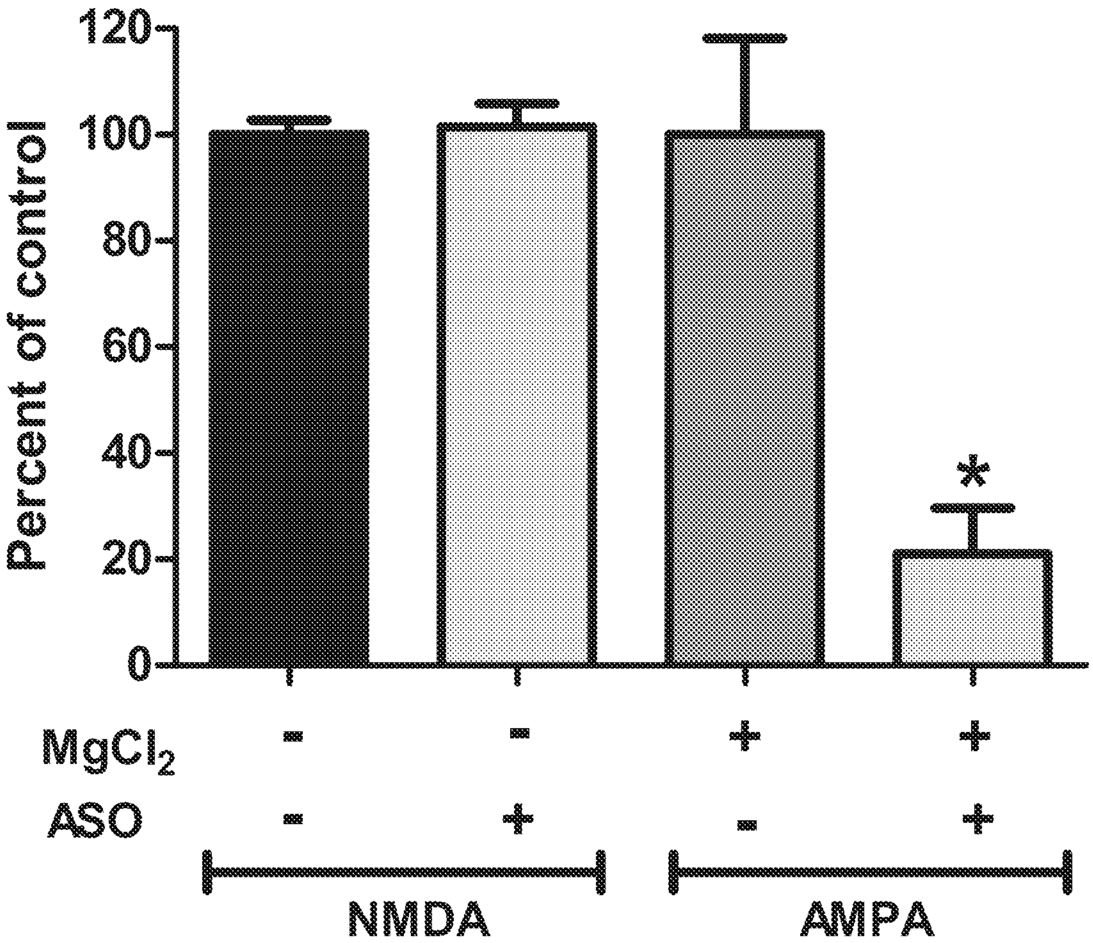
FIG. 5 is a graph showing inhibition of AMPA mediated calcium oscillations by antisense oligomers as an indication of neuronal network activity disruption. Antisense oligomer inhibition of spontaneous calcium oscillations mediated by either NMDA or AMPA was assessed in the presence or absence of 1 mM $MgCl_2$ (representing 100% control in each case). Addition of 25 μM antisense oligomers (TGTgatgcaggaGTT) (SEQ ID NO: 304) (ASO-00007) inhibited AMPA receptor but not NMDA receptor mediated oscillations. The ASO and other oligomers that behaved similarly were shown to negatively impact central nervous system (CNS) network activity in vivo and electrophysiologic spontaneous neuronal activity in vitro (data not shown).

Antisense oligomer inhibition of spontaneous calcium oscillations mediated by either NMDA or AMPA was assessed in the presence or absence of 1 mM $MgCl_2$ (representing 100% control in each case; FIG. 5). Addition of 25 μM antisense oligomers (ASO) inhibited AMPA receptor but not NMDA receptor mediated oscillations (FIG. 5). ASO, and other oligos that behaved similarly, were shown to negatively impact central nervous system (CNS) network activity in vivo and electrophysiologic spontaneous neuronal activity in vitro (data not shown). The impact of Tau antisense oligonucleotides on spontaneous calcium oscillations in primary neurons is summarized in FIG. 6A to 6GG. See Murphy et al., *J. Neurosci.* 12, 4834-4845 (1992).

Calcium oscillation reduction was measured for the oligomers of the invention and summarized in FIG. 6A to 6GG. The oligomers showing greater than 25% of control in the calcium oscillation assay were selected for further analysis.

Example 4

Sequence Score Calculation

The present application also shows that the sequence score of an oligomer, as calculated herein, corresponds to the neurotoxicity of the oligomer. In certain aspects of the invention, the higher the sequence score the less neurotoxic the oligomer. Different cut off values, over which the sequence score indicates that the oligomer has reduced neurotoxicity, can be determined as described herein.

The sequence score of each oligomer was calculated to predict the suitability and neurotoxicity of the oligomers. Sequence score is a mathematical calculation determined for all oligomers and is based on the percent of G and C nucleotides, or analogs thereof, within a given oligomer sequence. The following formula was applied to all oligomers in order to calculate sequence score:

$$\frac{\text{number of } C \text{ nucleotides} - \text{number of } G \text{ nucleotides}}{\text{nucleotide length}} \qquad \text{(I)}$$

An example calculation is given for oligomer ASO-000013 (SEQ ID NO: 686; sequence score 0.25): ATTtccaaattcaCTT: 4-0/16=sequence score of 0.25.

The sequence score of the selected oligomers were calculated for further studies. To determine the cut off value for the sequence score, an in vivo tolerability study was performed as shown in Example 5.

Example 5

In Vivo Tolerability and In Vivo Tau mRNA Reduction

The in vivo tolerability of the oligomers was tested to see how the oligomer was tolerated when injected into an animal.

Subjects

In vivo tolerability of the oligomers were tested in mice and rats. Animals for Tau qPCR and behavioral studies were adult, C57B1/6J female mice (20-30 g; Jackson Laboratories, Bar Harbor, Me.) housed 3-4 per cage. Animals were held in colony rooms maintained at constant temperature (21±2° C.) and humidity (50±10%) and illuminated for 12 hours per day (lights on at 0600 hours). In some cases, male and female transgenic mice (30-40 g) expressing a tau transgene derived from a human PAC, H1 haplotype driven by the tau promoter (Polydoro et. al., *J. Neurosci.* (2009) 29(34): 10741-9), and in which the native mouse Tau gene was deleted, were used to assess pharmacodynamic endpoints and tissue drug concentrations. For intrathecal infusion studies, female Sprague-Dawley rats (180-225 g at testing; Harlan) were singly housed in colony rooms maintained at a constant temperature (21±2° C.) and humidity (50±10%) and illuminated for 12 hours per day (lights on at 0600 h). All animals had ad libitum access to food and water throughout the studies. Behavioral studies were conducted between 0700 and 1500 hours. Animals were maintained in accordance with the guidelines of the Animal Care and Use Committee of the Bristol-Myers Squibb Company, and the "Guide for Care and Use of Laboratory Animals" published by the National Institutes of Health. Research protocols were approved by the Bristol-Myers Squibb Company Animal Care and Use Committee.

Administration Routes—Intra-Cerebroventricular or Intrathecal Injections.

The oligomers were administered to mice by either intracerebroventricular (ICV) injection or intrathecal injection. Intracerebroventricular injections were performed using a Hamilton micro syringe fitted with a 27 or 30-gauge needle, according to the method of Haley and McCormick. The needle was equipped with a polyethylene guard at 2.5 mm from the tip in order to limit its penetration into the brain.

Mice were anesthetized using isoflurane anesthetic (1.5-4%). The mouse to be injected, weighing 20-30 g, was held by the loose skin at the back of the neck with the thumb and first fingers of one hand. Applying gentle but firm pressure, the head of the animal was then immobilized by pressing against a firm flat level surface. The needle tip was then inserted through the scalp and the skull, about 1 mm lateral and 1 mm caudal to bregma. Once the needle was positioned, antisense oligonucleotide was given in a volume of 5 microliters in saline vehicle and injected into the right (or left) lateral ventricle over 20-30 seconds. The needle was left in place for 10 seconds before removal. This procedure required no surgery or incision. Animals were warmed on heating pads until they recovered from the procedure. Brain tissue (right, frontal cortical region) was collected on dry ice or RNAlater for drug concentration analysis and Tau qPCR respectively at multiple time points following dosing, e.g., 1 week through 16 weeks post-dosing.

For intrathecal (IT) injections of mice, animals were maintained under light isoflurane anesthesia (1.5-5%). The mouse was held securely in one hand by the pelvic girdle and inserting a 30 G ½ inch needle connected to a Hamilton syringe into the tissue between the dorsal aspects of L5 and L6, perpendicular to the vertebral column. When the needle enters the subarachnoid space, a sudden lateral movement of the tail was observed. This reflex was used as an indicator of successful placement of the needle for IT administration. A 5-10 μL volume of antisense oligonucleotide was injected slowly (over approximately 60 seconds) into the subarachnoid space.

For intrathecal injections in rat, intrathecal catheters were surgically implanted using methods described by Yaksh and Rudy, Physiol. Behav. (1976) 17(6): 1031-6. The rat was mounted to a stereotaxic frame with isoflurane anesthesia maintained through a nose cone. A skin incision was made beginning approximately at the line joining the ears and extending caudally about 3 cm along the midline. The muscle where it attached to the occipital crest of the skull was cut about 3 mm lateral on both sides of the muscle midline. Using retractors or forceps, the muscle was peeled caudally to expose the cisternal membrane at the base of the skull. The fascia and tissue were carefully removed from the membrane. The bent beveled end of a 16-22 gauge needle was used to make a 1-2 mm lateral incision in the cisternal membrane. A sterilized IT catheter, made of polyethylene tubing (PE10 tubing stretched to approximately 1.3 mm outer diameter), was inserted through the incision and carefully advanced caudally through the subarachnoid space while it was rotated between thumb and forefinger and while the base of the tail was gently pulled to align the spinal cord using the other hand. If any resistance was encountered, the catheter was retracted slightly, and slowly advanced again. Once the catheter had been advanced to the desired area, it was flushed with 20 μL sterile saline and the cranial end was passed through the skin using a 19 gauge needle about 1 cm from the incision. The catheter was plugged with a pin. Rats were given oral antibiotics for 5 days following the surgery. At least five days after surgery, a single antisense oligonucleotide injection was diluted in water and delivered via a programmable infusion pump (Knopf) at a rate of 10 μl/minute in a volume of 10 to 50 μl. A brief saline flush of 5 μl was given just prior to the antisense oligonucleotide delivery and a 10 μl saline flush was given just following the oligonucleotide delivery at a rate of 10 μl/minute to cover the dead volume of the catheter (6-7 μl). A saline flush of 20 μl was also given to animals 1-2×/week until used for an experiment.

Acute Tolerability Behavioral Assessments

For one hour following the single injection of antisense oligonucleotide ICV (intra-cerebroventricular) or IT (intrathecal), animals were observed for behavioral side effects and scored for the severity of side effects on a scale of zero (no side effects) to 20 (convulsions resulting in euthanasia). The tolerability scale was divided into 5 neurobehavioral categories: 1) hyperactivity 2) decreased activity and arousal 3) motor dysfunction/ataxia 4) abnormal posture and breathing and 5) tremor/convulsions. Each category was scored on a scale of 0-4, with the worst possible total score of 20. Animals were observed for changes in behavior in the home cage, and then they were removed from the home cage for more detailed observations which included measurement of grip strength and righting reflex.

Novel Object Recognition

Short term recognition memory was measured using the novel object recognition (NOR) task. NOR testing was based on the spontaneous behavior of rodents to explore a novel object more than a familiar one (Dodart et. al., *Neuroreport* (1997) 8(5): 1173-8; Ennaceur and Delacour, *Behav. Brain Res.* (1988) 31 (1):47-59). After a one hour retention interval between training (T1) and testing (T2) sessions, mice remembering the objects from the training session will show a preference for the novel object on the test session. For these experiments, animals were handled for 3 days and habituated to the chamber (48 cm×38 cm×20 cm) on the day prior to the test session. The chamber was made of polyethylene and lined with vinyl flooring. On the test day, animals were placed in the rectangular test chamber and allowed to explore two identical objects (7.6 cm high×5.1 cm wide) for a 15 minute training period. One hour later, mice were placed back into the test chamber for a 10 minute test session, this time with one object they had observed during training and one novel object. Objects were cleaned thoroughly with 25% ethanol between training and testing sessions and between subjects, and were cleaned again at the end of the day with mild detergent. Object exploration was only considered when the animal's nose was pointed at the object. Exploration was recorded using ObjectScan tracking software (Cleversys, Reston, Va.). Data are reported as percent of time spent exploring objects (i.e., novel time/novel+familiar time*100).

Morris Water Maze

Spatial learning and memory was assessed based on Morris Water Maze assay (Morris *J. Neurosci.* (1984) 11(1): 47-60). Water maze represents a pool with the diameter of 120 cm. Water was made opaque using white, non-toxic tempura paint (20° C.±1). The pool was surrounded with distinct extra-maze cues.

Prior to hidden platform training, all mice were exposed to the water maze pool by allowing them to swim down the rectangular channel during 2 pre-training trials. The escape platform was placed in the middle of the channel. If a mouse was not able to find and mount the platform during 60 sec trial, it was guided to it and allowed to sit for up to 10 sec. After pre-training, mice underwent hidden platform training, during which a 10×10 cm platform was submerged 1.5 cm below the surface. The platform location remained the same throughout training whereas the drop location varied randomly between the four daily trials as well as across the 4 days of training. Mice received 2 sessions per day for 4 consecutive days. Each session consisted of 2 trials with a 10-min inter-trial interval. The maximum time allowed per trial was 60 sec. If a mouse did not find or mount the platform, it was guided to the platform by the experimenter. All mice were allowed to sit on the platform for 10 sec after each training trial.

For probe trials, the platform was removed and each mouse was allowed to swim for 60 sec. The drop location for the probe trials was 180° from the platform location used during hidden platform training. After 60 sec, mice were guided to the platform location before retrieval from the pool. For early memory retrieval mice were probed 2 h after the last hidden platform training; long term memory recall was assessed 16 h following the last hidden platform training. 2 h following the 16 h probe trial, all mice underwent the visible platform training, where a local cue (pole built using legos) was placed above the hidden platform. Mice were given 2 training trials. All behavior was recorded with a video tracking system (Cleversys, Inc). Escape latencies, distance traveled, swim paths, swim speeds, and platform crossings were recorded automatically for subsequent analysis.

Catwalk

The Catwalk (Noldus, The Netherlands) is an automated and computerized gait-analysis technique that allows objective quantification of multiple static and dynamic gait parameters. Mice were placed on one end of the catwalk and allowed free exploration for 3 min or until they have 5 compliant trials, whichever comes first. Data were exported and classified using the Catwalk software. An average of classified trials was used for data analysis. Measures of interest include but are not limited to: print position or the distance between the position of the hind paw and previous placement of the ipsilateral front paw, initial and terminal dual stances, paw swing speed, and paw stand or the duration of paw contact with the glass plate in a step cycle.

Behavioral Statistics

Statistical analyses for all behavioral tests were conducted using GraphPad Prism (GraphPad Software, Inc., La Jolla, Calif.). For NOR, data were analyzed using either a paired t-test for within-group analyses or by an ANOVA followed by a Dunnett's post-hoc test for between group analyses. For MWM, a repeated MWM ANOVA was used to analyze the acquisition phase and a one-way ANOVA followed by Dunnett's post-hoc for probe trial analyses.

Brain Tau mRNA Analysis

Brain Homogenization

Mouse brain tissue was homogenized in a 10× volume of a high salt/sucrose buffer (10 mM Tris-HCl, pH 7.4, 800 mM NaCl, 10% sucrose (w/v), 1 mM EGTA) supplemented with phosphatase inhibitor cocktail sets 2 and 3, 1 mM PMSF (Sigma, Saint Louis, Mo.), and complete protease inhibitor cocktail EDTA-free (Roche, Indianapolis, Ind.) using a Quiagen TissueLyzer II. The homogenate was centrifuged at 20,000×g for 20 minutes at 4° C. The supernatant was centrifuged at 100,000×g for 1 hour at 4° C. and the supernatant was analyzed.

RT-PCR assays

For cDNA synthesis and subsequent PCR, 300 ng of RNA from brain tissue was added to 1 well of a 96 well plate (Axygen, PCR-96-C-S). To each well 7.5 μl of master mix (5 μL of 2.5 mM NTP mix and 2.5 μL random primers per reaction) was added and the plate was centrifuged at 1000 rpm and placed in thermocycler for 3 min at 70° C. Plates were immediately cooled on ice and 4 μl of reaction master mix was added. Prior to PCR, plates were briefly centrifuged to collect sample in bottom of well. cDNA synthesis was carried out at 42° C. for 60 min, 95° C. for 10 min followed by a hold at 4° C. cDNA Samples were diluted 1:3 with molecular biology grade water and stored at −20° C. until further use.

For PCR, each sample was run in triplicate with two probe sets (MAPT: Taqman Expression assays Hs00902193_m1; RhoA: Taqman Expression assays; GAPDH Taqman Expression assays Hs01922876_u1). To each reaction 4 μl of previously diluted cDNA and 6 μL of master mix was added and plates were centrifuged. Samples were incubated at 95° C. for 20 sec follow by 40 cycles at 95° C. for 1 sec and 60° C. for 20 sec.

Data was analyzed using the delta delta Ct method where each sample is first normalized to GAPDH and then expressed as percent of untreated control animals (see FIG. 7A to 7E).

Results

Figure 8A:
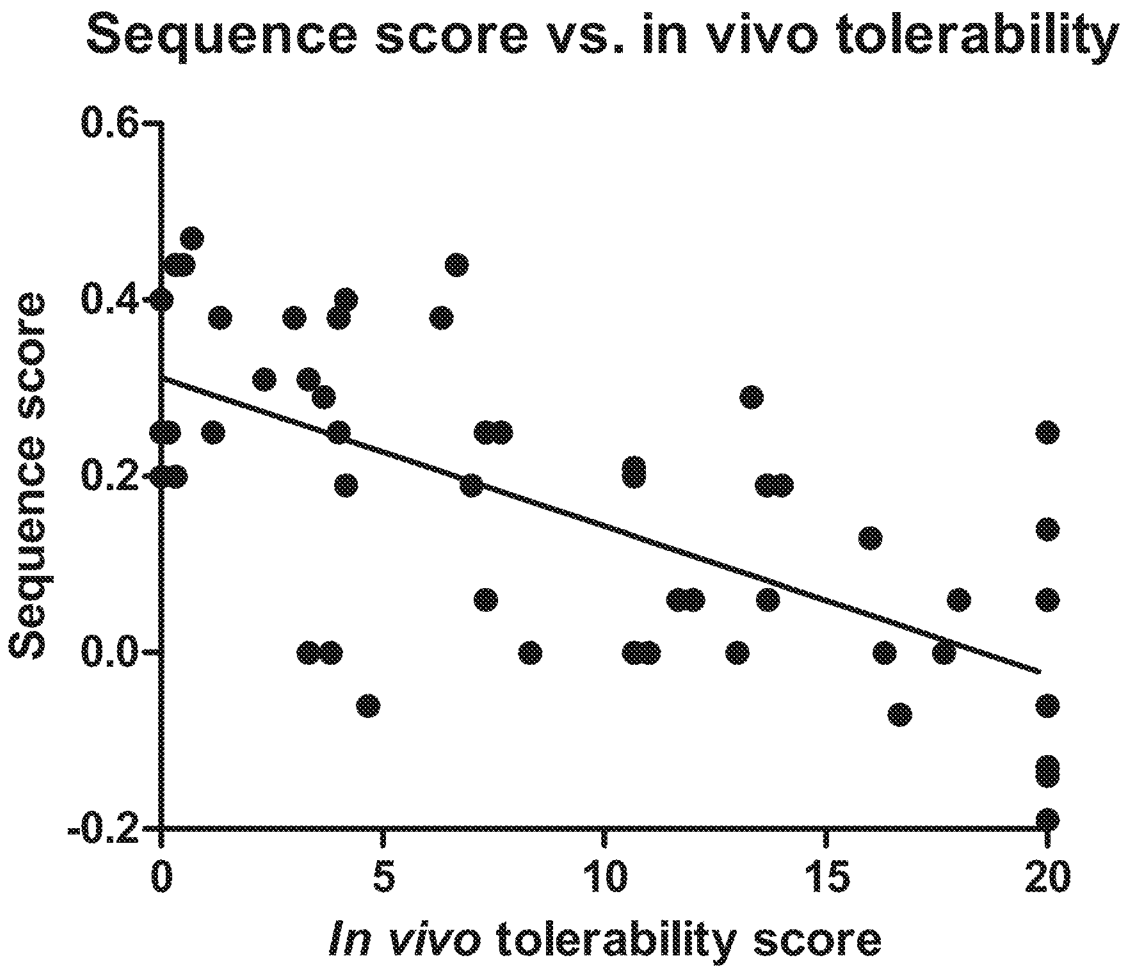
FIG. 8A shows correlation analysis of sequence score vs. in vivo tolerability score. Sequence score for each oligomer was calculated by inserting appropriate numbers in the formula: ((number of C nucleotides or its analogs −number of G nucleotides)/nucleotide length (i.e., number)). In vivo tolerability scores were calculated based upon observations following a single intra-cerebroventricular (ICV) administration of 100 μg oligomers in mice or intrathecal (i.t.) administration of 900 μg or up to 1500 μg oligomers in rats. The rodents were observed under five categories: 1) hyperactivity; 2) decreased activity and arousal; 3) motor dysfunction and/or ataxia; 4) abnormal posture and breathing; and 5) tremor and/or convulsions. The total in vivo tolerability score is the sum of five unit scores; each of the unit scores is measured on a scale of 0-4. Therefore, the total score of in vivo tolerability can range from 0 to 20. The sequence score calculated by the formula is on the X-axis, and the in vivo tolerability score is on the Y-axis.
Figure 8B:
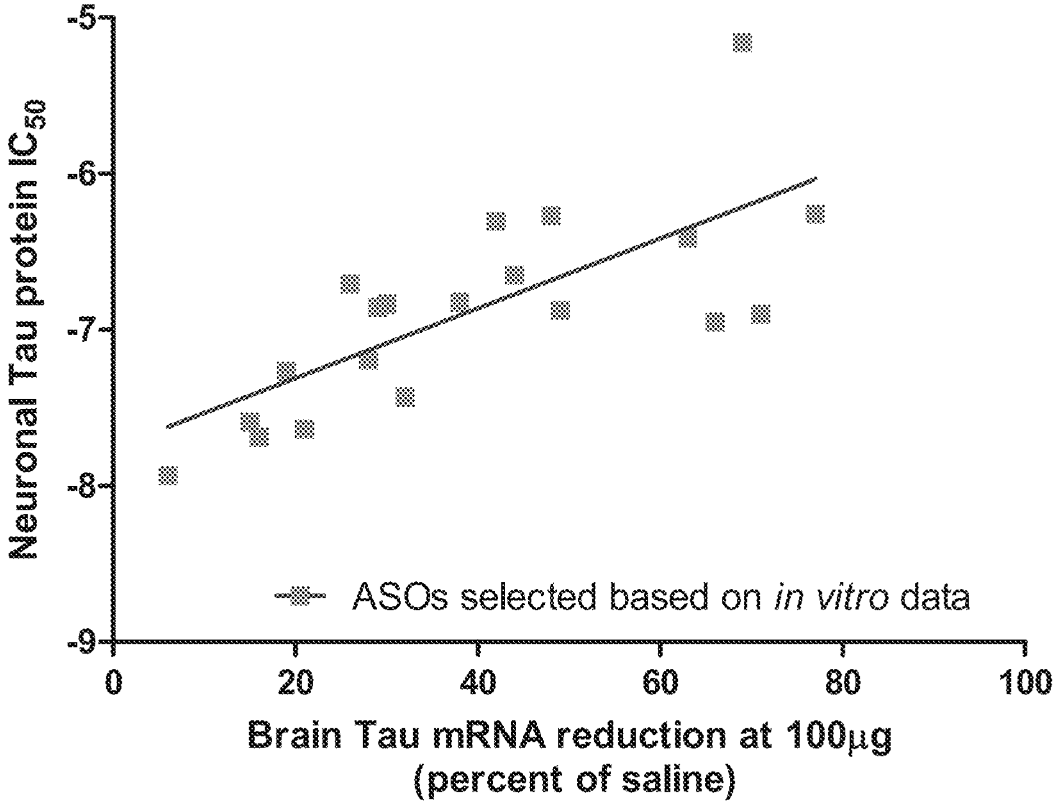
FIG. 8B shows correlation of in vitro potency (Y-axis) and in vivo Tau mRNA reduction (X-axis). In vitro potency ($IC_{50}$) was correlated with in vivo Tau mRNA reduction following administration of 100 μg ASOs, 2 weeks post-dose in mice ($r^2$=0.54; p<0.001). Squares represent oligomers prioritized based on the in vitro Tau protein reduction and primary neuronal health as assessed by tubulin and spontaneous calcium oscillations (FIGS. 3A to 3Z, 4, 6A to 6GG, and 7A to 7E).

In vivo cumulative tolerability threshold following an ICV injection of 100 μg of an antisense oligonucleotide was set at 4. The correlation analysis in FIG. 8A shows that the oligomers having in vivo tolerability lower than 4 tend to have a sequence score equal to or higher than 0.2. Squares in FIG. 8B represent oligomers prioritized based on not only on in vitro Tau protein reduction, but also on primary neuronal health and activity assessed by tubulin and spontaneous calcium oscillations criteria outlined above. In vitro potency data concorded well with in vivo tau mRNA reduction allowing for additional prioritization of oligomers. Potent LNA oligonucleotides targeting MAPT at or partially overlapping nucleotides in the 3'UTR were identified and found to be well tolerated in primary neurons in vitro and following ICV administration in vivo (See FIG. 7A to 7E).

The in vivo acute tolerability score and brain tau mRNA % control data shown in FIG. 7A to 7E show that selected oligomers that hybridize to target MAPT mRNA sequences are both well tolerated and potently reduce Tau mRNA in vivo (e.g., ASO-000013-ATTtccaaattcaCTT- SEQ. ID No. 686: 138,888-138,903).

Example 6

Oligomer Prioritization

The assays described herein can be used in combination to selected oligomers for further testing. Properties of selected oligomers can be described as shown in Table 1. Based on these criteria, certain oligomers were selected for additional dose-response testing in vitro and in vivo.

TABLE 1

Summary of criteria used to prioritize oligomers for additional testing.

| Assay | Prioritization Criteria |
|---|---|
| Tau protein reduction | >70% reduction in Tau protein (5 μM oligomer) |
| Calcium oscillations | <25% reduction in calcium oscillations |
| Sequence score | Sequence score ≥0.20 |

In another embodiment, oligomers can be selected based on the following characteristics: (1) Tau protein reduction >30% reduction in Tau protein (5 μM oligomer); (2) calcium oscillations <25% reduction in calcium oscillations; and (3) sequence score equal to or higher than 0.2.

Example 7

In Vivo Data

Oligomers were injected into animals to determine their effect on Tau expression and on the behavioral properties of the animal.

Research Animals and Administration Routes

The animals used in this Example are the same mice and rats described in Example 5 and were handled in the same manner as described in Example 5. Animals were injected as described in Example 5.

RT-PCR assays were performed as described in Example 5.

Running Wheel Assay

The Home Cage Running Wheel assay measures spontaneous activity in a voluntary free-spinning running wheel (Columbus Instruments). Each wheel has a magnetic sensor that connects to a computer interface and records wheel revolutions at user-specified intervals. In this study, mice were placed individually into cages with a running wheel and wheel rotations were monitored continuously in 15 min increments. To allow for habituation and establish baseline activity levels, control and test mice were tested over 7 days, after which they were transferred into clean cages and dosed with either saline or 100 ug ASO-000774 by ICV injection. Two weeks post treatment mice were returned to the running wheel cages to evaluate treatment effects over 7 days.

Brain Tau mRNA Analysis

Brain Homogenization

Mouse brain tissue was homogenized as described in Example 5. Survival and Febrile Seizure Data (Gheyara et. al., *Ann Neurol.* 2014; 76(3): 443-456.)

Heat-Induced Seizures: Seizures were induced in P30-45 mice using a heat lamp as described (Oakley et al., *Proc Natl Acad Sci USA* 2009; 106:3994-3999) except that a 2-minute acclimation period was used. Survival and febrile seizure data were analyzed by Cox proportional hazards regression using the R survival package (Therneau T M. Survival analysis. R package version 2.37-4 ed2013) and corrected for multiple comparisons with the method of Holm (Holm S. *Scand J Stat* 1979; 6:65-70) For analysis of drug-induced epileptic activity in brain slices, a linear mixed effects model (Laird et al., *Biometrics* 1982; 38:963-974.) was fitted using the R package. Random intercepts were included for each mouse and each genotype such that multiple comparison corrections were not needed due to "partial pooling." Five thousand draws were obtained of parameter estimates, and 95% confidence intervals (CIs) were estimated as the 2.5th and 97.5th quantiles of these draws. Probability values were calculated by inverting the simulated CIs around the differences. Analyses of log(spike frequency 10.1) and log(burst frequency 10.1) were conducted separately.

CSF Collection

All animal protocols were approved by the Wallingford BMS Animal Care and Use Committee. CSF was collected from the cisterna magna of mice following exsanguination as described by Barten, et al., *J Alz. Res.* 24: 127-141 (2011). In brief, CSF was collected with a P20 pipettor after puncturing the dura with a 30 gauge needle under a dissecting microscope. Body temperature was monitored and maintained at normal levels using heating pads and lamps. CSF was collected from rats after exposure of the cisterna magna and withdrawal using a 1 ml insulin syringe. CSF was placed on ice, centrifuged briefly to remove any red blood cells, transferred to another tube while measuring the volume, and frozen on dry ice. CSF Tau protein reduction measured by Tau Protein Enzyme-Linked ImmunoSorbant Assay (ELISA described below) was observed after 4 weeks following a single bolus ICV injection of ASO-000013 (data not shown).

Tau Protein Enzyme-Linked ImmunoSorbant Assay (ELISA)

For brain tissue, BT2 (antibody to Tau amino acid 194-198, Thermo Scientific) was used to coat 96 well black ELISA plates (Costar) at a concentration of 2.5 μg/ml for 1 hour at 37° C. After washing in TBST, the plates were blocked with 3% bovine serum albumin in TBS. Recombinant human Tau441 (rPeptide; Bogart, Ga.) or a 1:5000 dilution of the brain homogenates were diluted in 1% BSA+0.05% Tween-20 in TBS. Alkaline phosphatase conjugated Tau-5 (antibody to Tau amino acid 210-230, Covance, Emeryville, Calif.) was added to the samples at a 1:2000 dilution for co-incubation overnight at 4° C. with shaking. After washing in TBST, the signal was amplified with the Tropix CDP Star detection reagent from Applied Biosystems. The chemiluminescent signal was read on an Envision (Perkin Elmer). For CSF samples, this ELISA was done in a 384 well format to minimize the volume of CSF needed. 10 IA of a 1:2 dilution of CSF was added to each well.

In-Situ Hybridization

In-situ hybridization (ISH) detection of Tau mRNA or ASO-000013 was performed on 20 μm fresh frozen brain sections mounted. Slides were thawed, fixed in 4% paraformaldehyde for 10 minutes at room temperature, washed in phosphate buffered saline (PBS) and acetylated with 0.25% acetic anhydride/0.1M triethanolamine for 10 minutes at room temperature (RT). Following PBS washes, each slide was pre-hybridized in 0.7 ml pre-warmed hybridization buffer (HB), 50% formamide/5× saline sodium citrate (SSC), 100 μg/ml yeast tRNA, lx Denhardt's, for 30 minutes at 67° C. 5' FAM-labeled ASO-000013 sense probe (complementary all LNA probe, ASO-000067=SPC-11404) was heated to 90° C. for 4 minutes, cooled on ice then diluted in HB. Slides were hybridized in 0.45 ml for 30 minutes at 67° C. with a hybrislip (Electron Microscopy Sciences, Hatfield, Pa.). They were subsequently dipped in 0.1×SSC then washed three times in 0.1×SSC at 67° C. Slides were then treated in 3% hydrogen peroxide for 10 minutes, washed in PBS, and blocked for 15 minutes at RT in 0.1M Tris-HCl, pH 7.5, 0.15M NaCl, 0.5% blocking agent (FP1020, Perkin Elmer Waltham, Mass.). This was followed by incubation in rabbit anti-fluorescein-horse radish peroxidase for 30 minutes at RT. Following TBST washes (Tris buffered saline with 0.05% Tween 20), tyramide signal amplification was performed (TSA Plus, Perkin Elmer). Slides were washed in TBST, nuclei stained using DAPI, and coverslip mounted using Prolong Gold (Invitrogen, Carlsbad, Calif.). For chromogenic detection, slides (post-TSA washes) were incubated for a second time with anti-fluorescein-HRP for 30 minutes at RT, washed in TBST and developed using DAB substrate (Quanto, Thermo Scientific, Freemont, Calif.). Tau mRNA and ASO-00013 oligomer ISH indicate uniform distribution of tau mRNA reduction and oligomer across the mouse brain following a single ICV bolus injection of 100 μg ASO-000013 (data not shown).

Results

Figure 9A:
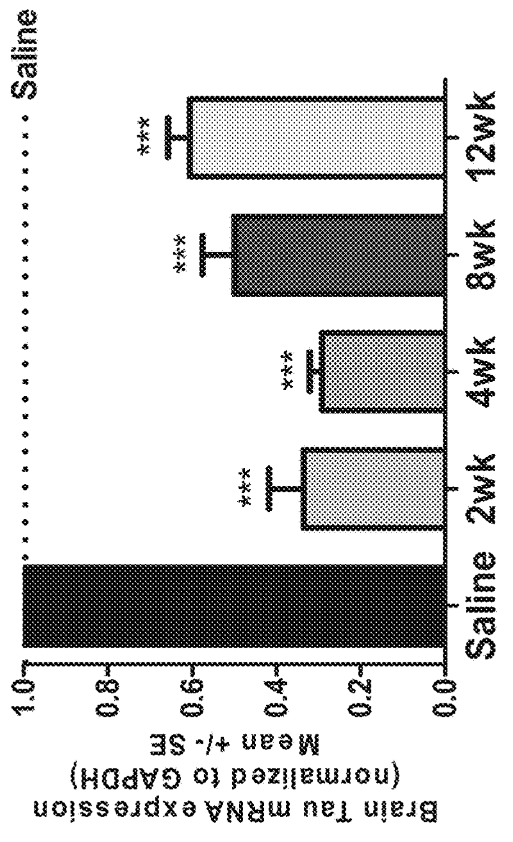
FIGS. 9A-9B are graphs showing brain Tau mRNA (9A) and Tau protein (9B) reduction over time following a single ICV bolus of 100 μg ASO-000013 (i.e., ATTtccaaattcaCTT, i.e., SEQ ID NO: 686 in which the upper case letters represent LNA nucleotides while the lower case letters represent DNA nucleotides) administration into wild type C57 mice (N=12). Tau mRNA expression (normalized to GAPDH) was measured at 2, 4, 8 and 12 weeks post injection. Tau protein (% of saline) level was measured at 2, 4, 8 and 12 weeks post injection. (* p<0.01, ***p<0.001) Both Tau mRNA and protein returned to baseline at 20 weeks post-dose (data not shown).
Figure 9B:
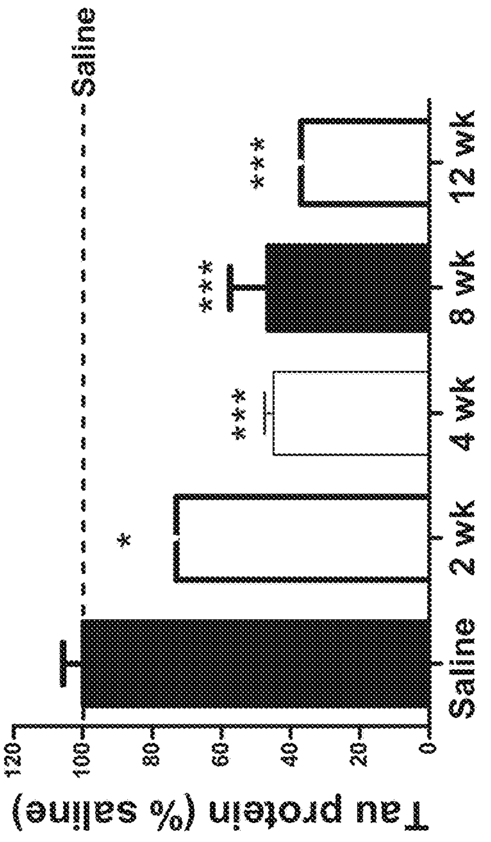
Figure 10:
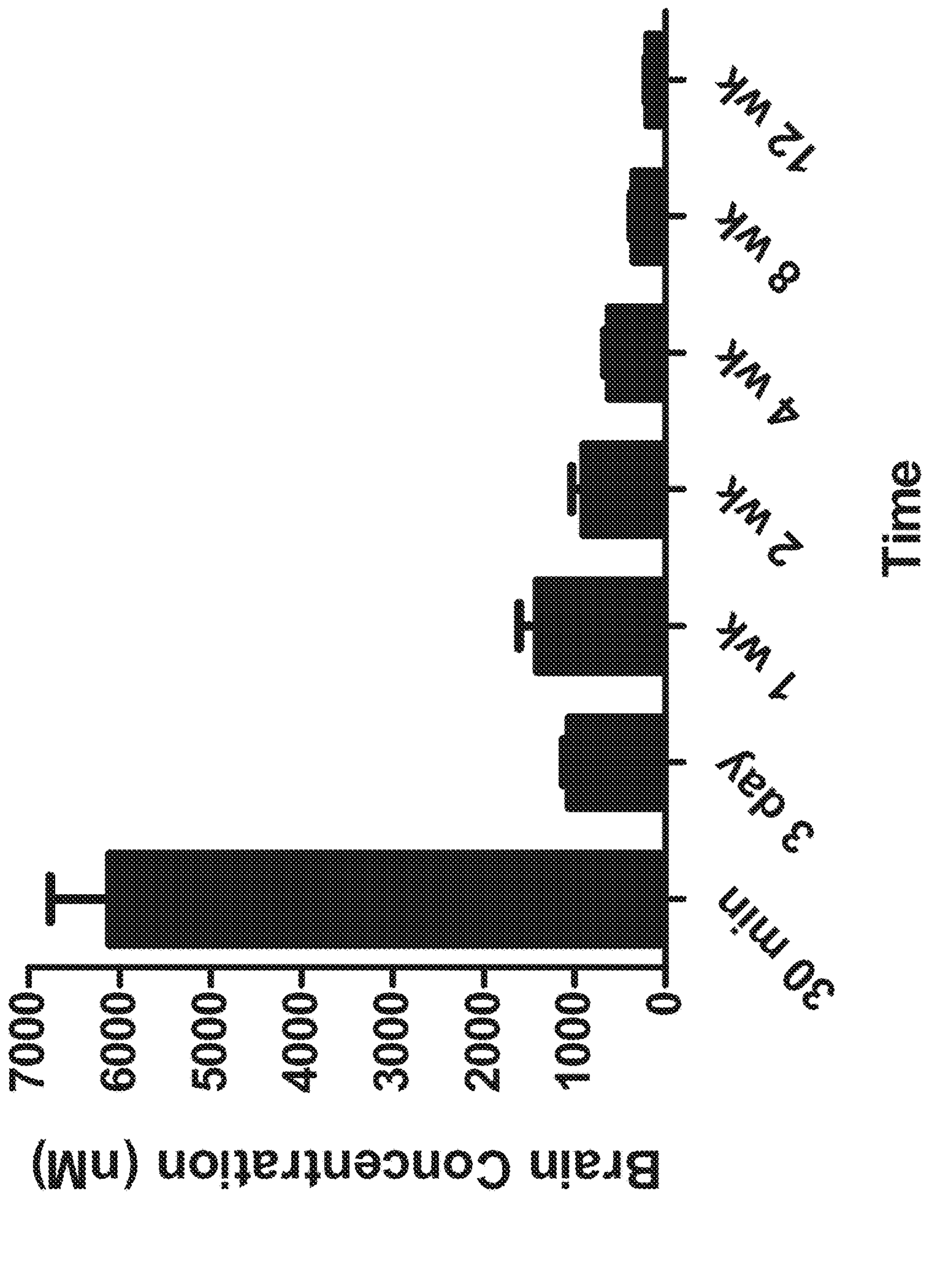
FIG. 10 is a graph showing that brain concentrations of ASO-000013 were detected up to 12 weeks following administration of a single ICV bolus of 100 μg into wild type C57 mice (N=12).

In vivo reduction of human tau mRNA level was measured in mice after the administration of various oligomers (FIG. 7A to 7E). As shown in FIGS. 9A and 9B, brain Tau mRNA and Tau protein reduction over time following a single ICV bolus of 100 μg ASO-000013 (i.e., ATTtccaaattcaCTT, in which the upper case letters represent LNA nucleotides while the lower case letters represent DNA nucleotides) administration into wild type C57 mice (N=12). Tau mRNA expression (normalized to GAPDH) was measured at 2, 4, 8 and 12 weeks post injection. Tau protein (% of saline) level was measured at 2, 4, 8 and 12 weeks post injection. This oligomer produced a durable reduction in Tau mRNA and protein with Tau protein remaining reduced following 12 weeks post single bolus ICV injection. Other oligomers defined within this invention exhibit more profound reductions in Tau mRNA, as measured by qRT-PCR, and protein with durable tissue oligomer exposure (FIG. 10) as measured by ELISA (further described below).

Tau mRNA Reduction

Oligonucleotides, or oligomers similar to ASO-000013, ASO-000757, ASO-000762, ASO-000761, ASO-000758, ASO-000760, and ASO-000759 show potent knockdown of Tau protein in primary hTau neurons with good tolerability in vitro and in vivo when administered directly into the cerebral spinal fluid (CSF) via intra-cerebroventricular or intrathecal dosing (see, e.g., FIG. 7A to 7E. They also display robust, durable tau reduction in the brain following intra-cerebroventricular administration of 100 ug in C57 b16 mice (FIG. 7A to 7E). Inhibition of calcium oscillations in primary neurons was not observed in primary neurons treated with these oligomers. This inhibition of calcium oscillations in primary neurons was a strong indication of acute in vivo tolerability issues related to network dysfunction when injected into CSF directly.

Oligomers like ASO-000013 produced sustained Tau reduction following a 100 μg intra-cerebroventricular (ICV) bolus injection (see FIG. 9). 100 μg/5 μl was injected into wt C57 mice, 3 Month study in wt mice; N=12. Robust and sustained Tau RNA (FIG. 9A) and protein (FIG. 9B) reduction was achieved; 3×33 ug intra-cerebroventricular bolus injections produced similar results (data not shown).

Figure 11:
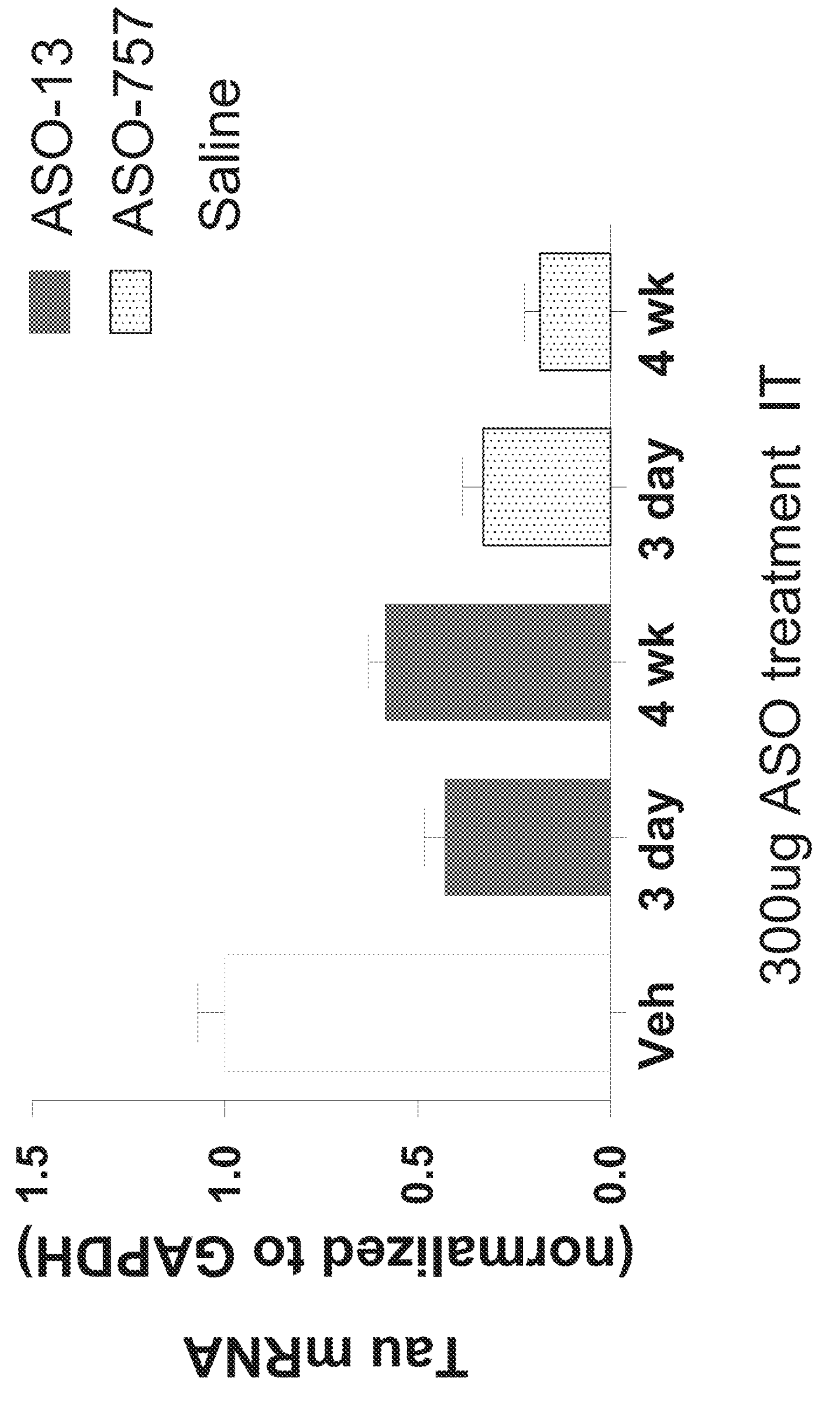
FIG. 11 is a graph showing brain Tau mRNA reduction following 3 day or 4 week post 300 μg single bolus intrathecal (IT) administration of oligomers (ASO-000013 and ASO-000757 (i.e., CTTTAtttccaaattCACTT (SEQ ID NO: 677)) in rat (N=6).

Dose dependent Tau RNA reduction was also observed following intrathecal (IT) injection of oligomers similar to ASO-000013 and ASO-000757 into lumbar ported rats (data not shown). A single bolus IT injection of 300 μg of ASO-000013 or ASO-000757 was injected into lumbar catheterized rats (as described above). Robust and sustained reduction of brain Tau mRNA was observed at both 3 days and 4 weeks following the single bolus administration using the proposed clinical route of administration of these representative oligomers (FIG. 11). IT administration is the preferred clinical route for the treatment of tau dependent disorders.

Tau Protein Reduction

Tau ASOs in the 3'UTR were administered at 100 μg intra-cerebroventricular (ICV) to hTau or wild type B16 mice in order to understand the hysteresis of Tau protein reduction with respect to mRNA reduction. During these studies, many of the Tau ASOs were not tolerated beyond 4 weeks following a single 100 μg ICV bolus dose. Some of the most potent Tau ASOs in this region also reduced expression of an unintended target Ras homolog gene family, member A ("RhoA"). RhoA is a small GTPase protein of Rho family. While the effects of RhoA activity are not all well known, it is primarily associated with cytoskeleton regulation, mostly actin stress fibers formation and actomyosin contractility. In humans, it is encoded by the gene RHOA. The RHOA gene contains the sequence of actttatttccaaatacacttcttt (SEQ ID NO: 959). FIG. 12 shows that the RHOA gene fragment has one to four basepair mismatches with selected oligomers (e.g., ASO-000757, ASO-000755, or ASO-000753).

Certain traditional gapmer sequences were further modified in the gap design and the wing design. In particular, the traditional gapmer design was converted to an alternating flank gapmer design (e.g., ASO-001967, ASO-001941, ASO-001933, and ASO-1940). FIG. 12 shows that the traditional gapmers are not tolerated beyond 4 weeks following a single 100 μg ICV bolus dose while the alternating flank gapmers exhibit tolerability beyond 4 weeks.

FIG. 12 also shows that tubulin (Tuj 1) was highly correlated with long term tolerability for the ASOs shown. Rho A reduction greater than 25% also correlated with lack of long term tolerability (greater than 4 weeks following a single ICV bolus injection of 100 μg of each ASO shown in FIG. 12).

Figure 13:
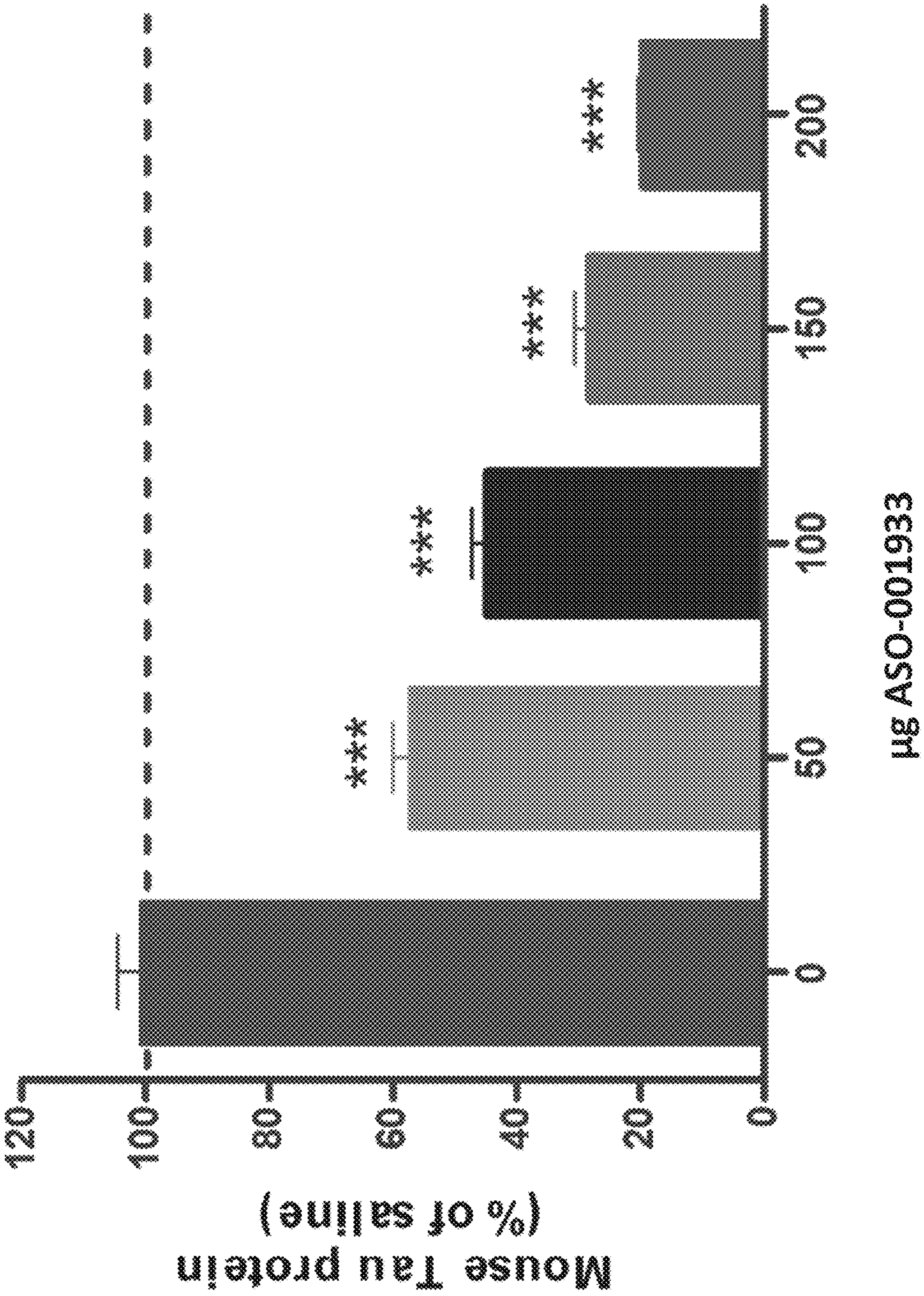
FIG. 13 shows that ASO-001933 produces dose responsive brain hTau protein reduction after a single ICV injection in hTau mouse brain. Saline or 50, 100, 150 or 200 μg of Tau ASO was injected ICV in hTau mice (n=10 per group). X-axis shows the dose of ASO-001933, and the Y-axis shows the hTau protein expression after the ASO injection compared to the hTau protein expression after the saline injection (% of saline).

ASO-001933 (100 μg-200 μg) was administered as a single bolus intracerebroventricularly (ICV) in mice, as described above, and produced greater than 50% reduction of brain Tau protein that was sustained for 4-12 weeks in hTau mice. At these dose levels, there were no clinical signs of toxicity and no gross or histologic findings observed over the 20-week period following a single ICV dose in mouse. ASO-000013 was also administered and gave results similar to ASO-001933. A single ICV bolus injection of 100 μg produced no adverse changes in cognition as assessed by novel object recognition or contextual fear conditioning, motor function as assessed by catwalk, rotorod and running wheel (data not shown). In a Tau knock out mouse carrying the entire human tau gene (hTau), the $EC_{50}$ for reduction of human Tau brain mRNA and protein was ~2.72 μg/g (414 nM). As FIG. 13 shows, ASO-001933 (Tau ASO) produces durable, dose responsive brain hTau protein reduction after a single intracerebroventricular (ICV) injection in hTau mouse brain. Saline or 50,100, 150 and 200 μg of Tau ASO was injected ICV in hTau mice (n=10 per group). The frontal cortical region was dissected eight weeks post dose to determine total Tau protein levels by ELISA (BT2/HT7). Two-way ANOVA and Bonferroni post hoc analysis were used ***$p<0.001$. Error bars represent SEM.

Figure 14A:
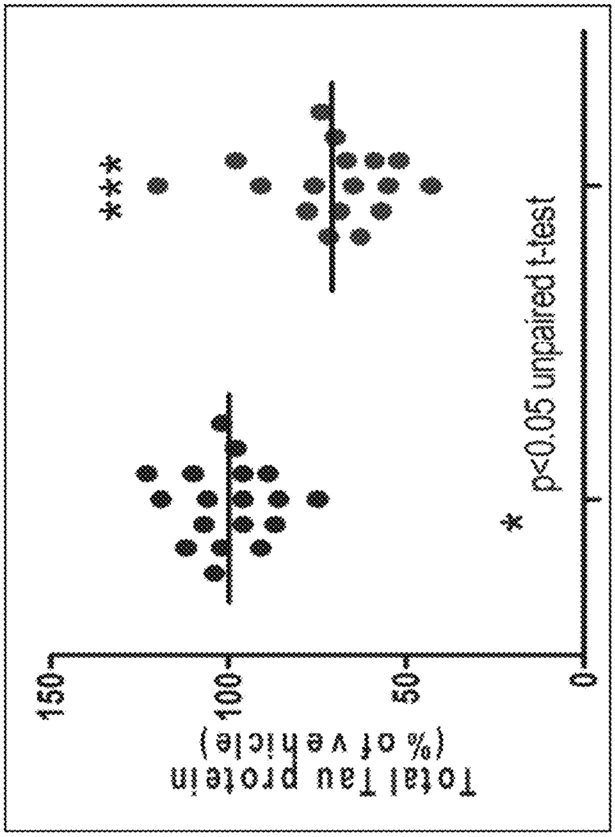
FIGS. 14A and 14B show that Tau ASO-000774 mediated insoluble and soluble Tau reduction rescued hyperactivity in a mouse model of tauopathy (Tg4510). Tau reduction reverses hyperactivity in Tg4510 mice in running wheel assay.
Figure 14B:
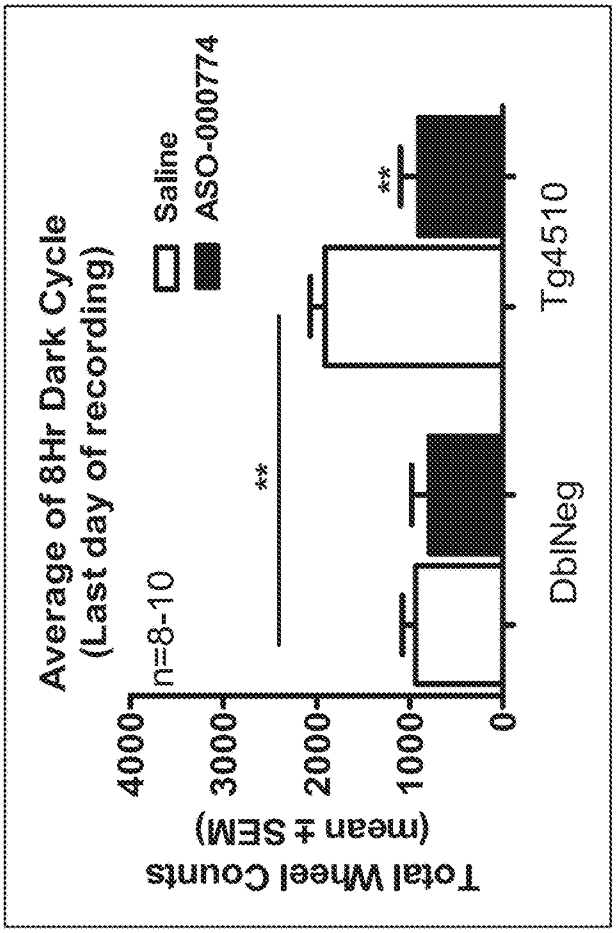

The relationship between the level of brain Tau protein suppression and functional outcome measures was studied in both tauopathy (Tg4510) and Dravet Syndrome mouse models. Initial data generated in these genetic mouse models (FIGS. 14 and 15) suggest that about 25-50% reduction of brain soluble and insoluble Tau protein compared to a control is sufficient for potential functional improvement in tauopathies like PSP and/or intractable early childhood epilepsies like Dravet. In particular, FIG. 14A shows that a single 100 μg ICV bolus of ASO-000774 reduced total Tau protein. The protein reduction was measured by using BT-2 and HT-7 ELISA described herein. $p<0.05$ unpaired t-test. In FIG. 14B, Tg4510 and double negative littermate controls (Dbl Neg) were assessed in a running wheel assay as described above. A single 100 μg ICV bolus of ASO-000774 reversed hyperactivity in Tg4510 to level of Dbl Neg littermate controls, $p<0.05$ Two-Way RMANOVA followed by Bonferroni's post test.

Figure 15A:
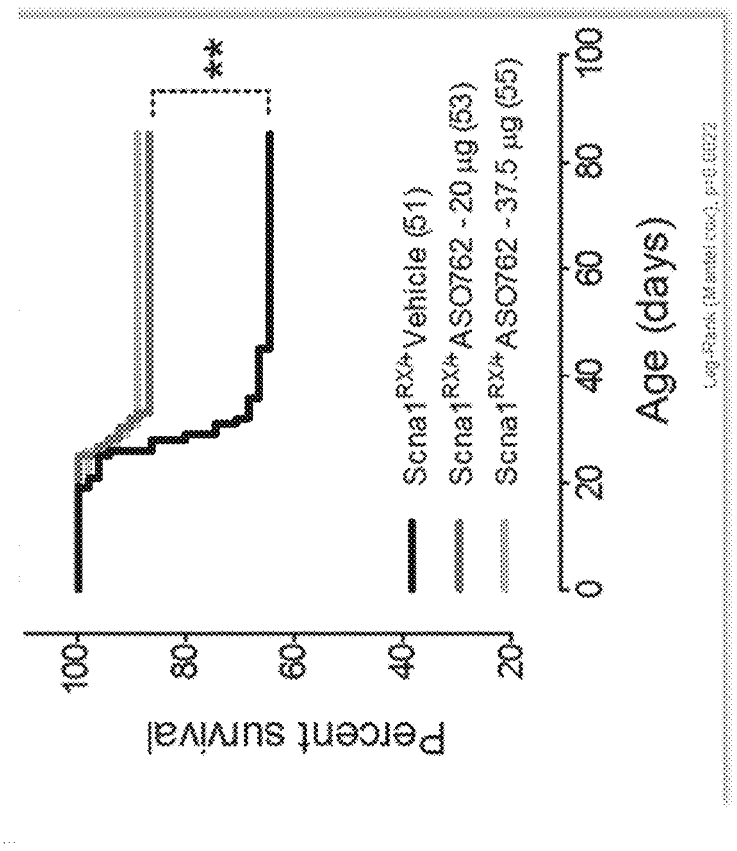
FIGS. 15A and 15B show that tau oligomers (e.g., ASO-000762) can rescue premature lethality and reduced tonic clonic seizure in a mouse model of Dravet Syndrome, respectively.
Figure 15B:
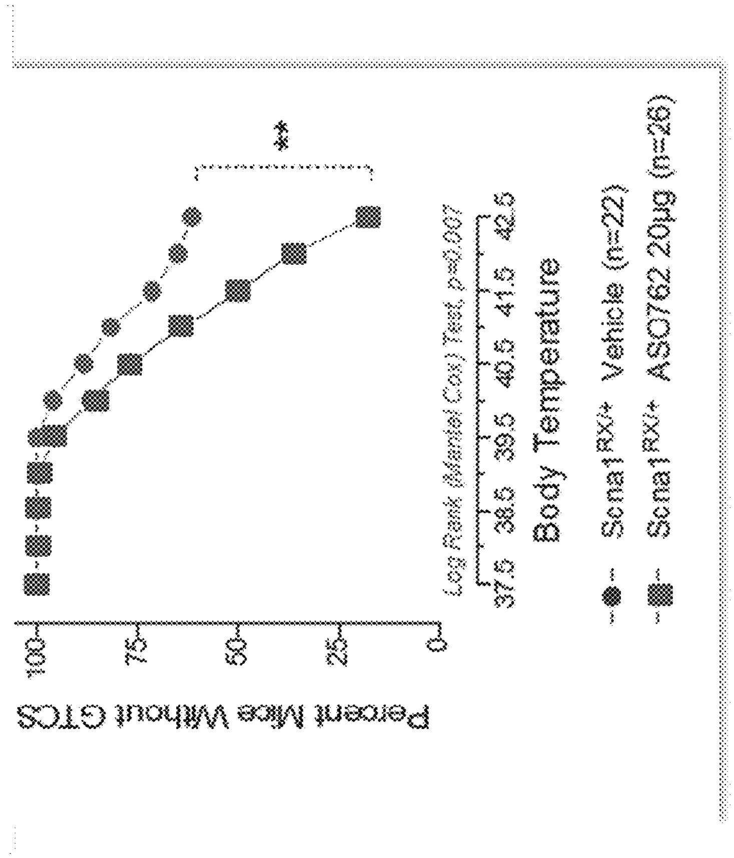

In addition, about 25-50% reduction of brain soluble and insoluble Tau protein compared to a control is sufficient to improve survival and heat induced seizure in Dravet mice, which possess a mutation in the SCNA1 gene (FIG. 15). Dravet mice treated with a single ICV administration of 20 or 37 μg of Tau ASO-000762 targeting the 3'-UTR region of Tau mRNA exhibited about 20-50% Tau protein reduction (data not shown) at 10 days postnatally. In addition, as FIG. 15A shows, the Dravet mice showed a greater percentage of live mice between 30-55 days when compared with littermate controls. Significant treatment effect has been shown by Cox proportional hazard regression. Dravet mice were tested to measure hyperthermia-induced Generalized Tonic-Clonic Seizures (GTCS). FIG. 15B shows that ASO-000762 at 20 μg protected against hyperthermia-induced Generalized Tonic-Clonic Seizures (GTCS) in Dravet mice after 8-9 weeks post-injection. Consistent with the in vivo Dravet studies, ASO-001933 tested in neurons derived from Dravet and human isogenic control Induced pluripotent stem cells ("iPSCs") corrected the network activity induced by neurotransmitter(s) (data not shown).

Example 8

Construction of Oligomers Targeting 5' UTR and/or Exon 2

A number of oligomers were designed to target the 5' UTR and/or exon 2 of MAPT pre-mRNA. See FIG. 1A to 1TT for genomic MAPT sequence. For example, the oligomers were constructed to target nucleotides 72,802-73,072 of SEQ ID NO: 1. The exemplary sequences of the oligomers are described in FIGS. 16A to 16C and 16D to 16K. In some embodiments, the oligomers were designed to be gapmers or mixmers. FIGS. 16A to 16C and 16D to 16K show non-limiting examples of the oligomer design for selected sequences. The same methods can be applied to any other sequences disclosed herein. The gapmers were constructed to contain locked nucleic acids—LNAs (upper case letters). For example, a gapmer can have Beta-deoxy LNA at the 5' end and the 3' end and have a phosphorothioate backbone. But the LNAs can also be substituted with any other nucleotide analogs and the backbone can be other types of backbones (e.g., a phosphodiester linkage, a phosphotriester linkage, a methylphosphonate linkage, a phosphoramidate linkage, or combinations thereof). A reference to a SEQ ID number includes a particular sequence, but does not include an oligomer design.

The oligomers were synthesized using methods well known in the art. Exemplary methods of preparing such oligomers are described in Barciszewski et al., Chapter 10—"Locked Nucleic Acid Aptamers" in *Nucleic Acid and Peptide Aptamers: Methods and Protocols*, vol. 535, Gunter Mayer (ed.) (2009), the entire contents of which is hereby expressly incorporated by reference herein.

Example 9

Tau mRNA and Protein Reduction in Cynomolgus Monkeys

Progressive supranuclear palsy (PSP) is a neurodegenerative syndrome that is clinically characterized by progressive postural instability, supranuclear gaze palsy, parkinsonism and cognitive impairment. PSP is defined neuropathologically by the accumulation of tau-positive neurofibrillary tangles in brain regions extending from the cerebral cortex, basal ganglia to the cerebellum and brainstem. The most severely affected brain regions include the brainstem substantia nigra, pontine nuclei and the cerebellar dentate nucleus. Tauopathy in these regions is believed to underpin several clinical features of PSP such as postural instability, dysarthria and gaze palsy. Suppression of Tau mRNA transcripts and, consequently, protein in the brain regions, can have therapeutic significance for treatment of PSP patients.

Subjects were male cynomolgus monkeys weighing 3.5-10.0 kg at the start of the study. Each was implanted with an intrathecal CSF catheter entering at the L3 or L4 vertebrae extending to approximately the L1 vertebra. The proximal end of the catheter was connected to a subcutaneous access port. CSF was collected through the port by gravity flow to a maximum of 0.5 ml CSF per sample. The CSF was centrifuged and the supernatent was kept at −90° C. until analyzed. Blood plasma obtained from an available vein was kept at −90° C. until analyzed.

Cynomolgus monkeys were administered with ASO-1933, which was dissolved in saline, at 0.33 ml/min in a 1.0 ml volume followed by a 0.5 ml sterile water flush. Total infusion time was 4.5 min.

Cynomolgus monkeys were administered the appropriate volume of a commercially available euthanasia solution while anesthetized with ketamine and isoflurane. Necropsy tissues were obtained immediately thereafter and the brain was transferred to wet ice for dissection. Areas of interest were dissected using 6 mm slices in an ASI Cyno Brain Matrix as well as free handed techniques. Samples were placed fresh in RNAlater, or frozen on dry ice for later analysis. Some slices were frozen intact for immunohistochemical analysis. Slices were placed in a weigh boat and floated on isopentane cooled with dry ice. Once frozen, slices were stored at −90° C. until analysis.

For brain block sectioning, the frozen brain blocks were cut on a cryostat coronal sections, and sections were thaw-mounted onto super frost slides, dried, re-frozen on dry ice, and stored at −80° C. until use. Brain sections collected from the cynomolgus monkey dosed with vehicle, ASO-1933 at 16 mg (1×16) or ASO-1933 at 16 mg twice (2×16, with 2 weeks apart) were used for the in situ hybridization (ISH) study.

In order to measure Tau mRNA expression using [$^{35}$S] labeled antisense ISH, a Tau DNA template and [$^{35}$S]labeled antisense probes were synthesized. A Tau DNA template (425 bp, 687-1111, accession number: XM_005584540.1) was amplified from a cynomolgus monkey cDNA library (Zyagen KD-201) by PCR using forward primer 5'-CAA GCT CGC ATG GTC AGT AA-3' (SEQ ID NO: 954) and reverse primer 5'-AAT TAA CCC TCA CTA AAG GGA GA TTC TCA GTG GAG CCG ATC TT-3' (SEQ ID NO: 955). Products of desired size were observed by gel electrophoresis. The Tau DNA template was transcripted with T3 RNA polymerase (Invitrogen AM1316) using [$^{35}$S]UTP (Perkin Elmer NEG-739) to produce a [$^{35}$S]labeled antisense ISH probe.

To measure Tau mRNA ISH using [$^{35}$S]labeled antisense probe, slides were thawed, fixed in 4% paraformaldehyde for 15 min at 4° C. followed by rinsing. Slides were then treated in acetic anhydride/triethanolamine followed by rinsing. Slides were pre-hybridized in pre-hybridization solution at 50° C. for 3 hours and hybridized with $1.5\times10^4$ cpm/ul [$^{35}$S]riboprobe (0.75 ml/slide) in hybridization solution. After hybridization, slides were washed at room temperature. Slides were then treated with Rnase A at 37° C., washed twice, followed by a high stringency wash. The sections were dehydrated in 90% alcohol containing 0.3 M $NH_4Ac$, dried, and exposed against phosphor screen (Perkin Elmer PPN 7001487). After exposure, autoradiographic images on the screen were captured and analyzed using Cyclone storage phosphor system and OptiQuant Acquisition and Analysis software (PerkinElmer, Waltham, Mass.).

QUANTIGENE® ViewRNA tissue ISH was used to detect Tau mRNA expression at the subnucleus and cellular levels. An antisense probe (type-1) targeting Tau mRNA (2344-3300, accession number: XM_005584529) was synthesized by Affymetrix. Slides were fixed in 4% formaldehyde in phosphate buffered saline (PBS). After passing through alcohol gradients for 10 minutes each, slides were dried, followed by protease QF digestion. Subsequently, sections were washed and hybridized with the target probe. Slides were then washed in wash buffer and stored in storage buffer overnight. Slides were then processed through a series of sequential PreAmp and Amp hybridization steps. The sections were incubated with Label Probe AP followed by incubation with Fast Red Substrate, rinsed in PBS, and counterstained using either Gill's Hematoxylin or DAPI. Slides were coverslipped using DAKO ultramount mounting medium and stored. Labeled Tau mRNA was visualized using either a Leica brightfield microscope or a Leica confocal fluorescence microscope (excitation: 630 nm; emission: 760).

To measure Tau protein expression, Tau12 (BioLegend, San Diego, Calif., epitope to amino acids 6-18 on tau 441 sequence) and BT2 (Thermo Scientific, Rockville, Ill., epitope to amino acids 194-198) were used to coat Costar 3925 ELISA plates at 2.5 and 1 μg/ml, respectively. Plates were incubated for 1 h at 37° C. before washing with TBS with 0.05% Tween-20 (TBST). Non-specific binding was blocked by the addition of 3% bovine serum albumin (BSA) in TBS with 0.1% Tween-20 for 4 h at room temperature with shaking. Plates were washed with TBST before the addition of samples or standard curve generated with recombinant h-tau441 protein, both of which were prepared in TBST plus 1% BSA. Plates containing standard curve and samples were incubated overnight at 4° C. with shaking. The following detection antibodies were conjugated with alkaline phosphatase (AP) using the Lightning Link Conjugation Kit (Novus Biologicals, Littleton, Colo.): BT2 and HT7 (Thermo Scientific, epitope of 159-163). AP-conjugated detection antibodies were diluted in TBST plus 1% BSA and co-incubated with samples and standard curve for 1 h at room temperature with shaking. After washing with TBST, Tropix CDP-Star Ready-to-Use with Sapphire-II AP substrate (Applied Biosystems, Bedford, Mass.) was added for 30 min. Chemiluminescent signal was determined using a Perkin Elmer EnVision microplate reader (Waltham, Mass.).

The N-terminal tau sandwich ELISA (Tau12-BT2) consists of the anti-tau antibody Tau12 as capture and detection with an alkaline phosphatase (AP) conjugate of the anti-tau antibody BT2. The mid-domain tau sandwich ELISA (BT2-HT7) consists of the anti-tau antibody BT2 as the capture antibody and detection with an alkaline phosphatase (AP) conjugate of the anti-tau antibody HT7 High binding black well ELISA plates (Costar, Corning, Tewksbury, Mass.) were coated with anti-Tau BT2 monoclonal antibody (Thermo, Waltham, Mass.) at 2.5 μg/ml or Tau12 anti-tau monoclonal antibody (Covance) at 5 μg/ml in tris buffered saline (50 μL/well). The plates were washed with tris buffered saline containing 0.05% tween-20 (TBS-T) followed by blocking at room temperature with shaking in 3% BSA/TBS (BSA from Roche, Indianapolis, Ind.). The plates were rewashed as listed above followed by sample addition in triplicate (50 μL/well). Cynomolgus monkey CSF samples were diluted 1:30 (BT2/HT7) or 1:25 (Tau12/BT2) in 1% BSA/TBS-T. A Tau 441 (R-peptide, Bogart, Ga.) standard curve was made. The samples were incubated on the ELISA plate overnight at 4° C. with shaking. AP conjugated HT7 or BT2 was diluted to 0.25 μg/ml (HT7) or 0.1 μg/ml (BT2) in 1% BSA/TBS-T was added to the plates (50 μL/well) for co-incubation with standards and samples for 1 hour at room temperature with shaking. The plates were re washed followed by the addition of chemiluminescent substrate (Tropix CDP Star, Applied Biosystems, Grand Island, N.Y.) (100 μL/well) and incubation at room temperature with shaking for 30 minutes. The plates were read on a Perkin Elmer TopCount. Unknown sample values were read off the Tau-441 standard curve using GraphPad Prism software.

Figures 17A, 17B:
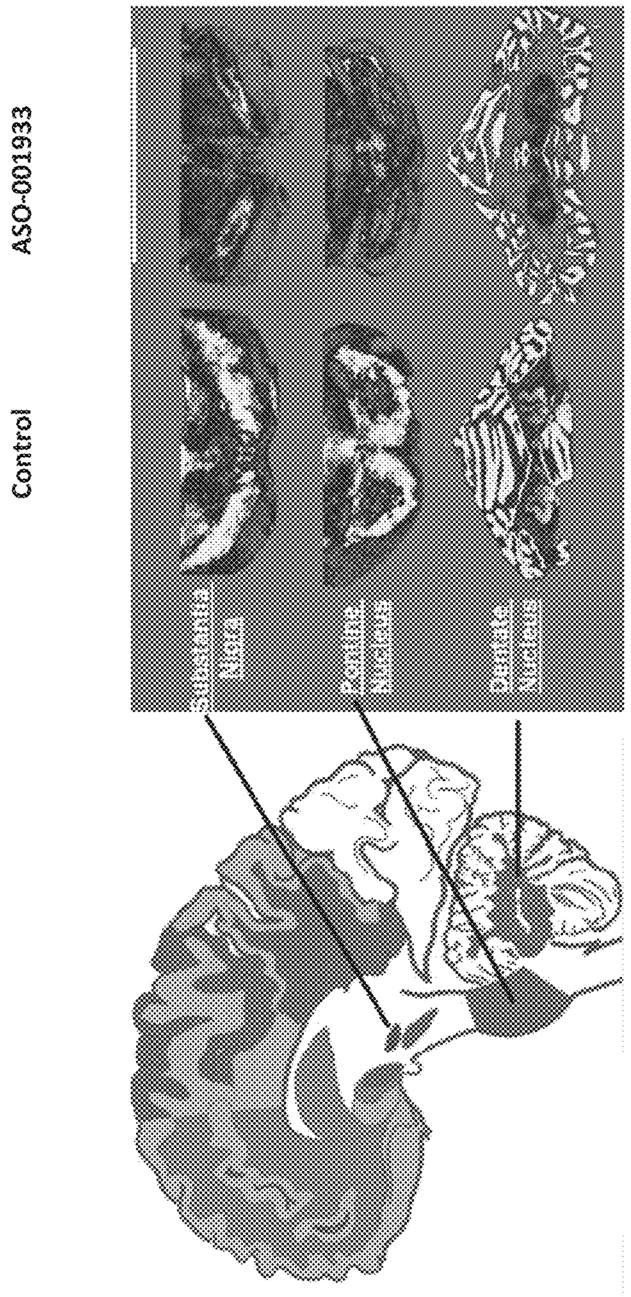
FIG. 17A is an image of brain regions showing pathologic Tau accumulation in PSP.
FIG. 17B shows regional Tau mRNA changes in a control monkey (left) or in a monkey that had received two single 16 mg intrathecal bolus doses of ASO-001933, one week apart (right). The Tau mRNA changes were assessed two weeks post-dosing by fluorescence in situ hybridization (FISH) using Tau mRNA specific probes in substantia nigra, pontine nucleus and central cerebellar dentate nucleus. Tau mRNA accumulation is shown as lighter shades.

These studies demonstrate that intrathecally-applied Tau ASO distributes to the substantia nigra, pontine nuclei and dentate nucleus and suppresses Tau mRNA expression in these brain regions in Cynomolgus monkeys following intrathecal administration of ASO-001933 following two doses (2 week apart) of 16 mg (2×16). FIG. 17A show in situ hybridization (ISH) autoradiographic images of tau mRNA expression (lighter shades) in the substantia nigra, pontine nuclei and dentate nucleus in the monkeys dosed with vehicle or ASO-001933 2×16 mg (1 week apart). As FIG. 17B shows, ASO-001933 produced profound suppression of Tau mRNA expression in all three regions in both monkeys. The Tau mRNA knockdown effect produced by ASO-001933 was further demonstrated using the QUANTIGENE® ViewRNA ISH assay (data not shown). FIG. 17B shows that in the vehicle-treated monkey, a high intensity Tau mRNA labeling was present, primarily, in neuronal cell bodies in the substantia nigra, pontine nuclei and dentate nucleus. In cynomolgus monkeys, two single 16 mg intrathecal doses of ASO-001933, one week apart were administered to assess anatomic distribution of Tau mRNA reduction in anatomic brain regions where pathologic Tau accumulates in PSP (FIG. 17A).

In monkeys, a single intrathecal (IT) dose of 4 mg of ASO-001933 produced Tau mRNA reductions between 58% to 80% in cortical brain regions and 63% in cerebellum within 2 weeks post dose (data not shown). These areas of the brain are believed to be important for treatment of Tau-dependent dysfunction in PSP (neurodegenerative tauopathies) and Dravet syndrome (epilepsy and autism spectrum disorders), leading indications for Tau antisense molecules like ASO-001933.

Figure 18B:
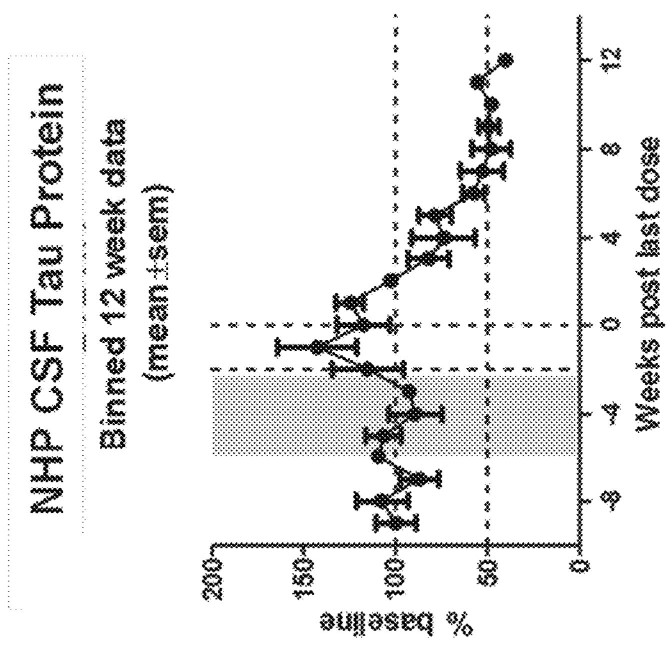
FIG. 18B shows Tau protein reduction in cerebrospinal fluid (CSF) following intrathecal dosing of ASO-001933 in nonhuman primates (NHPs). Y-axis shows percent baseline of Tau protein reduction in CSF, and X-axis shows weeks post last dose.
Figure 18A:
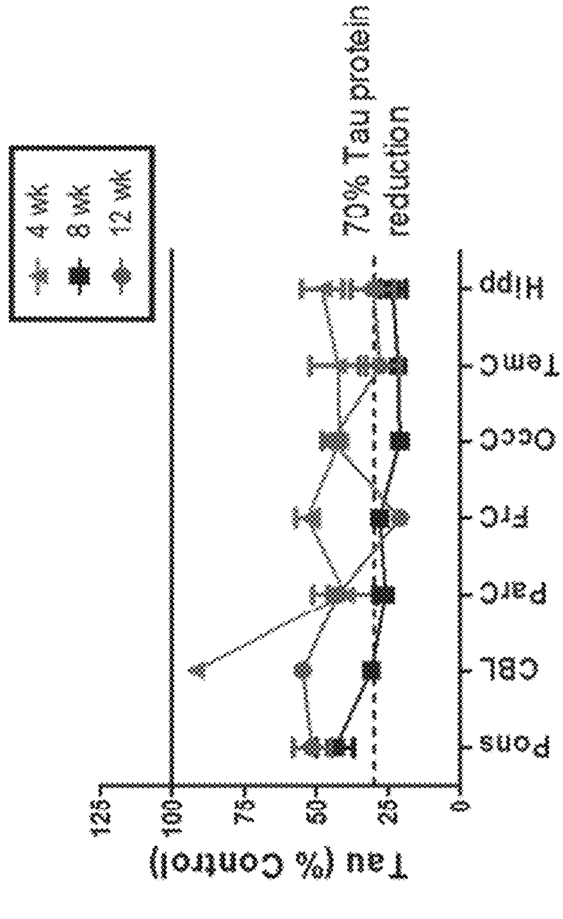
FIG. 18A shows Tau protein reduction in brain following intrathecal dosing of ASO-001933 in nonhuman primates (NHPs). Regional Tau mRNA changes in a control monkey or a monkey that had received two single 8 mg intrathecal bolus doses of ASO-001933, two weeks apart, were assessed 4, 8, or 12 weeks post-dosing by Tau ELISAs (BT2/HT7 or Tau12/BT2). The regional Tau mRNA changes were measured in pons, cerebellum (CBL), parietal cortex (ParC), frontal cortex (FrC), occipital cortex (OccC), temporal cortex (TemC), and hippocampus (Hipp).

Consistent with Tau mRNA, FIGS. 18A and 18B shows that the ASO-001933 administration as IT bolus injection (2 doses of 8 mg given 2 weeks apart) in monkeys is capable of reducing about 70% of Tau protein in the brain (FIG. 18A) about 60% in the CSF (FIG. 18B). The Tau protein expression was observed 12 weeks following the ASO administration. Similarly, the ASO-001933 administration as a single ICV intra-cerebroventricular injection (100 m) in mice is capable of reducing about 50% of Tau protein in the brain (data not shown) and about 34% of Tau protein in the CSF (data not shown). These data suggest that reduction of CSF Tau protein can be a clinically accessible biomarker of target engagement.

Figure 19A:
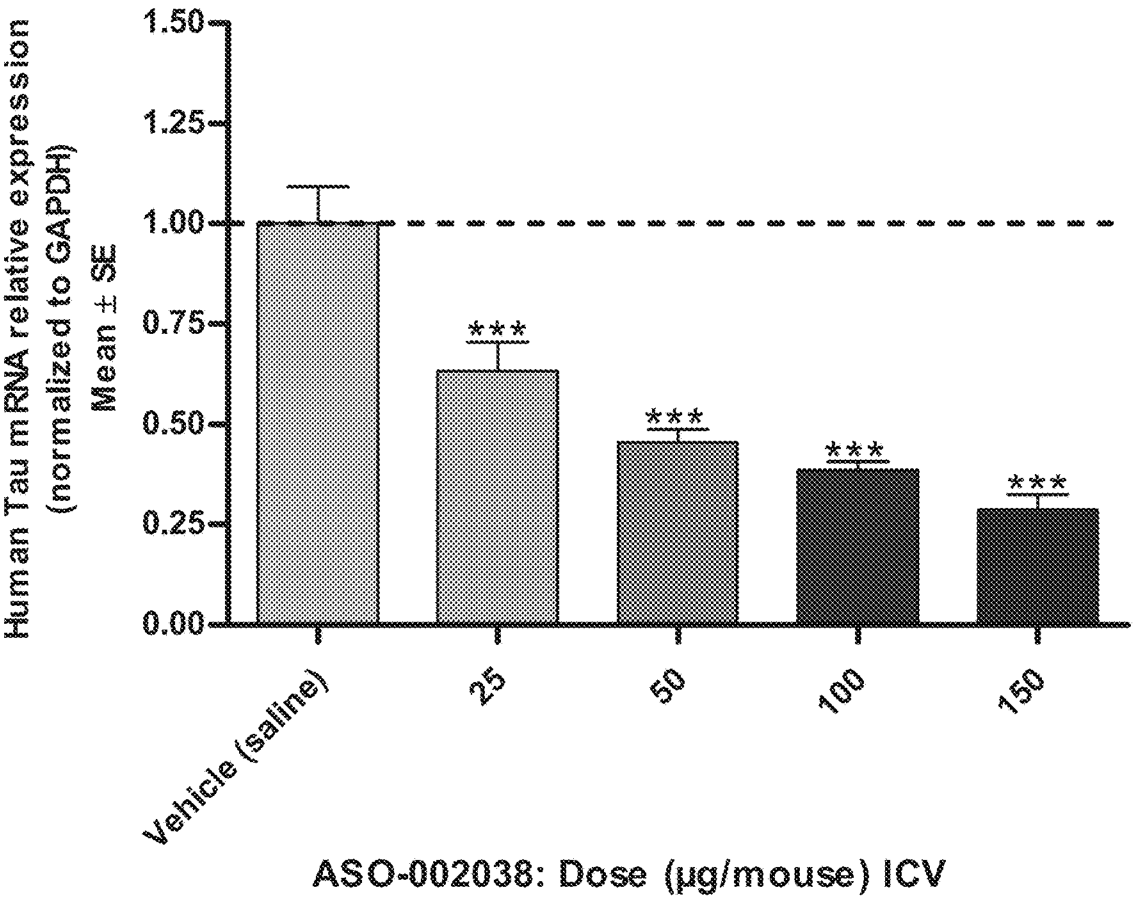
FIG. 19A shows that ASO-002038 (Tau ASO) produces durable, dose responsive brain hTau mRNA reduction after a single intracerebroventricular (ICV) injection in hTau mouse brain. Saline or 25, 50,100, and 150 μg of Tau ASO was injected ICV in hTau mice (n=10 per group). The frontal cortical region was dissected 1 week post dose to determine total Tau mRNA levels by qRT-PCR. 1-way ANOVA analysis was used ***p<0.001. Error bars represent mean+/−SEM.
Figure 19B:
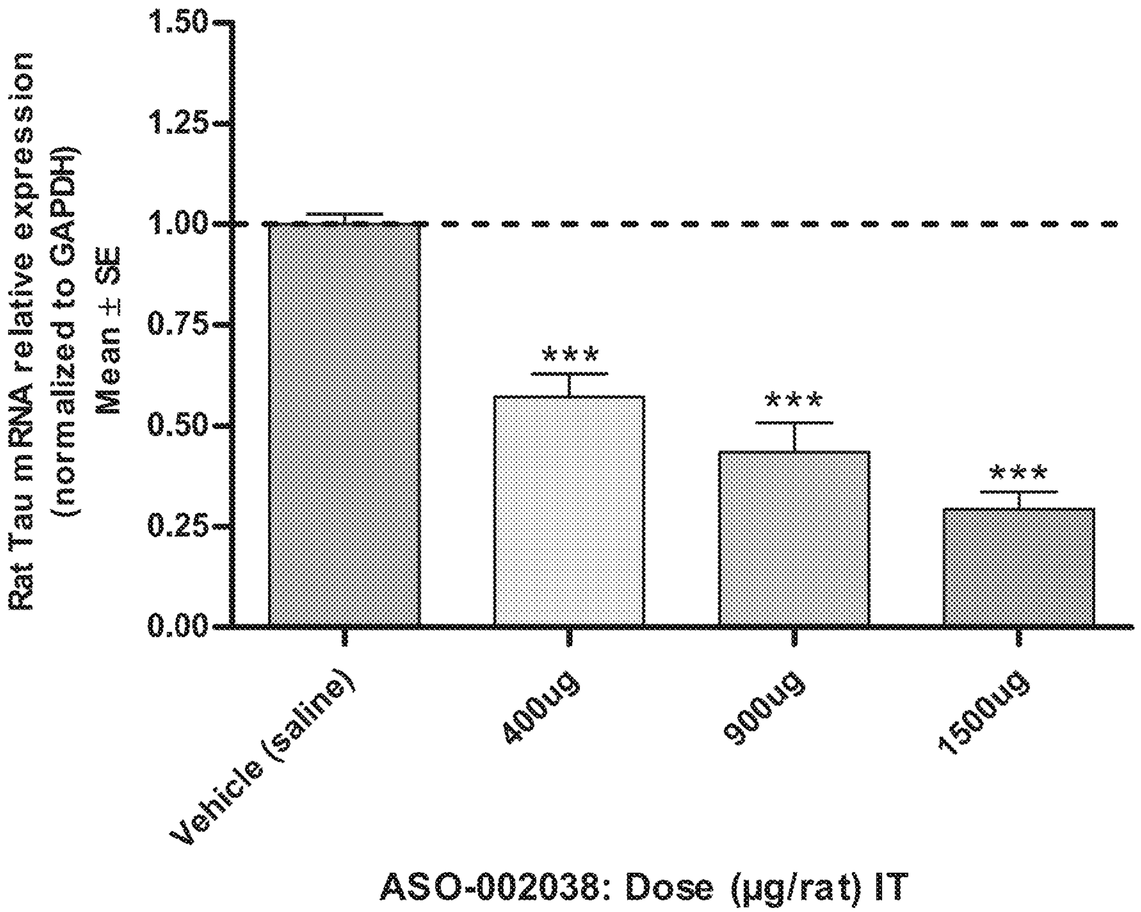
FIG. 19B shows that ASO-002038 (Tau ASO) produces durable, dose responsive brain hTau mRNA reduction after a single intrathecal (IT) injection in surgical lumbar catheterized rats. Saline or 400, 900, and 1500 μg of Tau ASO was injected IT in rats (n=10 per group). The frontal cortical region was dissected 1 week post dose to determine total Tau mRNA levels by qRT-PCR. 1-way ANOVA analysis was used ***$p<0.001$. Error bars represent mean+/−SEM.

ASO-002038 was administered as a single bolus intracerebroventricularly (FIG. 19A: ICV at 25-150 μg) or intrathecally (FIG. 19B: IT at 400-900 μg) in mice or in rats, as described in Example 5. ASO-002038 produced dose dependent hTau mRNA reduction in the brain with a calculated $EC_{50}$ value ~598 nM in mice. At these dose levels, there were no clinical signs of toxicity and no gross or histologic findings observed following a single ICV dose in mouse. Many ASOs including ASO-000013, ASO-001933, ASO-001967, ASO-001940, ASO-001941, and others produced similar hTau dose dependent reduction, $EC_{50}$ for reduction of human Tau brain mRNA, and were well tolerated in mice (data not shown).

Example 10

Quantigene Analysis of Tau, Rho and Tubulin mRNA Expression

To measure tau, rhoA and tubulin mRNA reduction, primary neuronal cultures were established from the forebrain of E18 transgenic mice expressing the human tau transgene on a mouse tau knockout background. (Andorfer et al. *J Neurochem* 86:582-590 (2003)). Cultures were prepared as described in Example 2. Alternatively, iNeurons from Cellular Dynamics Inc., were used per manufacturer specifications.

Lysis: Cells were plated on poly-D-lysine coated 96 well plates at 50,000 cells per well and maintained in Neurobasal media containing B27, glutamax and Penicillin-Streptomycin. ASOs were diluted in water and added to cells at DIV01 to a final concentration of 5 μM. For $IC_{50}$ determinations, neurons were treated with a top concentration of 5 uM and a concentration response dilution of 1:3 was used to define the $IC_{50}$. Following ASO treatment, neurons were incubated at 37° C. for 5 days to achieve steady state reduction of mRNA. Media was removed and cells were washed 1× in DPBS and lysed as follows. Measurement of lysate messenger RNA was performed using the Quantigene 2.0 Reagent System (Affymetrix), which quantitates RNA using a branched DNA-signal amplification method reliant on the specifically designed RNA capture probe set. The working cell lysis buffer solution was made by adding 50 μl proteinase K to 5 ml of pre-warmed Lysis mix and diluted to 1:4 final dilution with $dH_2O$. The working lysis buffer was added to the plate (150 μl/well), triturated to mix, sealed and incubated. Following lysis the wells were titrated to mix and stored at −80° C. or assayed immediately.

Assay: Lysates were diluted in lysis mix dependent on the specific capture probe used (tau, RhoA or tubulin). 80 μl/well total were then added to the capture plate (96 well polystyrene plate coated with capture probes). Working probe sets reagents were generated by combining nuclease-free water 12.1 lysis mixture 6.6 blocking reagent 1 specific 2.0 probe set 0.3 μl (human MAPT catalogue #15486, human RHOA catalogue # SA-11696, or human beta 3 tubulin catalogue # SA-15628) per manufacturer instructions (QuantiGene 2.0 Affymetrix). Then 20 μl working probe set reagents were added to 80 μl lysate dilution (or 80 μl lysis mix for background samples) on the capture plate. Plates were centrifuged and then incubated for 16-20 hours at 55° C. to hybridize (target RNA capture). Signal amplification and detection of target RNA was begun by washing plates with buffer 3 times to remove unbound material. 2.0 Pre-Amplifier hybridization reagent (100 μl/well) was added, incubated at 55° C. for 1 hour then aspirated and wash buffer was added and aspirated 3 times. The 2.0 Amplifier hybridization reagent was then added as described (100 μl/well), incubated for 1 hour at 55° C. and the wash was repeated as described previously. The 2.0 Label Probe hybridization reagent was added next (100 μl/well), incubated for 1 hour at 50° C. and the wash was repeated as described previously. Lastly, the plates were centrifuged to remove any excess wash buffer and 2.0 Substrate was added (100 μl/well). Plates were incubated for 5 minutes at room temperature and plates were imaged on a PerkinElmer Envision multilabel reader in luminometer mode within 15 minutes.

Data determination: For the gene of interest, the average assay background signal was subtracted from the average signal of each technical replicate. The background-subtracted, average signals were divided by the background subtracted average signal for the housekeeping tubulin RNA. The percent inhibition for the treated sample was calculated relative to control treated sample lysate. Results of Quantigene assays for cells treated with the oligomers (ASOs) are shown in FIGS. 20A and 20B to 20C.

The invention claimed is:

1. An oligomer consisting of the nucleic acid sequence AtTTCcaaattcactTTtAC (SEQ ID NO: 473), wherein upper case letters denote beta-D-oxy-LNA, and lower case letters denote DNA monomers.

2. The oligomer of claim 1, which comprises an internucleoside linkage selected from: a phosphodiester linkage, a phosphotriester linkage, a methylphosphonate linkage, a phosphoramidate linkage, a phosphorothioate linkage, and combinations thereof.

3. The oligomer of claim 1, wherein calcium oscillations of neuronal cells which are in contact with the oligomer are greater than or equal to 95%, greater than or equal to 90%, greater than or equal to 85%, greater than or equal to 80%, greater than or equal to 75%, or greater than or equal to 70% of oscillations in a cell not in contact with the oligomer.

4. The oligomer of claim 1, which has at least one property selected from: (1) reduces expression of Tau mRNA in a cell, compared to a control cell that has not been exposed to the oligomer; and (2) reduces expression of Tau protein in a cell, compared to a control cell that has not been exposed to the oligomer.

5. A conjugate comprising the oligomer of claim 1, wherein the oligomer is covalently attached to at least one non-nucleotide or non-polynucleotide moiety.

6. A composition comprising the oligomer of claim 1 and a pharmaceutically acceptable carrier.

7. A kit comprising the oligomer of claim 1 and instructions for use.

8. The oligomer of claim 1, wherein all internucleoside linkages are phosphorothioate linkages.

* * * * *

SEQUENCE LISTING

```
<160> NUMBER OF SEQ ID NOS: 960

<210> SEQ ID NO 1
<211> LENGTH: 140924
<212> TYPE: DNA
<213> ORGANISM: Artificial Sequence
<220> FEATURE:
<223> OTHER INFORMATION: MAPT Genomic Sequence

<400> SEQUENCE: 1

gggattacag gcgtgagcca ccacacccag cccagaatgt ttattagaat gcacaattaa     60

taccagaggc agtggggaag gaaggactga gcagaggagg aagttgagtt gtgattcaac    120

ccaacaactg cctggctggc atggggagct ctggagttaa atagggccat cagactttcc    180

cagtgtgggg ccaacatgac tgggtcttta tacccccacc tctgtcagtc actcaacgtg    240

gtctccctgc aacaaggtga ctcttgcagc cgagacaatc cctgaaggga cagaggctga    300

agcctgtctg ccaacagcac tcccagtggc tggaacaagt ccttccctat aggggaatct    360

gggcggcaca cctccatctc catgtccatc acatacgata tcacagacat ttaaatattt    420

tgataactgt acataagagt ttcctttata atcttataga tcttatttta tgcatttgaa    480

aatattcttc tgagacaggg cttttatcat attgccatag ggtgccacga tataaaaaag    540

gttaaatact ctctgattca gaagtatcca atgatgactt ctctctcatg catttaattg    600

aaaatctggt ttttctcctt ctctgctagt tctctacctc tctccccacc tcccacatca    660

tagcctattc acatatgtct gaatctcatg atagacaagt tcaggttctt ttcccaggtt    720

ctttttacca catcccccca cccccacata aaaagtatat atggcacagc ctaggttcca    780
```

-continued

```
cccaaatcct ttctcctctt cttcctgggc ccacaactct cctacataca ttggtatacc    840
ttgcgcttag ggatggccat gtgactaagt tctaacagtg gaacatgatc agatgccact    900
tccagcctct aagacagcca gtgtgtttcc tccataagct ccttctcttc ctcccaactg    960
gagactctaa atgatgaccc tgcctcaagc aagcaaacaa caagtccctc aggggtggtg   1020
taggctgcaa atggaaggag cttgagtccc aaaccttcca cggagaaggc tggctaccaa   1080
cctggatcac tcacccaaga ctgctcgaag agttggtttg aaccattgtg ttttggggtc   1140
tatttattac aacagtttag cttgctttgt gaatagattt agtggcagag cctccaaatt   1200
ctatagatac attgatctca gtcctaaccg catctggaac accattaaat aaaggaattg   1260
caaacccaga gaaggtaatg aatttgtcta aggtcataca agatggctag gatcaggacc   1320
caactctcca gttttctttc ttctctgcta ttctgccttc tgtgatccta cataagtggg   1380
catgattgta taacatatgc ggccatgaga tttctctttc agcaagagaa agggacagga   1440
agaaagagag ggaatgcatt ttcttggcct gaattagtgt gagccattag ttacctacat   1500
tgactaaatt atctggaatg aacattcaac tctacatcac atatagttaa aatgacagat   1560
ctgcttaaga ttgtttctag catacgttat ttcaatttag gcaaatgtga ccattcagtg   1620
tgaggggacc atactgtcat taggtccctg tcagttctca attatactgt tatcttagag   1680
ggggaaaaat gtgaaatttg aatgtagacg agtgttgatt tgactgctac agtttatttt   1740
acgtatagaa ataaaataat gtgtagcaaa agcattatta caaagatgat aatgaaataa   1800
ctagtattta taatagtata atagtatagt atttataata gtatgatagt ttaatgacta   1860
tttgtcagat gttgtgtaag aaactttata cacacacaca cacacacctc atttaattcc   1920
tgtatcaatc aggatacagg acgctgtggt aacaactcct caaatctcgg tggcttgcac   1980
aacaaatgct tatttctttt tttttttga caccaagtct tgctctgtaa caggctggag   2040
tgcaatggtg caatctcggc tcactgcagc ctctgcctcc tgggttcaag cgattctcct   2100
gcctcagtct ctcgagtagc tgggaacaca ggcacgcgcc accacatctg gctaattttt   2160
gtgattttag tagagatggg atttcaccat gttgctcagg ctggccttga actcctgacc   2220
tcaagcgatc cacccacctc agcctcccaa agtgctggga ttacaggcat gagccactgc   2280
gcccagcccc aaatgtttat ttcttgctca tgtgacatgt acttcctcga gtttttcctt   2340
cctgagatct aagctgaagg aacagctctc tggagccacg ccattctggt ggcggaaagg   2400
aagagtaaaa gtggtagaac cttgcaatgc tcttgaagcg cctatttgga atgtctacat   2460
catgtaaatg gtaatggaca agtatgtata atccccacac caaaaaaagg ggacactatt   2520
ggggacaata accacatttc aatgctgcaa gacggatatt gactgcaccc ccttcccact   2580
ttcagaaaga agaagagtaa ttttgctgaa ctccttctag agactggaaa tgtcccttcc   2640
agttggggtg attagggaag gctttggtaa aatttgagct agagtttgaa ggttaggtag   2700
actactggtg ggtgaagaaa gaacaaggac ctttgtaggc aaaggaaaac ctcagaatta   2760
cagaggtgga aaaagagttc tagtcaagcc acttcagctg gctacagagt aggtgggaaa   2820
gaaaatggga ggacaagggc tcagatgatg gggggttggg gcattggggg gacacttgaa   2880
agctaaacta aggggttgaa cttaatttag gaggcagtta gaagctttta catatttttg   2940
agcaagagag tgacataatt aaaatgatct gggccaggtg tggtggctca cacctgtaat   3000
cccagcactt tgggaggctg aggagcttgg gtcacctgag gtcaggagat cgagaccagc   3060
ctggccaaca tggtgaaatc ccgtcctact aaaaatacaa aaattagccg ggagtggtgg   3120
catatgcctg taatcccagt agctgggagg ctgagacagg aaaatcgctt gaacccggga   3180
```

-continued

```
aacaggttgc agtgagccga gatcgtgcca ctgcactcca gcctgggcaa cagagcgaga   3240
ctccatctca aaaaaacaaa acaaacacac acaaaaaacc aaaaataaat aaataaaatg   3300
atcacttctg aatactgatc taactagggg ttgcagggtg ggctgatata gggagaaact   3360
ggagagcaag gagatcacta aggtccctac atgtccagaa ccaagataga ggtcttgaac   3420
taggatggtg gcagttagaa caacaacaac aaaaagtcaa ttccaggctg agtgcagtgg   3480
ctcatgcttg taatcccaac gctttgggag gctgaggtgg gagttagaaa gcagcctggg   3540
caacactgca agacctcctc tctaaaaaaa aaaaaaaaaa aaagttagcc aggtgtggtg   3600
gtgcccacct gtagtcccag caactcagaa ggctgaggtg ggaagattgc ttgagcccca   3660
ggagttcaag cttgccgtga gctacgattg tgccactgca ctccagcctg agcaagacct   3720
tgtctccaaa aaaaggtcaa ttccactgac ttttctaagg tgtacaccat caaggggcag   3780
ctccatctcc aggccattgg ctcatgagac attctgtagt cagaaggcta gggcagattg   3840
ctttgagcaa gcccccatgg tggttctcac tcctacttct ttgggtatat gcccctctgt   3900
ttaaaaataa agttaatatg catttaaaaa aaaaaaggag aaaaaggtca gttccagaaa   3960
ctgtgtgaat aaagcatttt acttgctttt tctattaatc tataacatat gttgattttt   4020
taaaaagaat ataagagcta tgcaaattgg agcttcaaga caacttccca tctccctagg   4080
aggagatggc tgccctaaac ccccctacat agaaatcatc ccactgcttg ggcttaaact   4140
tgatgttggg gaaatgaaaa atccaagcta aggccgaagc ctggggcctg ggcgaccagc   4200
agaatgagga ccactggtca gtttcaggct gaggtgcgtc ttccagggga caatctctag   4260
ctggccctta aacattcaga cttcaagctc tatttacagc ataaaggtgt ttcaaaagac   4320
gtgatacaaa taactgcaaa tgctctgcga tgtgttaagc actgtttgaa attcgtctaa   4380
tttaagattt tttttctga cgtaacggtt agattcacgt ttctttttt ttaagtacag   4440
ttctactgta ttgtaactga gttagcttgc tttaagccga tttgttaagg aaaggattca   4500
ccttggtcag taacaaaaaa ggtgggaaaa aagcaaggag aaaggaagca gcctggggga   4560
aagagacctt agccaggggg gcggtttcgg gactacgaag ggtcggggcg gacggactcg   4620
agggccggcc acgtggaagg ccgctcagga cttctgtagg agaggacacc gccccaggct   4680
gactgaaagt aaagggcagc ggacccagcg gcggagccac tggccttgcc ccgaccccgc   4740
atggcccgaa ggaggacacc cacccccaca acgacacaaa gactccaact acaggaggtg   4800
gagaaagcgc gtgcgccacg gaacgcgcgt gcgcgctgcg gtcagcgccg cggcctgagg   4860
cgtagcggga gggggaccgc gaaagggcag cgccgagagg aacgagccgg gagacgccgg   4920
acggccgagc ggcagggcgc tcgcgcgcgc ccactagtgg ccggaggaga aggctcccgc   4980
ggaggccgcg ctgcccgccc cctcccctgg ggaggctcgc gttcccgctg ctcgcgcctg   5040
cgccgcccgc cggcctcagg aacgcgccct cttcgccggc gcgcgccctc gcagtcaccg   5100
ccacccacca gctccggcac caacagcagc gccgctgcca ccgcccacct tctgccgccg   5160
ccaccacagc caccttctcc tcctccgctg tcctctcccg tcctcgcctc tgtcgactat   5220
caggtaagcg ccgcggctcc gaaatctgcc tcgccgtccg cctctgtgca cccctgcgcc   5280
gccgcccctc gccctccctc tccgcagact ggggcttcgt gcgccgggca tcggtcgggg   5340
ccaccgcagg gcccctccct gcctccccctg ctcgggggct ggggccaggg cggcctggaa   5400
agggacctga gcaagggatg cacgcacgcg tgagtgcgcg cgtgtgtgtg tgctggaggg   5460
tcttcaccac cagattcgcg cagaccccag gtggaggctg tgccggcagg gtggggcgcg   5520
```

-continued gcggcggtga cttgggggag ggggctgccc ttcactctcg actgcagcct tttgccgcaa 5580
tgggcgtgtg tgtgtgtgtg tgtgtgtgtg tgtgtgtgtg tgtgtgtgtg gaggggtccg 5640
ataacgaccc ccgaaaccga atctgaaatc cgctgtccct gccgctgttc gccatcagct 5700
ctaagaaaga cgtggatcgg gttctagaaa agatgactcc ctgcacgccc ctccctgcac 5760
ctcccgagca gtgattccga cagggccttc actgcccctg attttaggcg gggccggcc 5820 ccctcccctt ttcctccttc agaaacccgt aggggacatt tgggggctgg gagaaatcga 5880
ggagatgggg aggggtccac gcgctgtcac tttagttgcc cttccccctg cgcacgcctg 5940
gcacagagac gcgagcagcg ccgtgcctga gaacagtgcg cggatcccac tgtgcacgct 6000
cgcaaaggca gggttcacct ggcctggcga tgtggacgga ctcggcggcc gctggtcccc 6060
gttcgcgggc acgcacagcc gcagccacgc acggatgggc gcggggctgc aggtgcatct 6120
cggggcggat ttctttctca gcgctcggag cgcagggcgc ccggcgtgtg cgctccctgc 6180
cggaggcgcg gggctggcgc gcagggctcg cccctcactg cggcagtggg tgtggaccct 6240
ggtgggcgag gaagggggag gataggctgt gcctcctccc actcccgccc ccagcccccc 6300
ttttttcccc cctcggaacg cgaggtgcca tctttttttcg gcgtgtcacg tctttacggt 6360
gccatgccaa accgggtggc cggggcttcat aggacagggc ggggcctggc attaaaggga 6420
gggggacaat cagcgctgaa atcttggcgt tttgctgctg cgggcgtgag cactgggggc 6480
gttcgcccag caccttcttc gggggctctt tgctttgtct gtagaggtta cgtgatctgc 6540
gctcccagcc ctggtttctg gcttttattc tgagggtgtt cagtcaacct ccccccctacg 6600 cccatgcgcc tctctttcct ttttcgctcc tcatttccga gcccattgtt ggatctcgag 6660
gcttgctggg ttcgatgaac tcgagtcaac cccccgaccc ccggcacgca tggaacgggc 6720
gtgaccgcgc gcagcctcgt ctcggagtct gccggcgccg ggaagcttct gaagggatgg 6780
gattcgagtc tccgtgcgcg ctgcgggcgg cggcagaggg atctcgcccc tccctacacc 6840
ccaagtgtcc tgagggccac gccacaccag gttgcccagc gagggacgct ggctacccat 6900
ccggggatgg gtggggagcc ctggcggggc ctctccggct ttacgccctg ttgcttcgcc 6960
tggccggaga atgtgaggaa ggggcataag gttactggtg cttcggccac acccatcttt 7020
ctgagcccac tggactgggc gcagaggggg gattgccatg gaaaccacag gtgtccggag 7080
aggggatctt ggggctggcc tcacccccttc cctgcggaga ttggggaccc tggggtaggg 7140
ggagccgcgc ccagtcggcc tcctggagga cacgggagga agccccgaac ccccgcgcct 7200
gaggctgttt ctgattggcc cctggaggcc gcagacacgc agataggcgg ccctgggtgt 7260
atttttatta atattatgtc cgtactgatt aatattattt atcttaaata aatttcaccc 7320
gtgtccaagt tcaccgcgcc cccaaaaccg agtctggggc ggcaggggga actcctggcc 7380
aacgaatcca tgcctcgccc tcctgtgatg aacctggtac gcacggtttt ctggttaatt 7440
ctatcgctga aaactggtgc ggggggcgca cttctgagac ggaagagcat ctaggagctg 7500
aatcctccac gcgggtcgcc caggttgatc tgaatttctg gggaatggct tggctgcccg 7560
cccgggacca ggccgaccct ccttgacggt ggcgtagagg gctggagcct gggtactgcg 7620
aggctcctcg catggctggg cccgccgcga ggggttgcag agcggctcag ggatcgattc 7680
aagcatcgtc tctcctccct cgcccccaga cagagctggg cgcggggttc cccttccaga 7740
tggagcgagg gtctcggggt ggccccggaa aaggggagcc cgcggccacg gctacgtatt 7800
gccatctcgc gagcagagat gtcacctcct gcctttggag gaaagggagc ccggtgggga 7860
tgagcgcatt tagcccaatg ctgggaacaa agcgcactcc gcgcttctgc gatttcgctc 7920

-continued

```
cattttgaaa tgtgttggcg ctttggtggg gccgctgcgg tgggcaaggc cgggggcgct   7980
gttaatggag gaacctcagg gggacggtcc ttcgtaggaa actctatcct ggctctgcgc   8040
gcgctttaag gaaatggctt ccctccagga cctcgaggga tgcagctttt gcgcggatga   8100
cggtggggtg ctgaaccagc cggtgcgcct ctggaaatgt ctgggcacgg atcctggggc   8160
catcgacgac tcctccccat tcccagcagg cgggagctct tacattccga gcgagtgacc   8220
cctctcaccc tctggcgctc acacacctgt aactccaaac ctccgtctca gaatggtcca   8280
ggctggaagg gatgatgggg gctccgacag cgactgccta gctcacccct ctgcgtgctc   8340
aggctccagg ctcagcagga ccaatttgag ttctatctga tccccctcgg ccccttaact   8400
gacccatcct acaggagaca gggaaatgtc tttcctaccg cggttgattc tggggtgtca   8460
ttttgtgttt tgtgatggct gcttatattt actgtataag cattgtattt actgtataag   8520
cattgtatta taattactgt ataagctgct tatatttact gtataagcat ctccaaatcc   8580
tccctctacg taaacaaatt aatggataaa cagataagtg tatcccctgc ccccacccct   8640
gctacgcagg tccggagtga ctcttgaagc tcatacattc cttggccaag tttgcttctc   8700
taacagatgt ttatatagca ataacctggc ttggctcttg ggttcacctt tggacgattt   8760
ggggaagggg cttgttggct ttgctgggtt ttggatgagt gacagtccat gactgttcct   8820
gctggaaggg cgtgactttt aagtggtttc taatatcagg cattgctcct ccgacaggaa   8880
caaaagaaat ggatactgcc cataaattgt tagaaaactt agaatcgctt tgattgagga   8940
aaggttagat ttattccggt tggaaaaagt ggcctttcta ttaaacgtgc cctttgaccc   9000
tcatgccctt ggaggtcggt gccagcctgg agatgggata agattgtggt tttccttctg   9060
cctttttaac atctgttgtt acagtccatt tgttgaaaat ttaaagaaac tgttttattc   9120
cactttccct cagcatttat gtgtgtggtt tcagtagctc tgtggctata tgtacgaaca   9180
cgtgttattt ttccaattgg acatgtgata attttccaac tggaccttgc cttctattga   9240
tgtatttatt tagcatcttc cttactccct ccttgaaaaa gaatcactca aaaacaaata   9300
aaaacagccg taggggccta atacagtgct agacatacaa gaggtattcg gtccatacca   9360
aatggatttt atccatgaag gataaatggg gaaatacagt gggaagcagg tgggaaactg   9420
cgtttgactc tgctctttcc tccaccacca ctttcctcat caccgtgttc agagaccccc   9480
aaagccccct cacactccca gaaacacccc cctggccact cctaacttgc catgcccagg   9540
agttaggtgc ttccactagt gacatggagc tggcgtttgg ggggcacctc agcaggtgac   9600
gggaagagaa gaccccagcc tcaccagctg ggctgcagca gggagaggag tcctcatgtt   9660
ccagcaggga ctctcagctg ttttcctgta aaaccatggt tctcaactgg gggccactga   9720
gatgtctaga gagatgtttt tgttttcaca actcggggag ggtgctactg acatcttgtg   9780
ggtagaggcc aggaatgctg ttaaacatcc tacaaggaag gcacaggaca gtctcctaca   9840
tcaaaatatg acccagtccc aatgtcacca ctgctggggt tgacactggc actgctatct   9900
taattacatt cattgagtgt cttttaggag gccctattct aagtgcttgc taagattatc   9960
tcatttaatc ctcacaacac ttccgctatg tagcaggtgc tgttattatc tccgtgatgg  10020
ggaaactgaa gcacagagag ggttagtaac ttgctaaagg tcacagagcc agtgggtggt  10080
ggagctggtt gcctgacact agttccctcc cctctcagcc acatgtgggt ttacttggcc  10140
attgtggact agtctgggaa cccagatatg atctataaca ttgacccagt agaatattga  10200
ttccaaaacc actgtctcac aaatgaattt ttacaagagt ctgtaatcgg agcatgaccc  10260
```

-continued

```
agaataaggt tagggagatg tggagttaaa gctctcaatt tcttatctgg ccccgacaca  10320
gagagcaagg catttcactc tacattggtg ctctgtttat aaaacaaaga gcaaatatct  10380
cttcctaagg tccttaaacc tcttccccca atccagggtt tctggactgc tctgccatat  10440
gacggggcag ctggtttgat tgacccaggg aaggctggaa atcaagactg ggggatcaag  10500
acgtagattc agtgtggcca aggtcaagtc tctgaggttt agggacatca gatccccagc  10560
ttaggttctg tacctcggca aggtgaaagc gttggcgccc actgatgagg cctgctctga  10620
gattgtgggt gtgggttgag ttgggtgggc ataggcaagt cctcttgtaa gaatcttttg  10680
gcaaagatgg gcctgggagg cttttctcac ttcctggggc ccaggctttg caataagtat  10740
tccattatac tgtggtacct tggggctacc tgagaatcct ctgtctcgcc cctgttgcct  10800
tgccaaagag tttgctgtcc aagaattcct ttcctgtctc caggtgccat gctcctgcca  10860
cctctgccag gttccctgcc tgcccagatg gctcccaact gagtgtgagg aggaatttga  10920
gacaggtttt gagctttctg ggttctccag ttaggaaact ttctgtaagc atgcagatag  10980
aatgggcttc agcaaaatac aaactcgaac aacttccatg tatagtccct taattttctt  11040
tgctttttc atatttcatc aggctccatg ctgagcccaa tcagggaccc gatagaaatc  11100
caaacaccat gtcagcgagt ccccaagaaa tgcattttgt gccaaggcta ttcaaggaag  11160
gtttgggagc agctcaaggg cagacactgt taccctcccc caggtcccca gtgcagggca  11220
gtgttctgca tgtggaggca gtttggccta atggttaagg aggtaggctc tgatcgggcc  11280
tcctgggcac aaatcccagc tccctgctca ctgtgagacc taagccatat tgtttagctg  11340
cttggagagt tttttgtcat ccacaacttg gagtatgatg gtacctgtct cacgggttgc  11400
catggggttc acacaagcta acccggtact cactagggcc aagcacatag taactgctca  11460
gtaaatggca tcatcggcgg tgtcctgtgg atgagtgctt gtgattggct gaatgaccag  11520
aggggtctaa agatcctggt gatggaatca gttgtacaga taaattgtta cactgagtag  11580
ggatcaagat aggaaaagtc ggcaactacc cagctcccct gcaccaaact gggcagaagt  11640
ggatcctctg aaaattgcac acacccatgt ttaaatgtac acacagaact cttgccacag  11700
gcaagcggag atttgtcatc tgctgtccct gcctcatctt cttcctgaaa tccactccat  11760
gccaggaata aactgcatgc tctccaccag cccaaactga cctgccttcc cgccagccat  11820
cccgggcagg gtgacctggc ttagtacatc gggttcagag atctttccag tttactcgtt  11880
gaataaaaag tgagggctga tcgagaaagt aatggcagtc agggaaggcg aaggaggtaa  11940
agaagagatt ttacaaatga agtaattcaa cagagtgctg acattggtaa actggcaaac  12000
agatttcagg gtggttggtt gagagtagag tagaaaagga ttaaataaag caaacttgtg  12060
gtgtactgaa tcttaggaat tccatgtatc caataagtat agtcatttat gaattaataa  12120
attcggccta agaagccttc ttatcgctta aatcaagact aagtaacaat atatcagttt  12180
taaaaagtca ttatatcaga aaatcattta aatgatacac atagatttcc aagattttac  12240
tttaaccgaa actatataaa tgtgaatttg ttcacccatc ttttgacaca gggctcaggt  12300
cttctcttgg tgtctggatc agccagttga aatttcttgt ctgttttgcc tatgccacat  12360
taataatgca ctgtctgggt cctccgattt cagtttggat tttgggttta cattgtggag  12420
tcatctgaat gcagaatcct tcagggattt tacttttttt tttttttttc atggtcttta  12480
ccatcccatt tgatagtaaa tattactcac ctttatgaag tctttccaaa acattcaact  12540
aaattttctt aaaatcattg aatgatttga agagcttatt cctcagcact tttactccat  12600
cagcttgcac cttatttttt aatctttttt tgagacggag tctcgctcta tcgcccaggc  12660
```

-continued

```
ttaagtgcaa tggcgcgatc ttggctcact gcgacctcca cctcctgggt tcaagcaatt  12720
ccgcctcagc ctccgccgta gccgggacta caggtacaca ccataatgct cggctgattt  12780
ttgtattttt gtagggatgg ggtatcgcca tgttggccag gctggtcccg aacttctgac  12840
ccaagtgatc cacccacctc ggcctcccaa agtgctggga ttacaggtgt gagccaccgc  12900
gcccggccag cttgcacctt atttaggata tgtgattatt atagcaagtc tggtgtacat  12960
acaagatttt gaatgggcac agatgacctt tagtaagtgc ttggctgtga taagaggcag  13020
tcctgactgc agatcaggct gtgtggaccc cagccttgca tgtttacaga ccttcatgtc  13080
ttattcttac agggtatcag aagaacacct actggggaaa cttataaatt agtaaaaggt  13140
gggcattctc cccgcccatc ttctgtctgt ctgccaggac tagcacagca ctttgaagtc  13200
attcacatag aatcccaact taagagggta aaatcctcct caacagactg aaaataagtt  13260
taaattccct ttgctatatt aactcccctg aggaaagagt cttagatcaa tgtccaacac  13320
taaaaacagt tttaaatcag caagtgagaa ttaaatctga agcaattgat aataatgttt  13380
cattcattcc tctcctttgg ccccgtccac cctactgcta aatccaggca tcaaagagaa  13440
gagggacata attatctcta gtcccagctg ctggttttcc ttccagccta tggcccagtt  13500
ttctgtttta ctgagaaggc tggtgatgtt atcttgggat ctaagtctgc agtttcacca  13560
caaaaagtcc agggatgcac tttcatgctt gtgtcctcct ccctgggata gcaaggatat  13620
tagaagaccc ctggctctgt aattgcttgt catgtgctct acagacgcca cagaatgcca  13680
agaacgaagt gctgggaagg acaaattcat ggaaccgtgg gacggtgctc ctcccccagc  13740
gtaaaggaca gctcctcctc ctgaattgga gccagcgttc taaatcatgt gtcaacagag  13800
ttgtcctgga tcggatccag ttctgccatt gatttgcagg tcatttcagt ggtacctgtt  13860
tccagttgtt cttaattgaa cagtggcacc aaactattgt cttgcctcat ccccctccca  13920
tggcctgtcc cccaaaaaga gacttcttgg gtaattaatc agggcaacat caggcagtct  13980
gggcgcggtg gctcacgcct gtaatcccag cactttggga ggccgaggcg ggcagatcat  14040
gaggttagga gattgagacc atcctggctt tgtgaaaccc cgtctctact aaaaatacaa  14100
aaaattagcc gggcgtggtg gcgggcgcct gtagtcccag ctactcgaga ggctgaggca  14160
ggggaatggc gtgaacccgg gaggtggagg ttgcagtgag ccgagatcgc accactgcac  14220
tctagcctgg gcgacagagc tagacttctt ctcaaaaaaa aaaaaaaaaa ggaatctctt  14280
tggttttata tatttttttt tatatatata atatatatta aaatataata tatatattta  14340
tataatataa tatataaata tattatatat tatatatttt tatatattat atattatata  14400
tattatatat tatatattta tatatttata tattatatat atttatatat tatatattta  14460
tatatattat atatttatat ataatatata ttatatatta tatattatat attatatatt  14520
atatatttat atatattata tattatatat attatatatt atatatttat atattatata  14580
tttatatata ttatatatta tatattatat atttatatat tatatattta tatattatat  14640
atatttatat atattatata ttatatatta tatatgtata tattatatat gttatatatt  14700
atatatattt atatatataa tatattgtat atattatata tctaatatat tatatatatt  14760
atatatatta tatattataa tatatattat atattatata tatttttata tatataatat  14820
gtataatata taatatatat aaaaacatat ataatatata ttatatatta tatatatatt  14880
atatatatta tatatattaa atatatttta tatatattat atatattata tatattaaat  14940
atattttata tatattatat atatatacac atatatatat ataaatgagg ccaggctcgg  15000
```

tggctcacac ttgtaatccc agcactgtgg gaggatcact tgaagccagg agtctgagac 15060
tagcctgggc aacaaaacaa gatcctgtct ctacaaaagg aaactgtaaa aattagctgg 15120
gcatgatggc atgtgtctgt agccctagct acttgggagg ccgaagcagg aggatcgctt 15180
gagcccagga gttcaaggct acagtgagct atgattgtcc catagcactc cagcctgggt 15240
aacacagcaa ggccctgtct ctaaactttt tttttttaat tctatttata tttacatgta 15300
tttaaatgtg aatattcact acctatttgt tgcatgcctg catttttat actgggcttg 15360 ccaaaaaccc gaacagcttt ctactttgac aatgtatcag aatttaaatc agcaatatgt 15420
taataagcca agcaaaggtt atatatgcaa ataaaactgt tgtctataac ctcctgttac 15480
actggggcac agcaaaagtc atggtgtagt cgcatgtgaa cctgtccctt tcatagctgc 15540
tcattgccag gaaacatcag gaatagccat ttggaagagt catcagccct cccaccatcc 15600
gttttctgtc ttgtcttttc cctatgagca ggggaaattc cacgctggcc ccaatcccca 15660
gtgcagcggc tcagcctctg cctctgctgc tggtccccat gaggccagct tagaaacgga 15720
ggattttgca gaacatccct aaatccgctt gaataatgaa gtgatcattc ataaactcac 15780
ctgaacctta ttaaaaccta tttaatattt ttcctggata atcctatagg gataacttgc 15840
ctcctgggct tctctccacc gggttcagtt cttcctttag tggtgaagtt cctcccttct 15900
tagcatctca actgtgcctg agaaaaggcc agtggcggct gcactctgtt ccctgtggag 15960
tgttaataaa gactgaataa attgaaataa atccctttca atgtcattaa gtgctataaa 16020
taatcatgaa ccaatgttcg atggctgatg agaaatgcaa gaaaaaattt ttaatcagta 16080
ggattcataa gttgacaatc tgggccaagt taaaaaaaat aaaaataaaa agacttttaa 16140
aaagatctta tcgtttgtta ccagtaagac tgaattccag aagcaagcta ctccctcatt 16200
tgtgggcccc tgttatcact ggctgcttag ggttgccaag ccctgaattc atttgtcaac 16260
taagagattt ttggccaaga ttaagatttc ccatgcctcc atatttccat ctgagaaatg 16320
gagattatac tgtcttcccc ctcagaatgg atgataatgt ggtctctctt ctgttcgcat 16380
agtcatagaa ctgaaataaa acaacttaag agaattcctt tgagcttctc agaagtgctg 16440
cagggctggg ggatgcctcc caggagccgc agtcaggtgc tgatctgaag tctttggtgg 16500
gctgacttta gcctgacctg aaatagtata gctgctgcca cctggctccc ttagcgtcag 16560
tcagacggtg cagctggttc ctaggggtga gggctgagcc agcagggtcc gtgcccagga 16620
gggatgcatg ggtggccaca gcccagcctg cactgatctt gtctgtcccc ttctttggaa 16680
ggaaggagcc ccaaaccagg gtgcaagaca gtgggtgggg gtgccttgag catgacctca 16740
agtgatttcc agcccctgcc agtgctgact tctctgggga agggctggga cttccttctg 16800
ggctcaagtc acgacccttg gatggaattt cctgggagct tttctgtttt ttctggagtt 16860
ttcagttttt tcctaaccag acagggactt ggtacagaat ctcatattct aattatgcct 16920
aggagcagcc tctccccacc actcacagtg tttagcatgt gacaggaatc gattaaggca 16980
tgagtgatta aattaaagcc aggcattgac ttggatggtg taatattctg acatctgttt 17040
ggtgtcaaag gcacggggca ggcgcgttaa ttgaactgct tgcacctggc atttgaattg 17100
agccagagcg gggctaaagt cagtttgcct tcaccctgta aatggagggt ttctccggag 17160
cgtggatggt gggaggtatt tcagggtgta tgcataaccc ccaccctgac aatggcccat 17220
ctcttctcca gcgtggccag gtttgagtgc cagtcctggg tgtccagtgg ccccatagcc 17280
ttgcgtttta gtaaaatgct gcccccatta ccacctggtc tgtgcacttc ggtcactgga 17340
atttgccatc ttccagtccc gaatgtggca agccatggag ccttaagctc ttctccctcc 17400

```
acatcctgga acagacccgc cagtttcttc caggcattgc ctcagtttgc ccctctgttt  17460
ccagtcacac tctcaccagc gataaaatga ttttagacct tatcatctca ccctcggatc  17520
cttatggaaa caataatgag ttgttccctg tttcaattcc aaaattcata tccaatccgt  17580
tttgcatgcc attgccaaat tcctcccaga gcaaccccgt cacctgccct ggccctctcc  17640
aagtgtggtc ctgccatggg catcgcctgc taagccaagc tggcctcgag ctgcctgccc  17700
gggtccccac accttggctc acctccctgc ccagtcccgc ctcctgccag cctgccctgt  17760
ggctccttca tagatgccgt gctctttctg ccccttgctc acccatggca gccttgcccc  17820
tctctccctg ccccaccccc tatttaaatt gacctgacct tcctcagtgt ccatcttccc  17880
cgaagctttc cccagccttg gcactcaagg tccagaggct acgcgtttcc tctcacctgt  17940
ggcagcgccg tgctccccag tgcctcacag tttccttctt gcccccgctt cctgtgtagg  18000
actcatctgc ccacaggttg cacgtcctgt gagggcaagg actgtgtctt atgtgacttt  18060
ccttctccag tcacagagct gggcacatag atagctcaaa accctcttta ttaacacagt  18120
tggatgttga gaaatcaaac aggccaatgt caaatgagct ctccttattt aaatcaagtc  18180
agttctccac ctcctagcac tcagttccag tactctatat acatggaaat aataaaaaac  18240
acatttcctt tgaaacattc tataatcgtt cctttgccct acttcagacc aacttaacgc  18300
actccccatt ggtccaaatg agttttgcta tacgaagatg ctgataataa tagcagcagt  18360
ggattattct gctaaaacca ttgcctcgtt aatcctcagt cccgaggtgg ggattattat  18420
cctcattttg cagagaagca aactgagact cagagatttc acagctgggg agggagccag  18480
ctcatccctc tgtccaggcc caagctctct cccgcttgcc ttcctgcctc tgcaacctca  18540
gagcatcccc catctggttc tactgcctgt gctagtcgtg caggagccaa aagacacgtc  18600
tttagtgcta aggactggag aagccatgcc ctccagcctc tgtgaatggg tcatatgtaa  18660
catgagcctg gagaaattat ttgaaaccaa aggcaagcct ctaaaccagg ctgctgcttc  18720
atggcgccgg tgacggcaga accaaattta gtgctgtggg caggtccaca cttatcaaat  18780
agagaagctc atttttcttc cggctcacat caagcatgaa aaatgttcac acataccccc  18840
cacacacaca tgctttccgg aggggtccat gtggctagag gctggaagat gtggatgaga  18900
ggagcctggc aggtaagccc agggaagatg acattcagct tcccagacag catctacagg  18960
gagaaattta attaaaagtg gggcggtttc cctgagcaag gcagacaaag tcagccctct  19020
actgttaaga aaaagggtca cagtgagagg ggaggtgagg agactgagtc tgtattttct  19080
agtctgttgg gctacactac ctgatccccc ttcctcaaaa atccacttta ctttccccat  19140
gtctacacca atgtggttca cactctggga ccaggaaaag ggggagtgat ggggaacaga  19200
gaagggagga gctcacacag ctgaggctgg ggttatgcat atcgaattac ttagaatttg  19260
caacctcaca gggtactttc atggcgttga aatacacttc ccacagccac cctccctcta  19320
actaaaagca agagtcattt ctcagttctg gtcttgcctc ccacgttctc ctccacattt  19380
aagaaaatcc accagctaca aagtgaagat accatatgtg atatcccacc ctagtttctg  19440
ttttatcagg gtttggagca ggtggagcag gcagagggat catttcagcc tataaattgt  19500
attaagggtg agtactgagt cattcttcaa gaaaagtttt agaagcatcc aaaactgaag  19560
ggtggagcca cctggagaca gtatcatcag tcctggcccc gagcatggcc tgcataggcc  19620
cccatggatc ccagcgggag ctgcagagtg cgggcacctt ggcacacagc cctgagtgca  19680
aaattaggag ctgggcagag ggcatctctc tgtcgccatt gggcagccca gggcacactg  19740
```

```
gtcatagcct tagaccacga acaccctgtg cccgggggac agatgcaacc agtgtgccct  19800
gggctgccca atggcaacag agagatcgac acctggaccc catgtcacgg ggactccact  19860
actaaggctc ctaagactgc caccttccag tgggataagc cctgcctcct actgggccca  19920
caatgtgcag agaacacttg ggactacctg gctttctgga tacacaaata ttgatccaat  19980
ctggactaat tagaaggtca gtcccaataa caaatcgaag tcagctgggc gtgatggctc  20040
actcctataa tcccagcact ttgggaggct gaggtgggca gatcatttga agccagaagt  20100
tcaagaccag cctgggcaac atagcaaaac cctgtctcta ctaaaaatac aaataattag  20160
gctgggtgtg gtggctcatg cctgtaatcc caacagtttg ggaggctgag gcaggtggtc  20220
acctgaggtc aggagtttga gaccagcctg gccaacaggg tgaaaccccg tgtctactaa  20280
aaacataaaa attagccaag catgatggca tgtgcctata atcctggcta ctagggaggc  20340
tgagacagga gagaatcgct tgaatccagg aggtggttgc agtgagctga gatggtgcca  20400
ctgcactcca gcctggttga cagagcaaga ctctgtctca aaaaaaaaaa aaaaaaaaaa  20460
aaaagccatg cctggtggag cactacgtgt aatctcagct atttgggagg ctgaggcacg  20520
agaatcactt gaacctggga ggcagtggtt gcagtgagct gagatcgcgc cactgcactc  20580
cagcctgggc gacagagtga gtgagactcc atttcaaaaa aataataaat ctgagtcact  20640
ttaatattgt tatttggatg tcaacctcta ggtgtttgag acaggagagt gatatggggg  20700
cactggaaac acacaggcac ggggtgtcct cacacttggg tagcccacac gatgtgattt  20760
cagggtgctg ggaggtcccc ccactcccca aattactaac aagtggatag tactttacag  20820
tttatatgat ctcatttgat tcttaacatg agcctgtgag tgaaaaattc cttcccctct  20880
tctacagatt aggacgttga gattcaggga ggttcagagg gattcaggga agtcaagtgg  20940
cacctggagt cccgtggcta atttgaggcc ggtaggggat tcgaacccag gatttgtgct  21000
tcttatgcct gggcttctgc tccctggggc atggtcttcc ccctagcttt cccattcact  21060
gctttagcct aggggtccta ccctttatta aactgccagt gcctcactgc ttttctcccc  21120
caaagacaaa aaaaaagtgt ttttgctttt gttttgtttt tcatgggcag agacctggaa  21180
tttcagcttg agaatttgtg ccatatgata aataaatcaa cagatggctt tttccttaaa  21240
aaaaaaaaaa aaaaaaacta agatgtattt gcagtgaggc ataatttgta ccaaaaagtg  21300
ctcaccacac tgtagtcatg gggcaggag gcagccgcgg gtgaagggag aaatcttgga  21360
gtccaggcag ccccccttctg ggctgaactg gggagctggg ggtgctgcca gccctgccag  21420
gttctcctag gaggcggcag ctcatatggc tgtgggagga ggcagaggga gcctcatatg  21480
cacccacatt tccagggatc tagaagacag aaggaggaaa accaccatca tgttaaagca  21540
gacagttagg taacacatcc tgtaatacaa gttatttttt ccacatctaa aggctaaaaa  21600
tagttgttag aatttaaaga taattggtaa atgagtttct atccttctag tttcacatca  21660
aatggaatca tgctgccttc acatcactag tgcccgttat ttgtgtttaa tttccacaat  21720
gttgtctaat tccactcttt gggcttcccc agggatccag cctccctcac tcgcccatcg  21780
cagggagatg ctttattcat ctttgtgtct tctgtgccgg gcatagcgca tggcacagaa  21840
taagcactca gtaattgatt cacgagtgaa taaatggatg agtgggtgag ttcaatattg  21900
actacaaaaa ccctaaggcc acactggtga gtggctgcgc ctgtagtccc agctgctggg  21960
gaatctgagg caggaggatc tcttgagccc aggagtttga aactagcctg ggcgatatag  22020
cgagaacctg tctcaaatga caaaaacagg gccaggtgca gtggctcacg cctggaatcc  22080
cagcacttta ggaggccaag atgggaggat cacttgaggc caggagtccg agaccagcct  22140
```

```
gggcaacata gggagaccct gtctctacaa aaaatttttt aaaaattagc tgggcatggc  22200
ggtgtgcgct tgtagtccca gctactcagg aggctgaggc aggaggatca cttgagccca  22260
ggaaattgag gctgcagcga gccatgatgg caccactgca ctgcagcctg ggcgtcagaa  22320
cgagacctgc tctcaaaaaa acaaacaaac aacaaaaaaa aaggctttct taaagagact  22380
tgagaacaga aaggggaaca gatacataac ttatatattt atttgttcat ctttccacct  22440
tcctggaggg tggaggggaa caggtctgta tttggagttt tgaatgctaa aagtgggaat  22500
acatgtactg tttgccatga tctgttcaaa agttaagcca aatgccttag attctcctga  22560
aaactggaat gccactgtaa actataagcc ccacttcaaa gataaaagat cttgatgaac  22620
agggctgggt ctgtggactg ggcctctccc caccacacaa ggaagggtgg tgccagttga  22680
aggaaaatca cttaaatcct tgctgtctcc taataaggtg tggtcccagg tagggctgtc  22740
agaattagca aattaaaaca cagggcatct gtgaaaatta gaatttcaga taacaacaaa  22800
taattggcat aggctgcata atgtccctca aagatatcag gtcctaatct ccagaacctg  22860
taaatgtgat cttatttgga aaaggggtct ttgtagatgt ggttaaatta aggattttga  22920
gatgggggga ttatcctgta ttatctaggt aggtcctaaa tgcagtcaca ctcatccttg  22980
taagaggaag gaagagagag atggaaaaca cagaagagaa gacaatgtgg tgatggaggc  23040
agagattgga gtgaggtggc cacaagccaa ggactgctgg cagctaccag cagccagaaa  23100
agtccaggaa ccaattctct cttggagctc cagagggagt gtggccctgc tgacacctta  23160
gcttcaacct agtgatcctg attttggact ttggccttca gaagtgtgag ggaatgaata  23220
tctgttgttt taagccacca agtttatggt catttcctac agcagccaca ggaatcaaaa  23280
acagtaagta tgtcccatgc aatgtttgtg acacacacca aaaatattac ttgttgttca  23340
cctgaaattc aaatttaact gggtctcctg tattttattt ggccaaccta gttcccaggc  23400
ccaaagaaag aggcttttga aatttgcaag aaagctggtt ggagctgtca gaaagtggac  23460
tttgtaaaca cagtaccacc gaaccaattt gaactgtact acctctagac aaaagagagg  23520
gcagtcagac agttgttcgt gatttcttct ttcaacagtc atttgagcac ttactacaaa  23580
acagaagcta tgtgtaaggg tggaggcgtt agctgttaat caggacctcc aggctaagtt  23640
tctgtattag tccgttttca cgctgctgat aaagacatac ccgagactgg ggaatttaca  23700
aaagaaagag gtttaattgg acttacagtt ccaagtggct ggggaagcct cacaatcatg  23760
gcagaaggca aggaggagca agccacatct tacatggatg gcagcagaca gacagggaga  23820
gagagcttgt gcaggggaac tcctcttttt aaaaccatca gatctcgtta gacttattca  23880
ctatcaagag aacagcacag aaaagacctg cccccatgat tcagttactt cccaccagat  23940
ccctcccaca acatgtggga attcaagatg agatttgtta ccatatcagt taccaaccct  24000
tccagataaa tcacgtgaaa tatcgccatt aacagagtga gctcaggtgg ttcttcagtg  24060
catttctgat acctgaacct tccctgggaa tttcacagac catcaggctc tccacccttt  24120
gatagcagga tagcagggcc caggttctgc aggaggagat gttaccacag gcctgaaagg  24180
gagggagggg cagatgctac aggaagatgc tggctctgga ttcgctggag gagctttcaa  24240
gggaagtaga tacacactgt ctccatcatt tcatgtccat cacactctaa aatgctttgg  24300
acaagaagca aatgttaaag acaaatgtgg cccattttcc tgtacaaaga gggctgctcc  24360
catgccaggc tattggcact ggtgggcatg aggcttctct gctgccctgg ccggggggtt  24420
ctctcactca ccattggctc tctgacacct ggagagacca ccacccttgg gctttcatga  24480
```

```
tgctcacaga atccacactg ttggagcttt aaggagcctg gatcaactgg aacaggcagg  24540
gagtactagg acagcccagc attgccccaa aatatccagg cctgataaaa gagaaaaaca  24600
ggtagctcac aggaaaagga taaaaaaagg aggagggatt taacatgaaa aggtgcttga  24660
tctccctcat aataaaaaga ctgctgattc catccaggca agtgacagaa aaaaaaaatt  24720
taatttaaaa agactgctga taaaaccaca gcgagacact gctgctcagg gatctgaggg  24780
tgtgggcagc caggctgcca cgcatcatgg gtcggagagg aagaccacac ccctggagca  24840
gagggcggct gatctgtcag atgccctttg acagcacctc agcttccaag aattaaccct  24900
ttctatgtga gcagaggcat ccatgggggg acacactggt gaatcatctg ttatgtagaa  24960
gtctggaaaa catcaggatg gaactggtga aataagtgtg gcctctgacg gaatggagcg  25020
gtccgtctgc actgctgcgg gtgcccctca gatcctgtgg gtcagtgaga aaagcagtga  25080
ggaacaaggc aggtactgtg tactgtcctc tgcgtgcaag gaaggccagc gcatgcaaca  25140
gagtccacac agacatagcc taactctgga aggaagaatg agaatgcagt ttcagtggtg  25200
gcctctggtg gggagaaact gggtgaaggg agatgtcatt tccatttctc tactattaat  25260
tttgtattac catgcttaaa tgttactttt taccttttttt ttttttttg agacagggtc  25320
tctctctgtt gcccaggcag gagtgcagtg gtacaatcat ggttcactgc agcctgaacc  25380
tcccaggctc aagcaatcct cccacctcag cctcctgagt agctgggact ataggcacgc  25440
ataccaccgt gcccagctat tttttttaat caagatggag tttttctatg ttgcccaggc  25500
tggtctcaag ctcctggact caagcaatcc tcctgcctca gcctcccaaa gggctgagat  25560
taaaacgtga gtcaccctgc ccagccaatt gctttttaaa aaagattaaa tgcatgtata  25620
cgctcaggca tcagcacact tggaaaggat gaaaatatcc ggaagaaggg ttcttttaaa  25680
aggctcctca agtgatgctg gcaggcatga cgaatgtccc tggtcacaaa agctctgatc  25740
tggcctaacc ctgtcatgtt agagactgga gtgcgtgtgt gtgcgcgcaa agtgtggggg  25800
gatgggggtg agtgtgtgtg gtgtgtaagc atgagtgtgt atgtgtgtgg tgtgggggtg  25860
tgtgctgtgt gagcgtgtgt gagtctgtgt gtgtagtgtg tgtgtgaagt atgtggtgtg  25920
tatgtgtgac gtgaggtgtg tgtggtgtgt gagttgtgta tggtgtgtgc atgagcatgt  25980
gtgtgggcat gtgatgtgtg tgtggtgtgt aagcatgtgt gagtgtgtat gtttgagcat  26040
gtgtggtgtg ttgtgatatg tgtgtggtgt gtgagcatgt gtgtgtgatg tgtctgtgtg  26100
tggtgtgtgt gagcatgtgt gttgtgtgtg tggtgcatgt gtgtggcgtg tgagcgtgtg  26160
tgtgcattgt gtctgtgagc atgtgtgagt gtgtgtgtgt tcagcatata taaggcatgt  26220
aactgaacac agcactttag agggctctcc tggagtcaga gggggtgggt aggaggagaa  26280
gggaggtggg ctagtgtgct gaagtatcta ctccttgtca tagtctgtga caacccagac  26340
tagcccatga gccaccctgt tccctgcatt tccaatgaga cctcggtgga catgttccct  26400
gaggtgaggc tgactgatgt catttgacga tcttgatgcc aaatcctttt atatcaaaaa  26460
caaccagaac actctctttt ctcttagtgc tttcacccag atgaccacat ttcatcctcc  26520
cagccactct gggccaggtg gcactgctgg tttgaaaggg aggtctcccc tggagtaact  26580
tccgtgggcg gattcacacc ctgcccacag tcctgtccca gtcagcccac catggtggtc  26640
tccggttcct ccagaattcc cgcttttcag ctcatcccca cattcccgga gggactgaga  26700
gcgcagcccc agggccctgc tctttggggg ccgtctctac acccagagaa gcagcaaggc  26760
attcctaggt ttctctttca gatgcagaac ttcagtgttc agagatgttc ccactggtcc  26820
tgagagggct cagttcagct ttaatgactg cgctgttgcg tgtgctctgc agagggcggg  26880
```

tggcccagcg tggctgactg cagttttcct gacgtggagc ccgagcctgc cccgctgttt 26940
attaattaag gatcactctg cttgcagaac cctgaactcc ccagaactgt gaggtgggag 27000
aaccccgaga ggccacctgg ccccacttcc cacctgctgc ccaaaccccc tctctgcctt 27060
cctgacagtc accccaactc ccagtgatcc ccatcaacca tctgacaagg ggactgagag 27120
ggaagagaaa ggaggggccc aaagaggaag gtaaaactgt cgggaacagc ccccaaatgt 27180
gtgacagcct tcagtggagt tgcccacttt cccttttctc ctccctgcag gacctccctt 27240
ctccccagtc ctccccaact tctgaggtta cattgagaaa agtctgcaga gaggtgccag 27300
catcacaagg tgttaaggac cacgagtttg gcattttaac agatgccaga gccacttgag 27360
aaatgtggta actaagccca gagaggtaca gttaacctcc ccagagtcac acagcaggtt 27420
catggcaaag ctggactagc acaggtgtcc ttcccctgca gatccccttc tgtgccccac 27480
atcacctccc tccagtgtct gggccacctg gagatgggcc ctcagactca cccggccaga 27540
ggtgccatct catgggagag gtctggccag gaagcatcga tatttgagat cccaagaaat 27600
gaagacttgg cctgtcagat gacagacttc ggtcatggga acacgtgatc tgttttacac 27660
atgcgtcccc tcagcagcag ctttccagaa cattcccact ttcttctgta gtgagaagaa 27720
ctctttccct gcagcctcct gcccaactcc tccttcagtg tctttgcttc agtgtctttg 27780
ataaaccatt ctgctttgca gagtgcgagc tctgccttgc agggttcgca tctgcctgtg 27840
ctgagtaacc aacgctaagg tcgagtggtc ggtcacctct cataagagct agggttgtct 27900
catgctgatg actaggactt gccctcaagg agaaaaataa atcaaaacaa aagcaaaaac 27960
agcaaacatg catctcttaa agaaggctct gagtccaggt aaatttcctt ccactgaagc 28020
agccaggctg aattcgaatt atctttgccc ctgcttaaaa actaatgcaa attttcctag 28080
agaatatcca ctaattcctg gagggggcat gggcattcct gatgcccatg agaggaccat 28140
ttgctcttcc ctcagtatgc taaataacag aagcgacatt tgttgctgga aagtatcagt 28200
gaagttaata aggtttttct tgcccagggt gagggaacag ttcccaatga caaatgctgt 28260
atgggaaggg gctgtagaac tgccagcccc tttggtccat ccgtaaagtg aactctgtgg 28320
atcctggagg attccagcgt cttttttttt ttttcttttt ttttaagaca gagccttgct 28380
gtcacccagg ctggagtgca gtggcacgat ctcagttcac tgcaacctcc gcctcccggg 28440
ttcaagcgat tctcatgtct cggcctcccg agcagcaaga ctacaggtgc gcaccaccat 28500
gcccgactaa tttttgtatt attagtagag acgggggttt cactctgttg gccaggctgg 28560
tctcaaactc ctgacctcag gtgatccacc cgcctcagcc tcccaaagtg ctgggattac 28620
aggcatgagc caccatgccc agccagcatc tttcattttt ctgtctgctt tggccctttc 28680
ctctctcact gtcttccttt tccatttcca aagtcagtcc atctcactat tagcacaaaa 28740
actgctagag cgcttgtcat tggtcatctc tccctgcacc tggctggtct gttcttggcc 28800
actgaagcgt ttcccccagc tgttgcttta atcattttat tgttattatg ccttacttaa 28860
gaaatggata tgagatgcat ttacctgtct cttcctgcca ctctgcagag ccagtaagat 28920
gtggtggaaa gggcccaggc tttggaggag ggctggctgg ggttggatct tggctgcccc 28980
ctactagctg tgtgaccttg ggtaagtagc tggacctctc tgagcctggt tcggaatcat 29040
agcacctctc tttcagggct gctgtaagga atagcagtgg tgtgtataaa gcagagcgca 29100
cagccagcaa ctggccccta gccacactgc tgagcaccta ctgtgataag ctgccattgt 29160
ggtgtgtgaa gcaaagggga aacatgcctg ctgtagtgag cttcctgtag ggcaggttgt 29220

```
agaaccagag gtgggttcca aggttacaaa gggactctta gtgtattagt ctgttctcac  29280
attactataa agacctacct gagactggat catttataaa gaaaagaggt ttaattggct  29340
cacattggct gggtgcggtg gctcacgcct gtaatcccag cattttggga ggccaaggcc  29400
ggcggatcac ttgaggtcag gaatttgaga ccagcctggc caacatggtg aaaccctgtc  29460
tcttctaaaa taaaatacaa aaattagctg gccatggtgg tgtgcgcctg gaatcccagc  29520
tactcaggag gctgaggtgg aagaattgct tgagcccggg aggtggaggt tgcagtgagc  29580
caagatcgcc ccactgcact ctagcctggg cagcagactg agactctgtc tcaataaaaa  29640
aaaaaaaaaa gaaaagaaaa agaattgcaa gaaataaatt attgtttatg agctatatgg  29700
tctgtggtac cttgttgtgg gactgggagt cttggcgtct ccctgaccct gcctgttgct  29760
gcagcaccgc tcagccctgc ctgctcccta cctgcctccc ctcggcctct cctgcctcca  29820
ccgggcccct ggtgcctcct ctagagacag tcctcctggg accgattgtg ttctcactta  29880
cacgaggcat ccaggactac agataaccag aggaaggggc gcccccccg cctgccctcc  29940
tccctggcat cctcacgctg cagaggtcag agcctcatcc cagcccctta cctgccccta  30000
ctctgtggag aaccgtggtc agttcgccag gccggatcca cgaacggcct tgtggaagat  30060
ggtgagctca cacccagagc tggctccgat gaccctgtct cctttacatg tttctacctt  30120
cccctcccta ccttccccca ctgctgggcg cagagtggag gcagatgagg tttaaagctc  30180
agaagggctt aaacgggttg gggcgcagtg gctcatgcct gtaatcccgg cactttggga  30240
ggccaaggca gaggatcact tgagcccagg agttcgagac caacctgagc aacatagtga  30300
gaccgcgtct ctacaaaaaa taaaataaat aaaattagct ttgcagggtg gcatgcacct  30360
gcagtccctg ctactcagaa ggctgaggtg ggaggatcgc ttgtgcccag gagtttgagg  30420
ctgcagtgag ctatgctggc accacagcac tccagcctga gtaacagaat gagatcctgt  30480
ctcaaaacaa acaaacaaac aaacaaaaga aggcttaaag gggctccag gtgggcttgg  30540
cagcacaaag ctatgaagtt ctatcttaga cacaagttct gttactgggc ctttgcaggc  30600
tggcctgggt acctggctgc catagacagg gaaccttcca gatgagctgc aggcgtggag  30660
cacaggagcc agggtgctct tcctgggctc tgtccacagg cagaacgtac acagtctttg  30720
tacacgtccg gcggctctgg tgcctatttt tgtttgtgtt tttcttttgt ttggggggat  30780
ggatttggtt tcccccgagc cctctgtcct cctgtcacct ggctggtgct cggcaatgtt  30840
gaccagctgc ctggctggag ttggcagtgg ctaaggctgt gacagctaac atgttcctga  30900
gtcctctcat ttcttcacca taatgccctg ttgagtttgc agatactgtc tctgttttta  30960
tctcccgggg aaactgaggc tcagagtggc taggccacct tcccatggtc cctcagctca  31020
tgagggccac acagggcatt gcggtggcct tctcctcagc cttgaccctc cggccccagc  31080
attgctgcct caaggggtct cctctgctga gccgtgcacc ttctgcctgg cagctccaac  31140
tctgtggctg tgttcagtgg ctcagcactg cccottgacc ctccctggcc ttctgcggat  31200
gccagactgg agcactctga caaggtctgg ggtggttgta tgggtcctgt gacctctata  31260
cacctcccag tgcctgggaa tcctgcagat acaccctcct tagccgtccc taaccataga  31320
ggacatttct gaggtccccg agagagtggg gcacccctgc aggatccaac tgctgggccc  31380
aggaaggata gcagcagcat gaggggttcc attagccaca aactcacggc atggaacctt  31440
cacccacctc gcccctcatc tgctgtttag cacctggcac gccgtgtata cttactgatt  31500
attacatttt aatggcaaat tatagtggca aacgtatgca tctttgcaca attgttgtac  31560
agcatgatga acaagtcatt aatagtaaag aataaatgtg aaagtgagaa aaatctgact  31620
```

gccaaagttt ttactccttc cttccctccc cagactttta aatgaaagtt tagggataat 31680
cccttagttg tcctgctagt aggacttgca attaaaagaa ttgggccaag aacacttcta 31740
cgcttctcct tttaggtttg ggtgtaaatt cggggtattt ctcactgatg aaagcctggt 31800
gcagggcaga ccgtgggaag ctttcatttc cggaatggac catcaacatc ccttggagaa 31860
gaattctctt ctccagaccc agacctggtg tcctggcacc cattgggcaa gtgggtccta 31920
gaagacaaac ctggtcagag cctggaggct gcttagcatt ccccacgcac attagcagct 31980
cggagagctc aggaagccgc agcccctcct tgcctcacca gcctggatca ggacagcatc 32040
ccctggaaga cacacagggc ctggcctctg attacccagc ctggagggaa agctcaatcg 32100
agcatcatgt cacccggtgc cccatgcag ggtggcactg gtgagacccc caagccaatg 32160
ataccacctc acaggagtgc aggcccattg tggccagatc atcttgactt ttcaagataa 32220
atcagaaatc gtatttccat gagatatccc tatttgcaag tgatggtgac taaattagaa 32280
gtttttgaat attgtaacat gttcgtaggc tgtttgtctg gtttaaactc tatctggagg 32340
aattcaagct agacttcagg aataacttct tgaggcaagg attttgagac cttagggaaa 32400
gaaggacgtc ttgggggtat tctgactgtt gtcctcctgg aagggaagaa cagagaacta 32460
gaagactgcc cttagcgaag ttcaaagcac ctaagcccgg gaccctcagc aagtgttctt 32520
gagtcacaga ttctccctga ggcgcctctt tctggctcca tagaatggct gattctgtaa 32580
ctcggtgagt ttgctttttt tttttcctcc atcacccagg ctggagtgca gtgaagctgg 32640
agtgccgtgg agcgatcact gcaacctctg tctcccaggt tcaagcaatt ctccttcctc 32700
agcctcccaa gtagctggga ttacaagcat gcagcaccac acctggctaa tttttgtgtt 32760
tttaatagag acggcccgaa gtgctaggat tacaggcatg agccaccgcg gccagccata 32820
actctgtgac tcttgttaca aaggccttat attttgctct ttgagggtgg ttttggtttg 32880
atgcctgttg gttgccatct tttaactagg gatgttttat caaaatgccc agccaaagtg 32940
tccaaacaaa ttataccta aagtttgaaa atgtctggca cttctaattc aatgcctgtt 33000
gtgccaggca ctgggctgct gaggaactga gtcccgtccc tgcaggctag ctagagaaca 33060
cacacacaca cacacacaca cacacacaca gagtggtctt acaagtcagt tttatattct 33120
acctatatgc aataaaggta ttattatgtt gaggtgcctt gatataaaaa tttttcttaa 33180
aggagaggat gcctaaaaca ggcattacct gaaacctcct ctctccagca ttggttgtct 33240
tctgtcatga ctcagggttt tcactgagaa tgggatggaa atgtggtcta aagatagggc 33300
caatgttggg actggatccc ctctgggaag tcagaccagg ctagggcagg tccttgaagc 33360
catcaggaaa agcctctgga gccagaaaca aaacaaaaaa aaaatggtgt taactaaact 33420
cagtctcaaa tcctgaatag gactcaagtc aagcaaaata attaaaggag ttagcaaagg 33480
gcaagtcaga gagaccgagc aacaccaatg tcttccggga gccctgtggc gagtgacaga 33540
gcctggactc tggagtagaa ctcatcttgt gtcttcttct gccactcgtt agctgggtga 33600
ccttgagcca agccccttaa cctcttggac cctatgttct tatctctaag taggggctgg 33660
taatatcttc ccctttgagg aatgccctct aaggggtgtt gtgaagattc ggtaaggtgg 33720
caggggtagg actcctggcc agaaacaggc acataataaa tgctaagtct ctccttctct 33780
ccacctgctg gatgctgtag atactaagga tttcgatgtg aatgagacaa aacccctgcc 33840
ttccaggagc ctttgagaat cagagaacta gacccatttc cagaacaagg ggatgcaggg 33900
tctggataaa gttttgggga tcaatagagc agagggctcc cagaggatcc catagggttg 33960

-continued

```
actcctaact caagggcatg agacaacccc caggaagggc accctggaag gggtccggct  34020
gtccctgatt tacttgtggg cactggggga atgcccggag ccatccagcc ctcagggctc  34080
tgtgtgattc tgggttcctc ccataaaaga taatcagatt ctttcacgtt aatgtctttc  34140
tccacctcat tgcacatcat gcagctattc attgactcag caagtatcag ctttgcatgc  34200
gaccttggcc tacccacttt agcttttagt aatagctccc ttcttgaata atacaaccag  34260
tggggaaaca gaacctaact cttacctctg ggaggcttat ttgctttgag aacatatgtc  34320
ctgcagtttt gttcatatgg cagtgaagtt tcgtgcacac actctagagc caggcagcct  34380
gggttcaaag cgcagctctg ccaggtccta actgcatgaa tttgggcaag tcgctcaacc  34440
tctccatgcc tgagtttcct catctgtaag attggagcaa tggtaatacc tgctttttag  34500
ggttgagaag agaattaaat gaattaagat gggtaaagtg cttagagtgg agctttgcaa  34560
gtagtaagtg ctatgtaagt gttcgattta aaatgaaaga cccttaaata cattctttgt  34620
tcatttcaca agcccttcat ttcacaacct tacatttcac aaccaagctc tgtctcccct  34680
ggaatccagc cataactctg ctcacaagtg tgagacaggc cccagcagag ctgcacgaag  34740
aggagagaag gcagcccccc agactcccaa ccccctgtcc aagatggcaa aaccagaaca  34800
cagcctctgt accaccccag caggtattca gaatctgcaa tctccaaagc ccacttcaat  34860
tgtaaatgta gagccacgtg cgctttaagt cacctgtcac tctggaggct cttttgctca  34920
gttcctcacc attagcaggg atgacaggga gtgcaggagt gcggtcgact cccagatatt  34980
ggagagcgct gggctagctg cccattctcc cggcctccac tcctctttgc tgtccagcca  35040
tcacttgctc tttgaaggca aacaaaacag aaaacagtgc caaaagtatg ggaagaaagc  35100
cagcttctcc cctggggtgc ctgtgatgcc atgcccaccc tccctgacca cgcagcccct  35160
gtggaccctc agggccccaa gcccccattt ccatcacatg cgtacaccca tgtgtgtcca  35220
tagccgccca tctcagtcaa taaggctgct cctgcccact tggaatagtg gtgacaacca  35280
ggagtggctt atgggaacta tcccaatggc ctgacagcat gtccgctgca aaccgctgag  35340
gtaggacact gccctcatgt ctagctgatc agcaagaggc gcagttgctt tcttaggtaa  35400
cattgctgct gtgtcctggc cattgctggg gggtggcact taatctacac cagatttttc  35460
cctcctgtat cttccaagct gcttggatct tggtgctgaa ttaggttgga ctttgtcttg  35520
tggggaaggg aggactatag accctcaacg taagcaatgg tcagactatt ctaagaaaac  35580
tcgccgaatt aaagcatgag gtaaatttag ttctgacttc tgtccacccc actgccactg  35640
tcccctttta tcccatgatc ccttgctttt cttttcctcc tctctcccta tctcttgtgt  35700
ttgacgcatg ataggaattc agaaatatat gtttgtggat ttgtttattc acgtagcaaa  35760
ccatttcttg agtgcctacc atgggccagg tagaatgggc ggccccgggc tgcagtggtt  35820
tcttcagccc ctctccaggg tttacactgt gcaagacggt ttgtgatggg tcctcccatc  35880
gaggaccaca ctcttctttc tctgtgcccc ttggtcctca gtctctgacc ccacttcaaa  35940
ggcagcattc actcagggaa gctcccatac aatgctagtc agagtaaaag tttggacaaa  36000
ttgccaggaa gcagcttgtc agtatgcata aacagccttt aaaatattac tactctttga  36060
cccagaattt cacttctagg aatctgtcct aaggaagtag tcacatgcaa aagatttatg  36120
taccaagatg ttcatcaaag tgttgtttta taacaggaag tctcagaagc tggataaata  36180
tccaacctct ggaaatggtt agatagaata gtatgtagcc attagaaaat tatgtctatg  36240
gggtttaaaa tgtcatggga aaacacttct gacataaaag agcatgagaa ctgtatattt  36300
agcataatct taactatgtt ttagaatgca caggaaaaaa atgtacaaac atattcatag  36360
```

tgatgtctct ggtggtagga ttatgatcag taagtacttc tgtctcttca tattttcctg 36420
tatttgataa tacatgcata tgttgttttt aaaataagaa aaattttaag tttaaaattg 36480
gagctgaaaa gtgtttttag gtcaggcgag gtggctcaca cctgtaatag caccactttg 36540
ggaggctgag gcagtcagat cacttgagcc caggagttcg agaccagcct ggccaacatg 36600
gtgaaacccc atctctacta aaaataaaaa aattagccat gtgtggtggc acacatctgt 36660
aatcccagct acttgggagg ctgaggcatg agaattgctt gaacccagga ggtggaggtt 36720
gcagtgagcc aagatcgtgc cactgcactc tagtctgggc aacagagtaa gactctatgt 36780
caaagaaaaa aaaaaaagaa aagccttttt aaacagtagc agacataact atataatcct 36840
tactaagctg tcggtcaaat ttttatttat atatttattt tattcattta ttatttttag 36900
acagggtctc actctgttgc ccaggctgga gtacagtggc gtgatcatgg ctctcttcaa 36960
acttgacctc ccgggctcaa gtgatcctcc catcttagcc tcccaagtag atgggaccac 37020
aggtgcatac caccacacct ggctaatttt ttttattttt tatttttaga gatggtgttt 37080
actatgttgc ccaggctagt ctcaaactcc tgggctcaag ctatcctccc acctcggcct 37140
cccgaagtgc tggggttacc agcatgagcc actgtaccca gccctcaaat ttttaaaaat 37200
ctataagaga cattattgga caattagaga aattcacata tggacttata atagtatcag 37260
agtgtgtggt gtgatggttc tggagggaat ggactttttc tttggagaca ggcttttcta 37320
tgcccaccct tttatcttgc taacttatca tcatccaggt tccagcagaa acattacttc 37380
ccccaggaaa tttcttaagg gtgcagtatc atgatgtctg cagcaaattc tcaaatagct 37440
caggaaaaaa gtacgtgtgt ggtatgagtg tgtgtatgta tgtgtgtata tatatacaca 37500
tatatacaca tatatataca tatatgtgta tatatataca tatatgtgta tatatataca 37560
cacacataca catatatata cacacacaca tacatacatg tatttttata taattatata 37620
tgcagagagt gcaaatgttg ccaagttaaa gattggtgag tctaggtgaa gggaatatgg 37680
tatttattgt attatttgtg caacttttct taagtttgaa aattttcaaa acaaaaaatt 37740
ggaggaagaa ggcatgccag tctaccccaa gccctccatt ggaatgctga aaatctaaac 37800
aatgtgattt ggcaatttca tttcttttct gttgtgggcc agtagtcctt agatgttggg 37860
gaagggggta gtcgctgagg tgtggttgac ttaggatgga agaagcagaa gtcaagactc 37920
ccagggtcaa agtggtttgc tctgctgacc caagtgtggg aggcccagag tcagcgtttc 37980
aggtgtgcta attcagcatg gttctattca cggccaaagt ccaccctggg cacctctctg 38040
gcagcaatct tgggtgactc tactaaggcc aggcctccat gaccctatgt ctggatccca 38100
tatctccacc tctcccactg tctcaggaac ggtgcttagc tttttctttt ccctctcctg 38160
tcttctttgc cagcatgtag aaagtttaaa taattcccct ctttacaaca aaacaaaaca 38220
tacccccttc agtcaaccac cctagctctc ttctcctttt cccagccaga tttttttaaa 38280
agcatcctag gccaggcgcg gtgactcacg cctgtaattc cagcactttg ggaggccaag 38340
gtgggtggat cacaaggtca ggagatcgag accatcctgg ctaacatggt gaaaccccat 38400
ctctactaaa aatacaaaaa agtagccggg agtggtggca ggtgcctgta gtcccagcta 38460
ctcgggaggc tgaggcagga gaatggcgtg aacctggtag gcggaggttg cagtgagccg 38520
agatggcgcc actgcactcc agcctgggtg acagagtgag actccgtctc aggaaaaaaa 38580
aaaaaaaaaa aaaaaaaagc atcctcagca ctttggcaac tccatctcct cccaacatgt 38640
ccctgttact ggaatccagc caggactcag ccccgatctt tctactctaa ccagttgtct 38700

-continued

```
cagttaacaa ggacaggttt atgctgcagt gacaaacaag atcccaaatt cttgtggctt  38760
cacacatctg gcaccacctc atcttccagc cttaggagtc atcttttagt tccttgaaaa  38820
ctctttacag ttttctgttg gggccttgtc atatactatt cccctggaat gttctttcct  38880
atcccctccc tttcaccttg ctaacttgtg cccatccttc aggtctcagc agaaacatca  38940
cttccttggg gaagttttct ccaacaccca cactacacag gtgtcccatc tacactccta  39000
tgactttgtg gtacttgtct cacttcattt tccactgcct tccccacaag gcacctgcac  39060
aagggcaagg accgtaccac tgtacctatg tcactcattg ctgtggtcac ctgcactctg  39120
gctgcctacc ttaactacac attagaatca cctgaggagc ttttaaagcc acaatgcaag  39180
actccaccct aggccaattg gatccaaatc cctggggtag ggccagacat cagtggagtt  39240
atatatacat atatatattt tgtttgtttg tttgtttgtt ttttgagaca gagttttgct  39300
ctgtcaccca ggctggagtg cagtggcgcg atcttggctc actgcaagct ccgcctctcg  39360
ggttcacacc attctcctgc ctcagcctcc tgagtggctg gaactacaag tgctcgccac  39420
cacgcccagc taattttttt gtgtttttag tagagatggg gtttcaccgt gttagccagg  39480
atggtctcga tctcctgacc tcatgatctg cctgcctcat cagcctccca gagtgctggg  39540
attacaggca tgagccactg cacccggcca tcagtggata tatttttaaa gcactgcaga  39600
gaattctgtt gcatcagctt gagaaccact gatctgcctt gtgcttcaca tttaaaactt  39660
tttttaatg aataaataaa ccccaaaaaa ttaatctccc taagcctccc tagaagatag  39720
gatggtaagg atattttcct aggtaaaaat atgttaattt catatttcat gaaatttcat  39780
gtttcatttc aatcaagctc tgtcatacac cttacatggg gcaagcccag tgcctgggca  39840
gggtgtaatt atactcatta cacaggcaag gaaaagtcac attaggtgat ggagcacaaa  39900
taggcagtta atggtttcag ggctagttag gatatgtttg tctttcaatt gcaagtaata  39960
gaagcccaaa gaaattggtt atttatataa tataattgat tggttcccaa atttgaaaaa  40020
ttcaggaata gacccagctt aggtacagct ggatccagtc actcaaacaa tgtcacaaag  40080
aaccctttga caggaatgta tcctgtgttg actctacttt gctctgagta gtctttcccc  40140
aggtgatgat aaaaatggtc atcatcgcca ggcttgtgtc ctgtttagta ggaatataca  40200
agaagagctc agtaaatgct ggccccacca ctaagcaaaa acaaaacttt tgttgttgtt  40260
attgttgttt taaataacag cttagacctt tcttctttcc ttgttattct ctttcatctg  40320
taatccagtt ttctacttct gaagtataga atgttctgat gatttattct tcattaccca  40380
caacttgcac atgtttattt aaaaatgcca ggattgcctg gccgttgtgt gctgttaacc  40440
tttgtttgct gttagtggat ccctgaagtt caggctccca ggggagcaga taatgggtat  40500
ccagttcctg caatatccac cctctggcaa gccaagttcc ttcctgggta aggttttgcc  40560
tacctgcatt cctagggaag tttctgggcc tgaccaccaa gccagctctg agaaggggtg  40620
cataagcccc accatgcttt ggctctgtcc ctatagaata ttttatgttg ttactgaaaa  40680
ctaaaggaag atgggtgcgg tggctcatgc ctgtaatccc agcactttgg gaggccaaga  40740
cagattgatc actcgatgcc aggagttcaa gaccagcctg gccaacatgg tgaaaccttg  40800
tctctacaaa aacaaaacaa aacaaaaatt agccgggtat ggtggcatgc acctgtggta  40860
ccagctactc aagaggctga ggcacaagaa tctcttgaac ctgggaggta gaggttgcag  40920
tgagccgaga tcgcactact gcattccagc ctgggtgaca gagcaagatt ctgtctccaa  40980
aaaaaaaaaa aaaaagaaaa ggaaagctaa aggagagaga ctaaaatgat atcaggttcc  41040
tggagaacaa acagacatga ttttgcttca tggcaggaca gccggaagaa gtgggattat  41100
```

```
atcctcacat tacaaataag aaaactgaga ctcagaatgg ttaagtcact tgtcccaggc  41160
cacacagcca gtaaattaca gaaacagaat ttgaacccaa atcttccagc tccaaagctt  41220
gtgttctttt cactacctcc tgcttaattt tttaatttct aagattagac ccttcatcta  41280
tccatgacac ctgcctgtca tcccctgaaa aaaggtgaac gccgttcaga aatttttcta  41340
gcctgagctc actcccagtt cacttatttt tgctttgtca tggctgccca gtccccactt  41400
gtagaccagg aataggtcat ggctgcgggg actacacgct gtcgctgctg caagggccgg  41460
cctctgtttc cggggctgag tgggggccag acctgccagg agcaccatct tctgtgggtc  41520
ctgcctggat gtcacatccc ggccccaaga agtcactgca aaccttcgta ttattgagct  41580
tcacatccta gaatttgctg tcactgtggc tgctgcatga agttgtcctg agagaaacgg  41640
gcattgtcat taacagggaa attgatggtc tgggggaaaa gtcatcctca ttctcttgca  41700
gatctatggg tgattgagac tggctgatgt tgaaggggtt tctcagccat cgtgtgccat  41760
gttatggaac agtggtgtag ccagccattt gacacccagc gctgaccttt gtttaacaac  41820
ctcacctata tatgacaaaa tgattgtcag aaataatcgt gtaatgaaat gactgtaata  41880
atggccagaa aagaaacgca gatagtaaaa tgtttctctt gttgaactct gtacatataa  41940
ttgcaccagg attttttca aataaaaagt aaatattata ctacaaaaaa gggaaaaagc  42000
acaagcattt attaaatagc tttctatatc tttctgagtt ttgatccttt gattgcagac  42060
tgatgtaata ttttatgtaa atcattgctt ggttactaag tgaactttaa gaaaagtgag  42120
acgtctgcag aagttgccca taatttagca gctactgtat tgtaccattg atgtacggct  42180
ttattttctt gattaattat ttaaacaata taattcacaa ttttaaaata ataaatttcc  42240
acttaaaatg gtatttaaac tcagcaaaat atatcatcta tgagtaaaat ttgtatttac  42300
caagcaaaaa tattacagtt tgtggttcac atgctgtctc actgttttaa attttaaata  42360
caaaaactcc aagtaggctg ggtgtggtgg ctcacacctg taatcccagt actttgggag  42420
gctgaggcag gcatatcgct tgagttcagg agttcaagat ttgcctgggc aacatagtga  42480
gatcctgtct ctactgaaaa caattagctg ggtgtggtgg cacatgcctg cggtcccagc  42540
tactcaggag gctgagatag gaggatcact tgaaccctgg gggacagagg ttgcagtgag  42600
gcaagattgc accactgcac tccagcctgg gtgacagatt gagaccctgt ctcaaaaaaa  42660
gaaaaaaaaa aaagaaacac aaaaactcca ggtggtcgca cagaatgaca ggactgaagt  42720
aacttagctc caatttctgt cttcataatc actgtcctac cattgtctgt gcttagaatc  42780
tacttgctta atgcaggaac atgtgttctc acagagatgg aaaatgcaaa tggcgccaga  42840
agcaagctgg aaattctgaa ccattaagaa tttactctct gccaggcacg gtggctcacg  42900
cctgtaatcc caggactttg ggaggctgag gcaggcagat catctgaggt caggagttca  42960
agaccagcct ggccaacatg gtgaaacttc atctctacaa aaatacaaaa attagccagg  43020
catgatggtg ggtgcctgta atcccagcta ctcgggaggc tgaggcagga gaatcgcttg  43080
cacctgagag gtggaggttg cagtgagccg agatctatct gcaccattgc acttcagcct  43140
gggagacaga gtaagactcc atctcaaaaa aaaaaaaaaa aaaaaagaac ttactctcaa  43200
aataaatacg tgtggctgac tccacatatg gtagggccaa ctgtataact agaagttctc  43260
caaataactt ctgtggagaa aaaaaagttt attaaaggtt aacttttttta aagtgctaac  43320
tagaacctta ctaacactga gatcgcacca attgtttata acttagacag ggccgggtgc  43380
agtggctcat gcctataatc ccaacacttt gggaggccga ggcaggtgga tcacttgatg  43440
```

tcaggagttc gagaccagcc taaccaacat gatgaaaccc catctctact aaaaatacaa 43500
aaattagcca ggcacggtgg tacacgcctg taatcccagc tactggggag ggtgaggcag 43560
gagaatctct tgaacccagg aggcggagat tgcagtgggc caagatcgca ccattgcact 43620
ctagccccag caacaagagt gaaactctgt ttcaaacaaa caaacaaaaa aaaaaacctc 43680
ttggaccagg aaaatatttt ttaagggagg agtattttat cactggcatt gtttaggatt 43740
gcaggcacat gatgctaatg aaaagcagac taactattag ttggttttat tactgttttt 43800
gaactctctc tctccctttt tttttttttt gagacagagt ctctctctct gtcacccagg 43860
ctggaatgca gtgactgcag tctcagctca ctacatcctc tgcctcctca gttcaagtga 43920
ttctcgtgcc tcagcctccc gagtagctgg gattacaggg caccacacca ggctaagttt 43980
ttgtattttt agtagaggca gggtttcacc atgttgccca ggctggtctc aaactcctgg 44040
cctcaagcga tctgcccatc ttgacctccc aaagtgttgg gattacaggc gtgagccacc 44100
gtgcctagcc ctgtttttga actctctaga gacagtccag ccccttatta cttgtcctga 44160
ggcagctgct cccttcacct ggccccccgc attgtgttcc ggacccttgt cctggtggtg 44220
ctaaagaata tctctgtcga tcctttgggg actggggaaa ctgaggccca gtgccacgcg 44280
atgccatttg ttcagggaag attaggtcat ctgctaggtc cccagtcact tgaccttctt 44340
cccagacagg aagaagctgc tctgggtctc tcagtgctcc acgtgtcttt gcacattgaa 44400
atgttttctg attttttttt tttttttttt gctgttacat ttacttttaa aaaataacaa 44460
gcaataaaat gttacatttg agaaggttga aatgagaatt gatttgagtt aaattctagc 44520
agatttttct tagaagaatg atatcatcat ctccagctac ctgcaattga tctactctga 44580
attaagaaag agacttccat ttgttgttta tattttgcac tcttgatgtg tttctttaaa 44640
ttatggtcat gggccaggtg taggagctca cacctgtaat cccagcacct tgggactctg 44700
aggagggagg atcactggag gccaggagtt caagacctcg tctgtacagt aaattttaaa 44760
aattagccag gcatggtagc attcacctgt agtcttagct acttgggagg ctgagatggg 44820
aggattgctt gagccagaac tttgaggcta cagtgagtta ttttcacgcc actgccctct 44880
agcctggctg acagagcaag acctgcctca aaaaaataag taaaaaataa attaaatttc 44940
aatcattagc agtcattagg atatttaaat acagtatgtt gaatcaaagt tacgcatgtg 45000
tgtatttttt tttccagaga gttgtttatc atgtgggttt taatttaact ttaaaaaaat 45060
gttggctgga cagttgccca aatggtatca tcagccattt ggttgagaac gtatgtcctg 45120
cgggctcctc tgtcactgga gttttgctag ctgacagcca ctggctagtt agagactgca 45180
gtcagcacag atgcaggcgt ggacttgcgc acgtaaccat gtcaatgcaa agccatcact 45240
tcttaaaaat tctgaaccct gctgtctgag atggtggtgc agcggataga actctgctct 45300
aagaggcagt agctaattcc atgtcttctt tgcccttgac tagctgagtg actttgcaca 45360
tggggcttgc ctctctgttg ccttgtctgc aaagtggaat catcttttcc ttgctagaca 45420
gaaggtggac cctggaccta tggccttttt gagtttcccc cccgcttctt agaaggacct 45480
ctgatcctac tgagtttaat acccacgggt taataattgg gaaaagcaaa ggaagcgctt 45540
ctgtttaggt aattatatgc atgtttttgt ctttttctgg ctggaaagat atccaagcca 45600
ctgggaaggt ccgtggctac ccagggtagc cctctctggg gagggctgct atatccaaga 45660
gcccctcatg agaatttgaa aatcgaccat ggtagggcct gctgactttt gacagctaat 45720
ggtgtgctga gaattgtccc tccaaagatg cctttccatt ccctcgggag agtctgggca 45780
gcccctactg gggctggga tgctggctct tccctcagcc tccaccccaa ctgctctctt 45840

-continued

```
ccctcctccc ctccccagcc ccctaatttc tctcacaagg ctttgttctg cagcaacctt  45900
tcctaatgca gtcctggcct cttcgcagct tcattacata accttccgtg gactcctggt  45960
ccaaggatca ccccagaaag ccagtcagag gtaggcacgc agctggggtc catttactta  46020
ccttccccac cccctcggaa ctcagaggtg gtgcaggaat ttggactcca agaattaaca  46080
gctccaccac catcaccaga gccaaaactc aggatgcatg tgcttcatct gctgcttatt  46140
tccagctgag agccagtggt gccatggttc cttagggagc cggtcccctg atgccggctc  46200
ctggccccaa atctctctga tccgggctct tccagaatgt cttgtctcca ccatcgcctt  46260
tgaccaatgg tgtccctttg cctggtaatg tcccctttgc ctgatgatgg ccctgtcact  46320
cctctcttta gcacagagga ggctgtttca tcccttcaag cctgccctcc cttcaagtct  46380
tagctcaagt tcaccttctc cgcagagcct tctccaatct tcttgactac gtctcctctc  46440
agctccagca acctctgtct ctggcactga ttccttactt agctaagaga atcacagaca  46500
cttggggctc aggacaatct gctttctctc ttcttaccca tggccttgga ctgtgtgtac  46560
ctctttgtct ccactcccaa acccaacccc cagagggcag agagcatgtt gtctgtccct  46620
ttgctcagca tgaagccatg cgtgtggtag atcggcagag ttccataact tgtgttgacc  46680
gaggggtcac tttgctctga aattacccct gtgtccttca gtatttgcac agatagcttc  46740
ctggccagac cgaatatatc caagggcatg gcccacctct gctcctgttt ccaggtccct  46800
ggtgggggtt agttcatgcc ttcctcataa tctgcccact ggcctggtcc tcaaggtctt  46860
cccaactgct cagccagagt tgagaaaatg ggtcgctcca tcctgtttgt gtcgttctct  46920
ccttcctggc ccactctcct gcccacaggt atccaggggc tgcctgtagc attagaggac  46980
atacatgcac atgcgtgggc atgggacact cacgtagcct ccaagcacag catcaataat  47040
gcattctgtg ctttatagca tggaaagctg ctctaaactt tattacacag tggacatgtc  47100
tgaagcagct cccaaatcca cccctgagtg tgttggaatt ggcaagccta tcacttggga  47160
gtctagtttt tttgttcgtt aataatagat gcttcctgtg gccccagctt ggcaattttg  47220
atttaaagtg atcttaactg aagagactaa tggacgggtc tgaatttgtg ccttttaagc  47280
acaaagtatt gctcttaatt aactggattc tatcctttga gcaggcagag gccttccccc  47340
aagggcgtca ttaacgatcc acatctggac atcttccaaa gccttcttct gtttcaggcc  47400
aaccgcaggt gtgttcctga acacccagga ggctatgaga gccacatatg cctcccaaat  47460
acacacagtg tgcatgccca gggacataga gcagtgtgca aagtcccatt ccatctctct  47520
ccacctggga gaggatggct cttctgtctg attcatggct caaagtggta aaggagctcc  47580
ccactccccg tcccacgcct actcagagtc tgcaaatatg tatgcgatat gagagctcgt  47640
cagttagctg tcttcagtgt ggcgcacatt tgaggagtct gactcccctc cagcacaggc  47700
caatgtgcac tgctctccta tctttgtacc cccactgttg cactgtgcag aggttggagc  47760
catagaagta ccagagctgt gaaaggagag gccccctctc acctctgccc tggtctccat  47820
ccccactttc tctaggaagc tagtaggtgc tgacagggga gagaagggag gggaggggtc  47880
cagaaacagt ggctcatgcc tgcaatccta gcactttggg aggctgaggc aggaggatca  47940
tttgaggtca ggagtttgag accagcctgg gcaatgtagc aagaccctat ctctacaaaa  48000
agaaaaaatg taattagctg ggtgtggtgg tgggcacctg tagtcctagc tacttgggag  48060
gatgaggtgg gaggattgct tgagcccaag agtttgaggt tacagtaagc tgtgattgca  48120
ccactgcact ccagcctggg caacagagct gagaccctat ctcaaaaaaa gaaaaaaaaa  48180
```

-continued

```
aagaaaggag agagagagaa agaaaagaaa agaaaaaaaa aaaagaaggg aagggaaagc  48240
ccagaagagt gtggggagag gaggcggccg tcattctggg gccctcagtg tgcacaacca  48300
gataacacat gctctgtggg cttttgtacc attttgcttg agcataaaga aaggaaggct  48360
gcccctaaat agaaagcact ctggaggcaa acaaatctga ctccaatcct ggccctgcca  48420
ctttcccagc tgaggactta gacaagcacc ctagcctctt ggacattctc agagccatct  48480
gctgcaagtg ggtgctgcca tacccacctt actgggcagg cttgggggac caagggtggt  48540
aaatggctca gtctttcatg atgcggccac acagcaggtg cgccatccag gtccatttct  48600
ttccttcctt tcccccaaat caagttgtca ttaaagtact agtccacatt aatgaaatca  48660
actgtattaa ttttctattt gctgctataa taaatcatca gaaatttagt ggcttaaacc  48720
aacacaaatg tattacctta cagttctgga ggccagaagc cctccatagg tgtcactggg  48780
ctgaaatcaa ggttttggca aggttgcggt cctttctgga gggtccaggg gagaatccat  48840
tttcttcctt tttccagctt ctaaaggttt catgcattcc ttggctcatg atcttctata  48900
gctatagtca gaaaaatttt ccatcaatca tcttcaaagc cagcaatggc aggatgagtc  48960
ctcacatcac cttgctctga caccagttct ctgcctccct cttccacatg tcaggaccct  49020
catgattact ttgggctcac tctgataatc tgggatgatc tctctatttt agagtcagct  49080
gactgggaac cttaattcca tctacaaccc caattcctct ttgccatgta cagtgacata  49140
ttcacaggtt ctggggatta ggacgagcct gtctctgaaa ggctacttta catgaaaatt  49200
cattttttta attaagattt ttttttcctc ttgagacaag gtctcactct atggttcagg  49260
ctggagtgca gtggtatgat cacagctcac tgcagcctcg acgtctctgg gctcaggtga  49320
tcctcccacc tcagcttccc tagtagctgg aactacaggg gtgagccccc atgcccagct  49380
aatttttttt tttttttttt tttgagacag agtctcactc agtcacccag gctggtgtgc  49440
agtggtgcaa tctcagctca cagcaacctc cgcctcctgg gttcaagtga ttcttgtgcc  49500
tcagcctccc aaggagctgg gactacaggt gtgcaccacc acgcccgact aatttttgta  49560
tttttagtaa agatggggtt tcaccatgtt ggccaggctg gtctcaaact cctgatctca  49620
agtgatccac caacctcagc ctctcaaagt gctgggatta caggtgtaag ccaacatgcc  49680
cggccccagc taatttttaa atattttttt tgtagagatg ggttttacc attttgtcta  49740
ggctggtctt gaactcctgg gctcaagcaa acctcccacc ttggtctccc aaagtgctgg  49800
gattacagca tgagccactg cactcggcct taagagaaga tttaataatt aatactttac  49860
aacaagatct ggaagaggtg ggatgagtaa ctaaatgagg atacaagtaa cccgggtcat  49920
atttgctaat acccttggtc acattgaact tgatatctta tcagattttc ctaatcagct  49980
cctttagcag cagtgttgca gcatcttatc tcattttgtt ttttgttttt ttgcctagca  50040
catgcctgta aatcactgga ttgaggtgtt tagatgtttg ttgtcctttg gatgcttctt  50100
ataaatccat atttcatggc tccctggaaa gtgctatgca aatgataagc tgcaaggatg  50160
gaaaggaaat tgcagtgctc ctgaattgta aatgggcttt tacgaggagg tttctaatta  50220
ctcgctcttt ctcttgaact gaggagttga agtgtaggtg gcagatccat aacagataat  50280
catgtgtgtg atgtgacttc agcctgagcg tcgaggacca agtcacagag caggaacagc  50340
cactctccag tgtccttggg gctacgtctg aggagaacct gggatttcat atatgacctg  50400
cactggctgg ggggctctct tgacgtaacg tgttccctct gagcatgtta cagattctga  50460
cattcttatg ttccttctgt ggagagacat gtacttagtg acctaactca ctttagcata  50520
tttttgctca tcgtttgtgt agcttaaagg aatcagataa ttaccccctc cccactactt  50580
```

tcggaagcac aaatgcaatg ccctagaatt gtactgggga ctcaaaaaga aaagagagta 50640
gtaaaatcta ttaaagggga caaagacagc ctatatacta caagctttct atttttatgg 50700
cagagaatgc catttctaa gtaaacagag aactgcattt gacctgcaat atcaaatgca 50760
tggatttgat gctttggaaa gcaactgttt tctgcgttaa tctgggtgtc ttccgtgaaa 50820
tgtcctcctg cctttggctt aaacactagc tttgtctaca gccattccat cctgaacctg 50880
cccaatcttg tctgaatcct ggtttcacca ctgacaagct gtgtgtcctt gggcaagtta 50940
cttcacctgt ctgtgcttca gagtcctcat ctgtgagttg gggaatctgg acagaatcta 51000
ccccataggg cgtagtgagg atgtgttgaa ttatcccaag tggctacaca gagtaagcac 51060
tcaaatgatg tcatcgttgt catgattgct gttaccagag cctagagttc attctgatac 51120
tcgagtctgt ggcccatcca gcccaggtaa ggaatagttg gaggagttgg gcatgttcag 51180
cttgaagagg agacgacagg ggatatggga tagttgaatc tgtgaagggc cccctgggat 51240
gaagaactgg catgttctgt gtggctccag ggcactgagc aggacccatt tgccaaagtc 51300
tcagggacac agtttctagc tatagacaga aaaattttct gtcactcaga ggatgaaaat 51360
agaatgagcc cccttaagag gtaatgagct ccctgtcatt ggaaggattc cagaagagct 51420
aggtaaccac tttaggtgct atcaaggggc ttttttcttt aaagtccttt ccaaaagctt 51480
ctgagattgc ataaacaata ggaagccatc ttggtgcttt aacacaaact ctccccagtg 51540
atgagggttg agccaaagcc agattggcaa gcagagagga gacttgtgta caaggagttc 51600
ctcgagtcaa ttgctttttc cttgttctag ccagccagag ggctcctgtt ggaaaacagg 51660
agaccggaga ggctgaggcc tgaccaaacc agcttctgca ggccagctgg gaggccacaa 51720
ctcctaccta cgggaaaact gaagggcatc tctattttta gattagcaaa agaaaataaa 51780
tttaagtttg agtctccttt gcaactttta aaagacatct ttattgagat gatcattcac 51840
attctataaa attcccccac tttgagttac aattcagtgg ttttagtctt ccttgatgat 51900
tttgatggtc ttttcttaag gctcttggaa gacccagaag cctctcagac acaggtgggt 51960
gtggagggcg tagcacagag gcagacttct catttcctgg gtctcccctt taatgactct 52020
cagagacccc tccttccccc tgcccctggc ttctacccca ggggtgtaga gttttgccat 52080
tttccaagca gaacttcatt tcctcttctg tgtctacact ctttgtgctt ctttcttgcc 52140
agctttttct cctttgcccg cccttccttc cttccttccc tccctccctc cttccctcct 52200
tccctctttc cctccttccc cccttccacc cttccccccct tccccccttc cctccttcct 52260
tccttccctc cttccttcct tccttcctgc cttccttcct tcctgccttc cttccttcct 52320
gccttccttc cttccttcct tccttccttc cttccttcct ggtatgtgac taatttctgt 52380
ttcaggacat aaatgttgtc caggctgttc tttggtcttt ctgttggata atggacattt 52440
ggcattgaga gaggctgctt tttctgaaat catgttcttg gggcccagaa cctaggtgtg 52500
tgcttctgac tttgttttct tcctgatcca aattctgata tgtccattta aattgatcta 52560
gacccacagg gcactgtggg acagatcctc agtggaacat gactctgtaa cgagagcatt 52620
ttgttttgtc aaaatgagaa catattattg cctttcatct gattgtaaac ataatacatg 52680
tttataaaac agtataatga gacaaaaatg tagacactaa taagggaaaa tctccctaat 52740
tgtatttctc ttcacagaga aagcccctgt tgggcatata tactctagtt tgtttatttg 52800
tttgactaca catatatgta ttcttttctt atgtataaaa attctgaaca tgcacatttc 52860
tgcaactact gttttcactt gatgatgcat ggacctctct agagtgtacg tttcttcttc 52920
cttacaaagc agttggcttc gcccagggta caccaggaca cggttttggc tctgtcccca 52980
gggtgtcacg ggaccagggg atgatctcac agggtctgcc atctgccctg cctggccgga 53040
ggctgcatcg agagggccaa ggggcaccac gtgtcgtggg tactgtcaaa caagagcctt 53100
cagagccttc cacagtcttt cttttgcttc ccagcattgc ttccccgctg gtggactctg 53160
aatctagaac tagctccagg cgcctctcca aattcagacg ggagctgggg cactattata 53220
atgcaaatct aggcaaagcc ctcccaatac caggatccag aatggggtgg ggccctttgc 53280
cctgaaaagc tgtttagttt gaaaatacaa acaggagaca gaaaagtttg gctaaattaa 53340
tggataaagt tttaacgatg gtaaccatag tagggttcat cgacagccag cgatggttct 53400
gaacacttga catgtattaa ctcacctaat ccccacattt tacagacaat gcaaaggagg 53460
ctctgggagg ttgagtgact tgccccaaag tcgcacagct cctaagtgaa ggattcggag 53520
tggactccag gcagcctggt ctgactccct gcactgcgct gtgcttatct ctggccccaa 53580
tgccgccatg cagaagtgtc tgggggcact ttgtctctgt cagacagaat tcggagatgt 53640
gtatgcttgc cctggtatgg cacttctctt tttttgagac agaatctcac tctgtcaccc 53700
tggctggagt gcagtggcat gatctcagct cactgcaacc tccgcctccc aggttcaagc 53760
aattcttgtg cctcagcctc ccaagtagct gggattatag atgtgcacca tcgtgcctag 53820
ctaaattttt gtacttttag taaagatgtt gttttgctgt gttggccaag ctgatctcga 53880
acttttggcc tcaagtgatc tgcctacctc agcctcccaa agtgctggga ttacaggcat 53940
gagccaccat gcctggcagt gtggcacttc ttacgtgtgt tcagcggaca ctgtttatct 54000
tctgtccctc caagacggtg ctgagctcag gtcgttcatt actggcagac aactgctgat 54060
ttccaacaga attgccatcc tcttctcccc tgcgactttc agagtgtgac ctcagactca 54120
aaaattagaa gtgaaaacat cttaaaaact atcacctttt cttcctaatc ctcctctccc 54180
ctccctgtct tccttgttgt ccccatctaa tgaactatca tggcaaaaag agcccatttc 54240
tggtcatttt ctgtggcctt tcaaactccc acctacccca ctgctcctgg gtgcattacc 54300
cgaaagctga gacttcagtg cagaaagtgc caggccctct gtccccccag atcgccttcc 54360
ttgtcttccc tgtgcttgcc tgtcacattg tgtgggttcc agcgctggaa ggaatgagga 54420
acagattctc tggttctcct tttgaagttt accttcgctc caccacttct gagaccttcc 54480
cggaagttgc cccttgtttc tctcctctcc agggctgccc cagagctgcc tctcacctct 54540
tcctgctgtc accccaccac catcagggca gaagttggga caaagcctct cctactggct 54600
cctgcttttc tcccttaggt ccagcctcct cttctccatc ttcaggagtc tccttctcca 54660
ctcacacgtc atgacttcag cacctcgcat cagtccagaa tatgactgct tgttcaagtg 54720
ccacctttct catgcatttt tttctagtga caatcacagc caccctgtgg ggcaggagtg 54780
tcatcatccc catgtttcaa atgaagaatt gcagttcaga gagggcaagt gactggccca 54840
gcctcaacag ctagccagtg gaccccacca gggcttctga ctccagtccg ggttcccttt 54900
ccacccaaat ccatggaggg agctgagccg agaacaggtg tccttcagga agacgtgaag 54960
ccaaagcctc cacctccaaa ctcaggggcc cagggagtcc aggcacccat ccactcacaa 55020
ggctggatat ggtgcattcc aggagagggg ttgggggcga gtggcctctc tgtgtacccg 55080
tggggataga tgcgcaagtg gcatcgccac atcgtgagtc ctggcttcat gggtgagctc 55140
caggtccaac gagaagccaa gcagggggcc cttcaagctc agctttgggc ccgggtcggg 55200
gtacagggta gagcgggcct ccccagcccc tgccatgagg ccaaggcagt gcatcgttcg 55260
cagcgtacat tcagaaacca aagcctagga gctggttatc attccggttt acagctgatg 55320
gaagagcagg tgcttccgag aacccacagt gctctttggc cagtgaccca agggtgcctc 55380
tgagaggcct cgcagcaccc ggaggtgctg ctgaggcaac gccctgactg taagaaggac 55440
cattcatcct cagagagtgg ccgtgatgct gctgcgacag tcccaccatc cctcccgact 55500
ctcactccca acagacttcc cactgtaaag ctgaactctc cagcaaatca cctctcgcca 55560
gactctctcc tcactctctc tgggtccact agaggttcct cagcctctct ttgccttggt 55620
tttcccagct gtaaaatgga gcaaagaggg cctatgtacc cacaaaggtg tggttggagc 55680
gactcctcct acattagggc ctcgagtggg gcttcatgat tggttggtgg aggtctccaa 55740
acccacccag tgccaccgaa ggctgagact gcagatgcaa tgccacaggt gtccttcctc 55800
agcctgggca gctgaacatc atgtgtaaaa cggggataat aagataataa cagccccttg 55860
cacctatgtg gctgtgagga ttaaacaaga taaatgtgta acagtgcctg gctatagaaa 55920
tatttactct tgttattaag ggaagaatat gtgtggctaa aaagggatcg aagatgtaaa 55980
agccaatccc tccccctcta gcatatttaa gggtaatgtt gagttggttt gtggaccatt 56040
tgctgcctgt tagagctgga aggtagggac cccctctcaa cagcgatgct acaaattata 56100
cccattggag gtcaaccaaa agacaaagct tattggctgg acatggtggc tcacacctgt 56160
aatcctagca ctttgggagg ccaaggcagg cggatcactt gagatcagga gttcgagacc 56220
agcctggcca acatggtgaa accccatccc tactaaaaat acaaaaatta gctgggcgtg 56280
gtggtgcaca cctgtaatcc cagctactca ggaggctgag gcaggagaat cactagaacc 56340
caggaggtga aggttgcagt gagccgagat cgcaccactg tactcaaacc gaggcaacag 56400
agggagacgc aatctcaaaa aaaagaaaaa aagacaaagc ttgttaatac cagcatattg 56460
ttaagggaat aaagtaggct gcagaacaac tggtgtaata tggtgccatg tagggaaaat 56520
tacatgtgtg cataggagag gggtctgcaa ggttgtgccc taagatgtta gagtggttcc 56580
tttgcttttc tcttttataa ttttgtattt gacttttaaa taaggaccat aaatcacttt 56640
tataaaatac attctctcca gcccctacta ctcctttaaa gaataagagt ggtttgccca 56700
agaaagacag tttttttgc tctggttttc ttgattctga catcagagga aactccttct 56760
catccacttg gggctctggg ttcaggggat tcatttcagg cagattaaag tggtgaccag 56820
gggcattcgt ggacacaggg agggacagga gcaccatcag tttgtctcac acaaccactg 56880
tcatcctcac tgaaggctgt tgcctgatca aaaacagtat tgggccaggc acggtggctc 56940
acacctgtaa taccaccact ttgggaggct gaggtgagtg gatcacttga ggtcaggagt 57000
tcgagatcaa cctggccaac atggtgaaac cttgtctcta ctaaaagttc aaaaattagc 57060
caggcgtggt gggtgcctgt agtcccagct acttgggagg ctgaggcagg agaattgctt 57120
gaacccgaga ggtagaggtt gcagtgagcc gagatggcac caccacactc cagcctgggc 57180
gaccgagggg gactctgtct taaaaaaaaa aaaaaaaaaa aaaaatatat atatatatat 57240
atgtcaaaaa tggggtagtt tttagatcta tagtagttct aaaaacaaag gccatccaag 57300
catgacagat ttacaagcac tattggctat tccagtagtt acaatggagg agagaagctt 57360
ttagttaaaa caaacaaaca acacaacaaa cccagaaacc ttaggtcaaa accaaaattg 57420
tcctctcaga cacaatctgg gaattttctc atgacagtgg gcattagcca actgacatca 57480
gcagcaacca tccgtgtgca cacagtggca ccacctcctc ccaaaaagca gccttcatct 57540
atgccctcat acaatcgttg attattctct ttggattgag gcccggaatt atttaagttt 57600
cttcttgcca gcatgagtct ttcctttctg tatgctcctt atcttctctc tttaatttgg 57660
cagttctgct tgaaatctgg gtctttcatt agtagtagtt caatttggtt ccagaacatt 57720
ctgtggtgtg atgcaatgtg accagagctc acacttcaga gctcttcaag ggccagtctt 57780
actgagcacc tcccagtggc tgcctgtgtg ctgggcgcca cttgtggtgg gcaggagaga 57840
ggaggggaca caaaaggaga cacagctcct tcttagaagc tcaaagttgg ggaccagctg 57900
ccacagaaga gtatgtttag catctgagac accaagatcc agcgtcacaa gggtgtttat 57960
taagcctcct catctctttc tttttctttt tttttttttt tttcctcagg cagtcttact 58020
ctgtcaccca ggctggagtg cagtggcatg atctcggctc actgcatgca accaccacct 58080
cccgggttta agcaattctc ctgcctcagc ctccccagta gctgggatta caggtgccca 58140
ccaccacacc cagctaattt ttgtgttttt agtagagaca gggtttcacc atgttggtca 58200
ggctggtctc gaactcctga cctcagatga ttcacccacc tcggcctccc agtgtgctgg 58260
gattacaggt gtgagccacc gcgcctggcc ttgctgttga ttcatctata gtatgtttga 58320
cttgatgacc tccagttacc ttagacagag gttctcatct aagctccaac tttccatttc 58380
ctttgtcctc gtctttcccc ttaacccctc cacatttctc tcaaaatcac cccacttcta 58440
aaaaatactg tttatttttc ttttaaattt caaattatct atactcattg aaataaatca 58500
aaatagcatg gaataagcga aaaaaatgga tcccaccctt ccccactccc attccctagg 58560
gctaaccata gttaaccatt taatgactag gttttttttgt tgttgttatt ttttatttat 58620
ttattttgag acagagtctt actctgtcac ccaggctgga gtgcagtggt gtgatctcgg 58680
ctcactgcaa cctctgcctc ccaggttcaa gcattctcct gcctctgcct cctgagtagc 58740
tgggattaca ggtgcctgcc accacacctg gctaattttt gtacttttgg tagagacagg 58800
gtttctcaat gttagccagg ctggtctcga actcctggcc tcaagtgatc tgcccacctt 58860
ggccttccaa aatactggga ttaaggtatg agccaccgca cccagccctc ctgggctctt 58920
ttcctttagt tgcactcgct ccccgctcct ggagtagagg gatttccgag agactgtggg 58980
ctccagcctt cacctaggcc caggactagg atgcctgccc taacatttat ctttatacct 59040
taaagcaaaa cagctggacc ataagcattc aagaacaaac tgtgaataag gagaaagttc 59100
tcccaggaaa caagagcttt agttatgttg ggccagccct tatattcctt agctgttacc 59160
agtcactgct tgatttaatc tcggctatca cttggcctga caggtctgct gctggtgcca 59220
ggatgtctgg gttttgaagc ctggctccat tacatacttc ctgtgtgacc ttgggcaact 59280
tactcaacct gtctgttcct cagtttcccc agctgtatta tgtcagcata atagtttgtt 59340
gtgtgaatta aatgaggtaa taactggaaa tgcttcaaac atggttccta tcatgagaaa 59400
tcctgctttc cgcctaaatg tgctggaaaa ttcctggtgg tgcagaacag gagaccagag 59460
caaaggaaag acagggtgca gaagccaaaa attaccttgg agaacaaagc gcatgttaag 59520
gttatttttg gattctaggt ttatctctgc ttggtcttca gttacctaca agagatccat 59580
ttaggggatt tttgtttgtt tttaacgata gctttattga gatataattc atatgccata 59640
aaagtcactc ttttaaaatg tttccggtat attcacaagg ctgtgcagcc ttccctgtcc 59700
ttgattccag tctgagtttt taactgaagg gataaggagg accacgcttt ccccagacca 59760
gaaccgcggg ccagggggcg attccgctga gtcaccgcgg gcgcctggtg cgcggcggcg 59820
gagcccggga ccttccttgg ctgcccccta gcgagggccg cagcgcagcc tgagacaccc 59880
gccggggccg ctccacggcc gtcggattta gactggaagc tcggtccagg tccccagctt 59940
gatgcgcccg cggtgtagga gaccagcccg actcgagctt cccctgagcc cctggactct 60000
tgactccagc agggcctggg taatgaacgt cagctcccct ttcccaaagg ggttgctctg 60060
ttgggaaggc acccgtttga tacagtagca tagagatggg ttttagcatc aaaatatcag 60120
aattcaagcc ttgctctctg cttactagct gtgtgaccct aaaaaggttt ctgaacgtct 60180
ctgagcttca gtttcctcat cattccttct cacggggtgg ttgtgagcat tacagagatc 60240
ctctctgtga agcccctgtg agtggctcat cctgagggct gaaataaaca tgttattaat 60300
aatccaaaac tggcaaggga tgttgactgg tccccctccc ttgcccaagg agctttctag 60360
aacctgagtt atcattacca aactgtactg ccttgagtaa gaaagttaga aggaatggga 60420
aggatggtgg caggtggagg aaggcggatt ggtcatcacc tccttgcagc aagaaacagc 60480
cccagatcgt gggaaaccta cagacctgct agacagacta ggagcaaaag ctggggcttt 60540
aagaatcccc agggaggttc tcctgagaga gtagccagtt ggattttgta agcagagatt 60600
tgtttgggga ggaggtgaca acgtagggag cagaggggca aagctgtcgg gaatcctgcc 60660
ttgagggcag ggatgtgtgt tggggggagt tgggtcactg gggctcggtg gccttgggca 60720
agtttctacc tctcaggtcc tttacccacc tagggtcgcc atcctgccca cctcacaggt 60780
tacagtgagc ctggatgcac tgtcatgggc aggtgcccag gaaaatggca gacatgttcc 60840
aaacagcacg cagcattccc cagtgatgcc cagggtcacc ttggaggtgg gcgagatgcc 60900
tggggtttct cgtccacccc acaacacctc aggggacagc caaagctgtc ccttcaggta 60960
agctgcacag aagatgtgaa ctctgctgca aagactctat tctttgggag caaaagggac 61020
ccagggtctc acctgcacat ccctgtccct gagggcctag gggttcttgg aggccccagc 61080
cttggcaaaa tgaggaagaa ggtgaaggtt gtctgggccc ctgccaggct ccttcctcgg 61140
ccacgcactc cccttcctgc acacacaccc ttctccctcc accccatctc cattgttgtc 61200
agaaaagtca caataaaaag gtccatattg tctagttccc atacttttaa tttttaaaat 61260
tttatttatt tatttattta tgtatttttt gagacagagt cttaacccag gctggagttc 61320
agtggcatga tctaggctca ctgcaacctc tccctcctgg gttcaagtga ttctcatgcc 61380
tcagcctccc gagtagctga gattacagat atgtgccact atgcccagct aatttttgta 61440
tttttagtag agacggggtt tcaccatgtt ggccaggctg gtctcgaact cctggcctca 61500
agtgatctgc ctgcctgagc ctccggaagt gctgggattt caggtgtgag ccaccgcact 61560
cggctccaca cttttcactt attaaaagac tgtggtgtcc atcaatggat gaatgaataa 61620
accaatgtgg actatccctc ccattaccca aggaatgaag cacggagccg tgccaagatc 61680
tggattcaca gtgaaagaag ccagtcacca aaagccacgt gctgtgtgac ttcccttata 61740
cgaaatatcc agaagagata catccatggt gacagaaagt agatgagcag ctggggactg 61800
gcgaagggga gaagggggag cagctgtcta tgaggtccag cctttcttct gggtttggtg 61860
agaatgtttt ggaactagat agaggtgata gttgtacaac attgtgaatg tactaaatgc 61920
cactgaatca ttcattttaa atcgttcttt acgttgcatg aattttaagt caatcaaaaa 61980
cagttgtttg aaaagagaaa agcctatggg tagcggcagc agtgattgga tttatgattc 62040
gattccatgg ctcatccctc ccctgcctca ccccctcgcc ctccgacgtc ttcttctttt 62100
actctgaact gttatctttg ttctcatctc tctctctctc tctcaaccct gcagacactt 62160
ttccctttct ttgtctgccc ccaccctcca gatttccgtg tctccagtgt ctccctacga 62220
ggcatgaatt gagactggga gggtgtgatt ctgaagaagg caccaacagt gactcagcta 62280
gccccttccc ccaccccgcc ccccgggcct caatttagct aaaaaaccac agggacggac 62340
tcaggaggca ataccttccc aagggtccct aaaaaatgtc ccattttagt gtccaggttt 62400

-continued

```
cactcaactt tagtgcctcc cctaaaatgt gttccttacc tcccacccca ctgcatctaa  62460
gtcactgcct gagaaaacag gattgaggaa aggagaaagg aagagagaga gagaggagga  62520
gagagagaga gagggaggaa ggctgatgga tttagaaaag aagaaaacaa gtggtctgag  62580
gaaaacagcc ttggtgtgtt tattttcctg tctgtgtatc gcttctcggc cttttggcta  62640
agatcaagtg tattttcctg tctgtgtgtc tcgcttagat tacagggatc tgtgggtgat  62700
gacacgtctg gtccaggctg cgtagtcacc tcaagggcat gcttattgat gtgtttttca  62760
attcactatc tttgcatggg agtcccaggc caagaggcac agctgcgcca tttgtctgtt  62820
ggtttagata tcctttatcc agttcttcca gagaaatcat cctgcccttc tggaggaggt  62880
gggcagcagg ggtcagagat gggagggaaa ggaaggagcc aggtccttgg ctaggatgcc  62940
agggtcccct gcctctcacc tggcctgggc tggaggcctc ctgctgtcct gtcactgatc  63000
actaccccgc cccagcctcc tgagttagaa gacacaggct aaagtagagt atttcttcat  63060
tgaaaaaccc atacaaaata aaggttcata aaaaataaaa atttagactg ggtgctgtgg  63120
ctcacacctg tgatcccagc actttgggag gccaaggcag gtggatcgct tgagccctgg  63180
ggttcatgac cagcctgggc aacatagtga aaccccatct ctacaaaaaa tacaaaaaat  63240
tagccaggca tggtggtgca tacctgtggt cccagcttct cagcctatgg acccacatag  63300
aatacaatgt cagcataaga agggagccct ggggtcacca aatggtttgg gcggcaaaga  63360
acctgaaggt tgagagaagt ggcttggtta cccagctgtt ggatgtgaga cctggccact  63420
gcttcttcca taccctagac ctgcaccctg acatctcaag taaaaagttg ggggatgttt  63480
tatggtccag gatgaaggaa gggcagtgag gggcagcgga gcatcacttt gcatttctgt  63540
ctgcctctta ctggctgtgt gacctggggc aggtaacttc ccagactcct gggaatcata  63600
acacctatga tgatgatgat gatgatgatg atgatgatga tgacacctac ctcaaggatt  63660
gccctgaagg gtcacagaga tgcctgcaag gcacctgcat ggagcaagcg ccccttctct  63720
ggcaggtgct gggtgagcac tacctgctgc caggccctgg ggctatggca ctgcgtgacc  63780
ctgcaagtcc tacctggcga agctgtcgtt cttgtgctca gtcagtgttg gttgtaagac  63840
tgagaagagt cacttcattt tgctctccag ggacatcttt ctgggtccta ttttctgcct  63900
atgtcaagta gcgcctcaag gatgctcctg aaaatgggct tgtctttctt aacatggcag  63960
gtaggtccca aagcattagc atggggcagc tgacctagcc cagccaatgc agtgcagtga  64020
ctcttgcaac cgagtctaat cagaaggtcc atgaacctac gagcatttcc tgtcccagga  64080
tcagggtgga ggctgagcct ccctgcttag agattcttcc catgcattcc actttttttcc  64140
ccaaaagaaa atattgaccc ttgagaggca cacagtttat ttattttgca tagtaaatag  64200
tagcctgtat tttaaggatg agttgatttc tgcatcagcc cctgtaggtc atcagccttc  64260
tattggtgca tctgactctc tctagccctg cagggatggt ggagggggag gggaaggagg  64320
gatctttatt ggaaaccagg acagtgagac tcattgccct gtcatctgct ctgtggtgct  64380
gaatgaggca gcccaacaga gaaataccct gagcgagcat ccccagcctc caaaacagtg  64440
gcgcattgcc ctgagtcctg ggaatgacct ttgattctcc tgctcctgac ttggaaccca  64500
tggaaacctc tagaagcagc tgaggaaaac ccaacatgaa aagcagaact ccacactgag  64560
aatataggag gtgatcggaa catacaatga ttcttgctaa gaccgattca cagtttttct  64620
ttttttcga tcgaagaaat actggagaag cctaaagaag gagtctaaaa actctggcac  64680
gtgggccaaa actgtccttg agctaagaat gattttcaca tttttaagtg gttgaaaaat  64740
gaaataaaat aagatgatgt tttgtgacac atgaaagcta tgggaaattc aaattctaat  64800
```

atctataaat agtgttttat cagaacacag tcatgctcat ttatttatgc tcgatggctg 64860
ctttcccgct acaattacgt tgagcagtta caacagagac cacgtggccc acaaagcctt 64920
acaatattta ctatctggcc ctttccagaa aaaaatgtgc cgactcttga ccttaacctc 64980
agcaatttgg gaggccgagg caggcggatc gcttgagctc tggagttcat gaccagcctg 65040
ggcaacatag taagactcca tctctacaaa aaatacaaaa cattagccag gcatggtggt 65100
gcacacctgt ggtcctagcc actcgggaga ctgaggtggg aggatcgcct gagcccagga 65160
agtcgaggct gcagtgagct gtgatggcac cactgcacct cagcctgggc gacagagcaa 65220
gaccttgtct ccaaataaat aaataatgca aagtaaaata aataaaacca tataaaaagg 65280
aatcaattta aaattataat gaaagctggc cgggcatggt ggctcacgcc tgtaatccca 65340
gcactttggg aggctgaggt gggtggatca cgaggccagg agatcgagac catcttggct 65400
aacacggtga aaccccgtct ctactaaaaa tacaaaaaaa aaattagccg ggcacagtgg 65460
cgggcgcctg tagtcccagc tactcgggag gctgaggcag gagaatgtct tgaacccggg 65520
aggtggagct tgcagtgagc cgagatcgtg ccacttgcag tccagcctgg gcgaaagagc 65580
gagactccgt ctcaaaaaca aaaacaaaaa caaaaacaaa aaaaaattat aatgaaagcc 65640
aaggggcata gtagaacaaa ttttctagag ctcattaagt caaatgagtc accagttagt 65700
aaaacgcagt cacggggaag agagggcagg attctttgaa gcagcggctc tcctaaaaac 65760
aacccaccct tgtccagctg ccttccctcc tgagggtgtt ccctttgact gtgtgacccc 65820
catcccctat ttcccaaccg tccaagccca cctctagcat aatacgagct tttaatccct 65880
ctccctgacc ccaacccgat tttgaagccc agtctagtat tttctcaaat acacttcttg 65940
gctccattcc ttcctttcca tcacctctgc cttttcactg catgcttgga ccactgcagt 66000
cagctcccta tgaacagttg ctctctaccc atccaatcgg ccccgcctgc tgctgccaaa 66060
ttcaccgagg gcacctctgt ggtgctgcct gtggacaaag tccaagccag ccacctcacc 66120
cacctacagg tgagtgggga gcagccagcg tgtccagtgg tttaccccat cgccacagac 66180
ttggtgatgt gtcgatgtgc agagaagggg tgttggcagc cacaacacaa gcaaccccgc 66240
cccatgtgag atctaagatg ggcgtgctgg gagccacctc tgagaatcca acagaaggca 66300
gaggggagaa cggctcacac ggcacaaaca ctccttcctt ttttttttt ctttttcctt 66360 tttgaaagga gtctcactct attgcccagg caggagtgca gtggtgcaat ctcagctcac 66420
tgcaacctcc gcctcctagg ttcaagcgat tctccagcct cagcttccca agtagctggg 66480
attacaggta cactccacca tgcccggcta atttttgtgt ttttagtaga gacggggttt 66540
ccctatgttg gccaggctgg tcttgagctc ctgacctcag gtgatctgcc tgccttggcc 66600
tcccaaagtg ctgggattac aggtgtgagc catggggcct agcctccttc catttaaatg 66660
tatgcctaat ttgcccattg agaacggctg agacgcattt taagtggcca gggtctactt 66720
agagttagtg ctcatgacca ggcccaggtc aagcctggct ggccagatgg tgcctttgac 66780
ctgctctgtc tctgtgcaaa ggaatgagct gaaggatggg ggtgcagtgt gtgggcagtg 66840
ggctggggct ggcaggactc agtgactaag ggaagagaac tttcctcact accagcctgt 66900
cttttcaggg caccgcgggg ggctttggga cttggtgatg aacacagcac agagagctgt 66960
ccagcatgcg ggtccctggc ttctcacact tcccaggctc cttcagaggc tctctccaaa 67020
gggagctgct ctctctagaa cccatgaatt tggaatatag gcaaccactg cattggggac 67080
cactgacctc aaacatagag accagagcaa atggggctca tcacgtgaaa ctcatctgga 67140

```
actctagcag gttcttttat atatatatat atatatatat attttttatt attatacttt  67200
aagttctagg gtacatgtgc acaacatgca ggtttgttac atatgtatac atgtgccatg  67260
ttggtgtgct gcacccatta attcatcatt tacattaggt atatctccta atgctatccc  67320
tccccactcc ccccacccca caacaggccc cagtgtgtga tgttcccctt cctgtgtcca  67380
agtgttctca ttgttcaatt cccacctacg agtgagaaca tgctgtgttt ggtttttttg  67440
tccttgcgat agtttgctga gaatgatggt ttccagcttc atccatgtcc ctacaaagga  67500
catgaactca tcatttttta tggctgcata gtattccatg gtgtatatgt gccacatttt  67560
cttaatccag tctatcattg ttggacattt gggttggttc caagtctttg ctattgtgaa  67620
tagtgccgca ataaacatac gtgtgcatgt gtctttataa cagcatgatt tatattcctt  67680
tggttatata cccagtaatg agatggctgg gtcaaatggt atttctagtt ctagatccct  67740
gaggaatcgc cacactgtct tccacaatgg ttgaactagt ttacagtcct accaacagtg  67800
taaaagtgtt cctatttctc cacatcctct ccagcagctg ttgtttcctg actttttaat  67860
gatcgccatt ctaactggtg tgagatgtta tctcatggtg gttttgattt gcatttctct  67920
gatggccagt gatgatgagc attttttcac atgtctgttg gcgaactcta gcagcttctt  67980
ttcacaagtt catggagaga ggtttcccac tgagggaatc acatctgtct gatcaaaaga  68040
ggcttgggaa atggctctcc tgttcattcc ctgaaaacct ctgatggaac cactgccact  68100
gtggcagccc cagcactggc accccagcca tgattggtgc cccagccaca tctctgctgt  68160
gagccccaga gccctggtta attaatcatc cacgtgttga tggggagagg cccattcaca  68220
aaagcgacat aaagcccagg gagacgtggc cgtggcaaga agggtgtggg actacattcc  68280
gcccccaact gagagattca gaaaccagaa aaaaatggaa aaacatactg tgctcttggg  68340
tgggaaaact aaatatcatg aagggagcaa tttttatagt tttggcctat aatacaattc  68400
cagccgaaat cccagtggaa ctttgagaat ttgcaggaaa aaaaaaaatg tctaaagtac  68460
atctggaaga caaacttaca agaaggtcaa ataattttga aaaagaaaat gatatctaag  68520
cccacctaga gaataagact tgagatccaa agctaaatca ggaggctcta gcaaaattga  68580
cagataagca ggacagagtg catggtgcat tcacctgggg aagagggcag attggtctac  68640
aaataggcct gggtccactg actttagctg ttatatttgg ggagaaactt ttcaacctca  68700
ctccatctta aacctaaaaa tattccagat gaattaataa atataaaaaa ttagaccact  68760
aaaaatgtag aagaaaatgg atgatctttc tataccatag agcaatggaa taaatcacaa  68820
aggaaaacag atttgactat ataaaactta aaccctgccc atcaaaaacc atcagaaacc  68880
aaaataaaag gcaaccaact ggagaagata gttgccacaa atatgatcaa gggttaatgt  68940
tattcataaa ttaagagccc acacaagtca ttagaataag cactgagacc tgaacagaca  69000
agcaaaaaga atgagagtgg gtcggcgcgg cggctcatgc ctgtaatccc agcactttgg  69060
aaggctgaag caggcggatc acttgatccc aggagttcca acaccagcct gagcaacatg  69120
gtgaaaccct gcctctacaa aagtcataaa tattagccgg gtgtgatggc acacgcctgt  69180
agtcccagct actcaggagg ctgaggtggg tggatcactt gagcccggga ggtagagtct  69240
gcagtgagcc aagatcacac cgctgcactc cagctggagc aacagagtga gaccctgact  69300
taaaagaaaa aaaaaaaaaa agaggagaaa aatgctgatc tcactagtaa ttaaaacatc  69360
aggccaggcg cagtggctca cacctttaat cccagcactc tgggaggctg aggcaggcag  69420
atcacttgag atcaggagtt ctagaccagc ttggccaaca tggtgaaatc ccgtctctac  69480
aaaaaataca aaaattcgcc aagcgtggtg gcacatgcct gtgatcccag ctactcggga  69540
```

ggctgagaca ggagaattgc ttgaacacgg gaggcagagg ttgcagtaag ctgagatcgt 69600
accattccag tccagcctgg gctacagagc gagactctgt cccagaaaaa attaaaacat 69660
cacatattta aacaactcta ggatatcatt taaaaaaaca ttaatagact gttttttaga 69720
gcacttttag gttcacagtg aaactgagtg gaaggtacag agacttcccg tatgttccct 69780
gccctccacg tacagcctcc cccactgcca acgtcctgca ccagagtggt acacttgtta 69840
caaccaatga atcctcatta acatatcatt atcacccaag ttcatagttt acattagtaa 69900
aacatcatct ttcatctata agcacaaaaa ttttttggca tttatttagg tgtatgatta 69960
actcagtgtt gacaagactc acacttcata cccacttgca ctgcatctga gaagcaattg 70020
gtgtctacag ccgctacacc ctcaacaagc ccgatcttgt ttgaaaagca attggtgatg 70080
cttctcaaaa ttctatggac aaagtcagcc gggcatggtg gctcatgcct gtaatcccta 70140
aactttggga ggccgaggca ggcagatcac ctgaggtctg gtgaaaccct gtctctacta 70200
aaaatgcaaa aattacccag gcatggtggc tggggcctgt aatcccagct actcgggagg 70260
ctgaggcagg agaatcgctt gaagcaagga ggcggaggtt tcagtgagcc aagattgcac 70320
cactgcactc cagcctgggt gacaagagtg aaactccatc taaaaaaaaa aaattatgga 70380
caaagttttt caaaaagata tttaatgcaa ctttatttgt aatattggaa catctgaggc 70440
catttcagtg ctaactatta ggggatggtt aggaaaatat ggtacatatg tggaaaggaa 70500
catttggtag ttagtgcccc tgatgtttac aaaggctttt agtgaccaac aaatgctcat 70560
gctataatct tatgtgaaaa aagcaagtag cataattgca actatatttt taatgcatag 70620
aataaaaggc tagaaggaaa tatcacagat ccttgacata cattcccaaa cctttgtaaa 70680
tccgcggatt catgaaaaca gacacatttg cacaagtgcc tgatcttttc tgttatacat 70740
tcattagaag tcaagccctg gtgccacaaa gtatctgcct tttcaaatgt gatcagaatg 70800
ttctcttttg cttcaaggcc atttttcacg aagcagtggc atttttgcct cttcatcaga 70860
gtcaccgtgt gccctggagg actgagaaca gcagagccgt tttaggatgg gacagggcag 70920
ccaggaggat tgggctcact ccctactgag tgcctcactc ccgtacagcc cccatagagg 70980
aagaggggtt caaatttatt cctcagccag atggcatgtg ccgcctgtcc tggaatttca 71040
catcacttat gatggaccaa aattccaaaa gctgaatcca tgattgtcaa agtctggtat 71100
ggcaggatgt caacagtaat cgtttctggg cagagggatg attttctctt cccatcttgc 71160
tttgtataaa tacattttct ataataaggt tgtattactt ttctcatcaa gaaatagcaa 71220
agtactgttt tactcaaaat atgaatagag ccaggcatgg tggcagctta tgcctgtaat 71280
cccaacactt tgagaggcgg atatgggagg atcactttag cccaggagtt tgagaccagc 71340
ctgggcaaca tagtgagacc cccgtcccca ctcccccaaa gaaaacccac aaagcattta 71400
tcctggatta ttcacagggg ccaaaaaaaa aaaaaaattc aggcctccta tagccatgag 71460
ctacgaatat gaaaatatgc aaatgtgtaa gaaaagccag cacatccgat ttttactttt 71520
actttcacac ctctgtccac catgttccaa gagaagaaac ttggtcattg aaaggaatag 71580
atcaaatcca aagaacaaaa ccactgtgct cattaaactt cttagtgttc acaaagcttt 71640
agctgcaggt tgaatggggc aacccgaatt ggctggctca cctgggctgc agggagcaga 71700
gatcgcgaca ctgcactcca gcctgggcaa caaagcgaga ctctatctca aaaaaaaaaa 71760
agttcataaa ttcaaagtta tgaattattt ttaaaataat aataatttac aataaagatg 71820
aggacaaagt gtgagtaaat ggtggtttct atccagctct gttgagctga agtggcatct 71880

-continued

```
ccctgctggg gcttttgggg aagaagggtg tgtgttgctc ttcagatccc aagcctcatg  71940
cccctactgg gccctgtggg gtgcttctca gcccaccagg agagccaccg ttggaacaca  72000
cacgtggggg acctggtggg tgccggtgtg gtgaatgggg gccacagcct gactccagga  72060
agccagcaaa ctcggagctg gaggagtcag gacacccccg atgagtcaag agttggtttt  72120
gctgccagtt gacatctgat tgaaccatct cttcacttct ccgtgcctca ctttccttac  72180
cagacaggct ctgctgatgc tgtccctctc ctgttcagtc gtgccctcac cgttaaagag  72240
aaagagcaaa ctgctgggca gcagcattga ttttttaat gaagtggaaa gagagctggg  72300
aataacaagt cgggcccacc tcacctgcct cacctggtgg gtttatttgt tttgtttttt  72360
tttttttgtt ttgagacaga gtttcaccct gtcacccagg ctggagtgca gtggtgtaat  72420
ctcagctcac tgcaacctcc acctgccagg ttcaattgat tctcctgcct cagcctcccc  72480
agtagctggg attacaggca cctgccacat gcctggctaa ttattgtatt tttagtagag  72540
atggggtttt accatgttgg ccaggctggt ctcgatctcc tgacctcagg tgatccaccc  72600
acctcggcct cccaaagtgc tgagatcaca ggcgtgagcc accatgcctg gccgtcacct  72660
ggtggtgttg aatatgaact gctgcggtgt tggtaaatta agcaagcaga tagatgtaaa  72720
taacgcttgg gcaggaatat ggagcacggg atgaggatgg gcggccaact gttagagagg  72780
gtagcaggga ggctgagatc tgcctgccat gaactgggag gagaggctcc tctctctctt  72840
cacccccact ctgcccccca acactcctca gaacttatcc tctcctcttc tttccccagg  72900
tgaactttga accaggatgg ctgagccccg ccaggagttc gaagtgatgg aagatcacgc  72960
tgggacgtac gggttggggg acaggaaaga tcagggggc tacaccatgc accaagacca  73020
agagggtgac acggacgctg gcctgaaagg ttagtggaca gccatgcaca gcaggcccag  73080
atcactgcaa gccaaggggt ggcgggaaca gtttgcatcc agaattgcaa agaaatttta  73140
aatacattat tgtcttagac tgtcagtaaa gtaaagcctc attaatttga gtgggccaag  73200
ataactcaag cagtgagata atggccagac acggtggctc acgcctgtaa tcccagcact  73260
ttggaaggcc caggcaggag gatcccttga ggccaggaat ttgagaccgg cctgggcaac  73320
atagcaagac cccgtctcta aaataattta aaaattagcc aggtgttgtg gtgcatgtct  73380
atagtcctag ctactcagga tgctgaggca gaaggatcac ttgagcccag gagttcaagg  73440
ttgcagtaag ctgtgattat aaaactgcac tccagcctga gcaacagagc aagaccctgt  73500
caaaaaaaaa agaaaagaaa aaagaaagaa agaaatttac cttgagttac ccacatgagt  73560
gaatgtaggg acagagattt tagggcctta acaatctctc aaatacaggg tactttttga  73620
ggcattagcc acacctgtta gcttataaat cagtggtatt gattagcatg taaaatatgt  73680
gactttaaac attgcttttt atctcttact tagatcaggc ctgagtggcc tctctttagc  73740
aagagttggt tagccctggg attcttactg tagccacatt aataaacaac atcgacttct  73800
aaacattcta taataccatc ttttggccaa attgacttcg cctcttcctc tctctttcca  73860
aatgaaatgt gtttcatttc actgtcagac cacatggttg gggaccccac agagcacaca  73920
gccctccctc tgccttccca tgctggccct tcacccactg ctggagtgcc aggttggtcc  73980
aagggttgga ccaagttgtc tgaggttgtc tcaaggttgg tcgaggctgt ctccgcgctg  74040
ggttgtgcta caaggagccc ttctttccat gggtgtggct ggcagtgagt gctcacagca  74100
acagcccaca gtgcagcccg agggcaggat ggactcagtc cctgcctcca tacccatttc  74160
taaggaggca aaatggcaaa cactctactt ttctctttta atgctaaaaa taagaaaaca  74220
ccttgcagcc cagggtatgg gtagtgcatg gaagccgtgg agttgtgagg tgggaagtga  74280
```

cctctgctgg atatgtctat tcaggaagat tgctggagtg ggtggggtct ctgggaggtc 74340
ccctgagtgt gggaagctgg gaccaccagc tttctcgcac agggagtggc catcccagct 74400
tggagaggtt ccaggactgg ttgggaggca cgtttcagat ttctatctgt tgaatcagcg 74460
aagatattgg attatgagga atttgggaat taggaaagtg ggtgcaggtg ggttgggggt 74520
aggtgaagga agacatgggc gtattggggg agcaggggct gctcagaggt gttccagaag 74580
ctctgggtga ggaggtgaga gggaccgggg aatgcagctc ggcccagcct ccctgcctga 74640
ggtcagccat cacgtggtga tggcaagatg gaaatgtgct ttctgactgc tccagccagt 74700
gctgccagat tcagctcccc agggagggca cctgagaggc tccaagccag gagatctgtt 74760
ttctcctttg ttttgttttt ttttgttttg ttttgtttta ttatacttta agttctaggg 74820
tacatgtgca caacgtgcag gtttgttaca tatgtataca tgtgccatgt tggtgtgctg 74880
cacccatcaa cttgtcattt acattaggta tatctcctaa tgctatccct ccccccctccc 74940
cccacccccct gttttctcct ttgaatcctt cttagaggcc gggtgcggtg gctcacgcct 75000
gtaatcccag cactttggga ggctgcggca ggaggattgc ttgagcccag gagttccaga 75060
ccagcctggg caacatagtg agacctcgtc tctacagata ataattttaa aaattatccg 75120
ggcatagtgg catgcaccta tagtcccagc tactcaagag gcagaggcag gaggatcact 75180
tgagcccagg aggcggaggt tgccgtgagc caagatccca ccactgcact ccagcctggg 75240
cgacagagac ccccatgtca aataataata ataataaata aatccttctc agtcccttcc 75300
tcactgtgtc cccctccact gaatttttcc acctcctctc ccacttcccc cactcccgct 75360
ttccctctcc ttctctcccc actccatctt tttctttctc tgctgtttct cgtccctccc 75420
tcctctccat cccacaacac tgcctaccct gtccctgccc caccctggtg ctcaggatgt 75480
gtgaagtgag gggtggtagc ccccaagacc tcaaccccga aggttagcct gttgaaacca 75540
ctttctccca gctgcccccc tggcagttgg tgctgctggg ggaaactggg attgggggcc 75600
agattttgcc tcttttcctg acaaagagag atgaagagtt ctctcaccag gtgcctggga 75660
ctggggtgtg ggtgtcccag cctatcccag cgcatctgtt ctgcatcatg attaatagtg 75720
ctgctttcag ccgggcgcgg tggctcacac ctgtaatccc agcactttgg gaggctaagg 75780
tgggcagatc acaaggtcag gagttcgaga ccagcctggc caacatggtg aaacctcgtc 75840
tctactaaaa atacaaaaat taaccaggtg tggtggtggg tgcctgtagt cccagctact 75900
tgggaggctg aggcaggaga atcacttgaa tctgggaagc agaggttgca gtgagccaag 75960
atcgtgccac tgcactccag cctgggtgac agagcgagac tccgtcctaa aaaaaaagga 76020
gttttgctct gtcgcccagg ctggagtgta gtggcgccat ctcggctcac cgcaacctgc 76080
gcctcccggg tgcaagcgat tctcctgcct cagcctccca agtagctagg attacaggcg 76140
cctaccacca cgcccggcca gttcttgtat ttttagaaga gacggggttt caccctgttg 76200
gccaggctcg tctgggactc ctgacctcag gtaatccgcc cacctcagcc tcccaaagtg 76260
ctgggattgc aggcatgagc caccgtgccc agtcaactcc ttctcaaaaa aaaaaaaata 76320
gtgctgcttt ctctttcaag tgtcctgatt tgggtgatag taaatgccac tctacttata 76380
agggatctac ctcagaatgc taattgggac atttttgtag cactctactg ttggcagcag 76440
gtgatgctca caacagcccg tgagggtgga tgacgtccgc ttcacagatg acaaaggagc 76500
ctcatgctca gaccgtgggc tgccagagca ggtccatggc tgcagcccca catggaccat 76560
atttcccccct tgtcactctt tccaccaagc tcccttggaa cttcagttat taagctctct 76620

-continued

```
tgggtggaat ccaagttaga atcacaacat gtgcctcata tggattgtgc cagtgaaaaa  76680
tgacattcta tttagaggca gggcagcctg gcttagagtc agtttaaaat atgtattatg  76740
ctgcaacaaa tgtaccatga tcctgtaaga tgttcacaac aagggaactg gatgtggggt  76800
atactgtctg tactaacttc acaagttttc tgtaaatcta aaactgttcc aaaataacaa  76860
gttcgtttaa aattaactcc aggagaccag gtacggtagc taatgcctat aatcccagca  76920
cttcggaagg ctgaggcagg tggattgctt gagcccagga gtttgagaca agcctgggca  76980
acatggtgaa atcctgtctc taaaaaaaat cacaaaaatt agccaggtgt ggtggcgcat  77040
tcctgtagtc ccagctactt gcggggctga ggtgggagaa tcatctgagc ccaggagttt  77100
gaggctgcag tgagctgtga ttgtaccact gcactccaac ctgggcaaca gagcaagacc  77160
ctgtctcaaa aaacaaaaat gaaataaagt ccaggaaaga agtaggtttt accactctta  77220
ttttctgaag agaaaactaa atttaatgtg taaagtgagg acaagttcac caagttagtg  77280
tttgagttgc ctaaaatatg tttgctaaaa ctattcaaag ctttcacata aaacatgatc  77340
agaagttcta tgccaaaaca tatgtgtgtg tatatatata tgcactatat atactgtata  77400
taaaaatgca aaatctaaat tgccaacctt ttagaaattg ctctgaaagg aaagcatttc  77460
aagataattt gcttacccaa agaatatact ttccaagaaa gcaagtaata cttaaggtgt  77520
tcataatcct catcaaatta attcttgcta ctgaaagctt acaaggagct gttttgatgt  77580
cgggtgtgac aggtttgact tggcagaagg tgtcacttta ctaacaacat tttaaataag  77640
tgacagaaga caagaaacta cacgttaaat gccagaacaa agagtgtcta agtggatgct  77700
aagagttgaa atatggctgg atacctgccc aagagagctg aaaagtagat gaaagttggt  77760
tacctataaa ctagtgcacc ctaatgaatt aaaaggtgtt gatgagttaa cttgttatgc  77820
cttccagata agacatgcaa atggggcttc ttcctccttc actacttcca agggatttaa  77880
caaggagacc aatgcaaatg ataaggactg tagggctcaa gctggggaca gattggggaa  77940
agggggacca tcatgcccat atagatgtcc ctgtgccctg gcagtcaagg ctgctgaaaa  78000
ataacaaaac ccagaagtct gcgtgatgct gcctctccat ttgtccaaag ccttcttgcg  78060
gcagtttgca ggcttttgca aaagctccag gaccaaggag ctatgttcat gctggaagct  78120
tgttcaggat tagctgttct ttgtgggatg ggtgcagcca gggccaggtg tccagggaca  78180
gtgttttaac aaagggcatg aggtgtctga tctcacagtg gaactccact tgcctttttt  78240
tcatcttctc attctgcttc atgcacagaa ccagccccat cctgaaactg actctaaatt  78300
actcccgccc caggtggagt gcctttctcg gagttcaaca gagccttcct gtcgcccaag  78360
ggacaactcc actgaatgcc caagccacac ccaaaaccta acaagtaaaa accaaattct  78420
gtgctccccc atcctgggcc attcctggtt tctctactgc tgttggtgat accaccatca  78480
gcttgtccat catgaccctg gccagttcct cccacaaccc tccacagcac ccagggacct  78540
cacctccatt ccatccgaca cagatctcct caccacaaac cttggttttg caacagcagc  78600
catgagacct ttacaccctc cgcccttcat cctgtccccc actgaggccc cagagccatt  78660
ccttaaagca gcgcgccaca aactataacc cacaagccaa ttctggtacc cagcctgttt  78720
tgcacagcca gtgaactgac aatgatcttt tcatacagcc agaaaaacaa aacaaaacaa  78780
aaaacaacaa aaaaaaaccc caccattctg agcatgtgac ttccatgttc aagatgtctc  78840
atgttcagaa aggcccctgg aaaaggagga aggggagctg ggcacaaagg gagaccctct  78900
cagctgagct cctcccatcc agacattttc ctggacttcc tatccaatga cttcccttag  78960
cttcttatca gccacccctg tctgcccagg aggctggaag atgtggcctt ttaactgggc  79020
```

acagctctgt cctctatcat atcagggctc tgttcccaag gagggtagag agaatggaca 79080
ccaggtggac cctcagcagt ctgtgccaca gagggagtgt ttgcaatttc cagactaaaa 79140
gtccccatgt gcttgacggg gtatgtgact acaacgtgat gcttgacttt tcctcatatg 79200
accagagcca ctttgtccat ctggtacaat gtcagctatc tgctaggggc cctccaggat 79260
tcccagtcaa ttccatatct gcatcaccac cattggcact aaataaaata aaatactcaa 79320
gttcctgctg gtgagcatga gcagtgctac actgggccct tcaaccaagg tgacatgata 79380
atgactgaaa ataatcactg ccacttattg gggacgtctc atctgccagg catggtacaa 79440
agtgctttaa ataagcattc aacaatttca tgctgacaga agccctgtga gccagtggag 79500
ctactactat gcccattata caggggagaa aactgaggca gagagaggtt aggtaattcg 79560
ctcagcctca cacaaccaat aggtggtgga gccaggattt gggccccatc tgcctgactc 79620
tctagaggct ctatcttcca gtcttccaga gttgagtcta agccatgaat aggacaatta 79680
gacagcagag gaaacccatt cagccaccat gtgcatgaag agtaaggaat ttctgtcata 79740
cagaggggag tgaattcact gagctgagag ctgaggaacc attgatctga tggctgagac 79800
accactggga agactggaga ggcttttctg ggcatgcagt gccaggcaca ggaggagctg 79860
agggaagatg actaagaggt actggcaaag aattcagaaa ttctgatgga agctttacat 79920
gttaccatca catccatcca tctatccacc catccatcca cccatatctt cctccctcca 79980
cccaatcatg catacatcca gtcatctata caccacccac ccacccatcc atccatccat 80040
ccatcccttc atccatccca tcatccatcc aattatacat acatccaatc atatatctgt 80100
acataatcca ttcttccctc ggttcatcca tccatccatt catccatcca tccacccatc 80160
ccttccttca tccttcctat catccatcca atcatatatc tgtacataat ccattcttcc 80220
ctcggttcat ccatccatcc attcatccat ccatccaccc atcccttcct tcatccttcc 80280
tatcatccat ccaatcatac atatatccaa tcatacatct gcacatcacc agctcatcca 80340
tctatccatt tatccatcca tccttccttc catccatcat tcatccatca tacatacatc 80400
taaccataca tctctacatc attcattctt ccatcgattc atccaattat ccatcattcc 80460
ttcctccatc catcccatta tccatttgat catacatata tcatctatac atcatccatt 80520
catccatcca tccatccatc cacccatatc ttcatccaat caatcataca tacatcgaat 80580
catctacaca tcacccatcc atccatccat ccattcatct atccacccat ccatccatcc 80640
atccatccat tcatctatcc acccatccat ccatccatcc atccatccat ccatgtaacc 80700
atccagtcat atatccaatt acacatccat ccagttatac attcatacat gcatctaatc 80760
attcaattat acatacacac atccatataa ttctacatcc aattatacct ccatccaatt 80820
acacattcat acacccacct aataaattat taattcatat atccatccat ataattatac 80880
atcaattata catccatcta atcattcagt aattcaccca ccatccagtc atctatccaa 80940
taatacattc atccaatcat ccatccatcc atccacccat tcatccatcc atccgtccgt 81000
ccacccatca tggtatgagc catgatttac cacgatggtc ccctgtggac agcccaggtg 81060
gggcagaact gaagggaagc ccagggctgc ccccataaac atttgcctcc tttacatgga 81120
tgagaactag atccacatgt ataaatcctc atgatttgaa ggtgctttta ccaacattca 81180
ctcatgggat tctcccagga gctctaggag gaggcaggta gagttgaggt catctcacgc 81240
attttacaga tgaggaaacg gaggccctga gaggcaggtc caaggccacc tgaccagaaa 81300
gaagtggaac tgggacttga acccagccat cttgcccctt ggtcccatgc tctctagcct 81360

-continued gtaactcctg cttcctggtg gggcatctcc aggaggaccc tatcggctgg ccatgggcct 81420
gccctggagt cttttgctct gtgtggccat ccttcctccc tcaggagagt gtgtgctccc 81480
agagcacagg ctgtatcttc tgagcatttt gtcccttccc agtacctagc actcagctct 81540
gtatacattg ggctctcaag aattctcaac cttccagagt gtaaggcctt gacctgctca 81600
gccctggata ctgcatgatg cattgataag cccataaaat aaccagggca gattgactcc 81660
cagtggccaa agtgccacag ggaagggaca attcagccct tctaggagga ggaggaggta 81720
gttttctcat ttctattaag gcaacaaaag ctgccttact aaggacattc ttggtggagg 81780
gcgtgactgt caaccactgt gatcatttgg gcctctcttg cccaggcttc ccattctgaa 81840
aggacagttt tattgtaggt acacatggct gccatttcaa atgtaactca cagcttgtcc 81900
atcagtcctt ggaggtcttt ctatgaaagg agcttggtgg cgtccaaaca ccacccaatg 81960
tccacttaga agtaagcacc gtgtctgccc tgagctgact ccttttccaa ggaaggggtt 82020
ggatcgctga gtgtttttcc aggtgtctac ttgttgttaa ttaatagcaa tgacaaagca 82080
gaaggttcat gcgtagctcg gctttctggt atttgctgcc cgttgaccaa tggaagataa 82140
acctttgcct caggtggcac cactagctgg ttaagaggca ctttgtcctt tcacccagga 82200
gcaaacgcac atcacctgtg tcctcatctg atggccctgg tgtggggcac agtcgtgttg 82260
gcagggaggg aggtggggtt ggtccccttt gtgggtttgt tgcgaggccg tgttccagct 82320
gtttccacag ggagcgattt tcagctccac aggacactgc tccccagttc ctcctgagaa 82380
caaaaggggg cgctggggag aggccaccgt tctgagggct cactgtatgt gttccagaat 82440
ctcccctgca gacccccact gaggacggat ctgaggaacc gggctctgaa acctctgatg 82500
ctaagagcac tccaacagcg gaaggtgggc ccccccttcag acgcccccctc catgcctcca 82560 gcctgtgctt agccgtgctt tgagcctccc tcctggctgc atctgctgct ccccctggct 82620
gagagatgtg ctcactcctt cggtgctttg caggacagcg tggtgggagc tgagccttgc 82680
gtcgatgcct tgcttgctgg tgctgagtgt gggcaccttc atcccgtgtg tgctctggag 82740
gcagccaccc ttggacagtc ccgcgcacag ctccacaaag ccccgctcca tacgattgtc 82800
ctcccacacc cccttcaaaa gccccctcct ctctctttct tcaggggcca gtaggtccca 82860
gagcagccat ttggctgagg gaaggggcag gtcagtggac atctgatctt ggtttagtat 82920
ccttcatttt gggggctctg ggtgtggcct gggcctctgg actttggcca cggtgtttgt 82980
tccagccctt ctcctaacct gtcctttcca gacactcggc atctaggtta ttagcacctc 83040
gcatactttc tgacatgctc ctcagtcctg attttgacca tcttctcttg cttcccatct 83100
gtgtcagtca agactgcatt tggctgtaag aaacagaaac cccaactaac tgtggcattt 83160
acatgaagag gtttactttt ctcacataat cagatgtcta gacttggcca gcacctcaag 83220
ggtcattgat gctctcctgt ctttattttc tgtcatcttt agtggttgga ttgttgcctc 83280
atggttacaa agtggctgct gcacttccag gcatcacatc tgcctttgaa gcaggaacaa 83340
gttgcaaagt aaagtggcca aaagggccct gaaactaaat gtgtcccctt aggaaagcag 83400
gagttttctt gcaagtggca atcttctgct tatgtctcat tggccagagc tgggtcttac 83460
ggccacccct tgctgcgagc aaggctggga cattgagcat tttgccgtcc aacctcttta 83520
gcagaataaa ccaaggggga agaacgttaa tagtggcttt tgagtcacta gttggcagta 83580
tctgcccctc tatctttcca tcctccccat ggagtttcaa ggttcctttc tcagtacttc 83640
ttcaggctct gcacgttcat ttggatcttg tgtcttgggg tgaaaaactg gcccaagtgt 83700
ctccccaagc atccaccttt ggattaattt ggaaaatggc tgtcaagtgc ccgcctcttg 83760

```
cttggtataa tgctacagct ttagaggacg cagcaggcat gggccttgcc gctgaggttc  83820
ttagcctcat gagaatatcc agatcagatt ctcttggctc cttcttagag ccagtgatgc  83880
aagacacttc ctgctcatct tgtcgggacg gttttacaag ttgcctgcca tcctgagaaa  83940
gtctacaaaa cgatgccaga cctcatgcca gcttcccaag ccttgactct cagtgctccc  84000
tcaacaggat tctggaagaa tctcccaaac aagtcgcaat cccctctgga ccctgtgcag  84060
gcatgagact caagagcatt ggctcccacc cctggtggag ggaacactgc tggggctggg  84120
atcttgcctg gttgctccgc ctgcacccaa gacaaccata attaaaatgt ccttcattga  84180
acttggaaag ccttcaaagc tgacaactcc ttatgtgtac ccggaaaggc ctgggagtgt  84240
gccagggcat tgctcgggag ggacgctgat ttggaagcat ttacctgatg agagactgac  84300
agcagctcct ggtagccgag ctttccctcc tgcctctgct gtgaaggtgg acccatccaa  84360
cagtcaaatg cctgactctg gacaggagcg gacctattta ttgccatgca agggactctg  84420
cacttttgaa ttgtgggtca tgggcttgga tttaggggtt agagctggga gaagtcttgg  84480
aagtcaccta gagatgacac tgccattttg cagatgagga aaccgtccaa tcaaaatgga  84540
ccaaggactt gcccaaagcc tcacagcaaa accataggcc cccgcactaa ccccagagtc  84600
cctgtgctgt cttaagaatc aaatagttgt aagcaatcat ctggttttca gtatttcttc  84660
ttttaaaatg cctggggcca tgcccagcag tctgtttcac tgcagcgttt acacagggct  84720
gccgggcttt cctggtggat gagctgggcg gttcatgagc cagaaccact cagcagcatg  84780
tcagtgtgct tcctggggag ctggtagcag gggctccggg ccctacttca gggctgcttt  84840
ctggcatatg gctgatcccc tcctcactcc tcctccctgc attgctcctg cgcaagaagc  84900
aaaggtgagg ggctgggtat ggctcgtcct ggcccctcta aggtggatct cggtggtttc  84960
tagatgtgac agcaccctta gtggatgagg gagctcccgg caagcaggct gccgcgcagc  85020
cccacacgga gatcccagaa ggaaccacag gtgagggtaa gccccagaga cccccaggca  85080
gtcaaggccc tgctgggtgc cccagctgac ctgtgacaga agtgagggag ctttgcgtgt  85140
ttatcctcct gtggggcagg aacatgggtg gattctggct cctgggaatc ttgggttgtg  85200
agtagctcga tgccttggtg ctcagttacc tccctggctg cctgccagcc tctcagagca  85260
tttagggcct tctggacttc tagatgctcc tcatcttgcc tcagtcagcg cgtcagttcc  85320
agagacttct ctgcagggtt ttctggggca ggtggtggca gacccgtgcc ttcttgacac  85380
ctgaggtcag tccaccctcc tgctcagact gcccagcaca gggtcacctc ccaaggggtg  85440
gaccccaaga tcacctgagc gcacagaggg tgcagatgac tggaccacac cttttggtga  85500
tcttaatgag gtggtcccag aggagctcag acatgcaatc tagcatccag ttctgggact  85560
ctgtctcctt ttcaaacgta ttcatgtaga acaggcatga cgagaatgcc ttgtcaacat  85620
gggtgatggg gaatcaatca gacagggcgc cgggctcaag gctgcagtca cccaagagtg  85680
gctcagccca ccaggcccta ggaaacgcct gcacagcctg gagctcctgg agtcatttcc  85740
ttcatgtctt cttcactgca cttacgtaaa gatgccagcc attggtttgg tgatttggag  85800
ggtgcccagt tgcccaacaa gaaatgcaga agaggcctag ccaggatttc accagcagtg  85860
gagagtagag aagatgtggc cagaaaagag tttcctttcc ctcctaaaga tggtactccc  85920
tgcagctact ggggaagcct gcagcattct ctagggctct gtgtgttgag agcagcccca  85980
ccctggcccc ttctgagtgc atttctgctt tgtgacttga tccgtgaagt cccctgagat  86040
gggcagaggg gatgtcctcg aagctggggc agagcctcat ccttgaacgt gaaggacgtt  86100
```

tgaagactgt ggcatgatca caggatgaga tcacagggaa cttgagtttc tctcctcctc 86160
tcccttcaca gttatttcac tgagggaaat ccctcccctg cccagaatga aaactctagc 86220
caactcttga cttttccatc actccaaagt agttgaaagt acattagtct ccacagtggc 86280
aaaacagtgt gcaaaagcta aataattaga acagccagtc ccatgtgaca gtcaaagctt 86340
ctaactccat tcaaagttgc agccattccc ctcgagggct ggcagggagg ggaggggtaa 86400
gagaaacagg aaggttctta ctgagttggt cctggtgtga gctgcgtcac actccctgca 86460
gaggtttcaa ggagactctc tctctctctg tctccatggg gaccttattt gaattcttct 86520
actcttaccc cagcctgcca tctccagcta tcctcccctg aagagccctt ctgctgcgct 86580
ggattctggt ggccatgtca tctcctcggc cccgtgggag tctgaagatc tggctgcagc 86640
ctcacctctg aggtcctgct agttgccacc tcttaaacat gatctgaggc tcccatgcac 86700
tctgacctgt gcccacatgg ggcccacggg aaacacgctg gcaagcaaac tgtgggtgtg 86760
cagacggttc tcagggctgc agcacctgtc ctttgctctg cccccaaagc aaggccagcc 86820
catcttccat cctctagtgt tccttggtgg ggccctgacc acagtccacc aggtccctaa 86880
ccagagggga cacacaccag gtgtcctcaa tgtattgcct tgaaacagtt gtgctgggac 86940
tgtgatgggg ggtggccatg tagccacccc caccaccccc aagccactct ctccaaggaa 87000
atcctcctaa agatcccttt acatcctcca tgtggtgggg aggttctaga gttgggtgca 87060
tgtgtcttca gctactgaca atgcagacct tagttggcac ctcgctctgg cctatcctgt 87120
ttgctgttct tggcgctcca gtgaaactcc ccatgggcca tccagttggg gtgcagtgtg 87180 gccacccccct tgcaggttcc tgccttgctg gagagcacag ggccctcctg gctcttgtaa 87240
aacactcccc atggtacaga gaggccagca gtgatgtgag gcccaacctc cctccatggt 87300
gttcccaagc agctcccttt ctggggtcaa ggggtggcaa agacagtgca gcgtccaatt 87360
tctgactcaa gccgggcctg gctatcgcag ctctgcactg tgtgtgacag caaggcaact 87420
cacccagtgc cgtggcagtg accgtgtccg aggaagcctc ctcacaccct ctgtctcaag 87480
gactctggca tttagctgga cttgctgtag ctctgagcct ttctgccatt gccatcacct 87540
tgtcagaaac tcaggccgaa tctgcactca gagttgtgcc caggcagttg agccaacact 87600
tgctcagcga tattgtcaca tgacaaggca ctgtcaccac tgggcgtcgt gggtagcgca 87660
gtgtcggctg gatggacccg gagggtgtct gtgtcatgct agtgctagtg atgggagccc 87720
cgtgagccca ttgcccgccc tcccatgccc tcagcagctg cctggggaca gccaatggcc 87780
tgggtgtttc tgaggctacc acatggcttc caggaaactc gagaaccttt ctctcccttg 87840
cctacactct tcacacaggc ctgtgctggc cagcggtggg gatccggcat tcctatctta 87900
ggtgcagaaa gtgactgact cattgcaggc ctgggagata agactgatgg cccagccagc 87960
aagatgtatg gatttctcag aggcagtggc ctctgtcatt gtcctcagga aatgctggtg 88020
attctggtgg cctgaggtca atgcatgtca acgtggccaa cttgccttat aaactttttt 88080
tctggacaat tgcgtgcact gtcctgtaac agtgtcctgt tgtttatgat gcagaaatag 88140
gtgtttttaa agcctattga ttttggtact attaatgtgg tcaggaactt tctcagtctt 88200
tcttgtttgg ggtgagctgt ggcttcctaa acaggaaccc aagacacccc caaaagctgc 88260
tcaccagcac tgccagcctc cctcttacca agtagcaccc gttcaggaca ttctgcgaaa 88320
ggcatttgcc cagaagttgg gaggaaggaa atgtaacatt ttggggcacc taccatatgc 88380
caggcaccag gctaaacgtg ttcacacaaa ttctcttact aaccctcacc atccttctac 88440
aagacaaact agtatcttca tcttggggtt caagatgagg aaatggaggc tcagagaggt 88500
tgaatgaatg ccggtgcctg gatatgaacc ccatctgcct gactccgcaa cccaggcaaa 88560
gtctttcctt gaacttccca gcagccactg cttagacaca gcctccacaa ccatggctca 88620
gcagcaaatt gcttctctga cctcactcag cctgtgtgtc cttgttgagt gaggcattca 88680
ggaccctggt cccaaagtgg agaaagtctt tcctactagg tcatagctac acctgcatgt 88740
gggtgctgtg ccttttgttt agtgaacttt tatcaccagc atcctcagca atgacatttg 88800
cagagaagcc agagctgagg caccttggta ttcttgggat gtgactttcc tgaatgttta 88860
agggaaaatg cccgaaggta cagagagctt ggtttctagt aaacaataac tgtcttgctt 88920 ttaccccccct tcatttgctg acacatacac cagctgaaga agcaggcatt ggagacaccc 88980
ccagcctgga agacgaagct gctggtcacg tgacccaagg tcagtgaact ggaattgcct 89040
gccatgactt gggggttggg gggagggaca tggggtgggc tctgccctga aaagatcatt 89100
tggacctgag ctctaattca caagtccagg agattttagg gagttggttc ttatcaaagg 89160
ttggctactc agatatagaa agagccctag tggtttttttt ctaataccat ttctgggtaa 89220
ttcctaaggc atttagtgtt ctgaaagatg ctagccttgt ccagcctggg agttgagaat 89280
gaatgtctaa cagaaactct aggccgggcg tggtggctca cgcctctaat cccagcacta 89340
tgggagaccc aggtgggcag atcacctgag gtcaggagtt tgagaccagc ctggccaaca 89400
tgtgaaatcc tgtctcacta caaataaaaa aattagccgg gtgtggtggt aggtgcctat 89460
aatcccagct actcaggagg ctgaggcagg acaatcgctc gaacccagga ggtggacgtt 89520
gcagtgagcc gagatcgcat cattgcactc cagcctgggc aacaaaagca aaactccgtc 89580
tcaaaaaaaa aaaagaaact caaatatgtg tgacaggcga ttctcactgc aggctgccct 89640
gtggctgatc caggagcaag gccttaacca tgtcatcccc aagcgattgc ttgtaaactt 89700
tcttctgtgc agccttcaac ccttattatg attttcttct caggaaccaa actgctgtat 89760
tcaagaaagg cagctttgtg taatcattta tcataaatat cttaagaaaa atcctagaga 89820
ttcctaattt taggaaatgg gagacctatg gtactgatat aatgtgggct gggcttgttt 89880
tctgtcattt gctagataaa tgaacttgag agcctactgt aaaatgtgga agcttctaga 89940
ttgcagaagg gctggaaaga cactgttctt ttctcccgag tgatgggatc tgtccagtat 90000
ttagagctgc ctctgaggcc atctgattct aggagactct gcctcgttga ggatattttg 90060
aggcctaact acacattcct gcccccagag aggtcacagc ctatagcagg ctgatgtttc 90120
tcatgtcaca tggcacagaa aggcacattt tcgttctcag gctaacaaag agcttcaaaa 90180
actattagaa gggacagtgg ctataagaga agaacctcag tcaatgtgtg aaattaacta 90240
ggaacctggc tcctgtttct tttaggtcat gtttttcagc ttaggtaaaa ctagaggctt 90300
tgataaagca tgacctctag aaatcattgc ttttcataaa tggaagtggg tttgagtttt 90360
ttctactgat tgttagtgca ggtgatgtct acatgccccc agaacatatt ccatgcaaca 90420
aaaaaagccc aggtcaccgt ctttgctggg aacttgactt ttgtgctcac tgaattttaa 90480
gctttctgac agcagcctgg aatcatggag ggataaagta cctattagta agatggaaaa 90540
aggtgtttca ggttggagct gcagtctgtt gagagtaagc tatgggaagg cctgtatacg 90600
aggggtggac ttttcttctg taagtgtcca gagaccaggc ctcctgaaga gggcatgggg 90660
gcttaactta cctggactac tgtgtttaca atactcattt atcttgaact cctcctaacc 90720
cctgagaatt gctacattta gtatttgctg agtacttcct agcatcctag ggaatcaata 90780
gaacattctc ccaaccaggc tgggtgcggt ggctcatgtc tgtaatccca gcactttggg 90840

-continued

```
aggccaaggt aggcagatcc cttgaggcca ggagtgcaag actagcctgg ctgacatggt  90900
gaaaccccgt ctttactaaa aatacaaaag ttagccaggc atggtggtac acacctgtaa  90960
tcccagctac atgggaggag taggaggcag gagaattgct tgaacctggg aggtggaggt  91020
tgctgtgagc cgagatcatg ccactgcact ccagcctggg cgacagagtg agtgagactc  91080
tgtttaaaaa aaaaaaaaaa aaagaacatt ctcctaacct ggcttcttcc tccaggggtg  91140
taattaatca tgtcagtttc ctcattgata cacacacaca cacactacaa tcctgtatcc  91200
attacttttc aaggtacatt tactatttac gtttggggtc cttgtctctt ttttaatagt  91260
gtttcttaaa gtcttgtatt atatcagagt acagtaacat cccagtcaag agcactctag  91320
taagctctag gaggaaagcg acttccggaa ggcagtggag acctgtcctg ttggggcagc  91380
ataggggcag cccctgcctc tggtcagttc tggcgctcag gctcagggtt gcctctgggc  91440
tgttcttccc agagactgac aaagggctcc cataaggcac ctgcagagcc tgtgagaagc  91500
tgaagtcaat gttttcctga caccagttga tctgtgcagg atccattgat ttaaccacct  91560
gctgtgtggc atgcactgtg gtcgatgcca ggaacaggaa ttggaggggc ccatgagcat  91620
ggccagtatc acaggctgga ggtgctgctg cgctctgacc gggcctcttg gggatgagcc  91680
catgtcaacc accttgcctc cgatggggtc gggcccacag gttacctttg tgtgtccatg  91740
accacacctt cctccccgac ctcatccaaa tctctttctt ttccaagccc ctgaatcctt  91800
cagggctgca ggttttgttt aaagcagagc tggtgagttg cataggttgt tgcgttggga  91860
ctagatgggg tgttcaaaga gttgggagtt aaaaaacata aagggtattt attaggagaa  91920
ccaaggagtg taattctcct gttcttaata tgcggccagg ttaatgaatg tcacgtgaat  91980
gaaccagaaa aaaatgaagt gtgcccttga tcagctgggt tggtgtgcag caagctgtgt  92040
gaccagggga cagcagtggt cctgagggcc gtcactgtct gccgtgcaga gcccttcctc  92100
ccacgggggc ctacctcacc tgtgccaagg gcttgtctgt ggtcagtgac ctggatagat  92160
ctgaatgggg cttctttttc gaggagtctt atggcaggtc tctcagtaaa gactccattc  92220
ttgatgatca cacattttgg attttccaaa tctgtcagag aatgggcttg aggcggggtt  92280
tgtgggcact agtttcactg gtttcattta ccaaaaaggg gagcagaagt caagtatggt  92340
ggctcatccc tgtaatccca gaggcaagag aattgcttga gcccaggagt tcgagaccag  92400
cctgagcaac ataaggagac cccgtctcca caaaaatgaa aaataacatt ttagtcagac  92460
gtggtggcat gcatctgtgg tcccagctgc ttgggagggt gagatgggag ggttgtttga  92520
gccctggagt taaagttgca atgagctgtg attgcaccac tgcactctag cctgggtgac  92580
agaacgagac cctgtctcaa aaaaaaaaaa aaagaaagaa aaaaaggaaa aaaaaaactc  92640
atgcctgtaa tcccagcact ttggggaccg gggtgggcag atcacgaggt caggagatca  92700
agactatcct agccaacatg gtgaaacccc gtttctacta aaaatacaaa aattagccag  92760
gtgtggtggc acgtgcctgt aatcccagtt actcgggagg ctgaggcagg agaatcgctt  92820
gaaccaggga gtcagaggtt gcagtgagct gagatcgtgc cactgtactc cagcctgggc  92880
gacagagtga gactctgtct caaaccaaaa aaaaggggtg gggggcgggg gcaggagaac  92940
agtgagaggt agggagagga aaggggattc tcgctacacc caaaccagat accatctaga  93000
ggctagaatc tttgggaggc tcaaattccc tagaaagcag gagaagcttc tgtagccctc  93060
ccgctttccc agtagattaa gcccagggcg gctccagatg tgtgacatgc tctgtgccca  93120
accagagccc atcataggca gaggaataac acccacacca gaagggccct cggaggtcac  93180
cacgtccaag aaccctcttt acagatgagg aaactgaggc ccagagaggg gagagccacc  93240
```

tagcgagctg gtggcggcta gaccaggaga gctgtcattc caagcaagca aaggcaacga 93300
gacgagccca gagctgtgct cccatctctt tgttaggggg cctgggatgc cctctcagtg 93360
tcattttgtc caggatgatg ctccctctct taagcgatta atgcgccctt gctaaccttt 93420
tgctatcgct gcctcttcaa accagaggag ttgagagttc cgggccggca gaggaaggcg 93480
cctgaaaggc ccctggccaa tgagattagc gcccacgtcc agcctggacc ctgcggagag 93540
gcctctgggg tctctgggcc gtgcctcggg gagaaagagc cagaagctcc cgtcccgctg 93600
accgcgagcc ttcctcagca ccgtcccgtt tgcccagcgc ctcctccaac aggaggccct 93660
caggagccct ccctggagtg gggacaaaaa ggcggggact gggccgagaa gggtccggcc 93720
tttccgaagc ccgccaccac tgcgtatctc cacacagagc ctgaaagtgg taaggtggtc 93780
caggaaggct tcctccgaga gccaggcccc ccaggtctga gccaccagct catgtccggc 93840
atgcctgggg ctcccctcct gcctgagggc cccagagagg ccacacgcca accttcgggg 93900
acaggacctg aggacacaga gggcggccgc cacgcccctg agctgctcaa gcaccagctt 93960
ctaggagacc tgcaccagga ggggccgccg ctgaaggggg cagggggcaa agagaggccg 94020
gggagcaagg aggaggtgga tgaagaccgc gacgtcgatg agtcctcccc ccaagactcc 94080
cctccctcca aggcctcccc agcccaagat gggcggcctc cccagacagc cgccagagaa 94140
gccaccagca tcccaggctt cccagcggag ggtgccatcc ccctccctgt ggatttcctc 94200
tccaaagttt ccacagagat cccagcctca gagcccgacg ggcccagtgt agggcgggcc 94260
aaagggcagg atgccccccct ggagttcacg tttcacgtgg aaatcacacc caacgtgcag 94320
aaggagcagg cgcactcgga ggagcatttg ggaagggctg catttccagg ggcccctgga 94380
gaggggccag aggcccgggg cccctctttg ggagaggaca caaaagaggc tgaccttcca 94440
gagccctctg aaaagcagcc tgctgctgct ccgcgggggga agcccgtcag ccgggtccct 94500
caactcaaag gtctgtgtct tgagcttctt cgctccttcc ctggggacct cccaggcctc 94560
ccaggctgcg ggcactgcca ctgagcttcc aggcctcccg actcctgctg cttctgacgt 94620
tcctaggacg ccactaaatc gacacctggg tgcagctgct ccactccctc ggcctcctcc 94680
cgtgctcagg ctgtggccgc acgcgcccct cacgcttgcc cgccactctg catgtcacca 94740
gcacccccgc tccgtgctcc ccaccttgtt tgactctctg gccacttgat ttgtccacaa 94800
cggcccatca gcccacagga ggtttggtgg gtgccttcca ccgacaggat gacgggtgcc 94860
ctcatggtgt ctagaactct ccaaccctcc catgtaggca taagcagccc cactttgcag 94920
atgaggaaac ggaggctcag agaagtacag taacttgccg aaggccaatg agtagtaagt 94980
gacagagcca ggtttgggat ccaggtaggt tgtctctgaa agacacgcct gtcctgcatc 95040
ccacaacgcc tcccaggagg tgctggagtg tggacgccta acacagagat gtgcagggca 95100
cacacagcag gtgacacaca cagcatccag aggtggccca gagctcatgc tgtgcctttg 95160
gcccagtgcc ctgccccccac ccactctgcc ttgtggcagg aagacaagga gcagacacaa 95220
gatctccctg gtccacatgc caccacctcc ctctgcagag gacaagggga tcctcatgct 95280
ggcattggag gggttgagc agggcccacc ttgagccctc aggagcacga ccacagcagc 95340
cctgcaggga gggattggtg ggaggagagt cccaagtatc agggagagga gagttggtgt 95400
cccacaggag acctcagagc cacaaggcga gcttgttcat aaatttggga cccttagcat 95460
ttcacagtta tttgcagagc ccagaaatgg atgttactga agctcacagt tgcaagcatc 95520
tgttaaattt ttattagatt ttacttttag ggaaaacttt gaaatgctat aaagaagcct 95580
gtgtttaaaa gttaagacag aggctggggg cgatggctca cgcctgtaat ctcagcactt 95640
tgggaggcca aggcaggtgg atcatttgag gttaggagtt cgagaccagc ctggccaaca 95700
tggtgagacc ctgtctctac taaaattaca aaaaattagc tgggcgtggt ggcgggcacc 95760
tgtagtccca gctactgggg aggctgaagc aggataagtg cttgaaccca ggaggcggag 95820
gttacagtga gccaagatca caccactgta ccctaagcct gggcgacaga gtgagactct 95880
gtctcaaaaa ataaaataaa ataaagttaa gagagaaaaa aatatatcct atatcctttg 95940
ttaaattcca aaacagtagg ggacaaataa ctgacttgac aggttactac aatatttcct 96000
gaaatgatgt tttcttgaat actggcctac tagaggttca taggtgtgtt tggattaaaa 96060
aagagttcca tggcccagtg actgggggaa aaaaataaaa gactaaagta agttaaacag 96120
gcttttctgc tgcaggactt gtcagagcct ttaatgtact aatggccatt gtgaccctct 96180
gagaaggtca cagagtgggt ttcccaaact tacttgattc tacctgctaa catttcctgg 96240
aggaagtttg ggaaatgccg atttagcaga ttcttttgtt gtgccgtgga tggtgctggt 96300
tgatgtgggc aaaacaaaga acacgtgagt cagatccgcc tggggctctt actaaagtgc 96360
aggttcccag gtgccacttt aggcttacag acccagttgt ggggtaagcc tgggagtctt 96420
ttagcaggtg attctgccac atagtatagt tggaaaacct ctgggcatac tcattgctgg 96480
tccctctaga aatccaggtg acaatagcca atgagaagct ccaagagacc cagttgtcca 96540
tggggtagag ggaatgtgat attgaaacca aagaagaaaa tctatgatca gttttcagca 96600
gtgactgtca agagaaggag aagggtgagt tagcgctgat gctggctgac aggtcagcgg 96660
gttggtttca ccaaggagtg tgatgaaggc tgatgttgtc tgtgggaatg tatgatggta 96720
actggtttgt agctaatttg gggaagcagt gagaattcgt gccctttgaa gaccagtaag 96780
tggcaagaaa cccaccaggc ctggctcagg gctgggctgg gcttggctcg tctcagagca 96840
gctggggctg gtggccaaag ccaccattag tgaggggcag gccctggggg tacaaccagc 96900
aactagggga caaagacaac cctgccagcc tctcctattc tggaggcgtg tgaccagaaa 96960
tggagatggg ttggtcagca taagatggcc aggaaggtgg aaatcaggac tgctggcaat 97020
ctagccacat gggcagggga gccgggtggt tccaggcagt ttccaaggcc aagagggtga 97080
gcaggcacct cacagggaat cagggccaag cctggctgca gtgtggagac aatgcaccca 97140
cccccatcct tggatcttgc aggaggctgg gtcctcactg agctaccaac atccatggcc 97200
ctgaggcttt taaaacaccc atccatggag tggggctggt cccagtgggg tgaggctgac 97260
cctggcagaa acagggcagg agcctgtggg ttagggagac tgcaccttcc ttagatagcc 97320
tccatgccat catgtccccg tgacagtttc tgctgcgtcc cctctgcatg gtcccaccct 97380
cggccagcct gctgcccccct cttgccaggt tgcgctaatc agtgacccca gtgtgctgtg 97440
ttgatactaa caatgcgagg cctagcagat tcaagggaaa agagaaccaa ctgggtttcc 97500
accagaccca actaaacaaa catggaccta tcccagagaa atccagcttc accacagctg 97560
gctttctgtg aacagtgaaa atggagtgtg acaagcattc ttattttata ttttatcagc 97620
tcgcatggtc agtaaaagca aagacgggac tggaagcgat gacaaaaaag ccaaggtaag 97680
ctgacgatgc cacggagctc tgcagctggt caagtttaca gagaagctgt gctttatgtc 97740
tgattcattc tcatatataa tgtggggagt atttgtcact aaagtacagc tgtcatttaa 97800
agtgctttgt attttggggc aggcttttaa aaagtccagc atttattagt tttgatactt 97860
accccaggga agagcagttg gcaggttcat gaagtcatgc tcctaattcc agctttctta 97920
gtgtactttc agtgagaccc tgacagtaaa tgaaggtgtg tttgaaaacc aaacccagga 97980
cagtaaatga aggtgtgttt gaaaaccagc cctaggacag taaatgaagc catcttctca 98040
ctgcataaac tgcacccaga tctttgccca tccttctcag tatttcactt cacccattgt 98100
ttactgtctc aatgactggg gaaatgtctg gggaaatgct cccgtaattg cacagtggcg 98160
tttttcctgg aaaatcccac catggctcta gataagacct atttttctta aaggtatcta 98220
aaatttccag cataaattct gtctgaaaca cctgaatttt aatcagtact ggagcccgga 98280
gggcatctcc agttgccaca tagctctgag cattcagtgg tgtgttgagg gctgctcccg 98340
gaagtgcctg cagagtcagg gctccccagc ctcatctagt gaggcagtgg aagggcctgt 98400
ggggatttgg agagctggcc tgggtctctg aagtgatagt gacagctgct tgtcaatcac 98460
ggtgcacatt tagtgccggg ggcagggggc agggaatacc agcctcatgc atgcatgcat 98520
tcatttgttc cttccttcat tcattcattc agtacacatg ggtacaacat ccctgccctg 98580
gagttgccca gagtctaggg aggggaaaga tctattaccc tgggcctcgg ccagctgggg 98640
agtgctgctg gtggagaggg gccgtgtgca gcgagggaag gaggagtcgt caataccccc 98700
accccagctt tgctttcttg tcatcagccc cagggcccca gcctgtgtcc ctcctctccc 98760
attgctactt catctcctgg gtcctcctta ccaagcctga ccacacagag ggccttggcc 98820
gcttccatgg ggaattggaa agcaataaga tagcatcccc tagaagccca gtgaagtctg 98880
ggacaggacc cttctctgag ctctgacttg ctcttggaaa cacttcgagg cttagcctcc 98940
ccactttgtt tcccaagagt gtgacctgtt cccctccaaa caccccctc tcctccaggg 99000
ccatgcccac ccgtcaaaat cccccacggg caggacgaac tgtgggtgtc agtcaccatc 99060
tatcctgcat cctggttcca gggccccccc cagccccgcc tccataggga caggcgtgca 99120
gacacccgtc cctggctgct tcctcttgtg gaatgggttc aaaagtaagc agtgttgttt 99180
acactgacaa actgaaaaaa aaagaaaaag agataacatt ggaggcttgg cacagtggct 99240
catgcctgta atcccagcac tttgggaggc taaggtggga ggatgtcccc agcccaagag 99300
ttctagacca gcctgggcaa catagcaaga ccccatctca aaaaaaaaat ttaattggcc 99360
aggcagaggt gggaggatca cttgaaccca aagggtggag gctgcagtga gccgtgatgg 99420
caccactgca ctccagccag ggcaacagag ggagaccctg tctctaaaac aaacaaacaa 99480
acaaacaaac aaaagagtta acattggcca gattaggatt caccagatag tgttaatatt 99540
agtttgattt gagactttaa tcagaaagca catgtgtggt gggggtgggt gtaacctaag 99600
tcaggtagaa tctttccaac ttgggggggg cacactcctg attgtagcca tatgagtctg 99660
tcagtgtggt ggaagagacc atgggttaat gggcaggtaa aaaagcacct tgcctggaat 99720
tgagtagaaa gtaaggccct tcagaccccg tgacacactt ggggacattt tcttgagtaa 99780
catcctaaga ttcatgtacc ttgatgatct ccatcaactt actcatgtga agcaccttta 99840
aaccagtcgt ctccaaattc aggggcacag taacatccaa caggctggag aaagaacgta 99900
ctagaacttc cattcctttt tcatgtcctc ttctaaaagc tttgtcaggg ccaggcgcgg 99960
tggctcacgc ctgtaatccc agcactttgg gaggccgaga cgggtggatc acgaggtcag 100020
gagatcgaga ccatcctggc taacacagtg aaaccccatc tctactaaaa atacaaaaaa 100080
acgagccggg cgtggtggtg ggcgcctgta gtcccagcta ctcgggaggc tgaggcagga 100140
gaatggcgtg aacccaggag gcagagcttg cagtgagccg agattgcacc actgcagtcc 100200
agcctgggcg acagagcgag actccgtctc aaaaaagaaa aagaaaaaga aaaagaactg 100260
tgattgggga ggacggtcac tttcctgttc ttactgatca gaagggatat taagggtacc 100320
tgattcaaac agcctggaga tcactgcttt caaccattac ctgccttatt tatttttagt 100380
tactgtcctt ttttcagttt gtttccctcc tccatgtgct gacttttatt ttgattttat 100440
ttatgtttat gtttaagaca tccacacgtt cctctgctaa aaccttgaaa aataggcctt 100500
gccttagccc caaacacccc actcctggta gctcagaccc tctgatccaa ccctccagcc 100560
ctgctgtgtg cccagagcca ccttcctctc ctaaacacgt ctcttctgtc acttcccgaa 100620
ctggcagttc tggagcaaag gagatgaaac tcaaggtaag gaaaccacct ttgaaaagaa 100680
ccaggctgct ctgctgtggt ttgcaaatgt ggggtttgtt tatttgtttt ttagcctcaa 100740
agacctttct tcaaatgagt tctggcatag aagcaccgtg taaaatagtt agaattctgg 100800
gcaaagggga aaagagagct gggggccatc cctctcagca ccccacaggc tctcatagca 100860
gcagctccta agacacctgg tgggaccttg gtttcgaaat cgctactcta aggctgggca 100920
cggtggctca cacctgtaat cccagctctt taggaggccg aggagggtgg atcacctgag 100980
atcaggagtt cgagaccagc ctggctaaca tggcaaaacc ctgtctctac taaaaataca 101040
aaaattagcc gggcgtggtg ttatgcgtgg tggtaatcgc agctactcgg gaggctgagg 101100
cacaaggatt gcttgaaccc cagaggcaga ggttgtagtt agctccagct tgggcgacag 101160
agcaagaccc tgtcgcaaaa attgtttaaa aaacaaaccc aaaattgcta ctctcattgg 101220
gttcctttgc ccattcctga ttttggcaag agaaatgctt ccagattgcc ctgatctggg 101280
taggacagca tcacgccata gcaacactgc cccgtgagct cactgccccc tcaactagct 101340
tgtggtcctt ggttaatgtc agtttctttt ttgagtttgt gttatgtcta agggtcatct 101400
gctgggtaac ggaacccagg gactgcccta gtccctagac tgtgccatgc ccgactctgc 101460
cagctttgtc agtgatgctg gtgctcgcct cctcgggtgc tcgcctggtc tgagcacacc 101520
caaggagttc ttgaggcctt agggttgttt gcgagagaat gaaagaacac gacctagctc 101580
tctttagcat ccttggtcag gttcaacact gcccccaggg gcctctggtg gagccaacca 101640
ccatcagcca aataaatcca taattagagt cagaaaatgg atgtctgcat atgtgtagtg 101700
cactaatgtc ctgccgatga ttgacatgga gtggagagtg acctgatcat tgctgtgagc 101760
tctgctggcc ttggcacaac tcatgctgat aactaatgca cacagttcct ctgggaggaa 101820
atgtcctcag ggaacttgga gtttgggtgg ggatgtgggt ttgtgtgccc agcaagccct 101880
tgtggttgta gcagacacta gtggcatcta ggaggcaaag ggtcacccca gtcttagcca 101940
cgttttgagt caaggtggcg gagtggggct ggtgttgact cttggtggca gtaacttttc 102000
ccaatggtga aaaacccctc tatcatgttt catttacagg gggctgatgg taaaacgaag 102060
atcgccacac cgcggggagc agcccctcca ggccagaagg gccaggccaa cgccaccagg 102120
attccagcaa aaaccccgcc cgctccaaag acaccaccca gctctggtaa gaagaacgtt 102180
ctcttgaatc ttagaggaag ctgaagctct cagaggtaca gccttcattt taggaggcct 102240
taggccactg agaatgaata accccctggca gctggtcagc agcttgcagt ttactaagca 102300
ctggagtctt cattgccttc tcagtccttt tgatttctga ggcaaatgtt gaatccctac 102360
cttttttttt ttttttcttt tgagacagag tttcgctttt gttatccagg ccggagtgca 102420
gtggtgtgat ctcagctcac tgcatcctcc acctcccagg ttcaagcgat tctcctacct 102480
cagcctccct agtagctggg attacaggca cctgccacta tgcccggcta attttttgta 102540
tttttagtag agacagggtt tcaccatgtt ggccaggctg gtctcgaacg cctgacctca 102600
ggtgatccac ctgcctcggc ctcccaaagt gctgggatta caggcatgag ccaccactcc 102660
cagcctgaat cctcactttt tatcaatgaa gaaattgagg ctgattctgc agcatgataa 102720

-continued aaaaaaatac agaaaaagga aaaaaaagaa agaaatcgag cctctgagag tttgcttgac 102780
tgagtctaac cagctcattt taaacccgag gaaaatgcag tcacatgact actaagtggc 102840
agctctcgga gcctctctgg ccccaagtcc agggttccat agaggcagcc ccagcatggc 102900
atgttttcag tccccaaatg agactctgga gacaaatgtc tctggagaca gagcagcagc 102960
ctggataagt cacaatgggt gacgtcactc agggctcaac ccctgggcag cttaacttgc 103020
tagggacgtt aggagtctgc tgcaaaacct gagggtctta gctgagcagt cacaggctgg 103080
gcccgttgcc ctgggctcct gtgagtaaaa cccagtcaat tttgagtacc cagtaaggca 103140
tccattgagt tattttgcag ccaggagtgc tattaagaac agtcgcggct gggcgtggtg 103200
gctcatgcct gtaatcccag cactttggga ggccaaggtg ggcggatcac ctgaggtcag 103260
gagttcgaga ccagcttggc caacatggca aaaccccgtc tctaataaaa atacaaaata 103320
attagctggg cgtggtggcg ggcgcctgta atcccagctt ctcaggaggg tgaggaagga 103380
gaatcacttg aacccaggag gcagaggttg cagtgagctg agatcgcacc attgcactcc 103440
agcctggatg acaaaagtga gattccttct caaaaaaaaa aaaaaaaaaa cagtcgtcct 103500
ctttggggat tagggacagc ctgcctgcct gcccgagcac ttctctcttc cattgcccca 103560
gtgaagtatt ccaggcccct gggtttagac tctgcaccat gtaggggtgt ctgacctgca 103620
cttgctcctt ggtggcacgg gcagcctatg gcacttgctg cgggctgtga ccaaagcctg 103680
gcctggatct tggatcttgg tgactctgct tctccctggc ctgagggagc tgcccagagc 103740
ctgcccacca cctgctgcgt gtctttgcgg tggcatttct cgcacacatg ccgtgcggtg 103800
gcacccccaa ggatggccat tcactaaggc ccattgtttt tgtcttttcg cttcgtgttt 103860
tctggcctgg tgtttttctc atatacatgt gatccaggga taattcccag aattttgaca 103920
ggattttaag tagcgtttgg atcctgctgt tttttttca cttaacatcg ggccagttga 103980
ctcacactct gtttttttgtt gttgtttttt tgagacggag tctcactgtg tcacccaggc 104040
tgaagtgcag tggcacaatc ttggcatact gcaacctctg cttcccaaat tcaagcagtt 104100
ttcctgcctc agcctcctga gtagctggga ctacaggcac aggccaccac gccctgctaa 104160
tttttgtatt tttagtaaag acagggtttc accattttgg ccagcctagt ctcgaactcc 104220
tgacctcaag tgatccgccc acctcggcct cccaaagtgc tgggattaca ggggactcac 104280
actttgtaac aacctgaaac aacgtgatgc atttcccttt gggtcttacc tgctcttcgg 104340
tggctgcctg caggtggaga gaccctcccc cttgggcccc tcgaccttgt ttcagaatgg 104400
ggcccctgct gggccagctg tgggtgcctg ccacgtgaag gactcattaa ggccctgttt 104460
aagcctgatg ataataaggc tttcgtggat ttttctcttt aagcgactaa gcaagtccag 104520
agaagaccac cccctgcagg gcccagatct gagagaggta ctcgggagcc tacttcgctg 104580
ggagcagcct ccctttgcgt gtgtggccat tcactggctt gtgtttctag agccgggagg 104640
accctttttct gcaatgcagg gttcacacag ggttcgcagc ctgaagatgg agcagtccga 104700
attctcttcc ctgtgcagtt tgcgcagctg tgtttgtctg atgggctttc taatcctgtg 104760
tgctctcctt gacttcaggg acaatggcat tacaggcatg agccaccatg cctggctgtc 104820
tccctatgtt tcagatgaag acataggctt aaggaggtca ggtgacttgc ccacgaccac 104880
tctgtaaata agaggcatga aaagtatttg gagccaccac caccaagccc actggtcacc 104940
ctgggtctct gaagtcaggg aggcaggagg atgggaggtc tgaggaggca gagaggctga 105000
gcctggaggc cctggaggcc gaggccccat ctgttgtttc cttatgtgga aaataagagg 105060

-continued

```
cttcatttgt cctattgcca cagagcgtac tacttcagga acatccaaga catggaaatc 105120
cgcagggcac ggtggctcac gtctataatc ccggcacttt gggaggttga ggtgggagaa 105180
tcgcttgagg ccagaagttc aagaccagcc tgagcaacat agtcagaccc cgtctctata 105240
aaaaacatta tttttaaaaa agacatggaa gtcaaattct aaaaactggt gctggctggg 105300
tgcggtggct catgcctata atcccagcac tttgggaggc cgaggcgggt ggatcacctg 105360
aggtcaggag ttcaagacca gcctggccaa catggtaaaa cctctactaa agaaatcttt 105420
actgaaaata caaaaatcca gtctctacta aaataagtct ctactaaaaa tacaaaaatt 105480
agccaggcgt ggtgctgcac acctgtaata tcagctactc gggaggctga ggcaggagac 105540
tcgcttgatc ccatgcagcg gaggttgcag tgagccgaga tcacgccatt gcactccagc 105600
ctgggcatca gaataagact ccgtctcaaa aaaaaaacca caaaaaaaca aaacaacaac 105660
aaaagaaaac tagtgcttat tcgtcactgg ccaagctgcc cattggctac atgggtgctt 105720
caaagagctg cccttctcca ggtctggcca gcaggtatgt gttacagcaa atgcctgggg 105780
cagcggcagg ggcattgctg cgggaagctt ctggacttgc aggaaagcta agttctcaga 105840
ctgcagggga gctaagcaca cctcggcaca gggtgaggcc tgcggttctc agacttcagt 105900
ctttgtggag cttgagaaaa atgaggcttt gcaggtccca cccctagaga ttctgctcta 105960
tccactcttg aaggggatcg agaaatttgc attttgcaac tcccactttc ctccttgaaa 106020
gctccggaga ttctgacgca gggttccgtg ggccacactt tggaaaatac agacccatga 106080
gatagaatac cagactgttg aagtgtaacg gggcctggg aagtgcagta acagaagcaa 106140
gtttgagggt aaaggacacc cagaggaggg agggacagca tctgcatgga gaggagaaga 106200
gacccccag cagcttccag ggtgttggaa gggtgcgcta gtaactgcta tgcatggcag 106260
gtggggaact gtacgtcagg gcacagcagc atgaagcggt atggctcgtg tggacagcta 106320
gggacaggca ggcgtggagc aggcatcctg ttctgaaggc caaatcccac agaggagcca 106380
gggtgctggc aggagccctg aactagccga acagctgaac agctgaacat tcaccctgtg 106440
gggaaagggt cagaagcgtc caggcttgag ggcacagctg ggtctcgtca ctgcatcacc 106500
cttatttagg ataaaggccc tgaagaattg tattagaggt tggcaaagca tatctaccac 106560
ctcctggagc cacgctggcc gcagggatta taattatttc cattttcaaa ttaaggcctc 106620
tgagctcaga gaggggaagt tacttgtctg aggccacaca gcttgttgga gcccatctct 106680
tgacccaaag actgtggagc cgagttggcc acctctctgg gagcgggtat tggatggtgg 106740
ttgatggttt tccattgctt tcctgggaaa ggggtgtctc tgtccctaag caaaaaggca 106800
gggaggaaga gatgcttccc cagggcagcc gtctgctgta gctgcgcttc caacctggct 106860
tccacctgcc taacccagtg gtgagcctgg gaatggaccc acgggacagg cagcccccag 106920
ggccttttct gaccccaccc actcgagtcc tggcttcact cccttccttc cttcccaggt 106980
gaacctccaa aatcagggga tcgcagcggc tacagcagcc ccggctcccc aggcactccc 107040
ggcagccgct cccgcacccc gtcccttcca accccaccca cccgggagcc caagaaggtg 107100
gcagtggtcc gtactccacc caagtcgccg tcttccgcca agagccgcct gcagacagcc 107160
cccgtgccca tgccagacct gaagaatgtc aagtccaaga tcggctccac tgagaacctg 107220
aagcaccagc cgggaggcgg gaaggtgaga gtggctggct gcgcgtggag gtgtgggggg 107280
ctgcgcctgg aggggtaggg ctgtgcctgg aagggtaggg ctgcgcctgg aggtgcgcgg 107340
ttgagcgtgg agtcgtggga ctgtgcatgg aggtgtgggg ctccccgcac ctgagcaccc 107400
ccgcataaca ccccagtccc ctctggaccc tcttcaagga agttcagttc tttattgggc 107460
```

tctccactac actgtgagtg ccctcctcag gcgagagaac gttctggctc ttctcttgcc 107520
ccttcagccc ctgttaatcg gacagagatg gcagggctgt gtctccacgg ccggaggctc 107580
tcatagtcag ggcacccaca gcggttcccc acctgccttc tgggcagaat acactgccac 107640
ccataggtca gcatctccac tcgtgggcca tctgcttagg ttgggttcct ctggattctg 107700
gggagattgg gggttctgtt ttgatcagct gattcttctg ggagcaagtg ggtgctcgcg 107760
agctctccag cttcctaaag gtggagaagc acagacttcg gggcctggc ctggatccct 107820 ttccccattc ctgtccctgt gcccctcgtc tgggtgcgtt agggctgaca tacaaagcac 107880
cacagtgaaa gaacagcagt atgcctcctc actagccagg tgtgggcggg tgggtttctt 107940
ccaaggcctc tctgtggccg tgggtagcca cctctgtcct gcaccgctgc agtcttccct 108000
ctgtgtgtgc tcctggtagc tctgcgcatg ctcatcttct tataagaaca ccatggcagc 108060
tgggcgtagt ggctcacgcc tataatccca gcactttggg aggctgaggc aggcagatca 108120
cgaggtcagg agttcgagac caacctgacc aacagggtga aacctcgtct ctactaaaaa 108180
tacaaaaata cctgggcgtg gtggtggtgc gcgcctataa tcccagctac tcaggaggct 108240
gaggcaggag aatcgcttga acccaggagg cagaggttgc agtgagccga gatagtgcca 108300
ctgcactcca gtttgagcaa cagagcgaga ctctgtctca aaacaaaata aaacaaacca 108360
aaaaaaccca ccatggctta gggcccagcc tgatgacctc atttttcact tagtcacctc 108420
tctaaaggcc ctgtctccaa atagagtcac attctaaggt acgggggtgt tggggagggg 108480
ggttagggct tcaacatgtg aatttgcggg gaccacaatt cagcccagga ccccgctccc 108540
gccacccagc actggggagc tggggaaggg tgaagaggag gctgggggtg agaaggacca 108600
cagctcactc tgaggctgca gatgtgctgg gccttctggg cactgggcct cggggagcta 108660
gggggctttc tggaaccctg ggcctgcgtg tcagcttgcc tcccccacgc aggcgctctc 108720
cacaccattg aagttcttat cacttgggtc tgagcctggg gcatttggac ggagggtggc 108780
caccagtgca catgggcacc ttgcctcaaa ccctgccacc tccccccacc caggatcccc 108840
cctgcccccg aacaagcttg tgagtgcagt gtcacatccc atcgggatgg aaatggacgg 108900
tcgggttaaa agggacgcat gtgtagaccc tgcctctgtg catcaggcct cttttgagag 108960
tccctgcgtg ccaggcggtg cacagaggtg gagaagactc ggctgtgccc cagagcacct 109020
cctctcatcg aggaaaggac agacagtggc tcccctgtgg ctgtggggac aagggcagag 109080
ctccctggaa cacaggaggg agggaaggaa gagaacatct cagaatctcc ctcctgatgg 109140
caaacgatcc gggttaaatt aaggtccggc cttttcctgc tcaggcatgt ggagcttgta 109200
gtggaagagg ctctctggac cctcatccac cacagtggcc tggttagaga ccttggggaa 109260
ataactcaca ggtgacccag ggcctctgtc ctgtaccgca gctgagggaa actgtcctgc 109320
gcttccactg gggacaatgc gctccctcgt ctccagactt tccagtcctc attcggttct 109380
cgaaagtcgc ctccagaagc cccatcttgg gaccaccgtg actttcattc tccagggtgc 109440
ctggccttgg tgctgcccaa gaccccagag gggccctcac tggcctttcc tgccttttct 109500
cccattgccc acccatgcac ccccatcctg ctccagcacc cagactgcca tccaggatct 109560
cctcaagtca cataacaagc agcacccaca aggtgctccc ttccccctag cctgaatctg 109620
ctgctccccg tctggggttc cccgcccatg cacctctggg ggcccctggg ttctgccata 109680
ccctgccctg tgtcccatgg tggggaatgt ccttctctcc ttatctcttc ccttccctta 109740
aatccaagtt cagttgccat ctcctccagg aagtcttcct ggattcccct ctctcttctt 109800
aaagcccctg taaactctga ccacactgag catgtgtctg ctgctcccta gtctgggcca 109860
tgagtgaggg tggaggccaa gtctcatgca tttttgcagc ccccacaaga ctgtgcaggt 109920
ggccggccct cattgaatgc ggggttaatt taactcagcc tctgtgtgag tggatgattc 109980
aggttgccag agacagaacc ctcagcttag catgggaagt agcttccctg ttgaccctga 110040
gttcatctga ggttggcttg gaaggtgtgg gcaccatttg gcccagttct tacagctctg 110100
aagagagcag caggaatggg gctgagcagg gaagacaact ttccattgaa ggcccctttc 110160
agggccagaa ctgtccctcc caccctgcag ctgccctgcc tctgcccatg aggggtgaga 110220
gtcaggcgac ctcatgccaa gtgtagaaag gggcagacgg gagccccagg ttatgacgtc 110280
accatgctgg gtggaggcag cacgtccaaa tctactaaag ggttaaagga gaaagggtga 110340
cttgactttt cttgagatat tttgggggac gaagtgtgga aaagtggcag aggacacagt 110400
cacagcctcc cttaaatgcc aggaaagcct agaaaaattg tctgaaacta aacctcagcc 110460
ataacaaaga ccaacacatg aatctccagg aaaaaagaaa aagaaaaatg tcatacaggg 110520
tccatgcaca agagccttta aaatgacccg ctgaagggtg tcaggcctcc tcctcctgga 110580
ctggcctgaa ggctccacga gcttttgctg agacctttgg gtccctgtgg cctcatgtag 110640
tacccagtat gcagtaagtg ctcaataaat gtttggctac aaaagaggca aagctggcgg 110700
agtctgaaga atccctcaac cgtgccggaa cagatgctaa caccaaaggg aaaagagcag 110760
gagccaagtc acgtttggga acctgcagag gctgaaaact gccgcagatt gctgcaaatc 110820
attgggggaa aaacggaaaa cgtctgtttt cccctttgtg cttttctctg ttttcttctt 110880
tgtgcttttc tctgttttca ggatttgcta cagtgaacat agattgcttt ggggccccaa 110940
atggaattat tttgaaagga aaatgcagat aatcaggtgg ccgcactgga gcaccagctg 111000
ggtaggggta gagattgcag gcaaggagga ggagctgggt ggggtgccag gcaggaagag 111060
cccgtaggcc ccgccgatct tgtgggagtc gtgggtggca gtgttccctc cagactgtaa 111120
aagggagcac ctggcgggaa gagggaattc ttttaaacat cattccagtg cccgagcctc 111180
ctggacctgt tgtcatcttg aggtgggcct cccctgggtg actctagtgt gcagcctggc 111240
tgagactcag tggccctggg ttcttactgc tgacacctac cctcaacctc aaccactgcg 111300
gcctcctgtg caccctgatc cagtggctca ttttccactt tcagtcccag ctctatccct 111360
atttgcagtt tccaagtgcc tggtcctcag tcagctcaga cccagccagg ccagcccctg 111420
gttcccacat cccctttgcc aagctcatcc ccgccctgtt tggcctgcgg gagtgggagt 111480
gtgtccagac acagagacaa aggaccagct tttaaaacat tttgttgggg ccaggtgtgg 111540
tggctcacac ctaatcccaa cacctgggga ggccaaggca gaaggatcac ttgagtccag 111600
gagttcaaga ccagcctggg caacataggg agaccctgtc tctacaattt tttttttaat 111660
tagctgggcc tgttggcact ctcctgtagt tccagctact ctagaggctg aggtgggagg 111720
actgcttgag cctgggaggt cagggctgca atgagccatg ttcacaccac tgaacgccag 111780
cctgggcgag accctgtatc aaaaaagtaa agtaaaatga atcctgtacg ttatattaag 111840
gtgccccaaa ttgtacttag aaggatttca tagttttaaa tacttttgtt atttaaaaaa 111900
ttaaatgact gcagcatata aattaggttc ttaatggagg ggaaaaagag tacaagaaaa 111960
gaaataagaa tctagaaaca aagataagag cagaaataaa ccagaaaaca caaccttgca 112020
ctcctaactt aaaaaaaaaa atgaagaaaa cacaaccagt aaaacaacat ataacagcat 112080
taagagctgg ctcctggctg ggcgcggtgg cgcatgcctg taatcccaac actttgggag 112140
gccgatgctg gaggatcact tgagaccagg agttcaaggt tgcagtgagc tatgatcata 112200
ccactacacc ctagcctggg caacacagtg agactgagac tctattaaaa aaaaaatgct 112260
ggttccttcc ttatttcatt cctttattca ttcattcaga caacatttat ggggcacttc 112320
tgagcaccag gctctgtgct aagagctttt gcccccaggg tccaggccag gggacagggg 112380
caggtgagca gagaaacagg gccagtcaca gcagcaggag gaatgtagga tggagagctt 112440
ggccaggcaa ggacatgcag gggagcagc ctgcacaagt cagcaagcca gagaagacag 112500
gcagaccctt gtttgggacc tgttcagtgg cctttgaaag gacagccccc acccggagtg 112560
ctgggtgcag gagctgaagg aggatagtgg aacactgcaa cgtggagctc ttcagagcaa 112620
aagcaaaata aacaactgga ggcagctggg gcagcagagg gtgtgtgttc agcactaagg 112680
ggtgtgaagc ttgagcgcta ggagagttca cactggcaga agagaggttg gggcagctgc 112740
aagcctctgg acatcgcccg acaggacaga gggtggtgga cggtggccct gaagagaggc 112800
tcagttcagc tggcagtggc cgtgggagtg ctgaagcagg caggctgtcg gcatctgctg 112860
gggacggtta agcaggggtg agggcccagc ctcagcagcc cttcttgggg ggtcgctggg 112920
aaacatagag gagaactgaa gaagcaggga gtcccagggt ccatgcaggg cgagagagaa 112980
gttgctcatg tggggcccag gctgcaggat caggagaact ggggaccctg tgactgccag 113040
cggggagaag gggtgtgca ggatcatgcc cagggaaggg cccaggggcc caagcatggg 113100
ggggcctggt tggctctgag aagatggagc taaagtcact ttctcggagg atgtccaggc 113160
caatagttgg gatgtgaaga cgtgaagcag cacagagcct ggaagcccag gatggacaga 113220
aacctacctg agcagtgggg ctttgaaagc cttggggcgg ggggtgcaat attcaagatg 113280
gccacaagat ggcaatagaa tgctgtaact ttcttggttc tgggccgcag cctgggtggc 113340
tgcttccttc cctgtgtgta ttgatttgtt tctctttttt gagacagagt cttgctgggt 113400
tgcccaggct ggagtgcagt ggtgcgatca tagctcactg cagccttgaa gtcctgagct 113460
caagagatcc ttccacctca gcctcctgag tagttgggac cacaggcttg caccacagtg 113520
cccaactaat ttcttatatt ttttgtagag atggggtttc actgtgtcgc ccaggatggt 113580
cttgaactcc tgggctcaag tgatcctcct gcctcagcct cgcaaattgc tgggattaca 113640
ggtgtgagcc accatgcccg accttctctt tttaagggcg tgtgtgtgtg tgtgtgtgtg 113700
tgggcgcact ctcgtcttca ccttccccca gccttgctct gtctctaccc agtcacctct 113760
gcccatctct ccgatctgtt tctctctcct tttacccctc tttcctccct cctcatacac 113820
cactgaccat tatagagaac tgagtattct aaaaatacat tttatttatt tattttgaga 113880
cagagtctca ctctgtcacc caggctggag tgcagtggtg caatctcggc tcactgcaac 113940
ctccgcctcc caggttgaag caactctcct gcctcagcct ccctagtagc tgggattaca 114000
agcacacacc accatgccta gcaaattttt atatttttag tagaggagga gtgtcaccat 114060
gtttgccaag ctggtctcaa actcctggcc tcaggtgatc tgcctacctt ggtctcccaa 114120
agtgctggga ttacaggtgt gagccaccac gcctgccctt aaaaatacat tatatttaat 114180
agcaaagccc cagttgtcac tttaaaaagc atctatgtag aacatttatg tggaataaat 114240
acagtgaatt tgtacgtgga atcgtttgcc tctcctcaat cagggccagg gatgcaggtg 114300
agcttgggct gagatgtcag accccacagt aagtgggggg cagagccagg ctgggaccct 114360
cctctaggac agctctgtaa ctctgagacc ctccaggcat cttttcctgt acctcagtgc 114420
ttctgaaaaa tctgtgtgaa tcaaatcatt ttaaaggagc ttgggttcat cactgtttaa 114480
aggacagtgt aaataattct gaaggtgact ctaccctgtt atttgatctc ttctttggcc 114540
agctgactta acaggacata gacaggtttt cctgtgtcag ttcctaagct gatcaccttg 114600
gacttgaaga ggaggcttgt gtgggcatcc agtgcccacc ccgggttaaa ctcccagcag 114660
agtattgcac tgggcttgct gagcctggtg aggcaaagca cagcacagcg agcaccaggc 114720
agtgctggag acaggccaag tctgggccag cctgggagcc aactgtgagg cacggacggg 114780
gctgtggggc tgtggggctg caggcttggg gccagggagg gagggctggg ctctttggaa 114840
cagccttgag agaactgaac ccaaacaaaa ccagatcaag gtctagtgag agcttagggc 114900
tgctttgggt gctccaggaa attgattaaa ccaagtggac acacaccccc agccccacct 114960
caccacagcc tctccttcag ggtcaaactc tgaccacaga catttctccc ctgactagga 115020
gttccctgga tcaaaattgg gagcttgcaa cacatcgttc tctcccttga tggtttttgt 115080
cagtgtctat ccagagctga agtgtaatat atatgttact gtagctgaga aattaaattt 115140
caggattctg atttcataat gacaaccatt cctcttttct ctcccttctg taaatctaag 115200
attctataaa cggtgttgac ttaatgtgac aattggcagt agttcaggtc tgctttgtaa 115260
ataccettgt gtctattgta aaatctcaca aaggcttgtt gccttttttg tggggttaga 115320
acaagaaaaa gccacatgga aaaaaaattt cttttttgtt tttttgtttg cttgtttttt 115380
tgagacagag tttcactctg tcgcccaggc tggagtgcag tggtgcgatc tccgcccact 115440
gcaagctcca cctcccgggt tcatgctatt ctcctgtctc agcctcccaa gtagctggga 115500
ctgcaggtgc ccgccaccac acctggctaa ttttttgta tttttagtag agacggggtt 115560
tcaccgtgtt agccaggatg gtctcaatct cctgacctcg tcatctgcct gcctcggcct 115620
cccaaagtgc tgagattaca ggcgtgagcc accgtgcccg gccagaaaaa aacatttcta 115680
agtatgtggc agatactgaa ttattgctta atgtcctttg attcatttgt ttaatttctt 115740
taatggatta gtacagaaaa caaagttctc ttccttgaaa aactggtaag ttttctttgt 115800
cagataagga gagttaaata acccatgaca tttccctttt tgcctcggct tccaggaagc 115860
tcaaagttaa atgtaatgat cactcttgta attatcagtg ttgatgccct tcccttcttc 115920
taatgttact ctttacattt tcctgcttta ttattgtgtg tgttttctaa ttctaagctg 115980
ttcccactcc tttctgaaag caggcaaatc ttctaagcct tatccactga aaagttatga 116040
ataaaaaatg atcgtcaagc ctacaggtgc tgaggctact ccagaggctg aggccagagg 116100
accacttgag cccaggaatt tgagacctgg gctgggcagc atagcaagac tctatctcca 116160
ttaaaactat tttttttat ttaaaaaata atccgcaaag aaggagttta tgtgggattc 116220
cttaaaatcg gagggtggca tgaattgatt caaagacttg tgcagagggc gacagtgact 116280
ccttgagaag cagtgtgaga aagcctgtcc cacctccttc cgcagctcca gcctgggctg 116340
aggcactgtc acagtgtctc cttgctggca ggagagaatt tcaacattca ccaaaaagta 116400
gtattgtttt tattaggttt atgaggctgt agccttgagg acagcccagg acaactttgt 116460
tgtcacatag atagcctgtg gctacaaact ctgagatcta gattcttctg cggctgcttc 116520
tgacctgaga aagttgcgga acctcagcga gcctcacatg gcctccttgt ccttaacgtg 116580
gggacggtgg gcaagaaagg tgatgtggca ctagagattt atccatctct aaaggaggag 116640
tggattgtac attgaaacac cagagaagga attacaaagg aagaatttga gtatctaaaa 116700
atgtaggtca ggcgctcctg tgttgattgc agggctattc acaatagcca agatttggaa 116760
gcaacccaag tgtccatcaa cagacaaatg gataaagaaa atgtggtgca tatacacaat 116820
ggaatactat tcagccatga aaaagaatga gaatctgtca tttgaaacaa catggatgga 116880
actggaggac attatgttaa gtgaaataag ccagacagaa ggacagactt cacatgttct 116940
cacacatttg tgggagctaa aaattaaact catggagata gagagtagaa ggatggttac 117000
cagaggctga ggagggtgga ggggagcagg gagaaagtag ggatggttaa tgggtacaaa 117060
aacgtagtta gcatgcatag atctagtatt ggatagcaca gcagggtgac gacagccaac 117120
agtaatttat agtacattta aaaacaacta aaagagtgta actggactgg ctaacatggt 117180
gaaaccccgt ctctactaaa aatacaaaaa ttagctgggc acggtggctc acgcctgtaa 117240
tcccagcact ttgggaggcc gaggcgggcc gatcacgagg tcaggagatc gagaccatcc 117300
tagctaacat ggtgaaaccc cgtctctact acaaatacaa aaaaaagaaa aaattagccg 117360
ggcatggtgg tgggcgcctg tagtcccagc tactcgggag gctgaggcag gagaatggcg 117420
tgaacccggg aggcggagct tgcagtgagc cgagatcgcg ccactgcact ccagcctggg 117480
cgacaaggca agattctatc tcaaaaaaat aaaaataaaa taaaataaaa taataaaata 117540
aaataaaata aaataaaata aaataaataa aataaaatgt ataattggaa tgtttataac 117600
acaagaaatg ataaatgctt gaggtgatag ataccccatt caccgtgatg tgattattgc 117660
acaatgtatg tctgtatcta aatatctcat gtaccccaca agtatataca cctactatgt 117720
acccatataa atttaaaatt aaaaaattat aaaacaaaaa taaataagta aattaaaatg 117780
taggctggac accgtggttc acgcctgtaa tcccagtgct ttgtgaggct gaggtgagag 117840
aatcacttga gcccaggagt ttgagaccgg cctgggtgac atagcgagac cccatcatca 117900
caaagaattt ttaaaaatta gctgggcgtg gtagcacata ccggtagttc cagctacttg 117960
ggagaccgag gcaggaggat tgcttgagcc caggagttta aggctgcagt gagctacgat 118020
ggcgccactg cattccagcc tgggtgacag agtgagagct tgtctctatt ttaaaaataa 118080
taaaaagaat aaataaaaat aaattaaaat gtaaatatgt gcatgttaga aaaaatacac 118140
ccatcagcaa aaagggggta aaggagcgat ttcagtcata attggagaga tgcagaataa 118200
gccagcaatg cagtttcttt tattttggtc aaaaaaaata agcaaaacaa tgttgtaaac 118260
acccagtgct ggcagcaatg tggtgaggct ggctctctca ccagggctca cagggaaaac 118320
tcatgcaacc cttttagaaa gccatgtgga gagttgtacc gagaggtttt agaatattta 118380
taactttgac ccagaaattc tattctagga ctctgtgtta tgaaaataac ccatcatatg 118440
gaaaaagctc ctttcagaaa gaggttcatg ggaggctgtt tgtatttttt ttttctttgc 118500
atcaaatcca gctcctgcag gactgtttgt attattgaag tacaaagtgg aatcaataca 118560
aatgttggat agcaggggaa caatattcac aaaatggaat gggacatagt attaaacata 118620
gtgcttctga tgaccgtaga ccatagacaa tgcttaggat atgatatcac ttcttttgtt 118680 gtttttgta ttttgagacg aagtctcatt ctgtcaccca ggctggagtt cagtggcgcc 118740
atctcagctc actgcaacct ccatctcccg ggttcaagct attctccttc ctcaacctcc 118800
cgagtagctg ggttgcgcac caccatgcct ggctaacttt tgtattttta gtacagacgg 118860
ggtttcacca cgttggccag gctgctcttg aactcctgac gtcaggtgat ccaccagcct 118920
tgacctccca aagtgctagg attacaggag ccactgtacc cagcctagga tatgatatca 118980
cttcttagag caagatacaa aattgcatgt gcacaataat tctaccaagt ataggtatac 119040
aggggtagtt atatataaat gagacttcaa ggaaatacaa caaaatgcaa tcgtgattgt 119100
gttagggtgg taagaaaacg gtttttgctt tgatgagctc tgttttttaa aatcgttata 119160
ttttctaata aaaatacata gtcttttgaa ggaacataaa agattatgaa gaaatgagtt 119220
agatattgat tcctattgaa gattcagaca agtaaaatta aggggaaaaa aaacgggatg 119280
aaccagaagt caggctggag ttccaacccc agatccgaca gcccaggctg atggggcctc 119340
cagggcagtg gtttccaccc agcattctca aaagagccac tgaggtctca gtgccatttt 119400
caagatttcg gaagcggcct gggcacggct ggtccttcac tgggatcacc acttggcaat 119460
tatttacacc tgagacgaat gaaaaccaga gtgctgagat tacaggcatg gtggcttacg 119520
cttgtaatcg gctttgggaa gccgaggtgg gctgattgct tgagcccagg agtttcaaac 119580
tatcctggac aacatagcat gacctcgtct ctacaaaaaa tacaaaaaat ttgccaggtg 119640
tggtggcatg tgcctgtggt cccagctact tgggaggctg aagtaggaga atcccctgag 119700
ccctgggaag tcgaggctgc actgagccgt gatggtgtca ctgcactcca gcctgggtga 119760
caaagtgaga ccctatctca caaagaaaaa aaacaaaaca aaaaacccaa agcacactgt 119820
ttccactgtt tccagagttc ctgagaggaa aggtcaccgg gtgaggaaga cgttctcact 119880
gatctggcag agaaaatgtc cagtttttcc aactccctaa accatggttt tctatttcat 119940
agttcttagg caaattggta aaaatcattt ctcatcaaaa cgctgatatt ttcacacctc 120000
cctggtgtct gcagaaagaa ccttccagaa atgcagtcgt gggagaccca tccaggccac 120060
ccctgcttat ggaagagctg agaaaaagcc ccacgggagc atttgctcag cttccgttac 120120
gcacctagtg gcattgtggg tgggagaggg ctggtgggtg gatggaagga gaaggcacag 120180
cccccccttg cagggacaga gccctcgtac agaagggaca ccccacattt gtcttcccca 120240
caaagcggcc tgtgtcctgc ctacggggtc agggcttctc aaacctggct gtgtgtcaga 120300
atcaccaggg gaacttttca aaactagaga gactgaagcc agactcctag attctaattc 120360
taggtcaggg ctaggggctg agattgtaaa aatccacagg tgattctgat gcccggcagg 120420
cttgagaaca gccgcaggga gttctctggg aatgtgccgg tgggtctagc caggtgtgag 120480
tggagatgcc ggggaacttc ctattactca ctcgtcagtg tggccgaaca catttttcac 120540
ttgacctcag gctggtgaac gctcccctct ggggttcagg cctcacgatg ccatcctttt 120600
gtgaagtgag gacctgcaat cccagcttcg taaagcccgc tggaaatcac tcacacttct 120660
gggatgcctt cagagcagcc ctctatccct tcagctcccc tgggatgtga ctcgacctcc 120720
cgtcactccc cagactgcct ctgccaagtc cgaaagtgga ggcatccttg cgagcaagta 120780
ggcgggtcca gggtggcgca tgtcactcat cgaaagtgga ggcgtccttg cgagcaagca 120840
ggcgggtcca gggtggcgtg tcactcatcc tttttctgg ctaccaaagg tgcagataat 120900
taataagaag ctggatctta gcaacgtcca gtccaagtgt ggctcaaagg ataatatcaa 120960
acacgtcccg ggaggcggca gtgtgagtac cttcacacgt cccatgcgcc gtgctgtggc 121020
ttgaattatt aggaagtggt gtgagtgcgt acacttgcga gacactgcat agaataaatc 121080
cttcttgggc tctcaggatc tggctgcgac ctctgggtga atgtagcccg gctccccaca 121140
ttcccccaca cggtccactg ttcccagaag ccccttcctc atattctagg agggggtgtc 121200
ccagcatttc tgggtccccc agcctgcgca ggctgtgtgg acagaatagg gcagatgacg 121260
gaccctctct ccggaccctg cctgggaagc tgagaatacc catcaaagtc tccttccact 121320
catgcccagc cctgtcccca ggagccccat agcccattgg aagttgggct gaaggtggtg 121380
gcacctgaga ctgggctgcc gcctcctccc ccgacacctg ggcaggttga cgttgagtgg 121440
ctccactgtg gacaggtgac ccgtttgttc tgatgagcgg acaccaaggt cttactgtcc 121500
tgctcagctg ctgctcctac acgttcaagg caggagccga ttcctaagcc tccagcttat 121560
gcttagcctg cgccaccctc tggcagagac tccagatgca aagagccaaa ccaaagtgcg 121620
acaggtccct ctgcccagcg ttgaggtgtg gcagagaaat gctgcttttg gccctttag 121680 atttggctgc ctcttgccag gagtggtggc tcgtgcctgt aattccagca ctttgggaga 121740
ctaaggcggg aggttcgctt gagcccagga gttcaagacc agcctgggca acaatgagac 121800
ccctgtgtct acaaaaagaa ttaaaattag ccaggtgtgg tggcacgcac ctgtagtccc 121860
agctacttgg gaggctgagg tgggaggatt gcctgagtcc gggaggcgga agttgcaagg 121920
agccatgatc gcgccactgc acttcaacct aggcaacaga gtgagacttt gtctcaaaaa 121980
acaatcatat aataatttta aaataaatag atttggcttc ctctaaatgt ccccggggac 122040
tccgtgcatc ttctgtggag tgtctccgtg agattcggga ctcagatcct caagtgcaac 122100
tgacccaccc gataagctga ggcttcatca tcccctggcc ggtctatgtc gactgggcac 122160
ccgaggctcc tctcccacca gctctcttgg tcagctgaaa gcaaactgtt aacaccctgg 122220
ggagctggac gtatgagacc cttggggtgg gaggcgttga tttttgagag caatcacctg 122280
gccctggctg gcagtaccgg gacactgctg tggctccggg gtgggctgtc tccagaaaat 122340
gcctggcctg aggcagccac ccgcatccag cccagagggt ttattcttgc aatgtgctgc 122400
tgcttcctgc cctgagcacc tggatcccgg cttctgccct gaggcccctt gagtcccaca 122460
ggtagcaagc gcttgccctg cggctgctgc atggggctaa ctaacgcttc ctcaccagtg 122520
tctgctaagt gtctcctctg tctcccacgc cctgctctcc tgtcccccca gtttgtctgc 122580
tgtgagggga cagaagaggt gtgtgccgcc cccacccctg cccgggccct tgttcctggg 122640
attgctgttt tcagctgttt gagctttgat cctggttctc tggcttcctc aaagtgagct 122700
cggccagagg aggaaggcca tgtgctttct ggttgaagtc aagtctggtg ccctggtgga 122760
ggctgtgctg ctgaggcgga gctggggaga gagtgcacac gggctgcgtg gccaacccct 122820
ctgggtagct gatgcccaaa gacgctgcag tgcccaggac atctgggacc tccctggggc 122880
ccgcccgtgt gtcccgcgct gtgttcatct gcgggctagc ctgtgacccg cgctgtgctc 122940
gtctgcgggc tagcctgtgt cccgcgctct gcttgtctgc ggtctagcct gtgacctggc 123000
agagagccac cagatgtccc gggctgagca ctgccctctg agcaccttca caggaagccc 123060
ttctcctggt gagaagagat gccagcccct ggcatctggg ggcactggat ccctggcctg 123120
agccctagcc tctccccagc ctgggggccc cttcccagca ggctggccct gctccttctc 123180
tacctgggac ccttctgcct cctggctgga ccctggaagc tctgcagggc ctgctgtccc 123240
cctccctgcc ctccaggtat cctgaccacc ggccctggct cccactgcca tccactcctc 123300
tcctttctgg ccgttccctg gtccctgtcc cagccccccct cccccctctca cgagttacct 123360
cacccaggcc agagggaaga gggaaggagg ccctggtcat accagcacgt cctcccacct 123420
ccctcggccc tggtccaccc cctcagtgct ggcctcagag cacagctctc tccaagccag 123480
gccgcgcgcc atccatcctc cctgtccccc aacgtccttg ccacagatca tgtccgccct 123540
gacacacatg ggtctcagcc atctctgccc cagttaactc cccatccata aagagcacat 123600
gccagccgac accaaaataa ttcgggatgg ttccagttta gacctaagtg gaaggagaaa 123660
ccaccacctg ccctgcacct tgttttttgg tgaccttgat aaaccatctt cagccatgaa 123720
gccagctgtc tcccaggaag ctccagggcg gtgcttcctc gggagctgac tgataggtgg 123780
gaggtggctg ccccccttgca ccctcaggtg accccacaca aggccactgc tggaggccct 123840
ggggactcca ggaatgtcaa tcagtgacct gccccccagg ccccacacag ccatggctgc 123900
atagaggcct gcctccaagg gacctgtctg tctgccactg tggagtccct acagcgtgcc 123960
ccccacaggg gagctggttc tttgactgag atcagctggc agctcagggt catcattccc 124020
agagggagcg gtgccctgga ggccacaggc ctcctcatgt gtgtctgcgt ccgctcgagc 124080
ttactgagac actaaatctg ttggtttctg ctgtgccacc tacccaccct gttggtgttg 124140
ctttgttcct attgctaaag acaggaatgt ccaggacact gagtgtgcag gtgcctgctg 124200
gttctcacgt ccgagctgct gaactccgct gggtcctgct tactgatggt ctttgctcta 124260
gtgctttcca gggtccgtgg aagcttttcc tggaataaag cccacgcatc gaccctcaca 124320
gcgcctcccc tctttgaggc ccagcagata ccccactcct gcctttccag caagattttt 124380
cagatgctgt gcatactcat catattgatc acttttttct tcatgcctga ttgtgatctg 124440
tcaatttcat gtcaggaaag ggagtgacat ttttacactt aagcgtttgc tgagcaaatg 124500
tctgggtctt gcacaatgac aatgggtccc tgtttttccc agaggctctt ttgttctgca 124560
gggattgaag acactccagt cccacagtcc ccagctcccc tggggcaggg ttggcagaat 124620
ttcgacaaca catttttcca ccctgactag gatgtgctcc tcatggcagc tgggaaccac 124680
tgtccaataa gggcctgggc ttacacagct gcttctcatt gagttacacc cttaataaaa 124740
taatcccatt ttatcctttt tgtctctctg tcttcctctc tctctgcctt tcctcttctc 124800
tctcctcctc tctcatctcc aggtgcaaat agtctacaaa ccagttgacc tgagcaaggt 124860
gacctccaag tgtggctcat taggcaacat ccatcataaa ccaggtagcc ctgtggaagg 124920
tgagggttgg gacgggaggg tgcagggggt ggaggagtcc tggtgaggct ggaactgctc 124980
cagacttcag aaggggctgg aaaggatatt ttaggtagac ctacatcaag gaaagtgttg 125040
agtgtgaaac ttgcgggagc ccaggaggcg tggtggctcc agctcgctcc tgcccaggcc 125100
atgctgccca agacaaggtg aggcgggagt gaagtgaaat aaggcaggca cagaaagaaa 125160
gcacatattc tcggccgggc gctgtggctc acgcctgtaa ttccagcact ttgggaggcc 125220
aaggtgggtg gatcatgagg tcaggagatt gagaccatcc tggctaacac agtgaaaccc 125280
cgtctctact aaaaatacaa aaaattagcc gggcgtggtg gtgggcgcct gtagtcccag 125340
ctactccgga ggctgaggca ggaaaatggc gtgaacccgg aaggcggagc ttgcagtgag 125400
cggagtgagc agagatcgcg ccactgcact ccagcctggg cgacagagcg agactccgtc 125460
tcaaaaaaaa aaagcacatg ttctcgcttc tttgtgggat ccaggagata gagaatagaa 125520
ggatggttac cagaggctgg gaagggtagt gaggggatgg tggggggatg gtcaatgggt 125580
acaaaaaaaa tagaataaga cctagtattt gatagtgcaa cagggtgact atagtcaata 125640
ataatttaat tgtacattta aaaataacta aaagatagcc gggtgcagtg gcttacgtct 125700
gtaatcccag tactttggga ggctgaggtg ggcgtttgag accagcctgg ccaacatggt 125760
gaaaccccat ctctactaaa aatacaaaaa ttagccaggc atggtggcgg gcgcctgtaa 125820
tcccagctac tcgggaggct gaggcaggag aatcacttga acctgggagg cagaggttgc 125880
agtgagccga gatcttgcca ctgcactcca gcctgggtga cagtgaaact ccgtctcaaa 125940
aataaaaata aaaatacagc tgggcacggt ggctcacgcc tgtaatccca gcactttggg 126000
aggccgaggc gagcggatca caaggtcagg agatatagac catcctggct aacacggtga 126060
aacccggtct ctactaaaaa tacaaaaaat tagccaggcg tggtggcagg tgcctatagt 126120
cccagctact cacaaggctg aggcaggaga atggcatgaa cctgggaggc ggagcttgca 126180
gtgagccgag attgtgccac tgcactccag cctgggcgag agagtgagac tccgtctcaa 126240
aacaaaaaca aaaacaaaaa caaaaacaaa cacacaacaa aaacctaaaa gaatataaat 126300
ggattgtttg taacacaaag gacaaatgtt tgaggggatg gataccccat tttccatgat 126360
gtgattatta tacattgtgt gtctgtatca aaacatctca tgagccccat aaatatatac 126420
acctaactat gtacccacaa aaattaaaaa aatatatttt ttaaggtgaa gagggaggcg 126480
agatgctggc cttaacccct aacccgttgt tctccctgca agctgtccac agggcctctc 126540
agactcgagg ttcagctata tggatgcatg agcttggtcc ccagccaaca tgggagacac 126600
ttcaccatcg gcagcagcta cagcacagga accctgggtc actgccatgt cccctctgtg 126660
actttgttta aacagaaaat gatgctctgg gccggctgtg gtggcccaca cctataatcc 126720
cagcaccttg ggaggcgggg gtgggcagat tgcctgaggt caggagttgg agatcagcct 126780
ggccgacatg gcgaaacccc atgtctacta aaaatacaaa aactagccag gcatggtggc 126840
acatgcctgt aatcccagct acttgggagg ctgaagcagg agaatcactt gaacccagga 126900
ggcagaggct gagtgagcca agatcgtgcc aatgcactcc agcttgggtg agggagtgag 126960
actccgtctc aaaaaaaaaa aaaaagaaag aaaaagaaaa gaaagtgatc ctactggaac 127020
catgcttact cccctcccca cctcacactg tgtagaaatt agtgctgtcg gccaggcgcg 127080
gtggctcatg cctgtaatcg cagcactttg ggaggccaag gcaggcggat cacgaggtca 127140
ggagatcaag accatcctgg ctaacacagt gaaaccctgt ctctactaaa aatacaaaaa 127200
attagccggg catggtggca ggcacctgta gtcccaacta cttgggaggc tgaggcagga 127260
gaatggcatg aacctgggag gcggagcttg cagtgagcca agatcgcgcc actgcatacc 127320
agcctaggtg acagagtgag actcagcaaa aaaagaaaga aagaaagaaa gaaatcagtg 127380
ctgtctatac ttctttctgc agtgatggaa atattctgta tctgtgctgt ccagtatagt 127440
agccactagc tacatgtggc acttgaaaca tggctggtac agttgaggaa gagtggctgc 127500
catatcggac gacacagcta tagattctgt caccccaccc cgagagtcca gagcggggac 127560
ttctgcctta ggccctattc agggctgatt tttacttgaa cccttactgt gggaagagaa 127620
ggccatgaga agttcagtct agaatgtgac tccttatttt ctggctccct tggacacttt 127680
gtgggattta gtctccctgt ggaaagtatt ccacaagtgg tgccactacc ccagctgtga 127740
gagcagctgg gagctgcttt tgtcatcttt ccctggaaag tcctgtgggc tgtctcttcc 127800
tcatgccttg tcccatgctt gggcatggtg tcaagcgtca ggagggagaa agggtcctta 127860
tttatttatt tagagaggga cccttcttct gttcccaggc tggagtgcag tggtgcgatc 127920
tcggctcact gcaacctccg cctcctgggt tcaagtgatt ctcctgcctc agcctcctga 127980
gtagctgaga ttacaggcac atgccaacat gcccggctaa tttttttttt tttttttttt 128040
tttttttttt tttttttttt gagatggagt tgtactctca ttgcccaggc tggaatgtaa 128100
tggcacaatc tcggctcact gcaacctcca cctcctggat tcaagcaatt ctcctgtctc 128160
agcttcccaa gtagctggga ttacaggtgc ccgccaccat gctcaactaa tttttgtatt 128220
tttttttag tagagacgag gtttcaccat gttggtcaga ctggtctcaa actcctgacc 128280
tcaggtgatc cacctgcctc ggcctcccaa agtgctagga ttacaggcat gagccaccac 128340
gcccggcctg aaagggttct tatttagtgt gcattttgac attcaattta attccaaggt 128400
cttgtggggt catggtttac aggatgttga tatagaaaag acttcactta atgggccggg 128460
cgcagtggct catgcctgta atcccagcac tttgggaggc cgaggcaggc agatcaggag 128520
gtcaggagat tgagaccatc ctggctaaca cagtgaaacc ccatctctac tgaaaataca 128580
aaaaattagc tgggcgtggt ggcaggcacc tgtagtccca gccactcggt tggctgaggc 128640
aggagaatgg catgaacccg ggaggcggag cttgcagtga gcagagacca tgccactgca 128700
ctccagcctg ggcgacagag caagactctg tctcaagaaa aaaaaaaaaa aacagacttt 128760
acttactgga agccaaccaa tgtatattta gagtaatttt tcctgggctg agctgtcatt 128820
tacttttgca gtatctcaag aagaagagtt tacagtgtaa atatttgatg cacactttga 128880
ttatatagat gaagcaaact attttcaaga gctttgcaag gacttacttg tatccaaaca 128940
ccattctaaa aggagtctta cctacttcta aaggctggtc tctacttgga accacttgct 129000
tggccctggt tcaagtcctg ctgcaaacct ggaagtcctg tcattgtctt cttccctcca 129060
gagcagtggc acccaatcta atttttgctg tgccccagca gcccctggca ctttgccctg 129120
tagactgcag acctcatgta atgtatgtta agtccacaga accacagaag atgatggcaa 129180
gatgctcttg tgtgtgttgt gttctaggag gtggccaggt ggaagtaaaa tctgagaagc 129240
ttgacttcaa ggacagagtc cagtcgaaga ttgggtccct ggacaatatc acccacgtcc 129300
ctggcggagg aaataaaaag gtaaaggggg tagggtgggt tggatgctgc ccttgggtat 129360
atgggcatta atcaagttga gtggacaaag gctggtccag ttcccagagg aggaaaacag 129420
aggcttctgt gttgactggc tggatgtggg ccctcagcag catccagtgg gtctccactg 129480
cctgtctcaa tcacctggag ctttagcacg tttcacacct gggccccaac ctggagaggc 129540
tgaccaatgg gtctcagggg cagctcggtt gctggagttt ttgtttttat ttatttttat 129600
gtatttaagg cagggtctct gtattagtcc attctcacac tgctaataaa gacataccca 129660
agactgggta atttataaag gaaagaggtt taatggactc acagttccac atggctgggg 129720
aggcctcaaa atcatggcgg aaggcaaagg agaagcaaag gcatttctta catggcgaca 129780
ggcaagagag cgtgtgcagg ggaactccca tttataaaac catcagacct catgagattt 129840
attcactatc atgagaacag catgggaaag acccgccccc atgattcagt tacctcccac 129900
tgggtccctc ccatgacaca tggaattatg ggagctacaa ttcaagatga gatttgggtg 129960
gggacacagc caaaccatat cagtctccct ctgtcatcca ggctggagtg cactggcatg 130020
atctcggctc actgcagcct ctacctccct gggtcaggtg atcttcccac ctcagcctcc 130080
caggtagctg gaactacagg tacctgccac tatgcctggc taaatatttt gtatttcctg 130140
tggagacgag gttttgccac gttgcccagg ctggtcttga actcctgagg tcaagcaata 130200
tgcccacctc ggcctcccaa ggtgctggga ttacaggtgt gagccacagt gctcggccta 130260
agtcactgca gtttttaaag ctcccaggtg attcttcagt gcagtcaaaa gtgagaactg 130320
gctgggtgcg gtggctcatg cctgtaatcc cagcaccttg ggaggcgaag gtgggcagat 130380
ggcttgaggt caggagttca agaccagcct ggccaacatg gtaaaacccc atctctacta 130440
aaaatacaaa agttagctgg gtgtggtggt gcgtgcctgt aatcccagct acttgggagg 130500
ctgaggcatg agaattgctt gaacccaggg gacagaggtt gtagtgagcc gagatcgtgc 130560
cactgcactc cagcctgggc aacagagtga gattccatct cacaaaaaaa aaaaaaagcg 130620
agaaccactg tcctaggccc tgatgtttgc aggcaactaa aaaaggaagt ggacatcccc 130680
agtcagctgt ggcgcaccaa gaacaagtca tgggaacata acctaatttt ctaaatgggt 130740
tactaggcac ttagagcaaa acaatgatgc cgaaatcctg atttcagcaa agcctctgcc 130800
tgcctgtctt ggaagtatcc acatgaggct gctggggcct tggtgtcccc agcagtttct 130860
agtctctagg tcttgctgtg ggtgtctgtg cagtgagggt gtgtgtggcg ctgggtgagc 130920
tctgtctagg cctggcacag gatgcggtct ggtagctgct gcttctcttc tgcagaagcg 130980
cagccaagca ccctctgggg tttcaggccc acacccagcc tgaagttctg ggagtggctc 131040
actttccaac cttcagggtc tcccagcagc tgactgggga gtggtggagg gaaaagggat 131100
tgtattagtc cgttttcacg ccgctgatga agacataccc gatactgggc agtctaaaag 131160
atagaggtct gatggactca cagttccacg tgactgggga ggcctgacaa tcatggtgga 131220
aggtgaaagg cttgtctcac acggtggcag acaagagaaa agagcttgtg caggggaact 131280
ccccttata aaaccatcag atctcgggag acttattcac tatcatgaga acagcacggg 131340
aaagaccctc ctctatgatt caattacctc ccaccaggtc cctcccacaa catgtaggaa 131400
ttgtgggaac tacaattcaa gatgacattt gggtggggac acagccaaac catatcaggg 131460
cgtcccagaa agggtatagg gtctgagacc caagtcagca tgagaaagta tgcttctcat 131520
ggtggcccag ttgggtggaa gtggcagccg ggccgtcttt ccaccaggcc actcaagtag 131580
cagctgagag accctgccc tggccagtcc ccgccctccc ctcttgccac tgcctctggt 131640
tctgaacaga tgggcaccct catcttgtat ttgtgattaa tgtctaacaa tgtagttttg 131700
tgagaagggt ttgctgatac agccttgctg cagatgctgc gaactgtggc ctggggcaga 131760
ccttacctcc agacacgccc tgaggcaggg gagggcactg gcccgtagct ggccgagagc 131820
tctcgggttg cgcgacaggg atacttttca gcggctgggt cgctatccaa agtgagaaaa 131880
cgaggaggga ccaggaggct gtccgcctca agagatgtgg gggccaggtc cagttatctg 131940
gggaagcagt aagcttctct gctgtttcta accccaggcc tcccctggtc taaggcaggg 132000
cctcccagcc tcggggcact ttaaagatat ctgggcctgg ccccatcccc acagtctgac 132060
tgagtgggtc tggatagggc ctgagcattg gtgatttcct gggtgaaagg aggcccctca 132120
cagtctctgg aagcttctct gtgttaggaa aagctctggg cttgactctg ctttgaaagt 132180
caagatccgc aaatcctctc agcctcagtt tctccttcag caagatgaaa tggaaatgct 132240
gtacctacgt cccggggtgg ttgtgagacc caaaaaagac aatgttctgg aaggttcctg 132300
gtgcgttgca gtcctctaag aacctgagtt agagccacgc tgagtctcag cttcttggct 132360
ccttctgttt caaactcgtc catgtgatag ctcaggaagg gtaggcaggg ccctgccccc 132420
tactcagaaa acaccatcct ggtcctgggg atccccgcag cattagtccc ctgttttccc 132480
agtgtattga gaaaaattgc taacaagcag tggggcacac caccagcctc ctgggttcct 132540
ttcagtttgg ggatttttgg acattcccag gaatgtctta aaaaacactt caaaaaacat 132600
taacataaat atttttatca aagcctgtat taaatggtct ttcaagaaaa tacagtaaca 132660
ggtcaggcat ggtggctcat gcctgtaacc ccagcacttt gggaggccaa ggcaggcaga 132720
tcacctgaaa tcaggagttc aagaccaacc tggccaacac agccaaatcc catctctaca 132780
aaaaatacaa aaattagctg ggtgtggtgg cacacacctg tagtcccagc tacttgggag 132840
gccgaggcag gagaattgct tgatcccgga ggcggaggtt gcagtgagcc gagatcgtgc 132900
cactgcactc cagcgtgggt gacaaggtga atctttgtct caaaaaaaaa aaaaaaaaaa 132960
agataaaata cagtatacag taatagagaa caatcctttt ttcaaagtag tgaccccaaa 133020
tgaacaaaat atgcatctag cttaaatgcg aacctggttt tctctacgcc cattcaagcc 133080
cctgcaatag gggcccttca ccccgcatcc atggactcct aaaattatat ggaaaatggc 133140
tgtgtgtgag tgtggatgga catgtgcaca catatttttg gctttaccag atgctcaaag 133200
agcctaggac ccaaaaaggg ctgagaatga ccgtgtcggc cacttcaggg tcatcaggaa 133260
ttgctgtgca ctgctcactt ctccagtgaa cactttctgc ttctgtgttt cctggtatcc 133320
tttgggactc ctggctaggt catgtgtttc tctactttca aaagggcttc agccaggcac 133380
gatggcatga gcctgtagtc ccagttgctc tggaggttaa ggtgggaaga ttgcttgagc 133440
ccaggaattt gaggccagcc tgggcaagta gataggtaga tgattgatag atagatagat 133500

-continued agataaatag atggatagat aagtcgctag acagtcatcc atccacccat ccacacataa 133560
aaaggccttt gtcatgtcat gttttgtggc ccacctgcca gtgttgccca cagttgctgc 133620
ccctccaaac tcatcagtca ctggcaaaca ggaggaatgt gtggctcatg tctgggcatc 133680
agtggctgtg ggagacatcc ttgatcttct ccagcttctc cttccacatt ttcctttgca 133740
atctggcaat atctattaaa ataaaatgtg catgcctttt gacctaagag cttcacttct 133800
aggacccact tacacgtgtg tgacatgatg ttcatacggg tttatttatc tgaggttgtt 133860
catacacacc attgcctgta atcactaaag gcgggagcag cctacacatc catccacaga 133920
ggagtagatg ccttttggta catccgtggc gacggaatac taagcagcct gtgtatctat 133980
acactcacac gtgtttgttt atgtgtggaa tatctctgga gggtacacaa gaaacttaaa 134040
atgatcactg tctctgggga gggtacctgg gtgcctggga ggcaggtcag ggaaggagtg 134100
ggcacaggta ttaccaattg gaagacaata aaaacaacag ctcctggcca ggcgcagtgg 134160
ctcacgcctg taatggcagc actctgagag gctgaggcgg gcagattgct tgcgtccagg 134220
agttcaagac cagcctgggc aacatagcaa aaccccgttt ctattaaaaa tacaaaaaat 134280
tagccaggtg tggtggcatg cacctgtaat cccagctact cgggaggctg aggtgggaga 134340
atcacctgag cctgggaggt caaggctgca gtgaggtgag attgtgccac cgcactctag 134400
cctgggcgat agagcaagac cctgtctcaa aaacaaacaa aaaacagtcc ctggcactct 134460
gggccaggcc tggcagggca gttggcaggg ctggtctttc tctggcactt catctcaccc 134520
tccctccctt cctcttcttg cagattgaaa cccacaagct gaccttccgc gagaacgcca 134580
aagccaagac agaccacggg gcggagatcg tgtacaagtc gccagtggtg tctggggaca 134640
cgtctccacg gcatctcagc aatgtctcct ccaccggcag catcgacatg gtagactcgc 134700
cccagctcgc cacgctagct gacgaggtgt ctgcctccct ggccaagcag ggtttgtgat 134760
caggcccctg gggcggtcaa taattgtgga gaggagagaa tgagagagtg tggaaaaaaa 134820
aagaataatg acccggcccc cgccctctgc ccccagctgc tcctcgcagt tcggttaatt 134880
ggttaatcac ttaacctgct tttgtcactc ggctttggct cgggacttca aaatcagtga 134940
tgggagtaag agcaaatttc atctttccaa attgatgggt gggctagtaa taaaatattt 135000
aaaaaaaaac attcaaaaac atggccacat ccaacatttc ctcaggcaat tccttttgat 135060
tctttttct tccccctcca tgtagaagag ggagaaggag aggctctgaa agctgcttct 135120
gggggatttc aagggactgg gggtgccaac cacctctggc cctgttgtgg gggtgtcaca 135180
gaggcagtgg cagcaacaaa ggatttgaaa cttggtgtgt tcgtggagcc acaggcagac 135240
gatgtcaacc ttgtgtgagt gtgacggggg ttggggtggg gcgggaggcc acgggggagg 135300
ccgaggcagg ggctgggcag aggggagagg aagcacaaga agtgggagtg ggagaggaag 135360
ccacgtgctg gagagtagac atccccctcc ttgccgctgg gagagccaag gcctatgcca 135420
cctgcagcgt ctgagcggcc gcctgtcctt ggtggccggg ggtgggggcc tgctgtgggt 135480
cagtgtgcca ccctctgcag ggcagcctgt gggagaaggg acagcgggta aaaagagaag 135540
gcaagctggc aggagggtgg cacttcgtgg atgacctcct tagaaaagac tgaccttgat 135600
gtcttgagag cgctggcctc ttcctccctc cctgcagggt agggggcctg agttgagggg 135660
cttccctctg ctccacagaa accctgtttt attgagttct gaaggttgga actgctgcca 135720
tgattttggc cactttgcag acctgggact ttagggctaa ccagttctct ttgtaaggac 135780
ttgtgcctct tgggagacgt ccacccgttt ccaagcctgg gccactggca tctctggagt 135840
gtgtgggggt ctgggaggca ggtcccgagc cccctgtcct tcccacggcc actgcagtca 135900
cccctgtctg cgccgctgtg ctgttgtctg ccgtgagagc ccaatcactg cctatacccc 135960
tcatcacacg tcacaatgtc ccgaattccc agcctcacca ccccttctca gtaatgaccc 136020
tggttggttg caggaggtac ctactccata ctgagggtga aattaaggga aggcaaagtc 136080
caggcacaag agtgggaccc cagcctctca ctctcagttc cactcatcca actgggaccc 136140
tcaccacgaa tctcatgatc tgattcggtt ccctgtctcc tcctcccgtc acagatgtga 136200
gccagggcac tgctcagctg tgaccctagg tgtttctgcc ttgttgacat ggagagagcc 136260
ctttcccctg agaaggcctg gccccttcct gtgctgagcc cacagcagca ggctgggtgt 136320
cttggttgtc agtggtggca ccaggatgga agggcaaggc acccagggca ggcccacagt 136380
cccgctgtcc cccacttgca ccctagcttg tagctgccaa cctcccagac agcccagccc 136440
gctgctcagc tccacatgca tagtatcagc cctccacacc cgacaaaggg gaacacaccc 136500
ccttggaaat ggttcttttc ccccagtccc agctggaagc catgctgtct gttctgctgg 136560
agcagctgaa catatacata gatgttgccc tgccctcccc atctgcaccc tgttgagttg 136620
tagttggatt tgtctgttta tgcttggatt caccagagtg actatgatag tgaaaagaaa 136680
aaaaaaaaaa aaaaaggacg catgtatctt gaaatgcttg taaagaggtt tctaacccac 136740
cctcacgagg tgtctctcac ccccacactg ggactcgtgt ggcctgtgtg gtgccaccct 136800
gctggggcct cccaagtttt gaaaggcttt cctcagcacc tgggacccaa cagagaccag 136860
cttctagcag ctaaggaggc cgttcagctg tgacgaaggc ctgaagcaca ggattaggac 136920
tgaagcgatg atgtcccctt ccctacttcc ccttggggct ccctgtgtca gggcacagac 136980
taggtcttgt ggctggtctg gcttgcggcg cgaggatggt tctctctggt catagcccga 137040
agtctcatgg cagtcccaaa ggaggcttac aactcctgca tcacaagaaa aaggaagcca 137100
ctgccagctg gggggatctg cagctcccag aagctccgtg agcctcagcc acccctcaga 137160
ctgggttcct ctccaagctc gccctctgga ggggcagcgc agcctcccac caagggccct 137220
gcgaccacag cagggattgg gatgaattgc ctgtcctgga tctgctctag aggcccaagc 137280
tgcctgcctg aggaaggatg acttgacaag tcaggagaca ctgttcccaa agccttgacc 137340
agagcacctc agcccgctga ccttgcacaa actccatctg ctgccatgag aaaagggaag 137400
ccgcctttgc aaaacattgc tgcctaaaga aactcagcag cctcaggccc aattctgcca 137460
cttctggttt gggtacagtt aaaggcaacc ctgagggact tggcagtaga aatccagggc 137520
ctcccctggg gctggcagct tcgtgtgcag ctagagcttt acctgaaagg aagtctctgg 137580
gcccagaact ctccaccaag agcctccctg ccgttcgctg agtcccagca attctcctaa 137640
gttgaaggga tctgagaagg agaaggaaat gtggggtaga tttggtggtg gttagagata 137700
tgcccccctc attactgcca acagtttcgg ctgcatttct tcacgcacct cggttcctct 137760
tcctgaagtt cttgtgccct gctcttcagc accatgggcc ttcttatacg gaaggctctg 137820
ggatctcccc cttgtggggg caggctcttg gggccagcct aagatcatgg tttagggtga 137880
tcagtgctgg cagataaatt gaaaaggcac gctggcttgt gatcttaaat gaggacaatc 137940
cccccagggc tgggcactcc tcccctcccc tcacttctcc cacctgcaga gccagtgtcc 138000
ttgggtgggc tagataggat atactgtatg ccggctcctt caagctgctg actcacttta 138060
tcaatagttc catttaaatt gacttcagtg gtgagactgt atcctgtttg ctattgcttg 138120
ttgtgctatg gggggagggg ggaggaatgt gtaagatagt taacatgggc aaagggagat 138180
cttggggtgc agcacttaaa ctgcctcgta accctttttca tgatttcaac cacatttgct 138240
agagggaggg agcagccacg gagttagagg cccttggggt ttctcttttc cactgacagg 138300
ctttcccagg cagctggcta gttcattccc tccccagcca ggtgcaggcg taggaatatg 138360
gacatctggt tgctttggcc tgctgccctc tttcaggggt cctaagccca caatcatgcc 138420
tccctaagac cttggcatcc ttccctctaa gccgttggca cctctgtgcc acctctcaca 138480
ctggctccag acacacagcc tgtgcttttg gagctgagat cactcgcttc accctcctca 138540
tctttgttct ccaagtaaag ccacgaggtc ggggcgaggg cagaggtgat cacctgcgtg 138600
tcccatctac agacctgcgg cttcataaaa cttctgattt ctcttcagct ttgaaaaggg 138660
ttaccctggg cactggccta gagcctcacc tcctaataga cttagcccca tgagtttgcc 138720
atgttgagca ggactatttc tggcacttgc aagtcccatg atttcttcgg taattctgag 138780
ggtgggggga gggacatgaa atcatcttag cttagctttc tgtctgtgaa tgtctatata 138840
gtgtattgtg tgttttaaca aatgatttac actgactgtt gctgtaaaag tgaatttgga 138900
aataaagtta ttactctgat taaataaggt ctccattcat ggattccaag gacaagaaag 138960
tcatatagaa tgtctatttt ttaagttctt tcccacgcac ccttagataa tttagctcag 139020
aacaggaaat gatagtatta ataaaagctg gacatcagga ttaacagctc tctctggggc 139080
cctgaaggtg agagttctca gacttgctca tttgcagttg cttctttgtg atgctggcaa 139140
accatcctag tcccattcaa agggcaatac aaagccttgt ggctgacctc acgatgcagc 139200
actcagtttg caagaccggc accagtgtat gcaaacctga gaaggttggg gatgaggata 139260
tgggatcttt catccctgga aatttagtcc agaggcctgg ggctggagca gaacaccaag 139320
ccaatcagct taatgaatgg cttagattcc tgctaggttt gcagagctgc cttctttcct 139380
ttggtacctt attatagatt gaggagtatt tctgctaaac caagataggg ataaccagat 139440
agcatcttca tagcaatgcc acaaaggaaa acaaaaacaa aacagtaatc catcatatta 139500
ttccttagta actatgccaa ggtcatgata ctgaatcctt agattgtttc aaaatactac 139560
ttttctttgc tcttcctgat gtgtttgcca ccgcaggcag atgtttaagt aaaacagatt 139620
ttaactgcag ctacaaaagc agcaacaggc cagcaaaaga gaagtgctat ctcagagagc 139680
atggctttca gagccacaag agacagcctc actggctgtt tcagcttgac tgccatgcaa 139740
agaagagagc agagggagaa ccagccccac ccacttattc atcttgtaca aaaaaaaagc 139800
acctaccagc ctaggctaca tagtgagaca ctatctccac aaaaaaccca cgaaaactag 139860
ctgggtatgg tggcacatgc ctacagtccc agctactggt aaggctgtgg tgggaggatc 139920
tcttgaggcc aggaaggaga tccaggctgc agtgagccaa gattgcacca ctgcactcca 139980
gtctggacaa tcgagcaaga tcccatctca aacaataaaa aaaaaaagcg tgtaacctcc 140040
tcagaagaaa gatgttataa tctcaggcag caggcaagaa ccaatccagg ctctaagcaa 140100
attatgtatc tcactgaccc caccaaacct cagaaaaatt taacagtgag aagcaaaatc 140160
tcctttaaag agcaacttag aacagataga aaatatcata cagctgactt cactagagag 140220
aaagtgcatc aactgctttc actcaacaaa aagaaaaaag agatgatcaa tgcagatccc 140280
ctctcctcct ggcagccctt accctcagtg aaaagccacc accattctct ctctggtggc 140340
catcagatca acctgcggcg ttcccacaag acagaatgga gattttccaa ggtatagagc 140400
aagtcagagt accccaaaga acggcggcag agagccagct ccgaaactgc caacactacc 140460
atgcatacac agttcagtaa gtcaagaaag gcctggtaca cagcattctg taactttttt 140520
ttttattttt ttcaattttt ccttcttttt tttttttaag cactagtctg tgctttgcga 140580
acagaatcaa gacattaaca aagatcagct tctctgaaga aaagcatttc tatagaacaa 140640
agacagctac atgtttcgct gccattacac agctccaaag caggaaaaga aaatatttac 140700
aaaatacaag gttttttttt tccatttttt gtttttgttt ttttttcaa tgctaaaagg 140760 gttattcaga attttcaacc ttataaatag aagaagcact ttatgcatag ggatatggtg 140820
cattattgta ttttttttta aagaaacaat gacaaaccct ttaacttgca aacagaaaaa 140880
aaaatcacta atgttgaaaa ttgtgaaaaa accccaacca ttaa 140924

<210> SEQ ID NO 2
<211> LENGTH: 6762
<212> TYPE: DNA
<213> ORGANISM: Artificial Sequence
<220> FEATURE:
<223> OTHER INFORMATION: MAPT cDNA Sequence

<400> SEQUENCE: 2
acggccgagc ggcagggcgc tcgcgcgcgc ccactagtgg ccggaggaga aggctcccgc 60
ggaggccgcg ctgcccgccc cctcccctgg ggaggctcgc gttcccgctg ctcgcgcctg 120
cgccgcccgc cggcctcagg aacgcgccct cttcgccggc gcgcgccctc gcagtcaccg 180
ccacccacca gctccggcac caacagcagc gccgctgcca ccgcccacct tctgccgccg 240
ccaccacagc caccttctcc tcctccgctg tcctctcccg tcctcgcctc tgtcgactat 300
caggtgaact ttgaaccagg atggctgagc cccgccagga gttcgaagtg atggaagatc 360
acgctgggac gtacgggttg gggacagga aagatcaggg gggctacacc atgcaccaag 420
accaagaggg tgacacggac gctggcctga aagaatctcc cctgcagacc cccactgagg 480
acggatctga ggaaccgggc tctgaaacct ctgatgctaa gagcactcca acagcggaag 540
atgtgacagc acccttagtg gatgagggag ctcccggcaa gcaggctgcc gcgcagcccc 600
acacggagat cccagaagga accacagctg aagaagcagg cattggagac acccccagcc 660
tggaagacga agctgctggt cacgtgaccc aagagcctga aagtggtaag gtggtccagg 720
aaggcttcct ccgagagcca ggccccccag gtctgagcca ccagctcatg tccggcatgc 780
ctggggctcc cctcctgcct gagggcccca gagaggccac acgccaacct tcggggacag 840
gacctgagga cacagagggc ggccgccacg cccctgagct gctcaagcac cagcttctag 900
gagacctgca ccaggagggg ccgccgctga agggggcagg gggcaaagag aggccgggga 960
gcaaggagga ggtggatgaa gaccgcgacg tcgatgagtc ctccccccaa gactcccctc 1020
cctccaaggc ctccccagcc caagatgggc ggcctcccca gacagccgcc agagaagcca 1080
ccagcatccc aggcttccca gcggagggtg ccatcccccct ccctgtggat ttcctctcca 1140
aagtttccac agagatccca gcctcagagc ccgacgggcc cagtgtaggg cgggccaaag 1200
ggcaggatgc ccccctggag ttcacgtttc acgtggaaat cacacccaac gtgcagaagg 1260
agcaggcgca ctcggaggag catttgggaa gggctgcatt tccaggggcc cctggagagg 1320
ggccagaggc ccggggcccc tctttgggag aggacacaaa agaggctgac cttccagagc 1380
cctctgaaaa gcagcctgct gctgctccgc gggggaagcc cgtcagccgg gtccctcaac 1440
tcaaagctcg catggtcagt aaaagcaaag acgggactgg aagcgatgac aaaaaagcca 1500
agacatccac acgttcctct gctaaaacct tgaaaaatag gccttgcctt agccccaaac 1560
accccactcc tggtagctca gaccctctga tccaaccctc cagccctgct gtgtgcccag 1620
agccaccttc ctctcctaaa cacgtctctt ctgtcacttc ccgaactggc agttctggag 1680
caaaggagat gaaactcaag gggctgatg gtaaaacgaa gatcgccaca ccgcggggag 1740

-continued cagcccctcc aggccagaag ggccaggcca acgccaccag gattccagca aaaaccccgc 1800
ccgctccaaa gacaccaccc agctctggtg aacctccaaa atcaggggat cgcagcggct 1860
acagcagccc cggctcccca ggcactcccg gcagccgctc ccgcaccccg tcccttccaa 1920
ccccacccac ccgggagccc aagaaggtgg cagtggtccg tactccaccc aagtcgccgt 1980
cttccgccaa gagccgcctg cagacagccc ccgtgcccat gccagacctg aagaatgtca 2040
agtccaagat cggctccact gagaacctga agcaccagcc gggaggcggg aaggtgcaga 2100
taattaataa gaagctggat cttagcaacg tccagtccaa gtgtggctca aaggataata 2160
tcaaacacgt cccgggaggc ggcagtgtgc aaatagtcta caaaccagtt gacctgagca 2220
aggtgacctc caagtgtggc tcattaggca acatccatca taaaccagga ggtggccagg 2280
tggaagtaaa atctgagaag cttgacttca aggacagagt ccagtcgaag attgggtccc 2340
tggacaatat cacccacgtc cctggcggag gaaataaaaa gattgaaacc cacaagctga 2400
ccttccgcga gaacgccaaa gccaagacag accacggggc ggagatcgtg tacaagtcgc 2460
cagtggtgtc tggggacacg tctccacggc atctcagcaa tgtctcctcc accggcagca 2520
tcgacatggt agactcgccc cagctcgcca cgctagctga cgaggtgtct gcctccctgg 2580
ccaagcaggg tttgtgatca ggcccctggg gcggtcaata attgtggaga ggagagaatg 2640
agagagtgtg gaaaaaaaaa gaataatgac ccggcccccg ccctctgccc ccagctgctc 2700
ctcgcagttc ggttaattgg ttaatcactt aacctgcttt tgtcactcgg ctttggctcg 2760
ggacttcaaa atcagtgatg ggagtaagag caaatttcat ctttccaaat tgatgggtgg 2820
gctagtaata aaatatttaa aaaaaaacat tcaaaaacat ggccacatcc aacatttcct 2880
caggcaattc cttttgattc tttttcttc cccctccatg tagaagaggg agaaggagag 2940
gctctgaaag ctgcttctgg gggatttcaa gggactgggg gtgccaacca cctctggccc 3000
tgttgtgggg gtgtcacaga ggcagtggca gcaacaaagg atttgaaact tggtgtgttc 3060
gtggagccac aggcagacga tgtcaacctt gtgtgagtgt gacgggggtt ggggtggggc 3120
gggaggccac gggggaggcc gaggcagggg ctgggcagag gggagaggaa gcacaagaag 3180
tgggagtggg agaggaagcc acgtgctgga gagtagacat ccccctcctt gccgctggga 3240
gagccaaggc ctatgccacc tgcagcgtct gagcggccgc ctgtccttgg tggccggggg 3300
tgggggcctg ctgtgggtca gtgtgccacc ctctgcaggg cagcctgtgg gagaagggac 3360
agcgggtaaa aagagaaggc aagctggcag gagggtggca cttcgtggat gacctcctta 3420
gaaaagactg accttgatgt cttgagagcg ctggcctctt cctccctccc tgcagggtag 3480
ggggcctgag ttgaggggct tccctctgct ccacagaaac cctgttttat tgagttctga 3540
aggttggaac tgctgccatg attttggcca ctttgcagac ctgggacttt agggctaacc 3600
agttctcttt gtaaggactt gtgcctcttg ggagacgtcc acccgtttcc aagcctgggc 3660
cactggcatc tctggagtgt gtgggggtct gggaggcagg tcccgagccc cctgtccttc 3720
ccacggccac tgcagtcacc cctgtctgcg ccgctgtgct gttgtctgcc gtgagagccc 3780
aatcactgcc tatacccctc atcacacgtc acaatgtccc gaattcccag cctcaccacc 3840
ccttctcagt aatgaccctg gttggttgca ggaggtacct actccatact gagggtgaaa 3900
ttaagggaag gcaaagtcca ggcacaagag tgggacccca gcctctcact ctcagttcca 3960
ctcatccaac tgggaccctc accacgaatc tcatgatctg attcggttcc ctgtctcctc 4020
ctcccgtcac agatgtgagc cagggcactg ctcagctgtg accctaggtg tttctgcctt 4080
gttgacatgg agagagccct ttcccctgag aaggcctggc cccttcctgt gctgagccca 4140

```
cagcagcagg ctgggtgtct tggttgtcag tggtggcacc aggatggaag ggcaaggcac   4200
ccagggcagg cccacagtcc cgctgtcccc cacttgcacc ctagcttgta gctgccaacc   4260
tcccagacag cccagcccgc tgctcagctc cacatgcata gtatcagccc tccacacccg   4320
acaaagggga acacacccc ttggaaatgg ttcttttccc ccagtcccag ctggaagcca   4380
tgctgtctgt tctgctggag cagctgaaca tatacataga tgttgccctg ccctccccat   4440
ctgcaccctg ttgagttgta gttggatttg tctgtttatg cttggattca ccagagtgac   4500
tatgatagtg aaaagaaaaa aaaaaaaaaa aaaggacgca tgtatcttga aatgcttgta   4560
aagaggtttc taacccaccc tcacgaggtg tctctcaccc ccacactggg actcgtgtgg   4620
cctgtgtggt gccaccctgc tggggcctcc caagttttga aaggctttcc tcagcacctg   4680
ggacccaaca gagaccagct tctagcagct aaggaggccg ttcagctgtg acgaaggcct   4740
gaagcacagg attaggactg aagcgatgat gtccccttcc ctacttcccc ttggggctcc   4800
ctgtgtcagg gcacagacta ggtcttgtgg ctggtctggc ttgcggcgcg aggatggttc   4860
tctctggtca tagcccgaag tctcatggca gtcccaaagg aggcttacaa ctcctgcatc   4920
acaagaaaaa ggaagccact gccagctggg gggatctgca gctcccagaa gctccgtgag   4980
cctcagccac ccctcagact gggttcctct ccaagctcgc cctctggagg ggcagcgcag   5040
cctcccacca agggccctgc gaccacagca gggattggga tgaattgcct gtcctggatc   5100
tgctctagag gcccaagctg cctgcctgag gaaggatgac ttgacaagtc aggagacact   5160
gttcccaaag ccttgaccag agcacctcag cccgctgacc ttgcacaaac tccatctgct   5220
gccatgagaa aagggaagcc gcctttgcaa aacattgctg cctaaagaaa ctcagcagcc   5280
tcaggcccaa ttctgccact tctggtttgg gtacagttaa aggcaaccct gagggacttg   5340
gcagtagaaa tccagggcct cccctggggc tggcagcttc gtgtgcagct agagctttac   5400
ctgaaaggaa gtctctgggc ccagaactct ccaccaagag cctccctgcc gttcgctgag   5460
tcccagcaat tctcctaagt tgaagggatc tgagaaggag aaggaaatgt ggggtagatt   5520
tggtggtggt tagagatatg ccccctcat tactgccaac agtttcggct gcatttcttc   5580
acgcacctcg gttcctcttc ctgaagttct tgtgccctgc tcttcagcac catgggcctt   5640
cttatacgga aggctctggg atctccccct tgtgggggca ggctcttggg gccagcctaa   5700
gatcatggtt tagggtgatc agtgctggca gataaattga aaaggcacgc tggcttgtga   5760
tcttaaatga ggacaatccc cccagggctg ggcactcctc ccctccccctc acttctccca   5820
cctgcagagc cagtgtcctt gggtgggcta gataggatat actgtatgcc ggctccttca   5880
agctgctgac tcactttatc aatagttcca tttaaattga cttcagtggt gagactgtat   5940
cctgtttgct attgcttgtt gtgctatggg gggagggggg aggaatgtgt aagatagtta   6000
acatgggcaa agggagatct tggggtgcag cacttaaact gcctcgtaac ccttttcatg   6060
atttcaacca catttgctag agggagggag cagccacgga gttagaggcc cttggggttt   6120
ctcttttcca ctgacaggct ttcccaggca gctggctagt tcattccctc cccagccagg   6180
tgcaggcgta ggaatatgga catctggttg ctttggcctg ctgccctctt tcaggggtcc   6240
taagcccaca atcatgcctc cctaagacct tggcatcctt ccctctaagc cgttggcacc   6300
tctgtgccac ctctcacact ggctccagac acacagcctg tgcttttgga gctgagatca   6360
ctcgcttcac cctcctcatc tttgttctcc aagtaaagcc acgaggtcgg ggcgagggca   6420
gaggtgatca cctgcgtgtc ccatctacag acctgcggct tcataaaact tctgatttct   6480
```

-continued

```
cttcagcttt gaaaagggtt accctgggca ctggcctaga gcctcacctc ctaatagact   6540

tagccccatg agtttgccat gttgagcagg actatttctg gcacttgcaa gtcccatgat   6600

ttcttcggta attctgaggg tggggggagg gacatgaaat catcttagct tagctttctg   6660

tctgtgaatg tctatatagt gtattgtgtg ttttaacaaa tgatttacac tgactgttgc   6720

tgtaaaagtg aatttggaaa taaagttatt actctgatta aa                      6762


<210> SEQ ID NO 3
<211> LENGTH: 758
<212> TYPE: PRT
<213> ORGANISM: Artificial Sequence
<220> FEATURE:
<223> OTHER INFORMATION: Microtubule-associated protein tau (Tau)
      protein sequence

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
```

```
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735
```

```
Val Asp Ser Pro Gln Leu Ala Thr Leu Ala Asp Glu Val Ser Ala Ser
            740                 745                 750

Leu Ala Lys Gln Gly Leu
        755


<210> SEQ ID NO 4
<211> LENGTH: 20
<212> TYPE: DNA
<213> ORGANISM: Artificial Sequence
<220> FEATURE:
<223> OTHER INFORMATION: ASO-001167

<400> SEQUENCE: 4

aaagatgaaa tttgctctta                                                   20


<210> SEQ ID NO 5
<211> LENGTH: 20
<212> TYPE: DNA
<213> ORGANISM: Artificial Sequence
<220> FEATURE:
<223> OTHER INFORMATION: ASO-001168

<400> SEQUENCE: 5

gaaagatgaa atttgctctt                                                   20


<210> SEQ ID NO 6
<211> LENGTH: 20
<212> TYPE: DNA
<213> ORGANISM: Artificial Sequence
<220> FEATURE:
<223> OTHER INFORMATION: ASO-001169

<400> SEQUENCE: 6

ggaaagatga aatttgctct                                                   20


<210> SEQ ID NO 7
<211> LENGTH: 16
<212> TYPE: DNA
<213> ORGANISM: Artificial Sequence
<220> FEATURE:
<223> OTHER INFORMATION: ASO-000829

<400> SEQUENCE: 7

aagatgaaat ttgctc                                                       16


<210> SEQ ID NO 8
<211> LENGTH: 20
<212> TYPE: DNA
<213> ORGANISM: Artificial Sequence
<220> FEATURE:
<223> OTHER INFORMATION: ASO-001170

<400> SEQUENCE: 8

tggaaagatg aaatttgctc                                                   20


<210> SEQ ID NO 9
<211> LENGTH: 20
<212> TYPE: DNA
<213> ORGANISM: Artificial Sequence
<220> FEATURE:
<223> OTHER INFORMATION: ASO-001171

<400> SEQUENCE: 9

ttggaaagat gaaatttgct                                                   20
```

<210> SEQ ID NO 10
<211> LENGTH: 20
<212> TYPE: DNA
<213> ORGANISM: Artificial Sequence
<220> FEATURE:
<223> OTHER INFORMATION: ASO-001172

<400> SEQUENCE: 10
tttggaaaga tgaaatttgc 20

<210> SEQ ID NO 11
<211> LENGTH: 20
<212> TYPE: DNA
<213> ORGANISM: Artificial Sequence
<220> FEATURE:
<223> OTHER INFORMATION: ASO-001173

<400> SEQUENCE: 11
atttggaaag atgaaatttg 20

<210> SEQ ID NO 12
<211> LENGTH: 20
<212> TYPE: DNA
<213> ORGANISM: Artificial Sequence
<220> FEATURE:
<223> OTHER INFORMATION: ASO-001174

<400> SEQUENCE: 12
aatttggaaa gatgaaattt 20

<210> SEQ ID NO 13
<211> LENGTH: 20
<212> TYPE: DNA
<213> ORGANISM: Artificial Sequence
<220> FEATURE:
<223> OTHER INFORMATION: ASO-001175

<400> SEQUENCE: 13
caatttggaa agatgaaatt 20

<210> SEQ ID NO 14
<211> LENGTH: 20
<212> TYPE: DNA
<213> ORGANISM: Artificial Sequence
<220> FEATURE:
<223> OTHER INFORMATION: ASO-001176

<400> SEQUENCE: 14
tcaatttgga aagatgaaat 20

<210> SEQ ID NO 15
<211> LENGTH: 20
<212> TYPE: DNA
<213> ORGANISM: Artificial Sequence
<220> FEATURE:
<223> OTHER INFORMATION: ASO-001177

<400> SEQUENCE: 15
atcaatttgg aaagatgaaa 20

<210> SEQ ID NO 16
<211> LENGTH: 20
<212> TYPE: DNA
<213> ORGANISM: Artificial Sequence
<220> FEATURE:
<223> OTHER INFORMATION: ASO-001178

<400> SEQUENCE: 16
catcaatttg gaaagatgaa 20

<210> SEQ ID NO 17
<211> LENGTH: 20
<212> TYPE: DNA
<213> ORGANISM: Artificial Sequence
<220> FEATURE:
<223> OTHER INFORMATION: ASO-001179

<400> SEQUENCE: 17
acccatcaat ttggaaagat 20

<210> SEQ ID NO 18
<211> LENGTH: 20
<212> TYPE: DNA
<213> ORGANISM: Artificial Sequence
<220> FEATURE:
<223> OTHER INFORMATION: ASO-001180

<400> SEQUENCE: 18
ccatcaattt ggaaagatga 20

<210> SEQ ID NO 19
<211> LENGTH: 20
<212> TYPE: DNA
<213> ORGANISM: Artificial Sequence
<220> FEATURE:
<223> OTHER INFORMATION: ASO-001181

<400> SEQUENCE: 19
cccatcaatt tggaaagatg 20

<210> SEQ ID NO 20
<211> LENGTH: 20
<212> TYPE: DNA
<213> ORGANISM: Artificial Sequence
<220> FEATURE:
<223> OTHER INFORMATION: ASO-001182

<400> SEQUENCE: 20
cacccatcaa tttggaaaga 20

<210> SEQ ID NO 21
<211> LENGTH: 20
<212> TYPE: DNA
<213> ORGANISM: Artificial Sequence
<220> FEATURE:
<223> OTHER INFORMATION: ASO-001183

<400> SEQUENCE: 21
ccacccatca atttggaaag 20

<210> SEQ ID NO 22
<211> LENGTH: 20
<212> TYPE: DNA
<213> ORGANISM: Artificial Sequence
<220> FEATURE:
<223> OTHER INFORMATION: ASO-001184

<400> SEQUENCE: 22
cccacccatc aatttggaaa 20

<210> SEQ ID NO 23

<211> LENGTH: 20
<212> TYPE: DNA
<213> ORGANISM: Artificial Sequence
<220> FEATURE:
<223> OTHER INFORMATION: ASO-001062

<400> SEQUENCE: 23
gcccacccat caatttggaa 20

<210> SEQ ID NO 24
<211> LENGTH: 20
<212> TYPE: DNA
<213> ORGANISM: Artificial Sequence
<220> FEATURE:
<223> OTHER INFORMATION: ASO-001063

<400> SEQUENCE: 24
tagcccaccc atcaatttgg 20

<210> SEQ ID NO 25
<211> LENGTH: 20
<212> TYPE: DNA
<213> ORGANISM: Artificial Sequence
<220> FEATURE:
<223> OTHER INFORMATION: ASO-001064

<400> SEQUENCE: 25
ctagcccacc catcaatttg 20

<210> SEQ ID NO 26
<211> LENGTH: 20
<212> TYPE: DNA
<213> ORGANISM: Artificial Sequence
<220> FEATURE:
<223> OTHER INFORMATION: ASO-001065

<400> SEQUENCE: 26
actagcccac ccatcaattt 20

<210> SEQ ID NO 27
<211> LENGTH: 20
<212> TYPE: DNA
<213> ORGANISM: Artificial Sequence
<220> FEATURE:
<223> OTHER INFORMATION: ASO-001066

<400> SEQUENCE: 27
tactagccca cccatcaatt 20

<210> SEQ ID NO 28
<211> LENGTH: 16
<212> TYPE: DNA
<213> ORGANISM: Artificial Sequence
<220> FEATURE:
<223> OTHER INFORMATION: ASO-000830

<400> SEQUENCE: 28
tactagccca cccatc 16

<210> SEQ ID NO 29
<211> LENGTH: 16
<212> TYPE: DNA
<213> ORGANISM: Artificial Sequence
<220> FEATURE:
<223> OTHER INFORMATION: ASO-000260

<400> SEQUENCE: 29
ccctcttcta catgga 16

<210> SEQ ID NO 30
<211> LENGTH: 16
<212> TYPE: DNA
<213> ORGANISM: Artificial Sequence
<220> FEATURE:
<223> OTHER INFORMATION: ASO-000305

<400> SEQUENCE: 30
tgcctctgtg acaccc 16

<210> SEQ ID NO 31
<211> LENGTH: 16
<212> TYPE: DNA
<213> ORGANISM: Artificial Sequence
<220> FEATURE:
<223> OTHER INFORMATION: ASO-000304

<400> SEQUENCE: 31
ttcaaatcct ttgttg 16

<210> SEQ ID NO 32
<211> LENGTH: 16
<212> TYPE: DNA
<213> ORGANISM: Artificial Sequence
<220> FEATURE:
<223> OTHER INFORMATION: ASO-000324

<400> SEQUENCE: 32
cacacaaggt tgacat 16

<210> SEQ ID NO 33
<211> LENGTH: 16
<212> TYPE: DNA
<213> ORGANISM: Artificial Sequence
<220> FEATURE:
<223> OTHER INFORMATION: ASO-000268

<400> SEQUENCE: 33
cgtcacactc acacaa 16

<210> SEQ ID NO 34
<211> LENGTH: 16
<212> TYPE: DNA
<213> ORGANISM: Artificial Sequence
<220> FEATURE:
<223> OTHER INFORMATION: ASO-000223

<400> SEQUENCE: 34
gccaccaagg acaggc 16

<210> SEQ ID NO 35
<211> LENGTH: 16
<212> TYPE: DNA
<213> ORGANISM: Artificial Sequence
<220> FEATURE:
<223> OTHER INFORMATION: ASO-000224

<400> SEQUENCE: 35
cagcttgcct tctctt 16

<210> SEQ ID NO 36
<211> LENGTH: 16
<212> TYPE: DNA

<213> ORGANISM: Artificial Sequence
<220> FEATURE:
<223> OTHER INFORMATION: ASO-000319

<400> SEQUENCE: 36
atcaaggtca gtcttt 16

<210> SEQ ID NO 37
<211> LENGTH: 16
<212> TYPE: DNA
<213> ORGANISM: Artificial Sequence
<220> FEATURE:
<223> OTHER INFORMATION: ASO-000208

<400> SEQUENCE: 37
ccttcagaac tcaata 16

<210> SEQ ID NO 38
<211> LENGTH: 16
<212> TYPE: DNA
<213> ORGANISM: Artificial Sequence
<220> FEATURE:
<223> OTHER INFORMATION: ASO-000689

<400> SEQUENCE: 38
aaagtcccag gtctgc 16

<210> SEQ ID NO 39
<211> LENGTH: 16
<212> TYPE: DNA
<213> ORGANISM: Artificial Sequence
<220> FEATURE:
<223> OTHER INFORMATION: ASO-000434

<400> SEQUENCE: 39
ctaaagtccc aggtct 16

<210> SEQ ID NO 40
<211> LENGTH: 15
<212> TYPE: DNA
<213> ORGANISM: Artificial Sequence
<220> FEATURE:
<223> OTHER INFORMATION: ASO-000409

<400> SEQUENCE: 40
taaagtccca ggtct 15

<210> SEQ ID NO 41
<211> LENGTH: 16
<212> TYPE: DNA
<213> ORGANISM: Artificial Sequence
<220> FEATURE:
<223> OTHER INFORMATION: ASO-000432

<400> SEQUENCE: 41
cctaaagtcc caggtc 16

<210> SEQ ID NO 42
<211> LENGTH: 14
<212> TYPE: DNA
<213> ORGANISM: Artificial Sequence
<220> FEATURE:
<223> OTHER INFORMATION: ASO-000391

<400> SEQUENCE: 42
taaagtccca ggtc 14

<210> SEQ ID NO 43
<211> LENGTH: 20
<212> TYPE: DNA
<213> ORGANISM: Artificial Sequence
<220> FEATURE:
<223> OTHER INFORMATION: ASO-001779

<400> SEQUENCE: 43
tagccctaaa gtcccaggtc 20

<210> SEQ ID NO 44
<211> LENGTH: 15
<212> TYPE: DNA
<213> ORGANISM: Artificial Sequence
<220> FEATURE:
<223> OTHER INFORMATION: ASO-000899

<400> SEQUENCE: 44
ctaaagtccc aggtc 15

<210> SEQ ID NO 45
<211> LENGTH: 16
<212> TYPE: DNA
<213> ORGANISM: Artificial Sequence
<220> FEATURE:
<223> OTHER INFORMATION: ASO-000398

<400> SEQUENCE: 45
ccctaaagtc ccaggt 16

<210> SEQ ID NO 46
<211> LENGTH: 20
<212> TYPE: DNA
<213> ORGANISM: Artificial Sequence
<220> FEATURE:
<223> OTHER INFORMATION: ASO-001778

<400> SEQUENCE: 46
ttagccctaa agtcccaggt 20

<210> SEQ ID NO 47
<211> LENGTH: 16
<212> TYPE: DNA
<213> ORGANISM: Artificial Sequence
<220> FEATURE:
<223> OTHER INFORMATION: ASO-000414

<400> SEQUENCE: 47
gccctaaagt cccagg 16

<210> SEQ ID NO 48
<211> LENGTH: 15
<212> TYPE: DNA
<213> ORGANISM: Artificial Sequence
<220> FEATURE:
<223> OTHER INFORMATION: ASO-000403

<400> SEQUENCE: 48
ccctaaagtc ccagg 15

<210> SEQ ID NO 49
<211> LENGTH: 20
<212> TYPE: DNA
<213> ORGANISM: Artificial Sequence
<220> FEATURE:

<223> OTHER INFORMATION: ASO-001780

<400> SEQUENCE: 49
gttagcccta aagtcccagg 20

<210> SEQ ID NO 50
<211> LENGTH: 15
<212> TYPE: DNA
<213> ORGANISM: Artificial Sequence
<220> FEATURE:
<223> OTHER INFORMATION: ASO-000433

<400> SEQUENCE: 50
gccctaaagt cccag 15

<210> SEQ ID NO 51
<211> LENGTH: 14
<212> TYPE: DNA
<213> ORGANISM: Artificial Sequence
<220> FEATURE:
<223> OTHER INFORMATION: ASO-000411

<400> SEQUENCE: 51
ccctaaagtc ccag 14

<210> SEQ ID NO 52
<211> LENGTH: 20
<212> TYPE: DNA
<213> ORGANISM: Artificial Sequence
<220> FEATURE:
<223> OTHER INFORMATION: ASO-001781

<400> SEQUENCE: 52
ggttagccct aaagtcccag 20

<210> SEQ ID NO 53
<211> LENGTH: 16
<212> TYPE: DNA
<213> ORGANISM: Artificial Sequence
<220> FEATURE:
<223> OTHER INFORMATION: ASO-000389

<400> SEQUENCE: 53
tagccctaaa gtccca 16

<210> SEQ ID NO 54
<211> LENGTH: 16
<212> TYPE: DNA
<213> ORGANISM: Artificial Sequence
<220> FEATURE:
<223> OTHER INFORMATION: ASO-001939

<400> SEQUENCE: 54
tagccctaaa gtccca 16

<210> SEQ ID NO 55
<211> LENGTH: 16
<212> TYPE: DNA
<213> ORGANISM: Artificial Sequence
<220> FEATURE:
<223> OTHER INFORMATION: ASO-001932

<400> SEQUENCE: 55
tagccctaaa gtccca 16

<210> SEQ ID NO 56
<211> LENGTH: 16
<212> TYPE: DNA
<213> ORGANISM: Artificial Sequence
<220> FEATURE:
<223> OTHER INFORMATION: ASO-001925

<400> SEQUENCE: 56
tagccctaaa gtccca 16

<210> SEQ ID NO 57
<211> LENGTH: 16
<212> TYPE: DNA
<213> ORGANISM: Artificial Sequence
<220> FEATURE:
<223> OTHER INFORMATION: ASO-001924

<400> SEQUENCE: 57
tagccctaaa gtccca 16

<210> SEQ ID NO 58
<211> LENGTH: 16
<212> TYPE: DNA
<213> ORGANISM: Artificial Sequence
<220> FEATURE:
<223> OTHER INFORMATION: ASO-001952

<400> SEQUENCE: 58
tagccctaaa gtccca 16

<210> SEQ ID NO 59
<211> LENGTH: 16
<212> TYPE: DNA
<213> ORGANISM: Artificial Sequence
<220> FEATURE:
<223> OTHER INFORMATION: ASO-001931

<400> SEQUENCE: 59
tagccctaaa gtccca 16

<210> SEQ ID NO 60
<211> LENGTH: 16
<212> TYPE: DNA
<213> ORGANISM: Artificial Sequence
<220> FEATURE:
<223> OTHER INFORMATION: ASO-001953

<400> SEQUENCE: 60
tagccctaaa gtccca 16

<210> SEQ ID NO 61
<211> LENGTH: 16
<212> TYPE: DNA
<213> ORGANISM: Artificial Sequence
<220> FEATURE:
<223> OTHER INFORMATION: ASO-001945

<400> SEQUENCE: 61
tagccctaaa gtccca 16

<210> SEQ ID NO 62
<211> LENGTH: 16
<212> TYPE: DNA
<213> ORGANISM: Artificial Sequence
<220> FEATURE:
<223> OTHER INFORMATION: ASO-001946

<400> SEQUENCE: 62
tagccctaaa gtccca 16

<210> SEQ ID NO 63
<211> LENGTH: 16
<212> TYPE: DNA
<213> ORGANISM: Artificial Sequence
<220> FEATURE:
<223> OTHER INFORMATION: ASO-001971

<400> SEQUENCE: 63
tagccctaaa gtccca 16

<210> SEQ ID NO 64
<211> LENGTH: 16
<212> TYPE: DNA
<213> ORGANISM: Artificial Sequence
<220> FEATURE:
<223> OTHER INFORMATION: ASO-001938

<400> SEQUENCE: 64
tagccctaaa gtccca 16

<210> SEQ ID NO 65
<211> LENGTH: 16
<212> TYPE: DNA
<213> ORGANISM: Artificial Sequence
<220> FEATURE:
<223> OTHER INFORMATION: ASO-001959

<400> SEQUENCE: 65
tagccctaaa gtccca 16

<210> SEQ ID NO 66
<211> LENGTH: 16
<212> TYPE: DNA
<213> ORGANISM: Artificial Sequence
<220> FEATURE:
<223> OTHER INFORMATION: ASO-001965

<400> SEQUENCE: 66
tagccctaaa gtccca 16

<210> SEQ ID NO 67
<211> LENGTH: 20
<212> TYPE: DNA
<213> ORGANISM: Artificial Sequence
<220> FEATURE:
<223> OTHER INFORMATION: ASO-001782

<400> SEQUENCE: 67
tggttagccc taaagtccca 20

<210> SEQ ID NO 68
<211> LENGTH: 16
<212> TYPE: DNA
<213> ORGANISM: Artificial Sequence
<220> FEATURE:
<223> OTHER INFORMATION: ASO-000900

<400> SEQUENCE: 68
tagccctaaa gtccca 16

<210> SEQ ID NO 69
<211> LENGTH: 16

<212> TYPE: DNA
<213> ORGANISM: Artificial Sequence
<220> FEATURE:
<223> OTHER INFORMATION: ASO-000435

<400> SEQUENCE: 69
ttagccctaa agtccc 16

<210> SEQ ID NO 70
<211> LENGTH: 16
<212> TYPE: DNA
<213> ORGANISM: Artificial Sequence
<220> FEATURE:
<223> OTHER INFORMATION: ASO-000423

<400> SEQUENCE: 70
gttagcccta aagtcc 16

<210> SEQ ID NO 71
<211> LENGTH: 14
<212> TYPE: DNA
<213> ORGANISM: Artificial Sequence
<220> FEATURE:
<223> OTHER INFORMATION: ASO-000442

<400> SEQUENCE: 71
tagccctaaa gtcc 14

<210> SEQ ID NO 72
<211> LENGTH: 16
<212> TYPE: DNA
<213> ORGANISM: Artificial Sequence
<220> FEATURE:
<223> OTHER INFORMATION: ASO-000416

<400> SEQUENCE: 72
ggttagccct aaagtc 16

<210> SEQ ID NO 73
<211> LENGTH: 14
<212> TYPE: DNA
<213> ORGANISM: Artificial Sequence
<220> FEATURE:
<223> OTHER INFORMATION: ASO-000438

<400> SEQUENCE: 73
gttagcccta aagt 14

<210> SEQ ID NO 74
<211> LENGTH: 16
<212> TYPE: DNA
<213> ORGANISM: Artificial Sequence
<220> FEATURE:
<223> OTHER INFORMATION: ASO-000581

<400> SEQUENCE: 74
actggttagc cctaaa 16

<210> SEQ ID NO 75
<211> LENGTH: 16
<212> TYPE: DNA
<213> ORGANISM: Artificial Sequence
<220> FEATURE:
<223> OTHER INFORMATION: ASO-000639

<400> SEQUENCE: 75
aactggttag ccctaa 16

<210> SEQ ID NO 76
<211> LENGTH: 16
<212> TYPE: DNA
<213> ORGANISM: Artificial Sequence
<220> FEATURE:
<223> OTHER INFORMATION: ASO-000558

<400> SEQUENCE: 76
gaactggtta gcccta 16

<210> SEQ ID NO 77
<211> LENGTH: 16
<212> TYPE: DNA
<213> ORGANISM: Artificial Sequence
<220> FEATURE:
<223> OTHER INFORMATION: ASO-000597

<400> SEQUENCE: 77
gagaactggt tagccc 16

<210> SEQ ID NO 78
<211> LENGTH: 16
<212> TYPE: DNA
<213> ORGANISM: Artificial Sequence
<220> FEATURE:
<223> OTHER INFORMATION: ASO-000245

<400> SEQUENCE: 78
tacaaagaga actggt 16

<210> SEQ ID NO 79
<211> LENGTH: 16
<212> TYPE: DNA
<213> ORGANISM: Artificial Sequence
<220> FEATURE:
<223> OTHER INFORMATION: ASO-000897

<400> SEQUENCE: 79
cacaagtcct tacaaa 16

<210> SEQ ID NO 80
<211> LENGTH: 16
<212> TYPE: DNA
<213> ORGANISM: Artificial Sequence
<220> FEATURE:
<223> OTHER INFORMATION: ASO-000185

<400> SEQUENCE: 80
ggcacaagtc cttaca 16

<210> SEQ ID NO 81
<211> LENGTH: 15
<212> TYPE: DNA
<213> ORGANISM: Artificial Sequence
<220> FEATURE:
<223> OTHER INFORMATION: ASO-000426

<400> SEQUENCE: 81
aggcacaagt cctta 15

<210> SEQ ID NO 82
<211> LENGTH: 16
<212> TYPE: DNA
<213> ORGANISM: Artificial Sequence

<220> FEATURE:
<223> OTHER INFORMATION: ASO-000417

<400> SEQUENCE: 82
gaggcacaag tcctta 16

<210> SEQ ID NO 83
<211> LENGTH: 16
<212> TYPE: DNA
<213> ORGANISM: Artificial Sequence
<220> FEATURE:
<223> OTHER INFORMATION: ASO-000393

<400> SEQUENCE: 83
agaggcacaa gtcctt 16

<210> SEQ ID NO 84
<211> LENGTH: 16
<212> TYPE: DNA
<213> ORGANISM: Artificial Sequence
<220> FEATURE:
<223> OTHER INFORMATION: ASO-000449

<400> SEQUENCE: 84
aagaggcaca agtcct 16

<210> SEQ ID NO 85
<211> LENGTH: 15
<212> TYPE: DNA
<213> ORGANISM: Artificial Sequence
<220> FEATURE:
<223> OTHER INFORMATION: ASO-000406

<400> SEQUENCE: 85
agaggcacaa gtcct 15

<210> SEQ ID NO 86
<211> LENGTH: 16
<212> TYPE: DNA
<213> ORGANISM: Artificial Sequence
<220> FEATURE:
<223> OTHER INFORMATION: ASO-000392

<400> SEQUENCE: 86
ccaagaggca caagtc 16

<210> SEQ ID NO 87
<211> LENGTH: 15
<212> TYPE: DNA
<213> ORGANISM: Artificial Sequence
<220> FEATURE:
<223> OTHER INFORMATION: ASO-000444

<400> SEQUENCE: 87
caagaggcac aagtc 15

<210> SEQ ID NO 88
<211> LENGTH: 16
<212> TYPE: DNA
<213> ORGANISM: Artificial Sequence
<220> FEATURE:
<223> OTHER INFORMATION: ASO-000443

<400> SEQUENCE: 88
cccaagaggc acaagt 16

<210> SEQ ID NO 89
<211> LENGTH: 14
<212> TYPE: DNA
<213> ORGANISM: Artificial Sequence
<220> FEATURE:
<223> OTHER INFORMATION: ASO-000450

<400> SEQUENCE: 89
caagaggcac aagt 14

<210> SEQ ID NO 90
<211> LENGTH: 16
<212> TYPE: DNA
<213> ORGANISM: Artificial Sequence
<220> FEATURE:
<223> OTHER INFORMATION: ASO-000258

<400> SEQUENCE: 90
ctcccaagag gcacaa 16

<210> SEQ ID NO 91
<211> LENGTH: 16
<212> TYPE: DNA
<213> ORGANISM: Artificial Sequence
<220> FEATURE:
<223> OTHER INFORMATION: ASO-000205

<400> SEQUENCE: 91
tggccgtggg aaggac 16

<210> SEQ ID NO 92
<211> LENGTH: 16
<212> TYPE: DNA
<213> ORGANISM: Artificial Sequence
<220> FEATURE:
<223> OTHER INFORMATION: ASO-000213

<400> SEQUENCE: 92
ggtgaggctg ggaatt 16

<210> SEQ ID NO 93
<211> LENGTH: 15
<212> TYPE: DNA
<213> ORGANISM: Artificial Sequence
<220> FEATURE:
<223> OTHER INFORMATION: ASO-000293

<400> SEQUENCE: 93
gtgaggctgg gaatt 15

<210> SEQ ID NO 94
<211> LENGTH: 16
<212> TYPE: DNA
<213> ORGANISM: Artificial Sequence
<220> FEATURE:
<223> OTHER INFORMATION: ASO-000321

<400> SEQUENCE: 94
tggtgaggct gggaat 16

<210> SEQ ID NO 95
<211> LENGTH: 16
<212> TYPE: DNA
<213> ORGANISM: Artificial Sequence
<220> FEATURE:
<223> OTHER INFORMATION: ASO-000226

<400> SEQUENCE: 95
ctcagtatgg agtagg 16

<210> SEQ ID NO 96
<211> LENGTH: 16
<212> TYPE: DNA
<213> ORGANISM: Artificial Sequence
<220> FEATURE:
<223> OTHER INFORMATION: ASO-000682

<400> SEQUENCE: 96
aatttcaccc tcagta 16

<210> SEQ ID NO 97
<211> LENGTH: 16
<212> TYPE: DNA
<213> ORGANISM: Artificial Sequence
<220> FEATURE:
<223> OTHER INFORMATION: ASO-000673

<400> SEQUENCE: 97
ttaatttcac cctcag 16

<210> SEQ ID NO 98
<211> LENGTH: 16
<212> TYPE: DNA
<213> ORGANISM: Artificial Sequence
<220> FEATURE:
<223> OTHER INFORMATION: ASO-000578

<400> SEQUENCE: 98
cttaatttca ccctca 16

<210> SEQ ID NO 99
<211> LENGTH: 17
<212> TYPE: DNA
<213> ORGANISM: Artificial Sequence
<220> FEATURE:
<223> OTHER INFORMATION: ASO-000540-21

<400> SEQUENCE: 99
ccttaatttc accctca 17

<210> SEQ ID NO 100
<211> LENGTH: 17
<212> TYPE: DNA
<213> ORGANISM: Artificial Sequence
<220> FEATURE:
<223> OTHER INFORMATION: ASO-000540-22

<400> SEQUENCE: 100
ccttaatttc accctca 17

<210> SEQ ID NO 101
<211> LENGTH: 17
<212> TYPE: DNA
<213> ORGANISM: Artificial Sequence
<220> FEATURE:
<223> OTHER INFORMATION: ASO-000540-23

<400> SEQUENCE: 101
ccttaatttc accctca 17

<210> SEQ ID NO 102

<211> LENGTH: 17
<212> TYPE: DNA
<213> ORGANISM: Artificial Sequence
<220> FEATURE:
<223> OTHER INFORMATION: ASO-000540-24

<400> SEQUENCE: 102
tcccttaatt tcaccct 17

<210> SEQ ID NO 103
<211> LENGTH: 17
<212> TYPE: DNA
<213> ORGANISM: Artificial Sequence
<220> FEATURE:
<223> OTHER INFORMATION: ASO-000540-25

<400> SEQUENCE: 103
tcccttaatt tcaccct 17

<210> SEQ ID NO 104
<211> LENGTH: 17
<212> TYPE: DNA
<213> ORGANISM: Artificial Sequence
<220> FEATURE:
<223> OTHER INFORMATION: ASO-000540-26

<400> SEQUENCE: 104
tcccttaatt tcaccct 17

<210> SEQ ID NO 105
<211> LENGTH: 17
<212> TYPE: DNA
<213> ORGANISM: Artificial Sequence
<220> FEATURE:
<223> OTHER INFORMATION: ASO-000540-27

<400> SEQUENCE: 105
tcccttaatt tcaccct 17

<210> SEQ ID NO 106
<211> LENGTH: 17
<212> TYPE: DNA
<213> ORGANISM: Artificial Sequence
<220> FEATURE:
<223> OTHER INFORMATION: ASO-000540-28

<400> SEQUENCE: 106
tcccttaatt tcaccct 17

<210> SEQ ID NO 107
<211> LENGTH: 17
<212> TYPE: DNA
<213> ORGANISM: Artificial Sequence
<220> FEATURE:
<223> OTHER INFORMATION: ASO-000540-29

<400> SEQUENCE: 107
tcccttaatt tcaccct 17

<210> SEQ ID NO 108
<211> LENGTH: 17
<212> TYPE: DNA
<213> ORGANISM: Artificial Sequence
<220> FEATURE:
<223> OTHER INFORMATION: ASO-000540-3

<400> SEQUENCE: 108
cccttaattt caccctc 17

<210> SEQ ID NO 109
<211> LENGTH: 18
<212> TYPE: DNA
<213> ORGANISM: Artificial Sequence
<220> FEATURE:
<223> OTHER INFORMATION: ASO-000540-42

<400> SEQUENCE: 109
cccttaattt caccctca 18

<210> SEQ ID NO 110
<211> LENGTH: 18
<212> TYPE: DNA
<213> ORGANISM: Artificial Sequence
<220> FEATURE:
<223> OTHER INFORMATION: ASO-000540-43

<400> SEQUENCE: 110
cccttaattt caccctca 18

<210> SEQ ID NO 111
<211> LENGTH: 18
<212> TYPE: DNA
<213> ORGANISM: Artificial Sequence
<220> FEATURE:
<223> OTHER INFORMATION: ASO-000540-44

<400> SEQUENCE: 111
cccttaattt caccctca 18

<210> SEQ ID NO 112
<211> LENGTH: 18
<212> TYPE: DNA
<213> ORGANISM: Artificial Sequence
<220> FEATURE:
<223> OTHER INFORMATION: ASO-000540-45

<400> SEQUENCE: 112
cccttaattt caccctca 18

<210> SEQ ID NO 113
<211> LENGTH: 18
<212> TYPE: DNA
<213> ORGANISM: Artificial Sequence
<220> FEATURE:
<223> OTHER INFORMATION: ASO-000540-46

<400> SEQUENCE: 113
cccttaattt caccctca 18

<210> SEQ ID NO 114
<211> LENGTH: 18
<212> TYPE: DNA
<213> ORGANISM: Artificial Sequence
<220> FEATURE:
<223> OTHER INFORMATION: ASO-000540-47

<400> SEQUENCE: 114
cccttaattt caccctca 18

<210> SEQ ID NO 115
<211> LENGTH: 18
<212> TYPE: DNA

<213> ORGANISM: Artificial Sequence
<220> FEATURE:
<223> OTHER INFORMATION: ASO-000540-48

<400> SEQUENCE: 115
cccttaattt caccctca 18

<210> SEQ ID NO 116
<211> LENGTH: 18
<212> TYPE: DNA
<213> ORGANISM: Artificial Sequence
<220> FEATURE:
<223> OTHER INFORMATION: ASO-000540-49

<400> SEQUENCE: 116
cccttaattt caccctca 18

<210> SEQ ID NO 117
<211> LENGTH: 17
<212> TYPE: DNA
<213> ORGANISM: Artificial Sequence
<220> FEATURE:
<223> OTHER INFORMATION: ASO-000540-5

<400> SEQUENCE: 117
cccttaattt caccctc 17

<210> SEQ ID NO 118
<211> LENGTH: 18
<212> TYPE: DNA
<213> ORGANISM: Artificial Sequence
<220> FEATURE:
<223> OTHER INFORMATION: ASO-000540-50

<400> SEQUENCE: 118
cccttaattt caccctca 18

<210> SEQ ID NO 119
<211> LENGTH: 18
<212> TYPE: DNA
<213> ORGANISM: Artificial Sequence
<220> FEATURE:
<223> OTHER INFORMATION: ASO-000540-51

<400> SEQUENCE: 119
cccttaattt caccctca 18

<210> SEQ ID NO 120
<211> LENGTH: 18
<212> TYPE: DNA
<213> ORGANISM: Artificial Sequence
<220> FEATURE:
<223> OTHER INFORMATION: ASO-000540-52

<400> SEQUENCE: 120
tcccttaatt tcaccctc 18

<210> SEQ ID NO 121
<211> LENGTH: 18
<212> TYPE: DNA
<213> ORGANISM: Artificial Sequence
<220> FEATURE:
<223> OTHER INFORMATION: ASO-000540-53

<400> SEQUENCE: 121
tcccttaatt tcaccctc 18

<210> SEQ ID NO 122
<211> LENGTH: 18
<212> TYPE: DNA
<213> ORGANISM: Artificial Sequence
<220> FEATURE:
<223> OTHER INFORMATION: ASO-000540-54

<400> SEQUENCE: 122
tcccttaatt tcaccctc 18

<210> SEQ ID NO 123
<211> LENGTH: 18
<212> TYPE: DNA
<213> ORGANISM: Artificial Sequence
<220> FEATURE:
<223> OTHER INFORMATION: ASO-000540-55

<400> SEQUENCE: 123
tcccttaatt tcaccctc 18

<210> SEQ ID NO 124
<211> LENGTH: 19
<212> TYPE: DNA
<213> ORGANISM: Artificial Sequence
<220> FEATURE:
<223> OTHER INFORMATION: ASO-000540-69

<400> SEQUENCE: 124
tcccttaatt tcaccctca 19

<210> SEQ ID NO 125
<211> LENGTH: 19
<212> TYPE: DNA
<213> ORGANISM: Artificial Sequence
<220> FEATURE:
<223> OTHER INFORMATION: ASO-000540-70

<400> SEQUENCE: 125
tcccttaatt tcaccctca 19

<210> SEQ ID NO 126
<211> LENGTH: 19
<212> TYPE: DNA
<213> ORGANISM: Artificial Sequence
<220> FEATURE:
<223> OTHER INFORMATION: ASO-000540-71

<400> SEQUENCE: 126
tcccttaatt tcaccctca 19

<210> SEQ ID NO 127
<211> LENGTH: 19
<212> TYPE: DNA
<213> ORGANISM: Artificial Sequence
<220> FEATURE:
<223> OTHER INFORMATION: ASO-000540-72

<400> SEQUENCE: 127
tcccttaatt tcaccctca 19

<210> SEQ ID NO 128
<211> LENGTH: 19
<212> TYPE: DNA
<213> ORGANISM: Artificial Sequence
<220> FEATURE:

-continued

<223> OTHER INFORMATION: ASO-000540-73

<400> SEQUENCE: 128
tcccttaatt tcaccctca 19

<210> SEQ ID NO 129
<211> LENGTH: 19
<212> TYPE: DNA
<213> ORGANISM: Artificial Sequence
<220> FEATURE:
<223> OTHER INFORMATION: ASO-000540-74

<400> SEQUENCE: 129
tcccttaatt tcaccctca 19

<210> SEQ ID NO 130
<211> LENGTH: 19
<212> TYPE: DNA
<213> ORGANISM: Artificial Sequence
<220> FEATURE:
<223> OTHER INFORMATION: ASO-000540-75

<400> SEQUENCE: 130
tcccttaatt tcaccctca 19

<210> SEQ ID NO 131
<211> LENGTH: 19
<212> TYPE: DNA
<213> ORGANISM: Artificial Sequence
<220> FEATURE:
<223> OTHER INFORMATION: ASO-000540-76

<400> SEQUENCE: 131
tcccttaatt tcaccctca 19

<210> SEQ ID NO 132
<211> LENGTH: 19
<212> TYPE: DNA
<213> ORGANISM: Artificial Sequence
<220> FEATURE:
<223> OTHER INFORMATION: ASO-000540-77

<400> SEQUENCE: 132
tcccttaatt tcaccctca 19

<210> SEQ ID NO 133
<211> LENGTH: 17
<212> TYPE: DNA
<213> ORGANISM: Artificial Sequence
<220> FEATURE:
<223> OTHER INFORMATION: ASO-000540-8

<400> SEQUENCE: 133
cccttaattt caccctc 17

<210> SEQ ID NO 134
<211> LENGTH: 17
<212> TYPE: DNA
<213> ORGANISM: Artificial Sequence
<220> FEATURE:
<223> OTHER INFORMATION: ASO-000540-9

<400> SEQUENCE: 134
cccttaattt caccctc 17

<210> SEQ ID NO 135
<211> LENGTH: 17
<212> TYPE: DNA
<213> ORGANISM: Artificial Sequence
<220> FEATURE:
<223> OTHER INFORMATION: TBD-mm10

<400> SEQUENCE: 135
ccttgatttc gccctca 17

<210> SEQ ID NO 136
<211> LENGTH: 17
<212> TYPE: DNA
<213> ORGANISM: Artificial Sequence
<220> FEATURE:
<223> OTHER INFORMATION: TBD-mm11

<400> SEQUENCE: 136
ccttgatttc accctct 17

<210> SEQ ID NO 137
<211> LENGTH: 17
<212> TYPE: DNA
<213> ORGANISM: Artificial Sequence
<220> FEATURE:
<223> OTHER INFORMATION: TBD-mm12

<400> SEQUENCE: 137
ccttagtttc accctcg 17

<210> SEQ ID NO 138
<211> LENGTH: 18
<212> TYPE: DNA
<213> ORGANISM: Artificial Sequence
<220> FEATURE:
<223> OTHER INFORMATION: TBD-mm19

<400> SEQUENCE: 138
cccttgattt caccctca 18

<210> SEQ ID NO 139
<211> LENGTH: 18
<212> TYPE: DNA
<213> ORGANISM: Artificial Sequence
<220> FEATURE:
<223> OTHER INFORMATION: TBD-mm20

<400> SEQUENCE: 139
cccttaattt caccctcg 18

<210> SEQ ID NO 140
<211> LENGTH: 18
<212> TYPE: DNA
<213> ORGANISM: Artificial Sequence
<220> FEATURE:
<223> OTHER INFORMATION: TBD-mm21

<400> SEQUENCE: 140
cccttagttt caccctca 18

<210> SEQ ID NO 141
<211> LENGTH: 18
<212> TYPE: DNA
<213> ORGANISM: Artificial Sequence
<220> FEATURE:
<223> OTHER INFORMATION: TBD-mm22

<400> SEQUENCE: 141
cccttgattt cgccctca 18

<210> SEQ ID NO 142
<211> LENGTH: 18
<212> TYPE: DNA
<213> ORGANISM: Artificial Sequence
<220> FEATURE:
<223> OTHER INFORMATION: TBD-mm23

<400> SEQUENCE: 142
cccttgattt caccctcg 18

<210> SEQ ID NO 143
<211> LENGTH: 18
<212> TYPE: DNA
<213> ORGANISM: Artificial Sequence
<220> FEATURE:
<223> OTHER INFORMATION: TBD-mm24

<400> SEQUENCE: 143
cccttgattt caccctct 18

<210> SEQ ID NO 144
<211> LENGTH: 19
<212> TYPE: DNA
<213> ORGANISM: Artificial Sequence
<220> FEATURE:
<223> OTHER INFORMATION: TBD-mm31

<400> SEQUENCE: 144
tcccttgatt tcaccctca 19

<210> SEQ ID NO 145
<211> LENGTH: 19
<212> TYPE: DNA
<213> ORGANISM: Artificial Sequence
<220> FEATURE:
<223> OTHER INFORMATION: TBD-mm32

<400> SEQUENCE: 145
tcccttaatt tcaccctcg 19

<210> SEQ ID NO 146
<211> LENGTH: 19
<212> TYPE: DNA
<213> ORGANISM: Artificial Sequence
<220> FEATURE:
<223> OTHER INFORMATION: TBD-mm33

<400> SEQUENCE: 146
acccttaatt tcaccctca 19

<210> SEQ ID NO 147
<211> LENGTH: 19
<212> TYPE: DNA
<213> ORGANISM: Artificial Sequence
<220> FEATURE:
<223> OTHER INFORMATION: TBD-mm34

<400> SEQUENCE: 147
tcccttgatt tcgccctca 19

<210> SEQ ID NO 148
<211> LENGTH: 19

<212> TYPE: DNA
<213> ORGANISM: Artificial Sequence
<220> FEATURE:
<223> OTHER INFORMATION: TBD-mm35

<400> SEQUENCE: 148
tcccttagtt tcaccctcg 19

<210> SEQ ID NO 149
<211> LENGTH: 19
<212> TYPE: DNA
<213> ORGANISM: Artificial Sequence
<220> FEATURE:
<223> OTHER INFORMATION: TBD-mm36

<400> SEQUENCE: 149
acccttgatt tcaccctca 19

<210> SEQ ID NO 150
<211> LENGTH: 17
<212> TYPE: DNA
<213> ORGANISM: Artificial Sequence
<220> FEATURE:
<223> OTHER INFORMATION: TBD-mm7

<400> SEQUENCE: 150
ccttgatttc accctca 17

<210> SEQ ID NO 151
<211> LENGTH: 17
<212> TYPE: DNA
<213> ORGANISM: Artificial Sequence
<220> FEATURE:
<223> OTHER INFORMATION: TBD-mm8

<400> SEQUENCE: 151
ccttagtttc accctca 17

<210> SEQ ID NO 152
<211> LENGTH: 17
<212> TYPE: DNA
<213> ORGANISM: Artificial Sequence
<220> FEATURE:
<223> OTHER INFORMATION: TBD-mm9

<400> SEQUENCE: 152
ccttaatttc accctcg 17

<210> SEQ ID NO 153
<211> LENGTH: 16
<212> TYPE: DNA
<213> ORGANISM: Artificial Sequence
<220> FEATURE:
<223> OTHER INFORMATION: ASO-000540

<400> SEQUENCE: 153
ccttaatttc accctc 16

<210> SEQ ID NO 154
<211> LENGTH: 15
<212> TYPE: DNA
<213> ORGANISM: Artificial Sequence
<220> FEATURE:
<223> OTHER INFORMATION: ASO-000555

<400> SEQUENCE: 154
cttaatttca ccctc 15

<210> SEQ ID NO 155
<211> LENGTH: 14
<212> TYPE: DNA
<213> ORGANISM: Artificial Sequence
<220> FEATURE:
<223> OTHER INFORMATION: ASO-000579

<400> SEQUENCE: 155
ttaatttcac cctc 14

<210> SEQ ID NO 156
<211> LENGTH: 17
<212> TYPE: DNA
<213> ORGANISM: Artificial Sequence
<220> FEATURE:
<223> OTHER INFORMATION: ASO-000540-1

<400> SEQUENCE: 156
cccttaattt caccctc 17

<210> SEQ ID NO 157
<211> LENGTH: 17
<212> TYPE: DNA
<213> ORGANISM: Artificial Sequence
<220> FEATURE:
<223> OTHER INFORMATION: ASO-000540-10

<400> SEQUENCE: 157
cccttaattt caccctc 17

<210> SEQ ID NO 158
<211> LENGTH: 17
<212> TYPE: DNA
<213> ORGANISM: Artificial Sequence
<220> FEATURE:
<223> OTHER INFORMATION: ASO-000540-11

<400> SEQUENCE: 158
cccttaattt caccctc 17

<210> SEQ ID NO 159
<211> LENGTH: 17
<212> TYPE: DNA
<213> ORGANISM: Artificial Sequence
<220> FEATURE:
<223> OTHER INFORMATION: ASO-000540-12

<400> SEQUENCE: 159
cccttaattt caccctc 17

<210> SEQ ID NO 160
<211> LENGTH: 17
<212> TYPE: DNA
<213> ORGANISM: Artificial Sequence
<220> FEATURE:
<223> OTHER INFORMATION: ASO-000540-13

<400> SEQUENCE: 160
cccttaattt caccctc 17

<210> SEQ ID NO 161
<211> LENGTH: 17
<212> TYPE: DNA
<213> ORGANISM: Artificial Sequence

<220> FEATURE:
<223> OTHER INFORMATION: ASO-000540-14

<400> SEQUENCE: 161
ccttaatttc accctca 17

<210> SEQ ID NO 162
<211> LENGTH: 17
<212> TYPE: DNA
<213> ORGANISM: Artificial Sequence
<220> FEATURE:
<223> OTHER INFORMATION: ASO-000540-15

<400> SEQUENCE: 162
ccttaatttc accctca 17

<210> SEQ ID NO 163
<211> LENGTH: 17
<212> TYPE: DNA
<213> ORGANISM: Artificial Sequence
<220> FEATURE:
<223> OTHER INFORMATION: ASO-000540-16

<400> SEQUENCE: 163
ccttaatttc accctca 17

<210> SEQ ID NO 164
<211> LENGTH: 17
<212> TYPE: DNA
<213> ORGANISM: Artificial Sequence
<220> FEATURE:
<223> OTHER INFORMATION: ASO-000540-17

<400> SEQUENCE: 164
ccttaatttc accctca 17

<210> SEQ ID NO 165
<211> LENGTH: 17
<212> TYPE: DNA
<213> ORGANISM: Artificial Sequence
<220> FEATURE:
<223> OTHER INFORMATION: ASO-000540-18

<400> SEQUENCE: 165
ccttaatttc accctca 17

<210> SEQ ID NO 166
<211> LENGTH: 17
<212> TYPE: DNA
<213> ORGANISM: Artificial Sequence
<220> FEATURE:
<223> OTHER INFORMATION: ASO-000540-19

<400> SEQUENCE: 166
ccttaatttc accctca 17

<210> SEQ ID NO 167
<211> LENGTH: 17
<212> TYPE: DNA
<213> ORGANISM: Artificial Sequence
<220> FEATURE:
<223> OTHER INFORMATION: ASO-000540-2

<400> SEQUENCE: 167
cccttaattt caccctc 17

<210> SEQ ID NO 168
<211> LENGTH: 17
<212> TYPE: DNA
<213> ORGANISM: Artificial Sequence
<220> FEATURE:
<223> OTHER INFORMATION: ASO-000540-20

<400> SEQUENCE: 168
ccttaatttc accctca 17

<210> SEQ ID NO 169
<211> LENGTH: 18
<212> TYPE: DNA
<213> ORGANISM: Artificial Sequence
<220> FEATURE:
<223> OTHER INFORMATION: ASO-000540-56

<400> SEQUENCE: 169
tcccttaatt tcaccctc 18

<210> SEQ ID NO 170
<211> LENGTH: 18
<212> TYPE: DNA
<213> ORGANISM: Artificial Sequence
<220> FEATURE:
<223> OTHER INFORMATION: ASO-000540-57

<400> SEQUENCE: 170
tcccttaatt tcaccctc 18

<210> SEQ ID NO 171
<211> LENGTH: 18
<212> TYPE: DNA
<213> ORGANISM: Artificial Sequence
<220> FEATURE:
<223> OTHER INFORMATION: ASO-000540-58

<400> SEQUENCE: 171
tcccttaatt tcaccctc 18

<210> SEQ ID NO 172
<211> LENGTH: 18
<212> TYPE: DNA
<213> ORGANISM: Artificial Sequence
<220> FEATURE:
<223> OTHER INFORMATION: ASO-000540-59

<400> SEQUENCE: 172
tcccttaatt tcaccctc 18

<210> SEQ ID NO 173
<211> LENGTH: 17
<212> TYPE: DNA
<213> ORGANISM: Artificial Sequence
<220> FEATURE:
<223> OTHER INFORMATION: ASO-000540-6

<400> SEQUENCE: 173
cccttaattt caccctc 17

<210> SEQ ID NO 174
<211> LENGTH: 18
<212> TYPE: DNA
<213> ORGANISM: Artificial Sequence
<220> FEATURE:
<223> OTHER INFORMATION: ASO-000540-60

<400> SEQUENCE: 174
tcccttaatt tcaccctc 18

<210> SEQ ID NO 175
<211> LENGTH: 18
<212> TYPE: DNA
<213> ORGANISM: Artificial Sequence
<220> FEATURE:
<223> OTHER INFORMATION: ASO-000540-61

<400> SEQUENCE: 175
tcccttaatt tcaccctc 18

<210> SEQ ID NO 176
<211> LENGTH: 18
<212> TYPE: DNA
<213> ORGANISM: Artificial Sequence
<220> FEATURE:
<223> OTHER INFORMATION: ASO-000540-62

<400> SEQUENCE: 176
tcccttaatt tcaccctc 18

<210> SEQ ID NO 177
<211> LENGTH: 18
<212> TYPE: DNA
<213> ORGANISM: Artificial Sequence
<220> FEATURE:
<223> OTHER INFORMATION: ASO-000540-63

<400> SEQUENCE: 177
tcccttaatt tcaccctc 18

<210> SEQ ID NO 178
<211> LENGTH: 18
<212> TYPE: DNA
<213> ORGANISM: Artificial Sequence
<220> FEATURE:
<223> OTHER INFORMATION: ASO-000540-64

<400> SEQUENCE: 178
tcccttaatt tcaccctc 18

<210> SEQ ID NO 179
<211> LENGTH: 18
<212> TYPE: DNA
<213> ORGANISM: Artificial Sequence
<220> FEATURE:
<223> OTHER INFORMATION: ASO-000540-65

<400> SEQUENCE: 179
tcccttaatt tcaccctc 18

<210> SEQ ID NO 180
<211> LENGTH: 19
<212> TYPE: DNA
<213> ORGANISM: Artificial Sequence
<220> FEATURE:
<223> OTHER INFORMATION: ASO-000540-66

<400> SEQUENCE: 180
tcccttaatt tcaccctca 19

<210> SEQ ID NO 181

<211> LENGTH: 19
<212> TYPE: DNA
<213> ORGANISM: Artificial Sequence
<220> FEATURE:
<223> OTHER INFORMATION: ASO-000540-67

<400> SEQUENCE: 181
tcccttaatt tcaccctca 19

<210> SEQ ID NO 182
<211> LENGTH: 19
<212> TYPE: DNA
<213> ORGANISM: Artificial Sequence
<220> FEATURE:
<223> OTHER INFORMATION: ASO-000540-68

<400> SEQUENCE: 182
tcccttaatt tcaccctca 19

<210> SEQ ID NO 183
<211> LENGTH: 16
<212> TYPE: DNA
<213> ORGANISM: Artificial Sequence
<220> FEATURE:
<223> OTHER INFORMATION: ASO-000540-mm1

<400> SEQUENCE: 183
ccttgatttc accctc 16

<210> SEQ ID NO 184
<211> LENGTH: 16
<212> TYPE: DNA
<213> ORGANISM: Artificial Sequence
<220> FEATURE:
<223> OTHER INFORMATION: ASO-000540-mm2

<400> SEQUENCE: 184
ccttaatttc gccctc 16

<210> SEQ ID NO 185
<211> LENGTH: 16
<212> TYPE: DNA
<213> ORGANISM: Artificial Sequence
<220> FEATURE:
<223> OTHER INFORMATION: ASO-000540-mm3

<400> SEQUENCE: 185
ccttagtttc accctc 16

<210> SEQ ID NO 186
<211> LENGTH: 16
<212> TYPE: DNA
<213> ORGANISM: Artificial Sequence
<220> FEATURE:
<223> OTHER INFORMATION: ASO-000540-mm4

<400> SEQUENCE: 186
ccttgatttc gccctc 16

<210> SEQ ID NO 187
<211> LENGTH: 16
<212> TYPE: DNA
<213> ORGANISM: Artificial Sequence
<220> FEATURE:
<223> OTHER INFORMATION: ASO-000540-mm5

<400> SEQUENCE: 187
ccttggtttc accctc 16

<210> SEQ ID NO 188
<211> LENGTH: 16
<212> TYPE: DNA
<213> ORGANISM: Artificial Sequence
<220> FEATURE:
<223> OTHER INFORMATION: ASO-000540-mm6

<400> SEQUENCE: 188
ccttagtttc gccctc 16

<210> SEQ ID NO 189
<211> LENGTH: 17
<212> TYPE: DNA
<213> ORGANISM: Artificial Sequence
<220> FEATURE:
<223> OTHER INFORMATION: TBD-mm1

<400> SEQUENCE: 189
cccttgattt caccctc 17

<210> SEQ ID NO 190
<211> LENGTH: 17
<212> TYPE: DNA
<213> ORGANISM: Artificial Sequence
<220> FEATURE:
<223> OTHER INFORMATION: TBD-mm2

<400> SEQUENCE: 190
cccttagttt caccctc 17

<210> SEQ ID NO 191
<211> LENGTH: 18
<212> TYPE: DNA
<213> ORGANISM: Artificial Sequence
<220> FEATURE:
<223> OTHER INFORMATION: TBD-mm25

<400> SEQUENCE: 191
tcccttgatt tcaccctc 18

<210> SEQ ID NO 192
<211> LENGTH: 18
<212> TYPE: DNA
<213> ORGANISM: Artificial Sequence
<220> FEATURE:
<223> OTHER INFORMATION: TBD-mm26

<400> SEQUENCE: 192
tcccttaatt tcgccctc 18

<210> SEQ ID NO 193
<211> LENGTH: 18
<212> TYPE: DNA
<213> ORGANISM: Artificial Sequence
<220> FEATURE:
<223> OTHER INFORMATION: TBD-mm27

<400> SEQUENCE: 193
tcccttagtt tcaccctc 18

<210> SEQ ID NO 194
<211> LENGTH: 18
<212> TYPE: DNA

<213> ORGANISM: Artificial Sequence
<220> FEATURE:
<223> OTHER INFORMATION: TBD-mm28

<400> SEQUENCE: 194
tcccttgatt tcgccctc 18

<210> SEQ ID NO 195
<211> LENGTH: 18
<212> TYPE: DNA
<213> ORGANISM: Artificial Sequence
<220> FEATURE:
<223> OTHER INFORMATION: TBD-mm29

<400> SEQUENCE: 195
tcccttagtt tcgccctc 18

<210> SEQ ID NO 196
<211> LENGTH: 17
<212> TYPE: DNA
<213> ORGANISM: Artificial Sequence
<220> FEATURE:
<223> OTHER INFORMATION: TBD-mm3

<400> SEQUENCE: 196
cccttaattt cgccctc 17

<210> SEQ ID NO 197
<211> LENGTH: 18
<212> TYPE: DNA
<213> ORGANISM: Artificial Sequence
<220> FEATURE:
<223> OTHER INFORMATION: TBD-mm30

<400> SEQUENCE: 197
acccttgatt tcaccctc 18

<210> SEQ ID NO 198
<211> LENGTH: 17
<212> TYPE: DNA
<213> ORGANISM: Artificial Sequence
<220> FEATURE:
<223> OTHER INFORMATION: TBD-mm4

<400> SEQUENCE: 198
cccttgattt cgccctc 17

<210> SEQ ID NO 199
<211> LENGTH: 17
<212> TYPE: DNA
<213> ORGANISM: Artificial Sequence
<220> FEATURE:
<223> OTHER INFORMATION: TBD-mm5

<400> SEQUENCE: 199
cccttggttt caccctc 17

<210> SEQ ID NO 200
<211> LENGTH: 17
<212> TYPE: DNA
<213> ORGANISM: Artificial Sequence
<220> FEATURE:
<223> OTHER INFORMATION: TBD-mm6

<400> SEQUENCE: 200
cccttagttt cgccctc 17

<210> SEQ ID NO 201
<211> LENGTH: 16
<212> TYPE: DNA
<213> ORGANISM: Artificial Sequence
<220> FEATURE:
<223> OTHER INFORMATION: ASO-000662

<400> SEQUENCE: 201
cccttaattt caccct 16

<210> SEQ ID NO 202
<211> LENGTH: 15
<212> TYPE: DNA
<213> ORGANISM: Artificial Sequence
<220> FEATURE:
<223> OTHER INFORMATION: ASO-000566

<400> SEQUENCE: 202
ccttaatttc accct 15

<210> SEQ ID NO 203
<211> LENGTH: 17
<212> TYPE: DNA
<213> ORGANISM: Artificial Sequence
<220> FEATURE:
<223> OTHER INFORMATION: ASO-000540-30

<400> SEQUENCE: 203
tcccttaatt tcaccct 17

<210> SEQ ID NO 204
<211> LENGTH: 17
<212> TYPE: DNA
<213> ORGANISM: Artificial Sequence
<220> FEATURE:
<223> OTHER INFORMATION: ASO-000540-31

<400> SEQUENCE: 204
tcccttaatt tcaccct 17

<210> SEQ ID NO 205
<211> LENGTH: 17
<212> TYPE: DNA
<213> ORGANISM: Artificial Sequence
<220> FEATURE:
<223> OTHER INFORMATION: ASO-000540-32

<400> SEQUENCE: 205
tcccttaatt tcaccct 17

<210> SEQ ID NO 206
<211> LENGTH: 17
<212> TYPE: DNA
<213> ORGANISM: Artificial Sequence
<220> FEATURE:
<223> OTHER INFORMATION: ASO-000540-33

<400> SEQUENCE: 206
tcccttaatt tcaccct 17

<210> SEQ ID NO 207
<211> LENGTH: 17
<212> TYPE: DNA
<213> ORGANISM: Artificial Sequence
<220> FEATURE:

<223> OTHER INFORMATION: ASO-000540-34

<400> SEQUENCE: 207
tcccttaatt tcaccct 17

<210> SEQ ID NO 208
<211> LENGTH: 17
<212> TYPE: DNA
<213> ORGANISM: Artificial Sequence
<220> FEATURE:
<223> OTHER INFORMATION: ASO-000540-35

<400> SEQUENCE: 208
tcccttaatt tcaccct 17

<210> SEQ ID NO 209
<211> LENGTH: 17
<212> TYPE: DNA
<213> ORGANISM: Artificial Sequence
<220> FEATURE:
<223> OTHER INFORMATION: ASO-000540-36

<400> SEQUENCE: 209
tcccttaatt tcaccct 17

<210> SEQ ID NO 210
<211> LENGTH: 18
<212> TYPE: DNA
<213> ORGANISM: Artificial Sequence
<220> FEATURE:
<223> OTHER INFORMATION: ASO-000540-37

<400> SEQUENCE: 210
cccttaattt caccctca 18

<210> SEQ ID NO 211
<211> LENGTH: 18
<212> TYPE: DNA
<213> ORGANISM: Artificial Sequence
<220> FEATURE:
<223> OTHER INFORMATION: ASO-000540-38

<400> SEQUENCE: 211
cccttaattt caccctca 18

<210> SEQ ID NO 212
<211> LENGTH: 18
<212> TYPE: DNA
<213> ORGANISM: Artificial Sequence
<220> FEATURE:
<223> OTHER INFORMATION: ASO-000540-39

<400> SEQUENCE: 212
cccttaattt caccctca 18

<210> SEQ ID NO 213
<211> LENGTH: 17
<212> TYPE: DNA
<213> ORGANISM: Artificial Sequence
<220> FEATURE:
<223> OTHER INFORMATION: ASO-000540-4

<400> SEQUENCE: 213
cccttaattt caccctc 17

<210> SEQ ID NO 214
<211> LENGTH: 18
<212> TYPE: DNA
<213> ORGANISM: Artificial Sequence
<220> FEATURE:
<223> OTHER INFORMATION: ASO-000540-40

<400> SEQUENCE: 214
cccttaattt caccctca 18

<210> SEQ ID NO 215
<211> LENGTH: 18
<212> TYPE: DNA
<213> ORGANISM: Artificial Sequence
<220> FEATURE:
<223> OTHER INFORMATION: ASO-000540-41

<400> SEQUENCE: 215
cccttaattt caccctca 18

<210> SEQ ID NO 216
<211> LENGTH: 17
<212> TYPE: DNA
<213> ORGANISM: Artificial Sequence
<220> FEATURE:
<223> OTHER INFORMATION: TBD-mm13

<400> SEQUENCE: 216
tcccttgatt tcaccct 17

<210> SEQ ID NO 217
<211> LENGTH: 17
<212> TYPE: DNA
<213> ORGANISM: Artificial Sequence
<220> FEATURE:
<223> OTHER INFORMATION: TBD-mm14

<400> SEQUENCE: 217
tcccttaatt tcaccca 17

<210> SEQ ID NO 218
<211> LENGTH: 17
<212> TYPE: DNA
<213> ORGANISM: Artificial Sequence
<220> FEATURE:
<223> OTHER INFORMATION: TBD-mm15

<400> SEQUENCE: 218
tcccttaatt tcgccct 17

<210> SEQ ID NO 219
<211> LENGTH: 17
<212> TYPE: DNA
<213> ORGANISM: Artificial Sequence
<220> FEATURE:
<223> OTHER INFORMATION: TBD-mm16

<400> SEQUENCE: 219
tcccttgatt tcaccca 17

<210> SEQ ID NO 220
<211> LENGTH: 17
<212> TYPE: DNA
<213> ORGANISM: Artificial Sequence
<220> FEATURE:
<223> OTHER INFORMATION: TBD-mm17

<400> SEQUENCE: 220
tcccttgatt tcacccg 17

<210> SEQ ID NO 221
<211> LENGTH: 17
<212> TYPE: DNA
<213> ORGANISM: Artificial Sequence
<220> FEATURE:
<223> OTHER INFORMATION: TBD-mm18

<400> SEQUENCE: 221
tcccttagtt tcgccct 17

<210> SEQ ID NO 222
<211> LENGTH: 14
<212> TYPE: DNA
<213> ORGANISM: Artificial Sequence
<220> FEATURE:
<223> OTHER INFORMATION: ASO-000628

<400> SEQUENCE: 222
ccttaatttc accc 14

<210> SEQ ID NO 223
<211> LENGTH: 15
<212> TYPE: DNA
<213> ORGANISM: Artificial Sequence
<220> FEATURE:
<223> OTHER INFORMATION: ASO-000642

<400> SEQUENCE: 223
cccttaattt caccc 15

<210> SEQ ID NO 224
<211> LENGTH: 16
<212> TYPE: DNA
<213> ORGANISM: Artificial Sequence
<220> FEATURE:
<223> OTHER INFORMATION: ASO-000274

<400> SEQUENCE: 224
tcccttaatt tcaccc 16

<210> SEQ ID NO 225
<211> LENGTH: 14
<212> TYPE: DNA
<213> ORGANISM: Artificial Sequence
<220> FEATURE:
<223> OTHER INFORMATION: ASO-000339

<400> SEQUENCE: 225
ccttaatttc accc 14

<210> SEQ ID NO 226
<211> LENGTH: 16
<212> TYPE: DNA
<213> ORGANISM: Artificial Sequence
<220> FEATURE:
<223> OTHER INFORMATION: ASO-000536

<400> SEQUENCE: 226
ttcccttaat ttcacc 16

<210> SEQ ID NO 227
<211> LENGTH: 15

<212> TYPE: DNA
<213> ORGANISM: Artificial Sequence
<220> FEATURE:
<223> OTHER INFORMATION: ASO-000603

<400> SEQUENCE: 227
tcccttaatt tcacc 15

<210> SEQ ID NO 228
<211> LENGTH: 14
<212> TYPE: DNA
<213> ORGANISM: Artificial Sequence
<220> FEATURE:
<223> OTHER INFORMATION: ASO-000666

<400> SEQUENCE: 228
tcccttaatt tcac 14

<210> SEQ ID NO 229
<211> LENGTH: 16
<212> TYPE: DNA
<213> ORGANISM: Artificial Sequence
<220> FEATURE:
<223> OTHER INFORMATION: ASO-000272

<400> SEQUENCE: 229
agagtgagag gctggg 16

<210> SEQ ID NO 230
<211> LENGTH: 16
<212> TYPE: DNA
<213> ORGANISM: Artificial Sequence
<220> FEATURE:
<223> OTHER INFORMATION: ASO-000255

<400> SEQUENCE: 230
tggatgagtg gaactg 16

<210> SEQ ID NO 231
<211> LENGTH: 14
<212> TYPE: DNA
<213> ORGANISM: Artificial Sequence
<220> FEATURE:
<223> OTHER INFORMATION: ASO-000336

<400> SEQUENCE: 231
ggatgagtgg aact 14

<210> SEQ ID NO 232
<211> LENGTH: 15
<212> TYPE: DNA
<213> ORGANISM: Artificial Sequence
<220> FEATURE:
<223> OTHER INFORMATION: ASO-000206

<400> SEQUENCE: 232
gttggatgag tggaa 15

<210> SEQ ID NO 233
<211> LENGTH: 15
<212> TYPE: DNA
<213> ORGANISM: Artificial Sequence
<220> FEATURE:
<223> OTHER INFORMATION: ASO-000271

<400> SEQUENCE: 233
agttggatga gtgga 15

<210> SEQ ID NO 234
<211> LENGTH: 14
<212> TYPE: DNA
<213> ORGANISM: Artificial Sequence
<220> FEATURE:
<223> OTHER INFORMATION: ASO-000340

<400> SEQUENCE: 234
gttggatgag tgga 14

<210> SEQ ID NO 235
<211> LENGTH: 16
<212> TYPE: DNA
<213> ORGANISM: Artificial Sequence
<220> FEATURE:
<223> OTHER INFORMATION: ASO-000229

<400> SEQUENCE: 235
cagggaaccg aatcag 16

<210> SEQ ID NO 236
<211> LENGTH: 16
<212> TYPE: DNA
<213> ORGANISM: Artificial Sequence
<220> FEATURE:
<223> OTHER INFORMATION: ASO-000273

<400> SEQUENCE: 236
gccctggctc acatct 16

<210> SEQ ID NO 237
<211> LENGTH: 16
<212> TYPE: DNA
<213> ORGANISM: Artificial Sequence
<220> FEATURE:
<223> OTHER INFORMATION: ASO-000264

<400> SEQUENCE: 237
acaaggcaga aacacc 16

<210> SEQ ID NO 238
<211> LENGTH: 14
<212> TYPE: DNA
<213> ORGANISM: Artificial Sequence
<220> FEATURE:
<223> OTHER INFORMATION: ASO-000341

<400> SEQUENCE: 238
tgtcaacaag gcag 14

<210> SEQ ID NO 239
<211> LENGTH: 16
<212> TYPE: DNA
<213> ORGANISM: Artificial Sequence
<220> FEATURE:
<223> OTHER INFORMATION: ASO-000198

<400> SEQUENCE: 239
tgccctgggt gccttg 16

<210> SEQ ID NO 240
<211> LENGTH: 16
<212> TYPE: DNA
<213> ORGANISM: Artificial Sequence

<220> FEATURE:
<223> OTHER INFORMATION: ASO-000210

<400> SEQUENCE: 240
agcgggactg tgggcc 16

<210> SEQ ID NO 241
<211> LENGTH: 14
<212> TYPE: DNA
<213> ORGANISM: Artificial Sequence
<220> FEATURE:
<223> OTHER INFORMATION: ASO-000342

<400> SEQUENCE: 241
gggacagcgg gact 14

<210> SEQ ID NO 242
<211> LENGTH: 16
<212> TYPE: DNA
<213> ORGANISM: Artificial Sequence
<220> FEATURE:
<223> OTHER INFORMATION: ASO-000333

<400> SEQUENCE: 242
gcgggctggg ctgtct 16

<210> SEQ ID NO 243
<211> LENGTH: 16
<212> TYPE: DNA
<213> ORGANISM: Artificial Sequence
<220> FEATURE:
<223> OTHER INFORMATION: ASO-000199

<400> SEQUENCE: 243
cagaacagac agcatg 16

<210> SEQ ID NO 244
<211> LENGTH: 16
<212> TYPE: DNA
<213> ORGANISM: Artificial Sequence
<220> FEATURE:
<223> OTHER INFORMATION: ASO-000280

<400> SEQUENCE: 244
tctatgtata tgttca 16

<210> SEQ ID NO 245
<211> LENGTH: 16
<212> TYPE: DNA
<213> ORGANISM: Artificial Sequence
<220> FEATURE:
<223> OTHER INFORMATION: ASO-000211

<400> SEQUENCE: 245
atctatgtat atgttc 16

<210> SEQ ID NO 246
<211> LENGTH: 15
<212> TYPE: DNA
<213> ORGANISM: Artificial Sequence
<220> FEATURE:
<223> OTHER INFORMATION: ASO-000347

<400> SEQUENCE: 246
catctatgta tatgt 15

<210> SEQ ID NO 247
<211> LENGTH: 16
<212> TYPE: DNA
<213> ORGANISM: Artificial Sequence
<220> FEATURE:
<223> OTHER INFORMATION: ASO-000352

<400> SEQUENCE: 247
acatctatgt atatgt 16

<210> SEQ ID NO 248
<211> LENGTH: 16
<212> TYPE: DNA
<213> ORGANISM: Artificial Sequence
<220> FEATURE:
<223> OTHER INFORMATION: ASO-000232

<400> SEQUENCE: 248
caacagggtg cagatg 16

<210> SEQ ID NO 249
<211> LENGTH: 16
<212> TYPE: DNA
<213> ORGANISM: Artificial Sequence
<220> FEATURE:
<223> OTHER INFORMATION: ASO-000257

<400> SEQUENCE: 249
agcataaaca gacaaa 16

<210> SEQ ID NO 250
<211> LENGTH: 16
<212> TYPE: DNA
<213> ORGANISM: Artificial Sequence
<220> FEATURE:
<223> OTHER INFORMATION: ASO-000388

<400> SEQUENCE: 250
atagtcactc tggtga 16

<210> SEQ ID NO 251
<211> LENGTH: 15
<212> TYPE: DNA
<213> ORGANISM: Artificial Sequence
<220> FEATURE:
<223> OTHER INFORMATION: ASO-000390

<400> SEQUENCE: 251
tagtcactct ggtga 15

<210> SEQ ID NO 252
<211> LENGTH: 14
<212> TYPE: DNA
<213> ORGANISM: Artificial Sequence
<220> FEATURE:
<223> OTHER INFORMATION: ASO-000413

<400> SEQUENCE: 252
agtcactctg gtga 14

<210> SEQ ID NO 253
<211> LENGTH: 16
<212> TYPE: DNA
<213> ORGANISM: Artificial Sequence
<220> FEATURE:
<223> OTHER INFORMATION: ASO-000405

<400> SEQUENCE: 253
catagtcact ctggtg 16

<210> SEQ ID NO 254
<211> LENGTH: 14
<212> TYPE: DNA
<213> ORGANISM: Artificial Sequence
<220> FEATURE:
<223> OTHER INFORMATION: ASO-000430

<400> SEQUENCE: 254
tagtcactct ggtg 14

<210> SEQ ID NO 255
<211> LENGTH: 16
<212> TYPE: DNA
<213> ORGANISM: Artificial Sequence
<220> FEATURE:
<223> OTHER INFORMATION: ASO-000447

<400> SEQUENCE: 255
tcatagtcac tctggt 16

<210> SEQ ID NO 256
<211> LENGTH: 14
<212> TYPE: DNA
<213> ORGANISM: Artificial Sequence
<220> FEATURE:
<223> OTHER INFORMATION: ASO-000396

<400> SEQUENCE: 256
tacatgcgtc cttt 14

<210> SEQ ID NO 257
<211> LENGTH: 16
<212> TYPE: DNA
<213> ORGANISM: Artificial Sequence
<220> FEATURE:
<223> OTHER INFORMATION: ASO-000395

<400> SEQUENCE: 257
gatacatgcg tccttt 16

<210> SEQ ID NO 258
<211> LENGTH: 16
<212> TYPE: DNA
<213> ORGANISM: Artificial Sequence
<220> FEATURE:
<223> OTHER INFORMATION: ASO-000394

<400> SEQUENCE: 258
aagatacatg cgtcct 16

<210> SEQ ID NO 259
<211> LENGTH: 16
<212> TYPE: DNA
<213> ORGANISM: Artificial Sequence
<220> FEATURE:
<223> OTHER INFORMATION: ASO-000421

<400> SEQUENCE: 259
ttcaagatac atgcgt 16

<210> SEQ ID NO 260

<211> LENGTH: 16
<212> TYPE: DNA
<213> ORGANISM: Artificial Sequence
<220> FEATURE:
<223> OTHER INFORMATION: ASO-000400

<400> SEQUENCE: 260
atttcaagat acatgc 16

<210> SEQ ID NO 261
<211> LENGTH: 16
<212> TYPE: DNA
<213> ORGANISM: Artificial Sequence
<220> FEATURE:
<223> OTHER INFORMATION: ASO-000248

<400> SEQUENCE: 261
gcatttcaag atacat 16

<210> SEQ ID NO 262
<211> LENGTH: 16
<212> TYPE: DNA
<213> ORGANISM: Artificial Sequence
<220> FEATURE:
<223> OTHER INFORMATION: ASO-000451

<400> SEQUENCE: 262
aagcatttca agatac 16

<210> SEQ ID NO 263
<211> LENGTH: 16
<212> TYPE: DNA
<213> ORGANISM: Artificial Sequence
<220> FEATURE:
<223> OTHER INFORMATION: ASO-000707

<400> SEQUENCE: 263
acaagcattt caagat 16

<210> SEQ ID NO 264
<211> LENGTH: 16
<212> TYPE: DNA
<213> ORGANISM: Artificial Sequence
<220> FEATURE:
<223> OTHER INFORMATION: ASO-000619

<400> SEQUENCE: 264
ttacaagcat ttcaag 16

<210> SEQ ID NO 265
<211> LENGTH: 16
<212> TYPE: DNA
<213> ORGANISM: Artificial Sequence
<220> FEATURE:
<223> OTHER INFORMATION: ASO-000671

<400> SEQUENCE: 265
aacctcttta caagca 16

<210> SEQ ID NO 266
<211> LENGTH: 16
<212> TYPE: DNA
<213> ORGANISM: Artificial Sequence
<220> FEATURE:
<223> OTHER INFORMATION: ASO-000221

<400> SEQUENCE: 266
gttagaaacc tcttta 16

<210> SEQ ID NO 267
<211> LENGTH: 16
<212> TYPE: DNA
<213> ORGANISM: Artificial Sequence
<220> FEATURE:
<223> OTHER INFORMATION: ASO-000298

<400> SEQUENCE: 267
ccacacaggc cacacg 16

<210> SEQ ID NO 268
<211> LENGTH: 16
<212> TYPE: DNA
<213> ORGANISM: Artificial Sequence
<220> FEATURE:
<223> OTHER INFORMATION: ASO-000311

<400> SEQUENCE: 268
gtctctgttg ggtccc 16

<210> SEQ ID NO 269
<211> LENGTH: 16
<212> TYPE: DNA
<213> ORGANISM: Artificial Sequence
<220> FEATURE:
<223> OTHER INFORMATION: ASO-000290

<400> SEQUENCE: 269
tgaacggcct ccttag 16

<210> SEQ ID NO 270
<211> LENGTH: 16
<212> TYPE: DNA
<213> ORGANISM: Artificial Sequence
<220> FEATURE:
<223> OTHER INFORMATION: ASO-000437

<400> SEQUENCE: 270
ctgtgcttca ggcctt 16

<210> SEQ ID NO 271
<211> LENGTH: 16
<212> TYPE: DNA
<213> ORGANISM: Artificial Sequence
<220> FEATURE:
<223> OTHER INFORMATION: ASO-000446

<400> SEQUENCE: 271
tcctgtgctt caggcc 16

<210> SEQ ID NO 272
<211> LENGTH: 16
<212> TYPE: DNA
<213> ORGANISM: Artificial Sequence
<220> FEATURE:
<223> OTHER INFORMATION: ASO-000685

<400> SEQUENCE: 272
aatcctgtgc ttcagg 16

<210> SEQ ID NO 273
<211> LENGTH: 14
<212> TYPE: DNA

<213> ORGANISM: Artificial Sequence
<220> FEATURE:
<223> OTHER INFORMATION: ASO-000410

<400> SEQUENCE: 273
tcctgtgctt cagg 14

<210> SEQ ID NO 274
<211> LENGTH: 15
<212> TYPE: DNA
<213> ORGANISM: Artificial Sequence
<220> FEATURE:
<223> OTHER INFORMATION: ASO-000604

<400> SEQUENCE: 274
aatcctgtgc ttcag 15

<210> SEQ ID NO 275
<211> LENGTH: 16
<212> TYPE: DNA
<213> ORGANISM: Artificial Sequence
<220> FEATURE:
<223> OTHER INFORMATION: ASO-000490

<400> SEQUENCE: 275
taatcctgtg cttcag 16

<210> SEQ ID NO 276
<211> LENGTH: 14
<212> TYPE: DNA
<213> ORGANISM: Artificial Sequence
<220> FEATURE:
<223> OTHER INFORMATION: ASO-000529

<400> SEQUENCE: 276
aatcctgtgc ttca 14

<210> SEQ ID NO 277
<211> LENGTH: 16
<212> TYPE: DNA
<213> ORGANISM: Artificial Sequence
<220> FEATURE:
<223> OTHER INFORMATION: ASO-000532

<400> SEQUENCE: 277
ctaatcctgt gcttca 16

<210> SEQ ID NO 278
<211> LENGTH: 15
<212> TYPE: DNA
<213> ORGANISM: Artificial Sequence
<220> FEATURE:
<223> OTHER INFORMATION: ASO-000508

<400> SEQUENCE: 278
taatcctgtg cttca 15

<210> SEQ ID NO 279
<211> LENGTH: 16
<212> TYPE: DNA
<213> ORGANISM: Artificial Sequence
<220> FEATURE:
<223> OTHER INFORMATION: ASO-000219

<400> SEQUENCE: 279
cctaatcctg tgcttc 16

<210> SEQ ID NO 280
<211> LENGTH: 14
<212> TYPE: DNA
<213> ORGANISM: Artificial Sequence
<220> FEATURE:
<223> OTHER INFORMATION: ASO-000656

<400> SEQUENCE: 280
taatcctgtg cttc 14

<210> SEQ ID NO 281
<211> LENGTH: 15
<212> TYPE: DNA
<213> ORGANISM: Artificial Sequence
<220> FEATURE:
<223> OTHER INFORMATION: ASO-000522

<400> SEQUENCE: 281
ctaatcctgt gcttc 15

<210> SEQ ID NO 282
<211> LENGTH: 15
<212> TYPE: DNA
<213> ORGANISM: Artificial Sequence
<220> FEATURE:
<223> OTHER INFORMATION: ASO-000513

<400> SEQUENCE: 282
cctaatcctg tgctt 15

<210> SEQ ID NO 283
<211> LENGTH: 16
<212> TYPE: DNA
<213> ORGANISM: Artificial Sequence
<220> FEATURE:
<223> OTHER INFORMATION: ASO-000640

<400> SEQUENCE: 283
tcctaatcct gtgctt 16

<210> SEQ ID NO 284
<211> LENGTH: 14
<212> TYPE: DNA
<213> ORGANISM: Artificial Sequence
<220> FEATURE:
<223> OTHER INFORMATION: ASO-000661

<400> SEQUENCE: 284
ctaatcctgt gctt 14

<210> SEQ ID NO 285
<211> LENGTH: 16
<212> TYPE: DNA
<213> ORGANISM: Artificial Sequence
<220> FEATURE:
<223> OTHER INFORMATION: ASO-000478

<400> SEQUENCE: 285
gtcctaatcc tgtgct 16

<210> SEQ ID NO 286
<211> LENGTH: 15
<212> TYPE: DNA
<213> ORGANISM: Artificial Sequence
<220> FEATURE:

<223> OTHER INFORMATION: ASO-000500

<400> SEQUENCE: 286
tcctaatcct gtgct 15

<210> SEQ ID NO 287
<211> LENGTH: 14
<212> TYPE: DNA
<213> ORGANISM: Artificial Sequence
<220> FEATURE:
<223> OTHER INFORMATION: ASO-000601

<400> SEQUENCE: 287
cctaatcctg tgct 14

<210> SEQ ID NO 288
<211> LENGTH: 16
<212> TYPE: DNA
<213> ORGANISM: Artificial Sequence
<220> FEATURE:
<223> OTHER INFORMATION: ASO-000643

<400> SEQUENCE: 288
agtcctaatc ctgtgc 16

<210> SEQ ID NO 289
<211> LENGTH: 15
<212> TYPE: DNA
<213> ORGANISM: Artificial Sequence
<220> FEATURE:
<223> OTHER INFORMATION: ASO-000600

<400> SEQUENCE: 289
gtcctaatcc tgtgc 15

<210> SEQ ID NO 290
<211> LENGTH: 14
<212> TYPE: DNA
<213> ORGANISM: Artificial Sequence
<220> FEATURE:
<223> OTHER INFORMATION: ASO-000525

<400> SEQUENCE: 290
tcctaatcct gtgc 14

<210> SEQ ID NO 291
<211> LENGTH: 16
<212> TYPE: DNA
<213> ORGANISM: Artificial Sequence
<220> FEATURE:
<223> OTHER INFORMATION: ASO-000453

<400> SEQUENCE: 291
tcagtcctaa tcctgt 16

<210> SEQ ID NO 292
<211> LENGTH: 16
<212> TYPE: DNA
<213> ORGANISM: Artificial Sequence
<220> FEATURE:
<223> OTHER INFORMATION: ASO-000553

<400> SEQUENCE: 292
cttcagtcct aatcct 16

<210> SEQ ID NO 293
<211> LENGTH: 15
<212> TYPE: DNA
<213> ORGANISM: Artificial Sequence
<220> FEATURE:
<223> OTHER INFORMATION: ASO-000622

<400> SEQUENCE: 293
gcttcagtcc taatc 15

<210> SEQ ID NO 294
<211> LENGTH: 16
<212> TYPE: DNA
<213> ORGANISM: Artificial Sequence
<220> FEATURE:
<223> OTHER INFORMATION: ASO-000325

<400> SEQUENCE: 294
ctgacacagg gagccc 16

<210> SEQ ID NO 295
<211> LENGTH: 16
<212> TYPE: DNA
<213> ORGANISM: Artificial Sequence
<220> FEATURE:
<223> OTHER INFORMATION: ASO-000215

<400> SEQUENCE: 295
gccagaccag ccacaa 16

<210> SEQ ID NO 296
<211> LENGTH: 14
<212> TYPE: DNA
<213> ORGANISM: Artificial Sequence
<220> FEATURE:
<223> OTHER INFORMATION: ASO-000482

<400> SEQUENCE: 296
caggagttgt aagc 14

<210> SEQ ID NO 297
<211> LENGTH: 16
<212> TYPE: DNA
<213> ORGANISM: Artificial Sequence
<220> FEATURE:
<223> OTHER INFORMATION: ASO-000337

<400> SEQUENCE: 297
tgcaggagtt gtaagc 16

<210> SEQ ID NO 298
<211> LENGTH: 16
<212> TYPE: DNA
<213> ORGANISM: Artificial Sequence
<220> FEATURE:
<223> OTHER INFORMATION: ASO-000480

<400> SEQUENCE: 298
atgcaggagt tgtaag 16

<210> SEQ ID NO 299
<211> LENGTH: 16
<212> TYPE: DNA
<213> ORGANISM: Artificial Sequence
<220> FEATURE:
<223> OTHER INFORMATION: ASO-000644

<400> SEQUENCE: 299
gatgcaggag ttgtaa 16

<210> SEQ ID NO 300
<211> LENGTH: 14
<212> TYPE: DNA
<213> ORGANISM: Artificial Sequence
<220> FEATURE:
<223> OTHER INFORMATION: ASO-000695

<400> SEQUENCE: 300
tgcaggagtt gtaa 14

<210> SEQ ID NO 301
<211> LENGTH: 16
<212> TYPE: DNA
<213> ORGANISM: Artificial Sequence
<220> FEATURE:
<223> OTHER INFORMATION: ASO-000455

<400> SEQUENCE: 301
tgatgcagga gttgta 16

<210> SEQ ID NO 302
<211> LENGTH: 16
<212> TYPE: DNA
<213> ORGANISM: Artificial Sequence
<220> FEATURE:
<223> OTHER INFORMATION: ASO-000531

<400> SEQUENCE: 302
gtgatgcagg agttgt 16

<210> SEQ ID NO 303
<211> LENGTH: 16
<212> TYPE: DNA
<213> ORGANISM: Artificial Sequence
<220> FEATURE:
<223> OTHER INFORMATION: ASO-000651

<400> SEQUENCE: 303
tgtgatgcag gagttg 16

<210> SEQ ID NO 304
<211> LENGTH: 15
<212> TYPE: DNA
<213> ORGANISM: Artificial Sequence
<220> FEATURE:
<223> OTHER INFORMATION: ASO-00007

<400> SEQUENCE: 304
tgtgatgcag gagtt 15

<210> SEQ ID NO 305
<211> LENGTH: 14
<212> TYPE: DNA
<213> ORGANISM: Artificial Sequence
<220> FEATURE:
<223> OTHER INFORMATION: ASO-000419

<400> SEQUENCE: 305
gtgatgcagg agtt 14

<210> SEQ ID NO 306
<211> LENGTH: 15

<212> TYPE: DNA
<213> ORGANISM: Artificial Sequence
<220> FEATURE:
<223> OTHER INFORMATION: ASO-000730

<400> SEQUENCE: 306
tgtgatgcag gagtt 15

<210> SEQ ID NO 307
<211> LENGTH: 15
<212> TYPE: DNA
<213> ORGANISM: Artificial Sequence
<220> FEATURE:
<223> OTHER INFORMATION: ASO-000728

<400> SEQUENCE: 307
tgtgatgcag gagtt 15

<210> SEQ ID NO 308
<211> LENGTH: 15
<212> TYPE: DNA
<213> ORGANISM: Artificial Sequence
<220> FEATURE:
<223> OTHER INFORMATION: ASO-000729

<400> SEQUENCE: 308
tgtgatgcag gagtt 15

<210> SEQ ID NO 309
<211> LENGTH: 15
<212> TYPE: DNA
<213> ORGANISM: Artificial Sequence
<220> FEATURE:
<223> OTHER INFORMATION: ASO-000727

<400> SEQUENCE: 309
tgtgatgcag gagtt 15

<210> SEQ ID NO 310
<211> LENGTH: 15
<212> TYPE: DNA
<213> ORGANISM: Artificial Sequence
<220> FEATURE:
<223> OTHER INFORMATION: ASO-000715

<400> SEQUENCE: 310
tgtgatgcag gagtt 15

<210> SEQ ID NO 311
<211> LENGTH: 12
<212> TYPE: DNA
<213> ORGANISM: Artificial Sequence
<220> FEATURE:
<223> OTHER INFORMATION: ASO-000716

<400> SEQUENCE: 311
gatgcaggag tt 12

<210> SEQ ID NO 312
<211> LENGTH: 15
<212> TYPE: DNA
<213> ORGANISM: Artificial Sequence
<220> FEATURE:
<223> OTHER INFORMATION: ASO-000721

<400> SEQUENCE: 312
tgtgatgcag gagtt 15

<210> SEQ ID NO 313
<211> LENGTH: 15
<212> TYPE: DNA
<213> ORGANISM: Artificial Sequence
<220> FEATURE:
<223> OTHER INFORMATION: ASO-000722

<400> SEQUENCE: 313
tgtgatgcag gagtt 15

<210> SEQ ID NO 314
<211> LENGTH: 15
<212> TYPE: DNA
<213> ORGANISM: Artificial Sequence
<220> FEATURE:
<223> OTHER INFORMATION: ASO-000723

<400> SEQUENCE: 314
tgtgatgcag gagtt 15

<210> SEQ ID NO 315
<211> LENGTH: 15
<212> TYPE: DNA
<213> ORGANISM: Artificial Sequence
<220> FEATURE:
<223> OTHER INFORMATION: ASO-000724

<400> SEQUENCE: 315
tgtgatgcag gagtt 15

<210> SEQ ID NO 316
<211> LENGTH: 15
<212> TYPE: DNA
<213> ORGANISM: Artificial Sequence
<220> FEATURE:
<223> OTHER INFORMATION: ASO-000725

<400> SEQUENCE: 316
tgtgatgcag gagtt 15

<210> SEQ ID NO 317
<211> LENGTH: 15
<212> TYPE: DNA
<213> ORGANISM: Artificial Sequence
<220> FEATURE:
<223> OTHER INFORMATION: ASO-000726

<400> SEQUENCE: 317
tgtgatgcag gagtt 15

<210> SEQ ID NO 318
<211> LENGTH: 15
<212> TYPE: DNA
<213> ORGANISM: Artificial Sequence
<220> FEATURE:
<223> OTHER INFORMATION: ASO-000731

<400> SEQUENCE: 318
tgtgatgcag gagtt 15

<210> SEQ ID NO 319
<211> LENGTH: 12
<212> TYPE: DNA
<213> ORGANISM: Artificial Sequence

<220> FEATURE:
<223> OTHER INFORMATION: ASO-000718

<400> SEQUENCE: 319
tgatgcagga gt 12

<210> SEQ ID NO 320
<211> LENGTH: 14
<212> TYPE: DNA
<213> ORGANISM: Artificial Sequence
<220> FEATURE:
<223> OTHER INFORMATION: ASO-000445

<400> SEQUENCE: 320
ttgtgatgca ggag 14

<210> SEQ ID NO 321
<211> LENGTH: 15
<212> TYPE: DNA
<213> ORGANISM: Artificial Sequence
<220> FEATURE:
<223> OTHER INFORMATION: ASO-000436

<400> SEQUENCE: 321
cttgtgatgc aggag 15

<210> SEQ ID NO 322
<211> LENGTH: 12
<212> TYPE: DNA
<213> ORGANISM: Artificial Sequence
<220> FEATURE:
<223> OTHER INFORMATION: ASO-000717

<400> SEQUENCE: 322
gtgatgcagg ag 12

<210> SEQ ID NO 323
<211> LENGTH: 16
<212> TYPE: DNA
<213> ORGANISM: Artificial Sequence
<220> FEATURE:
<223> OTHER INFORMATION: ASO-000570

<400> SEQUENCE: 323
ttcttgtgat gcagga 16

<210> SEQ ID NO 324
<211> LENGTH: 15
<212> TYPE: DNA
<213> ORGANISM: Artificial Sequence
<220> FEATURE:
<223> OTHER INFORMATION: ASO-000408

<400> SEQUENCE: 324
tcttgtgatg cagga 15

<210> SEQ ID NO 325
<211> LENGTH: 14
<212> TYPE: DNA
<213> ORGANISM: Artificial Sequence
<220> FEATURE:
<223> OTHER INFORMATION: ASO-000401

<400> SEQUENCE: 325
cttgtgatgc agga 14

<210> SEQ ID NO 326
<211> LENGTH: 12
<212> TYPE: DNA
<213> ORGANISM: Artificial Sequence
<220> FEATURE:
<223> OTHER INFORMATION: ASO-000719

<400> SEQUENCE: 326
tgtgatgcag ga 12

<210> SEQ ID NO 327
<211> LENGTH: 16
<212> TYPE: DNA
<213> ORGANISM: Artificial Sequence
<220> FEATURE:
<223> OTHER INFORMATION: ASO-000313

<400> SEQUENCE: 327
cagagggcga gcttgg 16

<210> SEQ ID NO 328
<211> LENGTH: 16
<212> TYPE: DNA
<213> ORGANISM: Artificial Sequence
<220> FEATURE:
<223> OTHER INFORMATION: ASO-000331

<400> SEQUENCE: 328
aatccctgct gtggtc 16

<210> SEQ ID NO 329
<211> LENGTH: 14
<212> TYPE: DNA
<213> ORGANISM: Artificial Sequence
<220> FEATURE:
<223> OTHER INFORMATION: ASO-000251

<400> SEQUENCE: 329
aggcaattca tccc 14

<210> SEQ ID NO 330
<211> LENGTH: 16
<212> TYPE: DNA
<213> ORGANISM: Artificial Sequence
<220> FEATURE:
<223> OTHER INFORMATION: ASO-000574

<400> SEQUENCE: 330
tggtcaaggc tttggg 16

<210> SEQ ID NO 331
<211> LENGTH: 16
<212> TYPE: DNA
<213> ORGANISM: Artificial Sequence
<220> FEATURE:
<223> OTHER INFORMATION: ASO-000218

<400> SEQUENCE: 331
tctggtcaag gctttg 16

<210> SEQ ID NO 332
<211> LENGTH: 16
<212> TYPE: DNA
<213> ORGANISM: Artificial Sequence
<220> FEATURE:
<223> OTHER INFORMATION: ASO-000634

<400> SEQUENCE: 332
ctctggtcaa ggcttt 16

<210> SEQ ID NO 333
<211> LENGTH: 16
<212> TYPE: DNA
<213> ORGANISM: Artificial Sequence
<220> FEATURE:
<223> OTHER INFORMATION: ASO-000497

<400> SEQUENCE: 333
ggtgctctgg tcaagg 16

<210> SEQ ID NO 334
<211> LENGTH: 14
<212> TYPE: DNA
<213> ORGANISM: Artificial Sequence
<220> FEATURE:
<223> OTHER INFORMATION: ASO-000569

<400> SEQUENCE: 334
ggtgctctgg tcaa 14

<210> SEQ ID NO 335
<211> LENGTH: 16
<212> TYPE: DNA
<213> ORGANISM: Artificial Sequence
<220> FEATURE:
<223> OTHER INFORMATION: ASO-000565

<400> SEQUENCE: 335
gctgaggtgc tctggt 16

<210> SEQ ID NO 336
<211> LENGTH: 16
<212> TYPE: DNA
<213> ORGANISM: Artificial Sequence
<220> FEATURE:
<223> OTHER INFORMATION: ASO-000296

<400> SEQUENCE: 336
agtttgtgca aggtca 16

<210> SEQ ID NO 337
<211> LENGTH: 16
<212> TYPE: DNA
<213> ORGANISM: Artificial Sequence
<220> FEATURE:
<223> OTHER INFORMATION: ASO-000663

<400> SEQUENCE: 337
gagtttgtgc aaggtc 16

<210> SEQ ID NO 338
<211> LENGTH: 15
<212> TYPE: DNA
<213> ORGANISM: Artificial Sequence
<220> FEATURE:
<223> OTHER INFORMATION: ASO-000670

<400> SEQUENCE: 338
agtttgtgca aggtc 15

<210> SEQ ID NO 339

<211> LENGTH: 16
<212> TYPE: DNA
<213> ORGANISM: Artificial Sequence
<220> FEATURE:
<223> OTHER INFORMATION: ASO-000261

<400> SEQUENCE: 339
ggagtttgtg caaggt 16

<210> SEQ ID NO 340
<211> LENGTH: 15
<212> TYPE: DNA
<213> ORGANISM: Artificial Sequence
<220> FEATURE:
<223> OTHER INFORMATION: ASO-000262

<400> SEQUENCE: 340
ggagtttgtg caagg 15

<210> SEQ ID NO 341
<211> LENGTH: 16
<212> TYPE: DNA
<213> ORGANISM: Artificial Sequence
<220> FEATURE:
<223> OTHER INFORMATION: ASO-000275

<400> SEQUENCE: 341
tggagtttgt gcaagg 16

<210> SEQ ID NO 342
<211> LENGTH: 16
<212> TYPE: DNA
<213> ORGANISM: Artificial Sequence
<220> FEATURE:
<223> OTHER INFORMATION: ASO-000247

<400> SEQUENCE: 342
atggagtttg tgcaag 16

<210> SEQ ID NO 343
<211> LENGTH: 15
<212> TYPE: DNA
<213> ORGANISM: Artificial Sequence
<220> FEATURE:
<223> OTHER INFORMATION: ASO-000303

<400> SEQUENCE: 343
tggagtttgt gcaag 15

<210> SEQ ID NO 344
<211> LENGTH: 15
<212> TYPE: DNA
<213> ORGANISM: Artificial Sequence
<220> FEATURE:
<223> OTHER INFORMATION: ASO-000299

<400> SEQUENCE: 344
atggagtttg tgcaa 15

<210> SEQ ID NO 345
<211> LENGTH: 16
<212> TYPE: DNA
<213> ORGANISM: Artificial Sequence
<220> FEATURE:
<223> OTHER INFORMATION: ASO-000270

<400> SEQUENCE: 345
agatggagtt tgtgca 16

<210> SEQ ID NO 346
<211> LENGTH: 16
<212> TYPE: DNA
<213> ORGANISM: Artificial Sequence
<220> FEATURE:
<223> OTHER INFORMATION: ASO-000297

<400> SEQUENCE: 346
agcagatgga gtttgt 16

<210> SEQ ID NO 347
<211> LENGTH: 16
<212> TYPE: DNA
<213> ORGANISM: Artificial Sequence
<220> FEATURE:
<223> OTHER INFORMATION: ASO-000259

<400> SEQUENCE: 347
ttctttaggc agcaat 16

<210> SEQ ID NO 348
<211> LENGTH: 16
<212> TYPE: DNA
<213> ORGANISM: Artificial Sequence
<220> FEATURE:
<223> OTHER INFORMATION: ASO-000220

<400> SEQUENCE: 348
tgtacccaaa ccagaa 16

<210> SEQ ID NO 349
<211> LENGTH: 15
<212> TYPE: DNA
<213> ORGANISM: Artificial Sequence
<220> FEATURE:
<223> OTHER INFORMATION: ASO-000278

<400> SEQUENCE: 349
gttgccttta actgt 15

<210> SEQ ID NO 350
<211> LENGTH: 16
<212> TYPE: DNA
<213> ORGANISM: Artificial Sequence
<220> FEATURE:
<223> OTHER INFORMATION: ASO-000334

<400> SEQUENCE: 350
gccctggatt tctact 16

<210> SEQ ID NO 351
<211> LENGTH: 16
<212> TYPE: DNA
<213> ORGANISM: Artificial Sequence
<220> FEATURE:
<223> OTHER INFORMATION: ASO-000241

<400> SEQUENCE: 351
tggtggagag ttctgg 16

<210> SEQ ID NO 352
<211> LENGTH: 16
<212> TYPE: DNA

<213> ORGANISM: Artificial Sequence
<220> FEATURE:
<223> OTHER INFORMATION: ASO-000289

<400> SEQUENCE: 352
ttctcagatc ccttca 16

<210> SEQ ID NO 353
<211> LENGTH: 16
<212> TYPE: DNA
<213> ORGANISM: Artificial Sequence
<220> FEATURE:
<223> OTHER INFORMATION: ASO-000233

<400> SEQUENCE: 353
ctctaaccac caccaa 16

<210> SEQ ID NO 354
<211> LENGTH: 16
<212> TYPE: DNA
<213> ORGANISM: Artificial Sequence
<220> FEATURE:
<223> OTHER INFORMATION: ASO-000201

<400> SEQUENCE: 354
agggcacaag aacttc 16

<210> SEQ ID NO 355
<211> LENGTH: 15
<212> TYPE: DNA
<213> ORGANISM: Artificial Sequence
<220> FEATURE:
<223> OTHER INFORMATION: ASO-000645

<400> SEQUENCE: 355
atcttaggct ggccc 15

<210> SEQ ID NO 356
<211> LENGTH: 16
<212> TYPE: DNA
<213> ORGANISM: Artificial Sequence
<220> FEATURE:
<223> OTHER INFORMATION: ASO-000546

<400> SEQUENCE: 356
gatcttaggc tggccc 16

<210> SEQ ID NO 357
<211> LENGTH: 16
<212> TYPE: DNA
<213> ORGANISM: Artificial Sequence
<220> FEATURE:
<223> OTHER INFORMATION: ASO-000692

<400> SEQUENCE: 357
tgatcttagg ctggcc 16

<210> SEQ ID NO 358
<211> LENGTH: 15
<212> TYPE: DNA
<213> ORGANISM: Artificial Sequence
<220> FEATURE:
<223> OTHER INFORMATION: ASO-000511

<400> SEQUENCE: 358
gatcttaggc tggcc 15

<210> SEQ ID NO 359
<211> LENGTH: 15
<212> TYPE: DNA
<213> ORGANISM: Artificial Sequence
<220> FEATURE:
<223> OTHER INFORMATION: ASO-000538

<400> SEQUENCE: 359
tgatcttagg ctggc 15

<210> SEQ ID NO 360
<211> LENGTH: 16
<212> TYPE: DNA
<213> ORGANISM: Artificial Sequence
<220> FEATURE:
<223> OTHER INFORMATION: ASO-000214

<400> SEQUENCE: 360
atgatcttag gctggc 16

<210> SEQ ID NO 361
<211> LENGTH: 14
<212> TYPE: DNA
<213> ORGANISM: Artificial Sequence
<220> FEATURE:
<223> OTHER INFORMATION: ASO-000653

<400> SEQUENCE: 361
gatcttaggc tggc 14

<210> SEQ ID NO 362
<211> LENGTH: 16
<212> TYPE: DNA
<213> ORGANISM: Artificial Sequence
<220> FEATURE:
<223> OTHER INFORMATION: ASO-000615

<400> SEQUENCE: 362
catgatctta ggctgg 16

<210> SEQ ID NO 363
<211> LENGTH: 16
<212> TYPE: DNA
<213> ORGANISM: Artificial Sequence
<220> FEATURE:
<223> OTHER INFORMATION: ASO-000524

<400> SEQUENCE: 363
ccatgatctt aggctg 16

<210> SEQ ID NO 364
<211> LENGTH: 15
<212> TYPE: DNA
<213> ORGANISM: Artificial Sequence
<220> FEATURE:
<223> OTHER INFORMATION: ASO-000492

<400> SEQUENCE: 364
catgatctta ggctg 15

<210> SEQ ID NO 365
<211> LENGTH: 16
<212> TYPE: DNA
<213> ORGANISM: Artificial Sequence
<220> FEATURE:

<223> OTHER INFORMATION: ASO-000468

<400> SEQUENCE: 365
accatgatct taggct 16

<210> SEQ ID NO 366
<211> LENGTH: 15
<212> TYPE: DNA
<213> ORGANISM: Artificial Sequence
<220> FEATURE:
<223> OTHER INFORMATION: ASO-000698

<400> SEQUENCE: 366
ccatgatctt aggct 15

<210> SEQ ID NO 367
<211> LENGTH: 14
<212> TYPE: DNA
<213> ORGANISM: Artificial Sequence
<220> FEATURE:
<223> OTHER INFORMATION: ASO-000593

<400> SEQUENCE: 367
catgatctta ggct 14

<210> SEQ ID NO 368
<211> LENGTH: 16
<212> TYPE: DNA
<213> ORGANISM: Artificial Sequence
<220> FEATURE:
<223> OTHER INFORMATION: ASO-000519

<400> SEQUENCE: 368
aaaccatgat cttagg 16

<210> SEQ ID NO 369
<211> LENGTH: 16
<212> TYPE: DNA
<213> ORGANISM: Artificial Sequence
<220> FEATURE:
<223> OTHER INFORMATION: ASO-000582

<400> SEQUENCE: 369
ctaaaccatg atctta 16

<210> SEQ ID NO 370
<211> LENGTH: 16
<212> TYPE: DNA
<213> ORGANISM: Artificial Sequence
<220> FEATURE:
<223> OTHER INFORMATION: ASO-000635

<400> SEQUENCE: 370
ccctaaacca tgatct 16

<210> SEQ ID NO 371
<211> LENGTH: 16
<212> TYPE: DNA
<213> ORGANISM: Artificial Sequence
<220> FEATURE:
<223> OTHER INFORMATION: ASO-000471

<400> SEQUENCE: 371
caccctaaac catgat 16

<210> SEQ ID NO 372
<211> LENGTH: 16
<212> TYPE: DNA
<213> ORGANISM: Artificial Sequence
<220> FEATURE:
<223> OTHER INFORMATION: ASO-000701

<400> SEQUENCE: 372
atcaccctaa accatg 16

<210> SEQ ID NO 373
<211> LENGTH: 16
<212> TYPE: DNA
<213> ORGANISM: Artificial Sequence
<220> FEATURE:
<223> OTHER INFORMATION: ASO-000533

<400> SEQUENCE: 373
tgatcaccct aaacca 16

<210> SEQ ID NO 374
<211> LENGTH: 16
<212> TYPE: DNA
<213> ORGANISM: Artificial Sequence
<220> FEATURE:
<223> OTHER INFORMATION: ASO-000323

<400> SEQUENCE: 374
gaggagtgcc cagccc 16

<210> SEQ ID NO 375
<211> LENGTH: 16
<212> TYPE: DNA
<213> ORGANISM: Artificial Sequence
<220> FEATURE:
<223> OTHER INFORMATION: ASO-000329

<400> SEQUENCE: 375
tgcaggtggg agaagt 16

<210> SEQ ID NO 376
<211> LENGTH: 14
<212> TYPE: DNA
<213> ORGANISM: Artificial Sequence
<220> FEATURE:
<223> OTHER INFORMATION: ASO-000194

<400> SEQUENCE: 376
tatctagccc accc 14

<210> SEQ ID NO 377
<211> LENGTH: 15
<212> TYPE: DNA
<213> ORGANISM: Artificial Sequence
<220> FEATURE:
<223> OTHER INFORMATION: ASO-000192

<400> SEQUENCE: 377
ctatctagcc caccc 15

<210> SEQ ID NO 378
<211> LENGTH: 14
<212> TYPE: DNA
<213> ORGANISM: Artificial Sequence
<220> FEATURE:
<223> OTHER INFORMATION: ASO-000343

<400> SEQUENCE: 378
tatcctatct agcc 14

<210> SEQ ID NO 379
<211> LENGTH: 15
<212> TYPE: DNA
<213> ORGANISM: Artificial Sequence
<220> FEATURE:
<223> OTHER INFORMATION: ASO-000212

<400> SEQUENCE: 379
ttgataaagt gagtc 15

<210> SEQ ID NO 380
<211> LENGTH: 15
<212> TYPE: DNA
<213> ORGANISM: Artificial Sequence
<220> FEATURE:
<223> OTHER INFORMATION: ASO-000230

<400> SEQUENCE: 380
attgataaag tgagt 15

<210> SEQ ID NO 381
<211> LENGTH: 15
<212> TYPE: DNA
<213> ORGANISM: Artificial Sequence
<220> FEATURE:
<223> OTHER INFORMATION: ASO-000188

<400> SEQUENCE: 381
aactattgat aaagt 15

<210> SEQ ID NO 382
<211> LENGTH: 14
<212> TYPE: DNA
<213> ORGANISM: Artificial Sequence
<220> FEATURE:
<223> OTHER INFORMATION: ASO-000415

<400> SEQUENCE: 382
gaactattga taaa 14

<210> SEQ ID NO 383
<211> LENGTH: 14
<212> TYPE: DNA
<213> ORGANISM: Artificial Sequence
<220> FEATURE:
<223> OTHER INFORMATION: ASO-000448

<400> SEQUENCE: 383
ggaactattg ataa 14

<210> SEQ ID NO 384
<211> LENGTH: 16
<212> TYPE: DNA
<213> ORGANISM: Artificial Sequence
<220> FEATURE:
<223> OTHER INFORMATION: ASO-000190

<400> SEQUENCE: 384
aaatggaact attgat 16

<210> SEQ ID NO 385
<211> LENGTH: 14

<212> TYPE: DNA
<213> ORGANISM: Artificial Sequence
<220> FEATURE:
<223> OTHER INFORMATION: ASO-000191

<400> SEQUENCE: 385
aatggaacta ttga 14

<210> SEQ ID NO 386
<211> LENGTH: 15
<212> TYPE: DNA
<213> ORGANISM: Artificial Sequence
<220> FEATURE:
<223> OTHER INFORMATION: ASO-000348

<400> SEQUENCE: 386
tcaatttaaa tggaa 15

<210> SEQ ID NO 387
<211> LENGTH: 15
<212> TYPE: DNA
<213> ORGANISM: Artificial Sequence
<220> FEATURE:
<223> OTHER INFORMATION: ASO-000349

<400> SEQUENCE: 387
gtcaatttaa atgga 15

<210> SEQ ID NO 388
<211> LENGTH: 16
<212> TYPE: DNA
<213> ORGANISM: Artificial Sequence
<220> FEATURE:
<223> OTHER INFORMATION: ASO-000200

<400> SEQUENCE: 388
ggatacagtc tcacca 16

<210> SEQ ID NO 389
<211> LENGTH: 16
<212> TYPE: DNA
<213> ORGANISM: Artificial Sequence
<220> FEATURE:
<223> OTHER INFORMATION: ASO-000630

<400> SEQUENCE: 389
gcaaacagga tacagt 16

<210> SEQ ID NO 390
<211> LENGTH: 15
<212> TYPE: DNA
<213> ORGANISM: Artificial Sequence
<220> FEATURE:
<223> OTHER INFORMATION: ASO-000614

<400> SEQUENCE: 390
caaacaggat acagt 15

<210> SEQ ID NO 391
<211> LENGTH: 14
<212> TYPE: DNA
<213> ORGANISM: Artificial Sequence
<220> FEATURE:
<223> OTHER INFORMATION: ASO-000563

<400> SEQUENCE: 391
aaacaggata cagt 14

<210> SEQ ID NO 392
<211> LENGTH: 16
<212> TYPE: DNA
<213> ORGANISM: Artificial Sequence
<220> FEATURE:
<223> OTHER INFORMATION: ASO-000527

<400> SEQUENCE: 392
tagcaaacag gataca 16

<210> SEQ ID NO 393
<211> LENGTH: 16
<212> TYPE: DNA
<213> ORGANISM: Artificial Sequence
<220> FEATURE:
<223> OTHER INFORMATION: ASO-000617

<400> SEQUENCE: 393
atagcaaaca ggatac 16

<210> SEQ ID NO 394
<211> LENGTH: 16
<212> TYPE: DNA
<213> ORGANISM: Artificial Sequence
<220> FEATURE:
<223> OTHER INFORMATION: ASO-000539

<400> SEQUENCE: 394
aatagcaaac aggata 16

<210> SEQ ID NO 395
<211> LENGTH: 16
<212> TYPE: DNA
<213> ORGANISM: Artificial Sequence
<220> FEATURE:
<223> OTHER INFORMATION: ASO-000691

<400> SEQUENCE: 395
caatagcaaa caggat 16

<210> SEQ ID NO 396
<211> LENGTH: 15
<212> TYPE: DNA
<213> ORGANISM: Artificial Sequence
<220> FEATURE:
<223> OTHER INFORMATION: ASO-000589

<400> SEQUENCE: 396
aatagcaaac aggat 15

<210> SEQ ID NO 397
<211> LENGTH: 16
<212> TYPE: DNA
<213> ORGANISM: Artificial Sequence
<220> FEATURE:
<223> OTHER INFORMATION: ASO-000509

<400> SEQUENCE: 397
gcaatagcaa acagga 16

<210> SEQ ID NO 398
<211> LENGTH: 15
<212> TYPE: DNA
<213> ORGANISM: Artificial Sequence

<220> FEATURE:
<223> OTHER INFORMATION: ASO-000674

<400> SEQUENCE: 398
caatagcaaa cagga 15

<210> SEQ ID NO 399
<211> LENGTH: 15
<212> TYPE: DNA
<213> ORGANISM: Artificial Sequence
<220> FEATURE:
<223> OTHER INFORMATION: ASO-000488

<400> SEQUENCE: 399
gcaatagcaa acagg 15

<210> SEQ ID NO 400
<211> LENGTH: 16
<212> TYPE: DNA
<213> ORGANISM: Artificial Sequence
<220> FEATURE:
<223> OTHER INFORMATION: ASO-000507

<400> SEQUENCE: 400
agcaatagca aacagg 16

<210> SEQ ID NO 401
<211> LENGTH: 15
<212> TYPE: DNA
<213> ORGANISM: Artificial Sequence
<220> FEATURE:
<223> OTHER INFORMATION: ASO-000521

<400> SEQUENCE: 401
agcaatagca aacag 15

<210> SEQ ID NO 402
<211> LENGTH: 16
<212> TYPE: DNA
<213> ORGANISM: Artificial Sequence
<220> FEATURE:
<223> OTHER INFORMATION: ASO-000288

<400> SEQUENCE: 402
aagcaatagc aaacag 16

<210> SEQ ID NO 403
<211> LENGTH: 15
<212> TYPE: DNA
<213> ORGANISM: Artificial Sequence
<220> FEATURE:
<223> OTHER INFORMATION: ASO-000552

<400> SEQUENCE: 403
aagcaatagc aaaca 15

<210> SEQ ID NO 404
<211> LENGTH: 16
<212> TYPE: DNA
<213> ORGANISM: Artificial Sequence
<220> FEATURE:
<223> OTHER INFORMATION: ASO-000250

<400> SEQUENCE: 404
caaatgtggt tgaaat 16

<210> SEQ ID NO 405
<211> LENGTH: 16
<212> TYPE: DNA
<213> ORGANISM: Artificial Sequence
<220> FEATURE:
<223> OTHER INFORMATION: ASO-000294

<400> SEQUENCE: 405
gcaaatgtgg ttgaaa 16

<210> SEQ ID NO 406
<211> LENGTH: 16
<212> TYPE: DNA
<213> ORGANISM: Artificial Sequence
<220> FEATURE:
<223> OTHER INFORMATION: ASO-000318

<400> SEQUENCE: 406
tagcaaatgt ggttga 16

<210> SEQ ID NO 407
<211> LENGTH: 16
<212> TYPE: DNA
<213> ORGANISM: Artificial Sequence
<220> FEATURE:
<223> OTHER INFORMATION: ASO-000308

<400> SEQUENCE: 407
cccaagggcc tctaac 16

<210> SEQ ID NO 408
<211> LENGTH: 16
<212> TYPE: DNA
<213> ORGANISM: Artificial Sequence
<220> FEATURE:
<223> OTHER INFORMATION: ASO-000254

<400> SEQUENCE: 408
aaagcaacca gatgtc 16

<210> SEQ ID NO 409
<211> LENGTH: 16
<212> TYPE: DNA
<213> ORGANISM: Artificial Sequence
<220> FEATURE:
<223> OTHER INFORMATION: ASO-000545

<400> SEQUENCE: 409
aagagggcag caggcc 16

<210> SEQ ID NO 410
<211> LENGTH: 16
<212> TYPE: DNA
<213> ORGANISM: Artificial Sequence
<220> FEATURE:
<223> OTHER INFORMATION: ASO-000476

<400> SEQUENCE: 410
gaaagagggc agcagg 16

<210> SEQ ID NO 411
<211> LENGTH: 16
<212> TYPE: DNA
<213> ORGANISM: Artificial Sequence
<220> FEATURE:
<223> OTHER INFORMATION: ASO-000620

<400> SEQUENCE: 411
ctgaaagagg gcagca 16

<210> SEQ ID NO 412
<211> LENGTH: 16
<212> TYPE: DNA
<213> ORGANISM: Artificial Sequence
<220> FEATURE:
<223> OTHER INFORMATION: ASO-000477

<400> SEQUENCE: 412
ccctgaaaga gggcag 16

<210> SEQ ID NO 413
<211> LENGTH: 16
<212> TYPE: DNA
<213> ORGANISM: Artificial Sequence
<220> FEATURE:
<223> OTHER INFORMATION: ASO-000562

<400> SEQUENCE: 413
tgattgtggg cttagg 16

<210> SEQ ID NO 414
<211> LENGTH: 16
<212> TYPE: DNA
<213> ORGANISM: Artificial Sequence
<220> FEATURE:
<223> OTHER INFORMATION: ASO-000547

<400> SEQUENCE: 414
atgattgtgg gcttag 16

<210> SEQ ID NO 415
<211> LENGTH: 15
<212> TYPE: DNA
<213> ORGANISM: Artificial Sequence
<220> FEATURE:
<223> OTHER INFORMATION: ASO-000696

<400> SEQUENCE: 415
tgattgtggg cttag 15

<210> SEQ ID NO 416
<211> LENGTH: 14
<212> TYPE: DNA
<213> ORGANISM: Artificial Sequence
<220> FEATURE:
<223> OTHER INFORMATION: ASO-000279

<400> SEQUENCE: 416
gattgtgggc ttag 14

<210> SEQ ID NO 417
<211> LENGTH: 16
<212> TYPE: DNA
<213> ORGANISM: Artificial Sequence
<220> FEATURE:
<223> OTHER INFORMATION: ASO-000543

<400> SEQUENCE: 417
catgattgtg ggctta 16

<210> SEQ ID NO 418

<211> LENGTH: 14
<212> TYPE: DNA
<213> ORGANISM: Artificial Sequence
<220> FEATURE:
<223> OTHER INFORMATION: ASO-000626

<400> SEQUENCE: 418
tgattgtggg ctta 14

<210> SEQ ID NO 419
<211> LENGTH: 15
<212> TYPE: DNA
<213> ORGANISM: Artificial Sequence
<220> FEATURE:
<223> OTHER INFORMATION: ASO-000650

<400> SEQUENCE: 419
atgattgtgg gctta 15

<210> SEQ ID NO 420
<211> LENGTH: 15
<212> TYPE: DNA
<213> ORGANISM: Artificial Sequence
<220> FEATURE:
<223> OTHER INFORMATION: ASO-000599

<400> SEQUENCE: 420
catgattgtg ggctt 15

<210> SEQ ID NO 421
<211> LENGTH: 16
<212> TYPE: DNA
<213> ORGANISM: Artificial Sequence
<220> FEATURE:
<223> OTHER INFORMATION: ASO-000542

<400> SEQUENCE: 421
gcatgattgt gggctt 16

<210> SEQ ID NO 422
<211> LENGTH: 16
<212> TYPE: DNA
<213> ORGANISM: Artificial Sequence
<220> FEATURE:
<223> OTHER INFORMATION: ASO-000463

<400> SEQUENCE: 422
ggcatgattg tgggct 16

<210> SEQ ID NO 423
<211> LENGTH: 15
<212> TYPE: DNA
<213> ORGANISM: Artificial Sequence
<220> FEATURE:
<223> OTHER INFORMATION: ASO-000605

<400> SEQUENCE: 423
gcatgattgt gggct 15

<210> SEQ ID NO 424
<211> LENGTH: 14
<212> TYPE: DNA
<213> ORGANISM: Artificial Sequence
<220> FEATURE:
<223> OTHER INFORMATION: ASO-000479

<400> SEQUENCE: 424
catgattgtg ggct 14

<210> SEQ ID NO 425
<211> LENGTH: 14
<212> TYPE: DNA
<213> ORGANISM: Artificial Sequence
<220> FEATURE:
<223> OTHER INFORMATION: ASO-000474

<400> SEQUENCE: 425
gcatgattgt gggc 14

<210> SEQ ID NO 426
<211> LENGTH: 15
<212> TYPE: DNA
<213> ORGANISM: Artificial Sequence
<220> FEATURE:
<223> OTHER INFORMATION: ASO-000675

<400> SEQUENCE: 426
ggcatgattg tgggc 15

<210> SEQ ID NO 427
<211> LENGTH: 16
<212> TYPE: DNA
<213> ORGANISM: Artificial Sequence
<220> FEATURE:
<223> OTHER INFORMATION: ASO-000537

<400> SEQUENCE: 427
aggcatgatt gtgggc 16

<210> SEQ ID NO 428
<211> LENGTH: 16
<212> TYPE: DNA
<213> ORGANISM: Artificial Sequence
<220> FEATURE:
<223> OTHER INFORMATION: ASO-000287

<400> SEQUENCE: 428
agggaggcat gattgt 16

<210> SEQ ID NO 429
<211> LENGTH: 15
<212> TYPE: DNA
<213> ORGANISM: Artificial Sequence
<220> FEATURE:
<223> OTHER INFORMATION: ASO-000292

<400> SEQUENCE: 429
gggaggcatg attgt 15

<210> SEQ ID NO 430
<211> LENGTH: 16
<212> TYPE: DNA
<213> ORGANISM: Artificial Sequence
<220> FEATURE:
<223> OTHER INFORMATION: ASO-000216

<400> SEQUENCE: 430
ttagggaggc atgatt 16

<210> SEQ ID NO 431
<211> LENGTH: 15
<212> TYPE: DNA

<213> ORGANISM: Artificial Sequence
<220> FEATURE:
<223> OTHER INFORMATION: ASO-000266

<400> SEQUENCE: 431
ttagggaggc atgat 15

<210> SEQ ID NO 432
<211> LENGTH: 16
<212> TYPE: DNA
<213> ORGANISM: Artificial Sequence
<220> FEATURE:
<223> OTHER INFORMATION: ASO-000256

<400> SEQUENCE: 432
tcttagggag gcatga 16

<210> SEQ ID NO 433
<211> LENGTH: 16
<212> TYPE: DNA
<213> ORGANISM: Artificial Sequence
<220> FEATURE:
<223> OTHER INFORMATION: ASO-000269

<400> SEQUENCE: 433
gaggtggcac agaggt 16

<210> SEQ ID NO 434
<211> LENGTH: 15
<212> TYPE: DNA
<213> ORGANISM: Artificial Sequence
<220> FEATURE:
<223> OTHER INFORMATION: ASO-000350

<400> SEQUENCE: 434
cagtgtgaga ggtgg 15

<210> SEQ ID NO 435
<211> LENGTH: 14
<212> TYPE: DNA
<213> ORGANISM: Artificial Sequence
<220> FEATURE:
<223> OTHER INFORMATION: ASO-000353

<400> SEQUENCE: 435
cagtgtgaga ggtg 14

<210> SEQ ID NO 436
<211> LENGTH: 16
<212> TYPE: DNA
<213> ORGANISM: Artificial Sequence
<220> FEATURE:
<223> OTHER INFORMATION: ASO-000310

<400> SEQUENCE: 436
acaaagatga ggaggg 16

<210> SEQ ID NO 437
<211> LENGTH: 16
<212> TYPE: DNA
<213> ORGANISM: Artificial Sequence
<220> FEATURE:
<223> OTHER INFORMATION: ASO-000309

<400> SEQUENCE: 437
aacaaagatg aggagg 16

<210> SEQ ID NO 438
<211> LENGTH: 16
<212> TYPE: DNA
<213> ORGANISM: Artificial Sequence
<220> FEATURE:
<223> OTHER INFORMATION: ASO-000263

<400> SEQUENCE: 438
gaagagaaat cagaag 16

<210> SEQ ID NO 439
<211> LENGTH: 16
<212> TYPE: DNA
<213> ORGANISM: Artificial Sequence
<220> FEATURE:
<223> OTHER INFORMATION: ASO-000197

<400> SEQUENCE: 439
tctaggccag tgccca 16

<210> SEQ ID NO 440
<211> LENGTH: 14
<212> TYPE: DNA
<213> ORGANISM: Artificial Sequence
<220> FEATURE:
<223> OTHER INFORMATION: ASO-000239

<400> SEQUENCE: 440
agtctattag gagg 14

<210> SEQ ID NO 441
<211> LENGTH: 16
<212> TYPE: DNA
<213> ORGANISM: Artificial Sequence
<220> FEATURE:
<223> OTHER INFORMATION: ASO-000267

<400> SEQUENCE: 441
gctcaacatg gcaaac 16

<210> SEQ ID NO 442
<211> LENGTH: 15
<212> TYPE: DNA
<213> ORGANISM: Artificial Sequence
<220> FEATURE:
<223> OTHER INFORMATION: ASO-000306

<400> SEQUENCE: 442
tgcaagtgcc agaaa 15

<210> SEQ ID NO 443
<211> LENGTH: 14
<212> TYPE: DNA
<213> ORGANISM: Artificial Sequence
<220> FEATURE:
<223> OTHER INFORMATION: ASO-000345

<400> SEQUENCE: 443
gcaagtgcca gaaa 14

<210> SEQ ID NO 444
<211> LENGTH: 16
<212> TYPE: DNA
<213> ORGANISM: Artificial Sequence
<220> FEATURE:

<223> OTHER INFORMATION: ASO-000193

<400> SEQUENCE: 444
aatcatggga cttgca 16

<210> SEQ ID NO 445
<211> LENGTH: 16
<212> TYPE: DNA
<213> ORGANISM: Artificial Sequence
<220> FEATURE:
<223> OTHER INFORMATION: ASO-000284

<400> SEQUENCE: 445
gatttcatgt ccctcc 16

<210> SEQ ID NO 446
<211> LENGTH: 15
<212> TYPE: DNA
<213> ORGANISM: Artificial Sequence
<220> FEATURE:
<223> OTHER INFORMATION: ASO-000209

<400> SEQUENCE: 446
gctaagctaa gatga 15

<210> SEQ ID NO 447
<211> LENGTH: 14
<212> TYPE: DNA
<213> ORGANISM: Artificial Sequence
<220> FEATURE:
<223> OTHER INFORMATION: ASO-000207

<400> SEQUENCE: 447
ctaagctaag atga 14

<210> SEQ ID NO 448
<211> LENGTH: 15
<212> TYPE: DNA
<213> ORGANISM: Artificial Sequence
<220> FEATURE:
<223> OTHER INFORMATION: ASO-000301

<400> SEQUENCE: 448
tagacattca cagac 15

<210> SEQ ID NO 449
<211> LENGTH: 15
<212> TYPE: DNA
<213> ORGANISM: Artificial Sequence
<220> FEATURE:
<223> OTHER INFORMATION: ASO-000234

<400> SEQUENCE: 449
tatagacatt cacag 15

<210> SEQ ID NO 450
<211> LENGTH: 16
<212> TYPE: DNA
<213> ORGANISM: Artificial Sequence
<220> FEATURE:
<223> OTHER INFORMATION: ASO-000332

<400> SEQUENCE: 450
aaacacacaa tacact 16

<210> SEQ ID NO 451
<211> LENGTH: 16
<212> TYPE: DNA
<213> ORGANISM: Artificial Sequence
<220> FEATURE:
<223> OTHER INFORMATION: SPC-15693-01

<400> SEQUENCE: 451
cagcaacagt cagtgt 16

<210> SEQ ID NO 452
<211> LENGTH: 16
<212> TYPE: DNA
<213> ORGANISM: Artificial Sequence
<220> FEATURE:
<223> OTHER INFORMATION: SPC-15692-01

<400> SEQUENCE: 452
acagcaacag tcagtg 16

<210> SEQ ID NO 453
<211> LENGTH: 16
<212> TYPE: DNA
<213> ORGANISM: Artificial Sequence
<220> FEATURE:
<223> OTHER INFORMATION: SPC-15691-01

<400> SEQUENCE: 453
tacagcaaca gtcagt 16

<210> SEQ ID NO 454
<211> LENGTH: 16
<212> TYPE: DNA
<213> ORGANISM: Artificial Sequence
<220> FEATURE:
<223> OTHER INFORMATION: SPC-15690-01

<400> SEQUENCE: 454
ttacagcaac agtcag 16

<210> SEQ ID NO 455
<211> LENGTH: 16
<212> TYPE: DNA
<213> ORGANISM: Artificial Sequence
<220> FEATURE:
<223> OTHER INFORMATION: SPC-15689-01

<400> SEQUENCE: 455
tttacagcaa cagtca 16

<210> SEQ ID NO 456
<211> LENGTH: 16
<212> TYPE: DNA
<213> ORGANISM: Artificial Sequence
<220> FEATURE:
<223> OTHER INFORMATION: SPC-15688-01

<400> SEQUENCE: 456
ttttacagca acagtc 16

<210> SEQ ID NO 457
<211> LENGTH: 16
<212> TYPE: DNA
<213> ORGANISM: Artificial Sequence
<220> FEATURE:
<223> OTHER INFORMATION: SPC-15687-01

<400> SEQUENCE: 457
cttttacagc aacagt 16

<210> SEQ ID NO 458
<211> LENGTH: 16
<212> TYPE: DNA
<213> ORGANISM: Artificial Sequence
<220> FEATURE:
<223> OTHER INFORMATION: SPC-15686-01

<400> SEQUENCE: 458
acttttacag caacag 16

<210> SEQ ID NO 459
<211> LENGTH: 16
<212> TYPE: DNA
<213> ORGANISM: Artificial Sequence
<220> FEATURE:
<223> OTHER INFORMATION: SPC-15685-01

<400> SEQUENCE: 459
cacttttaca gcaaca 16

<210> SEQ ID NO 460
<211> LENGTH: 16
<212> TYPE: DNA
<213> ORGANISM: Artificial Sequence
<220> FEATURE:
<223> OTHER INFORMATION: SPC-15684-01

<400> SEQUENCE: 460
tcacttttac agcaac 16

<210> SEQ ID NO 461
<211> LENGTH: 16
<212> TYPE: DNA
<213> ORGANISM: Artificial Sequence
<220> FEATURE:
<223> OTHER INFORMATION: SPC-15683-01

<400> SEQUENCE: 461
ttcactttta cagcaa 16

<210> SEQ ID NO 462
<211> LENGTH: 16
<212> TYPE: DNA
<213> ORGANISM: Artificial Sequence
<220> FEATURE:
<223> OTHER INFORMATION: SPC-15682-01

<400> SEQUENCE: 462
attcactttt acagca 16

<210> SEQ ID NO 463
<211> LENGTH: 16
<212> TYPE: DNA
<213> ORGANISM: Artificial Sequence
<220> FEATURE:
<223> OTHER INFORMATION: SPC-15681-01

<400> SEQUENCE: 463
aattcacttt tacagc 16

<210> SEQ ID NO 464
<211> LENGTH: 16

<212> TYPE: DNA
<213> ORGANISM: Artificial Sequence
<220> FEATURE:
<223> OTHER INFORMATION: SPC-15680-01

<400> SEQUENCE: 464
aaattcactt ttacag 16

<210> SEQ ID NO 465
<211> LENGTH: 16
<212> TYPE: DNA
<213> ORGANISM: Artificial Sequence
<220> FEATURE:
<223> OTHER INFORMATION: SPC-15679-01

<400> SEQUENCE: 465
caaattcact tttaca 16

<210> SEQ ID NO 466
<211> LENGTH: 20
<212> TYPE: DNA
<213> ORGANISM: Artificial Sequence
<220> FEATURE:
<223> OTHER INFORMATION: ASO-002090

<400> SEQUENCE: 466
atttccaaat tcacttttac 20

<210> SEQ ID NO 467
<211> LENGTH: 20
<212> TYPE: DNA
<213> ORGANISM: Artificial Sequence
<220> FEATURE:
<223> OTHER INFORMATION: ASO-002043

<400> SEQUENCE: 467
atttccaaat tcacttttac 20

<210> SEQ ID NO 468
<211> LENGTH: 20
<212> TYPE: DNA
<213> ORGANISM: Artificial Sequence
<220> FEATURE:
<223> OTHER INFORMATION: ASO-002076

<400> SEQUENCE: 468
atttccaaat tcacttttac 20

<210> SEQ ID NO 469
<211> LENGTH: 20
<212> TYPE: DNA
<213> ORGANISM: Artificial Sequence
<220> FEATURE:
<223> OTHER INFORMATION: ASO-002062

<400> SEQUENCE: 469
atttccaaat tcacttttac 20

<210> SEQ ID NO 470
<211> LENGTH: 20
<212> TYPE: DNA
<213> ORGANISM: Artificial Sequence
<220> FEATURE:
<223> OTHER INFORMATION: ASO-002082

<400> SEQUENCE: 470
atttccaaat tcacttttac 20

<210> SEQ ID NO 471
<211> LENGTH: 20
<212> TYPE: DNA
<213> ORGANISM: Artificial Sequence
<220> FEATURE:
<223> OTHER INFORMATION: ASO-000753

<400> SEQUENCE: 471
atttccaaat tcacttttac 20

<210> SEQ ID NO 472
<211> LENGTH: 20
<212> TYPE: DNA
<213> ORGANISM: Artificial Sequence
<220> FEATURE:
<223> OTHER INFORMATION: ASO-001940

<400> SEQUENCE: 472
atttccaaat tcacttttac 20

<210> SEQ ID NO 473
<211> LENGTH: 20
<212> TYPE: DNA
<213> ORGANISM: Artificial Sequence
<220> FEATURE:
<223> OTHER INFORMATION: ASO-001933

<400> SEQUENCE: 473
atttccaaat tcacttttac 20

<210> SEQ ID NO 474
<211> LENGTH: 20
<212> TYPE: DNA
<213> ORGANISM: Artificial Sequence
<220> FEATURE:
<223> OTHER INFORMATION: ASO-001919

<400> SEQUENCE: 474
atttccaaat tcacttttac 20

<210> SEQ ID NO 475
<211> LENGTH: 20
<212> TYPE: DNA
<213> ORGANISM: Artificial Sequence
<220> FEATURE:
<223> OTHER INFORMATION: ASO-002094

<400> SEQUENCE: 475
atttccaaat tcacttttac 20

<210> SEQ ID NO 476
<211> LENGTH: 20
<212> TYPE: DNA
<213> ORGANISM: Artificial Sequence
<220> FEATURE:
<223> OTHER INFORMATION: ASO-002034

<400> SEQUENCE: 476
atttccaaat tcacttttac 20

<210> SEQ ID NO 477
<211> LENGTH: 20
<212> TYPE: DNA
<213> ORGANISM: Artificial Sequence

<220> FEATURE:
<223> OTHER INFORMATION: ASO-002036

<400> SEQUENCE: 477
atttccaaat tcacttttac 20

<210> SEQ ID NO 478
<211> LENGTH: 20
<212> TYPE: DNA
<213> ORGANISM: Artificial Sequence
<220> FEATURE:
<223> OTHER INFORMATION: ASO-002084

<400> SEQUENCE: 478
atttccaaat tcacttttac 20

<210> SEQ ID NO 479
<211> LENGTH: 20
<212> TYPE: DNA
<213> ORGANISM: Artificial Sequence
<220> FEATURE:
<223> OTHER INFORMATION: ASO-002037

<400> SEQUENCE: 479
atttccaaat tcacttttac 20

<210> SEQ ID NO 480
<211> LENGTH: 20
<212> TYPE: DNA
<213> ORGANISM: Artificial Sequence
<220> FEATURE:
<223> OTHER INFORMATION: ASO-002058

<400> SEQUENCE: 480
atttccaaat tcacttttac 20

<210> SEQ ID NO 481
<211> LENGTH: 20
<212> TYPE: DNA
<213> ORGANISM: Artificial Sequence
<220> FEATURE:
<223> OTHER INFORMATION: ASO-002057

<400> SEQUENCE: 481
atttccaaat tcacttttac 20

<210> SEQ ID NO 482
<211> LENGTH: 20
<212> TYPE: DNA
<213> ORGANISM: Artificial Sequence
<220> FEATURE:
<223> OTHER INFORMATION: ASO-001926

<400> SEQUENCE: 482
atttccaaat tcacttttac 20

<210> SEQ ID NO 483
<211> LENGTH: 20
<212> TYPE: DNA
<213> ORGANISM: Artificial Sequence
<220> FEATURE:
<223> OTHER INFORMATION: ASO-002092

<400> SEQUENCE: 483
atttccaaat tcacttttac 20

<210> SEQ ID NO 484
<211> LENGTH: 20
<212> TYPE: DNA
<213> ORGANISM: Artificial Sequence
<220> FEATURE:
<223> OTHER INFORMATION: ASO-002023

<400> SEQUENCE: 484
atttccaaat tcacttttac 20

<210> SEQ ID NO 485
<211> LENGTH: 20
<212> TYPE: DNA
<213> ORGANISM: Artificial Sequence
<220> FEATURE:
<223> OTHER INFORMATION: ASO-000758

<400> SEQUENCE: 485
atttccaaat tcacttttac 20

<210> SEQ ID NO 486
<211> LENGTH: 20
<212> TYPE: DNA
<213> ORGANISM: Artificial Sequence
<220> FEATURE:
<223> OTHER INFORMATION: ASO-002065

<400> SEQUENCE: 486
atttccaaat tcacttttac 20

<210> SEQ ID NO 487
<211> LENGTH: 20
<212> TYPE: DNA
<213> ORGANISM: Artificial Sequence
<220> FEATURE:
<223> OTHER INFORMATION: ASO-002038

<400> SEQUENCE: 487
atttccaaat tcacttttac 20

<210> SEQ ID NO 488
<211> LENGTH: 20
<212> TYPE: DNA
<213> ORGANISM: Artificial Sequence
<220> FEATURE:
<223> OTHER INFORMATION: ASO-002039

<400> SEQUENCE: 488
atttccaaat tcacttttac 20

<210> SEQ ID NO 489
<211> LENGTH: 20
<212> TYPE: DNA
<213> ORGANISM: Artificial Sequence
<220> FEATURE:
<223> OTHER INFORMATION: ASO-000763

<400> SEQUENCE: 489
atttccaaat tcacttttac 20

<210> SEQ ID NO 490
<211> LENGTH: 20
<212> TYPE: DNA
<213> ORGANISM: Artificial Sequence
<220> FEATURE:
<223> OTHER INFORMATION: ASO-000768

<400> SEQUENCE: 490
atttccaaat tcacttttac 20

<210> SEQ ID NO 491
<211> LENGTH: 17
<212> TYPE: DNA
<213> ORGANISM: Artificial Sequence
<220> FEATURE:
<223> OTHER INFORMATION: 17-18-19mer-1

<400> SEQUENCE: 491
tccaaattca cttttac 17

<210> SEQ ID NO 492
<211> LENGTH: 17
<212> TYPE: DNA
<213> ORGANISM: Artificial Sequence
<220> FEATURE:
<223> OTHER INFORMATION: 17-18-19mer-10

<400> SEQUENCE: 492
tccaaattca cttttac 17

<210> SEQ ID NO 493
<211> LENGTH: 17
<212> TYPE: DNA
<213> ORGANISM: Artificial Sequence
<220> FEATURE:
<223> OTHER INFORMATION: 17-18-19mer-13

<400> SEQUENCE: 493
tccaaattca cttttac 17

<210> SEQ ID NO 494
<211> LENGTH: 18
<212> TYPE: DNA
<213> ORGANISM: Artificial Sequence
<220> FEATURE:
<223> OTHER INFORMATION: 17-18-19mer-16

<400> SEQUENCE: 494
ttccaaattc acttttac 18

<210> SEQ ID NO 495
<211> LENGTH: 18
<212> TYPE: DNA
<213> ORGANISM: Artificial Sequence
<220> FEATURE:
<223> OTHER INFORMATION: 17-18-19mer-22

<400> SEQUENCE: 495
ttccaaattc acttttac 18

<210> SEQ ID NO 496
<211> LENGTH: 18
<212> TYPE: DNA
<213> ORGANISM: Artificial Sequence
<220> FEATURE:
<223> OTHER INFORMATION: 17-18-19mer-28

<400> SEQUENCE: 496
ttccaaattc acttttac 18

<210> SEQ ID NO 497

<211> LENGTH: 18
<212> TYPE: DNA
<213> ORGANISM: Artificial Sequence
<220> FEATURE:
<223> OTHER INFORMATION: 17-18-19mer-34

<400> SEQUENCE: 497
ttccaaattc acttttac 18

<210> SEQ ID NO 498
<211> LENGTH: 17
<212> TYPE: DNA
<213> ORGANISM: Artificial Sequence
<220> FEATURE:
<223> OTHER INFORMATION: 17-18-19mer-4

<400> SEQUENCE: 498
tccaaattca cttttac 17

<210> SEQ ID NO 499
<211> LENGTH: 18
<212> TYPE: DNA
<213> ORGANISM: Artificial Sequence
<220> FEATURE:
<223> OTHER INFORMATION: 17-18-19mer-40

<400> SEQUENCE: 499
ttccaaattc acttttac 18

<210> SEQ ID NO 500
<211> LENGTH: 19
<212> TYPE: DNA
<213> ORGANISM: Artificial Sequence
<220> FEATURE:
<223> OTHER INFORMATION: 17-18-19mer-46

<400> SEQUENCE: 500
tttccaaatt cacttttac 19

<210> SEQ ID NO 501
<211> LENGTH: 19
<212> TYPE: DNA
<213> ORGANISM: Artificial Sequence
<220> FEATURE:
<223> OTHER INFORMATION: 17-18-19mer-52

<400> SEQUENCE: 501
tttccaaatt cacttttac 19

<210> SEQ ID NO 502
<211> LENGTH: 19
<212> TYPE: DNA
<213> ORGANISM: Artificial Sequence
<220> FEATURE:
<223> OTHER INFORMATION: 17-18-19mer-58

<400> SEQUENCE: 502
tttccaaatt cacttttac 19

<210> SEQ ID NO 503
<211> LENGTH: 19
<212> TYPE: DNA
<213> ORGANISM: Artificial Sequence
<220> FEATURE:
<223> OTHER INFORMATION: 17-18-19mer-64

<400> SEQUENCE: 503
tttccaaatt cacttttac  19

<210> SEQ ID NO 504
<211> LENGTH: 17
<212> TYPE: DNA
<213> ORGANISM: Artificial Sequence
<220> FEATURE:
<223> OTHER INFORMATION: 17-18-19mer-7

<400> SEQUENCE: 504
tccaaattca cttttac  17

<210> SEQ ID NO 505
<211> LENGTH: 19
<212> TYPE: DNA
<213> ORGANISM: Artificial Sequence
<220> FEATURE:
<223> OTHER INFORMATION: 17-18-19mer-70

<400> SEQUENCE: 505
tttccaaatt cacttttac  19

<210> SEQ ID NO 506
<211> LENGTH: 20
<212> TYPE: DNA
<213> ORGANISM: Artificial Sequence
<220> FEATURE:
<223> OTHER INFORMATION: ASO-001933-mm1

<400> SEQUENCE: 506
gtttccaaat tcacttttac  20

<210> SEQ ID NO 507
<211> LENGTH: 20
<212> TYPE: DNA
<213> ORGANISM: Artificial Sequence
<220> FEATURE:
<223> OTHER INFORMATION: ASO-001933-mm2

<400> SEQUENCE: 507
atttccagat tcacttttac  20

<210> SEQ ID NO 508
<211> LENGTH: 20
<212> TYPE: DNA
<213> ORGANISM: Artificial Sequence
<220> FEATURE:
<223> OTHER INFORMATION: ASO-001933-mm3

<400> SEQUENCE: 508
ttttccaaat tcacttttac  20

<210> SEQ ID NO 509
<211> LENGTH: 20
<212> TYPE: DNA
<213> ORGANISM: Artificial Sequence
<220> FEATURE:
<223> OTHER INFORMATION: ASO-001933-mm4

<400> SEQUENCE: 509
gtttccagat tcacttttac  20

<210> SEQ ID NO 510
<211> LENGTH: 20
<212> TYPE: DNA

<213> ORGANISM: Artificial Sequence
<220> FEATURE:
<223> OTHER INFORMATION: ASO-001933-mm5

<400> SEQUENCE: 510
atttccaagt tcacttttgc 20

<210> SEQ ID NO 511
<211> LENGTH: 20
<212> TYPE: DNA
<213> ORGANISM: Artificial Sequence
<220> FEATURE:
<223> OTHER INFORMATION: ASO-001933-mm6

<400> SEQUENCE: 511
atttccagat tcgcttttac 20

<210> SEQ ID NO 512
<211> LENGTH: 16
<212> TYPE: DNA
<213> ORGANISM: Artificial Sequence
<220> FEATURE:
<223> OTHER INFORMATION: SPC-15678-01

<400> SEQUENCE: 512
ccaaattcac ttttac 16

<210> SEQ ID NO 513
<211> LENGTH: 20
<212> TYPE: DNA
<213> ORGANISM: Artificial Sequence
<220> FEATURE:
<223> OTHER INFORMATION: SPC-15857-01

<400> SEQUENCE: 513
atttccaaat tcacttttac 20

<210> SEQ ID NO 514
<211> LENGTH: 20
<212> TYPE: DNA
<213> ORGANISM: Artificial Sequence
<220> FEATURE:
<223> OTHER INFORMATION: SPC-15858-01

<400> SEQUENCE: 514
atttccaaat tcacttttac 20

<210> SEQ ID NO 515
<211> LENGTH: 20
<212> TYPE: DNA
<213> ORGANISM: Artificial Sequence
<220> FEATURE:
<223> OTHER INFORMATION: SPC-15860-01

<400> SEQUENCE: 515
atttccaaat tcacttttac 20

<210> SEQ ID NO 516
<211> LENGTH: 20
<212> TYPE: DNA
<213> ORGANISM: Artificial Sequence
<220> FEATURE:
<223> OTHER INFORMATION: SPC-15864-01

<400> SEQUENCE: 516
atttccaaat tcacttttac 20

<210> SEQ ID NO 517
<211> LENGTH: 20
<212> TYPE: DNA
<213> ORGANISM: Artificial Sequence
<220> FEATURE:
<223> OTHER INFORMATION: SPC-15868-01

<400> SEQUENCE: 517
atttccaaat tcacttttac 20

<210> SEQ ID NO 518
<211> LENGTH: 20
<212> TYPE: DNA
<213> ORGANISM: Artificial Sequence
<220> FEATURE:
<223> OTHER INFORMATION: SPC-15872-01

<400> SEQUENCE: 518
atttccaaat tcacttttac 20

<210> SEQ ID NO 519
<211> LENGTH: 20
<212> TYPE: DNA
<213> ORGANISM: Artificial Sequence
<220> FEATURE:
<223> OTHER INFORMATION: SPC-15873-01

<400> SEQUENCE: 519
atttccaaat tcacttttac 20

<210> SEQ ID NO 520
<211> LENGTH: 20
<212> TYPE: DNA
<213> ORGANISM: Artificial Sequence
<220> FEATURE:
<223> OTHER INFORMATION: SPC-15874-01

<400> SEQUENCE: 520
atttccaaat tcacttttac 20

<210> SEQ ID NO 521
<211> LENGTH: 20
<212> TYPE: DNA
<213> ORGANISM: Artificial Sequence
<220> FEATURE:
<223> OTHER INFORMATION: SPC-15878-01

<400> SEQUENCE: 521
atttccaaat tcacttttac 20

<210> SEQ ID NO 522
<211> LENGTH: 20
<212> TYPE: DNA
<213> ORGANISM: Artificial Sequence
<220> FEATURE:
<223> OTHER INFORMATION: SPC-15879-01

<400> SEQUENCE: 522
atttccaaat tcacttttac 20

<210> SEQ ID NO 523
<211> LENGTH: 20
<212> TYPE: DNA
<213> ORGANISM: Artificial Sequence
<220> FEATURE:

<223> OTHER INFORMATION: SPC-15880-01

<400> SEQUENCE: 523
atttccaaat tcacttttac 20

<210> SEQ ID NO 524
<211> LENGTH: 20
<212> TYPE: DNA
<213> ORGANISM: Artificial Sequence
<220> FEATURE:
<223> OTHER INFORMATION: SPC-15883-01

<400> SEQUENCE: 524
atttccaaat tcacttttac 20

<210> SEQ ID NO 525
<211> LENGTH: 20
<212> TYPE: DNA
<213> ORGANISM: Artificial Sequence
<220> FEATURE:
<223> OTHER INFORMATION: SPC-15888-01

<400> SEQUENCE: 525
atttccaaat tcacttttac 20

<210> SEQ ID NO 526
<211> LENGTH: 20
<212> TYPE: DNA
<213> ORGANISM: Artificial Sequence
<220> FEATURE:
<223> OTHER INFORMATION: ASO-000754

<400> SEQUENCE: 526
tatttccaaa ttcactttta 20

<210> SEQ ID NO 527
<211> LENGTH: 20
<212> TYPE: DNA
<213> ORGANISM: Artificial Sequence
<220> FEATURE:
<223> OTHER INFORMATION: ASO-002055

<400> SEQUENCE: 527
tatttccaaa ttcactttta 20

<210> SEQ ID NO 528
<211> LENGTH: 20
<212> TYPE: DNA
<213> ORGANISM: Artificial Sequence
<220> FEATURE:
<223> OTHER INFORMATION: ASO-002035

<400> SEQUENCE: 528
tatttccaaa ttcactttta 20

<210> SEQ ID NO 529
<211> LENGTH: 20
<212> TYPE: DNA
<213> ORGANISM: Artificial Sequence
<220> FEATURE:
<223> OTHER INFORMATION: ASO-002048

<400> SEQUENCE: 529
tatttccaaa ttcactttta 20

<210> SEQ ID NO 530
<211> LENGTH: 20
<212> TYPE: DNA
<213> ORGANISM: Artificial Sequence
<220> FEATURE:
<223> OTHER INFORMATION: ASO-002053

<400> SEQUENCE: 530
tatttccaaa ttcactttta 20

<210> SEQ ID NO 531
<211> LENGTH: 20
<212> TYPE: DNA
<213> ORGANISM: Artificial Sequence
<220> FEATURE:
<223> OTHER INFORMATION: ASO-002067

<400> SEQUENCE: 531
tatttccaaa ttcactttta 20

<210> SEQ ID NO 532
<211> LENGTH: 20
<212> TYPE: DNA
<213> ORGANISM: Artificial Sequence
<220> FEATURE:
<223> OTHER INFORMATION: ASO-001954

<400> SEQUENCE: 532
tatttccaaa ttcactttta 20

<210> SEQ ID NO 533
<211> LENGTH: 20
<212> TYPE: DNA
<213> ORGANISM: Artificial Sequence
<220> FEATURE:
<223> OTHER INFORMATION: ASO-001947

<400> SEQUENCE: 533
tatttccaaa ttcactttta 20

<210> SEQ ID NO 534
<211> LENGTH: 20
<212> TYPE: DNA
<213> ORGANISM: Artificial Sequence
<220> FEATURE:
<223> OTHER INFORMATION: ASO-002081

<400> SEQUENCE: 534
tatttccaaa ttcactttta 20

<210> SEQ ID NO 535
<211> LENGTH: 20
<212> TYPE: DNA
<213> ORGANISM: Artificial Sequence
<220> FEATURE:
<223> OTHER INFORMATION: ASO-001966

<400> SEQUENCE: 535
tatttccaaa ttcactttta 20

<210> SEQ ID NO 536
<211> LENGTH: 20
<212> TYPE: DNA
<213> ORGANISM: Artificial Sequence
<220> FEATURE:
<223> OTHER INFORMATION: ASO-002025

<400> SEQUENCE: 536
tatttccaaa ttcactttta 20

<210> SEQ ID NO 537
<211> LENGTH: 20
<212> TYPE: DNA
<213> ORGANISM: Artificial Sequence
<220> FEATURE:
<223> OTHER INFORMATION: ASO-002033

<400> SEQUENCE: 537
tatttccaaa ttcactttta 20

<210> SEQ ID NO 538
<211> LENGTH: 20
<212> TYPE: DNA
<213> ORGANISM: Artificial Sequence
<220> FEATURE:
<223> OTHER INFORMATION: ASO-001960

<400> SEQUENCE: 538
tatttccaaa ttcactttta 20

<210> SEQ ID NO 539
<211> LENGTH: 20
<212> TYPE: DNA
<213> ORGANISM: Artificial Sequence
<220> FEATURE:
<223> OTHER INFORMATION: ASO-002056

<400> SEQUENCE: 539
tatttccaaa ttcactttta 20

<210> SEQ ID NO 540
<211> LENGTH: 20
<212> TYPE: DNA
<213> ORGANISM: Artificial Sequence
<220> FEATURE:
<223> OTHER INFORMATION: ASO-002063

<400> SEQUENCE: 540
tatttccaaa ttcactttta 20

<210> SEQ ID NO 541
<211> LENGTH: 20
<212> TYPE: DNA
<213> ORGANISM: Artificial Sequence
<220> FEATURE:
<223> OTHER INFORMATION: ASO-002089

<400> SEQUENCE: 541
tatttccaaa ttcactttta 20

<210> SEQ ID NO 542
<211> LENGTH: 20
<212> TYPE: DNA
<213> ORGANISM: Artificial Sequence
<220> FEATURE:
<223> OTHER INFORMATION: ASO-002073

<400> SEQUENCE: 542
tatttccaaa ttcactttta 20

<210> SEQ ID NO 543
<211> LENGTH: 20

<212> TYPE: DNA
<213> ORGANISM: Artificial Sequence
<220> FEATURE:
<223> OTHER INFORMATION: ASO-002027

<400> SEQUENCE: 543
tatttccaaa ttcactttta 20

<210> SEQ ID NO 544
<211> LENGTH: 20
<212> TYPE: DNA
<213> ORGANISM: Artificial Sequence
<220> FEATURE:
<223> OTHER INFORMATION: ASO-002075

<400> SEQUENCE: 544
tatttccaaa ttcactttta 20

<210> SEQ ID NO 545
<211> LENGTH: 20
<212> TYPE: DNA
<213> ORGANISM: Artificial Sequence
<220> FEATURE:
<223> OTHER INFORMATION: ASO-002028

<400> SEQUENCE: 545
tatttccaaa ttcactttta 20

<210> SEQ ID NO 546
<211> LENGTH: 20
<212> TYPE: DNA
<213> ORGANISM: Artificial Sequence
<220> FEATURE:
<223> OTHER INFORMATION: ASO-002085

<400> SEQUENCE: 546
tatttccaaa ttcactttta 20

<210> SEQ ID NO 547
<211> LENGTH: 20
<212> TYPE: DNA
<213> ORGANISM: Artificial Sequence
<220> FEATURE:
<223> OTHER INFORMATION: ASO-002083

<400> SEQUENCE: 547
tatttccaaa ttcactttta 20

<210> SEQ ID NO 548
<211> LENGTH: 20
<212> TYPE: DNA
<213> ORGANISM: Artificial Sequence
<220> FEATURE:
<223> OTHER INFORMATION: ASO-000759

<400> SEQUENCE: 548
tatttccaaa ttcactttta 20

<210> SEQ ID NO 549
<211> LENGTH: 20
<212> TYPE: DNA
<213> ORGANISM: Artificial Sequence
<220> FEATURE:
<223> OTHER INFORMATION: ASO-000769

<400> SEQUENCE: 549
tatttccaaa ttcactttta 20

<210> SEQ ID NO 550
<211> LENGTH: 20
<212> TYPE: DNA
<213> ORGANISM: Artificial Sequence
<220> FEATURE:
<223> OTHER INFORMATION: ASO-000764

<400> SEQUENCE: 550
tatttccaaa ttcactttta 20

<210> SEQ ID NO 551
<211> LENGTH: 17
<212> TYPE: DNA
<213> ORGANISM: Artificial Sequence
<220> FEATURE:
<223> OTHER INFORMATION: 17-18-19mer-11

<400> SEQUENCE: 551
ttccaaattc actttta 17

<210> SEQ ID NO 552
<211> LENGTH: 17
<212> TYPE: DNA
<213> ORGANISM: Artificial Sequence
<220> FEATURE:
<223> OTHER INFORMATION: 17-18-19mer-14

<400> SEQUENCE: 552
ttccaaattc actttta 17

<210> SEQ ID NO 553
<211> LENGTH: 18
<212> TYPE: DNA
<213> ORGANISM: Artificial Sequence
<220> FEATURE:
<223> OTHER INFORMATION: 17-18-19mer-17

<400> SEQUENCE: 553
tttccaaatt cactttta 18

<210> SEQ ID NO 554
<211> LENGTH: 17
<212> TYPE: DNA
<213> ORGANISM: Artificial Sequence
<220> FEATURE:
<223> OTHER INFORMATION: 17-18-19mer-2

<400> SEQUENCE: 554
ttccaaattc actttta 17

<210> SEQ ID NO 555
<211> LENGTH: 18
<212> TYPE: DNA
<213> ORGANISM: Artificial Sequence
<220> FEATURE:
<223> OTHER INFORMATION: 17-18-19mer-23

<400> SEQUENCE: 555
tttccaaatt cactttta 18

<210> SEQ ID NO 556
<211> LENGTH: 18
<212> TYPE: DNA
<213> ORGANISM: Artificial Sequence
<220> FEATURE:
<223> OTHER INFORMATION: 17-18-19mer-29

<400> SEQUENCE: 556
tttccaaatt cactttta 18

<210> SEQ ID NO 557
<211> LENGTH: 18
<212> TYPE: DNA
<213> ORGANISM: Artificial Sequence
<220> FEATURE:
<223> OTHER INFORMATION: 17-18-19mer-35

<400> SEQUENCE: 557
tttccaaatt cactttta 18

<210> SEQ ID NO 558
<211> LENGTH: 18
<212> TYPE: DNA
<213> ORGANISM: Artificial Sequence
<220> FEATURE:
<223> OTHER INFORMATION: 17-18-19mer-41

<400> SEQUENCE: 558
tttccaaatt cactttta 18

<210> SEQ ID NO 559
<211> LENGTH: 19
<212> TYPE: DNA
<213> ORGANISM: Artificial Sequence
<220> FEATURE:
<223> OTHER INFORMATION: 17-18-19mer-47

<400> SEQUENCE: 559
atttccaaat tcactttta 19

<210> SEQ ID NO 560
<211> LENGTH: 17
<212> TYPE: DNA
<213> ORGANISM: Artificial Sequence
<220> FEATURE:
<223> OTHER INFORMATION: 17-18-19mer-5

<400> SEQUENCE: 560
ttccaaattc actttta 17

<210> SEQ ID NO 561
<211> LENGTH: 19
<212> TYPE: DNA
<213> ORGANISM: Artificial Sequence
<220> FEATURE:
<223> OTHER INFORMATION: 17-18-19mer-53

<400> SEQUENCE: 561
atttccaaat tcactttta 19

<210> SEQ ID NO 562
<211> LENGTH: 19
<212> TYPE: DNA
<213> ORGANISM: Artificial Sequence
<220> FEATURE:
<223> OTHER INFORMATION: 17-18-19mer-59

<400> SEQUENCE: 562
atttccaaat tcactttta 19

<210> SEQ ID NO 563
<211> LENGTH: 19
<212> TYPE: DNA
<213> ORGANISM: Artificial Sequence
<220> FEATURE:
<223> OTHER INFORMATION: 17-18-19mer-65

<400> SEQUENCE: 563
atttccaaat tcactttta 19

<210> SEQ ID NO 564
<211> LENGTH: 19
<212> TYPE: DNA
<213> ORGANISM: Artificial Sequence
<220> FEATURE:
<223> OTHER INFORMATION: 17-18-19mer-71

<400> SEQUENCE: 564
atttccaaat tcactttta 19

<210> SEQ ID NO 565
<211> LENGTH: 17
<212> TYPE: DNA
<213> ORGANISM: Artificial Sequence
<220> FEATURE:
<223> OTHER INFORMATION: 17-18-19mer-8

<400> SEQUENCE: 565
ttccaaattc actttta 17

<210> SEQ ID NO 566
<211> LENGTH: 20
<212> TYPE: DNA
<213> ORGANISM: Artificial Sequence
<220> FEATURE:
<223> OTHER INFORMATION: ASO-001954-mm1

<400> SEQUENCE: 566
tatttccaga ttcactttta 20

<210> SEQ ID NO 567
<211> LENGTH: 20
<212> TYPE: DNA
<213> ORGANISM: Artificial Sequence
<220> FEATURE:
<223> OTHER INFORMATION: ASO-001954-mm2

<400> SEQUENCE: 567
tatttccgaa ttcactttta 20

<210> SEQ ID NO 568
<211> LENGTH: 20
<212> TYPE: DNA
<213> ORGANISM: Artificial Sequence
<220> FEATURE:
<223> OTHER INFORMATION: ASO-001954-mm3

<400> SEQUENCE: 568
gatttccaaa ttcactttta 20

<210> SEQ ID NO 569
<211> LENGTH: 20
<212> TYPE: DNA
<213> ORGANISM: Artificial Sequence
<220> FEATURE:
<223> OTHER INFORMATION: ASO-001954-mm4

<400> SEQUENCE: 569
ggtttccaaa ttcactttta 20

<210> SEQ ID NO 570
<211> LENGTH: 20
<212> TYPE: DNA
<213> ORGANISM: Artificial Sequence
<220> FEATURE:
<223> OTHER INFORMATION: ASO-001954-mm5

<400> SEQUENCE: 570
aatttccaga ttcactttta 20

<210> SEQ ID NO 571
<211> LENGTH: 20
<212> TYPE: DNA
<213> ORGANISM: Artificial Sequence
<220> FEATURE:
<223> OTHER INFORMATION: ASO-001954-mm6

<400> SEQUENCE: 571
tatttccaag ttcgctttta 20

<210> SEQ ID NO 572
<211> LENGTH: 16
<212> TYPE: DNA
<213> ORGANISM: Artificial Sequence
<220> FEATURE:
<223> OTHER INFORMATION: SPC-15677-01

<400> SEQUENCE: 572
tccaaattca ctttta 16

<210> SEQ ID NO 573
<211> LENGTH: 20
<212> TYPE: DNA
<213> ORGANISM: Artificial Sequence
<220> FEATURE:
<223> OTHER INFORMATION: SPC-15859-01

<400> SEQUENCE: 573
tatttccaaa ttcactttta 20

<210> SEQ ID NO 574
<211> LENGTH: 20
<212> TYPE: DNA
<213> ORGANISM: Artificial Sequence
<220> FEATURE:
<223> OTHER INFORMATION: SPC-15861-01

<400> SEQUENCE: 574
tatttccaaa ttcactttta 20

<210> SEQ ID NO 575
<211> LENGTH: 20
<212> TYPE: DNA
<213> ORGANISM: Artificial Sequence
<220> FEATURE:
<223> OTHER INFORMATION: SPC-15862-01

<400> SEQUENCE: 575
tatttccaaa ttcactttta 20

<210> SEQ ID NO 576

<211> LENGTH: 20
<212> TYPE: DNA
<213> ORGANISM: Artificial Sequence
<220> FEATURE:
<223> OTHER INFORMATION: SPC-15863-01

<400> SEQUENCE: 576
tatttccaaa ttcactttta 20

<210> SEQ ID NO 577
<211> LENGTH: 20
<212> TYPE: DNA
<213> ORGANISM: Artificial Sequence
<220> FEATURE:
<223> OTHER INFORMATION: SPC-15865-01

<400> SEQUENCE: 577
tatttccaaa ttcactttta 20

<210> SEQ ID NO 578
<211> LENGTH: 20
<212> TYPE: DNA
<213> ORGANISM: Artificial Sequence
<220> FEATURE:
<223> OTHER INFORMATION: SPC-15867-01

<400> SEQUENCE: 578
tatttccaaa ttcactttta 20

<210> SEQ ID NO 579
<211> LENGTH: 20
<212> TYPE: DNA
<213> ORGANISM: Artificial Sequence
<220> FEATURE:
<223> OTHER INFORMATION: SPC-15869-01

<400> SEQUENCE: 579
tatttccaaa ttcactttta 20

<210> SEQ ID NO 580
<211> LENGTH: 20
<212> TYPE: DNA
<213> ORGANISM: Artificial Sequence
<220> FEATURE:
<223> OTHER INFORMATION: SPC-15871-01

<400> SEQUENCE: 580
tatttccaaa ttcactttta 20

<210> SEQ ID NO 581
<211> LENGTH: 20
<212> TYPE: DNA
<213> ORGANISM: Artificial Sequence
<220> FEATURE:
<223> OTHER INFORMATION: SPC-15882-01

<400> SEQUENCE: 581
tatttccaaa ttcactttta 20

<210> SEQ ID NO 582
<211> LENGTH: 20
<212> TYPE: DNA
<213> ORGANISM: Artificial Sequence
<220> FEATURE:
<223> OTHER INFORMATION: SPC-15886-01

<400> SEQUENCE: 582
tatttccaaa ttcactttta 20

<210> SEQ ID NO 583
<211> LENGTH: 20
<212> TYPE: DNA
<213> ORGANISM: Artificial Sequence
<220> FEATURE:
<223> OTHER INFORMATION: SPC-15887-01

<400> SEQUENCE: 583
tatttccaaa ttcactttta 20

<210> SEQ ID NO 584
<211> LENGTH: 20
<212> TYPE: DNA
<213> ORGANISM: Artificial Sequence
<220> FEATURE:
<223> OTHER INFORMATION: SPC-15890-01

<400> SEQUENCE: 584
tatttccaaa ttcactttta 20

<210> SEQ ID NO 585
<211> LENGTH: 20
<212> TYPE: DNA
<213> ORGANISM: Artificial Sequence
<220> FEATURE:
<223> OTHER INFORMATION: SPC-15893-01

<400> SEQUENCE: 585
tatttccaaa ttcactttta 20

<210> SEQ ID NO 586
<211> LENGTH: 20
<212> TYPE: DNA
<213> ORGANISM: Artificial Sequence
<220> FEATURE:
<223> OTHER INFORMATION: ASO-002072

<400> SEQUENCE: 586
ttatttccaa attcactttt 20

<210> SEQ ID NO 587
<211> LENGTH: 20
<212> TYPE: DNA
<213> ORGANISM: Artificial Sequence
<220> FEATURE:
<223> OTHER INFORMATION: ASO-000755

<400> SEQUENCE: 587
ttatttccaa attcactttt 20

<210> SEQ ID NO 588
<211> LENGTH: 20
<212> TYPE: DNA
<213> ORGANISM: Artificial Sequence
<220> FEATURE:
<223> OTHER INFORMATION: ASO-002071

<400> SEQUENCE: 588
ttatttccaa attcactttt 20

<210> SEQ ID NO 589
<211> LENGTH: 20
<212> TYPE: DNA

<213> ORGANISM: Artificial Sequence
<220> FEATURE:
<223> OTHER INFORMATION: ASO-000760

<400> SEQUENCE: 589
ttatttccaa attcactttt 20

<210> SEQ ID NO 590
<211> LENGTH: 20
<212> TYPE: DNA
<213> ORGANISM: Artificial Sequence
<220> FEATURE:
<223> OTHER INFORMATION: ASO-001920

<400> SEQUENCE: 590
ttatttccaa attcactttt 20

<210> SEQ ID NO 591
<211> LENGTH: 20
<212> TYPE: DNA
<213> ORGANISM: Artificial Sequence
<220> FEATURE:
<223> OTHER INFORMATION: ASO-002080

<400> SEQUENCE: 591
ttatttccaa attcactttt 20

<210> SEQ ID NO 592
<211> LENGTH: 20
<212> TYPE: DNA
<213> ORGANISM: Artificial Sequence
<220> FEATURE:
<223> OTHER INFORMATION: ASO-001927

<400> SEQUENCE: 592
ttatttccaa attcactttt 20

<210> SEQ ID NO 593
<211> LENGTH: 20
<212> TYPE: DNA
<213> ORGANISM: Artificial Sequence
<220> FEATURE:
<223> OTHER INFORMATION: ASO-001941

<400> SEQUENCE: 593
ttatttccaa attcactttt 20

<210> SEQ ID NO 594
<211> LENGTH: 20
<212> TYPE: DNA
<213> ORGANISM: Artificial Sequence
<220> FEATURE:
<223> OTHER INFORMATION: ASO-002045

<400> SEQUENCE: 594
ttatttccaa attcactttt 20

<210> SEQ ID NO 595
<211> LENGTH: 20
<212> TYPE: DNA
<213> ORGANISM: Artificial Sequence
<220> FEATURE:
<223> OTHER INFORMATION: ASO-001934

<400> SEQUENCE: 595
ttatttccaa attcactttt 20

<210> SEQ ID NO 596
<211> LENGTH: 20
<212> TYPE: DNA
<213> ORGANISM: Artificial Sequence
<220> FEATURE:
<223> OTHER INFORMATION: ASO-002074

<400> SEQUENCE: 596
ttatttccaa attcactttt 20

<210> SEQ ID NO 597
<211> LENGTH: 20
<212> TYPE: DNA
<213> ORGANISM: Artificial Sequence
<220> FEATURE:
<223> OTHER INFORMATION: ASO-002093

<400> SEQUENCE: 597
ttatttccaa attcactttt 20

<210> SEQ ID NO 598
<211> LENGTH: 20
<212> TYPE: DNA
<213> ORGANISM: Artificial Sequence
<220> FEATURE:
<223> OTHER INFORMATION: ASO-002054

<400> SEQUENCE: 598
ttatttccaa attcactttt 20

<210> SEQ ID NO 599
<211> LENGTH: 20
<212> TYPE: DNA
<213> ORGANISM: Artificial Sequence
<220> FEATURE:
<223> OTHER INFORMATION: ASO-002091

<400> SEQUENCE: 599
ttatttccaa attcactttt 20

<210> SEQ ID NO 600
<211> LENGTH: 20
<212> TYPE: DNA
<213> ORGANISM: Artificial Sequence
<220> FEATURE:
<223> OTHER INFORMATION: ASO-002064

<400> SEQUENCE: 600
ttatttccaa attcactttt 20

<210> SEQ ID NO 601
<211> LENGTH: 20
<212> TYPE: DNA
<213> ORGANISM: Artificial Sequence
<220> FEATURE:
<223> OTHER INFORMATION: ASO-002066

<400> SEQUENCE: 601
ttatttccaa attcactttt 20

<210> SEQ ID NO 602
<211> LENGTH: 20
<212> TYPE: DNA
<213> ORGANISM: Artificial Sequence
<220> FEATURE:

<223> OTHER INFORMATION: ASO-002044

<400> SEQUENCE: 602
ttatttccaa attcactttt 20

<210> SEQ ID NO 603
<211> LENGTH: 20
<212> TYPE: DNA
<213> ORGANISM: Artificial Sequence
<220> FEATURE:
<223> OTHER INFORMATION: ASO-002047

<400> SEQUENCE: 603
ttatttccaa attcactttt 20

<210> SEQ ID NO 604
<211> LENGTH: 20
<212> TYPE: DNA
<213> ORGANISM: Artificial Sequence
<220> FEATURE:
<223> OTHER INFORMATION: ASO-002046

<400> SEQUENCE: 604
ttatttccaa attcactttt 20

<210> SEQ ID NO 605
<211> LENGTH: 20
<212> TYPE: DNA
<213> ORGANISM: Artificial Sequence
<220> FEATURE:
<223> OTHER INFORMATION: ASO-000765

<400> SEQUENCE: 605
ttatttccaa attcactttt 20

<210> SEQ ID NO 606
<211> LENGTH: 20
<212> TYPE: DNA
<213> ORGANISM: Artificial Sequence
<220> FEATURE:
<223> OTHER INFORMATION: ASO-000770

<400> SEQUENCE: 606
ttatttccaa attcactttt 20

<210> SEQ ID NO 607
<211> LENGTH: 17
<212> TYPE: DNA
<213> ORGANISM: Artificial Sequence
<220> FEATURE:
<223> OTHER INFORMATION: 17-18-19mer-12

<400> SEQUENCE: 607
tttccaaatt cactttt 17

<210> SEQ ID NO 608
<211> LENGTH: 17
<212> TYPE: DNA
<213> ORGANISM: Artificial Sequence
<220> FEATURE:
<223> OTHER INFORMATION: 17-18-19mer-15

<400> SEQUENCE: 608
tttccaaatt cactttt 17

<210> SEQ ID NO 609
<211> LENGTH: 18
<212> TYPE: DNA
<213> ORGANISM: Artificial Sequence
<220> FEATURE:
<223> OTHER INFORMATION: 17-18-19mer-18

<400> SEQUENCE: 609
atttccaaat tcactttt 18

<210> SEQ ID NO 610
<211> LENGTH: 18
<212> TYPE: DNA
<213> ORGANISM: Artificial Sequence
<220> FEATURE:
<223> OTHER INFORMATION: 17-18-19mer-24

<400> SEQUENCE: 610
atttccaaat tcactttt 18

<210> SEQ ID NO 611
<211> LENGTH: 17
<212> TYPE: DNA
<213> ORGANISM: Artificial Sequence
<220> FEATURE:
<223> OTHER INFORMATION: 17-18-19mer-3

<400> SEQUENCE: 611
tttccaaatt cactttt 17

<210> SEQ ID NO 612
<211> LENGTH: 18
<212> TYPE: DNA
<213> ORGANISM: Artificial Sequence
<220> FEATURE:
<223> OTHER INFORMATION: 17-18-19mer-30

<400> SEQUENCE: 612
atttccaaat tcactttt 18

<210> SEQ ID NO 613
<211> LENGTH: 18
<212> TYPE: DNA
<213> ORGANISM: Artificial Sequence
<220> FEATURE:
<223> OTHER INFORMATION: 17-18-19mer-36

<400> SEQUENCE: 613
atttccaaat tcactttt 18

<210> SEQ ID NO 614
<211> LENGTH: 18
<212> TYPE: DNA
<213> ORGANISM: Artificial Sequence
<220> FEATURE:
<223> OTHER INFORMATION: 17-18-19mer-42

<400> SEQUENCE: 614
atttccaaat tcactttt 18

<210> SEQ ID NO 615
<211> LENGTH: 19
<212> TYPE: DNA
<213> ORGANISM: Artificial Sequence
<220> FEATURE:
<223> OTHER INFORMATION: 17-18-19mer-48

<400> SEQUENCE: 615
tatttccaaa ttcactttt 19

<210> SEQ ID NO 616
<211> LENGTH: 19
<212> TYPE: DNA
<213> ORGANISM: Artificial Sequence
<220> FEATURE:
<223> OTHER INFORMATION: 17-18-19mer-54

<400> SEQUENCE: 616
tatttccaaa ttcactttt 19

<210> SEQ ID NO 617
<211> LENGTH: 17
<212> TYPE: DNA
<213> ORGANISM: Artificial Sequence
<220> FEATURE:
<223> OTHER INFORMATION: 17-18-19mer-6

<400> SEQUENCE: 617
tttccaaatt cactttt 17

<210> SEQ ID NO 618
<211> LENGTH: 19
<212> TYPE: DNA
<213> ORGANISM: Artificial Sequence
<220> FEATURE:
<223> OTHER INFORMATION: 17-18-19mer-60

<400> SEQUENCE: 618
tatttccaaa ttcactttt 19

<210> SEQ ID NO 619
<211> LENGTH: 19
<212> TYPE: DNA
<213> ORGANISM: Artificial Sequence
<220> FEATURE:
<223> OTHER INFORMATION: 17-18-19mer-66

<400> SEQUENCE: 619
tatttccaaa ttcactttt 19

<210> SEQ ID NO 620
<211> LENGTH: 19
<212> TYPE: DNA
<213> ORGANISM: Artificial Sequence
<220> FEATURE:
<223> OTHER INFORMATION: 17-18-19mer-72

<400> SEQUENCE: 620
tatttccaaa ttcactttt 19

<210> SEQ ID NO 621
<211> LENGTH: 17
<212> TYPE: DNA
<213> ORGANISM: Artificial Sequence
<220> FEATURE:
<223> OTHER INFORMATION: 17-18-19mer-9

<400> SEQUENCE: 621
tttccaaatt cactttt 17

<210> SEQ ID NO 622
<211> LENGTH: 20

<212> TYPE: DNA
<213> ORGANISM: Artificial Sequence
<220> FEATURE:
<223> OTHER INFORMATION: ASO-001941-mm1

<400> SEQUENCE: 622
atatttccaa attcactttt 20

<210> SEQ ID NO 623
<211> LENGTH: 20
<212> TYPE: DNA
<213> ORGANISM: Artificial Sequence
<220> FEATURE:
<223> OTHER INFORMATION: ASO-001941-mm2

<400> SEQUENCE: 623
ttatttccaa attcacttta 20

<210> SEQ ID NO 624
<211> LENGTH: 20
<212> TYPE: DNA
<213> ORGANISM: Artificial Sequence
<220> FEATURE:
<223> OTHER INFORMATION: ASO-001941-mm3

<400> SEQUENCE: 624
ttatttccaa attcactttg 20

<210> SEQ ID NO 625
<211> LENGTH: 20
<212> TYPE: DNA
<213> ORGANISM: Artificial Sequence
<220> FEATURE:
<223> OTHER INFORMATION: ASO-001941-mm4

<400> SEQUENCE: 625
atatttccag attcactttt 20

<210> SEQ ID NO 626
<211> LENGTH: 20
<212> TYPE: DNA
<213> ORGANISM: Artificial Sequence
<220> FEATURE:
<223> OTHER INFORMATION: ASO-001941-mm5

<400> SEQUENCE: 626
ttatttccaa gttcactttc 20

<210> SEQ ID NO 627
<211> LENGTH: 20
<212> TYPE: DNA
<213> ORGANISM: Artificial Sequence
<220> FEATURE:
<223> OTHER INFORMATION: ASO-001941-mm6

<400> SEQUENCE: 627
ttatttccag attcgctttt 20

<210> SEQ ID NO 628
<211> LENGTH: 16
<212> TYPE: DNA
<213> ORGANISM: Artificial Sequence
<220> FEATURE:
<223> OTHER INFORMATION: SPC-15676-01

<400> SEQUENCE: 628
ttccaaattc actttt 16

<210> SEQ ID NO 629
<211> LENGTH: 20
<212> TYPE: DNA
<213> ORGANISM: Artificial Sequence
<220> FEATURE:
<223> OTHER INFORMATION: SPC-15866-01

<400> SEQUENCE: 629
ttatttccaa attcactttt 20

<210> SEQ ID NO 630
<211> LENGTH: 20
<212> TYPE: DNA
<213> ORGANISM: Artificial Sequence
<220> FEATURE:
<223> OTHER INFORMATION: SPC-15870-01

<400> SEQUENCE: 630
ttatttccaa attcactttt 20

<210> SEQ ID NO 631
<211> LENGTH: 20
<212> TYPE: DNA
<213> ORGANISM: Artificial Sequence
<220> FEATURE:
<223> OTHER INFORMATION: SPC-15875-01

<400> SEQUENCE: 631
ttatttccaa attcactttt 20

<210> SEQ ID NO 632
<211> LENGTH: 20
<212> TYPE: DNA
<213> ORGANISM: Artificial Sequence
<220> FEATURE:
<223> OTHER INFORMATION: SPC-15876-01

<400> SEQUENCE: 632
ttatttccaa attcactttt 20

<210> SEQ ID NO 633
<211> LENGTH: 20
<212> TYPE: DNA
<213> ORGANISM: Artificial Sequence
<220> FEATURE:
<223> OTHER INFORMATION: SPC-15877-01

<400> SEQUENCE: 633
ttatttccaa attcactttt 20

<210> SEQ ID NO 634
<211> LENGTH: 20
<212> TYPE: DNA
<213> ORGANISM: Artificial Sequence
<220> FEATURE:
<223> OTHER INFORMATION: SPC-15881-01

<400> SEQUENCE: 634
ttatttccaa attcactttt 20

<210> SEQ ID NO 635
<211> LENGTH: 20
<212> TYPE: DNA
<213> ORGANISM: Artificial Sequence

<220> FEATURE:
<223> OTHER INFORMATION: SPC-15884-01

<400> SEQUENCE: 635
ttatttccaa attcactttt 20

<210> SEQ ID NO 636
<211> LENGTH: 20
<212> TYPE: DNA
<213> ORGANISM: Artificial Sequence
<220> FEATURE:
<223> OTHER INFORMATION: SPC-15885-01

<400> SEQUENCE: 636
ttatttccaa attcactttt 20

<210> SEQ ID NO 637
<211> LENGTH: 20
<212> TYPE: DNA
<213> ORGANISM: Artificial Sequence
<220> FEATURE:
<223> OTHER INFORMATION: SPC-15889-01

<400> SEQUENCE: 637
ttatttccaa attcactttt 20

<210> SEQ ID NO 638
<211> LENGTH: 20
<212> TYPE: DNA
<213> ORGANISM: Artificial Sequence
<220> FEATURE:
<223> OTHER INFORMATION: SPC-15891-01

<400> SEQUENCE: 638
ttatttccaa attcactttt 20

<210> SEQ ID NO 639
<211> LENGTH: 20
<212> TYPE: DNA
<213> ORGANISM: Artificial Sequence
<220> FEATURE:
<223> OTHER INFORMATION: SPC-15892-01

<400> SEQUENCE: 639
ttatttccaa attcactttt 20

<210> SEQ ID NO 640
<211> LENGTH: 20
<212> TYPE: DNA
<213> ORGANISM: Artificial Sequence
<220> FEATURE:
<223> OTHER INFORMATION: SPC-15894-01

<400> SEQUENCE: 640
ttatttccaa attcactttt 20

<210> SEQ ID NO 641
<211> LENGTH: 20
<212> TYPE: DNA
<213> ORGANISM: Artificial Sequence
<220> FEATURE:
<223> OTHER INFORMATION: SPC-15895-01

<400> SEQUENCE: 641
ttatttccaa attcactttt 20

<210> SEQ ID NO 642
<211> LENGTH: 20
<212> TYPE: DNA
<213> ORGANISM: Artificial Sequence
<220> FEATURE:
<223> OTHER INFORMATION: SPC-15896-01

<400> SEQUENCE: 642
ttatttccaa attcactttt 20

<210> SEQ ID NO 643
<211> LENGTH: 25
<212> TYPE: DNA
<213> ORGANISM: Artificial Sequence
<220> FEATURE:
<223> OTHER INFORMATION: ASO-002020

<400> SEQUENCE: 643
actttatttc caaattcact tttac 25

<210> SEQ ID NO 644
<211> LENGTH: 20
<212> TYPE: DNA
<213> ORGANISM: Artificial Sequence
<220> FEATURE:
<223> OTHER INFORMATION: ASO-000756

<400> SEQUENCE: 644
tttatttcca aattcacttt 20

<210> SEQ ID NO 645
<211> LENGTH: 20
<212> TYPE: DNA
<213> ORGANISM: Artificial Sequence
<220> FEATURE:
<223> OTHER INFORMATION: ASO-001967

<400> SEQUENCE: 645
tttatttcca aattcacttt 20

<210> SEQ ID NO 646
<211> LENGTH: 20
<212> TYPE: DNA
<213> ORGANISM: Artificial Sequence
<220> FEATURE:
<223> OTHER INFORMATION: ASO-001955

<400> SEQUENCE: 646
tttatttcca aattcacttt 20

<210> SEQ ID NO 647
<211> LENGTH: 20
<212> TYPE: DNA
<213> ORGANISM: Artificial Sequence
<220> FEATURE:
<223> OTHER INFORMATION: ASO-001948

<400> SEQUENCE: 647
tttatttcca aattcacttt 20

<210> SEQ ID NO 648
<211> LENGTH: 25
<212> TYPE: DNA
<213> ORGANISM: Artificial Sequence
<220> FEATURE:
<223> OTHER INFORMATION: ASO-002086

<400> SEQUENCE: 648
actttatttc caaattcact tttac 25

<210> SEQ ID NO 649
<211> LENGTH: 25
<212> TYPE: DNA
<213> ORGANISM: Artificial Sequence
<220> FEATURE:
<223> OTHER INFORMATION: ASO-002029

<400> SEQUENCE: 649
actttatttc caaattcact tttac 25

<210> SEQ ID NO 650
<211> LENGTH: 20
<212> TYPE: DNA
<213> ORGANISM: Artificial Sequence
<220> FEATURE:
<223> OTHER INFORMATION: ASO-001961

<400> SEQUENCE: 650
tttatttcca aattcacttt 20

<210> SEQ ID NO 651
<211> LENGTH: 25
<212> TYPE: DNA
<213> ORGANISM: Artificial Sequence
<220> FEATURE:
<223> OTHER INFORMATION: ASO-002095

<400> SEQUENCE: 651
actttatttc caaattcact tttac 25

<210> SEQ ID NO 652
<211> LENGTH: 25
<212> TYPE: DNA
<213> ORGANISM: Artificial Sequence
<220> FEATURE:
<223> OTHER INFORMATION: ASO-002059

<400> SEQUENCE: 652
actttatttc caaattcact tttac 25

<210> SEQ ID NO 653
<211> LENGTH: 25
<212> TYPE: DNA
<213> ORGANISM: Artificial Sequence
<220> FEATURE:
<223> OTHER INFORMATION: ASO-002077

<400> SEQUENCE: 653
actttatttc caaattcact tttac 25

<210> SEQ ID NO 654
<211> LENGTH: 25
<212> TYPE: DNA
<213> ORGANISM: Artificial Sequence
<220> FEATURE:
<223> OTHER INFORMATION: ASO-002021

<400> SEQUENCE: 654
actttatttc caaattcact tttac 25

<210> SEQ ID NO 655

<211> LENGTH: 20
<212> TYPE: DNA
<213> ORGANISM: Artificial Sequence
<220> FEATURE:
<223> OTHER INFORMATION: ASO-000761

<400> SEQUENCE: 655
tttatttcca aattcacttt 20

<210> SEQ ID NO 656
<211> LENGTH: 25
<212> TYPE: DNA
<213> ORGANISM: Artificial Sequence
<220> FEATURE:
<223> OTHER INFORMATION: ASO-002068

<400> SEQUENCE: 656
actttatttc caaattcact tttac 25

<210> SEQ ID NO 657
<211> LENGTH: 20
<212> TYPE: DNA
<213> ORGANISM: Artificial Sequence
<220> FEATURE:
<223> OTHER INFORMATION: ASO-000766

<400> SEQUENCE: 657
tttatttcca aattcacttt 20

<210> SEQ ID NO 658
<211> LENGTH: 20
<212> TYPE: DNA
<213> ORGANISM: Artificial Sequence
<220> FEATURE:
<223> OTHER INFORMATION: ASO-000771

<400> SEQUENCE: 658
tttatttcca aattcacttt 20

<210> SEQ ID NO 659
<211> LENGTH: 18
<212> TYPE: DNA
<213> ORGANISM: Artificial Sequence
<220> FEATURE:
<223> OTHER INFORMATION: 17-18-19mer-19

<400> SEQUENCE: 659
tatttccaaa ttcacttt 18

<210> SEQ ID NO 660
<211> LENGTH: 18
<212> TYPE: DNA
<213> ORGANISM: Artificial Sequence
<220> FEATURE:
<223> OTHER INFORMATION: 17-18-19mer-25

<400> SEQUENCE: 660
tatttccaaa ttcacttt 18

<210> SEQ ID NO 661
<211> LENGTH: 18
<212> TYPE: DNA
<213> ORGANISM: Artificial Sequence
<220> FEATURE:
<223> OTHER INFORMATION: 17-18-19mer-31

<400> SEQUENCE: 661
tatttccaaa ttcacttt 18

<210> SEQ ID NO 662
<211> LENGTH: 18
<212> TYPE: DNA
<213> ORGANISM: Artificial Sequence
<220> FEATURE:
<223> OTHER INFORMATION: 17-18-19mer-37

<400> SEQUENCE: 662
tatttccaaa ttcacttt 18

<210> SEQ ID NO 663
<211> LENGTH: 18
<212> TYPE: DNA
<213> ORGANISM: Artificial Sequence
<220> FEATURE:
<223> OTHER INFORMATION: 17-18-19mer-43

<400> SEQUENCE: 663
tatttccaaa ttcacttt 18

<210> SEQ ID NO 664
<211> LENGTH: 19
<212> TYPE: DNA
<213> ORGANISM: Artificial Sequence
<220> FEATURE:
<223> OTHER INFORMATION: 17-18-19mer-49

<400> SEQUENCE: 664
ttatttccaa attcacttt 19

<210> SEQ ID NO 665
<211> LENGTH: 19
<212> TYPE: DNA
<213> ORGANISM: Artificial Sequence
<220> FEATURE:
<223> OTHER INFORMATION: 17-18-19mer-55

<400> SEQUENCE: 665
ttatttccaa attcacttt 19

<210> SEQ ID NO 666
<211> LENGTH: 19
<212> TYPE: DNA
<213> ORGANISM: Artificial Sequence
<220> FEATURE:
<223> OTHER INFORMATION: 17-18-19mer-61

<400> SEQUENCE: 666
ttatttccaa attcacttt 19

<210> SEQ ID NO 667
<211> LENGTH: 19
<212> TYPE: DNA
<213> ORGANISM: Artificial Sequence
<220> FEATURE:
<223> OTHER INFORMATION: 17-18-19mer-67

<400> SEQUENCE: 667
ttatttccaa attcacttt 19

<210> SEQ ID NO 668
<211> LENGTH: 19
<212> TYPE: DNA

<213> ORGANISM: Artificial Sequence
<220> FEATURE:
<223> OTHER INFORMATION: 17-18-19mer-73

<400> SEQUENCE: 668
ttatttccaa attcacttt 19

<210> SEQ ID NO 669
<211> LENGTH: 20
<212> TYPE: DNA
<213> ORGANISM: Artificial Sequence
<220> FEATURE:
<223> OTHER INFORMATION: ASO-001967-mm1

<400> SEQUENCE: 669
attatttcca aattcacttt 20

<210> SEQ ID NO 670
<211> LENGTH: 20
<212> TYPE: DNA
<213> ORGANISM: Artificial Sequence
<220> FEATURE:
<223> OTHER INFORMATION: ASO-001967-mm2

<400> SEQUENCE: 670
tttatttcca agttcacttt 20

<210> SEQ ID NO 671
<211> LENGTH: 20
<212> TYPE: DNA
<213> ORGANISM: Artificial Sequence
<220> FEATURE:
<223> OTHER INFORMATION: ASO-001967-mm3

<400> SEQUENCE: 671
gttatttcca aattcacttt 20

<210> SEQ ID NO 672
<211> LENGTH: 20
<212> TYPE: DNA
<213> ORGANISM: Artificial Sequence
<220> FEATURE:
<223> OTHER INFORMATION: ASO-001967-mm4

<400> SEQUENCE: 672
attatttcca gattcacttt 20

<210> SEQ ID NO 673
<211> LENGTH: 20
<212> TYPE: DNA
<213> ORGANISM: Artificial Sequence
<220> FEATURE:
<223> OTHER INFORMATION: ASO-001967-mm5

<400> SEQUENCE: 673
tttatttcca ggttcacttt 20

<210> SEQ ID NO 674
<211> LENGTH: 20
<212> TYPE: DNA
<213> ORGANISM: Artificial Sequence
<220> FEATURE:
<223> OTHER INFORMATION: ASO-001967-mm6

<400> SEQUENCE: 674
cttatttcca agttcacttt 20

<210> SEQ ID NO 675
<211> LENGTH: 16
<212> TYPE: DNA
<213> ORGANISM: Artificial Sequence
<220> FEATURE:
<223> OTHER INFORMATION: SPC-15675-01

<400> SEQUENCE: 675
tttccaaatt cacttt 16

<210> SEQ ID NO 676
<211> LENGTH: 20
<212> TYPE: DNA
<213> ORGANISM: Artificial Sequence
<220> FEATURE:
<223> OTHER INFORMATION: ASO-002006

<400> SEQUENCE: 676
ctttatttcc aaattcactt 20

<210> SEQ ID NO 677
<211> LENGTH: 20
<212> TYPE: DNA
<213> ORGANISM: Artificial Sequence
<220> FEATURE:
<223> OTHER INFORMATION: ASO-000757

<400> SEQUENCE: 677
ctttatttcc aaattcactt 20

<210> SEQ ID NO 678
<211> LENGTH: 20
<212> TYPE: DNA
<213> ORGANISM: Artificial Sequence
<220> FEATURE:
<223> OTHER INFORMATION: ASO-002017

<400> SEQUENCE: 678
ctttatttcc aaattcactt 20

<210> SEQ ID NO 679
<211> LENGTH: 20
<212> TYPE: DNA
<213> ORGANISM: Artificial Sequence
<220> FEATURE:
<223> OTHER INFORMATION: ASO-001928

<400> SEQUENCE: 679
ctttatttcc aaattcactt 20

<210> SEQ ID NO 680
<211> LENGTH: 21
<212> TYPE: DNA
<213> ORGANISM: Artificial Sequence
<220> FEATURE:
<223> OTHER INFORMATION: ASO-001968

<400> SEQUENCE: 680
actttatttc caaattcact t 21

<210> SEQ ID NO 681
<211> LENGTH: 20
<212> TYPE: DNA
<213> ORGANISM: Artificial Sequence
<220> FEATURE:

<223> OTHER INFORMATION: ASO-001921

<400> SEQUENCE: 681
ctttatttcc aaattcactt 20

<210> SEQ ID NO 682
<211> LENGTH: 20
<212> TYPE: DNA
<213> ORGANISM: Artificial Sequence
<220> FEATURE:
<223> OTHER INFORMATION: ASO-001989

<400> SEQUENCE: 682
ctttatttcc aaattcactt 20

<210> SEQ ID NO 683
<211> LENGTH: 20
<212> TYPE: DNA
<213> ORGANISM: Artificial Sequence
<220> FEATURE:
<223> OTHER INFORMATION: ASO-001942

<400> SEQUENCE: 683
ctttatttcc aaattcactt 20

<210> SEQ ID NO 684
<211> LENGTH: 15
<212> TYPE: DNA
<213> ORGANISM: Artificial Sequence
<220> FEATURE:
<223> OTHER INFORMATION: ASO-000128

<400> SEQUENCE: 684
tttccaaatt cactt 15

<210> SEQ ID NO 685
<211> LENGTH: 20
<212> TYPE: DNA
<213> ORGANISM: Artificial Sequence
<220> FEATURE:
<223> OTHER INFORMATION: ASO-001935

<400> SEQUENCE: 685
ctttatttcc aaattcactt 20

<210> SEQ ID NO 686
<211> LENGTH: 16
<212> TYPE: DNA
<213> ORGANISM: Artificial Sequence
<220> FEATURE:
<223> OTHER INFORMATION: ASO-000013

<400> SEQUENCE: 686
atttccaaat tcactt 16

<210> SEQ ID NO 687
<211> LENGTH: 20
<212> TYPE: DNA
<213> ORGANISM: Artificial Sequence
<220> FEATURE:
<223> OTHER INFORMATION: ASO-002002

<400> SEQUENCE: 687
ctttatttcc aaattcactt 20

<210> SEQ ID NO 688
<211> LENGTH: 20
<212> TYPE: DNA
<213> ORGANISM: Artificial Sequence
<220> FEATURE:
<223> OTHER INFORMATION: ASO-000762

<400> SEQUENCE: 688
ctttatttcc aaattcactt 20

<210> SEQ ID NO 689
<211> LENGTH: 20
<212> TYPE: DNA
<213> ORGANISM: Artificial Sequence
<220> FEATURE:
<223> OTHER INFORMATION: ASO-002010

<400> SEQUENCE: 689
ctttatttcc aaattcactt 20

<210> SEQ ID NO 690
<211> LENGTH: 20
<212> TYPE: DNA
<213> ORGANISM: Artificial Sequence
<220> FEATURE:
<223> OTHER INFORMATION: ASO-002005

<400> SEQUENCE: 690
ctttatttcc aaattcactt 20

<210> SEQ ID NO 691
<211> LENGTH: 20
<212> TYPE: DNA
<213> ORGANISM: Artificial Sequence
<220> FEATURE:
<223> OTHER INFORMATION: ASO-001998

<400> SEQUENCE: 691
ctttatttcc aaattcactt 20

<210> SEQ ID NO 692
<211> LENGTH: 20
<212> TYPE: DNA
<213> ORGANISM: Artificial Sequence
<220> FEATURE:
<223> OTHER INFORMATION: ASO-002001

<400> SEQUENCE: 692
ctttatttcc aaattcactt 20

<210> SEQ ID NO 693
<211> LENGTH: 20
<212> TYPE: DNA
<213> ORGANISM: Artificial Sequence
<220> FEATURE:
<223> OTHER INFORMATION: ASO-001994

<400> SEQUENCE: 693
ctttatttcc aaattcactt 20

<210> SEQ ID NO 694
<211> LENGTH: 20
<212> TYPE: DNA
<213> ORGANISM: Artificial Sequence
<220> FEATURE:
<223> OTHER INFORMATION: ASO-002013

<400> SEQUENCE: 694
ctttatttcc aaattcactt 20

<210> SEQ ID NO 695
<211> LENGTH: 20
<212> TYPE: DNA
<213> ORGANISM: Artificial Sequence
<220> FEATURE:
<223> OTHER INFORMATION: ASO-002009

<400> SEQUENCE: 695
ctttatttcc aaattcactt 20

<210> SEQ ID NO 696
<211> LENGTH: 20
<212> TYPE: DNA
<213> ORGANISM: Artificial Sequence
<220> FEATURE:
<223> OTHER INFORMATION: ASO-000767

<400> SEQUENCE: 696
ctttatttcc aaattcactt 20

<210> SEQ ID NO 697
<211> LENGTH: 20
<212> TYPE: DNA
<213> ORGANISM: Artificial Sequence
<220> FEATURE:
<223> OTHER INFORMATION: ASO-000772

<400> SEQUENCE: 697
ctttatttcc aaattcactt 20

<210> SEQ ID NO 698
<211> LENGTH: 20
<212> TYPE: DNA
<213> ORGANISM: Artificial Sequence
<220> FEATURE:
<223> OTHER INFORMATION: BMT-214296

<400> SEQUENCE: 698
ctttacttcc aaattcactt 20

<210> SEQ ID NO 699
<211> LENGTH: 16
<212> TYPE: DNA
<213> ORGANISM: Artificial Sequence
<220> FEATURE:
<223> OTHER INFORMATION: ASO-000013-mm1

<400> SEQUENCE: 699
gtttccaaat tcactt 16

<210> SEQ ID NO 700
<211> LENGTH: 16
<212> TYPE: DNA
<213> ORGANISM: Artificial Sequence
<220> FEATURE:
<223> OTHER INFORMATION: ASO-000013-mm2

<400> SEQUENCE: 700
atttccaagt tcactt 16

<210> SEQ ID NO 701
<211> LENGTH: 16

<212> TYPE: DNA
<213> ORGANISM: Artificial Sequence
<220> FEATURE:
<223> OTHER INFORMATION: ASO-000013-mm3

<400> SEQUENCE: 701
atttccgaat tcactt 16

<210> SEQ ID NO 702
<211> LENGTH: 16
<212> TYPE: DNA
<213> ORGANISM: Artificial Sequence
<220> FEATURE:
<223> OTHER INFORMATION: ASO-000013-mm4

<400> SEQUENCE: 702
gtttccagat tcactt 16

<210> SEQ ID NO 703
<211> LENGTH: 16
<212> TYPE: DNA
<213> ORGANISM: Artificial Sequence
<220> FEATURE:
<223> OTHER INFORMATION: ASO-000013-mm5

<400> SEQUENCE: 703
gtttccaaat tcacta 16

<210> SEQ ID NO 704
<211> LENGTH: 16
<212> TYPE: DNA
<213> ORGANISM: Artificial Sequence
<220> FEATURE:
<223> OTHER INFORMATION: ASO-000013-mm6

<400> SEQUENCE: 704
atttccagat tcactc 16

<210> SEQ ID NO 705
<211> LENGTH: 16
<212> TYPE: DNA
<213> ORGANISM: Artificial Sequence
<220> FEATURE:
<223> OTHER INFORMATION: ASO-000898

<400> SEQUENCE: 705
atttccaaat tcactt 16

<210> SEQ ID NO 706
<211> LENGTH: 20
<212> TYPE: DNA
<213> ORGANISM: Artificial Sequence
<220> FEATURE:
<223> OTHER INFORMATION: ASO-001942-mm1

<400> SEQUENCE: 706
ctttatttcc agattcactt 20

<210> SEQ ID NO 707
<211> LENGTH: 20
<212> TYPE: DNA
<213> ORGANISM: Artificial Sequence
<220> FEATURE:
<223> OTHER INFORMATION: ASO-001942-mm2

<400> SEQUENCE: 707
ctttatttcc aaattcactg 20

<210> SEQ ID NO 708
<211> LENGTH: 20
<212> TYPE: DNA
<213> ORGANISM: Artificial Sequence
<220> FEATURE:
<223> OTHER INFORMATION: ASO-001942-mm3

<400> SEQUENCE: 708
ctttatttcc aaattcgctt 20

<210> SEQ ID NO 709
<211> LENGTH: 20
<212> TYPE: DNA
<213> ORGANISM: Artificial Sequence
<220> FEATURE:
<223> OTHER INFORMATION: ASO-001942-mm4

<400> SEQUENCE: 709
ctttatttcc agattcacta 20

<210> SEQ ID NO 710
<211> LENGTH: 20
<212> TYPE: DNA
<213> ORGANISM: Artificial Sequence
<220> FEATURE:
<223> OTHER INFORMATION: ASO-001942-mm5

<400> SEQUENCE: 710
ctttatttcc aggttcactt 20

<210> SEQ ID NO 711
<211> LENGTH: 20
<212> TYPE: DNA
<213> ORGANISM: Artificial Sequence
<220> FEATURE:
<223> OTHER INFORMATION: ASO-001942-mm6

<400> SEQUENCE: 711
ctttatttcc gagttcactt 20

<210> SEQ ID NO 712
<211> LENGTH: 16
<212> TYPE: DNA
<213> ORGANISM: Artificial Sequence
<220> FEATURE:
<223> OTHER INFORMATION: SPC-15674-01

<400> SEQUENCE: 712
atttccaaat tcactt 16

<210> SEQ ID NO 713
<211> LENGTH: 19
<212> TYPE: DNA
<213> ORGANISM: Artificial Sequence
<220> FEATURE:
<223> OTHER INFORMATION: ASO-002004

<400> SEQUENCE: 713
ctttatttcc aaattcact 19

<210> SEQ ID NO 714
<211> LENGTH: 19
<212> TYPE: DNA
<213> ORGANISM: Artificial Sequence

<220> FEATURE:
<223> OTHER INFORMATION: ASO-002012

<400> SEQUENCE: 714
ctttatttcc aaattcact 19

<210> SEQ ID NO 715
<211> LENGTH: 20
<212> TYPE: DNA
<213> ORGANISM: Artificial Sequence
<220> FEATURE:
<223> OTHER INFORMATION: ASO-001962

<400> SEQUENCE: 715
actttatttc caaattcact 20

<210> SEQ ID NO 716
<211> LENGTH: 20
<212> TYPE: DNA
<213> ORGANISM: Artificial Sequence
<220> FEATURE:
<223> OTHER INFORMATION: ASO-001956

<400> SEQUENCE: 716
actttatttc caaattcact 20

<210> SEQ ID NO 717
<211> LENGTH: 20
<212> TYPE: DNA
<213> ORGANISM: Artificial Sequence
<220> FEATURE:
<223> OTHER INFORMATION: ASO-001949

<400> SEQUENCE: 717
actttatttc caaattcact 20

<210> SEQ ID NO 718
<211> LENGTH: 19
<212> TYPE: DNA
<213> ORGANISM: Artificial Sequence
<220> FEATURE:
<223> OTHER INFORMATION: ASO-001987

<400> SEQUENCE: 718
ctttatttcc aaattcact 19

<210> SEQ ID NO 719
<211> LENGTH: 19
<212> TYPE: DNA
<213> ORGANISM: Artificial Sequence
<220> FEATURE:
<223> OTHER INFORMATION: ASO-001991

<400> SEQUENCE: 719
ctttatttcc aaattcact 19

<210> SEQ ID NO 720
<211> LENGTH: 19
<212> TYPE: DNA
<213> ORGANISM: Artificial Sequence
<220> FEATURE:
<223> OTHER INFORMATION: ASO-001995

<400> SEQUENCE: 720
ctttatttcc aaattcact 19

<210> SEQ ID NO 721
<211> LENGTH: 19
<212> TYPE: DNA
<213> ORGANISM: Artificial Sequence
<220> FEATURE:
<223> OTHER INFORMATION: ASO-001992

<400> SEQUENCE: 721
ctttatttcc aaattcact 19

<210> SEQ ID NO 722
<211> LENGTH: 19
<212> TYPE: DNA
<213> ORGANISM: Artificial Sequence
<220> FEATURE:
<223> OTHER INFORMATION: ASO-002000

<400> SEQUENCE: 722
ctttatttcc aaattcact 19

<210> SEQ ID NO 723
<211> LENGTH: 19
<212> TYPE: DNA
<213> ORGANISM: Artificial Sequence
<220> FEATURE:
<223> OTHER INFORMATION: ASO-001996

<400> SEQUENCE: 723
ctttatttcc aaattcact 19

<210> SEQ ID NO 724
<211> LENGTH: 19
<212> TYPE: DNA
<213> ORGANISM: Artificial Sequence
<220> FEATURE:
<223> OTHER INFORMATION: ASO-002008

<400> SEQUENCE: 724
ctttatttcc aaattcact 19

<210> SEQ ID NO 725
<211> LENGTH: 19
<212> TYPE: DNA
<213> ORGANISM: Artificial Sequence
<220> FEATURE:
<223> OTHER INFORMATION: ASO-002015

<400> SEQUENCE: 725
ctttatttcc aaattcact 19

<210> SEQ ID NO 726
<211> LENGTH: 19
<212> TYPE: DNA
<213> ORGANISM: Artificial Sequence
<220> FEATURE:
<223> OTHER INFORMATION: ASO-002016

<400> SEQUENCE: 726
ctttatttcc aaattcact 19

<210> SEQ ID NO 727
<211> LENGTH: 19
<212> TYPE: DNA
<213> ORGANISM: Artificial Sequence
<220> FEATURE:
<223> OTHER INFORMATION: ASO-001986

<400> SEQUENCE: 727
ctttatttcc aaattcact 19

<210> SEQ ID NO 728
<211> LENGTH: 19
<212> TYPE: DNA
<213> ORGANISM: Artificial Sequence
<220> FEATURE:
<223> OTHER INFORMATION: 17-18-19mer-50

<400> SEQUENCE: 728
ctttatttcc aaattcact 19

<210> SEQ ID NO 729
<211> LENGTH: 19
<212> TYPE: DNA
<213> ORGANISM: Artificial Sequence
<220> FEATURE:
<223> OTHER INFORMATION: 17-18-19mer-62

<400> SEQUENCE: 729
ctttatttcc aaattcact 19

<210> SEQ ID NO 730
<211> LENGTH: 19
<212> TYPE: DNA
<213> ORGANISM: Artificial Sequence
<220> FEATURE:
<223> OTHER INFORMATION: 17-18-19mer-68

<400> SEQUENCE: 730
ctttatttcc aaattcact 19

<210> SEQ ID NO 731
<211> LENGTH: 19
<212> TYPE: DNA
<213> ORGANISM: Artificial Sequence
<220> FEATURE:
<223> OTHER INFORMATION: 17-18-19mer-74

<400> SEQUENCE: 731
ctttatttcc aaattcact 19

<210> SEQ ID NO 732
<211> LENGTH: 19
<212> TYPE: DNA
<213> ORGANISM: Artificial Sequence
<220> FEATURE:
<223> OTHER INFORMATION: ASO-001995-mm1

<400> SEQUENCE: 732
ctttatttcc agattcact 19

<210> SEQ ID NO 733
<211> LENGTH: 19
<212> TYPE: DNA
<213> ORGANISM: Artificial Sequence
<220> FEATURE:
<223> OTHER INFORMATION: ASO-001995-mm2

<400> SEQUENCE: 733
ctttgtttcc aaattcact 19

<210> SEQ ID NO 734

<211> LENGTH: 19
<212> TYPE: DNA
<213> ORGANISM: Artificial Sequence
<220> FEATURE:
<223> OTHER INFORMATION: ASO-001995-mm3

<400> SEQUENCE: 734
ctttatttcc aaattcacg 19

<210> SEQ ID NO 735
<211> LENGTH: 19
<212> TYPE: DNA
<213> ORGANISM: Artificial Sequence
<220> FEATURE:
<223> OTHER INFORMATION: ASO-001995-mm4

<400> SEQUENCE: 735
ctttgtttcc agattcact 19

<210> SEQ ID NO 736
<211> LENGTH: 19
<212> TYPE: DNA
<213> ORGANISM: Artificial Sequence
<220> FEATURE:
<223> OTHER INFORMATION: ASO-001995-mm5

<400> SEQUENCE: 736
ctttgtttcc aagttcact 19

<210> SEQ ID NO 737
<211> LENGTH: 19
<212> TYPE: DNA
<213> ORGANISM: Artificial Sequence
<220> FEATURE:
<223> OTHER INFORMATION: ASO-001995-mm6

<400> SEQUENCE: 737
ctttatttcc gagttcact 19

<210> SEQ ID NO 738
<211> LENGTH: 16
<212> TYPE: DNA
<213> ORGANISM: Artificial Sequence
<220> FEATURE:
<223> OTHER INFORMATION: SPC-15673-01

<400> SEQUENCE: 738
tatttccaaa ttcact 16

<210> SEQ ID NO 739
<211> LENGTH: 18
<212> TYPE: DNA
<213> ORGANISM: Artificial Sequence
<220> FEATURE:
<223> OTHER INFORMATION: ASO-002003

<400> SEQUENCE: 739
ctttatttcc aaattcac 18

<210> SEQ ID NO 740
<211> LENGTH: 18
<212> TYPE: DNA
<213> ORGANISM: Artificial Sequence
<220> FEATURE:
<223> OTHER INFORMATION: ASO-002007

<400> SEQUENCE: 740
ctttatttcc aaattcac 18

<210> SEQ ID NO 741
<211> LENGTH: 18
<212> TYPE: DNA
<213> ORGANISM: Artificial Sequence
<220> FEATURE:
<223> OTHER INFORMATION: ASO-002011

<400> SEQUENCE: 741
ctttatttcc aaattcac 18

<210> SEQ ID NO 742
<211> LENGTH: 18
<212> TYPE: DNA
<213> ORGANISM: Artificial Sequence
<220> FEATURE:
<223> OTHER INFORMATION: ASO-001988

<400> SEQUENCE: 742
ctttatttcc aaattcac 18

<210> SEQ ID NO 743
<211> LENGTH: 18
<212> TYPE: DNA
<213> ORGANISM: Artificial Sequence
<220> FEATURE:
<223> OTHER INFORMATION: ASO-001999

<400> SEQUENCE: 743
ctttatttcc aaattcac 18

<210> SEQ ID NO 744
<211> LENGTH: 18
<212> TYPE: DNA
<213> ORGANISM: Artificial Sequence
<220> FEATURE:
<223> OTHER INFORMATION: ASO-001993

<400> SEQUENCE: 744
ctttatttcc aaattcac 18

<210> SEQ ID NO 745
<211> LENGTH: 18
<212> TYPE: DNA
<213> ORGANISM: Artificial Sequence
<220> FEATURE:
<223> OTHER INFORMATION: ASO-001997

<400> SEQUENCE: 745
ctttatttcc aaattcac 18

<210> SEQ ID NO 746
<211> LENGTH: 18
<212> TYPE: DNA
<213> ORGANISM: Artificial Sequence
<220> FEATURE:
<223> OTHER INFORMATION: 17-18-19mer-26

<400> SEQUENCE: 746
ctttatttcc aaattcac 18

<210> SEQ ID NO 747
<211> LENGTH: 18
<212> TYPE: DNA

<213> ORGANISM: Artificial Sequence
<220> FEATURE:
<223> OTHER INFORMATION: 17-18-19mer-32

<400> SEQUENCE: 747
ctttatttcc aaattcac 18

<210> SEQ ID NO 748
<211> LENGTH: 18
<212> TYPE: DNA
<213> ORGANISM: Artificial Sequence
<220> FEATURE:
<223> OTHER INFORMATION: 17-18-19mer-44

<400> SEQUENCE: 748
ctttatttcc aaattcac 18

<210> SEQ ID NO 749
<211> LENGTH: 19
<212> TYPE: DNA
<213> ORGANISM: Artificial Sequence
<220> FEATURE:
<223> OTHER INFORMATION: 17-18-19mer-51

<400> SEQUENCE: 749
actttatttc caaattcac 19

<210> SEQ ID NO 750
<211> LENGTH: 19
<212> TYPE: DNA
<213> ORGANISM: Artificial Sequence
<220> FEATURE:
<223> OTHER INFORMATION: 17-18-19mer-57

<400> SEQUENCE: 750
actttatttc caaattcac 19

<210> SEQ ID NO 751
<211> LENGTH: 19
<212> TYPE: DNA
<213> ORGANISM: Artificial Sequence
<220> FEATURE:
<223> OTHER INFORMATION: 17-18-19mer-63

<400> SEQUENCE: 751
actttatttc caaattcac 19

<210> SEQ ID NO 752
<211> LENGTH: 19
<212> TYPE: DNA
<213> ORGANISM: Artificial Sequence
<220> FEATURE:
<223> OTHER INFORMATION: 17-18-19mer-69

<400> SEQUENCE: 752
actttatttc caaattcac 19

<210> SEQ ID NO 753
<211> LENGTH: 19
<212> TYPE: DNA
<213> ORGANISM: Artificial Sequence
<220> FEATURE:
<223> OTHER INFORMATION: 17-18-19mer-75

<400> SEQUENCE: 753
actttatttc caaattcac 19

<210> SEQ ID NO 754
<211> LENGTH: 18
<212> TYPE: DNA
<213> ORGANISM: Artificial Sequence
<220> FEATURE:
<223> OTHER INFORMATION: ASO-001997-mm1

<400> SEQUENCE: 754
ctttatttcc agattcac 18

<210> SEQ ID NO 755
<211> LENGTH: 18
<212> TYPE: DNA
<213> ORGANISM: Artificial Sequence
<220> FEATURE:
<223> OTHER INFORMATION: ASO-001997-mm2

<400> SEQUENCE: 755
ctttatttcc gaattcac 18

<210> SEQ ID NO 756
<211> LENGTH: 18
<212> TYPE: DNA
<213> ORGANISM: Artificial Sequence
<220> FEATURE:
<223> OTHER INFORMATION: ASO-001997-mm3

<400> SEQUENCE: 756
ctttgtttcc aaattcac 18

<210> SEQ ID NO 757
<211> LENGTH: 18
<212> TYPE: DNA
<213> ORGANISM: Artificial Sequence
<220> FEATURE:
<223> OTHER INFORMATION: ASO-001997-mm4

<400> SEQUENCE: 757
ctttgtttcc agattcac 18

<210> SEQ ID NO 758
<211> LENGTH: 18
<212> TYPE: DNA
<213> ORGANISM: Artificial Sequence
<220> FEATURE:
<223> OTHER INFORMATION: ASO-001997-mm5

<400> SEQUENCE: 758
ctttatttcc aggttcac 18

<210> SEQ ID NO 759
<211> LENGTH: 18
<212> TYPE: DNA
<213> ORGANISM: Artificial Sequence
<220> FEATURE:
<223> OTHER INFORMATION: ASO-001997-mm6

<400> SEQUENCE: 759
ctttgtttcc aagttcac 18

<210> SEQ ID NO 760
<211> LENGTH: 16
<212> TYPE: DNA
<213> ORGANISM: Artificial Sequence
<220> FEATURE:

<223> OTHER INFORMATION: SPC-15672-01

<400> SEQUENCE: 760
ttatttccaa attcac 16

<210> SEQ ID NO 761
<211> LENGTH: 18
<212> TYPE: DNA
<213> ORGANISM: Artificial Sequence
<220> FEATURE:
<223> OTHER INFORMATION: 17-18-19mer-21

<400> SEQUENCE: 761
actttatttc caaattca 18

<210> SEQ ID NO 762
<211> LENGTH: 18
<212> TYPE: DNA
<213> ORGANISM: Artificial Sequence
<220> FEATURE:
<223> OTHER INFORMATION: 17-18-19mer-27

<400> SEQUENCE: 762
actttatttc caaattca 18

<210> SEQ ID NO 763
<211> LENGTH: 18
<212> TYPE: DNA
<213> ORGANISM: Artificial Sequence
<220> FEATURE:
<223> OTHER INFORMATION: 17-18-19mer-33

<400> SEQUENCE: 763
actttatttc caaattca 18

<210> SEQ ID NO 764
<211> LENGTH: 18
<212> TYPE: DNA
<213> ORGANISM: Artificial Sequence
<220> FEATURE:
<223> OTHER INFORMATION: 17-18-19mer-39

<400> SEQUENCE: 764
actttatttc caaattca 18

<210> SEQ ID NO 765
<211> LENGTH: 18
<212> TYPE: DNA
<213> ORGANISM: Artificial Sequence
<220> FEATURE:
<223> OTHER INFORMATION: 17-18-19mer-45

<400> SEQUENCE: 765
actttatttc caaattca 18

<210> SEQ ID NO 766
<211> LENGTH: 16
<212> TYPE: DNA
<213> ORGANISM: Artificial Sequence
<220> FEATURE:
<223> OTHER INFORMATION: SPC-15671-01

<400> SEQUENCE: 766
tttatttcca aattca 16

<210> SEQ ID NO 767
<211> LENGTH: 16
<212> TYPE: DNA
<213> ORGANISM: Artificial Sequence
<220> FEATURE:
<223> OTHER INFORMATION: SPC-15670-01

<400> SEQUENCE: 767
ctttatttcc aaattc 16

<210> SEQ ID NO 768
<211> LENGTH: 16
<212> TYPE: DNA
<213> ORGANISM: Artificial Sequence
<220> FEATURE:
<223> OTHER INFORMATION: SPC-15669-01

<400> SEQUENCE: 768
actttatttc caaatt 16

<210> SEQ ID NO 769
<211> LENGTH: 16
<212> TYPE: DNA
<213> ORGANISM: Artificial Sequence
<220> FEATURE:
<223> OTHER INFORMATION: ASO-000139

<400> SEQUENCE: 769
aactttattt ccaaat 16

<210> SEQ ID NO 770
<211> LENGTH: 16
<212> TYPE: DNA
<213> ORGANISM: Artificial Sequence
<220> FEATURE:
<223> OTHER INFORMATION: SPC-15668-01

<400> SEQUENCE: 770
aactttattt ccaaat 16

<210> SEQ ID NO 771
<211> LENGTH: 16
<212> TYPE: DNA
<213> ORGANISM: Artificial Sequence
<220> FEATURE:
<223> OTHER INFORMATION: SPC-15667-01

<400> SEQUENCE: 771
taactttatt tccaaa 16

<210> SEQ ID NO 772
<211> LENGTH: 16
<212> TYPE: DNA
<213> ORGANISM: Artificial Sequence
<220> FEATURE:
<223> OTHER INFORMATION: SPC-15666-01

<400> SEQUENCE: 772
ataactttat ttccaa 16

<210> SEQ ID NO 773
<211> LENGTH: 16
<212> TYPE: DNA
<213> ORGANISM: Artificial Sequence
<220> FEATURE:
<223> OTHER INFORMATION: ASO-000118

<400> SEQUENCE: 773
aataacttta tttcca 16

<210> SEQ ID NO 774
<211> LENGTH: 16
<212> TYPE: DNA
<213> ORGANISM: Artificial Sequence
<220> FEATURE:
<223> OTHER INFORMATION: SPC-15665-01

<400> SEQUENCE: 774
aataacttta tttcca 16

<210> SEQ ID NO 775
<211> LENGTH: 16
<212> TYPE: DNA
<213> ORGANISM: Artificial Sequence
<220> FEATURE:
<223> OTHER INFORMATION: ASO-000101

<400> SEQUENCE: 775
taataacttt atttcc 16

<210> SEQ ID NO 776
<211> LENGTH: 16
<212> TYPE: DNA
<213> ORGANISM: Artificial Sequence
<220> FEATURE:
<223> OTHER INFORMATION: SPC-15664-01

<400> SEQUENCE: 776
taataacttt atttcc 16

<210> SEQ ID NO 777
<211> LENGTH: 16
<212> TYPE: DNA
<213> ORGANISM: Artificial Sequence
<220> FEATURE:
<223> OTHER INFORMATION: ASO-000148

<400> SEQUENCE: 777
gtaataactt tatttc 16

<210> SEQ ID NO 778
<211> LENGTH: 15
<212> TYPE: DNA
<213> ORGANISM: Artificial Sequence
<220> FEATURE:
<223> OTHER INFORMATION: ASO-000184

<400> SEQUENCE: 778
taataacttt atttc 15

<210> SEQ ID NO 779
<211> LENGTH: 15
<212> TYPE: DNA
<213> ORGANISM: Artificial Sequence
<220> FEATURE:
<223> OTHER INFORMATION: ASO-000112

<400> SEQUENCE: 779
gtaataactt tattt 15

<210> SEQ ID NO 780
<211> LENGTH: 16

<212> TYPE: DNA
<213> ORGANISM: Artificial Sequence
<220> FEATURE:
<223> OTHER INFORMATION: ASO-000170

<400> SEQUENCE: 780
agtaataact ttattt 16

<210> SEQ ID NO 781
<211> LENGTH: 16
<212> TYPE: DNA
<213> ORGANISM: Artificial Sequence
<220> FEATURE:
<223> OTHER INFORMATION: ASO-000154

<400> SEQUENCE: 781
gagtaataac tttatt 16

<210> SEQ ID NO 782
<211> LENGTH: 15
<212> TYPE: DNA
<213> ORGANISM: Artificial Sequence
<220> FEATURE:
<223> OTHER INFORMATION: ASO-000125

<400> SEQUENCE: 782
agtaataact ttatt 15

<210> SEQ ID NO 783
<211> LENGTH: 15
<212> TYPE: DNA
<213> ORGANISM: Artificial Sequence
<220> FEATURE:
<223> OTHER INFORMATION: ASO-000167

<400> SEQUENCE: 783
gagtaataac tttat 15

<210> SEQ ID NO 784
<211> LENGTH: 16
<212> TYPE: DNA
<213> ORGANISM: Artificial Sequence
<220> FEATURE:
<223> OTHER INFORMATION: ASO-000134

<400> SEQUENCE: 784
agagtaataa ctttat 16

<210> SEQ ID NO 785
<211> LENGTH: 16
<212> TYPE: DNA
<213> ORGANISM: Artificial Sequence
<220> FEATURE:
<223> OTHER INFORMATION: ASO-000175

<400> SEQUENCE: 785
cagagtaata acttta 16

<210> SEQ ID NO 786
<211> LENGTH: 15
<212> TYPE: DNA
<213> ORGANISM: Artificial Sequence
<220> FEATURE:
<223> OTHER INFORMATION: ASO-000178

<400> SEQUENCE: 786
agagtaataa cttta 15

<210> SEQ ID NO 787
<211> LENGTH: 15
<212> TYPE: DNA
<213> ORGANISM: Artificial Sequence
<220> FEATURE:
<223> OTHER INFORMATION: ASO-000138

<400> SEQUENCE: 787
cagagtaata acttt 15

<210> SEQ ID NO 788
<211> LENGTH: 16
<212> TYPE: DNA
<213> ORGANISM: Artificial Sequence
<220> FEATURE:
<223> OTHER INFORMATION: ASO-000171

<400> SEQUENCE: 788
tcagagtaat aacttt 16

<210> SEQ ID NO 789
<211> LENGTH: 16
<212> TYPE: DNA
<213> ORGANISM: Artificial Sequence
<220> FEATURE:
<223> OTHER INFORMATION: ASO-000236

<400> SEQUENCE: 789
atcagagtaa taactt 16

<210> SEQ ID NO 790
<211> LENGTH: 15
<212> TYPE: DNA
<213> ORGANISM: Artificial Sequence
<220> FEATURE:
<223> OTHER INFORMATION: ASO-000127

<400> SEQUENCE: 790
tcagagtaat aactt 15

<210> SEQ ID NO 791
<211> LENGTH: 14
<212> TYPE: DNA
<213> ORGANISM: Artificial Sequence
<220> FEATURE:
<223> OTHER INFORMATION: ASO-000177

<400> SEQUENCE: 791
cagagtaata actt 14

<210> SEQ ID NO 792
<211> LENGTH: 16
<212> TYPE: DNA
<213> ORGANISM: Artificial Sequence
<220> FEATURE:
<223> OTHER INFORMATION: ASO-000238

<400> SEQUENCE: 792
aatcagagta ataact 16

<210> SEQ ID NO 793
<211> LENGTH: 16
<212> TYPE: DNA
<213> ORGANISM: Artificial Sequence

<220> FEATURE:
<223> OTHER INFORMATION: ASO-000222

<400> SEQUENCE: 793
taatcagagt aataac 16

<210> SEQ ID NO 794
<211> LENGTH: 15
<212> TYPE: DNA
<213> ORGANISM: Artificial Sequence
<220> FEATURE:
<223> OTHER INFORMATION: ASO-000307

<400> SEQUENCE: 794
aatcagagta ataac 15

<210> SEQ ID NO 795
<211> LENGTH: 16
<212> TYPE: DNA
<213> ORGANISM: Artificial Sequence
<220> FEATURE:
<223> OTHER INFORMATION: ASO-000204

<400> SEQUENCE: 795
ttaatcagag taataa 16

<210> SEQ ID NO 796
<211> LENGTH: 15
<212> TYPE: DNA
<213> ORGANISM: Artificial Sequence
<220> FEATURE:
<223> OTHER INFORMATION: ASO-000330

<400> SEQUENCE: 796
taatcagagt aataa 15

<210> SEQ ID NO 797
<211> LENGTH: 16
<212> TYPE: DNA
<213> ORGANISM: Artificial Sequence
<220> FEATURE:
<223> OTHER INFORMATION: ASO-000326

<400> SEQUENCE: 797
tttaatcaga gtaata 16

<210> SEQ ID NO 798
<211> LENGTH: 15
<212> TYPE: DNA
<213> ORGANISM: Artificial Sequence
<220> FEATURE:
<223> OTHER INFORMATION: ASO-000249

<400> SEQUENCE: 798
tttaatcaga gtaat 15

<210> SEQ ID NO 799
<211> LENGTH: 20
<212> TYPE: DNA
<213> ORGANISM: Artificial Sequence
<220> FEATURE:
<223> OTHER INFORMATION: ASO-002022

<400> SEQUENCE: 799
ttatttccaa attcactttt 20

<210> SEQ ID NO 800
<211> LENGTH: 20
<212> TYPE: DNA
<213> ORGANISM: Artificial Sequence
<220> FEATURE:
<223> OTHER INFORMATION: ASO-002026

<400> SEQUENCE: 800
ttatttccaa attcactttt 20

<210> SEQ ID NO 801
<211> LENGTH: 20
<212> TYPE: DNA
<213> ORGANISM: Artificial Sequence
<220> FEATURE:
<223> OTHER INFORMATION: ASO-002024

<400> SEQUENCE: 801
ttatttccaa attcactttt 20

<210> SEQ ID NO 802
<211> LENGTH: 25
<212> TYPE: DNA
<213> ORGANISM: Artificial Sequence
<220> FEATURE:
<223> OTHER INFORMATION: ASO-002049

<400> SEQUENCE: 802
actttatttc caaattcact tttac 25

<210> SEQ ID NO 803
<211> LENGTH: 25
<212> TYPE: DNA
<213> ORGANISM: Artificial Sequence
<220> FEATURE:
<223> OTHER INFORMATION: ASO-002019

<400> SEQUENCE: 803
actttatttc caaattcact tttac 25

<210> SEQ ID NO 804
<211> LENGTH: 14
<212> TYPE: DNA
<213> ORGANISM: Artificial Sequence
<220> FEATURE:
<223> OTHER INFORMATION: ASO-000050

<400> SEQUENCE: 804
gcgtgatctt ccat 14

<210> SEQ ID NO 805
<211> LENGTH: 16
<212> TYPE: DNA
<213> ORGANISM: Artificial Sequence
<220> FEATURE:
<223> OTHER INFORMATION: ASO-000054

<400> SEQUENCE: 805
agcgtgatct tccatc 16

<210> SEQ ID NO 806
<211> LENGTH: 16
<212> TYPE: DNA
<213> ORGANISM: Artificial Sequence
<220> FEATURE:
<223> OTHER INFORMATION: ASO-000237

<400> SEQUENCE: 806
agccatcctg gttcaa 16

<210> SEQ ID NO 807
<211> LENGTH: 16
<212> TYPE: DNA
<213> ORGANISM: Artificial Sequence
<220> FEATURE:
<223> OTHER INFORMATION: ASO-000461

<400> SEQUENCE: 807
ccagcgtgat cttcca 16

<210> SEQ ID NO 808
<211> LENGTH: 14
<212> TYPE: DNA
<213> ORGANISM: Artificial Sequence
<220> FEATURE:
<223> OTHER INFORMATION: ASO-000462

<400> SEQUENCE: 808
ccagcgtgat cttc 14

<210> SEQ ID NO 809
<211> LENGTH: 16
<212> TYPE: DNA
<213> ORGANISM: Artificial Sequence
<220> FEATURE:
<223> OTHER INFORMATION: ASO-000472

<400> SEQUENCE: 809
gcgtgatctt ccatca 16

<210> SEQ ID NO 810
<211> LENGTH: 16
<212> TYPE: DNA
<213> ORGANISM: Artificial Sequence
<220> FEATURE:
<223> OTHER INFORMATION: ASO-000495

<400> SEQUENCE: 810
tcccagcgtg atcttc 16

<210> SEQ ID NO 811
<211> LENGTH: 16
<212> TYPE: DNA
<213> ORGANISM: Artificial Sequence
<220> FEATURE:
<223> OTHER INFORMATION: ASO-000520

<400> SEQUENCE: 811
cgtgatcttc catcac 16

<210> SEQ ID NO 812
<211> LENGTH: 16
<212> TYPE: DNA
<213> ORGANISM: Artificial Sequence
<220> FEATURE:
<223> OTHER INFORMATION: ASO-000573

<400> SEQUENCE: 812
cagcgtgatc ttccat 16

<210> SEQ ID NO 813

<211> LENGTH: 14
<212> TYPE: DNA
<213> ORGANISM: Artificial Sequence
<220> FEATURE:
<223> OTHER INFORMATION: ASO-000587

<400> SEQUENCE: 813
tcccagcgtg atct 14

<210> SEQ ID NO 814
<211> LENGTH: 14
<212> TYPE: DNA
<213> ORGANISM: Artificial Sequence
<220> FEATURE:
<223> OTHER INFORMATION: ASO-000596

<400> SEQUENCE: 814
cgtgatcttc catc 14

<210> SEQ ID NO 815
<211> LENGTH: 16
<212> TYPE: DNA
<213> ORGANISM: Artificial Sequence
<220> FEATURE:
<223> OTHER INFORMATION: ASO-000633

<400> SEQUENCE: 815
cccagcgtga tcttcc 16

<210> SEQ ID NO 816
<211> LENGTH: 14
<212> TYPE: DNA
<213> ORGANISM: Artificial Sequence
<220> FEATURE:
<223> OTHER INFORMATION: ASO-000659

<400> SEQUENCE: 816
cccagcgtga tctt 14

<210> SEQ ID NO 817
<211> LENGTH: 16
<212> TYPE: DNA
<213> ORGANISM: Artificial Sequence
<220> FEATURE:
<223> OTHER INFORMATION: ASO-000773

<400> SEQUENCE: 817
atcacttcga actcct 16

<210> SEQ ID NO 818
<211> LENGTH: 16
<212> TYPE: DNA
<213> ORGANISM: Artificial Sequence
<220> FEATURE:
<223> OTHER INFORMATION: ASO-000774

<400> SEQUENCE: 818
catcacttcg aactcc 16

<210> SEQ ID NO 819
<211> LENGTH: 16
<212> TYPE: DNA
<213> ORGANISM: Artificial Sequence
<220> FEATURE:
<223> OTHER INFORMATION: ASO-000775

<400> SEQUENCE: 819
ccatcacttc gaactc 16

<210> SEQ ID NO 820
<211> LENGTH: 20
<212> TYPE: DNA
<213> ORGANISM: Artificial Sequence
<220> FEATURE:
<223> OTHER INFORMATION: ASO-000945

<400> SEQUENCE: 820
tccatcactt cgaactcctg 20

<210> SEQ ID NO 821
<211> LENGTH: 20
<212> TYPE: DNA
<213> ORGANISM: Artificial Sequence
<220> FEATURE:
<223> OTHER INFORMATION: ASO-000946

<400> SEQUENCE: 821
ttccatcact tcgaactcct 20

<210> SEQ ID NO 822
<211> LENGTH: 20
<212> TYPE: DNA
<213> ORGANISM: Artificial Sequence
<220> FEATURE:
<223> OTHER INFORMATION: ASO-000947

<400> SEQUENCE: 822
cttccatcac ttcgaactcc 20

<210> SEQ ID NO 823
<211> LENGTH: 20
<212> TYPE: DNA
<213> ORGANISM: Artificial Sequence
<220> FEATURE:
<223> OTHER INFORMATION: ASO-000948

<400> SEQUENCE: 823
tcttccatca cttcgaactc 20

<210> SEQ ID NO 824
<211> LENGTH: 20
<212> TYPE: DNA
<213> ORGANISM: Artificial Sequence
<220> FEATURE:
<223> OTHER INFORMATION: ASO-001783

<400> SEQUENCE: 824
ccagcgtgat cttccatcac 20

<210> SEQ ID NO 825
<211> LENGTH: 20
<212> TYPE: DNA
<213> ORGANISM: Artificial Sequence
<220> FEATURE:
<223> OTHER INFORMATION: ASO-001784

<400> SEQUENCE: 825
cccagcgtga tcttccatca 20

<210> SEQ ID NO 826
<211> LENGTH: 20
<212> TYPE: DNA

<213> ORGANISM: Artificial Sequence
<220> FEATURE:
<223> OTHER INFORMATION: ASO-001922

<400> SEQUENCE: 826
ccagcgtgat cttccatcac 20

<210> SEQ ID NO 827
<211> LENGTH: 20
<212> TYPE: DNA
<213> ORGANISM: Artificial Sequence
<220> FEATURE:
<223> OTHER INFORMATION: ASO-001923

<400> SEQUENCE: 827
tcccagcgtg atcttccatc 20

<210> SEQ ID NO 828
<211> LENGTH: 20
<212> TYPE: DNA
<213> ORGANISM: Artificial Sequence
<220> FEATURE:
<223> OTHER INFORMATION: ASO-001929

<400> SEQUENCE: 828
ccagcgtgat cttccatcac 20

<210> SEQ ID NO 829
<211> LENGTH: 20
<212> TYPE: DNA
<213> ORGANISM: Artificial Sequence
<220> FEATURE:
<223> OTHER INFORMATION: ASO-001930

<400> SEQUENCE: 829
tcccagcgtg atcttccatc 20

<210> SEQ ID NO 830
<211> LENGTH: 20
<212> TYPE: DNA
<213> ORGANISM: Artificial Sequence
<220> FEATURE:
<223> OTHER INFORMATION: ASO-001936

<400> SEQUENCE: 830
ccagcgtgat cttccatcac 20

<210> SEQ ID NO 831
<211> LENGTH: 20
<212> TYPE: DNA
<213> ORGANISM: Artificial Sequence
<220> FEATURE:
<223> OTHER INFORMATION: ASO-001937

<400> SEQUENCE: 831
tcccagcgtg atcttccatc 20

<210> SEQ ID NO 832
<211> LENGTH: 20
<212> TYPE: DNA
<213> ORGANISM: Artificial Sequence
<220> FEATURE:
<223> OTHER INFORMATION: ASO-001943

<400> SEQUENCE: 832
ccagcgtgat cttccatcac 20

<210> SEQ ID NO 833
<211> LENGTH: 20
<212> TYPE: DNA
<213> ORGANISM: Artificial Sequence
<220> FEATURE:
<223> OTHER INFORMATION: ASO-001944

<400> SEQUENCE: 833
tcccagcgtg atcttccatc 20

<210> SEQ ID NO 834
<211> LENGTH: 20
<212> TYPE: DNA
<213> ORGANISM: Artificial Sequence
<220> FEATURE:
<223> OTHER INFORMATION: ASO-001950

<400> SEQUENCE: 834
cccagcgtga tcttccatca 20

<210> SEQ ID NO 835
<211> LENGTH: 20
<212> TYPE: DNA
<213> ORGANISM: Artificial Sequence
<220> FEATURE:
<223> OTHER INFORMATION: ASO-001951

<400> SEQUENCE: 835
cgtcccagcg tgatcttcca 20

<210> SEQ ID NO 836
<211> LENGTH: 20
<212> TYPE: DNA
<213> ORGANISM: Artificial Sequence
<220> FEATURE:
<223> OTHER INFORMATION: ASO-001957

<400> SEQUENCE: 836
cccagcgtga tcttccatca 20

<210> SEQ ID NO 837
<211> LENGTH: 20
<212> TYPE: DNA
<213> ORGANISM: Artificial Sequence
<220> FEATURE:
<223> OTHER INFORMATION: ASO-001958

<400> SEQUENCE: 837
cgtcccagcg tgatcttcca 20

<210> SEQ ID NO 838
<211> LENGTH: 20
<212> TYPE: DNA
<213> ORGANISM: Artificial Sequence
<220> FEATURE:
<223> OTHER INFORMATION: ASO-001963

<400> SEQUENCE: 838
cccagcgtga tcttccatca 20

<210> SEQ ID NO 839
<211> LENGTH: 20
<212> TYPE: DNA
<213> ORGANISM: Artificial Sequence
<220> FEATURE:

<223> OTHER INFORMATION: ASO-001964

<400> SEQUENCE: 839
cgtcccagcg tgatcttcca 20

<210> SEQ ID NO 840
<211> LENGTH: 20
<212> TYPE: DNA
<213> ORGANISM: Artificial Sequence
<220> FEATURE:
<223> OTHER INFORMATION: ASO-001969

<400> SEQUENCE: 840
cccagcgtga tcttccatca 20

<210> SEQ ID NO 841
<211> LENGTH: 20
<212> TYPE: DNA
<213> ORGANISM: Artificial Sequence
<220> FEATURE:
<223> OTHER INFORMATION: ASO-001970

<400> SEQUENCE: 841
cgtcccagcg tgatcttcca 20

<210> SEQ ID NO 842
<211> LENGTH: 20
<212> TYPE: DNA
<213> ORGANISM: Artificial Sequence
<220> FEATURE:
<223> OTHER INFORMATION: ASO-001978

<400> SEQUENCE: 842
tcccagcgtg atcttccatc 20

<210> SEQ ID NO 843
<211> LENGTH: 16
<212> TYPE: DNA
<213> ORGANISM: Artificial Sequence
<220> FEATURE:
<223> OTHER INFORMATION: ASO-002100

<400> SEQUENCE: 843
catcacttcg aactcc 16

<210> SEQ ID NO 844
<211> LENGTH: 16
<212> TYPE: DNA
<213> ORGANISM: Artificial Sequence
<220> FEATURE:
<223> OTHER INFORMATION: ASO-002101

<400> SEQUENCE: 844
ccatcacttc gaactc 16

<210> SEQ ID NO 845
<211> LENGTH: 17
<212> TYPE: DNA
<213> ORGANISM: Artificial Sequence
<220> FEATURE:
<223> OTHER INFORMATION: ASO-002102

<400> SEQUENCE: 845
catcacttcg aactcct 17

<210> SEQ ID NO 846
<211> LENGTH: 17
<212> TYPE: DNA
<213> ORGANISM: Artificial Sequence
<220> FEATURE:
<223> OTHER INFORMATION: ASO-002103

<400> SEQUENCE: 846
tccatcactt cgaactc 17

<210> SEQ ID NO 847
<211> LENGTH: 18
<212> TYPE: DNA
<213> ORGANISM: Artificial Sequence
<220> FEATURE:
<223> OTHER INFORMATION: ASO-002104

<400> SEQUENCE: 847
cttccatcac ttcgaact 18

<210> SEQ ID NO 848
<211> LENGTH: 20
<212> TYPE: DNA
<213> ORGANISM: Artificial Sequence
<220> FEATURE:
<223> OTHER INFORMATION: ASO-002105

<400> SEQUENCE: 848
cttccatcac ttcgaactcc 20

<210> SEQ ID NO 849
<211> LENGTH: 22
<212> TYPE: DNA
<213> ORGANISM: Artificial Sequence
<220> FEATURE:
<223> OTHER INFORMATION: ASO-002106

<400> SEQUENCE: 849
tcttccatca cttcgaactc ct 22

<210> SEQ ID NO 850
<211> LENGTH: 16
<212> TYPE: DNA
<213> ORGANISM: Artificial Sequence
<220> FEATURE:
<223> OTHER INFORMATION: ASO-002112

<400> SEQUENCE: 850
catcacttcg aactcc 16

<210> SEQ ID NO 851
<211> LENGTH: 16
<212> TYPE: DNA
<213> ORGANISM: Artificial Sequence
<220> FEATURE:
<223> OTHER INFORMATION: ASO-002113

<400> SEQUENCE: 851
ccatcacttc gaactc 16

<210> SEQ ID NO 852
<211> LENGTH: 17
<212> TYPE: DNA
<213> ORGANISM: Artificial Sequence
<220> FEATURE:
<223> OTHER INFORMATION: ASO-002114

<400> SEQUENCE: 852
ccatcacttc gaactcc 17

<210> SEQ ID NO 853
<211> LENGTH: 17
<212> TYPE: DNA
<213> ORGANISM: Artificial Sequence
<220> FEATURE:
<223> OTHER INFORMATION: ASO-002115

<400> SEQUENCE: 853
tccatcactt cgaactc 17

<210> SEQ ID NO 854
<211> LENGTH: 18
<212> TYPE: DNA
<213> ORGANISM: Artificial Sequence
<220> FEATURE:
<223> OTHER INFORMATION: ASO-002116

<400> SEQUENCE: 854
tccatcactt cgaactcc 18

<210> SEQ ID NO 855
<211> LENGTH: 20
<212> TYPE: DNA
<213> ORGANISM: Artificial Sequence
<220> FEATURE:
<223> OTHER INFORMATION: ASO-002117

<400> SEQUENCE: 855
cttccatcac ttcgaactcc 20

<210> SEQ ID NO 856
<211> LENGTH: 22
<212> TYPE: DNA
<213> ORGANISM: Artificial Sequence
<220> FEATURE:
<223> OTHER INFORMATION: ASO-002118

<400> SEQUENCE: 856
tcttccatca cttcgaactc ct 22

<210> SEQ ID NO 857
<211> LENGTH: 16
<212> TYPE: DNA
<213> ORGANISM: Artificial Sequence
<220> FEATURE:
<223> OTHER INFORMATION: ASO-002124

<400> SEQUENCE: 857
catcacttcg aactcc 16

<210> SEQ ID NO 858
<211> LENGTH: 16
<212> TYPE: DNA
<213> ORGANISM: Artificial Sequence
<220> FEATURE:
<223> OTHER INFORMATION: ASO-002125

<400> SEQUENCE: 858
ccatcacttc gaactc 16

<210> SEQ ID NO 859
<211> LENGTH: 17

<212> TYPE: DNA
<213> ORGANISM: Artificial Sequence
<220> FEATURE:
<223> OTHER INFORMATION: ASO-002126

<400> SEQUENCE: 859
ccatcacttc gaactcc 17

<210> SEQ ID NO 860
<211> LENGTH: 17
<212> TYPE: DNA
<213> ORGANISM: Artificial Sequence
<220> FEATURE:
<223> OTHER INFORMATION: ASO-002127

<400> SEQUENCE: 860
tccatcactt cgaactc 17

<210> SEQ ID NO 861
<211> LENGTH: 18
<212> TYPE: DNA
<213> ORGANISM: Artificial Sequence
<220> FEATURE:
<223> OTHER INFORMATION: ASO-002128

<400> SEQUENCE: 861
tccatcactt cgaactcc 18

<210> SEQ ID NO 862
<211> LENGTH: 20
<212> TYPE: DNA
<213> ORGANISM: Artificial Sequence
<220> FEATURE:
<223> OTHER INFORMATION: ASO-002129

<400> SEQUENCE: 862
tcttccatca cttcgaactc 20

<210> SEQ ID NO 863
<211> LENGTH: 16
<212> TYPE: DNA
<213> ORGANISM: Artificial Sequence
<220> FEATURE:
<223> OTHER INFORMATION: ASO-002136

<400> SEQUENCE: 863
catcacttcg aactcc 16

<210> SEQ ID NO 864
<211> LENGTH: 16
<212> TYPE: DNA
<213> ORGANISM: Artificial Sequence
<220> FEATURE:
<223> OTHER INFORMATION: ASO-002137

<400> SEQUENCE: 864
ccatcacttc gaactc 16

<210> SEQ ID NO 865
<211> LENGTH: 17
<212> TYPE: DNA
<213> ORGANISM: Artificial Sequence
<220> FEATURE:
<223> OTHER INFORMATION: ASO-002138

<400> SEQUENCE: 865
ccatcacttc gaactcc 17

<210> SEQ ID NO 866
<211> LENGTH: 18
<212> TYPE: DNA
<213> ORGANISM: Artificial Sequence
<220> FEATURE:
<223> OTHER INFORMATION: ASO-002139

<400> SEQUENCE: 866
ccatcacttc gaactcct 18

<210> SEQ ID NO 867
<211> LENGTH: 18
<212> TYPE: DNA
<213> ORGANISM: Artificial Sequence
<220> FEATURE:
<223> OTHER INFORMATION: ASO-002140

<400> SEQUENCE: 867
tccatcactt cgaactcc 18

<210> SEQ ID NO 868
<211> LENGTH: 20
<212> TYPE: DNA
<213> ORGANISM: Artificial Sequence
<220> FEATURE:
<223> OTHER INFORMATION: ASO-002141

<400> SEQUENCE: 868
tcttccatca cttcgaactc 20

<210> SEQ ID NO 869
<211> LENGTH: 16
<212> TYPE: DNA
<213> ORGANISM: Artificial Sequence
<220> FEATURE:
<223> OTHER INFORMATION: ASO-002148

<400> SEQUENCE: 869
catcacttcg aactcc 16

<210> SEQ ID NO 870
<211> LENGTH: 16
<212> TYPE: DNA
<213> ORGANISM: Artificial Sequence
<220> FEATURE:
<223> OTHER INFORMATION: ASO-002149

<400> SEQUENCE: 870
ccatcacttc gaactc 16

<210> SEQ ID NO 871
<211> LENGTH: 17
<212> TYPE: DNA
<213> ORGANISM: Artificial Sequence
<220> FEATURE:
<223> OTHER INFORMATION: ASO-002150

<400> SEQUENCE: 871
ccatcacttc gaactcc 17

<210> SEQ ID NO 872
<211> LENGTH: 18
<212> TYPE: DNA
<213> ORGANISM: Artificial Sequence

<220> FEATURE:
<223> OTHER INFORMATION: ASO-002151

<400> SEQUENCE: 872
ccatcacttc gaactcct 18

<210> SEQ ID NO 873
<211> LENGTH: 18
<212> TYPE: DNA
<213> ORGANISM: Artificial Sequence
<220> FEATURE:
<223> OTHER INFORMATION: ASO-002152

<400> SEQUENCE: 873
tccatcactt cgaactcc 18

<210> SEQ ID NO 874
<211> LENGTH: 20
<212> TYPE: DNA
<213> ORGANISM: Artificial Sequence
<220> FEATURE:
<223> OTHER INFORMATION: ASO-002153

<400> SEQUENCE: 874
ttccatcact tcgaactcct 20

<210> SEQ ID NO 875
<211> LENGTH: 16
<212> TYPE: DNA
<213> ORGANISM: Artificial Sequence
<220> FEATURE:
<223> OTHER INFORMATION: ASO-002160

<400> SEQUENCE: 875
catcacttcg aactcc 16

<210> SEQ ID NO 876
<211> LENGTH: 17
<212> TYPE: DNA
<213> ORGANISM: Artificial Sequence
<220> FEATURE:
<223> OTHER INFORMATION: ASO-002161

<400> SEQUENCE: 876
catcacttcg aactcct 17

<210> SEQ ID NO 877
<211> LENGTH: 17
<212> TYPE: DNA
<213> ORGANISM: Artificial Sequence
<220> FEATURE:
<223> OTHER INFORMATION: ASO-002162

<400> SEQUENCE: 877
ccatcacttc gaactcc 17

<210> SEQ ID NO 878
<211> LENGTH: 18
<212> TYPE: DNA
<213> ORGANISM: Artificial Sequence
<220> FEATURE:
<223> OTHER INFORMATION: ASO-002163

<400> SEQUENCE: 878
ccatcacttc gaactcct 18

<210> SEQ ID NO 879
<211> LENGTH: 18
<212> TYPE: DNA
<213> ORGANISM: Artificial Sequence
<220> FEATURE:
<223> OTHER INFORMATION: ASO-002164

<400> SEQUENCE: 879
ttccatcact tcgaactc 18

<210> SEQ ID NO 880
<211> LENGTH: 20
<212> TYPE: DNA
<213> ORGANISM: Artificial Sequence
<220> FEATURE:
<223> OTHER INFORMATION: ASO-002165

<400> SEQUENCE: 880
ttccatcact tcgaactcct 20

<210> SEQ ID NO 881
<211> LENGTH: 16
<212> TYPE: DNA
<213> ORGANISM: Artificial Sequence
<220> FEATURE:
<223> OTHER INFORMATION: ASO-002172

<400> SEQUENCE: 881
catcacttcg aactcc 16

<210> SEQ ID NO 882
<211> LENGTH: 17
<212> TYPE: DNA
<213> ORGANISM: Artificial Sequence
<220> FEATURE:
<223> OTHER INFORMATION: ASO-002173

<400> SEQUENCE: 882
catcacttcg aactcct 17

<210> SEQ ID NO 883
<211> LENGTH: 17
<212> TYPE: DNA
<213> ORGANISM: Artificial Sequence
<220> FEATURE:
<223> OTHER INFORMATION: ASO-002174

<400> SEQUENCE: 883
tccatcactt cgaactc 17

<210> SEQ ID NO 884
<211> LENGTH: 18
<212> TYPE: DNA
<213> ORGANISM: Artificial Sequence
<220> FEATURE:
<223> OTHER INFORMATION: ASO-002175

<400> SEQUENCE: 884
ccatcacttc gaactcct 18

<210> SEQ ID NO 885
<211> LENGTH: 18
<212> TYPE: DNA
<213> ORGANISM: Artificial Sequence
<220> FEATURE:
<223> OTHER INFORMATION: ASO-002176

<400> SEQUENCE: 885
ttccatcact tcgaactc 18

<210> SEQ ID NO 886
<211> LENGTH: 20
<212> TYPE: DNA
<213> ORGANISM: Artificial Sequence
<220> FEATURE:
<223> OTHER INFORMATION: ASO-002177

<400> SEQUENCE: 886
ttccatcact tcgaactcct 20

<210> SEQ ID NO 887
<211> LENGTH: 16
<212> TYPE: DNA
<213> ORGANISM: Artificial Sequence
<220> FEATURE:
<223> OTHER INFORMATION: ASO-002184

<400> SEQUENCE: 887
ccatcacttc gaactc 16

<210> SEQ ID NO 888
<211> LENGTH: 17
<212> TYPE: DNA
<213> ORGANISM: Artificial Sequence
<220> FEATURE:
<223> OTHER INFORMATION: ASO-002185

<400> SEQUENCE: 888
catcacttcg aactcct 17

<210> SEQ ID NO 889
<211> LENGTH: 17
<212> TYPE: DNA
<213> ORGANISM: Artificial Sequence
<220> FEATURE:
<223> OTHER INFORMATION: ASO-002186

<400> SEQUENCE: 889
tccatcactt cgaactc 17

<210> SEQ ID NO 890
<211> LENGTH: 18
<212> TYPE: DNA
<213> ORGANISM: Artificial Sequence
<220> FEATURE:
<223> OTHER INFORMATION: ASO-002187

<400> SEQUENCE: 890
cttccatcac ttcgaact 18

<210> SEQ ID NO 891
<211> LENGTH: 18
<212> TYPE: DNA
<213> ORGANISM: Artificial Sequence
<220> FEATURE:
<223> OTHER INFORMATION: ASO-002188

<400> SEQUENCE: 891
ttccatcact tcgaactc 18

<210> SEQ ID NO 892

<211> LENGTH: 20
<212> TYPE: DNA
<213> ORGANISM: Artificial Sequence
<220> FEATURE:
<223> OTHER INFORMATION: ASO-002189

<400> SEQUENCE: 892
ttccatcact tcgaactcct 20

<210> SEQ ID NO 893
<211> LENGTH: 16
<212> TYPE: DNA
<213> ORGANISM: Artificial Sequence
<220> FEATURE:
<223> OTHER INFORMATION: ASO-002623

<400> SEQUENCE: 893
catcacttcg aactcc 16

<210> SEQ ID NO 894
<211> LENGTH: 16
<212> TYPE: DNA
<213> ORGANISM: Artificial Sequence
<220> FEATURE:
<223> OTHER INFORMATION: ASO-002667

<400> SEQUENCE: 894
catcacttcg aactcc 16

<210> SEQ ID NO 895
<211> LENGTH: 16
<212> TYPE: DNA
<213> ORGANISM: Artificial Sequence
<220> FEATURE:
<223> OTHER INFORMATION: ASO-002674

<400> SEQUENCE: 895
catcacttcg aactcc 16

<210> SEQ ID NO 896
<211> LENGTH: 16
<212> TYPE: DNA
<213> ORGANISM: Artificial Sequence
<220> FEATURE:
<223> OTHER INFORMATION: ASO-002631

<400> SEQUENCE: 896
catcacttcg aactcc 16

<210> SEQ ID NO 897
<211> LENGTH: 16
<212> TYPE: DNA
<213> ORGANISM: Artificial Sequence
<220> FEATURE:
<223> OTHER INFORMATION: ASO-002639

<400> SEQUENCE: 897
catcacttcg aactcc 16

<210> SEQ ID NO 898
<211> LENGTH: 16
<212> TYPE: DNA
<213> ORGANISM: Artificial Sequence
<220> FEATURE:
<223> OTHER INFORMATION: ASO-002624

<400> SEQUENCE: 898
catcacttcg aactcc 16

<210> SEQ ID NO 899
<211> LENGTH: 16
<212> TYPE: DNA
<213> ORGANISM: Artificial Sequence
<220> FEATURE:
<223> OTHER INFORMATION: ASO-002637

<400> SEQUENCE: 899
catcacttcg aactcc 16

<210> SEQ ID NO 900
<211> LENGTH: 16
<212> TYPE: DNA
<213> ORGANISM: Artificial Sequence
<220> FEATURE:
<223> OTHER INFORMATION: ASO-002651

<400> SEQUENCE: 900
catcacttcg aactcc 16

<210> SEQ ID NO 901
<211> LENGTH: 16
<212> TYPE: DNA
<213> ORGANISM: Artificial Sequence
<220> FEATURE:
<223> OTHER INFORMATION: ASO-002625

<400> SEQUENCE: 901
tagccctaaa gtccca 16

<210> SEQ ID NO 902
<211> LENGTH: 16
<212> TYPE: DNA
<213> ORGANISM: Artificial Sequence
<220> FEATURE:
<223> OTHER INFORMATION: ASO-002675

<400> SEQUENCE: 902
tagccctaaa gtccca 16

<210> SEQ ID NO 903
<211> LENGTH: 16
<212> TYPE: DNA
<213> ORGANISM: Artificial Sequence
<220> FEATURE:
<223> OTHER INFORMATION: ASO-002633

<400> SEQUENCE: 903
tagccctaaa gtccca 16

<210> SEQ ID NO 904
<211> LENGTH: 17
<212> TYPE: DNA
<213> ORGANISM: Artificial Sequence
<220> FEATURE:
<223> OTHER INFORMATION: ASO-002640

<400> SEQUENCE: 904
ccttaatttc accctca 17

<210> SEQ ID NO 905
<211> LENGTH: 17
<212> TYPE: DNA

<213> ORGANISM: Artificial Sequence
<220> FEATURE:
<223> OTHER INFORMATION: ASO-002632

<400> SEQUENCE: 905
ccttaatttc accctca 17

<210> SEQ ID NO 906
<211> LENGTH: 17
<212> TYPE: DNA
<213> ORGANISM: Artificial Sequence
<220> FEATURE:
<223> OTHER INFORMATION: ASO-002647

<400> SEQUENCE: 906
ccttaatttc accctca 17

<210> SEQ ID NO 907
<211> LENGTH: 16
<212> TYPE: DNA
<213> ORGANISM: Artificial Sequence
<220> FEATURE:
<223> OTHER INFORMATION: ASO-002655

<400> SEQUENCE: 907
ccttaatttc accctc 16

<210> SEQ ID NO 908
<211> LENGTH: 16
<212> TYPE: DNA
<213> ORGANISM: Artificial Sequence
<220> FEATURE:
<223> OTHER INFORMATION: ASO-002641

<400> SEQUENCE: 908
ccttaatttc accctc 16

<210> SEQ ID NO 909
<211> LENGTH: 16
<212> TYPE: DNA
<213> ORGANISM: Artificial Sequence
<220> FEATURE:
<223> OTHER INFORMATION: ASO-002648

<400> SEQUENCE: 909
ccttaatttc accctc 16

<210> SEQ ID NO 910
<211> LENGTH: 20
<212> TYPE: DNA
<213> ORGANISM: Artificial Sequence
<220> FEATURE:
<223> OTHER INFORMATION: ASO-002666

<400> SEQUENCE: 910
atttccaaat tcacttttac 20

<210> SEQ ID NO 911
<211> LENGTH: 20
<212> TYPE: DNA
<213> ORGANISM: Artificial Sequence
<220> FEATURE:
<223> OTHER INFORMATION: ASO-002659

<400> SEQUENCE: 911
atttccaaat tcacttttac 20

<210> SEQ ID NO 912
<211> LENGTH: 20
<212> TYPE: DNA
<213> ORGANISM: Artificial Sequence
<220> FEATURE:
<223> OTHER INFORMATION: ASO-002652

<400> SEQUENCE: 912
atttccaaat tcacttttac 20

<210> SEQ ID NO 913
<211> LENGTH: 20
<212> TYPE: DNA
<213> ORGANISM: Artificial Sequence
<220> FEATURE:
<223> OTHER INFORMATION: ASO-002645

<400> SEQUENCE: 913
atttccaaat tcacttttac 20

<210> SEQ ID NO 914
<211> LENGTH: 20
<212> TYPE: DNA
<213> ORGANISM: Artificial Sequence
<220> FEATURE:
<223> OTHER INFORMATION: ASO-002638

<400> SEQUENCE: 914
atttccaaat tcacttttac 20

<210> SEQ ID NO 915
<211> LENGTH: 20
<212> TYPE: DNA
<213> ORGANISM: Artificial Sequence
<220> FEATURE:
<223> OTHER INFORMATION: ASO-003270

<400> SEQUENCE: 915
atttccaaat tcacttttac 20

<210> SEQ ID NO 916
<211> LENGTH: 20
<212> TYPE: DNA
<213> ORGANISM: Artificial Sequence
<220> FEATURE:
<223> OTHER INFORMATION: ASO-003269

<400> SEQUENCE: 916
atttccaaat tcacttttac 20

<210> SEQ ID NO 917
<211> LENGTH: 20
<212> TYPE: DNA
<213> ORGANISM: Artificial Sequence
<220> FEATURE:
<223> OTHER INFORMATION: ASO-003268

<400> SEQUENCE: 917
atttccaaat tcacttttac 20

<210> SEQ ID NO 918
<211> LENGTH: 20
<212> TYPE: DNA
<213> ORGANISM: Artificial Sequence
<220> FEATURE:

<223> OTHER INFORMATION: ASO-002673

<400> SEQUENCE: 918
atttccaaat tcacttttac 20

<210> SEQ ID NO 919
<211> LENGTH: 20
<212> TYPE: DNA
<213> ORGANISM: Artificial Sequence
<220> FEATURE:
<223> OTHER INFORMATION: ASO-002661

<400> SEQUENCE: 919
tttatttcca aattcacttt 20

<210> SEQ ID NO 920
<211> LENGTH: 20
<212> TYPE: DNA
<213> ORGANISM: Artificial Sequence
<220> FEATURE:
<223> OTHER INFORMATION: ASO-002654

<400> SEQUENCE: 920
tttatttcca aattcacttt 20

<210> SEQ ID NO 921
<211> LENGTH: 20
<212> TYPE: DNA
<213> ORGANISM: Artificial Sequence
<220> FEATURE:
<223> OTHER INFORMATION: ASO-002668

<400> SEQUENCE: 921
tttatttcca aattcacttt 20

<210> SEQ ID NO 922
<211> LENGTH: 16
<212> TYPE: DNA
<213> ORGANISM: Artificial Sequence
<220> FEATURE:
<223> OTHER INFORMATION: ASO-002676

<400> SEQUENCE: 922
atttccaaat tcactt 16

<210> SEQ ID NO 923
<211> LENGTH: 16
<212> TYPE: DNA
<213> ORGANISM: Artificial Sequence
<220> FEATURE:
<223> OTHER INFORMATION: ASO-002669

<400> SEQUENCE: 923
atttccaaat tcactt 16

<210> SEQ ID NO 924
<211> LENGTH: 16
<212> TYPE: DNA
<213> ORGANISM: Artificial Sequence
<220> FEATURE:
<223> OTHER INFORMATION: ASO-002662

<400> SEQUENCE: 924
atttccaaat tcactt 16

<210> SEQ ID NO 925
<211> LENGTH: 16
<212> TYPE: DNA
<213> ORGANISM: Artificial Sequence
<220> FEATURE:
<223> OTHER INFORMATION: ASO-002672

<400> SEQUENCE: 925
tagccctaaa gtccca 16

<210> SEQ ID NO 926
<211> LENGTH: 17
<212> TYPE: DNA
<213> ORGANISM: Artificial Sequence
<220> FEATURE:
<223> OTHER INFORMATION: ASO-002658

<400> SEQUENCE: 926
ccttaatttc accctca 17

<210> SEQ ID NO 927
<211> LENGTH: 16
<212> TYPE: DNA
<213> ORGANISM: Artificial Sequence
<220> FEATURE:
<223> OTHER INFORMATION: ASO-002622

<400> SEQUENCE: 927
ccttaatttc accctc 16

<210> SEQ ID NO 928
<211> LENGTH: 20
<212> TYPE: DNA
<213> ORGANISM: Artificial Sequence
<220> FEATURE:
<223> OTHER INFORMATION: ASO-002629

<400> SEQUENCE: 928
atttccaaat tcacttttac 20

<210> SEQ ID NO 929
<211> LENGTH: 20
<212> TYPE: DNA
<213> ORGANISM: Artificial Sequence
<220> FEATURE:
<223> OTHER INFORMATION: ASO-002621

<400> SEQUENCE: 929
atttccaaat tcacttttac 20

<210> SEQ ID NO 930
<211> LENGTH: 20
<212> TYPE: DNA
<213> ORGANISM: Artificial Sequence
<220> FEATURE:
<223> OTHER INFORMATION: ASO-002665

<400> SEQUENCE: 930
tttatttcca aattcacttt 20

<210> SEQ ID NO 931
<211> LENGTH: 16
<212> TYPE: DNA
<213> ORGANISM: Artificial Sequence
<220> FEATURE:
<223> OTHER INFORMATION: ASO-002630

<400> SEQUENCE: 931
atttccaaat tcactt 16

<210> SEQ ID NO 932
<211> LENGTH: 20
<212> TYPE: DNA
<213> ORGANISM: Artificial Sequence
<220> FEATURE:
<223> OTHER INFORMATION: ASO-002399

<400> SEQUENCE: 932
atttccaaat tcacttttac 20

<210> SEQ ID NO 933
<211> LENGTH: 20
<212> TYPE: DNA
<213> ORGANISM: Artificial Sequence
<220> FEATURE:
<223> OTHER INFORMATION: ASO-002482

<400> SEQUENCE: 933
atttccaaat tcacttttac 20

<210> SEQ ID NO 934
<211> LENGTH: 20
<212> TYPE: DNA
<213> ORGANISM: Artificial Sequence
<220> FEATURE:
<223> OTHER INFORMATION: ASO-002437

<400> SEQUENCE: 934
atttccaaat tcacttttac 20

<210> SEQ ID NO 935
<211> LENGTH: 20
<212> TYPE: DNA
<213> ORGANISM: Artificial Sequence
<220> FEATURE:
<223> OTHER INFORMATION: ASO-002425

<400> SEQUENCE: 935
atttccaaat tcacttttac 20

<210> SEQ ID NO 936
<211> LENGTH: 16
<212> TYPE: DNA
<213> ORGANISM: Artificial Sequence
<220> FEATURE:
<223> OTHER INFORMATION: ASO-000069

<400> SEQUENCE: 936
atttccaaat tcactt 16

<210> SEQ ID NO 937
<211> LENGTH: 16
<212> TYPE: DNA
<213> ORGANISM: Artificial Sequence
<220> FEATURE:
<223> OTHER INFORMATION: ASO-000070

<400> SEQUENCE: 937
atttccaaat tcactt 16

<210> SEQ ID NO 938
<211> LENGTH: 17

<212> TYPE: DNA
<213> ORGANISM: Artificial Sequence
<220> FEATURE:
<223> OTHER INFORMATION: ASO-002107

<400> SEQUENCE: 938
cccttaattt caccctc 17

<210> SEQ ID NO 939
<211> LENGTH: 20
<212> TYPE: DNA
<213> ORGANISM: Artificial Sequence
<220> FEATURE:
<223> OTHER INFORMATION: ASO-257283

<400> SEQUENCE: 939
atttccaaat tcacttttac 20

<210> SEQ ID NO 940
<211> LENGTH: 20
<212> TYPE: DNA
<213> ORGANISM: Artificial Sequence
<220> FEATURE:
<223> OTHER INFORMATION: ASO-257284

<400> SEQUENCE: 940
atttccaaat tcacttttac 20

<210> SEQ ID NO 941
<211> LENGTH: 16
<212> TYPE: DNA
<213> ORGANISM: Artificial Sequence
<220> FEATURE:
<223> OTHER INFORMATION: ASO-002627

<400> SEQUENCE: 941
ccaaattcac ttttac 16

<210> SEQ ID NO 942
<211> LENGTH: 17
<212> TYPE: DNA
<213> ORGANISM: Artificial Sequence
<220> FEATURE:
<223> OTHER INFORMATION: ASO-002677

<400> SEQUENCE: 942
tccaaattca cttttac 17

<210> SEQ ID NO 943
<211> LENGTH: 18
<212> TYPE: DNA
<213> ORGANISM: Artificial Sequence
<220> FEATURE:
<223> OTHER INFORMATION: ASO-002670

<400> SEQUENCE: 943
ttccaaattc acttttac 18

<210> SEQ ID NO 944
<211> LENGTH: 19
<212> TYPE: DNA
<213> ORGANISM: Artificial Sequence
<220> FEATURE:
<223> OTHER INFORMATION: ASO-002663

<400> SEQUENCE: 944
tttccaaatt cacttttac 19

<210> SEQ ID NO 945
<211> LENGTH: 15
<212> TYPE: DNA
<213> ORGANISM: Artificial Sequence
<220> FEATURE:
<223> OTHER INFORMATION: ASO-002635

<400> SEQUENCE: 945
caaattcact tttac 15

<210> SEQ ID NO 946
<211> LENGTH: 18
<212> TYPE: DNA
<213> ORGANISM: Artificial Sequence
<220> FEATURE:
<223> OTHER INFORMATION: ASO-002643

<400> SEQUENCE: 946
tttccaaatt cacttta 18

<210> SEQ ID NO 947
<211> LENGTH: 16
<212> TYPE: DNA
<213> ORGANISM: Artificial Sequence
<220> FEATURE:
<223> OTHER INFORMATION: ASO-002671

<400> SEQUENCE: 947
tccaaattca ctttta 16

<210> SEQ ID NO 948
<211> LENGTH: 17
<212> TYPE: DNA
<213> ORGANISM: Artificial Sequence
<220> FEATURE:
<223> OTHER INFORMATION: ASO-002664

<400> SEQUENCE: 948
ttccaaattc actttta 17

<210> SEQ ID NO 949
<211> LENGTH: 19
<212> TYPE: DNA
<213> ORGANISM: Artificial Sequence
<220> FEATURE:
<223> OTHER INFORMATION: ASO-002626

<400> SEQUENCE: 949
atttccaaat tcactttta 19

<210> SEQ ID NO 950
<211> LENGTH: 18
<212> TYPE: DNA
<213> ORGANISM: Artificial Sequence
<220> FEATURE:
<223> OTHER INFORMATION: ASO-002634

<400> SEQUENCE: 950
atttccaaat tcactttt 18

<210> SEQ ID NO 951
<211> LENGTH: 17
<212> TYPE: DNA
<213> ORGANISM: Artificial Sequence

<220> FEATURE:
<223> OTHER INFORMATION: ASO-002642

<400> SEQUENCE: 951
atttccaaat tcacttt 17

<210> SEQ ID NO 952
<211> LENGTH: 16
<212> TYPE: DNA
<213> ORGANISM: Artificial Sequence
<220> FEATURE:
<223> OTHER INFORMATION: ASO-002649

<400> SEQUENCE: 952
atttccaaat tcactt 16

<210> SEQ ID NO 953
<211> LENGTH: 15
<212> TYPE: DNA
<213> ORGANISM: Artificial Sequence
<220> FEATURE:
<223> OTHER INFORMATION: ASO-002656

<400> SEQUENCE: 953
atttccaaat tcact 15

<210> SEQ ID NO 954
<211> LENGTH: 20
<212> TYPE: DNA
<213> ORGANISM: Artificial Sequence
<220> FEATURE:
<223> OTHER INFORMATION: Forward primer

<400> SEQUENCE: 954
caagctcgca tggtcagtaa 20

<210> SEQ ID NO 955
<211> LENGTH: 43
<212> TYPE: DNA
<213> ORGANISM: Artificial Sequence
<220> FEATURE:
<223> OTHER INFORMATION: Reverse primer

<400> SEQUENCE: 955
aattaaccct cactaaaggg agattctcag tggagccgat ctt 43

<210> SEQ ID NO 956
<211> LENGTH: 16
<212> TYPE: DNA
<213> ORGANISM: Artificial Sequence
<220> FEATURE:
<223> OTHER INFORMATION: SAN-002678

<400> SEQUENCE: 956
ttccaaattc actttt 16

<210> SEQ ID NO 957
<211> LENGTH: 17
<212> TYPE: DNA
<213> ORGANISM: Artificial Sequence
<220> FEATURE:
<223> OTHER INFORMATION: SAN-002650

<400> SEQUENCE: 957
tttccaaatt cactttt 17

-continued

```
<210> SEQ ID NO 958
<211> LENGTH: 16
<212> TYPE: DNA
<213> ORGANISM: Artificial Sequence
<220> FEATURE:
<223> OTHER INFORMATION: SAN-002657

<400> SEQUENCE: 958

tttccaaatt cacttt                                                    16


<210> SEQ ID NO 959
<211> LENGTH: 25
<212> TYPE: DNA
<213> ORGANISM: Artificial Sequence
<220> FEATURE:
<223> OTHER INFORMATION: RhoA

<400> SEQUENCE: 959

actttatttc caaatacact tcttt                                          25


<210> SEQ ID NO 960
<211> LENGTH: 16
<212> TYPE: DNA
<213> ORGANISM: Artificial Sequence
<220> FEATURE:
<223> OTHER INFORMATION: ASO-000071

<400> SEQUENCE: 960

atttccaaat tcactt                                                    16
```